United States Patent
Bair et al.

(10) Patent No.: US 9,422,281 B2
(45) Date of Patent: Aug. 23, 2016

(54) BENZOPIPERAZINE COMPOSITIONS AS BET BROMODOMAIN INHIBITORS

(71) Applicant: Forma Therapeutics, Inc., Watertown, MA (US)

(72) Inventors: Kenneth W. Bair, Wellesley, MA (US); Torsten Herbertz, Stow, MA (US); Goss S. Kauffman, Ledyard, CT (US); Katherine J. Kayser-Bricker, Branford, CT (US); George P. Luke, Clinton, CT (US); Matthew W. Martin, Arlington, MA (US); David S. Millan, Watertown, MA (US); Shawn E. R. Schiller, Haverhill, MA (US); Adam C. Talbot, Giulford, CT (US); Mark J. Tebbe, Arlington, MA (US)

(73) Assignee: Forma Therapeutics, Inc., Watertown, MA (US)

( * ) Notice: Subject to any disclaimer, the term of this patent is extended or adjusted under 35 U.S.C. 154(b) by 0 days.

(21) Appl. No.: 14/546,896

(22) Filed: Nov. 18, 2014

(65) Prior Publication Data
US 2015/0232465 A1 Aug. 20, 2015

Related U.S. Application Data

(60) Provisional application No. 62/054,806, filed on Sep. 24, 2014, provisional application No. 61/905,633, filed on Nov. 18, 2013.

(51) Int. Cl.

| | | |
|---|---|---|
| *C07D 241/12* | (2006.01) |
| *A61K 31/53* | (2006.01) |
| *C07D 471/04* | (2006.01) |
| *C07D 403/04* | (2006.01) |
| *A61K 31/498* | (2006.01) |
| *C07D 405/14* | (2006.01) |
| *C07D 417/14* | (2006.01) |
| *C07D 417/10* | (2006.01) |
| *C07D 241/42* | (2006.01) |
| *C07D 409/14* | (2006.01) |
| *C07D 405/06* | (2006.01) |
| *C07D 413/14* | (2006.01) |
| *C07D 413/04* | (2006.01) |
| *C07D 401/04* | (2006.01) |
| *C07D 403/14* | (2006.01) |
| *A61K 31/4985* | (2006.01) |
| *A61K 31/5377* | (2006.01) |
| *A61K 31/541* | (2006.01) |
| *A61K 31/551* | (2006.01) |

(52) U.S. Cl.
CPC ............ *C07D 471/04* (2013.01); *A61K 31/498* (2013.01); *A61K 31/4985* (2013.01); *A61K 31/5377* (2013.01); *A61K 31/541* (2013.01); *A61K 31/551* (2013.01); *C07D 241/42* (2013.01); *C07D 401/04* (2013.01); *C07D 403/04* (2013.01); *C07D 403/14* (2013.01); *C07D 405/06* (2013.01); *C07D 405/14* (2013.01); *C07D 409/14* (2013.01); *C07D 413/04* (2013.01); *C07D 413/14* (2013.01); *C07D 417/10* (2013.01); *C07D 417/14* (2013.01)

(58) Field of Classification Search
CPC .. C07D 241/42; C07D 401/04; C07D 403/04; C07D 403/14; C07D 405/06; C07D 405/14; C07D 409/14; C07D 413/04; C07D 413/14; C07D 417/10; C07D 417/14; C07D 471/04; A61K 31/53; A61K 31/77; A61K 31/541; A61K 31/551; A61K 31/4985; A61K 31/498
See application file for complete search history.

(56) References Cited

U.S. PATENT DOCUMENTS

| | | |
|---|---|---|
| 4,576,954 A | 3/1986 | Bourzat et al. |
| 5,041,454 A | 8/1991 | Van Daele et al. |
| 5,244,898 A | 9/1993 | Ogawa et al. |
| 5,256,625 A | 10/1993 | Bussler et al. |
| 5,378,726 A | 1/1995 | Yanagi et al. |
| 5,462,965 A | 10/1995 | Roba et al. |
| 5,521,170 A | 5/1996 | Setoi et al. |
| 5,719,141 A | 2/1998 | Rasetti et al. |
| 5,739,130 A | 4/1998 | Matsuo et al. |
| 5,994,379 A | 11/1999 | Bayly et al. |
| 6,159,966 A | 12/2000 | Lohray et al. |
| 6,315,928 B1 | 11/2001 | Mann et al. |

(Continued)

FOREIGN PATENT DOCUMENTS

| | | |
|---|---|---|
| EP | 0028765 | 5/1981 |
| EP | 0190105 | 8/1986 |

(Continued)

OTHER PUBLICATIONS

Cartigny, J ORg Chem, vol. 77, 4544-4556, 2012.*

(Continued)

*Primary Examiner* — D M Seaman
(74) *Attorney, Agent, or Firm* — Cooley LLP

(57) ABSTRACT

The present invention relates to inhibitors of bromo and extra terminal (BET) br'omodomains that are useful for the treatment of cancer, inflammatory diseases, diabetes, and obesity, having Formula (I):

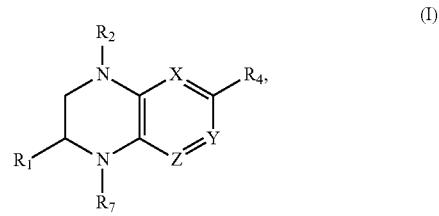

wherein X, Y, Z, $R_1$, $R_2$, $R_4$ and $R_7$ are defined herein.

35 Claims, No Drawings

(56) References Cited

U.S. PATENT DOCUMENTS

| | | | |
|---|---|---|---|
| 6,329,389 B1 | 12/2001 | Suzuki et al. |
| 6,632,814 B1 | 10/2003 | Bourzat et al. |
| 6,642,228 B1 | 11/2003 | Hayashi et al. |
| 6,696,448 B2 | 2/2004 | Tang et al. |
| 6,720,420 B2 | 4/2004 | Zhao et al. |
| 6,809,095 B2 | 10/2004 | Lohray et al. |
| 6,930,104 B2 | 8/2005 | Kakihana et al. |
| 7,135,434 B2 | 11/2006 | Ziemer et al. |
| 7,297,696 B2 | 11/2007 | Laborde et al. |
| 7,388,095 B2 | 6/2008 | Nettekoven et al. |
| 7,459,555 B2 | 12/2008 | Melzig et al. |
| 7,741,317 B2 | 6/2010 | Chao et al. |
| 7,745,479 B2 | 6/2010 | Nettekoven et al. |
| 7,807,672 B2 | 10/2010 | Deng et al. |
| 7,879,845 B2 | 2/2011 | Ackermann et al. |
| 7,897,773 B2 | 3/2011 | Aletru et al. |
| 7,902,184 B2 | 3/2011 | Nettekoven et al. |
| 7,906,619 B2 | 3/2011 | Phadke et al. |
| 7,947,834 B2 | 5/2011 | Braun et al. |
| 7,951,950 B2 | 5/2011 | Little et al. |
| 8,119,656 B2 | 2/2012 | Roth et al. |
| 8,153,631 B2 | 4/2012 | Powers et al. |
| 8,188,073 B2 | 5/2012 | Iijima et al. |
| 8,222,417 B2 | 7/2012 | Suzuki et al. |
| 8,288,377 B2 | 10/2012 | Storck et al. |
| 8,309,734 B2 | 11/2012 | Bissantz et al. |
| 8,394,825 B2 | 3/2013 | Leese et al. |
| 8,637,507 B2 | 1/2014 | Zhou et al. |
| 8,722,633 B2 | 5/2014 | Bebernitz et al. |
| 8,729,091 B2 | 5/2014 | Bissantz et al. |
| 8,865,918 B2 | 10/2014 | Zhi et al. |
| 2003/0216398 A1 | 11/2003 | Kakihana et al. |
| 2004/0043985 A1 | 3/2004 | Hicks et al. |
| 2004/0138199 A1 | 7/2004 | Gogliotti et al. |
| 2006/0122224 A1 | 6/2006 | Bechle et al. |
| 2007/0010670 A1 | 1/2007 | Hirata et al. |
| 2009/0005344 A1 | 1/2009 | Burns et al. |
| 2009/0012045 A1 | 1/2009 | Hitoshi et al. |
| 2009/0018118 A1 | 1/2009 | Urleb et al. |
| 2009/0088371 A1 | 4/2009 | Grossbard |
| 2009/0264384 A1 | 10/2009 | Didsbury et al. |
| 2010/0234422 A1 | 9/2010 | McComas et al. |
| 2012/0165370 A1 | 6/2012 | Tang et al. |
| 2013/0190258 A1 | 7/2013 | Cashman et al. |
| 2014/0088094 A1 | 3/2014 | Glick et al. |
| 2014/0205567 A1 | 7/2014 | Zhan |
| 2014/0206673 A1 | 7/2014 | Cao et al. |

FOREIGN PATENT DOCUMENTS

| | | |
|---|---|---|
| EP | 0480902 | 4/1992 |
| EP | 1968598 | 9/2008 |
| WO | WO 96/33723 | 10/1996 |
| WO | WO98/35939 | 8/1998 |
| WO | WO99/18951 | 4/1999 |
| WO | WO02/080895 | 10/2002 |
| WO | 2004085401 | * 10/2004 |
| WO | WO2005/028451 | 3/2005 |
| WO | WO2005/112932 | 11/2005 |
| WO | WO2006/009819 | 1/2006 |
| WO | WO2006/094210 | 9/2006 |
| WO | WO2007/146230 | 12/2007 |

OTHER PUBLICATIONS

Li, Bioorg Med Chem Lett, vol. 19, 3952-3954, 2009.*
Asangani, Nature, Jun. 12, 2014, 510(7504), 278-282.*
Vlcek, Collect Czech Chem COmmun, vol. 64, 1999, 633-648.*
Xiao, Rheumatology Oxford Journals, www.rheumatology.oxfordjournals.org, 2015, 1-12.*
Muller, www.expertreviews.org, doi:10.1017/S1462399411001992; vol. 13; e29; Sep. 2011, pp. 1-5.*
Liao, Oncotarget, vol. 7(8), 9491-9500, Jan. 2016.*
Wei, International Immunopharmacology, vol. 29, 314-319, 2015.*
Lenhart, Molecular Cancer Therapeutics, vol. 14, 2167-2174, Aug. 2015.*
Aguilera, Roland, et al. "Nuclear Magnetic Resonance Study of the Conformation of 1,2,3,4-Tetrahydroquinoxaline Derivatives" Div. Chim. Pharmacol., Centre Rech. Serv. Sante Armees, Lyons, Fr. (1968), (11), 4491-7.
Baxter, I.; et al. "Reductive Formylation of Some Quinoxaline Derivatives", Journal of the Chemical Society [Section] C: Organic, (1968), (19), 2471-4.
Cartigny, Damien et al., "General Asymmetric Hydrogenation of 2-Alkyl-and 2-Aryl-Substituted Quinoxaline Derivatives Catalyzed by Iridium-Difluorphos: Unusual Halide Effect and Synthetic Application" Journal of Organic Chemistry (2012), 77(10), 4544-4556.
Chen, Ying-Chun et al., "Organocatalytic Enantioselective Hetero-Diels-Alder Reaction of Aldehydes and O-Benzoquinone Diimide:Synthesis of Optically Active Hydroquinoxalines", Bioorganic & Medicinal Chemistry Letters (2009).
Eary, C. Todd, et al., "Tetrazole and Ester Substituted Tetrahydroquinoxalines as Potent Cholesteryl Ester Transfer Protein Inhibitors", Bioorganic & Medicinal Chemistry Letters (2007),17(9), 2608-2613.
Fisher, George H.et al., "Quinoxaline Studies. XXII. Tosylation and Chiralities of 2-Substituted 1,2,3,4-Tetrahydroquinoxalines" Journal of Organic Chemistry (1974), 39(5), 635-40.
Fisher, George H.et al., "Quinoxaline Studies. XVI. Unequivocal Synthesis of (S)-2-Methyl-1,2,3,4-Tetrahydroquinoxaline", Journal of Organic Chemistry (1970), 35(7), 2240-2.
Friedrichsen, W., et al. "Cycloadditions With O-Benzoquinone Diimines, II. Reactions of O-Benzoquinone Diimines With Olefins" Justus Liebigs Annalen der Chemie (1978), (7), 1129-38.
Friedrichsen, W., et al. "Cycloaddition Reactions of O-Benzoquinone Dibenzimines" Tetrahedron Letters (1974), (33), 2827-30.
Gorczyca, M., et al., "Search for New Xanthine Drugs. XXVII. 1-(*-Hydroxy-*- Dialkylaminopropyl)Theobromines", Farmaco, Edizione Scientifica (1966), 21(5), 338-45.
Landriani, L. et al. "C-Alkylpiperazines. XII. Synthesis and Diuretic Activity of Compounds Structurally Related to Clopamide" Farmaco, Edizione Scientifica (1987), 42(3), 191-204.
Maffei, Silvio, et al., "Hydrogenation of Phenazines and Quinoxalines" Gazzetta Chimica Italiana (1958), 88, 556-63.
Mantlo, Nathan B., et al., "Update on the Discovery and Development of Cholesteryl Ester Transfer Protein Inhibitors for Reducing Residual Cardiovascular Risk" Journal of Medical Chemistry (2014), 57(1), 1-17.
Maidwell, Nicola L., "On the Development of NAD(P)H-Sensitive Fluorescent Probes" Perkin 1 (2000), (10), 1541-1546.
Chen et al., "Stereochemistry of Fully Acetylated Tetrahydropterins and Tetrahydroquinoxalines" Heterocycles (2005), 65(12), 2917-2924.
Russell, James R., "Model Studies Related to the Cofactor of Oxomolybdoenzymes. Part 4. Reduction of the Pyrazine Ring in Quinoxalines and Pteridines", Journal of the Chemical Society, Perkin Transactions 1: Organic and Bio-Organic Chemistry (1972-1999) (1992), (10), 1245-9.
Schuyler, Peter, et al., "Synthesis of Potential Antineoplastic Agents. XV. Some 1,4-Bisamides of 1,2,3,4-Tetrahydroquinoxaline" Journal of Medicinal Chemistry (1966), 9(5), 704-7.
Walser, A., et al., "Quinazolines and 1,4-Benzodiazepines. L. Ring Contraction of 4-Hydroxy-5-Phenyltetrahydro-1,4-Benzodiazepines to Tetrahydroquinoxalines" Journal of Organic Chemistry (1971), 36(9), 1248-51.
Zellner, H., et al., "Syntheses of Quinoxaline Derivatives" Helvetica Chimica Acta (1966), 49(2), 913-39.

* cited by examiner

BENZOPIPERAZINE COMPOSITIONS AS BET BROMODOMAIN INHIBITORS

PRIORITY

This application claims priority to, and the benefit of, U.S. provisional application No. 61/905,633, filed Nov. 18, 2013 and U.S. provisional application No. 62/054,806, filed Sep. 24, 2014, the entire disclosures of which are incorporated herein by reference in their entirety.

FIELD OF THE INVENTION

The present invention is directed to inhibitors of the bromo and extra terminal (BET) family of bromodomains useful in the treatment of disease or disorders associated with the inhibition of the bromo and extra terminal (BET) family of bromodomains. Specifically, the invention is concerned with compounds and compositions for inhibition of the bromo and extra terminal (BET) family of bromodomains, methods of treating, preventing, or ameliorating diseases or disorders associated with the inhibition of bromo and extra terminal (BET) family of bromodomains, and methods of synthesis of these compounds.

BACKGROUND OF THE INVENTION

The bromo and extra terminal (BET) family proteins contain four members in mammals, BRD2, BRD3, BRD4, and BRDT, with each of these containing two bromodomains (BRD): a conserved N-terminal bromodomain (bromodomain 1 [BD1]) and a C-terminal bromodomain (bromodomain 2 [BD2]). BET family proteins have been shown to have a critical role in cellular proliferation and cell cycle progression.

Bromodomain containing proteins are known to be involved in transcriptional regulation. In general, bromodomains are found in proteins that regulate chromatin structure and gene expression. The presence of these proteins is required for the systematic expression of various growth and antiapoptotic genes. Additionally, these proteins play a role in the omnipresent cell cycle progression, as many nuclear proteins have bromodomains that interact with chromatin such as histone acetyltransferases. Dysfunction of bromodomain containing proteins has been linked to the development of a number of diseases, particularly to the development of cancer. (Muller, S. Filippakopoulos, P. Knapp, S. (2011), Bromodomains as therapeutic targets. *Expert Rev. Mol. Med.* 13: e29). Bromodomains have also been implicated in inflammatory processes (Nicodeme et al, *Nature*, 2010, Vol. 468, pg. 1119).

BRD4 protein, as a gene product, contains 1362 amino acids. BRD4 BD1 is ~75-147; BRD4 BD2 is ~368-440; thus each is 73 residues long. For the purpose of biochemical screening, biophysics or X-ray crystallography various protein constructs with additional N- and C-terminal residues added for both bromodomains are expressed and used. In addition, protein constructs with both bromodomains expressed within the same protein have also been used (~400 aa residues total).

The protein is comprised of four alpha helices, all left hand oriented, which is in stark contrast to the highly diverse sequential nature of the proteins. The helices ($\alpha_Z$, $\alpha_A$, $\alpha_C$, and $\alpha_B$) are arranged in such a way that the Z and A helices interact forming the long "ZA loop" and the C and B helices interact forming the short "BC loop." (Dhalluin C., Carlson J. E., Zeng L., He C., Aggarwal A. K., Zhou M. M. (1999), Structure and ligand of a histone acetyltransferase bromodomain. *Nature*. 399, 491-6.). These loops form hydrophobic pockets in the protein where the protein interacts with acetylated lysine residues. Mutagenesis studies suggest that tertiary contacts amongst the hydrophobic and aromatic residues between the two inter-helical loops contribute directly to the structural stability of the protein. ((Dhalluin C., Carlson J. E., Zeng L., He C., Aggarwal A. K., Zhou M. M. (1999), Structure and ligand of a histone acetyltransferase bromodomain. *Nature*. 399, 491-6.).

It has long been suggested that bromodomains play an important role on chromatin remodeling. In recent years, certain proteins of the double bromodomain family, including BRD2, BRD3, BRD4, and BRDT have been identified as major epigenetic regulators in human cancer. As such, these double bromodomains appear to play a particularly vital role in human cancer proliferation and differentiation. For example, BRD4 affects the breast cancer microenvironment and survival rates. (Crawford, N. P, Alsarraj, J., Lukes, L., Walker, R. C., Officewala, J. S., Yang, H. H., Lee, M. P., Ozato, K., Hunter, K. W. (2008), Bromodomain 4 Activation Predicts Breast Cancer Survival. *Proc. Natl. Acad. Sci. USA*. 105(17): 6380-6385.). BRD4 also plays a role in Kaposi's sarcoma and BRD2 factors in to some mixed lineage leukemias. (Guo, N., Faller, D. V., Denis, G. V., Activation-Induced Nuclear Translocation of RING3 (2001), *J. Cell Sci*. 113(17): 3085-3091.). In addition, genetic knockdown by RNAi or exposure of cells to BET inhibitors has resulted in significant transcriptional downregulation of MYC, a mutated version of which is found in many cancers. (Delmore J. E., Issa G. C., Lemieux M. E., Rahl, P. B., Shi J., Jacobs H. M. (2011), BET Bromodomain Inhibition as a Therapeutic Strategy to Target c-Myc. *Cell*. 146: 904-17.). Thus, inhibition of these interactions and exposure of cells to BET inhibitors results in a significant transcriptional downregulation. This, in turn, provides the medical community with a novel pharmacological strategy for the treatment of cancer.

The highly differentiated sequential nature of bromodomains has remained a severe obstacle in the discovery of potent and efficacious bromodomain inhibitors. (Dawson, M. A, Prinjha, R. K., Dittman, A. Giotopoulos, G. Bantcheff, M., Chan, W-I., Robson, S. C., Chung, C., Hopf, C., Savitski, M. M., Hutmacher, C., Gudgin, E., Lugo, D., Beinke, S., Chapman. T. D., Roberts, E. J., Soden. P. E., Auger, K. R., Mirguet, O., Doehner, K., Delwel, R., Burnett, A. K., Jeffrey, P., Drewes, G., Lee, K., Huntly, B. J. P. and Kouzarides, T. (2011), Inhibition of BET recruitment of chromatin as an effective treatment of MLL-fusion leukemia. *Nature*. 0: 1-5; Picaud, S., Da Costa, D. Thanasopoulou, A., Filippakopoulos, P., Fish, P., Philpott, M., Federov, O. Brennan, P., Bunnage, M. E., Owen, D. R., Bradner, J. E., Taniere, P., O'Sullivan, B., Muller, S, Schwaller, J., Stankovic, T., Knapp, S., PFI-1—A highly Selective Protein Interaction Inhibitor Targeting BET Bromodomains, *Cancer Res*., 73(11), 2013, 3336-3346). As a result, there are currently no approved bromodomain inhibitors available on the market despite their well-recognized potential as anti-cancer therapeutic agents. For these reasons, there remains a considerable need for novel and potent small molecule modulators of BET bromodomains.

SUMMARY OF THE INVENTION

One aspect of the present invention relates to compounds of Formula (I):

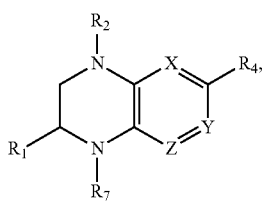

and pharmaceutically acceptable salts, enantiomers, hydrates, solvates, prodrugs, isomers, or tautomers thereof, wherein:

X is selected from N or $CR_3$;
Y is selected from N or $CR_5$;
Z is selected from N or $CR_6$;
$R_1$ is hydrogen, $C_1$-$C_6$ alkyl, or $C_1$-$C_6$ haloalkyl;
$R_2$ is —C(O)(CR$^k$R$^l$)$_n$O(CR$^k$R$^l$)$_m$R$^d$, —C(O)(CR$^k$R$^l$)$_n$R$^e$, —S(O)$_2$(CR$^k$R$^l$)$_n$R$^f$, —(CR$^k$R$^l$)$_n$R$^g$, —C(O)(CR$^k$R$^l$)$_n$NR$^a$R$^g$ or —C(O)(CR$^k$R$^l$)$_n$S(CR$^k$R$^l$)$_m$R$^f$;
$R_3$ and $R_6$ are each independently selected from hydrogen or halogen;
$R_4$ is hydrogen, halogen, $C_1$-$C_6$ alkyl, $C_3$-$C_6$ cycloalkyl, $C_6$-$C_{10}$ aryl, heterocycloalkyl, heteroaryl, —NR$^a$R$^b$, —C(O)R$^h$, —OR$^h$, $C_1$-$C_6$ haloalkyl, $C_2$-$C_6$ alkenyl, $C_2$-$C_6$ alkynyl, —$C_1$-$C_4$ alkyl(aryl), —$C_1$-$C_4$ alkyl(heteroaryl), or —$C_1$-$C_4$ alkyl(heterocycloalkyl), wherein the cycloalkyl, aryl, heterocycloalkyl, heteroaryl, and alkyl are optionally substituted with one or more $R_{10}$;
$R_5$ is hydrogen, halogen, $C_1$-$C_6$ alkyl, nitro, —NH$_2$, $C_1$-$C_6$ alkylamino, $C_1$-$C_6$ dialkylamino, $C_1$-$C_6$ aminoalkyl, $C_1$-$C_6$ aminoalkoxy, CN, $C_1$-$C_6$ alkoxy, —C(O)NR$^a$R$^b$, —NR$^a$S(O)$_2$R$^b$, —NR$^a$C(O)R$^b$, —NR$^a$C(O)OR$^b$, —NR$^a$C(O)NR$^b$R$^c$, $C_1$-$C_6$ haloalkyl, $C_1$-$C_6$ haloalkoxy, —S(O)$_2$NR$^a$R$^b$, or —S(O)$_2$R$^a$;
$R_7$ is —C(O)R$_8$, —C(O)OR$_8$, —C(O)NR$_8$R$_9$, or —S(O)$_2$R$_8$;
$R_8$ and $R_9$ are each independently hydrogen, —(CR$^k$R$^l$)$_m$OR$^a$, $C_1$-$C_6$ alkyl, $C_1$-$C_6$ haloalkyl, $C_3$-$C_6$ cycloalkyl, heterocycloalkyl, aryl, or heteroaryl;
each $R_{10}$ is independently at each occurrence selected from the group consisting of $C_1$-$C_6$ alkyl, $C_1$-$C_6$ alkoxy, $C_1$-$C_6$ hydroxyalkyl, $C_1$-$C_6$ haloalkyl, $C_1$-$C_6$ haloalkoxy, —OR$^i$, —NR$^a$R$^i$, CN, oxo, —(CR$^k$R$^l$)$_n$S(O)$_2$R$^i$, —(CR$^k$R$^l$)$_n$NR$^a$S(O)$_2$R$^i$, —(CR$^k$R$^l$)$_n$S(O)$_2$NR$^a$R$^i$, —(CR$^k$R$^l$)$_n$NR$^a$R$^i$S(O)$_2$NR$^a$R$^i$, —(CR$^k$R$^l$)$_n$C(O)OR$^a$, —(CR$^k$R$^l$)$_n$C(O)R$^i$, —(CR$^k$R$^l$)$_n$C(O)NR$^a$R$^i$, —(CR$^k$R$^l$)$_n$R$^i$, —(CR$^k$R$^l$)$_n$NR$^a$C(O)NR$^b$, —(CR$^k$R$^l$)$_n$NR$^a$C(O)OR$^b$, and oxo, wherein each alkyl is substituted with one or more $R_{11}$; or
two $R_{10}$ together when on adjacent carbons form an aryl ring optionally substituted with one or more $R_{11}$; or two $R_{10}$ together when on adjacent carbons form a heteroaryl ring optionally substituted with one or more $R_{11}$; or two $R_{10}$ together when on adjacent carbons form a heterocycloalkyl ring optionally substituted with one or more $R_{11}$;
each $R_{11}$ is independently at each occurrence selected from halogen, $C_1$-$C_6$ alkyl, $C_1$-$C_6$ alkoxy, $C_1$-$C_6$ haloalkyl, $C_1$-$C_6$ haloalkoxy, hydroxy, CN, $C_1$-$C_6$ hydroxyalkyl, —(CR$^k$R$^l$)$_m$NH$_2$, $C_1$-$C_6$ alkylamino, $C_1$-$C_6$ dialkylamino, —C(O)NR$^a$R$^b$, —C(O)OR$^a$, —C(O)R$^a$, —S(O)$_2$R$^a$, —C(O)H, —NR$^a$C(O)OR$^a$, —NR$^a$C(O)$C_1$-$C_6$ alkyl, or oxo;
or two $R_{11}$ together can form a heterocycloalkyl ring;
R$^a$, R$^b$, and R$^c$ are each independently at each occurrence hydrogen, $C_1$-$C_6$ alkyl, —$C_1$-$C_4$ alkyl(aryl), or aryl, wherein the alkyl and aryl are optionally substituted with one or more $R_{10}$;

R$^d$ is $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, CN, —C(O)$C_1$-$C_6$ alkyl, $C_3$-$C_7$ cycloalkyl, aryl, heteroaryl, or heterocycloalkyl, wherein cycloalkyl, aryl, heteroaryl, and heterocycloalkyl are optionally substituted with one or more $R_{12}$;
R$^e$ is hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_1$-$C_6$ alkoxy, CN, $C_3$-$C_7$ cycloalkyl, aryl, heteroaryl, or heterocycloalkyl, wherein cycloalkyl, aryl, heteroaryl, and heterocycloalkyl are optionally substituted with one or more $R_{12}$;
R$^f$ is $C_3$-$C_7$ cycloalkyl, aryl, heteroaryl, or heterocycloalkyl, wherein cycloalkyl, aryl, heteroaryl and heterocycloalkyl are optionally substituted with one or more $R_{12}$;
R$^g$ is $C_1$-$C_6$ alkyl, $C_3$-$C_7$ cycloalkyl, —$C_1$-$C_4$ alkyl($C_3$-$C_7$ cycloalkyl), aryl, —$C_1$-$C_4$ alkyl(aryl), heteroaryl, —$C_1$-$C_4$ alkyl(heteroaryl), heterocycloalkyl, or —$C_1$-$C_4$ alkyl(heterocycloalkyl), wherein cycloalkyl, aryl, heteroaryl, and heterocycloalkyl are optionally substituted with one or more $R_{12}$;
R$^h$ is $C_3$-$C_7$ cycloalkyl, aryl, heteroaryl, or heterocycloalkyl, wherein cycloalkyl, aryl, heteroaryl, and heterocycloalkyl are optionally substituted with one or more $R_{10}$;
R$^i$ is hydrogen, $C_1$-$C_6$ alkyl, $C_1$-$C_6$ alkoxy, $C_1$-$C_6$ hydroxyalkyl, $C_1$-$C_6$ haloalkyl, —(CH$_2$)$_q$N(H)$C_1$-$C_6$ alkyl, —(CH$_2$)$_q$N($C_1$-$C_6$ alkyl)$_2$, —(CR$^k$R$^l$)$_m$$C_3$-$C_7$ cycloalkyl, —(CR$^k$R$^l$)$_m$aryl, —(CR$^k$R$^l$)$_m$heteroaryl, or —(CR$^k$R$^l$)$_m$heterocycloalkyl, wherein alkyl, cycloalkyl, aryl, heteroaryl, and heterocycloalkyl are optionally substituted with one or more $R^{11}$;
each $R_{12}$ is independently at each occurrence selected from $C_1$-$C_6$ alkyl, halogen, CN, $C_1$-$C_6$ alkoxy, $C_1$-$C_6$ haloalkyl, $C_1$-$C_6$ haloalkoxy, hydroxy, NO$_2$, —NH$_2$, CH$_2$NH$_2$, —(CH$_2$)$_q$N($C_1$-$C_6$ alkyl)$_2$, $C_1$-$C_6$ alkylamino, $C_1$-$C_6$ dialkylamino, —O(CH$_2$)$_q$N(H)$C_1$-$C_6$ alkyl, —O(CH$_2$)$_q$N($C_1$-$C_6$ alkyl)$_2$, aryl, heteroaryl, —NH-heteroaryl, —O-aryl, —S(O)$_p$—$C_1$-$C_6$ alkyl, —S(O)$_p$—N(H)$C_1$-$C_6$ alkyl, —S(O)$_p$—N($C_1$-$C_6$ alkyl)$_2$, —C(O)$C_1$-$C_6$ alkyl, —C(O)OC$_1$-$C_6$ alkyl, —NHC(O)($C_1$-$C_6$ alkyl), or oxo, wherein aryl and heteroaryl are optionally substituted with one or more substituents selected from $C_1$-$C_6$ alkyl, halogen, CN, $C_1$-$C_6$ alkoxy, hydroxy, NO$_2$, —NH$_2$, $C_1$-$C_6$ alkylamino, or $C_1$-$C_6$ dialkylamino; or
two $R_{12}$ together with the carbon to which they are attached can form a 4- to 6 membered heterospirocycle; or two $R_{12}$ together when on adjacent carbons form a $C_4$-$C_6$ cycloalkyl optionally substituted with one or more $R_{13}$; or two $R_{12}$ together when on adjacent carbons form an aryl optionally substituted with one or more $R_{13}$; or two $R_{12}$ together when on adjacent carbons form a heteroaryl optionally substituted with one or more $R_{13}$; or two $R_{12}$ together when on adjacent carbons form a heterocycloalkyl optionally substituted with one or more $R_{13}$; or $R_{12}$ with the carbon to which it is attached and the adjacent carbon form a $C_3$ cycloalkyl optionally substituted with one or more $R_{13}$;
each $R_{13}$ is independently at each occurrence selected from $C_1$-$C_6$ alkyl, halogen, CN, $C_1$-$C_6$ alkoxy, $C_1$-$C_6$ haloalkyl, $C_1$-$C_6$ haloalkoxy, hydroxy, NO$_2$, —NH$_2$, CH$_2$NH$_2$, —(CH$_2$)$_q$N($C_1$-$C_6$ alkyl)$_2$, $C_1$-$C_6$ alkylamino, $C_1$-$C_6$ dialkylamino, —O(CH$_2$)$_q$N(H)$C_1$-$C_6$ alkyl, —O(CH$_2$)$_q$N($C_1$-$C_6$ alkyl)$_2$, aryl, heteroaryl, —NH-heteroaryl, —O-aryl, —S(O)$_p$—$C_1$-$C_6$ alkyl, —S(O)$_p$—N(H)$C_1$-$C_6$ alkyl, —S(O)$_p$—N($C_1$-$C_6$ alkyl)$_2$, —C(O)$C_1$-$C_6$ alkyl, —NHC(O)($C_1$-$C_6$ alkyl), or oxo, wherein aryl and heteroaryl are optionally substituted with one or more substituents selected from the group consisting of $C_1$-$C_6$ alkyl, halogen, CN, $C_1$-$C_6$ alkoxy, hydroxy, NO$_2$, —NH$_2$, $C_1$-$C_6$ alkylamino, and $C_1$-$C_6$ dialkylamino;
R$^k$ and R$^l$ are each independently at each occurrence selected from H, $C_1$-$C_6$ alkyl, $C_1$-$C_6$ alkoxy, $C_1$-$C_6$ haloalkyl, or halogen;

each m, n, and p is independently at each occurrence 0, 1, or 2; and each q is independently at each occurrence 1, 2, 3 or 4;

provided that when m is 0, $R^d$ is not $C_1$-$C_6$ alkoxy, $C_1$-$C_6$ haloalkoxy, or CN.

Another aspect of the present invention relates to a pharmaceutical composition comprising a compound of Formula (I), or a pharmaceutically acceptable salt, hydrate, solvate, prodrug, stereoisomer, or tautomer thereof and a pharmaceutically acceptable carrier.

In another aspect, the present invention relates to a method of modulating one or more of BET-family bromodomains. The method comprises administering to a patient in need thereof a therapeutically effective amount of a compound of Formula (I), or a pharmaceutically acceptable salt, hydrate, solvate, prodrug, stereoisomer, or tautomer thereof.

Another aspect of the present invention relates to a method of inhibiting one or more of BET-family bromodomains. The method comprises administering to a patient in need thereof a therapeutically effective amount of a compound of Formula (I), or a pharmaceutically acceptable salt, hydrate, solvate, prodrug, stereoisomer, or tautomer thereof.

In another aspect, the present invention relates to a method of inhibiting one or more of BET-family bromodomains. The method comprises administering to a patient in need thereof a therapeutically effective amount of the pharmaceutical composition of Formula (I).

Another aspect of the present invention relates to a method of treating, preventing, inhibiting, or eliminating a disease or condition in a patient associated with the inhibition of one or more of BET-family bromodomains. The method comprises administering to a patient in need thereof a therapeutically effective amount of a compound of Formula (I), or a pharmaceutically acceptable salt, hydrate, solvate, prodrug, stereoisomer, or tautomer thereof, wherein said disease or condition is selected from the group consisting of cancer, inflammatory disorders, irritable bowel syndrome, inflammatory bowel disease, rheumatoid arthritis, obesity and diabetes.

In another aspect, the present invention relates to a male contraceptive comprising a therapeutically effective amount of a compound of Formula (I), or a pharmaceutically acceptable salt, hydrate, solvate, prodrug, stereoisomer, or tautomer thereof.

The present invention provides inhibitors of BET domains that are therapeutic agents in the treatment of diseases such as cancer, inflammation, metabolic and neurological disorders, and infectious diseases.

The present invention further provides compounds and compositions with an improved efficacy and safety profile relative to known BET domain inhibitors. The present disclosure also provides agents with novel mechanisms of action toward BET proteins in the treatment of various types of diseases including cancers, inflammations, metabolic and neurological disorders, and infectious diseases. Ultimately the present invention provides the medical community with a novel pharmacological strategy for the treatment of diseases and disorders associated with BET proteins.

DETAILED DESCRIPTION OF THE INVENTION

The present invention relates to compounds and compositions that are capable of modulating the activity of the BET family bromodomains, e.g., BRD2, BRD3, BRD4, and BRDT bromodomains. The invention features methods of treating, preventing or ameliorating a disease or disorder in which BET bromodomains play a role by administering to a patient in need thereof a therapeutically effective amount of a compound of Formula (I)-(VI), or a pharmaceutically acceptable salt, hydrate, solvate, prodrug, stereoisomer, or tautomer thereof. The methods of the present invention can be used in the treatment of a variety of BET bromodomain dependent diseases and disorders by inhibiting the activity of a BET bromodomains. Inhibition of BET bromodomains provides a novel approach to the treatment, prevention, or amelioration of diseases including, but not limited to, cancer, inflammatory diseases, diabetes and obesity, and to develop male contraceptives.

In a first aspect of the invention, the compounds of Formula (I) are described:

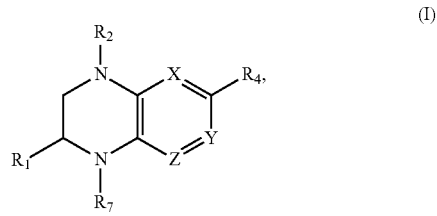

(I)

and pharmaceutically acceptable salts, enantiomers, hydrates, solvates, prodrugs, isomers, and tautomers thereof, wherein X, Y, Z, $R_1$, $R_2$, $R_4$, and $R_7$ are described as above.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

DEFINITIONS

As used herein, the terms "including," "containing," and "comprising" are used in their open, non-limiting sense.

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently A "patient" is a mammal, e.g., a human, mouse, rat, guinea pig, dog, cat, horse, cow, pig, or non-human primate, such as a monkey, chimpanzee, baboon or rhesus. "Patient includes both human and animals.

The term "inhibitor" refers to a molecule such as a compound, a drug, an enzyme activator or a hormone that blocks or otherwise interferes with a particular biologic activity.

The term "bromodomain inhibitor" denotes a compound which inhibits binding of a bromodomain with its cognate acetylated proteins. In one embodiment the bromodomain inhibitor is a compound which inhibits the binding of any one or a combination of bromodomains to acetylated lysine residues. In a further embodiment the bromodomain inhibitor is a compound which inhibits the binding of a bromodomain to acetylated lysine residues on histones, particularly histones H3 and H4.

The term "BET family bromodomain inhibitor" or "inhibitor of bromodomain of the BET family proteins" means a compound that inhibits binding of BET (bromo and extra terminal) bromodomains BRD2 BD1, BRD2 BD2, BRD3 BD1, BRD3 BD2, BRD4 BD1, BRD4 BD2, BRDT BD1, or BRDT BD2. In one embodiment BET family bromodomain inhibitors are compounds according to Formulae I-VI.

The terms "effective amount" or "therapeutically effective amount" when used in connection with a compound refer to a sufficient amount of the compound to provide the desired biological result. That result can be reduction and/or alleviation of the signs, symptoms, or causes of a disease, or any other desired alteration of a biological system. For example, an "effective amount" for therapeutic use is the amount of the composition comprising a compound as disclosed herein, or the compound itself, required to provide a clinically significant decrease in a disease. An appropriate "effective amount" in any individual case may be determined by one of ordinary skill in the art using routine experimentation. Thus, the expression "effective amount" generally refers to the quantity for which the active substance has therapeutic effects. In the present case the active substance is the inhibitor of the bromodomains of the BET proteins.

As used herein, the terms "treat" or "treatment" are synonymous with the term "prevent" and are meant to indicate a postponement of development of diseases, preventing the development of diseases, and/or reducing severity of such symptoms that will or are expected to develop. Thus, these terms include ameliorating existing disease symptoms, preventing additional symptoms, ameliorating or preventing the underlying causes of symptoms, inhibiting the disorder or disease, e.g., arresting the development of the disorder or disease, relieving the disorder or disease, causing regression of the disorder or disease, relieving a condition caused by the disease or disorder, or stopping or alleviating the symptoms of the disease or disorder.

The term "disorder" or "disease" is used in this disclosure to mean, and is used interchangeably with, the terms disease, condition, or illness, unless otherwise indicated.

By using the terms "pharmaceutically acceptable" or "pharmacologically acceptable" it is intended to mean a material which is not biologically or otherwise undesirable— the material may be administered to an individual without causing any substantially undesirable biological effects or interacting in a deleterious manner with any of the components of the composition in which it is contained.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject. Excipients should be selected on the basis of compatibility and the release profile properties of the desired dosage form. Exemplary carrier materials include, e.g., binders, suspending agents, disintegration agents, filling agents, surfactants, solubilizers, stabilizers, lubricants, wetting agents, diluents, and the like.

"Pharmaceutically compatible carrier materials" may comprise, e.g., acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate carrageenan, monoglyceride, diglyceride, pregelatinized starch, and the like. See, e.g., Hoover, John E., *Remington's Pharmaceutical Sciences*, Mack Publishing Co., Easton, Pa. 1975.

As used herein, the term "subject" encompasses mammals and non-mammals. Examples of mammals include, but are not limited to, any member of the class Mammalia: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the present invention, the mammal is a human.

The present invention also includes "prodrugs" of compounds of the invention. The term "prodrug" means a compound which is convertible in vivo by metabolic means (I, by hydrolysis) to a disclosed compound or active ingredient. Prodrugs can be prepared by techniques known to one skilled in the art. These techniques generally modify appropriate functional, e.g., a hydroxy, amino, carboxylic, etc., groups in a given compound. These modified functional groups, however, regenerate original functional groups by routine manipulation or in vivo. Examples of prodrugs include, but are not limited to esters (e.g., acetate, formate, and benzoate derivatives), carbamates (e.g., N,N-dimethylaminocarbonyl) of hydroxy or amino functional groups in compounds of the invention, amides (e.g., trifluoroacetylamino, acetylamino, and the like), and the like. Since prodrugs are known to enhance numerous desirable qualities of pharmaceuticals (e.g., solubility, bioavailability, manufacturing, transport, pharmacodynamics, etc.), the compounds of the present invention may be delivered in prodrug form. Prodrugs, for instance, may be bioavailable by oral administration even when the parent drug is not. Thus, the present invention is intended to cover prodrugs of the presently claimed compounds, methods of delivering the same, and compositions containing the same. Generally speaking, prodrugs are derivatives of per se drugs that after administration undergo conversion or metabolism to the physiologically active species. The conversion may be spontaneous, such as hydrolysis in the physiological environment, or may be enzyme-catalyzed. Prodrugs include compounds that can be oxidized, reduced, aminated, deaminated, hydroxylated, dehydroxylated, hydrolyzed, esterified, alkylated, dealkylated, acylated, deacylated, phosphorylated, and/or dephosphorylated to produce the active compound.

The term "$IC_{50}$", as used herein, refers to concentrations at which a measurable activity, phenotype or response, for example growth or proliferation of cells such as tumor cells, is inhibited by 50%. $IC_{50}$ values can be estimated from an appropriate dose-response curve, for example by eye or by using appropriate curve fitting or statistical software. More accurately, $IC_{50}$ values may be determined using non-linear regression analysis.

The terms "administered", "administration", or "administering" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body, including an animal, in need of treatment by bringing such individual in contact with, or otherwise exposing such individual to, such compound.

As used herein, "alkyl" means a straight chain or branched saturated chain having from 1 to 10 carbon atoms. Representative saturated alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl and the like, and longer alkyl groups, such as heptyl, and octyl and the like. An alkyl group can be unsubstituted or substituted. Alkyl groups containing three or more carbon atoms may be straight or branched. As used herein, "lower alkyl" means an alkyl having from 1 to 6 carbon atoms.

As used herein, an "alkenyl" includes an unbranched or branched hydrocarbon chain containing 2-12 carbon atoms. The "alkenyl" group contains at least one double bond. The double bond of an alkenyl group can be unconjugated or conjugated to another unsaturated group. Examples of alkenyl groups include, but are not limited to, ethylenyl, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl and the like. An alkenyl group can be unsubstituted or substituted. Alkenyl, as herein defined, may be straight or branched.

As used herein, "alkynyl" includes an unbranched or branched unsaturated hydrocarbon chain containing 2-12 carbon atoms. The "alkynyl" group contains at least one triple bond. The triple bond of an alkynyl group can be unconjugated or conjugated to another unsaturated group. Examples of alkynyl groups include, but are not limited to, ethynyl, propynyl, butynyl, pentynyl, hexynyl, methylpropynyl, 4-methyl-1-butynyl, 4-propyl-2-pentynyl, 4-butyl-2-hexynyl and the like. An alkynyl group can be unsubstituted or substituted.

The term "alkylene" or "alkylenyl" refers to a divalent alkyl radical. Any of the above mentioned monovalent alkyl groups may be an alkylene by abstraction of a second hydrogen atom from the alkyl. As herein defined, alkylene may also be a $C_1$-$C_6$ alkylene. An alkylene may further be a $C_1$-$C_4$ alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

The terms "trifluoromethyl", "sulfonyl", and "carboxyl" refer $CF_3$, $S(O)_2$, and $C(O)OH$, respectively.

The term "hydroxyl" or "hydroxy" means an OH group;

The term "hydroxyalkyl" means an alkyl group as defined above, where the alkyl group is substituted with one or more OH groups. Examples of hydroxyalkyl groups include HO—$CH_2$—, HO—$CH_2$—$CH_2$— and $CH_3$—$CH(OH)$—.

The term "alkoxy" as used herein refers to a straight or branched chain saturated hydrocarbon containing 1-12 carbon atoms containing a terminal "O" in the chain, i.e., —O(alkyl). Examples of alkoxy groups include, without limitation, methoxy, ethoxy, propoxy, butoxy, t-butoxy, or pentoxy groups.

"Aralkyl" or "arylalkyl" means an a $C_1$-$C_6$ alkyl group, as defined herein above, substituted with an aryl ring containing from 3 to 24 ring atoms per ring. For example, arylalkyl groups herein described can have the following formula

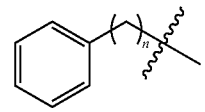

where n is an integer from 1 to 6. Non-limiting examples of suitable aralkyl groups include benzyl, 2-phenethyl and naphthalenylmethyl. The bond to the parent moiety is through the alkyl.

"Cycloalkylalkyl" means monocyclic saturated carbon rings containing 3-18 carbon atoms further substituted with $C_1$-$C_6$ alkyl groups. In general cycloalkylalkyl groups herein described display the following formula

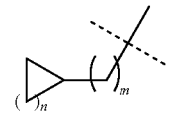

where m is an integer from 1 to 6 and n is an integer from 1 to 16.

"Heterocycloalkyl-alkyl" means an a $C_1$-$C_6$ alkyl group, as defined herein above, substituted with an heterocycloalkyl ring containing from 3 to 24 ring atoms per ring. For example, an heterocycloalkyl-alkyl group can have the following structure

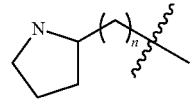

where n is an integer from 1 to 6. The bond to the parent moiety is through the alkyl.

"Heteroaryl alkyl" means an a $C_1$-$C_6$ alkyl group, as defined herein above, substituted with a heteroaryl ring containing from 5 to 24 ring atoms per ring. For example, a heteroarylalkyl group can have the following structure

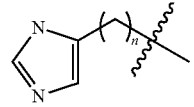

where n is an integer from 1 to 6. The bond to the parent moiety is through the alkyl.

It should also be noted that any carbon as well as heteroatom with unsatisfied valences in the text, schemes, examples and Tables herein is assumed to have the sufficient number of hydrogen atom(s) to satisfy the valences.

As used herein, references to hydrogen may also refer to a deuterium substitution if desired. The term "deuterium" as used herein means a stable isotope of hydrogen having odd numbers of protons and neutrons.

The term "halo" or "halogen" refers to fluorine, chlorine, bromine, or iodine.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkyl groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., C≡N.

The term "amine" as used herein refers to primary (R—$NH_2$, R≠H), secondary ($R_2$—NH, $R_2$≠H) and tertiary ($R_3$—N, R≠H) amines. A substituted amine is intended to mean an amine where at least one of the hydrogen atoms has been replaced by the substituent.

The term "amino" as used herein means a substituent containing at least one nitrogen atom. Specifically, $NH_2$, —NH(alkyl) or alkylamino, —N(alkyl)$_2$ or dialkylamino, amide-, carbamide-, urea, and sulfamide substituents are included in the term "amino".

The term "(amino)alkoxy" or "aminoalkoxy" as used herein means an alkoxy group, as defined herein above, where the straight or branched chain saturated hydrocarbon of the alkoxy is substituted with one or more amino groups.

The term "aminoalkyl" or "amino(alkyl)" as used herein refers to an alkyl group, as defined herein, which is substituted one or more times with one or more amino groups.

The term "alkylamino" as used herein refers to an amino or $NH_2$ group where one of the hydrogens has been replaced with an alkyl group, as defined herein above, i.e., —NH-alkyl. Example of alkylamino groups include, but are not limited to, methylamino (i.e., —$NHCH_3$), ethylamino, propylamino, iso-propylamino, n-butylamino, sec-butylamino, and tert-butylamino.

The term "dialkylamino" as used herein refers to an amino or $NH_2$ group where both of the hydrogens have been replaced with alkyl groups, as defined herein above, i.e., —N(alkyl)$_2$. The alkyl groups on the amino group can be the same ore different alkyl groups. Example of alkylamino groups include, but are not limited to, dimethylamino (i.e., —N($CH_3$)$_2$), diethylamino, dipropylamino, diiso-propylamino, di-n-butylamino, di-sec-butylamino, di-tert-butylamino, methyl(ethyl)amino, methyl(butylamino), etc.

The term "aryloxy" refers to an aryl ring as defined herein containing a terminal "O", i.e., Aryl-O—. Examples of aryloxy groups include, without limitation, phenoxy, biphenoxy, and naphtyloxy.

The term "methylenedioxy" as used herein means a functional group with the structural formula —O—$CH_2$—O— which is connected to the molecule by two chemical bonds via the oxygens.

As used herein, "alkoxyalkyl" means an alkyl group as defined herein further substituted with one or more alkoxy groups as defined herein, i.e., alkyl-O-alkyl-.

The term "(alkoxyalkyl)amino" as used herein means an amino group substituent having at least one alkoxyalkyl group as defined above and at least one amino group as defined above.

Unless otherwise specifically defined, the term "aryl" refers to cyclic, aromatic hydrocarbon groups that have 1 to 4 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. The substituents can themselves be optionally substituted. Furthermore when containing two fused rings the aryl groups herein defined may have an unsaturated or partially saturated ring fused with a fully saturated ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic aromatic radical of 5 to 24 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. The substituents can themselves be optionally substituted. Examples include, but are not limited to, benzothiophene, furyl, thienyl, pyrrolyl, pyridyl, pyrazinyl, pyrazolyl, pyridazinyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, benzoimidazolyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydropyrrolo[1,2-a]pyrimidinyl, 3,4-dihydro-2H-1λ$^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo[1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo[1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore when containing two fused rings the heteroaryl groups herein defined may have an unsaturated or partially saturated ring fused with a fully saturated ring.

As used herein, the term "cycloalkyl" refers to a saturated or partially saturated, monocyclic, fused or spiro polycyclic, carbocycle having from 3 to 24 carbon atoms per ring. The cycloalkyl ring or carbocycle may be optionally substituted by one or more substituents, e.g., 1 to 5 substituents, at any point of attachment. The substituents can themselves be optionally substituted. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, bicyclo[2.2.2]octenyl, decahydronaphthalenyl, octahydro-1H-indenyl, cyclopentenyl, cyclohexenyl, cyclohexa-1,4-dienyl, cyclohexa-1,3-dienyl, 1,2,3,4-tetrahydronaphthalenyl, octahydropentalenyl, 3a,4,5,6,7,7a-hexahydro-1H-indenyl, 1,2,3,3a-tetrahydropentalenyl, bicyclo[3.1.0]hexanyl, bicyclo[2.1.0]pentanyl, spiro[3.3]heptanyl, bicyclo[2.2.1]heptanyl, bicyclo[2.2.1]hept-2-enyl, bicyclo[2.2.2]octanyl, 6-methylbicyclo[3.1.1]heptanyl, 2,6,6-trimethylbicyclo[3.1.1]heptanyl, and derivatives thereof.

As used herein, the term "heterocycloalkyl" refers to a saturated or partially saturated monocyclic, or fused or spiro, polycyclic, ring structure containing carbon and heteroatoms taken from oxygen, nitrogen, or sulfur and wherein there is not delocalized π electrons (aromaticity) shared among the ring carbon or heteroatoms. The heterocycloalkyl ring structure may be substituted by one or more substituents. The substituents can themselves be optionally substituted. Examples of heterocyclyl rings include, but are not limited to, oxetanyl, azetidinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, homotropanyl, dihydrothiophen-2(3H)-onyl, tetrahydrothiophene 1,1-dioxide, 2,5-dihydro-1H-pyrrolyl, imidazolidin-2-one, pyrrolidin-2-one, dihydrofuran-2(3H)-one, 1,3-dioxolan-2-one, isothiazolidine 1,1-dioxide, 4,5-dihydro-1H-imidazolyl, 4,5-dihydrooxazolyl, oxiranyl, pyrazolidinyl, 4H-1,4-thiazinyl, thiomorpholinyl, 1,2,3,4-tetrahydropyridinyl, 1,2,3,4-tetrahydropyrazinyl, 1,3-oxazinan-2-one, tetrahydro-2H-thiopyran 1,1-dioxide, 7-oxabicyclo[2.2.1]heptanyl, 1,2-thiazepane 1,1-dioxide, octahydro-2H-quinolizinyl, 1,3-diazabicyclo[2.2.2]octanyl, 2,3-dihydrobenzo[b][1,4]dioxine, 3-azabicyclo[3.2.1]octanyl, 8-azaspiro[4.5]decane, 8-oxa-3-azabicyclo[3.2.1]octanyl, 2-azabicyclo[2.2.1]heptane, 2,8-diazaspiro[5.5]undecanyl, 2-azaspiro[5.5]undecanyl, 3-azaspiro[5.5]undecanyl, decahydroisoquinolinyl, 1-oxa-8-azaspiro[4.5]decanyl, 8-azabicyclo[3.2.1]octanyl, 1,4'-bipiperidinyl, azepanyl, 8-oxa-3-azabicyclo[3.2.1]octanyl, 3,4-dihydro-2H-benzo[b][1,4]oxazinyl, 5,6,7,8-tetrahydroimidazo[1,2-a]pyridinyl, 1,4-diazepanyl, phenoxathiinyl, benzo[d][1,3]dioxolyl, 2,3-dihydrobenzofuranyl, 2,3-dihydrobenzo[b][1,4]dioxinyl, 4-(piperidin-4-yl)morpholinyl, 3-azaspiro[5.5]undecanyl, decahydroquinolinyl, piperazin-2-one, 1-(pyrrolidin-2-ylmethyl)pyrrolidinyl, 1,3'-bipyrrolidinyl, 6,7,8,9-tetrahydro-1H,5H-pyrazolo[1,2-a][1,2]diazepinyl.

Numerical ranges, as used herein, are intended to include sequential integers. For example, a range expressed as "from 0 to 4" would include 0, 1, 2, 3 and 4.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, oxo, -halogen, $C_1$-$C_6$ alkyl, $C_1$-$C_6$ alkoxy, $C_1$-$C_6$ haloalkyl, $C_1$-$C_6$ haloalkoxy, —$OC_1$-$C_6$ alkenyl, —$OC_1$-$C_6$ alkynyl, —$C_1$-$C_6$ alkenyl, —$C_1$-$C_6$ alkynyl, —OH, CN (cyano), —$CH_2CN$, —$OP(O)(OH)_2$, —C(O)OH, —$OC(O)C_1$-$C_6$ alkyl, —$C(O)C_1$-$C_6$ alkyl, —C(O)—$C_0$-$C_6$ alkylenyl-cycloalkyl, —C(O)—$C_0$-$C_6$ alkylenyl-heterocycloalkyl, —C(O)—$C_0$-$C_6$ alkylenyl-aryl, —C(O)—$C_0$-$C_6$ alkylenyl-heteroaryl, —$OC(O)OC_1$-$C_6$ alkyl, —$NH_2$, $NH(C_1$-$C_6$ alkyl), $N(C_1$-$C_6$ alkyl)$_2$, —$C(O)NH_2$, —C(O)NH($C_1$-$C_6$ alkyl), —$C(O)N(C_1$-$C_6$ alkyl)$_2$, —C(O)NH cycloalkyl, —$C(O)N(C_1$-$C_6$ alkyl)cycloalkyl, —C(O)NH-heterocycloalkyl, —$C(O)N(C_1$-$C_6$ alkyl)heterocycloalkyl, —C(O)NHaryl, —$C(O)N(C_1$-$C_6$ alkyl)aryl, —C(O)NHheteroaryl, —$C(O)N(C_1$-$C_6$ alkyl)heteroaryl, —$S(O)_2$—$C_1$-$C_6$ alkyl, —$S(O)_2$—$C_1$-$C_6$ haloalkyl, —$S(O)_2$-cycloalkyl, —$S(O)_2$-heterocycloalkyl, —$S(O)_2$-aryl, —$S(O)_2$-heteroaryl —$C_0$-$C_6$ alkylenyl-$S(O)_2NH_2$, —$S(O)_2NHC_1$-$C_6$ alkyl, —$S(O)_2N(C_1$-$C_6$ alkyl)$_2$, —$S(O)_2$NHcycloalkyl, —$S(O)_2$NHheterocycloalkyl, —$S(O)_2$NHaryl, —$S(O)_2$NHhetereoaryl, —$NHS(O)_2C_1$-$C_6$ alkyl, —$N(C_1$-$C_6$ alkyl)$S(O)_2$ ($C_1$-$C_6$ alkyl), —$NHS(O)_2$aryl, —$N(C_1$-$C_6$ alkyl)$S(O)_2$ aryl, —$NHS(O)_2$ heteroaryl, —$N(C_1$-$C_6$ alkyl)$S(O)_2$ heteroaryl, —$NHS(O)_2$ cycloalkyl, —$N(C_1$-$C_6$ alkyl)$S(O)_2$ cycloalkyl, —$NHS(O)_2$ heterocycloalkyl, —$N(C_1$-$C_6$ alkyl)$S(O)_2$ heterocycloalkyl, —$N(C_1$-$C_6$ alkyl)$S(O)_2$ aryl, —$C_0$-$C_6$ alkylenyl-aryl, —$C_0$-$C_6$ alkylenyl-heteroaryl, —$C_0$-$C_6$ alkylenyl-cycloalkyl, —$C_0$-$C_6$ alkylenyl-heterocycloalkyl, —O-aryl, —NH-aryl, and $N(C_1$-$C_6$ alkyl)aryl. The substituents can themselves be optionally substituted. When a multifunctional moiety is shown, the point of attachment to the core is indicated by a line, e.g., (cycloalkyloxy)alkyl- refers to alkyl being the point of attachment to the core while cycloalkyl is attached to alkyl via the oxy group. "Optionally substituted" as used herein also refers to substituted or unsubstituted whose meaning is described above.

The term "oxy" as used herein refers to an "—O—" group.

The term "oxo" as used herein refers to an "=O" group.

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atoms and may occur as racemates, racemic mixtures and as individual enantiomers or diastereomers.

When used as a therapeutic agent the inhibitors of the BET Bromodomains described herein may be administered with one or more physiologically acceptable excipients. A physiologically acceptable carrier or excipient is a formulation to which the compound can be added to dissolve it or otherwise facilitate its administration.

The term "salt(s)", as employed herein, denotes acidic salts formed with inorganic and/or organic acids, as well as basic salts formed with inorganic and/or organic bases. In addition, when a compound of the Formula contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Compounds of the Invention

The present invention relates to compounds, or pharmaceutically acceptable salts or isomers thereof, capable of modulating BET family bromodomains, including BRD2, BRD3, BRD4 and BRDT, which are useful for the treatment of diseases and disorders associated with modulation of BET family bromodomains. The invention further relates to compounds, or pharmaceutically acceptable salts or isomers thereof, which are useful for inhibiting BET family bromodomains.

It should also be noted that any carbon as well as heteroatom with unsatisfied valences in the text, schemes, examples and Tables herein is assumed to have the sufficient number of hydrogen atom(s) to satisfy the valences. When any variable (e.g., aryl, heterocycle, $R^2$, etc.) occurs more than one time in any constituent or in the Formulae, its definition on each occurrence is independent of its definition at every other occurrence.

In a first aspect of the invention, the compounds of Formula (I) are described:

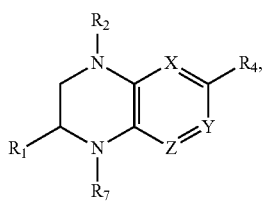

I and pharmaceutically acceptable salts, enantiomers, hydrates, solvates, prodrugs, isomers, and tautomers thereof, where X, Y, Z, $R_1$, $R_2$, $R_4$, and $R_7$ are described as above.

In one embodiment, the compounds of Formula (I) have the structure of Formula (II):

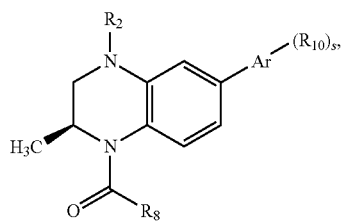

(II)

and pharmaceutically acceptable salts, enantiomers, hydrates, solvates, prodrugs, isomers, and tautomers thereof, wherein:

Ar is $C_6$-$C_{10}$ aryl or heteroaryl;

$R_2$ is —$C(O)(CR^kR^i)_nO(CR^kR^i)_mR^d$, —$C(O)(CR^kR^i)_nR^e$, —$S(O)_2(CR^kR^i)_nR^f$, —$(CR^kR^i)_nR^g$, —$C(O)(CR^kR^i)_nNR^aR^g$ or —$C(O)(CR^kR^i)_nS(CR^kR^i)_mR^f$;

$R_8$ is —$(CR^kR^i)_mOR^a$, $C_1$-$C_6$ alkyl, or $C_3$-$C_6$ cycloalkyl;

each $R_{10}$ is independently at each occurrence selected from the group consisting of $C_1$-$C_6$ alkyl, $C_1$-$C_6$ alkoxy, $C_1$-$C_6$ hydroxyalkyl, $C_1$-$C_6$ haloalkyl, $C_1$-$C_6$ haloalkoxy, —$OR^i$, —$NR^aR^i$, CN, oxo, —$(CR^kR^i)_nS(O)_2R^i$, —$(CR^kR^i)_nNR^aS(O)_2R^i$, —$(CR^kR^i)_nS(O)_2NR^aR^i$, —$(CR^kR^i)_nNR^aR^iS(O)_2NR^aR^i$, —$(CR^kR^i)_nC(O)OR^a$, —$(CR^kR^i)_nC(O)R^i$, —$(CR^kR^i)_nC(O)NR^aR^i$, —$(CR^kR^i)_nR^i$, —$(CR^kR^i)_nNR^aC(O)NR^b$, and —$(CR^kR^i)_nNR^aC(O)OR^b$, wherein each alkyl is substituted with one or more $R_{11}$; or two $R_{10}$ together when on adjacent carbons form an aryl ring optionally substituted with one or more $R_{11}$; or two $R_{10}$ together when on adjacent carbons form a heteroaryl ring optionally substituted with one or more $R_{11}$; or two $R_{10}$ together when on adjacent carbons form a heterocycloalkyl ring optionally substituted with one or more $R_{11}$;

each $R_{11}$ is independently at each occurrence selected from halogen, $C_1$-$C_6$ alkyl, $C_1$-$C_6$ alkoxy, $C_1$-$C_6$ haloalkyl, hydroxy, CN, $C_1$-$C_6$ hydroxyalkyl, —$(CR^kR^i)_mNH_2$, $C_1$-$C_6$ alkylamino, $C_1$-$C_6$ dialkylamino, —$C(O)NR^aR^b$, —$C(O)OR^a$, —$C(O)R^a$, —$S(O)_2R^a$, —$C(O)H$, —$NR^aC(O)OR^a$, —$NR^aC(O)C_1$-$C_6$ alkyl, or oxo;

or two $R_{11}$ together can form a heterocycloalkyl ring;

$R^a$ and $R^b$ are each independently at each occurrence hydrogen, $C_1$-$C_6$ alkyl, —$C_1$-$C_4$ alkyl(aryl), or aryl, wherein the alkyl and aryl are optionally substituted with one or more $R_{10}$;

$R^d$ is $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, CN, —$C(O)C_1$-$C_6$ alkyl, $C_3$-$C_7$ cycloalkyl, aryl, heteroaryl, or heterocycloalkyl, wherein cycloalkyl, aryl, heteroaryl, and heterocycloalkyl are optionally substituted with one or more $R_{12}$;

$R^e$ is hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_1$-$C_6$ alkoxy, CN, $C_3$-$C_7$ cycloalkyl, aryl, heteroaryl, or heterocycloalkyl, wherein cycloalkyl, aryl, heteroaryl, and heterocycloalkyl are optionally substituted with one or more $R_{12}$;

$R^f$ is $C_3$-$C_7$ cycloalkyl, aryl, heteroaryl, or heterocycloalkyl, wherein cycloalkyl, aryl, heteroaryl, and heterocycloalkyl are optionally substituted with one or more $R_{12}$;

$R^g$ is $C_1$-$C_6$ alkyl, $C_3$-$C_7$ cycloalkyl, $C_3$-$C_7$ cycloalkyl, —$C_1$-$C_4$ alkyl(cycloalkyl), aryl, —$C_1$-$C_4$ alkyl(aryl), heteroaryl, —$C_1$-$C_4$ alkyl(heteroaryl), heterocycloalkyl, or —$C_1$-$C_4$ alkyl(heterocycloalkyl), wherein cycloalkyl, aryl, heteroaryl, and heterocycloalkyl are optionally substituted with one or more $R_{12}$;

$R^i$ is hydrogen, $C_1$-$C_6$ alkyl, $C_1$-$C_6$ alkoxy, $C_1$-$C_6$ hydroxyalkyl, $C_1$-$C_6$ haloalkyl, —$(CH_2)_qN(H)C_1$-$C_6$ alkyl, —$(CH_2)_qN(C_1$-$C_6$ alkyl$)_2$, —$(CR^kR^i)_mC_3$-$C_7$ cycloalkyl, —$(CR^kR^i)_m$ aryl, —$(CR^kR^i)_m$heteroaryl, or —$(CR^kR^i)_m$heterocycloalkyl, wherein alkyl, cycloalkyl, aryl, heteroaryl, and heterocycloalkyl are optionally substituted with one or more $R^{11}$;

each $R_{12}$ is independently at each occurrence selected from $C_1$-$C_6$ alkyl, halogen, CN, $C_1$-$C_6$ alkoxy, $C_1$-$C_6$ haloalkyl, $C_1$-$C_6$ haloalkoxy, hydroxy, $NO_2$, —$NH_2$, $CH_2NH_2$, —$(CH_2)_qN(C_1$-$C_6$ alkyl$)_2$, $C_1$-$C_6$ alkylamino, $C_1$-$C_6$ dialkylamino, —$O(CH_2)_qN(H)C_1$-$C_6$ alkyl, —$O(CH_2)_qN(C_1$-$C_6$ alkyl$)_2$, aryl, heteroaryl, —NH-heteroaryl, —O-aryl, —$S(O)_p$—$C_1$-$C_6$ alkyl, —$S(O)_p$—$N(H)C_1$-$C_6$ alkyl, —$S(O)_p$—$N(C_1$-$C_6$ alkyl$)_2$, —$C(O)C_1$-$C_6$ alkyl, —$C(O)OC_1$-$C_6$ alkyl, —$NHC(O)(C_1$-$C_6$ alkyl), or oxo, wherein aryl and heteroaryl are optionally substituted with one or more substituents selected from $C_1$-$C_6$ alkyl, halogen, CN, $C_1$-$C_6$ alkoxy, hydroxy, $NO_2$, —$NH_2$, $C_1$-$C_6$ alkylamino, or $C_1$-$C_6$ dialkylamino; or two $R_{12}$ together with the carbon to which they are attached can form a 4- to 6 membered heterospirocycle; or two $R_{12}$ together when on adjacent carbons form a $C_4$-$C_6$ cycloalkyl optionally substituted with one or more $R_{13}$; or two $R_{12}$ together when on adjacent carbons form an aryl optionally substituted with one or more $R_{13}$; or two $R_{12}$ together when on adjacent carbons form a heteroaryl optionally substituted with one or more $R_{13}$; or two $R_{12}$ together when on adjacent carbons form a heterocycloalkyl optionally substituted with one or more $R_{13}$; or $R_{12}$ with the carbon to which it is attached and the adjacent carbon form a $C_3$ cycloalkyl optionally substituted with one or more $R_{13}$;

each $R_{13}$ is independently at each occurrence selected from $C_1$-$C_6$ alkyl, halogen, CN, $C_1$-$C_6$ alkoxy, $C_1$-$C_6$ haloalkyl, $C_1$-$C_6$ haloalkoxy, hydroxy, $NO_2$, —$NH_2$, $CH_2NH_2$, —$(CH_2)_q$N$(C_1$-$C_6$ alkyl$)_2$, $C_1$-$C_6$ alkylamino, $C_1$-$C_6$ dialkylamino, —O$(CH_2)_q$N(H)$C_1$-$C_6$ alkyl, —O$(CH_2)_q$N$(C_1$-$C_6$ alkyl$)_2$, aryl, heteroaryl, —NH-heteroaryl, —O-aryl, —S(O)$_p$—$C_1$-$C_6$ alkyl, —S(O)$_p$—N(H)$C_1$-$C_6$ alkyl, —S(O)$_p$—N$(C_1$-$C_6$ alkyl$)_2$, —C(O)$C_1$-$C_6$ alkyl, —NHC(O)$(C_1$-$C_6$ alkyl), or oxo, wherein aryl and heteroaryl are optionally substituted with one or more substituents selected from the group consisting of $C_1$-$C_6$ alkyl, halogen, CN, $C_1$-$C_6$ alkoxy, hydroxy, $NO_2$, —$NH_2$, $C_1$-$C_6$ alkylamino, and $C_1$-$C_6$ dialkylamino;

$R^k$ and $R^l$ are each independently at each occurrence selected from H, $C_1$-$C_6$ alkyl, $C_1$-$C_6$ alkoxy, $C_1$-$C_6$ haloalkyl, or halogen;

each m, n, and p is independently at each occurrence 0, 1, or 2;

each q is independently at each occurrence 1, 2, 3 or 4; and s is 1, 2, 3, 4, or 5;

provided that when m is 0, $R^d$ is not $C_1$-$C_6$ alkoxy, $C_1$-$C_6$ haloalkoxy, or CN.

In another embodiment, the compounds of Formula (I) have the structure of Formula (III):

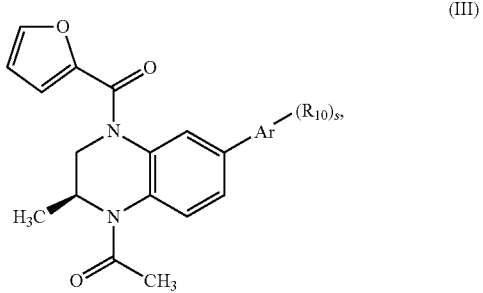

(III)

and pharmaceutically acceptable salts, enantiomers, hydrates, solvates, prodrugs, isomers, and tautomers thereof, wherein:

Ar is $C_6$-$C_{10}$ aryl or heteroaryl;

each $R_{10}$ is independently at each occurrence selected from the group consisting of $C_1$-$C_6$ alkyl, $C_1$-$C_6$ alkoxy, $C_1$-$C_6$ hydroxyalkyl, $C_1$-$C_6$ haloalkyl, $C_1$-$C_6$ haloalkoxy, —OR$^i$, —NR$^a$R$^i$, CN, oxo, —(CR$^k$R$^l$)$_n$S(O)$_2$R$^i$, —(CR$^k$R$^l$)$_n$NR$^a$S(O)$_2$R$^i$, —(CR$^k$R$^l$)$_n$S(O)$_2$NR$^a$R$^i$, —(CR$^k$R$^l$)$_n$NR$^a$R$^i$S(O)$_2$NR$^a$R$^i$, —(CR$^k$R$^l$)$_n$C(O)OR$^a$, —(CR$^k$R$^l$)$_n$C(O)R$^i$, —(CR$^k$R$^l$)$_n$C(O)NR$^a$R$^i$, —(CR$^k$R$^l$)$_n$R$^i$, —(CR$^k$R$^l$)$_n$NR$^a$C(O)NR$^b$, and —(CR$^k$R$^l$)$_n$NR$^a$C(O)OR$^b$, wherein each alkyl is substituted with one or more $R_{11}$; or two $R_{10}$ together when on adjacent carbons form an aryl ring optionally substituted with one or more $R_{11}$; or two $R_{10}$ together when on adjacent carbons form a heteroaryl ring optionally substituted with one or more $R_{11}$; or two $R_{10}$ together when on adjacent carbons form a heterocycloalkyl ring optionally substituted with one or more $R_{11}$;

each $R_{11}$ is independently at each occurrence selected from halogen, $C_1$-$C_6$ alkyl, $C_1$-$C_6$ alkoxy, $C_1$-$C_6$ haloalkyl, hydroxy, CN, $C_1$-$C_6$ hydroxyalkyl, —(CR$^k$R$^l$)$_m$NH$_2$, $C_1$-$C_6$ alkylamino, $C_1$-$C_6$ dialkylamino, —C(O)NR$^a$R$^b$, —C(O)OR$^a$, —C(O)R$^a$, —S(O)$_2$R$^a$, —C(O)H, —NR$^a$C(O)OR$^a$, —NR$^a$C(O)$C_1$-$C_6$ alkyl, or oxo;

or two $R_{11}$ together can form a heterocycloalkyl ring;

$R^a$ and $R^b$ are each independently at each occurrence hydrogen, $C_1$-$C_6$ alkyl, —$C_1$-$C_4$ alkyl(aryl), or aryl, wherein the alkyl and aryl are optionally substituted with one or more $R_{10}$;

$R^i$ is hydrogen, $C_1$-$C_6$ alkyl, $C_1$-$C_6$ alkoxy, $C_1$-$C_6$ hydroxyalkyl, $C_1$-$C_6$ haloalkyl, —(CH$_2$)$_q$N(H)$C_1$-$C_6$ alkyl, —(CH$_2$)$_q$N$(C_1$-$C_6$alkyl)$_2$, —(CR$^k$R$^l$)$_m$C$_3$-$C_7$ cycloalkyl, —(CR$^k$R$^l$)$_m$ aryl, —(CR$^k$R$^l$)$_m$heteroaryl, or —(CR$^k$R$^l$)$_m$heterocycloalkyl, wherein alkyl, cycloalkyl, aryl, heteroaryl, and heterocycloalkyl are optionally substituted with one or more $R^{11}$;

$R^k$ and $R^l$ are each independently at each occurrence selected from H, $C_1$-$C_6$ alkyl, $C_1$-$C_6$ alkoxy, $C_1$-$C_6$ haloalkyl, or halogen;

each m and n is independently at each occurrence 0, 1, or 2;

each q is independently at each occurrence 1, 2, 3 or 4; and s is 1, 2, 3, 4, or 5.

Another embodiment of the present invention is directed to compounds of Formula (I) having the structure of Formula (IV):

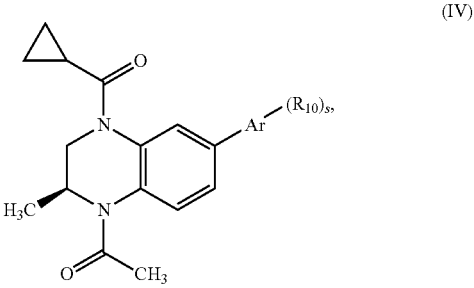

(IV)

and pharmaceutically acceptable salts, enantiomers, hydrates, solvates, prodrugs, isomers, and tautomers thereof, wherein:

Ar is $C_6$-$C_{10}$ aryl or heteroaryl;

each $R_{10}$ is independently at each occurrence selected from the group consisting of $C_1$-$C_6$ alkyl, $C_1$-$C_6$ alkoxy, $C_1$-$C_6$ hydroxyalkyl, $C_1$-$C_6$ haloalkyl, $C_1$-$C_6$ haloalkoxy, —OR$^i$, —NR$^a$R$^i$, CN, oxo, —(CR$^k$R$^l$)$_n$S(O)$_2$R$^i$, —(CR$^k$R$^l$)$_n$NR$^a$S(O)$_2$R$^i$, —(CR$^k$R$^l$)$_n$S(O)$_2$NR$^a$R$^i$, —(CR$^k$R$^l$)$_n$NR$^a$R$^i$S(O)$_2$NR$^a$R$^i$, —(CR$^k$R$^l$)$_n$C(O)OR$^a$, —(CR$^k$R$^l$)$_n$C(O)R$^i$, —(CR$^k$R$^l$)$_n$C(O)NR$^a$R$^i$, —(CR$^k$R$^l$)$_n$R$^i$, —(CR$^k$R$^l$)$_n$NR$^a$C(O)NR$^b$, and —(CR$^k$R$^l$)$_n$NR$^a$C(O)OR$^b$, wherein each alkyl is substituted with one or more $R_{11}$; or two $R_{10}$ together when on adjacent carbons form an aryl ring optionally substituted with one or more $R_{11}$; or two $R_{10}$ together when on adjacent carbons form a heteroaryl ring optionally substituted with one or more $R_{11}$; or two $R_{10}$ together when on adjacent carbons form a heterocycloalkyl ring optionally substituted with one or more $R_{11}$;

each $R_{11}$ is independently at each occurrence selected from halogen, $C_1$-$C_6$ alkyl, $C_1$-$C_6$ alkoxy, $C_1$-$C_6$ haloalkyl, hydroxy, CN, $C_1$-$C_6$ hydroxyalkyl, —$(CR^kR^i)_m$NH$_2$, $C_1$-$C_6$ alkylamino, $C_1$-$C_6$ dialkylamino, —C(O)NR$^a$R$^b$, —C(O)OR$^a$, —C(O)R$^a$, —S(O)$_2$R$^a$, —C(O)H, —NR$^a$C(O)OR$^a$, —NR$^a$C(O)C$_1$-C$_6$ alkyl, or oxo;

or two $R_{11}$ together can form a heterocycloalkyl ring;

$R^a$ and $R^b$ are each independently at each occurrence hydrogen, $C_1$-$C_6$ alkyl, —$C_1$-$C_4$ alkyl(aryl), or aryl, wherein the alkyl and aryl are optionally substituted with one to three $R_{10}$;

$R^i$ is hydrogen, $C_1$-$C_6$ alkyl, $C_1$-$C_6$ alkoxy, $C_1$-$C_6$ hydroxyalkyl, $C_1$-$C_6$ haloalkyl, —(CH$_2$)$_q$N(H)C$_1$-C$_6$ alkyl, —(CH$_2$)$_q$N(C$_1$-C$_6$ alkyl)$_2$, —(CR$^k$R$^i$)$_m$C$_3$-C$_7$ cycloalkyl, —(CR$^k$R$^i$)$_m$ aryl, —(CR$^k$R$^i$)$_m$heteroaryl, or —(CR$^k$R$^i$)$_m$ heterocycloalkyl, wherein alkyl, cycloalkyl, aryl, heteroaryl, and heterocycloalkyl are optionally substituted with one or more $R^{11}$;

$R^k$ and $R^l$ are each independently at each occurrence selected from H, $C_1$-$C_6$ alkyl, $C_1$-$C_6$ alkoxy, $C_1$-$C_6$ haloalkyl, or halogen;

each m and n is independently at each occurrence 0, 1, or 2;
each q is independently at each occurrence 1, 2, 3 or 4; and
s is 1, 2, 3, 4, or 5.

In another embodiment, the present invention relates to compounds of Formula (I) having the structure of Formula (V):

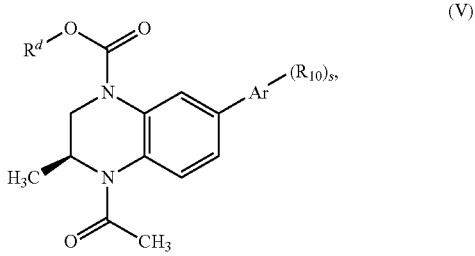

(V)

and pharmaceutically acceptable salts, enantiomers, hydrates, solvates, prodrugs, isomers, and tautomers thereof, wherein:

Ar is $C_6$-$C_{10}$ aryl or heteroaryl;

each $R_{10}$ is independently at each occurrence selected from the group consisting of $C_1$-$C_6$ alkyl, $C_1$-$C_6$ alkoxy, $C_1$-$C_6$ hydroxyalkyl, $C_1$-$C_6$ haloalkyl, $C_1$-$C_6$ haloalkoxy, —OR$^i$, —NR$^a$R$^i$, CN, oxo, —(CR$^k$R$^i$)$_n$S(O)$_2$R$^i$, —(CR$^k$R$^i$)$_n$NR$^a$S(O)$_2$R$^i$, —(CR$^k$R$^i$)$_n$S(O)$_2$NR$^a$R$^i$, —(CR$^k$R$^i$)$_n$NR$^a$R$^i$S(O)$_2$NR$^a$R$^i$, —(CR$^k$R$^i$)$_n$C(O)OR$^a$, —(CR$^k$R$^i$)$_n$C(O)R$^i$, —(CR$^k$R$^i$)$_n$C(O)NR$^a$R$^i$, —(CR$^k$R$^i$)$_n$R$^i$, —(CR$^k$R$^i$)$_n$NR$^a$C(O)NR$^b$, and —(CR$^k$R$^i$)$_n$NR$^a$C(O)OR$^b$, wherein each alkyl is substituted with one or more $R_{11}$; or two $R_{10}$ together when on adjacent carbons form an aryl ring optionally substituted with one or more $R_{11}$; or two $R_{10}$ together when on adjacent carbons form a heteroaryl ring optionally substituted with one or more $R_{11}$; or two $R_{10}$ together when on adjacent carbons form a heterocycloalkyl ring optionally substituted with one or more $R_{11}$;

each $R_{11}$ is independently at each occurrence selected from halogen, $C_1$-$C_6$ alkyl, $C_1$-$C_6$ alkoxy, $C_1$-$C_6$ haloalkyl, hydroxy, CN, $C_1$-$C_6$ hydroxyalkyl, —(CR$^k$R$^i$)$_m$NH$_2$, $C_1$-$C_6$ alkylamino, $C_1$-$C_6$ dialkylamino, —C(O)NR$^a$R$^b$, —C(O)OR$^a$, —C(O)R$^a$, —S(O)$_2$R$^a$, —C(O)H, —NR$^a$C(O)OR$^a$, —NR$^a$C(O)C$_1$-C$_6$ alkyl, or oxo;

or two $R_{11}$ together can form a heterocycloalkyl ring;

$R^a$ and $R^b$ are each independently at each occurrence hydrogen, $C_1$-$C_6$ alkyl, —$C_1$-$C_4$ alkyl(aryl), or aryl, wherein the alkyl and aryl are optionally substituted with one or more $R_{10}$;

$R^d$ is $C_1$-$C_6$ alkyl, $C_1$-$C_6$ haloalkyl, $C_3$-$C_7$ cycloalkyl, aryl, heteroaryl, or heterocycloalkyl, wherein cycloalkyl, aryl, heteroaryl, and heterocycloalkyl are optionally substituted with one or more $R_{12}$;

$R^i$ is hydrogen, $C_1$-$C_6$ alkyl, $C_1$-$C_6$ alkoxy, $C_1$-$C_6$ hydroxyalkyl, $C_1$-$C_6$ haloalkyl, —(CH$_2$)$_q$N(H)C$_1$-C$_6$ alkyl, —(CH$_2$)$_q$N(C$_1$-C$_6$ alkyl)$_2$, —(CR$^k$R$^i$)$_m$C$_3$-C$_7$ cycloalkyl, —(CR$^k$R$^i$)$_m$ aryl, —(CR$^k$R$^i$)$_m$heteroaryl, or —(CR$^k$R$^i$)$_m$heterocycloalkyl, wherein alkyl, cycloalkyl, aryl, heteroaryl, and heterocycloalkyl are optionally substituted with one or more $R^{11}$;

each $R_{12}$ is independently at each occurrence selected from $C_1$-$C_6$ alkyl, halogen, CN, $C_1$-$C_6$ alkoxy, $C_1$-$C_6$ haloalkyl, $C_1$-$C_6$ haloalkoxy, hydroxy, NO$_2$, —NH$_2$, CH$_2$NH$_2$, —(CH$_2$)$_q$N(C$_1$-C$_6$ alkyl)$_2$, $C_1$-$C_6$ alkylamino, $C_1$-$C_6$ dialkylamino, —O(CH$_2$)$_q$N(H)C$_1$-C$_6$ alkyl, —O(CH$_2$)$_q$N(C$_1$-C$_6$ alkyl)$_2$, aryl, heteroaryl, —NH-heteroaryl, —O-aryl, —S(O)$_p$—C$_1$-C$_6$ alkyl, —S(O)$_p$—N(H)C$_1$-C$_6$ alkyl, —S(O)$_p$—N(C$_1$-C$_6$ alkyl)$_2$, —C(O)C$_1$-C$_6$ alkyl, —C(O)OC$_1$-C$_6$ alkyl, —NHC(O)(C$_1$-C$_6$ alkyl), or oxo, wherein aryl and heteroaryl are optionally substituted with one or more substituents selected from $C_1$-$C_6$ alkyl, halogen, CN, $C_1$-$C_6$ alkoxy, hydroxy, NO$_2$, —NH$_2$, $C_1$-$C_6$ alkylamino, or $C_1$-$C_6$ dialkylamino; or two $R_{12}$ together with the carbon to which they are attached can form a 4- to 6 membered heterospirocycle; or two $R_{12}$ together when on adjacent carbons form a $C_4$-$C_6$ cycloalkyl optionally substituted with one or more $R_{13}$; or two $R_{12}$ together when on adjacent carbons form an aryl optionally substituted with one or more $R_{13}$; or two $R_{12}$ together when on adjacent carbons form a heteroaryl optionally substituted with one or more $R_{13}$; or two $R_{12}$ together when on adjacent carbons form a heterocycloalkyl optionally substituted with one or more $R_{13}$; or $R_{12}$ with the carbon to which it is attached and the adjacent carbon form a $C_3$ cycloalkyl optionally substituted with one or more $R_{13}$;

each $R_{13}$ is independently at each occurrence selected from $C_1$-$C_6$ alkyl, halogen, CN, $C_1$-$C_6$ alkoxy, $C_1$-$C_6$ haloalkyl, $C_1$-$C_6$ haloalkoxy, hydroxy, NO$_2$, —NH$_2$, CH$_2$NH$_2$, —(CH$_2$)$_q$N(C$_1$-C$_6$ alkyl)$_2$, $C_1$-$C_6$ alkylamino, $C_1$-$C_6$ dialkylamino, —O(CH$_2$)$_q$N(H)C$_1$-C$_6$ alkyl, —O(CH$_2$)$_q$N(C$_1$-C$_6$ alkyl)$_2$, aryl, heteroaryl, —NH-heteroaryl, —O-aryl, —S(O)$_p$—C$_1$-C$_6$ alkyl, —S(O)$_p$—N(H)C$_1$-C$_6$ alkyl, —S(O)$_p$—N(C$_1$-C$_6$ alkyl)$_2$, —C(O)C$_1$-C$_6$ alkyl, —NHC(O)(C$_1$-C$_6$ alkyl), or oxo, wherein aryl and heteroaryl are optionally substituted with one or more substituents selected from the group consisting of $C_1$-$C_6$ alkyl, halogen, CN, $C_1$-$C_6$ alkoxy, hydroxy, NO$_2$, —NH$_2$, $C_1$-$C_6$ alkylamino, and $C_1$-$C_6$ dialkylamino;

$R^k$ and $R^l$ are each independently at each occurrence selected from H, $C_1$-$C_6$ alkyl, $C_1$-$C_6$ alkoxy, $C_1$-$C_6$ haloalkyl, or halogen;

each m, n, and p is independently at each occurrence 0, 1, or 2;
each q is independently at each occurrence 1, 2, 3 or 4; and
s is 1, 2, 3, 4, or 5;
provided that when m is 0, $R^d$ is not $C_1$-$C_6$ alkoxy, $C_1$-$C_6$ haloalkoxy, or CN.

Another embodiment of the present invention relates to compounds of Formula (I) having the structure of Formula (VI):

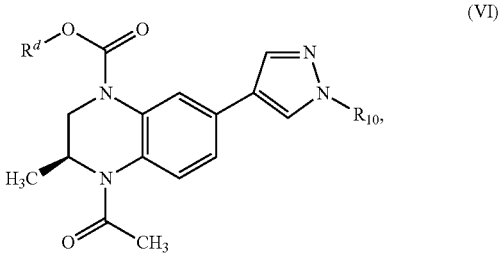

(VI)

and pharmaceutically acceptable salts, enantiomers, hydrates, solvates, prodrugs, isomers, and tautomers thereof, wherein:

$R_{10}$ is independently selected from the group consisting of $C_1$-$C_6$ alkyl, $C_1$-$C_6$ alkoxy, $C_1$-$C_6$ hydroxyalkyl, $C_1$-$C_6$ haloalkyl, $C_1$-$C_6$ haloalkoxy, —$OR^i$, —$NR^aR^i$, CN, oxo, —$(CR^kR^l)_nS(O)_2R^i$, —$(CR^kR^l)_nNR^aS(O)_2R^i$, —$(CR^kR^l)_nS(O)_2NR^aR^i$, —$(CR^kR^l)_nNR^aR^iS(O)_2NR^aR^i$, —$(CR^kR^l)_nC(O)OR^a$, —$(CR^kR^l)_nC(O)R^i$, —$(CR^kR^l)_nC(O)NR^aR^i$, —$(CR^kR^l)_nR^i$, —$(CR^kR^l)_nNR^aC(O)NR^b$, and —$(CR^kR^l)_nNR^aC(O)OR^b$, wherein each alkyl is substituted with one or more $R_{11}$; or two $R_{10}$ together when on adjacent carbons form an aryl ring optionally substituted with one or more $R_{11}$; or two $R_{10}$ together when on adjacent carbons form a heteroaryl ring optionally substituted with one or more $R_{11}$; or two $R_{10}$ together when on adjacent carbons form a heterocycloalkyl ring optionally substituted with one or more $R_{11}$;

each $R_{11}$ is independently at each occurrence selected from halogen, $C_1$-$C_6$ alkyl, $C_1$-$C_6$ alkoxy, $C_1$-$C_6$ haloalkyl, hydroxy, CN, $C_1$-$C_6$ hydroxyalkyl, —$(CR^kR^l)_mNH_2$, $C_1$-$C_6$ alkylamino, $C_1$-$C_6$ dialkylamino, —$C(O)NR^aR^b$, —$C(O)OR^a$, —$C(O)R^a$, —$S(O)_2R^a$, —$C(O)H$, —$NR^aC(O)OR^a$, —$NR^aC(O)C_1$-$C_6$ alkyl, or oxo;

or two $R_{11}$ together can form a heterocycloalkyl ring;

$R^a$ and $R^b$ are each independently hydrogen, $C_1$-$C_6$ alkyl, —$C_1$-$C_4$ alkyl(aryl), or aryl, wherein the alkyl and aryl are optionally substituted with one or more $R_{10}$;

$R^d$ is $C_1$-$C_6$ alkyl, $C_1$-$C_6$ haloalkyl, $C_3$-$C_7$ cycloalkyl, aryl, heteroaryl, or heterocycloalkyl, wherein cycloalkyl, aryl, heteroaryl, and heterocycloalkyl are optionally substituted with one or more $R_{12}$;

$R^i$ is hydrogen, $C_1$-$C_6$ alkyl, $C_1$-$C_6$ alkoxy, $C_1$-$C_6$ hydroxyalkyl, $C_1$-$C_6$ haloalkyl, —$(CH_2)_qN(H)C_1$-$C_6$ alkyl, —$(CH_2)_qN(C_1$-$C_6$ alkyl$)_2$, —$(CR^kR^l)_mC_3$-$C_7$ cycloalkyl, —$(CR^kR^l)_m$ aryl, —$(CR^kR^l)_m$heteroaryl, or —$(CR^kR^l)_m$ heterocycloalkyl, wherein alkyl, cycloalkyl, aryl, heteroaryl, and heterocycloalkyl are optionally substituted with one or more $R^{11}$;

each $R_{12}$ is independently at each occurrence selected from $C_1$-$C_6$ alkyl, halogen, CN, $C_1$-$C_6$ alkoxy, $C_1$-$C_6$ haloalkyl, $C_1$-$C_6$ haloalkoxy, hydroxy, $NO_2$, —$NH_2$, $CH_2NH_2$, —$(CH_2)_qN(C_1$-$C_6$ alkyl$)_2$, $C_1$-$C_6$ alkylamino, $C_1$-$C_6$ dialkylamino, —$O(CH_2)_qN(H)C_1$-$C_6$ alkyl, —$O(CH_2)_qN(C_1$-$C_6$ alkyl$)_2$, aryl, heteroaryl, —NH-heteroaryl, —O-aryl, —$S(O)_p$—$C_1$-$C_6$ alkyl, —$S(O)_p$—$N(H)C_1$-$C_6$ alkyl, —$S(O)_p$—$N(C_1$-$C_6$ alkyl$)_2$, —$C(O)C_1$-$C_6$ alkyl, —$C(O)OC_1$-$C_6$ alkyl, —$NHC(O)(C_1$-$C_6$ alkyl), or oxo, wherein aryl and heteroaryl are optionally substituted with one or more substituents selected from $C_1$-$C_6$ alkyl, halogen, CN, $C_1$-$C_6$ alkoxy, hydroxy, $NO_2$, —$NH_2$, $C_1$-$C_6$ alkylamino, or $C_1$-$C_6$ dialkylamino; or two $R_{12}$ together with the carbon to which they are attached can form a 4- to 6 membered heterospirocycle; or two $R_{12}$ together when on adjacent carbons form a $C_4$-$C_6$ cycloalkyl optionally substituted with one or more $R_{13}$; or two $R_{12}$ together when on adjacent carbons form an aryl optionally substituted with one or more $R_{13}$; or two $R_{12}$ together when on adjacent carbons form a heteroaryl optionally substituted with one or more $R_{13}$; or two $R_{12}$ together when on adjacent carbons form a heterocycloalkyl optionally substituted with one or more $R_{13}$; or $R_{12}$ with the carbon to which it is attached and the adjacent carbon form a $C_3$ cycloalkyl optionally substituted with one or more $R_{13}$;

each $R_{13}$ is independently at each occurrence selected from $C_1$-$C_6$ alkyl, halogen, CN, $C_1$-$C_6$ alkoxy, $C_1$-$C_6$ haloalkyl, $C_1$-$C_6$ haloalkoxy, hydroxy, $NO_2$, —$NH_2$, $CH_2NH_2$, —$(CH_2)_qN(C_1$-$C_6$ alkyl$)_2$, $C_1$-$C_6$ alkylamino, $C_1$-$C_6$ dialkylamino, —$O(CH_2)_qN(H)$ $C_1$-$C_6$ alkyl, —$O(CH_2)_qN(C_1$-$C_6$ alkyl$)_2$, aryl, heteroaryl, —NH-heteroaryl, —O-aryl, —$S(O)_p$—$C_1$-$C_6$ alkyl, —$S(O)_p$—$N(H)C_1$-$C_6$ alkyl, —$S(O)_p$—$N(C_1$-$C_6$ alkyl$)_2$, —$C(O)C_1$-$C_6$ alkyl, —$NHC(O)$ $(C_1$-$C_6$ alkyl), or oxo, wherein aryl and heteroaryl are optionally substituted with one or more substituents selected from consisting of $C_1$-$C_6$ alkyl, halogen, CN, $C_1$-$C_6$ alkoxy, hydroxy, $NO_2$, —$NH_2$, $C_1$-$C_6$ alkylamino, and $C_1$-$C_6$ dialkylamino;

$R^k$ and $R^l$ are each independently at each occurrence selected from H, $C_1$-$C_6$ alkyl, $C_1$-$C_6$ alkoxy, $C_1$-$C_6$ haloalkyl, or halogen;

each m, n, and p is independently at each occurrence 0, 1, or 2; and each q is independently at each occurrence 1, 2, 3 or 4;

provided that when m is 0, $R^d$ is not $C_1$-$C_6$ alkoxy, $C_1$-$C_6$ haloalkoxy, or CN.

In some embodiments of the Formulae above, $R_1$ is hydrogen, $C_1$-$C_6$ alkyl, or $C_1$-$C_6$ haloalkyl. In one embodiment, $R_1$ is hydrogen, $C_1$-$C_3$ alkyl, or $C_1$-$C_3$ haloalkyl. In yet another embodiment, $R_1$ is hydrogen, $C_1$-$C_2$ alkyl, or $C_1$-$C_2$ haloalkyl. In another embodiment, $R_1$ is hydrogen, methyl, ethyl, propyl, iso-propyl, $CF_3$, $CHF_2$, $CH_2F$, $CH_2CF_3$, $CH_2CHF_2$, $CH_2CH_2F$, $CHFCH_3$, $CF_2CH_3$, $CHFCH_2F$, $CF_2CH_2F$, $CHFCHF_2$, $CF_2CHF_2$, $CHFCF_3$, or $CF_2CF_3$. In another embodiment, $R_1$ is hydrogen, methyl, ethyl, or $CHF_2$. In yet another embodiment, $R_1$ is methyl.

In some embodiments of the Formulae above, $R_2$ is —$C(O)(CR^kR^l)_nO(CR^kR^l)_mR^d$, —$C(O)(CR^kR^l)_nR^e$, —$S(O)_2(CR^kR^l)_nR^f$, —$(CR^kR^l)_nR^g$, —$C(O)(CR^kR^l)_nNR^aR^g$ or —$C(O)(CR^kR^l)_nS(CR^kR^l)_mR^f$. In another embodiment, $R_2$ is —$C(O)(CR^kH)_nO(CR^kH)_mR^d$, —$C(O)(CR^kH)_nR^e$, —$S(O)_2(CR^kH)_nR^f$, —$(CR^kH)_nR^g$, —$C(O)(CR^kH)_nNR^aR^g$ or —$C(O)(CR^kH)_nS(CR^kH)_mR^f$. In yet another embodiment, $R_2$ is —$C(O)(CR^kH)_nO(CR^kH)_mR^d$, —$C(O)(CR^kH)_nR^e$, —$S(O)_2(CR^kH)_nR^f$, —$(CR^kH)_nR^g$, or —$C(O)(CR^kH)_n$—$NR^aR^g$. In another embodiment, $R_2$ is —$C(O)O(CR^kH)_mR^d$ or —$C(O)(CR^kH)_nR^e$. In another embodiment, $R_2$ is —$C(O)OR_d$, —$C(O)R_e$, or $R_g$.

In some embodiments of the Formulae above, $R_3$ may be hydrogen or F. In another embodiment, $R_3$ is hydrogen. In yet another embodiment, $R_3$ is F.

In some embodiments of the Formulae above, $R_4$ is hydrogen, $C_3$-$C_6$ cycloalkyl, $C_6$-$C_{10}$ aryl, heterocycloalkyl, heteroaryl, —$NR^aR^b$, —$C(O)R^h$, or —$OR^h$. In another embodiment, the cycloalkyl, aryl, heterocycloalkyl, heteroaryl, and alkyl of $R_4$ are optionally substituted with one or more $R_{10}$.

In some embodiments of the Formulae above, $R_4$ is selected from the group consisting of:

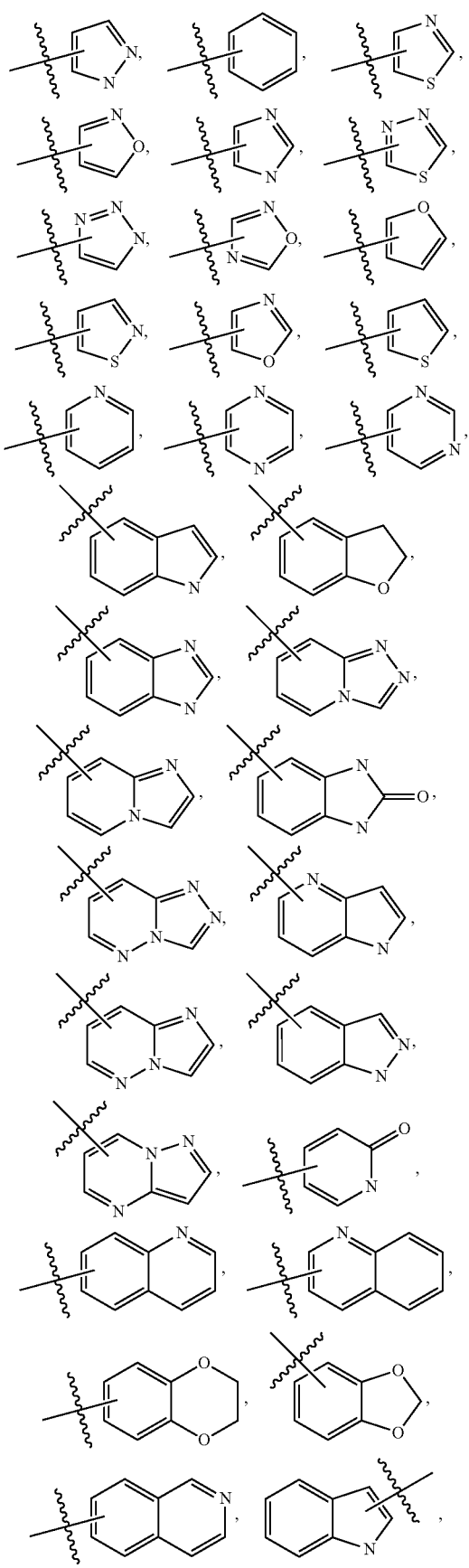

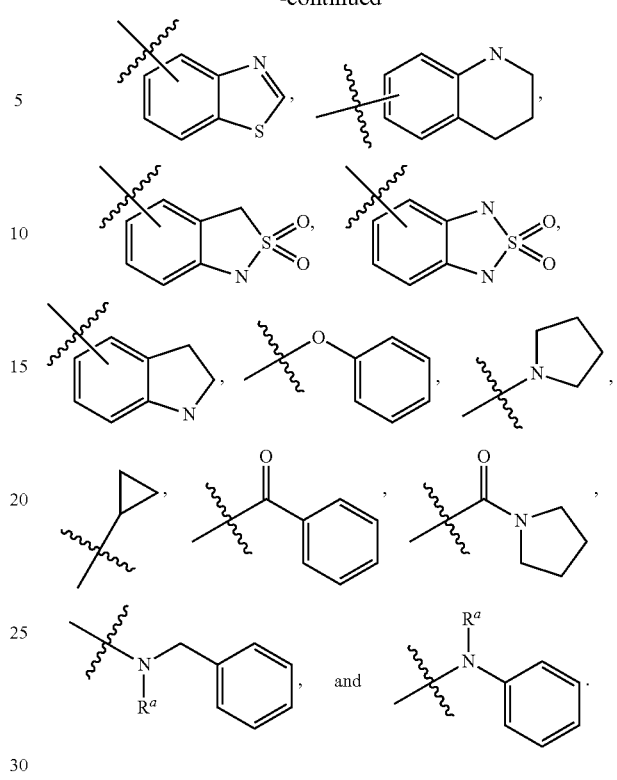

In other embodiments, $R_4$ is phenyl, pyridine, pyridazine, pyrimidine or pyrazole.

In some embodiments of the Formulae above, $R_6$ is hydrogen or F. In another embodiment, $R_6$ is hydrogen. In another embodiment, $R_6$ is F.

In some embodiments of the Formulae above, $R_7$ is —C(O)$R_8$, —C(O)O$R_8$, —C(O)N$R_8R_9$, or —S(O)$_2R_8$. In another embodiment, $R_7$ is —C(O)$R_8$, —C(O)O$R_8$, or —C(O)N$R_8R_9$.

In another embodiment, $R_7$ is —C(O)CH$_3$, —C(O)OCH$_3$, —S(O)$_2$CH$_3$, —C(O)H, —C(O)CF$_3$, —C(O)N(H)CH$_3$, —C(O)N(CH$_3$)$_2$, —C(O)NH$_2$,

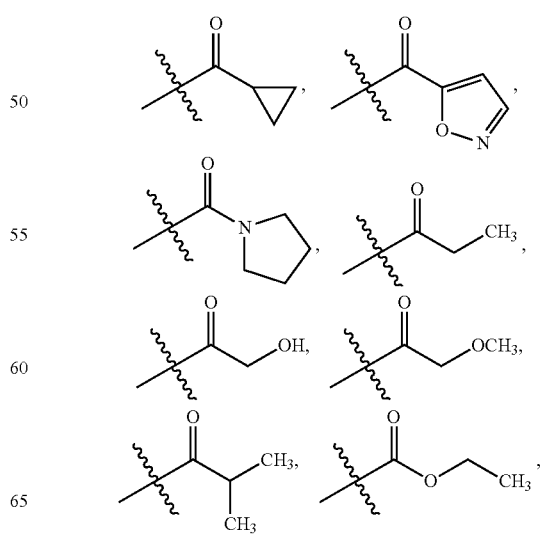

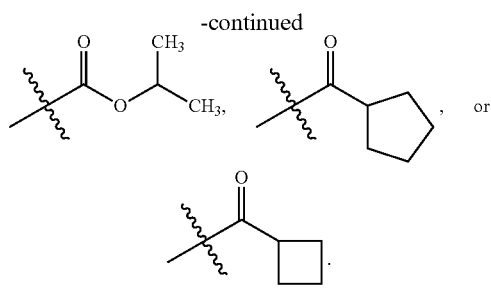

In some embodiments of the Formulae above, $R_8$ is hydrogen, $-(CR^kR^l)_mOR^a$, $C_1$-$C_4$ alkyl, $C_1$-$C_3$ haloalkyl, $C_3$-$C_6$ cycloalkyl, heterocycloalkyl, aryl, or heteroaryl. In another embodiment, $R_8$ is hydrogen, $-(CH_2)_mOR^a$, $C_1$-$C_2$ alkyl, $C_1$-$C_2$ haloalkyl, $C_3$-$C_6$ cycloalkyl, heterocycloalkyl, aryl, or heteroaryl. In yet another embodiment, $R_8$ is hydrogen, $C_1$-$C_2$ alkyl, $C_1$-$C_2$ haloalkyl, $C_3$-$C_6$ cycloalkyl, heterocycloalkyl or heteroaryl. In another embodiment, $R_8$ is hydrogen, $-CH_3$, $-CF_3$, or cyclopropyl. In yet another embodiment, $R_8$ is $-CH_3$, or cyclopropyl.

In some embodiments of the Formulae above, $R_9$ is hydrogen, $-(CR^kR^l)_mOR^a$, $C_1$-$C_4$ alkyl, $C_1$-$C_3$ haloalkyl, $C_3$-$C_6$ cycloalkyl, heterocycloalkyl, aryl, or heteroaryl. In another embodiment, $R_9$ is hydrogen, $-(CH_2)_mOR^a$, $C_1$-$C_2$ alkyl, $C_1$-$C_2$ haloalkyl, $C_3$-$C_6$ cycloalkyl, heterocycloalkyl, aryl, or heteroaryl. In yet another embodiment, $R_9$ is hydrogen, $C_1$-$C_2$ alkyl, $C_1$-$C_2$ haloalkyl, or $C_3$-$C_6$ cycloalkyl. In another embodiment, $R_9$ is hydrogen, or $C_1$-$C_2$ alkyl. In yet another embodiment, $R_9$ is hydrogen or $-CH_3$.

In some embodiments of the Formulae above, $R^a$ is independently hydrogen, $C_1$-$C_6$ alkyl, $-C_1$-$C_3$ alkyl(aryl), or aryl, where the alkyl and aryl are optionally substituted with one or more $R_{10}$. In one embodiment, $R^a$ is hydrogen, $C_1$-$C_6$ alkyl, $-C_1$-$C_3$ alkyl(aryl), or aryl, where the alkyl and aryl are optionally substituted with one or three $R_{10}$. In another embodiment, $R^a$ is hydrogen, methyl, ethyl, propyl, iso-propyl, butyl, iso-butyl, tert-butyl, benzyl, or phenyl, where the alkyl and phenyl are optionally substituted with one or more $R_{10}$.

In some embodiments of the Formulae above, $R^b$ is hydrogen, $C_1$-$C_6$ alkyl, $-C_1$-$C_3$ alkyl(aryl), or aryl, where the alkyl and aryl are optionally substituted with one or more $R_{10}$. In one embodiment, $R^b$ is hydrogen, $C_1$-$C_6$ alkyl, $-C_1$-$C_3$ alkyl(aryl), or aryl, where the alkyl and aryl are optionally substituted with one or three $R_{10}$. In another embodiment, $R^b$ is hydrogen, methyl, ethyl, propyl, iso-propyl, butyl, iso-butyl, tert-butyl, benzyl, or phenyl, where the alkyl and phenyl are optionally substituted with one or more $R_{10}$.

In some embodiments of the Formulae above, $R^c$ is hydrogen, $C_1$-$C_6$ alkyl, $-C_1$-$C_3$ alkyl(aryl), or aryl, where the alkyl and aryl are optionally substituted with one or more $R_{10}$. In one embodiment, $R^c$ is hydrogen, $C_1$-$C_6$ alkyl, $-C_1$-$C_3$ alkyl(aryl), or aryl, where the alkyl and aryl are optionally substituted with one to three $R_{10}$. In another embodiment, $R^c$ is hydrogen, methyl, ethyl, propyl, iso-propyl, butyl, iso-butyl, tert-butyl, benzyl, or phenyl, where the alkyl and phenyl are optionally substituted with one or more $R_{10}$.

In some embodiments of the Formulae above, $R^d$ is $C_1$-$C_3$ alkyl, $C_2$-$C_4$ alkenyl, $C_2$-$C_4$ alkynyl, $C_1$-$C_3$ alkoxy, $C_1$-$C_3$ haloalkyl, $C_1$-$C_3$ haloalkoxy, CN, $-C(O)C_1$-$C_3$ alkyl, $C_3$-$C_7$ cycloalkyl, aryl, heteroaryl, or heterocycloalkyl, where cycloalkyl, aryl, heteroaryl, and heterocycloalkyl are optionally substituted with one or more $R_{12}$. In another embodiment, $R^d$ is $C_1$-$C_3$ alkyl, $C_2$-$C_4$ alkenyl, $C_2$-$C_4$ alkynyl, $C_1$-$C_3$ alkoxy, $C_1$-$C_3$ haloalkyl, $C_1$-$C_3$ haloalkoxy, CN, $-C(O)C_1$-$C_3$ alkyl, $C_3$-$C_7$ cycloalkyl, aryl, heteroaryl, or heterocycloalkyl, where cycloalkyl, aryl, heteroaryl, and heterocycloalkyl are optionally substituted with one to three $R_{12}$. In yet another embodiment, $R^d$ is cyclopropyl, cyclobutyl, cyclopentyl, methyl, ethyl, propyl, or iso-propyl. In another embodiment, $R^d$ is cyclopropyl, cyclobutyl, iso-propyl, or methyl. In another embodiment, $R^d$ is $C_3$-$C_7$ cycloalkyl, aryl, heteroaryl, or heterocycloalkyl, where cycloalkyl, aryl, heteroaryl, and heterocycloalkyl are optionally substituted with one or more $R_{12}$.

In some embodiments of the Formulae above, $R^e$ is $C_1$-$C_3$ alkyl, $C_2$-$C_4$ alkynyl, $C_1$-$C_3$ haloalkyl, $C_1$-$C_3$ haloalkoxy, $C_1$-$C_4$ alkoxy, CN, $C_3$-$C_7$ cycloalkyl, aryl, heteroaryl, or heterocycloalkyl, where cycloalkyl, aryl, heteroaryl, and heterocycloalkyl are optionally substituted with one or more $R_{12}$. In another embodiment, $R^e$ is $C_1$-$C_3$ alkyl, $C_2$-$C_4$ alkynyl, $C_1$-$C_3$ haloalkyl, $C_1$-$C_3$ haloalkoxy, $C_1$-$C_4$ alkoxy, CN, $C_3$-$C_7$ cycloalkyl, aryl, heteroaryl, or heterocycloalkyl, where cycloalkyl, aryl, heteroaryl, and heterocycloalkyl are optionally substituted with one to three $R_{12}$. In yet another embodiment, $R^e$ is cyclopropyl, cyclobutyl, cyclopentyl, methyl, ethyl, propyl, or iso-propyl. In another embodiment, $R^e$ is cyclopropyl, cyclobutyl, iso-propyl, or methyl. In another embodiment, $R^e$ is $C_3$-$C_7$ cycloalkyl, aryl, heteroaryl, or heterocycloalkyl, where cycloalkyl, aryl, heteroaryl, and heterocycloalkyl are optionally substituted with one or more $R_{12}$.

In some embodiments of the Formulae above, $R^f$ is $C_3$-$C_7$ cycloalkyl, aryl, heteroaryl, or heterocycloalkyl, where cycloalkyl, aryl, heteroaryl and heterocycloalkyl are optionally substituted with one or more $R_{12}$. In another embodiment, $R^f$ is $C_3$-$C_7$ cycloalkyl, aryl, heteroaryl, or heterocycloalkyl, where cycloalkyl, aryl, heteroaryl and heterocycloalkyl are optionally substituted with one to three $R_{12}$.

In some embodiments of the Formulae above, $R^g$ is $C_1$-$C_6$ alkyl, $C_3$-$C_7$ cycloalkyl, $-C_1$-$C_3$ alkyl($C_3$-$C_7$ cycloalkyl), aryl, $-C_1$-$C_3$ alkyl(aryl), heteroaryl, $-C_1$-$C_3$ alkyl(heteroaryl), heterocycloalkyl or $-C_1$-$C_3$ alkyl(heterocycloalkyl), where cycloalkyl, aryl, heteroaryl, and heterocycloalkyl are optionally substituted with one or more $R_{12}$. In another embodiment, $R^g$ is $C_1$-$C_3$ alkyl, $C_3$-$C_6$ cycloalkyl, $-C_1$-$C_2$ alkyl($C_3$-$C_6$ cycloalkyl), aryl, $-C_1$-$C_2$ alkyl(aryl), heteroaryl, $-C_1$-$C_2$ alkyl(heteroaryl), heterocycloalkyl or $-C_1$-$C_2$ alkyl(heterocycloalkyl), where cycloalkyl, aryl, heteroaryl, and heterocycloalkyl are optionally substituted with one or more $R_{12}$. In another embodiment, $R^g$ is $C_1$-$C_3$ alkyl, $C_3$-$C_6$ cycloalkyl, $-C_1$-$C_2$ alkyl($C_3$-$C_6$ cycloalkyl), aryl, $-C_1$-$C_2$ alkyl(aryl), heteroaryl, $-C_1$-$C_2$ alkyl(heteroaryl), heterocycloalkyl or $-C_1$-$C_2$ alkyl(heterocycloalkyl), where cycloalkyl, aryl, heteroaryl, and heterocycloalkyl are optionally substituted with one to three $R_{12}$.

In some embodiments of the Formulae above, $R^h$ is $C_3$-$C_7$ cycloalkyl, aryl, heteroaryl, or heterocycloalkyl, where cycloalkyl, aryl, heteroaryl, and heterocycloalkyl are optionally substituted with one or more $R_{10}$. In one embodiment, $R^h$ is $C_3$-$C_7$ cycloalkyl, aryl, heteroaryl, or heterocycloalkyl, where cycloalkyl, aryl, heteroaryl, and heterocycloalkyl are optionally substituted with one to three $R_{10}$.

In some embodiments of the Formulae above, $R^k$ is at each occurrence selected from H, $C_1$-$C_3$ alkyl, $C_1$-$C_3$ alkoxy, $C_1$-$C_3$ haloalkyl, or halogen. In another embodiment, $R^k$ is at each occurrence selected from H, methyl, ethyl, propyl, iso-propyl, methoxy, ethoxy, $CF_3$, $CHF_2$, $CH_2F$, F, or Cl.

In some embodiments of the Formulae above, $R^l$ is at each occurrence selected from H, $C_1$-$C_3$ alkyl, $C_1$-$C_3$ alkoxy, $C_1$-$C_3$ haloalkyl, or halogen. In another embodiment, $R^l$ is at each occurrence selected from H, methyl, ethyl, propyl, isopropyl, methoxy, ethoxy, $CF_3$, $CHF_2$, $CH_2F$, F, or Cl.

In some embodiments of the Formulae above, m is 0. In another embodiment, m is 1. In yet another embodiment, m is 2.

In some embodiments of the Formulae above, n is 0. In another embodiment, n is 1. In yet another embodiment, n is 2.

In some embodiments of the Formulae above, p is 0. In another embodiment, p is 1. In yet another embodiment, p is 2.

In some embodiments of the Formulae above, q is 1. In another embodiment, q is 2. In yet another embodiment, q is 3. In another embodiment, q is 4.

In some embodiments of the Formulae above, X is N or $CR_3$. In another embodiment, X is N or CH. In yet another embodiment, X is CH. In another embodiment, X is N.

In some embodiments of the Formulae above, Y is N or $CR_5$. In another embodiment, Y is N. In yet another embodiment, Y is $CR_5$ and $R_5$ is hydrogen, halogen, nitro, $-NH_2$, CN, $C_1$-$C_3$ alkoxy, $-C(O)NR^aR^b$, $-NR^aS(O)_2R^b$, $-NR^aC(O)R^b$, $-NR^aC(O)OR^b$, or $-NR^aC(O)NR^bR^c$. In another embodiment, Y is $CR_5$ and $R_5$ is hydrogen, halogen, nitro, $-NH_2$, CN, $C_1$-$C_3$ alkoxy, $-C(O)NHR^b$, $-NHS(O)_2R^b$, $-NHC(O)R^b$, $-NHC(O)OR^b$, or $-NHC(O)NR^bR^c$. In yet another embodiment, Y is $CR_5$ and $R_5$ is H, $NO_2$, $-NH_2$, $-NHS(O)_2CH_3$, $-NHC(O)CH_3$, $-NHC(O)NHCH_3$, $-NHC(O)OCH_3$, $-OCH_3$, $-C(O)NH_2$, F, Cl, Br, or CN In some embodiments of the Formulae above, Z is selected from N or $CR_6$. In another embodiment, Z is independently selected from N or CH. In yet another embodiment, Z is CH. In another embodiment, Z is N.

In some embodiments of the Formulae above, Ar is selected from the group consisting of:

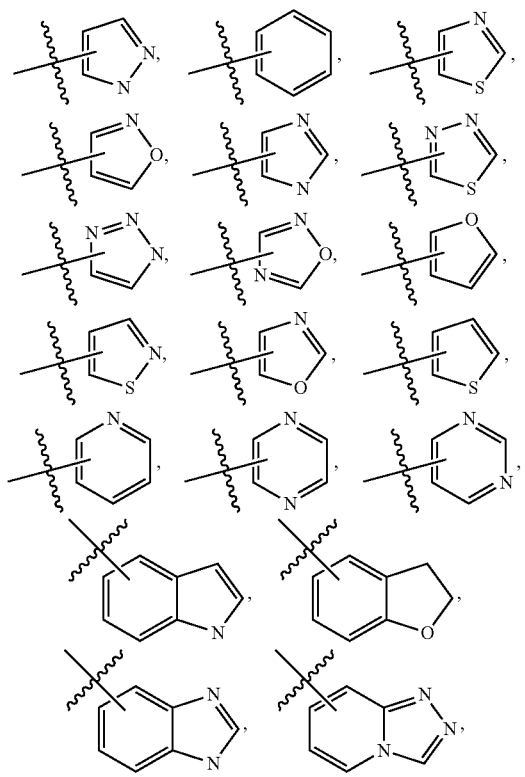

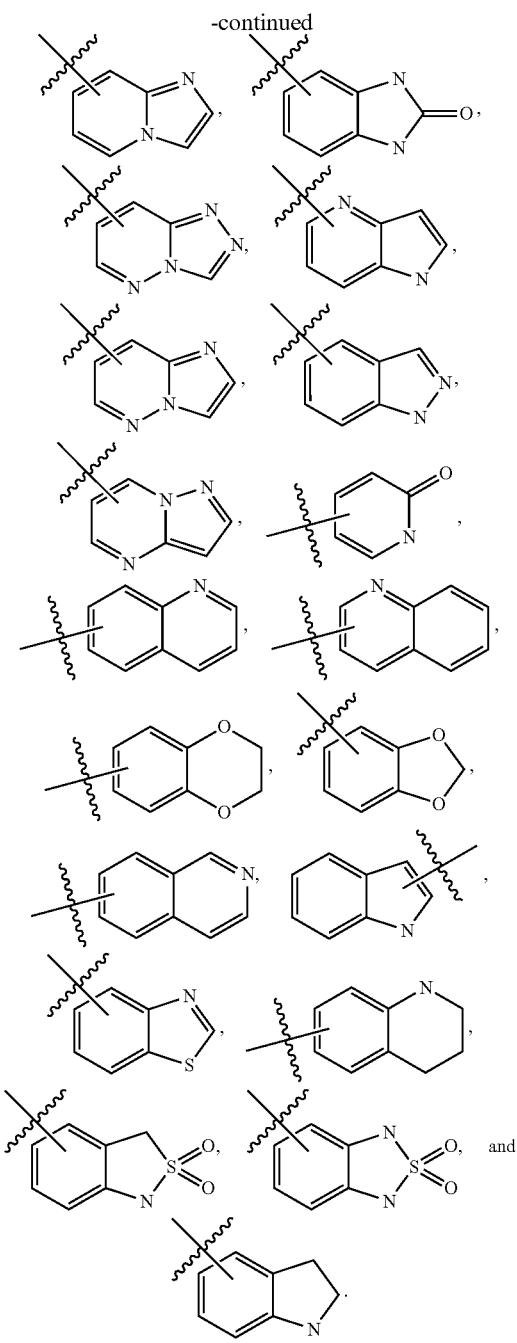

In another embodiment, Ar is phenyl, pyridine, pyridazine, pyrimidine or pyrazole.

In some embodiments of the Formulae above, X is CH, Y is CH, and Z is CH. In another embodiment, X is CH, Y is CH, Z is CH, and $R_1$ is methyl. In yet another embodiment, X is CH, Y is CH, Z is CH, $R_1$ is methyl and $R_2$ is $-C(O)O(CH_2)_m R^d$ or $-C(O)(CH_2)_n R^e$. In another embodiment, X is CH, Y is CH, Z is CH, $R_1$ is methyl, $R_2$ is $-C(O)O(CH_2)_m R^d$ or $-C(O)(CH_2)_n R^e$, and $R_4$ is phenyl, pyridine, pyridazine, pyrimidine, or pyrazole.

In another embodiment, $R^8$ is alkoxy or $-CH_3$; $R_2$ is C(O)$R^b$, or substituted or unsubstituted bicyclic heteroaryl having two heteroatoms independently selected from O, S, and N; and $R^b$ is substituted or unsubstituted cyclopropyl, heterocyclopropyl with a single O, S, or N heteroatom, substituted branched alkyl, or heteroaryl with a single O, S, or N heteroatom.

In some embodiments of the Formulae above, X is CH. In another embodiment, X is CH and Y is $CR_5$. In yet another embodiment, X is CH, Y is $CR_5$, and Z is CH. In another embodiment, X is CH, Y is $CR_5$, Z is CH, and $R_1$ is $C_1$-$C_6$ alkyl. In another embodiment, X is CH, Y is $CR_5$, Z is CH, $R_1$ is methyl and $R_2$ is —C(O)$OR_d$, —C(O)$R_e$, or $R_g$. In yet another embodiment, X is CH, Y is $CR_5$, Z is CH, $R_1$ is methyl, $R_2$ is —C(O)$OR_d$, —C(O)$R_e$, or $R_g$, and $R_7$ is —C(O)$R_8$. In another embodiment, X is CH, Y is $CR_5$, Z is CH, $R_1$ is methyl, $R_2$ is —C(O)$OR_d$, —C(O)$R_e$, or $R_g$, $R_7$ is —C(O)$R_8$, and $R_8$ is $C_1$-$C_6$ alkyl or $C_3$-$C_6$ cycloalkyl. In yet another embodiment of the Formulae above, X is CH, Y is $CR_5$, Z is CH, $R_1$ is methyl, $R_2$ is —C(O)$OR_d$, —C(O)$R_e$, or $R_g$, $R_7$ is —C(O)$R_8$, $R_8$ is $C_1$-$C_6$ alkyl or $C_3$-$C_6$ cycloalkyl, and $R_d$ is $C_3$-$C_7$ cycloalkyl, $C_1$-$C_6$ alkyl, or heterocycloalkyl optionally substituted with the preferred substituents. In another embodiment, X is CH, Y is $CR_5$, Z is CH, $R_1$ is methyl, $R_2$ is —C(O)$OR_d$, —C(O)$R_e$, or $R_g$, $R_7$ is —C(O)$R_8$, $R_8$ is $C_1$-$C_6$ alkyl or $C_3$-$C_6$ cycloalkyl, $R_d$ is $C_3$-$C_7$ cycloalkyl, $C_1$-$C_6$ alkyl, or heterocycloalkyl optionally substituted with the preferred substituents, and $R_e$ is $C_1$-$C_6$ alkyl or heterocycloalkyl optionally substituted with the preferred substituents. In another embodiment, X is CH, Y is $CR_5$, Z is CH, $R_1$ is methyl, $R_2$ is —C(O)$OR_d$, —C(O)$R_e$, or $R_g$, $R_7$ is —C(O)$R_8$, $R_8$ is $C_1$-$C_6$ alkyl or $C_3$-$C_6$ cycloalkyl, $R_d$ is $C_3$-$C_7$ cycloalkyl, $C_1$-$C_6$ alkyl, or heterocycloalkyl optionally substituted with the preferred substituents, $R_e$ is $C_1$-$C_6$ alkyl or heterocycloalkyl optionally substituted with the preferred substituents, and $R_g$ is heteroaryl optionally substituted with the preferred substituents. In yet another embodiment, X is CH, Y is $CR_5$, Z is CH, $R_1$ is methyl, $R_2$ is —C(O)$OR_d$, —C(O)$R_e$, or $R_g$, $R_7$ is —C(O)$R_8$, $R_8$ is $C_1$-$C_6$ alkyl or $C_3$-$C_6$ cycloalkyl, $R_d$ is $C_3$-$C_7$ cycloalkyl, $C_1$-$C_6$ alkyl, or heterocycloalkyl optionally substituted with the preferred substituents, $R_e$ is $C_1$-$C_6$ alkyl or heterocycloalkyl optionally substituted with the preferred substituents, $R_g$ is heteroaryl optionally substituted with the preferred substituents, and $R_4$ is aryl or heteroaryl optionally substituted with one or more $R_{10}$.

In some embodiments of the Formulae above, X is CH. In another embodiment, X is CH and Y is CH. In yet another embodiment, X is CH, Y is CH, and Z is CH. In another embodiment, X is CH, Y is CH, Z is CH, and $R_1$ is methyl. In another embodiment, X is CH, Y is CH, Z is CH, $R_1$ is methyl and $R_2$ is —C(O)$OR_d$, —C(O)$R_e$, or $R_g$. In yet another embodiment, X is CH, Y is CH, Z is CH, $R_1$ is methyl, $R_2$ is —C(O)$OR_d$, —C(O)$R_e$, or $R_g$, and $R_7$ is —C(O)$R_8$. In another embodiment, X is CH, Y is CH, Z is CH, $R_1$ is methyl, $R_2$ is —C(O)$OR_d$, —C(O)$R_e$, or $R_g$, $R_7$ is —C(O)$R_8$, and $R_8$ is $C_1$-$C_6$ alkyl or $C_3$-$C_6$ cycloalkyl. In yet another embodiment of the Formulae above, X is CH, Y is CH, Z is CH, $R_1$ is methyl, $R_2$ is —C(O)$OR_d$, —C(O)$R_e$, or $R_g$, $R_7$ is —C(O)$R_8$, $R_8$ is $C_1$-$C_6$ alkyl or $C_3$-$C_6$ cycloalkyl, and $R_d$ is $C_3$-$C_7$ cycloalkyl, $C_1$-$C_6$ alkyl, or heterocycloalkyl optionally substituted with the preferred substituents. In another embodiment, X is CH, Y is CH, Z is CH, $R_1$ is methyl, $R_2$ is —C(O)$OR_d$, —C(O)$R_e$, or $R_g$, $R_7$ is —C(O)$R_8$, $R_8$ is $C_1$-$C_6$ alkyl or $C_3$-$C_6$ cycloalkyl, $R_d$ is $C_3$-$C_7$ cycloalkyl, $C_1$-$C_6$ alkyl, or heterocycloalkyl optionally substituted with the preferred substituents, and $R_e$ is $C_1$-$C_6$ alkyl or heterocycloalkyl optionally substituted with the preferred substituents. In another embodiment, X is CH, Y is CH, Z is CH, $R_1$ is methyl, $R_2$ is —C(O)$OR_d$, —C(O)$R_e$, or $R_g$, $R_7$ is —C(O)$R_8$, $R_8$ is $C_1$-$C_6$ alkyl or $C_3$-$C_6$ cycloalkyl, $R_d$ is $C_3$-$C_7$ cycloalkyl, $C_1$-$C_6$ alkyl, or heterocycloalkyl optionally substituted with the preferred substituents, $R_e$ is $C_1$-$C_6$ alkyl or heterocycloalkyl optionally substituted with the preferred substituents, and $R_g$ is heteroaryl optionally substituted with the preferred substituents. In yet another embodiment, X is CH, Y is $CR_5$, Z is CH, $R_1$ is methyl, $R_2$ is —C(O)$OR_d$, —C(O)$R_e$, or $R_g$, $R_7$ is —C(O)$R_8$, $R_8$ is $C_1$-$C_6$ alkyl or $C_3$-$C_6$ cycloalkyl, $R_d$ is $C_3$-$C_7$ cycloalkyl, $C_1$-$C_6$ alkyl, or heterocycloalkyl optionally substituted with the preferred substituents, $R_e$ is $C_1$-$C_6$ alkyl or heterocycloalkyl optionally substituted with the preferred substituents, $R_g$ is heteroaryl optionally substituted with the preferred substituents, and $R_4$ phenyl, pyridine, pyridazine, pyrimidine or pyrazole optionally substituted with one or more $R_{10}$. In another embodiment, X is CH, Y is $CR_5$, Z is CH, $R_1$ is methyl, $R_2$ is —C(O)$OR_d$, —C(O)$R_e$, or $R_g$, $R_7$ is —C(O)$R_8$, $R_8$ is $C_1$-$C_6$ alkyl or $C_3$-$C_6$ cycloalkyl, $R_d$ is $C_3$-$C_7$ cycloalkyl, $C_1$-$C_6$ alkyl, or heterocycloalkyl optionally substituted with the preferred substituents, $R_e$ is $C_1$-$C_6$ alkyl or heterocycloalkyl optionally substituted with the preferred substituents, $R_g$ is heteroaryl optionally substituted with the preferred substituents, $R_4$ phenyl, pyridine, pyridazine, pyrimidine or pyrazole optionally substituted with one or more $R_{10}$, and $R_{10}$ is $C_1$-$C_6$ alkyl, heterocycloalkyl, —S(O)$_2R^i$, $NR^aS(O)R^i$, or $R^i$. In yet another embodiment, X is CH, Y is $CR_5$, Z is CH, $R_1$ is methyl, $R_2$ is —C(O)$OR_d$, —C(O)$R_e$, or $R_g$, $R_7$ is —C(O)$R_8$, $R_8$ is $C_1$-$C_6$ alkyl or $C_3$-$C_6$ cycloalkyl, $R_d$ is $C_3$-$C_7$ cycloalkyl, $C_1$-$C_6$ alkyl, or heterocycloalkyl optionally substituted with the preferred substituents, $R_e$ is $C_1$-$C_6$ alkyl or heterocycloalkyl optionally substituted with the preferred substituents, $R_g$ is heteroaryl optionally substituted with the preferred substituents, $R_4$ phenyl, pyridine, pyridazine, pyrimidine or pyrazole optionally substituted with one or more $R_{10}$, and $R_{10}$ is $C_1$-$C_6$ alkyl and 2 $R_{10}$ together when on adjacent carbons form a heterocycloalkyl.

Non-limiting illustrative compounds of the invention include:

3,3-difluorocyclobutyl (3S)-4-acetyl-7-[1-(1,1-dioxo-1λ$^6$-thietan-3-yl)-1H-pyrazol-4-yl]-3-methyl-1,2,3,4-tetrahydroquinoxaline-1-carboxylate;

4,4-difluorocyclohexyl (3S)-4-acetyl-3-methyl-7-[1-(oxan-4-yl)-1H-pyrazol-4-yl]-1,2,3,4-tetrahydroquinoxaline-1-carboxylate;

2-methoxyphenyl (3S)-4-acetyl-3-methyl-7-[1-(oxetan-3-yl)-1H-pyrazol-4-yl]-1,2,3,4-tetrahydroquinoxaline-1-carboxylate;

3,3-difluorocyclobutyl (3S)-4-acetyl-3-methyl-7-[1-(oxan-4-yl)-1H-pyrazol-4-yl]-1,2,3,4-tetrahydroquinoxaline-1-carboxylate;

3,3-difluorocyclobutyl (3S)-4-acetyl-7-(4-methanesulfonylphenyl)-3-methyl-1,2,3,4-tetrahydroquinoxaline-1-carboxylate;

1-[(2S)-4-cyclopropanecarbonyl-6-(1-cyclopropyl-1H-pyrazol-4-yl)-2-methyl-1,2,3,4-tetrahydroquinoxalin-1-yl]ethan-1-one;

ethyl (3S)-4-acetyl-3-methyl-7-[1-(oxetan-3-yl)-1H-pyrazol-4-yl]-1,2,3,4-tetrahydroquinoxaline-1-carboxylate;

1-[(2S)-4-cyclopropanecarbonyl-2-methyl-6-[1-(oxetan-3-yl)-1H-pyrazol-4-yl]-1,2,3,4-tetrahydroquinoxalin-1-yl]ethan-1-one;

1-[(2S)-4-cyclobutanecarbonyl-2-methyl-6-[1-(oxetan-3-yl)-1H-pyrazol-4-yl]-1,2,3,4-tetrahydroquinoxalin-1-yl]ethan-1-one;

propan-2-yl (3S)-4-acetyl-7-[1-(2-hydroxyethyl)-1H-pyrazol-4-yl]-3-methyl-1,2,3,4-tetrahydroquinoxaline-1-carboxylate;

1-[(2S)-4-(furan-2-carbonyl)-2-methyl-6-(1H-pyrazol-4-yl)-1,2,3,4-tetrahydroquinoxalin-1-yl]ethan-1-one;

1-[(2S)-4-(furan-2-carbonyl)-2-methyl-6-(1H-pyrazol-3-yl)-1,2,3,4-tetrahydroquinoxalin-1-yl]ethan-1-one;

1-[(2S)-4-(furan-2-carbonyl)-2-methyl-6-(2-methyl-1,3-thiazol-5-yl)-1,2,3,4-tetrahydroquinoxalin-1-yl]ethan-1-one;

phenyl (3S)-4-acetyl-3-methyl-7-(1H-pyrazol-4-yl)-1,2,3,4-tetrahydroquinoxaline-1-carboxylate;

propan-2-yl (3S)-4-acetyl-7-[1-(2-methoxyethyl)-1H-pyrazol-4-yl]-3-methyl-1,2,3,4-tetrahydroquinoxaline-1-carboxylate;

1-[(2S)-4-(furan-2-carbonyl)-6-[1-(2-methoxyethyl)-1H-pyrazol-4-yl]-2-methyl-1,2,3,4-tetrahydroquinoxalin-1-yl]ethan-1-one;

ethyl (3S)-4-acetyl-3-methyl-7-(1H-pyrazol-4-yl)-1,2,3,4-tetrahydroquinoxaline-1-carboxylate;

cyclopentyl (3S)-4-acetyl-3-methyl-7-(1H-pyrazol-4-yl)-1,2,3,4-tetrahydroquinoxaline-1-carboxylate;

ethyl (3S)-4-acetyl-7-(1-cyclopropyl-1H-pyrazol-4-yl)-3-methyl-1,2,3,4-tetrahydroquinoxaline-1-carboxylate;

propan-2-yl (3S)-4-acetyl-7-(1-cyclopropyl-1H-pyrazol-4-yl)-3-methyl-1,2,3,4-tetrahydroquinoxaline-1-carboxylate;

cyclopentyl (3S)-4-acetyl-7-(1-cyclopropyl-1H-pyrazol-4-yl)-3-methyl-1,2,3,4-tetrahydroquinoxaline-1-carboxylate;

propan-2-yl (3S)-4-acetyl-7-(1-cyclobutyl-1H-pyrazol-4-yl)-3-methyl-1,2,3,4-tetrahydroquinoxaline-1-carboxylate;

cyclopentyl (3S)-4-acetyl-7-(1-cyclobutyl-1H-pyrazol-4-yl)-3-methyl-1,2,3,4-tetrahydroquinoxaline-1-carboxylate;

3,3-difluorocyclobutyl (3S)-4-acetyl-7-(1-cyclopropyl-1H-pyrazol-4-yl)-3-methyl-1,2,3,4-tetrahydroquinoxaline-1-carboxylate;

3,3-difluorocyclobutyl (3S)-4-acetyl-7-[1-(2-hydroxyethyl)-1H-pyrazol-4-yl]-3-methyl-1,2,3,4-tetrahydroquinoxaline-1-carboxylate;

3,3-difluorocyclobutyl (3S)-4-acetyl-7-[1-(2-hydroxy-2-methylpropyl)-1H-pyrazol-4-yl]-3-methyl-1,2,3,4-tetrahydroquinoxaline-1-carboxylate;

3,3-difluorocyclobutyl (3S)-4-acetyl-7-[4-(1,1-dioxo-1λ$^6$,2-thiazolidin-2-yl)phenyl]-3-methyl-1,2,3,4-tetrahydroquinoxaline-1-carboxylate;

3,3-difluorocyclobutyl (3S)-4-acetyl-7-(4-methanesulfonamidophenyl)-3-methyl-1,2,3,4-tetrahydroquinoxaline-1-carboxylate;

4,4-difluorocyclohexyl (3S)-4-acetyl-7-(4-methanesulfonamidophenyl)-3-methyl-1,2,3,4-tetrahydroquinoxaline-1-carboxylate;

4,4-difluorocyclohexyl (3S)-4-acetyl-7-(4-methanesulfonylphenyl)-3-methyl-1,2,3,4-tetrahydroquinoxaline-1-carboxylate;

4,4-difluorocyclohexyl (3S)-4-acetyl-7-(1-cyclopropyl-1H-pyrazol-4-yl)-3-methyl-1,2,3,4-tetrahydroquinoxaline-1-carboxylate;

4,4-difluorocyclohexyl (3S)-4-acetyl-7-[1-(2-hydroxyethyl)-1H-pyrazol-4-yl]-3-methyl-1,2,3,4-tetrahydroquinoxaline-1-carboxylate;

4,4-difluorocyclohexyl (3S)-4-acetyl-7-[1-(2-hydroxy-2-methylpropyl)-1H-pyrazol-4-yl]-3-methyl-1,2,3,4-tetrahydroquinoxaline-1-carboxylate;

4,4-difluorocyclohexyl (3S)-4-acetyl-7-[4-(1,1-dioxo-1λ$^6$,2-thiazolidin-2-yl)phenyl]-3-methyl-1,2,3,4-tetrahydroquinoxaline-1-carboxylate;

oxan-4-yl (3S)-4-acetyl-7-[1-(1,1-dioxo-1λ$^6$-thietan-3-yl)-1H-pyrazol-4-yl]-3-methyl-1,2,3,4-tetrahydroquinoxaline-1-carboxylate;

oxan-4-yl (3S)-4-acetyl-3-methyl-7-[1-(oxan-4-yl)-1H-pyrazol-4-yl]-1,2,3,4-tetrahydroquinoxaline-1-carboxylate;

cyclobutyl (3S)-4-acetyl-3-methyl-7-[1-(oxan-4-yl)-1H-pyrazol-4-yl]-1,2,3,4-tetrahydroquinoxaline-1-carboxylate;

4-cyclopentyl 1-methyl (2S)-6-(1-cyclopropyl-1H-pyrazol-4-yl)-2-methyl-1,2,3,4-tetrahydroquinoxaline-1,4-dicarboxylate;

cyclopentyl (3S)-4-cyclopropanecarbonyl-7-(1-cyclopropyl-1H-pyrazol-4-yl)-3-methyl-1,2,3,4-tetrahydroquinoxaline-1-carboxylate;

methyl (2S)-4-cyclopropanecarbonyl-6-(1-cyclopropyl-1H-pyrazol-4-yl)-2-methyl-1,2,3,4-tetrahydroquinoxaline-1-carboxylate;

1-methyl 4-propan-2-yl (2S)-6-(1-cyclopropyl-1H-pyrazol-4-yl)-2-methyl-1,2,3,4-tetrahydroquinoxaline-1,4-dicarboxylate;

1-[(2S)-4-(1,3-benzoxazol-2-yl)-6-(1-cyclopropyl-1H-pyrazol-4-yl)-2-methyl-1,2,3,4-tetrahydroquinoxalin-1-yl]ethan-1-one;

1-[(2S)-6-(4-methanesulfonylphenyl)-2-methyl-4-(pyrimidin-2-yl)-1,2,3,4-tetrahydroquinoxalin-1-yl]ethan-1-one;

1-[(2S)-4-(1,3-benzoxazol-2-yl)-6-(4-methanesulfonylphenyl)-2-methyl-1,2,3,4-tetrahydroquinoxalin-1-yl]ethan-1-one;

1-[(2S)-6-(4-methanesulfonylphenyl)-2-methyl-4-(pyridin-2-yl)-1,2,3,4-tetrahydroquinoxalin-1-yl]ethan-1-one;

1-[(2S)-6-(4-methanesulfonylphenyl)-2-methyl-4-(quinazolin-2-yl)-1,2,3,4-tetrahydroquinoxalin-1-yl]ethan-1-one;

1-[(2S)-6-(4-methanesulfonylphenyl)-2-methyl-4-(4-phenylpyrimidin-2-yl)-1,2,3,4-tetrahydroquinoxalin-1-yl]ethan-1-one;

1-[(2S)-6-(4-methanesulfonylphenyl)-2-methyl-4-(5-phenylpyrimidin-2-yl)-1,2,3,4-tetrahydroquinoxalin-1-yl]ethan-1-one;

1-[(2S)-6-(1-cyclopropyl-1H-pyrazol-4-yl)-2-methyl-4-(quinazolin-2-yl)-1,2,3,4-tetrahydroquinoxalin-1-yl]ethan-1-one;

1-[(2S)-6-(1-cyclopropyl-1H-pyrazol-4-yl)-2-methyl-4-(1-methyl-1H-indazol-3-yl)-1,2,3,4-tetrahydroquinoxalin-1-yl]ethan-1-one;

1-[(2S)-2-methyl-4-(1-methyl-1H-indazol-3-yl)-6-[1-(oxetan-3-yl)-1H-pyrazol-4-yl]-1,2,3,4-tetrahydroquinoxalin-1-yl]ethan-1-one;

1-[(2S)-6-(1-cyclopropyl-1H-pyrazol-4-yl)-4-(6-fluoro-1-methyl-1H-indazol-3-yl)-2-methyl-1,2,3,4-tetrahydroquinoxalin-1-yl]ethan-1-one;

1-[(2S)-6-(1-cyclopropyl-1H-pyrazol-4-yl)-4-(5-fluoro-1-methyl-1H-indazol-3-yl)-2-methyl-1,2,3,4-tetrahydroquinoxalin-1-yl]ethan-1-one;

1-[(2S)-4-(1,3-benzoxazol-2-yl)-6-[1-(1,3-benzoxazol-2-yl)-1H-pyrazol-4-yl]-2-methyl-1,2,3,4-tetrahydroquinoxalin-1-yl]ethan-1-one;

1-[(3S-1-(furan-2-carbonyl)-7-(4-methanesulfonylphenyl)-3-methyl-1H,2H,3H,4H-pyrido[3,4-b]pyrazin-4-yl]ethan-1-one;

propan-2-yl (3S)-4-acetyl-7-(4-methanesulfonylphenyl)-3-methyl-1H,2H,3H,4H-pyrido[3,4-b]pyrazine-1-carboxylate;

oxetan-3-yl (3S)-4-acetyl-3-methyl-7-[1-(oxetan-3-yl)-1H-pyrazol-4-yl]-1,2,3,4-tetrahydroquinoxaline-1-carboxylate;

cyclobutylmethyl (3S)-4-acetyl-3-methyl-7-[1-(oxetan-3-yl)-1H-pyrazol-4-yl]-1,2,3,4-tetrahydroquinoxaline-1-carboxylate;

(3-methyloxetan-3-yl)methyl (3S)-4-acetyl-3-methyl-7-[1-(oxetan-3-yl)-1H-pyrazol-4-yl]-1,2,3,4-tetrahydroquinoxaline-1-carboxylate;

2,2-dichloroethyl (3S)-4-acetyl-3-methyl-7-[1-(oxetan-3-yl)-1H-pyrazol-4-yl]-1,2,3,4-tetrahydroquinoxaline-1-carboxylate;

(3-ethyloxetan-3-yl)methyl (3S)-4-acetyl-3-methyl-7-[1-(oxetan-3-yl)-1H-pyrazol-4-yl]-1,2,3,4-tetrahydroquinoxaline-1-carboxylate;

oxetan-3-ylmethyl (3S)-4-acetyl-3-methyl-7-[1-(oxetan-3-yl)-1H-pyrazol-4-yl]-1,2,3,4-tetrahydroquinoxaline-1-carboxylate;

3,3-difluorocyclobutyl (3S)-4-acetyl-3-methyl-7-[1-(oxetan-3-yl)-1H-pyrazol-4-yl]-1,2,3,4-tetrahydroquinoxaline-1-carboxylate;

(3-fluorooxetan-3-yl)methyl (3S)-4-acetyl-3-methyl-7-[1-(oxetan-3-yl)-1H-pyrazol-4-yl]-1,2,3,4-tetrahydroquinoxaline-1-carboxylate;

2-(oxetan-3-yl)ethyl (3S)-4-acetyl-3-methyl-7-[1-(oxetan-3-yl)-1H-pyrazol-4-yl]-1,2,3,4-tetrahydroquinoxaline-1-carboxylate;

2,2-difluoropropyl (3S)-4-acetyl-3-methyl-7-[1-(oxetan-3-yl)-1H-pyrazol-4-yl]-1,2,3,4-tetrahydroquinoxaline-1-carboxylate;

3,3,3-trifluoropropyl (3S)-4-acetyl-3-methyl-7-[1-(oxetan-3-yl)-1H-pyrazol-4-yl]-1,2,3,4-tetrahydroquinoxaline-1-carboxylate;

2-oxaspiro[3.3]heptan-6-yl (3S)-4-acetyl-3-methyl-7-[1-(oxetan-3-yl)-1H-pyrazol-4-yl]-1,2,3,4-tetrahydroquinoxaline-1-carboxylate;

2,2,2-trifluoroethyl (3S)-4-acetyl-3-methyl-7-[1-(oxetan-3-yl)-1H-pyrazol-4-yl]-1,2,3,4-tetrahydroquinoxaline-1-carboxylate;

1,3-difluoropropan-2-yl (3S)-4-acetyl-3-methyl-7-[1-(oxetan-3-yl)-1H-pyrazol-4-yl]-1,2,3,4-tetrahydroquinoxaline-1-carboxylate;

(2,2-dimethylcyclopropyl)methyl (3S)-4-acetyl-3-methyl-7-[1-(oxetan-3-yl)-1H-pyrazol-4-yl]-1,2,3,4-tetrahydroquinoxaline-1-carboxylate;

bicyclo[3.1.0]hexan-3-yl (3S)-4-acetyl-3-methyl-7-[1-(oxetan-3-yl)-1H-pyrazol-4-yl]-1,2,3,4-tetrahydroquinoxaline-1-carboxylate;

(2,2-difluorocyclopropyl)methyl (3S)-4-acetyl-3-methyl-7-[1-(oxetan-3-yl)-1H-pyrazol-4-yl]-1,2,3,4-tetrahydroquinoxaline-1-carboxylate;

1-methylcyclopropyl (3S)-4-acetyl-3-methyl-7-[1-(oxetan-3-yl)-1H-pyrazol-4-yl]-1,2,3,4-tetrahydroquinoxaline-1-carboxylate;

2-fluoro-2-methylpropyl (3S)-4-acetyl-3-methyl-7-[1-(oxetan-3-yl)-1H-pyrazol-4-yl]-1,2,3,4-tetrahydroquinoxaline-1-carboxylate;

3,3,3-trifluoropropyl (3S)-4-acetyl-7-(1-cyclopropyl-1H-pyrazol-4-yl)-3-methyl-1,2,3,4-tetrahydroquinoxaline-1-carboxylate;

2,2,2-trifluoroethyl (3S)-4-acetyl-7-(1-cyclopropyl-1H-pyrazol-4-yl)-3-methyl-1,2,3,4-tetrahydroquinoxaline-1-carboxylate;

1,3-difluoropropan-2-yl (3S)-4-acetyl-7-(1-cyclopropyl-1H-pyrazol-4-yl)-3-methyl-1,2,3,4-tetrahydroquinoxaline-1-carboxylate;

3,3,3-trifluoropropyl (3S)-4-acetyl-7-[1-(2-hydroxyethyl)-1H-pyrazol-4-yl]-3-methyl-1,2,3,4-tetrahydroquinoxaline-1-carboxylate;

2,2,2-trifluoroethyl (3S)-4-acetyl-7-[1-(2-hydroxyethyl)-1H-pyrazol-4-yl]-3-methyl-1,2,3,4-tetrahydroquinoxaline-1-carboxylate;

1,3-difluoropropan-2-yl (3S)-4-acetyl-7-[1-(2-hydroxyethyl)-1H-pyrazol-4-yl]-3-methyl-1,2,3,4-tetrahydroquinoxaline-1-carboxylate;

2,2-difluoroethyl (3S)-4-acetyl-3-methyl-7-[1-(oxetan-3-yl)-1H-pyrazol-4-yl]-1,2,3,4-tetrahydroquinoxaline-1-carboxylate;

4-fluorophenyl (3S)-4-acetyl-3-methyl-7-[1-(oxetan-3-yl)-1H-pyrazol-4-yl]-1,2,3,4-tetrahydroquinoxaline-1-carboxylate;

cyclohexyl (3S)-4-acetyl-3-methyl-7-[1-(oxetan-3-yl)-1H-pyrazol-4-yl]-1,2,3,4-tetrahydroquinoxaline-1-carboxylate;

4-methoxyphenyl (3S)-4-acetyl-3-methyl-7-[1-(oxetan-3-yl)-1H-pyrazol-4-yl]-1,2,3,4-tetrahydroquinoxaline-1-carboxylate;

phenyl (3S)-4-acetyl-3-methyl-7-[1-(oxetan-3-yl)-1H-pyrazol-4-yl]-1,2,3,4-tetrahydroquinoxaline-1-carboxylate;

pyridin-3-yl (3S)-4-acetyl-3-methyl-7-[1-(oxetan-3-yl)-1H-pyrazol-4-yl]-1,2,3,4-tetrahydroquinoxaline-1-carboxylate;

pyridin-4-yl (3S)-4-acetyl-3-methyl-7-[1-(oxetan-3-yl)-1H-pyrazol-4-yl]-1,2,3,4-tetrahydroquinoxaline-1-carboxylate;

pyridin-2-yl (3S)-4-acetyl-3-methyl-7-[1-(oxetan-3-yl)-1H-pyrazol-4-yl]-1,2,3,4-tetrahydroquinoxaline-1-carboxylate;

(2S)-4-(1,3-benzoxazol-2-yl)-1-cyclopropanecarbonyl-6-(1-cyclopropyl-1H-pyrazol-4-yl)-2-methyl-1,2,3,4-tetrahydroquinoxaline;

1-[(2S)-6-(1-cyclopropyl-1H-pyrazol-4-yl)-4-(1H-indazol-3-yl)-2-methyl-1,2,3,4-tetrahydroquinoxalin-1-yl]ethan-1-one;

1-[(2S)-4-(1H-indazol-3-yl)-6-(4-methanesulfonylphenyl)-2-methyl-1,2,3,4-tetrahydroquinoxalin-1-yl]ethan-1-one;

1-[(2S)-4-(1,2-benzoxazol-3-yl)-6-(1-cyclopropyl-1H-pyrazol-4-yl)-2-methyl-1,2,3,4-tetrahydroquinoxalin-1-yl]ethan-1-one;

(2S)-4-(furan-2-carbonyl-1-methanesulfonyl-6-(4-methanesulfonylphenyl)-2-methyl-1,2,3,4-tetrahydroquinoxaline;

1-[(2S)-4-cyclopropanecarbonyl-2-methyl-6-phenoxy-1H,2H,3H,4H-pyrido[2,3-b]pyrazine-1-yl]ethan-1-one;

cyclobutyl (3S)-4-acetyl-7-[1-(1,1-dioxo-1λ$^6$-thietan-3-yl)-1H-pyrazol-4-yl]-3-methyl-1,2,3,4-tetrahydroquinoxaline-1-carboxylate;

phenyl (3S)-4-acetyl-3-methyl-7-[4-(piperazine-1-carbonyl)phenyl]-1,2,3,4-tetrahydroquinoxaline-1-carboxylate;

1-[(2S)-6-(4-methanesulfonylphenyl)-2-methyl-4-(pyrrolidine-1-carbonyl)-1,2,3,4-tetrahydroquinoxalin-1-yl]ethan-1-one;

1-[(2S)-4-(furan-2-carbonyl)-2-methyl-6-(pyrrolidine-1-carbonyl)-1,2,3,4-tetrahydroquinoxalin-1-yl]ethan-1-one;

(3S)-4-acetyl-7-(4-methanesulfonylphenyl)-3-methyl-1,2,3,4-tetrahydroquinoxaline-1-carbaldehyde;

(2S)-4-(furan-2-carbonyl)-6-(4-methanesulfonylphenyl)-2-methyl-1,2,3,4-tetrahydroquinoxaline-1-carbaldehyde;

1-[(2S)-6-(4-methanesulfonylphenyl)-2,4-dimethyl-1,2,3,4-tetrahydroquinoxalin-1-yl]ethan-1-one;

1-[(3S)-4-acetyl-3-methyl-7-[1-(oxetan-3-yl)-1H-pyrazol-4-yl]-1,2,3,4-tetrahydroquinoxalin-1-yl]-3-methylbutan-1-one;

1-[(3S)-4-acetyl-3-methyl-7-[1-(oxetan-3-yl)-1H-pyrazol-4-yl]-1,2,3,4-tetrahydroquinoxalin-1-yl]-2,2-difluoroethan-1-one;

1-[(3S)-4-acetyl-3-methyl-7-[1-(oxetan-3-yl)-1H-pyrazol-4-yl]-1,2,3,4-tetrahydroquinoxalin-1-yl]-2-cyclopropylethan-1-one;

1-[(3S)-4-acetyl-3-methyl-7-[1-(oxetan-3-yl)-1H-pyrazol-4-yl]-1,2,3,4-tetrahydroquinoxalin-1-yl]-3,3,3-trifluoropropan-1-one;

1-[(3S)-4-acetyl-3-methyl-7-[1-(oxetan-3-yl)-1H-pyrazol-4-yl]-1,2,3,4-tetrahydroquinoxalin-1-yl]-2-methylpropan-1-one;

1-[(2S)-2-methyl-4-(oxane-4-carbonyl)-6-[1-(oxetan-3-yl)-1H-pyrazol-4-yl]-1,2,3,4-tetrahydroquinoxalin-1-yl]ethan-1-one;

1-[(3S)-4-acetyl-3-methyl-7-[1-(oxetan-3-yl)-1H-pyrazol-4-yl]-1,2,3,4-tetrahydroquinoxalin-1-yl]-2-cyclopentylethan-1-one;

1-[(2S)-4-[(1S)-2,2-dichlorocyclopropanecarbonyl]-2-methyl-6-[1-(oxetan-3-yl)-1H-pyrazol-4-yl]-1,2,3,4-tetrahydroquinoxalin-1-yl]ethan-1-one;

1-[(2S)-4-[(1R)-2,2-dichlorocyclopropanecarbonyl]-2-methyl-6-[1-(oxetan-3-yl)-1H-pyrazol-4-yl]-1,2,3,4-tetrahydroquinoxalin-1-yl]ethan-1-one;

1-[(2S)-2-methyl-4-(1-methylcyclopropanecarbonyl)-6-[1-(oxetan-3-yl)-1H-pyrazol-4-yl]-1,2,3,4-tetrahydroquinoxalin-1-yl]ethan-1-one;

1-[(3S)-4-acetyl-3-methyl-7-[1-(oxetan-3-yl)-1H-pyrazol-4-yl]-1,2,3,4-tetrahydroquinoxalin-1-yl]-2-chloro-2-methylpropan-1-one;

propan-2-yl (3S)-4-acetyl-3-methyl-7-[1-(pyrazin-2-ylmethyl)-1H-pyrazol-4-yl]-1,2,3,4-tetrahydroquinoxaline-1-carboxylate;

propan-2-yl (3S)-4-acetyl-3-methyl-7-[1-(pyridin-4-ylmethyl)-1H-pyrazol-4-yl]-1,2,3,4-tetrahydroquinoxaline-1-carboxylate;

1-[(2S)-4-cyclopropanecarbonyl-2-methyl-6-[1-(pyridin-4-ylmethyl)-1H-pyrazol-4-yl]-1,2,3,4-tetrahydroquinoxalin-1-yl]ethan-1-one;

propan-2-yl (3S)-4-acetyl-3-methyl-7-[1-(pyridin-3-ylmethyl)-1H-pyrazol-4-yl]-1,2,3,4-tetrahydroquinoxaline-1-carboxylate;

propan-2-yl (3S)-4-acetyl-3-methyl-7-[1-(pyridin-2-ylmethyl)-1H-pyrazol-4-yl]-1,2,3,4-tetrahydroquinoxaline-1-carboxylate;

1-[(2S)-4-cyclopropanecarbonyl-2-methyl-6-[1-(pyridin-2-ylmethyl)-1H-pyrazol-4-yl]-1,2,3,4-tetrahydroquinoxalin-1-yl]ethan-1-one;

1-[(2S)-4-cyclopropanecarbonyl-2-methyl-6-[1-(pyridin-3-ylmethyl)-1H-pyrazol-4-yl]-1,2,3,4-tetrahydroquinoxalin-1-yl]ethan-1-one;

1-[(2S)-4-cyclopropanecarbonyl-2-methyl-6-[1-(pyrazin-2-ylmethyl)-1H-pyrazol-4-yl]-1,2,3,4-tetrahydroquinoxalin-1-yl]ethan-1-one;

1-[(2S)-4-cyclopropanecarbonyl-2-methyl-6-{1-[(3-methyloxetan-3-yl)methyl]-1H-pyrazol-4-yl}-1,2,3,4-tetrahydroquinoxalin-1-yl]ethan-1-one;

2-{4-[(2S)-1-acetyl-4-cyclopropanecarbonyl-2-methyl-1,2,3,4-tetrahydroquinoxalin-6-yl]-1H-pyrazol-1-yl}-1-(morpholin-4-yl)ethan-1-one;

1-[(2S)-4-cyclopropanecarbonyl-2-methyl-6-[1-(pyrimidin-2-ylmethyl)-1H-pyrazol-4-yl]-1,2,3,4-tetrahydroquinoxalin-1-yl]ethan-1-one;

1-[(2S)-4-cyclopropanecarbonyl-6-[1-(1H-imidazol-4-ylmethyl)-1H-pyrazol-4-yl]-2-methyl-1,2,3,4-tetrahydroquinoxalin-1-yl]ethan-1-one;

1-[(2S)-4-cyclopropanecarbonyl-2-methyl-6-[1-(pyrimidin-5-ylmethyl)-1H-pyrazol-4-yl]-1,2,3,4-tetrahydroquinoxalin-1-yl]ethan-1-one;

propan-2-yl (3S)-4-acetyl-7-{1-[2-(dimethylamino)ethyl]-1H-pyrazol-4-yl}-3-methyl-1,2,3,4-tetrahydroquinoxaline-1-carboxylate;

2-{4-[(2S)-1-acetyl-2-methyl-4-[(propan-2-yloxy)carbonyl]-1,2,3,4-tetrahydroquinoxalin-6-yl]-1H-pyrazol-1-yl}acetic acid;

propan-2-yl (3S)-4-acetyl-3-methyl-7-[1-(1,2-oxazol-5-ylmethyl)-1H-pyrazol-4-yl]-1,2,3,4-tetrahydroquinoxaline-1-carboxylate;

2-{4-[(2S)-1-acetyl-4-cyclopropanecarbonyl-2-methyl-1,2,3,4-tetrahydroquinoxalin-6-yl]-1H-pyrazol-1-yl}-N-methylacetamide;

propan-2-yl (3S)-4-acetyl-7-{1-[(3-fluorooxetan-3-yl)methyl]-1H-pyrazol-4-yl}-3-methyl-1,2,3,4-tetrahydroquinoxaline-1-carboxylate;

propan-2-yl (3S)-4-acetyl-3-methyl-7-{1-[(methylcarbamoyl)methyl]-1H-pyrazol-4-yl}-1,2,3,4-tetrahydroquinoxaline-1-carboxylate;

propan-2-yl (3S)-4-acetyl-3-methyl-7-[1-(2,2-difluoroethyl)-1H-pyrazol-4-yl]-3-methyl-1,2,3,4-tetrahydroquinoxaline-1-carboxylate;

3-{4-[(2S)-1-acetyl-4-cyclopropanecarbonyl-2-methyl-1,2,3,4-tetrahydroquinoxalin-6-yl]-1H-pyrazol-1-yl}propanoic acid;

propan-2-yl (3S)-4-acetyl-7-[1-(3-hydroxypropyl)-1H-pyrazol-4-yl]-3-methyl-1,2,3,4-tetrahydroquinoxaline-1-carboxylate;

propan-2-yl (3S)-4-acetyl-7-[1-(1-carbamoyl-1-methylethyl)-1H-pyrazol-4-yl]-3-methyl-1,2,3,4-tetrahydroquinoxaline-1-carboxylate;

propan-2-yl (3S)-4-acetyl-3-methyl-7-{1-[2-(1H-1,2,4-triazol-1-yl)ethyl]-1H-pyrazol-4-yl}-1,2,3,4-tetrahydroquinoxaline-1-carboxylate;
propan-2-yl (3S)-4-acetyl-7-[1-(2-fluoro-2-methylpropyl)-1H-pyrazol-4-yl]-3-methyl-1,2,3,4-tetrahydroquinoxaline-1-carboxylate;
propan-2-yl (3S)-4-acetyl-3-methyl-7-{1-[(3-methyl-1,2-oxazol-5-yl)methyl]-1H-pyrazol-4-yl}-1,2,3,4-tetrahydroquinoxaline-1-carboxylate;
propan-2-yl (3S)-4-acetyl-3-methyl-7-[1-(3,3,3-trifluoropropyl)-1H-pyrazol-4-yl]-1,2,3,4-tetrahydroquinoxaline-1-carboxylate;
propan-2-yl (3S)-4-acetyl-3-methyl-7-[1-(1,3-thiazol-5-ylmethyl)-1H-pyrazol-4-yl]-1,2,3,4-tetrahydroquinoxaline-1-carboxylate;
propan-2-yl (3S)-4-acetyl-3-methyl-7-[1-(oxetan-3-yl)-1H-pyrazol-4-yl]-1,2,3,4-tetrahydroquinoxaline-1-carboxylate;
1-[(2S)-4-cyclopropanecarbonyl-6-[1-(2-fluoro-2-methylpropyl)-1H-pyrazol-4-yl]-2-methyl-1,2,3,4-tetrahydroquinoxalin-1-yl]ethan-1-one;
1-[(2S)-4-cyclopropanecarbonyl-6-{1-[2-(dimethylamino)ethyl]-1H-pyrazol-4-yl}-2-methyl-1,2,3,4-tetrahydroquinoxalin-1-yl]ethan-1-one;
1-[(2S)-4-cyclopropanecarbonyl-2-methyl-6-{1-[(4-methyl-1,2,5-oxadiazol-3-yl)methyl]-1H-pyrazol-4-yl}-1,2,3,4-tetrahydroquinoxalin-1-yl]ethan-1-one;
1-[(2S)-4-cyclopropanecarbonyl-6-{1-[(2,2-difluorocyclopropyl)methyl]-1H-pyrazol-4-yl}-2-methyl-1,2,3,4-tetrahydroquinoxalin-1-yl]ethan-1-one;
1-[(2S)-4-cyclopropanecarbonyl-2-methyl-6-{1-[(3-methyl-1,2-oxazol-5-yl)methyl]-1H-pyrazol-4-yl}-1,2,3,4-tetrahydroquinoxalin-1-yl]ethan-1-one;
1-[(2S)-4-cyclopropanecarbonyl-2-methyl-6-[1-(3,3,3-trifluoropropyl)-1H-pyrazol-4-yl]-1,2,3,4-tetrahydroquinoxalin-1-yl]ethan-1-one;
1-[(2S)-4-cyclopropanecarbonyl-2-methyl-6-{1-[2-(morpholin-4-yl)ethyl]-1H-pyrazol-4-yl}-1,2,3,4-tetrahydroquinoxalin-1-yl]ethan-1-one;
4,4-difluorocyclohexyl (3S)-4-acetyl-7-[1-(azetidin-3-yl)-1H-pyrazol-4-yl]-3-methyl-1,2,3,4-tetrahydroquinoxaline-1-carboxylate;
4,4-difluorocyclohexyl (3S)-4-acetyl-3-methyl-7-[1-(piperidin-4-yl)-1H-pyrazol-4-yl]-1,2,3,4-tetrahydroquinoxaline-1-carboxylate;
cyclobutyl (3S)-4-acetyl-7-[1-(1,1-dioxo-1$\lambda^6$-thian-4-yl)-1H-pyrazol-4-yl]-3-methyl-1,2,3,4-tetrahydroquinoxaline-1-carboxylate;
oxan-4-yl (3S)-4-acetyl-7-[1-(1,1-dioxo-1$\lambda^6$-thian-4-yl)-1H-pyrazol-4-yl]-3-methyl-1,2,3,4-tetrahydroquinoxaline-1-carboxylate;
propan-2-yl (3S)-4-acetyl-7-[1-(1,1-dioxo-1$\lambda^6$-thian-4-yl)-1H-pyrazol-4-yl]-3-methyl-1,2,3,4-tetrahydroquinoxaline-1-carboxylate;
4-{4-[(2S)-1-acetyl-4-cyclopropanecarbonyl-2-methyl-1,2,3,4-tetrahydroquinoxalin-6-yl]-1H-pyrazol-1-yl}-1$\lambda^6$-thiane-1,1-dione;
cyclobutyl (3S)-4-acetyl-7-[1-(1,1-dioxo-1$\lambda^6$-thian-3-yl)-1H-pyrazol-4-yl]-3-methyl-1,2,3,4-tetrahydroquinoxaline-1-carboxylate;
propan-2-yl (3S)-4-acetyl-3-methyl-7-{1-[(2S)-2-methylazetidin-3-yl]-1H-pyrazol-4-yl}-1,2,3,4-tetrahydroquinoxaline-1-carboxylate;
1-[(2S)-4-cyclopropanecarbonyl-2-methyl-6-{1-[(2S)-2-methylazetidin-3-yl]-1H-pyrazol-4-yl}-1,2,3,4-tetrahydroquinoxalin-1-yl]ethan-1-one;

oxan-4-yl (3S)-4-acetyl-7-[1-(1,1-dioxo-1$\lambda^6$-thian-3-yl)-1H-pyrazol-4-yl]-3-methyl-1,2,3,4-tetrahydroquinoxaline-1-carboxylate;
3,3-difluorocyclobutyl (3S)-4-acetyl-7-[1-(1,1-dioxo-1$\lambda^6$-thian-3-yl)-1H-pyrazol-4-yl]-3-methyl-1,2,3,4-tetrahydroquinoxaline-1-carboxylate;
oxan-4-yl (3S)-4-acetyl-3-methyl-7-[1-(2-oxopiperidin-4-yl)-1H-pyrazol-4-yl]-1,2,3,4-tetrahydroquinoxaline-1-carboxylate;
3,3-difluorocyclobutyl (3S)-4-acetyl-3-methyl-7-[1-(2-oxopiperidin-4-yl)-1H-pyrazol-4-yl]-1,2,3,4-tetrahydroquinoxaline-1-carboxylate;
4,4-difluorocyclohexyl (3S)-4-acetyl-3-methyl-7-[1-(2-oxopiperidin-4-yl)-1H-pyrazol-4-yl]-1,2,3,4-tetrahydroquinoxaline-1-carboxylate;
propan-2-yl (3S)-4-acetyl-3-methyl-7-[1-(2-oxopiperidin-4-yl)-1H-pyrazol-4-yl]-1,2,3,4-tetrahydroquinoxaline-1-carboxylate;
4-{4-[(2S)-1-acetyl-4-cyclopropanecarbonyl-2-methyl-1,2,3,4-tetrahydroquinoxalin-6-yl]-1H-pyrazol-1-yl}piperidin-2-one;
3,3-difluorocyclobutyl (3S)-4-acetyl-3-methyl-7-{1-[(2S)-2-methylazetidin-3-yl]-1H-pyrazol-4-yl}-1,2,3,4-tetrahydroquinoxaline-1-carboxylate;
cyclopropylmethyl (3S)-4-acetyl-7-[1-(1,1-dioxo-1$\lambda^6$-thian-4-yl)-1H-pyrazol-4-yl]-3-methyl-1,2,3,4-tetrahydroquinoxaline-1-carboxylate;
cyclobutyl (3S)-4-acetyl-3-methyl-7-{1-[(2R)-2-methylazetidin-3-yl]-1H-pyrazol-4-yl}-1,2,3,4-tetrahydroquinoxaline-1-carboxylate;
cyclopropylmethyl (3S)-4-acetyl-7-{1-[(3R)-1,1-dioxo-1$\lambda^6$-thian-3-yl]-1H-pyrazol-4-yl}-3-methyl-1,2,3,4-tetrahydroquinoxaline-1-carboxylate;
cyclopropylmethyl (3S)-4-acetyl-7-{1-[(3S)-1,1-dioxo-1$\lambda^6$-thian-3-yl]-1H-pyrazol-4-yl}-3-methyl-1,2,3,4-tetrahydroquinoxaline-1-carboxylate;
cyclobutyl (3S)-4-acetyl-7-{1-[(3R)-1,1-dioxo-1$\lambda^6$-thian-3-yl]-1H-pyrazol-4-yl}-3-methyl-1,2,3,4-tetrahydroquinoxaline-1-carboxylate;
cyclobutyl (3S)-4-acetyl-7-{1-[(3S)-1,1-dioxo-1$\lambda^6$-thian-3-yl]-1H-pyrazol-4-yl}-3-methyl-1,2,3,4-tetrahydroquinoxaline-1-carboxylate;
cyclobutyl (3S)-4-acetyl-3-methyl-7-[1-(2-oxopiperidin-4-yl)-1H-pyrazol-4-yl]-1,2,3,4-tetrahydroquinoxaline-1-carboxylate;
cyclobutyl (3S)-4-acetyl-3-methyl-7-{1-[(4R)-2-oxopiperidin-4-yl]-1H-pyrazol-4-yl}-1,2,3,4-tetrahydroquinoxaline-1-carboxylate;
cyclobutyl (3S)-4-acetyl-3-methyl-7-{1-[(4S)-2-oxopiperidin-4-yl]-1H-pyrazol-4-yl}-1,2,3,4-tetrahydroquinoxaline-1-carboxylate;
cyclobutyl (3S)-4-acetyl-3-methyl-7-{1-[(2S)-2-methylazetidin-3-yl]-1H-pyrazol-4-yl}-1,2,3,4-tetrahydroquinoxaline-1-carboxylate;
1-[(2S)-6-(1-cyclopropyl-1H-pyrazol-4-yl)-4-(7-fluoro-1-methyl-1H-indazol-3-yl)-2-methyl-1,2,3,4-tetrahydroquinoxalin-1-yl]ethan-1-one;
1-[(2S)-4-(7-fluoro-1-methyl-1H-indazol-3-yl)-6-[1-(2-hydroxyethyl)-1H-pyrazol-4-yl]-2-methyl-1,2,3,4-tetrahydroquinoxalin-1-yl]ethan-1-one;
1-[(2S)-2-methyl-4-(1-methyl-1H-indazol-3-yl)-6-[1-(piperidin-4-yl)-1H-pyrazol-4-yl]-1,2,3,4-tetrahydroquinoxalin-1-yl]ethan-1-one;
1-[(2S)-2-methyl-4-{1-methyl-1H-pyrazolo[3,4-c]pyridin-3-yl}-6-[1-(piperidin-4-yl)-1H-pyrazol-4-yl]-1,2,3,4-tetrahydroquinoxalin-1-yl]ethan-1-one;

1-[(2S)-6-(1-cyclopropyl-1H-pyrazol-4-yl)-4-(4-fluoro-1-methyl-1H-indazol-3-yl)-2-methyl-1,2,3,4-tetrahydroquinoxalin-1-yl]ethan-1-one;
1-[(2S)-6-(1-cyclopropyl-1H-pyrazol-4-yl)-2-methyl-4-{1-methyl-1H-pyrazolo[3,4-b]pyridin-3-yl}-1,2,3,4-tetrahydroquinoxalin-1-yl]ethan-1-one;
1-[(2S)-6-(1-cyclopropyl-1H-pyrazol-4-yl)-2-methyl-4-{1-methyl-1H-pyrazolo[3,4-c]pyridin-3-yl}-1,2,3,4-tetrahydroquinoxalin-1-yl]ethan-1-one;
1-[(2S)-6-(1-cyclopropyl-1H-pyrazol-4-yl)-2-methyl-4-{1-methyl-1H-pyrazolo[4,3-c]pyridin-3-yl}-1,2,3,4-tetrahydroquinoxalin-1-yl]ethan-1-one;
1-[(2S)-6-(1-cyclopropyl-1H-pyrazol-4-yl)-2-methyl-4-{1-methyl-1H-pyrazolo[4,3-b]pyridin-3-yl}-1,2,3,4-tetrahydroquinoxalin-1-yl]ethan-1-one;
1-[(2S)-4-(6-fluoro-1-methyl-1H-indazol-3-yl)-6-[1-(2-hydroxyethyl)-1H-pyrazol-4-yl]-2-methyl-1,2,3,4-tetrahydroquinoxalin-1-yl]ethan-1-one;
1-[(2S)-4-(5-fluoro-1-methyl-1H-indazol-3-yl)-6-[1-(2-hydroxyethyl)-1H-pyrazol-4-yl]-2-methyl-1,2,3,4-tetrahydroquinoxalin-1-yl]ethan-1-one;
1-[(2S)-4-(4-fluoro-1-methyl-1H-indazol-3-yl)-6-[1-(2-hydroxyethyl)-1H-pyrazol-4-yl]-2-methyl-1,2,3,4-tetrahydroquinoxalin-1-yl]ethan-1-one;
propan-2-yl (3S)-4-cyclopropanecarbonyl-3-methyl-7-(1H-pyrazol-4-yl)-1,2,3,4-tetrahydroquinoxaline-1-carboxylate;
propan-2-yl (3S)-4-acetyl-3-methyl-7-(1H-pyrazol-4-yl)-1,2,3,4-tetrahydroquinoxaline-1-carboxylate;
1-methyl 4-propan-2-yl (2S)-2-methyl-6-(1H-pyrazol-4-yl)-1,2,3,4-tetrahydroquinoxaline-1,4-dicarboxylate;
phenyl (3S)-4-acetyl-7-(4-methanesulfonylphenyl)-3-methyl-1,2,3,4-tetrahydroquinoxaline-1-carboxylate;
ethyl (3S)-4-acetyl-7-(4-methanesulfonylphenyl)-3-methyl-1,2,3,4-tetrahydroquinoxaline-1-carboxylate;
2-chlorophenyl (3S)-4-acetyl-7-(4-methanesulfonylphenyl)-3-methyl-1,2,3,4-tetrahydroquinoxaline-1-carboxylate;
4-chlorophenyl (3S)-4-acetyl-7-(4-methanesulfonylphenyl)-3-methyl-1,2,3,4-tetrahydroquinoxaline-1-carboxylate;
2-methoxyphenyl (3S)-4-acetyl-7-(4-methanesulfonylphenyl)-3-methyl-1,2,3,4-tetrahydroquinoxaline-1-carboxylate;
4-nitrophenyl (3S)-4-acetyl-7-(4-methanesulfonylphenyl)-3-methyl-1,2,3,4-tetrahydroquinoxaline-1-carboxylate;
4-(methoxycarbonyl)phenyl (3S)-4-acetyl-7-(4-methanesulfonylphenyl)-3-methyl-1,2,3,4-tetrahydroquinoxaline-1-carboxylate;
benzyl (3S)-4-acetyl-7-(4-methanesulfonylphenyl)-3-methyl-1,2,3,4-tetrahydroquinoxaline-1-carboxylate;
butyl (3S)-4-acetyl-7-(4-methanesulfonylphenyl)-3-methyl-1,2,3,4-tetrahydroquinoxaline-1-carboxylate;
4-methylphenyl (3S)-4-acetyl-7-(4-methanesulfonylphenyl)-3-methyl-1,2,3,4-tetrahydroquinoxaline-1-carboxylate;
4-methoxyphenyl (3S)-4-acetyl-7-(4-methanesulfonylphenyl)-3-methyl-1,2,3,4-tetrahydroquinoxaline-1-carboxylate;
4-fluorophenyl (3S)-4-acetyl-7-(4-methanesulfonylphenyl)-3-methyl-1,2,3,4-tetrahydroquinoxaline-1-carboxylate;
methyl (3S)-4-acetyl-7-(4-methanesulfonylphenyl)-3-methyl-1,2,3,4-tetrahydroquinoxaline-1-carboxylate;
cyclopentyl (3S)-4-acetyl-7-(4-methanesulfonylphenyl)-3-methyl-1,2,3,4-tetrahydroquinoxaline-1-carboxylate;
3-(trifluoromethyl)phenyl (3S)-4-acetyl-7-(4-methanesulfonylphenyl)-3-methyl-1,2,3,4-tetrahydroquinoxaline-1-carboxylate;
cyclohexyl (3S)-4-acetyl-7-(4-methanesulfonylphenyl)-3-methyl-1,2,3,4-tetrahydroquinoxaline-1-carboxylate;
naphthalen-2-yl (3S)-4-acetyl-7-(4-methanesulfonylphenyl)-3-methyl-1,2,3,4-tetrahydroquinoxaline-1-carboxylate;
prop-2-yn-1-yl (3S)-4-acetyl-7-(4-methanesulfonylphenyl)-3-methyl-1,2,3,4-tetrahydroquinoxaline-1-carboxylate;
1-[(3S)-4-acetyl-7-(4-methanesulfonylphenyl)-3-methyl-1,2,3,4-tetrahydroquinoxalin-1-yl]ethan-1-one;
1-[(3S)-4-acetyl-7-(4-methanesulfonylphenyl)-3-methyl-1,2,3,4-tetrahydroquinoxalin-1-yl]-2-methylpropane-1-one;
1-[(3S)-4-acetyl-7-(4-methanesulfonylphenyl)-3-methyl-1,2,3,4-tetrahydroquinoxalin-1-yl]-2,2-dimethylpropane-1-one;
1-[(2S)-4-cyclopentanecarbonyl-6-(4-methanesulfonylphenyl)-2-methyl-1,2,3,4-tetrahydroquinoxalin-1-yl]ethan-1-one;
1-[(2S)-4-cyclobutanecarbonyl-6-(4-methanesulfonylphenyl)-2-methyl-1,2,3,4-tetrahydroquinoxalin-1-yl]ethan-1-one;
1-[(3S)-4-acetyl-7-(4-methanesulfonylphenyl)-3-methyl-1,2,3,4-tetrahydroquinoxalin-1-yl]-2-cyclopentylethan-1-one;
3-[(3S)-4-acetyl-7-(4-methanesulfonylphenyl)-3-methyl-1,2,3,4-tetrahydroquinoxalin-1-yl]-3-oxopropanenitrile;
(3S)-4-acetyl-7-(4-methanesulfonylphenyl)-N,N,3-trimethyl-1,2,3,4-tetrahydroquinoxalin-1-carboxamide;
2-methoxyethyl (3S)-4-acetyl-7-(4-methanesulfonylphenyl)-3-methyl-1,2,3,4-tetrahydroquinoxaline-1-carboxylate;
2-methylpropyl (3S)-4-acetyl-7-(4-methanesulfonylphenyl)-3-methyl-1,2,3,4-tetrahydroquinoxaline-1-carboxylate;
naphthalen-1-yl (3S)-4-acetyl-7-(4-methanesulfonylphenyl)-3-methyl-1,2,3,4-tetrahydroquinoxaline-1-carboxylate;
propyl (3S)-4-acetyl-7-(4-methanesulfonylphenyl)-3-methyl-1,2,3,4-tetrahydroquinoxaline-1-carboxylate;
(3S)-4-acetyl-7-(4-methanesulfonylphenyl)-N,3-dimethyl-1,2,3,4-tetrahydroquinoxalin-1-carboxamide;
propan-2-yl (2S)-1-acetyl-6-(4-methanesulfonylphenyl)-2-methyl-1H,2H,3H,4H-pyrido[2,3-b]pyrazine-4-carboxylate;
propan-2-yl (2S)-1-acetyl-6-(1-cyclopropyl-1H-pyrazol-4-yl)-2-methyl-1H,2H,3H,4H-pyrido[2,3-b]pyrazine-4-carboxylate;
phenyl (3S)-4-acetyl-7-(1-cyclopropyl-1H-pyrazol-4-yl)-3-methyl-1,2,3,4-tetrahydroquinoxaline-1-carboxylate;
2-chlorophenyl (3S)-4-acetyl-7-(1-cyclopropyl-1H-pyrazol-4-yl)-3-methyl-1,2,3,4-tetrahydroquinoxaline-1-carboxylate;
2-methoxyphenyl (3S)-4-acetyl-7-(1-cyclopropyl-1H-pyrazol-4-yl)-3-methyl-1,2,3,4-tetrahydroquinoxaline-1-carboxylate;
3-(trifluoromethyl)phenyl (3S)-4-acetyl-7-(1-cyclopropyl-1H-pyrazol-4-yl)-3-methyl-1,2,3,4-tetrahydroquinoxaline-1-carboxylate;
4-chlorophenyl (3S)-4-acetyl-7-(1-cyclopropyl-1H-pyrazol-4-yl)-3-methyl-1,2,3,4-tetrahydroquinoxaline-1-carboxylate;
4-fluorophenyl (3S)-4-acetyl-7-(1-cyclopropyl-1H-pyrazol-4-yl)-3-methyl-1,2,3,4-tetrahydroquinoxaline-1-carboxylate;
4-(methoxycarbonyl)phenyl (3S)-4-acetyl-7-(1-cyclopropyl-1H-pyrazol-4-yl)-3-methyl-1,2,3,4-tetrahydroquinoxaline-1-carboxylate;

4-methoxyphenyl (3S)-4-acetyl-7-(1-cyclopropyl-1H-pyrazol-4-yl)-3-methyl-1,2,3,4-tetrahydroquinoxaline-1-carboxylate;
4-methylphenyl (3S)-4-acetyl-7-(1-cyclopropyl-1H-pyrazol-4-yl)-3-methyl-1,2,3,4-tetrahydroquinoxaline-1-carboxylate;
naphthalen-1-yl (3S)-4-acetyl-7-(1-cyclopropyl-1H-pyrazol-4-yl)-3-methyl-1,2,3,4-tetrahydroquinoxaline-1-carboxylate;
4-fluoro-3-methylphenyl (3S)-4-acetyl-7-(1-cyclopropyl-1H-pyrazol-4-yl)-3-methyl-1,2,3,4-tetrahydroquinoxaline-1-carboxylate;
4-[(2S)-1-acetyl-4-(furan-2-carbonyl)-2-methyl-1,2,3,4-tetrahydroquinoxalin-6-yl]-N-cyclopropylbenzene-1-sulfonamide;
1-[(2S)-4-(furan-2-carbonyl)-2-methyl-6-(1-propyl-1H-pyrazol-4-yl)-1,2,3,4-tetrahydroquinoxalin-1-yl]ethan-1-one;
1-[(2S)-6-(1,5-dimethyl-1H-pyrazol-4-yl)-4-(furan-2-carbonyl)-2-methyl-1,2,3,4-tetrahydroquinoxalin-1-yl]ethan-1-one;
1-[(3S-1-(furan-2-carbonyl)-7-(4-methanesulfonylphenyl)-3-methyl-1H,2H,3H,4H-pyrido[2,3-b]pyrazin-4-yl]ethan-1-one;
4-[(3S)-4-acetyl-1-(furan-2-carbonyl)-3-methyl-1H,2H,3H,4H-pyrido[2,3-b]pyrazin-7-yl]-N,N-dimethylbenzamide;
1-[(3S-1-(furan-2-carbonyl)-3-methyl-7-(1-propyl-1H-pyrazol-4-yl)-1H,2H,3H,4H-pyrido[2,3-b]pyrazin-4-yl]ethan-1-one;
4-[(2S)-1-acetyl-4-(furan-2-carbonyl)-2-methyl-1,2,3,4-tetrahydroquinoxalin-6-yl]-N-(propan-2-yl)benzene-1-sulfonamide;
1-[(2S)-4-(furan-2-carbonyl)-2-methyl-6-[4-(morpholine-4-sulfonyl)phenyl]-1,2,3,4-tetrahydroquinoxalin-1-yl]ethan-1-one;
1-[(2S)-6-{4-[2-(dimethylamino)ethoxy]phenyl}-4-(furan-2-carbonyl)-2-methyl-1,2,3,4-tetrahydroquinoxalin-1-yl]ethan-1-one;
4-[(2S)-1-acetyl-4-(furan-2-carbonyl)-2-methyl-1,2,3,4-tetrahydroquinoxalin-6-yl]-N,N-dimethylbenzene-1-sulfonamide;
1-[(2S)-4-(furan-2-carbonyl)-2-methyl-6-{4-[(4-methylpiperazine-1-yl)sulfonyl]phenyl}-1,2,3,4-tetrahydroquinoxalin-1-yl]ethan-1-one;
N-{4-[(2S)-1-acetyl-4-(furan-2-carbonyl)-2-methyl-1,2,3,4-tetrahydroquinoxalin-6-yl]phenyl}methanesulfonamide;
{4-[(2S)-1-acetyl-4-(furan-2-carbonyl)-2-methyl-1,2,3,4-tetrahydroquinoxalin-6-yl]phenyl}urea;
4-[(2S)-1-acetyl-4-(furan-2-carbonyl)-2-methyl-1,2,3,4-tetrahydroquinoxalin-6-yl]benzene-1-sulfonamide;
1-[(2S)-4-(furan-2-carbonyl)-2-methyl-6-[4-(pyrrolidine-1-carbonyl)phenyl]-1,2,3,4-tetrahydroquinoxalin-1-yl]ethan-1-one;
1-[(2S)-4-(furan-2-carbonyl)-2-methyl-6-[4-(morpholine-4-carbonyl)phenyl]-1,2,3,4-tetrahydroquinoxalin-1-yl]ethan-1-one;
1-{4-[(2S)-1-acetyl-4-(furan-2-carbonyl)-2-methyl-1,2,3,4-tetrahydroquinoxalin-6-yl]phenyl}-3,3-dimethylurea;
N-{4-[(2S)-1-acetyl-4-(furan-2-carbonyl)-2-methyl-1,2,3,4-tetrahydroquinoxalin-6-yl]phenyl}morpholine-4-carboxamide;
1-[(2S)-4-(furan-2-carbonyl)-2-methyl-6-[4-(pyrrolidine-1-sulfonyl)phenyl]-1,2,3,4-tetrahydroquinoxalin-1-yl]ethan-1-one;
N-{4-[(2S)-1-acetyl-4-(furan-2-carbonyl)-2-methyl-1,2,3,4-tetrahydroquinoxalin-6-yl]phenyl}cyclopropanesulfonamide;
1-[(2S)-4-(furan-2-carbonyl)-2-methyl-6-[4-(propane-2-sulfonyl)phenyl]-1,2,3,4-tetrahydroquinoxalin-1-yl]ethan-1-one;
1-[(2S)-6-[4-(azetidine-1-sulfonyl)phenyl]-4-(furan-2-carbonyl)-2-methyl-1,2,3,4-tetrahydroquinoxalin-1-yl]ethan-1-one;
4-[(2S)-1-acetyl-4-(furan-2-carbonyl)-2-methyl-1,2,3,4-tetrahydroquinoxalin-6-yl]-N-(2-hydroxyethyl)benzamide;
1-[(2S)-6-[4-(cyclopropanesulfonyl)phenyl]-4-(furan-2-carbonyl)-2-methyl-1,2,3,4-tetrahydroquinoxalin-1-yl]ethan-1-one;
4-[(2S)-1-acetyl-4-(furan-2-carbonyl)-2-methyl-1,2,3,4-tetrahydroquinoxalin-6-yl]-N-cyclopropylbenzamide;
S-{4-[(2S)-1-acetyl-4-(furan-2-carbonyl)-2-methyl-1,2,3,4-tetrahydroquinoxalin-6-yl]phenyl}-2-hydroxyethan-1-sulfonamido;
propan-2-yl (3S)-4-acetyl-7-(4-methanesulfonylphenyl)-3-methyl-1,2,3,4-tetrahydroquinoxaline-1-carboxylate;
1-[(2S)-6-(6-aminopyridin-3-yl)-4-(furan-2-carbonyl)-2-methyl-1,2,3,4-tetrahydroquinoxalin-1-yl]ethan-1-one;
1-[(2S)-6-(2-aminopyrimidin-5-yl)-4-(furan-2-carbonyl)-2-methyl-1,2,3,4-tetrahydroquinoxalin-1-yl]ethan-1-one;
propan-2-yl (3R)-4-acetyl-7-(4-methanesulfonylphenyl)-3-methyl-1,2,3,4-tetrahydroquinoxaline-1-carboxylate;
1-[(2S)-4-(furan-2-carbonyl)-2-methyl-6-[4-(pyrrolidin-1-yl)phenyl]-1,2,3,4-tetrahydroquinoxalin-1-yl]ethan-1-one;
1-[(2S)-4-(furan-2-carbonyl)-6-(1-methanesulfonyl-2,3-dihydro-1H-indol-5-yl)-2-methyl-1,2,3,4-tetrahydroquinoxalin-1-yl]ethan-1-one;
1-[(2S)-4-(furan-2-carbonyl)-6-(4-methanesulfonylphenyl)-2-methyl-1H,2H,3H,4H-pyrido[2,3-b]pyrazine-1-yl]ethan-1-one;
1-[(2S)-4-cyclopropanecarbonyl-6-(4-methanesulfonylphenyl)-2-methyl-1H,2H,3H,4H-pyrido[2,3-b]pyrazine-1-yl]ethan-1-one;
1-[(2S)-6-cyclopropyl-4-(furan-2-carbonyl)-2-methyl-1,2,3,4-tetrahydroquinoxalin-1-yl]ethan-1-one;
propan-2-yl (3S)-4-acetyl-7-[1-(2-methanesulfonylethyl)-1H-pyrazol-4-yl]-3-methyl-1,2,3,4-tetrahydroquinoxaline-1-carboxylate;
propan-2-yl (3S)-4-acetyl-7-[1-(carbamoylmethyl)-1H-pyrazol-4-yl]-3-methyl-1,2,3,4-tetrahydroquinoxaline-1-carboxylate;
propan-2-yl (3S)-4-acetyl-7-{1-[(dimethylcarbamoyl)methyl]-1H-pyrazol-4-yl}-3-methyl-1,2,3,4-tetrahydroquinoxaline-1-carboxylate;
propan-2-yl (3S)-4-acetyl-3-methyl-7-{1-[2-(morpholin-4-yl)ethyl]-1H-pyrazol-4-yl}-1,2,3,4-tetrahydroquinoxaline-1-carboxylate;
propan-2-yl (3S)-4-acetyl-3-methyl-7-[1-(oxan-4-yl)-1H-pyrazol-4-yl]-1,2,3,4-tetrahydroquinoxaline-1-carboxylate;
propan-2-yl (3S)-4-acetyl-7-[1-(cyclopropylmethyl)-1H-pyrazol-4-yl]-3-methyl-1,2,3,4-tetrahydroquinoxaline-1-carboxylate;
propan-2-yl (3S)-4-cyclopropanecarbonyl-7-[1-(2-methanesulfonylethyl)-1H-pyrazol-4-yl]-3-methyl-1,2,3,4-tetrahydroquinoxaline-1-carboxylate;
propan-2-yl (3S)-7-[1-(carbamoylmethyl)-1H-pyrazol-4-yl]-4-cyclopropanecarbonyl-3-methyl-1,2,3,4-tetrahydroquinoxaline-1-carboxylate;
propan-2-yl (3S)-4-cyclopropanecarbonyl-7-{1-[(dimethylcarbamoyl)methyl]-1H-pyrazol-4-yl}-3-methyl-1,2,3,4-tetrahydroquinoxaline-1-carboxylate;

propan-2-yl (3S)-4-cyclopropanecarbonyl-3-methyl-7-{1-[2-(morpholin-4-yl)ethyl]-1H-pyrazol-4-yl}-1,2,3,4-tetrahydroquinoxaline-1-carboxylate;

propan-2-yl (3S)-4-cyclopropanecarbonyl-3-methyl-7-[1-(oxan-4-yl)-1H-pyrazol-4-yl]-1,2,3,4-tetrahydroquinoxaline-1-carboxylate;

propan-2-yl (3S)-4-cyclopropanecarbonyl-7-[1-(2-methoxyethyl)-1H-pyrazol-4-yl]-3-methyl-1,2,3,4-tetrahydroquinoxaline-1-carboxylate;

propan-2-yl (3S)-4-cyclopropanecarbonyl-7-[1-(2-hydroxyethyl)-1H-pyrazol-4-yl]-3-methyl-1,2,3,4-tetrahydroquinoxaline-1-carboxylate;

propan-2-yl (3S)-4-cyclopropanecarbonyl-7-[1-(cyclopropylmethyl)-1H-pyrazol-4-yl]-3-methyl-1,2,3,4-tetrahydroquinoxaline-1-carboxylate;

propan-2-yl (3S)-4-cyclopropanecarbonyl-3-methyl-7-[1-(oxetan-3-yl)-1H-pyrazol-4-yl]-1,2,3,4-tetrahydroquinoxaline-1-carboxylate;

1-methyl 4-propan-2-yl (2S)-6-[1-(2-methanesulfonylethyl)-1H-pyrazol-4-yl]-2-methyl-1,2,3,4-tetrahydroquinoxaline-1,4-dicarboxylate;

1-methyl 4-propan-2-yl (2S)-6-[1-(carbamoylmethyl)-1H-pyrazol-4-yl]-2-methyl-1,2,3,4-tetrahydroquinoxaline-1,4-dicarboxylate;

1-methyl 4-propan-2-yl (2S)-6-{1-[(dimethylcarbamoyl)methyl]-1H-pyrazol-4-yl}-2-methyl-1,2,3,4-tetrahydroquinoxaline-1,4-dicarboxylate;

1-methyl 4-propan-2-yl (2S)-2-methyl-6-{1-[2-(morpholin-4-yl)ethyl]-1H-pyrazol-4-yl}-1,2,3,4-tetrahydroquinoxaline-1,4-dicarboxylate;

1-methyl 4-propan-2-yl (2S)-2-methyl-6-[1-(oxan-4-yl)-1H-pyrazol-4-yl]-1,2,3,4-tetrahydroquinoxaline-1,4-dicarboxylate;

1-methyl 4-propan-2-yl (2S)-6-[1-(2-methoxyethyl)-1H-pyrazol-4-yl]-2-methyl-1,2,3,4-tetrahydroquinoxaline-1,4-dicarboxylate;

1-methyl 4-propan-2-yl (2S)-6-[1-(2-hydroxyethyl)-1H-pyrazol-4-yl]-2-methyl-1,2,3,4-tetrahydroquinoxaline-1,4-dicarboxylate;

1-methyl 4-propan-2-yl (2S)-6-[1-(cyclopropylmethyl)-1H-pyrazol-4-yl]-2-methyl-1,2,3,4-tetrahydroquinoxaline-1,4-dicarboxylate;

1-methyl 4-propan-2-yl (2S)-2-methyl-6-[1-(oxetan-3-yl)-1H-pyrazol-4-yl]-1,2,3,4-tetrahydroquinoxaline-1,4-dicarboxylate;

propan-2-yl (3S)-4-acetyl-7-[1-(2-hydroxy-2-methylpropyl)-1H-pyrazol-4-yl]-3-methyl-1,2,3,4-tetrahydroquinoxaline-1-carboxylate;

propan-2-yl (3S)-4-cyclopropanecarbonyl-7-[1-(2-hydroxy-2-methylpropyl)-1H-pyrazol-4-yl]-3-methyl-1,2,3,4-tetrahydroquinoxaline-1-carboxylate;

1-methyl 4-propan-2-yl (2S)-6-[1-(2-hydroxy-2-methylpropyl)-1H-pyrazol-4-yl]-2-methyl-1,2,3,4-tetrahydroquinoxaline-1,4-dicarboxylate;

propan-2-yl (3S)-4-acetyl-7-(1-tert-butyl-1H-pyrazol-4-yl)-3-methyl-1,2,3,4-tetrahydroquinoxaline-1-carboxylate;

propan-2-yl (3S)-7-(1-tert-butyl-1H-pyrazol-4-yl)-4-cyclopropanecarbonyl-3-methyl-1,2,3,4-tetrahydroquinoxaline-1-carboxylate;

1-methyl 4-propan-2-yl (2S)-6-(1-tert-butyl-1H-pyrazol-4-yl)-2-methyl-1,2,3,4-tetrahydroquinoxaline-1,4-dicarboxylate;

propan-2-yl (3S)-4-acetyl-7-(3,5-dimethyl-1H-pyrazol-4-yl)-3-methyl-1,2,3,4-tetrahydroquinoxaline-1-carboxylate;

propan-2-yl (3S)-4-acetyl-3-methyl-7-(1-phenyl-1H-pyrazol-4-yl)-1,2,3,4-tetrahydroquinoxaline-1-carboxylate;

propan-2-yl (3S)-4-acetyl-3-methyl-7-[3-(trifluoromethyl)-1H-pyrazol-4-yl]-1,2,3,4-tetrahydroquinoxaline-1-carboxylate;

propan-2-yl (3S)-4-acetyl-7-[1-(difluoromethyl)-1H-pyrazol-4-yl]-3-methyl-1,2,3,4-tetrahydroquinoxaline-1-carboxylate;

propan-2-yl (3S)-4-acetyl-3-methyl-7-(3-methyl-1H-pyrazol-4-yl)-1,2,3,4-tetrahydroquinoxaline-1-carboxylate;

propan-2-yl (3S)-4-acetyl-7-(1,3-dimethyl-1H-pyrazol-4-yl)-3-methyl-1,2,3,4-tetrahydroquinoxaline-1-carboxylate;

propan-2-yl (3S)-4-acetyl-7-(1,5-dimethyl-1H-pyrazol-4-yl)-3-methyl-1,2,3,4-tetrahydroquinoxaline-1-carboxylate;

2-{4-[(2S)-1-cyclopropanecarbonyl-2-methyl-4-[(propan-2-yloxy)carbonyl]-1,2,3,4-tetrahydroquinoxalin-6-yl]-1H-pyrazol-1-yl}acetic acid;

2-{4-[(2S)-1-(methoxycarbonyl)-2-methyl-4-[(propan-2-yloxy)carbonyl]-1,2,3,4-tetrahydroquinoxalin-6-yl]-1H-pyrazol-1-yl}acetic acid;

1-[(2S)-4-cyclopropanecarbonyl-6-[1-(2-hydroxyethyl)-1H-pyrazol-4-yl]-2-methyl-1,2,3,4-tetrahydroquinoxalin-1-yl]ethan-1-one;

1-[(2S)-4-cyclopropanecarbonyl-6-[1-(2-hydroxy-2-methylpropyl)-1H-pyrazol-4-yl]-2-methyl-1,2,3,4-tetrahydroquinoxalin-1-yl]ethan-1-one;

1-{4-cyclopropanecarbonyl-6-[1-(2-methanesulfonylethyl)-1H-pyrazol-4-yl]-2-methyl-1,2,3,4-tetrahydroquinoxalin-1-yl}ethan-1-one;

propan-2-yl (3S)-4-acetyl-7-(4-methanesulfonamidophenyl)-3-methyl-1,2,3,4-tetrahydroquinoxaline-1-carboxylate;

propan-2-yl (3S)-4-acetyl-3-methyl-7-[4-(N-methylmethanesulfonamido)phenyl]-1,2,3,4-tetrahydroquinoxaline-1-carboxylate;

propan-2-yl (3S)-4-acetyl-7-(1-methanesulfonyl-2,3-dihydro-1H-indol-5-yl)-3-methyl-1,2,3,4-tetrahydroquinoxaline-1-carboxylate;

N-{4-[(2S)-1-acetyl-4-cyclopropanecarbonyl-2-methyl-1,2,3,4-tetrahydroquinoxalin-6-yl]phenyl}methanesulfonamide;

N-{4-[(2S)-1-acetyl-4-cyclopropanecarbonyl-2-methyl-1,2,3,4-tetrahydroquinoxalin-6-yl]phenyl}-N-methylmethanesulfonamide;

propan-2-yl (3S)-4-acetyl-3-methyl-7-[1-(piperidin-4-yl)-1H-pyrazol-4-yl]-1,2,3,4-tetrahydroquinoxaline-1-carboxylate;

propan-2-yl (3S)-4-cyclopropanecarbonyl-3-methyl-7-[1-(piperidin-4-yl)-1H-pyrazol-4-yl]-1,2,3,4-tetrahydroquinoxaline-1-carboxylate;

1-methyl 4-propan-2-yl (2S)-2-methyl-6-[1-(piperidin-4-yl)-1H-pyrazol-4-yl]-1,2,3,4-tetrahydroquinoxaline-1,4-dicarboxylate;

propan-2-yl (3S)-4-acetyl-7-[1-(azetidin-3-yl)-1H-pyrazol-4-yl]-3-methyl-1,2,3,4-tetrahydroquinoxaline-1-carboxylate;

propan-2-yl (3S)-7-[1-(azetidin-3-yl)-1H-pyrazol-4-yl]-4-cyclopropanecarbonyl-3-methyl-1,2,3,4-tetrahydroquinoxaline-1-carboxylate;

1-methyl 4-propan-2-yl (2S)-6-[1-(azetidin-3-yl)-1H-pyrazol-4-yl]-2-methyl-1,2,3,4-tetrahydroquinoxaline-1,4-dicarboxylate;

1-[(2S)-4-cyclopropanecarbonyl-2-methyl-6-[1-(piperidin-4-yl)-1H-pyrazol-4-yl]-1,2,3,4-tetrahydroquinoxalin-1-yl]ethan-1-one;

1-[(2S)-6-[1-(azetidin-3-yl)-1H-pyrazol-4-yl]-4-cyclopropanecarbonyl-2-methyl-1,2,3,4-tetrahydroquinoxalin-1-yl]ethan-1-one;
2,2,2-trifluoro-1-[(2S)-4-(furan-2-carbonyl)-6-(4-methanesulfonylphenyl)-2-methyl-1,2,3,4-tetrahydroquinoxalin-1-yl]ethan-1-one;
4-[(2S)-4-(furan-2-carbonyl)-2-methyl-1-(trifluoroacetyl)-1,2,3,4-tetrahydroquinoxalin-6-yl]-N,N-dimethylbenzamide;
2,2,2-trifluoro-1-[(2S)-4-(furan-2-carbonyl)-2-methyl-6-(1-propyl-1H-pyrazol-4-yl)-1,2,3,4-tetrahydroquinoxalin-1-yl]ethan-1-one;
(2S)-1-cyclopropanecarbonyl-4-(furan-2-carbonyl)-6-(4-methanesulfonylphenyl)-2-methyl-1,2,3,4-tetrahydroquinoxaline;
1-[(2S)-4-(furan-2-carbonyl)-6-(4-methanesulfonylphenyl)-2-methyl-1,2,3,4-tetrahydroquinoxalin-1-yl]propane-1-one;
methyl (2S)-4-(furan-2-carbonyl)-6-(4-methanesulfonylphenyl)-2-methyl-1,2,3,4-tetrahydroquinoxaline-1-carboxylate;
1-[(2S)-4-(furan-2-carbonyl)-6-(4-methanesulfonylphenyl)-2-methyl-1,2,3,4-tetrahydroquinoxalin-1-yl]-2-hydroxyethan-1-one;
1-[(2S)-4-(furan-2-carbonyl)-6-(4-methanesulfonylphenyl)-2-methyl-1,2,3,4-tetrahydroquinoxalin-1-yl]-2-methoxyethan-1-one;
(2S)-4-(furan-2-carbonyl)-6-(4-methanesulfonylphenyl)-N,N,2-trimethyl-1,2,3,4-tetrahydroquinoxaline-1-carboxamide;
1-[(2S)-4-(furan-2-carbonyl)-6-(4-methanesulfonylphenyl)-2-methyl-1,2,3,4-tetrahydroquinoxalin-1-yl]-2-methylpropane-1-one;
ethyl (2S)-4-(furan-2-carbonyl)-6-(4-methanesulfonylphenyl)-2-methyl-1,2,3,4-tetrahydroquinoxaline-1-carboxylate;
propan-2-yl (2S)-4-(furan-2-carbonyl)-6-(4-methanesulfonylphenyl)-2-methyl-1,2,3,4-tetrahydroquinoxaline-1-carboxylate;
(2S)-1-cyclopentanecarbonyl-4-(furan-2-carbonyl)-6-(4-methanesulfonylphenyl)-2-methyl-1,2,3,4-tetrahydroquinoxaline;
(2S)-1-cyclobutanecarbonyl-4-(furan-2-carbonyl)-6-(4-methanesulfonylphenyl)-2-methyl-1,2,3,4-tetrahydroquinoxaline;
(2S)-4-(furan-2-carbonyl)-6-(4-methanesulfonylphenyl)-2-methyl-1-(1,2-oxazole-5-carbonyl)-1,2,3,4-tetrahydroquinoxaline;
(2S)-4-(furan-2-carbonyl)-6-(4-methanesulfonylphenyl)-2-methyl-1-(pyrrolidine-1-carbonyl)-1,2,3,4-tetrahydroquinoxaline;
(2S)-1,4-dicyclopropanecarbonyl-6-(1-cyclopropyl-1H-pyrazol-4-yl)-2-methyl-1,2,3,4-tetrahydroquinoxaline;
propan-2-yl (3S)-4-cyclopropanecarbonyl-7-(1-cyclopropyl-1H-pyrazol-4-yl)-3-methyl-1,2,3,4-tetrahydroquinoxaline-1-carboxylate;
ethyl (3S)-4-cyclopropanecarbonyl-7-(1-cyclopropyl-1H-pyrazol-4-yl)-3-methyl-1,2,3,4-tetrahydroquinoxaline-1-carboxylate;
4-ethyl 1-methyl (2S)-6-(1-cyclopropyl-1H-pyrazol-4-yl)-2-methyl-1,2,3,4-tetrahydroquinoxaline-1,4-dicarboxylate;
1-[(2S)-4-(furan-2-carbonyl)-2-methyl-6-(pyridin-2-yl)-1,2,3,4-tetrahydroquinoxalin-1-yl]ethan-1-one;
1-[(2S)-4-(furan-2-carbonyl)-6-{imidazo[1,2-a]pyridin-6-yl}-2-methyl-1,2,3,4-tetrahydroquinoxalin-1-yl]ethan-1-one;
1-[(2S)-4-(furan-2-carbonyl)-2-methyl-6-(pyrimidin-2-yl)-1,2,3,4-tetrahydroquinoxalin-1-yl]ethan-1-one;
1-[(2S)-4-(furan-2-carbonyl)-2-methyl-6-(pyrazin-2-yl)-1,2,3,4-tetrahydroquinoxalin-1-yl]ethan-1-one;
1-[(2S)-4-(furan-2-carbonyl)-6-(1H-indol-5-yl)-2-methyl-1,2,3,4-tetrahydroquinoxalin-1-yl]ethan-1-one 1-[(2S)-6-(2,3-dihydro-1-benzofuran-7-yl)-4-(furan-2-carbonyl)-2-methyl-1,2,3,4-tetrahydroquinoxalin-1-yl]ethan-1-one;
5-[(2S)-1-acetyl-4-(furan-2-carbonyl)-2-methyl-1,2,3,4-tetrahydroquinoxalin-6-yl]pyrazine-2-carbonitrile;
1-[(2S)-4-(furan-2-carbonyl)-2-methyl-6-(1-methyl-1H-imidazol-2-yl)-1,2,3,4-tetrahydroquinoxalin-1-yl]ethan-1-one;
1-[(2S)-4-(furan-2-carbonyl)-2-methyl-6-(1-methyl-1H-imidazol-5-yl)-1,2,3,4-tetrahydroquinoxalin-1-yl]ethan-1-one;
1-[(2S)-4-(furan-2-carbonyl)-2-methyl-6-(1,2-oxazol-4-yl)-1,2,3,4-tetrahydroquinoxalin-1-yl]ethan-1-one;
1-[(2S)-4-(furan-2-carbonyl)-6-{imidazo[1,2-a]pyridin-3-yl}-2-methyl-1,2,3,4-tetrahydroquinoxalin-1-yl]ethan-1-one;
6-[(2S)-1-acetyl-4-(furan-2-carbonyl)-2-methyl-1,2,3,4-tetrahydroquinoxalin-6-yl]pyridine-3-carbonitrile;
1-[(2S)-4-(furan-2-carbonyl)-2-methyl-6-{3-methyl-[1,2,4]triazolo[4,3-a]pyridin-6-yl}-1,2,3,4-tetrahydroquinoxalin-1-yl]ethan-1-one;
5-[(2S)-1-acetyl-4-(furan-2-carbonyl)-2-methyl-1,2,3,4-tetrahydroquinoxalin-6-yl]-2,3-dihydro-1H-1,3-benzodiazol-2-one;
5-[(2S)-1-acetyl-4-(furan-2-carbonyl)-2-methyl-1,2,3,4-tetrahydroquinoxalin-6-yl]-1,3-dimethyl-2,3-dihydro-1H-1,3-benzodiazol-2-one;
1-[(2S)-4-(furan-2-carbonyl)-2-methyl-6-{[1,2,4]triazolo[4,3-b]pyridazin-6-yl}-1,2,3,4-tetrahydroquinoxalin-1-yl]ethan-1-one;
1-[(2S)-4-(furan-2-carbonyl)-2-methyl-6-{1H-pyrrolo[3,2-b]pyridin-5-yl}-1,2,3,4-tetrahydroquinoxalin-1-yl]ethan-1-one;
1-[(2S)-4-(furan-2-carbonyl)-6-{imidazo[1,2-b]pyridazin-6-yl}-2-methyl-1,2,3,4-tetrahydroquinoxalin-1-yl]ethan-1-one;
1-[(2S)-4-(furan-2-carbonyl)-2-methyl-6-(1-methyl-1H-1,3-benzodiazol-6-yl)-1,2,3,4-tetrahydroquinoxalin-1-yl]ethan-1-one;
1-[(2S)-4-(furan-2-carbonyl)-2-methyl-6-(1-methyl-1H-1,3-benzodiazol-5-yl)-1,2,3,4-tetrahydroquinoxalin-1-yl]ethan-1-one;
1-[(2S)-4-(furan-2-carbonyl)-2-methyl-6-(1-methyl-1H-imidazol-4-yl)-1,2,3,4-tetrahydroquinoxalin-1-yl]ethan-1-one;
1-[(2S)-4-(furan-2-carbonyl)-2-methyl-6-[3-(5-methyl-1,2,4-oxadiazol-3-yl)phenyl]-1,2,3,4-tetrahydroquinoxalin-1-yl]ethan-1-one;
1-[(2S)-4-(furan-2-carbonyl)-2-methyl-6-(5-methyl-1,3,4-thiadiazol-2-yl)-1,2,3,4-tetrahydroquinoxalin-1-yl]ethan-1-one;
1-[(2S)-4-(furan-2-carbonyl)-2-methyl-6-(2-methyl-2H-indazol-5-yl)-1,2,3,4-tetrahydroquinoxalin-1-yl]ethan-1-one;
1-[(2S)-4-(furan-2-carbonyl)-2-methyl-6-[3-(pyrimidin-2-yl)phenyl]-1,2,3,4-tetrahydroquinoxalin-1-yl]ethan-1-one;
1-[(2S)-4-(furan-2-carbonyl)-6-{imidazo[1,2-a]pyrimidin-7-yl}-2-methyl-1,2,3,4-tetrahydroquinoxalin-1-yl]ethan-1-one;

1-[(2S)-4-(furan-2-carbonyl)-6-(5-methanesulfonylpyridin-2-yl)-2-methyl-1,2,3,4-tetrahydroquinoxalin-1-yl]ethan-1-one;
1-[(2S)-6-benzoyl-4-(furan-2-carbonyl)-2-methyl-1,2,3,4-tetrahydroquinoxalin-1-yl]ethan-1-one;
1-[(2S)-6-(1-benzyl-1H-pyrazol-4-yl)-4-(furan-2-carbonyl)-2-methyl-1,2,3,4-tetrahydroquinoxalin-1-yl]ethan-1-one;
4-[(2S)-1-acetyl-4-(furan-2-carbonyl)-2-methyl-1,2,3,4-tetrahydroquinoxalin-6-yl]-N,N-dimethyl-1H-imidazol-1-sulfonamide;
5-[(2S)-1-acetyl-4-(furan-2-carbonyl)-2-methyl-1,2,3,4-tetrahydroquinoxalin-6-yl]-1-methyl-1,2-dihydropyridin-2-one;
1-[(2S)-4-(furan-2-carbonyl)-2-methyl-6-[4-(1,3-oxazol-2-yl)phenyl]-1,2,3,4-tetrahydroquinoxalin-1-yl]ethan-1-one;
1-[(2S)-6-(5-aminopyrazin-2-yl)-4-(furan-2-carbonyl)-2-methyl-1,2,3,4-tetrahydroquinoxalin-1-yl]ethan-1-one;
methyl N-{4-[(2S)-1-acetyl-4-(furan-2-carbonyl)-2-methyl-1,2,3,4-tetrahydroquinoxalin-6-yl]phenyl}carbamate;
1-[(2S)-4-(furan-2-carbonyl)-6-[4-(3-hydroxyoxetan-3-yl)phenyl]-2-methyl-1,2,3,4-tetrahydroquinoxalin-1-yl]ethan-1-one;
1-[(2S)-4-(furan-2-carbonyl)-2-methyl-6-[4-(1,3,4-oxadiazol-2-yl)phenyl]-1,2,3,4-tetrahydroquinoxalin-1-yl]ethan-1-one;
4-{4-[(2S)-1-acetyl-4-(furan-2-carbonyl)-2-methyl-1,2,3,4-tetrahydroquinoxalin-6-yl]phenyl}-1$\lambda^6$-thiomorpholine-1,1-dione;
{4-[(2S)-1-acetyl-4-(furan-2-carbonyl)-2-methyl-1,2,3,4-tetrahydroquinoxalin-6-yl]phenyl}methanesulfonamide;
1-[(2S)-4-(furan-2-carbonyl)-2-methyl-6-(2-methyl-2H-1,2,3-triazol-4-yl)-1,2,3,4-tetrahydroquinoxalin-1-yl]ethan-1-one;
1-[(2S)-4-(furan-2-carbonyl)-2-methyl-6-(1-methyl-1H-1,2,3-triazol-4-yl)-1,2,3,4-tetrahydroquinoxalin-1-yl]ethan-1-one;
3-{4-[(2S)-1-acetyl-4-(furan-2-carbonyl)-2-methyl-1,2,3,4-tetrahydroquinoxalin-6-yl]phenyl}-1H-pyrazole-5-carboxylic acid;
1-[(2S)-4-(furan-2-carbonyl)-2-methyl-6-[4-(piperazine-1-carbonyl)phenyl]-1,2,3,4-tetrahydroquinoxalin-1-yl]ethan-1-one;
1-[(2S)-4-(furan-2-carbonyl)-6-[4-(2-hydroxyethanesulfonyl)phenyl]-2-methyl-1,2,3,4-tetrahydroquinoxalin-1-yl]ethan-1-one;
2-{4-[(2S)-1-acetyl-4-(furan-2-carbonyl)-2-methyl-1,2,3,4-tetrahydroquinoxalin-6-yl]phenyl}-1$\lambda^6$,2-thiazolidine-1,1-dione;
1-[(2S)-6-[4-(2-aminoethanesulfonyl)phenyl]-4-(furan-2-carbonyl)-2-methyl-1,2,3,4-tetrahydroquinoxalin-1-yl]ethan-1-one;
4-[(2S)-1-acetyl-4-(furan-2-carbonyl)-2-methyl-1,2,3,4-tetrahydroquinoxalin-6-yl]-N-(2-aminoethyl)benzamide;
2-({4-[(2S)-1-acetyl-4-(furan-2-carbonyl)-2-methyl-1,2,3,4-tetrahydroquinoxalin-6-yl]phenyl}methyl)-1$\lambda^6$,2-thiazolidine-1,1-dione;
3-{4-[(2S)-1-acetyl-4-(furan-2-carbonyl)-2-methyl-1,2,3,4-tetrahydroquinoxalin-6-yl]phenoxy}propanenitrile;
1-[(2S)-4-(furan-2-carbonyl)-6-[4-(1H-imidazol-2-yl)phenyl]-2-methyl-1,2,3,4-tetrahydroquinoxalin-1-yl]ethan-1-one;
1-[(2S)-6-(5-amino-1,3,4-thiadiazol-2-yl)-4-(furan-2-carbonyl)-2-methyl-1,2,3,4-tetrahydroquinoxalin-1-yl]ethan-1-one;
1-[(2S)-6-(5-amino-1,3-thiazol-2-yl)-4-(furan-2-carbonyl)-2-methyl-1,2,3,4-tetrahydroquinoxalin-1-yl]ethan-1-one;
1-[(2S)-4-(furan-2-carbonyl)-2-methyl-6-(1,2-thiazol-4-yl)-1,2,3,4-tetrahydroquinoxalin-1-yl]ethan-1-one;
2-{4-[(2S)-1-acetyl-4-(furan-2-carbonyl)-2-methyl-1,2,3,4-tetrahydroquinoxalin-6-yl]benzenesulfonyl}-N,N-dimethylacetamide;
1-[(2S)-4-(furan-2-carbonyl)-2-methyl-6-(1,2-thiazol-5-yl)-1,2,3,4-tetrahydroquinoxalin-1-yl]ethan-1-one;
4-{4-[(2S)-1-acetyl-4-cyclopropanecarbonyl-2-methyl-1,2,3,4-tetrahydroquinoxalin-6-yl]phenyl}-1$\lambda^6$-thiomorpholine-1,1-dione;
4-{4-[(2S)-1,4-dicyclopropanecarbonyl-2-methyl-1,2,3,4-tetrahydroquinoxalin-6-yl]phenyl}-1$\lambda^6$-thiomorpholine-1,1-dione;
1-[(2S)-4-cyclopropanecarbonyl-2-methyl-6-[4-(piperazine-1-carbonyl)phenyl]-1,2,3,4-tetrahydroquinoxalin-1-yl]ethan-1-one;
(2S)-1,4-dicyclopropanecarbonyl-2-methyl-6-[4-(piperazine-1-carbonyl)phenyl]-1,2,3,4-tetrahydroquinoxaline;
2-{4-[(2S)-1-acetyl-4-cyclopropanecarbonyl-2-methyl-1,2,3,4-tetrahydroquinoxalin-6-yl]phenyl}-1$\lambda^6$,2-thiazolidine-1,1-dione;
2-{4-[(2S)-1,4-dicyclopropanecarbonyl-2-methyl-1,2,3,4-tetrahydroquinoxalin-6-yl]phenyl}-1$\lambda^6$,2-thiazolidine-1,1-dione;
1-[(2S)-6-(5-aminopyrazin-2-yl)-4-cyclopropanecarbonyl-2-methyl-1,2,3,4-tetrahydroquinoxalin-1-yl]ethan-1-one;
5-[(2S)-1,4-dicyclopropanecarbonyl-2-methyl-1,2,3,4-tetrahydroquinoxalin-6-yl]pyrazin-2-amine;
1-[(2S)-4-cyclopropanecarbonyl-6-[4-(3-hydroxyoxetan-3-yl)phenyl]-2-methyl-1,2,3,4-tetrahydroquinoxalin-1-yl]ethan-1-one;
3-{4-[(2S)-1,4-dicyclopropanecarbonyl-2-methyl-1,2,3,4-tetrahydroquinoxalin-6-yl]phenyl}oxetan-3-ol;
{4-[(2S)-1-acetyl-4-cyclopropanecarbonyl-2-methyl-1,2,3,4-tetrahydroquinoxalin-6-yl]phenyl}methanesulfonamide;
{4-[(2S)-1,4-dicyclopropanecarbonyl-2-methyl-1,2,3,4-tetrahydroquinoxalin-6-yl]phenyl}methanesulfonamide;
1-[(2S)-6-[4-(2-aminoethanesulfonyl)phenyl]-4-cyclopropanecarbonyl-2-methyl-1,2,3,4-tetrahydroquinoxalin-1-yl]ethan-1-one;
2-{4-[(2S)-1,4-dicyclopropanecarbonyl-2-methyl-1,2,3,4-tetrahydroquinoxalin-6-yl]benzenesulfonyl}ethan-1-amine;
1-[(2S)-4-cyclopropanecarbonyl-6-[4-(2-hydroxyethanesulfonyl)phenyl]-2-methyl-1,2,3,4-tetrahydroquinoxalin-1-yl]ethan-1-one;
2-{4-[(2S)-1,4-dicyclopropanecarbonyl-2-methyl-1,2,3,4-tetrahydroquinoxalin-6-yl]benzenesulfonyl}ethan-1-ol;
4-[(2S)-1-acetyl-4-cyclopropanecarbonyl-2-methyl-1,2,3,4-tetrahydroquinoxalin-6-yl]-N-(2-aminoethyl)benzamide;
N-(2-aminoethyl)-4-[(2S)-1,4-dicyclopropanecarbonyl-2-methyl-1,2,3,4-tetrahydroquinoxalin-6-yl]benzamide;
1-[(2S)-4-cyclopropanecarbonyl-2-methyl-6-(1-methyl-1H-1,2,3-triazol-4-yl)-1,2,3,4-tetrahydroquinoxalin-1-yl]ethan-1-one;
(2S)-1,4-dicyclopropanecarbonyl-2-methyl-6-(1-methyl-1H-1,2,3-triazol-4-yl)-1,2,3,4-tetrahydroquinoxaline;
methyl (2S)-4-cyclopropanecarbonyl-6-[4-(1,1-dioxo-1$\lambda^6$-thiomorpholin-4-yl)phenyl]-2-methyl-1,2,3,4-tetrahydroquinoxaline-1-carboxylate;
methyl (2S)-4-cyclopropanecarbonyl-6-[4-(piperazine-1-carbonyl)phenyl]-1,2,3,4-tetrahydroquinoxaline-1-carboxylate;
methyl (2S)-4-cyclopropanecarbonyl-6-[4-(1,1-dioxo-1$\lambda^6$,2-thiazolidin-2-yl)phenyl]-2-methyl-1,2,3,4-tetrahydroquinoxaline-1-carboxylate;

methyl (2S)-6-(5-aminopyrazin-2-yl)-4-cyclopropanecarbonyl-2-methyl-1,2,3,4-tetrahydroquinoxaline-1-carboxylate;
methyl (2S)-4-cyclopropanecarbonyl-6-[4-(3-hydroxyoxetan-3-yl)phenyl]-2-methyl-1,2,3,4-tetrahydroquinoxaline-1-carboxylate;
methyl (2S)-4-cyclopropanecarbonyl-2-methyl-6-[4-(sulfamoylmethyl)phenyl]-1,2,3,4-tetrahydroquinoxaline-1-carboxylate;
methyl (2S)-6-[4-(2-aminoethanesulfonyl)phenyl]-4-cyclopropanecarbonyl-2-methyl-1,2,3,4-tetrahydroquinoxaline-1-carboxylate;
methyl (2S)-4-cyclopropanecarbonyl-6-[4-(2-hydroxyethanesulfonyl)phenyl]-2-methyl-1,2,3,4-tetrahydroquinoxaline-1-carboxylate;
methyl (2S)-6-{4-[(2-aminoethyl)carbamoyl]phenyl}-4-cyclopropanecarbonyl-2-methyl-1,2,3,4-tetrahydroquinoxaline-1-carboxylate;
methyl (2S)-4-cyclopropanecarbonyl-2-methyl-6-(1-methyl-1H-1,2,3-triazol-4-yl)-1,2,3,4-tetrahydroquinoxaline-1-carboxylate;
propan-2-yl (3S)-4-acetyl-3-methyl-7-(1-methyl-1H-1,2,3-triazol-4-yl)-1,2,3,4-tetrahydroquinoxaline-1-carboxylate;
1-methyl 4-propan-2-yl (2S)-6-[4-(2-hydroxyethanesulfonyl)phenyl]-2-methyl-1,2,3,4-tetrahydroquinoxaline-1,4-dicarboxylate;
propan-2-yl (3S)-4-acetyl-7-[4-(1,1-dioxo-1λ$^6$-thiomorpholin-4-yl)phenyl]-3-methyl-1,2,3,4-tetrahydroquinoxaline-1-carboxylate;
propan-2-yl (3S)-4-cyclopropanecarbonyl-7-[4-(1,1-dioxo-1λ$^6$-thiomorpholin-4-yl)phenyl]-3-methyl-1,2,3,4-tetrahydroquinoxaline-1-carboxylate;
propan-2-yl (3S)-4-acetyl-7-[4-(1,1-dioxo-1λ$^6$,2-thiazolidin-2-yl)phenyl]-3-methyl-1,2,3,4-tetrahydroquinoxaline-1-carboxylate;
propan-2-yl (3S)-4-cyclopropanecarbonyl-7-[4-(1,1-dioxo-1λ$^6$,2-thiazolidin-2-yl)phenyl]-3-methyl-1,2,3,4-tetrahydroquinoxaline-1-carboxylate propan-2-yl (3S)-4-acetyl-7-(5-aminopyrazin-2-yl)-3-methyl-1,2,3,4-tetrahydroquinoxaline-1-carboxylate;
propan-2-yl (3S)-7-(5-aminopyrazin-2-yl)-4-cyclopropanecarbonyl-3-methyl-1,2,3,4-tetrahydroquinoxaline-1-carboxylate;
propan-2-yl (3S)-4-acetyl-7-[4-(3-hydroxyoxetan-3-yl)phenyl]-3-methyl-1,2,3,4-tetrahydroquinoxaline-1-carboxylate;
propan-2-yl (3S)-4-cyclopropanecarbonyl-7-[4-(3-hydroxyoxetan-3-yl)phenyl]-3-methyl-1,2,3,4-tetrahydroquinoxaline-1-carboxylate;
propan-2-yl (3S)-4-acetyl-3-methyl-7-[4-(sulfamoylmethyl)phenyl]-1,2,3,4-tetrahydroquinoxaline-1-carboxylate;
propan-2-yl (3S)-4-cyclopropanecarbonyl-3-methyl-7-[4-(sulfamoylmethyl)phenyl]-1,2,3,4-tetrahydroquinoxaline-1-carboxylate;
propan-2-yl (3S)-4-acetyl-7-[4-(2-aminoethanesulfonyl)phenyl]-3-methyl-1,2,3,4-tetrahydroquinoxaline-1-carboxylate
propan-2-yl (3S)-4-acetyl-7-[4-(2-hydroxyethanesulfonyl)phenyl]-3-methyl-1,2,3,4-tetrahydroquinoxaline-1-carboxylate;
propan-2-yl (3S)-4-cyclopropanecarbonyl-7-[4-(2-hydroxyethanesulfonyl)phenyl]-3-methyl-1,2,3,4-tetrahydroquinoxaline-1-carboxylate;
propan-2-yl (3S)-4-acetyl-7-{4-[(2-aminoethyl)carbamoyl]phenyl}-3-methyl-1,2,3,4-tetrahydroquinoxaline-1-carboxylate;
propan-2-yl (3S)-7-{4-[(2-aminoethyl)carbamoyl]phenyl}-4-cyclopropanecarbonyl-3-methyl-1,2,3,4-tetrahydroquinoxaline-1-carboxylate;
propan-2-yl (3S)-4-cyclopropanecarbonyl-3-methyl-7-(1-methyl-1H-1,2,3-triazol-4-yl)-1,2,3,4-tetrahydroquinoxaline-1-carboxylate;
1-methyl 4-propan-2-yl (2S)-6-[4-(1,1-dioxo-1λ$^6$-thiomorpholin-4-yl)phenyl]-2-methyl-1,2,3,4-tetrahydroquinoxaline-1,4-dicarboxylate;
1-methyl 4-propan-2-yl (2S)-6-[4-(1,1-dioxo-1λ$^6$,2-thiazolidin-2-yl)phenyl]-2-methyl-1,2,3,4-tetrahydroquinoxaline-1,4-dicarboxylate;
1-methyl 4-propan-2-yl (2S)-6-(5-aminopyrazin-2-yl)-2-methyl-1,2,3,4-tetrahydroquinoxaline-1,4-dicarboxylate;
1-methyl 4-propan-2-yl (2S)-6-[4-(3-hydroxyoxetan-3-yl)phenyl]-2-methyl-1,2,3,4-tetrahydroquinoxaline-1,4-dicarboxylate;
1-methyl 4-propan-2-yl (2S)-2-methyl-6-[4-(sulfamoylmethyl)phenyl]-1,2,3,4-tetrahydroquinoxaline-1,4-dicarboxylate;
1-methyl 4-propan-2-yl (2S)-6-[4-(2-aminoethanesulfonyl)phenyl]-2-methyl-1,2,3,4-tetrahydroquinoxaline-1,4-dicarboxylate;
1-methyl 4-propan-2-yl (2S)-6-{4-[(2-aminoethyl)carbamoyl]phenyl}-2-methyl-1,2,3,4-tetrahydroquinoxaline-1,4-dicarboxylate;
1-methyl 4-propan-2-yl (2S)-2-methyl-6-(1-methyl-1H-1,2,3-triazol-4-yl)-1,2,3,4-tetrahydroquinoxaline-1,4-dicarboxylate;
1-[(2S)-4-(furan-2-carbonyl)-2-methyl-6-(1,3-oxazol-2-yl)-1,2,3,4-tetrahydroquinoxalin-1-yl]ethan-1-one;
N-{4-[(2S)-1-acetyl-4-(furan-2-carbonyl)-2-methyl-1,2,3,4-tetrahydroquinoxalin-6-yl]phenyl}-N-methylmethanesulfonamide;
cyclobutyl (3S)-4-acetyl-7-(4-methanesulfonylphenyl)-3-methyl-1,2,3,4-tetrahydroquinoxaline-1-carboxylate;
butan-2-yl (3S)-4-acetyl-7-(4-methanesulfonylphenyl)-3-methyl-1,2,3,4-tetrahydroquinoxaline-1-carboxylate;
cyclopropylmethyl (3S)-4-acetyl-7-(4-methanesulfonylphenyl)-3-methyl-1,2,3,4-tetrahydroquinoxaline-1-carboxylate;
oxan-4-yl (3S)-4-acetyl-7-(4-methanesulfonylphenyl)-3-methyl-1,2,3,4-tetrahydroquinoxaline-1-carboxylate;
oxetan-3-yl (3S)-4-acetyl-7-(4-methanesulfonylphenyl)-3-methyl-1,2,3,4-tetrahydroquinoxaline-1-carboxylate;
oxan-4-yl (3S)-4-acetyl-3-methyl-7-[4-(piperazine-1-carbonyl)phenyl]-1,2,3,4-tetrahydroquinoxaline-1-carboxylate;
2,4-difluorophenyl (3S)-4-acetyl-7-(1-cyclopropyl-1H-pyrazol-4-yl)-3-methyl-1,2,3,4-tetrahydroquinoxaline-1-carboxylate;
3-methoxyphenyl (3S)-4-acetyl-7-(1-cyclopropyl-1H-pyrazol-4-yl)-3-methyl-1,2,3,4-tetrahydroquinoxaline-1-carboxylate;
3-cyanophenyl (3S)-4-acetyl-7-(1-cyclopropyl-1H-pyrazol-4-yl)-3-methyl-1,2,3,4-tetrahydroquinoxaline-1-carboxylate;
3-fluorophenyl (3S)-4-acetyl-7-(1-cyclopropyl-1H-pyrazol-4-yl)-3-methyl-1,2,3,4-tetrahydroquinoxaline-1-carboxylate;
2,5-difluorophenyl (3S)-4-acetyl-7-(1-cyclopropyl-1H-pyrazol-4-yl)-3-methyl-1,2,3,4-tetrahydroquinoxaline-1-carboxylate;
2-chloro-4-methylphenyl (3S)-4-acetyl-7-(1-cyclopropyl-1H-pyrazol-4-yl)-3-methyl-1,2,3,4-tetrahydroquinoxaline-1-carboxylate;

2-chloro-4-methoxyphenyl (3S)-4-acetyl-7-(1-cyclopropyl-1H-pyrazol-4-yl)-3-methyl-1,2,3,4-tetrahydroquinoxaline-1-carboxylate;
2-methoxy-4-methylphenyl (3S)-4-acetyl-7-(1-cyclopropyl-1H-pyrazol-4-yl)-3-methyl-1,2,3,4-tetrahydroquinoxaline-1-carboxylate;
4-cyano-2-methoxyphenyl (3S)-4-acetyl-7-(1-cyclopropyl-1H-pyrazol-4-yl)-3-methyl-1,2,3,4-tetrahydroquinoxaline-1-carboxylate;
2-methoxy-5-methylphenyl (3S)-4-acetyl-7-(1-cyclopropyl-1H-pyrazol-4-yl)-3-methyl-1,2,3,4-tetrahydroquinoxaline-1-carboxylate;
2-methylphenyl (3S)-4-acetyl-7-(1-cyclopropyl-1H-pyrazol-4-yl)-3-methyl-1,2,3,4-tetrahydroquinoxaline-1-carboxylate;
pyridin-3-yl (3S)-4-acetyl-7-(1-cyclopropyl-1H-pyrazol-4-yl)-3-methyl-1,2,3,4-tetrahydroquinoxaline-1-carboxylate;
6-methylpyridin-3-yl (3S)-4-acetyl-7-(1-cyclopropyl-1H-pyrazol-4-yl)-3-methyl-1,2,3,4-tetrahydroquinoxaline-1-carboxylate;
quinolin-6-yl (3S)-4-acetyl-7-(1-cyclopropyl-1H-pyrazol-4-yl)-3-methyl-1,2,3,4-tetrahydroquinoxaline-1-carboxylate;
2-methylquinolin-6-yl (3S)-4-acetyl-7-(1-cyclopropyl-1H-pyrazol-4-yl)-3-methyl-1,2,3,4-tetrahydroquinoxaline-1-carboxylate;
2-methylpyridin-3-yl (3S)-4-acetyl-7-(1-cyclopropyl-1H-pyrazol-4-yl)-3-methyl-1,2,3,4-tetrahydroquinoxaline-1-carboxylate;
2-methylquinolin-8-yl (3S)-4-acetyl-7-(1-cyclopropyl-1H-pyrazol-4-yl)-3-methyl-1,2,3,4-tetrahydroquinoxaline-1-carboxylate;
2,4-dimethylphenyl (3S)-4-acetyl-7-(1-cyclopropyl-1H-pyrazol-4-yl)-3-methyl-1,2,3,4-tetrahydroquinoxaline-1-carboxylate;
3-methylphenyl (3S)-4-acetyl-7-(1-cyclopropyl-1H-pyrazol-4-yl)-3-methyl-1,2,3,4-tetrahydroquinoxaline-1-carboxylate;
3-chlorophenyl (3S)-4-acetyl-7-(1-cyclopropyl-1H-pyrazol-4-yl)-3-methyl-1,2,3,4-tetrahydroquinoxaline-1-carboxylate;
2-fluorophenyl (3S)-4-acetyl-7-(1-cyclopropyl-1H-pyrazol-4-yl)-3-methyl-1,2,3,4-tetrahydroquinoxaline-1-carboxylate;
5-methylpyridin-3-yl (3S)-4-acetyl-7-(1-cyclopropyl-1H-pyrazol-4-yl)-3-methyl-1,2,3,4-tetrahydroquinoxaline-1-carboxylate;
2-methoxypyridin-3-yl (3S)-4-acetyl-7-(1-cyclopropyl-1H-pyrazol-4-yl)-3-methyl-1,2,3,4-tetrahydroquinoxaline-1-carboxylate;
3-methoxy-2-methylpyridin-4-yl (3S)-4-acetyl-7-(1-cyclopropyl-1H-pyrazol-4-yl)-3-methyl-1,2,3,4-tetrahydroquinoxaline-1-carboxylate;
2-fluoro-4-methoxyphenyl (3S)-4-acetyl-7-(1-cyclopropyl-1H-pyrazol-4-yl)-3-methyl-1,2,3,4-tetrahydroquinoxaline-1-carboxylate;
2-fluoro-5-methoxyphenyl (3S)-4-acetyl-7-(1-cyclopropyl-1H-pyrazol-4-yl)-3-methyl-1,2,3,4-tetrahydroquinoxaline-1-carboxylate;
isoquinolin-4-yl (3S)-4-acetyl-7-(1-cyclopropyl-1H-pyrazol-4-yl)-3-methyl-1,2,3,4-tetrahydroquinoxaline-1-carboxylate;
5-cyano-2-methoxyphenyl (3S)-4-acetyl-7-(1-cyclopropyl-1H-pyrazol-4-yl)-3-methyl-1,2,3,4-tetrahydroquinoxaline-1-carboxylate;
1,3-benzothiazol-6-yl (3S)-4-acetyl-7-(1-cyclopropyl-1H-pyrazol-4-yl)-3-methyl-1,2,3,4-tetrahydroquinoxaline-1-carboxylate;
2-chloro-4-cyanophenyl (3S)-4-acetyl-7-(1-cyclopropyl-1H-pyrazol-4-yl)-3-methyl-1,2,3,4-tetrahydroquinoxaline-1-carboxylate;
4-chloro-2-methoxyphenyl (3S)-4-acetyl-7-(1-cyclopropyl-1H-pyrazol-4-yl)-3-methyl-1,2,3,4-tetrahydroquinoxaline-1-carboxylate;
5-chloro-2-methoxyphenyl (3S)-4-acetyl-7-(1-cyclopropyl-1H-pyrazol-4-yl)-3-methyl-1,2,3,4-tetrahydroquinoxaline-1-carboxylate;
2-chloro-5-methoxyphenyl (3S)-4-acetyl-7-(1-cyclopropyl-1H-pyrazol-4-yl)-3-methyl-1,2,3,4-tetrahydroquinoxaline-1-carboxylate;
propan-2-yl (3S)-4-acetyl-7-{4-[(3R)-3-aminopyrrolidine-1-carbonyl]phenyl}-3-methyl-1,2,3,4-tetrahydroquinoxaline-1-carboxylate;
propan-2-yl (3S)-4-acetyl-7-(4-{[2-(dimethylamino)ethyl]carbamoyl}phenyl)-3-methyl-1,2,3,4-tetrahydroquinoxaline-1-carboxylate;
propan-2-yl (3S)-4-acetyl-7-{4-[(carbamoylmethyl)carbamoyl]phenyl}-3-methyl-1,2,3,4-tetrahydroquinoxaline-1-carboxylate;
propan-2-yl (3S)-4-acetyl-3-methyl-7-[4-(phenylcarbamoyl)phenyl]-1,2,3,4-tetrahydroquinoxaline-1-carboxylate;
propan-2-yl (3S)-4-acetyl-7-[4-(diethylcarbamoyl)phenyl]-3-methyl-1,2,3,4-tetrahydroquinoxaline-1-carboxylate;
propan-2-yl (3S)-4-acetyl-3-methyl-7-[4-(piperidin-1-carbonyl)phenyl]-1,2,3,4-tetrahydroquinoxaline-1-carboxylate;
propan-2-yl (3S)-4-acetyl-3-methyl-7-[4-(thiomorpholine-4-carbonyl)phenyl]-1,2,3,4-tetrahydroquinoxaline-1-carboxylate;
propan-2-yl (3S)-4-acetyl-7-(4-{[2-(dimethylamino)ethyl](methyl)carbamoyl}phenyl)-3-methyl-1,2,3,4-tetrahydroquinoxaline-1-carboxylate;
propan-2-yl (3S)-4-acetyl-7-{4-[(3R)-3-acetamidopyrrolidine-1-carbonyl]phenyl}-3-methyl-1,2,3,4-tetrahydroquinoxaline-1-carboxylate;
propan-2-yl (3S)-4-acetyl-7-{4-[(3S)-3-acetamidopyrrolidine-1-carbonyl]phenyl}-3-methyl-1,2,3,4-tetrahydroquinoxaline-1-carboxylate;
propan-2-yl (3S)-4-acetyl-7-{4-[(3R)-3-(dimethylamino)pyrrolidine-1-carbonyl]phenyl}-3-methyl-1,2,3,4-tetrahydroquinoxaline-1-carboxylate;
propan-2-yl (3S)-4-acetyl-7-{4-[(3S)-3-(dimethylamino)pyrrolidine-1-carbonyl]phenyl}-3-methyl-1,2,3,4-tetrahydroquinoxaline-1-carboxylate;
propan-2-yl (3S)-4-acetyl-3-methyl-7-[4-(4-methylpiperazine-1-carbonyl)phenyl]-1,2,3,4-tetrahydroquinoxaline-1-carboxylate;
propan-2-yl (3S)-4-acetyl-7-[4-(4-formylpiperazine-1-carbonyl)phenyl]-3-methyl-1,2,3,4-tetrahydroquinoxaline-1-carboxylate;
propan-2-yl (3S)-4-acetyl-7-{4-[4-(methoxycarbonyl)piperazine-1-carbonyl]phenyl}-3-methyl-1,2,3,4-tetrahydroquinoxaline-1-carboxylate;
propan-2-yl (3S)-4-acetyl-3-methyl-7-[4-(3-oxopiperazine-1-carbonyl)phenyl]-1,2,3,4-tetrahydroquinoxaline-1-carboxylate;
propan-2-yl (3S)-4-acetyl-7-[4-(4-acetylpiperazine-1-carbonyl)phenyl]-3-methyl-1,2,3,4-tetrahydroquinoxaline-1-carboxylate;
propan-2-yl (3S)-4-acetyl-7-[4-(4-methanesulfonylpiperazine-1-carbonyl)phenyl]-3-methyl-1,2,3,4-tetrahydroquinoxaline-1-carboxylate;

propan-2-yl (3S)-4-acetyl-7-(4-{[(dimethylcarbamoyl)methyl](methyl)carbamoyl}phenyl)-3-methyl-1,2,3,4-tetrahydroquinoxaline-1-carboxylate;

propan-2-yl (3S)-4-acetyl-3-methyl-7-(4-{methyl[2-(pyrrolidin-1-yl)ethyl]carbamoyl}phenyl)-1,2,3,4-tetrahydroquinoxaline-1-carboxylate;

propan-2-yl (3S)-4-acetyl-3-methyl-7-{4-[methyl(pyridin-2-yl)carbamoyl]phenyl}-1,2,3,4-tetrahydroquinoxaline-1-carboxylate;

propan-2-yl (3S)-4-acetyl-3-methyl-7-[4-(4-methyl-1,4-diazepan-1-carbonyl)phenyl]-1,2,3,4-tetrahydroquinoxaline-1-carboxylate;

propan-2-yl (3S)-4-acetyl-3-methyl-7-(4-{methyl[(methylcarbamoyl)methyl]carbamoyl}phenyl)-1,2,3,4-tetrahydroquinoxaline-1-carboxylate;

propan-2-yl (3S)-7-{4-[(3aR,6aR)-1-methyl-octahydropyrrolo[3,4-b]pyrrole-5-carbonyl]phenyl}-4-acetyl-3-methyl-1,2,3,4-tetrahydroquinoxaline-1-carboxylate;

propan-2-yl (3S)-4-acetyl-7-{4-[(1R,5S)-3-{[(tert-butoxy)carbonyl]amino}-8-azabicyclo[3.2.1]octane-8-carbonyl]phenyl}-3-methyl-1,2,3,4-tetrahydroquinoxaline-1-carboxylate;

propan-2-yl (3S)-4-acetyl-3-methyl-7-[4-(piperazine-1-carbonyl)phenyl]-1,2,3,4-tetrahydroquinoxaline-1-carboxylate;

propan-2-yl (3S)-4-cyclopropanecarbonyl-3-methyl-7-[4-(piperazine-1-carbonyl)phenyl]-1,2,3,4-tetrahydroquinoxaline-1-carboxylate;

1-methyl 4-propan-2-yl (2S)-2-methyl-6-[4-(piperazine-1-carbonyl)phenyl]-1,2,3,4-tetrahydroquinoxaline-1,4-dicarboxylate;

propan-2-yl (3S)-4-cyclopropanecarbonyl-7-(4-{[(dimethylcarbamoyl)methyl](methyl) carbamoyl}phenyl)-3-methyl-1,2,3,4-tetrahydroquinoxaline-1-carboxylate;

1-methyl 4-propan-2-yl (2S)-6-(4-{[(dimethylcarbamoyl)methyl](methyl)carbamoyl}phenyl)-2-methyl-1,2,3,4-tetrahydroquinoxaline-1,4-dicarboxylate;

propan-2-yl (3S)-4-cyclopropanecarbonyl-3-methyl-7-(4-{methyl[(methylcarbamoyl)methyl]carbamoyl}phenyl)-1,2,3,4-tetrahydroquinoxaline-1-carboxylate;

1-methyl 4-propan-2-yl (2S)-2-methyl-6-(4-{methyl[(methylcarbamoyl)methyl]carbamoyl}phenyl)-1,2,3,4-tetrahydroquinoxaline-1,4-dicarboxylate;

propan-2-yl (3S)-4-cyclopropanecarbonyl-7-{4-[(3R)-3-(dimethylamino)pyrrolidine-1-carbonyl]phenyl}-3-methyl-1,2,3,4-tetrahydroquinoxaline-1-carboxylate;

1-methyl 4-propan-2-yl (2S)-6-{4-[(3R)-3-(dimethylamino)pyrrolidine-1-carbonyl]phenyl}-2-methyl-1,2,3,4-tetrahydroquinoxaline-1,4-dicarboxylate;

propan-2-yl (3S)-4-cyclopropanecarbonyl-7-{4-[(3S)-3-(dimethylamino)pyrrolidine-1-carbonyl]phenyl}-3-methyl-1,2,3,4-tetrahydroquinoxaline-1-carboxylate;

1-methyl 4-propan-2-yl (2S)-6-{4-[(3S)-3-(dimethylamino)pyrrolidine-1-carbonyl]phenyl}-2-methyl-1,2,3,4-tetrahydroquinoxaline-1,4-dicarboxylate;

propan-2-yl (3S)-4-cyclopropanecarbonyl-7-{4-[(3R)-3-acetamidopyrrolidine-1-carbonyl]phenyl}-3-methyl-1,2,3,4-tetrahydroquinoxaline-1-carboxylate;

1-methyl 4-propan-2-yl (2S)-6-{4-[(3R)-3-acetamidopyrrolidine-1-carbonyl]phenyl}-2-methyl-1,2,3,4-tetrahydroquinoxaline-1,4-dicarboxylate;

propan-2-yl (3S)-4-cyclopropanecarbonyl-7-{4-[(3S)-3-acetamidopyrrolidine-1-carbonyl]phenyl}-3-methyl-1,2,3,4-tetrahydroquinoxaline-1-carboxylate;

1-methyl 4-propan-2-yl (2S)-6-{4-[(3S)-3-acetamidopyrrolidine-1-carbonyl]phenyl}-2-methyl-1,2,3,4-tetrahydroquinoxaline-1,4-dicarboxylate;

propan-2-yl (3S)-4-cyclopropanecarbonyl-7-[4-(4-methanesulfonylpiperazine-1-carbonyl)phenyl]-3-methyl-1,2,3,4-tetrahydroquinoxaline-1-carboxylate;

1-methyl 4-propan-2-yl (2S)-6-[4-(4-methanesulfonylpiperazine-1-carbonyl)phenyl]-2-methyl-1,2,3,4-tetrahydroquinoxaline-1,4-dicarboxylate;

propan-2-yl (3S)-4-cyclopropanecarbonyl-7-{4-[(3S)-3-hydroxypyrrolidine-1-carbonyl]phenyl}-3-methyl-1,2,3,4-tetrahydroquinoxaline-1-carboxylate;

1-methyl 4-propan-2-yl (2S)-6-{4-[(3S)-3-hydroxypyrrolidine-1-carbonyl]phenyl}-2-methyl-1,2,3,4-tetrahydroquinoxaline-1,4-dicarboxylate;

propan-2-yl (3S)-4-cyclopropanecarbonyl-7-{4-[(3R)-3-hydroxypyrrolidine-1-carbonyl]phenyl}-3-methyl-1,2,3,4-tetrahydroquinoxaline-1-carboxylate;

1-methyl 4-propan-2-yl (2S)-6-{4-[(3R)-3-hydroxypyrrolidine-1-carbonyl]phenyl}-2-methyl-1,2,3,4-tetrahydroquinoxaline-1,4-dicarboxylate;

propan-2-yl (3S)-4-cyclopropanecarbonyl-7-[4-(3-hydroxyazetidine-1-carbonyl)phenyl]-3-methyl-1,2,3,4-tetrahydroquinoxaline-1-carboxylate;

1-methyl 4-propan-2-yl (2S)-6-[4-(3-hydroxyazetidine-1-carbonyl)phenyl]-2-methyl-1,2,3,4-tetrahydroquinoxaline-1,4-dicarboxylate;

propan-2-yl (3S)-4-acetyl-7-{4-[(3S)-3-hydroxypyrrolidine-1-carbonyl]phenyl}-3-methyl-1,2,3,4-tetrahydroquinoxaline-1-carboxylate;

propan-2-yl (3S)-4-acetyl-7-{4-[(3R)-3-hydroxypyrrolidine-1-carbonyl]phenyl}-3-methyl-1,2,3,4-tetrahydroquinoxaline-1-carboxylate;

propan-2-yl (3S)-4-acetyl-7-[4-(3-hydroxyazetidine-1-carbonyl)phenyl]-3-methyl-1,2,3,4-tetrahydroquinoxaline-1-carboxylate;

1-methyl 4-propan-2-yl (2S)-2-methyl-6-{4-[(1,3-oxazol-2-ylmethyl)carbamoyl]phenyl}-1,2,3,4-tetrahydroquinoxaline-1,4-dicarboxylate;

propan-2-yl (3S)-4-acetyl-3-methyl-7-{4-[(1,3-oxazol-2-ylmethyl)carbamoyl]phenyl}-1,2,3,4-tetrahydroquinoxaline-1-carboxylate;

propan-2-yl (3S)-4-cyclopropanecarbonyl-3-methyl-7-{4-[(1,3-oxazol-2-ylmethyl)carbamoyl]phenyl}-1,2,3,4-tetrahydroquinoxaline-1-carboxylate;

propan-2-yl (3S)-4-acetyl-7-[4-(3-aminopyrrolidine-1-carbonyl)phenyl]-3-methyl-1,2,3,4-tetrahydroquinoxaline-1-carboxylate;

propan-2-yl (3S)-4-acetyl-7-{4-[(3R)-3-aminopyrrolidine-1-carbonyl]phenyl}-3-methyl-1,2,3,4-tetrahydroquinoxaline-1-carboxylate;

propan-2-yl (3S)-4-acetyl-7-{4-[(3S)-3-aminopyrrolidine-1-carbonyl]phenyl}-3-methyl-1,2,3,4-tetrahydroquinoxaline-1-carboxylate;

propan-2-yl (3S)-4-acetyl-7-{4-[(3R)-3-aminopiperidin-1-carbonyl]phenyl}-3-methyl-1,2,3,4-tetrahydroquinoxaline-1-carboxylate;

propan-2-yl (3S)-4-acetyl-7-[4-(4-aminopiperidin-1-carbonyl)phenyl]-3-methyl-1,2,3,4-tetrahydroquinoxaline-1-carboxylate;

propan-2-yl (3S)-4-acetyl-7-{4-[2-(aminomethyl)piperidin-1-carbonyl]phenyl}-3-methyl-1,2,3,4-tetrahydroquinoxaline-1-carboxylate;

propan-2-yl (3S)-4-acetyl-7-{4-[(2R)-2-(aminomethyl)pyrrolidine-1-carbonyl]phenyl}-3-methyl-1,2,3,4-tetrahydroquinoxaline-1-carboxylate;

propan-2-yl (3S)-4-acetyl-7-{4-[(1S,4S)-2,5-diazabicyclo[2.2.1]heptane-2-carbonyl]phenyl}-3-methyl-1,2,3,4-tetrahydroquinoxaline-1-carboxylate;

propan-2-yl (3S)-4-acetyl-7-(4-{[(1R,3 S,5 S)-8-azabicyclo[3.2.1]octan-3-yl]carbamoyl}phenyl)-3-methyl-1,2,3,4-tetrahydroquinoxaline-1-carboxylate;

propan-2-yl (3S)-4-acetyl-7-{1-[(1,1-dioxo-1λ⁶-thian-4-yl)methyl]-1H-pyrazol-4-yl}-3-methyl-1,2,3,4-tetrahydroquinoxaline-1-carboxylate;

propan-2-yl (3S)-4-acetyl-7-(1-{[cyclopropyl(methyl)carbamoyl]methyl}-1H-pyrazol-4-yl)-3-methyl-1,2,3,4-tetrahydroquinoxaline-1-carboxylate;

propan-2-yl (3S)-4-acetyl-7-{1-[2-(1,1-dioxo-1λ⁶,2-thiazolidin-2-yl)ethyl]-1H-pyrazol-4-yl}-3-methyl-1,2,3,4-tetrahydroquinoxaline-1-carboxylate;

propan-2-yl (3S)-4-acetyl-7-{1-[2-(1H-imidazo-1-yl)ethyl]-1H-pyrazol-4-yl}-3-methyl-1,2,3,4-tetrahydroquinoxaline-1-carboxylate;

propan-2-yl (3S)-4-acetyl-3-methyl-7-{1-[2-oxo-2-(piperidin-1-yl)ethyl]-1H-pyrazol-4-yl}-1,2,3,4-tetrahydroquinoxaline-1-carboxylate;

propan-2-yl (3S)-4-acetyl-7-(1-{[3-(hydroxymethyl)oxetan-3-yl]methyl}-1H-pyrazol-4-yl)-3-methyl-1,2,3,4-tetrahydroquinoxaline-1-carboxylate;

propan-2-yl (3S)-4-acetyl-7-[1-(1H-imidazol-4-ylmethyl)-1H-pyrazol-4-yl]-3-methyl-1,2,3,4-tetrahydroquinoxaline-1-carboxylate;

propan-2-yl (3S)-4-acetyl-7-{1-[(dimethyl-1,2-oxazol-4-yl)methyl]-1H-pyrazol-4-yl}-3-methyl-1,2,3,4-tetrahydroquinoxaline-1-carboxylate;

propan-2-yl (3S)-4-acetyl-7-[1-(cyclobutylmethyl)-1H-pyrazol-4-yl]-3-methyl-1,2,3,4-tetrahydroquinoxaline-1-carboxylate;

propan-2-yl (3S)-4-acetyl-3-methyl-7-[1-(2,2,2-trifluoroethyl)-1H-pyrazol-4-yl]-1,2,3,4-tetrahydroquinoxaline-1-carboxylate;

propan-2-yl (3S)-4-acetyl-3-methyl-7-{1-[(3-methyloxetan-3-yl)methyl]-1H-pyrazol-4-yl}-1,2,3,4-tetrahydroquinoxaline-1-carboxylate;

propan-2-yl (3S)-4-acetyl-7-[1-(2-carbamoylethyl)-1H-pyrazol-4-yl]-3-methyl-1,2,3,4-tetrahydroquinoxaline-1-carboxylate;

propan-2-yl (3S)-4-acetyl-7-[1-(cyanomethyl)-1H-pyrazol-4-yl]-3-methyl-1,2,3,4-tetrahydroquinoxaline-1-carboxylate;

propan-2-yl (3S)-4-acetyl-3-methyl-7-[1-(oxan-4-ylmethyl)-1H-pyrazol-4-yl]-1,2,3,4-tetrahydroquinoxaline-1-carboxylate;

propan-2-yl (3S)-4-cyclopropanecarbonyl-7-{1-[(1,1-dioxo-1λ⁶-thian-4-yl)methyl]-1H-pyrazol-4-yl}-3-methyl-1,2,3,4-tetrahydroquinoxaline-1-carboxylate;

propan-2-yl (3S)-4-cyclopropanecarbonyl-7-(1-{[cyclopropyl(methyl)carbamoyl]methyl}-1H-pyrazol-4-yl)-3-methyl-1,2,3,4-tetrahydroquinoxaline-1-carboxylate;

propan-2-yl (3S)-4-cyclopropanecarbonyl-7-{1-[2-(1,1-dioxo-1λ⁶,2-thiazolidin-2-yl)ethyl]-1H-pyrazol-4-yl}-3-methyl-1,2,3,4-tetrahydroquinoxaline-1-carboxylate;

propan-2-yl (3S)-4-cyclopropanecarbonyl-7-{1-[2-(1H-imidazo-1-yl)ethyl]-1H-pyrazol-4-yl}-3-methyl-1,2,3,4-tetrahydroquinoxaline-1-carboxylate;

propan-2-yl (3S)-4-cyclopropanecarbonyl-7-[1-(2-methanesulfonamidoethyl)-1H-pyrazol-4-yl]-3-methyl-1,2,3,4-tetrahydroquinoxaline-1-carboxylate;

propan-2-yl (3S)-4-cyclopropanecarbonyl-3-methyl-7-{1-[2-oxo-2-(piperidin-1-yl)ethyl]-1H-pyrazol-4-yl}-1,2,3,4-tetrahydroquinoxaline-1-carboxylate;

propan-2-yl (3S)-4-cyclopropanecarbonyl-7-(1-{[3-(hydroxymethyl)oxetan-3-yl]methyl}-1H-pyrazol-4-yl)-3-methyl-1,2,3,4-tetrahydroquinoxaline-1-carboxylate;

propan-2-yl (3S)-4-cyclopropanecarbonyl-7-[1-(1H-imidazol-4-ylmethyl)-1H-pyrazol-4-yl]-3-methyl-1,2,3,4-tetrahydroquinoxaline-1-carboxylate;

propan-2-yl (3S)-4-cyclopropanecarbonyl-7-{1-[(dimethyl-1,2-oxazol-4-yl)methyl]-1H-pyrazol-4-yl}-3-methyl-1,2,3,4-tetrahydroquinoxaline-1-carboxylate;

propan-2-yl (3S)-7-[1-(cyclobutylmethyl)-1H-pyrazol-4-yl]-4-cyclopropanecarbonyl-3-methyl-1,2,3,4-tetrahydroquinoxaline-1-carboxylate;

propan-2-yl (3S)-4-cyclopropanecarbonyl-3-methyl-7-[1-(2,2,2-trifluoroethyl)-1H-pyrazol-4-yl]-1,2,3,4-tetrahydroquinoxaline-1-carboxylate;

propan-2-yl (3S)-4-cyclopropanecarbonyl-3-methyl-7-{1-[(3-methyloxetan-3-yl)methyl]-1H-pyrazol-4-yl}-1,2,3,4-tetrahydroquinoxaline-1-carboxylate;

propan-2-yl (3S)-7-[1-(2-carbamoylethyl)-1H-pyrazol-4-yl]-4-cyclopropanecarbonyl-3-methyl-1,2,3,4-tetrahydroquinoxaline-1-carboxylate;

propan-2-yl (3S)-7-[1-(cyanomethyl)-1H-pyrazol-4-yl]-4-cyclopropanecarbonyl-3-methyl-1,2,3,4-tetrahydroquinoxaline-1-carboxylate;

propan-2-yl (3S)-4-cyclopropanecarbonyl-3-methyl-7-[1-(oxan-4-ylmethyl)-1H-pyrazol-4-yl]-1,2,3,4-tetrahydroquinoxaline-1-carboxylate;

1-methyl 4-propan-2-yl (2S)-6-{1-[(1,1-dioxo-1λ⁶-thian-4-yl)methyl]-1H-pyrazol-4-yl}-2-methyl-1,2,3,4-tetrahydroquinoxaline-1,4-dicarboxylate;

1-methyl 4-propan-2-yl (2S)-6-(1-{[cyclopropyl(methyl)carbamoyl]methyl}-1H-pyrazol-4-yl)-2-methyl-1,2,3,4-tetrahydroquinoxaline-1,4-dicarboxylate;

1-methyl 4-propan-2-yl (2S)-6-{1-[2-(1,1-dioxo-1λ⁶,2-thiazolidin-2-yl)ethyl]-1H-pyrazol-4-yl}-2-methyl-1,2,3,4-tetrahydroquinoxaline-1,4-dicarboxylate;

1-methyl 4-propan-2-yl (2S)-6-{1-[2-(1H-imidazo-1-yl)ethyl]-1H-pyrazol-4-yl}-2-methyl-1,2,3,4-tetrahydroquinoxaline-1,4-dicarboxylate;

1-methyl 4-propan-2-yl (2S)-2-methyl-6-{1-[2-(2-oxopyrrolidin-1-yl)ethyl]-1H-pyrazol-4-yl}-1,2,3,4-tetrahydroquinoxaline-1,4-dicarboxylate;

1-methyl 4-propan-2-yl (2S)-2-methyl-6-{1-[2-oxo-2-(piperidin-1-yl)ethyl]-1H-pyrazol-4-yl}-1,2,3,4-tetrahydroquinoxaline-1,4-dicarboxylate;

1-methyl 4-propan-2-yl (2S)-6-(1-{[3-(hydroxymethyl)oxetan-3-yl]methyl}-1H-pyrazol-4-yl)-2-methyl-1,2,3,4-tetrahydroquinoxaline-1,4-dicarboxylate;

1-methyl 4-propan-2-yl (2S)-6-[1-(1H-imidazol-4-ylmethyl)-1H-pyrazol-4-yl]-2-methyl-1,2,3,4-tetrahydroquinoxaline-1,4-dicarboxylate;

1-methyl 4-propan-2-yl (2S)-2-methyl-6-[1-(pyrimidin-5-ylmethyl)-1H-pyrazol-4-yl]-1,2,3,4-tetrahydroquinoxaline-1,4-dicarboxylate;

1-methyl 4-propan-2-yl (2S)-2-methyl-6-[1-(pyrazin-2-ylmethyl)-1H-pyrazol-4-yl]-1,2,3,4-tetrahydroquinoxaline-1,4-dicarboxylate;

1-methyl 4-propan-2-yl (2S)-6-{1-[(dimethyl-1,2-oxazol-4-yl)methyl]-1H-pyrazol-4-yl}-2-methyl-1,2,3,4-tetrahydroquinoxaline-1,4-dicarboxylate;

1-methyl 4-propan-2-yl (2S)-6-[1-(cyclobutylmethyl)-1H-pyrazol-4-yl]-2-methyl-1,2,3,4-tetrahydroquinoxaline-1,4-dicarboxylate;

1-methyl 4-propan-2-yl (2S)-2-methyl-6-[1-(2,2,2-trifluoroethyl)-1H-pyrazol-4-yl]-1,2,3,4-tetrahydroquinoxaline-1,4-dicarboxylate;

1-methyl 4-propan-2-yl (2S)-2-methyl-6-{1-[(3-methyloxetan-3-yl)methyl]-1H-pyrazol-4-yl}-1,2,3,4-tetrahydroquinoxaline-1,4-dicarboxylate;

1-methyl 4-propan-2-yl (2S)-6-[1-(2-carbamoylethyl)-1H-pyrazol-4-yl]-2-methyl-1,2,3,4-tetrahydroquinoxaline-1,4-dicarboxylate;

1-methyl 4-propan-2-yl (2S)-6-[1-(cyanomethyl)-1H-pyrazol-4-yl]-2-methyl-1,2,3,4-tetrahydroquinoxaline-1,4-dicarboxylate;

1-methyl 4-propan-2-yl (2S)-2-methyl-6-[1-(pyridin-4-ylmethyl)-1H-pyrazol-4-yl]-1,2,3,4-tetrahydroquinoxaline-1,4-dicarboxylate;

1-methyl 4-propan-2-yl (2S)-2-methyl-6-[1-(oxan-4-ylmethyl)-1H-pyrazol-4-yl]-1,2,3,4-tetrahydroquinoxaline-1,4-dicarboxylate;

propan-2-yl (3S)-4-acetyl-3-methyl-7-[1-(oxetan-3-ylmethyl)-1H-pyrazol-4-yl]-1,2,3,4-tetrahydroquinoxaline-1-carboxylate;

propan-2-yl (3S)-4-cyclopropanecarbonyl-3-methyl-7-[1-(oxetan-3-ylmethyl)-1H-pyrazol-4-yl]-1,2,3,4-tetrahydroquinoxaline-1-carboxylate;

1-methyl 4-propan-2-yl (2S)-2-methyl-6-[1-(oxetan-3-ylmethyl)-1H-pyrazol-4-yl]-1,2,3,4-tetrahydroquinoxaline-1,4-dicarboxylate;

1-methyl 4-propan-2-yl (2S)-6-{1-[2-(dimethylamino)ethyl]-1H-pyrazol-4-yl}-2-methyl-1,2,3,4-tetrahydroquinoxaline-1,4-dicarboxylate;

propan-2-yl (3S)-4-cyclopropanecarbonyl-7-{1-[2-(dimethylamino)ethyl]-1H-pyrazol-4-yl}-3-methyl-1,2,3,4-tetrahydroquinoxaline-1-carboxylate;

1-[(2S)-4-cyclopropanecarbonyl-2-methyl-6-[1-(propan-2-yl)-1H-pyrazol-4-yl]-1,2,3,4-tetrahydroquinoxalin-1-yl]ethan-1-one;

2-{4-[(2S)-1-acetyl-4-cyclopropanecarbonyl-2-methyl-1,2,3,4-tetrahydroquinoxalin-6-yl]-1H-pyrazol-1-yl}-2-methylpropanamide;

1-[(2S)-4-cyclopropanecarbonyl-6-{1-[(3-fluorooxetan-3-yl)methyl]-1H-pyrazol-4-yl}-2-methyl-1,2,3,4-tetrahydroquinoxalin-1-yl]ethan-1-one;

3-{4-[(2S)-1-acetyl-4-cyclopropanecarbonyl-2-methyl-1,2,3,4-tetrahydroquinoxalin-6-yl]-1H-pyrazol-1-yl}propanenitrile;

1-[(2S)-4-cyclopropanecarbonyl-6-[1-(2,2-difluoroethyl)-1H-pyrazol-4-yl]-2-methyl-1,2,3,4-tetrahydroquinoxalin-1-yl]ethan-1-one;

1-[(2S)-4-cyclopropanecarbonyl-2-methyl-6-{1-[(1-methyl-1H-pyrazol-5-yl)methyl]-1H-pyrazol-4-yl}-1,2,3,4-tetrahydroquinoxalin-1-yl]ethan-1-one;

propan-2-yl (3S)-4-acetyl-3-methyl-7-[1-(propan-2-yl)-1H-pyrazol-4-yl]-1,2,3,4-tetrahydroquinoxaline-1-carboxylate;

propan-2-yl (3S)-4-acetyl-3-methyl-7-{1-[2-(morpholin-4-yl)-2-oxoethyl]-1H-pyrazol-4-yl}-1,2,3,4-tetrahydroquinoxaline-1-carboxylate;

2-{4-[(2S)-1-acetyl-4-cyclopropanecarbonyl-2-methyl-1,2,3,4-tetrahydroquinoxalin-6-yl]-1H-pyrazol-1-yl}acetamide;

1-[(2S)-6-[1-(cyclobutylmethyl)-1H-pyrazol-4-yl]-4-cyclopropanecarbonyl-2-methyl-1,2,3,4-tetrahydroquinoxalin-1-yl]ethan-1-one;

1-[(2S)-4-cyclopropanecarbonyl-2-methyl-6-[1-(oxan-4-ylmethyl)-1H-pyrazol-4-yl]-1,2,3,4-tetrahydroquinoxalin-1-yl]ethan-1-one;

2-{4-[(2S)-1-acetyl-4-cyclopropanecarbonyl-2-methyl-1,2,3,4-tetrahydroquinoxalin-6-yl]-1H-pyrazol-1-yl}-N-cyclopropyl-N-methylacetamide;

2-(2-{4-[(2S)-1-acetyl-4-cyclopropanecarbonyl-2-methyl-1,2,3,4-tetrahydroquinoxalin-6-yl]-1H-pyrazol-1-yl}ethyl)-1$\lambda^6$,2-thiazolidine-1,1-dione;

1-(2-{4-[(2S)-1-acetyl-4-cyclopropanecarbonyl-2-methyl-1,2,3,4-tetrahydroquinoxalin-6-yl]-1H-pyrazol-1-yl}ethyl)pyrrolidin-2-one;

2-{4-[(2S)-1-acetyl-4-cyclopropanecarbonyl-2-methyl-1,2,3,4-tetrahydroquinoxalin-6-yl]-1H-pyrazol-1-yl}-1-(piperidin-1-yl)ethan-1-one;

1-[(2S)-4-cyclopropanecarbonyl-6-(1-{[3-(hydroxymethyl)oxetan-3-yl]methyl}-1H-pyrazol-4-yl)-2-methyl-1,2,3,4-tetrahydroquinoxalin-1-yl]ethan-1-one;

1-[(2S)-4-cyclopropanecarbonyl-2-methyl-6-[1-(1,2-oxazol-5-ylmethyl)-1H-pyrazol-4-yl]-1,2,3,4-tetrahydroquinoxalin-1-yl]ethan-1-one;

propan-2-yl (3S)-4-acetyl-7-{1-[(ethylcarbamoyl)methyl]-1H-pyrazol-4-yl}-3-methyl-1,2,3,4-tetrahydroquinoxaline-1-carboxylate;

propan-2-yl (3S)-4-acetyl-3-methyl-7-{1-[(5-methyl-1,2-oxazol-3-yl)methyl]-1H-pyrazol-4-yl}-1,2,3,4-tetrahydroquinoxaline-1-carboxylate;

propan-2-yl (3S)-4-acetyl-7-[1-(2-fluoroethyl)-1H-pyrazol-4-yl]-3-methyl-1,2,3,4-tetrahydroquinoxaline-1-carboxylate;

propan-2-yl (3S)-4-acetyl-7-{1-[2-(azetidin-1-yl)-2-oxoethyl]-1H-pyrazol-4-yl}-3-methyl-1,2,3,4-tetrahydroquinoxaline-1-carboxylate;

1-[(2S)-4-cyclopropanecarbonyl-2-methyl-6-{1-[(5-methyl-1,2,4-oxadiazol-3-yl)methyl]-1H-pyrazol-4-yl}-1,2,3,4-tetrahydroquinoxalin-1-yl]ethan-1-one;

1-[(2S)-4-cyclopropanecarbonyl-2-methyl-6-{1-[(5-methyl-1,2-oxazol-3-yl)methyl]-1H-pyrazol-4-yl}-1,2,3,4-tetrahydroquinoxalin-1-yl]ethan-1-one;

1-[(2S)-4-cyclopropanecarbonyl-2-methyl-6-[1-(2-methylpropyl)-1H-pyrazol-4-yl]-1,2,3,4-tetrahydroquinoxalin-1-yl]ethan-1-one;

1-[(2S)-4-cyclopropanecarbonyl-6-[1-(2-fluoroethyl)-1H-pyrazol-4-yl]-2-methyl-1,2,3,4-tetrahydroquinoxalin-1-yl]ethan-1-one;

2-{4-[(2S)-1-acetyl-4-cyclopropanecarbonyl-2-methyl-1,2,3,4-tetrahydroquinoxalin-6-yl]-1H-pyrazol-1-yl}-1-(azetidin-1-yl)ethan-1-one;

1-[(2S)-4-cyclopropanecarbonyl-6-[1-(3-hydroxypropyl)-1H-pyrazol-4-yl]-2-methyl-1,2,3,4-tetrahydroquinoxalin-1-yl]ethan-1-one;

3-{4-[(2S)-1-acetyl-4-cyclopropanecarbonyl-2-methyl-1,2,3,4-tetrahydroquinoxalin-6-yl]-1H-pyrazol-1-yl}propanamide;

2-{4-[(2S)-1-acetyl-4-cyclopropanecarbonyl-2-methyl-1,2,3,4-tetrahydroquinoxalin-6-yl]-1H-pyrazol-1-yl}acetonitrile;

2-{4-[(2S)-1-acetyl-4-cyclopropanecarbonyl-2-methyl-1,2,3,4-tetrahydroquinoxalin-6-yl]-1H-pyrazol-1-yl}acetic acid;

propan-2-yl (3S)-4-acetyl-3-methyl-7-{1-[(4-methyl-1,2,5-oxadiazol-3-yl)methyl]-1H-pyrazol-4-yl}-1,2,3,4-tetrahydroquinoxaline-1-carboxylate;

propan-2-yl (3S)-4-acetyl-7-{1-[(2,2-difluorocyclopropyl)methyl]-1H-pyrazol-4-yl}-3-methyl-1,2,3,4-tetrahydroquinoxaline-1-carboxylate;

propan-2-yl (3S)-4-acetyl-7-[1-(2-cyanoethyl)-1H-pyrazol-4-yl]-3-methyl-1,2,3,4-tetrahydroquinoxaline-1-carboxylate;

propan-2-yl (3S)-4-acetyl-3-methyl-7-{1-[(1-methyl-1H-pyrazol-5-yl)methyl]-1H-pyrazol-4-yl}-1,2,3,4-tetrahydroquinoxaline-1-carboxylate;

2-{4-[(2S)-1-acetyl-4-cyclopropanecarbonyl-2-methyl-1,2,3,4-tetrahydroquinoxalin-6-yl]-1H-pyrazol-1-yl}-N-ethylacetamide;

1-[(2S)-4-cyclopropanecarbonyl-2-methyl-6-{1-[(1-methyl-1H-pyrazol-3-yl)methyl]-1H-pyrazol-4-yl}-1,2,3,4-tetrahydroquinoxalin-1-yl]ethan-1-one;

2-{4-[(2S)-1-acetyl-4-cyclopropanecarbonyl-2-methyl-1,2,3,4-tetrahydroquinoxalin-6-yl]-1H-pyrazol-1-yl}-N,N-dimethylacetamide;

4-({4-[(2S)-1-acetyl-4-cyclopropanecarbonyl-2-methyl-1,2,3,4-tetrahydroquinoxalin-6-yl]-1H-pyrazol-1-yl}methyl)-1$\lambda^6$-thiane-1,1-dione;

propan-2-yl (3S)-4-acetyl-3-methyl-7-{1-[(5-methyl-1,2,4-oxadiazol-3-yl)methyl]-1H-pyrazol-4-yl}-1,2,3,4-tetrahydroquinoxaline-1-carboxylate;

1-[(2S)-4-cyclopropanecarbonyl-2-methyl-6-[1-(1,3-thiazol-5-ylmethyl)-1H-pyrazol-4-yl]-1,2,3,4-tetrahydroquinoxalin-1-yl]ethan-1-one;

propan-2-yl (3S)-4-acetyl-3-methyl-7-{1-[(3R)-pyrrolidin-3-ylmethyl]-1H-pyrazol-4-yl}-1,2,3,4-tetrahydroquinoxaline-1-carboxylate;

propan-2-yl (3S)-4-acetyl-3-methyl-7-{1-[(3S)-pyrrolidin-3-ylmethyl]-1H-pyrazol-4-yl}-1,2,3,4-tetrahydroquinoxaline-1-carboxylate;

propan-2-yl (3S)-4-cyclopropanecarbonyl-3-methyl-7-{1-[(3R)-pyrrolidin-3-ylmethyl]-1H-pyrazol-4-yl}-1,2,3,4-tetrahydroquinoxaline-1-carboxylate;

propan-2-yl (3S)-4-cyclopropanecarbonyl-3-methyl-7-{1-[(3S)-pyrrolidin-3-ylmethyl]-1H-pyrazol-4-yl}-1,2,3,4-tetrahydroquinoxaline-1-carboxylate;

1-methyl 4-propan-2-yl (2S)-2-methyl-6-{1-[(3R)-pyrrolidin-3-ylmethyl]-1H-pyrazol-4-yl}-1,2,3,4-tetrahydroquinoxaline-1,4-dicarboxylate;

1-methyl 4-propan-2-yl (2S)-2-methyl-6-{1-[(3S)-pyrrolidin-3-ylmethyl]-1H-pyrazol-4-yl}-1,2,3,4-tetrahydroquinoxaline-1,4-dicarboxylate;

1-[(3S)-4-acetyl-3-methyl-1,2,3,4-tetrahydroquinoxalin-1-yl]-3-(dimethylamino)propane-1-one;

1-[(2S)-4-benzoyl-2-methyl-1,2,3,4-tetrahydroquinoxalin-1-yl]ethan-1-one;

1-[(3S)-4-acetyl-3-methyl-1,2,3,4-tetrahydroquinoxalin-1-yl]-2-phenylethan-1-one;

1-[(3S)-4-acetyl-3-methyl-1,2,3,4-tetrahydroquinoxalin-1-yl]-3-phenylpropan-1-one;

1-[(2S)-4-cyclohexanecarbonyl-2-methyl-1,2,3,4-tetrahydroquinoxalin-1-yl]ethan-1-one;

1-[(3S)-4-acetyl-3-methyl-1,2,3,4-tetrahydroquinoxalin-1-yl]-2-(4-methoxyphenyl) ethan-1-one;

1-[(3S)-4-acetyl-3-methyl-1,2,3,4-tetrahydroquinoxalin-1-yl]-2-(3-methoxyphenyl)ethan-1-one;

1-[(3S)-4-acetyl-3-methyl-1,2,3,4-tetrahydroquinoxalin-1-yl]-3-methoxypropan-1-one;

1-[(2S)-4-(2H-1,3-benzodioxole-5-carbonyl)-2-methyl-1,2,3,4-tetrahydroquinoxalin-1-yl]ethan-1-one;

1-[(2S)-4-(2-methoxybenzoyl)-2-methyl-1,2,3,4-tetrahydroquinoxalin-1-yl]ethan-1-one;

1-[(2S)-2-methyl-4-(4-phenylbenzoyl)-1,2,3,4-tetrahydroquinoxalin-1-yl]ethan-1-one;

1-[(2S)-2-methyl-4-(pyridine-4-carbonyl)-1,2,3,4-tetrahydroquinoxalin-1-yl]ethan-1-one;

1-[(2S)-2-methyl-4-(2-methyl-1,3-thiazole-4-carbonyl)-1,2,3,4-tetrahydroquinoxalin-1-yl]ethan-1-one;

1-[(3S)-4-acetyl-3-methyl-1,2,3,4-tetrahydroquinoxalin-1-yl]-2-(oxan-4-yl)ethan-1-one 1-[(3S)-4-acetyl-3-methyl-1,2,3,4-tetrahydroquinoxalin-1-yl]-2-(4-phenylphenyl)ethan-1-one;

1-[(3S)-4-acetyl-3-methyl-1,2,3,4-tetrahydroquinoxalin-1-yl]-3-methylbutan-1-one;

1-[(3S)-4-acetyl-3-methyl-1,2,3,4-tetrahydroquinoxalin-1-yl]-2-(2H-1,3-benzodioxol-5-yl)ethan-1-one;

1-[(3S)-4-acetyl-3-methyl-1,2,3,4-tetrahydroquinoxalin-1-yl]-2-[3-(trifluoromethyl)phenyl]ethan-1-one;

1-[(3S)-4-acetyl-3-methyl-1,2,3,4-tetrahydroquinoxalin-1-yl]-2-(2-methoxyphenyl) ethan-1-one;

1-[(3S)-4-acetyl-3-methyl-1,2,3,4-tetrahydroquinoxalin-1-yl]-2-phenoxyethan-1-one;

1-[(3S)-4-acetyl-3-methyl-1,2,3,4-tetrahydroquinoxalin-1-yl]-2-cyclopentylethan-1-one;

1-[(2S)-4-cyclopentanecarbonyl-2-methyl-1,2,3,4-tetrahydroquinoxalin-1-yl]ethan-1-one;

(2R)-1-[(3S)-4-acetyl-3-methyl-1,2,3,4-tetrahydroquinoxalin-1-yl]-2-phenylpropan-1-one;

1-[(2S)-2-methyl-4-(naphthalene-2-carbonyl)-1,2,3,4-tetrahydroquinoxalin-1-yl]ethan-1-one;

1-[(2S)-4-(2,3-dihydro-1-benzofuran-5-carbonyl)-2-methyl-1,2,3,4-tetrahydroquinoxalin-1-yl]ethan-1-one;

1-[(2S)-4-(3-chlorobenzoyl)-2-methyl-1,2,3,4-tetrahydroquinoxalin-1-yl]ethan-1-one;

1-[(2S)-2-methyl-4-(naphthalene-1-carbonyl)-1,2,3,4-tetrahydroquinoxalin-1-yl]ethan-1-one;

1-[(2S)-4-(furan-2-carbonyl)-2-methyl-1,2,3,4-tetrahydroquinoxalin-1-yl]ethan-1-one;

1-[(2S)-2-methyl-4-(5-methylpyrazine-2-carbonyl)-1,2,3,4-tetrahydroquinoxalin-1-yl]ethan-1-one;

1-[(2S)-2-methyl-4-(5-methyl-1,2-oxazole-3-carbonyl)-1,2,3,4-tetrahydroquinoxalin-1-yl]ethan-1-one;

1-[(2S)-2-methyl-4-[4-(1H-pyrazol-1-yl)benzoyl]-1,2,3,4-tetrahydroquinoxalin-1-yl]ethan-1-one;

1-[(2S)-4-(1,3-benzothiazole-6-carbonyl)-2-methyl-1,2,3,4-tetrahydroquinoxalin-1-yl]ethan-1-one;

1-[(2S)-2-methyl-4-{2-[(pyridin-3-yl)amino]-1,3-thiazole-4-carbonyl}-1,2,3,4-tetrahydroquinoxalin-1-yl]ethan-1-one;

1-[(2S)-2-methyl-4-[2-(pyridin-3-yl)-1,3-thiazole-5-carbonyl]-1,2,3,4-tetrahydroquinoxalin-1-yl]ethan-1-one;

1-[(3S)-4-acetyl-3-methyl-1,2,3,4-tetrahydroquinoxalin-1-yl]-2-(phenylsulfanyl)ethan-1-one;

1-[(2S)-2-methyl-4-[5-(propan-2-yl)pyridine-2-carbonyl]-1,2,3,4-tetrahydroquinoxalin-1-yl]ethan-1-one;

1-[(2S)-2-methyl-4-[6-(propan-2-yl)pyridine-3-carbonyl]-1,2,3,4-tetrahydroquinoxalin-1-yl]ethan-1-one;

1-[(2S)-4-(1H-indole-2-carbonyl)-2-methyl-1,2,3,4-tetrahydroquinoxalin-1-yl]ethan-1-one;

1-[(3S)-4-acetyl-3-methyl-1,2,3,4-tetrahydroquinoxalin-1-yl]-2-(thiophen-2-yl)ethan-1-one;

1-[(3S)-4-acetyl-3-methyl-1,2,3,4-tetrahydroquinoxalin-1-yl]-2-(4-chlorophenoxyl)ethan-1-one;

1-[(3S)-4-acetyl-3-methyl-1,2,3,4-tetrahydroquinoxalin-1-yl]-2-(4-methoxyphenoxyl)ethan-1-one;

1-[(3S)-4-acetyl-3-methyl-1,2,3,4-tetrahydroquinoxalin-1-yl]-2-(naphthalen-2-yloxy)ethan-1-one;

1-[(3S)-4-acetyl-3-methyl-1,2,3,4-tetrahydroquinoxalin-1-yl]-2-(4-fluorophenoxyl)ethan-1-one;

1-[(3S)-4-acetyl-3-methyl-1,2,3,4-tetrahydroquinoxalin-1-yl]-2-(naphthalen-1-yloxy)ethan-1-one;

1-[(2S)-4-(2,3-dihydro-1,4-benzodioxine-2-carbonyl)-2-methyl-1,2,3,4-tetrahydroquinoxalin-1-yl]ethan-1-one;

1-[(3S)-4-acetyl-3-methyl-1,2,3,4-tetrahydroquinoxalin-1-yl]-2-methoxyethan-1-one;

1-[(3S)-4-acetyl-3-methyl-1,2,3,4-tetrahydroquinoxalin-1-yl]-2-(5-chloro-1-benzothiophen-3-yl)ethan-1-one;

(2R)-1-[(3S)-4-acetyl-3-methyl-1,2,3,4-tetrahydroquinoxalin-1-yl]-2-methoxy-2-phenylethan-1-one;

(2S)-1-[(3S)-4-acetyl-3-methyl-1,2,3,4-tetrahydroquinoxalin-1-yl]-2-methoxy-2-phenylethan-1-one;

1-[(2S)-2-methyl-4-(4-phenoxybenzoyl)-1,2,3,4-tetrahydroquinoxalin-1-yl]ethan-1-one;

1-[(2S)-4-(4-chlorobenzoyl)-2-methyl-1,2,3,4-tetrahydroquinoxalin-1-yl]ethan-1-one;
1-[(2S)-2-methyl-4-(2-phenoxybenzoyl)-1,2,3,4-tetrahydroquinoxalin-1-yl]ethan-1-one;
1-[(2S)-2-methyl-4-(thiophene-2-carbonyl)-1,2,3,4-tetrahydroquinoxalin-1-yl]ethan-1-one;
1-[(2S)-4-(1-benzothiophene-2-carbonyl)-2-methyl-1,2,3,4-tetrahydroquinoxalin-1-yl]ethan-1-one;
1-[(2S)-4-(4-methoxythiophene-3-carbonyl)-2-methyl-1,2,3,4-tetrahydroquinoxalin-1-yl]ethan-1-one;
1-[(2S)-2-methyl-4-(1-methyl-1H-indole-2-carbonyl)-1,2,3,4-tetrahydroquinoxalin-1-yl]ethan-1-one;
1-[(2S)-4-(2,5-dimethylfuran-3-carbonyl)-2-methyl-1,2,3,4-tetrahydroquinoxalin-1-yl]ethan-1-one;
1-[(2S)-4-(4,5-dimethylfuran-2-carbonyl)-2-methyl-1,2,3,4-tetrahydroquinoxalin-1-yl]ethan-1-one;
1-[(2S)-4-(1-benzofuran-2-carbonyl)-2-methyl-1,2,3,4-tetrahydroquinoxalin-1-yl]ethan-1-one;
1-[(2S)-2-methyl-4-(quinoline-3-carbonyl)-1,2,3,4-tetrahydroquinoxalin-1-yl]ethan-1-one;
1-[(2S)-4-(4-methoxyquinoline-2-carbonyl)-2-methyl-1,2,3,4-tetrahydroquinoxalin-1-yl]ethan-1-one;
1-[(2S)-2-methyl-4-(quinoline-4-carbonyl)-1,2,3,4-tetrahydroquinoxalin-1-yl]ethan-1-one;
1-[(2S)-4-(1,5-dimethyl-1H-pyrazole-3-carbonyl)-2-methyl-1,2,3,4-tetrahydroquinoxalin-1-yl]ethan-1-one;
1-[(2S)-2-methyl-4-[1-phenyl-5-(trifluoromethyl)-1H-pyrazole-4-carbonyl]-1,2,3,4-tetrahydroquinoxalin-1-yl]ethan-1-one;
1-[(2S)-2-methyl-4-(4-methyl-1,2,3-thiadiazole-5-carbonyl)-1,2,3,4-tetrahydroquinoxalin-1-yl]ethan-1-one;
1-[(2S)-4-(2-methoxypyridine-3-carbonyl)-2-methyl-1,2,3,4-tetrahydroquinoxalin-1-yl]ethan-1-one;
1-[(2S)-4-(5-chloro-1-benzofuran-2-carbonyl)-2-methyl-1,2,3,4-tetrahydroquinoxalin-1-yl]ethan-1-one;
1-[(2S)-4-(1H-indole-6-carbonyl)-2-methyl-1,2,3,4-tetrahydroquinoxalin-1-yl]ethan-1-one;
1-[(2S)-2-methyl-4-[2-(trifluoromethyl)-1,3-thiazole-4-carbonyl]-1,2,3,4-tetrahydroquinoxalin-1-yl]ethan-1-one;
1-[(3S)-4-acetyl-3-methyl-1,2,3,4-tetrahydroquinoxalin-1-yl]-2-(1-methanesulfonylpiperidin-4-yl)ethan-1-one;
1-[(2S)-4-(5-fluoropyridine-2-carbonyl)-2-methyl-1,2,3,4-tetrahydroquinoxalin-1-yl]ethan-1-one;
1-{2-[(3S)-4-acetyl-3-methyl-1,2,3,4-tetrahydroquinoxalin-1-yl]-2-oxoethyl}azepan-2-one;
1-{3-[(3S)-4-acetyl-3-methyl-1,2,3,4-tetrahydroquinoxalin-1-yl]-3-oxopropyl}azepan-2-one;
1-[(3S)-4-acetyl-3-methyl-1,2,3,4-tetrahydroquinoxalin-1-yl]-2-(1H-1,3-benzodiazol-1-yl)ethan-1-one;
4-{2-[(3S)-4-acetyl-3-methyl-1,2,3,4-tetrahydroquinoxalin-1-yl]-2-oxoethyl}-1λ⁶-thiomorpholine-1,1-dione;
1-[(2S)-4-(dimethyl-1,2-oxazole-4-carbonyl)-2-methyl-1,2,3,4-tetrahydroquinoxalin-1-yl]ethan-1-one;
1-[(3S)-4-acetyl-3-methyl-1,2,3,4-tetrahydroquinoxalin-1-yl]-2-(5-methyl-2-phenyl-1,3-oxazol-4-yl)ethan-1-one;
1-[(2S)-4-(1H-indole-4-carbonyl)-2-methyl-1,2,3,4-tetrahydroquinoxalin-1-yl]ethan-1-one;
1-[(2S)-2-methyl-4-{pyrazolo[1,5-a]pyridine-2-carbonyl}-1,2,3,4-tetrahydroquinoxalin-1-yl]ethan-1-one;
1-[(3S)-4-acetyl-3-methyl-1,2,3,4-tetrahydroquinoxalin-1-yl]-2-(2-methylpropoxy)ethan-1-one;
1-[(2S)-2-methyl-4-{5H,6H,7H-pyrazolo[3,2-b][1,3]oxazine-3-carbonyl}-1,2,3,4-tetrahydroquinoxalin-1-yl]ethan-1-one;
1-[(2S)-2-methyl-4-{4H,5H,6H-pyrrolo[1,2-b]pyrazole-2-carbonyl}-1,2,3,4-tetrahydroquinoxalin-1-yl]ethan-1-one;
1-[(2S)-2-methyl-4-{thieno[2,3-c]pyridine-2-carbonyl}-1,2,3,4-tetrahydroquinoxalin-1-yl]ethan-1-one;
1-[(2S)-4-{imidazo[1,2-a]pyridine-6-carbonyl}-2-methyl-1,2,3,4-tetrahydroquinoxalin-1-yl]ethan-1-one;
1-[(2S)-4-{furo[2,3-c]pyridine-2-carbonyl}-2-methyl-1,2,3,4-tetrahydroquinoxalin-1-yl]ethan-1-one;
1-[(2S)-6-(4-methanesulfonylphenyl)-2-methyl-4-{1H-pyrrolo[3,2-c]pyridine-2-carbonyl}-1,2,3,4-tetrahydroquinoxalin-1-yl]ethan-1-one;
1-[(2S)-4-{imidazo[1,2-a]pyrazine-2-carbonyl}-6-(4-methanesulfonylphenyl)-2-methyl-1,2,3,4-tetrahydroquinoxalin-1-yl]ethan-1-one;
1-[(2S)-6-(4-methanesulfonylphenyl)-2-methyl-4-[4-(trifluoromethyl)benzoyl]-1,2,3,4-tetrahydroquinoxalin-1-yl]ethan-1-one;
1-[(2S)-4-cyclopropanecarbonyl-6-(4-methanesulfonylphenyl)-2-methyl-1,2,3,4-tetrahydroquinoxalin-1-yl]ethan-1-one;
1-[(2S)-6-(4-methanesulfonylphenyl)-2-methyl-4-(pyridine-2-carbonyl)-1,2,3,4-tetrahydroquinoxalin-1-yl]ethan-1-one;
1-[(2S)-6-(4-methanesulfonylphenyl)-2-methyl-4-(1,2,3-thiadiazole-4-carbonyl)-1,2,3,4-tetrahydroquinoxalin-1-yl]ethan-1-one;
1-[(2S)-6-(4-methanesulfonylphenyl)-2-methyl-4-(1-methyl-1H-imidazole-2-carbonyl)-1,2,3,4-tetrahydroquinoxalin-1-yl]ethan-1-one;
1-[(2S)-4-(5-chloro-1H-indole-2-carbonyl)-6-(4-methanesulfonylphenyl)-2-methyl-1,2,3,4-tetrahydroquinoxalin-1-yl]ethan-1-one;
1-[(2S)-4-(5-hydroxy-1H-indole-2-carbonyl)-6-(4-methanesulfonylphenyl)-2-methyl-1,2,3,4-tetrahydroquinoxalin-1-yl]ethan-1-one;
1-[(2S)-4-(6-chloro-1H-indole-2-carbonyl)-6-(4-methanesulfonylphenyl)-2-methyl-1,2,3,4-tetrahydroquinoxalin-1-yl]ethan-1-one;
1-[(2S)-6-(4-methanesulfonylphenyl)-2-methyl-4-[5-(trifluoromethoxy)-1H-indole-2-carbonyl]-1,2,3,4-tetrahydroquinoxalin-1-yl]ethan-1-one;
1-[(2S)-6-(4-methanesulfonylphenyl)-2-methyl-4-{1H-pyrrolo[2,3-b]pyridine-2-carbonyl}-1,2,3,4-tetrahydroquinoxalin-1-yl]ethan-1-one;
1-[(2S)-6-(4-methanesulfonylphenyl)-2-methyl-4-(3-phenyl-1-benzofuran-2-carbonyl)-1,2,3,4-tetrahydroquinoxalin-1-yl]ethan-1-one;
1-[(3S)-4-acetyl-3-methyl-7-(quinolin-6-yl)-1,2,3,4-tetrahydroquinoxalin-1-yl]-2-phenoxyethan-1-one;
1-[(3S)-4-acetyl-3-methyl-7-(3-phenylphenyl)-1,2,3,4-tetrahydroquinoxalin-1-yl]-2-phenoxyethan-1-one;
1-[(2S)-4-(furan-2-carbonyl)-2-methyl-6-(3-phenylphenyl)-1,2,3,4-tetrahydroquinoxalin-1-yl]ethan-1-one;
1-[(3S)-4-acetyl-7-(2-fluorophenyl)-3-methyl-1,2,3,4-tetrahydroquinoxalin-1-yl]-2-phenoxyethan-1-one;
1-[(2S)-6-(2-fluorophenyl)-4-(furan-2-carbonyl)-2-methyl-1,2,3,4-tetrahydroquinoxalin-1-yl]ethan-1-one;
1-[(2S)-4-(furan-2-carbonyl)-2-methyl-6-(1-methyl-1H-indol-5-yl)-1,2,3,4-tetrahydroquinoxalin-1-yl]ethan-1-one;
1-[(3S)-4-acetyl-3-methyl-7-(4-phenylphenyl)-1,2,3,4-tetrahydroquinoxalin-1-yl]-2-phenoxyethan-1-one;
1-[(2S)-4-(furan-2-carbonyl)-2-methyl-6-(4-phenylphenyl)-1,2,3,4-tetrahydroquinoxalin-1-yl]ethan-1-one;
4-[(2S)-1-acetyl-4-(furan-2-carbonyl)-2-methyl-1,2,3,4-tetrahydroquinoxalin-6-yl]benzoic acid;
1-[(2S)-4-(furan-2-carbonyl)-2-methyl-6-[6-(morpholin-4-yl)pyridin-3-yl]-1,2,3,4-tetrahydroquinoxalin-1-yl]ethan-1-one;

3-[(2S)-1-acetyl-4-(furan-2-carbonyl)-2-methyl-1,2,3,4-tetrahydroquinoxalin-6-yl]-N-methylbenzamide;
3-[(2S)-1-acetyl-4-(furan-2-carbonyl)-2-methyl-1,2,3,4-tetrahydroquinoxalin-6-yl]-N-cyclopropylbenzamide;
1-[(2S)-4-(furan-2-carbonyl)-2-methyl-6-[4-(1H-pyrazol-1-yl)phenyl]-1,2,3,4-tetrahydroquinoxalin-1-yl]ethan-1-one;
1-[(2S)-4-(furan-2-carbonyl)-2-methyl-6-phenyl-1,2,3,4-tetrahydroquinoxalin-1-yl]ethan-1-one;
1-[(2S)-6-(4-chlorophenyl)-4-(furan-2-carbonyl)-2-methyl-1,2,3,4-tetrahydroquinoxalin-1-yl]ethan-1-one;
1-[(2S)-6-(2H-1,3-benzodioxol-5-yl)-4-(furan-2-carbonyl)-2-methyl-1,2,3,4-tetrahydroquinoxalin-1-yl]ethan-1-one;
1-[(2S)-4-(furan-2-carbonyl)-6-(4-methoxyphenyl)-2-methyl-1,2,3,4-tetrahydroquinoxalin-1-yl]ethan-1-one;
1-[(2S)-4-(furan-2-carbonyl)-2-methyl-6-[4-(trifluoromethoxy)phenyl]-1,2,3,4-tetrahydroquinoxalin-1-yl]ethan-1-one;
4-[(2S)-1-acetyl-4-(furan-2-carbonyl)-2-methyl-1,2,3,4-tetrahydroquinoxalin-6-yl]-N,N-dimethylbenzamide;
4-[(2S)-1-acetyl-4-(furan-2-carbonyl)-2-methyl-1,2,3,4-tetrahydroquinoxalin-6-yl]benzamide;
4-[(2S)-1-acetyl-4-(furan-2-carbonyl)-2-methyl-1,2,3,4-tetrahydroquinoxalin-6-yl]benzonitrile;
3-[(2S)-1-acetyl-4-(furan-2-carbonyl)-2-methyl-1,2,3,4-tetrahydroquinoxalin-6-yl]benzonitrile;
1-[(2S)-4-(furan-2-carbonyl)-2-methyl-6-(4-phenoxyphenyl)-1,2,3,4-tetrahydroquinoxalin-1-yl]ethan-1-one;
1-[(2S)-6-[3-fluoro-4-(1H-pyrazol-1-yl)phenyl]-4-(furan-2-carbonyl)-2-methyl-1,2,3,4-tetrahydroquinoxalin-1-yl]ethan-1-one;
1-[(2S)-4-(furan-2-carbonyl)-2-methyl-6-[4-(trifluoromethyl)phenyl]-1,2,3,4-tetrahydroquinoxalin-1-yl]ethan-1-one;
1-[(2S)-6-(dimethyl-1,2-oxazol-4-yl)-4-(furan-2-carbonyl)-2-methyl-1,2,3,4-tetrahydroquinoxalin-1-yl]ethan-1-one;
1-[(2S)-4-(furan-2-carbonyl)-6-(4-methanesulfonylphenyl)-2-methyl-1,2,3,4-tetrahydroquinoxalin-1-yl]ethan-1-one;
1-[(2S)-6-(4-fluorophenyl)-4-(furan-2-carbonyl)-2-methyl-1,2,3,4-tetrahydroquinoxalin-1-yl]ethan-1-one;
1-[(2S)-4-(furan-2-carbonyl)-2-methyl-6-(pyridin-3-yl)-1,2,3,4-tetrahydroquinoxalin-1-yl]ethan-1-one;
1-[(2S)-4-(furan-2-carbonyl)-2-methyl-6-(pyridin-4-yl)-1,2,3,4-tetrahydroquinoxalin-1-yl]ethan-1-one;
1-[(2S)-4-(furan-2-carbonyl)-2-methyl-6-(pyrimidin-5-yl)-1,2,3,4-tetrahydroquinoxalin-1-yl]ethan-1-one;
1-[(2S)-4-(furan-2-carbonyl)-2-methyl-6-(1-methyl-1H-pyrazol-4-yl)-1,2,3,4-tetrahydroquinoxalin-1-yl]ethan-1-one;
1-[(2S)-4-(furan-2-carbonyl)-2-methyl-6-(quinolin-3-yl)-1,2,3,4-tetrahydroquinoxalin-1-yl]ethan-1-one;
4-[(2S)-1-acetyl-4-(furan-2-carbonyl)-2-methyl-1,2,3,4-tetrahydroquinoxalin-6-yl]-N-methylbenzamide;
1-[(2S)-6-(2,3-dihydro-1,4-benzodioxin-6-yl)-4-(furan-2-carbonyl)-2-methyl-1,2,3,4-tetrahydroquinoxalin-1-yl]ethan-1-one;
1-[(2S)-6-(4-fluoro-2-methoxyphenyl)-4-(furan-2-carbonyl)-2-methyl-1,2,3,4-tetrahydroquinoxalin-1-yl]ethan-1-one;
N-{2-[(2S)-1-acetyl-4-(furan-2-carbonyl)-2-methyl-1,2,3,4-tetrahydroquinoxalin-6-yl]phenyl}methanesulfonamide;
1-[(2S)-6-(4-fluoro-3-methoxyphenyl)-4-(furan-2-carbonyl)-2-methyl-1,2,3,4-tetrahydroquinoxalin-1-yl]ethan-1-one;
5-[(2S)-1-acetyl-4-(furan-2-carbonyl)-2-methyl-1,2,3,4-tetrahydroquinoxalin-6-yl]-2-fluoro-N-(propan-2-yl)benzamide;
1-[(2S)-6-(5-fluoropyridin-3-yl)-4-(furan-2-carbonyl)-2-methyl-1,2,3,4-tetrahydroquinoxalin-1-yl]ethan-1-one;
1-[(2S)-6-[2-(dimethylamino)pyrimidin-5-yl]-4-(furan-2-carbonyl)-2-methyl-1,2,3,4-tetrahydroquinoxalin-1-yl]ethan-1-one;
1-[(2S)-6-(5-chloropyridin-3-yl)-4-(furan-2-carbonyl)-2-methyl-1,2,3,4-tetrahydroquinoxalin-1-yl]ethan-1-one;
1-[(2S)-4-(furan-2-carbonyl)-6-(6-methoxypyridin-3-yl)-2-methyl-1,2,3,4-tetrahydroquinoxalin-1-yl]ethan-1-one;
1-[(2S)-4-(furan-2-carbonyl)-6-(2-methoxypyrimidin-5-yl)-2-methyl-1,2,3,4-tetrahydroquinoxalin-1-yl]ethan-1-one;
1-[(2S)-4-(furan-2-carbonyl)-6-(5-methoxypyridin-3-yl)-2-methyl-1,2,3,4-tetrahydroquinoxalin-1-yl]ethan-1-one;
5-[(2S)-1-acetyl-4-(furan-2-carbonyl)-2-methyl-1,2,3,4-tetrahydroquinoxalin-6-yl]-N-methylpyridine-2-carboxamide;
1-[(2S)-4-(furan-2-carbonyl)-2-methyl-6-[6-(trifluoromethyl)pyridin-3-yl]-1,2,3,4-tetrahydroquinoxalin-1-yl]ethan-1-one;
1-[(2S)-4-(furan-2-carbonyl)-2-methyl-6-[3-(morpholine-4-carbonyl)phenyl]-1,2,3,4-tetrahydroquinoxalin-1-yl]ethan-1-one;
1-[(2S)-4-(furan-2-carbonyl)-2-methyl-6-(1-methyl-1H-indol-2-yl)-1,2,3,4-tetrahydroquinoxalin-1-yl]ethan-1-one;
1-[(2S)-4-(furan-2-carbonyl)-2-methyl-6-(2-methyl-2H-indazol-6-yl)-1,2,3,4-tetrahydroquinoxalin-1-yl]ethan-1-one;
3-[(2S)-1-acetyl-4-(furan-2-carbonyl)-2-methyl-1,2,3,4-tetrahydroquinoxalin-6-yl]benzene-1-sulfonamide;
1-[(2S)-4-(furan-2-carbonyl)-2-methyl-6-(1-methyl-1H-indazol-7-yl)-1,2,3,4-tetrahydroquinoxalin-1-yl]ethan-1-one;
1-[(2S)-4-(furan-2-carbonyl)-2-methyl-6-(1-methyl-1H-indazol-6-yl)-1,2,3,4-tetrahydroquinoxalin-1-yl]ethan-1-one;
N-{3-[(2S)-1-acetyl-4-(furan-2-carbonyl)-2-methyl-1,2,3,4-tetrahydroquinoxalin-6-yl]phenyl}methanesulfonamide;
3-[(2S)-1-acetyl-4-(furan-2-carbonyl)-2-methyl-1,2,3,4-tetrahydroquinoxalin-6-yl]-N,N-dimethylbenzene-1-sulfonamide;
1-[(2S)-4-(furan-2-carbonyl)-6-(1H-indol-4-yl)-2-methyl-1,2,3,4-tetrahydroquinoxalin-1-yl]ethan-1-one;
1-[(2S)-4-(furan-2-carbonyl)-6-(3-methanesulfonylphenyl)-2-methyl-1,2,3,4-tetrahydroquinoxalin-1-yl]ethan-1-one;
3-[(2S)-1-acetyl-4-(furan-2-carbonyl)-2-methyl-1,2,3,4-tetrahydroquinoxalin-6-yl]-N,N-dimethylbenzamide;
1-[(2S)-6-(2H-1,3-benzodioxol-4-yl)-4-(furan-2-carbonyl)-2-methyl-1,2,3,4-tetrahydroquinoxalin-1-yl]ethan-1-one;
1-[(2S)-4-(furan-2-carbonyl)-2-methyl-6-[4-(morpholin-4-yl)phenyl]-1,2,3,4-tetrahydroquinoxalin-1-yl]ethan-1-one;
1-[(2S)-4-(furan-2-carbonyl)-2-methyl-6-[1-methyl-3-(trifluoromethyl)-1H-pyrazol-5-yl]-1,2,3,4-tetrahydroquinoxalin-1-yl]ethan-1-one;
1-[(2S)-4-(furan-2-carbonyl)-2-methyl-6-(1-methyl-1H-indazol-5-yl)-1,2,3,4-tetrahydroquinoxalin-1-yl]ethan-1-one;
1-[(2S)-4-(furan-2-carbonyl)-2-methyl-6-[3-(1H-pyrazol-1-yl)phenyl]-1,2,3,4-tetrahydroquinoxalin-1-yl]ethan-1-one;
1-[(2S)-4-(furan-2-carbonyl)-2-methyl-6-[3-(5-methyl-1,3,4-oxadiazol-2-yl)phenyl]-1,2,3,4-tetrahydroquinoxalin-1-yl]ethan-1-one;
1-[(2S)-4-(furan-2-carbonyl)-6-[3-(furan-2-yl)phenyl]-2-methyl-1,2,3,4-tetrahydroquinoxalin-1-yl]ethan-1-one;
3-[(2S)-1-acetyl-4-(furan-2-carbonyl)-2-methyl-1,2,3,4-tetrahydroquinoxalin-6-yl]benzamide;

1-[(2S)-6-[3-(3,5-dimethyl-1H-pyrazol-1-yl)phenyl]-4-(furan-2-carbonyl)-2-methyl-1,2,3,4-tetrahydroquinoxalin-1-yl]ethan-1-one;
1-[(2S)-4-(furan-2-carbonyl)-2-methyl-6-(1-methyl-1H-indazol-4-yl)-1,2,3,4-tetrahydroquinoxalin-1-yl]ethan-1-one;
N-{3-[(2S)-1-acetyl-4-(furan-2-carbonyl)-2-methyl-1,2,3,4-tetrahydroquinoxalin-6-yl]phenyl}-4-methylbenzene-1-sulfonamide;
N-{4-[(2S)-1-acetyl-4-(furan-2-carbonyl)-2-methyl-1,2,3,4-tetrahydroquinoxalin-6-yl]phenyl}-4-methylbenzene-1-sulfonamide;
1-[(2S)-4-(furan-2-carbonyl)-2-methyl-6-[2-(trifluoromethyl)pyridin-4-yl]-1,2,3,4-tetrahydroquinoxalin-1-yl]ethan-1-one;
1-[(2S)-4-(furan-2-carbonyl)-2-methyl-6-[2-(morpholin-4-yl)pyridin-4-yl]-1,2,3,4-tetrahydroquinoxalin-1-yl]ethan-1-one;
1-[(2S)-4-(furan-2-carbonyl)-6-(2-methoxypyridin-4-yl)-2-methyl-1,2,3,4-tetrahydroquinoxalin-1-yl]ethan-1-one;
1-[(2S)-4-(furan-2-carbonyl)-6-(isoquinolin-6-yl)-2-methyl-1,2,3,4-tetrahydroquinoxalin-1-yl]ethan-1-one;
1-[(2S)-6-(1,3-benzothiazol-5-yl)-4-(furan-2-carbonyl)-2-methyl-1,2,3,4-tetrahydroquinoxalin-1-yl]ethan-1-one;
1-[(2S)-4-(furan-2-carbonyl)-2-methyl-6-(4-trifluoromethanesulfonylphenyl)-1,2,3,4-tetrahydroquinoxalin-1-yl]ethan-1-one;
1-[(2S)-4-(furan-2-carbonyl)-2-methyl-6-[3-(piperidin-1-yl)phenyl]-1,2,3,4-tetrahydroquinoxalin-1-yl]ethan-1-one;
3-[1-acetyl-4-(furan-2-carbonyl)-1,2,3,4-tetrahydroquinoxalin-6-yl]-N-methylbenzamide;
1-[(2S)-6-(3,5-difluorophenyl)-4-(furan-2-carbonyl)-2-methyl-1,2,3,4-tetrahydroquinoxalin-1-yl]ethan-1-one;
1-[(2S)-6-[3-(dimethylamino)phenyl]-4-(furan-2-carbonyl)-2-methyl-1,2,3,4-tetrahydroquinoxalin-1-yl]ethan-1-one;
1-[(2S)-6-[4-(dimethylamino)phenyl]-4-(furan-2-carbonyl)-2-methyl-1,2,3,4-tetrahydroquinoxalin-1-yl]ethan-1-one;
1-[(2S)-4-(furan-2-carbonyl)-2-methyl-6-(5-methylthiophen-2-yl)-1,2,3,4-tetrahydroquinoxalin-1-yl]ethan-1-one;
1-[(2S)-6-(1-benzothiophen-7-yl)-4-(furan-2-carbonyl)-2-methyl-1,2,3,4-tetrahydroquinoxalin-1-yl]ethan-1-one;
1-[(2S)-4-(furan-2-carbonyl)-2-methyl-6-[4-(4-methylpiperazin-1-yl)phenyl]-1,2,3,4-tetrahydroquinoxalin-1-yl]ethan-1-one;
4-[(2S)-1-acetyl-4-(furan-2-carbonyl)-2-methyl-1,2,3,4-tetrahydroquinoxalin-6-yl]-N-methylbenzene-1-sulfonamide;
N-{3-[(2S)-1-acetyl-4-(furan-2-carbonyl)-2-methyl-1,2,3,4-tetrahydroquinoxalin-6-yl]phenyl}ethan-1-sulfonamide;
1-[(2S)-6-(4-methanesulfonylphenyl)-4-(4-methoxybenzoyl)-2-methyl-1,2,3,4-tetrahydroquinoxalin-1-yl]ethan-1-one;
1-[(2S)-4-(4-fluorobenzoyl)-6-(4-methanesulfonylphenyl)-2-methyl-1,2,3,4-tetrahydroquinoxalin-1-yl]ethan-1-one;
1-[(2S)-6-(4-methanesulfonylphenyl)-2-methyl-4-[4-(trifluoromethoxy)benzoyl]-1,2,3,4-tetrahydroquinoxalin-1-yl]ethan-1-one;
1-[(2S)-4-[5-(3,5-dichlorophenoxyl)furan-2-carbonyl]-6-(4-methanesulfonylphenyl)-2-methyl-1,2,3,4-tetrahydroquinoxalin-1-yl]ethan-1-one;
1-[(2S)-6-(4-methanesulfonylphenyl)-2-methyl-4-(1-methyl-1H-imidazole-4-carbonyl)-1,2,3,4-tetrahydroquinoxalin-1-yl]ethan-1-one;
1-[(2S)-6-(4-methanesulfonylphenyl)-4-(5-methoxy-1H-indole-2-carbonyl)-2-methyl-1,2,3,4-tetrahydroquinoxalin-1-yl]ethan-1-one;
1-[(2S)-6-(4-methanesulfonylphenyl)-4-(4-methoxy-1H-indole-2-carbonyl)-2-methyl-1,2,3,4-tetrahydroquinoxalin-1-yl]ethan-1-one;
1-[(2S)-6-(4-methanesulfonylphenyl)-2-methyl-4-(5-methyl-1,3-oxazole-4-carbonyl)-1,2,3,4-tetrahydroquinoxalin-1-yl]ethan-1-one;
1-[(2S)-6-(4-methanesulfonylphenyl)-2-methyl-4-(2-phenyl-1,3-thiazole-4-carbonyl)-1,2,3,4-tetrahydroquinoxalin-1-yl]ethan-1-one;
1-[(2S)-6-(4-methanesulfonylphenyl)-2-methyl-4-(5-phenylfuran-2-carbonyl)-1,2,3,4-tetrahydroquinoxalin-1-yl]ethan-1-one;
1-[(2S)-6-(4-methanesulfonylphenyl)-2-methyl-4-[5-(trifluoromethyl)furan-2-carbonyl]-1,2,3,4-tetrahydroquinoxalin-1-yl]ethan-1-one;
1-[(2S)-4-(5-methanesulfonylfuran-2-carbonyl)-6-(4-methanesulfonylphenyl)-2-methyl-1,2,3,4-tetrahydroquinoxalin-1-yl]ethan-1-one;
N-{3-[(3S)-4-acetyl-7-(4-methanesulfonylphenyl)-3-methyl-1,2,3,4-tetrahydroquinoxalin-1-carbonyl]phenyl}acetamide;
1-[(2S)-4-[5-(aminomethyl)furan-2-carbonyl]-6-(4-methanesulfonylphenyl)-2-methyl-1,2,3,4-tetrahydroquinoxalin-1-yl]ethan-1-one;
1-[(2S)-4-{[4-(dimethylamino)phenyl]methyl}-2-methyl-1,2,3,4-tetrahydroquinoxalin-1-yl]ethan-1-one;
1-[(2S)-2-methyl-4-{[4-(propan-2-yl)phenyl]methyl}-1,2,3,4-tetrahydroquinoxalin-1-yl]ethan-1-one;
1-[(2S)-2-methyl-4-[(3-methylphenyl)methyl]-1,2,3,4-tetrahydroquinoxalin-1-yl]ethan-1-one;
1-[(2S)-4-[(2,4-dichlorophenyl)methyl]-2-methyl-1,2,3,4-tetrahydroquinoxalin-1-yl]ethan-1-one;
1-[(2S)-2-methyl-4-[(4-methylphenyl)methyl]-1,2,3,4-tetrahydroquinoxalin-1-yl]ethan-1-one;
1-[(2S)-2-methyl-4-[(2-methylphenyl)methyl]-1,2,3,4-tetrahydroquinoxalin-1-yl]ethan-1-one;
1-[(2S)-4-[(2,4-difluorophenyl)methyl]-2-methyl-1,2,3,4-tetrahydroquinoxalin-1-yl]ethan-1-one;
1-[(2S)-4-[(4-chloro-3-fluorophenyl)methyl]-2-methyl-1,2,3,4-tetrahydroquinoxalin-1-yl]ethan-1-one;
1-[(2S)-2-methyl-4-{[3-(trifluoromethyl)phenyl]methyl}-1,2,3,4-tetrahydroquinoxalin-1-yl]ethan-1-one;
1-[(2S)-4-{[3,5-bis(trifluoromethyl)phenyl]methyl}-2-methyl-1,2,3,4-tetrahydroquinoxalin-1-yl]ethan-1-one;
1-[(2S)-4-[(4-ethylphenyl)methyl]-2-methyl-1,2,3,4-tetrahydroquinoxalin-1-yl]ethan-1-one;
1-[(2S)-4-[(3,5-dimethoxyphenyl)methyl]-2-methyl-1,2,3,4-tetrahydroquinoxalin-1-yl]ethan-1-one;
1-[(2S)-4-[(2,5-dimethylphenyl)methyl]-2-methyl-1,2,3,4-tetrahydroquinoxalin-1-yl]ethan-1-one;
1-[(2S)-4-[(4-hydroxy-3-methylphenyl)methyl]-2-methyl-1,2,3,4-tetrahydroquinoxalin-1-yl]ethan-1-one;
1-[(2S)-4-[(1,3-dimethyl-1H-pyrazol-5-yl)methyl]-2-methyl-1,2,3,4-tetrahydroquinoxalin-1-yl]ethan-1-one;
1-[(2S)-4-({2-[2-(dimethylamino)ethoxy]phenyl}methyl)-2-methyl-1,2,3,4-tetrahydroquinoxalin-1-yl]ethan-1-one;
1-[(2S)-4-({4-[2-(dimethylamino)ethoxy]phenyl}methyl)-2-methyl-1,2,3,4-tetrahydroquinoxalin-1-yl]ethan-1-one;
1-[(2S)-4-({3-[2-(dimethylamino)ethoxy]phenyl}methyl)-2-methyl-1,2,3,4-tetrahydroquinoxalin-1-yl]ethan-1-one;
1-[(2S)-4-benzyl-2-methyl-1,2,3,4-tetrahydroquinoxalin-1-yl]ethan-1-one;
1-[(2S)-4-(cyclohexylmethyl)-2-methyl-1,2,3,4-tetrahydroquinoxalin-1-yl]ethan-1-one;
1-[(2S)-2-methyl-4-{[6-(trifluoromethyl)pyridin-3-yl]methyl}-1,2,3,4-tetrahydroquinoxalin-1-yl]ethan-1-one;

1-[(2S)-2-methyl-4-(pyridin-4-ylmethyl)-1,2,3,4-tetrahydroquinoxalin-1-yl]ethan-1-one;
1-[(2S)-2-methyl-4-(pyridin-2-ylmethyl)-1,2,3,4-tetrahydroquinoxalin-1-yl]ethan-1-one;
1-[(2S)-4-[(5-methoxypyridin-3-yl)methyl]-2-methyl-1,2,3,4-tetrahydroquinoxalin-1-yl]ethan-1-one;
1-[(2S)-2-methyl-4-(1,3-thiazol-2-ylmethyl)-1,2,3,4-tetrahydroquinoxalin-1-yl]ethan-1-one;
1-[(2S)-2-methyl-4-[(4-phenylphenyl)methyl]-1,2,3,4-tetrahydroquinoxalin-1-yl]ethan-1-one;
1-[(2S)-2-methyl-4-{[4-(propan-2-yloxy)phenyl]methyl}-1,2,3,4-tetrahydroquinoxalin-1-yl]ethan-1-one;
1-[(2S)-2-methyl-4-[(3-phenoxyphenyl)methyl]-1,2,3,4-tetrahydroquinoxalin-1-yl]ethan-1-one;
1-[(2S)-2-methyl-4-[(4-phenoxyphenyl)methyl]-1,2,3,4-tetrahydroquinoxalin-1-yl]ethan-1-one;
1-[(2S)-4-(2H-1,3-benzodioxol-5-ylmethyl)-2-methyl-1,2,3,4-tetrahydroquinoxalin-1-yl]ethan-1-one;
1-[(2S)-4-(2H-1,3-benzodioxol-4-ylmethyl)-2-methyl-1,2,3,4-tetrahydroquinoxalin-1-yl]ethan-1-one;
1-[(2S)-2-methyl-4-{[6-(morpholin-4-yl)pyridin-3-yl]methyl}-1,2,3,4-tetrahydroquinoxalin-1-yl]ethan-1-one;
1-[(2S)-4-[(4-hydroxyphenyl)methyl]-2-methyl-1,2,3,4-tetrahydroquinoxalin-1-yl]ethan-1-one;
1-[(2S)-2-methyl-4-(pyridin-3-ylmethyl)-1,2,3,4-tetrahydroquinoxalin-1-yl]ethan-1-one;
1-[(2S)-2-methyl-4-(oxan-4-ylmethyl)-1,2,3,4-tetrahydroquinoxalin-1-yl]ethan-1-one;
1-[(2S)-2-methyl-4-[(1-methyl-1H-imidazol-5-yl)methyl]-1,2,3,4-tetrahydroquinoxalin-1-yl]ethan-1-one;
1-[(2S)-2-methyl-4-(2-methylpentyl)-1,2,3,4-tetrahydroquinoxalin-1-yl]ethan-1-one;
1-[(2S)-4-[(1-acetylpiperidin-3-yl)methyl]-2-methyl-1,2,3,4-tetrahydroquinoxalin-1-yl]ethan-1-one;
1-[(2S)-2-methyl-4-{[1-(propan-2-yl)piperidin-4-yl]methyl}-1,2,3,4-tetrahydroquinoxalin-1-yl]ethan-1-one;
1-[(2S)-4-(2,5-dimethoxybenzenesulfonyl)-2-methyl-1,2,3,4-tetrahydroquinoxalin-1-yl]ethan-1-one;
1-[(2S)-4-(2-fluorobenzenesulfonyl)-2-methyl-1,2,3,4-tetrahydroquinoxalin-1-yl]ethan-1-one;
1-[(2S)-4-(benzenesulfonyl)-2-methyl-1,2,3,4-tetrahydroquinoxalin-1-yl]ethan-1-one;
1-[(2S)-2-methyl-4-[(1-methyl-1H-pyrazol-3-yl)sulfonyl]-1,2,3,4-tetrahydroquinoxalin-1-yl]ethan-1-one;
1-[(2S)-2-methyl-4-(pyridine-3-sulfonyl)-1,2,3,4-tetrahydroquinoxalin-1-yl]ethan-1-one;
1-[(2S)-4-(4-chlorobenzenesulfonyl)-2-methyl-1,2,3,4-tetrahydroquinoxalin-1-yl]ethan-1-one;
1-[(2S)-4-(4-methoxybenzenesulfonyl)-2-methyl-1,2,3,4-tetrahydroquinoxalin-1-yl]ethan-1-one;
1-[(2S)-2-methyl-4-[4-(trifluoromethyl)benzenesulfonyl]-1,2,3,4-tetrahydroquinoxalin-1-yl]ethan-1-one;
4-{[(3S)-4-acetyl-3-methyl-1,2,3,4-tetrahydroquinoxalin-1-yl]sulfonyl}benzonitrile;
1-[(2S)-2-methyl-4-[4-(trifluoromethoxy)benzenesulfonyl]-1,2,3,4-tetrahydroquinoxalin-1-yl]ethan-1-one;
1-[(2S)-2-methyl-4-(4-methylbenzenesulfonyl)-1,2,3,4-tetrahydroquinoxalin-1-yl]ethan-1-one;
1-[(2S)-2-methyl-4-(2-methylbenzenesulfonyl)-1,2,3,4-tetrahydroquinoxalin-1-yl]ethan-1-one;
1-[(2S)-4-(2-chlorobenzenesulfonyl)-2-methyl-1,2,3,4-tetrahydroquinoxalin-1-yl]ethan-1-one;
2-{[(3S)-4-acetyl-3-methyl-1,2,3,4-tetrahydroquinoxalin-1-yl]sulfonyl}benzonitrile;
3-{[(3S)-4-acetyl-3-methyl-1,2,3,4-tetrahydroquinoxalin-1-yl]sulfonyl}benzonitrile;
1-[(2S)-4-(3-methoxybenzenesulfonyl)-2-methyl-1,2,3,4-tetrahydroquinoxalin-1-yl]ethan-1-one;
1-[(2S)-4-(3-chlorobenzenesulfonyl)-2-methyl-1,2,3,4-tetrahydroquinoxalin-1-yl]ethan-1-one;
1-[(2S)-2-methyl-4-[3-(trifluoromethyl)benzenesulfonyl]-1,2,3,4-tetrahydroquinoxalin-1-yl]ethan-1-one;
1-[(2S)-2-methyl-4-(3-methylbenzenesulfonyl)-1,2,3,4-tetrahydroquinoxalin-1-yl]ethan-1-one;
1-[(2S)-4-(2,4-dimethylbenzenesulfonyl)-2-methyl-1,2,3,4-tetrahydroquinoxalin-1-yl]ethan-1-one;
1-[(2S)-4-(2,4-dimethoxybenzenesulfonyl)-2-methyl-1,2,3,4-tetrahydroquinoxalin-1-yl]ethan-1-one;
1-[(2S)-2-methyl-4-{[6-(trifluoromethyl)pyridin-3-yl]sulfonyl}-1,2,3,4-tetrahydroquinoxalin-1-yl]ethan-1-one;
1-[(2S)-4-(cyclopropanesulfonyl)-2-methyl-1,2,3,4-tetrahydroquinoxalin-1-yl]ethan-1-one;
1-[(2S)-4-[(2-chlorophenyl)methanesulfonyl]-2-methyl-1,2,3,4-tetrahydroquinoxalin-1-yl]ethan-1-one;
1-[(2S)-2-methyl-4-phenylmethanesulfonyl-1,2,3,4-tetrahydroquinoxalin-1-yl]ethan-1-one;
1-[(2S)-4-[(3-chlorophenyl)methanesulfonyl]-2-methyl-1,2,3,4-tetrahydroquinoxalin-1-yl]ethan-1-one;
1-[(2S)-4-[(1,2-dimethyl-1H-imidazol-4-yl)sulfonyl]-2-methyl-1,2,3,4-tetrahydroquinoxalin-1-yl]ethan-1-one;
1-[(2S)-4-(4-acetylbenzenesulfonyl)-2-methyl-1,2,3,4-tetrahydroquinoxalin-1-yl]ethan-1-one;
3-({[(3S)-4-acetyl-3-methyl-1,2,3,4-tetrahydroquinoxalin-1-yl]sulfonyl}methyl)benzonitrile;
1-[(2S)-4-(4-chloro-2-methoxybenzenesulfonyl)-2-methyl-1,2,3,4-tetrahydroquinoxalin-1-yl]ethan-1-one;
1-[(2S)-4-(4-methoxy-2-methylbenzenesulfonyl)-2-methyl-1,2,3,4-tetrahydroquinoxalin-1-yl]ethan-1-one;
1-[(2S)-2-methyl-4-[(1-methyl-1H-imidazol-4-yl)sulfonyl]-1,2,3,4-tetrahydroquinoxalin-1-yl]ethan-1-one;
1-[(2S)-4-[(4-chlorophenyl)methanesulfonyl]-2-methyl-1,2,3,4-tetrahydroquinoxalin-1-yl]ethan-1-one;
4-({[(3S)-4-acetyl-3-methyl-1,2,3,4-tetrahydroquinoxalin-1-yl]sulfonyl}methyl)benzonitrile;
(3S)-4-acetyl-7-(4-methanesulfonylphenyl)-3-methyl-N-phenyl-1,2,3,4-tetrahydroquinoxalin-1-carboxamide;
(3S)-4-acetyl-N-ethyl-7-(4-methanesulfonylphenyl)-3-methyl-1,2,3,4-tetrahydroquinoxalin-1-carboxamide;
(3S)-4-acetyl-7-(4-methanesulfonylphenyl)-3-methyl-N-(2-methylphenyl)-1,2,3,4-tetrahydroquinoxaline-1-carboxamide;
(3S)-4-acetyl-7-(4-methanesulfonylphenyl)-N-(3-methoxyphenyl)-3-methyl-1,2,3,4-tetrahydroquinoxaline-1-carboxamide;
(3S)-4-acetyl-N-cyclopentyl-7-(4-methanesulfonylphenyl)-3-methyl-1,2,3,4-tetrahydroquinoxaline-1-carboxamide;
(3S)-4-acetyl-N-(3-chlorophenyl)-7-(4-methanesulfonylphenyl)-3-methyl-1,2,3,4-tetrahydroquinoxaline-1-carboxamide;
(3S)-4-acetyl-7-(4-methanesulfonylphenyl)-N-(2-methoxyphenyl)-3-methyl-1,2,3,4-tetrahydroquinoxaline-1-carboxamide;
(3S)-4-acetyl-7-(4-methanesulfonylphenyl)-3-methyl-N-(3-methylphenyl)-1,2,3,4-tetrahydroquinoxaline-1-carboxamide;
(3S)-4-acetyl-7-(4-methanesulfonylphenyl)-N-[(2-methoxyphenyl)methyl]-3-methyl-1,2,3,4-tetrahydroquinoxaline-1-carboxamide;
(3S)-4-acetyl-N-(2-chlorophenyl)-7-(4-methanesulfonylphenyl)-3-methyl-1,2,3,4-tetrahydroquinoxaline-1-carboxamide;

(3S)-4-acetyl-7-(4-methanesulfonylphenyl)-3-methyl-N-(4-methylphenyl)-1,2,3,4-tetrahydroquinoxaline-1-carboxamide;

(3S)-4-acetyl-N-(4-chlorophenyl)-7-(4-methanesulfonylphenyl)-3-methyl-1,2,3,4-tetrahydroquinoxaline-1-carboxamide;

(3S)-4-acetyl-7-(4-methanesulfonylphenyl)-3-methyl-N-[(4-methylphenyl)methyl]-1,2,3,4-tetrahydroquinoxaline-1-carboxamide;

(3S)-4-acetyl-N-[(2-chlorophenyl)methyl]-7-(4-methanesulfonylphenyl)-3-methyl-1,2,3,4-tetrahydroquinoxaline-1-carboxamide;

(3S)-4-acetyl-7-(4-methanesulfonylphenyl)-3-methyl-N-(2-methylpropyl)-1,2,3,4-tetrahydroquinoxaline-1-carboxamide;

(3S)-4-acetyl-7-(4-methanesulfonylphenyl)-3-methyl-N-(thiophen-3-yl)-1,2,3,4-tetrahydroquinoxaline-1-carboxamide;

(3S)-4-acetyl-N-(furan-2-ylmethyl)-7-(4-methanesulfonylphenyl)-3-methyl-1,2,3,4-tetrahydroquinoxaline-1-carboxamide;

1-[(2S)-6-(4-methanesulfonylphenyl)-2-methyl-4-(5-methyl-1H-pyrazole-3-carbonyl)-1,2,3,4-tetrahydroquinoxalin-1-yl]ethan-1-one;

1-[(2S)-4-(1H-imidazole-2-carbonyl)-6-(4-methanesulfonylphenyl)-2-methyl-1,2,3,4-tetrahydroquinoxalin-1-yl]ethan-1-one;

5-[(3S)-4-acetyl-7-(4-methanesulfonylphenyl)-3-methyl-1,2,3,4-tetrahydroquinoxalin-1-carbonyl]-N,N-dimethylfuran-2-sulfonamide;

1-[(2S)-4-{5-[(dimethylamino)methyl]furan-2-carbonyl}-6-(4-methanesulfonylphenyl)-2-methyl-1,2,3,4-tetrahydroquinoxalin-1-yl]ethan-1-one;

1-[(2S)-4-(3-aminobenzoyl)-6-(4-methanesulfonylphenyl)-2-methyl-1,2,3,4-tetrahydroquinoxalin-1-yl]ethan-1-one;

1-[(2S)-4-(4-aminobenzoyl)-6-(4-methanesulfonylphenyl)-2-methyl-1,2,3,4-tetrahydroquinoxalin-1-yl]ethan-1-one;

(2S)-4-(furan-2-carbonyl)-6-(4-methanesulfonylphenyl)-2-methyl-1,2,3,4-tetrahydroquinoxaline-1-carboxamide;

(2S)-4-(furan-2-carbonyl)-6-(4-methanesulfonylphenyl)-N,2-dimethyl-1,2,3,4-tetrahydroquinoxaline-1-carboxamide;

1-[(2S)-6-(benzylamino)-4-(furan-2-carbonyl)-2-methyl-1,2,3,4-tetrahydroquinoxalin-1-yl]ethan-1-one;

1-[(2S)-6-[benzyl(methyl)amino]-4-(furan-2-carbonyl)-2-methyl-1,2,3,4-tetrahydroquinoxalin-1-yl]ethan-1-one;

1-[(2S)-4-(furan-2-carbonyl)-2-methyl-6-(phenylamino)-1,2,3,4-tetrahydroquinoxalin-1-yl]ethan-1-one;

1-[(2S)-4-(furan-2-carbonyl)-2-methyl-6-[methyl(phenyl)amino]-1,2,3,4-tetrahydroquinoxalin-1-yl]ethan-1-one;

1-[(2S)-4-(furan-2-carbonyl)-2-methyl-6-(pyrrolidin-1-yl)-1,2,3,4-tetrahydroquinoxalin-1-yl]ethan-1-one;

cyclopropylmethyl (3S)-4-acetyl-7-(1-cyclopropyl-1H-pyrazol-4-yl)-3-methyl-1,2,3,4-tetrahydroquinoxaline-1-carboxylate;

cyclopropylmethyl (3S)-4-cyclopropanecarbonyl-7-(1-cyclopropyl-1H-pyrazol-4-yl)-3-methyl-1,2,3,4-tetrahydroquinoxaline-1-carboxylate;

4-cyclopropylmethyl 1-methyl (2S)-6-(1-cyclopropyl-1H-pyrazol-4-yl)-2-methyl-1,2,3,4-tetrahydroquinoxaline-1,4-dicarboxylate;

oxetan-3-yl(3S)-4-acetyl-7-(1-cyclopropyl-1H-pyrazol-4-yl)-3-methyl-1,2,3,4-tetrahydroquinoxaline-1-carboxylate;

oxetan-3-yl(3S)-4-cyclopropanecarbonyl-7-(1-cyclopropyl-1H-pyrazol-4-yl)-3-methyl-1,2,3,4-tetrahydroquinoxaline-1-carboxylate;

1-methyl 4-oxetan-3-yl (2S)-6-(1-cyclopropyl-1H-pyrazol-4-yl)-2-methyl-1,2,3,4-tetrahydroquinoxaline-1,4-dicarboxylate;

oxan-4-yl (3S)-4-acetyl-7-(1-cyclopropyl-1H-pyrazol-4-yl)-3-methyl-1,2,3,4-tetrahydroquinoxaline-1-carboxylate;

oxan-4-yl(3S)-4-cyclopropanecarbonyl-7-(1-cyclopropyl-1H-pyrazol-4-yl)-3-methyl-1,2,3,4-tetrahydroquinoxaline-1-carboxylate;

1-methyl 4-oxan-4-yl(2S)-6-(1-cyclopropyl-1H-pyrazol-4-yl)-2-methyl-1,2,3,4-tetrahydroquinoxaline-1,4-dicarboxylate;

cyclobutyl (3S)-4-acetyl-7-(1-cyclopropyl-1H-pyrazol-4-yl)-3-methyl-1,2,3,4-tetrahydroquinoxaline-1-carboxylate;

cyclobutyl (3S)-4-cyclopropanecarbonyl-7-(1-cyclopropyl-1H-pyrazol-4-yl)-3-methyl-1,2,3,4-tetrahydroquinoxaline-1-carboxylate;

4-cyclobutyl 1-methyl (2S)-6-(1-cyclopropyl-1H-pyrazol-4-yl)-2-methyl-1,2,3,4-tetrahydroquinoxaline-1,4-dicarboxylate;

phenyl (3S)-4-acetyl-7-[1-(2-hydroxy-2-methylpropyl)-1H-pyrazol-4-yl]-3-methyl-1,2,3,4-tetrahydroquinoxaline-1-carboxylate;

pyridin-3-yl (3S)-4-acetyl-7-[1-(2-hydroxy-2-methylpropyl)-1H-pyrazol-4-yl]-3-methyl-1,2,3,4-tetrahydroquinoxaline-1-carboxylate;

1-[(2S)-2-ethyl-4-(furan-2-carbonyl)-6-(4-methanesulfonylphenyl)-1,2,3,4-tetrahydroquinoxalin-1-yl]ethan-1-one;

1-[2-(fluoromethyl)-4-(furan-2-carbonyl)-6-(4-methanesulfonylphenyl)-1,2,3,4-tetrahydroquinoxalin-1-yl]ethan-1-one;

1-[(2S)-4-cyclopropanecarbonyl-6-[4-(ethanesulfonyl)phenyl]-2-methyl-1,2,3,4-tetrahydroquinoxalin-1-yl]ethan-1-one;

1-[(2S)-4-cyclobutanecarbonyl-6-[4-(ethanesulfonyl)phenyl]-2-methyl-1,2,3,4-tetrahydroquinoxalin-1-yl]ethan-1-one;

ethyl (3S)-4-acetyl-7-[4-(ethanesulfonyl)phenyl]-3-methyl-1,2,3,4-tetrahydroquinoxalin-1-carboxylate;

propan-2-yl (3S)-4-acetyl-7-[4-(ethanesulfonyl)phenyl]-3-methyl-1,2,3,4-tetrahydroquinoxaline-1-carboxylate;

1-[(2S)-4-cyclopropanecarbonyl-6-[4-(cyclopropanesulfonyl)phenyl]-2-methyl-1,2,3,4-tetrahydroquinoxalin-1-yl]ethan-1-one;

1-[(2S)-4-cyclobutanecarbonyl-6-[4-(cyclopropanesulfonyl)phenyl]-2-methyl-1,2,3,4-tetrahydroquinoxalin-1-yl]ethan-1-one;

ethyl (3S)-4-acetyl-7-[4-(cyclopropanesulfonyl)phenyl]-3-methyl-1,2,3,4-tetrahydroquinoxaline-1-carboxylate;

propan-2-yl (3S)-4-acetyl-7-[4-(cyclopropanesulfonyl)phenyl]-3-methyl-1,2,3,4-tetrahydroquinoxaline-1-carboxylate;

S-{4-[(2S)-1-acetyl-4-cyclopropanecarbonyl-2-methyl-1,2,3,4-tetrahydroquinoxalin-6-yl]phenyl}-2-hydroxyethan-1-sulfonamido;

S-{4-[(2S)-1-acetyl-4-cyclobutanecarbonyl-2-methyl-1,2,3,4-tetrahydroquinoxalin-6-yl]phenyl}-2-hydroxyethan-1-sulfonamido;

ethyl (3S)-4-acetyl-7-{4-[(2-hydroxyethyl)sulfamoyl]phenyl}-3-methyl-1,2,3,4-tetrahydroquinoxaline-1-carboxylate;

propan-2-yl (3S)-4-acetyl-7-{4-[(2-hydroxyethyl)sulfamoyl]phenyl}-3-methyl-1,2,3,4-tetrahydroquinoxaline-1-carboxylate;

3-[(2S)-1-acetyl-4-cyclopropanecarbonyl-2-methyl-1,2,3,4-tetrahydroquinoxalin-6-yl]benzene-1-sulfonamide;

3-[(2S)-1-acetyl-4-cyclobutanecarbonyl-2-methyl-1,2,3,4-tetrahydroquinoxalin-6-yl]benzene-1-sulfonamide;
ethyl (3S)-4-acetyl-3-methyl-7-(3-sulfamoylphenyl)-1,2,3,4-tetrahydroquinoxalin-1-carboxylate;
propan-2-yl (3S)-4-acetyl-3-methyl-7-(3-sulfamoylphenyl)-1,2,3,4-tetrahydroquinoxalin-1-carboxylate;
N-{3-[(2S)-1-acetyl-4-cyclopropanecarbonyl-2-methyl-1,2,3,4-tetrahydroquinoxalin-6-yl]phenyl}methanesulfonamide;
N-{3-[(2S)-1-acetyl-4-cyclobutanecarbonyl-2-methyl-1,2,3,4-tetrahydroquinoxalin-6-yl]phenyl}methanesulfonamide;
ethyl (3S)-4-acetyl-7-(3-methanesulfonamidophenyl)-3-methyl-1,2,3,4-tetrahydroquinoxalin-1-carboxylate;
3-[(2S)-1-acetyl-4-cyclopropanecarbonyl-2-methyl-1,2,3,4-tetrahydroquinoxalin-6-yl]-N,N-dimethylbenzene-1-sulfonamide;
3-[(2S)-1-acetyl-4-cyclobutanecarbonyl-2-methyl-1,2,3,4-tetrahydroquinoxalin-6-yl]-N,N-dimethylbenzene-1-sulfonamide;
ethyl (3S)-4-acetyl-7-[3-(dimethylsulfamoyl)phenyl]-3-methyl-1,2,3,4-tetrahydroquinoxalin-1-carboxylate;
propan-2-yl (3S)-4-acetyl-7-[3-(dimethylsulfamoyl)phenyl]-3-methyl-1,2,3,4-tetrahydroquinoxaline-1-carboxylate;
1-[(2S)-4-cyclopropanecarbonyl-6-(3-methanesulfonylphenyl)-2-methyl-1,2,3,4-tetrahydroquinoxalin-1-yl]ethan-1-one;
1-[(2S)-4-cyclobutanecarbonyl-6-(3-methanesulfonylphenyl)-2-methyl-1,2,3,4-tetrahydroquinoxalin-1-yl]ethan-1-one;
ethyl (3S)-4-acetyl-7-(3-methanesulfonylphenyl)-3-methyl-1,2,3,4-tetrahydroquinoxalin-1-carboxylate;
propan-2-yl (3S)-4-acetyl-7-(3-methanesulfonylphenyl)-3-methyl-1,2,3,4-tetrahydroquinoxaline-1-carboxylate;
N-{3-[(2S)-1-acetyl-4-cyclopropanecarbonyl-2-methyl-1,2,3,4-tetrahydroquinoxalin-6-yl]phenyl}ethane-1-sulfonamide;
N-{3-[(2S)-1-acetyl-4-cyclobutanecarbonyl-2-methyl-1,2,3,4-tetrahydroquinoxalin-6-yl]phenyl}ethan-1-sulfonamide;
ethyl (3S)-4-acetyl-7-(3-ethanesulfonamidophenyl)-3-methyl-1,2,3,4-tetrahydroquinoxalin-1-carboxylate;
propan-2-yl (3S)-4-acetyl-7-(3-ethanesulfonamidophenyl)-3-methyl-1,2,3,4-tetrahydroquinoxaline-1-carboxylate;
1-[(2S)-4-cyclopropanecarbonyl-2-methyl-6-[4-(morpholin-4-yl)phenyl]-1,2,3,4-tetrahydroquinoxalin-1-yl]ethan-1-one;
1-[(2S)-4-cyclobutanecarbonyl-2-methyl-6-[4-(morpholin-4-yl)phenyl]-1,2,3,4-tetrahydroquinoxalin-1-yl]ethan-1-one;
ethyl (3S)-4-acetyl-3-methyl-7-[4-(morpholin-4-yl)phenyl]-1,2,3,4-tetrahydroquinoxalin-1-carboxylate;
propan-2-yl (3S)-4-acetyl-3-methyl-7-[4-(morpholin-4-yl)phenyl]-1,2,3,4-tetrahydroquinoxaline-1-carboxylate;
1-[(2S)-4-cyclopropanecarbonyl-2-methyl-6-[4-(propane-2-sulfonyl)phenyl]-1,2,3,4-tetrahydroquinoxalin-1-yl]ethan-1-one;
1-[(2S)-4-cyclobutanecarbonyl-2-methyl-6-[4-(propane-2-sulfonyl)phenyl]-1,2,3,4-tetrahydroquinoxalin-1-yl]ethan-1-one;
ethyl (3S)-4-acetyl-3-methyl-7-[4-(propane-2-sulfonyl)phenyl]-1,2,3,4-tetrahydroquinoxalin-1-carboxylate;
propan-2-yl (3S)-4-acetyl-3-methyl-7-[4-(propane-2-sulfonyl)phenyl]-1,2,3,4-tetrahydroquinoxaline-1-carboxylate;
4-[(2S)-1-acetyl-4-cyclopropanecarbonyl-2-methyl-1,2,3,4-tetrahydroquinoxalin-6-yl]benzene-1-sulfonamide;
4-[(2S)-1-acetyl-4-cyclobutanecarbonyl-2-methyl-1,2,3,4-tetrahydroquinoxalin-6-yl]benzene-1-sulfonamide;
ethyl (3S)-4-acetyl-3-methyl-7-(4-sulfamoylphenyl)-1,2,3,4-tetrahydroquinoxalin-1-carboxylate;
propan-2-yl (3S)-4-acetyl-3-methyl-7-(4-sulfamoylphenyl)-1,2,3,4-tetrahydroquinoxalin-1-carboxylate;
1-[(2S)-4-cyclopropanecarbonyl-2-methyl-6-[4-(propane-1-sulfonyl)phenyl]-1,2,3,4-tetrahydroquinoxalin-1-yl]ethan-1-one;
1-[(2S)-4-cyclobutanecarbonyl-2-methyl-6-[4-(propane-1-sulfonyl)phenyl]-1,2,3,4-tetrahydroquinoxalin-1-yl]ethan-1-one;
ethyl (3S)-4-acetyl-3-methyl-7-[4-(propane-1-sulfonyl)phenyl]-1,2,3,4-tetrahydroquinoxaline-1-carboxylate;
propan-2-yl (3S)-4-acetyl-3-methyl-7-[4-(propane-1-sulfonyl)phenyl]-1,2,3,4-tetrahydroquinoxaline-1-carboxylate;
1-[(2S)-4-cyclopropanecarbonyl-6-(4-cyclopropylmethanesulfonylphenyl)-2-methyl-1,2,3,4-tetrahydroquinoxalin-1-yl]ethan-1-one;
1-[(2S)-4-cyclobutanecarbonyl-6-(4-cyclopropylmethanesulfonylphenyl)-2-methyl-1,2,3,4-tetrahydroquinoxalin-1-yl]ethan-1-one;
ethyl (3S)-4-acetyl-7-(4-cyclopropylmethanesulfonylphenyl)-3-methyl-1,2,3,4-tetrahydroquinoxaline-1-carboxylate;
propan-2-yl (3S)-4-acetyl-7-(4-cyclopropylmethanesulfonylphenyl)-3-methyl-1,2,3,4-tetrahydroquinoxaline-1-carboxylate;
1-[(2S)-4-cyclopropanecarbonyl-2-methyl-6-[4-(2-methylpropanesulfonyl)phenyl]-1,2,3,4-tetrahydroquinoxalin-1-yl]ethan-1-one;
1-[(2S)-4-cyclobutanecarbonyl-2-methyl-6-[4-(2-methylpropanesulfonyl)phenyl]-1,2,3,4-tetrahydroquinoxalin-1-yl]ethan-1-one;
ethyl (3S)-4-acetyl-3-methyl-7-[4-(2-methylpropanesulfonyl)phenyl]-1,2,3,4-tetrahydroquinoxaline-1-carboxylate;
propan-2-yl (3S)-4-acetyl-3-methyl-7-[4-(2-methylpropanesulfonyl)phenyl]-1,2,3,4-tetrahydroquinoxaline-1-carboxylate;
1-[(2S)-4-cyclopropanecarbonyl-6-(3-fluoro-4-methanesulfonylphenyl)-2-methyl-1,2,3,4-tetrahydroquinoxalin-1-yl]ethan-1-one;
1-[(2S)-4-cyclobutanecarbonyl-6-(3-fluoro-4-methanesulfonylphenyl)-2-methyl-1,2,3,4-tetrahydroquinoxalin-1-yl]ethan-1-one;
ethyl (3S)-4-acetyl-7-(3-fluoro-4-methanesulfonylphenyl)-3-methyl-1,2,3,4-tetrahydroquinoxaline-1-carboxylate;
propan-2-yl (3S)-4-acetyl-7-(3-fluoro-4-methanesulfonylphenyl)-3-methyl-1,2,3,4-tetrahydroquinoxaline-1-carboxylate;
1-[(2S)-4-cyclopropanecarbonyl-6-[3-(cyclopropanesulfonyl)phenyl]-2-methyl-1,2,3,4-tetrahydroquinoxalin-1-yl]ethan-1-one;
1-[(2S)-4-cyclobutanecarbonyl-6-[3-(cyclopropanesulfonyl)phenyl]-2-methyl-1,2,3,4-tetrahydroquinoxalin-1-yl]ethan-1-one;
ethyl (3S)-4-acetyl-7-[3-(cyclopropanesulfonyl)phenyl]-3-methyl-1,2,3,4-tetrahydroquinoxaline-1-carboxylate;
propan-2-yl (3S)-4-acetyl-7-[3-(cyclopropanesulfonyl)phenyl]-3-methyl-1,2,3,4-tetrahydroquinoxaline-1-carboxylate;
1-[(2S)-4-cyclopropanecarbonyl-6-[3-(ethanesulfonyl)phenyl]-2-methyl-1,2,3,4-tetrahydroquinoxalin-1-yl]ethan-1-one;
1-[(2S)-4-cyclobutanecarbonyl-6-[3-(ethanesulfonyl)phenyl]-2-methyl-1,2,3,4-tetrahydroquinoxalin-1-yl]ethan-1-one;

ethyl (3S)-4-acetyl-7-[3-(ethanesulfonyl)phenyl]-3-methyl-1,2,3,4-tetrahydroquinoxaline-1-carboxylate;

propan-2-yl (3S)-4-acetyl-7-[3-(ethanesulfonyl)phenyl]-3-methyl-1,2,3,4-tetrahydroquinoxaline-1-carboxylate;

1-[(2S)-6-(3-chloro-5-methanesulfonylphenyl)-4-cyclopropanecarbonyl-2-methyl-1,2,3,4-tetrahydroquinoxalin-1-yl]ethan-1-one;

1-[(2S)-6-(3-chloro-5-methanesulfonylphenyl)-4-cyclobutanecarbonyl-2-methyl-1,2,3,4-tetrahydroquinoxalin-1-yl]ethan-1-one;

ethyl (3S)-4-acetyl-7-(3-chloro-5-methanesulfonylphenyl)-3-methyl-1,2,3,4-tetrahydroquinoxaline-1-carboxylate;

propan-2-yl (3S)-4-acetyl-7-(3-chloro-5-methanesulfonylphenyl)-3-methyl-1,2,3,4-tetrahydroquinoxaline-1-carboxylate;

1-[(2S)-4-cyclopropanecarbonyl-6-(4-fluoro-3-methanesulfonylphenyl)-2-methyl-1,2,3,4-tetrahydroquinoxalin-1-yl]ethan-1-one;

1-[(2S)-4-cyclobutanecarbonyl-6-(4-fluoro-3-methanesulfonylphenyl)-2-methyl-1,2,3,4-tetrahydroquinoxalin-1-yl]ethan-1-one;

ethyl (3S)-4-acetyl-7-(4-fluoro-3-methanesulfonylphenyl)-3-methyl-1,2,3,4-tetrahydroquinoxaline-1-carboxylate;

propan-2-yl (3S)-4-acetyl-7-(4-fluoro-3-methanesulfonylphenyl)-3-methyl-1,2,3,4-tetrahydroquinoxaline-1-carboxylate;

ethyl (3S)-4-acetyl-7-[4-(2-methanesulfonylethoxy)phenyl]-3-methyl-1,2,3,4-tetrahydroquinoxaline-1-carboxylate;

propan-2-yl (3S)-4-acetyl-7-[4-(2-methanesulfonylethoxy)phenyl]-3-methyl-1,2,3,4-tetrahydroquinoxaline-1-carboxylate;

3-[(2S)-1-acetyl-4-cyclopropanecarbonyl-2-methyl-1,2,3,4-tetrahydroquinoxalin-6-yl]-N-methylbenzene-1-sulfonamide;

3-[(2S)-1-acetyl-4-cyclobutanecarbonyl-2-methyl-1,2,3,4-tetrahydroquinoxalin-6-yl]-N-methylbenzene-1-sulfonamide;

ethyl (3S)-4-acetyl-3-methyl-7-[3-(methylsulfamoyl)phenyl]-1,2,3,4-tetrahydroquinoxaline-1-carboxylate;

propan-2-yl (3S)-4-acetyl-3-methyl-7-[3-(methylsulfamoyl)phenyl]-1,2,3,4-tetrahydroquinoxaline-1-carboxylate;

S-{3-[(2S)-1-acetyl-4-cyclopropanecarbonyl-2-methyl-1,2,3,4-tetrahydroquinoxalin-6-yl]phenyl}-2-hydroxyethan-1-sulfonamido;

S-{3-[(2S)-1-acetyl-4-cyclobutanecarbonyl-2-methyl-1,2,3,4-tetrahydroquinoxalin-6-yl]phenyl}-2-hydroxyethan-1-sulfonamido;

ethyl (3S)-4-acetyl-7-{3-[(2-hydroxyethyl)sulfamoyl]phenyl}-3-methyl-1,2,3,4-tetrahydroquinoxaline-1-carboxylate;

propan-2-yl (3S)-4-acetyl-7-{3-[(2-hydroxyethyl)sulfamoyl]phenyl}-3-methyl-1,2,3,4-tetrahydroquinoxaline-1-carboxylate;

5-[(2S)-1-acetyl-4-cyclopropanecarbonyl-2-methyl-1,2,3,4-tetrahydroquinoxalin-6-yl]-N,N-diethyl-2-methoxybenzene-1-sulfonamide;

5-[(2S)-1-acetyl-4-cyclobutanecarbonyl-2-methyl-1,2,3,4-tetrahydroquinoxalin-6-yl]-N,N-diethyl-2-methoxybenzene-1-sulfonamide;

ethyl (3S)-4-acetyl-7-[3-(diethylsulfamoyl)-4-methoxyphenyl]-3-methyl-1,2,3,4-tetrahydroquinoxaline-1-carboxylate;

propan-2-yl (3S)-4-acetyl-7-[3-(diethylsulfamoyl)-4-methoxyphenyl]-3-methyl-1,2,3,4-tetrahydroquinoxaline-1-carboxylate;

1-[(2S)-4-cyclobutanecarbonyl-2-methyl-6-[4-(1H-pyrazol-1-sulfonyl)phenyl]-1,2,3,4-tetrahydroquinoxalin-1-yl]ethan-1-one;

ethyl (3S)-4-acetyl-3-methyl-7-[4-(1H-pyrazol-1-sulfonyl)phenyl]-1,2,3,4-tetrahydroquinoxaline-1-carboxylate;

propan-2-yl (3S)-4-acetyl-3-methyl-7-[4-(1H-pyrazol-1-sulfonyl)phenyl]-1,2,3,4-tetrahydroquinoxaline-1-carboxylate;

4-[(2S)-1-acetyl-4-cyclopropanecarbonyl-2-methyl-1,2,3,4-tetrahydroquinoxalin-6-yl]-N-methylbenzene-1-sulfonamide;

4-[(2S)-1-acetyl-4-cyclobutanecarbonyl-2-methyl-1,2,3,4-tetrahydroquinoxalin-6-yl]-N-methylbenzene-1-sulfonamide;

ethyl (3S)-4-acetyl-3-methyl-7-[4-(methylsulfamoyl)phenyl]-1,2,3,4-tetrahydroquinoxaline-1-carboxylate;

propan-2-yl (3S)-4-acetyl-3-methyl-7-[4-(methylsulfamoyl)phenyl]-1,2,3,4-tetrahydroquinoxaline-1-carboxylate;

4-[(2S)-1-acetyl-4-cyclopropanecarbonyl-2-methyl-1,2,3,4-tetrahydroquinoxalin-6-yl]-N,N-dimethylbenzene-1-sulfonamide;

4-[(2S)-1-acetyl-4-cyclobutanecarbonyl-2-methyl-1,2,3,4-tetrahydroquinoxalin-6-yl]-N,N-dimethylbenzene-1-sulfonamide;

ethyl (3S)-4-acetyl-7-[4-(dimethylsulfamoyl)phenyl]-3-methyl-1,2,3,4-tetrahydroquinoxaline-1-carboxylate;

propan-2-yl (3S)-4-acetyl-7-[4-(dimethylsulfamoyl)phenyl]-3-methyl-1,2,3,4-tetrahydroquinoxaline-1-carboxylate;

4-[(2S)-1-acetyl-4-cyclopropanecarbonyl-2-methyl-1,2,3,4-tetrahydroquinoxalin-6-yl]-N-tert-butylbenzene-1-sulfonamide;

4-[(2S)-1-acetyl-4-cyclobutanecarbonyl-2-methyl-1,2,3,4-tetrahydroquinoxalin-6-yl]-N-tert-butylbenzene-1-sulfonamide;

ethyl (3S)-4-acetyl-7-[4-(tert-butylsulfamoyl)phenyl]-3-methyl-1,2,3,4-tetrahydroquinoxaline-1-carboxylate;

propan-2-yl (3S)-4-acetyl-7-[4-(tert-butylsulfamoyl)phenyl]-3-methyl-1,2,3,4-tetrahydroquinoxaline-1-carboxylate;

1-{4-[(2S)-1-acetyl-4-cyclopropanecarbonyl-2-methyl-1,2,3,4-tetrahydroquinoxalin-6-yl]phenyl}pyrrolidin-2-one;

1-{4-[(2S)-1-acetyl-4-cyclobutanecarbonyl-2-methyl-1,2,3,4-tetrahydroquinoxalin-6-yl]phenyl}pyrrolidin-2-one;

ethyl (3S)-4-acetyl-3-methyl-7-[4-(2-oxopyrrolidin-1-yl)phenyl]-1,2,3,4-tetrahydroquinoxaline-1-carboxylate;

propan-2-yl (3S)-4-acetyl-3-methyl-7-[4-(2-oxopyrrolidin-1-yl)phenyl]-1,2,3,4-tetrahydroquinoxaline-1-carboxylate;

N-{4-[(2S)-1-acetyl-4-cyclopropanecarbonyl-2-methyl-1,2,3,4-tetrahydroquinoxalin-6-yl]phenyl}ethan-1-sulfonamide;

N-{4-[(2S)-1-acetyl-4-cyclobutanecarbonyl-2-methyl-1,2,3,4-tetrahydroquinoxalin-6-yl]phenyl}ethan-1-sulfonamide;

ethyl (3S)-4-acetyl-7-(4-ethanesulfonamidophenyl)-3-methyl-1,2,3,4-tetrahydroquinoxaline-1-carboxylate;

propan-2-yl (3S)-4-acetyl-7-(4-ethanesulfonamidophenyl)-3-methyl-1,2,3,4-tetrahydroquinoxaline-1-carboxylate;

N-{5-[(2S)-1-acetyl-4-cyclopropanecarbonyl-2-methyl-1,2,3,4-tetrahydroquinoxalin-6-yl]-2-methoxyphenyl}methanesulfonamide;

N-{5-[(2S)-1-acetyl-4-cyclobutanecarbonyl-2-methyl-1,2,3,4-tetrahydroquinoxalin-6-yl]-2-methoxyphenyl}methanesulfonamide;

ethyl (3S)-4-acetyl-7-(3-methanesulfonamido-4-methoxyphenyl)-3-methyl-1,2,3,4-tetrahydroquinoxaline-1-carboxylate;
propan-2-yl (3S)-4-acetyl-7-(3-methanesulfonamido-4-methoxyphenyl)-3-methyl-1,2,3,4-tetrahydroquinoxaline-1-carboxylate;
1-[(2S)-4-cyclopropanecarbonyl-6-{3-[(dimethylsulfamoyl)amino]phenyl}-2-methyl-1,2,3,4-tetrahydroquinoxalin-1-yl]ethan-1-one;
1-[(2S)-4-cyclobutanecarbonyl-6-{3-[(dimethylsulfamoyl)amino]phenyl}-2-methyl-1,2,3,4-tetrahydroquinoxalin-1-yl]ethan-1-one;
ethyl (3S)-4-acetyl-7-{3-[(dimethylsulfamoyl)amino]phenyl}-3-methyl-1,2,3,4-tetrahydroquinoxaline-1-carboxylate;
propan-2-yl (3S)-4-acetyl-7-{3-[(dimethylsulfamoyl)amino]phenyl}-3-methyl-1,2,3,4-tetrahydroquinoxaline-1-carboxylate;
cyclopentyl (3S)-4-acetyl-3-methyl-7-[1-(oxan-4-yl)-1H-pyrazol-4-yl]-1,2,3,4-tetrahydroquinoxaline-1-carboxylate;
cyclopentyl (3S)-4-acetyl-7-[1-(1,1-dioxo-1$\lambda^6$-thian-3-yl)-1H-pyrazol-4-yl]-3-methyl-1,2,3,4-tetrahydroquinoxaline-1-carboxylate;
2-{3-[(2S)-1-acetyl-4-cyclopropanecarbonyl-2-methyl-1,2,3,4-tetrahydroquinoxalin-6-yl]phenyl}-1$\lambda^6$,2-thiazolidine-1,1-dione;
propan-2-yl (3S)-4-acetyl-7-[3-(1,1-dioxo-1$\lambda^6$,2-thiazolidin-2-yl)phenyl]-3-methyl-1,2,3,4-tetrahydroquinoxaline-1-carboxylate;
2-{4-[(2S)-1-acetyl-4-cyclobutanecarbonyl-2-methyl-1,2,3,4-tetrahydroquinoxalin-6-yl]-2-fluorophenyl}-1$\lambda^6$,2-thiazolidine-1,1-dione;
ethyl (3S)-4-acetyl-7-[4-(1,1-dioxo-1$\lambda^6$,2-thiazolidin-2-yl)-3-fluorophenyl]-3-methyl-1,2,3,4-tetrahydroquinoxaline-1-carboxylate;
propan-2-yl (3S)-4-acetyl-7-[4-(1,1-dioxo-1$\lambda^6$,2-thiazolidin-2-yl)-3-fluorophenyl]-3-methyl-1,2,3,4-tetrahydroquinoxaline-1-carboxylate;
1-[(2S)-4-cyclopropanecarbonyl-6-(1-methanesulfonyl-1,2,3,4-tetrahydroquinolin-6-yl)-2-methyl-1,2,3,4-tetrahydroquinoxalin-1-yl]ethan-1-one;
1-[(2S)-4-cyclobutanecarbonyl-6-(1-methanesulfonyl-1,2,3,4-tetrahydroquinolin-6-yl)-2-methyl-1,2,3,4-tetrahydroquinoxalin-1-yl]ethan-1-one;
ethyl (3S)-4-acetyl-7-(1-methanesulfonyl-1,2,3,4-tetrahydroquinolin-6-yl)-3-methyl-1,2,3,4-tetrahydroquinoxaline-1-carboxylate;
propan-2-yl (3S)-4-acetyl-7-(1-methanesulfonyl-1,2,3,4-tetrahydroquinolin-6-yl)-3-methyl-1,2,3,4-tetrahydroquinoxaline-1-carboxylate;
2-{3-[(2S)-1-acetyl-4-cyclobutanecarbonyl-2-methyl-1,2,3,4-tetrahydroquinoxalin-6-yl]phenyl}-1$\lambda^6$,2-thiazolidine-1,1-dione;
ethyl (3S)-4-acetyl-7-[3-(1,1-dioxo-1$\lambda^6$,2-thiazolidin-2-yl)phenyl]-3-methyl-1,2,3,4-tetrahydroquinoxaline-1-carboxylate;
2-{3-[(2S)-1-acetyl-4-cyclopropanecarbonyl-2-methyl-1,2,3,4-tetrahydroquinoxalin-6-yl]-5-(trifluoromethyl)phenyl}-1$\lambda^6$,2-thiazolidine-1,1-dione;
2-{3-[(2S)-1-acetyl-4-cyclobutanecarbonyl-2-methyl-1,2,3,4-tetrahydroquinoxalin-6-yl]-5-(trifluoromethyl)phenyl}-1$\lambda^6$,2-thiazolidine-1,1-dione;
ethyl (3S)-4-acetyl-7-[3-(1,1-dioxo-1$\lambda^6$,2-thiazolidin-2-yl)-5-(trifluoromethyl)phenyl]-3-methyl-1,2,3,4-tetrahydroquinoxaline-1-carboxylate;
propan-2-yl (3S)-4-acetyl-7-[3-(1,1-dioxo-1$\lambda^6$,2-thiazolidin-2-yl)-5-(trifluoromethyl)phenyl]-3-methyl-1,2,3,4-tetrahydroquinoxaline-1-carboxylate;
2-{5-[(2S)-1-acetyl-4-cyclopropanecarbonyl-2-methyl-1,2,3,4-tetrahydroquinoxalin-6-yl]-2-methoxyphenyl}-1$\lambda^6$,2-thiazolidine-1,1-dione;
2-{5-[(2S)-1-acetyl-4-cyclobutanecarbonyl-2-methyl-1,2,3,4-tetrahydroquinoxalin-6-yl]-2-methoxyphenyl}-1$\lambda^6$,2-thiazolidine-1,1-dione;
ethyl (3S)-4-acetyl-7-[3-(1,1-dioxo-1$\lambda^6$,2-thiazolidin-2-yl)-4-methoxyphenyl]-3-methyl-1,2,3,4-tetrahydroquinoxaline-1-carboxylate;
propan-2-yl (3S)-4-acetyl-7-[3-(1,1-dioxo-1$\lambda^6$,2-thiazolidin-2-yl)-4-methoxyphenyl]-3-methyl-1,2,3,4-tetrahydroquinoxaline-1-carboxylate;
N-{4-[(2S)-1-acetyl-4-cyclopropanecarbonyl-2-methyl-1,2,3,4-tetrahydroquinoxalin-6-yl]-2-methylphenyl}methanesulfonamide;
N-{4-[(2S)-1-acetyl-4-cyclobutanecarbonyl-2-methyl-1,2,3,4-tetrahydroquinoxalin-6-yl]-2-methylphenyl}methanesulfonamide;
ethyl (3S)-4-acetyl-7-(4-methanesulfonamido-3-methylphenyl)-3-methyl-1,2,3,4-tetrahydroquinoxaline-1-carboxylate;
propan-2-yl (3S)-4-acetyl-7-(4-methanesulfonamido-3-methylphenyl)-3-methyl-1,2,3,4-tetrahydroquinoxaline-1-carboxylate;
6-[(2S)-1-acetyl-4-cyclopropanecarbonyl-2-methyl-1,2,3,4-tetrahydroquinoxalin-6-yl]-1-methyl-1,3-dihydro-2$\lambda^6$,1,3-benzothiadiazole-2,2-dione;
6-[(2S)-1-acetyl-4-cyclobutanecarbonyl-2-methyl-1,2,3,4-tetrahydroquinoxalin-6-yl]-1-methyl-1,3-dihydro-2$\lambda^6$,1,3-benzothiadiazole-2,2-dione;
propan-2-yl (3S)-4-acetyl-3-methyl-7-(3-methyl-2,2-dioxo-1,3-dihydro-2$\lambda^6$,1,3-benzothiadiazol-5-yl)-1,2,3,4-tetrahydroquinoxaline-1-carboxylate;
5-[(2S)-1-acetyl-4-cyclopropanecarbonyl-2-methyl-1,2,3,4-tetrahydroquinoxalin-6-yl]-1,3-dihydro-2$\lambda^6$,1-benzothiazole-2,2-dione;
propan-2-yl (3S)-4-acetyl-7-(2,2-dioxo-1,3-dihydro-2$\lambda^6$,1-benzothiazol-5-yl)-3-methyl-1,2,3,4-tetrahydroquinoxaline-1-carboxylate;
N-{4-[(2S)-1-acetyl-4-cyclopropanecarbonyl-2-methyl-1,2,3,4-tetrahydroquinoxalin-6-yl]-2-fluorophenyl}methanesulfonamide;
N-{4-[(2S)-1-acetyl-4-cyclobutanecarbonyl-2-methyl-1,2,3,4-tetrahydroquinoxalin-6-yl]-2-fluorophenyl}methanesulfonamide;
ethyl (3S)-4-acetyl-7-(3-fluoro-4-methanesulfonamidophenyl)-3-methyl-1,2,3,4-tetrahydroquinoxaline-1-carboxylate;
propan-2-yl (3S)-4-acetyl-7-(3-fluoro-4-methanesulfonamidophenyl)-3-methyl-1,2,3,4-tetrahydroquinoxaline-1-carboxylate;
1-[(2S)-4-cyclopropanecarbonyl-6-(1-methanesulfonyl-1,2,3,4-tetrahydroquinolin-7-yl)-2-methyl-1,2,3,4-tetrahydroquinoxalin-1-yl]ethan-1-one;
propan-2-yl (3S)-4-acetyl-7-(1-methanesulfonyl-1,2,3,4-tetrahydroquinolin-7-yl)-3-methyl-1,2,3,4-tetrahydroquinoxaline-1-carboxylate;
5-chloropyridin-3-yl (3S)-4-acetyl-7-(1-cyclopropyl-1H-pyrazol-4-yl)-3-methyl-1,2,3,4-tetrahydroquinoxaline-1-carboxylate;
3-(trifluoromethyl)pyridin-2-yl (3S)-4-acetyl-7-(1-cyclopropyl-1H-pyrazol-4-yl)-3-methyl-1,2,3,4-tetrahydroquinoxaline-1-carboxylate;

5-fluoropyridin-3-yl (3S)-4-acetyl-7-(1-cyclopropyl-1H-pyrazol-4-yl)-3-methyl-1,2,3,4-tetrahydroquinoxaline-1-carboxylate;
2,6-dimethylpyridin-3-yl (3S)-4-acetyl-7-(1-cyclopropyl-1H-pyrazol-4-yl)-3-methyl-1,2,3,4-tetrahydroquinoxaline-1-carboxylate;
quinolin-5-yl (3S)-4-acetyl-7-(1-cyclopropyl-1H-pyrazol-4-yl)-3-methyl-1,2,3,4-tetrahydroquinoxaline-1-carboxylate;
isoquinolin-6-yl (3S)-4-acetyl-7-(1-cyclopropyl-1H-pyrazol-4-yl)-3-methyl-1,2,3,4-tetrahydroquinoxaline-1-carboxylate;
5-chloro-2-methoxypyridin-3-yl (3S)-4-acetyl-7-(1-cyclopropyl-1H-pyrazol-4-yl)-3-methyl-1,2,3,4-tetrahydroquinoxaline-1-carboxylate;
5-fluoro-2-methoxypyridin-3-yl (3S)-4-acetyl-7-(1-cyclopropyl-1H-pyrazol-4-yl)-3-methyl-1,2,3,4-tetrahydroquinoxaline-1-carboxylate;
5-chloro-2-methoxypyridin-4-yl (3S)-4-acetyl-7-(1-cyclopropyl-1H-pyrazol-4-yl)-3-methyl-1,2,3,4-tetrahydroquinoxaline-1-carboxylate;
2-methoxy-5-methylpyridin-3-yl (3S)-4-acetyl-7-(1-cyclopropyl-1H-pyrazol-4-yl)-3-methyl-1,2,3,4-tetrahydroquinoxaline-1-carboxylate;
4-fluoro-2-methoxyphenyl (3S)-4-acetyl-7-(1-cyclopropyl-1H-pyrazol-4-yl)-3-methyl-1,2,3,4-tetrahydroquinoxaline-1-carboxylate;
2,4-dichlorophenyl (3S)-4-acetyl-7-(1-cyclopropyl-1H-pyrazol-4-yl)-3-methyl-1,2,3,4-tetrahydroquinoxaline-1-carboxylate;
4-(1H-1,2,4-triazol-1-yl)phenyl (3S)-4-acetyl-7-(1-cyclopropyl-1H-pyrazol-4-yl)-3-methyl-1,2,3,4-tetrahydroquinoxaline-1-carboxylate;
quinolin-8-yl (3S)-4-acetyl-7-(1-cyclopropyl-1H-pyrazol-4-yl)-3-methyl-1,2,3,4-tetrahydroquinoxaline-1-carboxylate;
5-chloroquinolin-8-yl (3S)-4-acetyl-7-(1-cyclopropyl-1H-pyrazol-4-yl)-3-methyl-1,2,3,4-tetrahydroquinoxaline-1-carboxylate;
5,7-dichloroquinolin-8-yl(3S)-4-acetyl-7-(1-cyclopropyl-1H-pyrazol-4-yl)-3-methyl-1,2,3,4-tetrahydroquinoxaline-1-carboxylate;
2-fluoro-5-methylphenyl (3S)-4-acetyl-7-(1-cyclopropyl-1H-pyrazol-4-yl)-3-methyl-1,2,3,4-tetrahydroquinoxaline-1-carboxylate;
6-methoxypyridin-3-yl (3S)-4-acetyl-7-(1-cyclopropyl-1H-pyrazol-4-yl)-3-methyl-1,2,3,4-tetrahydroquinoxaline-1-carboxylate;
5-fluoro-2-methylphenyl (3S)-4-acetyl-7-(1-cyclopropyl-1H-pyrazol-4-yl)-3-methyl-1,2,3,4-tetrahydroquinoxaline-1-carboxylate;
5-fluoro-2-methoxyphenyl (3S)-4-acetyl-7-(1-cyclopropyl-1H-pyrazol-4-yl)-3-methyl-1,2,3,4-tetrahydroquinoxaline-1-carboxylate;
quinolin-7-yl(3S)-4-acetyl-7-(1-cyclopropyl-1H-pyrazol-4-yl)-3-methyl-1,2,3,4-tetrahydroquinoxaline-1-carboxylate;
quinolin-3-yl (3S)-4-acetyl-7-(1-cyclopropyl-1H-pyrazol-4-yl)-3-methyl-1,2,3,4-tetrahydroquinoxaline-1-carboxylate;
quinoxalin-5-yl (3S)-4-acetyl-7-(1-cyclopropyl-1H-pyrazol-4-yl)-3-methyl-1,2,3,4-tetrahydroquinoxaline-1-carboxylate;
1-methyl-1H-1,3-benzodiazol-5-yl (3S)-4-acetyl-7-(1-cyclopropyl-1H-pyrazol-4-yl)-3-methyl-1,2,3,4-tetrahydroquinoxaline-1-carboxylate;
isoquinolin-7-yl(3S)-4-acetyl-7-(1-cyclopropyl-1H-pyrazol-4-yl)-3-methyl-1,2,3,4-tetrahydroquinoxaline-1-carboxylate;
cyclohexyl (3S)-4-acetyl-7-[4-(ethanesulfonyl)phenyl]-3-methyl-1,2,3,4-tetrahydroquinoxaline-1-carboxylate;
oxan-4-yl (3S)-4-acetyl-7-[4-(ethanesulfonyl)phenyl]-3-methyl-1,2,3,4-tetrahydroquinoxaline-1-carboxylate;
cyclohexyl (3S)-4-acetyl-7-[4-(cyclopropanesulfonyl)phenyl]-3-methyl-1,2,3,4-tetrahydroquinoxaline-1-carboxylate;
oxan-4-yl (3S)-4-acetyl-7-[4-(cyclopropanesulfonyl)phenyl]-3-methyl-1,2,3,4-tetrahydroquinoxaline-1-carboxylate;
cyclohexyl (3S)-4-acetyl-7-{4-[(2-hydroxyethyl)sulfamoyl]phenyl}-3-methyl-1,2,3,4-tetrahydroquinoxaline-1-carboxylate;
oxan-4-yl (3S)-4-acetyl-7-{4-[(2-hydroxyethyl)sulfamoyl]phenyl}-3-methyl-1,2,3,4-tetrahydroquinoxaline-1-carboxylate;
cyclohexyl (3S)-4-acetyl-3-methyl-7-(3-sulfamoylphenyl)-1,2,3,4-tetrahydroquinoxalin-1-carboxylate;
oxan-4-yl (3S)-4-acetyl-3-methyl-7-(3-sulfamoylphenyl)-1,2,3,4-tetrahydroquinoxalin-1-carboxylate;
cyclohexyl (3S)-4-acetyl-7-(3-methanesulfonamidophenyl)-3-methyl-1,2,3,4-tetrahydroquinoxaline-1-carboxylate;
oxan-4-yl (3S)-4-acetyl-7-(3-methanesulfonamidophenyl)-3-methyl-1,2,3,4-tetrahydroquinoxaline-1-carboxylate;
cyclohexyl (3S)-4-acetyl-7-[3-(dimethylsulfamoyl)phenyl]-3-methyl-1,2,3,4-tetrahydroquinoxaline-1-carboxylate;
oxan-4-yl (3S)-4-acetyl-7-[3-(dimethylsulfamoyl)phenyl]-3-methyl-1,2,3,4-tetrahydroquinoxaline-1-carboxylate;
cyclohexyl (3S)-4-acetyl-7-(3-methanesulfonylphenyl)-3-methyl-1,2,3,4-tetrahydroquinoxaline-1-carboxylate;
oxan-4-yl (3S)-4-acetyl-7-(3-methanesulfonylphenyl)-3-methyl-1,2,3,4-tetrahydroquinoxalin-1-carboxylate;
cyclohexyl (3S)-4-acetyl-7-(3-ethanesulfonamidophenyl)-3-methyl-1,2,3,4-tetrahydroquinoxaline-1-carboxylate;
oxan-4-yl (3S)-4-acetyl-7-(3-ethanesulfonamidophenyl)-3-methyl-1,2,3,4-tetrahydroquinoxaline-1-carboxylate;
cyclohexyl (3S)-4-acetyl-3-methyl-7-[4-(morpholin-4-yl)phenyl]-1,2,3,4-tetrahydroquinoxaline-1-carboxylate;
oxan-4-yl(3S)-4-acetyl-3-methyl-7-[4-(morpholin-4-yl)phenyl]-1,2,3,4-tetrahydroquinoxaline-1-carboxylate;
cyclohexyl (3S)-4-acetyl-3-methyl-7-[4-(propane-2-sulfonyl)phenyl]-1,2,3,4-tetrahydroquinoxaline-1-carboxylate;
oxan-4-yl(3S)-4-acetyl-3-methyl-7-[4-(propane-2-sulfonyl)phenyl]-1,2,3,4-tetrahydroquinoxaline-1-carboxylate;
cyclohexyl (3S)-4-acetyl-3-methyl-7-(4-sulfamoylphenyl)-1,2,3,4-tetrahydroquinoxalin-1-carboxylate;
oxan-4-yl (3S)-4-acetyl-3-methyl-7-(4-sulfamoylphenyl)-1,2,3,4-tetrahydroquinoxalin-1-carboxylate;
cyclohexyl (3S)-4-acetyl-3-methyl-7-[4-(propane-1-sulfonyl)phenyl]-1,2,3,4-tetrahydroquinoxaline-1-carboxylate;
oxan-4-yl(3S)-4-acetyl-3-methyl-7-[4-(propane-1-sulfonyl)phenyl]-1,2,3,4-tetrahydroquinoxaline-1-carboxylate;
cyclohexyl (3S)-4-acetyl-7-(4-cyclopropylmethanesulfonylphenyl)-3-methyl-1,2,3,4-tetrahydroquinoxaline-1-carboxylate;
oxan-4-yl (3S)-4-acetyl-7-(4-cyclopropylmethanesulfonylphenyl)-3-methyl-1,2,3,4-tetrahydroquinoxaline-1-carboxylate;
cyclohexyl (3S)-4-acetyl-3-methyl-7-[4-(2-methylpropanesulfonyl)phenyl]-1,2,3,4-tetrahydroquinoxaline-1-carboxylate;
oxan-4-yl(3S)-4-acetyl-3-methyl-7-[4-(2-methylpropanesulfonyl)phenyl]-1,2,3,4-tetrahydroquinoxaline-1-carboxylate;

cyclohexyl (3S)-4-acetyl-7-(3-fluoro-4-methanesulfonylphenyl)-3-methyl-1,2,3,4-tetrahydroquinoxaline-1-carboxylate;
oxan-4-yl (3S)-4-acetyl-7-(3-fluoro-4-methanesulfonylphenyl)-3-methyl-1,2,3,4-tetrahydroquinoxaline-1-carboxylate;
cyclohexyl (3S)-4-acetyl-7-[3-(cyclopropanesulfonyl)phenyl]-3-methyl-1,2,3,4-tetrahydroquinoxaline-1-carboxylate;
oxan-4-yl(3S)-4-acetyl-7-[3-(cyclopropanesulfonyl)phenyl]-3-methyl-1,2,3,4-tetrahydroquinoxaline-1-carboxylate;
cyclohexyl (3S)-4-acetyl-7-[3-(ethanesulfonyl)phenyl]-3-methyl-1,2,3,4-tetrahydroquinoxaline-1-carboxylate;
oxan-4-yl (3S)-4-acetyl-7-[3-(ethanesulfonyl)phenyl]-3-methyl-1,2,3,4-tetrahydroquinoxaline-1-carboxylate;
cyclohexyl (3S)-4-acetyl-7-(3-chloro-5-methanesulfonylphenyl)-3-methyl-1,2,3,4-tetrahydroquinoxaline-1-carboxylate;
oxan-4-yl (3S)-4-acetyl-7-(3-chloro-5-methanesulfonylphenyl)-3-methyl-1,2,3,4-tetrahydroquinoxaline-1-carboxylate;
cyclohexyl (3S)-4-acetyl-7-(4-fluoro-3-methanesulfonylphenyl)-3-methyl-1,2,3,4-tetrahydroquinoxaline-1-carboxylate;
oxan-4-yl (3S)-4-acetyl-7-(4-fluoro-3-methanesulfonylphenyl)-3-methyl-1,2,3,4-tetrahydroquinoxaline-1-carboxylate;
cyclohexyl (3S)-4-acetyl-7-[4-(2-methanesulfonylethoxyl)phenyl]-3-methyl-1,2,3,4-tetrahydroquinoxaline-1-carboxylate;
oxan-4-yl(3S)-4-acetyl-7-[4-(2-methanesulfonylethoxyl)phenyl]-3-methyl-1,2,3,4-tetrahydroquinoxaline-1-carboxylate;
cyclohexyl (3S)-4-acetyl-3-methyl-7-[3-(methylsulfamoyl)phenyl]-1,2,3,4-tetrahydroquinoxaline-1-carboxylate;
oxan-4-yl(3S)-4-acetyl-3-methyl-7-[3-(methylsulfamoyl)phenyl]-1,2,3,4-tetrahydroquinoxaline-1-carboxylate;
cyclohexyl (3S)-4-acetyl-7-{3-[(2-hydroxyethyl)sulfamoyl]phenyl}-3-methyl-1,2,3,4-tetrahydroquinoxaline-1-carboxylate;
oxan-4-yl (3S)-4-acetyl-7-{3-[(2-hydroxyethyl)sulfamoyl]phenyl}-3-methyl-1,2,3,4-tetrahydroquinoxaline-1-carboxylate;
cyclohexyl (3S)-4-acetyl-7-[3-(diethylsulfamoyl)-4-methoxyphenyl]-3-methyl-1,2,3,4-tetrahydroquinoxaline-1-carboxylate;
oxan-4-yl (3S)-4-acetyl-7-[3-(diethylsulfamoyl)-4-methoxyphenyl]-3-methyl-1,2,3,4-tetrahydroquinoxaline-1-carboxylate;
cyclohexyl (3S)-4-acetyl-3-methyl-7-[4-(1H-pyrazol-1-sulfonyl)phenyl]-1,2,3,4-tetrahydroquinoxaline-1-carboxylate;
oxan-4-yl (3S)-4-acetyl-3-methyl-7-[4-(1H-pyrazol-1-sulfonyl)phenyl]-1,2,3,4-tetrahydroquinoxaline-1-carboxylate;
cyclohexyl (3S)-4-acetyl-3-methyl-7-[4-(methylsulfamoyl)phenyl]-1,2,3,4-tetrahydroquinoxaline-1-carboxylate;
oxan-4-yl (3S)-4-acetyl-3-methyl-7-[4-(methylsulfamoyl)phenyl]-1,2,3,4-tetrahydroquinoxaline-1-carboxylate;
cyclohexyl (3S)-4-acetyl-7-[4-(dimethylsulfamoyl)phenyl]-3-methyl-1,2,3,4-tetrahydroquinoxaline-1-carboxylate;
oxan-4-yl (3S)-4-acetyl-7-[4-(dimethylsulfamoyl)phenyl]-3-methyl-1,2,3,4-tetrahydroquinoxaline-1-carboxylate;
cyclohexyl (3S)-4-acetyl-7-[4-(tert-butylsulfamoyl)phenyl]-3-methyl-1,2,3,4-tetrahydroquinoxaline-1-carboxylate;
oxan-4-yl (3S)-4-acetyl-7-[4-(tert-butylsulfamoyl)phenyl]-3-methyl-1,2,3,4-tetrahydroquinoxaline-1-carboxylate;
cyclohexyl (3S)-4-acetyl-3-methyl-7-[4-(2-oxopyrrolidin-1-yl)phenyl]-1,2,3,4-tetrahydroquinoxaline-1-carboxylate;
oxan-4-yl (3S)-4-acetyl-3-methyl-7-[4-(2-oxopyrrolidin-1-yl)phenyl]-1,2,3,4-tetrahydroquinoxaline-1-carboxylate;
cyclohexyl (3S)-4-acetyl-7-(4-ethanesulfonamidophenyl)-3-methyl-1,2,3,4-tetrahydroquinoxaline-1-carboxylate;
oxan-4-yl (3S)-4-acetyl-7-(4-ethanesulfonamidophenyl)-3-methyl-1,2,3,4-tetrahydroquinoxaline-1-carboxylate;
cyclohexyl (3S)-4-acetyl-7-(3-methanesulfonamido-4-methoxyphenyl)-3-methyl-1,2,3,4-tetrahydroquinoxaline-1-carboxylate;
oxan-4-yl (3S)-4-acetyl-7-(3-methanesulfonamido-4-methoxyphenyl)-3-methyl-1,2,3,4-tetrahydroquinoxaline-1-carboxylate;
cyclohexyl (3S)-4-acetyl-7-{3-[(dimethylsulfamoyl)amino]phenyl}-3-methyl-1,2,3,4-tetrahydroquinoxaline-1-carboxylate;
oxan-4-yl (3S)-4-acetyl-7-{3-[(dimethylsulfamoyl)amino]phenyl}-3-methyl-1,2,3,4-tetrahydroquinoxaline-1-carboxylate;
propan-2-yl (3S)-4-acetyl-7-(4-cyclopropanesulfonamidophenyl)-3-methyl-1,2,3,4-tetrahydroquinoxaline-1-carboxylate;
N-{4-[(2S)-1-acetyl-4-cyclopropanecarbonyl-2-methyl-1,2,3,4-tetrahydroquinoxalin-6-yl]phenyl}cyclopropanesulfonamide;
1-[(2S)-4-cyclopropanecarbonyl-6-(1-methanesulfonyl-2,3-dihydro-1H-indol-5-yl)-2-methyl-1,2,3,4-tetrahydroquinoxalin-1-yl]ethan-1-one;
propan-2-yl (3S)-4-acetyl-7-[1-(1-hydroxy-2-methylpropan-2-yl)-1H-pyrazol-4-yl]-3-methyl-1,2,3,4-tetrahydroquinoxaline-1-carboxylate;
1-methyl 4-pyridin-3-yl (2S)-6-(4-methanesulfonylphenyl)-2-methyl-1,2,3,4-tetrahydroquinoxaline-1,4-dicarboxylate;
pyridin-3-yl (3S)-4-acetyl-7-(4-methanesulfonamidophenyl)-3-methyl-1,2,3,4-tetrahydroquinoxaline-1-carboxylate;
1-methyl 4-pyridin-3-yl (2S)-6-(4-methanesulfonamidophenyl)-2-methyl-1,2,3,4-tetrahydroquinoxaline-1,4-dicarboxylate;
pyridin-3-yl (3S)-4-acetyl-7-[1-(2-methanesulfonylethyl)-1H-pyrazol-4-yl]-3-methyl-1,2,3,4-tetrahydroquinoxaline-1-carboxylate;
1-methyl 4-pyridin-3-yl (2S)-6-[1-(2-methanesulfonylethyl)-1H-pyrazol-4-yl]-2-methyl-1,2,3,4-tetrahydroquinoxaline-1,4-dicarboxylate;
pyridin-3-yl (3S)-4-acetyl-7-[1-(2-hydroxyethyl)-1H-pyrazol-4-yl]-3-methyl-1,2,3,4-tetrahydroquinoxaline-1-carboxylate;
1-methyl 4-pyridin-3-yl (2S)-6-[1-(2-hydroxyethyl)-1H-pyrazol-4-yl]-2-methyl-1,2,3,4-tetrahydroquinoxaline-1,4-dicarboxylate;
1-methyl 4-pyridin-3-yl (2S)-6-(1-cyclopropyl-1H-pyrazol-4-yl)-2-methyl-1,2,3,4-tetrahydroquinoxaline-1,4-dicarboxylate;
pyridin-3-yl (3S)-4-acetyl-7-[1-(1-hydroxy-2-methylpropan-2-yl)-1H-pyrazol-4-yl]-3-methyl-1,2,3,4-tetrahydroquinoxaline-1-carboxylate;
1-methyl 4-pyridin-3-yl (2S)-6-[1-(1-hydroxy-2-methylpropan-2-yl)-1H-pyrazol-4-yl]-2-methyl-1,2,3,4-tetrahydroquinoxaline-1,4-dicarboxylate;
pyridin-3-yl (3S)-4-acetyl-7-[4-(1,1-dioxo-1$\lambda^{6}$,2-thiazolidin-2-yl)phenyl]-3-methyl-1,2,3,4-tetrahydroquinoxaline-1-carboxylate;

1-methyl 4-pyridin-3-yl (2S)-6-[4-(1,1-dioxo-1λ⁶,2-thiazolidin-2-yl)phenyl]-2-methyl-1,2,3,4-tetrahydroquinoxaline-1,4-dicarboxylate;
pyridin-3-yl (3S)-4-acetyl-7-[1-(2-cyanoethyl)-1H-pyrazol-4-yl]-3-methyl-1,2,3,4-tetrahydroquinoxaline-1-carboxylate;
1-methyl 4-pyridin-3-yl (2S)-6-[1-(2-cyanoethyl)-1H-pyrazol-4-yl]-2-methyl-1,2,3,4-tetrahydroquinoxaline-1,4-dicarboxylate;
pyridin-3-yl (3S)-4-acetyl-7-(1-methanesulfonyl-2,3-dihydro-1H-indol-5-yl)-3-methyl-1,2,3,4-tetrahydroquinoxaline-1-carboxylate;
1-methyl 4-pyridin-3-yl (2S)-6-(1-methanesulfonyl-2,3-dihydro-1H-indol-5-yl)-2-methyl-1,2,3,4-tetrahydroquinoxaline-1,4-dicarboxylate;
pyridin-3-yl (3S)-4-acetyl-3-methyl-7-[4-(N-methylmethanesulfonamido)phenyl]-1,2,3,4-tetrahydroquinoxaline-1-carboxylate;
1-methyl 4-pyridin-3-yl (2S)-2-methyl-6-[4-(N-methylmethanesulfonamido)phenyl]-1,2,3,4-tetrahydroquinoxaline-1,4-dicarboxylate;
pyridin-3-yl (3S)-4-acetyl-7-[1-(azetidin-3-yl)-1H-pyrazol-4-yl]-3-methyl-1,2,3,4-tetrahydroquinoxaline-1-carboxylate;
1-methyl 4-pyridin-3-yl (2S)-6-[1-(azetidin-3-yl)-1H-pyrazol-4-yl]-2-methyl-1,2,3,4-tetrahydroquinoxaline-1,4-dicarboxylate;
1-methyl 4-pyridin-3-yl (2S)-2-methyl-6-[1-(piperidin-4-yl)-1H-pyrazol-4-yl]-1,2,3,4-tetrahydroquinoxaline-1,4-dicarboxylate;
4-[(2S)-1-acetyl-4-cyclopropanecarbonyl-2-methyl-1,2,3,4-tetrahydroquinoxalin-6-yl]-2-fluorobenzene-1-sulfonamide;
propan-2-yl (3S)-4-acetyl-7-(3-fluoro-4-sulfamoylphenyl)-3-methyl-1,2,3,4-tetrahydroquinoxaline-1-carboxylate;
propan-2-yl (3S)-4-acetyl-7-[4-(dimethylsulfamoyl)-3-methylphenyl]-3-methyl-1,2,3,4-tetrahydroquinoxaline-1-carboxylate;
4-[(2S)-1-acetyl-4-cyclopropanecarbonyl-2-methyl-1,2,3,4-tetrahydroquinoxalin-6-yl]-N,N,2-trimethylbenzene-1-sulfonamide;
cyclohexyl (3S)-4-acetyl-3-methyl-7-[1-(oxan-4-yl)-1H-pyrazol-4-yl]-1,2,3,4-tetrahydroquinoxaline-1-carboxylate;
1-[(2S)-4-cyclopropanecarbonyl-2-methyl-6-[1-(oxan-4-yl)-1H-pyrazol-4-yl]-1,2,3,4-tetrahydroquinoxalin-1-yl]ethan-1-one;
cyclohexyl (3S)-4-acetyl-3-methyl-7-[1-(piperidin-4-yl)-1H-pyrazol-4-yl]-1,2,3,4-tetrahydroquinoxaline-1-carboxylate;
cyclohexyl (3S)-4-acetyl-7-[1-(azetidin-3-yl)-1H-pyrazol-4-yl]-3-methyl-1,2,3,4-tetrahydroquinoxaline-1-carboxylate;
3-{4-[(2S)-1-acetyl-4-cyclopropanecarbonyl-2-methyl-1,2,3,4-tetrahydroquinoxalin-6-yl]-1H-pyrazol-1-yl}-1λ⁶-thietane-1,1-dione;
propan-2-yl (3S)-4-acetyl-7-[1-(1,1-dioxo-1λ⁶-thietan-3-yl)-1H-pyrazol-4-yl]-3-methyl-1,2,3,4-tetrahydroquinoxaline-1-carboxylate;
cyclopentyl (3S)-4-acetyl-7-[1-(1,1-dioxo-1λ⁶-thietan-3-yl)-1H-pyrazol-4-yl]-3-methyl-1,2,3,4-tetrahydroquinoxaline-1-carboxylate;
cyclohexyl (3S)-4-acetyl-7-[1-(1,1-dioxo-1λ⁶-thietan-3-yl)-1H-pyrazol-4-yl]-3-methyl-1,2,3,4-tetrahydroquinoxaline-1-carboxylate;
propan-2-yl (3S)-4-acetyl-7-(1-cyclopropyl-1H-pyrazol-4-yl)-3-methyl-1H,2H,3H,4H-pyrido[2,3-b]pyrazine-1-carboxylate;
3-{4-[(2S)-1-acetyl-4-cyclopropanecarbonyl-2-methyl-1,2,3,4-tetrahydroquinoxalin-6-yl]-1H-pyrazol-1-yl}-1λ⁶-thiane-1,1-dione;
propan-2-yl (3S)-4-acetyl-7-[1-(1,1-dioxo-1λ⁶-thian-3-yl)-1H-pyrazol-4-yl]-3-methyl-1,2,3,4-tetrahydroquinoxaline-1-carboxylate;
cyclohexyl (3S)-4-acetyl-7-[1-(1,1-dioxo-1λ⁶-thian-3-yl)-1H-pyrazol-4-yl]-3-methyl-1,2,3,4-tetrahydroquinoxaline-1-carboxylate;
1-methyl 4-pyridin-2-yl (2S)-6-[1-(1-hydroxy-2-methylpropan-2-yl)-1H-pyrazol-4-yl]-2-methyl-1,2,3,4-tetrahydroquinoxaline-1,4-dicarboxylate;
pyridin-2-yl (3S)-4-acetyl-7-(4-methanesulfonylphenyl)-3-methyl-1,2,3,4-tetrahydroquinoxaline-1-carboxylate;
1-methyl 4-pyridin-2-yl (2S)-6-(4-methanesulfonylphenyl)-2-methyl-1,2,3,4-tetrahydroquinoxaline-1,4-dicarboxylate;
pyridin-2-yl (3S)-4-acetyl-7-(4-methanesulfonamidophenyl)-3-methyl-1,2,3,4-tetrahydroquinoxaline-1-carboxylate;
1-methyl 4-pyridin-2-yl (2S)-6-(4-methanesulfonamidophenyl)-2-methyl-1,2,3,4-tetrahydroquinoxaline-1,4-dicarboxylate;
pyridin-2-yl (3S)-4-acetyl-7-[1-(2-methanesulfonylethyl)-1H-pyrazol-4-yl]-3-methyl-1,2,3,4-tetrahydroquinoxaline-1-carboxylate;
1-methyl 4-pyridin-2-yl (2S)-6-[1-(2-methanesulfonylethyl)-1H-pyrazol-4-yl]-2-methyl-1,2,3,4-tetrahydroquinoxaline-1,4-dicarboxylate;
pyridin-2-yl (3S)-4-acetyl-7-[1-(2-hydroxy-2-methylpropyl)-1H-pyrazol-4-yl]-3-methyl-1,2,3,4-tetrahydroquinoxaline-1-carboxylate;
1-methyl 4-pyridin-2-yl (2S)-6-[1-(2-hydroxy-2-methylpropyl)-1H-pyrazol-4-yl]-2-methyl-1,2,3,4-tetrahydroquinoxaline-1,4-dicarboxylate;
pyridin-2-yl (3S)-4-acetyl-7-(1-cyclopropyl-1H-pyrazol-4-yl)-3-methyl-1,2,3,4-tetrahydroquinoxaline-1-carboxylate;
1-methyl 4-pyridin-2-yl (2S)-6-(1-cyclopropyl-1H-pyrazol-4-yl)-2-methyl-1,2,3,4-tetrahydroquinoxaline-1,4-dicarboxylate;
pyridin-2-yl (3S)-4-acetyl-7-[4-(1,1-dioxo-1λ⁶,2-thiazolidin-2-yl)phenyl]-3-methyl-1,2,3,4-tetrahydroquinoxaline-1-carboxylate;
1-methyl 4-pyridin-2-yl (2S)-6-[4-(1,1-dioxo-1λ⁶,2-thiazolidin-2-yl)phenyl]-2-methyl-1,2,3,4-tetrahydroquinoxaline-1,4-dicarboxylate;
pyridin-2-yl (3S)-4-acetyl-7-[1-(2-cyanoethyl)-1H-pyrazol-4-yl]-3-methyl-1,2,3,4-tetrahydroquinoxaline-1-carboxylate;
1-methyl 4-pyridin-2-yl (2S)-6-[1-(2-cyanoethyl)-1H-pyrazol-4-yl]-2-methyl-1,2,3,4-tetrahydroquinoxaline-1,4-dicarboxylate;
pyridin-2-yl (3S)-4-acetyl-7-(1-methanesulfonyl-2,3-dihydro-1H-indol-5-yl)-3-methyl-1,2,3,4-tetrahydroquinoxaline-1-carboxylate;
1-methyl 4-pyridin-2-yl (2S)-6-(1-methanesulfonyl-2,3-dihydro-1H-indol-5-yl)-2-methyl-1,2,3,4-tetrahydroquinoxaline-1,4-dicarboxylate;
pyridin-2-yl (3S)-4-acetyl-3-methyl-7-[4-(N-methylmethanesulfonamido)phenyl]-1,2,3,4-tetrahydroquinoxaline-1-carboxylate;

1-methyl 4-pyridin-2-yl(2S)-2-methyl-6-[4-(N-methyl-methanesulfonamido)phenyl]-1,2,3,4-tetrahydroquinoxaline-1,4-dicarboxylate;

pyridin-2-yl(3S)-4-acetyl-3-methyl-7-[1-(piperidin-4-yl)-1H-pyrazol-4-yl]-1,2,3,4-tetrahydroquinoxaline-1-carboxylate;

1-methyl 4-pyridin-2-yl(2S)-2-methyl-6-[1-(piperidin-4-yl)-1H-pyrazol-4-yl]-1,2,3,4-tetrahydroquinoxaline-1,4-dicarboxylate;

pyridin-2-yl(3S)-4-acetyl-7-[1-(2-hydroxyethyl)-1H-pyrazol-4-yl]-3-methyl-1,2,3,4-tetrahydroquinoxaline-1-carboxylate;

1-methyl 4-pyridin-2-yl(2S)-6-[1-(2-hydroxyethyl)-1H-pyrazol-4-yl]-2-methyl-1,2,3,4-tetrahydroquinoxaline-1,4-dicarboxylate;

2,4-difluorophenyl (3S)-4-acetyl-7-[1-(2-hydroxy-2-methylpropyl)-1H-pyrazol-4-yl]-3-methyl-1,2,3,4-tetrahydroquinoxaline-1-carboxylate;

4-chloro-2-methylphenyl (3S)-4-acetyl-7-(1-cyclopropyl-1H-pyrazol-4-yl)-3-methyl-1,2,3,4-tetrahydroquinoxaline-1-carboxylate;

4-fluorophenyl (3S)-4-acetyl-7-[1-(2-hydroxyethyl)-1H-pyrazol-4-yl]-3-methyl-1,2,3,4-tetrahydroquinoxaline-1-carboxylate;

4-fluorophenyl (3S)-4-acetyl-7-[1-(2-hydroxy-2-methylpropyl)-1H-pyrazol-4-yl]-3-methyl-1,2,3,4-tetrahydroquinoxaline-1-carboxylate;

4-fluorophenyl (3S)-4-acetyl-7-[1-(2-methanesulfonylethyl)-1H-pyrazol-4-yl]-3-methyl-1,2,3,4-tetrahydroquinoxaline-1-carboxylate;

4-fluorophenyl (3S)-4-acetyl-7-[1-(2-cyanoethyl)-1H-pyrazol-4-yl]-3-methyl-1,2,3,4-tetrahydroquinoxaline-1-carboxylate;

4-fluorophenyl (3S)-4-acetyl-7-(4-methanesulfonamidophenyl)-3-methyl-1,2,3,4-tetrahydroquinoxaline-1-carboxylate;

4-fluorophenyl (3S)-4-acetyl-3-methyl-7-[1-(piperidin-4-yl)-1H-pyrazol-4-yl]-1,2,3,4-tetrahydroquinoxaline-1-carboxylate;

4-fluorophenyl (3S)-4-acetyl-7-[1-(azetidin-3-yl)-1H-pyrazol-4-yl]-3-methyl-1,2,3,4-tetrahydroquinoxaline-1-carboxylate;

4-fluorophenyl (3S)-4-acetyl-7-[1-(1-hydroxy-2-methylpropan-2-yl)-1H-pyrazol-4-yl]-3-methyl-1,2,3,4-tetrahydroquinoxaline-1-carboxylate;

2,4-difluorophenyl (3S)-4-acetyl-7-[1-(2-hydroxyethyl)-1H-pyrazol-4-yl]-3-methyl-1,2,3,4-tetrahydroquinoxaline-1-carboxylate;

2,4-difluorophenyl (3S)-4-acetyl-7-(4-methanesulfonylphenyl)-3-methyl-1,2,3,4-tetrahydroquinoxaline-1-carboxylate;

2,4-difluorophenyl (3S)-4-acetyl-7-[4-(1,1-dioxo-1$\lambda^6$,2-thiazolidin-2-yl)phenyl]-3-methyl-1,2,3,4-tetrahydroquinoxaline-1-carboxylate;

2,4-difluorophenyl (3S)-4-acetyl-7-[1-(2-cyanoethyl)-1H-pyrazol-4-yl]-3-methyl-1,2,3,4-tetrahydroquinoxaline-1-carboxylate;

2,4-difluorophenyl (3S)-4-acetyl-7-(4-methanesulfonamidophenyl)-3-methyl-1,2,3,4-tetrahydroquinoxaline-1-carboxylate;

2,4-difluorophenyl (3S)-4-acetyl-7-[1-(1-hydroxy-2-methylpropan-2-yl)-1H-pyrazol-4-yl]-3-methyl-1,2,3,4-tetrahydroquinoxaline-1-carboxylate;

4-fluorophenyl (3S)-4-acetyl-7-[4-(1,1-dioxo-1$\lambda^6$,2-thiazolidin-2-yl)phenyl]-3-methyl-1,2,3,4-tetrahydroquinoxaline-1-carboxylate;

2,4-difluorophenyl (3S)-4-acetyl-3-methyl-7-[1-(piperidin-4-yl)-1H-pyrazol-4-yl]-1,2,3,4-tetrahydroquinoxaline-1-carboxylate;

4-(4-fluorophenyl) 1-methyl (2S)-6-[1-(2-hydroxyethyl)-1H-pyrazol-4-yl]-2-methyl-1,2,3,4-tetrahydroquinoxaline-1,4-dicarboxylate;

4-(4-fluorophenyl) 1-methyl (2S)-6-[1-(2-hydroxy-2-methylpropyl)-1H-pyrazol-4-yl]-2-methyl-1,2,3,4-tetrahydroquinoxaline-1,4-dicarboxylate;

4-(4-fluorophenyl) 1-methyl (2S)-6-[1-(1-hydroxy-2-methylpropan-2-yl)-1H-pyrazol-4-yl]-2-methyl-1,2,3,4-tetrahydroquinoxaline-1,4-dicarboxylate;

4-(4-fluorophenyl) 1-methyl (2S)-6-[1-(2-cyanoethyl)-1H-pyrazol-4-yl]-2-methyl-1,2,3,4-tetrahydroquinoxaline-1,4-dicarboxylate;

4-(4-fluorophenyl) 1-methyl (2S)-2-methyl-6-[1-(piperidin-4-yl)-1H-pyrazol-4-yl]-1,2,3,4-tetrahydroquinoxaline-1,4-dicarboxylate;

2S-1-acetyl-6-(1-cyclopropyl-1H-pyrazol-4-yl)-N-(4-fluorophenyl)-2-methyl-1H,2H,3H,4H-pyrido[2,3-b]pyrazine-4-carboxamide;

(2S)-1-acetyl-6-(1-cyclopropyl-1H-pyrazol-4-yl)-2-methyl-N-(propan-2-yl)-1H,2H,3H,4H-pyrido[2,3-b]pyrazine-4-carboxamide;

4-fluorophenyl (3S)-4-acetyl-7-(1-methanesulfonyl-2,3-dihydro-1H-indol-5-yl)-3-methyl-1,2,3,4-tetrahydroquinoxaline-1-carboxylate;

propan-2-yl(3S)-4-acetyl-7-(1-cyclopropyl-1H-pyrazol-4-yl)-3-methyl-6-nitro-1,2,3,4-tetrahydroquinoxaline-1-carboxylate;

propan-2-yl(3S)-4-acetyl-6-amino-7-(1-cyclopropyl-1H-pyrazol-4-yl)-3-methyl-1,2,3,4-tetrahydroquinoxaline-1-carboxylate;

propan-2-yl(3S)-4-acetyl-7-(1-cyclopropyl-1H-pyrazol-4-yl)-6-methanesulfonamido-3-methyl-1,2,3,4-tetrahydroquinoxaline-1-carboxylate;

propan-2-yl(3S)-4-acetyl-7-(1-cyclopropyl-1H-pyrazol-4-yl)-6-acetamido-3-methyl-1,2,3,4-tetrahydroquinoxaline-1-carboxylate;

propan-2-yl(3S)-4-acetyl-7-(1-cyclopropyl-1H-pyrazol-4-yl)-3-methyl-6-[(methylcarbamoyl)amino]-1,2,3,4-tetrahydroquinoxaline-1-carboxylate;

(3S)-4-acetyl-7-[1-(2-hydroxyethyl)-1H-pyrazol-4-yl]-N,3-dimethyl-N-(propan-2-yl)-1,2,3,4-tetrahydroquinoxaline-1-carboxamide;

(3S)-4-acetyl-7-[1-(2-hydroxyethyl)-1H-pyrazol-4-yl]-N,3-dimethyl-N-phenyl-1,2,3,4-tetrahydroquinoxaline-1-carboxamide;

propan-2-yl (3S)-4-acetyl-6-bromo-7-(4-methanesulfonylphenyl)-3-methyl-1,2,3,4-tetrahydroquinoxaline-1-carboxylate;

propan-2-yl (3S)-4-acetyl-6-chloro-7-(4-methanesulfonylphenyl)-3-methyl-1,2,3,4-tetrahydroquinoxaline-1-carboxylate;

propan-2-yl (3S)-4-acetyl-6-cyano-7-(4-methanesulfonylphenyl)-3-methyl-1,2,3,4-tetrahydroquinoxaline-1-carboxylate;

propan-2-yl (3S)-4-acetyl-6-fluoro-7-(4-methanesulfonylphenyl)-3-methyl-1,2,3,4-tetrahydroquinoxaline-1-carboxylate;

propan-2-yl (3S)-4-acetyl-6-acetamido-7-(4-methanesulfonylphenyl)-3-methyl-1,2,3,4-tetrahydroquinoxaline-1-carboxylate;

propan-2-yl (3S)-4-acetyl-7-(4-methanesulfonylphenyl)-6-[(methoxycarbonyl)amino]-3-methyl-1,2,3,4-tetrahydroquinoxaline-1-carboxylate;

propan-2-yl (3S)-4-acetyl-6-amino-7-(4-methanesulfonylphenyl)-3-methyl-1,2,3,4-tetrahydroquinoxaline-1-carboxylate;
propan-2-yl (3S)-4-acetyl-7-(4-methanesulfonylphenyl)-6-methoxy-3-methyl-1,2,3,4-tetrahydroquinoxaline-1-carboxylate;
propan-2-yl (3S)-4-acetyl-6-acetamido-3-methyl-1,2,3,4-tetrahydroquinoxaline-1-carboxylate;
propan-2-yl (3S)-4-acetyl-6-methanesulfonamido-3-methyl-1,2,3,4-tetrahydroquinoxaline-1-carboxylate;
propan-2-yl (3S)-4-acetyl-6-[(methoxycarbonyl)amino]-3-methyl-1,2,3,4-tetrahydroquinoxaline-1-carboxylate
propan-2-yl (3S)-4-acetyl-7-bromo-6-acetamido-3-methyl-1,2,3,4-tetrahydroquinoxaline-1-carboxylate;
propan-2-yl (3S)-4-acetyl-7-(1-cyclopropyl-1H-pyrazol-4-yl)-6-[(methoxycarbonyl)amino]-3-methyl-1,2,3,4-tetrahydroquinoxaline-1-carboxylate;
propan-2-yl (3S)-4-acetyl-6-acetamido-7-[1-(2-hydroxy-2-methylpropyl)-1H-pyrazol-4-yl]-3-methyl-1,2,3,4-tetrahydroquinoxaline-1-carboxylate;
propan-2-yl(3S)-4-acetyl-7-(1-cyclopropyl-1H-pyrazol-4-yl)-6-fluoro-3-methyl-1,2,3,4-tetrahydroquinoxaline-1-carboxylate;
propan-2-yl(3S)-4-acetyl-6-chloro-7-(1-cyclopropyl-1H-pyrazol-4-yl)-3-methyl-1,2,3,4-tetrahydroquinoxaline-1-carboxylate;
propan-2-yl (3S)-4-acetyl-6-bromo-7-(1-cyclopropyl-1H-pyrazol-4-yl)-3-methyl-1,2,3,4-tetrahydroquinoxaline-1-carboxylate;
propan-2-yl(3S)-4-acetyl-7-(1-cyclopropyl-1H-pyrazol-4-yl)-6-methoxy-3-methyl-1,2,3,4-tetrahydroquinoxaline-1-carboxylate;
propan-2-yl(3S)-4-acetyl-6-cyano-7-(1-cyclopropyl-1H-pyrazol-4-yl)-3-methyl-1,2,3,4-tetrahydroquinoxaline-1-carboxylate;
propan-2-yl(3S)-4-acetyl-6-carbamoyl-7-(1-cyclopropyl-1H-pyrazol-4-yl)-3-methyl-1,2,3,4-tetrahydroquinoxaline-1-carboxylate; and
propan-2-yl(3S)-7-(1-cyclopropyl-1H-pyrazol-4-yl)-3-methyl-4-(methylcarbamoyl)-1H,2H,3H,4H-pyrido[2,3-b]pyrazine-1-carboxylate In another embodiment, suitable compounds of the invention include:
cyclobutyl (S)-4-acetyl-7-(1-(1,1-dioxidotetrahydro-2H-thiopyran-4-yl)-1H-pyrazol-4-yl)-3-methyl-3,4-dihydroquinoxaline-1(2H)-carboxylate;
cyclobutyl (S)-4-acetyl-3-methyl-7-(1-((S)-2-oxopiperidin-4-yl)-1H-pyrazol-4-yl)-3,4-dihydroquinoxaline-1(2H)-carboxylate;
cyclobutyl (S)-4-acetyl-3-methyl-7-(1-((R)-2-oxopiperidin-4-yl)-1H-pyrazol-4-yl)-3,4-dihydroquinoxaline-1(2H)-carboxylate;
isopropyl (3S)-4-acetyl-3-methyl-7-(1-((2S)-2-methylazetidin-3-yl)-1H-pyrazol-4-yl)-3,4-dihydroquinoxaline-1(2H)-carboxylate;
cyclobutyl (S)-4-acetyl-7-(1-(1,1-dioxidothietan-3-yl)-1H-pyrazol-4-yl)-3-methyl-3,4-dihydroquinoxaline-1(2H)-carboxylate;
(S)-1-(4-(cyclopropanecarbonyl)-2-methyl-6-(1-(tetrahydro-2H-pyran-4-yl)-1H-pyrazol-4-yl)-3,4-dihydroquinoxaline-1(2H)-yl)ethan-1-one;
tetrahydro-2H-pyran-4-yl (S)-4-acetyl-3-methyl-7-(1-(tetrahydro-2H-pyran-4-yl)-1H-pyrazol-4-yl)-3,4-dihydroquinoxaline-1(2H)-carboxylate;
(S)-1-(2-methyl-4-(1-methyl-1H-indazol-3-yl)-6-(1-(piperidin-4-yl)-1H-pyrazol-4-yl)-3,4-dihydroquinoxaline-1(2H)-yl)ethan-1-one;
(S)-1-(4-(cyclopropanecarbonyl)-2-methyl-6-(1-(methylsulfonyl)indolin-5-yl)-3,4-dihydroquinoxaline-1(2H)-yl)ethan-1-one;
(S)-1-(4-(cyclopropanecarbonyl)-6-(4-(1,1-dioxidothiomorpholino)phenyl)-2-methyl-3,4-dihydroquinoxaline-1(2H)-yl)ethan-1-one;
cyclobutyl (S)-4-acetyl-7-(1-((R)-1,1-dioxidotetrahydro-2H-thiopyran-3-yl)-1H-pyrazol-4-yl)-3-methyl-3,4-dihydroquinoxaline-1(2H)-carboxylate;
cyclobutyl (S)-4-acetyl-7-(1-((S)-1,1-dioxidotetrahydro-2H-thiopyran-3-yl)-1H-pyrazol-4-yl)-3-methyl-3,4-dihydroquinoxaline-1(2H)-carboxylate;
(S)-3-(1-acetyl-4-(cyclopropanecarbonyl)-2-methyl-1,2,3,4-tetrahydroquinoxalin-6-yl)benzenesulfonamide;
1,3-difluoropropan-2-yl (S)-4-acetyl-7-(1-cyclopropyl-1H-pyrazol-4-yl)-3-methyl-3,4-dihydroquinoxaline-1(2H)-carboxylate;
(S)-N-(4-(1-acetyl-4-(cyclopropanecarbonyl)-2-methyl-1,2,3,4-tetrahydroquinoxalin-6-yl)phenyl)methanesulfonamide;
1-((2S)-4-(cyclopropanecarbonyl)-6-(1-((2,2-difluorocyclopropyl)methyl-1H-pyrazol-4-yl)-2-methyl-3,4-dihydroquinoxaline-1(2H)-yl)ethan-1-one;
isopropyl (S)-4-acetyl-7-(1-(2-cyanoethyl)-1H-pyrazol-4-yl)-3-methyl-3,4-dihydroquinoxaline-1(2H)-carboxylate;
(S)-1-(4-(cyclopropanecarbonyl)-2-methyl-6-(1-((tetrahydro-2H-pyran-4-yl)methyl-1H-pyrazol-4-yl)-3,4-dihydroquinoxaline-1(2H)-yl)ethan-1-one;
(S)-3-(4-(1-acetyl-4-(cyclopropanecarbonyl)-2-methyl-1,2,3,4-tetrahydroquinoxalin-6-yl)-1H-pyrazol-1-yl)propanenitrile;
isopropyl (S)-4-(cyclopropanecarbonyl)-3-methyl-7-(1-(2,2,2-trifluoroethyl-1H-pyrazol-4-yl)-3,4-dihydroquinoxaline-1(2H)-carboxylate;
isopropyl (S)-4-acetyl-7-(1-(2-hydroxy-2-methylpropyl)-1H-pyrazol-4-yl)-3-methyl-3,4-dihydroquinoxaline-1(2H)-carboxylate;
isopropyl (S)-4-acetyl-3-methyl-7-(1-(piperidin-4-yl)-1H-pyrazol-4-yl)-3,4-dihydroquinoxaline-1(2H)-carboxylate;
isopropyl (S)-4-acetyl-7-(1-(2-hydroxyethyl)-1H-pyrazol-4-yl)-3-methyl-3,4-dihydroquinoxaline-1(2H)-carboxylate;
isopropyl (S)-4-acetyl-3-methyl-7-(1-(2-(methylsulfonyl)ethyl)-1H-pyrazol-4-yl)-3,4-dihydroquinoxaline-1(2H)-carboxylate;
(S)-1-(4-(cyclopropanecarbonyl)-6-(1-cyclopropyl-1H-pyrazol-4-yl)-2-methyl-3,4-dihydroquinoxaline-1(2H)-yl)ethan-1-one;
isopropyl (S)-4-acetyl-7-(4-(2-aminoethyl)carbamoyl)phenyl)-3-methyl-3,4-dihydroquinoxaline-1(2H)-carboxylate;
isopropyl (S)-4-acetyl-7-(4-(1,1-dioxidoisothiazolidin-2-yl)phenyl)-3-methyl-3,4-dihydroquinoxaline-1(2H)-carboxylate;
isopropyl (S)-4-acetyl-7-(4-(1,1-dioxidothiomorpholino)phenyl)-3-methyl-3,4-dihydroquinoxaline-1(2H)-carboxylate;
(S)-1-(4-(cyclopropanecarbonyl)-6-(4-(1,1-dioxidoisothiazolidin-2-yl)phenyl)-2-methyl-3,4-dihydroquinoxaline-1(2H)-yl)ethan-1-one;
ethyl (S)-4-acetyl-7-(1-cyclopropyl-1H-pyrazol-4-yl)-3-methyl-3,4-dihydroquinoxaline-1(2H)-carboxylate;
isopropyl (S)-4-acetyl-3-methyl-7-(4-(methylsulfonyl)phenyl)-3,4-dihydroquinoxaline-1(2H)-carboxylate;
(S)-1-(4-(furan-2-carbonyl)-2-methyl-6-(1-methyl-1H-pyrazol-4-yl)-3,4-dihydroquinoxalin-1(2H)-yl)ethan-1-one;

(S)-1-(4-(furan-2-carbonyl)-2-methyl-6-(4-(methylsulfonyl)phenyl)-3,4-dihydroquinoxalin-1(2H)-yl)ethan-1-one;
(S)-4-(1-acetyl-4-(furan-2-carbonyl)-2-methyl-1,2,3,4-tetrahydroquinoxalin-6-yl)benzamide; and
(S)-4-(1-acetyl-4-(furan-2-carbonyl)-2-methyl-1,2,3,4-tetrahydroquinoxalin-6-yl)-N,N-dimethylbenzamide.

In another embodiment of the invention, the compounds of Formula (I)-(VI) are enantiomers. In some embodiments the compounds are the (S)-enantiomer. In other embodiments the compounds are the (R)-enantiomer. In yet other embodiments, the compounds of Formula (I) may be (+) or (−) enantiomers.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the various Formulae, and salts, solvates, esters and prodrugs thereof, may exist in their tautomeric form (for example, as an amide or imino ether). All such tautomeric forms are contemplated herein as part of the present invention.

The compounds of the various Formulae may contain asymmetric or chiral centers, and, therefore, exist in different stereoisomeric forms. It is intended that all stereoisomeric forms of the compounds of the various Formulae as well as mixtures thereof, including racemic mixtures, form part of the present invention. In addition, the present invention embraces all geometric and positional isomers. For example, if a compound of the various Formulae incorporates a double bond or a fused ring, both the cis- and trans-forms, as well as mixtures, are embraced within the scope of the invention. Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the various Formulae may be atropisomers (e.g., substituted biaryls) and are considered as part of this invention. Enantiomers can also be separated by use of a chiral HPLC column.

It is also possible that the compounds of the various Formulae may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of the various Formulae incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$ (or D), $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of the various Formulae (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of the various Formulae can generally be prepared by following procedures analogous to those disclosed in the Schemes and/or in the Examples herein below, by substituting an appropriate isotopically labelled reagent for a non-isotopically labelled reagent.

The compounds of Formulae (I) to (VI) may form salts which are also within the scope of this invention. Reference to a compound of the Formula herein is understood to include reference to salts thereof, unless otherwise indicated.

The present invention relates to compounds which are modulators of one or more bromodomains of the BET family. In one embodiment, the compounds of the present invention are inhibitors of one or more bromodomains of the BET family.

The invention is directed to compounds as described herein and pharmaceutically acceptable salts, enantiomers, hydrates, solvates, prodrugs, isomers, or tautomers thereof, and pharmaceutical compositions comprising one or more compounds as described herein, or pharmaceutically acceptable salts, enantiomers, hydrates, solvates, prodrugs, isomers, or tautomers thereof.

Method of Synthesizing the Compounds

The compounds of the present invention may be made by a variety of methods, including standard chemistry. Suitable synthetic routes are depicted in the Schemes given below.

The compounds of the present invention, i.e., compounds of Formulae (I)-(VI), or a pharmaceutically acceptable salt, enantiomer, hydrate, solvate, prodrug, isomer, or tautomer thereof, may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formulae (I)-(VI).

Those skilled in the art will recognize if a stereocenter exists in the compounds of Formulae (I)-(VI). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Illustrative methods include but are not limited to those methods described below. Compounds of the present invention can be synthesized by following the steps outlined in General Schemes 1 and 2, which comprise different sequences of assembling intermediates. Starting materials are either commercially available or made by known procedures in the reported literature or as illustrated.

Scheme 1

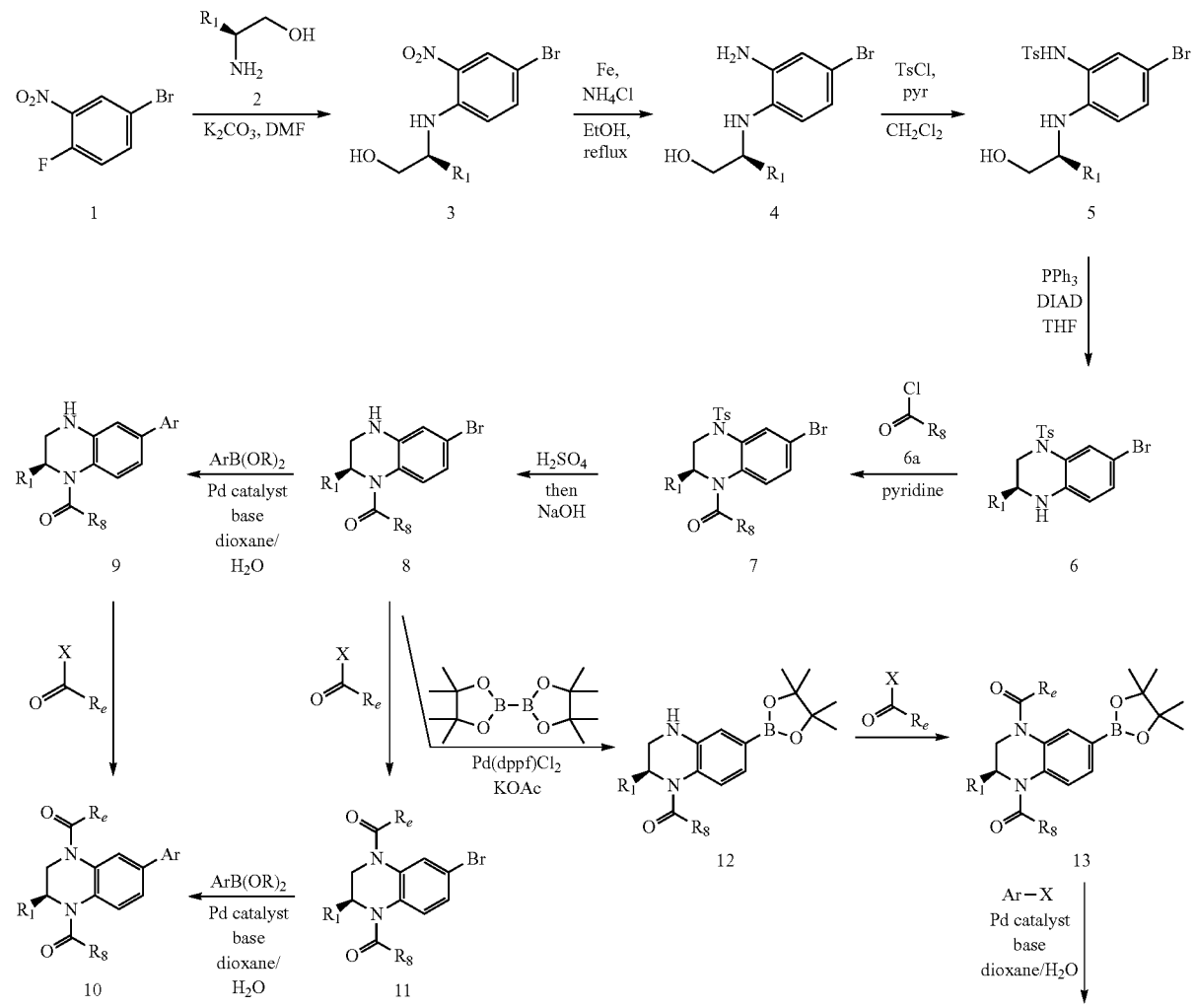

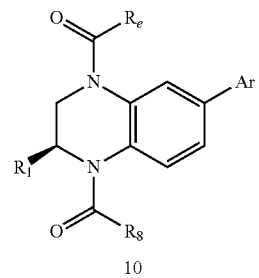

wherein $R_1$, $R_8$ and $R_e$ are as defined above.

The substituted benzopiperazines (10) described herein can be prepared according to the general procedures outlined in Scheme 1. Nucleophilic displacement of 4-bromo-1-fluoro-2-nitrobenzene (1) with an amino alcohol (2) affords nitroaniline 3. Reduction of the nitro group with a metal, i.e. iron, yields bis-aniline 4, which can be reacted with p-toluenesulfonylchloride to provide sulfonamide 5. Subsequent treatment of 5 with triphenylphosphine and a dehydrogenating agent, i.e. diisopropyl azodicarboxylate or diethyl azodicarboxylate, affords 1,2,3,4-tetrahydroquinoxaline 6 via an intramolecular Mitsunobu reaction. Acylation with an acetyl chloride (6a) and subsequent removal of the N-tosyl protecting group with sulfuric acid provides aryl bromide 8, which can be transformed into the desired target molecules through a number of routes. A palladium-catalyzed Suzuki reaction of 8 with an aryl boronic acid (or boronic ester) affords 6-aryl-1,2,3,4-tetrahydroquinoxaline 9, which is converted to the desired benzopiperazine 10 via an acylation with the appropriate acid chloride (or chloroformate) or via a coupling with the appropriate carboxylic acid and coupling reagent (i.e. HATU). Aryl bromide 8 can also be treated with an acid chloride (or chloroformate) or with the appropriate carboxylic acid and coupling reagent to afford intermediate 11. Subsequent palladium-catalyzed Suzuki coupling with the appropriate aryl boronic acid (or boronic ester) yields benzopiperazine 10. Alternatively, aryl bromide 8 could be converted to the corresponding aryl boronic ester 12 via a palladium-catalyzed cross coupling with bis(pinacolato)diboron. Boronic ester 12 can be acylated with the appropriate acid chloride (or chloroformate) or treated with the appropriate carboxylic acid and coupling reagent to provide intermediate 13, which can undergo a palladium-catalyzed Suzuki reaction with the desired aryl halide to afford the desired benzopiperazine 10.

Scheme 2

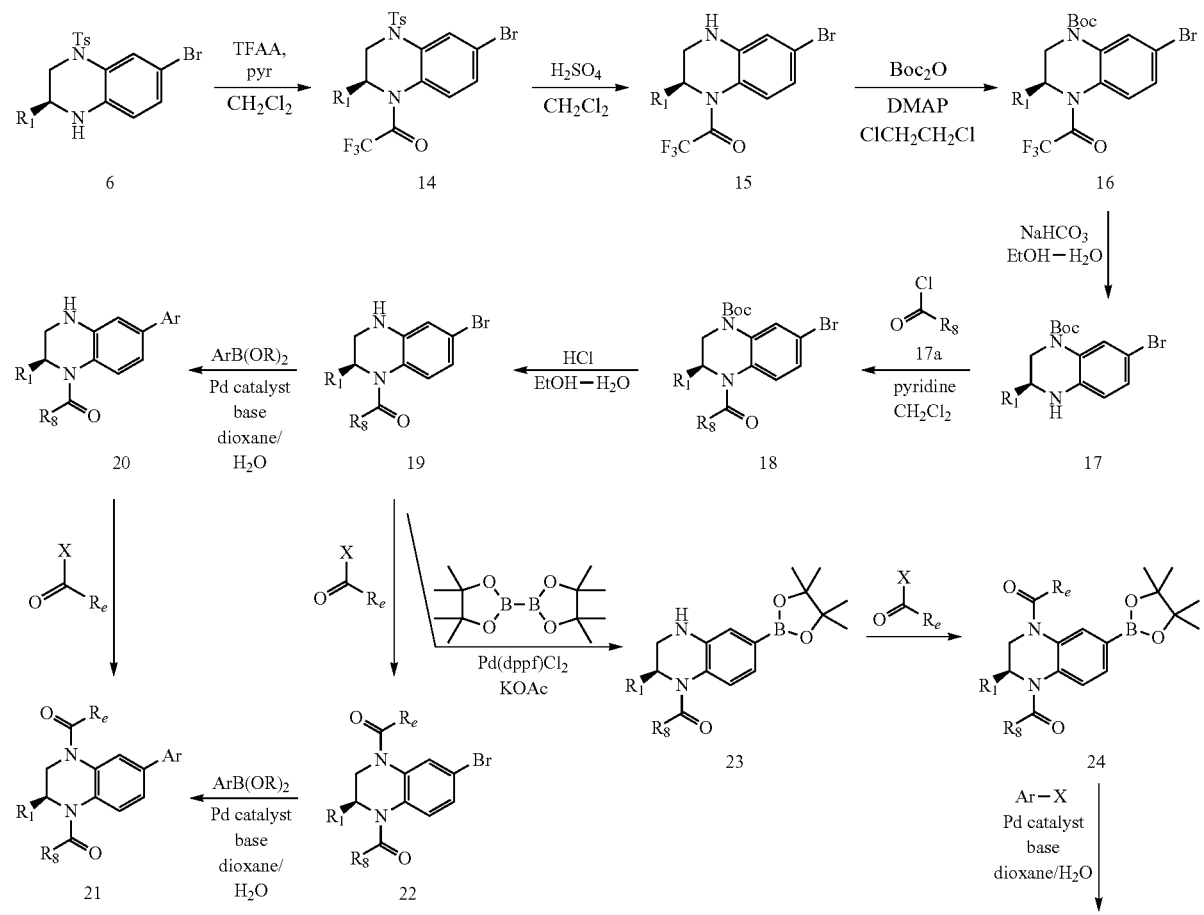

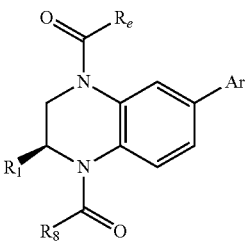

21 wherein $R_1$, $R_8$ and $R_e$ are as defined above.

Alternatively, benzopiperazines (10) could be prepared according to the procedures outlined in Scheme 2. 1,2,3,4-Tetrahydroquinoxaline 6 can be treated with trifluoroacetic anhydride to provide intermediate 14. Removal of the N-tosyl protecting group with sulfuric acid and re-protection of the free amine with di-tert-butyl dicarbonate provides 16. Removal of the trifluoroacetate group with sodium bicarbonate yields 17 which can be acylated with the appropriate acid chloride or chloroformate to afford N-Boc-protected tetrahydroquinoxaline 18. Removal of the tert-butoxycarbonyl protecting group with hydrochloric acid provides aryl bromide 19, which can be transformed into the desired target molecules through a number of routes. A palladium-catalyzed Suzuki reaction of 19 with an aryl boronic acid (or boronic ester) affords 6-aryl-1,2,3,4-tetrahydroquinoxaline 20 which is converted to the desired benzopiperazine 21 via an acylation with the appropriate acid chloride (or chloroformate) or via a coupling with the appropriate carboxylic acid and coupling reagent (i.e. HATU). Aryl bromide 19 can also be treated with an acid chloride (or chloroformate) or with the appropriate carboxylic acid and coupling reagent to afford tetrahydroquinoxaline 22. Subsequent palladium-catalyzed Suzuki coupling with the appropriate aryl boronic acid (or boronic ester) yields benzopiperazine 21. Alternatively, aryl bromide 19 could be converted to the corresponding aryl boronic ester via a palladium-catalyzed cross coupling with bis(pinacolato)diboron. The resulting boronic ester 23 can be acylated with the appropriate acid chloride (or chloroformate) or treated with the appropriate carboxylic acid and coupling reagent to provide intermediate 24, which can undergo a palladium-catalyzed Suzuki reaction with the desired aryl halide to afford the desired benzopiperazine 21.

Methods of Using the Disclosed Compounds

One aspect of the present invention relates to a method of modulating one or more of BET-family bromodomains, comprising administering to a patient in need thereof a therapeutically effective amount of a compound of Formula (I).

Another aspect of the present invention relates to a method of inhibiting one or more of BET-family bromodomains, comprising administering to a patient in need thereof a therapeutically effective amount of a compound of Formula (I).

In another aspect, the present invention relates to a method of inhibiting one or more of BET-family bromodomains, comprising administering to a patient in need thereof a therapeutically effective amount of the pharmaceutical composition of Formula (I).

Another aspect of the present invention relates to a method of treating, preventing, inhibiting, or eliminating a disease or condition in a patient associated with the inhibition of one or more of BET-family bromodomains, the method comprising administering a therapeutically effective amount of a compound of Formula (I). In one embodiment, the disease or condition is selected from the group consisting of cancer, inflammatory disorders, irritable bowel syndrome, inflammatory bowel disease, rheumatoid arthritis, obesity and diabetes.

The present invention also relates to the use of an inhibitor of BET family bromodomains for the preparation of a medicament used in the treatment, prevention, inhibition or elimination of a disease or condition mediated by BET family bromodomains, wherein the medicament comprises a compound of Formula (I).

In another aspect, the present invention the present invention relates to a method for the manufacture of a medicament for treating, preventing, inhibiting, or eliminating a disease or condition mediated by BET family bromodomains, wherein the medicament comprises a compound of Formula (I).

Another aspect of the present invention relates to a pharmaceutical composition for use in a method for treating a disease or condition mediated by BET family bromodomains, wherein the pharmaceutical composition comprises a compound of Formula (I).

In yet another aspect, the present invention relates to a compound for use in a method for treating a disease or condition mediated by BET family bromodomains, wherein the compound comprises a compound of Formula (I).

The present invention also relates to the use of an inhibitor of BET family bromodomains for the preparation of a medicament used in the treatment, prevention, inhibition or elimination of tumors, wherein the medicament comprises a compound of Formula (I).

The present invention further relates to the use of an inhibitor of BET family bromodomains for the preparation of a medicament used in the treatment, prevention, inhibition or elimination of cancer, wherein the medicament comprises a compound of Formula (I).

In one embodiment, the present invention relates to the use of an inhibitor of BET family bromodomains for the preparation of a medicament used in treatment, prevention, inhibition or elimination of diseases associated with chronic autoimmune, inflammatory conditions, acute inflammatory conditions, systemic inflammatory response syndrome, virus, bacterial, or fungal infections, diabetes, and/or obesity. In one embodiment, the medicament prepared comprises a compound of Formula (I), or a pharmaceutically acceptable salt, enantiomer, hydrate, solvate, prodrug, isomer, or tautomer thereof. In another embodiment, the present invention relates to the use of an inhibitor of BET family bromodomains for the preparation of a male contraceptive, wherein the inhibitor comprises a compound of Formula (I).

Another embodiment of the present invention relates to a compound of Formula (I), or a pharmaceutically acceptable salt, enantiomer, hydrate, solvate, prodrug, isomer, or tautomer thereof, or a pharmaceutical composition comprising a compound of the present invention, or a pharmaceutically acceptable salt, enantiomer, hydrate, solvate, prodrug, isomer, or tautomer thereof, and a pharmaceutically acceptable carrier which provides, upon administration to a human, a decrease in tumor burden and/or metastases. The pharmaceutical composition can be administered by oral means or other suitable means.

In another embodiment, the present invention relates to a compound of Formula (I) or a pharmaceutical composition comprising a compound of the present invention and a pharmaceutically acceptable carrier used for the treatment of cancers including but not limited to cervix, colon, breast, lung, and stomach cancers; hematologic cancer, such as but not limited to leukaemia, lymphoma and multiple myeloma; midline carcinomas, mesenchymal, hepatic, renal and neurological tumors; and melanoma, squamous cell carcinoma and cutaneous T-cell lymphoma.

In another embodiment, the present invention relates to a compound of Formula (I) or a pharmaceutical composition comprising a compound of the present invention and a pharmaceutically acceptable carrier used for the treatment of a variety of diseases or conditions related to systemic or tissue inflammation, inflammatory responses to infection or hypoxia, cellular activation and proliferation, lipid metabolism, fibrosis and in the prevention and treatment of viral infections. In one embodiment, the pharmaceutical composition is used.

Another embodiment of the present invention relates to a compound of Formula (I) or a pharmaceutical composition comprising a compound of the present invention and a pharmaceutically acceptable carrier used for the treatment of a variety of chronic and inflammatory conditions, including but not limited to rheumatoid arthritis, osteoarthritis, acute gout, psoriasis, systemic lupus erythematosus, multiple sclerosis, Crohn's disease, ulcerative colitis, asthma, chronic obstructive airways disease, pneumonitis, myocarditis, pericarditis, myositis, eczema, dermatitis, alopecia, vitiligo, bullous skin disease, nephritis, vasculitis, atherosclerosis, Alzheimer's disease, depression, Sjogren's syndrome, siloadenitis, central retinal vein occlusion, branched retinal vein occlusion, Irvine-Gass syndrome, parafoveal telangiectasis, retinitis pigmentosa, pars planitis, birdshot retinochoroidopathy, epiretinal membrane, cystic macular edema, maculopathies, vitreomacular traction syndromes, retinal detachment, neuroretinitis, idiopathic macular edema, retinitis, dry eye, vernal keratoconjuctivitis, atopic keratoconjuctivitis, anterior uveitis, pan uveitis, posterior uveitis, uveitis-associated macular edema, scleritis, diabetic retinopathy, diabetic macular edema, age-related macular dystrophy, hepatitis, pancreatitis, primary biliary cirrhosis, sclerosing cholangitis, Addison's disease, hypophysitis, thyroiditis, type I diabetes and acute rejection of transplanted organisms.

In another embodiment, the present invention relates to a compound of Formula (I) or a pharmaceutical composition comprising a compound of the present invention and a pharmaceutically acceptable carrier used for the treatment of a variety of acute inflammatory conditions such as acute gout, giant cell arteritis, nephritis including lupus nephritis, vasculitis with organ involvement such as glomerulonephritis, vasculitis including giant cell arteritis, Wegner's granulomatosis, Polyarteritis nodosa, Becet's disease, Kawasaki disease, Takayasu's arteritis, pyoderma gangrenosum, vasculitis with organ involvement and acute rejection of transplanted organs.

Another embodiment of the present invention relates to a compound of Formula (I) or a pharmaceutical composition comprising a compound of the present invention and a pharmaceutically acceptable carrier used for the treatment of a variety of diseases or conditions which involve inflammatory responses to infections with bacteria, viruses, fungi, parasites or their toxins, such as but not limited to sepsis, sepsis syndrome, septic shock, endotoxaemia, systemic inflammatory response syndrome, multi organ dysfunction syndrome, toxic shock syndrome, acute lung injury, acute respiratory distress syndrome, acute renal failure, fulminant hepatitis, burns, acute pancreatitis, post-surgical syndromes, sarcoidosis, Herxheimer reactions, encephalitis, myelitis, meningitis, malaria, systemic inflammatory responses associated with viral infections, such as but not limited to influenza, herpes zoster, herpes simplex and coronavirus.

In another embodiment, the present invention relates to a compound of Formula (I) or a pharmaceutical composition comprising a compound of the present invention and a pharmaceutically acceptable carrier used for the treatment of a variety of conditions associated with ischaemia reperfusion injury such as myocardial infarction, cerebro-vascular ischaemia, acute coronary syndromes, renal reperfusion injury, organ transplantation, coronary artery bypass procedures, cardio-, pulmonary and bypass procedures, pulmonary, renal, hepatic, gastrointestinal or peripheral limb embolism.

Another embodiment of the present invention relates to a compound of Formula (I) or a pharmaceutical composition comprising a compound of the present invention and a pharmaceutically acceptable carrier used for treatment of a variety of disorders of lipid metabolisms such as hypercholesterolemia, atherosclerosis and Alzheimer disease.

In another embodiment, the present invention relates to a compound of Formula (I) or a pharmaceutical composition comprising a compound of the present invention and a pharmaceutically acceptable carrier used for the treatment of a variety of fibrotic conditions such as, but not limited to idiopathic pulmonary fibrosis, renal fibrosis, post-operative structure, keloid scar formation, scleroma and cardial fibrosis.

Another embodiment of the present invention relates to a compound of Formula (I) or a pharmaceutical composition comprising a compound of the present invention used for the treatment of a variety of viral infections such as, but not limited to herpes virus, human papilloma virus, adenovirus, poxvirus, and DNA-viruses in general.

In another embodiment, the present invention relates to a compound of Formula (I) or a pharmaceutical composition comprising a compound of the present invention and a pharmaceutically acceptable carrier used for the treatment of a variety of conditions such as non-malignant melanoma, actinic keratosis, basal cell melanoma, in situ melanoma, squamous cell carcinoma and cutaneous T-cell lymphoma.

Another embodiment of the present invention relates to a compound of Formula (I) or a pharmaceutical composition comprising a compound of the present invention and a pharmaceutically acceptable carrier used for the treatment of obesity.

In another embodiment, the present invention relates to a compound of Formula (I) or a pharmaceutical composition comprising a pharmaceutically acceptable compound of the present invention and a pharmaceutically acceptable carrier used for male contraceptive.

Another embodiment of the present invention relates to a method of treating a disease associated with systemic inflammatory response syndrome, such as but not limited to sepsis, burns, pancreatitis, major trauma, hemorrhage and ischaemia, the method comprising administering a compound of Formulae (I), (II), (III), (IV), (V) or (VI).

In another embodiment, the present invention relates to a method to reduce incidence of SIRS, onset of shock, multi-organ dysfunction syndrome, acute lung injury, acute renal hepatic, cardiac and gastrointestinal injury at the point of diagnosis by administering a compound of Formulae (I), (II), (III), (IV), (V) or (VI).

Another embodiment of the present invention relates to a method to reduce incidence of sepsis, hemorrhage, tissue damage, and multiple organ dysfunction before surgery or any procedure with high risk of sepsis, the method comprising administering a compound of Formulae (I), (II), (III), (IV), (V) or (VI).

The disclosed compounds of the invention can be administered in effective amounts to treat or prevent a disorder and/or prevent the development thereof in subjects.

The present invention also relates to a pharmaceutical composition comprising a compound of Formula (I) and a pharmaceutically acceptable carrier. The pharmaceutical acceptable carrier may further include an excipient, diluent, additive, or surfactant.

The compounds or pharmaceutical compositions of the invention may be administered via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compounds or compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

In one embodiment, the present invention relates to a method of preparing a pharmaceutical composition of the present invention by mixing at least one pharmaceutically acceptable compound of the present invention, and, optionally, one or more pharmaceutically acceptable carriers, additives, or excipients.

In another embodiment, the present invention relates to a method of preparing a pharmaceutical composition of the present invention by mixing at least one pharmaceutically acceptable compound of the present invention and one or more additional therapeutic agents.

According to one embodiment of the invention, the additional therapeutic agents may be selected from the group consisting of cytotoxic agent, cisplatin, doxorubicin, taxotere, taxol, etoposide, irinotecan, camptostar, topotecan, paclitaxel, docetaxel, the epothilones, tamoxifen, 5-fluorouracil, methotrexate, temozolomide, cyclophosphamide, SCH 66336, tipifarnib (Zarnestra®), R115777, L778,123, BMS 214662, Iressa®, Tarceva®, C225, GLEEVEC®, Intron®, Peg-Intron®, aromatase combinations, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, leucovirin, oxaliplatin (ELOXATIN®), Pentostatine, Vinblastine, Vincristine, Vindesine, Bleomycin, Dactinomycin, Daunorubicin, Epirubicin, Idarubicin, Mithramycin™, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrol acetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Rituximab, C225, Campath, leucovorin, dexamethasone, bicalutamide, carboplatin, letrozole, megestrol, and valrubicin.

The dosage forms of the present invention, may contain a mixture of one or more compounds of this invention, and may include additional materials known to those skilled in the art as pharmaceutical excipients. Stabilizing additives may be incorporated into the delivery agent solution. With some drugs, the presence of such additives promotes the stability and dispersibility of the agent in solution. The stabilizing additives may be employed at a concentration ranging from about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. In one embodiment, the stabilizing additives are gum acacia, gelatin and methyl cellulose.

Examples of pharmaceutical excipients and additives include, but are not limited to: acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Aerosol propellants (butane, dichlorodifluoro-methane, dichlorotetrafluoroethane, isobutane, propane, trichloromonofluoromethane); Air displacements (carbon dioxide, nitrogen); Alcohol denaturants (denatonium benzoate, methyl isobutyl ketone, sucrose octaacetate); Alkalizing agents (strong ammonia solution, ammonium carbonate, diethanolamine, diisopropanolamine, potassium hydroxide, sodium bicarbonate, sodium borate, sodium carbonate, sodium hydroxide, trolamine); Anticaking agents (see glidant); Antifoaming agents (dimethicone, simethicone); Antimicrobial preservatives (benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Antioxidants (ascorbic acid, ascorbyl palmitate, butylated hydroxyanisole, butylated hydroxytoluene, hypophosphorous acid, monothioglycerol, propyl gallate sodium formaldehyde sulfoxylate sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Capsule lubricants (see tablet and capsule lubricant); Chelating agents (edetate disodium, ethylenediaminetetraacetic acid and salts, edetic acid); Coating agents (sodium carboxymethylcellulose, cellulose acetate, cellulose acetate phthalate ethylcellulose, gelatin, pharmaceutical glaze, hydroxypropyl cellulose, hydroxypropyl methylcellulose, hydroxypropyl methylcellulose phthalate methacrylic acid copolymer, methylcellulose, polyethylene glycol, polyvinyl acetate phthalate shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolamide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, lecithin, mono- and diglycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate monosodium glutamate, orange flower oil, peppermint, peppermint oil, peppermint spirit, rose oil, stronger rose water, thymol, tolu balsam tincture, vanilla, vanilla tincture, vanillin); Glidants and/or anticaking agents (calcium silicate, magnesium silicate, colloidal silicon dioxide, talc); Humectants (glycerin, hexylene glycol, propylene glycol, sorbitol); Plasticizers (castor oil, diacetylated monoglycerides, diethyl phthalate glycerin, mono- and di-acetylated monoglycerides, polyethylene glycol, propylene glycol, triacetin, triethyl citrate); Polymers (e.g., cellulose acetate, alkyl celluloses, hydroxyalkylcelluloses, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer 934p, carboxymethylcellulose calcium, carboxymethylcellulose sodium, carboxymethylcellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methylcellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); Tablet disintegrants (alginic acid, microcrystalline cellulose, croscarmellose sodium, crospovidone, polacrilin potassium, sodium starch glycolate starch, pregelatinized starch); Tablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, sesame oil, soybean oil, squalane); Vehicle: solid carrier (sugar spheres); Vehicle: sterile (bacteriostatic water for injection, bacteriostatic sodium chloride injection); Viscosity-increasing (see suspending agent); Water repelling agent (cyclomethicone, dimethicone, simethicone); and Wetting and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaurate, sorbitan monooleate, sorbitan monopalmitate, sorbitan monostearate, tyloxapol) may be used as excipients. This list is not meant to be exclusive, but instead merely representative of the classes of excipients and the particular excipients which may be used in dosage forms of the present invention.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

For preparing pharmaceutical compositions from the compounds described in this disclosure inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. For example, water or water-propylene glycol solutions for parenteral injection or addition of sweeteners and opacifiers for oral solutions, suspensions and emulsions. Liquid form preparations may also include solutions for intra-nasal administration.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

If formulated as a fixed dose, such combination products employ the compounds of this invention within the dosage range described herein, or as known to those skilled in the art.

Since the compounds of this invention are intended for use in pharmaceutical compositions a skilled artisan will understand that they can be provided in substantially pure forms for example, at least 60% pure, more suitably at least 75% pure, preferably at least 85% pure and most preferably at least 98% pure (w/w).

The pharmaceutical preparation may be in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, from about 1 mg to about 500 mg, from about 1 mg to about 250 mg, or from about 1 mg to about 25 mg, according to the particular application.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. A typical recommended daily dosage regimen for oral administration can range from about 1 mg/day to about 500 mg/day or 1 mg/day to 200 mg/day, in two to four divided doses.

The compounds of Formulae (I) to (VI) can form salts which are also within the scope of this invention. Reference to a compound of the Formula herein is understood to include reference to salts thereof, unless otherwise indicated.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-V C H; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

The synthetic schemes are presented for the synthesis of certain compounds herein disclosed. The process and results for the assays testing BET family bromodomain inhibition and effects on a cancer cell line proliferation are also described.

Definitions used in the following Schemes and elsewhere herein are:

Ac$_2$O acetic anhydride
Boc tert-butoxycarbonyl
DCE 1,2-dichloroethane
DIAD diisopropyl azodicarboxylate
DCM dichloromethane or methylene chloride
DIPEA N,N-diisopropylethylamine
DMA N,N-dimethylacetamide
DMAP 4-(dimethylamino)pyridine
DMC 2-chloro-1,3-dimethylimidazolidinium chloride
DMF N,N-dimethylformamide
DMSO dimethylsulfoxide
dppf bis(diphenylphosphino)ferrocene
Et$_3$N triethylamine
EtOAc ethyl acetate
EtOH ethanol
h hours
HATU 2-(3H-[1,2,3]triazolo[4,5-b]pyridin-3-yl)-1,1,3,3-tetramethylisouronium hexafluorophosphate
HCl hydrogen chloride
HPLC high performance liquid chromatography
(i-Pr)$_2$NEt N,N-diisopropylethylamine
LC/MS liquid chromatography/mass spectrometry
K$_2$CO$_3$ potassium carbonate
MS mass spectrometry
NBS N-bromosuccinimide
Ph$_3$P triphenylphosphine
PhCHO benzaldehyde
Pd$_2$(dba)$_3$ tris(dibenzylideneacetone)dipalladium
p-TsOH para-toluenesulfonic acid
rt room temperature
TFAA trifluoroacetic anhydride
THF tetrahydrofuran
Ts p-tolulenesulfonyl
XPhos 2-dicyclohexylphosphino-2',4',6'-triisopropylbiphenyl Analytical Methods, Materials, and Instrumentation Unless otherwise noted, all materials were obtained from commercial suppliers and were used without further purification. Anhydrous solvents were obtained from Sigma-Aldrich (Milwaukee, Wis.) and used directly. All reactions involving air- or moisture-sensitive reagents were performed under a nitrogen atmosphere.

Unless otherwise noted, mass-triggered HPLC purification and/or purity and low resolution mass spectral data were measured using either: (1) Waters Acquity ultra performance liquid chromatography (UPLC) system (Waters Acquity UPLC with Sample Organizer and Waters Micromass ZQ Mass Spectrometer) with UV detection at 220 nm and a low resonance electrospray positive ion mode (ESI) (Column: Acquity UPLC BEH C$_{18}$ 1.7 µm 2.1×50 mm; gradient: 5-100% Solvent B (95/5/0.09%: Acetonitrile/Water/Formic Acid) in Solvent A (95/5/0.1%: 10 mM Ammonium Formate/Acetonitrile/Formic Acid) for 2.2 min then 100-5% Solvent B in Solvent A for 0.01 min then hold at 5% Solvent B in Solvent A for 0.29 min) or (2) Waters HT2790 Alliance high performance liquid chromatography (HPLC) system (Waters 996 PDA and Waters ZQ Single Quad Mass Spectrometer) with UV detection at 220 nm and 254 nm and a low resonance electrospray ionization (positive/negative) mode (ESI) (Column: XBridge Phenyl or C18, 5 µm 4.6×50 mm; gradient: 5-95% Solvent B (95% methanol/5% water with 0.1% Formic Acid) in Solvent A (95% water/5% methanol with 0.1% Formic Acid) for 2.5 min then hold at 95% Solvent B in Solvent A for 1 min (purity and low resolution MS only).

Example 1

Intermediate 1. (S)-1-(6-bromo-2-methyl-3,4-dihydroquinoxaline-1(2H)-yl)-2,2,2-trifluoroethanone

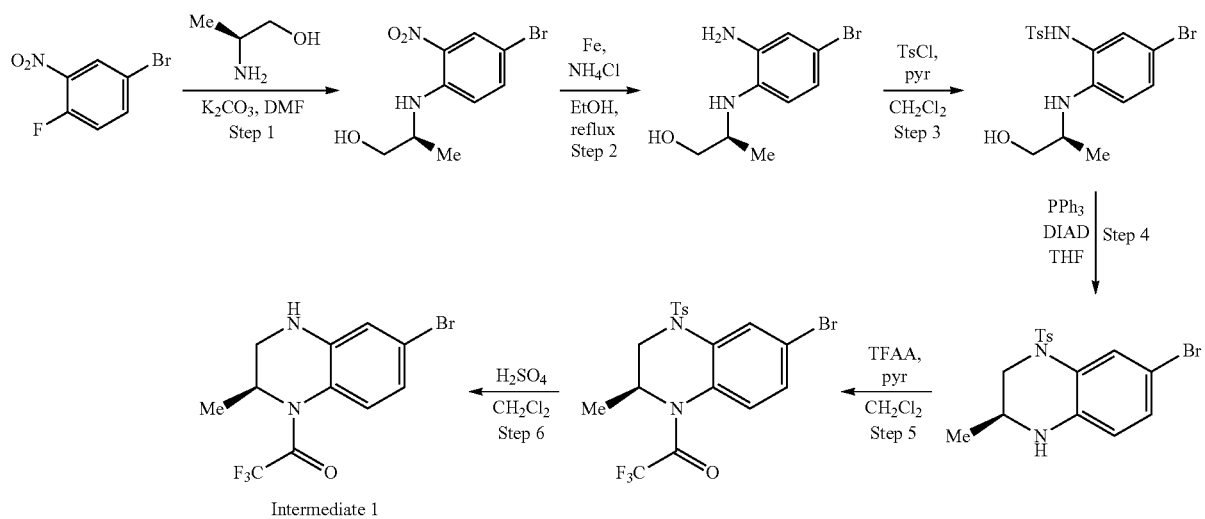

Intermediate 1

Step 1. (S)-2-(4-bromo-2-nitrophenylamino)propane-1-ol

A 1-L, three-necked, round bottomed flask fitted with a nitrogen inlet, overhead stirrer, thermocouple, and condenser was charged with 4-bromo-1-fluoro-2-nitrobenzene (46 g, 209 mmol), DMF (230 mL), potassium carbonate (31.8 g, 230 mmol), and (S)-2-aminopropane-1-ol (17.9 mL, 230 mmol). The reaction mixture was heated to 60° C. for 6 h and then cooled to rt and stirred overnight. The mixture was slowly diluted with water (690 mL), and the resulting slurry stirred at rt for 3 h and was then filtered. The solids were washed with water (120 mL) and dried under house vacuum (ca 17 Torr) overnight to afford (S)-2-(4-bromo-2-nitrophenylamino)propane-1-ol (72.98 g) as a yellow-orange solid which contained excess water, and was used in next step without further drying or purification. MS (ESI, pos. ion) m/z 275 [M+1]$^+$.

Step 2. (S)-2-(2-amino-4-bromophenylamino)propane-1-ol

A 2-L, three-necked, round bottomed flask fitted with a nitrogen inlet, overhead stirrer, thermocouple, and condenser was charged with iron power (117 g, 2090 mmol), ammonium chloride (1.118 g, 20.90 mmol), ethanol (375 mL), and water (201 mL). The mixture was heated to 80° C., and a solution of (S)-2-(4-bromo-2-nitrophenylamino)propane-1-ol (57.5 g, 209 mmol) in ethanol (200 mL) was slowly added. The mixture stirred at 80° C. for 4 h. The reaction mixture was filtered through a pad of Celite and washed with ethanol (100 mL). The filtrate was concentrated under reduced pressure to remove the ethanol, and the resulting aqueous slurry stirred at rt for 3 h. The slurry was then filtered, and the solids were washed with water (100 mL) and dried under a nitrogen atmosphere overnight to afford (S)-2-(2-amino-4-bromophenylamino)propane-1-ol (47.55 g, 89%) as an off-white solid. MS (ESI, pos. ion) m/z 245 [M+1]$^+$.

Step 3. (S)-N-(5-bromo-2-(1-hydroxypropan-2-ylamino)phenyl)-4-methylbenzene sulfonamide A 1-L, round bottomed flask fitted with a nitrogen inlet, magnetic stir bar, and thermocouple was charged with (S)-2-(2-amino-4-bromophenylamino)propane-1-ol (47.55 g, 194 mmol), and pyridine (475 mL). The mixture was cooled to 0° C. and p-toluene sulfonyl chloride (37.0 g, 194 mmol) was added in portions of 12.6 and 24.4 g. The internal temperature rose from 1.5 to 15.6° C. following each addition. The reaction mixture stirred at 0° C. for 1.5 h and was then warmed to room temperature. The pyridine was removed under reduced pressure, and the residue was diluted with ethyl acetate (300 mL) and washed with water (100 mL). The combined organic phases were washed with half saturated brine (100 mL) and concentrated under reduced pressure. The residue was dissolved in toluene (250 mL), and the solution concentrated under reduced pressure (in order to remove some residual pyridine). The crude product was purified by column chromatography on silica gel (eluting with 1:1 hexanes-ethyl acetate). The product-containing fractions were combined and concentrated under reduced pressure. Toluene (250 mL) was added, and the mixture was concentrated under reduced pressure to removed trace pyridine. The material was dried under vacuum (ca 17 Torr) to afford (S)-N-(5-bromo-2-(1-hydroxypropan-2-ylamino)phenyl)-4-methylbenzenesulfonamide (88 g, 110%) as a viscous yellow oil that contains 11 wt % toluene. MS (ESI, pos. ion) m/z 399 [M+1]$^+$.

Step 4. (S)-7-bromo-3-methyl-1-tosyl-1,2,3,4-tetrahydroquinoxaline

A 3-L, three-necked, round bottomed flask fitted with a nitrogen inlet, overhead stirrer, and thermocouple was charged with (S)-N-(5-bromo-2-(1-hydroxypropan-2-ylamino)phenyl)-4-methylbenzenesulfonamide (77.0 g, 193 mmol), THF (1925 mL), and triphenylphosphine (60.7 g, 231 mmol). The solution was cooled to 0° C., and diisopropyl azodicarboxylate (DIAD) (41.2 mL, 212 mmol) was slowly added while maintaining the internal temperature below 7° C. The reaction mixture stirred at 0° C. for 1.5 h and was then warmed to room temperature. The mixture was concentrated and the residue was purified by column chromatography on silica gel (eluting with dichloromethane). The product-containing fraction were combined and concentrated under reduced pressure. The material was treated with a mixture of 4:1 hexanes-dichloromethane, and the slurry was stirred for 3 h and then filtered. The solids were rinsed with cold (ca. 0° C.) solution of 4:1 hexanes-dichloromethane (50 mL) and dried to afford (S)-7-bromo-3-methyl-1-tosyl-1,2,3,4-tetrahydroquinoxaline (61.8 g, 84%) as a white solid. MS (ESI, pos. ion) m/z 381 [M+1]+.

Step 5. (S)-1-(6-bromo-2-methyl-4-tosyl-3,4-dihydroquinoxaline-1(2H)-yl)-2,2,2-trifluoroethanone A 3-L, three-necked, round bottomed flask fitted with a nitrogen inlet, overhead stirrer, and thermocouple was charged with (S)-7-bromo-3-methyl-1-tosyl-1,2,3,4-tetrahydroquinoxaline (90.43 g, 237 mmol), dichloromethane (1720 mL), and pyridine (28.8 mL, 356 mmol). The solution was cooled to 0° C., and 2,2,2-trifluoroacetic anhydride (40.2 mL, 285 mmol) was slowly added while maintaining the internal temperature below 10° C. Once the addition was complete, the reaction mixture was stirred at 0° C. for 30 min and then warmed to rt. After 1.5 h at rt, the reaction mixture was washed with water (200 mL), 1 M aqueous HCl solution (200 mL) and water (200 mL). The combined organic layers were concentrated under reduced pressure. The crude product was further dried under vacuum (ca 17 Torr) at rt during which time the product crystallized to afford (S)-1-(6-bromo-2-methyl-4-tosyl-3,4-dihydroquinoxaline-1(2H)-yl)-2,2,2-trifluoroethanone (113 g, 99%) as a tan solid. MS (ESI, pos. ion) m/z 477[M+1]+.

Step 6. (S)-1-(6-bromo-2-methyl-3,4-dihydroquinoxaline-1(2H)-yl)-2,2,2-trifluoroethanone A 3-L, three-necked, round bottomed flask fitted with a nitrogen inlet, magnetic stir bar, and thermocouple was charged with (S)-1-(6-bromo-2-methyl-4-tosyl-3,4-dihydroquinoxaline-1(2H)-yl)-2,2,2-trifluoroethanone (106.81 g, 224 mmol), dichloromethane (1070 mL), and sulfuric acid (18 M, 119 mL, 2238 mmol). The reaction mixture stirred at rt for 1 h and was then cooled to 0° C. Water (1070 mL) was slowly added in 100 mL portions, while maintaining the internal temperature at ca. 0° C. (Note: the internal temperature rose from ca. 2.6° C. to 23.8° C. with each addition). After the final water addition, the internal temperature was 34° C., and the mixture was cooled to rt. The aqueous layer was separated extracted with dichloromethane (700 mL). The combined organic layers were washed with water (700 mL) and then concentrated under reduced pressure. The crude product was purified by column chromatography on silica gel (eluting with 100% dichloromethane). The product-containing fractions were combined and concentrated under reduced pressure. Further drying under vacuum (ca. 17 Torr) at rt afforded (S)-1-(6-bromo-2-methyl-3,4-dihydroquinoxaline-1(2H)-yl)-2,2,2-trifluoroethanone (71.8 g, 99%) as a brown solid. MS (ESI, pos. ion) m/z 323[M+1]+.

Example 2

Intermediate 2. (S)-1-(6-bromo-2-methyl-3,4-dihydroquinoxaline-1(2H)-yl)ethanone

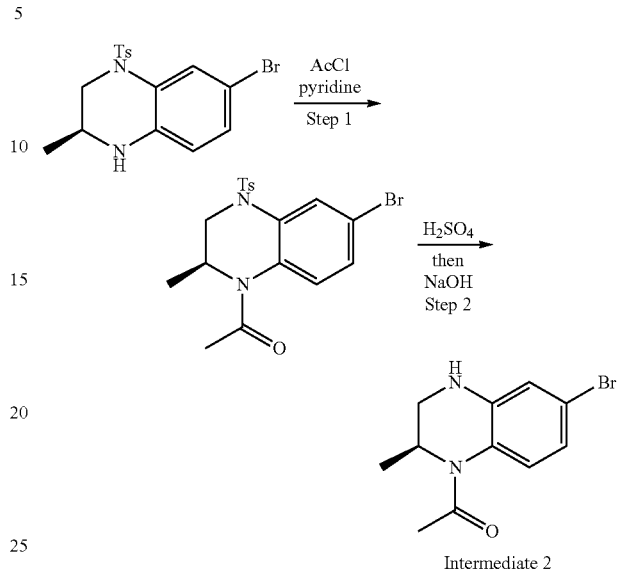

Step 1. (S)-1-(6-bromo-2-methyl-4-tosyl-3,4-dihydroquinoxaline-1(2H)-yl)ethanone A 2-L, three-necked, round bottomed flask fitted with a nitrogen inlet, overhead stirring, and thermocouple was charged with (S)-7-bromo-3-methyl-1-tosyl-1,2,3,4-tetrahydroquinoxaline (45.0 g, 118 mmol), dichloromethane (900 mL), and pyridine (14.32 mL, 177 mmol). The mixture was cooled to 0° C. and acetyl chloride (10.07 mL, 142 mmol) was added slowly while maintaining the internal temperature below 10° C. The reaction mixture was held cold (ca. 30 min) and then warmed to rt. After 1 h, the reaction was diluted with dichloromethane (200 mL), and the solution was washed with 1 M aqueous HCl (2×100 mL) and water (100 mL). The organic layer was concentrated under reduced pressure and the crude product was purified by column chromatography on silica gel (eluting with 3:1 dichloromethane-ethyl acetate) to afford (S)-1-(6-bromo-2-methyl-4-tosyl-3,4-dihydroquinoxaline-1(2H)-yl)ethanone (54.15 g, 108%), which contained 4.1 wt % ethyl acetate, as a colorless to yellow oil. MS (ESI, pos. ion) m/z 424 [M+1]+.

Step 2. (S)-1-(6-bromo-2-methyl-3,4-dihydroquinoxaline-1(2H)-yl)ethanone

A 1-L round bottomed flask was charged with (S)-1-(6-bromo-2-methyl-4-tosyl-3,4-dihydroquinoxaline-1(2H)-yl) ethanone (13.32 g, 31.5 mmol) and sulfuric acid (67.1 mL, 1259 mmol). The reaction mixture was stirred until all the viscous oil had dissolved (ca. 1 h). The reaction mixture was then quenched over crushed ice (ca. 50 g). The mixture was carefully neutralized with 10 N sodium hydroxide (157 mL, 1573 mmol) while not allowing internal temperature to exceed 10° C. The mixture was diluted with dichloromethane (200 mL) and the layers separated. The aqueous layer was extracted with dichloromethane (100 mL). The organic layers were combined and concentrated under reduced pressure. The crude product was purified by column chromatography (eluting with 4:1 dichloromethane-ethyl acetate) to afford (S)-1-(6-bromo-2-methyl-3,4-dihydroquinoxaline-1(2H)-yl)ethanone (7.18 g, 85%) as an off-white solid. MS (ESI, pos. ion) m/z 269 [M+1]+.

Example 3

Intermediate 3. (S)-(6-bromo-2-methyl-3,4-dihydroquinoxaline-1(2H)-yl)(cyclopropyl)methanone

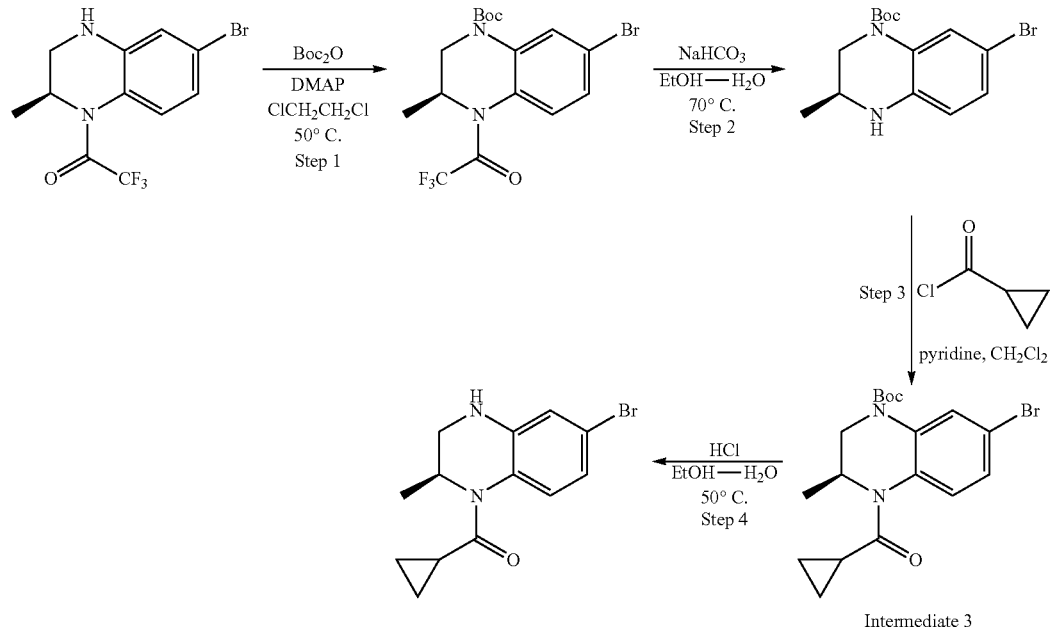

Intermediate 3

Step 1. (S)-tert-butyl 7-bromo-3-methyl-4-(2,2,2-trifluoroacetyl)-3,4-dihydroquinoxaline-1(2H)-carboxylate A 500-mL three neck round bottomed flask fitted with a nitrogen inlet, magnetic stir bar, thermocouple, and condenser was charged with (S)-1-(6-bromo-2-methyl-3,4-dihydroquinoxaline-1(2H)-yl)-2,2,2-trifluoroethanone (10 g, 30.9 mmol), dichloroethane (150 mL), N,N-dimethylpyridin-4-amine (0.378 g, 3.09 mmol), and di-tert-butyl dicarbonate (9.46 g, 43.3 mmol), and the reaction mixture was heated to 50° C. for 1 h. The reaction mixture was cooled to room temperature and concentrated under reduce pressure to afford (S)-tert-butyl 7-bromo-3-methyl-4-(2,2,2-trifluoroacetyl)-3,4-dihydroquinoxaline-1(2H)-carboxylate (13.10 g, 100%) as a white solid. MS (ESI, pos. ion) m/z 423, 425 [M+1]⁺.

Step 2. (S)-tert-butyl 7-bromo-3-methyl-3,4-dihydroquinoxaline-1(2H)-carboxylate A 500-mL round bottomed flask fitted with a nitrogen inlet, magnetic stir bar, and condenser was charged with (S)-tert-butyl 7-bromo-3-methyl-4-(2,2,2-trifluoroacetyl)-3,4-dihydroquinoxaline-1(2H)-carboxylate (13.10 g, 31.0 mmol), ethanol (130 mL), and half-saturated aqueous sodium bicarbonate solution (130 mL, 31.0 mmol). The reaction mixture was heated to 70° C. for 24 h and then cooled to room temperature. The ethanol was removed under reduced pressure, and the residue was extracted into dichloromethane (250 mL). The combined organic layers were concentrated under reduced pressure. The crude product was purified by column chromatography on silica gel (eluting with 4:1 hexanes-ethyl acetate) to afford (S)-tert-butyl 7-bromo-3-methyl-3,4-dihydroquinoxaline-1(2H)-carboxylate (9.78 g, 97%) as a white solid. MS (ESI, pos. ion) m/z 327, 329 [M+1]⁺.

Step 3. (S)-tert-butyl 7-bromo-4-(cyclopropanecarbonyl)-3-methyl-3,4-dihydroquinoxaline-1(2H)-carboxylate A 100-mL round bottomed flask fitted with a nitrogen inlet and magnetic stir bar was charged with (S)-tert-butyl 7-bromo-3-methyl-3,4-dihydroquinoxaline-1(2H)-carboxylate (4.75 g, 14.52 mmol), dichloromethane (50 mL), pyridine (1.996 mL, 24.68 mmol), and cyclopropanecarbonyl chloride (1.976 mL, 21.77 mmol). The reaction mixture was stirred at rt for 2 h and then 1 M aqueous HCl solution (25 mL) was added. The organic layer was separated and concentrated under reduced pressure to afford (S)-tert-butyl 7-bromo-4-(cyclopropanecarbonyl)-3-methyl-3,4-dihydroquinoxaline-1(2H)-carboxylate (5.72 g, 99%) as a solid, which was used directly in next step. MS (ESI, pos. ion) m/z 395, 397 [M+1]⁺.

Step 4. (S)-(6-bromo-2-methyl-3,4-dihydroquinoxaline-1(2H)-yl)(cyclopropyl)methanone A 200-mL round bottomed flask fitted with a nitrogen inlet, magnetic stir bar, and condenser was charged with (S)-tert-butyl 7-bromo-4-(cyclopropanecarbonyl)-3-methyl-3,4-dihydroquinoxaline-1(2H)-carboxylate (5.74 g, 14.52 mmol), ethanol (100 mL), water (25 mL), and 6 M hydrochloric acid solution (2.66 mL, 15.97 mmol). The reaction mixture was heated to 50° C. for 24 h and then cooled to room temperature. The ethanol was removed under reduced pressure, the residue was extracted into dichloromethane (100 mL), and the extract was concentrated under reduced pressure. The crude material was purified by column chromatography on silica gel (eluting with 3:2 hexanes-ethyl acetate) to afford (S)-(6-bromo-2-methyl-3,4-dihydroquinoxaline-1(2H)-yl)(cyclopropyl)methanone (4.00 g, 93%) as an off-white solid. MS (ESI, pos. ion) m/z 295, 297 [M+1]⁺.

Example 4

Intermediate 4. (S)-methyl 6-bromo-2-methyl-3,4-dihydroquinoxaline-1(2H)-carboxylate

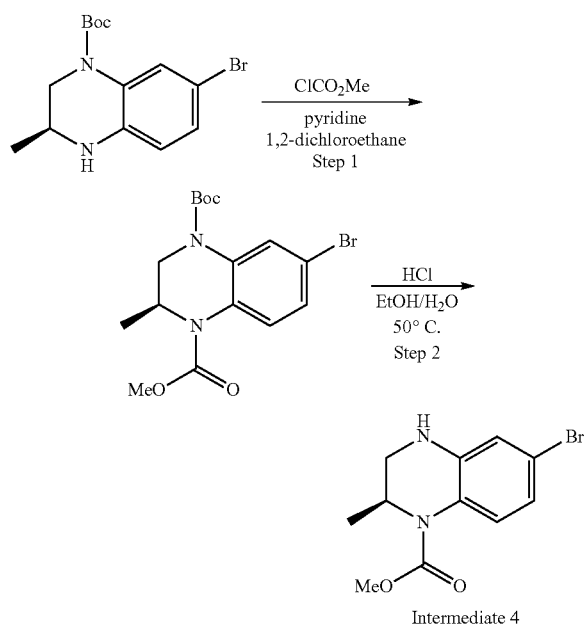

Intermediate 4

Step 1. (S)-4-tert-butyl 1-methyl 6-bromo-2-methyl-2,3-dihydroquinoxaline-1,4-dicarboxylate A 100-mL round bottom flask fitted with nitrogen inlet and magnetic stir bar was charged with (S)-tert-butyl 7-bromo-3-methyl-3,4-dihydroquinoxaline-1(2H)-carboxylate (4.95 g, 15.13 mmol), 1,2-dichloroethane (50 mL), and pyridine (2.45 mL, 30.3 mmol). The reaction was cooled to 0° C. and methyl chloroformate (1.758 ml, 22.69 mmol) was added slowly. The reaction mixture stirred at 0° C. for 30 min and was then warmed to room temperature. After 2 h the reaction was diluted with 1,2-dichloroethane (20 mL) and washed with 1 M aqueous HCl solution (25 mL). The organic was concentrated under reduced pressure to afford (S)-4-tert-butyl 1-methyl 6-bromo-2-methyl-2,3-dihydroquinoxaline-1,4-dicarboxylate (5.83 g, 100%) as an amber oil. The material was used without further purification. MS (ESI, pos. ion) m/z 385 $[M+1]^+$.

Step 2. (S)-methyl 6-bromo-2-methyl-3,4-dihydroquinoxaline-1(2H)-carboxylate (S)-Methyl 6-bromo-2-methyl-3,4-dihydroquinoxaline-1(2H)-carboxylate (4.09 g, 95%) was prepared as a white solid following the procedure outlined in Step 4 of the synthesis of (S)-(6-bromo-2-methyl-3,4-dihydroquinoxalin-1 (2H)-yl)(cyclopropyl)methanone (Example 3). M/S (ESI, pos. ion) m/z 285 $[M+1]^+$.

Example 5

Intermediate 5. (S)-1-(7-bromo-3-methyl-2,3-dihydropyrido[3,2-b]pyrazin-4(1H)-yl)ethanone

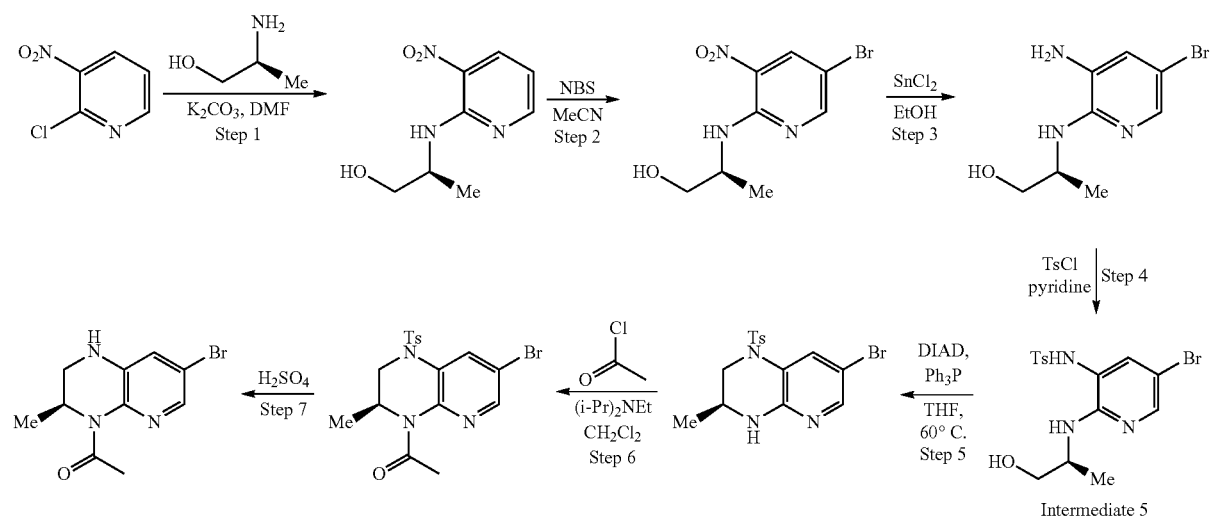

Intermediate 5

Step 1. (S)-2-(3-nitropyridin-2-ylamino)propane-1-ol

A 100-mL round bottomed flask equipped with a magnetic stir bar was charged with 2-chloro-3-nitropyridine (4.0 g, 25.2 mmol), potassium carbonate (4.18 g, 30.3 mmol), and DMF (25 mL). Next, (S)-2-aminopropane-1-ol (1.990 g, 26.5 mmol) was added at rt. The yellow mixture was stirred at rt for 45 min, then was heated to 50° C. for 22 h. Heating was discontinued, and after the mixture had cooled, it was diluted with water (50 mL) and extracted with ethyl acetate. The organic phase was separated and washed with 5% aqueous sodium chloride solution (3×25 mL). The combined aqueous layers were extracted with ethyl acetate. The combined organic phases were concentrated to yield (S)-2-(3-nitropyridin-2-ylamino)propane-1-ol (5.68 g, 28.8 mmol, 114%) as a dark yellow syrup. MS (ESI, pos. ion) m/z 198 [M+1]$^+$.

Step 2. (S)-2-(5-bromo-3-nitropyridin-2-ylamino) propane-1-ol

A solution of (S)-2-(3-nitropyridin-2-ylamino)propane-1-ol (4.88 g, 24.75 mmol) in acetonitrile (50 mL) was cooled to 0° C. and treated with N-bromosuccinimide (4.40 g, 24.75 mmol) in one portion. The ice bath was left in place and allowed to slowly expire over 15 h. The solution was then concentrated under reduced pressure in order to remove most (>90%) of the acetonitrile. The concentrated solution was dissolved in ethyl acetate and washed with half-saturated aqueous sodium bicarbonate solution (2×75 mL) and 5% aqueous sodium chloride solution (1×75 mL). The ethyl acetate solution was then concentrated under reduced pressure to afford (S)-2-(5-bromo-3-nitropyridin-2-ylamino)propane-1-ol (7.11 g) as a dark yellow solution which was used in the next step without purification. MS (ESI, pos. ion) m/z 276. 278 [M+1]$^+$.

Step 3. (S)-2-(3-amino-5-bromopyridin-2-ylamino) propane-1-ol

A 500-mL round bottomed flask equipped with a magnetic stir bar was charged with a solution of (S)-2-(5-bromo-3-nitropyridin-2-ylamino)propane-1-ol (6.8 g, 24.63 mmol) in ethanol (55 mL). Tin(II) chloride dihydrate (22.23 g, 99 mmol) was added, and the mixture was heated to 75° C. The dark orange color faded to a pale orange color over time. After 3 h, heating was discontinued. After the reaction mixture had cooled to ambient temperature, it was slowly diluted with 2 M sodium hydroxide solution (100 mL, 200 mmol). The thick slurry was further diluted with ethyl acetate. The biphasic mixture was rapidly stirred for 10-15 min, and then the organic layer was decanted into a separatory funnel. The small aqueous layer that carried with the ethyl acetate was drained, and the ethyl acetate extract was washed with 5% aqueous sodium chloride solution (2×100 mL). The original aqueous slurry was extracted with ethyl acetate, and the extract subsequently washed with the 5% aqueous sodium chloride solution. The combined ethyl acetate extracts were concentrated under reduced pressure. The biphasic residue was dissolved in acetonitrile (ca. 100 mL), which was then removed under reduced pressure. The process was repeated to yield crude (S)-2-(3-amino-5-bromopyridin-2-ylamino)propane-1-ol (5.95 g, 24.18 mmol, 98%) as a dark purple-green syrup, which eventually solidified upon standing. MS (ESI, pos. ion) m/z 246, 248 [M+1]$^+$.

Step 4. (S)-N-(5-bromo-2-(1-hydroxypropan-2-ylamino)pyridin-3-yl)-4-methylbenzene sulfonamide A solution of crude (S)-2-(3-amino-5-bromopyridin-2-ylamino)propane-1-ol (5.85 g, 23.77 mmol) dissolved in pyridine (58 mL) was cooled to 0° C. and treated with p-toluenesulfonyl chloride (4.53 g, 23.77 mmol) in one portion. The reaction mixture was stirred at 0° C. After 45 min, the solution was concentrated under reduced pressure. The residue was partitioned between water (60 mL) and ethyl acetate. The ethyl acetate layer was separated and washed with 5% aqueous sodium chloride solution (2×50 mL) and concentrated under reduced pressure. The resulting syrup was dissolved in toluene (100 mL), which was then removed under reduced pressure in an effort to remove residual pyridine. The crude product (10.4 g) was purified by column chromatography on silica gel (eluting with 3:1 dichloromethane-ethyl acetate followed by 2:1 dichloromethane-ethyl acetate and finally 3:2 dichloromethane-ethyl acetate). The product-containing fractions were combined and concentrated. The resulting syrup was dissolved in dichloromethane and the solution diluted with heptane. The mixture was concentrated under reduced pressure to yield (S)-N-(5-bromo-2-(1-hydroxypropan-2-ylamino)pyridin-3-yl)-4-methylbenzenesulfonamide (8.6 g, 21.5 mmol, 90%) as a nearly colorless foam/solid. MS (ESI, pos. ion) m/z 400, 402 [M+1]$^+$.

Step 5. (S)-7-bromo-3-methyl-1-tosyl-1,2,3,4-tetrahydropyrido[3,2-b]pyrazine

A solution of (S)-N-(5-bromo-2-(1-hydroxypropan-2-ylamino)pyridin-3-yl)-4-methylbenzenesulfonamide (6.39 g, 15.96 mmol) and triphenylphosphine (5.02 g, 19.16 mmol) in THF (160 ml) was heated to 60° C. whereupon diisopropyl azodicarboxylate (3.72 mL, 19.16 mmol) was added dropwise to the warm solution over a 5 minute period. Heating was discontinued after 5 minutes, and after cooling briefly, the solution was concentrated under reduced pressure. The residue was dissolved in dichloromethane and purified by column chromatography on silica gel (eluting with 6:1 dichloromethane-ethyl acetate followed by 5:1 dichloromethane-ethyl acetate) to afford (S)-7-bromo-3-methyl-1-tosyl-1,2,3,4-tetrahydropyrido[3,2-b]pyrazine a tan, waxy solid (3.12 g) which was used without further purification. MS (ESI, pos. ion) m/z 382, 384 [M+1]$^+$.

Step 6. (S)-1-(7-bromo-3-methyl-1-tosyl-2,3-dihydropyrido[3,2-b]pyrazin-4(1H)-yl) ethanone A solution of (S)-7-bromo-3-methyl-1-tosyl-1,2,3,4-tetrahydropyrido[3,2-b]pyrazine (3.12 g, 8.11 mmol) in dichloromethane (31 mL) was treated with pyridine (0.984 mL, 12.16 mmol), N,N-dimethylaminopyridine (0.099 g, 0.811 mmol), and acetyl chloride (0.692 mL, 9.73 mmol) at rt. The reaction mixture stirred at rt for 7 h, and was then heated at 35° C. for 1 h. The reaction mixture was cooled to room temperature and diluted with dichloromethane. The resulting mixture was washed with 1 N aqueous hydrogen chloride solution (2×15 mL), half-saturated aqueous sodium bicarbonate solution (15 mL), and 5% aqueous sodium chloride solution (15 mL). The combined organic layers was concentrated under reduced pressure to afford a dark syrup. The crude product was purified by column chromatography on silica gel (eluting with 20:1 dichloromethane-methyl tert-butyl ether followed by 15:1 dichloromethane-methyl tert-butyl ether) to afford a nearly colorless gum (1.5 g) that crystallized upon standing. The material was recrystallized from methyl tert-butyl ether-hexanes to afford colorless crystals. The mother liquors were re-purified by flash chromatography on silica gel (eluting with 1:1 methyl tert-butyl ether-hexanes followed by 3:2 methyl tert-butyl ether-hexanes) to afford additional product. The material was combined to afford (S)-1-(7-bromo-3-methyl-1-tosyl-2,3-dihydropyrido[3,2-b]pyrazin-4(1H)-yl)ethanone (1.213 g, 35%). MS (ESI, pos. ion) m/z 424, 426 [M+1]$^+$.

Step 7. (S)-1-(7-bromo-3-methyl-2,3-dihydropyrido[3,2-b]pyrazin-4(1H)-yl)ethanone A 50-mL round bottomed flask was charged with (S)-1-(7-bromo-3-methyl-1-tosyl-2,3-dihydropyrido[3,2-b]pyrazin-4(1H)-yl)ethanone (1.2 g, 2.83 mmol) and sulfuric acid (5.79 mL, 109 mmol). A slight exotherm was observed. The mixture was stirred until all the substrate dissolved (ca. 20-30 min). After a total of 30-45 min, the pale yellow solution was carefully pipetted onto crushed ice (50 g). The flask was rinsed with a small portion of water (ca. 2 mL), which was also added to the crushed ice. The crushed ice/aqueous solution mixture was then stirred as 10 N aqueous sodium hydroxide solution was slowly added while maintaining the internal temperature below 9° C. (with the aid of an external crushed ice/water bath). The pH was adjusted to 11-12 (a total of ca. 22 mL 10 N aqueous sodium hydroxide solution was added). After the addition was complete, the mixture was poured into a separatory funnel and extracted with dichloromethane. The dichloromethane layer was washed with water (2×30 mL) and concentrated under reduced pressure. The crude product was purified by column chromatography on silica gel (eluting with 4:1 dichloromethane-ethyl acetate) to afford (5)-1-(7-bromo-3-methyl-2,3-dihydropyrido[3,2-b]pyrazin-4(1H)-yl)ethanone (384 mg, 50%) as a colorless foam. MS (ESI, pos. ion) m/z 270, 272 [M+1]$^+$.

Example 6

Intermediate 6. (S)-1-(6-bromo-2-methyl-3,4-dihydropyrido[2,3-b]pyrazin-1(2H)-yl) ethanone (1.349 mL, 13.31 mmol), and magnesium sulfate (4.81 g, 39.9 mmol), and the mixture stirred at rt for 24 h. The slurry was filtered through a medium frit Buchner funnel and the solids were washed with additional dichloromethane. The filtrate was concentrated to a colorless syrup. The crude imine (2.171 g, 13.3 mmol) was dissolved in methanol (30 mL) and treated with sodium borohydride (0.503 g, 13.30 mmol) in two portions (0.200 g then 0.303 g 5 min later) at rt. The solution was stirred at rt for 4 h and then concentrated under reduced pressure. The residue was dissolved in 1 N aqueous hydrogen chloride solution (40 mL). This aqueous solution was washed with ethyl acetate (2×40 mL). The aqueous layer was made basic by the addition of 10 N aqueous sodium hydroxide solution (8 mL) and extracted with dichloromethane. The dichloromethane layer was washed with 5% aqueous sodium chloride solution (20 mL) and concentrated under reduced pressure to afford (R)-1-(benzylamino)propan-2-ol (1.61 g, 73%) as a colorless syrup. MS (ESI, pos. ion) m/z 166 [M+1]$^+$.

Step 2. (R)-1-(benzyl(6-bromo-3-nitropyridin-2-yl)amino)propan-2-ol 2,6-Dibromo-3-nitropyridine (2.59 g, 9.20 mmol) and triethylamine (2.70 mL, 19.37 mmol) were added to a solution of (R)-1-(benzylamino)propan-2-ol (1.6 g, 9.68 mmol) in ethanol (35 mL). The solution was stirred at rt for 17 h and then concentrated under reduced pressure. The residue was partitioned between ethyl acetate and saturated aqueous sodium bicarbonate solution (25 mL). The layers were separated, and the organic layer was washed with 5% aqueous

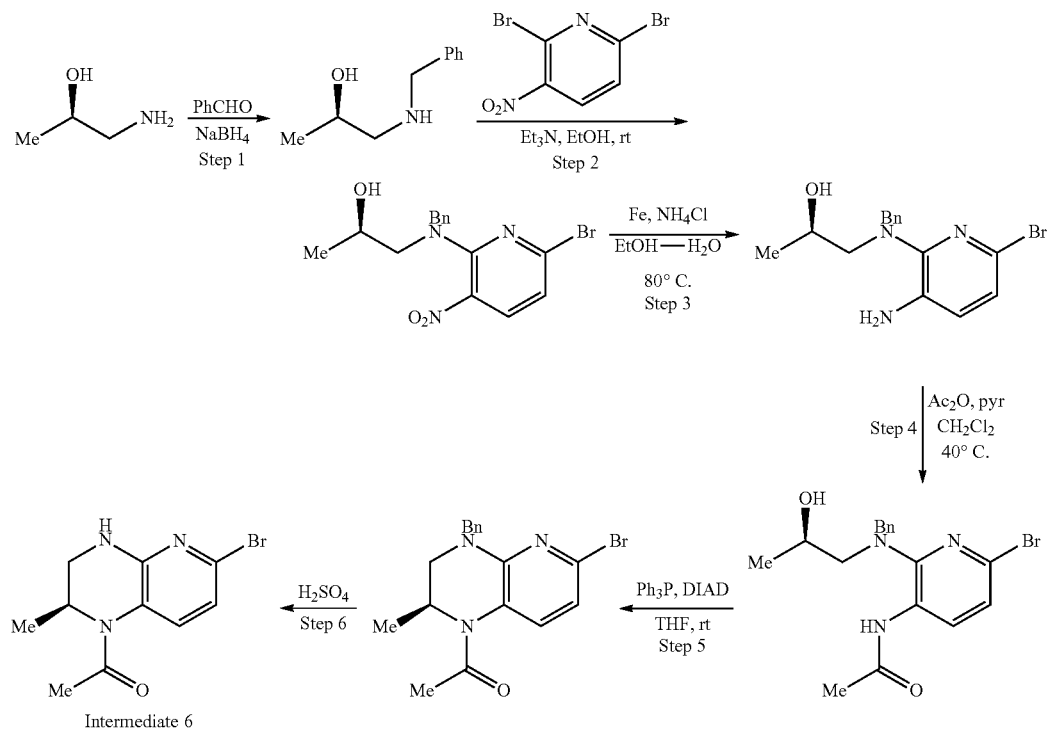

Intermediate 6

Step 1. (R)-1-(benzylamino)propan-2-ol

A 100-mL round bottomed flask equipped with a magnetic stir bar was charged with (R)-1-aminopropan-2-ol (1.0 g, 13.31 mmol), dichloromethane (25 mL), benzaldehyde sodium chloride solution (25 mL). The ethyl acetate layer was concentrated under reduced pressure to afford an orange syrup. The crude product was purified by column chromatography on silica gel (eluting with 5:1 hexanes-ethyl acetate followed by 3:1 hexanes-ethyl acetate) to afford (R)-1-(benzyl(6-bromo-3-nitropyridin-2-yl)amino)propan-2-ol (3.01 g, 85%) as a bright yellow syrup. MS (ESI, pos. ion) m/z 388, 390 [M+Na]+.

Step 3. (R)-1-((3-amino-6-bromopyridin-2-yl)(benzyl)amino)propan-2-ol

A 100-mL round bottomed flask equipped with a magnetic stir bar was charged with ammonium chloride (0.044 g, 0.820 mmol), water (8.2 mL), iron powder (4.58 g, 82 mmol), and ethanol (21.8 mL). The mixture was heated to 80° C., and a solution of (R)-1-(benzyl(6-bromo-3-nitropyridin-2-yl)amino)propan-2-ol (3.00 g, 8.2 mmol) in ethanol (8.20 mL) was slowly added over 2 min. The reaction mixture was stirred at 80° C. After 90 min, heating was discontinued and the reaction mixture filtered through a pad of Celite. The flask and Celite pad were rinsed with ethanol. The filtrate was concentrated. The residue was then partitioned between ethyl acetate and saturated aqueous sodium bicarbonate solution (20 mL). The ethyl acetate layer was washed with 5% aqueous sodium chloride solution (20 mL) and concentrated under reduced pressure to afford crude (R)-1-((3-amino-6-bromopyridin-2-yl)(benzyl)amino)propan-2-ol (2.22 g) as a dark syrup. MS (ESI, pos. ion) m/z 336, 338 [M+1]+.

Step 4. (R)-N-(2-(benzyl(2-hydroxypropyl)amino)-6-bromopyridin-3-yl)acetamide Acetic anhydride (0.623 mL, 6.60 mmol) was added to a solution of crude (R)-1-((3-amino-6-bromopyridin-2-yl)(benzyl)amino)propan-2-ol (2.22 g, 6.60 mmol) and pyridine (1.60 mL, 19.8 mmol) in dichloromethane (60 mL). The reaction mixture was then heated to 40° C. for 39 h. The reaction mixture was concentrated under reduced pressure. The crude residue was dissolved in toluene (ca. 100 mL), which was then concentrated under reduced pressure in order to remove residual pyridine. The crude product was purified by column chromatography on silica gel (eluting with 2:1 dichloromethane-ethyl acetate followed by 3:2 dichloromethane-ethyl acetate) to afford (R)-N-(2-(benzyl(2-hydroxypropyl)amino)-6-bromopyridin-3-yl)acetamide (1.39 g, 56% yield). MS (ESI, pos. ion) m/z 378, 380 [M+1]+.

Step 5. (S)-1-(4-benzyl-6-bromo-2-methyl-3,4-dihydropyrido[2,3-b]pyrazine-1(2H)-yl)ethanone Diisopropyl azodicarboxylate (0.763 mL, 3.93 mmol) was slowly added to a solution of (R)-N-(2-(benzyl(2-hydroxypropyl)amino)-6-bromopyridin-3-yl)acetamide (1.35 g, 3.57 mmol) and triphenylphosphine (1.030 g, 3.93 mmol) in THF (35.7 mL). A mild exotherm was observed. The reaction mixture stirred at room temperature for 30 minutes and was then concentrated under reduced pressure. The crude product was purified by column chromatography on silica gel (eluting with 10:1 dichloromethane-ethyl acetate) to afford (S)-1-(4-benzyl-6-bromo-2-methyl-3,4-dihydropyrido[2,3-b]pyrazine-1 (2H)-yl)ethanone (0.93 g, 72%). MS (ESI, pos. ion) m/z 360, 362 [M+1]+.

Step 6. (S)-1-(6-bromo-2-methyl-3,4-dihydropyrido[2,3-b]pyrazine-1(2H)-yl)ethanone A 50-mL round bottomed flask equipped with a magnetic stir bar was charged with a solution of (S)-1-(4-benzyl-6-bromo-2-methyl-3,4-dihydropyrido[2,3-b]pyrazine-1(2H)-yl)ethanone (0.93 g, 2.58 mmol) in dichloromethane (10 mL). Sulfuric acid (1.376 mL, 25.8 mmol) was added at rt, and a slight exotherm was observed. The mixture stirred rapidly at ambient temperature for 1 h, and additional sulfuric acid (1.376 mL, 25.8 mmol) was added. After 3 h, the dark reaction mixture was cooled to 0° C., and slowly diluted with water (20 mL). The cold mixture was further neutralized to pH=9-10 by the addition of ammonium hydroxide (7 mL) (while maintaining the internal temperature below 15° C.). Dichloromethane was added, and the organic layer was separated and washed with 5% aqueous sodium chloride solution (20 mL) and concentrated under reduced pressure to yield 1.0 g of a pale yellow foam. The crude product was purified by column chromatography on silica gel (eluting with 3:1 dichloromethane-ethyl acetate followed by 1:1 dichloromethane-ethyl acetate and finally 100% ethyl acetate) to afford (S)-1-(6-bromo-2-methyl-3,4-dihydropyrido[2,3-b]pyrazine-1(2H)-yl)ethanone (0.59 g, 85%) as a colorless foam. MS (ESI, pos. ion) m/z 270, 272 [M+1]+.

Example 7

Intermediate 7. (S)-1-(2-methyl-3,4-dihydroquinoxaline-1(2H)-yl)ethanone

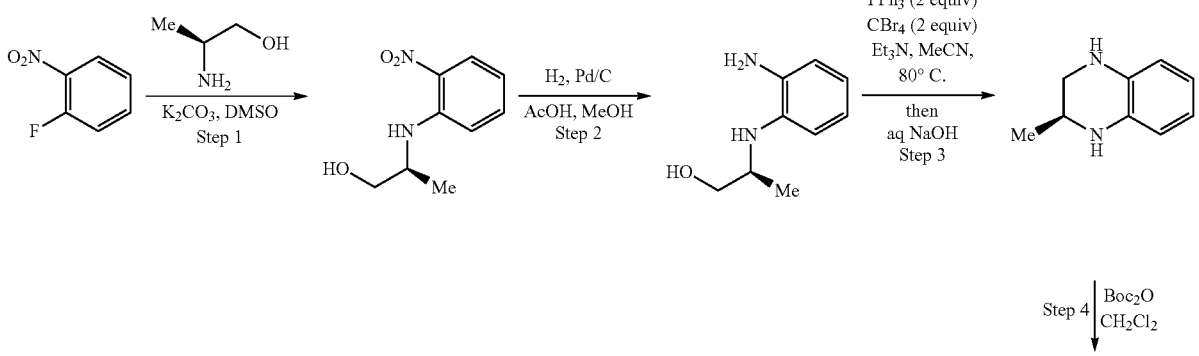

-continued

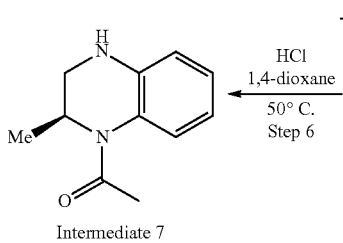 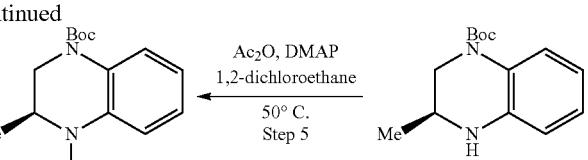

Intermediate 7

Step 1. (S)-2-(2-nitrophenylamino)propane-1-ol

A 200-mL round bottomed flask equipped with a magnetic stir bar was charged with 1-fluoro-2-nitrobenzene (8.25 g, 58.5 mmol), DMSO (29 mL), potassium carbonate (8.89 g, 64.3 mmol), and (S)-2-aminopropane-1-ol (4.83 g, 64.3 mmol). The mixture was heated to 60° C. for 6 h and then cooled to room temperature. The reaction mixture was diluted with water (60 mL). The mixture was stirred for several minutes, then extracted with ethyl acetate (ca. 200-250 mL). The ethyl acetate extract was washed thrice with 5 wt % aqueous sodium chloride (3×50 mL) and concentrated under reduced pressure to afford crude (S)-2-(2-nitrophenylamino) propane-1-ol (12.0 g, 105%) as a bright orange syrup. MS (ESI, pos. ion) m/z 197 [M+1]$^+$.

Step 2. (S)-2-(2-aminophenylamino)propane-1-ol

A 1-L round bottomed flask containing (S)-2-(2-nitrophenylamino)propane-1-ol (6.9 g, 35.2 mmol) and equipped with a magnetic stir bar was charged with methanol (138 mL), acetic acid (6.04 mL, 106 mmol), and 10% palladium on carbon (0.700 g, 0.658 mmol). The flask was fitted with a three-way stopper with a balloon of hydrogen attached. A vacuum line was connected, and the flask was gently evacuated, then back filled with hydrogen, twice. The reaction mixture was then stirred under a hydrogen atmosphere at rt. After 4 h, the reaction mixture was filtered through a pad of Celite, and the filter cake and catalyst were rinsed with fresh methanol. The filtrate was concentrated under reduce pressure to a dark syrup. The material was redissolved in toluene (ca. 200 mL), which was then removed under reduced pressure. The residue was then dissolved in ethyl acetate and washed with saturated aqueous sodium bicarbonate (75 mL) followed by 5 wt % aqueous sodium chloride (50 mL). The ethyl acetate extract was then concentrated under reduced pressure to afford (S)-2-(2-aminophenylamino)propane-1-ol (5.12 g, 88%) as a dark purple solid. MS (ESI, pos. ion) m/z 167 [M+1]$^+$.

Step 3. (S)-2-methyl-1,2,3,4-tetrahydroquinoxaline

A 1-L round bottomed flask containing (S)-2-(2-aminophenylamino)propane-1-ol (5.12 g, 30.8 mmol) was charged with acetonitrile (400 mL). The solution was concentrated partially in order to azeotropically dry the solution (ca. 100 mL of acetonitrile were removed). Triphenylphosphine (17.77 g, 67.8 mmol) was added, and once the triphenylphosphine had dissolved, carbon tetrabromide (22.47 g, 67.8 mmol) was added. The internal temperature gradually increased to a high of 35° C. After 10 min, triethylamine (18.89 mL, 136 mmol) was added. After 15 min, the reaction mixture was heated to 80° C. After 4 h, heating was discontinued and the reaction mixture stirred at rt overnight. The reaction mixture was diluted with aqueous sodium hydroxide and the mixture stirred at rt until hydrolysis of the iminophosphorane was complete. The mixture was extracted with dichloromethane. The dichloromethane extract was concentrated under reduced pressure. The crude product was purified by flash chromatography on silica gel. The product-containing fractions were concentrated to afford (S)-2-methyl-1,2,3, 4-tetrahydroquinoxaline (1.9 g, 41%). MS (ESI, pos. ion) m/z 149 [M+1]$^+$.

Step 4. (S)-tert-butyl 3-methyl-3,4-dihydroquinoxaline-1(2H)-carboxylate

A 200-mL round bottomed flask equipped with a magnetic stir bar was charged with a solution of (S)-2-methyl-1,2,3,4-tetrahydroquinoxaline (1.9 g, 12.82 mmol) in dichloromethane (30 mL). The solution was cooled to 0° C. and then di-tert-butyl dicarbonate (2.98 mL, 12.82 mmol) was added in one portion. The ice bath was left in place and allowed to slowly expire while the reaction mixture slowly warmed to rt. After 48 h, the reaction mixture was concentrated and the residue was purified via column chromatography on silica gel (eluting with 7:1 hexanes-ethyl acetate) to afford (S)-tert-butyl 3-methyl-3,4-dihydroquinoxaline-1(2H)-carboxylate (1.7 g, 53%) that was contaminated with ca. 2% of the undesired regioisomer. MS (ESI, pos. ion) m/z 149 [M−99].

Step 5. (S)-tert-butyl 4-acetyl-3-methyl-3,4-dihydroquinoxaline-1(2H)-carboxylate A 40 mL reaction vial was charged with (S)-tert-butyl 3-methyl-3,4-dihydroquinoxaline-1(2H)-carboxylate (0.3 g, 1.21 mmol) and 1,2-dichloroethane (10 mL). 4-Dimethylaminopyridine (DMAP) (0.030 g, 0.242 mmol) was added as a solid followed by the addition of acetic anhydride (0.456 ml, 4.83 mmol). The reaction mixture was heated to 50° C. for 16 h on a heater shaker. The reaction mixture was concentrated under reduced pressure, and the residue was dissolved in ethyl acetate (20 mL) and washed with saturated aqueous sodium bicarbonate (20 mL). The organic layer was removed and set aside. The aqueous layer was washed with another portion of ethyl acetate (20 mL) and the organic layers were combined and concentrated under reduced pressure to yield (S)-tert-butyl 4-acetyl-3-methyl-3,4-dihydroquinoxaline-1 (2H)-carboxylate (0.35 g) which was used without further purification. MS (ESI, Na+ ion) m/z 313 [M+1]$^+$.

Step 6. ((S)-1-(2-methyl-3,4-dihydroquinoxaline-1 (2H)-yl)ethanone

A 40 mL reaction vial was charged with (S)-tert-butyl 4-acetyl-3-methyl-3,4-dihydroquinoxaline-1(2H)-carboxylate (0.35 g, 1.21 mmol) and 1,4-dioxane (6 mL). HCl (4 M solution in 1,4-dioxane, 3.0 mL, 12.1 mmol) was then added, and the reaction mixture was heated to 50° C. for 2 hrs on a heater shaker. The reaction concentrated under reduced pressure and the residue was dissolved in ethyl acetate (20 mL) and washed with saturated aqueous sodium bicarbonate (20 mL). The organic layer was removed and set aside. The aqueous layer was washed with another portion of ethyl acetate (20 mL) and the organic layers were combined and concentrated under reduced pressure. The residue was purified by column chromatography on silica gel (gradient elution with 2:1 hexanes-ethyl acetate to 1:1 hexanes-ethyl acetate) to afford ((S)-1-(2-methyl-3,4-dihydroquinoxaline-1(2H)-yl) ethanone (0.2 g, 1.05 mmol, 87% yield) as a colorless oil. MS poor ionization (ESI, -acetate fragment) m/z 149 [M+1]$^+$.

Example 8

Intermediate 8. (S)-1-(2-methyl-6-(4-(methylsulfonyl)phenyl)-3,4-dihydroquinoxaline-1(2H)-yl) ethanone

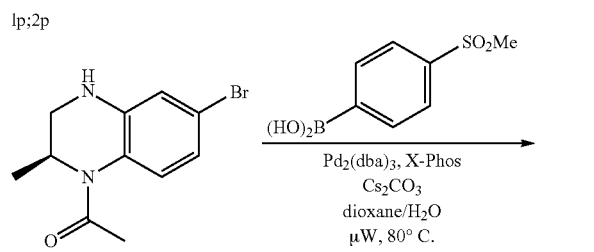

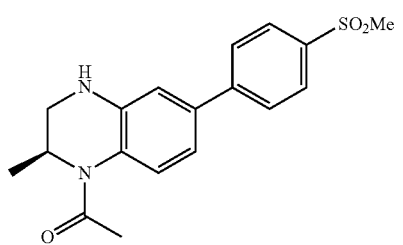

Intermediate 8

A mixture of (S)-1-(6-bromo-2-methyl-3,4-dihydroquinoxaline-1(2H)-yl)ethanone (0.100 g, 0.372 mmol), 4-(methylsulfonyl)phenylboronic acid (0.074 g, 0.372 mmol), tris (dibenzylideneacetone)dipalladium (0.017 g, 0.019 mmol), X-Phos (0.018 g, 0.037 mmol) and cesium carbonate (0.363 g, 1.115 mmol) in 1,4-dioxane (3.0 mL) and water (0.60 mL) was heated in the microwave at 80° C. for 1 h. The reaction mixture was filtered through Celite and concentrated to afford an orange oil. This material was purified via column chromatography on silica gel (Biotage 25 g column, gradient elution with 50-100% ethyl acetate-hexane) to afford (S)-1-(2-methyl-6-(4-(methylsulfonyl)phenyl)-3,4-dihydroquinoxaline-1(2H)-yl)ethanone (0.121 g, 95%) as a yellow solid. MS (ESI, pos. ion) m/z 345 [M+1]$^+$.

Example 9

Intermediate 9. (S)-1-(6-(1-cyclopropyl-1H-pyrazol-4-yl)-2-methyl-3,4-dihydroquinoxaline-1(2H)-yl) ethanone

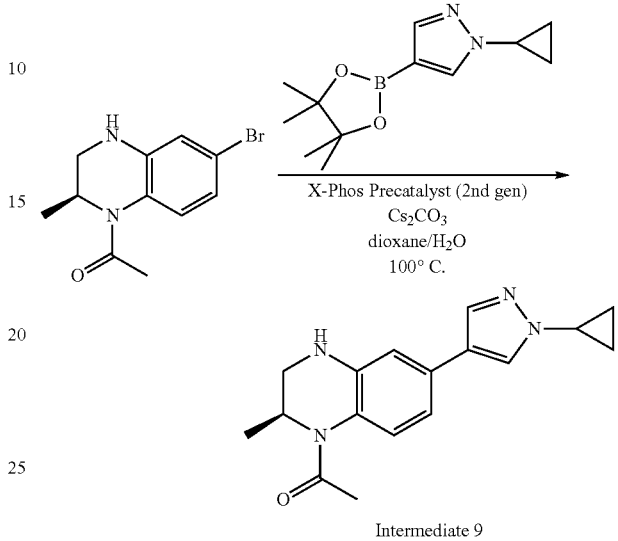

Intermediate 9

A mixture of (S)-1-(6-bromo-2-methyl-3,4-dihydroquinoxaline-1(2H)-yl)ethanone (0.500 g, 1.858 mmol), 1-cyclopropyl-4-(4,4,5,5-tetramethyl-1,3,2-dioxaborolan-2-yl)-1H-pyrazole (0.457 g, 1.951 mmol), chloro(2-dicyclohexylphosphino-2',4',6'-tri-i-propyl-1,1'-biphenyl) (2'-amino-1,1'-biphenyl-2-yl) palladium(II) (XPhos 2nd generation precatalyst) (0.146 g, 0.186 mmol), and cesium carbonate (1.816 g, 5.57 mmol) in 1,4-dioxane (7.5 mL) and water (1.50 mL) was heated at 100° C. for 16 h. The reaction mixture was filtered through Celite and concentrated to afford an orange oil. This material was purified via column chromatography on silica gel (Biotage 25 g column, gradient elution with 50-100% ethyl acetate-hexane) to afford (S)-1-(6-(1-cyclopropyl-1H-pyrazol-4-yl)-2-methyl-3,4-dihydroquinoxaline-1(2H)-yl)ethanone (0.335 g, 61%) as an off-white solid. MS (ESI, pos. ion) m/z 297 [M+1]$^+$.

Example 10

Intermediate 10. (S)-1-(2-methyl-6-(1-(oxetan-3-yl)-1H-pyrazol-4-yl)-3,4-dihydroquinoxaline-1(2H)-yl) ethanone

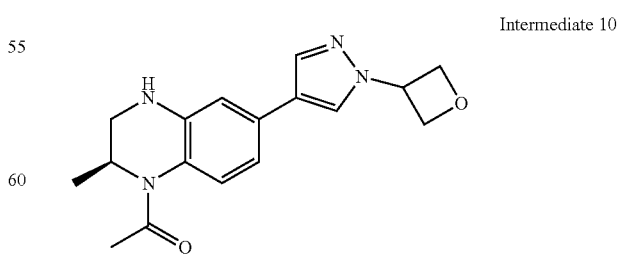

Intermediate 10

(S)-1-(2-methyl-6-(1-(oxetan-3-yl)-1H-pyrazol-4-yl)-3,4-dihydroquinoxaline-1(2H)-yl)ethanone was prepared from (S)-1-(6-bromo-2-methyl-3,4-dihydroquinoxaline-1(2H)- yl)ethanone and 1-(oxetan-3-yl)-4-(4,4,5,5-tetramethyl-1,3,2-dioxaborolan-2-yl)-1H-pyrazole according to the procedure outlined above for (S)-1-(6-(1-cyclopropyl-1H-pyrazol-4-yl)-2-methyl-3,4-dihydroquinoxaline-1(2H)-yl)ethanone. MS (ESI, pos. ion) m/z 313 [M+1]$^+$.

Example 11

Intermediate 11. (S)-isopropyl 4-acetyl-7-bromo-3-methyl-3,4-dihydroquinoxaline-1(2H)-carboxylate

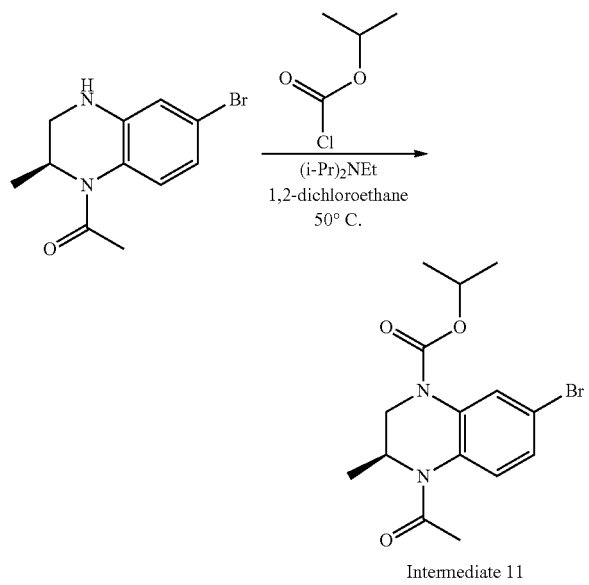

Intermediate 11

N,N-Diisopropylethylamine (0.973 mL, 5.57 mmol) was added to a solution of (S)-1-(6-bromo-2-methyl-3,4-dihydroquinoxaline-1(2H)-yl)ethanone (0.500 g, 1.858 mmol) and isopropyl chloroformate (1.0 M in toluene, 2.79 mL, 2.79 mmol) in 1,2-dichloroethane (10.0 mL), and the mixture stirred at 50° C. for 16 h. The reaction mixture was concentrated to afford a yellow oil. This material was purified via column chromatography on silica gel (Biotage 25 g column, gradient elution with 0-50% ethyl acetate-hexane) to afford (S)-isopropyl 4-acetyl-7-bromo-3-methyl-3,4-dihydroquinoxaline-1(2H)-carboxylate (0.558 g, 85%) as an off-white solid. MS (ESI, pos. ion) m/z 355, 357 [M+1]$^+$.

Example 12

Intermediate 12. (S)-isopropyl 7-bromo-4-(cyclopropanecarbonyl)-3-methyl-3,4-dihydroquinoxalin-1(2H)carboxylate

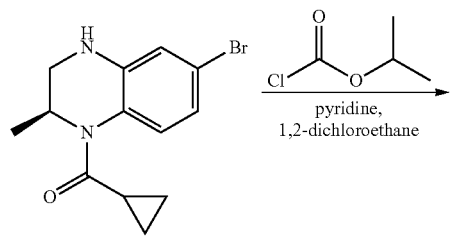

-continued

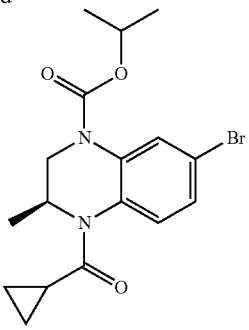

Intermediate 12

A 100-mL round bottomed flask fitted with a nitrogen inlet and magnetic stir bar was charged with (S)-(6-bromo-2-methyl-3,4-dihydroquinoxalin-1 (2H)-yl)(cyclopropyl)methanone (0.62 g, 2.1 mmol), dichloroethane (25 mL), and pyridine (0.254 mL, 3.15 mmol). The mixture was cooled to 0° C. in an ice bath. A solution of isopropyl chloroformate (1 M in toluene, 2.52 mL, 2.52 mmol) was then added dropwise over several minutes. The reaction mixture was stirred for 30 min in an ice bath before warming to ambient temperature for 1 h. The reaction mixture was diluted with dichloromethane (20 mL) and washed with 1 M aqueous HCl solution (25 mL). The organic layer was separated and concentrated under reduced pressure. The oil was put through a silica pad using 1:1 hexane/ethyl acetate and the eluent was concentrated in vacuo. This afforded (S)-isopropyl 7-bromo-4-(cyclopropanecarbonyl)-3-methyl-3,4-dihydroquinoxalin-1(2H)carboxylate (0.83 g, 100%) as a solid, which was used directly in next step. MS (ESI, pos. ion) m/z 381, 383 [M+1]$^+$.

Example 13

Intermediate 13. 4-isopropyl 1-methyl (S)-6-bromo-2-methyl-2,3-dihydroquinoxaline-1,4-dicarboxylate

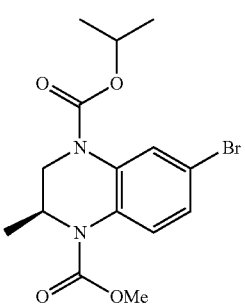

Intermediate 13

4-isopropyl 1-methyl (S)-6-bromo-2-methyl-2,3-dihydroquinoxaline-1,4-dicarboxylate was synthesized from (S)-methyl 6-bromo-2-methyl-3,4-dihydroquinoxaline-1(2H)-carboxylate according to the procedure outlined above for (S)-isopropyl 7-bromo-4-(cyclopropanecarbonyl)-3-methyl-3,4-dihydroquinoxalin-1(2H)carboxylate. MS (ESI, pos. ion) m/z 393, 395 [M+Na]$^+$.

Example 14

Intermediate 14. (S)-1-(6-bromo-4-(furan-2-carbonyl)-2-methyl-3,4-dihydroquinoxaline-1(2H)-yl)ethanone

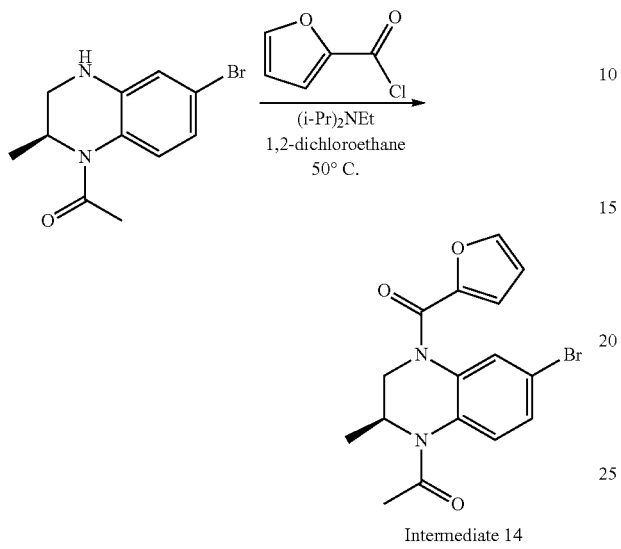

Intermediate 14

A 100 mL round bottomed flask fitted with a nitrogen inlet was charged with (S)-1-(6-bromo-2-methyl-3,4-dihydroquinoxaline-1(2H)-yl)ethanone (0.500 g, 1.858 mmol), 1,2-dichloroethane (20 mL), N,N-diisopropylethylamine (1.0 mL, 5.73 mmol), and furan-2-carbonyl chloride (0.366 mL, 3.72 mmol). The reaction mixture was heated to 50° C. for 2 h with magnetic stirring. After for 2 h, the reaction was washed with 1 N aqueous sodium hydroxide solution (15 mL). The organic layer was removed and set aside. The aqueous layer was washed with 1,2-dichloroethane (20 mL) and the organic layers were combined and concentrated under reduced pressure. The crude product was purified by column chromatography on silica gel (eluting with 2:1 hexanes-ethyl acetate) to afford (S)-1-(6-bromo-4-(furan-2-carbonyl)-2-methyl-3,4-dihydroquinoxaline-1(2H)-yl)ethanone (0.58 g, 86% yield) as a viscous yellow oil. MS (ESI, pos. ion) m/z 417 [M+1]$^+$.

Example 15

Intermediate 15. (S)-1-(6-bromo-4-(cyclopropanecarbonyl)-2-methyl-3,4-dihydroquinoxaline-1(2H)-yl)ethan-1-one

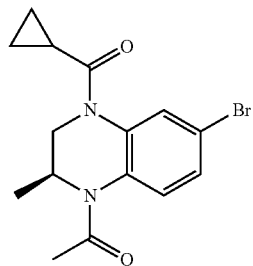

Intermediate 15

A 250-mL 3-necked round-bottom flask was charged with a solution of (S)-1-(6-bromo-2-methyl-3,4-dihydroquinoxaline-1(2H)-yl)ethan-1-one (7 g, 26.01 mmol) and pyridine (4 mL, 49.4 mmol) in dichloromethane (80 mL). This was followed by the addition of cyclopropanecarbonyl chloride (3.6 mL, 40.0 mmol) dropwise with stirring at 0° C. The resulting solution was stirred for 14 h at room temperature. The reaction mixture was concentrated under vacuum. The residue was purified via column chromatography on silica gel (eluting with 20:1, dichloromethane/methanol) to afford (S)-1-(6-bromo-2-methyl-3,4-dihydroquinoxaline-1(2H)-yl)ethan-1-one (8.2 g, 94%) as a yellow solid. MS (ESI, pos. ion) m/z 337, 339 [M+1]$^+$.

Example 16

Intermediate 16. (S)-1-(2-methyl-6-(4,4,5,5-tetramethyl-1,3,2-dioxaborolan-2-yl)-3,4-dihydroquinoxaline-1(2H)-yl)ethanone

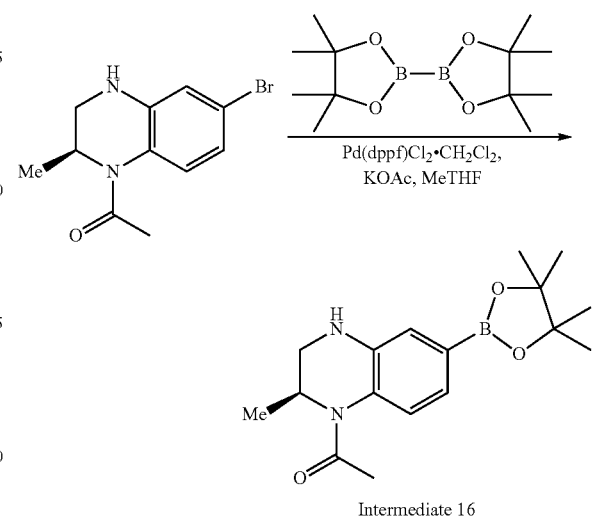

Intermediate 16

A 200 mL round bottom flask fitted with a nitrogen inlet, stir bar, and condenser was charged with (S)-1-(6-bromo-2-methyl-3,4-dihydroquinoxaline-1(2H)-yl)ethanone (4.4 g, 16.35 mmol), 2-methyltetrahydrofuran (93 mL), potassium acetate (4.01 g, 40.9 mmol), and bis(pinacolato)diboron (4.57 g, 17.98 mmol). Nitrogen was bubble through the mixture for 30 min and then [1,1'-bis(diphenylphosphino)ferrocene]dichloropalladium(II) dichloromethane adduct (0.134 g, 0.163 mmol) was added. The reaction mixture was heated to 80° C. for 24 h, and then additional bis(pinacolato)diboron (2.29 g, 8.99 mmol) and [1,1'-bis(diphenylphosphino)ferrocene]dichloropalladium(II) dichloromethane adduct (0.134 g, 0.163 mmol) were added. The mixture was heated at 80° C. for 30 h, and then the mixture was cooled to rt and diluted with 2-methyltetrahydrofuran (90 mL). The organic layer was separated and washed with water (50 mL) and brine (50 mL). The combined organic layers were concentrated under reduced pressure. The crude product was purified by column chromatography on silica gel (gradient elution with 20-33% ethyl acetate-dichloromethane) to yield a solid which was further purified by crystallizing from 4:1 hexanes-ethyl acetate to afford (S)-1-(2-methyl-6-(4,4,5,5-tetramethyl-1,3,2-dioxaborolan-2-yl)-3,4-dihydroquinoxaline-1(2H)-yl)ethanone (3.45 g, 67%) as an off-white solid. MS (ESI, pos. ion) m/z 317 [M+1]$^+$.

Example 17

Intermediate 17. (S)-1-(4-(furan-2-carbonyl)-2-methyl-6-(4,4,5,5-tetramethyl-1,3,2-dioxaborolan-2-yl)-3,4-dihydroquinoxaline-1(2H)-yl)ethanone

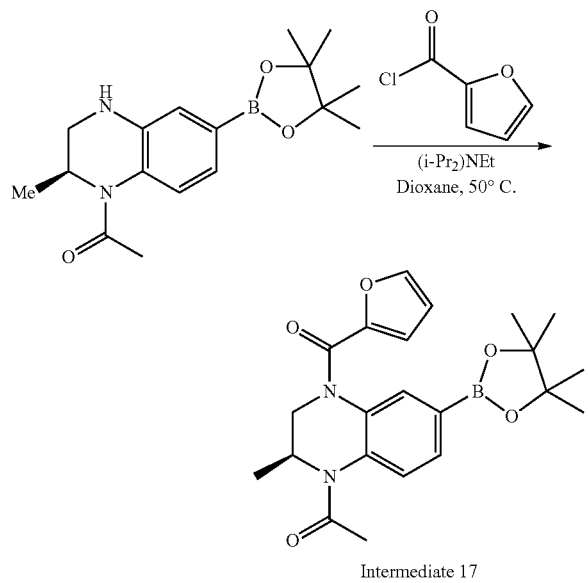

Intermediate 17

A 100 mL round bottom flask fitted with a nitrogen inlet, and stir bar was charged with (S)-1-(2-methyl-6-(4,4,5,5-tetramethyl-1,3,2-dioxaborolan-2-yl)-3,4-dihydroquinoxalin-1(2H)-yl)ethanone (0.8 g, 2.53 mmol), 1,4-dioxane (30 ml), N,N-diisopropylethylamine (2.65 mL, 15.18 mmol) and furan-2-carbonyl chloride (0.991 g, 7.59 mmol). The reaction mixture was purged with nitrogen and heated to 50° C. for 2 h. The mixture was cooled to rt and diluted with ethyl acetate (100 mL). The mixture was then washed with brine (50 mL), and the organic layer was concentrated under reduced pressure. The crude product was purified by column chromatography on silica gel (eluting with 9:1 hexanes-ethyl acetate) to afford (S)-1-(4-(furan-2-carbonyl)-2-methyl-6-(4,4,5,5-tetramethyl-1,3,2-dioxaborolan-2-yl)-3,4-dihydroquinoxalin-1(2H)-yl)ethanone (0.69 g, 66% yield) as a colorless foam. MS (ESI, pos. ion) m/z 411 [M+1]$^+$.

Example 18

Intermediate 18. S)-cyclopropyl(3-methyl-7-(4,4,5,5-tetramethyl-1,3,2-dioxaborolan-2-yl)-3,4-dihydroquinoxaline-1(2H)-yl)methanone

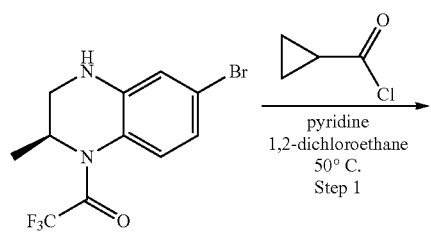

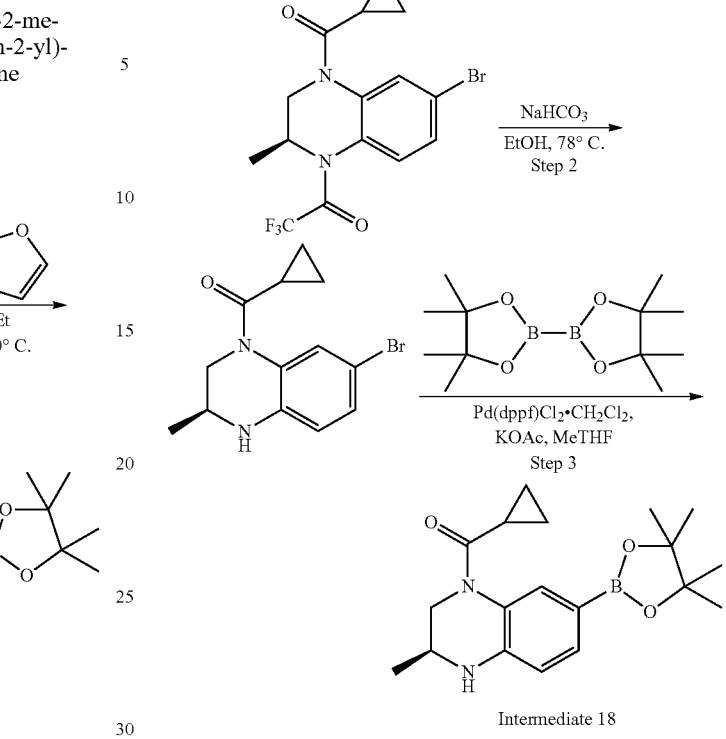

Intermediate 18

Step 1. (S)-1-(6-bromo-4-(cyclopropanecarbonyl)-2-methyl-3,4-dihydroquinoxaline-1(2H)-yl)-2,2,2-trifluoroethanone A 250-mL, three-necked, round bottomed flask fitted with a nitrogen inlet, magnetic stir bar, and thermocouple was charged with (S)-1-(6-bromo-2-methyl-3,4-dihydroquinoxalin-1(2H)-yl)-2,2,2-trifluoroethanone (7.0 g, 21.66 mmol), dichloromethane (140 mL), and pyridine (2.63 mL, 32.5 mmol). The mixture was cooled to 0° C. and cyclopropanecarbonyl chloride (2.36 mL, 26.0 mmol) was slowly added while maintaining the internal temperature below 7° C. The reaction mixture was stirred cold for 30 min. and then warmed to rt. The reaction mixture was washed with 1 M aqueous HCl solution (25 mL) and water (25 mL), and the combined organic layers were concentrated under reduced pressure. The crude product was purified by column chromatography on silica gel (eluting with 4:1 hexanes-ethyl acetate) to afford (S)-1-(6-bromo-4-(cyclopropanecarbonyl)-2-methyl-3,4-dihydroquinoxaline-1(2H)-yl)-2,2,2-trifluoroethanone (8.26 g, 97%) as an off-white solid. MS (ESI, pos. ion) m/z 392 [M+1]$^+$.

Step 2. (S)-(7-bromo-3-methyl-3,4-dihydroquinoxaline-1(2H)-yl)(cyclopropyl)methanone A 250-mL, three-necked round bottom flask fitted with a nitrogen inlet, magnetic stir bar, thermocouple, and condenser was charged with (S)-1-(6-bromo-4-(cyclopropanecarbonyl)-2-methyl-3,4-dihydroquinoxaline-1(2H)-yl)-2,2,2-trifluoroethanone (8.26 g, 21.12 mmol), ethanol (82 mL), and half-saturated sodium bicarbonate (82 mL, 422 mmol). The reaction mixture was heated to 78° C. for 3 h and then cooled to rt. The ethanol was removed under reduced pressure, and the resulting solution was extracted with dichloromethane (2×125 mL). The combined organic layers were concentrated under reduced pressure. The crude product was diluted with 2-methyltetrahydrofuran (100 mL), and the resulting solution concentrated to remove trace water. This afforded (S)-(7-bromo-3-methyl-3,4-dihydroquinoxaline-1(2H)-yl)(cyclopropyl)methanone (6.25 g, 100%) as an oil, which was used as is for the next step. MS (ESI, pos. ion) m/z 296. [M+1]+.

Step 3. (S)-cyclopropyl(3-methyl-7-(4,4,5,5-tetramethyl-1,3,2-dioxaborolan-2-yl)-3,4-dihydroquinoxaline-1(2H)-yl)methanone A 500-mL round bottom flask fitted with a nitrogen inlet, magnetic stir bar, and condenser was charged with (S)-(7-bromo-3-methyl-3,4-dihydroquinoxaline-1(2H)-yl)(cyclopropyl)methanone (6.25 g, 21.17 mmol), 2-methyltetrahydrofuran (132 mL), potassium acetate (5.20 g, 52.9 mmol), and bis(pinacolato)diboron (5.91 g, 23.29 mmol). Nitrogen was bubbled through the mixture for 30 min and then [1,1'-bis(diphenylphosphino)ferrocene]dichloropalladium(II) dichloromethane adduct (0.173 g, 0.212 mmol) was added. The mixture was heated to 75° C. for 24 h and then cooled to room temperature. Water was added, and the organic phase was separated and washed with and brine (50 mL), and concentrated under reduced pressure. The crude product was purified by column chromatography on silica gel (eluting with 4:1 dichloromethane-ethyl acetate followed by a second column eluting with 8:1 dichloromethane-ethyl acetate) to afford a solid which was crystallized from 10:1 hexanes-ethyl acetate to afford (S)-cyclopropyl(3-methyl-7-(4,4,5,5-tetramethyl-1,3,2-dioxaborolan-2-yl)-3,4-dihydroquinoxaline-1(2H)-yl)methanone (4.37 g, 60%) as an off-white solid. MS (ESI, pos. ion) m/z 343 [M+1]+.

Example 19

Intermediate 19. (S)-furan-2-yl(3-methyl-7-(4-(methylsulfonyl)phenyl)-3,4-dihydroquinoxaline-1(2H)-yl)methanone

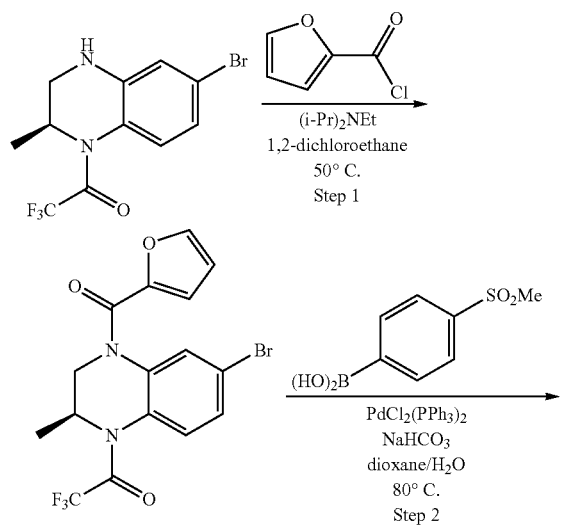

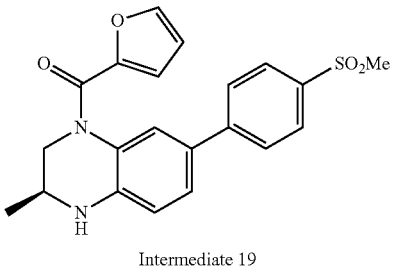

Intermediate 19

Step 1. (S)-1-(6-bromo-4-(furan-2-carbonyl)-2-methyl-3,4-dihydroquinoxaline-1(2H)-yl)-2,2,2-trifluoroethanone A 100 mL round bottomed flask fitted with a nitrogen inlet was charged with (S)-1-(6-bromo-2-methyl-3,4-dihydroquinoxaline-1(2H)-yl)-2,2,2-trifluoroethanone (1.54 g, 4.77 mmol), 1,2-dichloroethane (45 mL), and N,N-diisopropylethyl amine (2.497 mL, 14.30 mmol). The mixture stirred for 5 min and then furan-2-carbonyl chloride (0.940 mL, 9.53 mmol) was slowly added. The reaction stirred at room temperature for 2 h and was then concentrated. The residue was purified via column chromatography (eluting with 3:2 hexanes/ethyl acetate) to afford (S)-1-(6-bromo-4-(furan-2-carbonyl)-2-methyl-3,4-dihydroquinoxaline-1(2H)-yl)-2,2,2-trifluoroethanone (1.07 g, 54%) as an off-white solid. MS (ESI, pos. ion) m/z 417, 419 [M+1]+.

Step 2. (S)-furan-2-yl(3-methyl-7-(4-(methylsulfonyl)phenyl)-3,4-dihydroquinoxaline-1(2H)-yl)methanone A 100 mL round bottomed flask fitted with a nitrogen inlet was charged with (S)-1-(6-bromo-4-(furan-2-carbonyl)-2-methyl-3,4-dihydroquinoxaline-1(2H)-yl)-2,2,2-trifluoroethanone (0.626 g, 1.5 mmol), 1,4-dioxane (15 mL), 4-(methylsulfonyl)phenylboronic acid (0.360 g, 1.8 mmol), and sodium bicarbonate as a 1M solution in water (4.5 mL, 4.5 mmol). The reaction mixture was purged with nitrogen. Bis(triphenylphosphine)palladium(II) dichloride (0.01 M solution in DMF, 7.5 mL, 0.075 mmol) was added, and the reaction mixture was purged with nitrogen and heated to 80° C. overnight. The reaction was diluted with ethyl acetate (30 mL) and washed with brine (15 mL). The aqueous layer was separated and washed with ethyl acetate (30 mL) and the combined organic layers were concentrated under reduced pressure. The crude product was purified by column chromatography on silica gel (eluting with 1:1 hexanes-ethyl acetate) to afford (S)-furan-2-yl(3-methyl-7-(4-(methylsulfonyl)phenyl)-3,4-dihydroquinoxaline-1(2H)-yl)methanone (0.33 g, 55% yield) as a viscous yellow oil. MS (ESI, pos. ion) m/z 397 [M+1]+.

Example 20

Intermediate 20. ethyl (S)-7-(1-cyclopropyl-1H-pyrazol-4-yl)-3-methyl-3,4-dihydro-quinoxaline-1(2H)-carboxylate

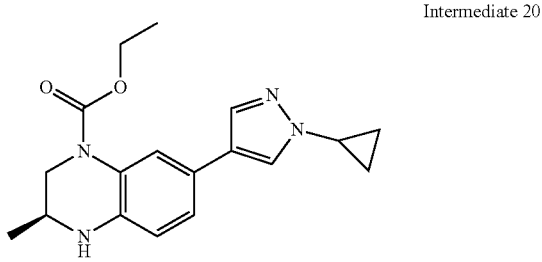 [SMILES: CCOC(=O)N1C[C@H](C)Nc2ccc(-c3cnn(C4CC4)c3)cc21]

Intermediate 20

Ethyl (S)-7-(1-cyclopropyl-1H-pyrazol-4-yl)-3-methyl-3,4-dihydroquinoxaline-1(2H)-carboxylate was prepared according to the procedure outlined for (S)-furan-2-yl(3-methyl-7-(4-(methylsulfonyl)phenyl)-3,4-dihydroquinoxaline-1(2H)-yl)methanone, substituting ethyl chloroformate for furan-2-carbonyl chloride in Step 1 and 1-cyclopropyl-4-(4,4,5,5-tetramethyl-1,3,2-dioxaborolan-2-yl)-1H-pyrazole for 4-(methylsulfonyl)phenylboronic acid in Step 2 to afford the desired product. MS (ESI, pos. ion) m/z 327 [M+1]+.

Example 21

Intermediate 21. (S)-isopropyl 4-(cyclopropanecarbonyl)-3-methyl-7-(1H-pyrazol-4-yl)-3,4-dihydro-quinoxaline-1(2H)-carboxylate

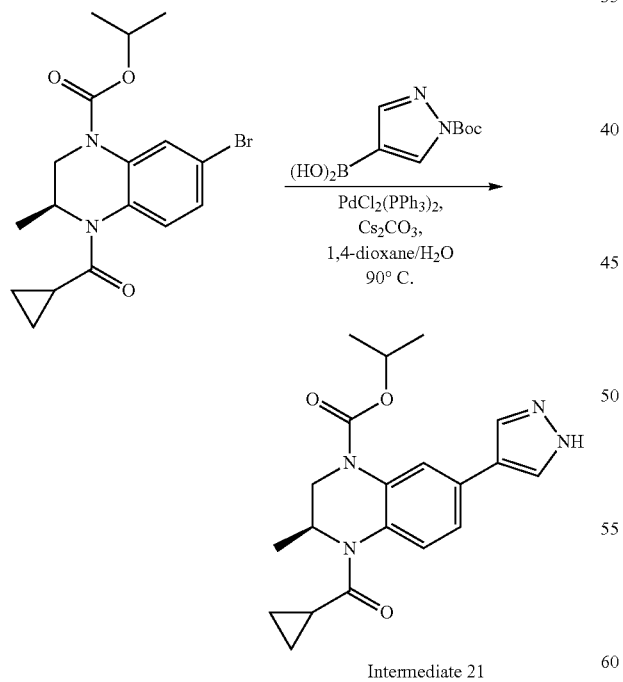

Intermediate 21

A 50-mL round bottomed flask fitted with a nitrogen inlet and magnetic stir bar was charged with (S)-isopropyl 7-bromo-4-(cyclopropanecarbonyl)-3-methyl-3,4-dihydro-quinoxaline-1(2H)-carboxylate (0.801 g, 2.1 mmol), dioxane (11 mL), and water (4.6 mL). Cesium carbonate (2.053 g, 6.30 mmol) and tert-butyl 4-(4,4,5,5-tetramethyl-1,3,2-dioxaborolan-2-yl)-1H-pyrazol-1-carboxylate (0.927 g, 3.15 mmol) were then added. The reaction was purged with nitrogen and bis(triphenylphosphine)palladium (II) dichloride (0.177 g, 0.252 mmol) was added. The mixture was heated at 90° C. with vigorous stirring for 5 h and then cooled to ambient temperature. Water (25 mL) was added, and the mixture was extracted with ethyl acetate (3×25 mL). The combined organic extracts were concentrated to afford a viscous oil and purified via column chromatography (gradient elution with 75-100% ethyl acetate-hexanes). The resulting material was triturated with diethyl ether (2×10 mL) to afford (S)-isopropyl 4-(cyclopropanecarbonyl)-3-methyl-7-(1H-pyrazol-4-yl)-3,4-dihydroquinoxaline-1(2H)-carboxylate (0.55 g, 71% yield) as a solid. MS (ESI, pos. ion) m/z 369 [M+1]+.

Example 22

Intermediate 22. isopropyl (S)-4-acetyl-3-methyl-7-(1H-pyrazol-4-yl)-3,4-dihydroquinoxaline-1(2H)-carboxylate

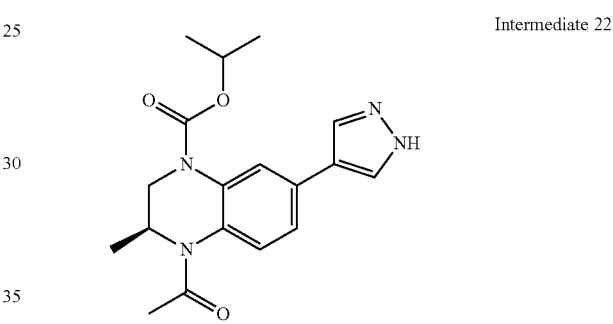

Intermediate 22

Isopropyl (S)-4-acetyl-3-methyl-7-(1H-pyrazol-4-yl)-3,4-dihydroquinoxaline-1 (2H)-carboxylate was synthesized from (S)-isopropyl 4-acetyl-7-bromo-3-methyl-3,4-dihydro-quinoxaline-1(2H)-carboxylate according to the procedure outlined above for (S)-isopropyl 4-(cyclopropanecarbonyl)-3-methyl-7-(1H-pyrazol-4-yl)-3,4-dihydroquinoxaline-1(2H)-carboxylate. MS (ESI, pos. ion) m/z 343 [M+1]+.

Example 23

Intermediate 23. 4-isopropyl 1-methyl (S)-2-methyl-6-(1H-pyrazol-4-yl)-2,3-dihydroquinoxaline-1,4-dicarboxylate

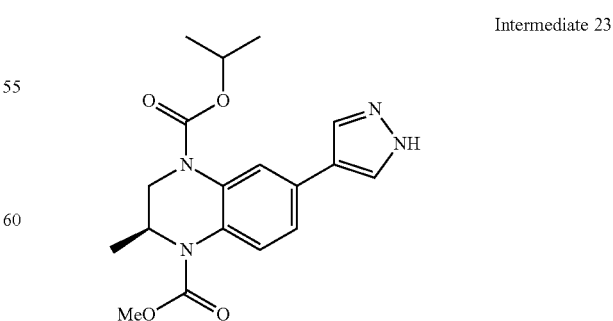

Intermediate 23

4-Isopropyl 1-methyl (S)-2-methyl-6-(1H-pyrazol-4-yl)-2,3-dihydroquinoxaline-1,4-dicarboxylate was synthesized from 4-isopropyl 1-methyl (S)-6-bromo-2-methyl-2,3-dihydroquinoxaline-1,4-dicarboxylate according to the procedure outlined above for (S)-isopropyl 4-(cyclopropanecarbonyl)-3-methyl-7-(1H-pyrazol-4-yl)-3,4-dihydroquinoxaline-1(2H)-carboxylate. MS (ESI, pos. ion) m/z 359 [M+1]$^+$.

Example 24

Intermediate 24. (S)-1-(4-(cyclopropanecarbonyl)-2-methyl-6-(1H-pyrazol-4-yl)-3,4-dihydroquinoxaline-1(2H)-yl)ethan-1-one

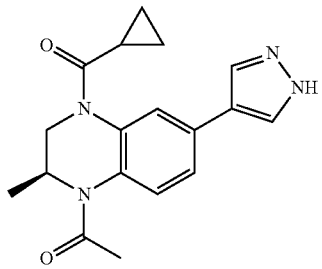

Intermediate 24

(S)-1-(4-(Cyclopropanecarbonyl)-2-methyl-6-(1H-pyrazol-4-yl)-3,4-dihydroquinoxalin-1 (2H)-yl)ethan-1-one was synthesized from (S)-1-(6-bromo-4-(cyclopropanecarbonyl)-2-methyl-3,4-dihydroquinoxalin-1 (2H)-yl)ethan-1-one according to the procedure outlined above for (S)-isopropyl 4-(cyclopropanecarbonyl)-3-methyl-7-(1H-pyrazol-4-yl)-3,4-dihydroquinoxaline-1(2H)-carboxylate. MS (ESI, pos. ion) m/z 359 [M+1]$^+$.

Example 25

Intermediate 25. (S)-4-(1-acetyl-4-(isopropoxycarbonyl)-2-methyl-1,2,3,4-tetrahydroquinoxalin-6-yl)benzoic acid

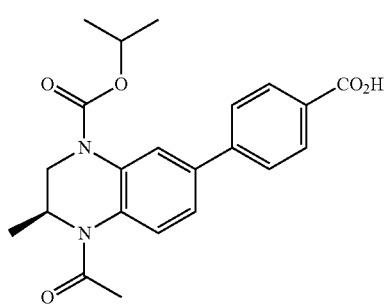

Intermediate 25

(S)-4-(1-acetyl-4-(isopropoxycarbonyl)-2-methyl-1,2,3,4-tetrahydroquinoxalin-6-yl)benzoic acid was synthesized from (S)-isopropyl 4-acetyl-7-bromo-3-methyl-3,4-dihydroquinoxaline-1(2H)-carboxylate and 4-carboxyphenylboronic acid according to the procedure outlined above for (S)-isopropyl 4-(cyclopropanecarbonyl)-3-methyl-7-(1H-pyrazol-4-yl)-3,4-dihydroquinoxaline-1(2H)-carboxylate. MS (ESI, pos. ion) m/z 419 [M+Na]$^+$

Example 26

Intermediate 26. (S)-1-(6-(1-(2-hydroxyethyl-1H-pyrazol-4-yl)-2-methyl-3,4-dihydroquinoxalin-1(2H)-yl)ethan-1-one

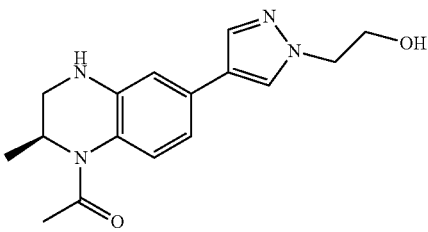

Intermediate 26

(S)-1-(6-(1-(2-Hydroxyethyl-1H-pyrazol-4-yl)-2-methyl-3,4-dihydroquinoxalin-1(2H)-yl)ethan-1-one was prepared from (S)-1-(6-bromo-2-methyl-3,4-dihydroquinoxalin-1(2H)-yl)ethanone and 2-(4-(4,4,5,5-tetramethyl-1,3,2-dioxaborolan-2-yl)-1H-pyrazol-1-yl)ethanol according to the procedure outlined above for (S)-1-(6-(1-cyclopropyl-1H-pyrazol-4-yl)-2-methyl-3,4-dihydroquinoxaline-1(2H)-yl)ethanone. MS (ESI, pos. ion) m/z 301 [M+1]$^+$.

Example 27

Intermediate 27. ethyl (S)-4-acetyl-7-bromo-3-methyl-3,4-dihydroquinoxaline-1(2H)-carboxylate

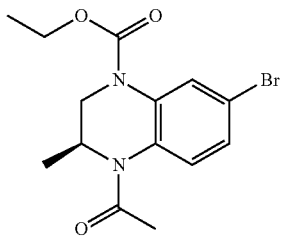

Intermediate 27

Ethyl (S)-4-acetyl-7-bromo-3-methyl-3,4-dihydroquinoxaline-1 (2H)-carboxylate was prepared from (S)-1-(6-bromo-2-methyl-3,4-dihydroquinoxaline-1(2H)-yl)ethanone and ethyl chloroformate according to the procedure outlined above for (S)-isopropyl 4-acetyl-7-bromo-3-methyl-3,4-dihydroquinoxaline-1(2H)-carboxylate. MS (ESI, pos. ion) m/z 341, 343 [M+1]$^+$.

Example 28

Intermediate 28. cyclopentyl (S)-4-acetyl-7-bromo-3-methyl-3,4-dihydroquinoxaline-1(2H)-carboxylate

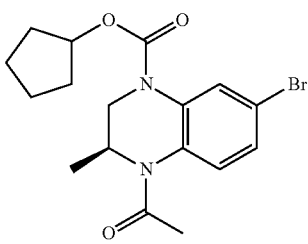

Intermediate 28

Cyclopentyl (S)-4-acetyl-7-bromo-3-methyl-3,4-dihydroquinoxaline-1 (2H)-carboxylate was prepared from (S)-1-(6-bromo-2-methyl-3,4-dihydroquinoxaline-1(2H)-yl)ethanone and cyclopentyl chloroformate according to the procedure outlined above for (S)-isopropyl 4-acetyl-7-bromo-3-methyl-3,4-dihydroquinoxaline-1 (2H)-carboxylate. MS (ESI, pos. ion) m/z 381, 383 [M+1]$^+$.

Example 29

Intermediate 29. phenyl (S)-4-acetyl-7-bromo-3-methyl-3,4-dihydroquinoxaline-1(2H)-carboxylate

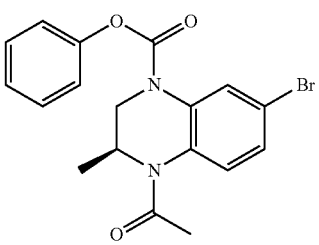

Intermediate 29

Phenyl (S)-4-acetyl-7-bromo-3-methyl-3,4-dihydroquinoxaline-1(2H)-carboxylate was prepared from (S)-1-(6-bromo-2-methyl-3,4-dihydroquinoxaline-1(2H)-yl)ethanone and phenyl chloroformate according to the procedure outlined above for (S)-isopropyl 4-acetyl-7-bromo-3-methyl-3,4-dihydroquinoxaline-1(2H)-carboxylate. MS (ESI, pos. ion) m/z 389, 391 [M+1]$^+$.

Example 30

Intermediate 30. 3,3-difluorocyclobutyl (S)-4-acetyl-7-bromo-3-methyl-3,4-dihydroquinoxaline-1(2H)-carboxylate

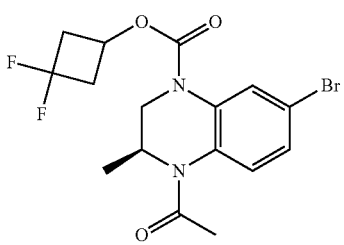

Intermediate 30

A 250-mL round-bottom flask was charged with 3,3-difluorocyclobutan-1-ol (2.41 g, 22.3 mmol), 1,2-dichloroethane (50 mL), N,N-diisopropylethyl amine (3.5 mL, 20 mmol) and triphosgene (1.33 g, 4.48 mmol). The resulting solution stirred 30 minutes at 50° C., and then a solution of (S)-1-(6-bromo-2-methyl-3,4-dihydroquinoxaline-1(2H)-yl)ethan-1-one (600 mg, 2.23 mmol) and N,N-diisopropylethyl amine (3.5 mL, 20 mmol) in 1,2-dichloroethane (30 mL) was added. The resulting solution stirred overnight at 50° C. After cooling to room temperature, the reaction mixture was concentrated under vacuum. The residue was dissolved in ethyl acetate (50 mL), washed with saturated sodium carbonate solution (2×50 mL), dried over anhydrous sodium sulfate and concentrated under vacuum. The residue was purified via column chromatography on silica gel (eluting with 2:3, ethyl acetate/petroleum ether) to afford 3,3-difluorocyclobutyl (S)-4-acetyl-7-bromo-3-methyl-3,4-dihydroquinoxaline-1(2H)-carboxylate (800 mg, 89%) as a brown solid. MS (ESI, pos. ion) m/z 404, 405 [M+1]$^+$.

Example 31

Intermediate 31. 4,4-difluorocyclohexyl (S)-4-acetyl-7-bromo-3-methyl-3,4-dihydro-quinoxaline-1(2H)-carboxylate

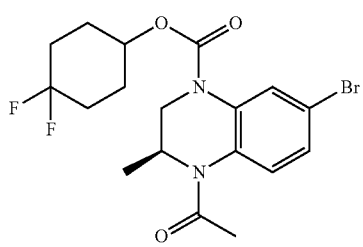

Intermediate 31

4,4-Difluorocyclohexyl (S)-4-acetyl-7-bromo-3-methyl-3,4-dihydroquinoxaline-1(2H)-carboxylate was prepared from 4,4-difluorocyclohexan-1-ol and (S)-1-(6-bromo-2-methyl-3,4-dihydroquinoxaline-1(2H)-yl)ethan-1-one according to the procedure outlined above for 3,3-difluorocyclobutyl (S)-4-acetyl-7-bromo-3-methyl-3,4-dihydroquinoxaline-1(2H)-carboxylate. MS (ESI, pos. ion) m/z 431, 433 [M+1]$^+$.

Example 32

Intermediate 32. cyclobutyl (S)-4-acetyl-7-bromo-3-methyl-3,4-dihydroquinoxaline-1(2H)-carboxylate

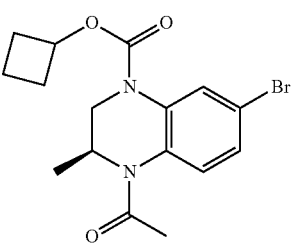

Intermediate 32

A solution of cyclobutanol (28.8 g, 399 mmol), 1,2-dichloroethane (450 mL), triphosgene (22.1 g, 74.41 mmol) and N,N-diisopropylethyl amine (58.0 mL, 333 mmol) was stirred at 50° C. for 2 hr. A solution of (S)-1-(6-bromo-2-methyl-3,4-dihydroquinoxaline-1(2H)-yl)ethan-1-one (10.0 g, 37.2 mmol) and N,N-diisopropylethyl amine (58.0 mL, 333 mmol) in 1,2-dichloroethane (180 mL) was added dropwise. The resulting solution was stirred for 5 h at 50° C. After cooling to room temperature, the reaction mixture was concentrated under vacuum. The residue was purified via column chromatography on silica gel (eluting with 25% ethyl acetate-petroleum ether) to afford cyclobutyl (S)-4-acetyl-7-bromo-3-methyl-3,4-dihydroquinoxaline-1(2H)-carboxylate (20 g, 73%) as yellow oil. MS (ESI, pos. ion) m/z 367, 369 [M+1]$^+$.

Example 33

Intermediate 33. tetrahydro-2H-pyran-4-yl (S)-4-acetyl-7-bromo-3-methyl-3,4-dihydroquinoxaline-1 (2H)-carboxylate

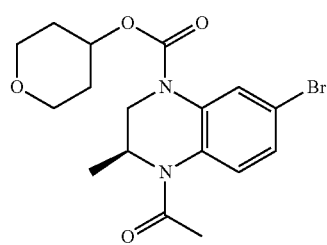

Intermediate 33

Tetrahydro-2H-pyran-4-yl (S)-4-acetyl-7-bromo-3-methyl-3,4-dihydroquinoxaline-1(2H)-carboxylate was prepared from tetrahydro-2H-pyran-4-ol and (S)-1-(6-bromo-2-methyl-3,4-dihydroquinoxaline-1(2H)-yl)ethan-1-one according to the procedure outlined above for 3,3-difluorocyclobutyl (S)-4-acetyl-7-bromo-3-methyl-3,4-dihydroquinoxaline-1(2H)-carboxylate. MS (ESI, pos. ion) m/z 397, 399 [M+1]$^+$.

Example 34

Intermediate 34. cyclopropylmethyl (3S)-4-acetyl-7-bromo-3-methyl-1,2,3,4-tetrahydroquinoxaline-1-carboxylate

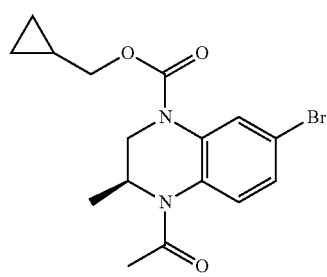

Intermediate 34

A 250-mL round-bottom flask was charged with cyclopropylmethanol (1.90 g, 26.3 mmol), triphosgene (1.50 g, 5.28 mmol), N,N-diisopropylethylamine (4.0 mL, 23 mmol) and 1,2-dichloroethane (100 mL). The resulting solution was stirred for 1 h at 50° C. 1-[(2S)-6-Bromo-2-methyl-1,2,3,4-tetrahydroquinoxalin-1-yl]ethan-1-one (710 mg, 2.64 mmol) and N,N-diisopropylethylamine (4.0 mL, 23 mmol) in 1,2-dichloroethane (20 mL) were added, and the resulting solution stirred overnight at 50° C. After cooling to room temperature, the reaction mixture was poured into water (30 mL). The aqueous layer was separated and extracted with ethyl acetate (3×50 mL). The combined organic layers were dried over anhydrous sodium sulfate, filtered, and concentrated. The residue was purified via column chromatography on silica gel (eluting with 1:12, ethyl acetate/petroleum ether) to afford cyclopropylmethyl (3S)-4-acetyl-7-bromo-3-methyl-1,2,3,4-tetrahydroquinoxaline-1-carboxylate in (850 mg, 88%) as a yellow solid. MS (ESI, pos. ion) m/z 367, 369 [M+1]$^+$.

Example 35

Intermediate 35. cyclobutyl (S)-4-acetyl-3-methyl-7-(1H-pyrazol-4-yl)-3,4-dihydroquinoxaline-1(2H)-carboxylate

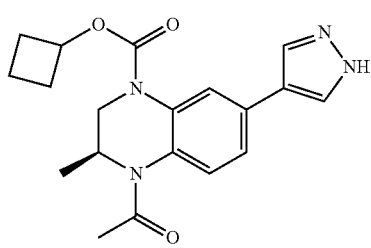

Intermediate 35

A 500-mL round-bottom flask was purged with nitrogen and charged with cyclobutyl (S)-4-acetyl-7-bromo-3-methyl-3,4-dihydroquinoxaline-1(2H)-carboxylate (15.0 g, 40.9 mmol), tert-butyl 4-(tetramethyl-1,3,2-dioxaborolan-2-yl)-1H-pyrazole-1-carboxylate (20 g, 68 mmol), cesium carbonate (40.0 g, 123 mmol), [1,1'-bis(diphenylphosphino)ferrocene]dichloropalladium(II) dichloromethane complex (2.0 g, 2.45 mmol), 1,4-dioxane (150 mL), and water (15 mL). The resulting mixture was stirred overnight at 100° C. After cooling to room temperature, the reaction mixture was diluted with ethyl acetate (200 mL) and washed with water (100 mL). The combined organic phases were washed with brine (100 mL), dried over anhydrous sodium sulfate, filtered, and concentrated under vacuum. The residue was purified via column chromatography on silica gel (eluting with 1:3, ethyl acetate/petroleum ether) to afford cyclobutyl (S)-4-acetyl-3-methyl-7-(1H-pyrazol-4-yl)-3,4-dihydroquinoxaline-1(2H)-carboxylate (9.0 g, 62%) of as a yellow solid. MS (ESI, pos. ion) m/z 355 [M+H]$^+$.

Example 36

Intermediate 36. (S)-1-(6-bromo-2-ethyl-3,4-dihydroquinoxaline-1(2H)-yl)ethan-1-one

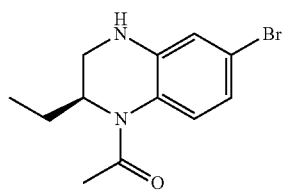

Intermediate 36

(S)-1-(6-bromo-2-ethyl-3,4-dihydroquinoxaline-1(2H)-yl)ethan-1-one was synthesized according to the procedure outlined for (S)-1-(6-bromo-2-methyl-3,4-dihydroquinoxaline-1(2H)-yl)ethanone substituting (S)-2-aminobutan-1-ol for (S)-2-aminopropan-1-ol in the initial step. MS (ESI, pos. ion) m/z 241, 243 [M–42 (acyl)]$^+$.

Example 37

Intermediate 37. (S)-1-(6-bromo-2-ethyl-4-(furan-2-carbonyl)-3,4-dihydroquinoxaline-1(2H)-yl)ethan-1-one

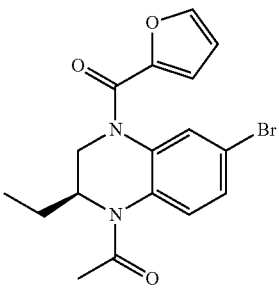

Intermediate 37

(S)-1-(6-bromo-2-ethyl-4-(furan-2-carbonyl)-3,4-dihydroquinoxalin-1 (2H)-yl)ethan-1-one was synthesized from (S)-1-(6-bromo-2-ethyl-3,4-dihydroquinoxaline-1(2H)-yl)ethan-1-one and furan-2-carbonyl chloride according to the procedure outlined for (S)-1-(6-bromo-4-(furan-2-carbonyl)-2-methyl-3,4-dihydroquinoxaline-1(2H)-yl)ethanone. MS (ESI, pos. ion) m/z 335, 337 [M–42 (acyl)]$^+$.

Example 38

Intermediate 38. 1-(6-bromo-2-(fluoromethyl)-3,4-dihydroquinoxaline-1(2H)-yl)ethan-1-one

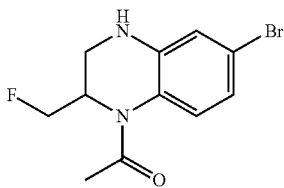

Intermediate 38

1-(6-bromo-2-(fluoromethyl)-3,4-dihydroquinoxalin-1 (2H)-yl)ethan-1-one was synthesized according to the procedure outlined for (S)-1-(6-bromo-2-methyl-3,4-dihydroquinoxaline-1(2H)-yl)ethanone substituting racemic 2-amino-3-fluoropropane-1-ol for (S)-2-aminopropan-1-ol in the initial step. MS (ESI, pos. ion) m/z 245, 247 [M–42 (acyl)]$^+$.

Example 39

Intermediate 39. 1-(6-bromo-2-(fluoromethyl)-4-(furan-2-carbonyl)-3,4-dihydro-quinoxaline-1(2H)-yl)ethan-1-one

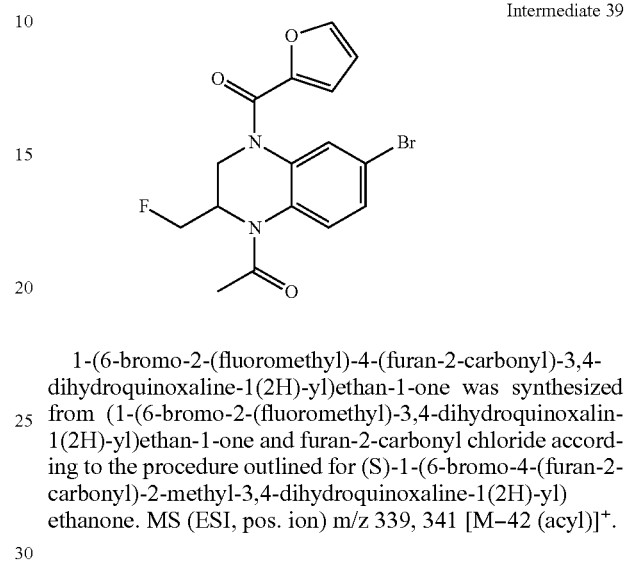

Intermediate 39

1-(6-bromo-2-(fluoromethyl)-4-(furan-2-carbonyl)-3,4-dihydroquinoxaline-1(2H)-yl)ethan-1-one was synthesized from (1-(6-bromo-2-(fluoromethyl)-3,4-dihydroquinoxalin-1(2H)-yl)ethan-1-one and furan-2-carbonyl chloride according to the procedure outlined for (S)-1-(6-bromo-4-(furan-2-carbonyl)-2-methyl-3,4-dihydroquinoxaline-1(2H)-yl)ethanone. MS (ESI, pos. ion) m/z 339, 341 [M–42 (acyl)]$^+$.

EXAMPLES

Example 40

(S)-1-(4-(cyclopropanecarbonyl)-6-(1-cyclopropyl-1H-pyrazol-4-yl)-2-methyl-3,4-dihydroquinoxaline-1(2H)-yl)ethanone (I-8)

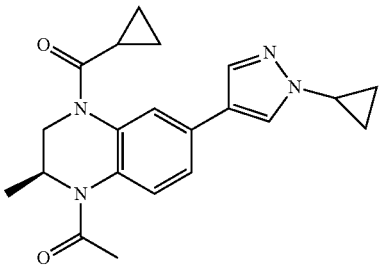

I-8

N,N-Diisopropylethylamine (0.120 mL, 0.688 mmol) was added to a solution of (S)-1-(6-(1-cyclopropyl-1H-pyrazol-4-yl)-2-methyl-3,4-dihydroquinoxaline-1(2H)-yl)ethanone (0.068 g, 0.229 mmol) and cyclopropanecarbonyl chloride (0.031 mL, 0.344 mmol) in 1,2-dichloroethane (2.0 mL), and the mixture stirred at 50° C. for 16 h. The reaction mixture was concentrated to afford an orange oil. This material was purified via column chromatography on silica gel (Biotage 25 g column, gradient elution with 50-100% ethyl acetate-hexane) to afford (S)-1-(4-(cyclopropanecarbonyl)-6-(1-cyclopropyl-1H-pyrazol-4-yl)-2-methyl-3,4-dihydroquinoxaline-1(2H)-yl)ethanone (0.060 g, 72%) as an off-white solid. $^1$H NMR (300 MHz, DMSO-d$_6$) δ ppm 0.68-0.77 (m, 1 H), 0.83-1.02 (m, 5 H), 1.02-1.08 (m, 5 H), 1.87-2.04 (m, 1 H), 2.12 (s, 3 H), 3.33 (m, 1 H), 3.74 (tt, J=7.33, 3.81 Hz, 1 H), 4.61 (m, 1 H), 4.69-4.86 (m, 1 H), 7.37-7.57 (m, 2 H), 7.65 (s, 1 H), 7.85 (s, 1 H), 8.25 (s, 1 H). MS (ESI, pos. ion) m/z 365. [M+1]⁺.

The following examples were made according to the Procedure Outlined for Example 40

Example 41

(S)-ethyl 4-acetyl-3-methyl-7-(1-(oxetan-3-yl)-1H-pyrazol-4-yl)-3,4-dihydroquinoxaline-1(2H)-carboxylate (I-9)

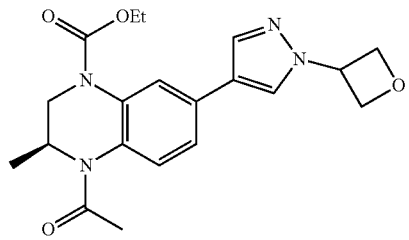 [SMILES: CCOC(=O)N1C[C@H](C)N(C(C)=O)c2ccc(-c3cnn(C4COC4)c3)cc21]

¹H NMR (300 MHz, DMSO-d₆) δ ppm 0.92-1.04 (m, 3 H), 1.25 (t, J=7.04 Hz, 3H), 2.14 (s, 3 H), 3.48 (m, 1 H), 3.87-4.08 (m, 2 H), 4.08-4.31 (m, 2 H), 4.79-5.01 (m, 4 H), 5.59 (quin, J=7.04 Hz, 1 H), 7.34 (dd, J=8.35, 1.91 Hz, 1 H), 7.45 (m, 1 H), 7.96 (s, 2 H), 8.31 (s, 1 H). MS (ESI, pos. ion) m/z 385 [M+1]⁺.

Example 42

(S)-1-(4-(cyclopropanecarbonyl)-2-methyl-6-(1-(oxetan-3-yl)-1H-pyrazol-4-yl)-3,4-dihydroquinoxaline-1(2H)-yl)ethanone (I-10)

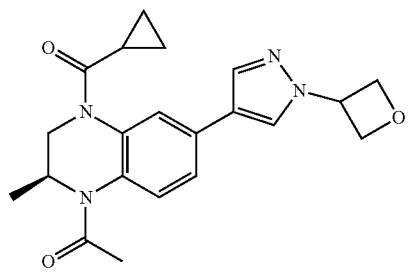 [SMILES: CC(=O)N1c2ccc(-c3cnn(C4COC4)c3)cc2N(C(=O)C2CC2)C[C@@H]1C]

¹H NMR (300 MHz, DMSO-d₆) δ ppm 0.72-0.97 (m, 4 H), 1.05 (d, J=6.45 Hz, 3H), 1.89-2.04 (m, 1 H), 2.13 (s, 3 H), 2.94 (m, 1 H), 4.61 (m, 1 H), 4.68-4.85 (m, 1 H), 4.85-5.01 (m, 4 H), 5.59 (quin, J=7.04 Hz, 1 H), 7.38-7.61 (m, 2 H), 7.69 (s, 1 H), 8.03 (s, 1 H), 8.38 (s, 1 H). MS (ESI, pos. ion) m/z 381 [M+1]⁺.

Example 43

(S)-1-(4-(cyclobutanecarbonyl)-2-methyl-6-(1-(oxetan-3-yl)-1H-pyrazol-4-yl)-3,4-dihydroquinoxaline-1(2H)-yl)ethanone (I-11)

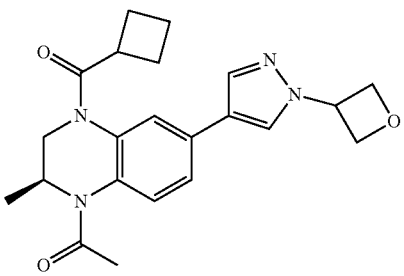 [SMILES: CC(=O)N1c2ccc(-c3cnn(C4COC4)c3)cc2N(C(=O)C2CCC2)C[C@@H]1C]

¹H NMR (300 MHz, DMSO-d₆) δ ppm 1.05 (d, J=6.16 Hz, 3 H), 1.56-1.93 (m, 4H), 2.00-2.15 (m, 1 H), 2.08 (s, 3 H), 2.18-2.40 (m, 1 H), 3.64 (br d, J=8.79 Hz, 1 H), 4.73 (m, 2 H), 4.83-5.03 (m, 5 H), 5.59 (quin, J=7.04 Hz, 1 H), 7.47 (br s, 2 H), 7.68 (m, 1 H), 8.07 (s, 1H), 8.42 (s, 1H). MS (ESI, pos. ion) m/z 395 [M+1]⁺.

Example 44

(S)-isopropyl 4-acetyl-7-(1-(2-hydroxyethyl)-1H-pyrazol-4-yl)-3-methyl-3,4-dihydroquinoxaline-1(2H)-carboxylate (I-12)

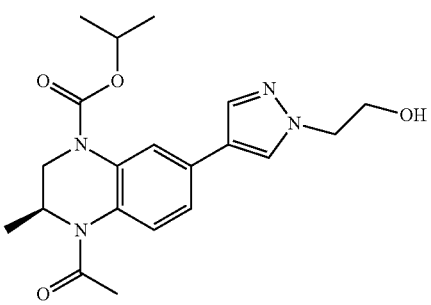 [SMILES: CC(=O)N1c2ccc(-c3cnn(CCO)c3)cc2N(C(=O)OC(C)C)C[C@@H]1C]

A mixture of (S)-isopropyl 4-acetyl-7-bromo-3-methyl-3,4-dihydroquinoxaline-1(2H)-carboxylate (0.050 g, 0.141 mmol), 2-(4-(4,4,5,5-tetramethyl-1,3,2-dioxaborolan-2-yl)-1H-pyrazol-1-yl)ethanol (0.050 g, 0.211 mmol), chloro(2-dicyclohexylphosphino-2',4',6'-tri-i-propyl-1,1'-biphenyl)(2'-amino-1,1'-biphenyl-2-yl) palladium(II) (XPhos 2nd generation precatalyst) (5.54 mg, 7.04 µmol), and cesium carbonate (0.138 g, 0.422 mmol) in 1,4-dioxane (2.0 mL) and water (0.40 mL) was stirred in the microwave at 100° C. for 1 h. The reaction mixture was filtered through Celite and concentrated to afford a yellow oil. This material was purified via column chromatography on silica gel (Biotage 25 g column, gradient elution with 0-10% methanol-ethyl acetate) to afford (S)-isopropyl 4-acetyl-7-(1-(2-hydroxyethyl)-1H-pyrazol-4-yl)-3-methyl-3,4-dihydroquinoxaline-1(2H)-carboxylate (0.052 g, 96%) as an off-white solid.

¹H NMR (300 MHz, DMSO-d₆) δ ppm 0.98 (d, J=6.74 Hz, 3 H), 1.26 (dd, J=9.67, 6.16 Hz, 6 H), 2.14 (s, 3 H), 3.51 (m, 1 H), 3.66-3.81 (m, 2 H), 3.92 (br dd, J=10.85, 7.04 Hz, 1 H), 4.09-4.21 (m, 2 H), 4.71-5.05 (m, 3 H), 7.29 (dd, J=8.35, 1.91 Hz, 1 H), 7.45 (m, 1 H), 7.80 (s, 1 H), 7.93 (s, 1 H), 8.07 (s, 1 H) MS (ESI, pos. ion) m/z 387 [M+1]⁺.

The following examples were made according to the procedure outlined for Example 44

Example 45

(S)-1-(4-(furan-2-carbonyl)-2-methyl-6-(1H-pyrazol-4-yl)-3,4-dihydroquinoxalin-1(2H)-yl)ethanone (I-13)

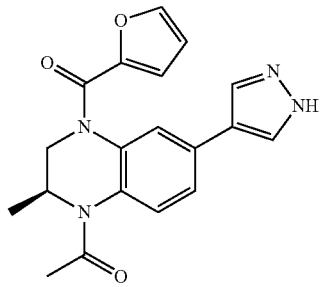 [SMILES: CC(=O)N1c2ccc(-c3cn[nH]c3)cc2N(C(=O)c2ccco2)C[C@@H]1C]

¹H NMR (300 MHz, DMSO-d₆) δ ppm 1.08 (d, J=6.45 Hz, 3 H), 2.16 (s, 3 H), 3.35-3.43 (m, 1 H), 4.63 (br s, 1 H), 4.85 (br d, J=7.33 Hz, 1 H), 6.57 (dd, J=3.52, 1.76 Hz, 1 H), 6.84 (br d, J=3.22 Hz, 1 H), 7.19-7.32 (m, 1 H), 7.46 (br d, J=8.21 Hz, 1 H), 7.54 (br s, 1 H), 7.70-7.83 (m, 2 H), 8.07 (s, 1 H), 12.92 (br s, 1 H). MS (ESI, pos. ion) m/z 351 [M+1]⁺.

Example 46

(S)-1-(4-(furan-2-carbonyl)-2-methyl-6-(1H-pyrazol-3-yl)-3,4-dihydroquinoxalin-1(2H)-yl)ethanone (I-14)

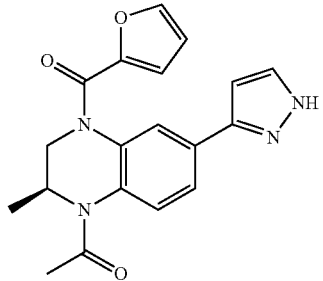 [SMILES: CC(=O)N1c2ccc(-c3cc[nH]n3)cc2N(C(=O)c2ccco2)C[C@@H]1C]

¹H NMR (300 MHz, DMSO-d₆) δ ppm 1.09 (d, J=6.45 Hz, 3 H), 2.18 (s, 3 H), 3.21 (m, 1 H), 4.60 (m, 1 H), 4.85 (m, 1 H), 6.49-6.63 (m, 2 H), 6.88 (m, 1 H), 7.38-7.54 (m, 1 H), 7.54-7.69 (m, 2 H), 7.69-7.84 (m, 2 H), 12.86 (br s, 1 H). MS (ESI, pos. ion) m/z 351 [M+1]⁺.

Example 47

(S)-1-(4-(furan-2-carbonyl)-2-methyl-6-(2-methylthiazol-5-yl)-3,4-dihydroquinoxaline-1(2H)-yl)ethanone (I-15)

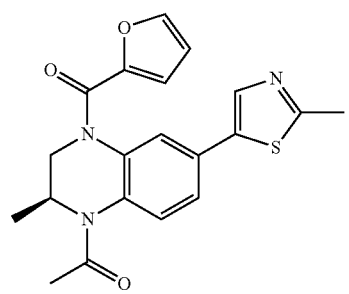

¹H NMR (300 MHz, DMSO-d₆) δ ppm 1.09 (d, J=6.45 Hz, 3 H), 2.20 (s, 3 H), 2.40-2.44 (m, 1 H), 2.62 (s, 3 H), 4.47 (m, 1 H), 4.73-4.92 (m, 1 H), 6.62 (dd, J=3.52, 1.76 Hz, 1H), 6.97 (d, J=3.52 Hz, 1 H), 7.27 (d, J=2.05 Hz, 1 H), 7.44 (dd, J=8.35, 2.20 Hz, 1 H), 7.71 (m, 1 H), 7.79 (dd, J=1.76, 0.88 Hz, 1 H), 7.87 (s, 1 H). MS (ESI, pos. ion) m/z 382 [M+1]⁺.

Example 48

(S)-phenyl 4-acetyl-3-methyl-7-(1H-pyrazol-4-yl)-3,4-dihydroquinoxaline-1(2H)-carboxylate (I-16)

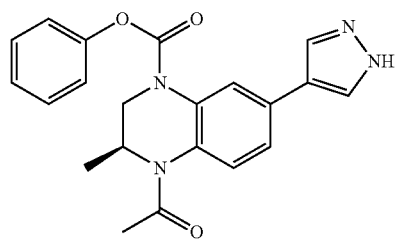 [SMILES: CC(=O)N1c2ccc(-c3cn[nH]c3)cc2N(C(=O)Oc2ccccc2)C[C@@H]1C]

¹H NMR (300 MHz, DMSO-d₆) δ ppm 1.02-1.10 (m, 3 H), 2.19 (s, 3 H), 3.35-3.45 (m, 1 H), 4.20 (m, 1 H), 4.97 (m, 1 H), 7.18-7.33 (m, 2 H), 7.36-7.58 (m, 5 H), 7.86 (br s, 1H), 8.05 (s, 1 H), 8.15 (s, 1 H), 12.96 (br s, 1 H). MS (ESI, pos. ion) m/z 377 [M+1]⁺.

Example 49

(S)-isopropyl 4-acetyl-7-(1-(2-methoxyethyl)-1H-pyrazol-4-yl)-3-methyl-3,4-dihydroquinoxaline-1(2H)-carboxylate (I-17)

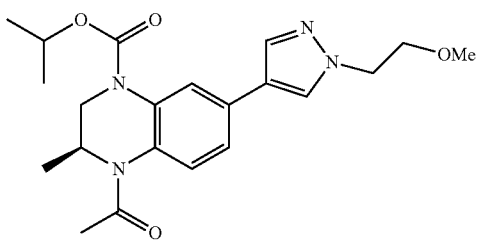 [SMILES: COCCn1cc(-c2ccc3c(c2)N(C(=O)OC(C)C)C[C@H](C)N3C(C)=O)cn1]

$^1$H NMR (300 MHz, DMSO-d$_6$) δ ppm 0.98 (d, J=6.74 Hz, 3 H), 1.26 (dd, J=10.26, 6.16 Hz, 6 H), 2.14 (s, 3 H), 3.22 (s, 3 H), 3.63-3.76 (m, 2 H), 3.85-4.05 (m, 2 H), 4.20-4.33 (m, 2 H), 4.91 (dq, J=12.50, 6.29 Hz, 2 H), 7.23-7.35 (m, 1 H), 7.45 (br s, 1 H), 7.81 (s, 1 H), 7.92 (s, 1 H), 8.09 (s, 1 H). MS (ESI, pos. ion) m/z 401 [M+1]$^+$.

Example 50

(S)-1-(4-(furan-2-carbonyl)-6-(1-(2-methoxyethyl)-1H-pyrazol-4-yl)-2-methyl-3,4-dihydroquinoxaline-1(2H)-yl)ethanone (I-18)

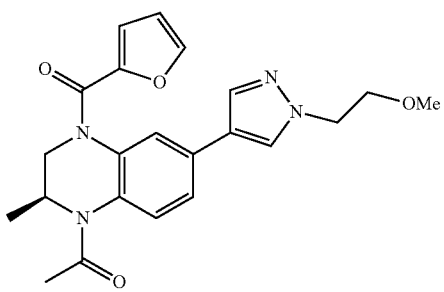 [SMILES: COCCn1cc(-c2ccc3c(c2)N(C(=O)c2ccco2)C[C@H](C)N3C(C)=O)cn1]

$^1$H NMR (300 MHz, DMSO-d$_6$) δ ppm 1.08 (d, J=6.45 Hz, 3 H), 2.16 (s, 3 H), 3.20 (s, 3 H), 3.39 (br s, 1 H), 3.66 (t, J=5.28 Hz, 2 H), 4.22 (t, J=5.28 Hz, 2 H), 4.61 (br s, 1 H), 4.74-4.92 (m, 1 H), 6.58 (dd, J=3.52, 1.47 Hz, 1 H), 6.85 (d, J=3.22 Hz, 1 H), 7.26 (d, J=1.47 Hz, 1 H), 7.35-7.47 (m, 1 H), 7.55 (br s, 1 H), 7.73 (s, 1 H), 7.75-7.81 (m, 1 H), 8.04 (s, 1H). MS (ESI, pos. ion) m/z 409 [M+1]$^+$.

Example 51

(S)-ethyl 4-acetyl-3-methyl-7-(1H-pyrazol-4-yl)-3,4-dihydroquinoxaline-1(2H)-carboxylate (I-19)

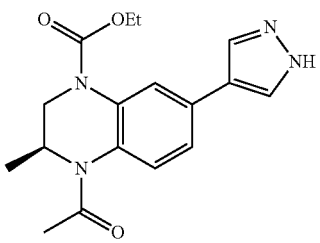 [SMILES: CCOC(=O)N1C[C@H](C)N(C(C)=O)c2ccc(-c3cn[nH]c3)cc21]

$^1$H NMR (300 MHz, CDCl$_3$) δ ppm 1.10 (br d, J=6.45 Hz, 3 H), 1.36 (br t, J=6.89 Hz, 3 H), 2.23 (s, 3 H), 3.46 (br d, J=9.67 Hz, 1 H), 4.12 (br d, J=6.74 Hz, 1 H), 4.19-4.46 (m, 2 H), 4.99-5.33 (m, 1 H), 7.17 (br s, 1 H), 7.88 (br s, 2 H), 8.08 (br s, 1 H). MS (ESI, pos. ion) m/z 329 [M+1]$^+$.

Example 52

(S)-cyclopentyl 4-acetyl-3-methyl-7-(1H-pyrazol-4-yl)-3,4-dihydroquinoxaline-1(2H)-carboxylate (I-20)

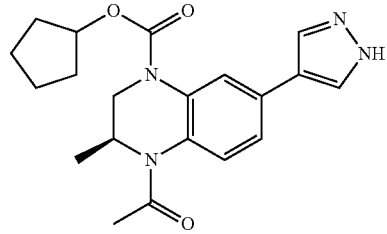 [SMILES: CC(=O)N1c2ccc(-c3cn[nH]c3)cc2N(C(=O)OC2CCCC2)C[C@@H]1C]

$^1$H NMR (300 MHz, DMSO-d$_6$) δ ppm 0.98 (d, J=6.45 Hz, 3 H), 1.34-1.88 (m, 8H), 2.14 (s, 3 H), 3.37-3.51 (m, 1 H), 3.81-4.07 (m, 1 H), 4.85 (br s, 1 H), 5.14 (br s, 1 H), 7.34 (br d, J=6.74 Hz, 1 H), 7.44 (br s, 1 H), 7.73-7.97 (m, 2 H), 8.13 (br s, 1 H), 12.97 (br s, 1 H). MS (ESI, pos. ion) m/z 369 [M+1]$^+$.

Example 53

(S)-ethyl 4-acetyl-7-(1-cyclopropyl-1H-pyrazol-4-yl)-3-methyl-3,4-dihydroquinoxaline-1(2H)-carboxylate (I-21)

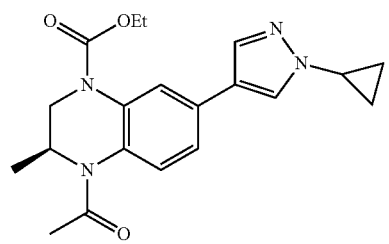 [SMILES: CCOC(=O)N1C[C@H](C)N(C(C)=O)c2ccc(-c3cnn(C4CC4)c3)cc21]

$^1$H NMR (300 MHz, DMSO-d$_6$) δ ppm 0.88-1.02 (m, 5 H), 1.02-1.12 (m, 2 H), 1.25 (t, J=7.04 Hz, 3 H), 2.13 (s, 3 H), 3.38-3.53 (m, 1 H), 3.64-3.85 (m, 1 H), 3.99 (br d, J=5.28 Hz, 1 H), 4.09-4.29 (m, 2 H), 4.87 (m, 1 H), 7.31 (dd, J=8.35, 1.91 Hz, 1 H), 7.43 (br s, 1 H), 7.78 (s, 1 H), 7.92 (s, 1 H), 8.19 (s, 1 H). MS (ESI, pos. ion) m/z 369 [M+1]$^+$.

Example 54

(S)-isopropyl 4-acetyl-7-(1-cyclopropyl-1H-pyrazol-4-yl)-3-methyl-3,4-dihydroquinoxaline-1(2H)-carboxylate (I-22)

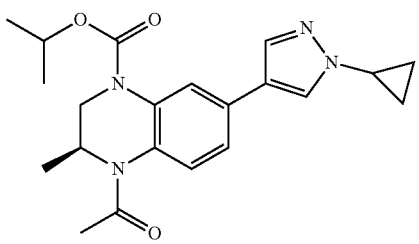 [SMILES: CC(=O)N1c2ccc(-c3cnn(C4CC4)c3)cc2N(C(=O)OC(C)C)C[C@@H]1C]

¹H NMR (300 MHz, DMSO-d₆) δ ppm 0.89-1.02 (m, 5 H), 1.02-1.13 (m, 2 H), 1.26 (dd, J=10.11, 6.30 Hz, 6 H), 2.14 (s, 3 H), 3.45 (br s, 1 H), 3.59-3.83 (m, 1 H), 3.92 (m, 1 H), 4.92 (dt, J=12.31, 6.16 Hz, 2 H), 7.30 (dd, J=8.50, 1.76 Hz, 1 H), 7.46 (br s, 1 H), 7.77 (s, 1 H), 7.91 (s, 1 H), 8.18 (s, 1 H). MS (ESI, pos. ion) m/z 383 [M+1]⁺.

Example 55

(S)-cyclopentyl 4-acetyl-7-(1-cyclopropyl-1H-pyrazol-4-yl)-3-methyl-3,4-dihydroquinoxaline-1(2H)-carboxylate (I-23)

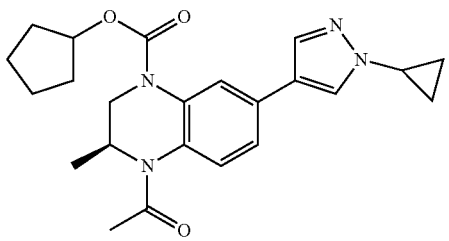 [SMILES: CC(=O)N1c2ccc(-c3cnn(C4CC4)c3)cc2N(C(=O)OC2CCCC2)C[C@@H]1C]

¹H NMR (300 MHz, DMSO-d₆) δ ppm 0.92-1.02 (m, 5 H), 1.02-1.10 (m, 2 H), 1.48-1.91 (m, 8 H), 2.14 (s, 3 H), 3.46 (m, 1 H), 3.74 (tt, J=7.33, 3.81 Hz, 1 H), 3.90 (m, 1H), 4.87 (br s, 1 H), 5.13 (td, J=5.42, 2.93 Hz, 1 H), 7.30 (dd, J=8.35, 1.91 Hz, 1 H), 7.45 (br s, 1 H), 7.76 (s, 1 H), 7.84-7.93 (m, 1 H), 8.17 (s, 1 H). MS (ESI, pos. ion) m/z 409 [M+1]⁺.

Example 56

(S)-isopropyl 4-acetyl-7-(1-cyclobutyl-1H-pyrazol-4-yl)-3-methyl-3,4-dihydroquinoxaline-1(2H)-carboxylate (I-24)

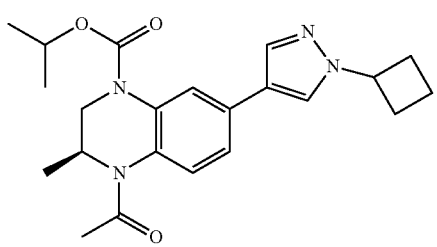 [SMILES: CC(=O)N1c2ccc(-c3cnn(C4CCC4)c3)cc2N(C(=O)OC(C)C)C[C@@H]1C]

¹H NMR (300 MHz, DMSO-d₆) δ ppm 0.98 (d, J=6.74 Hz, 3 H), 1.16-1.33 (m, 8H), 1.60-1.89 (m, 2 H), 2.14 (s, 3 H), 2.30-2.44 (m, 2 H), 3.50 (br s, 1 H), 3.77-4.07 (m, 1 H), 4.69-5.06 (m, 3 H), 7.24-7.36 (m, 1 H), 7.45 (br s, 1 H), 7.81 (s, 1 H), 7.92 (s, 1 H), 8.21 (s, 1H). MS (ESI, pos. ion) m/z 397 [M+1]⁺.

Example 57

(S)-cyclopentyl 4-acetyl-7-(1-cyclobutyl-1H-pyrazol-4-yl)-3-methyl-3,4-dihydroquinoxaline-1(2H)-carboxylate (I-25)

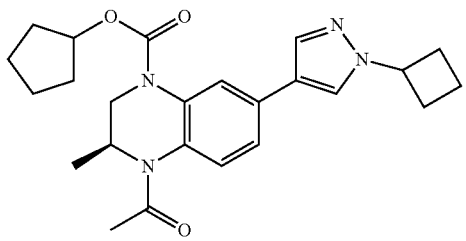 [SMILES: CC(=O)N1c2ccc(-c3cnn(C4CCC4)c3)cc2N(C(=O)OC2CCCC2)C[C@@H]1C]

¹H NMR (300 MHz, DMSO-d₆) δ ppm 1.05 (d, J=6.74 Hz, 3 H), 1.53-2.04 (m, 12H), 2.22 (s, 3 H), 2.39-2.50 (m, 3 H), 3.87-4.10 (m, 1 H), 4.73-5.03 (m, 2 H), 5.21 (br dd, J=4.98, 2.93 Hz, 1 H), 7.38 (dd, J=8.35, 1.91 Hz, 1 H), 7.53 (br s, 1 H), 7.88 (s, 1 H), 7.98 (s, 1 H), 8.29 (s, 1 H). MS (ESI, pos. ion) m/z 423 [M+1]⁺.

Example 58

(S)-3,3-difluorocyclobutyl 4-acetyl-7-(1-cyclopropyl-1H-pyrazol-4-yl)-3-methyl-3,4-dihydroquinoxaline-1(2H)-carboxylate (I-26)

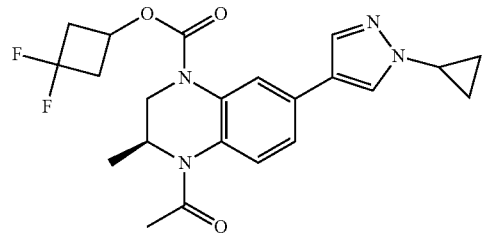 [SMILES: CC(=O)N1c2ccc(-c3cnn(C4CC4)c3)cc2N(C(=O)OC2CC(F)(F)C2)C[C@@H]1C]

¹H NMR (400 MHz, CD₃OD) δ ppm 1.01-1.19 (m, 7H), 2.20 (s, 3H), 2.67-2.95 (m, 2H), 3.05-3.19 (m, 2H), 3.55 (s, 1H), 3.63-3.80 (m, 1H), 4.11-4.23 (m, 1H), 5.00-5.21 (m, 2H), 7.45 (s, 2H), 7.80 (s, 1H), 8.01-8.13 (m, 2H). MS (ESI, pos. ion) m/z 431 [M+1]⁺.

Example 59

(S)-3,3-difluorocyclobutyl 4-acetyl-7-(1-(2-hydroxyethyl)-1H-pyrazol-4-yl)-3-methyl-3,4-dihydroquinoxaline-1(2H)-carboxylate (I-27)

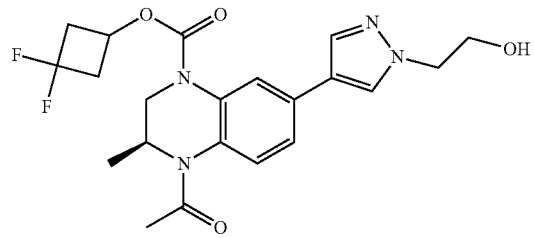 [SMILES: CC(=O)N1c2ccc(-c3cnn(CCO)c3)cc2N(C(=O)OC2CC(F)(F)C2)C[C@@H]1C]

¹H NMR (300 MHz, CD₃OD) δ ppm 1.12 (d, J=6.60 Hz, 3H), 2.20 (s, 3H), 2.67-2.99 (m, 2H), 3.00-3.17 (m, 2H), 3.50

(s, 1H), 3.87-4.02 (m, 2H), 4.12-4.38 (m, 3H), 4.97-5.15 (m, 2H), 7.47 (s, 2H), 7.83 (s, 1H), 8.06 (s, 2H). MS (ESI, pos. ion) m/z 435 [M+1]⁺.

Example 60

(S)-3,3-difluorocyclobutyl 4-acetyl-7-(1-(2-hydroxy-2-methylpropyl)-1H-pyrazol-4-yl)-3-methyl-3,4-dihydroquinoxaline-1(2H)-carboxylate (I-28)

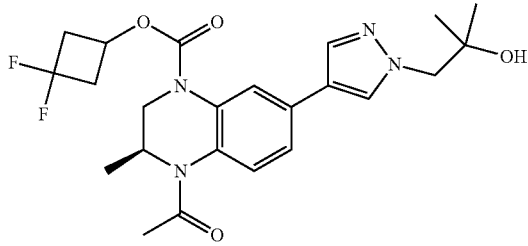 [SMILES: CC(=O)N1c2ccc(-c3cnn(CC(C)(C)O)c3)cc2N(C(=O)OC2CC(F)(F)C2)C[C@@H]1C]

¹H NMR (300 MHz, CD₃OD) δ ppm 1.10 (d, J=6.60 Hz, 3H), 1.21 (s, 6H), 2.22 (s, 3H), 2.67-2.89 (m, 2H), 3.00-3.16 (m, 2H), 3.50 (s, 1H), 4.12-4.38 (m, 3H), 4.97-5.15 (m, 2H), 7.39 (s, 2H), 7.84 (s, 1H), 7.98-8.10 (m, 2H). MS (ESI, pos. ion) m/z 463 [M+1]⁺.

Example 61

3,3-difluorocyclobutyl (3S)-4-acetyl-7-[4-(1,1-dioxo-1λ⁶,2-thiazolidin-2-yl)phenyl]-3-methyl-1,2,3,4-tetrahydroquinoxaline-1-carboxylate (I-29)

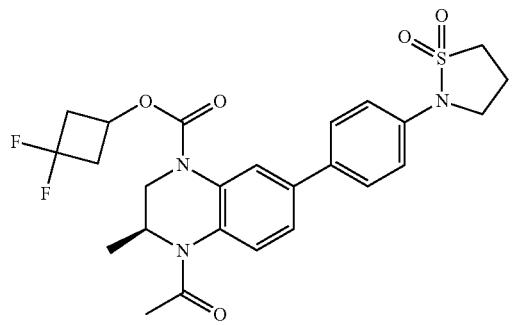 [SMILES: CC(=O)N1c2ccc(-c3ccc(N4CCCS4(=O)=O)cc3)cc2N(C(=O)OC2CC(F)(F)C2)C[C@@H]1C]

¹H NMR (300 MHz, CD₃OD) δ ppm 1.12 (d, J=6.60 Hz, 3H), 2.24 (s, 3H), 2.50-2.61 (m, 2H), 2.70-2.90 (m, 2H), 3.03-3.18 (m, 2H), 3.39-3.52 (m, 3H), 3.81-3.92 (m, 2H), 4.97-5.15 (m, 2H), 7.30-7.60 (m, 4H), 7.61-7.73 (m, 2H), 8.13 (s, 2H). MS (ESI, pos. ion) m/z 520 [M+1]⁺.

Example 62

(S)-3,3-difluorocyclobutyl 4-acetyl-3-methyl-7-(4-(methylsulfonamido)phenyl)-3,4-dihydroquinoxaline-1(2H)-carboxylate (I-30)

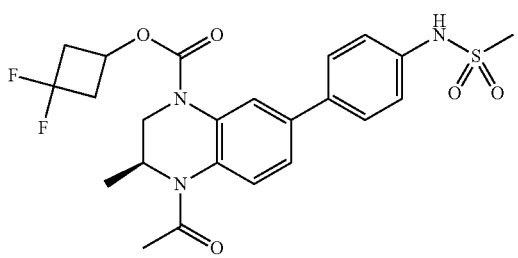 [SMILES: CC(=O)N1c2ccc(-c3ccc(NS(C)(=O)=O)cc3)cc2N(C(=O)OC2CC(F)(F)C2)C[C@@H]1C]

¹H NMR (300 MHz, CD₃OD) δ ppm 1.12 (d, J=6.60 Hz, 3H), 2.24 (s, 3H), 2.70-2.98 (m, 2H), 2.99-3.16 (m, 5H), 3.52 (s, 1H), 4.14-4.31 (m, 1H), 4.97-5.19 (m, 2H), 7.27-7.53 (m, 4H), 7.63 (d, J=8.70 Hz, 2H), 8.12 (s, 1H). MS (ESI, pos. ion) m/z 494 [M+1]⁺.

Example 63

(S)-4,4-difluorocyclohexyl 4-acetyl-3-methyl-7-(4-(methylsulfonamido)phenyl)-3,4-dihydroquinoxaline-1(2H)-carboxylate (I-31)

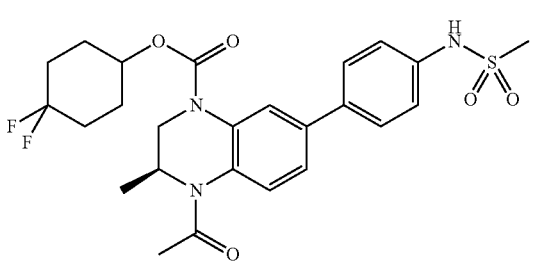 [SMILES: CC(=O)N1c2ccc(-c3ccc(NS(C)(=O)=O)cc3)cc2N(C(=O)OC2CCC(F)(F)CC2)C[C@@H]1C]

¹H NMR (400 MHz, CD₃OD) δ ppm 1.13 (d, J=5.40 Hz, 3H), 1.90-2.10 (m, 8H), 2.26 (s, 3H), 3.01 (s, 3H), 3.52 (s, 1H), 4.22 (s, 1H), 5.01-5.22 (m, 2H), 7.36 (d, J=8.40 Hz, 2H), 7.47 (s, 2H), 7.64 (d, J=8.40 Hz, 2H), 8.10 (s, 1H). MS (ESI, pos. ion) m/z 522 [M+1]⁺.

Example 64

(S)-4,4-difluorocyclohexyl 4-acetyl-3-methyl-7-(4-(methylsulfonyl)phenyl)-3,4-dihydroquinoxaline-1(2H)-carboxylate (I-32)

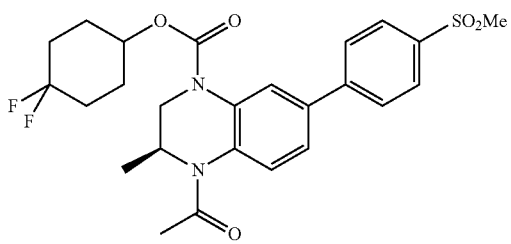 [SMILES: CC(=O)N1c2ccc(-c3ccc(S(C)(=O)=O)cc3)cc2N(C(=O)OC2CCC(F)(F)CC2)C[C@@H]1C]

$^1$H NMR (400 MHz, CD$_3$OD) δ ppm 1.16 (d, J=5.40 Hz, 3H), 1.90-2.13 (m, 8H), 2.28 (s, 3H), 3.18 (s, 3H), 3.64 (s, 1H), 4.17 (s, 1H), 5.01-5.22 (m, 2H), 7.54-7.56 (m, 2H), 7.92 (d, J=8.40 Hz, 2H), 7.05 (d, J=8.40 Hz, 2H), 8.27 (s, 1H). MS (ESI, pos. ion) m/z 507 [M+1]+.

Example 65

(S)-4,4-difluorocyclohexyl 4-acetyl-7-(1-cyclopropyl-1H-pyrazol-4-yl)-3-methyl-3,4-dihydroquinoxaline-1(2H)-carboxylate (I-33)

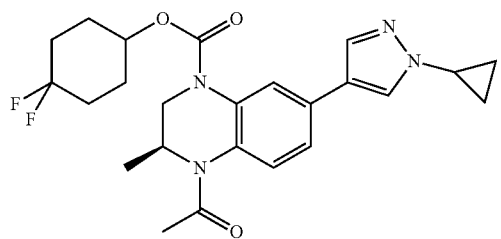 [SMILES: CC(=O)N1c2ccc(-c3cnn(C4CC4)c3)cc2N(C(=O)OC2CCC(F)(F)CC2)C[C@@H]1C]

$^1$H NMR (300 MHz, CD$_3$OD) δ ppm 1.01-1.19 (m, 7H), 1.85-2.11 (m, 8H), 2.21 (s, 3H), 3.44 (s, 1H), 3.64-3.79 (m, 1H), 4.21 (s, 1H), 4.98-5.19 (m, 2H), 7.39 (s, 1H), 7.81 (s, 1H), 7.98 (s, 1H), 8.05 (s, 1H). MS (ESI, pos. ion) m/z 458 [M+1]$^+$.

Example 66

(S)-4,4-difluorocyclohexyl 4-acetyl-7-(1-(2-hydroxyethyl)-1H-pyrazol-4-yl)-3-methyl-3,4-dihydroquinoxaline-1(2H)-carboxylate (I-34)

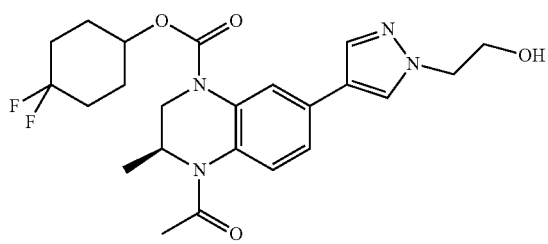 [SMILES: CC(=O)N1c2ccc(-c3cnn(CCO)c3)cc2N(C(=O)OC2CCC(F)(F)CC2)C[C@@H]1C]

$^1$H NMR (400 MHz, CD$_3$OD) δ ppm 1.11 (d, J=6.80 Hz, 3H), 1.95-2.11 (m, 8H), 2.23 (s, 3H), 3.44 (s, 1H), 3.87-3.98 (m, 2H), 4.12-4.31 (m, 3H), 4.98-5.19 (m, 2H), 7.41 (s, 1H), 7.86 (s, 1H), 7.96-8.19 (m, 2H). MS (ESI, pos. ion) m/z 463 [M+1]$^+$.

Example 67

(S)-4,4-difluorocyclohexyl 4-acetyl-7-(1-(2-hydroxy-2-methylpropyl)-1H-pyrazol-4-yl)-3-methyl-3,4-dihydroquinoxaline-1(2H)-carboxylate (I-35)

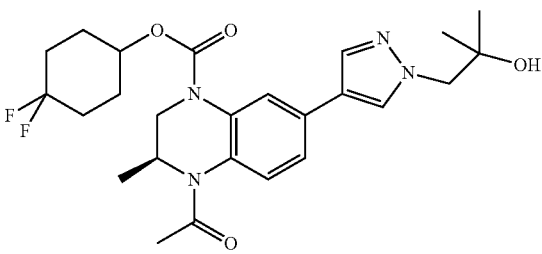 [SMILES: CC(=O)N1c2ccc(-c3cnn(CC(C)(C)O)c3)cc2N(C(=O)OC2CCC(F)(F)CC2)C[C@@H]1C]

$^1$H NMR (400 MHz, CD$_3$OD) δ ppm NMR (300 MHz, CD$_3$OD) δ ppm 1.10 (d, J=6.60 Hz, 3H), 1.21 (s, 6H), 1.90-2.11 (m, 8H), 2.22 (s, 3H), 3.44 (s, 1H), 4.11-4.29 (m, 3H), 4.98-5.19 (m, 2H), 7.40 (s, 1H), 7.84 (s, 1H), 8.00 (s, 2H). MS (ESI, pos. ion) m/z 491 [M+1]$^+$.

Example 68

4,4-difluorocyclohexyl (3S)-4-acetyl-7-[4-(1,1-dioxo-1λ$^6$,2-thiazolidin-2-yl)phenyl]-3-methyl-1,2,3,4-tetrahydroquinoxaline-1-carboxylate (I-36)

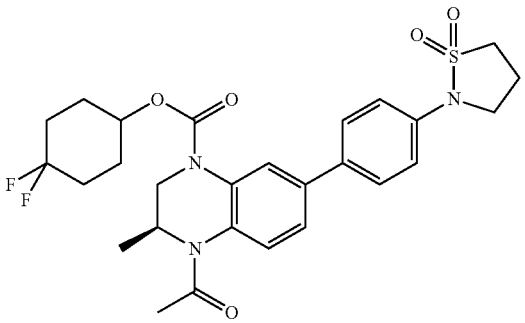 [SMILES: CC(=O)N1c2ccc(-c3ccc(N4CCCS4(=O)=O)cc3)cc2N(C(=O)OC2CCC(F)(F)CC2)C[C@@H]1C]

$^1$H NMR (400 MHz, CD$_3$OD) δ ppm 1.13 (d, J=6.80 Hz, 3H), 1.90-2.11 (m, 8H), 2.25 (s, 3H), 2.45-2.68 (m, 2H), 3.40-3.61 (m, 3H), 3.78-3.91 (m, 2H), 4.11-4.29 (m, 1H), 4.98-5.19 (m, 2H), 7.37 (d, J=8.80 Hz, 2H), 7.46 (s, 2H), 7.65 (d, J=8.80 Hz, 2H), 8.10 (s, 1H). MS (ESI, pos. ion) m/z 548 [M+1]$^+$.

Example 69 oxan-4-yl (3S)-4-acetyl-7-[1-(1,1-dioxo-1λ⁶-thietan-3-yl)-1H-pyrazol-4-yl]-3-methyl-1,2,3,4-tetrahydroquinoxaline-1-carboxylate (I-37)

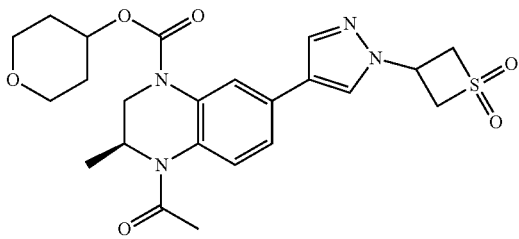 [SMILES: CC(=O)N1c2ccc(-c3cnn(C4CS(=O)(=O)C4)c3)cc2N(C(=O)OC2CCOCC2)C[C@@H]1C]

¹H NMR (300 MHz, CD$_3$OD) δ ppm 1.10 (d, J=6.90 Hz, 3H), 1.72-1.89 (m, 2H), 1.92-2.10 (m, 2H), 2.23 (s, 3H), 3.55-3.70 (m, 3H), 3.82-3.97 (m, 2H), 4.15-4.29 (m, 1H), 4.68-4.82 (m, 5H), 4.95-5.18 (m, 1.5H), 5.33-5.42 (m, 0.5H), 7.40 (s, 2H), 7.95 (s, 1H), 8.05 (s, 1H), 8.18 (s, 1H). MS (ESI, pos. ion) m/z 489 [M+1]⁺.

Example 70

(S)-tetrahydro-2H-pyran-4-yl 4-acetyl-3-methyl-7-(1-(tetrahydro-2H-pyran-4-yl)-1H-pyrazol-4-yl)-3,4-dihydroquinoxaline-1(2H)-carboxylate (I-38)

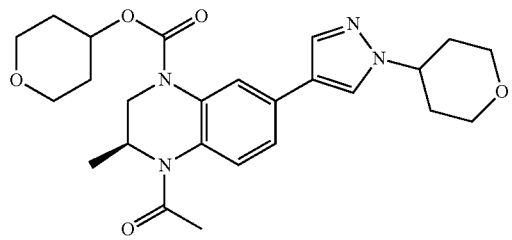 [SMILES: CC(=O)N1c2ccc(-c3cnn(C4CCOCC4)c3)cc2N(C(=O)OC2CCOCC2)C[C@@H]1C]

¹H NMR (400 MHz, CD$_3$OD) δ ppm 0.99 (s, 3H), 1.51-1.72 (m, 2H), 1.83-2.02 (m, 6H), 2.11 (s, 3H), 3.31-3.41 (m, 1H), 3.43-3.58 (m, 4H), 3.68-3.83 (m, 2H), 3.93-4.01 (m, 2H), 4.00-4.15 (m, 1H), 4.27-4.39 (m, 1H), 4.89-5.02 (m, 2H), 7.29 (s, 2H), 7.74 (s, 1H), 7.92 (s, 1H), 7.99 (s, 1H). MS (ESI, pos. ion) m/z 469 [M+1]⁺.

Example 71

(S)-cyclobutyl 4-acetyl-3-methyl-7-(1-(tetrahydro-2H-pyran-4-yl)-1H-pyrazol-4-yl)-3,4-dihydroquinoxaline-1(2H)-carboxylate (I-39)

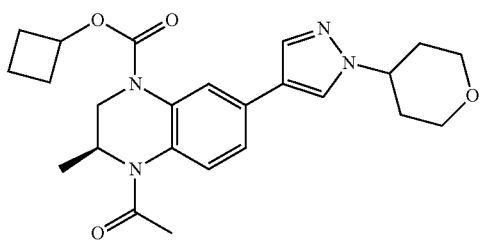 [SMILES: CC(=O)N1c2ccc(-c3cnn(C4CCOCC4)c3)cc2N(C(=O)OC2CCC2)C[C@@H]1C]

¹H NMR (300 MHz, CD$_3$OD) δ ppm 1.10 (d, J=6.60 Hz, 3H), 1.62-1.75 (m, 1H), 1.76-1.89 (m, 1H), 2.05-2.20 (m, 9H), 2.31-2.49 (m, 2H), 3.40-3.68 (m, 3H), 4.05-4.19 (m, 3H), 4.40-51 (m, 1H), 5.01-5.12 (m, 2H), 7.31-7.41 (m, 2H), 7.85 (s, 1H), 8.02 (s, 1H), 8.11 (s, 1H). MS (ESI, pos. ion) m/z 439 [M+I]

Example 72 cyclobutyl (3S)-4-acetyl-7-[1-(1,1-dioxo-1λ⁶-thietan-3-yl)-1H-pyrazol-4-yl]-3-methyl-1,2,3,4-tetrahydroquinoxaline-1-carboxylate (I-98)

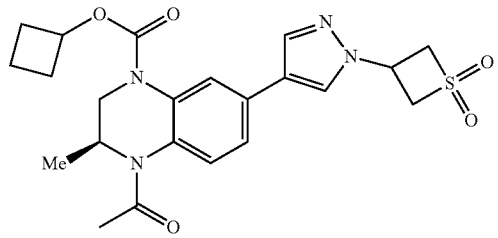 [SMILES: CC(=O)N1c2ccc(-c3cnn(C4CS(=O)(=O)C4)c3)cc2N(C(=O)OC2CCC2)C[C@@H]1C]

¹H NMR (400 MHz, CD$_3$OD) ppm 1.11 (d, J=6.40 Hz, 3H), 1.62-1.73 (m, 1H), 1.81-1.90 (m, 1H), 2.05-2.21 (m, 2H), 2.20 (s, 3H), 2.35-2.48 (m, 2H), 3.41-3.58 (m, 1H), 4.09-4.21 (m, 1H), 4.74 (d, J=7.20 Hz, 4H), 5.02-5.11 (m, 2H), 5.34-5.45 (m, 1H), 7.40 (s, 2H), 7.97 (s, 1H), 8.05 (s, 1H), 8.19 (s, 1H). MS (ESI, pos. ion) m/z 459 [M+1]⁺.

Example 73

3,3-difluorocyclobutyl (3S)-4-acetyl-7-[1-(1,1-dioxo-1λ⁶-thietan-3-yl)-1H-pyrazol-4-yl]-3-methyl-1,2,3,4-tetrahydroquinoxaline-1-carboxylate (I-1)

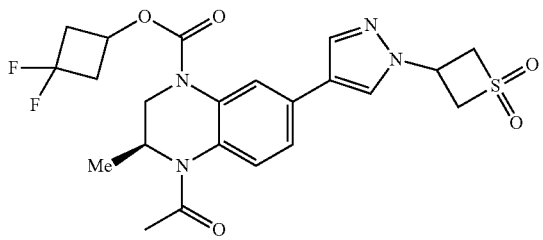 [SMILES: CC(=O)N1c2ccc(-c3cnn(C4CS(=O)(=O)C4)c3)cc2N(C(=O)OC2CC(F)(F)C2)C[C@@H]1C]

¹H NMR (400 MHz, CD$_3$OD) δ ppm 0.99 (d, J=6.40 Hz, 3H), 2.11 (s, 3H), 2.58-2.75 (m, 2H), 2.92-3.01 (m, 2H), 3.31-3.41 (m, 1H), 4.01-4.12 (m, 1H), 4.61-4.65 (m, 4H), 4.82-5.02 (m, 2H), 5.21-5.31 (m, 1H), 7.22-7.32 (m, 2H), 7.85 (s, 1H), 7.95 (s, 1H), 8.11 (s, 1H). MS (ESI, pos. ion) m/z 495 [M+1]+.

Example 74

(S)-4,4-difluorocyclohexyl 4-acetyl-3-methyl-7-(1-(tetrahydro-2H-pyran-4-yl)-1H-pyrazol-4-yl)-3,4-dihydroquinoxaline-1(2H)-carboxylate (I-2)

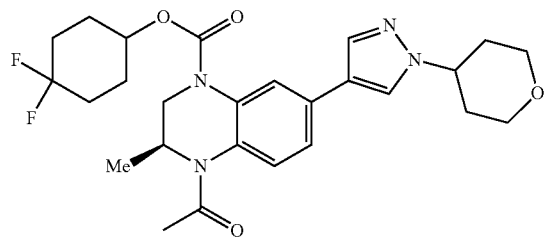 [SMILES: CC(=O)N1c2ccc(-c3cnn(C4CCOCC4)c3)cc2N(C(=O)OC2CCC(F)(F)CC2)C[C@@H]1C]

¹H NMR (300 MHz, CD₃OD) δ ppm 1.10 (d, J=6.60 Hz, 3H), 1.82-2.13 (m, 12H), 2.22 (s, 3H), 3.35-3.49 (m, 1H), 3.50-3.68 (m, 2H), 4.05-4.10 (m, 2H), 4.15-4.23 (m, 1H), 4.38-4.49 (m, 1H), 4.97-5.10 (m, 2H), 7.31-7.41 (m, 2H), 7.85 (s, 1H), 7.99 (s, 1H), 8.09 (s, 1H). MS (ESI, pos. ion) m/z 503 [M+1]⁺.

Example 75

(S)-3,3-difluorocyclobutyl 4-acetyl-3-methyl-7-(1-(tetrahydro-2H-pyran-4-yl)-1H-pyrazol-4-yl)-3,4-dihydroquinoxaline-1(2H)-carboxylate (I-4)

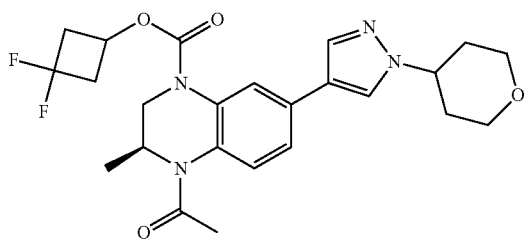 [SMILES: CC(=O)N1c2ccc(-c3cnn(C4CCOCC4)c3)cc2N(C(=O)OC2CC(F)(F)C2)C[C@@H]1C]

¹H NMR (300 MHz, CD₃OD) δ ppm 1.10 (d, J=6.60 Hz, 3H), 2.01-2.13 (m, 4H), 2.20 (s, 3H), 2.67-89 (m, 2H), 2.98-3.17 (m, 2H), 3.39-3.69 (m, 3H), 4.03-4.22 (m, 3H), 4.37-4.51 (m, 1H), 4.95-5.12 (m, 2H), 7.31-7.48 (m, 2H), 7.85 (s, 1H), 8.03 (s, 1H), 8.11 (s, 1H). MS (ESI, pos. ion) m/z 475 [M+1]⁺.

Example 76

(S)-3,3-difluorocyclobutyl 4-acetyl-3-methyl-7-(4-(methylsulfonyl)phenyl)-3,4-dihydroquinoxaline-1(2H)-carboxylate (I-5)

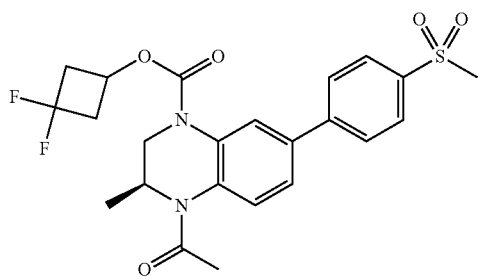 [SMILES: CC(=O)N1c2ccc(-c3ccc(S(C)(=O)=O)cc3)cc2N(C(=O)OC2CC(F)(F)C2)C[C@@H]1C]

¹H NMR (400 MHz, CD₃OD) δ ppm 1.14 (d, J=6.40 Hz, 3H), 2.28 (s, 3H), 2.70-2.90 (m, 2H), 3.01-3.15 (m, 2H), 3.19 (s, 3H), 3.55-3.70 (m, 1H), 4.09-4.19 (m, 1H), 4.95-5.15 (m, 2H), 7.50-7.62 (m, 2H), 7.92 (d, J=8.40 Hz, 2H), 8.06 (d, J=8.40 Hz, 2H), 8.25 (br s, 1H). MS (ESI, pos. ion) m/z 479 [M+H]⁺.

Example 77

(S)-1-(2-ethyl-4-(furan-2-carbonyl)-6-(4-(methylsulfonyl)phenyl)-3,4-dihydroquinoxaline-1(2H)-yl)ethan-1-one (I-6)

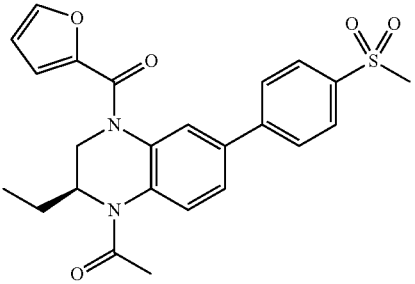 [SMILES: CC[C@H]1CN(C(=O)c2ccco2)c2cc(-c3ccc(S(C)(=O)=O)cc3)ccc2N1C(C)=O]

MS (ESI, pos. ion) m/z 453 [M+H]⁺.

Example 78

1-(2-(fluoromethyl)-4-(furan-2-carbonyl)-6-(4-(methylsulfonyl)phenyl)-3,4-dihydroquinoxaline-1(2H)-yl)ethan-1-one (I-7)

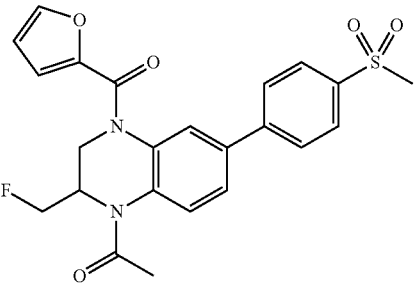 [SMILES: CC(=O)N1c2ccc(-c3ccc(S(C)(=O)=O)cc3)cc2N(C(=O)c2ccco2)CC1CF]

MS (ESI, pos. ion) m/z 457 [M+H]⁺.

Example 79

(S)-4-cyclopentyl 1-methyl 6-(1-cyclopropyl-1H-pyrazol-4-yl)-2-methyl-2,3-dihydroquinoxaline-1,4-dicarboxylate (I-40)

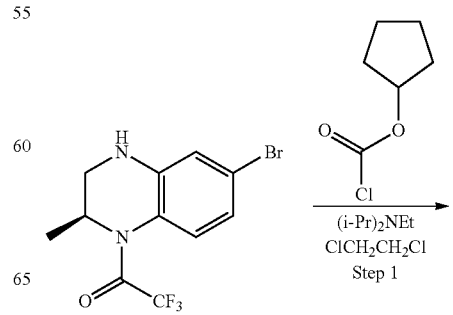

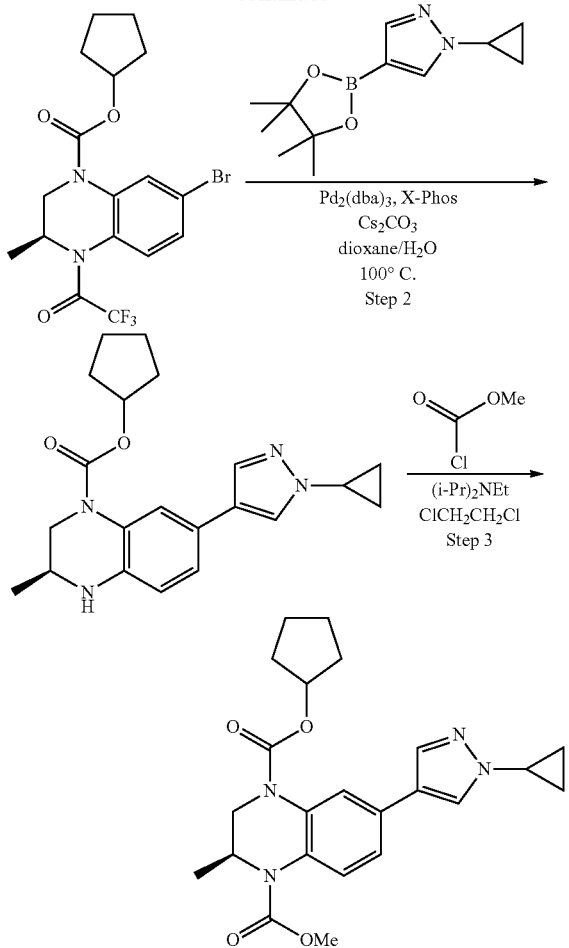

Step 1. (S)-cyclopentyl 7-bromo-3-methyl-4-(2,2,2-trifluoroacetyl)-3,4-dihydroquinoxaline-1(2H)-carboxylate N,N-Diisopropylethylamine (0.486 mL, 2.79 mmol) was added to a solution of (S)-1-(6-bromo-2-methyl-3,4-dihydroquinoxaline-1(2H)-yl)-2,2,2-trifluoroethanone (0.300 g, 0.928 mmol) and cyclopentyl chloroformate (0.144 mL, 1.114 mmol) in 1,2-dichloroethane (6.0 mL), and the mixture stirred at 50° C. for 3 days. Additional N,N-diisopropylethylamine (0.486 mL, 2.79 mmol) and cyclopentyl chloroformate (0.28 mL, 2.22 mmol) were added, and the mixture stirred at 50° C. for 16 h. The reaction mixture was concentrated to afford an off-white solid. This material was purified via column chromatography on silica gel (Biotage 25 g column, gradient elution with 0-25% ethyl acetate-hexane) to afford (S)-cyclopentyl 7-bromo-3-methyl-4-(2,2,2-trifluoroacetyl)-3,4-dihydroquinoxaline-1(2H)-carboxylate (0.390 g, 97%) as a yellow oil. MS (ESI, pos. ion) m/z 435, 437 [M+1]+.

Step 2. (S)-cyclopentyl 7-(1-cyclopropyl-1H-pyrazol-4-yl)-3-methyl-3,4-dihydroquinoxaline-1(2H)-carboxylate A mixture of (S)-cyclopentyl 7-bromo-3-methyl-4-(2,2,2-trifluoroacetyl)-3,4-dihydroquinoxaline-1(2H)-carboxylate (0.250 g, 0.574 mmol), 1-cyclopropyl-4-(4,4,5,5-tetramethyl-1,3,2-dioxaborolan-2-yl)-1H-pyrazole (0.148 g, 0.632 mmol), tris(dibenzylideneacetone)dipalladium (0.026 g, 0.029 mmol), X-Phos (0.027 g, 0.057 mmol) and cesium carbonate (0.561 g, 1.723 mmol) in 1,4-dioxane (5.0 mL) and water (1.0 mL) was heated at 100° C. for 17 h. The reaction mixture was filtered through Celite and concentrated to afford an orange oil. This material was purified via column chromatography on silica gel (Biotage 25 g column, gradient elution with 25-100% ethyl acetate-hexane) to afford (S)-cyclopentyl 7-(1-cyclopropyl-1H-pyrazol-4-yl)-3-methyl-3,4-dihydroquinoxaline-1(2H)-carboxylate (0.124 g, 59%) as a yellow solid. MS (ESI, pos. ion) m/z 367 [M+1]+.

Step 3. (S)-4-cyclopentyl 1-methyl 6-(1-cyclopropyl-1H-pyrazol-4-yl)-2-methyl-2,3-dihydroquinoxaline-1,4-dicarboxylate N,N-Diisopropylethylamine (0.148 mL, 0.846 mmol) was added to a solution of (S)-cyclopentyl 7-(1-cyclopropyl-1H-pyrazol-4-yl)-3-methyl-3,4-dihydroquinoxaline-1(2H)-carboxylate (0.062 g, 0.169 mmol) and methyl chloroformate (0.065 mL, 0.846 mmol) in 1,2-dichloroethane (2.0 mL), and the mixture stirred at 50° C. for 2.5 h. The reaction mixture was concentrated to afford a brown oil. This material was purified via column chromatography on silica gel (Biotage 25 g column, gradient elution with 0-50% ethyl acetate-hexane) to afford (S)-4-cyclopentyl 1-methyl 6-(1-cyclopropyl-1H-pyrazol-4-yl)-2-methyl-2,3-dihydroquinoxaline-1,4-dicarboxylate (0.057 g, 79%) as an off-white solid. $^1$H NMR (300 MHz, DMSO-$d_6$) δ ppm 0.90-1.02 (m, 2 H), 1.02-1.12 (m, 5 H), 1.37-1.93 (m, 9 H), 3.66-3.81 (m, 5 H), 4.49-4.72 (m, 1 H), 5.00-5.21 (m, 1 H), 7.17-7.39 (m, 1 H), 7.67-7.82 (m, 3 H), 8.13 (s, 1 H). MS (ESI, pos. ion) m/z 425. [M+1]+.

Example 80

(S)-cyclopentyl 4-(cyclopropanecarbonyl)-7-(1-cyclopropyl-1H-pyrazol-4-yl)-3-methyl-3,4-dihydroquinoxaline-1(2H)-carboxylate (I-41)

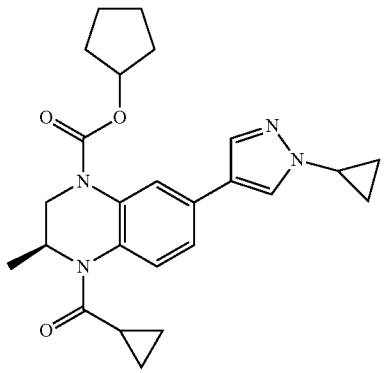 [SMILES: C[C@H]1CN(C(=O)OC2CCCC2)c2cc(-c3cnn(C4CC4)c3)ccc2N1C(=O)C1CC1]

N,N-Diisopropylethylamine (0.148 mL 0.846 mmol) was added to a solution of (S)-cyclopentyl 7-(1-cyclopropyl-1H-pyrazol-4-yl)-3-methyl-3,4-dihydroquinoxaline-1(2H)-carboxylate (0.062 g, 0.169 mmol) and cyclopropanecarbonyl chloride (0.077 mL, 0.846 mmol) in 1,2-dichloroethane (2.0 mL), and the mixture stirred at 50° C. for 2.5 h. The reaction mixture was concentrated to afford a brown oil. This material was purified via column chromatography on silica gel (Biotage 25 g column, gradient elution with 0-50% ethyl acetate-hexane) to afford (S)-cyclopentyl 4-(cyclopropanecarbonyl)-7-(1-cyclopropyl-1H-pyrazol-4-yl)-3-methyl-3,4-dihydroquinoxaline-1(2H)-carboxylate (0.056 g, 76%) as an off-white solid. $^1$H NMR (300 MHz, DMSO-$d_6$) δ ppm 0.71-0.91 (m, 3 H), 0.93-1.12 (m, 8 H), 1.48-1.99 (m, 9 H), 3.42-3.55 (m, 1 H), 3.75 (tt, J=7.33, 3.81 Hz, 1 H), 3.93 (br dd, J=12.75, 6.30 Hz, 1 H), 4.86-4.98 (m, 1 H), 5.14 (td, J=5.50, 2.79 Hz, 1 H), 7.29-7.44 (m, 2 H), 7.76 (s, 1 H), 7.91 (s, 1 H), 8.17 (s, 1 H). MS (ESI, pos. ion) m/z 435 [M+1]$^+$.

Example 81

(S)-methyl 4-(cyclopropanecarbonyl)-6-(1-cyclopropyl-1H-pyrazol-4-yl)-2-methyl-3,4-dihydroquinoxaline-1(2H)-carboxylate

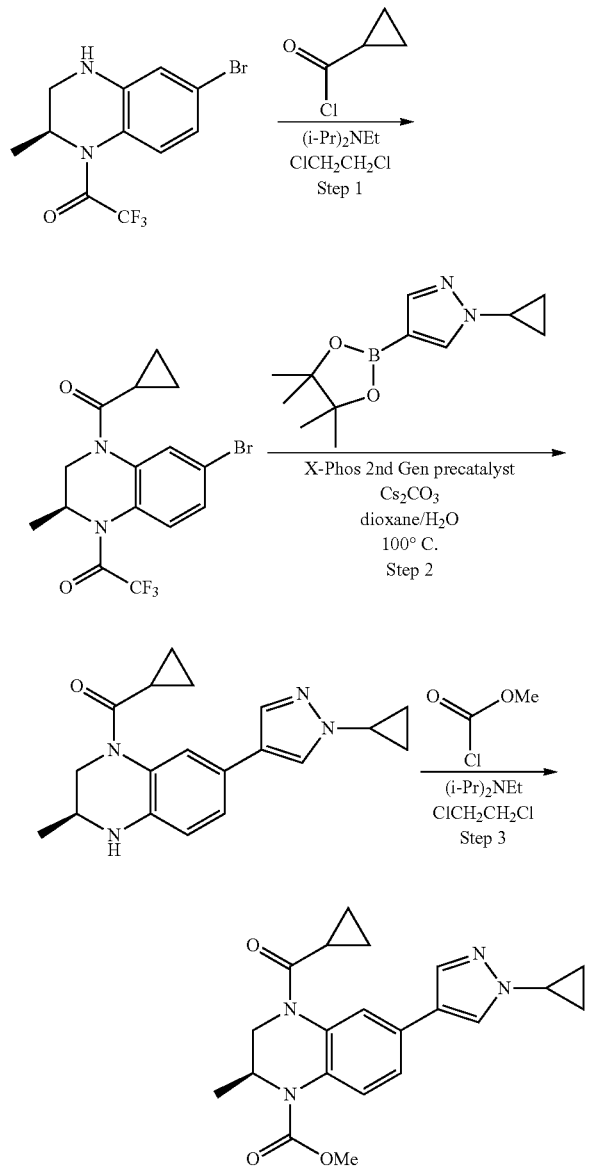

Step 1. (S)-1-(6-bromo-4-(cyclopropanecarbonyl)-2-methyl-3,4-dihydroquinoxaline-1(2H)-yl)-2,2,2-trifluoroethanone (I-42)

N,N-Diisopropylethylamine (0.486 mL, 2.79 mmol) was added to a solution of (S)-1-(6-bromo-2-methyl-3,4-dihydroquinoxaline-1(2H)-yl)-2,2,2-trifluoroethanone (0.300 g, 0.928 mmol) and cyclopropanecarbonyl chloride (0.126 mL, 1.39 mmol) in 1,2-dichloroethane (6.0 mL), and the mixture stirred at 50° C. for 16 h. The reaction mixture was concentrated to afford an orange oil. This material was purified via column chromatography on silica gel (Biotage 25 g column, gradient elution with 0-25% ethyl acetate-hexane) to afford (S)-1-(6-bromo-4-(cyclopropanecarbonyl)-2-methyl-3,4-dihydroquinoxaline-1(2H)-yl)-2,2,2-trifluoroethanone (0.355 g, 98%) as a yellow oil. MS (ESI, pos. ion) m/z 435, 437 [M+1]$^+$.

Step 2. (S)-cyclopropyl(7-(1-cyclopropyl-1H-pyrazol-4-yl)-3-methyl-3,4-dihydroquinoxalin-1(2H)-yl)methanone A mixture of (S)-1-(6-bromo-4-(cyclopropanecarbonyl)-2-methyl-3,4-dihydroquinoxaline-1(2H)-yl)-2,2,2-trifluoroethanone (0.100 g, 0.256 mmol), 1-cyclopropyl-4-(4,4,5,5-tetramethyl-1,3,2-dioxaborolan-2-yl)-1H-pyrazole (0.066 g, 0.281 mmol), chloro(2-dicyclohexyl phosphino-2',4',6'-tri-i-propyl-1,1'-biphenyl)(2'-amino-1,1'-biphenyl-2-yl) palladium(II) (XPhos Precatalyst 2nd Generation) (10.06 mg, 0.013 mmol), and cesium carbonate (0.250 g, 0.767 mmol) in dioxane (2.0 mL) and water (0.40 mL) was heated in the microwave at 100° C. for 16 h. The reaction mixture was filtered through Celite and concentrated to afford an orange oil. This material was purified via column chromatography on silica gel (Biotage 25 g column, gradient elution with 25-100% ethyl acetate-hexane) to afford (S)-cyclopropyl(7-(1-cyclopropyl-1H-pyrazol-4-yl)-3-methyl-3,4-dihydroquinoxaline-1(2H)-yl)methanone (0.065 g, 79%) as a yellow solid. MS (ESI, pos. ion) m/z 323 [M+1]$^+$.

Step 3. (S)-methyl 4-(cyclopropanecarbonyl)-6-(1-cyclopropyl-1H-pyrazol-4-yl)-2-methyl-3,4-dihydroquinoxaline-1(2H)-carboxylate N,N-Diisopropylethylamine (0.176 mL, 1.008 mmol) was added to a solution of (S)-cyclopropyl(7-(1-cyclopropyl-1H-pyrazol-4-yl)-3-methyl-3,4-dihydroquinoxalin-1 (2H)-yl) methanone (0.065 g, 0.202 mmol) and methyl chloroformate (0.078 mL, 1.008 mmol) in 1,2-dichloroethane (2.0 mL), and the mixture stirred at 50° C. for 2.5 h. The reaction mixture was concentrated to afford a brown oil. This material was purified via column chromatography on silica gel (Biotage 25 g column, gradient elution with 0-50% ethyl acetate-hexane) to afford (S)-methyl 4-(cyclopropanecarbonyl)-6-(1-cyclopropyl-1H-pyrazol-4-yl)-2-methyl-3,4-dihydro quinoxaline-1(2H)-carboxylate (0.057 g, 74%) as an off-white solid. $^1$H NMR (300 MHz, DMSO-$d_6$) δ ppm 0.84-1.09 (m, 8 H), 1.13 (d, J=6.16 Hz, 3 H), 1.93-2.06 (m, 1 H), 3.32-3.40 (m, 1 H), 3.68-3.77 (m, 1 H), 3.72 (s, 3 H), 4.26 (br dd, J=13.05, 6.30 Hz, 1 H), 4.41-4.57 (m, 1 H), 7.39 (dd, J=8.50, 2.05 Hz, 1 H), 7.58 (d, J=2.05 Hz, 1 H), 7.73 (d, J=8.50 Hz, 1 H), 7.80 (s, 1 H), 8.19 (s, 1 H). MS (ESI, pos. ion) m/z 381 [M+1]+.

Example 82

(S)-4-isopropyl 1-methyl 6-(1-cyclopropyl-1H-pyrazol-4-yl)-2-methyl-2,3-dihydroquinoxaline-1,4-dicarboxylate (I-43)

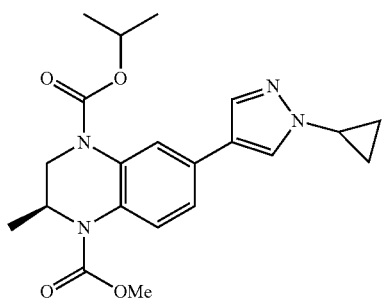 [SMILES: COC(=O)N1c2ccc(-c3cnn(C4CC4)c3)cc2N(C(=O)OC(C)C)C[C@@H]1C]

(S)-4-isopropyl 1-methyl 6-(1-cyclopropyl-1H-pyrazol-4-yl)-2-methyl-2,3-dihydroquinoxaline-1,4-dicarboxylate was prepared from 2-methyl-3,4-dihydroquinoxalin-1(2H)-yl)-2,2,2-trifluoroethanone following the procedure outlined above for (S)-4-cyclopentyl 1-methyl 6-(1-cyclopropyl-1H-pyrazol-4-yl)-2-methyl-2,3-dihydroquinoxaline-1,4-dicarboxylate and substituting isopropyl chloroformate (1.0 M solution in toluene) in Step 1. The desired product was obtained as an off-white solid (0.065 g, 79%). $^1$H NMR (300 MHz, DMSO-$d_6$) δ ppm 0.90-1.03 (m, 2 H), 1.07 (br d, J=6.16 Hz, 5 H), 1.26 (dd, J=5.86, 2.93 Hz, 6 H), 3.60-3.83 (m, 6 H), 4.49-4.71 (m, 1 H), 4.93 (dt, J=12.46, 6.08 Hz, 1 H), 7.28 (br d, J=7.04 Hz, 1 H), 7.65-7.87 (m, 3 H), 8.14 (s, 1 H). MS (ESI, pos. ion) m/z 399 [M+1]+.

Example 83

(S)-1-(4-(benzo[d]oxazol-2-yl)-6-(1-cyclopropyl-1H-pyrazol-4-yl)-2-methyl-3,4-dihydroquinoxaline-1(2H)-yl)ethanone (I-44)

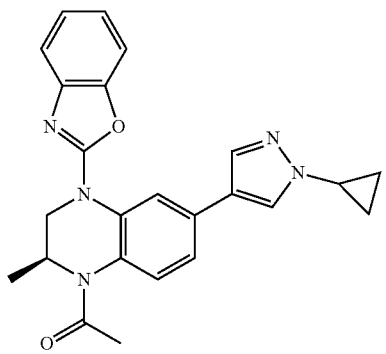 [SMILES: CC(=O)N1c2ccc(-c3cnn(C4CC4)c3)cc2N(c2nc3ccccc3o2)C[C@@H]1C]

A mixture of (S)-1-(6-(1-cyclopropyl-1H-pyrazol-4-yl)-2-methyl-3,4-dihydroquinoxaline-1(2H)-yl)ethanone (0.040 g, 0.135 mmol), 2-chlorobenzo[d]oxazole (0.031 mL, 0.270 mmol), tris(dibenzylideneacetone)dipalladium (0.012 g, 0.013 mmol), 4,5-bis(diphenylphosphino)-9,9-dimethylxanthene (Xantphos) (0.016 g, 0.027 mmol), and cesium carbonate (0.088 g, 0.270 mmol) in t-butanol (2.0 mL) was heated in the microwave at 80° C. for 1.5 h. Additional portions of Xantphos (0.016 g, 0.027 mmol), tris(dibenzylideneacetone)dipalladium (0.012 g, 0.013 mmol), and 2-chlorobenzo[d]oxazole (0.031 ml, 0.270 mmol) were added, and the mixture stirred at 100° C. for 2.5 h. The reaction mixture was filtered through Celite and concentrated to afford an orange oil. This material was purified via column chromatography on silica gel (Biotage 25 g column, gradient elution with 50-100% ethyl acetate-hexane) to afford (S)-1-(4-(benzo[d]oxazol-2-yl)-6-(1-cyclopropyl-1H-pyrazol-4-yl)-2-methyl-3,4-dihydroquinoxaline-1(2H)-yl)ethanone (0.049 g, 88%) as an off-white solid. $^1$H NMR (300 MHz, DMSO-$d_6$) δ ppm 0.89-1.03 (m, 2 H), 1.03-1.11 (m, 5 H), 2.18 (s, 3 H), 3.76 (tt, J=7.44, 3.85 Hz, 1 H), 4.01 (br d, J=10.26 Hz, 1 H), 4.07-4.19 (m, 1 H), 5.08 (br s, 1 H), 7.13-7.37 (m, 3 H), 7.53 (dd, J=18.03, 7.48 Hz, 3 H), 7.85 (s, 1 H), 8.24 (s, 1 H), 8.38 (d, J=2.05 Hz, 1H). MS (ESI, pos. ion) m/z 414 [M+1]+.

The following examples were made according to the procedure outlined for Example 83

Example 84

(S)-1-(2-methyl-6-(4-(methylsulfonyl)phenyl)-4-(pyrimidin-2-yl)-3,4-dihydroquinoxaline-1(2H)-yl)ethanone (I-45)

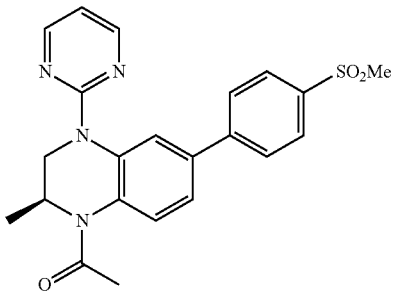 [SMILES: CC(=O)N1c2ccc(-c3ccc(S(C)(=O)=O)cc3)cc2N(c2ncccn2)C[C@@H]1C]

MS (ESI, pos. ion) m/z 423 [M+1]+.

Example 85

(S)-1-(4-(benzo[d]oxazol-2-yl)-2-methyl-6-(4-(methylsulfonyl)phenyl)-3,4-dihydroquinoxaline-1(2H)-yl)ethanone (I-46)

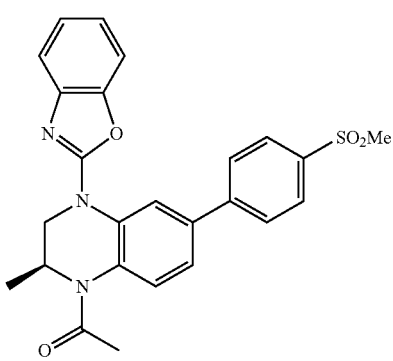 [SMILES: CC(=O)N1c2ccc(-c3ccc(S(C)(=O)=O)cc3)cc2N(c2nc3ccccc3o2)C[C@@H]1C]

¹H NMR (300 MHz, DMSO-d$_6$) δ ppm 1.09 (d, J=6.74 Hz, 3 H), 2.26 (s, 3 H), 3.27 (s, 3 H), 3.99-4.27 (m, 3 H), 5.08 (br s, 1 H), 7.11-7.22 (m, 1 H), 7.23-7.31 (m, 1 H), 7.46-7.55 (m, 2 H), 7.58 (d, J=7.92 Hz, 1 H), 7.73 (br s, 1 H), 7.94-8.08 (m, 4 H), 8.78 (d, J=2.05 Hz, 1 H). MS (ESI, pos. ion) m/z 462 [M+1]⁺.

Example 86

(S)-1-(2-methyl-6-(4-(methylsulfonyl)phenyl)-4-(pyridin-2-yl)-3,4-dihydroquinoxaline-1(2H)-yl)ethan-1-one (I-47)

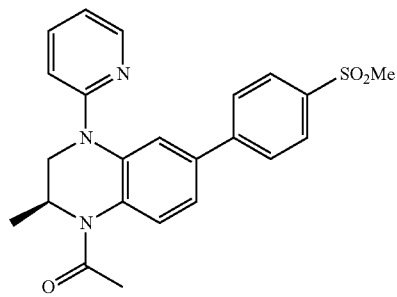 [SMILES: CC(=O)N1c2ccc(-c3ccc(S(C)(=O)=O)cc3)cc2N(c2ccccn2)C[C@@H]1C]

MS (ESI, pos. ion) m/z 422 [M+1]⁺.

Example 87

(S)-1-(2-methyl-6-(4-(methylsulfonyl)phenyl)-4-(quinazolin-2-yl)-3,4-dihydroquinoxaline-1(2H)-yl)ethanone (I-48)

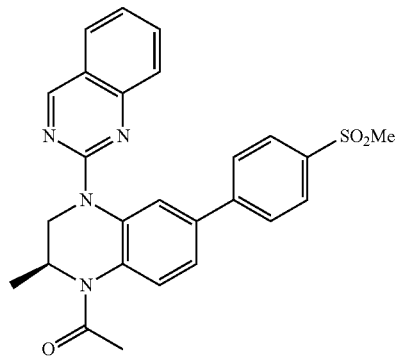 [SMILES: CC(=O)N1c2ccc(-c3ccc(S(C)(=O)=O)cc3)cc2N(c2ncc3ccccc3n2)C[C@@H]1C]

¹H NMR (300 MHz, DMSO-d$_6$) δ ppm 1.12 (d, J=6.45 Hz, 3H), 2.21 (s, 3 H), 3.25 (s, 3 H), 3.90 (m, 1 H), 4.53 (m, 1 H), 4.99 (m, 1 H), 7.29-7.59 (m, 2 H), 7.62-7.79 (m, 2 H), 7.79-7.92 (m, 1 H), 7.92-8.08 (m, 5 H), 8.34 (d, J=1.76 Hz, 1 H), 9.37 (s, 1 H). MS (ESI, pos. ion) m/z 473 [M+1]⁺.

Example 88

(S)-1-(2-methyl-6-(4-(methylsulfonyl)phenyl)-4-(4-phenylpyrimidin-2-yl)-3,4-dihydroquinoxaline-1(2H)-yl)ethanone (I-49)

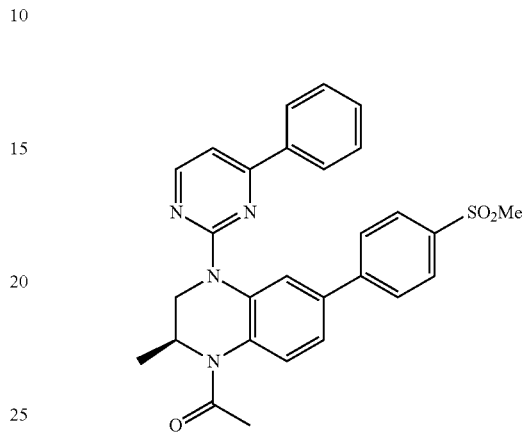

¹H NMR (300 MHz, DMSO-d$_6$) δ ppm 1.11 (d, J=6.45 Hz, 3 H), 2.21 (s, 3 H), 3.26 (s, 3 H), 3.82-4.06 (m, 1 H), 4.45 (m, 1 H), 4.99 (m, 1 H), 7.39-7.59 (m, 5 H), 7.71 (br d, J=8.21 Hz, 1 H), 7.94-8.00 (m, 4 H), 8.09-8.19 (m, 2 H), 8.45 (d, J=2.35 Hz, 1 H), 8.61 (d, J=5.28 Hz, 1 H). MS (ESI, pos. ion) m/z 499 [M+1]⁺.

Example 89

(S)-1-(2-methyl-6-(4-(methylsulfonyl)phenyl)-4-(5-phenylpyrimidin-2-yl)-3,4-dihydroquinoxaline-1(2H)-yl)ethanone (I-50)

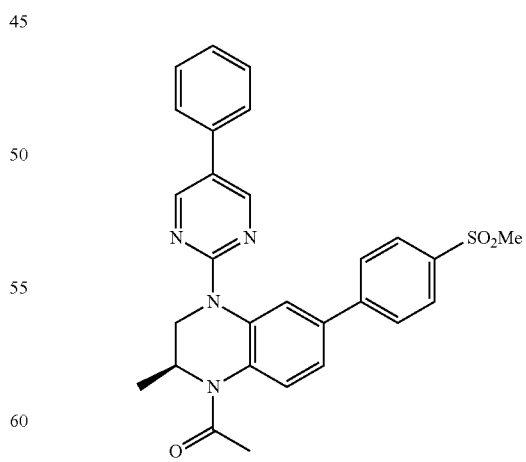

¹H NMR (300 MHz, DMSO-d$_6$) δ ppm 1.11 (d, J=6.45 Hz, 3 H), 2.21 (s, 3 H), 3.26 (s, 3 H), 3.86 (m, 1 H), 4.43 (m, 1 H), 4.98 (m, 1 H), 7.31-7.42 (m, 1 H), 7.42-7.57 (m, 3 H), 7.62-

7.82 (m, 3 H), 7.85-8.06 (m, 4 H), 8.30 (d, J=2.05 Hz, 1 H), 8.89 (s, 2 H). MS (ESI, pos. ion) m/z 499 [M+1]⁺.

Example 90

(S)-1-(6-(1-cyclopropyl-1H-pyrazol-4-yl)-2-methyl-4-(quinazolin-2-yl)-3,4-dihydroquinoxaline-1(2H)-yl)ethanone (I-51)

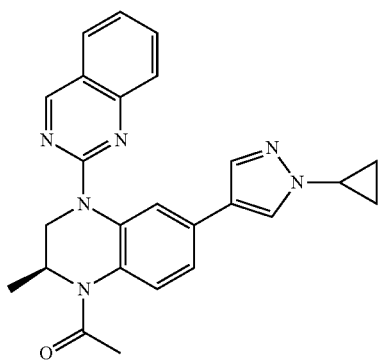 [SMILES: CC(=O)N1c2ccc(-c3cnn(C4CC4)c3)cc2N(c2ncc3ccccc3n2)C[C@@H]1C]

¹H NMR (300 MHz, DMSO-d₆) δ ppm 0.8-1.0 (m, 4 H), 1.12 (d, J=6.45 Hz, 3 H), 2.1 (s, 3 H), 3.4-3.6 (m, 1 H), 3.6-3.7 (m, 1 H), 4.5-4.7 (m, 1 H), 4.85-4.95 (m, 1 H), 7.2-7.6 (m, 5 H), 7.7-8.0 (m, 3 H), 8.1 (s, 1 H), 9.3 (s, 1 H). MS (ESI, pos. ion) m/z 425 [M+1]⁺.

Example 91

(S)-1-(6-(1-cyclopropyl-1H-pyrazol-4-yl)-2-methyl-4-(1-methyl-1H-indazol-3-yl)-3,4-dihydroquinoxaline-1(2H)-yl)ethanone (I-52)

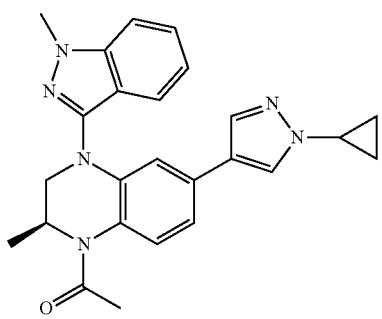 [SMILES: CC(=O)N1c2ccc(-c3cnn(C4CC4)c3)cc2N(c2nn(C)c3ccccc23)C[C@@H]1C]

¹H NMR (300 MHz, DMSO-d₆) δ ppm 0.78-1.03 (m, 4 H), 1.15 (br d, J=6.45 Hz, 3 H), 1.23 (br s, 1 H), 2.23 (s, 3 H), 3.50-3.74 (m, 2 H), 3.84 (br d, J=7.04 Hz, 1 H), 4.02 (s, 3H), 6.81 (d, J=1.76 Hz, 1 H), 6.97 (br d, J=8.21 Hz, 1 H), 7.01-7.11 (m, 1 H), 7.34 (d, J=7.92 Hz, 1 H), 7.37-7.49 (m, 3 H), 7.67 (d, J=8.79 Hz, 1 H), 7.88 (s, 1 H). MS (ESI, pos. ion) m/z 427 [M+1]⁺.

Example 92

(S)-1-(2-methyl-4-(1-methyl-1H-indazol-3-yl)-6-(1-(oxetan-3-yl)-1H-pyrazol-4-yl)-3,4-dihydroquinoxaline-1(2H)-yl)ethanone (I-53)

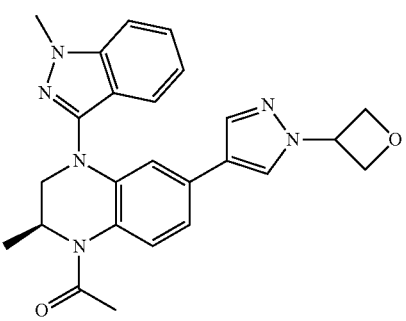 [SMILES: CC(=O)N1c2ccc(-c3cnn(C4COC4)c3)cc2N(c2nn(C)c3ccccc23)C[C@@H]1C]

¹H NMR (300 MHz, DMSO-d₆) δ ppm 1.09-1.22 (m, 3 H), 2.24 (s, 3 H), 3.67 (dd, J=11.87, 2.20 Hz, 1 H), 3.79-3.93 (m, 1 H), 4.02 (s, 3 H), 4.72-4.91 (m, 5 H), 5.48 (quin, J=6.96 Hz, 1 H), 6.81 (d, J=2.05 Hz, 1 H), 6.90-7.15 (m, 2 H), 7.26-7.47 (m, 2 H), 7.59-7.70 (m, 3 H), 7.97 (s, 1 H). MS (ESI, pos. ion) m/z 443 [M+1]⁺.

Example 93

(S)-1-(6-(1-cyclopropyl-1H-pyrazol-4-yl)-4-(6-fluoro-1-methyl-1H-indazol-3-yl)-2-methyl-3,4-dihydroquinoxaline-1(2H)-yl)ethanone (I-54)

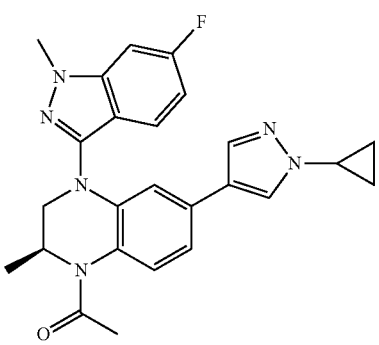 [SMILES: CC(=O)N1c2ccc(-c3cnn(C4CC4)c3)cc2N(c2nn(C)c3cc(F)ccc23)C[C@@H]1C]

¹H NMR (300 MHz, DMSO-d₆) δ ppm 0.74-1.06 (m, 4 H), 1.14 (br d, J=6.74 Hz, 3 H), 1.23 (br s, 1 H), 2.23 (s, 3 H), 3.66 (br d, J=11.14 Hz, 2 H), 3.86 (br d, J=11.43 Hz, 1H), 3.98 (s, 3 H), 6.85 (s, 1 H), 6.88-7.07 (m, 2 H), 7.22-7.41 (m, 2 H), 7.47 (s, 1 H), 7.57 (br d, J=9.67 Hz, 1 H), 7.91 (s, 1 H). MS (ESI, pos. ion) m/z 445 [M+1]+.

Example 94

(S)-1-(6-(1-cyclopropyl-1H-pyrazol-4-yl)-4-(5-fluoro-1-methyl-1H-indazol-3-yl)-2-methyl-3,4-dihydroquinoxaline-1(2H)-yl)ethanone (I-55)

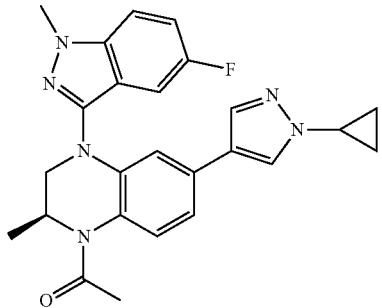 [SMILES: CC(=O)N1c2ccc(-c3cnn(C4CC4)c3)cc2N(c2nn(C)c3ccc(F)cc23)C[C@@H]1C]

For the synthesis of (S)-1-(6-(1-cyclopropyl-1H-pyrazol-4-yl)-4-(5-fluoro-1-methyl-1H-indazol-3-yl)-2-methyl-3,4-dihydroquinoxaline-1(2H)-yl)ethanone, RuPhos Precatalyst 2nd Generation (chloro(2-dicyclohexylphosphino-2',6'-di-isopropoxy-1,1'-biphenyl)[2-(2'-amino-1,1'-biphenyl)]palladium(II) was used in place of tris(dibenzylideneacetone)dipalladium and 4,5-bis(diphenylphosphino)-9,9-dimethylxanthene. $^1$H NMR (300 MHz, DMSO-$d_6$) δ ppm 0.76-1.03 (m, 4 H), 1.10-1.19 (m, 3 H), 1.22 (br s, 1 H), 2.21 (s, 3 H), 3.53-3.68 (m, 2 H), 3.68-3.81 (m, 1 H), 4.04 (s, 3 H), 6.64 (d, J=1.76 Hz, 1 H), 6.84 (dd, J=10.55, 7.62 Hz, 1 H), 6.94 (br d, J=8.21 Hz, 1 H), 7.35-7.56 (m, 4 H), 7.91 (s, 1 H). MS (ESI, pos. ion) m/z 445 [M+1]+.

Example 95

(S)-1-(4-(benzo[d]oxazol-2-yl)-6-(1-(benzo[d]oxazol-2-yl)-1H-pyrazol-4-yl)-2-methyl-3,4-dihydroquinoxaline-1(2H)-yl)ethanone (I-56)

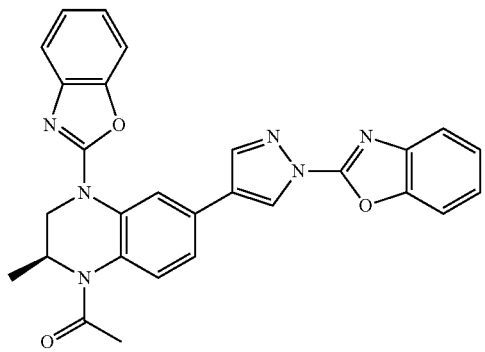 [SMILES: CC(=O)N1c2ccc(-c3cnn(-c4nc5ccccc5o4)c3)cc2N(c2nc3ccccc3o2)C[C@@H]1C]

$^1$H NMR (300 MHz, DMSO-$d_6$) δ ppm 1.08 (d, J=6.74 Hz, 3 H), 2.23 (s, 3 H), 3.96-4.23 (m, 2 H), 5.10 (br s, 1 H), 7.08-7.23 (m, 1 H), 7.23-7.33 (m, 1 H), 7.37-7.49 (m, 2 H), 7.57 (dt, J=16.27, 7.99 Hz, 4 H), 7.70-7.90 (m, 2 H), 8.55 (s, 1 H), 8.61 (s, 1 H), 9.18 (s, 1H). MS (ESI, pos. ion) m/z 491 [M+1]+.

Example 96

(S)-1-(1-(furan-2-carbonyl)-3-methyl-7-(4-(methylsulfonyl)phenyl)-2,3-dihydropyrido[3,4-b]pyrazin-4(1H)-yl)ethanone (I-57)

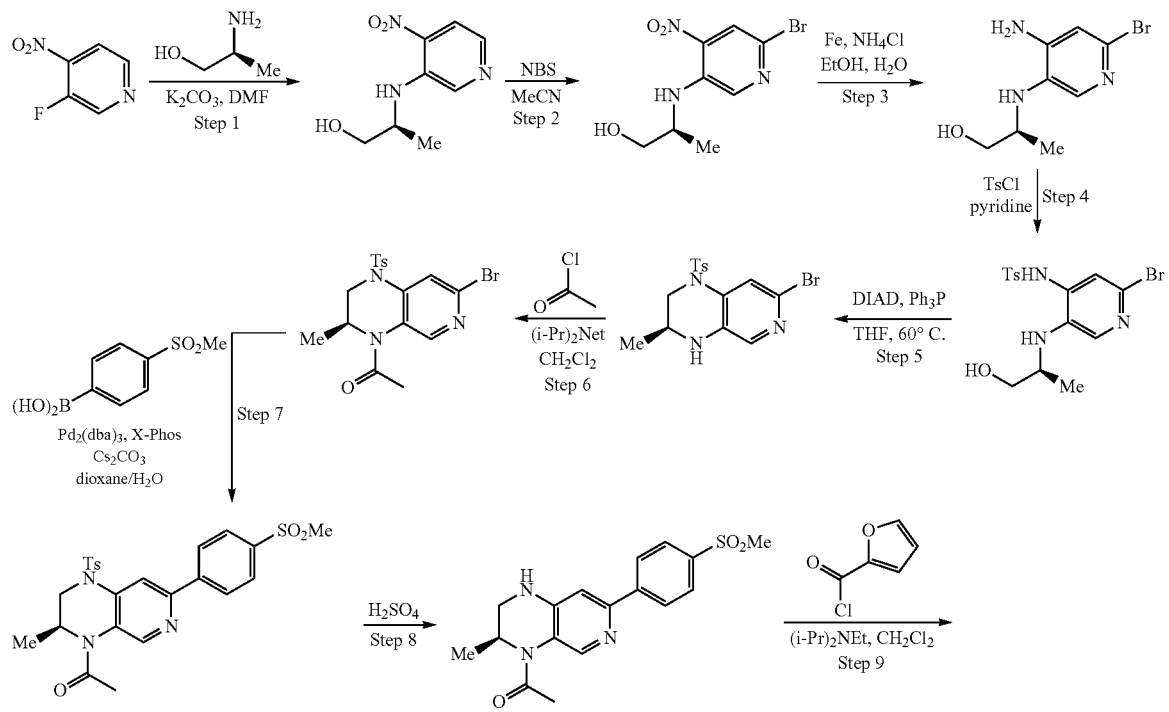

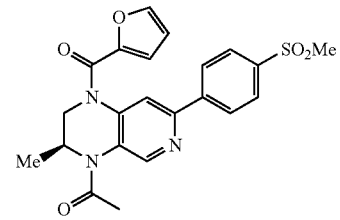

Step 1. (S)-2-(4-nitropyridin-3-ylamino)propane-1-ol

A mixture of 3-fluoro-4-nitropyridine (0.400 mL, 4.05 mmol), (S)-2-aminopropane-1-ol (0.347 mL, 4.46 mmol) and potassium carbonate (0.616 g, 4.46 mmol) in DMF (5.0 mL) was stirred at 60° C. for 2 h. Water was added and the mixture stirred at room temperature to afford a precipitate. The mixture was filtered to afford an orange solid. The filtrate was extracted with dichloromethane. The organic extracts were washed with brine, dried over anhydrous sodium sulfate, filtrate, and concentrated to afford an orange solid. The solids were combined and purified via column chromatography on silica gel (Biotage 50 g column, gradient elution with 0-10% methanol-dichloromethane) to afford (S)-2-(4-nitropyridin-3-ylamino)propane-1-ol (0.668 g, 84%) as an orange solid. MS (ESI, pos. ion) m/z 198.

Step 2. (S)-2-(6-bromo-4-nitropyridin-3-ylamino)propane-1-ol

N-Bromosuccinimide (0.090 g, 0.507 mmol) was added in one portion to a 0° C. solution of (S)-2-(4-nitropyridin-3-ylamino)propane-1-ol (0.100 g, 0.507 mmol) in acetonitrile (2.0 mL). The mixture stirred at 0° C. and was allowed to warm to room temperature over 16 h. The solution was then concentrated to remove most (>90%) of the acetonitrile. Ethyl acetate was added, and the solution was washed with saturated aqueous sodium bicarbonate solution and brine, dried over anhydrous sodium sulfate, filtered and concentrated to afford an orange oil. This material was purified via column chromatography on silica gel (Biotage 25 g column, gradient elution with 0-50% ethyl acetate-hexane) to afford (S)-2-(6-bromo-4-nitropyridin-3-ylamino)propane-1-ol (0.056 g, 40%) as an orange solid. MS (ESI, pos. ion) m/z 276, 278.

Step 3. (S)-2-(4-amino-6-bromopyridin-3-ylamino)propane-1-ol

Iron powder (0.101 g, 1.811 mmol) was added to a solution of (S)-2-(6-bromo-4-nitropyridin-3-ylamino)propane-1-ol (0.050 g, 0.181 mmol) and ammonium chloride (2.422 mg, 0.045 mmol) in ethanol (2.0 mL) and water (0.7 mL). The reaction mixture was heated at 80° C. for 2 h. The mixture was cooled to room temperature and filtered through celite (washing with methanol). The filtrate was concentrated and the residue was partitioned between ethyl acetate and saturated aqueous sodium bicarbonate solution. The aqueous phase was separated and extracted with ethyl acetate. The combined organic phases were washed with brine, dried over anhydrous sodium sulfate, filtered and concentrated to afford (S)-2-(4-amino-6-bromopyridin-3-ylamino)propane-1-ol (0.028 g, 63%) as a purple solid. MS (ESI, pos. ion) m/z 246, 248.

Step 4. (S)-N-(2-bromo-5-(1-hydroxypropan-2-ylamino)pyridin-4-yl)-4-methylbenzene sulfonamide p-Toluenesulfonyl chloride (0.022 g, 0.114 mmol) was added to a 0° C. solution of (S)-2-(4-amino-6-bromopyridin-3-ylamino)propane-1-ol (0.028 g, 0.114 mmol) in pyridine (2.0 mL). The reaction mixture stirred at 0° C. and was allowed to warm to room temperature over 16 h. A second portion of p-toluenesulfonyl chloride (0.022 g, 0.114 mmol) was added, and the mixture stirred at room temperature overnight. The mixture was concentrated and the residue was partitioned between ethyl acetate and water. The aqueous phase was separated and extracted with ethyl acetate. The combined organic phases were washed with brine, dried over anhydrous sodium sulfate, filtered and concentrated to afford a purple solid. This material was purified via column chromatography on silica gel (Biotage 10 g column, gradient elution with 0-5% methanol-ethyl acetate) to afford (S)-N-(2-bromo-5-(1-hydroxypropan-2-ylamino)pyridin-4-yl)-4-methylbenzenesulfonamide (0.022 g, 48%) as a purple solid. MS (ESI, pos. ion) m/z 400, 402.

Step 5. (S)-7-bromo-3-methyl-1-tosyl-1,2,3,4-tetrahydropyrido[4,3-b]pyrazine

Diisopropyl azodicarboxylate (0.013 ml, 0.066 mmol) was added dropwise to a 60° C. solution of (S)-N-(2-bromo-5-(1-hydroxypropan-2-ylamino)pyridin-4-yl)-4-methylbenzene sulfonamide (0.022 g, 0.055 mmol) and triphenylphosphine (0.017 g, 0.066 mmol) in THF (1.0 mL). The reaction mixture stirred at 60° C. for 10 min. The mixture was concentrated and the residue was purified via column chromatography on silica gel (Biotage 10 g column, gradient elution with 0-50% ethyl acetate-hexane) to afford (S)-7-bromo-3-methyl-1-tosyl-1,2,3,4-tetrahydropyrido[4,3-b]pyrazine (0.013 g, 62%) as a light purple solid. MS (ESI, pos. ion) m/z 382, 384.

Step 6. (S)-1-(7-bromo-3-methyl-1-tosyl-2,3-dihydropyrido[3,4-b]pyrazin-4(1H)-yl)ethanone N,N-Diisopropylethylamine (0.018 mL, 0.102 mmol) was added to a solution of (S)-7-bromo-3-methyl-1-tosyl-1,2,3,4-tetrahydropyrido[3,4-b]pyrazine (0.013 g, 0.034 mmol) and acetyl chloride (3.6 μL, 0.051 mmol) in dichloromethane (2.0 mL), and the mixture stirred at room temperature for 2 h. The reaction mixture was partitioned between dichloromethane and water. The aqueous phase was separated and extracted with dichloromethane. The combined organic phases were washed with brine, dried over anhydrous sodium sulfate, filtered, and concentrated to afford a yellow oil. This material was purified via column chromatography on silica gel (Biotage 10 g column, gradient elution with 50-100% ethyl acetate-hexane) to afford (S)-1-(7-bromo-3-methyl-1-tosyl-2,3-dihydropyrido[3,4-b]pyrazin-4(1H)-yl)ethanone (0.010 g, 69%) as an off-white solid. MS (ESI, pos. ion) m/z 424, 426.

Step 7. (S)-1-(3-methyl-7-(4-(methylsulfonyl)phenyl-1-tosyl-2,3-dihydropyrido[4,3-b]pyrazin-4(1H)-yl)ethanone A mixture of (S)-1-(7-bromo-3-methyl-1-tosyl-2,3-dihydropyrido[3,4-b]pyrazin-4(1H)-yl)ethanone (0.010 g, 0.024 mmol), 4-(methylsulfonyl)phenylboronic acid (4.95 mg, 0.025 mmol), tris(dibenzylideneacetone)dipalladium (1.1 mg, 1.2 µmol), 2-dicyclohexylphosphino-2',4',6'-triisopropylbiphenyl (XPhos) (1.1 mg, 2.4 µmol), and cesium carbonate (0.023 g, 0.071 mmol) in 1,4-dioxane (1.5 mL) and water (0.30 mL) were stirred at 80° C. for 2 h. The reaction mixture was filtered through Celite and concentrated to afford an orange solid. This material was purified via column chromatography on silica gel (Biotage 10 g column, gradient elution with 0-100% ethyl acetate-hexane) to afford (S)-1-(3-methyl-7-(4-(methylsulfonyl)phenyl)-1-tosyl-2,3-dihydropyrido[4,3-b]pyrazin-4(1H)-yl)ethanone (0.006 g, 51%) as an off-white solid. MS (ESI, pos. ion) m/z 500.

Step 8. (S)-1-(3-methyl-7-(4-(methylsulfonyl)phenyl)-2,3-dihydropyrido[4,3-b]pyrazin-4(1H)-yl)ethanone Sulfuric acid (0.5 mL, 9.4 mmol) was added to (S)-1-(3-methyl-7-(4-(methylsulfonyl)phenyl)-1-tosyl-2,3-dihydropyrido[4,3-b]pyrazin-4(1H)-yl)ethanone (0.006 g, 0.012 mmol) and the mixture was stirred until all the solid had dissolved (10 min). After 10 min, ice was added, and the solution was basified by the slow addition of 6 M aqueous sodium hydroxide solution. Dichloromethane was added and the layers were separated. The aqueous phase was extracted with dichloromethane and the combined organic phases were washed with brine, dried over anhydrous sodium sulfate, filtered, and concentrated to afford (S)-1-(3-methyl-7-(4-(methylsulfonyl)phenyl)-2,3-dihydropyrido[4,3-b]pyrazin-4(1H)-yl)ethanone (0.004 g, 96%) as an off-white solid. MS (ESI, pos. ion) m/z 346.

Step 9. (S)-1-(1-(furan-2-carbonyl)-3-methyl-7-(4-(methylsulfonyl)phenyl)-2,3-dihydro pyrido[3,4-b]pyrazin-4(1H)-yl)ethanone N,N-Diisopropylethylamine (0.3 mL, 1.718 mmol) was added to a solution of (S)-1-(3-methyl-7-(4-(methylsulfonyl)phenyl)-2,3-dihydropyrido[4,3-b]pyrazin-4(1H)-yl)ethanone (0.004 g, 0.012 mmol) and furan-2-carbonyl chloride (0.2 mL, 2.029 mmol) in dichloromethane (1.0 mL), and the mixture stirred at room temperature for 2 h. The reaction mixture was partitioned between dichloromethane and water. The aqueous phase was separated and extracted with dichloromethane. The combined organic phases were washed with brine, dried over anhydrous sodium sulfate, filtered, and concentrated to afford a yellow oil. This material was purified via column chromatography on silica gel (Biotage 25 g column, gradient elution with 0-50% ethyl acetate-hexane) to afford (S)-1-(1-(furan-2-carbonyl)-3-methyl-7-(4-(methylsulfonyl)phenyl)-2,3-dihydropyrido[3,4-b]pyrazin-4(1H)-yl)ethanone (0.0038 g, 75%) as an off-white solid. $^1$H NMR (300 MHz, CDCl$_3$) δ ppm 1.13-1.22 (m, 3 H), 2.25 (br s, 1 H), 2.31 (s, 3 H), 3.02 (s, 3 H), 3.88 (br s, 1 H), 4.05-4.18 (m, 1 H), 5.03 (br s, 1 H), 6.55 (dd, J=3.52, 1.76 Hz, 1 H), 7.20-7.26 (m, 1 H), 7.45 (dd, J=1.76, 0.88 Hz, 1 H), 7.78 (s, 1 H), 7.89-8.02 (m, 4 H). MS (ESI, pos. ion) m/z 440.

The following examples were made according to the procedure outlined for Example 96:

Example 97 isopropyl (S)-4-acetyl-3-methyl-7-(4-(methylsulfonyl)phenyl)-3,4-dihydro pyrido[3,4-b]pyrazine-1(2H)-carboxylate (I-58)

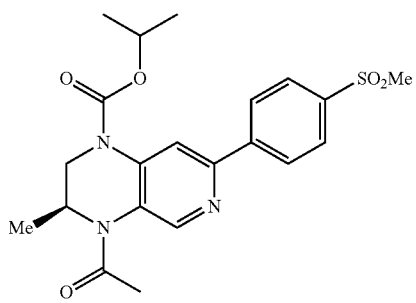 [SMILES: CC(=O)N1c2cnc(-c3ccc(S(C)(=O)=O)cc3)cc2N(C(=O)OC(C)C)C[C@@H]1C]

$^1$H NMR (300 MHz, CDCl$_3$) δ ppm $^1$H NMR (300 MHz, DMSO-d$_6$) δ ppm 1.03 (br d, J=6.74 Hz, 3 H), 1.14-1.40 (m, 6 H), 2.27 (s, 3 H), 3.27 (s, 3 H), 3.65 (br d, J=9.09 Hz, 1H), 3.96-4.15 (m, 1 H), 4.87 (br s, 1 H), 4.92-5.08 (m, 1 H), 8.04 (br d, J=8.21 Hz, 2 H), 8.16-8.31 (m, 2 H), 8.64-8.77 (m, 1 H), 8.92 (br s, 1 H). MS (ESI, pos. ion) m/z 432.

Example 98

(S)-oxetan-3-yl 4-acetyl-3-methyl-7-(1-(oxetan-3-yl)-1H-pyrazol-4-yl)-3,4-dihydroquinoxaline-1(2H)-carboxylate (I-59)

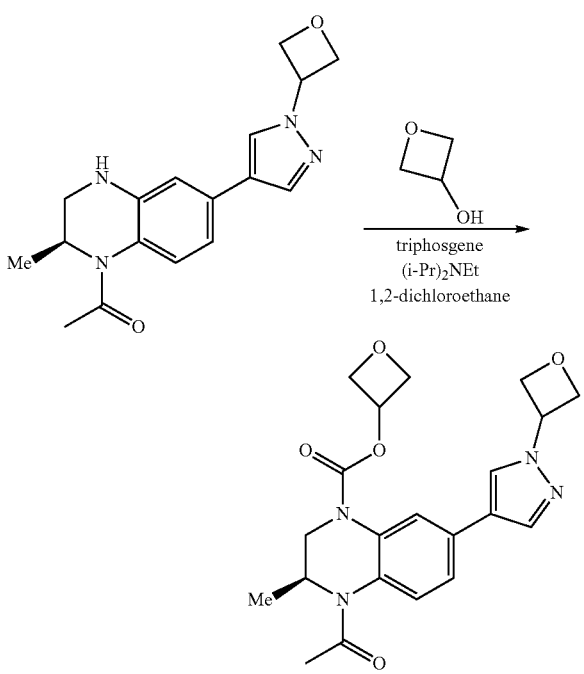

Triphosgene (0.057 g, 0.192 mmol) was added to a solution of oxetan-3-ol (0.034 mL, 0.576 mmol) and N,N-diisopropylethylamine (0.101 mL, 0.576 mmol) in 1,2-dichloroethane (2.0 mL). The mixture stirred at rt for 30 min. (S)-1-(2-methyl-6-(1-(oxetan-3-yl)-1H-pyrazol-4-yl)-3,4-dihydroquinoxaline-1(2H)-yl)ethanone (0.030 g, 0.096 mmol) and N,N-diisopropylethylamine (0.101 mL, 0.576 mmol) were added and the mixture stirred at 50° C. for 3 h. The reaction mixture was concentrated to afford an orange oil. This material was purified via column chromatography on silica gel (Biotage 25 g column, gradient elution with 50-100% ethyl acetate-hexane then 5-10% methanol-dichloromethane) to afford (S)-oxetan-3-yl 4-acetyl-3-methyl-7-(1-(oxetan-3-yl)-1H-pyrazol-4-yl)-3,4-dihydroquinoxaline-1(2H)-carboxylate (0.025 g, 63%) as a tan solid. $^1$H NMR (300 MHz, DMSO-d$_6$) δ ppm 0.95 (d, J=6.74 Hz, 3 H), 2.10 (s, 3 H), 3.49 (br s, 1 H), 3.98 (br dd, J=12.90, 5.86 Hz, 1 H), 4.51 (ddd, J=10.55, 7.18, 5.42 Hz, 2 H), 4.66-4.79 (m, 2 H), 4.79-4.94 (m, 5 H), 5.30-5.45 (m, 1 H), 5.53 (dq, J=14.07, 7.23 Hz, 1 H), 7.30 (dd, J=8.35, 1.91 Hz, 1 H), 7.41 (br s, 1 H), 7.86-8.00 (m, 2 H), 8.25 (s, 1 H). MS (ESI, pos. ion) m/z 413.

The following examples were made according to the procedure outlined for Example 98

Example 99

(S)-cyclobutylmethyl 4-acetyl-3-methyl-7-(1-(oxetan-3-yl)-1H-pyrazol-4-yl)-3,4-dihydroquinoxaline-1(2H)-carboxylate (I-60)

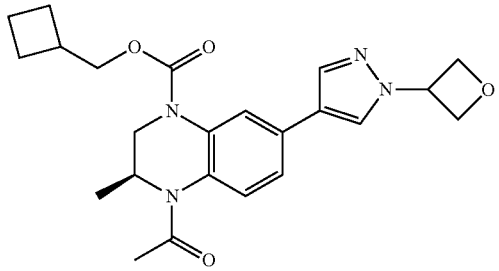 [SMILES: CC(=O)N1c2ccc(-c3cnn(C4COC4)c3)cc2N(C(=O)OCC2CCC2)C[C@@H]1C]

$^1$H NMR (400 MHz, CD$_3$OD) δ ppm 1.12 (d, J=6.40 Hz, 3H), 1.84-1.98 (m, 4H), 2.00-2.14 (m, 2H), 2.23 (s, 3H), 2.71-2.75 (m, 1H), 3.34 (m, 1H), 4.17-4.26 (m, 3H), 5.09 (d, J=6.80 Hz, 5H), 5.58-5.65 (m, 1H), 7.41 (m, 2H), 7.97 (s, 1H), 8.02 (s, 1H), 5.15 (s, 1H). MS (ESI, pos. ion) m/z 425 [M+H]$^+$.

Example 100

(S)-(3-methyloxetan-3-yl)methyl 4-acetyl-3-methyl-7-(1-(oxetan-3-yl)-1H-pyrazol-4-yl)-3,4-dihydroquinoxaline-1(2H)-carboxylate (I-61)

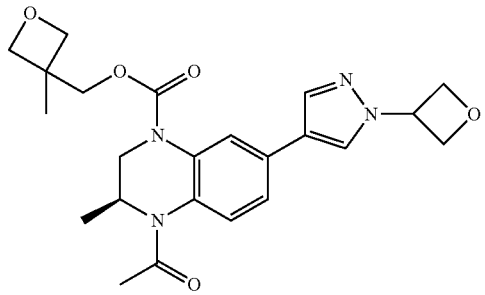 [SMILES: CC(=O)N1c2ccc(-c3cnn(C4COC4)c3)cc2N(C(=O)OCC2(C)COC2)C[C@@H]1C]

$^1$H NMR (300 MHz, CD$_3$OD) δ ppm 1.12 (d, J=6.60 Hz, 3H), 1.38 (s, 3H), 3.31 (s, 3H), 3.42-3.45 (m, 1H), 4.21-4.43 (m, 5H), 4.60-4.63 (m, 2H), 5.04-5.10 (m, 5H), 5.55-5.64 (m, 1H), 7.40-7.45 (m, 2H), 7.97 (s, 1H), 8.05 (s, 1H), 8.20 (s, 1H). MS (ESI, pos. ion) m/z 441 [M+H]$^+$.

Example 101

(S)-2,2-dichloroethyl 4-acetyl-3-methyl-7-(1-(oxetan-3-yl)-1H-pyrazol-4-yl)-3,4-dihydroquinoxaline-1(2H)-carboxylate (I-62)

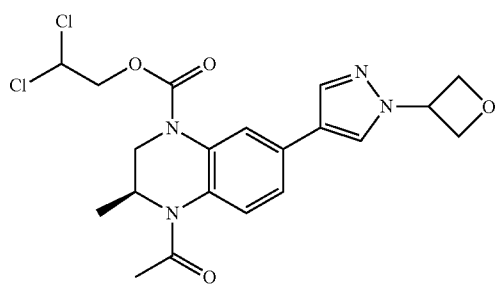 [SMILES: CC(=O)N1c2ccc(-c3cnn(C4COC4)c3)cc2N(C(=O)OCC(Cl)Cl)C[C@@H]1C]

$^1$H NMR (300 MHz, CD$_3$OD) δ ppm 1.12 (d, J=6.90 Hz, 3H), 2.22 (s, 3H), 3.47 (m, 1H), 4.26-4.28 (m, 1H), 4.53-4.70 (m, 2H), 5.07 (d, J=6.90 Hz, 5H), 5.56-5.65 (m, 1H), 6.26-6.29 (m, 1H), 7.42-7.45 (m, 2H), 7.97 (s, 1H), 8.04 (m, 1H), 8.17 (s, 1H). MS (ESI, pos. ion) m/z 454 [M+H]$^+$.

Example 102

(S)-(3-ethyloxetan-3-yl)methyl 4-acetyl-3-methyl-7-(1-(oxetan-3-yl)-1H-pyrazol-4-yl)-3,4-dihydroquinoxaline-1(2H)-carboxylate (I-63)

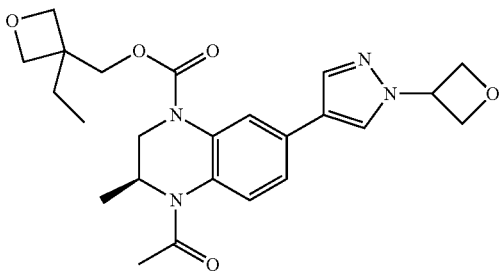 [SMILES: CCC1(COC(=O)N2C[C@H](C)N(C(C)=O)c3ccc(-c4cnn(C5COC5)c4)cc32)COC1]

$^1$H NMR (300 MHz, CD$_3$OD) δ ppm 0.92-0.98 (m, 3H), 1.12 (d, J=6.60 Hz, 3H), 1.74-1.82 (m, 2H), 2.22 (s, 3H), 3.42-3.55 (m, 1H), 4.28-4.32 (m, 2H), 4.42-4.49 (m, 3H), 4.51-4.58 (m, 2H), 5.07 (d, J=6.90 Hz, 5H), 5.55-5.64 (m, 1H), 7.41-7.44 (m, 2H), 7.97 (s, 1H), 8.05 (s, 1H), 8.19 (s, 1H). MS (ESI, pos. ion) m/z 455 [M+H]+.

Example 103

(S)-oxetan-3-ylmethyl 4-acetyl-3-methyl-7-(1-(oxetan-3-yl)-1H-pyrazol-4-yl)-3,4-dihydroquinoxaline-1(2H)-carboxylate (I-64)

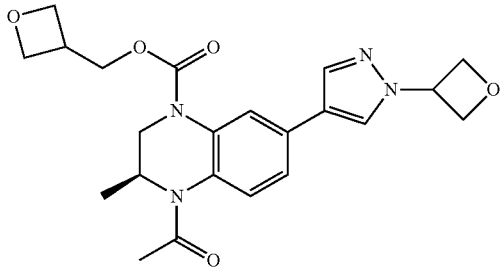 [SMILES: CC(=O)N1c2ccc(-c3cnn(C4COC4)c3)cc2N(C(=O)OCC2COC2)C[C@@H]1C]

$^1$H NMR (300 MHz, CD$_3$OD) δ ppm 1.12 (d, J=6.60 Hz, 3H), 2.22 (s, 3H), 3.33-3.46 (m, 2H), 4.22-4.28 (m, 1H), 4.35-4.39 (m, 1H), 4.41-4.59 (m, 3H), 4.80-4.82 (m, 2H), 5.08 (d, J=7.20 Hz, 5H), 5.55-5.64 (m, 1H), 7.41-7.44 (m, 2H), 7.97 (s, 1H), 8.05 (s, 1H), 8.19 (s, 1H). MS (ESI, pos. ion) m/z 427 [M+H]+.

Example 104

(S)-3,3-difluorocyclobutyl 4-acetyl-3-methyl-7-(1-(oxetan-3-yl)-1H-pyrazol-4-yl)-3,4-dihydroquinoxaline-1(2H)-carboxylate (I-65)

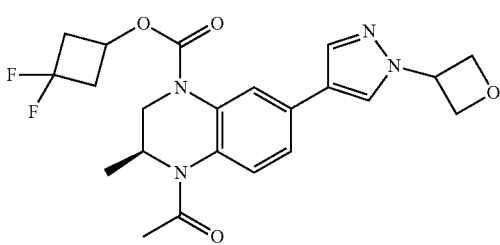 [SMILES: CC(=O)N1c2ccc(-c3cnn(C4COC4)c3)cc2N(C(=O)OC2CC(F)(F)C2)C[C@@H]1C]

$^1$H NMR (300 MHz, CD$_3$OD) δ ppm 1.12 (d, J=6.60 Hz, 3H), 2.22 (s, 3H), 2.74-2.88 (m, 2H), 3.02-3.16 (m, 2H), 3.47-3.49 (m, 1H), 4.16-4.23 (m, 1H), 4.96-5.20 (m, 5H), 5.56-5.65 (m, 1H), 7.41 (s, 1H), 7.96 (s, 1H), 8.06 (s, 1H), 8.17 (s, 1H). MS (ESI, pos. ion) m/z 447 [M+H]+.

Example 105

(S)-(3-fluorooxetan-3-yl)methyl 4-acetyl-3-methyl-7-(1-(oxetan-3-yl)-1H-pyrazol-4-yl)-3,4-dihydroquinoxaline-1(2H)-carboxylate (I-66)

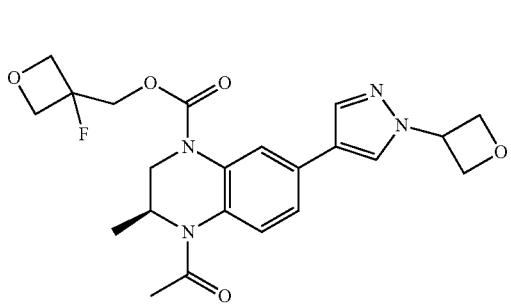 [SMILES: CC(=O)N1c2ccc(-c3cnn(C4COC4)c3)cc2N(C(=O)OCC2(F)COC2)C[C@@H]1C]

$^1$H NMR (300 MHz, CD$_3$OD) δ ppm 1.12 (d, J=6.60 Hz, 3H), 2.23 (s, 3H), 3.47-3.56 (m, 1H), 4.20-4.26 (m, 1H), 4.54-4.82 (m, 6H), 4.82-5.12 (m, 5H), 5.57-5.66 (m, 1H), 7.42-7.45 (m, 2H), 7.98-8.01 (m, 2H), 8.18 (s, 1H). MS (ESI, pos. ion) m/z 445 [M+H]+.

Example 106

(S)-2-(oxetan-3-yl)ethyl 4-acetyl-3-methyl-7-(1-(oxetan-3-yl)-1H-pyrazol-4-yl)-3,4-dihydroquinoxaline-1(2H)-carboxylate (I-67)

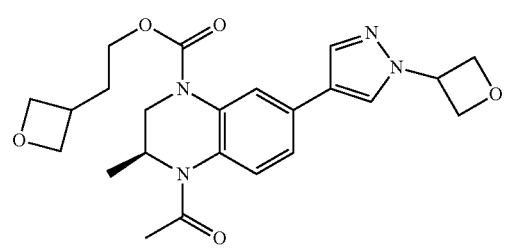 [SMILES: CC(=O)N1c2ccc(-c3cnn(C4COC4)c3)cc2N(C(=O)OCCC2COC2)C[C@@H]1C]

$^1$H NMR (300 MHz, CD$_3$OD) δ ppm 1.12 (d, J=6.60 Hz, 3H), 2.09-2.13 (m, 2H), 2.21 (s, 3H), 3.15-3.20 (m, 1H), 3.37-3.39 (m, 1H), 4.16-4.20 (m, 3H), 4.21-4.44 (m, 2H), 4.73-4.78 (m, 2H), 5.08 (d, J=6.90 Hz, 5H), 5.56-5.65 (m,

Example 107

(S)-2,2-difluoropropyl 4-acetyl-3-methyl-7-(1-(oxetan-3-yl)-1H-pyrazol-4-yl)-3,4-dihydroquinoxaline-1(2H)-carboxylate (I-68)

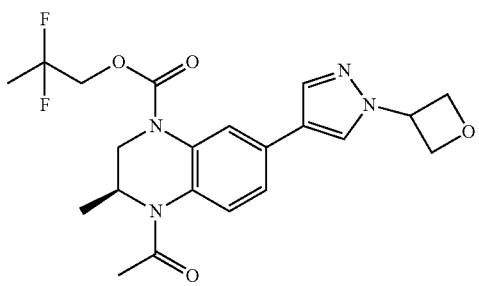 [SMILES: CC(=O)N1c2ccc(-c3cnn(C4COC4)c3)cc2N(C(=O)OCC(C)(F)F)C[C@@H]1C]

$^1$H NMR (300 MHz, CD$_3$OD) δ ppm 1.12 (d, J=6.90 Hz, 3H), 1.59-1.69 (m, 3H), 2.23 (s, 3H), 3.49-3.57 (m, 1H), 4.21-4.27 (m, 1H), 4.34-4.49 (m, 2H), 5.08 (d, J=6.90 Hz, 5H), 5.12-5.66 (m, 1H), 7.39-7.49 (m, 2H), 7.96 (s, 1H), 8.02 (s, 1H), 8.16 (s, 1H). MS (ESI, pos. ion) m/z 435 [M+H]$^+$.

Example 108

(S)-3,3,3-trifluoropropyl 4-acetyl-3-methyl-7-(1-(oxetan-3-yl)-1H-pyrazol-4-yl)-3,4-dihydroquinoxaline-1(2H)-carboxylate (I-69)

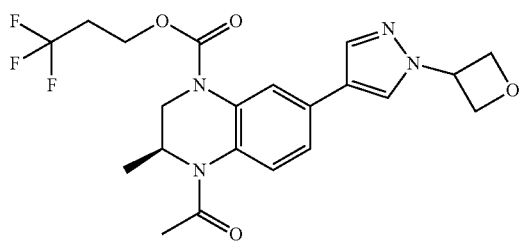 [SMILES: CC(=O)N1c2ccc(-c3cnn(C4COC4)c3)cc2N(C(=O)OCCC(F)(F)F)C[C@@H]1C]

$^1$H NMR (300 MHz, CD$_3$OD) δ ppm 1.12 (d, J=6.60 Hz, 3H), 2.22 (s, 3H), 2.61-2.74 (m, 2H), 3.42-3.44 (m, 1H), 4.18-4.24 (m, 1H), 4.40-4.53 (m, 2H), 5.08 (d, J=6.90 Hz, 5H), 5.56-5.65 (m, 1H), 7.41-7.44 (m, 2H), 7.97 (s, 1H), 8.05 (s, 1H), 8.19 (s, 1H). MS (ESI, pos. ion) m/z 453 [M+H]$^+$.

Example 109

2-oxaspiro[3.3]heptan-6-yl (3S)-4-acetyl-3-methyl-7-[1-(oxetan-3-yl)-1H-pyrazol-4-yl]-1,2,3,4-tetrahydroquinoxaline-1-carboxylate (I-70)

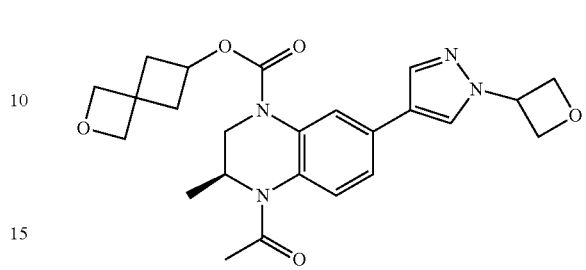

$^1$H NMR (300 MHz, CD$_3$OD) δ ppm 1.12 (d, J=6.60 Hz, 3H), 2.24 (s, 3H), 2.33-2.43 (m, 2H), 2.75-2.82 (m, 2H), 3.45-3.50 (m, 1H), 4.14-4.21 (m, 1H), 4.67-4.71 (m, 2H), 4.76 (s, 2H), 4.92-4.99 (m, 1H), 5.01-5.11 (m, 5H), 5.58-5.67 (m, 1H), 7.41 (s, 2H), 7.98 (s, 1H), 8.04 (s, 1H), 8.19 (s, 1H). MS (ESI, pos. ion) m/z 453 [M+H]$^+$.

Example 110

(S)-2,2,2-trifluoroethyl 4-acetyl-3-methyl-7-(1-(oxetan-3-yl)-1H-pyrazol-4-yl)-3,4-dihydroquinoxaline-1(2H)-carboxylate (I-71)

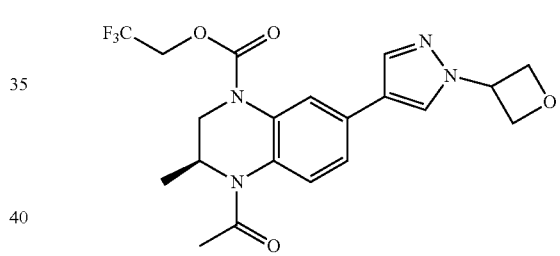

$^1$H NMR (300 MHz, CD$_3$OD) δ ppm 1.12 (d, J=6.90 Hz, 3H), 2.22 (s, 3H), 3.49 (m, 1H), 4.21-4.27 (m, 1H), 4.69-4.82 (m, 2H), 5.08 (d, J=6.90 Hz, 5H), 5.56-5.65 (m, 1H), 7.43-7.46 (m, 2H), 7.95-7.99 (m, 2H), 8.15 (s, 1H). MS (ESI, pos. ion) m/z 439 [M+H]$^+$.

Example 111

(S)-1,3-difluoropropan-2-yl 4-acetyl-3-methyl-7-(1-(oxetan-3-yl)-1H-pyrazol-4-yl)-3,4-dihydroquinoxaline-1(2H)-carboxylate (I-72)

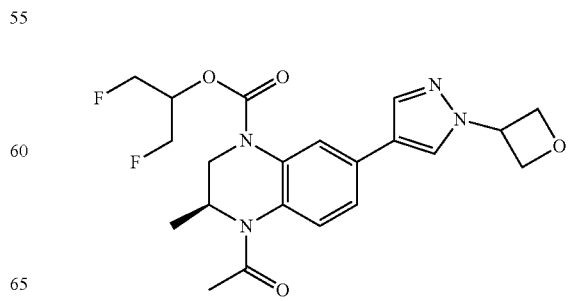

<sup>1</sup>H NMR (300 MHz, CD₃OD) δ ppm 1.12 (d, J=6.60 Hz, 3H), 2.23 (s, 3H), 3.32-3.33 (m, 1H), 4.18-4.25 (m, 1H), 4.56-4.80 (m, 4H), 5.08 (d, J=6.90 Hz, 5H), 5.22-5.38 (m, 1H), 7.42 (m, 2H), 7.95 (s, 1H), 8.02 (s, 1H), 8.16 (s, 1H). MS (ESI, pos. ion) m/z 435 [M+H]⁺.

Example 112

(2,2-dimethylcyclopropyl)methyl (3S)-4-acetyl-3-methyl-7-(1-(oxetan-3-yl)-1H-pyrazol-4-yl)-3,4-dihydroquinoxaline-1(2H)-carboxylate (I-73)

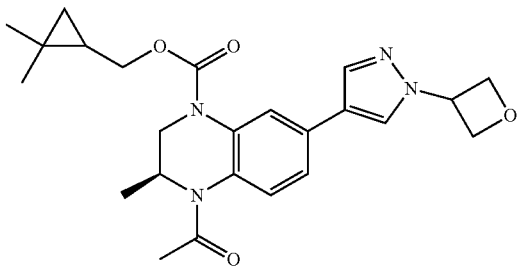 [SMILES: CC(=O)N1c2ccc(-c3cnn(C4COC4)c3)cc2N(C(=O)OCC2CC2(C)C)C[C@@H]1C]

¹H NMR (300 MHz, CD₃OD) δ ppm 0.25-0.35 (m, 1H), 0.55-0.65 (m, 1H), 0.95-1.15 (m, 10H), 2.22 (s, 3H), 3.35-3.50 (m, 1H), 3.95-4.08 (m, 1H), 4.10-4.21 (m, 1H), 4.37-4.48 (m, 1H), 4.99-5.09 (m, 5H), 5.55-5.65 (m, 1H), 7.40 (s, 2H), 7.96 (s, 1H), 8.03 (s, 1H), 8.17 (s, 1H). MS (ESI, pos. ion) m/z 439 [M+H]⁺.

Example 113

(3S)-bicyclo[3.1.0]hexan-3-yl 4-acetyl-3-methyl-7-(1-(oxetan-3-yl)-1H-pyrazol-4-yl)-3,4-dihydroquinoxaline-1(2H)-carboxylate (I-74)

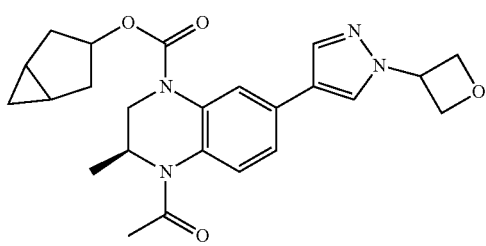 [SMILES: CC(=O)N1c2ccc(-c3cnn(C4COC4)c3)cc2N(C(=O)OC2CC3CC3C2)C[C@@H]1C]

¹H NMR (300 MHz, CD₃OD) δ ppm 0.30-0.34 (m, 1H), 0.42-0.49 (m, 1H), 1.10 (d, J=6.60 Hz, 3H), 1.30-1.41 (m, 2H), 1.86-1.96 (m, 2H), 2.22-2.30 (m, 5H), 3.40 (m, 1H), 4.11-4.15 (m, 1H), 4.96-5.09 (m, 5H), 5.30-5.34 (m, 1H), 5.56-5.66 (m, 1H), 7.45 (m, 2H), 7.97 (s, 2H), 8.16 (s, 1H). MS (ESI, pos. ion) m/z 437 [M+H]⁺.

Example 114

(3S)-(2,2-difluorocyclopropyl)methyl 4-acetyl-3-methyl-7-(1-(oxetan-3-yl)-1H-pyrazol-4-yl)-3,4-dihydroquinoxaline-1(2H)-carboxylate (I-75)

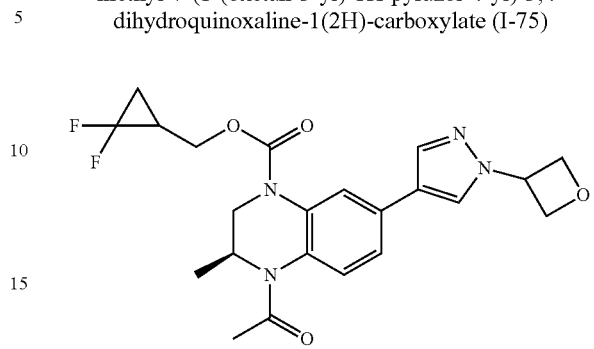

¹H NMR (300 MHz, CD₃OD) δ ppm 1.12 (d, J=6.60 Hz, 3H), 1.29-1.31 (m 1H), 1.60-1.71 (m, 1H), 2.10-2.24 (m, 4H), 3.46-3.49 (m, 1H), 4.14-4.26 (m, 2H), 4.43-4.52 (m, 1H), 5.10 (d, J=6.90 Hz, 5H), 5.58-5.67 (m, 1H), 7.36-7.47 (m, 2H), 7.98 (s, 1H), 8.04 (s, 1H), 8.18 (s, 1H). MS (ESI, pos. ion) m/z 447 [M+H]⁺.

Example 115

(S)-1-methylcyclopropyl 4-acetyl-3-methyl-7-(1-(oxetan-3-yl)-1H-pyrazol-4-yl)-3,4-dihydroquinoxaline-1(2H)-carboxylate (I-76)

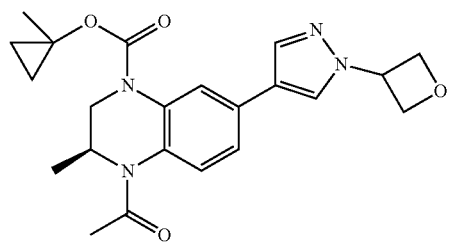 [SMILES: CC(=O)N1c2ccc(-c3cnn(C4COC4)c3)cc2N(C(=O)OC2(C)CC2)C[C@@H]1C]

¹H NMR (300 MHz, CD₃OD) δ ppm 0.70-0.74 (m, 2H), 0.80-1.00 (m, 2H), 1.09 (d, J=6.60 Hz, 3H), 1.62 (s, 3H), 2.22 (s, 3H), 3.38-3.42 (m, 1H), 4.07-4.13 (m, 1H), 5.03-5.09 (m, 5H), 5.57-5.66 (m, 1H), 7.39 (s, 2H), 7.96-8.00 (m, 2H), 8.17 (s, 1H). MS (ESI, pos. ion) m/z 411 [M+H]⁺.

Example 116

(S)-2-fluoro-2-methylpropyl 4-acetyl-3-methyl-7-(1-(oxetan-3-yl)-1H-pyrazol-4-yl)-3,4-dihydroquinoxaline-1(2H)-carboxylate (I-77)

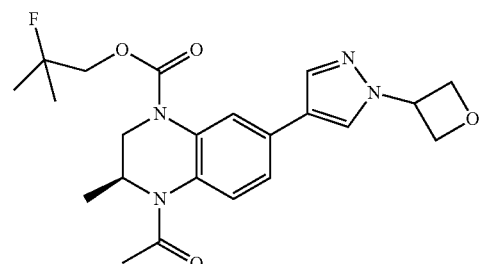

¹H NMR (300 MHz, CD₃OD) δ ppm 1.12 (d, J=6.60 Hz, 3H), 1.31-1.38 (m, 3H), 1.44-1.45 (m, 3H), 2.22 (s, 3H), 3.46-3.55 (m, 1H), 4.16-4.36 (m, 3H), 5.00-5.11 (m, 5H), 5.55-5.65 (m, 1H), 7.42 (s, 2H), 7.97 (s, 1H), 8.04 (s, 1H), 8.17 (s, 1H). MS (ESI, pos. ion) m/z 431 [M+H]⁺.

Example 117

(S)-3,3,3-trifluoropropyl 4-acetyl-7-(1-cyclopropyl-1H-pyrazol-4-yl)-3-methyl-3,4-dihydroquinoxaline-1(2H)-carboxylate (I-78)

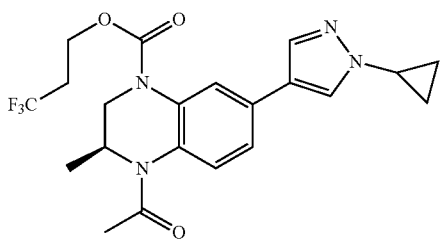 [SMILES: CC(=O)N1c2ccc(-c3cnn(C4CC4)c3)cc2N(C(=O)OCCC(F)(F)F)C[C@@H]1C]

¹H NMR (300 MHz, CD₃OD) δ ppm 1.06-1.21 (m, 7H), 2.22 (s, 3H), 2.61-2.79 (m, 2H), 3.42 (s, 1H), 3.67-3.75 (m, 1H), 4.21 (s, 1H), 4.40-4.65 (m, 2H), 5.08 (s, 1H), 7.40 (s, 2H), 7.87 (s, 1H), 8.02 (s, 1H), 8.06 (s, 1H). MS (ESI, pos. ion) m/z 437 [M+H]⁺.

Example 118

(S)-2,2,2-trifluoroethyl 4-acetyl-7-(1-cyclopropyl-1H-pyrazol-4-yl)-3-methyl-3,4-dihydroquinoxaline-1(2H)-carboxylate (I-79)

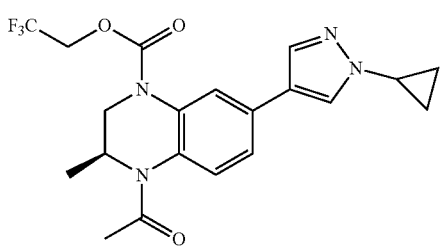 [SMILES: CC(=O)N1c2ccc(-c3cnn(C4CC4)c3)cc2N(C(=O)OCC(F)(F)F)C[C@@H]1C]

¹H NMR (300 MHz, CD₃OD) δ ppm 1.04-1.21 (m, 7H), 2.24 (s, 3H), 3.42 (s, 1H), 3.69-3.79 (m, 1H), 4.21 (s, 1H), 4.70-4.87 (m, 2H), 5.08 (s, 1H), 7.42 (s, 2H), 7.82 (s, 1H), 7.97 (s, 1H), 8.06 (s, 1H). MS (ESI, pos. ion) m/z 423 [M+H]⁺.

Example 119

(S)-1,3-difluoropropan-2-yl 4-acetyl-7-(1-cyclopropyl-1H-pyrazol-4-yl)-3-methyl-3,4-dihydroquinoxaline-1(2H)-carboxylate (I-80)

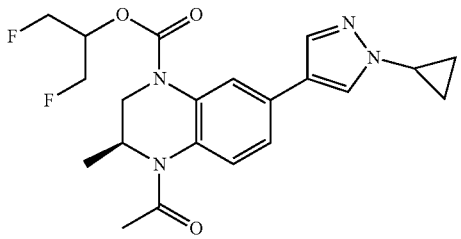 [SMILES: CC(=O)N1c2ccc(-c3cnn(C4CC4)c3)cc2N(C(=O)OC(CF)CF)C[C@@H]1C]

¹H NMR (300 MHz, CD₃OD) δ ppm 1.04-1.19 (m, 7H), 2.24 (s, 3H), 3.42 (s, 1H), 3.65-3.78 (m, 1H), 4.22 (s, 1H), 4.70-4.89 (m, 2H), 5.08 (s, 1H), 5.20-5.45 (m, 1H), 7.40 (s, 2H), 7.82 (s, 1H), 7.99 (s, 1H), 8.06 (s, 1H). MS (ESI, pos. ion) m/z 419 [M+H]⁺.

Example 120

(S)-3,3,3-trifluoropropyl 4-acetyl-7-(1-(2-hydroxyethyl)-1H-pyrazol-4-yl)-3-methyl-3,4-dihydroquinoxaline-1(2H)-carboxylate (I-81)

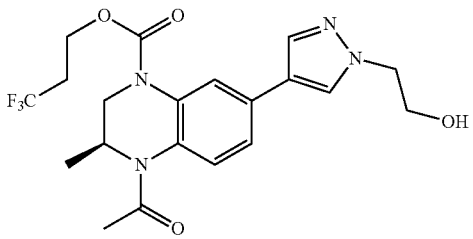 [SMILES: CC(=O)N1c2ccc(-c3cnn(CCO)c3)cc2N(C(=O)OCCC(F)(F)F)C[C@@H]1C]

¹H NMR (300 MHz, CD₃OD) δ ppm 1.01-1.29 (m, 3H), 2.21 (s, 3H), 2.55-2.83 (m, 2H), 3.41 (s, 1H), 3.85-4.09 (m, 2H), 4.11-4.39 (m, 3H), 4.40-4.59 (m, 2H), 5.05 (s, 1H), 7.39 (s, 2H), 8.00 (s, 2H), 8.03 (s, 2H). MS (ESI, pos. ion) m/z 441 [M+H]⁺.

Example 121

(S)-2,2,2-trifluoroethyl 4-acetyl-7-(1-(2-hydroxyethyl)-1H-pyrazol-4-yl)-3-methyl-3,4-dihydroquinoxaline-1(2H)-carboxylate (I-82)

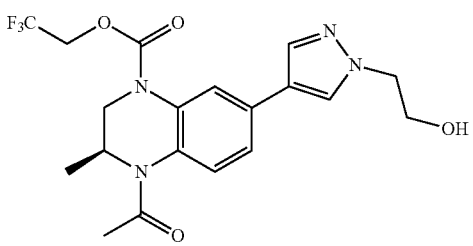 [SMILES: CC(=O)N1c2ccc(-c3cnn(CCO)c3)cc2N(C(=O)OCC(F)(F)F)C[C@@H]1C]

¹H NMR (300 MHz, CD₃OD) δ ppm 0.92-1.28 (m, 3H), 2.25 (s, 3H), 3.19-3.28 (m, 1H), 3.31-3.44 (m, 1H), 3.87-3.98 (m, 1H), 4.20-4.31 (m, 1H), 4.46-4.53 (m, 2H), 5.08 (s, 1H), 6.79-6.83 (m, 2H), 7.03 (s, 1H), 7.78 (d, J=5.70 Hz, 1H), 7.93 (s, 1H). MS (ESI, pos. ion) m/z 427 [M+H]⁺.

Example 122

(S)-1,3-difluoropropan-2-yl 4-acetyl-7-(1-(2-hydroxyethyl)-1H-pyrazol-4-yl)-3-methyl-3,4-dihydroquinoxaline-1(2H)-carboxylate (I-83)

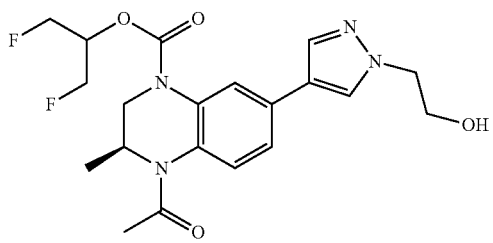 [SMILES: CC(=O)N1c2ccc(-c3cnn(CCO)c3)cc2N(C(=O)OC(CF)CF)C[C@@H]1C]

$^1$H NMR (300 MHz, CD$_3$OD) δ ppm 1.02-1.14 (m, 3H), 2.23 (s, 3H), 3.38-3.44 (m, 1H), 3.89-3.98 (m, 2H), 4.12-4.33 (m, 3H), 4.51-4.82 (m, 4H), 5.07 (s, 1H), 5.20-5.41 (m, 1H), 7.40 (s, 2H), 7.85 (s, 1H), 7.99-8.10 (m, 2H). MS (ESI, pos. ion) m/z 423 [M+H]$^+$.

Example 123

(S)-2,2-difluoroethyl 4-acetyl-3-methyl-7-(1-(oxetan-3-yl)-1H-pyrazol-4-yl)-3,4-dihydroquinoxaline-1(2H)-carboxylate (I-84)

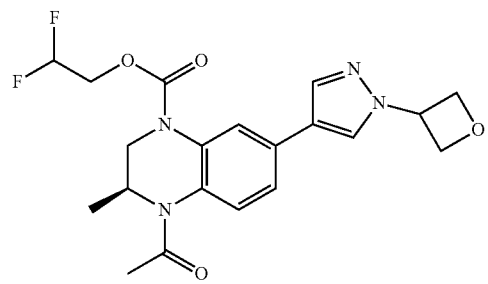 [SMILES: CC(=O)N1c2ccc(-c3cnn(C4COC4)c3)cc2N(C(=O)OCC(F)F)C[C@@H]1C]

$^1$H NMR (CD$_3$OD, 300 MHz) δ ppm 1.11 (d, J=6.60 Hz, 3H), 2.22 (s, 3H), 3.35-3.50 (m, 1H), 4.17-4.28 (m, 1H), 4.38-4.55 (m, 2H), 5.02-5.11 (m, 5H), 5.55-5.65 (m, 1H), 6.15 (tt, J=54.60, 3.60 Hz, 1H), 7.35-7.45 (m, 2H), 7.99 (s, 1H), 8.02 (s, 1H), 8.12 (s, 1H). MS (ESI, pos. ion) m/z 421 [M+H]$^+$.

Example 124

4-fluorophenyl (S)-4-acetyl-3-methyl-7-(1-(oxetan-3-yl)-1H-pyrazol-4-yl)-3,4-dihydroquinoxaline-1(2H)-carboxylate (I-85)

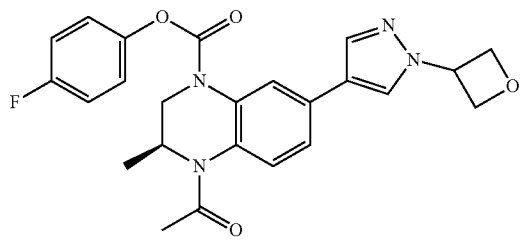 [SMILES: CC(=O)N1c2ccc(-c3cnn(C4COC4)c3)cc2N(C(=O)Oc2ccc(F)cc2)C[C@@H]1C]

$^1$H NMR (300 MHz, CD$_3$OD) δ ppm 1.18 (d, J=6.60 Hz, 3H), 2.25 (s, 3H), 3.65 (s, 1H), 4.28-4.47 (m, 1H), 5.00-5.19 (m, 5H), 5.50-5.70 (m, 1H), 7.05-7.19 (m, 2H), 7.20-7.35 (m, 2H), 7.45 (s, 2H), 7.95 (s, 1H), 8.09-8.20 (m, 2H). MS (ESI, pos. ion) m/z 451 [M+H]$^+$.

Example 125

(S)-cyclohexyl 4-acetyl-3-methyl-7-(1-(oxetan-3-yl)-1H-pyrazol-4-yl)-3,4-dihydroquinoxaline-1(2H)-carboxylate (I-86)

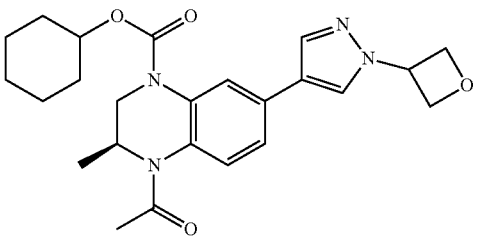 [SMILES: CC(=O)N1c2ccc(-c3cnn(C4COC4)c3)cc2N(C(=O)OC2CCCCC2)C[C@@H]1C]

$^1$H NMR (300 MHz, CD$_3$OD) δ ppm 1.16 (d, J=6.60 Hz, 3H), 1.29-2.08 (m, 10H), 2.22 (s, 3H), 3.51 (s, 1H), 4.13-4.20 (m, 1H), 4.75-4.89 (m, 1H), 4.99-5.21 (m, 5H), 5.50-5.70 (m, 1H), 7.39 (s, 2H), 7.95 (s, 1H), 8.03 (s, 1H), 8.16 (s, 1H). MS (ESI, pos. ion) m/z 489 [M+H]$^+$.

Example 126

(S)-4-methoxyphenyl 4-acetyl-3-methyl-7-(1-(oxetan-3-yl)-1H-pyrazol-4-yl)-3,4-dihydroquinoxaline-1(2H)-carboxylate (I-87)

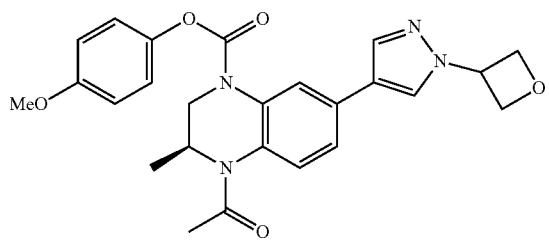 [SMILES: COc1ccc(OC(=O)N2C[C@H](C)N(C(C)=O)c3ccc(-c4cnn(C5COC5)c4)cc32)cc1]

$^1$H NMR (300 MHz, CD$_3$OD) δ ppm 1.18 (d, J=6.60 Hz, 3H), 2.22 (s, 3H), 3.61 (s, 1H), 3.88 (s, 3H), 4.25-4.40 (m, 1H), 5.00-5.19 (m, 5H), 5.50-5.70 (m, 1H), 6.90-7.01 (m, 2H), 7.08-7.19 (m, 2H), 7.40 (s, 2H), 7.95 (s, 1H), 8.09-8.20 (m, 2H). MS (ESI, pos. ion) m/z 463 [M+H]$^+$.

Example 127

(S)-phenyl 4-acetyl-3-methyl-7-(1-(oxetan-3-yl)-1H-pyrazol-4-yl)-3,4-dihydroquinoxaline-1(2H)-carboxylate (I-88)

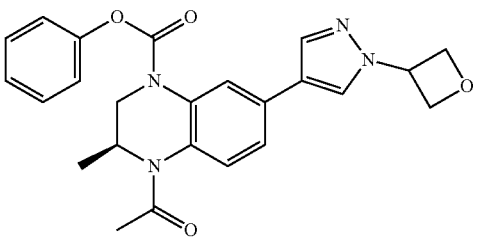 [SMILES: CC(=O)N1c2ccc(-c3cnn(C4COC4)c3)cc2N(C(=O)Oc2ccccc2)C[C@@H]1C]

Example 128

(S)-2-methoxyphenyl 4-acetyl-3-methyl-7-(1-(oxetan-3-yl)-1H-pyrazol-4-yl)-3,4-dihydroquinoxaline-1(2H)-carboxylate (I-3)

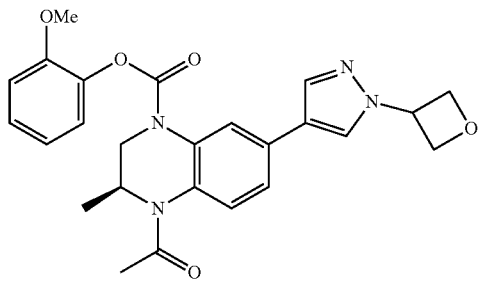 [SMILES: COc1ccccc1OC(=O)N1C[C@H](C)N(C(C)=O)c2ccc(-c3cnn(C4COC4)c3)cc21]

$^1$H NMR (300 MHz, CD$_3$OD) δ ppm 1.18 (d, J=6.60 Hz, 3H), 2.04 (s, 1H), 2.22 (s, 3H), 3.61 (s, 1H), 3.88 (s, 3H), 4.13-4.20 (m, 1H), 4.99-5.21 (m, 5H), 5.50-5.70 (m, 1H), 6.90-7.01 (m, 1H), 7.08-7.19 (m, 2H), 7.20-7.38 (m, 1H), 7.40-7.52 (s, 2H), 7.90 (s, 1H), 8.20 (d, J=8.40 Hz, 2H). MS (ESI, pos. ion) m/z 463[M+H]$^+$.

Example 129

(S)-pyridin-3-yl 4-acetyl-3-methyl-7-(1-(oxetan-3-yl)-1H-pyrazol-4-yl)-3,4-dihydroquinoxaline-1(2H)-carboxylate (I-89)

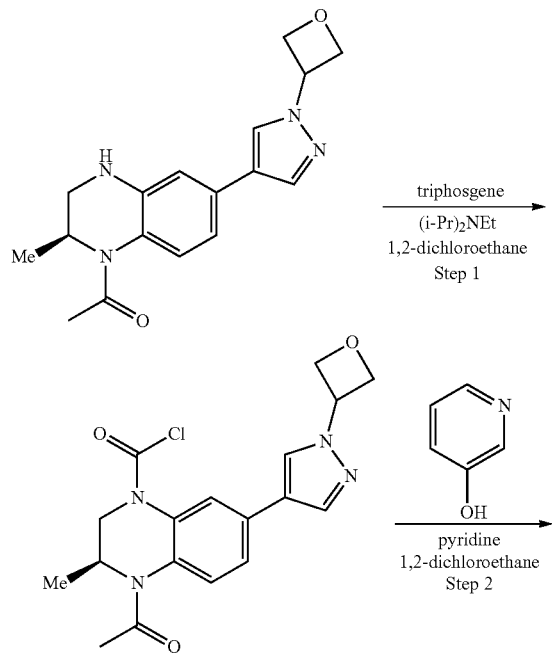

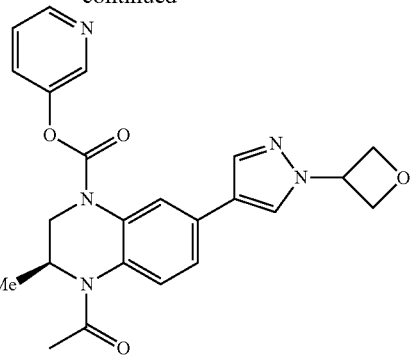

Step 1. (S)-4-acetyl-3-methyl-7-(1-(oxetan-3-yl)-1H-pyrazol-4-yl)-3,4-dihydroquinoxaline-1(2H)-carbonyl chloride Triphosgene (0.048 g, 0.16 mmol) was added slowly to a solution of (S)-1-(2-methyl-6-(1-(oxetan-3-yl)-1H-pyrazol-4-yl)-3,4-dihydroquinoxaline-1(2H)-yl)ethanone (0.050 g, 0.16 mmol) and N,N-diisopropylethylamine (0.413 g, 3.20 mmol) in 1,2-dichloroethane (20 mL) at room temperature. The resulting solution was stirred for 1 hour at room temperature and then concentrated under vacuum. The crude product was purified via preparative thin layer chromatography (eluting with 1:1 petroleum ether:ethyl acetate) to afford (S)-4-acetyl-3-methyl-7-(1-(oxetan-3-yl)-1H-pyrazol-4-yl)-3,4-dihydroquinoxaline-1(2H)-carbonyl chloride (0.040 g, 67%) as a yellow solid. $^1$H-NMR (300 MHz, CDCl$_3$, ppm): δ 7.92-7.80 (m, 3H), 7.41-7.38 (m, 1H), 7.26-7.23 (m, 1H), 5.55-5.45 (m, 1H), 5.13-5.08 (m, 5H), 4.58-4.53 (m, 1H), 3.33-3.20 (m, 1H), 2.23 (s, 3H), 1.10 (d, J=6.3 Hz, 3H). MS (ESI, pos. ion) m/z 375, 377 [M+H]$^+$.

Step 2. (S)-pyridin-3-yl 4-acetyl-3-methyl-7-(1-(oxetan-3-yl)-1H-pyrazol-4-yl)-3,4-dihydroquinoxaline-1(2H)-carboxylate A solution of (S)-4-acetyl-3-methyl-7-(1-(oxetan-3-yl)-1H-pyrazol-4-yl)-3,4-dihydroquinoxaline-1(2H)-carbonyl chloride (0.050 g, 0.13 mmol) in 1,2-dichloroethane (1 mL) was added dropwise to a 50° C. solution of pyridine-3-ol (0.053 g, 0.26 mmol) and pyridine (1 mL) in 1,2-dichloroethane (20 mL). The resulting solution was stirred for 6 h at 50° C. and then concentrated under vacuum. The residue was purified by preparative thin layer chromatography (eluting with 1-20% methanol-dichloromethane) and then by preparative-HPLC (conditions: Column, SunFire™Prep C18OBD™, 19×150 nm; Mobile phase, A: 0.05% ammonium carbonate, B: acetonitrile; Detector, 220 and 254 nm) to afford (S)-pyridin-3-yl 4-acetyl-3-methyl-7-(1-(oxetan-3-yl)-1H-pyrazol-4-yl)-3,4-dihydroquinoxaline-1(2H)-carboxylate (0.026 mg, 46%) as a white solid. $^1$H NMR (300 MHz, CD$_3$OD) 1.17 (d, J=6.60 Hz, 3H), 2.27 (s, 3H), 3.50-3.79 (m, 1H), 4.35-4.45 (m, 1H), 5.02-5.25 (m, 5H), 5.55-5.65 (m, 1H), 7.39-7.49 (m, 2H), 7.51-7.57 (m, 1H), 7.78-7.83 (m, 1H), 7.97 (s, 1H), 8.10-8.19 (m, 2H), 8.47-8.50 (m, 1H), 8.52-8.56 (m, 1H). MS (ESI, pos. ion) m/z 434 [M+H]$^+$.

The following examples were made according to the procedure outlined for Example 129

---

$^1$H NMR (300 MHz, CD$_3$OD) δ ppm 1.17 (d, J=6.60 Hz, 3H), 2.27 (s, 3H), 3.65 (s, 1H), 4.28-4.47 (m, 1H), 5.00-5.19 (m, 5H), 5.50-5.70 (m, 1H), 7.16-7.30 (m, 3H), 7.30-7.55 (m, 4H), 7.95 (s, 1H), 8.09-8.20 (m, 2H). MS (ESI, pos. ion) m/z 433[M+H]$^+$.

Example 130

(S)-pyridin-4-yl 4-acetyl-3-methyl-7-(1-(oxetan-3-yl)-1H-pyrazol-4-yl)-3,4-dihydroquinoxaline-1(2H)-carboxylate (I-90)

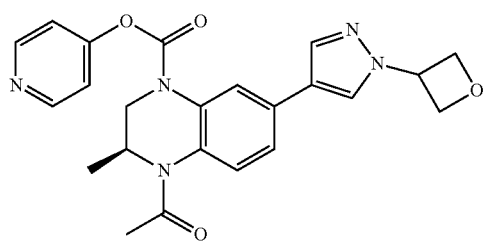 [SMILES: CC(=O)N1c2ccc(-c3cnn(C4COC4)c3)cc2N(C(=O)Oc2ccncc2)C[C@@H]1C]

$^1$H NMR (300 MHz, CD$_3$OD) δ ppm 1.16 (d, J=6.60 Hz, 3H), 2.26 (s, 3H), 3.61 (s, 1H), 4.38-4.47 (m, 1H), 5.04-5.14 (m, 5H), 5.54-5.63 (m, 1H), 7.41-7.49 (m, 4H), 7.96 (s, 1H), 8.11 (s, 1H), 8.16 (s, 1H), 8.49-8.60 (m, 2H). MS (ESI, pos. ion) m/z 434 [M+H]$^+$.

Example 131

(S)-pyridin-2-yl 4-acetyl-3-methyl-7-(1-(oxetan-3-yl)-1H-pyrazol-4-yl)-3,4-dihydroquinoxaline-1(2H)-carboxylate (I-91)

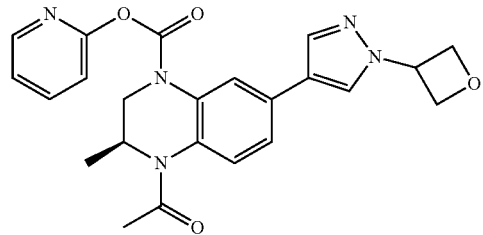 [SMILES: CC(=O)N1c2ccc(-c3cnn(C4COC4)c3)cc2N(C(=O)Oc2ccccn2)C[C@@H]1C]

$^1$H NMR (300 MHz, CD$_3$OD) δ ppm 1.18 (d, J=6.60 Hz, 3H), 2.27 (s, 3H), 3.65 (s, 1H), 4.28-4.47 (m, 1H), 5.00-5.21 (m, 5H), 5.50-5.70 (m, 1H), 7.29-7.49 (m, 4H), 7.87-8.02 (m, 2H), 8.09-8.20 (m, 2H), 8.40 (s, 1H). MS (ESI, pos. ion) m/z 434 [M+H]$^+$.

Example 132

(S)-(4-(benzo[d]oxazol-2-yl)-6-(1-cyclopropyl-1H-pyrazol-4-yl)-2-methyl-3,4-dihydroquinoxaline-1(2H)-yl)(cyclopropyl)methanone (I-92)

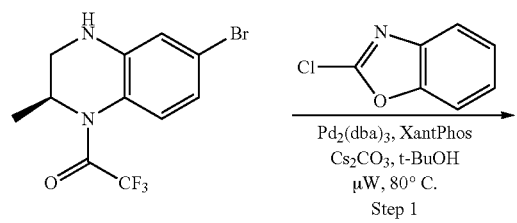

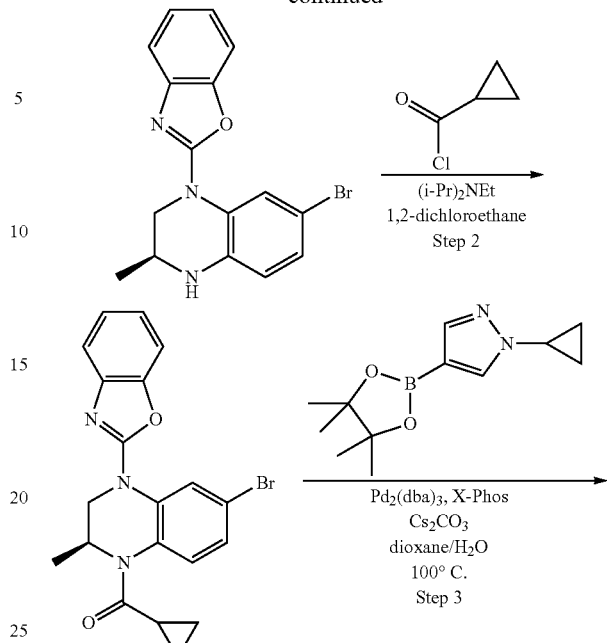

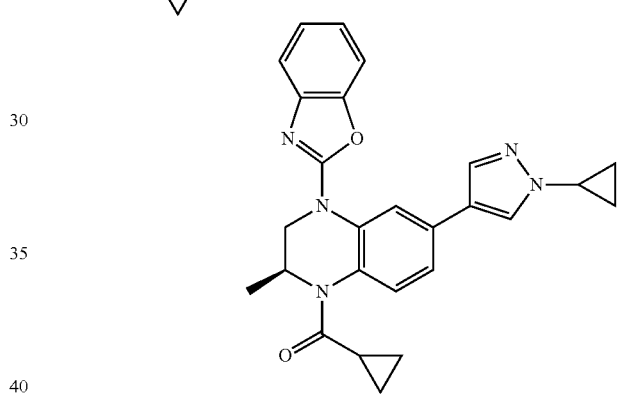

Step 1. (S)-2-(7-bromo-3-methyl-3,4-dihydroquinoxaline-1(2H)-yl)benzo[d]oxazole A mixture of (S)-1-(6-bromo-2-methyl-3,4-dihydroquinoxaline-1(2H)-yl)-2,2,2-trifluoroethanone (0.050 g, 0.155 mmol), 2-chlorobenzo[d]oxazole (0.035 mL, 0.309 mmol), tris(dibenzylideneacetone)dipalladium (7.09 mg, 7.74 µmol), 4,5-bis(diphenylphosphino)-9,9-dimethylxanthene (Xantphos) (0.018 g, 0.031 mmol) (0.015 g, 0.031 mmol) and cesium carbonate (0.101 g, 0.309 mmol) in t-butanol (2.0 mL) was heated in the microwave at 100° C. for 1.5 h. A second portion of Xantphos (0.018 g, 0.031 mmol) and tris(dibenzylideneacetone)dipalladium (7.09 mg, 7.74 µmol) were added, and the mixture stirred at 100° C. for 2.5 h. The reaction mixture was filtered through Celite and concentrated to afford an orange oil. This material was purified via column chromatography on silica gel (Biotage 25 g column, gradient elution with 0-50% ethyl acetate-hexane) to afford (S)-2-(7-bromo-3-methyl-3,4-dihydroquinoxaline-1(2H)-yl)benzo[d]oxazole (0.016 g, 30%) as an off-white solid. MS (ESI, pos. ion) m/z 344, 346 [M+H]$^+$.

Step 2. (S)-(4-(benzo[d]oxazol-2-yl)-6-bromo-2-methyl-3,4-dihydroquinoxaline-1(2H)-yl)(cyclopropyl)methanone N,N-Diisopropylethylamine (0.041 mL, 0.232 mmol) was added to a solution of (S)-2-(7-bromo-3-methyl-3,4-dihydroquinoxaline-1(2H)-yl)benzo[d]oxazole (0.016 g, 0.046 mmol) and cyclopropanecarbonyl chloride (0.021 mL, 0.232 mmol) in 1,2-dichloroethane (1.0 mL), and the mixture stirred at 50° C. for 2.5 h. The reaction mixture was partitioned between water and dichloromethane. The aqueous phase was separated and extracted with dichloromethane. The combined organic phases were washed with brine, dried over anhydrous sodium sulfate, filtered, and concentrated to afford (S)-(4-(benzo[d]oxazol-2-yl)-6-bromo-2-methyl-3,4-dihydroquinoxaline-1(2H)-yl)(cyclopropyl)methanone (0.019 g, 99%) as a brown oil. MS (ESI, pos. ion) m/z 412, 414 [M+H]+.

Step 3. (S)-(4-(benzo[d]oxazol-2-yl)-6-(1-cyclopropyl-1H-pyrazol-4-yl)-2-methyl-3,4-dihydroquinoxaline-1(2H)-yl)(cyclopropyl)methanone A mixture of (S)-(4-(benzo[d]oxazol-2-yl)-6-bromo-2-methyl-3,4-dihydroquinoxalin-1(2H)-yl)(cyclopropyl)methanone (0.019 g, 0.046 mmol), 1-cyclopropyl-4-(4,4,5,5-tetramethyl-1,3,2-dioxaborolan-2-yl)-1H-pyrazole (0.012 g, 0.051 mmol), tris(dibenzylideneacetone)dipalladium (2.1 mg, 2.3 µmol), 2-dicyclohexylphosphino-2',4',6'-triisopropylbiphenyl (XPhos) (2.2 mg, 4.6 µmol) and cesium carbonate (0.045 g, 0.138 mmol) in dioxane (1.0 mL) and water (0.20 mL) was heated in the microwave at 100° C. for 1.5 h. The reaction mixture was filtered through Celite and concentrated to afford an orange oil. This material was purified via column chromatography on silica gel (Biotage 25 g column, gradient elution with 50-100% ethyl acetate-hexane) to afford (S)-(4-(benzo[d]oxazol-2-yl)-6-(1-cyclopropyl-1H-pyrazol-4-yl)-2-methyl-3,4-dihydroquinoxaline-1(2H)-yl)(cyclopropyl)methanone (0.014 g, 69%) as an off-white solid. $^1$H NMR (300 MHz, DMSO-$d_6$) δ ppm 0.65-1.05 (m, 11 H), 1.85-2.02 (m, 1 H), 3.58-3.80 (m, 1H), 3.90-4.16 (m, 2 H), 5.02-5.18 (m, 1 H), 7.01-7.26 (m, 2 H), 7.31 (dd, J=8.21, 1.76 Hz, 1 H), 7.35-7.58 (m, 3 H), 7.79 (s, 1 H), 8.18 (s, 1 H), 8.36 (d, J=2.05 Hz, 1 H). MS (ESI, pos. ion) m/z 440 [M+H]+.

Example 133

(S)-1-(6-(1-cyclopropyl-1H-pyrazol-4-yl)-4-(1H-indazol-3-yl)-2-methyl-3,4-dihydroquinoxaline-1(2H)-yl)ethan-1-one (I-93)

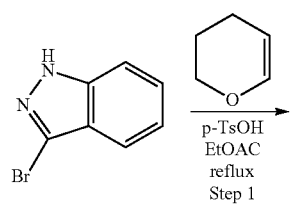

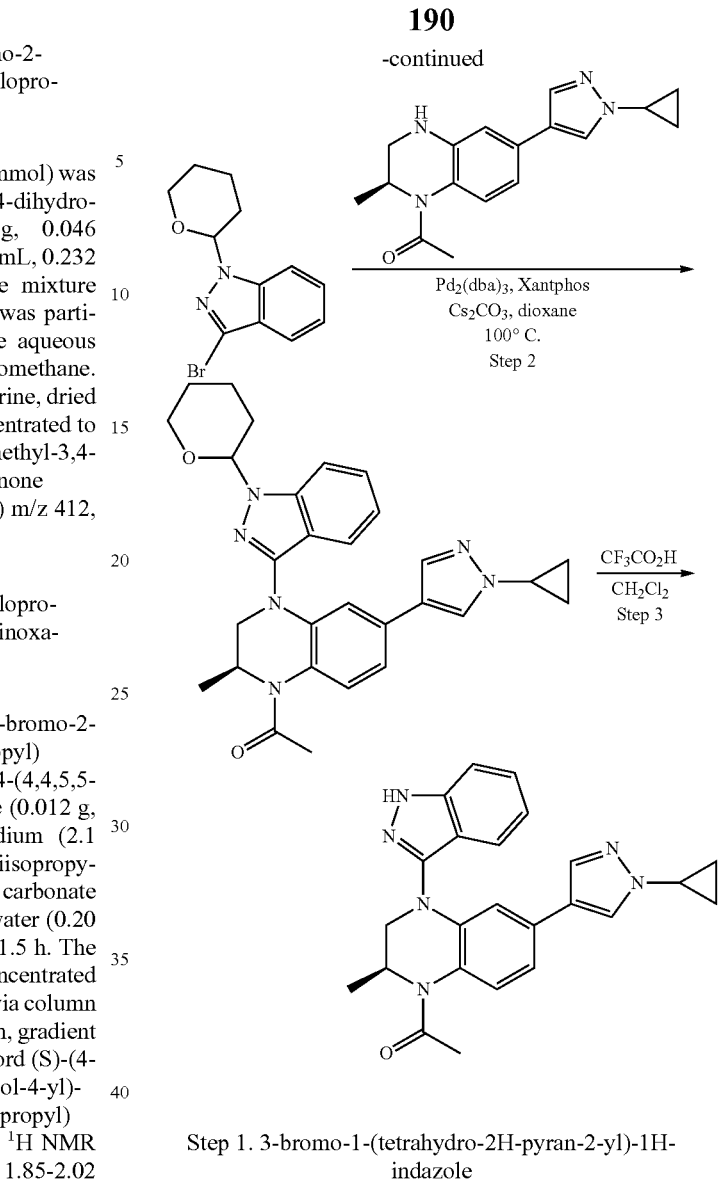

Step 1. 3-bromo-1-(tetrahydro-2H-pyran-2-yl)-1H-indazole 3,4-Dihydro-2H-pyran (0.232 mL, 2.54 mmol) and p-toluenesulfonic acid monohydrate (0.024 g, 0.127 mmol) were added to a solution of 3-bromo-1H-indazole (0.250 g, 1.269 mmol) in ethyl acetate (12.0 ml), and the mixture was heated at reflux for 48 h. The reaction mixture was partitioned between ethyl acetate and saturated aqueous sodium bicarbonate solution. The aqueous phase was separated and extracted with ethyl acetate. The combined organic phases were washed with brine, dried over anhydrous sodium sulfate, filtered, and concentrated to afford an orange oil. This material was purified via column chromatography on silica gel (Biotage 25 g column. gradient elution with 0-25% ethyl acetate-hexane) to afford 3-bromo-1-(tetrahydro-2H-pyran-2-yl)-1H-indazole (0.350 g, 98%) as a colorless oil. MS (ESI, pos. ion) m/z 281, 283 [M+H]+.

Step 2. 1-((2S)-6-(1-cyclopropyl-1H-pyrazol-4-yl)-2-methyl-4-(1-(tetrahydro-2H-pyran-2-yl)-1H-indazol-3-yl)-3,4-dihydroquinoxaline-1(2H)-yl)ethanone A mixture of (S)-1-(6-(1-cyclopropyl-1H-pyrazol-4-yl)-2-methyl-3,4-dihydroquinoxaline-1(2H)-yl)ethanone (0.050 g, 0.169 mmol), 3-bromo-1-(tetrahydro-2H-pyran-2-yl)-1H-indazole (0.071 g, 0.253 mmol), tris(dibenzylideneacetone)dipalladium (0.015 g, 0.017 mmol), 4,5-bis(diphenylphosphino)-9,9-dimethylxanthene (Xantphos) (0.020 g, 0.034 mmol), cesium carbonate (0.165 g, 0.506 mmol), and t-butanol (2.0 mL) was heated in the microwave at 100° C. for 4 h. A second portion of 3-bromo-1-(tetrahydro-2H-pyran-2-yl)-1H-indazole (0.071 g, 0.253 mmol), tris(dibenzylideneacetone)dipalladium (0.015 g, 0.017 mmol), Xantphos (0.020 g, 0.034 mmol), cesium carbonate (0.165 g, 0.506 mmol) and dioxane (2.0 mL) was added, and the mixture stirred at 100° C. for 4.5 h. A third portion of 3-bromo-1-(tetrahydro-2H-pyran-2-yl)-1H-indazole (0.071 g, 0.253 mmol), tris(dibenzylideneacetone)dipalladium (0.015 g, 0.017 mmol), Xantphos (0.020 g, 0.034 mmol), and cesium carbonate (0.165 g, 0.506 mmol) was added, and the mixture stirred at 100° C. for 18 h. The reaction mixture was filtered through Celite and concentrated to afford an orange oil. This material was purified via column chromatography on silica gel (Biotage 25 g column, gradient elution with 50-100% ethyl acetate-hexane) to afford 1-((2S)-6-(1-cyclopropyl-1H-pyrazol-4-yl)-2-methyl-4-(1-(tetrahydro-2H-pyran-2-yl)-1H-indazol-3-yl)-3,4-dihydroquinoxaline-1(2H)-yl)ethanone (0.048 g, 57%) as a tan solid. MS (ESI, pos. ion) m/z 497 [M+H]+.

Step 3. (S)-1-(6-(1-cyclopropyl-1H-pyrazol-4-yl)-4-(1H-indazol-3-yl)-2-methyl-3,4-dihydroquinoxalin-1(2H)-yl)ethanone Trifluoroacetic acid (0.5 mL, 6.49 mmol) was added to a solution of 1-((2S)-6-(1-cyclopropyl-1H-pyrazol-4-yl)-2-methyl-4-(1-(tetrahydro-2H-pyran-2-yl)-1H-indazol-3-yl)-3,4-dihydroquinoxaline-1(2H)-yl)ethanone (0.048 g, 0.097 mmol) in dichloromethane (2.0 mL) and the mixture stirred at rt for 4 h. The reaction mixture was concentrated and the residue was partitioned between dichloromethane and saturated aqueous sodium bicarbonate solution. The organic phase was separated, dried over anhydrous sodium sulfate, filtered, and concentrated to afford (S)-1-(6-(1-cyclopropyl-1H-pyrazol-4-yl)-4-(1H-indazol-3-yl)-2-methyl-3,4-dihydroquinoxalin-1(2H)-yl)ethanone (0.039 g, 98%) as a tan solid. $^1$H NMR (300 MHz, DMSO-$d_6$) δ ppm 0.76-1.04 (m, 4 H), 1.09-1.33 (m, 3 H), 2.23 (s, 3 H), 3.54-3.77 (m, 2 H), 3.78-3.99 (m, 1 H), 4.36 (br s, 1 H), 6.67-6.85 (m, 1 H), 6.87-7.14 (m, 2 H), 7.26-7.46 (m, 4 H), 7.53 (d, J=8.50 Hz, 1 H), 7.87 (s, 1 H), 12.70-12.87 (m, 1 H). MS (ESI, pos. ion) m/z 413 [M+H]+.

The following examples were made according to the procedure outlined for Example 133

Example 134

(S)-1-(4-(1H-indazol-3-yl)-2-methyl-6-(4-(methylsulfonyl)phenyl)-3,4-dihydroquinoxaline-1(2H)-yl)ethan-1-one (I-94)

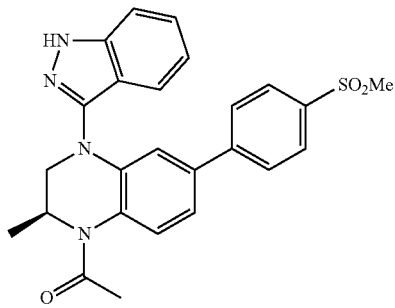 [SMILES: CC(=O)N1c2ccc(-c3ccc(S(C)(=O)=O)cc3)cc2N(c2n[nH]c3ccccc23)C[C@@H]1C]

$^1$H NMR (300 MHz, DMSO-$d_6$) δ ppm 1.22 (br d, J=5.57 Hz, 3 H), 2.29 (s, 3 H), 3.17 (s, 3 H), 3.35-3.48 (m, 1 H), 3.72 (br d, J=13.78 Hz, 1 H), 3.82-4.04 (m, 1 H), 6.90 (d, J=1.76 Hz, 1 H), 7.01-7.23 (m, 2 H), 7.31-7.48 (m, 2 H), 7.48-7.67 (m, 4 H), 7.84 (d, J=8.21 Hz, 2 H), 12.90 (s, 1 H). MS (ESI, pos. ion) m/z 461 [M+H]+.

Example 135

(S)-1-(4-(benzo[d]isoxazol-3-yl)-6-(1-cyclopropyl-1H-pyrazol-4-yl)-2-methyl-3,4-dihydroquinoxaline-1(2H)-yl)ethanone (I-95)

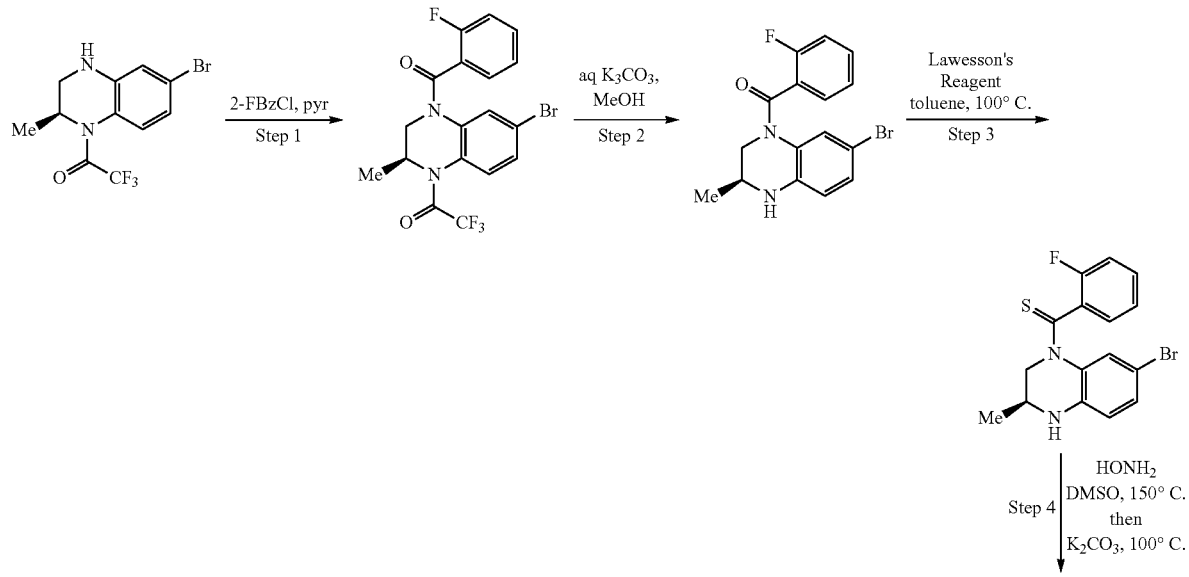

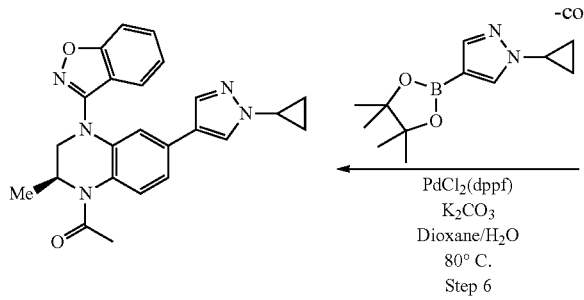 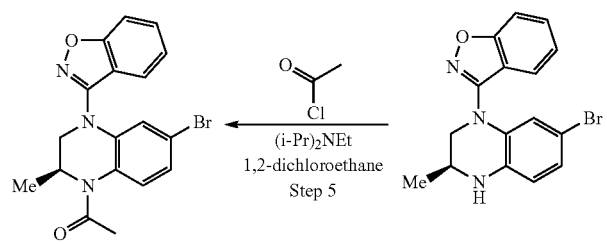

Step 1. (S)-1-(6-bromo-4-(2-fluorobenzoyl)-2-methyl-3,4-dihydroquinoxaline-1(2H)-yl)-2,2,2-trifluoroethanone A 50-mL round bottomed flask equipped with a magnetic stir bar was charged with (S)-1-(6-bromo-2-methyl-3,4-dihydroquinoxaline-1(2H)-yl)-2,2,2-trifluoroethanone (0.500 g, 1.547 mmol), dichloromethane (10 mL), and pyridine (0.188 mL, 2.321 mmol). The resulting solution was cooled to 0° C. and slowly treated with 2-fluorobenzoyl chloride (0.194 mL, 1.625 mmol). The solution was stirred at 0° C. for 1 h and then allowed to warm to rt. After stirring overnight at rt, the reaction mixture was diluted with dichloromethane and washed with 1 M aqueous HCl solution (10 mL) followed by 5% aqueous sodium chloride solution (10 mL). The dichloromethane extract was concentrated to afford crude (S)-1-(6-bromo-4-(2-fluorobenzoyl)-2-methyl-3,4-dihydroquinoxaline-1(2H)-yl)-2,2,2-trifluoroethanone (0.686 g, 100%). MS (ESI, pos. ion) m/z 445, 447 [M+1].

Step 2. (S)-(7-bromo-3-methyl-3,4-dihydroquinoxaline-1(2H)-yl)(2-fluorophenyl)methanone The crude (S)-1-(6-bromo-4-(2-fluorobenzoyl)-2-methyl-3,4-dihydroquinoxalin-1(2H)-yl)-2,2,2-trifluoroethanone (0.686 g, 1.54 mmol) was dissolved in methanol (ca. 5-10 mL) and 10% aqueous potassium carbonate solution (23 mL, 1.7 mmol) was added. After 10 min, the reaction mixture was concentrated under reduced pressure in order to remove the methanol. The residue was then partitioned between ethyl acetate and water (ca. 5-8 mL). The organic layer was separated and washed with 5% aqueous sodium chloride solution (8 mL) and then concentrated under reduced pressure. The crude product was dissolved in toluene and concentrated. The residue was purified by column chromatography on silica gel (eluting with 4:1 hexanes-ethyl acetate followed by 2:1 hexanes-ethyl acetate) to afford (S)-(7-bromo-3-methyl-3,4-dihydroquinoxaline-1(2H)-yl)(2-fluorophenyl)methanone (0.415 g, 77%). MS (ESI, pos. ion) m/z 349, 351 [M+1].

Step 3. (S)-(7-bromo-3-methyl-3,4-dihydroquinoxaline-1(2H)-yl)(2-fluorophenyl)methane thione A screw-cap vial equipped with a magnetic stir bar was charge with (S)-(7-bromo-3-methyl-3,4-dihydroquinoxaline-1(2H)-yl)(2-fluorophenyl)methanone (0.050 g, 0.143 mmol), toluene (1 mL), and 2,4-bis(4-methoxyphenyl)-1,3,2,4-dithiadiphosphetane-2,4-dithione (Lawesson's Reagent) (0.035 g, 0.086 mmol). The head space was flushed with nitrogen, the vial capped, and the mixture heated to 100° C. After about 10-15 min, the reaction mixture turned yellow. After 45 min, heating was discontinued. After cooling, the reaction mixture was loaded directly onto a preparative thin layer chromatography plate (1000 micron), and eluted with 4:1 hexanes-ethyl acetate. The non-polar, yellow band was isolated and afforded (S)-(7-bromo-3-methyl-3,4-dihydroquinoxaline-1(2H)-yl)(2-fluorophenyl)methanethione (0.042 g, 80%) as a bright yellow solid. MS (ESI, pos. ion) m/z 365, 367 [M+1].

Step 4. (S)-3-(7-bromo-3-methyl-3,4-dihydroquinoxaline-1(2H)-yl)benzo[d]isoxazole A screw-cap vial equipped with a magnetic stir bar was charged with a solution of (S)-(7-bromo-3-methyl-3,4-dihydroquinoxaline-1(2H)-yl)(2-fluorophenyl)methanethione (0.021 g, 0.057 mmol) in dimethylsulfoxide (0.5 mL) and hydroxylamine (50% in water, 0.035 mL, 0.575 mmol). The vial was capped, and the solution heated to 100° C. for 90 min. Heating was increased to 150° C. for 3 h, and then the solution was stirred at rt overnight. Additional hydroxylamine (50% in water, 0.035 mL, 0.575 mmol) was added and heating resumed at 150° C. for 5 h. Potassium carbonate (ca. 10-15 mg) was added and heating resumed at 100° C. for 5 h. The mixture was diluted with water (1 mL) and extracted with dichloromethane. The dichloromethane extract was washed with 5% aqueous sodium chloride solution (1 mL) and concentrated. The crude product was purified by preparative thin layer chromatography (1×1000 micron plate, eluting with 4:1 hexanes-ethyl acetate). The major band was isolated to afford (S)-3-(7-bromo-3-methyl-3,4-dihydroquinoxaline-1(2H)-yl)benzo[d]isoxazole (0.010 g, 51%). MS (ESI, pos. ion) m/z 344, 346 [M+1].

Step 5. (S)-1-(4-(benzo[d]isoxazol-3-yl)-6-bromo-2-methyl-3,4-dihydroquinoxaline-1(2H)-yl)ethanone A reaction vial was charged with (S)-3-(7-bromo-3-methyl-3,4-dihydroquinoxalin-1(2H)-yl)benzo[d]isoxazole (10.33 mg, 0.03 mmol) and 1,2-dichloroethane (0.30 mL). N,N-Diisopropylethylamine (0.026 mL, 0.150 mmol) and acetyl chloride (6.4 µl, 0.090 mmol) were added, and the mixture stirred at 50° C. for 1.5 h. The reaction was diluted with ethyl acetate and washed with brine. The aqueous layer was separated and washed with ethyl acetate, and the combined organic layers were concentrated under a stream of nitrogen to afford (S)-1-(4-(benzo[d]isoxazol-3-yl)-6-bromo-2-methyl-3,4-dihydroquinoxaline-1(2H)-yl)ethanone (0.012 g, 0.03 mmol) which was used without purification. MS (ESI, pos. ion) m/z 386

Step 6. (S)-1-(4-(benzo[d]isoxazol-3-yl)-6-(1-cyclopropyl-1H-pyrazol-4-yl)-2-methyl-3,4-dihydroquinoxaline-1(2H)-yl)ethanone A 1.5 mL reaction vial was charged with (S)-1-(4-(benzo[d]isoxazol-3-yl)-6-bromo-2-methyl-3,4-dihydroquinoxaline-1(2H)-yl)ethanone (0.012 g, 0.03 mmol), 1-cyclopropyl-4-(4,4,5,5-tetramethyl-1,3,2-dioxaborolan-2-yl)-1H- pyrazole (0.2 M in 1,4-dioxane, 225 μL, 0.03 mmol), and dioxane (0.1 mL). Potassium carbonate (1 M solution in water, 90 μL, 0.09 mmol) was added, and the reaction mixture was purged with nitrogen. [1,1'-Bis(diphenylphosphino)ferrocene]dichloropalladium(II) (0.02 M solution in 1,2-dichloroethane, 150 μL, 0.003 mmol) was added, the reaction was purged with nitrogen, and heated overnight at 80° C. on a heater shaker. The reaction was diluted with ethyl acetate and washed with 1 N aqueous sodium hydroxide solution. The aqueous layer was separated and washed with ethyl acetate and the combined organic layers were concentrated under a stream of nitrogen. The crude product was purified by mass triggered preparatory HPLC. The product-containing fractions were combined and concentrated in a Genevac to afford 1-[(2S)-4-[(furan-2-yl)carbonyl]-6-(5-methanesulfonylpyridin-2-yl)-2-methyl-1,2,3,4-tetrahydroquinoxalin-1-yl]ethan-1-one (0.0026 g, 22%). MS (ESI, pos. ion) m/z 414 [M+H]+.

Example 136

(S)-furan-2-yl(3-methyl-4-(methylsulfonyl)-7-(4-(methylsulfonyl)phenyl)-3,4-dihydroquinoxaline-1(2H)-yl)methanone (I-96)

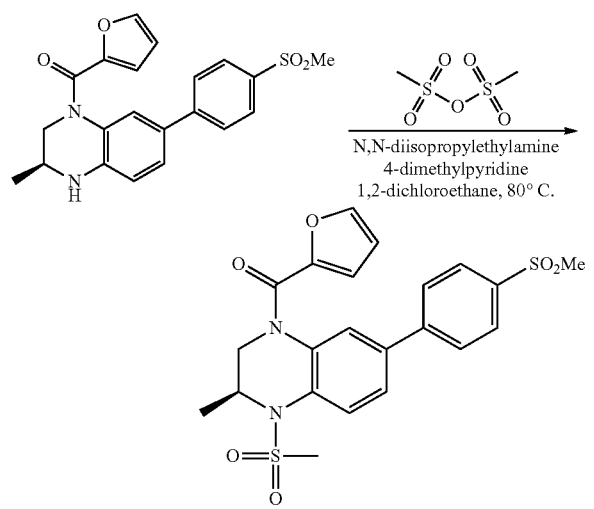

A 1.5 mL reaction vial was charged with (S)-furan-2-yl(3-methyl-7-(4-(methylsulfonyl)phenyl)-3,4-dihydroquinoxaline-1(2H)-yl)methanone (0.1M solution in 1,2-dichloroethane, 400 μL, 0.04 mmol). N,N-Diisopropylethylamine (50 μL, 0.28 mmol) was then added followed by the addition of methanesulfonic anhydride (0.035 g, 0.20 mmol) and 4-dimethylaminopyridine (4.89 mg, 0.040 mmol)). The reaction was heated on a heater shaker at 80° C. for 4 h. Benzoyl chloride (4.6 μL, 0.04 mmol) was added to the reaction mixture and the reaction was placed on a heater shaker at room temperature for 2 h. The reaction was diluted with ethyl acetate and washed with 1 N aqueous sodium hydroxide solution. The aqueous layer was separated and washed with ethyl acetate and the combined organic layers were concentrated under a stream of nitrogen. The crude product was purified by mass triggered preparatory HPLC. The product-containing fractions were combined and concentrated in a Genevac to afford (S)-furan-2-yl(3-methyl-4-(methylsulfonyl)-7-(4-(methylsulfonyl)phenyl)-3,4-dihydroquinoxaline-1(2H)-yl)methanone (0.0011 g, 5%). MS (ESI, pos. ion) m/z 575

Example 137

(S)-1-(4-(cyclopropanecarbonyl)-2-methyl-6-phenoxy-3,4-dihydropyrido[2,3-b]pyrazine-1(2H)-yl)ethanone (I-97)

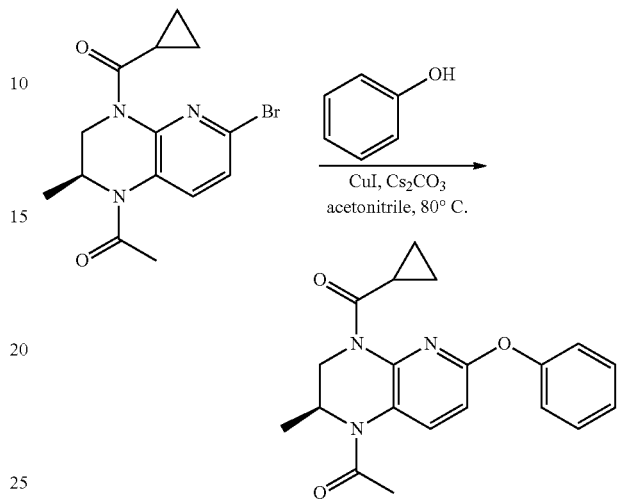

A 1.5 mL reaction vial was charged with (S)-1-(6-bromo-4-(cyclopropanecarbonyl)-2-methyl-3,4-dihydropyrido[2,3-b]pyrazine-1(2H)-yl)ethanone (synthesized from Intermediate 6 and cyclopropane carbonyl chloride according to the procedure used to prepare Intermediate 15, 6.76 mg, 0.02 mmol), phenol (3.76 mg, 0.040 mmol), copper (I) iodide (0.762 mg, 4.00 μmol), cesium carbonate (0.012 g, 0.036 mmol), and acetonitrile (250 μL). The reaction was heated on a heater shake at 80° C. for 18 hrs. The reaction was diluted with ethyl acetate and washed with 1 N aqueous sodium hydroxide solution. The aqueous layer was separated and washed with ethyl acetate and the combined organic layers were concentrated under a stream of nitrogen. The crude product was purified by mass triggered preparatory HPLC. The product-containing fractions were combined and concentrated in a Genevac to afford (S)-1-(4-(cyclopropanecarbonyl)-2-methyl-6-phenoxy-3,4-dihydropyrido[2,3-b]pyrazine-1 (2H)-yl)ethanone (0.0039 g, 56%). MS (ESI, pos. ion) m/z 352.

Example 138 phenyl (S)-4-acetyl-3-methyl-7-(4-(piperazine-1-carbonyl)phenyl)-3,4-dihydroquinoxaline-1(2H)-carboxylate (I-99)

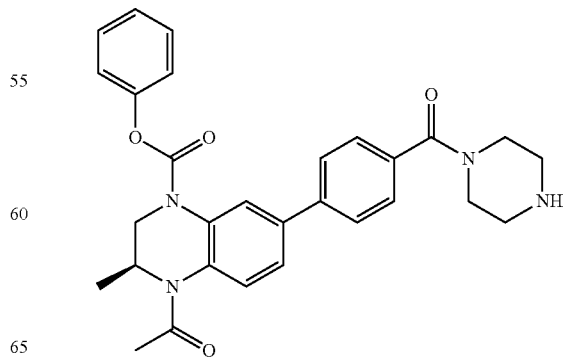

Step 1. (S)-tert-butyl 4-(4-(1-acetyl-2-methyl-1,2,3,4-tetrahydroquinoxalin-6-yl)benzoyl)piperazine-1-carboxylate A mixture of (S)-1-(6-bromo-2-methyl-3,4-dihydroquinoxaline-1(2H)-yl)ethanone (0.200 g, 0.743 mmol), tert-butyl 4-(4-(4,4,5,5-tetramethyl-1,3,2-dioxaborolan-2-yl)benzoyl)piperazine-1-carboxylate (0.340 g, 0.817 mmol), bis(triphenylphosphine)palladium (II) dichloride (0.052 g, 0.074 mmol), and sodium bicarbonate (1 M in water, 1.5 mL, 1.5 mmol) in 1,4-dioxane (3.7 mL) was heated at 80° C. for 16 h. The reaction mixture was filtered through Celite and concentrated to afford an orange oil. This material was purified via column chromatography on silica gel (gradient elution with 0-100% ethyl acetate-hexane) to afford (S)-tert-butyl 4-(4-(1-acetyl-2-methyl-1,2,3,4-tetrahydroquinoxalin-6-yl)benzoyl)piperazine-1-carboxylate (0.294 g, 83%) as an off-white solid. MS (ESI, pos. ion) m/z 479.

Step 2. phenyl (S)-4-acetyl-3-methyl-7-(4-(piperazine-1-carbonyl)phenyl)-3,4-dihydroquinoxaline-1(2H)-carboxylate A reaction vial was charged with (S)-tert-butyl 4-(4-(1-acetyl-2-methyl-1,2,3,4-tetrahydroquinoxalin-6-yl)benzoyl)piperazine-1-carboxylate (0.2 M in 1,2-dichloroethane, 100 µL, 0.02 mmol), N,N-diisopropylethyl amine (25 µL, 0.14 mmol), and phenyl chloroformate (6.23 mg, 0.04 mmol), and the mixture was shaken at 50° C. for 2 h. Methanol (50 µL) was added and the mixture was shaken at 50° C. for 10 min. HCl (4 M in dioxane, 0.075 mL, 0.30 mmol) was added and the reaction was shaken at 50° C. for 2 h. The mixture was concentrated and the residue was purified by mass triggered preparatory HPLC. The product-containing fractions were combined and concentrated in a Genevac to afford phenyl (S)-4-acetyl-3-methyl-7-(4-(piperazine-1-carbonyl)phenyl)-3,4-dihydroquinoxaline-1(2H)-carboxylate. MS (ESI, pos. ion) m/z 499.

Example 139

(S)-1-(2-methyl-6-(4-(methylsulfonyl)phenyl)-4-(pyrrolidine-1-carbonyl)-3,4-dihydroquinoxaline-1(2H)-yl)ethanone (I-100)

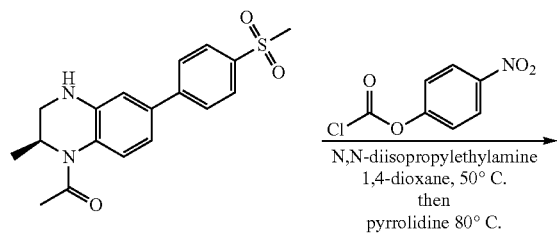

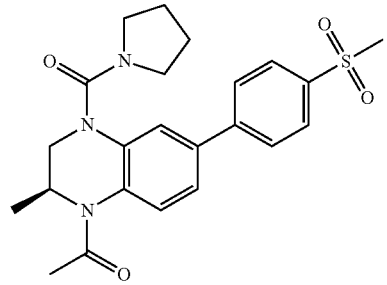

4-Nitrophenyl chloroformate (0.4 M in 1,4-dioxane, 0.075 mL, 0.030 mmol) and N,N-diisopropylethylamine (0.015 mL, 0.086 mmol) were added to (S)-1-(2-methyl-6-(4-(methylsulfonyl)phenyl)-3,4-dihydroquinoxaline-1(2H)-yl)ethanone (0.2 M in 1,4-dioxane, 0.100 mL, 0.020 mmol) and the mixture stirred at 50° C. for 1 h. Pyrrolidine (0.2 M in 1,4-dioxane, 0.200 mL, 0.040 mmol) was then added and the mixture was stirred at 80° C. for 16 h. The reaction was concentrated and the crude product was purified by mass-triggered preparatory HPLC. The product-containing fractions were combined and concentrated to afford (S)-1-(2-methyl-6-(4-(methylsulfonyl)phenyl)-4-(pyrrolidine-1-carbonyl)-3,4-dihydroquinoxaline-1(2H)-yl)ethanone (0.0038 g, 43% yield). MS (ESI, pos. ion) m/z 442

Example 140

(S)-1-(4-(furan-2-carbonyl)-2-methyl-6-(pyrrolidine-1-carbonyl)-3,4-dihydroquinoxaline-1(2H)-yl)ethanone (I-101)

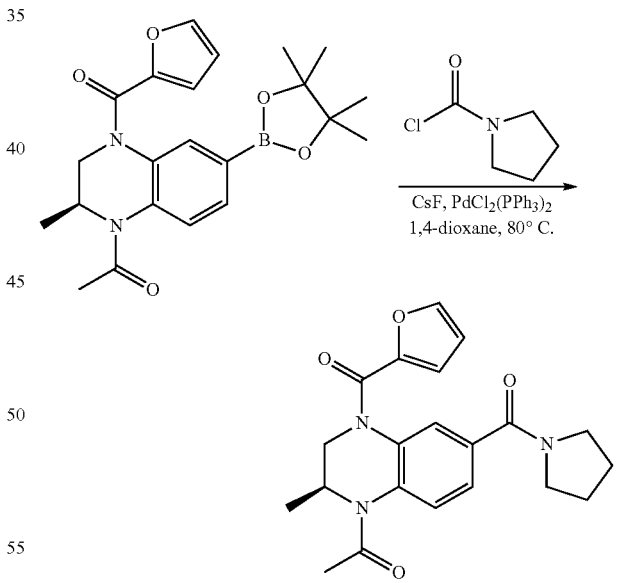

A 1.5 mL reaction vial was charged with (S)-1-(4-(furan-2-carbonyl)-2-methyl-6-(4,4,5,5-tetramethyl-1,3,2-dioxaborolan-2-yl)-3,4-dihydroquinoxalin-1(2H)-yl)ethanone (0.2 M in 1,4-dioxane, 150 µL, 0.03 mmol), and pyrrolidine-1-carbonyl chloride (4 mg, 0.030 mmol). Cesium fluoride was then added (5 mg, 0.030 mmol) and the reaction mixture was purged with nitrogen. Bis(triphenylphosphine)palladium (II) dichloride (1 mg, 0.0015) was then added, and the reaction was purged with nitrogen and heated overnight at 80° C. on a heater shaker. The reaction was diluted with ethyl acetate (0.5 mL) washed with brine (0.5 mL). The aqueous layer was separated and washed with ethyl acetate (1 mL) and the combined organic layers were concentrated under a stream of nitrogen. The crude product was purified by mass triggered preparatory HPLC. The product-containing fractions were combined and concentrated in a Genevac to afford (S)-1-(4-(furan-2-carbonyl)-2-methyl-6-(pyrrolidine-1-carbonyl)-3,4-dihydroquinoxaline-1(2H)-yl)ethanone (0.0009 g, 8%). MS (ESI, pos. ion) m/z 382.

Example 141

(S)-4-acetyl-3-methyl-7-(4-(methylsulfonyl)phenyl)-3,4-dihydroquinoxaline-1(2H)-carbaldehyde (I-102)

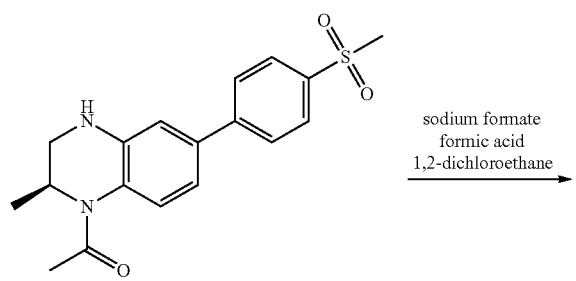

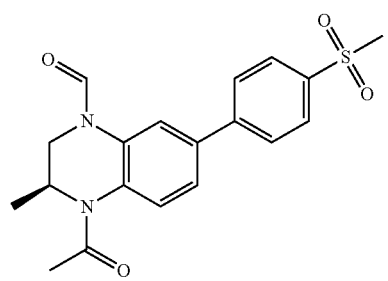

Sodium formate (14 mg, 0.200 mmol) and formic acid (46 mg, 1.0 mmol) were added to (S)-1-(2-methyl-6-(4-(methylsulfonyl)phenyl)-3,4-dihydroquinoxaline-1(2H)-yl)ethanone (0.2 M in 1,2-dichloroethane, 0.1 mL, 0.02 mmol) and shaken at room temperature for 5 h. The reaction was concentrated and the crude product was purified by mass-triggered preparatory HPLC. The product-containing fractions were combined and concentrated to afford (S)-4-acetyl-3-methyl-7-(4-(methylsulfonyl)phenyl)-3,4-dihydroquinoxaline-1 (2H)-carbaldehyde (0.0034 g, 46%). MS (ESI, pos. ion) m/z 373

Example 142

(S)-4-(furan-2-carbonyl)-2-methyl-6-(4-(methylsulfonyl)phenyl)-3,4-dihydroquinoxaline-1(2H)-carbaldehyde (I-103)

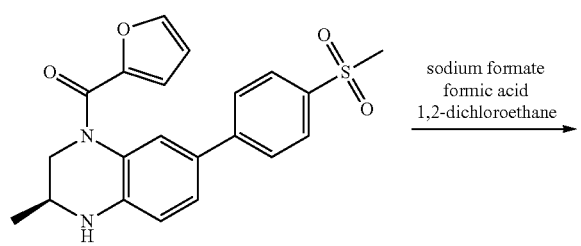

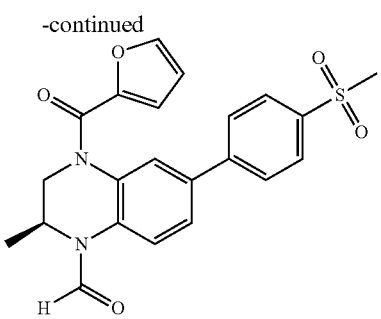

Sodium formate (14 mg, 0.200 mmol) and formic acid (46 mg, 1.0 mmol) were added to (S)-furan-2-yl(3-methyl-7-(4-(methylsulfonyl)phenyl)-3,4-dihydroquinoxaline-1(2H)-yl) methanone (0.2 M in 1,2-dichloroethane, 0.1 mL, 0.02 mmol) and shaken at room temperature for 5 h. The reaction was concentrated and the crude product was purified by mass-triggered preparatory HPLC. The product-containing fractions were combined and concentrated to afford (S)-4-(furan-2-carbonyl)-2-methyl-6-(4-(methylsulfonyl)phenyl)-3,4-dihydroquinoxaline-1(2H)-carbaldehyde (0.0061 g, 72%). MS (ESI, pos. ion) m/z 425.

Example 143

(S)-1-(2,4-dimethyl-6-(4-(methylsulfonyl)phenyl)-3,4-dihydroquinoxalin-1(2H)-yl)ethanone (I-104)

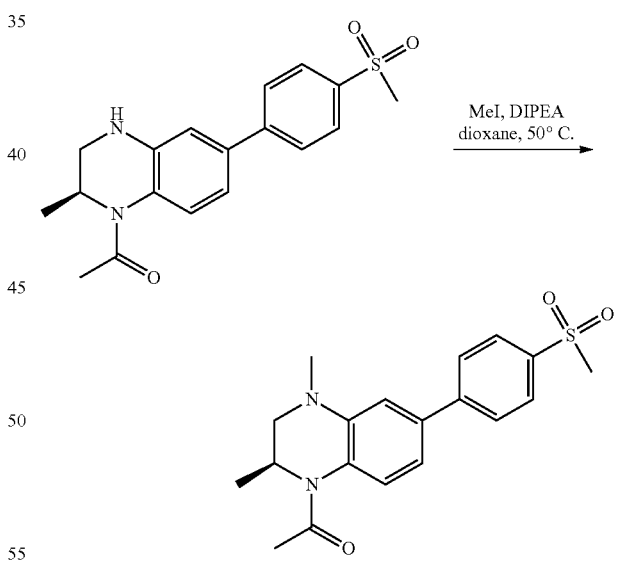

Iodomethane (0.025 mL, 0.400 mmol) was added to a solution of (S)-1-(2-methyl-6-(4-(methylsulfonyl)phenyl)-3,4-dihydroquinoxaline-1(2H)-yl)ethanone and the mixture was stirred at 50° C. for 16 h. The reaction was concentrated and the crude product was purified by mass-triggered preparatory HPLC. The product-containing fractions were combined and concentrated to afford (S)-1-(6-(5-amino-1,3,4-thiadiazol-2-yl)-4-(furan-2-carbonyl)-2-methyl-3,4-dihydroquinoxaline-1(2H)-yl)ethanone (0.0022 g, 30% yield). MS (ESI, pos. ion) m/z 359.

Example 144

(S)-1-(4-acetyl-3-methyl-7-(1-(oxetan-3-yl)-1H-pyrazol-4-yl)-3,4-dihydroquinoxalin-1(2H)-yl)-3-methylbutan-1-one (I-105)

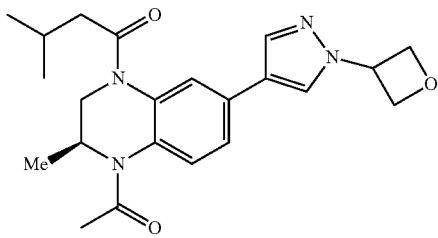 [SMILES: CC(=O)N1c2ccc(-c3cnn(C4COC4)c3)cc2N(C(=O)CC(C)C)C[C@@H]1C]

Step 1. 3-methylbutanoyl chloride

A 100-mL round-bottom flask was charged with 3-methylbutanoic acid (500 mg, 4.90 mmol) and thionyl chloride (20 mL). The resulting solution was stirred for 6 h at 80° C. in an oil bath and then concentrated under vacuum to afford 3-methylbutanoyl chloride (510 mg, 86%) as yellow oil, which was directly used into next step without any purification.

Step 2. (S)-1-(4-acetyl-3-methyl-7-(1-(oxetan-3-yl)-1H-pyrazol-4-yl)-3,4-dihydroquinoxalin-1(2H)-yl)-3-methylbutan-1-one A 100-mL round-bottom flask was charged with (S)-1-(2-methyl-6-(1-(oxetan-3-yl)-1H-pyrazol-4-yl)-3,4-dihydroquinoxaline-1(2H)-yl)ethanone (50 mg, 0.16 mmol), 3-methylbutanoyl chloride (93 mg, 0.77 mmol), pyridine (63 mg, 0.80 mmol, 5.00 equiv) and dichloromethane (30 mL). The resulting solution stirred for 30 min at 0° C. in a water/ice bath and an additional 3 h at room temperature. The reaction mixture was concentrated under vacuum. The residue was purified by column chromatography on silica gel (eluting with 2-50% ethyl acetate-petroleum ether) to afford (S)-1-(4-acetyl-3-methyl-7-(1-(oxetan-3-yl)-1H-pyrazol-4-yl)-3,4-dihydroquinoxaline-1(2H)-yl)-3-methylbutan-1-one (26.7 mg, 42%) of as light yellow oil. $^1$H NMR (300 MHz, CD$_3$OD) δ ppm 079 (br s, 3 H), 0.93 (d, J=6.60 Hz, 3 H), 1.18 (d, J=6.30 Hz, 3 H), 1.90-2.10 (m, 1 H), 2.42 (s, 3 H), 2.35-2.43 (m, 1 H), 2.48-2.50 (m, 1 H), 2.51-2.89 (m, 1 H), 4.80-4.95 (m, 2 H), 5.08 (d, J=6.90 Hz, 4 H), 5.55-5.65 (m, 1 H), 7.38-7.45 (m, 1 H), 7.55-7.75 (m, 2 H), 8.03 (s, 1 H), 8.24 (s, 1 H). MS (ESI, pos. ion) m/z 425 [M+H]$^+$.

The following examples were made according to the procedure outlined for Example 144

Example 145

(S)-1-(4-acetyl-3-methyl-7-(1-(oxetan-3-yl)-1H-pyrazol-4-yl)-3,4-dihydroquinoxaline-1(2H)-yl)-3,3,3-trifluoropropane-1-one (I-108)

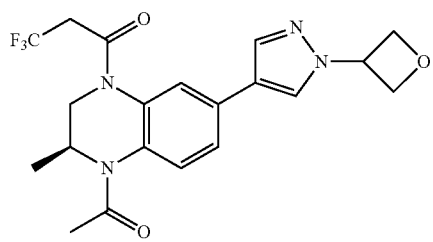 [SMILES: CC(=O)N1c2ccc(-c3cnn(C4COC4)c3)cc2N(C(=O)CC(F)(F)F)C[C@@H]1C]

$^1$H NMR (300 MHz, CD$_3$OD) δ ppm 1.20 (d, J=6.60 Hz, 3 H), 2.22 (s, 3 H), 2.80 (s, 1 H), 3.57-3.89 (m, 2 H), 4.89-5.06 (s, 2 H), 5.09-5.13 (m, 4 H), 5.58-5.67 (m, 1 H), 7.39-7.55 (m, 1 H), 7.56-7.90 (m, 2 H), 8.05 (s, 1 H), 8.26 (s, 1 H). MS (ESI, pos. ion) m/z 423[M+H]$^+$.

Example 146

(S)-1-(4-acetyl-3-methyl-7-(1-(oxetan-3-yl)-1H-pyrazol-4-yl)-3,4-dihydroquinoxaline-1(2H)-yl)-2-methylpropane-1-one (I-109)

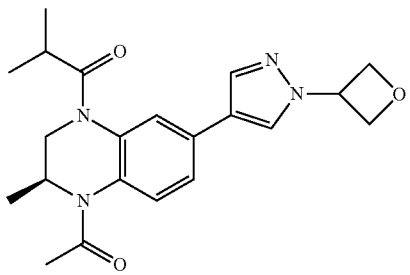 [SMILES: CC(=O)N1c2ccc(-c3cnn(C4COC4)c3)cc2N(C(=O)C(C)C)C[C@@H]1C]

$^1$H NMR (300 MHz, CD$_3$OD) δ ppm 0.97 (s, 3 H), 1.16-1.27 (m, 6 H), 2.21 (s, 3 H), 2.79 (s, 1 H), 3.10-3.23 (m, 1 H), 4.85-5.01 (s, 2 H), 5.02-5.15 (m, 4 H), 5.55-5.75 (m, 1 H), 7.35-7.55 (m, 1 H), 7.56-7.73 (m, 1 H), 7.73-7.77 (s, 1 H), 8.03 (s, 1 H), 8.25 (s, 1 H). MS (ESI, pos. ion) m/z 383 [M+H]$^+$.

Example 147

(S)-1-(2-methyl-6-(1-(oxetan-3-yl)-1H-pyrazol-4-yl)-4-(tetrahydro-2H-pyran-4-carbonyl)-3,4-dihydroquinoxaline-1(2H)-yl)ethanone (I-110)

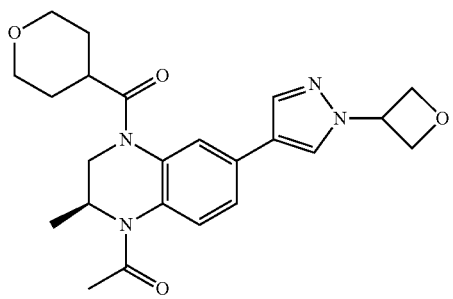 [SMILES: CC(=O)N1c2ccc(-c3cnn(C4COC4)c3)cc2N(C(=O)C2CCOCC2)C[C@@H]1C]

$^1$H NMR (300 MHz, CD$_3$OD) δ ppm 0.97 (s, 3 H), 1.20 (s, 3 H), 1.30-1.55 (m, 1 H), 1.56-1.78 (m, 1 H), 1.79-2.11 (m, 2 H), 2.23 (s, 3 H), 2.83 (s, 1 H), 3.10-3.30 (m, 2 H), 3.43-3.56 (m, 1 H), 3.86-3.96 (m, 1 H), 3.96-4.11 (m, 1 H), 4.85-5.01 (m, 2 H), 5.01-5.21 (m, 4 H), 5.50-5.67 (m, 1 H), 7.35-7.53 (m, 1 H), 7.53-7.65 (m, 1 H), 7.70 (s, 1 H), 8.03 (s, 1 H), 8.24 (s, 1 H). MS (ESI, pos. ion) m/z 425 [M+H]$^+$.

Example 148

(S)-1-(4-acetyl-3-methyl-7-(1-(oxetan-3-yl)-1H-pyrazol-4-yl)-3,4-dihydroquinoxaline-1(2H)-yl)-2-cyclopentylethanone (I-111)

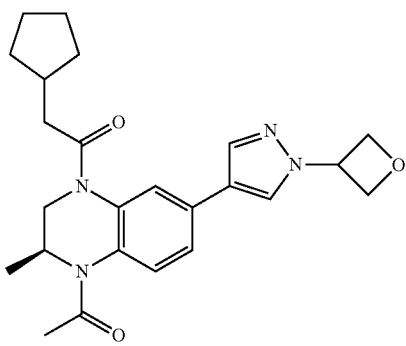 [SMILES: CC(=O)N1c2ccc(-c3cnn(C4COC4)c3)cc2N(C(=O)CC2CCCC2)C[C@@H]1C]

$^1$H NMR (300 MHz, DMSO-d$_6$) δ ppm 0.89 (s, 1 H), 1.09 (d, J=9.00 Hz, 4 H), 1.32-1.85 (m, 7 H), 2.03-2.18 (m, 4 H), 2.52-2.61 (m, 1 H), 2.72 (s, 1 H), 4.72 (s, 2 H), 2.88-5.03 (m, 4 H), 5.50-5.70 (m, 1 H), 7.50 (s, 2 H), 7.73 (s, 1 H), 8.08 (s, 1 H), 8.43 (s, 1 H). MS (ESI, pos. ion) m/z 423 [M+H]$^+$.

Example 149

1-((S)-4-((S)-2,2-dichlorocyclopropane-1-carbonyl)-2-methyl-6-(1-(oxetan-3-yl)-1H-pyrazol-4-yl)-3,4-dihydroquinoxaline-1(2H)-yl)ethan-1-one (I-112)

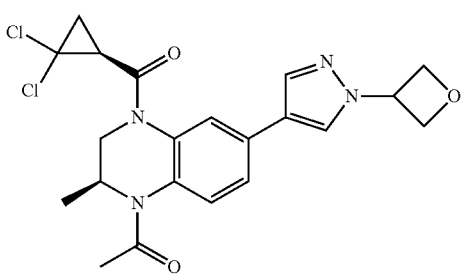 [SMILES: CC(=O)N1c2ccc(-c3cnn(C4COC4)c3)cc2N(C(=O)[C@@H]2CC2(Cl)Cl)C[C@@H]1C]

$^1$H NMR (300 MHz, CD$_3$OD) δ ppm 1.21-1.22 (m, 3 H), 1.89-2.03 (m, 1 H), 2.22 (s, 4 H), 2.78 (s, 1 H), 2.95 (s, 1 H), 3.58-3.69 (m, 1 H), 4.49-5.06 (m, 2 H), 5.08-5.13 (m, 4 H), 5.62-5.66 (m, 1 H), 7.50-7.53 (m, 1 H), 7.66-7.68 (m, 2 H), 8.10 (s, 1 H), 8.26 (s, 1 H). MS (ESI, pos. ion) m/z 449[M+H]$^+$ (stereochemistry of cyclopropane arbitrarily assigned).

Example 150

1-((S)-4-((R)-2,2-dichlorocyclopropane-1-carbonyl)-2-methyl-6-(1-(oxetan-3-yl)-1H-pyrazol-4-yl)-3,4-dihydroquinoxaline-1(2H)-yl)ethan-1-one (I-113)

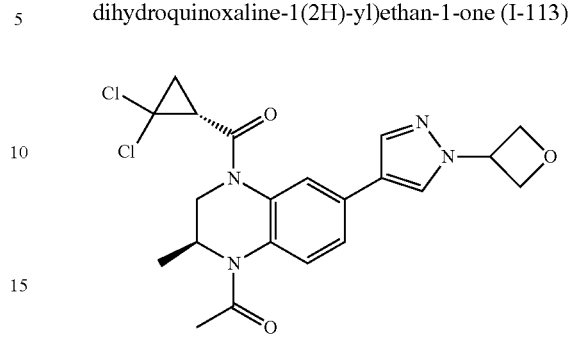

$^1$H NMR (300 MHz, CD$_3$OD) δ ppm 1.21-1.22 (m, 3 H), 1.89-1.92 (m, 2 H), 2.22 (s, 3 H), 2.83-3.10 (m, 1 H), 3.58-3.69 (m, 1 H), 4.79-4.88 (m, 2 H), 5.08-5.13 (m, 4 H), 5.62-5.66 (m, 1 H), 7.55-7.71 (m, 2 H), 7.78 (s, 1 H), 8.07 (s, 1 H), 8.28 (s, 1 H). MS (ESI, pos. ion) m/z 449[M+H]$^+$ (stereochemistry of cyclopropane arbitrarily assigned).

Example 151

(S)-1-(2-methyl-4-(1-methylcyclopropanecarbonyl)-6-(1-(oxetan-3-yl)-1H-pyrazol-4-yl)-3,4-dihydroquinoxaline-1(2H)-yl)ethanone (I-114)

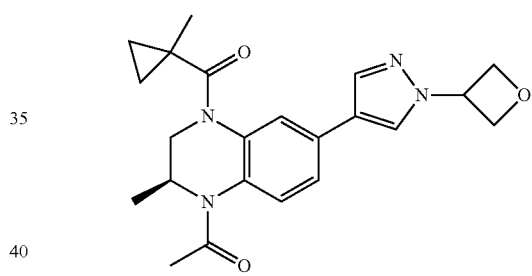

$^1$H NMR (300 MHz, CD$_3$OD) δ ppm 0.78-0.79 (m, 1 H), 0.80-0.82 (m, 1 H), 1.16-1.24 (m, 8 H), 2.23 (d, J=10.20 Hz, 3 H), 3.02 (s, 1 H), 4.80-4.84 (m, 1 H), 4.95-4.98 (m, 1 H), 5.09 (d, J=6.90 Hz, 4 H), 5.56-5.68 (m, 1 H), 7.45-7.57 (m, 2 H), 7.77 (s, 1 H), 8.01 (s, 1 H), 8.21 (s, 1 H). MS (ESI, pos. ion) m/z 395[M+H]$^+$.

Example 152

(S)-1-(4-acetyl-3-methyl-7-(1-(oxetan-3-yl)-1H-pyrazol-4-yl)-3,4-dihydroquinoxaline-1(2H)-yl)-2-chloro-2-methylpropane-1-one (I-115)

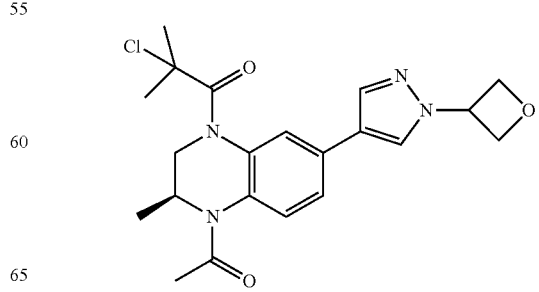

$^1$H NMR (300 MHz, DMSO-d$_6$) δ ppm 1.11 (d, J=6.00 Hz, 3 H), 1.77-1.85 (m, 6H), 2.09 (s, 3 H), 2.95 (s, 1 H), 4.70-4.85 (m, 1 H), 4.89-5.01 (m, 5 H), 7.48-7.55 (m, 2 H), 7.71 (s, 1 H), 8.03 (s, 1 H), 8.41 (s, 1 H). MS (ESI, pos. ion) m/z 417[M+H]$^+$.

Example 153

(S)-1-(4-acetyl-3-methyl-7-(1-(oxetan-3-yl)-1H-pyrazol-4-yl)-3,4-dihydroquinoxaline-1(2H)-yl)-2,2-difluoroethanone (I-106)

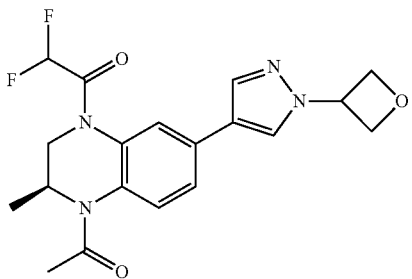 [SMILES: CC(=O)N1c2ccc(-c3cnn(C4COC4)c3)cc2N(C(=O)C(F)F)C[C@@H]1C]

$^1$H NMR (300 MHz, CD$_3$OD) δ ppm 1.2 (s, 3 H), 2.22 (s, 3 H), 2.86 (s, 1 H), 4.89-5.03 (m, 2 H), 5.06-5.17 (m, 4 H), 5.50-5.69 (m, 1 H), 6.47-6.74 (m, 1 H), 7.40-7.52 (m, 1 H), 7.52-7.78 (s, 2 H), 8.02 (s, 1 H), 8.22 (s, 1 H). MS (ESI, pos. ion) m/z 391[M+H]$^+$.

Example 154

(S)-1-(4-acetyl-3-methyl-7-(1-(oxetan-3-yl)-1H-pyrazol-4-yl)-3,4-dihydroquinoxaline-1(2H)-yl)-2-cyclopropylethanone (I-107)

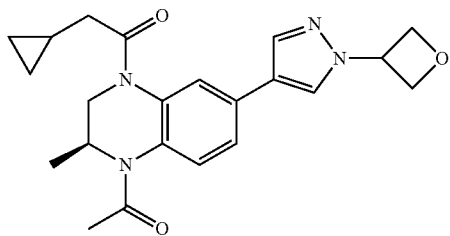 [SMILES: CC(=O)N1c2ccc(-c3cnn(C4COC4)c3)cc2N(C(=O)CC2CC2)C[C@@H]1C]

$^1$H NMR (300 MHz, CD$_3$OD) δ ppm 0.84 (s, 1 H), 0.19 (s, 1 H), 0.48-0.50 (s, 2 H), 0.97 (s, 1 H), 1.19 (d, J=4.00 Hz, 3 H), 2.22 (s, 3 H), 2.52 (d, J=6.90 Hz, 2 H), 2.81 (s, 1 H), 4.89-5.01 (m, 2 H), 5.09 (d, J=6.90 Hz, 4 H), 5.57-5.66 (m, 1 H), 7.44-7.47 (m, 1 H), 7.56-7.59 (m, 1 H), 7.72 (s, 1 H), 8.03 (s, 1 H), 8.25 (s, 1 H). MS (ESI, pos. ion) m/z 395[M+H]$^+$.

Example 155

(S)-isopropyl 4-acetyl-3-methyl-7-(1-(pyrazin-2-ylmethyl)-1H-pyrazol-4-yl)-3,4-dihydroquinoxaline-1(2H)-carboxylate (I-116)

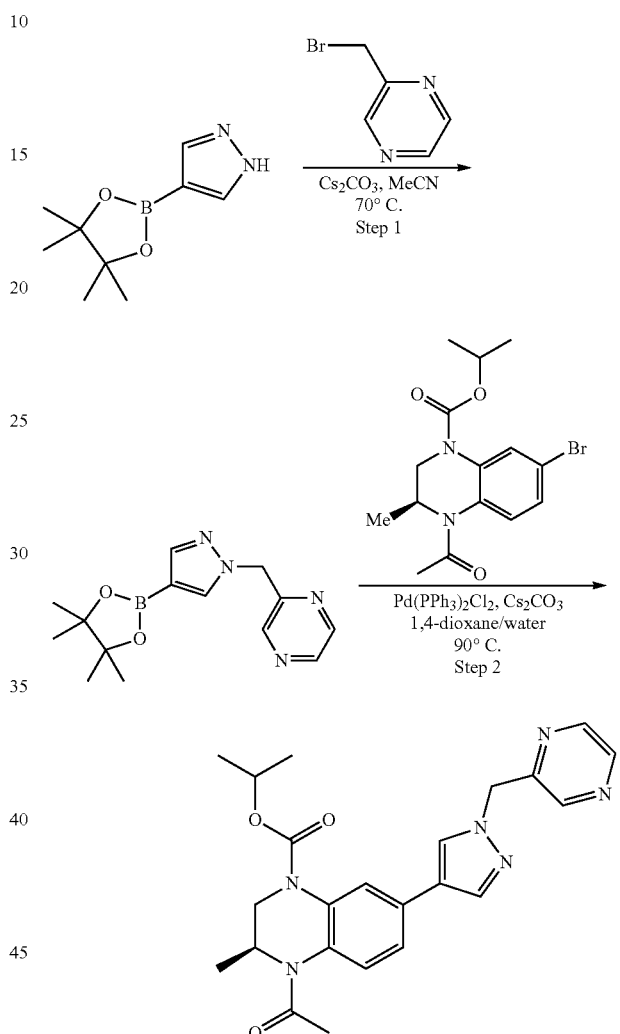

Step 1. 2-[[4-(tetramethyl-1,3,2-dioxaborolan-2-yl)-1H-pyrazol-1-yl]methyl]pyrazine A 100-mL round-bottom flask was charged with a solution of 4-(tetramethyl-1,3,2-dioxaborolan-2-yl)-1H-pyrazole (265 mg, 1.37 mmol), acetonitrile (40 mL), 2-(bromomethyl)pyrazine dihydrochloride (500 mg, 2.03 mmol) and cesium carbonate (2.23 g, 6.84 mmol). The resulting mixture stirred overnight at 70° C. After cooling to room temperature, the reaction mixture was filtered and the filtrate was concentrated under reduced pressure. The residue was purified by preparative thin layer chromatography (eluting with 2:1, ethyl acetate/petroleum ether) to afford 2-[[4-(tetramethyl-1,3,2-dioxaborolan-2-yl)-1H-pyrazol-1-yl]methyl]pyrazine (0.12 g, 31%) as red oil.

Step 2. (S)-isopropyl 4-acetyl-3-methyl-7-(1-(pyrazin-2-ylmethyl)-1H-pyrazol-4-yl)-3,4-dihydroquinoxaline-1(2H)-carboxylate A 100-mL round-bottom flask was charged with isopropyl (3S)-4-acetyl-7-bromo-3-methyl-1,2,3,4-tetrahydroquinoxaline-1-carboxylate (60 mg, 0.17 mmol), bis(triphenylphosphine)palladium(II) dichloride (12 mg, 0.02 mmol), water (8 mL), 1,4-dioxane (20 mL), cesium carbonate (165 mg, 0.50 mmol), and 2-[4-(tetramethyl-1,3,2-dioxaborolan-2-yl)-1H-pyrazol-1-yl]methylpyrazine (60 mg, 0.21 mmol). The resulting mixture stirred overnight at 70° C. After cooling to room temperature, the reaction mixture was passed through a short pad of celite and concentrated under vacuum. The residue was purified by Prep-HPLC with the following conditions (1#waters2767): Column, Xbridge Phenyl 19×150 mm; mobile phase, Phase A: water (0.05% NH$_4$HCO$_3$), Phase B: CH$_3$CN (15% CH$_3$CN up to 60% in 8 min); Detector, UV220&254 nm to afford (S)-isopropyl 4-acetyl-3-methyl-7-(1-(pyrazin-2-ylmethyl)-1H-pyrazol-4-yl)-3,4-dihydroquinoxaline-1(2H)-carboxylate (27.7 mg, 38%) as a white solid. $^1$H NMR (300 MHz, CD$_3$OD) δ ppm 1.10 (d, J=6.60 Hz, 3H), 1.27-1.37 (m, 6H), 2.22 (s, 3H), 3.35-3.50 (m, 1H), 4.05-4.17 (m, 1H), 4.95-5.10 (m, 2H), 5.58 (s, 2H), 7.39 (br s, 2H), 7.91 (s, 1H), 8.03 (s, 1H), 8.21 (s, 1H), 8.49 (s, 1H), 8.56 (d, J=2.70 Hz, 1H), 8.59-8.62 (m, 1H). MS (ESI, pos. ion) m/z 435 [M+H]$^+$.

The following examples were made according to the procedure outlined for Example 155

Example 156

PH-FMA-D4-081-0. (S)-isopropyl 4-acetyl-3-methyl-7-(1-(pyridin-4-ylmethyl)-1H-pyrazol-4-yl)-3,4-dihydroquinoxaline-1(2H)-carboxylate (I-117)

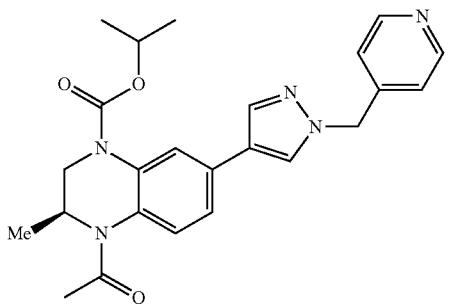 [SMILES: CC(=O)N1c2ccc(-c3cnn(Cc4ccncc4)c3)cc2N(C(=O)OC(C)C)C[C@@H]1C]

$^1$H NMR (300 MHz, CD$_3$OD) δ ppm 1.09 (d, J=6.60 Hz, 3H), 1.27-1.35 (m, 6H), 2.22 (s, 3H), 3.38-3.48 (m, 1H), 4.01-4.15 (m, 1H), 4.98-5.05 (m, 2H), 5.50 (s, 1H), 7.24 (d, J=6.30 Hz, 2H), 7.40 (s, 2H), 7.93 (s, 1H), 8.05 (s, 1H), 8.18 (s, 1H), 8.50-8.55 (m, 2H). MS (ESI, pos. ion) m/z 434 [M+H]$^+$.

Example 157

(S)-1-(4-(cyclopropanecarbonyl)-2-methyl-6-(1-(pyridin-4-ylmethyl)-1H-pyrazol-4-yl)-3,4-dihydroquinoxaline-1(2H)-yl)ethanone (I-118)

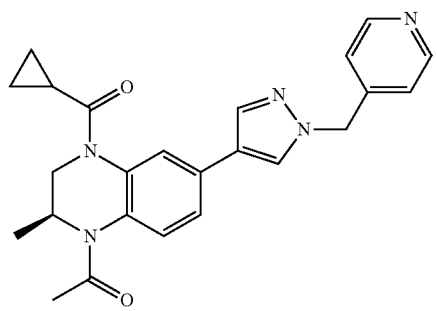 [SMILES: CC(=O)N1c2ccc(-c3cnn(Cc4ccncc4)c3)cc2N(C(=O)C2CC2)C[C@@H]1C]

$^1$H NMR (400 MHz, CDCl$_3$) δ ppm 0.72-0.80 (m, 1H), 0.85-0.93 (m, 1H), 1.01-1.11 (m, 1H), 1.12-1.19 (m, 3H), 1.19-1.25 (m, 1H), 1.90-1.99 (m, 1H), 2.22 (s, 3H), 2.96 (br s, 1H), 4.70-4.78 (m, 1H), 4.90-5.03 (m, 1H), 5.38 (s, 2H), 7.10 (d, J=5.20 Hz, 2H), 7.20-7.35 (m, 2H), 7.60 (s, 1H), 7.70 (s, 1H), 7.84 (s, 1H), 8.60-8.61 (m, 2H). MS (ESI, pos. ion) m/z 416 [M+H]$^+$.

Example 158

(S)-isopropyl 4-acetyl-3-methyl-7-(1-(pyridin-3-ylmethyl)-1H-pyrazol-4-yl)-3,4-dihydroquinoxaline-1(2H)-carboxylate (I-119)

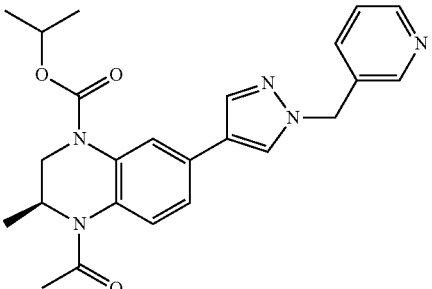

$^1$H NMR (300 MHz, CD$_3$OD) δ ppm 1.12 (d, J=6.60 Hz, 3H), 1.33-1.38 (m, 6H), 2.24 (s, 3H), 3.50 (m, 1H), 4.10-4.20 (m, 1H), 5.04-5.10 (m, 2H), 5.49 (s, 2H), 7.40 (s, 2H), 7.45-7.49 (m, 1H), 7.81 (d, J=8.10 Hz, 1H), 7.92 (s, 1H), 8.04 (s, 1H), 8.18 (s, 1H), 8.52-8.55 (m, 2H). MS (ESI, pos. ion) m/z 434 [M+H]$^+$.

Example 159

(S)-isopropyl 4-acetyl-3-methyl-7-(1-(pyridin-2-ylmethyl)-1H-pyrazol-4-yl)-3,4-dihydroquinoxaline-1(2H)-carboxylate (I-120)

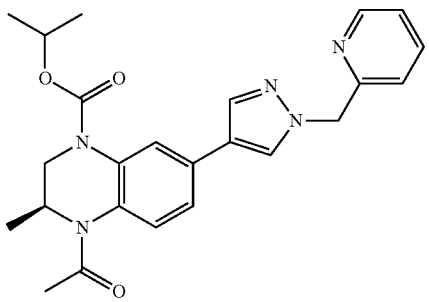 [SMILES: CC(=O)N1c2ccc(-c3cnn(Cc4ccccn4)c3)cc2N(C(=O)OC(C)C)C[C@@H]1C]

¹H NMR (300 MHz, CD₃OD) δ ppm 1.12 (d, J=6.90 Hz, 3H), 1.34-1.38 (m, 6H), 2.25 (s, 3H), 3.50 (m, 1H), 4.10-4.20 (m, 1H), 5.04-5.08 (m, 2H), 5.62 (s, 2H), 7.37-7.41 (m, 3H), 7.58-7.60 (m, 1H), 7.95 (s, 1H), 8.05-8.07 (m, 2H), 8.20 (s, 1H), 8.66 (d, J=4.50 Hz, 1H). MS (ESI, pos. ion) m/z 434 [M+H]+.

Example 160

(S)-1-(4-(cyclopropanecarbonyl)-2-methyl-6-(1-(pyridin-2-ylmethyl)-1H-pyrazol-4-yl)-3,4-dihydro-quinoxaline-1(2H)-yl)ethanone (I-121)

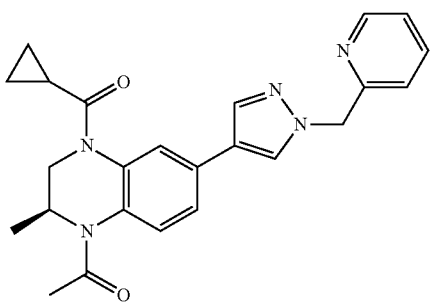 [SMILES: CC(=O)N1c2ccc(-c3cnn(Cc4ccccn4)c3)cc2N(C(=O)C2CC2)C[C@@H]1C]

¹H NMR (300 MHz, CD₃OD) δ ppm 0.83-0.85 (m, 1H), 0.99-1.12 (m, 3H), 1.19 (d, J=6.30 Hz, 3H), 2.09-2.13 (m, 1H), 2.24 (s, 3H), 2.95 (m, 1H), 4.81-4.85 (m, 1H), 4.94-4.99 (m, 1H), 5.53 (s, 2H), 7.21 (d, J=7.80 Hz, 1H), 7.37-7.39 (m, 1H), 7.41-7.59 (m, 2H), 7.77 (d, J=1.50 Hz, 1H), 7.82-7.88 (m, 1H), 7.97 (s, 1H), 8.24 (s, 1H), 8.57 (d, J=4.20 Hz, 1H). MS (ESI, pos. ion) m/z 416 [M+H]⁺.

Example 161

(S)-1-(4-(cyclopropanecarbonyl)-2-methyl-6-(1-(pyridin-3-ylmethyl)-1H-pyrazol-4-yl)-3,4-dihydro-quinoxaline-1(2H)-yl)ethan-1-one (I-122)

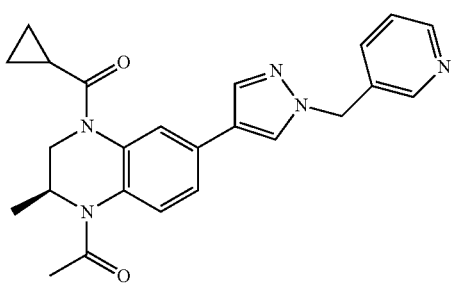 [SMILES: CC(=O)N1c2ccc(-c3cnn(Cc4cccnc4)c3)cc2N(C(=O)C2CC2)C[C@@H]1C]

¹H NMR (300 MHz, CD₃OD) δ ppm 0.75-0.85 (m, 1H), 0.95-1.15 (m, 3H), 1.18 (d, J=6.30 Hz, 3H), 1.98-2.15 (m, 1H), 2.24 (s, 3H), 2.92 (br s, 1H), 4.75-4.85 (m, 1H), 4.85-5.02 (m, 1H), 5.49 (s, 2H), 7.39-7.58 (m, 3H), 7.72-7.85 (m, 2H), 7.96 (s, 1H), 8.25 (s, 1H), 8.49-8.55 (m, 2H). MS (ESI, pos. ion) m/z 416 [M+H]⁺.

Example 162

(S)-1-(4-(cyclopropanecarbonyl)-2-methyl-6-(1-(pyrazin-2-ylmethyl)-1H-pyrazol-4-yl)-3,4-dihydro-quinoxaline-1(2H)-yl)ethanone (I-123)

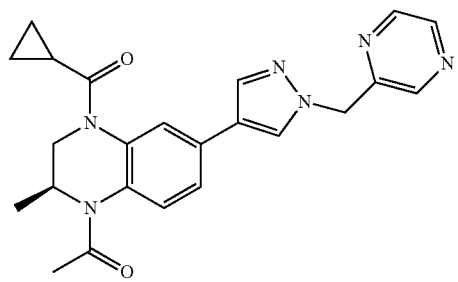 [SMILES: CC(=O)N1c2ccc(-c3cnn(Cc4cnccn4)c3)cc2N(C(=O)C2CC2)C[C@@H]1C]

¹H NMR (300 MHz, CD₃OD) δ ppm 0.72-0.85 (m, 1H), 0.91-1.10 (m, 3H), 1.17 (d, J=6.30 Hz, 3H), 2.06-2.11 (m, 1H), 2.22 (s, 3H), 2.95 (m, 1H), 4.82-4.83 (m, 1H), 4.92-4.97 (m, 1H), 5.58 (s, 2H), 7.46-7.58 (m, 2H), 7.75 (d, J=1.50 Hz, 1H), 7.95 (s, 1H), 8.26 (s, 1H), 8.49 (d, J=1.20 Hz, 1H), 8.56 (d, J=2.40 Hz, 1H), 8.61-8.62 (m, 1H). MS (ESI, pos. ion) m/z 417 [M+H]⁺.

Example 163

(S)-1-(4-(cyclopropanecarbonyl)-2-methyl-6-(1-(pyrazin-2-ylmethyl)-1H-pyrazol-4-yl)-3,4-dihydro-quinoxaline-1(2H)-yl)ethanone (I-124)

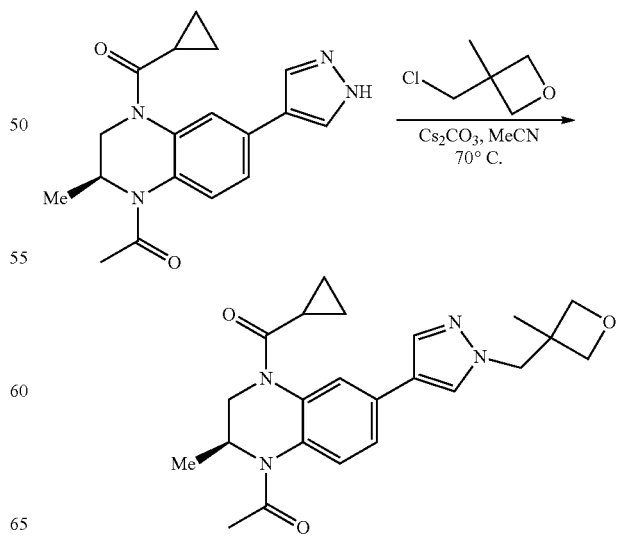

A 40-mL sealed tube was charged with (S)-1-(4-(cyclopropanecarbonyl)-2-methyl-6-(1H-pyrazol-4-yl)-3,4-dihydroquinoxaline-1(2H)-yl)ethan-1-one (100 mg, 0.31 mmol), 3-(chloromethyl)-3-methyloxetane (100 mg, 0.83 mmol), cesium carbonate (300 mg, 0.92 mmol), and acetonitrile (10 mL). The resulting mixture was stirred overnight at 70° C. After cooling to room temperature, the reaction mixture was filtered through a short pad of celite and concentrated under vacuum. The residue was purified by Prep-HPLC with the following conditions: Column, SunFire Prep C18, 19×150 mm; mobile phase, Phase A: water (0.05% $NH_4HCO_3$), Phase B: $CH_3CN$ (12% $CH_3CN$ up to 64% in 14 min); Detector, UV220&254 nm. This afforded (S)-1-(4-(cyclopropanecarbonyl)-2-methyl-6-(1-((3-methyloxetan-3-yl)methyl)-1H-pyrazol-4-yl)-3,4-dihydroquinoxaline-1(2H)-yl)ethanone (33.4 mg, 27%) as an off-white solid. $^1$H NMR (300 MHz, $CD_3OD$) δ ppm 0.75-0.88 (m, 1H), 0.95-1.10 (m, 3H), 1.17 (d, J=6.30 Hz, 3H), 1.27 (s, 3H), 2.01-2.10 (m, 1H), 2.22 (s, 3H), 2.85-2.98 (m, 1H), 4.35-4.42 (m, 4H), 4.73-4.78 (m, 3H), 4.89-5.01 (m, 1H), 7.39-7.56 (m, 2H), 7.73 (s, 1H), 7.90 (s, 1H), 8.11 (s, 1H). MS (ESI, pos. ion) m/z 409 [M+H]$^+$. The following examples were made according to the procedure outlined for Example 163

Example 164

(S)-isopropyl 4-acetyl-7-(1-(2,2-difluoroethyl)-1H-pyrazol-4-yl)-3-methyl-3,4-dihydroquinoxaline-1(2H)-carboxylate (I-135)

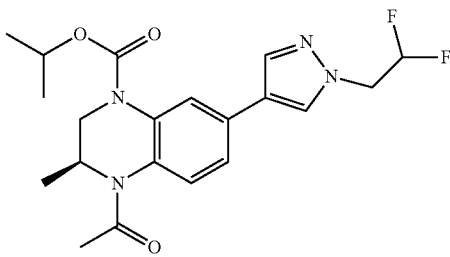 [SMILES: CC(=O)N1c2ccc(-c3cnn(CC(F)F)c3)cc2N(C(=O)OC(C)C)C[C@@H]1C]

$^1$H NMR (300 MHz, $CD_3OD$) δ ppm 1.11 (d, J=6.60 Hz, 3H), 1.32-1.37 (m, 6H), 2.22 (s, 3H), 3.47 (m, 1H), 4.12-4.20 (m, 1H), 4.56-4.66 (m, 2H), 5.00-5.09 (m, 2H), 6.04-6.40 (m, 1H), 7.39 (s, 2H), 7.90 (s, 1H), 8.02 (s, 1H), 8.07 (s, 2H). MS (ESI, pos. ion) m/z 407 [M+H]$^+$.

Example 165

(S)-1-(4-(cyclopropanecarbonyl)-6-(1-(2-fluoro-2-methylpropyl)-1H-pyrazol-4-yl)-2-methyl-3,4-dihydroquinoxaline-1(2H)-yl)ethanone (I-145)

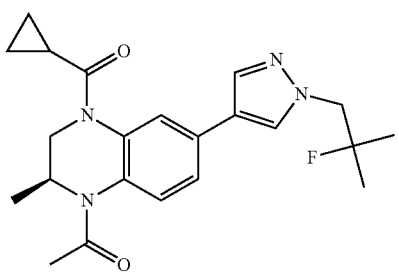 [SMILES: CC(=O)N1c2ccc(-c3cnn(CC(C)(C)F)c3)cc2N(C(=O)C2CC2)C[C@@H]1C]

$^1$H NMR (300 MHz, $CD_3OD$) δ ppm 0.79-0.83 (m, 1H), 0.95-1.14 (m, 3H), 1.17 (d, J=6.60 Hz, 3H), 1.31 (s, 3H), 1.38 (s, 3H), 1.85-2.09 (m, 1H), 2.22 (s, 3H), 2.95 (s, 1H), 4.32 (s, 1H), 4.38 (s, 1H), 4.72-4.88 (m, 1H), 4.93-5.14 (m, 1H), 7.39-7.58 (m, 2H), 7.74 (s, 1H), 7.91 (s, 1H), 8.05 (s, 1H). MS (ESI, pos. ion) m/z 399 [M+H]$^+$.

Example 166

(S)-1-(4-(cyclopropanecarbonyl)-6-(1-(2-(dimethylamino)ethyl)-1H-pyrazol-4-yl)-2-methyl-3,4-dihydroquinoxaline-1(2H)-yl)ethanone (I-146)

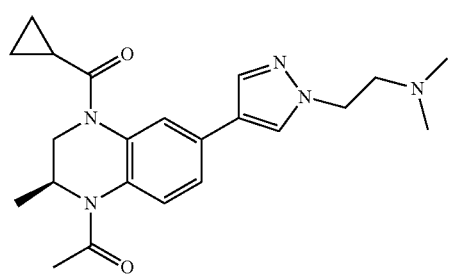 [SMILES: CC(=O)N1c2ccc(-c3cnn(CCN(C)C)c3)cc2N(C(=O)C2CC2)C[C@@H]1C]

$^1$H NMR (300 MHz, $CD_3OD$) δ ppm 0.81-0.89 (m, 1H), 1.00-1.14 (m, 3H), 1.19 (d, J=6.30 Hz, 3H), 2.06-2.10 (m, 1H), 2.12-2.33 (m, 9H), 2.85-2.90 (m, 3H), 4.32-4.37 (m, 2H), 4.64 (m, 1H), 4.81-4.84 (m, 1H), 7.47-7.57 (m, 2H), 7.74 (d, J=1.50 Hz, 1H), 7.91 (s, 1H), 8.13 (s, 1H). MS (ESI, pos. ion) m/z 396 [M+H]$^+$.

Example 167

(S)-1-(4-(cyclopropanecarbonyl)-2-methyl-6-(1-((4-methyl-1,2,5-oxadiazol-3-yl)methyl-1H-pyrazol-4-yl)-3,4-dihydroquinoxaline-1(2H)-yl)ethanone (I-147)

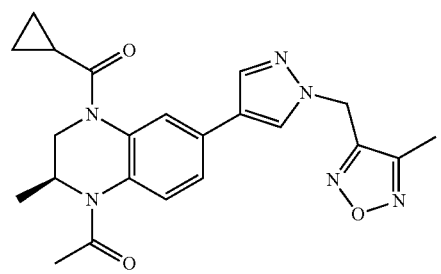 [SMILES: CC(=O)N1c2ccc(-c3cnn(Cc4nonc4C)c3)cc2N(C(=O)C2CC2)C[C@@H]1C]

$^1$H NMR (300 MHz, $CD_3OD$) δ ppm 0.81-0.89 (m, 1H), 0.95-1.14 (m, 3H), 1.17 (d, J=6.30 Hz, 3H), 1.95-2.17 (m, 1H), 2.21 (s, 3H), 2.29 (s, 3H), 2.95 (s, 1H), 4.72-4.83 (m, 1H), 4.91-5.02 (m, 1H), 5.63 (s, 2H), 7.39-7.63 (m, 2H), 7.74 (s, 1H), 7.93 (s, 1H), 8.22 (s, 1H). MS (ESI, pos. ion) m/z 421 [M+H]$^+$.

Example 168

1-((S)-4-(cyclopropanecarbonyl)-6-(1-((2,2-difluoro-cyclopropyl)methyl-1H-pyrazol-4-yl)-2-methyl-3,4-dihydroquinoxaline-1(2H)-yl)ethanone (I-148)

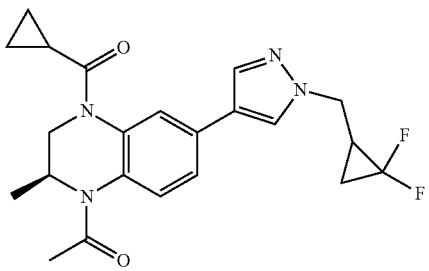 [SMILES: CC(=O)N1c2ccc(-c3cnn(CC4CC4(F)F)c3)cc2N(C(=O)C2CC2)C[C@@H]1C]

¹H NMR (300 MHz, CD₃OD) δ ppm 0.73-0.88 (m, 1H), 0.95-1.14 (m, 3H), 1.17 (d, J=6.30 Hz, 3H), 1.35-1.52 (m, 1H), 1.52-1.61 (m, 1H), 2.01-2.12 (m, 1H), 2.13-2.32 (m, 4H), 2.95 (s, 1H), 4.20-4.41 (m, 2H), 4.79-4.86 (m, 1H), 4.92-5.02 (m, 1H), 7.50-7.60 (m, 2H), 7.73 (s, 1H), 7.91 (s, 1H), 8.05 (s, 1H). MS (ESI, pos. ion) m/z 415 [M+H]⁺.

Example 169

(S)-1-(4-(cyclopropanecarbonyl)-2-methyl-6-(1-((3-methylisoxazol-5-yl)methyl-1H-pyrazol-4-yl)-3,4-dihydroquinoxaline-1(2H)-yl)ethanone (I-149)

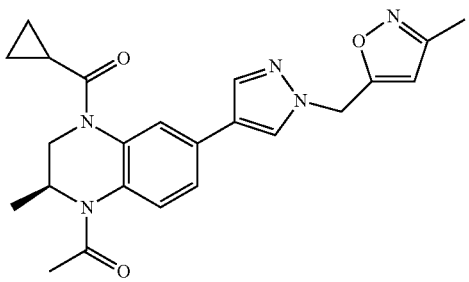 [SMILES: CC(=O)N1c2ccc(-c3cnn(Cc4cc(C)no4)c3)cc2N(C(=O)C2CC2)C[C@@H]1C]

¹H NMR (300 MHz, CD₃OD) δ ppm 0.68-0.95 (m, 1H), 0.96-1.12 (m, 3H), 1.17 (d, J=6.30 Hz, 3H), 1.95-2.19 (m, 1H), 2.22 (s, 3H), 2.27 (s, 3H), 2.95 (s, 1H), 4.71-4.85 (m, 1H), 4.90-5.04 (m, 1H), 5.51 (s, 2H), 6.25 (s, 1H), 7.40-7.60 (m, 2H), 7.73 (s, 1H), 7.93 (s, 1H), 8.20 (s, 1H). MS (ESI, pos. ion) m/z 420[M+H]⁺.

Example 170

(S)-1-(4-(cyclopropanecarbonyl)-2-methyl-6-(1-(3,3,3-trifluoropropyl)-1H-pyrazol-4-yl)-3,4-dihydroquinoxaline-1(2H)-yl)ethanone (I-150)

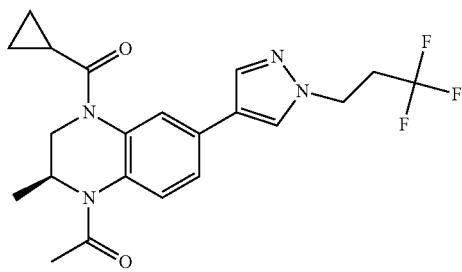 [SMILES: CC(=O)N1c2ccc(-c3cnn(CCC(F)(F)F)c3)cc2N(C(=O)C2CC2)C[C@@H]1C]

¹H NMR (300 MHz, CD₃OD) δ ppm 0.78-0.94 (m, 1H), 0.95-1.13 (m, 3H), 1.19 (d, J=6.30 Hz, 3H), 1.96-2.15 (m, 1H), 2.22 (s, 3H), 2.27 (s, 3H), 2.69-3.05 (m, 3H), 2.69-3.05 (m, 3H), 4.45-4.59 (m, 2H), 4.75-4.86 (m, 1H), 4.95-5.10 (m, 1H), 7.39-7.66 (m, 2H), 7.74 (s, 1H), 7.93 (s, 1H), 8.15 (s, 1H). MS (ESI, pos. ion) m/z 421 [M+H]⁺.

Example 171

(S)-1-(4-(cyclopropanecarbonyl)-2-methyl-6-(1-(2-morpholinoethyl)-1H-pyrazol-4-yl)-3,4-dihydroquinoxaline-1(2H)-yl)ethanone (I-151)

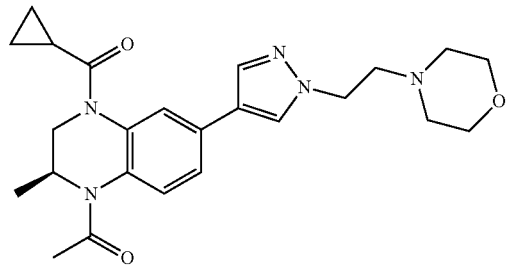 [SMILES: CC(=O)N1c2ccc(-c3cnn(CCN4CCOCC4)c3)cc2N(C(=O)C2CC2)C[C@@H]1C]

¹H NMR (400 MHz, CD₃OD) δ ppm 0.83-086 (m, 1H), 0.99-1.12 (m, 3H), 1.18 (d, J=6.40 Hz, 3H), 2.08-2.12 (m, 1H), 2.23 (s, 3H), 2.51-2.53 (m, 4H), 2.84-2.85 (m, 2H), 2.87 (m, 1H), 3.67-3.69 (m, 4H), 4.32-4.35 (m, 2H), 4.83-4.86 (m, 1H), 4.96-4.97 (m, 1H), 7.46-7.55 (m, 2H), 7.73 (s, 1H), 7.89 (s, 1H), 8.09 (s, 1H). MS (ESI, pos. ion) m/z 438 [M+H]⁺.

Example 172

(S)-2-(4-(1-acetyl-4-(cyclopropanecarbonyl)-2-methyl-1,2,3,4-tetrahydro quinoxalin-6-yl)-1H-pyrazol-1-yl)-1-morpholinoethanone (I-125)

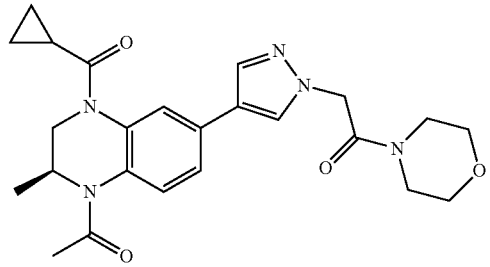 [SMILES: CC(=O)N1c2ccc(-c3cnn(CC(=O)N4CCOCC4)c3)cc2N(C(=O)C2CC2)C[C@@H]1C]

¹H NMR (400 MHz, CD₃OD) δ ppm 0.76-0.82 (m, 1H), 0.95-1.11 (m, 3H), 1.18 (d, J=6.40 Hz, 3H), 2.01-2.09 (m, 1H), 2.24 (s, 3H), 2.89 (br s, 1H), 3.59-3.75 (m, 8H), 4.75-4.85 (m, 1H), 4.88-4.99 (m, 1H), 5.21 (s, 2H), 7.39-7.45 (m, 1H), 7.50-7.55 (m, 1H), 7.74 (s, 1H), 7.93 (s, 1H), 8.07 (s, 1H). MS (ESI, pos. ion) m/z 452 [M+H]⁺.

Example 173

(S)-1-(4-(cyclopropanecarbonyl)-2-methyl-6-(1-(pyrimidin-2-ylmethyl)-1H-pyrazol-4-yl)-3,4-dihydroquinoxaline-1(2H)-yl)ethanone (I-126)

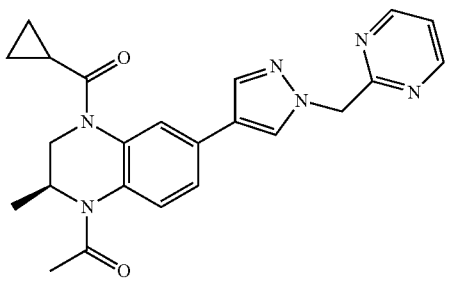 [SMILES: CC(=O)N1c2ccc(-c3cnn(Cc4ncccn4)c3)cc2N(C(=O)C2CC2)C[C@@H]1C]

¹H NMR (300 MHz, CD₃OD) δ ppm 0.78-0.86 (m, 1H), 0.98-1.13 (m, 3H), 1.18 (d, J=6.30 Hz, 3H), 2.05-2.13 (m, 1H), 2.23 (s, 3H), 2.95 (m, 1H), 4.79-4.84 (m, 1H), 4.92-4.97 (m, 1H), 5.62 (s, 2H), 7.40-7.48 (m, 2H), 7.55-7.58 (m, 1H), 7.75 (d, J=1.80 Hz, 1H), 7.92 (s, 1H), 8.23 (s, 1H), 8.76 (s, 2H). MS (ESI, pos. ion) m/z 417 [M+H]⁺.

Example 174

(S)-1-(6-(1-((1H-imidazol-4-yl)methyl-1H-pyrazol-4-yl)-4-(cyclopropanecarbonyl)-2-methyl-3,4-dihydroquinoxaline-1(2H)-yl)ethanone (I-127)

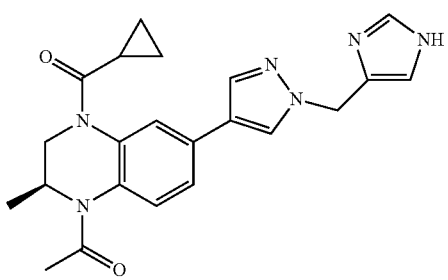 [SMILES: CC(=O)N1c2ccc(-c3cnn(Cc4c[nH]cn4)c3)cc2N(C(=O)C2CC2)C[C@@H]1C]

¹H NMR (300 MHz, CD₃OD) δ ppm 0.80-0.954 (m, 1H), 0.96-1.10 (m, 3H), 1.16 (d, J=6.30 Hz, 3H), 2.01-2.16 (m, 1H), 2.21 (s, 3H), 2.83-2.91 (m, 1H), 4.82 (m, 1H), 5.01-5.07 (m, 1H), 5.38 (s, 2H), 7.17 (s, 1H), 7.43-7.55 (m, 2H), 7.70 (s, 2H), 7.87 (s, 1H), 8.05 (s, 1H). MS (ESI, pos. ion) m/z 405 [M+H]⁺.

Example 175

(S)-1-(4-(cyclopropanecarbonyl)-2-methyl-6-(1-(pyrimidin-5-ylmethyl)-1H-pyrazol-4-yl)-3,4-dihydroquinoxaline-1(2H)-yl)ethanone (I-128)

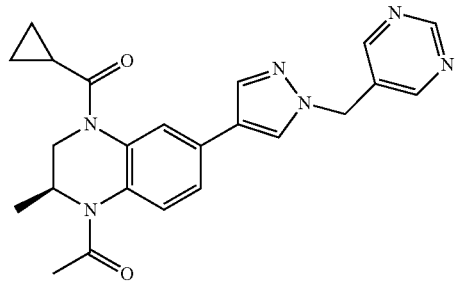 [SMILES: CC(=O)N1c2ccc(-c3cnn(Cc4cncnc4)c3)cc2N(C(=O)C2CC2)C[C@@H]1C]

¹H NMR (400 MHz, CD₃OD) δ ppm 0.75-0.85 (m, 1H), 0.90-1.12 (m, 3H), 1.17 (d, J=6.30 Hz, 3H), 2.04-2.12 (m, 1H), 2.22 (s, 3H), 2.93 (m, 1H), 4.789-4.85 (m, 1H), 4.94-4.96 (m, 1H), 5.49 (s, 2H), 7.45-7.56 (m, 2H), 7.74 (d, J=1.50 Hz, 1H), 7.96 (s, 1H) 8.25 (s, 1H), 8.77 (s, 1H), 9.12 (s, 1H). MS (ESI, pos. ion) m/z 417 [M+H]⁺.

Example 176

(S)-isopropyl 4-acetyl-7-(1-(2-(dimethylamino)ethyl)-1H-pyrazol-4-yl)-3-methyl-3,4-dihydroquinoxaline-1(2H)-carboxylate (I-129)

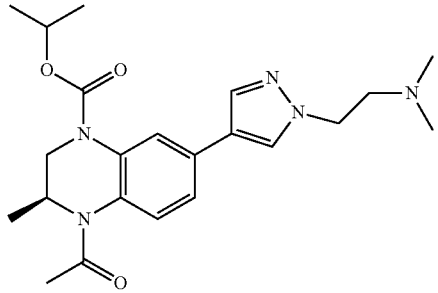

¹H NMR (300 MHz, CD₃OD) δ ppm 1.12 (d, J=6.90 Hz, 3H), 1.33-1.38 (m, 6H), 2.23 (s, 3H), 2.32-2.33 (m, 6H), 2.84-2.88 (m, 2H), 3.46 (m, 1H), 4.13-4.20 (m, 1H), 4.31-4.35 (m, 2H), 5.04-5.08 (m, 2H), 7.38 (s, 2H), 7.85 (s, 1H), 8.01 (s, 1H), 8.07 (s, 1H). MS (ESI, pos. ion) m/z 414 [M+H]⁺.

Example 177

(S)-2-(4-(1-acetyl-4-(isopropoxycarbonyl)-2-methyl-1,2,3,4-tetrahydro quinoxalin-6-yl)-1H-pyrazol-1-yl) acetic acid (I-130)

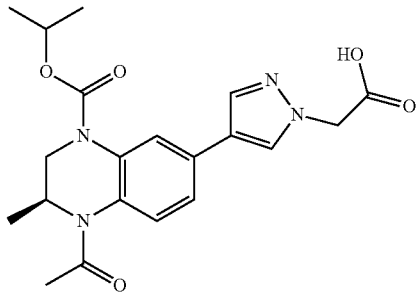 [SMILES: CC(=O)N1c2ccc(-c3cnn(CC(=O)O)c3)cc2N(C(=O)OC(C)C)C[C@@H]1C]

¹H NMR (300 MHz, CD₃OD) δ ppm 1.12 (d, J=6.60 Hz, 3H), 1.33-1.39 (m, 6H), 2.24 (s, 3H), 3.35 (m, 1H), 4.10-4.20 (m, 1H), 5.04-5.10 (m, 2H), 7.40 (s, 2H), 7.83 (s, 1H), 8.02 (s, 2H). MS (ESI, pos. ion) m/z 401 [M+H]⁺.

Example 178

(S)-isopropyl 4-acetyl-7-(1-(isoxazol-5-ylmethyl)-1H-pyrazol-4-yl)-3-methyl-3,4-dihydroquinoxaline-1(2H)-carboxylate (I-131)

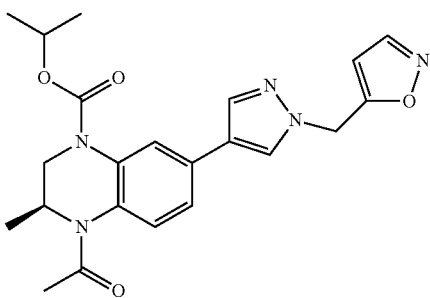 [SMILES: CC(=O)N1c2ccc(-c3cnn(Cc4ccno4)c3)cc2N(C(=O)OC(C)C)C[C@@H]1C]

¹H NMR (300 MHz, CD₃OD) δ ppm 1.10 (d, J=6.90 Hz, 3H), 1.32-1.36 (m, 6H), 2.22 (s, 3H), 3.48 (m, 1H), 4.11-4.17 (m, 1H), 4.98-5.10 (m, 2H), 5.60 (s, 2H), 6.38 (m, 1H), 7.38 (s, 2H), 7.89 (s, 1H), 8.02 (s, 1H), 8.15 (s, 1H), 8.37 (d, J=1.8 Hz, 1H). MS (ESI, pos. ion) m/z 424 [M+H]⁺.

Example 179

(S)-2-(4-(1-acetyl-4-(cyclopropanecarbonyl)-2-methyl-1,2,3,4-tetrahydro quinoxalin-6-yl)-1H-pyrazol-1-yl)-N-methylacetamide (I-132)

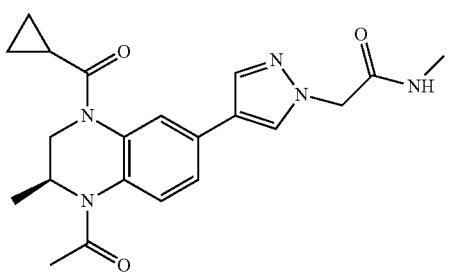 [SMILES: CNC(=O)Cn1cc(-c2ccc3c(c2)N(C(=O)C2CC2)C[C@H](C)N3C(C)=O)cn1]

¹H NMR (400 MHz, CD₃OD) δ ppm 0.75-0.85 (m, 1H), 0.98-1.14 (m, 3H), 1.19 (d, J=6.00 Hz, 3H), 2.06-2.13 (m, 1H), 2.23 (s, 3H), 2.80 (s, 3H), 2.97 (m, 1H), 4.81 (m, 1H), 4.90 (s, 2H), 4.96-4.98 (m, 1H), 7.48 (d, J=7.20 Hz, 1H), 7.55-7.57 (m, 1H), 7.75 (s, 1H), 7.94 (s, 1H), 8.11 (s, 1H). MS (ESI, pos. ion) m/z 396 [M+H]⁺.

Example 180

(S)-isopropyl 4-acetyl-7-(1-((3-fluorooxetan-3-yl)methyl-1H-pyrazol-4-yl)-3-methyl-3,4-dihydroquinoxaline-1(2H)-carboxylate (I-133)

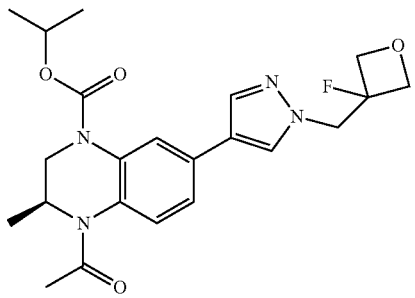 [SMILES: CC(=O)N1c2ccc(-c3cnn(CC4(F)COC4)c3)cc2N(C(=O)OC(C)C)C[C@@H]1C]

¹H NMR (300 MHz, CD₃OD) δ ppm 1.32-1.37 (m, 6H), 2.22 (s, 3H), 3.47 (m, 1H), 4.11-4.17 (m, 1H), 4.68-4.85 (m, 6H), 4.93-5.11 (m, 2H), 7.37 (s, 2H), 7.86 (s, 1H), 8.02 (d, J=6.30 Hz, 2H). MS (ESI, pos. ion) m/z 431 [M+H]⁺.

Example 181

(S)-isopropyl 4-acetyl-3-methyl-7-(1-(2-(methylamino)-2-oxoethyl-1H-pyrazol-4-yl)-3,4-dihydroquinoxaline-1(2H)-carboxylate (I-134)

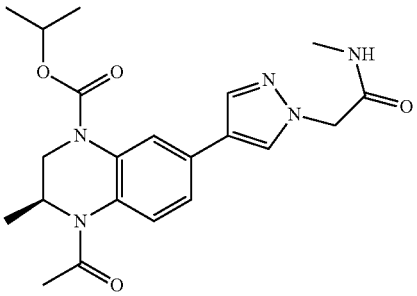 [SMILES: CNC(=O)Cn1cc(-c2ccc3c(c2)N(C(=O)OC(C)C)C[C@H](C)N3C(C)=O)cn1]

¹H NMR (300 MHz, CD₃OD) δ ppm 1.12 (d, J=6.60 Hz, 3H), 1.32-1.37 (m, 6H), 2.22 (s, 3H), 2.78 (s, 3H), 3.43-3.46 (m, 1H), 4.12 (m, 1H), 4.89 (s, 2H), 4.98-5.10 (m, 2H), 7.39 (s, 2H), 7.89 (s, 1H), 8.02-8.05 (m, 2H). MS (ESI, pos. ion) m/z 414 [M+H]⁺.

Example 182

(S)-3-(4-(1-acetyl-4-(cyclopropanecarbonyl)-2-methyl-1,2,3,4-tetrahydro quinoxalin-6-yl)-1H-pyrazol-1-yl)propanoic acid (I-136)

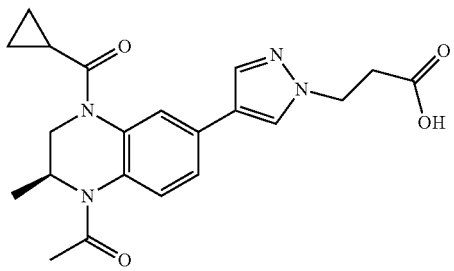 [SMILES: CC(=O)N1c2ccc(-c3cnn(CCC(=O)O)c3)cc2N(C(=O)C2CC2)C[C@@H]1C]

¹H NMR (400 MHz, CD₃OD) δ ppm 0.78-0.85 (m, 1H), 0.99-1.11 (m, 3H), 1.17 (d, J=6.30 Hz, 3H), 1.94-2.12 (s, 6H), 2.22 (s, 3H), 2.81-2.93 (m, 3H), 4.34-4.47 (m, 2H), 4.79-4.82 (m, 1H), 4.94-5.05 (m, 1H), 7.43-7.54 (m, 2H), 7.70 (s, 1H), 7.86 (s, 1H), 8.06 (s, 1H). MS (ESI, pos. ion) m/z 397 [M+H]⁺.

Example 183

(S)-isopropyl 4-acetyl-7-(1-(3-hydroxypropyl)-1H-pyrazol-4-yl)-3-methyl-3,4-dihydroquinoxaline-1(2H)-carboxylate (I-137)

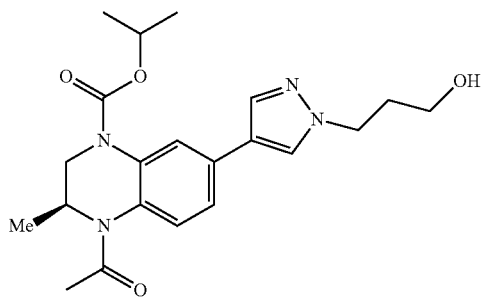 [SMILES: CC(=O)N1c2ccc(-c3cnn(CCCO)c3)cc2N(C(=O)OC(C)C)C[C@@H]1C]

¹H NMR (300 MHz, CD₃OD) δ ppm 1.11 (d, J=6.90 Hz, 3H), 1.27-1.41 (m, 6H), 2.02-2.13 (m, 2H), 2.23 (s, 3H), 3.35-3.48 (m, 1H), 3.39 (t, J=6.00 Hz, 2H), 4.08-4.18 (m, 1H), 4.17 (d, J=6.00 Hz, 2H), 4.98-5.13 (m, 2H), 7.38 (s, 2H), 7.85 (s, 1H), 8.03 (s, 2H). MS (ESI, pos. ion) m/z 401 [M+H]⁺.

Example 184

(S)-isopropyl 4-acetyl-3-methyl-7-(1-((5-methyl-1,2,4-oxadiazol-3-yl)methyl)-1H-pyrazol-4-yl)-3,4-dihydroquinoxaline-1(2H)-carboxylate (I-138)

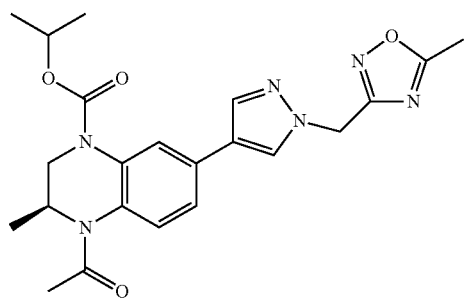

¹H NMR (300 MHz, CD₃OD) δ ppm 1.35-1.39 (m, 6H), 1.89 (s, 6H), 2.25 (s, 3H), 3.45 (m, 1H), 4.16 (m, 1H), 5.03-5.11 (m, 2H), 7.44-7.46 (m, 2H), 7.95 (s, 1H), 8.07 (s, 1H), 8.24 (s, 1H). MS (ESI, pos. ion) m/z 439 [M+H]⁺.

Example 185

(S)-isopropyl 7-(1-(2-(1H-1,2,4-triazol-1-yl)ethyl)-1H-pyrazol-4-yl)-4-acetyl-3-methyl-3,4-dihydroquinoxaline-1(2H)-carboxylate (I-139)

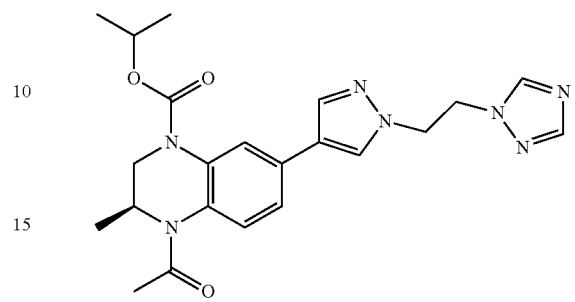

¹H NMR (300 MHz, CD₃OD) δ ppm 1.10 (d, J=6.60 Hz, 3H), 1.33-1.38 (m, 6H), 2.22 (s, 3H), 3.46 (m, 1H), 4.11-4.18 (m, 1H), 4.65-4.77 (m, 4H), 5.01-5.09 (m, 2H), 7.27-7.35 (m, 2H), 7.72 (s, 1H), 7.87 (s, 1H), 8.02 (s, 1H), 8.13 (s, 1H). MS (ESI, pos. ion) m/z 438 [M+H]⁺.

Example 186

(S)-isopropyl 4-acetyl-7-(1-(2-fluoro-2-methylpropyl)-1H-pyrazol-4-yl)-3-methyl-3,4-dihydroquinoxaline-1(2H)-carboxylate (I-140)

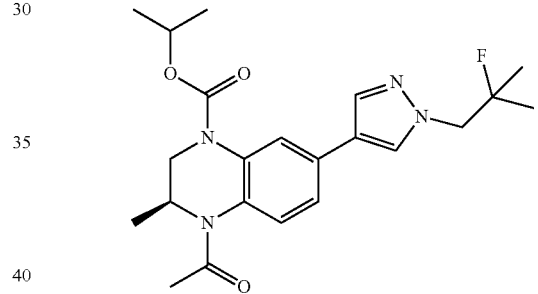

¹H NMR (300 MHz, CD₃OD) δ ppm 1.12 (d, J=6.60 Hz, 3H), 1.34-1.40 (m, 12H), 2.25 (s, 3H), 3.46 (m, 1H), 4.10-4.20 (m, 1H), 4.34-4.41 (m, 2H), 5.07 (m, 2H), 7.40 (s, 2H), 7.88 (s, 1H), 8.03 (d, J=5.70 Hz, 2H). MS (ESI, pos. ion) m/z 417 [M+H]⁺.

Example 187

(S)-isopropyl 4-acetyl-3-methyl-7-(1-((3-methylisoxazol-5-yl)methyl-1H-pyrazol-4-yl)-3,4-dihydroquinoxaline-1(2H)-carboxylate (I-141)

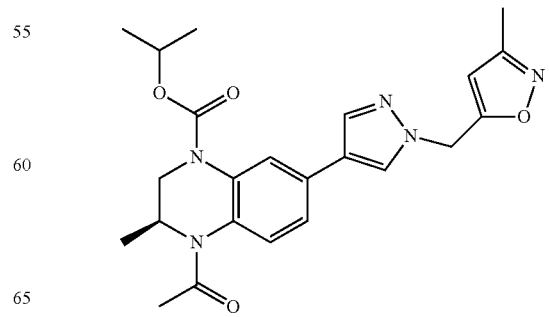

¹H NMR (300 MHz, CD₃OD) δ ppm 1.12 (d, J=6.60 Hz, 3H), 1.34-1.39 (m, 6H), 2.24 (s, 3H), 2.29 (s, 3H), 3.49 (m, 1H), 4.13-4.19 (m, 1H), 5.02-5.10 (m, 2H), 5.55 (s, 2H), 6.26 (m, 1H), 7.40 (s, 2H), 7.91 (s, 1H), 8.04 (s, 1H), 8.15 (s, 1H). MS (ESI, pos. ion) m/z 438 [M+H]⁺.

Example 188

(S)-isopropyl 4-acetyl-3-methyl-7-(1-(3,3,3-trifluoropropyl)-1H-pyrazol-4-yl)-3,4-dihydroquinoxaline-1(2H)-carboxylate (I-142)

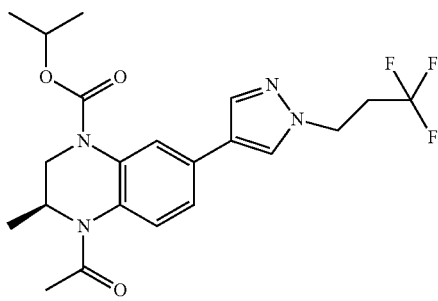 [SMILES: CC(=O)N1c2ccc(-c3cnn(CCC(F)(F)F)c3)cc2N(C(=O)OC(C)C)C[C@@H]1C]

¹H NMR (300 MHz, CD₃OD) δ ppm 1.12 (d, J=6.60 Hz, 3H), 1.34-1.39 (m, 6H), 2.24 (s, 3H), 2.83-2.91 (m, 3H), 3.46 (m, 1H), 4.10-4.20 (m, 1H), 4.47-4.52 (m, 2H), 5.02-5.11 (m, 2H), 7.40 (s, 2H), 7.89 (s, 1H), 8.03 (s, 1H), 8.09 (s, 1H). MS (ESI, pos. ion) m/z 439 [M+H]⁺.

Example 189

(S)-isopropyl 4-acetyl-3-methyl-7-(1-(thiazol-5-ylmethyl)-1H-pyrazol-4-yl)-3,4-dihydroquinoxaline-1(2H)-carboxylate (I-143)

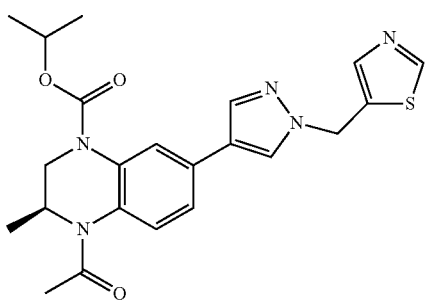 [SMILES: CC(=O)N1c2ccc(-c3cnn(Cc4cncs4)c3)cc2N(C(=O)OC(C)C)C[C@@H]1C]

¹H NMR (400 MHz, CD₃OD) δ ppm 1.11 (d, J=6.40 Hz, 3H), 1.33-1.37 (m, 6H), 2.23 (s, 3H), 4.14 (m, 1H), 5.00-5.10 (m, 2H), 5.68 (s, 2H), 7.38 (s, 2H), 7.89 (s, 1H), 7.94 (d, J=7.60 Hz, 1H), 8.02 (s, 1H), 8.13 (s, 1H), 9.00 (s, 1H). MS (ESI, pos. ion) m/z 440 [M+H]⁺.

Example 190

(S)-isopropyl 4-acetyl-3-methyl-7-(1-(oxetan-3-yl)-1H-pyrazol-4-yl)-3,4-dihydroquinoxaline-1(2H)-carboxylate (I-144)

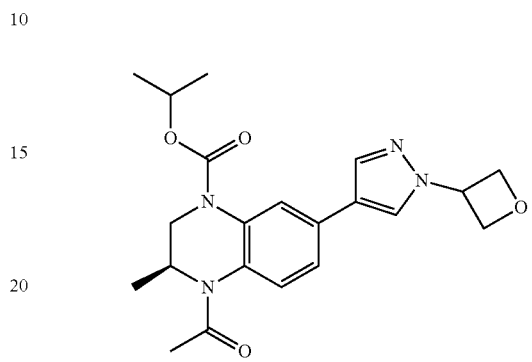

¹H NMR (300 MHz, DMSO-d₆) δ ppm 0.99 (d, J=6.74 Hz, 3 H), 1.27 (dd, J=9.53, 6.30 Hz, 6 H), 2.15 (s, 3 H), 3.49 (br s, 1 H), 3.84-4.07 (m, 1 H), 4.74-5.05 (m, 6 H), 5.60 (quin, J=7.04 Hz, 1 H), 7.33 (dd, J=8.50, 2.05 Hz, 1 H), 7.47 (br s, 1 H), 7.86-8.03 (m, 2 H), 8.30 (s, 1 H). MS (ESI, pos. ion) m/z 399 [M+H]⁺.

Example 191

(S)-3,3-difluorocyclobutyl 4-acetyl-7-(1-(azetidin-3-yl)-1H-pyrazol-4-yl)-3-methyl-3,4-dihydroquinoxaline-1(2H)-carboxylate (I-152)

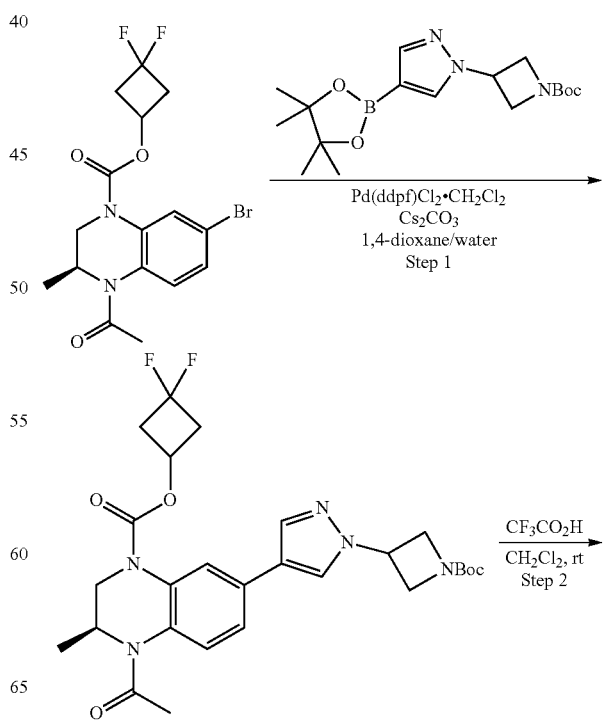

223

-continued

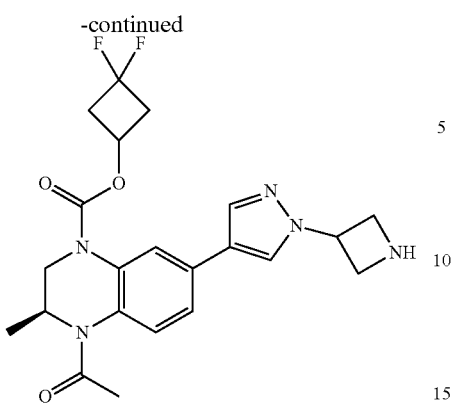

Step 1. 3,3-difluorocyclobutyl (S)-4-acetyl-7-(1-(1-(tert-butoxycarbonyl)azetidin-3-yl)-1H-pyrazol-4-yl)-3-methyl-3,4-dihydroquinoxaline-1(2H)-carboxylate A 100-mL round-bottom flask was purged with nitrogen and then charged with 3,3-difluorocyclobutyl (S)-4-acetyl-7-bromo-3-methyl-3,4-dihydroquinoxaline-1(2H)-carboxylate (300 mg, 0.70 mmol), tert-butyl 3-[4-(tetramethyl-1,3,2-dioxaborolan-2-yl)-1H-pyrazol-1-yl]azetidine-1-carboxylate (487 mg, 1.39 mmol), [1,1'-bis(diphenylphosphino)ferrocene]dichloropalladium(II) dichloromethane complex (69 mg, 0.08 mmol), cesium carbonate (456 mg, 1.40 mmol), 1,4-dioxane (10 mL) and water (3 mL). The resulting mixture stirred overnight at 90° C. in an oil bath. After cooling to room temperature, the resulting mixture was diluted with water (10 mL) and extracted with ethyl acetate (3×15 mL). The combined organic layers were dried over anhydrous sodium sulfate, filtered, and concentrated under vacuum. The residue was purified via column chromatography on silica gel (eluting with 8:1 ethyl acetate/petroleum ether) to afford 3,3-difluorocyclobutyl (S)-4-acetyl-7-(1-(1-(tert-butoxycarbonyl)azetidin-3-yl)-1H-pyrazol-4-yl)-3-methyl-3,4-dihydroquinoxaline-1(2H)-carboxylate (300 mg, 79%) as a yellow oil. MS (ESI, pos. ion) m/z 546 [M+H]$^+$.

Step 2. (S)-3,3-difluorocyclobutyl 4-acetyl-7-(1-(azetidin-3-yl)-1H-pyrazol-4-yl)-3-methyl-3,4-dihydroquinoxaline-1(2H)-carboxylate A 100-mL round-bottom flask was charged with (S)-4-acetyl-7-(1-(1-(tert-butoxycarbonyl)azetidin-3-yl)-1H-pyrazol-4-yl)-3-methyl-3,4-dihydroquinoxaline-1(2H)-carboxylate (300 mg, 0.51 mmol), trifluoroacetic acid (3 mL) and dichloromethane (5 mL). The resulting solution stirred for 1 h at room temperature. The pH of the solution was adjusted to 8 with 2 M aqueous potassium carbonate solution. The resulting mixture was extracted with dichloromethane (3×15 mL). The combined organic layers were dried over anhydrous sodium sulfate and concentrated under vacuum. The residue was purified by Prep-HPLC with the following conditions (Waters I): Column, Xbridge Prep C18 OBD column, Sum, 19×150 mm; mobile phase, Water (0.03% NH$_4$OH) and CH$_3$CN (16% CH$_3$CN up to 34% in 10 min); Detector, UV 220&254 nm. This afforded (S)-3,3-difluorocyclobutyl 4-acetyl-7-(1-(azetidin-3-yl)-1H-pyrazol-4-yl)-3-methyl-3,4-dihydroquinoxaline-1(2H)-carboxylate (40 mg, 16%) of as a yellow solid. $^1$H NMR (300 MHz, CD$_3$OD) δ ppm 1.16 (d,

224

J=6.90 Hz, 3H), 1.92-2.17 (m, 8H), 2.28 (s, 3H), 3.41-59 (m, 1H), 4.02-4.11 (m, 2H), 4.18-4.32 (m, 3H), 5.03-5.21 (m, 2H), 5.31-5.42 (m, 1H), 7.39-7.51 (m, 2H), 7.94 (s, 1H), 8.07 (s, 1H), 8.19 (s, 1H). MS (ESI, pos. ion) m/z 446 [M+H]$^+$.

The following examples were made according to the procedure outlined for Example 191

Example 192

(S)-4,4-difluorocyclohexyl 4-acetyl-3-methyl-7-(1-(piperidin-4-yl)-1H-pyrazol-4-yl)-3,4-dihydroquinoxaline-1(2H)-carboxylate (I-153)

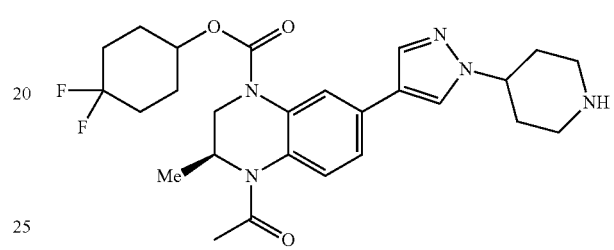

$^1$H NMR (300 MHz, CD$_3$OD) δ ppm 1.11 (d, J=6.60 Hz, 3H), 1.85-2.22 (m, 15H), 2.71-2.82 (m, 2H), 3.11-3.21 (m, 2H), 3.31-3.49 (m, 1H), 4.12-4.39 (m, 2H), 4.95-5.10 (m, 2H), 7.33-7.41 (m, 2H), 7.84 (s, 1H), 7.99 (s, 1H), 8.07 (s, 1H). MS (ESI, pos. ion) m/z 502 [M+H]$^+$.

Example 193 cyclobutyl (3S)-4-acetyl-7-[1-(1,1-dioxo-1λ$^6$-thian-4-yl)-1H-pyrazol-4-yl]-3-methyl-1,2,3,4-tetrahydroquinoxaline-1-carboxylate (I-154)

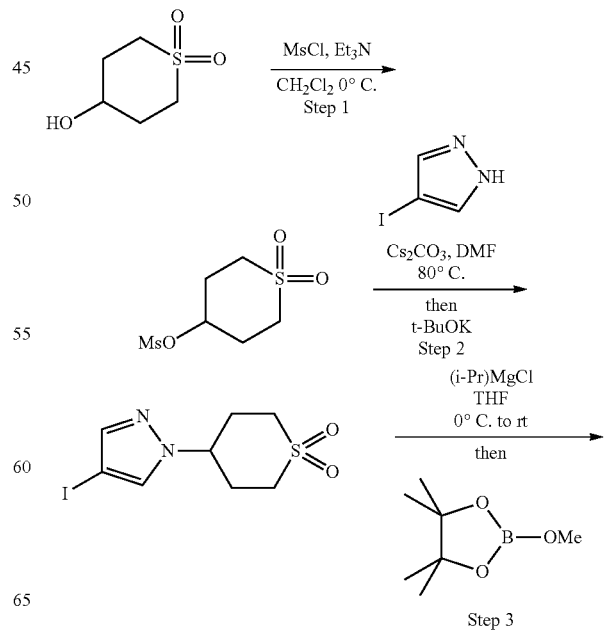

-continued

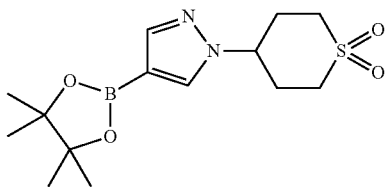

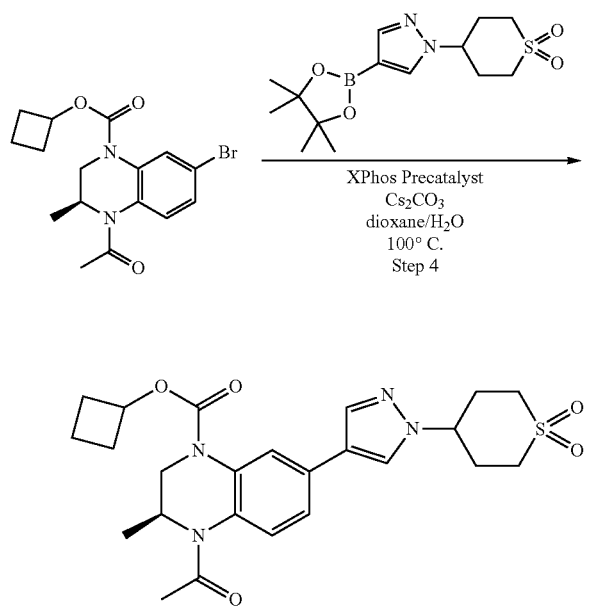

Step 1. 1,1-dioxidotetrahydro-2H-thiopyran-4-yl methanesulfonate

Triethylamine (7.80 mL, 55.9 mmol) was added to a solution of 4-hydroxytetrahydro-2H-thiopyran 1,1-dioxide (3.5 g, 23.3 mmol) in dichloromethane (35.0 mL). The reaction solution was cooled to 0° C. and methanesulfonyl chloride (3.25 ml, 41.9 mmol) was added. After 10 minutes, the reaction solution was warmed to room temperature and stirred for 3 h. The reaction was quenched via the addition of saturated aqueous ammonium chloride solution (15 mL). The organic layer was separated and washed with saturated aqueous sodium bicarbonate solution (15 mL) and brine (15 mL), dried over anhydrous sodium sulfate, filtered and concentrated in vacuo to afford an off-white solid. The solid residue was suspended in ethyl acetate (20 mL) and filtered. The filtered solid was then collected and dried in vacuo affording 1,1-dioxidotetrahydro-2H-thiopyran-4-yl methanesulfonate (5.1 g, 95%) as a white solid. $^1$H NMR (400 MHz, CDCl$_3$) δ ppm 2.38-2.56 (m, 4 H) 2.94-3.06 (m, 2 H) 3.10 (s, 3 H) 3.23-3.39 (m, 2 H) 5.03 (tt, J=4.74, 2.49 Hz, 1 H)

Step 2. 4-(4-iodo-1H-pyrazol-1-yl)tetrahydro-2H-thiopyran 1,1-dioxide

A suspension of 4-iodo-1H-pyrazole (1.00 g, 5.16 mmol), 1,1-dioxidotetrahydro-2H-thiopyran-4-yl methanesulfonate (1.77 g, 7.73 mmol) and cesium carbonate (2.52 g, 7.73 mmol) in DMF (10 mL) was heated to 80° C. for 2 h. The reaction was cooled to room temperature, and potassium tert-butoxide (0.578 g, 5.16 mmol) was added. The reaction mixture stirred at room temperature for 30 minutes and then water (30 mL) was added. The mixture stirred for 4 h and was then filtered. The filter cake was washed with water (10 mL) and dried in vacuo to afford 4-(4-iodo-1H-pyrazol-1-yl)tetrahydro-2H-thiopyran 1,1-dioxide (1.00 g, 60%) as an off-white solid. MS (ESI, pos. ion) m/z 327 [M+H]$^+$.

Step 3. 4-(4-(4,4,5,5-tetramethyl-1,3,2-dioxaborolan-2-yl)-1H-pyrazol-1-yl)tetrahydro-2H-thiopyran 1,1-dioxide Isopropylmagnesium chloride (2.0 M in THF, 1.23 mL, 2.45 mmol) was slowly added to a solution of 4-(4-iodo-1H-pyrazol-1-yl)tetrahydro-2H-thiopyran 1,1-dioxide (0.50 g, 1.533 mmol) in THF (6.0 mL) at −10° C. The reaction mixture was warmed to room temperature and stirred for 1 h. The reaction was then cooled to 0° C., 2-methoxy-4,4,5,5-tetramethyl-1,3,2-dioxaborolane (0.402 mL, 2.45 mmol) was added, and the reaction stirred at room temperature for an additional 1.5 h. The reaction solution was then concentrated in vacuo to remove the THF. The crude solid was dissolved in ether (200 mL) and filtered. The filtrate was slowly concentrated until a white precipitate formed. The solution was allowed to stand for 2 h, and the precipitate was filtered and dried in vacuo to afford 4-(4-(4,4,5,5-tetramethyl-1,3,2-dioxaborolan-2-yl)-1H-pyrazol-1-yl)tetrahydro-2H-thiopyran 1,1-dioxide (0.34 g, 68%) as a white powder. MS (ESI, pos. ion) m/z 327 [M+H]$^+$.

Step 4. cyclobutyl (3S)-4-acetyl-7-[1-(1,1-dioxo-1λ$^6$-thian-4-yl)-1H-pyrazol-4-yl]-3-methyl-1,2,3,4-tetrahydroquinoxaline-1-carboxylate A mixture of (S)-cyclobutyl 4-acetyl-7-bromo-3-methyl-3,4-dihydroquinoxaline-1(2H)-carboxylate (0.098 g, 0.267 mmol), 4-(4-(4,4,5,5-tetramethyl-1,3,2-dioxaborolan-2-yl)-1H-pyrazol-1-yl)tetrahydro-2H-thiopyran 1,1-dioxide (0.097 g, 0.296 mmol), XPhos Precatalyst 2nd Generation (0.021 g, 0.027 mmol), cesium carbonate (0.261 g, 0.801 mmol), 1,4-dioxane (1.2 mL) and water (0.2 mL) was heated at 80° C. overnight. The reaction mixture was cooled to room temperature, filtered through a pad of Celite, and concentrated. The residue was purified via column chromatography on silica gel (Biotage 25 g column, gradient elution with 10-100% ethyl acetate-hexane). The resulting off-white solid was further purified via column chromatography on silica gel (Biotage 25 g column, gradient elution with 2-5% methanol-dichloromethane) to afford cyclobutyl (3S)-4-acetyl-7-[1-(1,1-dioxo-1λ$^6$-thian-4-yl)-1H-pyrazol-4-yl]-3-methyl-1,2,3,4-tetrahydroquinoxaline-1-carboxylate (60 mg, 47%) as a white solid. $^1$H NMR (300 MHz, CDCl$_3$) δ ppm 1.07 (d, J=7.04 Hz, 3 H), 1.61-1.74 (m, 1 H), 1.76-1.91 (m, 1 H), 2.05-2.19 (m, 2 H), 2.21 (s, 3 H), 2.34-2.48 (m, 2 H), 2.52-2.76 (m, 4 H), 3.12 (ddd, J=13.63, 8.79, 4.25 Hz, 2 H), 3.41-3.57 (m, 3 H), 4.07 (dd, J=12.61, 6.45 Hz, 1 H), 4.48 (tt, J=7.66, 3.92 Hz, 1 H), 5.05 (quin, J=7.55 Hz, 1 H), 5.17 (br s, 1 H), 7.09-7.23 (m, 2 H), 7.68 (s, 1 H), 7.77 (s, 1 H), 8.08 (s, 1 H). MS (ESI, pos. ion) m/z 487 [M+H]$^+$.

The following examples were made according to the procedure outlined for Example 193

Example 194 oxan-4-yl (3S)-4-acetyl-7-[1-(1,1-dioxo-1λ⁶-thian-4-yl)-1H-pyrazol-4-yl]-3-methyl-1,2,3,4-tetrahydroquinoxaline-1-carboxylate (I-155)

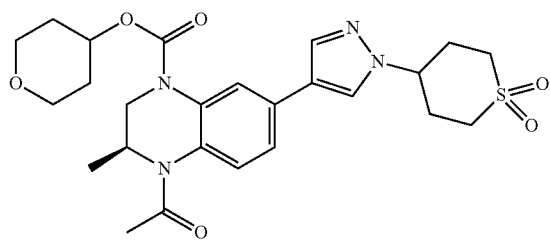 [SMILES: CC(=O)N1c2ccc(-c3cnn(C4CCS(=O)(=O)CC4)c3)cc2N(C(=O)OC2CCOCC2)C[C@@H]1C]

¹H NMR (300 MHz, CDCl₃) δ ppm 1.09 (d, 3H), 1.97-2.09 (m, 2H), 2.23 (s, 3H), 2.225-2.37 (m, 2H), 2.50-2.78 (m, 4H), 3.03-3.17 (m, 2H), 3.37-3.68 (m, 5H), 3.82-3.97 (m, 2H), 4.01-4.12 (m, 1H), 4.45-4.62 (m, 1H), 4.97-5.05 (m, 1H), 5.11-5.22 (m, 1H), 7.12-7.23 (m, 2H), 7.70 (s, 1H), 7.79 (s, 1H), 8.07 (s, 1H). MS (ESI, pos. ion) m/z 517 [M+H]⁺.

Example 195 propan-2-yl (3S)-4-acetyl-7-[1-(1,1-dioxo-1λ⁶-thian-4-yl)-1H-pyrazol-4-yl]-3-methyl-1,2,3,4-tetrahydroquinoxaline-1-carboxylate (I-156)

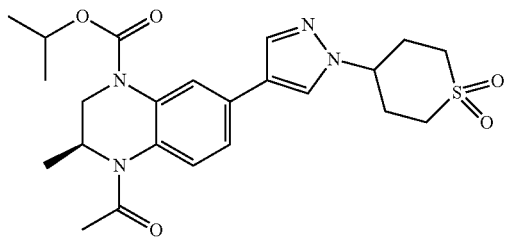 [SMILES: CC(=O)N1c2ccc(-c3cnn(C4CCS(=O)(=O)CC4)c3)cc2N(C(=O)OC(C)C)C[C@@H]1C]

¹H NMR (300 MHz, CDCl₃) δ ppm 1.08 (d, J=6.60 Hz, 3H), 1.34 (d, J=6.30 Hz, 6H), 2.22 (s, 3H), 2.50-2.78 (m, 4H), 3.05-3.19 (m, 2H), 3.40-3.59 (m, 3H), 3.99-4.12 (m, 1H), 4.40-4.53 (m, 1H), 4.99-5.21 (m, 2H), 7.05-7.19 (m, 2H), 7.70 (s, 1H), 7.87 (s, 1H), 8.09 (s, 1H). MS (ESI, pos. ion) m/z 475 [M+H]⁺.

Example 196

4-{4-[(2S)-1-acetyl-4-cyclopropanecarbonyl-2-methyl-1,2,3,4-tetrahydroquinoxalin-6-yl]-1H-pyrazol-1-yl}-1λ⁶-thiane-1,1-dione (I-157)

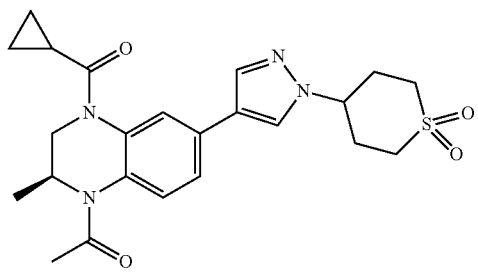 [SMILES: CC(=O)N1c2ccc(-c3cnn(C4CCS(=O)(=O)CC4)c3)cc2N(C(=O)C2CC2)C[C@@H]1C]

¹H NMR (300 MHz, CDCl₃) 0.72-0.82 (m, 1H), 0.85-0.94 (m, 1H), 1.02-1.29 (m, 5H), 1.87-2.01 (m, 1H), 2.23 (s, 3H), 2.53-2.75 (m, 4H), 2.89-3.02 (m, 1H), 3.05-3.18 (m, 2H), 3.40-3.56 (m, 2H), 4.42-4.58 (m, 1H), 4.72-4.89 (m, 1H), 4.91-5.05 (m, 1H), 7.30 (s, 2H), 7.58 (s, 1H), 7.67 (s, 1H), 7.77 (s, 1H). MS (ESI, pos. ion) m/z 457 [M+H]⁺.

Example 197 cyclobutyl (3S)-4-acetyl-7-[1-(1,1-dioxo-1λ⁶-thian-3-yl)-1H-pyrazol-4-yl]-3-methyl-1,2,3,4-tetrahydroquinoxaline-1-carboxylate (I-158)

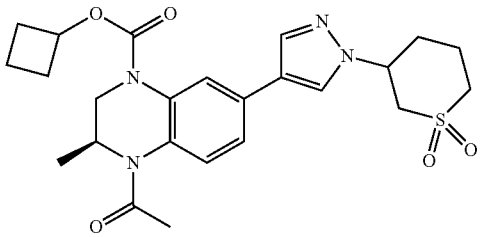 [SMILES: CC(=O)N1c2ccc(-c3cnn(C4CCCS(=O)(=O)C4)c3)cc2N(C(=O)OC2CCC2)C[C@@H]1C]

A 100-mL round-bottom flask was charged with cyclobutyl (3S)-4-acetyl-3-methyl-7-(1H-pyrazol-4-yl)-1,2,3,4-tetrahydroquinoxaline-1-carboxylate (1.67 g, 4.71 mmol), N,N-dimethylformamide (10 mL), 4-bromo-1λ⁶-thiane-1,1-dione (1.0 g, 4.7 mmol), and cesium carbonate (3.08 g, 9.45 mmol). The resulting mixture was stirred overnight at 100° C. After cooling to room temperature, the resulting solution was diluted with water (20 mL) and extracted with ethyl acetate (2×30 mL). The combined organic layers were washed with brine, dried over anhydrous sodium sulfate, filtered and concentrated. The residue was purified via column chromatography on silica gel (eluting with 1:1, ethyl acetate/petroleum ether). The material was further purified by Prep-HPLC with the following conditions (Waters III): Column, Xbridge RP18 Sum, 19×150 mm; mobile phase, water (0.05% ammonium bicarbonate) and acetonitrile (50% acetonitrile up to 100% in 10 min); Detector, UV 220&254 nm. This afforded cyclobutyl (3S)-4-acetyl-7-[1-(1,1-dioxo-1λ⁶-thian-3-yl)-1H-pyrazol-4-yl]-3-methyl-1,2,3,4-tetrahydroquinoxaline-1-carboxylate (1.01 g, 44%) as a white solid. ¹H NMR (300 MHz, CD₃OD) δ ppm 1.09 (d, J=6.60 Hz, 3H), 1.62-1.74 (m, 1H), 1.75-1.92 (m, 1H), 2.03-2.35 (m, 9H), 2.36-2.45 (m, 2H), 3.06-3.18 (m, 2H), 3.38-3.56 (m, 2H), 3.67 (t, J=13.20 Hz, 1H), 4.07-4.18 (m, 1H), 4.75-4.83 (m, 1H), 4.97-5.07 (m, 2H), 7.37 (s, 2H), 7.88 (s, 1H), 8.03 (s, 1H), 8.11 (s, 1H). MS (ESI, pos. ion) m/z 487 [M+H]

The following examples were made according to the procedure outlined for Example 197

Example 198 oxan-4-yl (3S)-4-acetyl-7-[1-(1,1-dioxo-1λ⁶-thian-3-yl)-1H-pyrazol-4-yl]-3-methyl-1,2,3,4-tetrahydroquinoxaline-1-carboxylate (I-161)

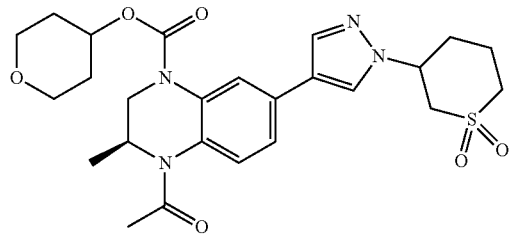 [SMILES: CC(=O)N1c2ccc(-c3cnn(C4CCCS(=O)(=O)C4)c3)cc2N(C(=O)OC2CCOCC2)C[C@@H]1C]

¹H NMR (400 MHz, CD₃OD) δ ppm 1.11 (d, J=6.80 Hz, 3H), 1.64-1.82 (m, 2H), 1.95-2.18 (m, 4H), 2.28 (s, 3H), 2.23-2.32 (m, 2H), 3.05-3.21 (m, 2H), 3.45-3.73 (m, 5H), 3.82-3.94 (m, 2H), 4.15-4.22 (m, 1H), 4.78-4.85 (m, 1H), 4.98-5.10 (m, 2H), 7.40 (s, 2H), 7.89 (s, 1H), 8.04 (s, 1H), 8.12 (s, 1H). MS (ESI, pos. ion) m/z 517 [M+H]⁺.

Example 199

3,3-difluorocyclobutyl (3S)-4-acetyl-7-[1-(1,1-dioxo-1λ⁶-thian-3-yl)-1H-pyrazol-4-yl]-3-methyl-1,2,3,4-tetrahydroquinoxaline-1-carboxylate (I-162)

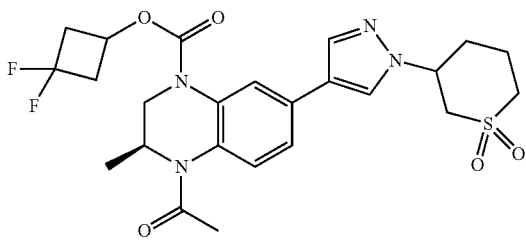 [SMILES: CC(=O)N1c2ccc(-c3cnn(C4CCCS(=O)(=O)C4)c3)cc2N(C(=O)OC2CC(F)(F)C2)C[C@@H]1C]

¹H NMR (400 MHz, CD₃OD) δ ppm 0.99 (d, J=6.80 Hz, 3H), 2.11 (s, 3H), 2.61-2.79 (m, 2H), 2.91-2.99 (m, 2H), 3.31-3.42 (m, 1H), 4.02-4.11 (m, 1H), 4.58-4.63 (m, 4H), 4.82-5.01 (m, 2H), 5.21-5.28 (m, 1H), 7.21-7.31 (m, 2H), 7.85 (s, 1H), 8.09 (s, 1H). MS (ESI, pos. ion) m/z 523 [M+H]

Example 200 oxan-4-yl (3S)-4-acetyl-3-methyl-7-[1-(2-oxopiperidin-4-yl)-1H-pyrazol-4-yl]-1,2,3,4-tetrahydroquinoxaline-1-carboxylate (I-163)

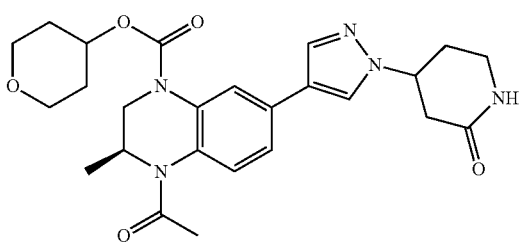 [SMILES: CC(=O)N1c2ccc(-c3cnn(C4CCNC(=O)C4)c3)cc2N(C(=O)OC2CCOCC2)C[C@@H]1C]

¹H NMR (300 MHz, CD₃OD) δ ppm 1.11 (d, J=6.60 Hz, 3H), 1.65-1.85 (m, 2H), 1.95-2.10 (m, 2H), 2.22 (s, 3H), 2.22-2.33 (m, 2H), 2.89 (d, J=7.50 Hz, 2H), 3.30-3.42 (m, 3H), 3.50-3.65 (m, 2H), 3.78-3.95 (m, 2H), 4.10-4.20 (m, 1H), 4.70-4.85 (m, 1H), 4.95-5.10 (m, 2H), 7.39 (br s, 2H), 7.87 (s, 1H), 8.03 (s, 1H), 8.09 (s, 1H). MS (ESI, pos. ion) m/z 482 [M+H]⁺.

Example 201

3,3-difluorocyclobutyl (3S)-4-acetyl-3-methyl-7-[1-(2-oxopiperidin-4-yl)-1H-pyrazol-4-yl]-1,2,3,4-tetrahydroquinoxaline-1-carboxylate (I-164)

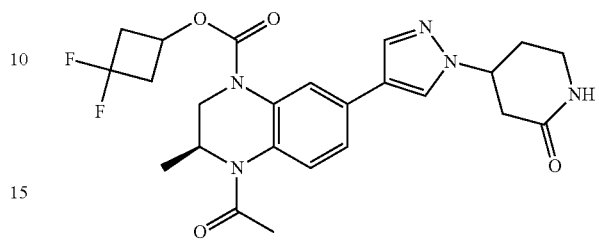

¹H NMR (400 MHz, CD₃OD) δ ppm 1.12 (d, J=6.80 Hz, 3H), 2.24 (s, 3H), 2.20-2.32 (m, 2H), 2.65-2.88 (m, 2H), 2.87-2.92 (m, 2H), 3.01-3.15 (m, 2H), 3.40-3.50 (m, 3H), 4.12-4.25 (m, 1H), 4.78-4.85 (m, 1H), 4.95-5.10 (m, 2H), 7.32-7.45 (m, 2H), 7.89 (s, 1H), 8.05 (s, 1H), 8.12 (s, 1H). MS (ESI, pos. ion) m/z 488[M+H]⁺.

Example 202

4,4-difluorocyclohexyl (3S)-4-acetyl-3-methyl-7-[1-(2-oxopiperidin-4-yl)-1H-pyrazol-4-yl]-1,2,3,4-tetrahydroquinoxaline-1-carboxylate (I-165)

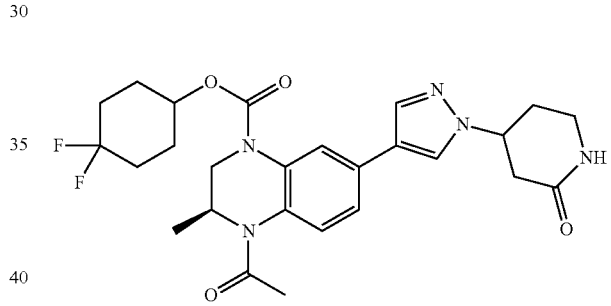

¹H NMR (400 MHz, CD₃OD) δ ppm 1.10 (d, J=6.80 Hz, 3H), 1.88-2.12 (m, 8H), 2.24 (s, 3H), 2.25-2.33 (m, 2H), 2.88-2.91 (m, 2H), 3.35-3.42 (m, 3H), 4.15-4.28 (m, 1H), 4.76-4.83 (m, 1H), 5.01-5.14 (m, 2H), 7.42 (s, 2H), 7.89 (s, 1H), 8.07 (s, 1H), 8.10 (s, 1H). MS (ESI, pos. ion) m/z 516[M+H]⁺.

Example 203 propan-2-yl (3S)-4-acetyl-3-methyl-7-[1-(2-oxopiperidin-4-yl)-1H-pyrazol-4-yl]-1,2,3,4-tetrahydroquinoxaline-1-carboxylate (I-166)

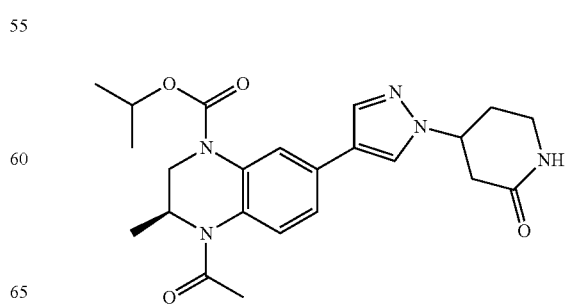

¹H NMR (300 MHz, CD₃OD) δ ppm 1.10 (d, J=6.60 Hz, 3H), 1.33 (d, J=8.40 Hz, 3H), 1.35 (d, J=8.40 Hz, 3H), 2.22 (s, 3H), 2.20-2.37 (m, 2H), 2.87-2.91 (m, 2H), 3.30-3.42 (m, 3H), 4.05-4.17 (m, 1H), 4.73-4.82 (m, 1H), 4.98-5.09 (m, 2H), 7.38 (s, 2H), 7.87 (s, 1H), 8.01 (s, 1H), 8.10 (s, 1H). MS (ESI, pos. ion) m/z 440 [M+H]⁺.

Example 204

4-{4-[(2S)-1-acetyl-4-cyclopropanecarbonyl-2-methyl-1,2,3,4-tetrahydroquinoxalin-6-yl]-1H-pyrazol-1-yl}piperidin-2-one (I-167)

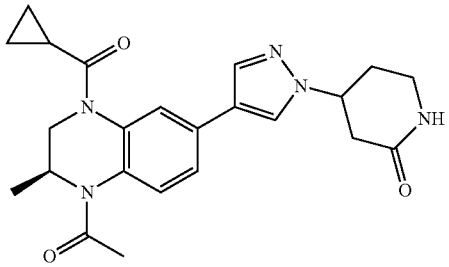 [SMILES: CC(=O)N1c2ccc(-c3cnn(C4CCNC(=O)C4)c3)cc2N(C(=O)C2CC2)C[C@@H]1C]

¹H NMR (400 MHz, CD₃OD) δ ppm 0.78-0.89 (m, 1H), 0.95-1.11 (m, 3H), 1.18 (d, J=6.40 Hz, 3H), 2.02-2.10 (m, 1H), 2.23 (s, 3H), 2.23-2.33 (m, 2H), 2.85-2.92 (m, 2H), 3.35-3.42 (m, 3H), 4.75-4.90 (m, 2H), 4.90-5.02 (m, 1H), 7.40-7.59 (m, 2H), 7.75 (s, 1H), 7.93 (s, 1H), 8.13 (s, 1H). MS (ESI, pos. ion) m/z 422 [M+H]⁺.

Example 205

3,3-difluorocyclobutyl (3S)-4-acetyl-3-methyl-7-{1-[(2S)-2-methylazetidin-3-yl]-1H-pyrazol-4-yl}-1,2,3,4-tetrahydroquinoxaline-1-carboxylate (I-168)

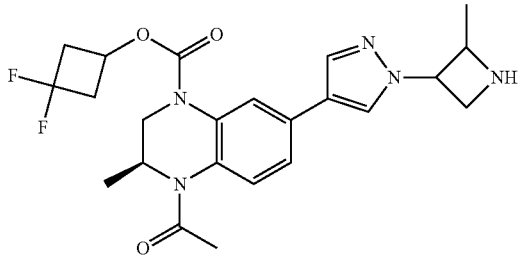 [SMILES: CC(=O)N1c2ccc(-c3cnn(C4CNC4C)c3)cc2N(C(=O)OC2CC(F)(F)C2)C[C@@H]1C]

Mixture of isomers. Major isomer: ¹H NMR (300 MHz, CD3OD) δ ppm 0.65-0.75 (m, 1H), 0.85-95 (m, 2H), 0.95-1.03 (m, 3H), 2.12 (s, 3H), 2.55-2.79 (m, 2H), 2.87-3.05 (m, 2H), 3.27-3.40 (m, 1H), 3.98-4.15 (m, 3H), 4.35-4.55 (m, 1H), 4.85-5.05 (m, 2H), 5.12-5.22 (m, 1H), 7.18-7.35 (m, 2H), 7.75-7.82 (m, 1H), 7.97 (br s, 1H), 8.05-8.20 (m, 1H).

Example 206 propan-2-yl (3S)-4-acetyl-3-methyl-7-{1-[(2S)-2-methylazetidin-3-yl]-1H-pyrazol-4-yl}-1,2,3,4-tetrahydroquinoxaline-1-carboxylate (I-159)

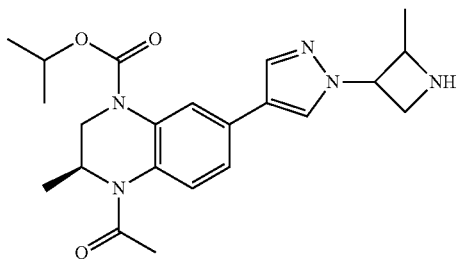 [SMILES: CC(=O)N1c2ccc(-c3cnn(C4CNC4C)c3)cc2N(C(=O)OC(C)C)C[C@@H]1C]

¹H NMR (400 MHz, CD₃OD) δ ppm 0.81-1.11 (m, 3H), 1.21-1.35 (m, 9H), 1.51-1.59 (m, 1H), 1.71-1.72 (m, 1H), 2.21 (s, 3H), 3.40-4.51 (m, 1H), 4.02-4.15 (m, 1H), 4.30-4.79 (m, 3H), 4.99-5.10 (m, 2H), 7.30-7.48 (m, 2H), 7.60-7.72 (m, 1H), 7.89-8.21 (m, 2H). MS (ESI, pos. ion) m/z 412 [M+H]⁺.

Example 207

1-[(2S)-4-cyclopropanecarbonyl-2-methyl-6-{1-[(2S)-2-methylazetidin-3-yl]-1H-pyrazol-4-yl}-1,2,3,4-tetrahydroquinoxalin-1-yl]ethan-1-one (I-160)

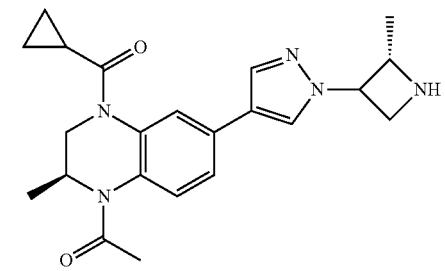 [SMILES: CC(=O)N1c2ccc(-c3cnn(C4CN[C@H]4C)c3)cc2N(C(=O)C2CC2)C[C@@H]1C]

¹H NMR (400 MHz, CD₃OD) δ ppm 0.78-0.84 (m, 1H), 0.97-1.10 (m, 3H), 1.18 (d, J=6.40 Hz, 3H), 1.30-1.35 (m, 1H), 1.35-1.42 (m, 3H), 2.01-2.11 (m, 1H), 2.23 (s, 3H), 2.80-3.05 (m, 1H), 3.75-3.82 (m, 1H), 4.01-4.09 (m, 1H), 4.38-4.45 (m, 1H), 4.75-4.99 (m, 2H), 7.40-7.55 (m, 2H), 7.75 (s, 1H), 7.90-7.95 (m, 1H), 8.15-8.20 (m, 1H). MS (ESI, pos. ion) m/z 394 [M+H]⁺.

Example 208 cyclopropylmethyl (3S)-4-acetyl-7-[1-(1,1-dioxo-1λ⁶-thian-4-yl)-1H-pyrazol-4-yl]-3-methyl-1,2,3,4-tetrahydroquinoxaline-1-carboxylate (I-169)

cyclopropylmethyl (3S)-4-acetyl-7-{1-[(3R)-1,1-dioxo-1λ⁶-thian-3-yl]-1H-pyrazol-4-yl}-3-methyl-1,2,3,4-tetrahydroquinoxaline-1-carboxylate (I-171)

cyclopropylmethyl (3S)-4-acetyl-7-{1-[(3S)-1,1-dioxo-1λ⁶-thian-3-yl]-1H-pyrazol-4-yl}-3-methyl-1,2,3,4-tetrahydroquinoxaline-1-carboxylate (I-172)

I-169

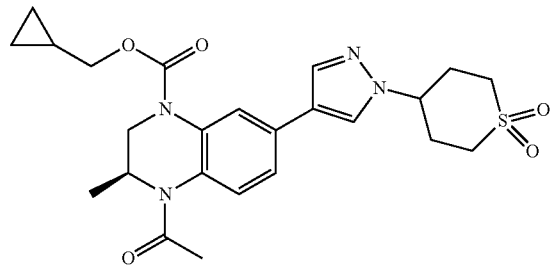

I-171

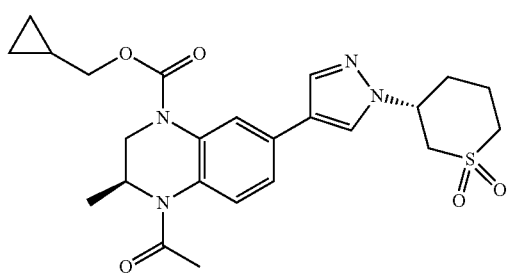

I-172

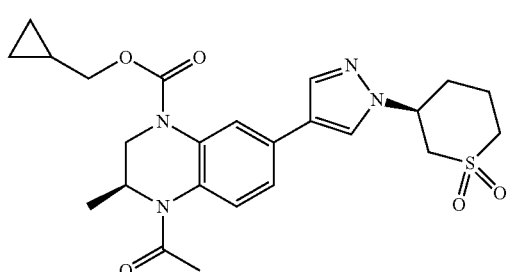

Step 1. cyclopropylmethyl (3S)-4-acetyl-3-methyl-7-(1H-pyrazol-4-yl)-1,2,3,4-tetrahydroquinoxaline-1-carboxylate A 100-mL round-bottom flask was purged with nitrogen and charged with cyclopropylmethyl (3S)-4-acetyl-7-bromo-3-methyl-1,2,3,4-tetrahydroquinoxaline-1-carboxylate (1 g, 2.72 mmol), tert-butyl 4-(tetramethyl-1,3,2-dioxaborolan-2-yl)-1H-pyrazol-1-carboxylate (953 mg, 3.24 mmol), sodium carbonate (573 mg, 5.41 mmol), [1,1'bis(diphenylphosphino)ferrocene]dichloropalladium(II) dichloromethane complex (265 mg, 0.326 mmol), 1,4-dioxane (9 mL), and water (3 mL). The resulting mixture was stirred overnight at 100° C. After cooling to room temperature, the reaction mixture was poured into water (20 mL). The aqueous layer was separated and extracted with ethyl acetate (4×40 mL). The combined organic layers were dried over anhydrous sodium sulfate, filtered, and concentrated under vacuum. The residue was purified via column chromatography on silica gel (eluting with 1:1, ethyl acetate/petroleum ether) to afford cyclopropylmethyl (3S)-4-acetyl-3-methyl-7-(1H-pyrazol-4-yl)-1,2,3,4-tetrahydroquinoxaline-1-carboxylate (400 mg, 41%) of as a yellow solid. MS (ESI, pos. ion) m/z 355 [M+H]⁺.

Step 2. cyclopropylmethyl (3S)-4-acetyl-7-[1-(1,1-dioxo-1λ⁶-thian-4-yl)-1H-pyrazol-4-yl]-3-methyl-1,2,3,4-tetrahydroquinoxaline-1-carboxylate, cyclopropylmethyl (3S)-4-acetyl-7-{1-[(3R)-1,1-dioxo-1λ⁶-thian-3-yl]-1H-pyrazol-4-yl}-3-methyl-1,2,3,4-tetrahydroquinoxaline-1-carboxylate, and cyclopropylmethyl (3S)-4-acetyl-7-{1-[(3S)-1,1-dioxo-1λ⁶-thian-3-yl]-1H-pyrazol-4-yl}-3-methyl-1,2,3,4-tetrahydroquinoxaline-1-carboxylate A 100-mL round-bottom flask was charged with cyclopropylmethyl (3S)-4-acetyl-3-methyl-7-(1H-pyrazol-4-yl)-1,2,3,4-tetrahydroquinoxaline-1-carboxylate (400 mg, 1.13 mmol), 1,1-dioxidotetrahydro-2H-thiopyran-4-yl methanesulfonate (276 mg, 1.21 mmol), cesium carbonate (715 mg, 2.19 mmol) and N,N-dimethylformamide (10 mL). The resulting mixture was stirred overnight at 100° C. After cooling to room temperature, the resulting mixture was diluted with ethyl acetate (100 mL), washed with water (3×20 mL), dried over anhydrous sodium sulfate, filtered, and concentrated. The residue was purified via column chromatography on silica gel (eluting with 1:2, ethyl acetate/petroleum ether). The crude product was further purified by Prep-HPLC with the following conditions: Column, XBridge RP C18, 19×150 mm, 5 um; mobile phase: water (0.05% NH₄HCO₃) and acetonitrile (5% acetonitrile to 58% in 7 min; Flow rate: 25 mL/min); Detector, 220&254 nm. This afforded:

cyclopropylmethyl (3S)-4-acetyl-7-[1-(1,1-dioxo-1λ⁶-thian-4-yl)-1H-pyrazol-4-yl]-3-methyl-1,2,3,4-tetrahydroquinoxaline-1-carboxylate (I-169) (134 mg, 24%) as a white solid. ¹H NMR (400 MHz, CD₃OD) δ ppm 0.35-0.39 (m, 2H), 0.58-0.63 (m, 2H), 1.11 (d, J=6.80 Hz, 3H), 1.28-1.31 (m, 1H), 2.01-2.15 (m, 2H), 2.23 (s, 3H), 2.24-2.31 (m, 2H), 3.09-3.19 (m, 2H), 3.40-3.53 (m, 2H), 3.68 (t, J=12.30 Hz, 1H), 4.08 (d, J=7.20 Hz, 2H), 4.11-4.21 (m, 1H), 4.73-4.87 (m, 1H), 5.01-5.12 (m, 1H), 7.31-7.41 (m, 2H), 7.90 (s, 1H), 8.04 (s, 1H), 8.12 (s, 1H). MS (ESI, pos. ion) m/z 487 [M+H]⁺; and cyclopropylmethyl (3S)-4-acetyl-7-[1-(1,1-dioxo-1λ⁶-thian-3-yl-1H-pyrazol-4-yl]-3-methyl-1,2,3,4-tetrahydroquinoxaline-1-carboxylate (90 mg, 16%) as a white solid. This material was further separated with Prep Chiral HPLC (Prep-HPLC-009): Column: Chiralpak IB2*25 cm, 5 μm, Chiral-P(IB)001IBOOCJ-KE002; Mobile Phase A: Hexane-HPLC, Mobile Phase B: ethanol; Flow rate: 20 mL/min; 220&254 nm; RT=1:20 min (Example 23-2); RT=2:26 min (Example 23-3) to afford:

cyclopropylmethyl (3S)-4-acetyl-7-{1-[(3R)-1,1-dioxo-1λ⁶-thian-3-yl]-1H-pyrazol-4-yl}-3-methyl-1,2,3,4-tetrahydroquinoxaline-1-carboxylate (I-171) (33.5 mg, 6%) as a white solid. ¹H NMR (400 MHz, CD₃OD) δ ppm 0.35-0.39 (m, 2H), 0.59-0.63 (m, 2H), 1.12 (d, J=6.40 Hz, 3H), 1.17-1.28 (m, 1H), 2.01-2.14 (m, 2H), 2.23 (s, 3H), 2.24-2.31 (m, 2H), 3.10-3.21 (m, 2H), 3.40-3.55 (m, 2H), 3.68 (t, J=12.00 Hz, 1H), 4.08 (d, J=7.20 Hz, 2H), 4.10-4.21 (m, 1H), 4.73-4.89 (m, 1H), 5.01-5.12 (m, 1H), 7.33-7.45 (m, 2H), 7.89 (s, 1H), 8.04 (s, 1H), 8.11 (s, 1H). MS (ESI, pos. ion) m/z 487 [M+H]⁺. Stereochemistry of tetrahydro-2H-thiopyran 1,1-dioxide tentatively assigned and cyclopropylmethyl (3S)-4-acetyl-7-{1-[(3S)-1,1-dioxo-1λ⁶-thian-3-yl]-1H-pyrazol-4-yl}-3-methyl-1,2,3,4-tetrahydroquinoxaline-1-carboxylate (I-172) (31.5 mg, 6%) as a white solid. ¹H NMR (400 MHz, CD₃OD) δ ppm 0.35-0.39 (m, 2H), 0.58-0.63 (m, 2H), 1.11 (d, J=6.80 Hz, 3H), 1.28-1.31 (m, 1H), 2.01-2.15 (m, 2H), 2.23 (s, 3H), 2.24-2.31 (m, 2H), 3.09-3.19 (m, 2H), 3.40-3.53 (m, 2H), 3.68 (t, J=12.30 Hz, 1H), 4.08 (d, J=7.20 Hz, 2H), 4.11-4.21 (m, 1H), 4.73-4.87 (m, 1H), 5.01-5.12 (m, 1H), 7.31-7.41 (m, 2H), 7.90 (s, 1H), 8.04 (s, 1H), 8.12 (s, 1H). MS (ESI, pos. ion) m/z 487 [M+H]⁺. Stereochemistry of tetrahydro-2H-thiopyran 1,1-dioxide tentatively assigned.

The following examples were made according to the procedure outlined for Examples 208:

Example 209 cyclobutyl (3S)-4-acetyl-7-{1-[(3R)-1,1-dioxo-1λ⁶-thian-3-yl]-1H-pyrazol-4-yl}-3-methyl-1,2,3,4-tetrahydroquinoxaline-1-carboxylate (I-173)

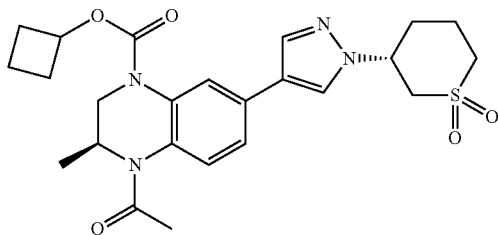 [SMILES: CC(=O)N1c2ccc(-c3cnn([C@@H]4CCCS(=O)(=O)C4)c3)cc2N(C(=O)OC2CCC2)C[C@@H]1C]

¹H NMR (300 MHz, CDCl₃) δ ppm 1.08 (d, J=6.80 Hz, 3H), 1.53-1.73 (m, 1H), 1.75-1.91 (m, 1H), 2.05-2.31 (m, 9H), 2.33-2.49 (m, 2H), 2.93-3.07 (m, 1H), 3.09-3.19 (m, 1H), 3.40-3.65 (m, 3H), 4.03-4.12 (m, 1H), 4.66-4.82 (m, 1H), 5.01-5.11 (m, 1H), 5.10-5.21 (m, 1H), 7.12-7.19 (m, 2H), 7.67 (s, 1H), 7.80 (s, 1H), 8.11 (s, 1H). MS (ESI, pos. ion) m/z 487 [M+H]⁺.

Example 210 cyclobutyl (3S)-4-acetyl-7-{1-[(3S)-1,1-dioxo-1λ⁶-thian-3-yl]-1H-pyrazol-4-yl}-3-methyl-1,2,3,4-tetrahydroquinoxaline-1-carboxylate (I-174)

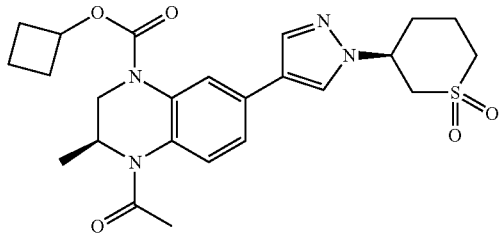 [SMILES: CC(=O)N1c2ccc(-c3cnn([C@H]4CCCS(=O)(=O)C4)c3)cc2N(C(=O)OC2CCC2)C[C@@H]1C]

¹H NMR (300 MHz, CDCl3) δ ppm 1.08 (d, J=6.80 Hz, 3H), 1.48-1.57 (m, 1H), 1.73-1.89 (m, 1H), 2.05-2.30 (m, 9H), 2.35-2.49 (m, 2H), 2.91-3.18 (m, 2H), 3.39-3.68 (m, 3H), 4.01-4.12 (m, 1H), 4.67-4.82 (m, 1H), 5.01-5.21 (m, 2H), 7.05-7.21 (m, 2H), 7.67 (s, 1H), 7.80 (s, 1H), 8.08 (s, 1H). MS (ESI, pos. ion) m/z 487 [M+H]⁺.

Example 211 cyclobutyl (3S)-4-acetyl-3-methyl-7-[1-(2-oxopiperidin-4-yl)-1H-pyrazol-4-yl]-1,2,3,4-tetrahydroquinoxaline-1-carboxylate (I-175)

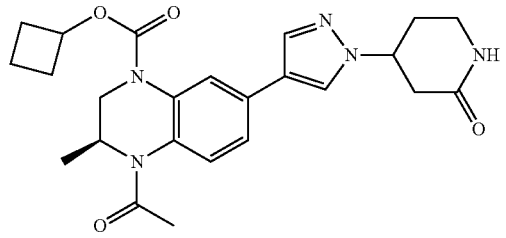 [SMILES: CC(=O)N1c2ccc(-c3cnn(C4CCNC(=O)C4)c3)cc2N(C(=O)OC2CCC2)C[C@@H]1C]

¹H NMR (400 MHz, CD₃OD) δ ppm 1.11 (d, J=6.80 Hz, 3H), 1.62-1.73 (m, 1H), 1.82-1.89 (m, 1H), 2.11-2.45 (m, 9H), 2.87-2.91 (m, 2H), 3.31-3.45 (m, 3H), 4.10-4.19 (m, 1H), 4.76-4.83 (m, 1H), 5.01-5.09 (m, 2H), 7.35-7.41 (m, 2H), 7.89 (s, 1H), 8.04 (s, 1H), 8.11 (s, 1H). MS (ESI, pos. ion) m/z 452 [M+H]⁺.

Example 212 cyclobutyl (3S)-4-acetyl-3-methyl-7-{1-[(4R)-2-oxopiperidin-4-yl]-1H-pyrazol-4-yl}-1,2,3,4-tetrahydroquinoxaline-1-carboxylate (I-176)

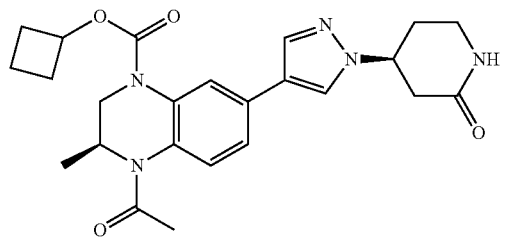 [SMILES: CC(=O)N1c2ccc(-c3cnn([C@H]4CCNC(=O)C4)c3)cc2N(C(=O)OC2CCC2)C[C@@H]1C]

¹H NMR (300 MHz, CD₃OD) δ ppm 1.10 (d, J=6.60 Hz, 3H), 1.62-1.75 (m, 1H), 1.78-1.89 (m, 1H), 2.09-2.48 (m, 9H), 2.87-2.91 (m, 2H), 3.31-3.42 (m, 3H), 4.09-4.21 (m, 1H), 4.75-4.83 (m, 1H), 4.98-5.11 (m, 2H), 7.38 (s, 2H), 7.88 (s, 1H), 8.02 (s, 1H), 8.09 (s, 1H). MS (ESI, pos. ion) m/z 452 [M+H]⁺. Stereochemistry of piperidin-2-one tentatively assigned.

Example 213 cyclobutyl (3S)-4-acetyl-3-methyl-7-{1-[(4S)-2-oxopiperidin-4-yl]-1H-pyrazol-4-yl}-1,2,3,4-tetrahydroquinoxaline-1-carboxylate (I-177)

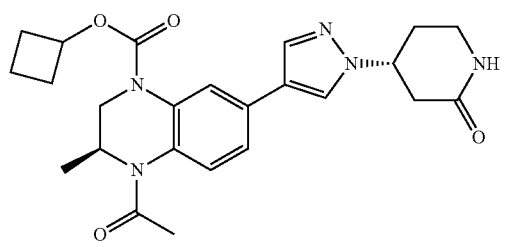 [SMILES: CC(=O)N1c2ccc(-c3cnn([C@@H]4CCNC(=O)C4)c3)cc2N(C(=O)OC2CCC2)C[C@@H]1C]

¹H NMR (300 MHz, CD₃OD) δ ppm 1.10 (d, J=6.90 Hz, 3H), 1.62-1.75 (m, 1H), 1.78-1.89 (m, 1H), 2.09-2.48 (m, 9H), 2.87-2.91 (m, 2H), 3.31-3.42 (m, 3H), 4.09-4.21 (m, 1H), 4.75-4.83 (m, 1H), 4.98-5.11 (m, 2H), 7.38 (s, 2H), 7.88 (s, 1H), 8.03 (s, 1H), 8.10 (s, 1H). MS (ESI, pos. ion) m/z 452 [M+H]⁺. Stereochemistry of piperidin-2-one tentatively assigned.

Example 214 cyclobutyl (3S)-4-acetyl-3-methyl-7-{1-[(2S)-2-methylazetidin-3-yl]-1H-pyrazol-4-yl}-1,2,3,4-tetrahydroquinoxaline-1-carboxylate (I-178)

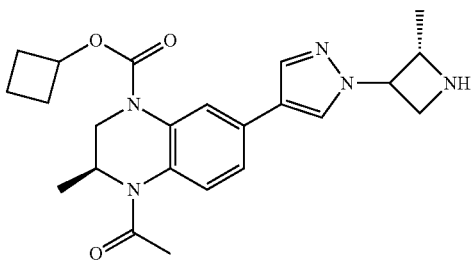 [SMILES: CC(=O)N1c2ccc(-c3cnn(C4CN[C@H]4C)c3)cc2N(C(=O)OC2CCC2)C[C@@H]1C]

¹H NMR (400 MHz, CD₃OD) δ ppm 0.99 (d, J=6.40 Hz, 3H), 1.07 (d, J=6.80 Hz, 3H), 1.51-1.63 (m, 1H), 1.68-1.75 (m, 1H), 1.95-2.15 (m, 3H), 2.12 (s, 3H), 2.23-2.33 (m, 2H), 3.31-3.42 (m, 1H), 3.95-4.09 (m, 1H), 4.37-4.43 (m, 1H), 4.53-4.62 (m, 1H), 4.89-5.01 (m, 2H), 5.20-5.31 (m, 1H), 7.08-7.19 (m, 1H), 7.23-7.35 (m, 2H), 7.91 (s, 1H), 7.97 (s, 1H), 8.02 (s, 1H). MS (ESI, pos. ion) m/z 424 [M+H]⁺. Stereochemistry of piperidin-2-one tentatively assigned.

Example 215 cyclobutyl (3S)-4-acetyl-3-methyl-7-{1-[(2R)-2-methylazetidin-3-yl]-1H-pyrazol-4-yl}-1,2,3,4-tetrahydroquinoxaline-1-carboxylate (I-170)

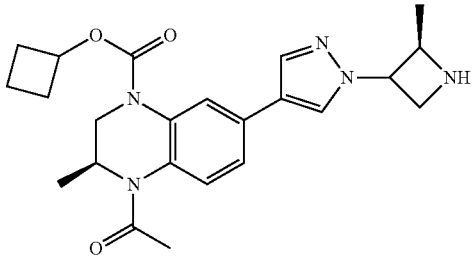 [SMILES: CC(=O)N1c2ccc(-c3cnn(C4CN[C@@H]4C)c3)cc2N(C(=O)OC2CCC2)C[C@@H]1C]

¹H NMR (400 MHz, CD₃OD) δ ppm 0.68-0.80 (m, 3H), 0.94-1.05 (m, 11H), 1.15-1.40 (m, 4H), 1.55-1.60 (m, 1H), 1.60-1.81 (m, 1H), 2.00-2.19 (m, 11H), 2.23-2.40 (m, 3H), 2.65-2.78 (m, 1H), 2.90-3.02 (m, 2H), 3.99-4.20 (m, 2H), 4.20-4.48 (m, 1H), 4.50 (s, 3H), 4.92-5.03 (m, 4H), 7.30 (s, 4H), 7.77 (s, 1H), 7.78 (s, 1H), 7.83 (s, 1H), 7.96 (s, 2H), 8.03 (s, 1H). MS (ESI, pos. ion) m/z 424 [M+H]⁺. Stereochemistry of piperidin-2-one tentatively assigned.

Example 216

1-[(2S)-6-(1-cyclopropyl-1H-pyrazol-4-yl)-4-(7-fluoro-1-methyl-1H-indazol-3-yl)-2-methyl-1,2,3,4-tetrahydroquinoxalin-1-yl]ethan-1-one (I-179)

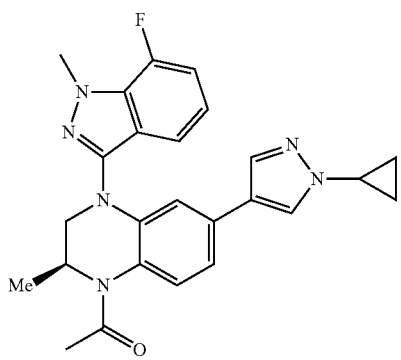 [SMILES: CC(=O)N1c2ccc(-c3cnn(C4CC4)c3)cc2N(c2nn(C)c3c(F)cccc23)C[C@@H]1C]

Step 1. (S)-1-(6-bromo-4-(7-fluoro-1-methyl-1H-indazol-3-yl)-2-methyl-3,4-dihydroquinoxalin-1(2H)-yl)ethan-1-one A 100-mL round-bottom flask was purged with an inert atmosphere of nitrogen and charged with (S)-1-(6-bromo-2-methyl-3,4-dihydroquinoxalin-1(2H)-yl)ethan-1-one (100 mg, 0.37 mmol), 4-3-bromo-7-fluoro-1-methyl-1H-indazole (128 mg, 0.56 mmol), XPhos 3ʳᵈ Generation precatalyst ((2-dicyclohexylphosphino-2',4',6'-triisopropyl-1,1'-biphenyl)[2-(2'-amino-1,1'-biphenyl)]palladium(II) methanesulfonate)(31 mg, 0.04 mmol), cesium carbonate (364 mg, 1.12 mmol), and 1,4-dioxane (40 mL). The resulting mixture stirred for 14 h at 110° C. in an oil bath. After cooling to room temperature, the reaction mixture was filtered through a short pad of celite and concentrated under vacuum. The residue was purified by preparative thin layer chromatography (eluting with 10% methanol-dichloromethane) to afford (S)-1-(6-bromo-4-(7-fluoro-1-methyl-1H-indazol-3-yl)-2-methyl-3,4-dihydroquinoxalin-1(2H)-yl)ethan-1-one (67 mg, 43%) of as a yellow solid. MS (ESI, pos. ion) m/z 417 [M+H]⁺.

Step 2. 1-[(2S)-6-(1-cyclopropyl-1H-pyrazol-4-yl)-4-(7-fluoro-1-methyl-1H-indazol-3-yl)-2-methyl-1,2,3,4-tetrahydroquinoxalin-1-yl]ethan-1-one A 100-mL round-bottom flask was purged with an inert atmosphere of nitrogen and charged with (S)-1-(6-bromo-4-(7-fluoro-1-methyl-1H-indazol-3-yl)-2-methyl-3,4-dihydroquinoxalin-1(2H)-yl)ethan-1-one (46 mg, 0.11 mmol), 1-cyclopropyl-4-(4,4,5,5-tetramethyl-1,3,2-dioxaborolan-2-yl)-1H-pyrazole (77.6 mg, 0.33 mmol), [1,1'-bis(diphenylphosphino)ferrocene]dichloropalladium(II) (8 mg, 0.01 mmol), potassium carbonate (46 mg, 0.33 mmol), 1,4-dioxane (20 mL) and water (2 mL). The resulting mixture stirred overnight at 100° C. After cooling to room temperature, the reaction mixture was filtered through a short pad of celite and concentrated under vacuum. The residue was purified via column chromatography on silica gel (eluting with 1:1, ethyl acetate/petroleum ether) to afford (S)-1-(6-(1-cyclopropyl-1H-pyrazol-4-yl)-4-(7-fluoro-1-methyl-1H-indazol-3-yl)-2-methyl-3,4-dihydroquinoxalin-1(2H)-yl)ethanone (13.1 mg, 27%) as a white solid. ¹H NMR (300 MHz, CDCl₃) δ ppm 1.01-1.14 (m, 4H), 1.26 (d, J=6.90 Hz, 3H), 2.32 (s, 3H), 3.55-3.65 (m, 1H), 3.67-3.75 (m, 1H), 3.90-4.01 (m, 1H), 4.23 (s, 3H), 6.76 (s, 1H), 6.85-6.98 (m, 2H), 7.01-7.15 (m, 3H), 7.49 (s, 1H), 7.56 (s, 1H). MS (ESI, pos. ion) m/z 445 [M+H]⁺.

The following examples were made according to the procedure outlined for Example 216

Example 217

1-[(2S)-6-(1-cyclopropyl-1H-pyrazol-4-yl)-4-(4-fluoro-1-methyl-1H-indazol-3-yl)-2-methyl-1,2,3,4-tetrahydroquinoxalin-1-yl]ethan-1-one (I-183)

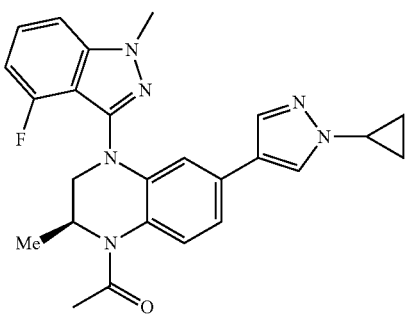 [SMILES: CC(=O)N1c2ccc(-c3cnn(C4CC4)c3)cc2N(c2nn(C)c3cccc(F)c23)C[C@@H]1C]

¹H NMR (400 MHz, CD₃OD) δ ppm 0.99-1.12 (m, 4H), 1.29 (s, 3H), 2.35 (s, 3H), 3.55-3.64 (m, 1H), 3.71-3.79 (m, 1H), 3.88-3.99 (m, 1H), 4.08 (s, 3H), 5.30 (s, 1H), 6.78 (s, 1H), 6.97-7.12 (m, 2H), 7.15-7.38 (m, 2H), 7.46 (s, 1H), 7.61-7.69 (m, 1H), 7.76 (s, 1H). MS (ESI, pos. ion) m/z 445 [M+H]⁺.

Example 218

1-[(2S)-6-(1-cyclopropyl-1H-pyrazol-4-yl)-2-methyl-4-{1-methyl-1H-pyrazolo[3,4-b]pyridin-3-yl}-1,2,3,4-tetrahydroquinoxalin-1-yl]ethan-1-one (I-184)

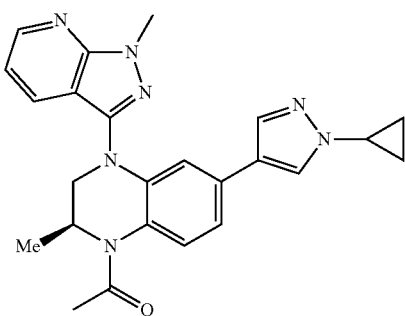 [SMILES: CC(=O)N1c2ccc(-c3cnn(C4CC4)c3)cc2N(c2nn(C)c3ncccc23)C[C@@H]1C]

¹H NMR (300 MHz, CDCl₃) δ ppm 0.95-1.10 (m, 3H), 1.10-1.44 (m, 4H), 2.25 (s, 3H), 3.52-3.67 (m, 1H), 3.75-3.90 (m, 1H), 3.90-4.03 (m, 1H), 4.03-4.17 (m, 3H), 4.77 (m, 1H), 5.05-5.35 (m, 1H), 7.02 (s, 1H), 7.09-7.21 (m, 2H), 7.28-7.61 (m, 2H), 7.80-8.00 (m, 2H), 8.55 (s, 1H). MS (ESI, pos. ion) m/z 428 [M+H]⁺.

Example 219

1-[(2S)-6-(1-cyclopropyl-1H-pyrazol-4-yl)-2-methyl-4-{1-methyl-1H-pyrazolo[3,4-c]pyridin-3-yl}-1,2,3,4-tetrahydroquinoxalin-1-yl]ethan-1-one (I-185)

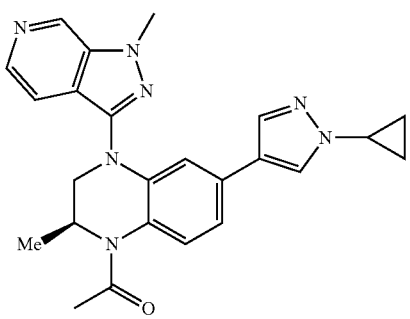 [SMILES: CC(=O)N1c2ccc(-c3cnn(C4CC4)c3)cc2N(c2nn(C)c3cnccc23)C[C@@H]1C]

¹H NMR (300 MHz, CD₃OD) δ ppm 0.90-1.09 (m, 4H), 1.20-1.31 (m, 3H), 2.33 (s, 3H), 3.50-3.65 (m, 1H), 3.78-3.92 (m, 1H), 3.92-4.03 (m, 1H), 4.20 (s, 3H), 5.25 (s, 1H), 6.91 (s, 1H), 7.06-7.20 (m, 1H), 7.27-7.45 (m, 2H), 7.55 (s, 1H), 7.77 (s, 1H), 8.14 (d, J=5.70 Hz, 1H), 9.09 (s, 1H). MS (ESI, pos. ion) m/z 428 [M+H]⁺.

Example 220

1-[(2S)-6-(1-cyclopropyl-1H-pyrazol-4-yl)-2-methyl-4-{1-methyl-1H-pyrazolo[4,3-c]pyridin-3-yl}-1,2,3,4-tetrahydroquinoxalin-1-yl]ethan-1-one (I-186)

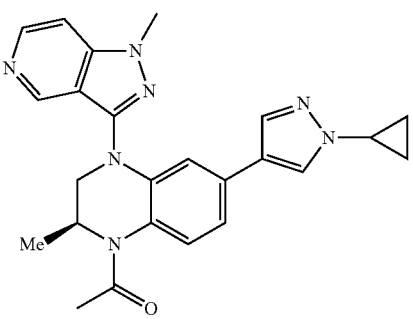 [SMILES: CC(=O)N1c2ccc(-c3cnn(C4CC4)c3)cc2N(c2nn(C)c3ccncc23)C[C@@H]1C]

¹H NMR (300 MHz, CD₃OD) δ ppm 0.91-1.10 (m, 5H), 1.25-1.32 (m, 6H), 2.35 (s, 3H), 3.52-3.67 (m, 1H), 3.75-3.90 (m, 1H), 3.96-4.08 (m, 1H), 4.21 (s, 3H), 5.25 (s, 1H), 6.92 (s, 1H), 7.13 (d, J=9.60 Hz, 1H), 7.43 (d, J=5.40 Hz, 1H), 7.51 (s, 1H), 7.79 (s, 1H), 8.16 (d, J=5.40 Hz, 1H), 9.11 (s, 1H). MS (ESI, pos. ion) m/z 428 [M+H]+.

Example 221

1-[(2S)-6-(1-cyclopropyl-1H-pyrazol-4-yl)-2-methyl-4-{1-methyl-1H-pyrazolo[4,3-b]pyridin-3-yl}-1,2,3,4-tetrahydroquinoxalin-1-yl]ethan-1-one (I-187)

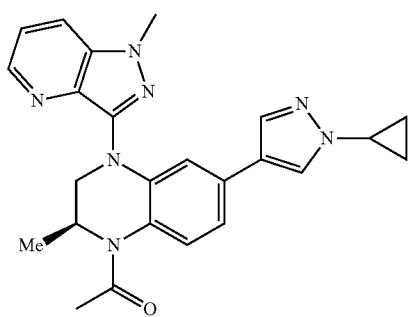 [SMILES: CC(=O)N1c2ccc(-c3cnn(C4CC4)c3)cc2N(c2nn(C)c3cccnc23)C[C@@H]1C]

¹H NMR (300 MHz, CD₃OD) δ ppm 0.91-1.10 (m, 4H), 1.20-1.32 (m, 3H), 2.33 (s, 3H), 3.52-3.67 (m, 1H), 3.80-3.95 (m, 1H), 3.96-4.21 (m, 4H), 5.21 (s, 1H), 6.95 (s, 1H), 7.02 (d, J=7.20 Hz, 1H), 7.25 (s, 1H), 7.56 (s, 2H), 7.75 (s, 1H), 8.10 (d, J=8.40 Hz, 1H), 8.45 (s, 1H). MS (ESI, pos. ion) m/z 428 [M+H]+.

Example 222

1-[(2S)-4-(6-fluoro-1-methyl-1H-indazol-3-yl)-6-[1-(2-hydroxyethyl)-1H-pyrazol-4-yl]-2-methyl-1,2,3,4-tetrahydroquinoxalin-1-yl]ethan-1-one (I-188)

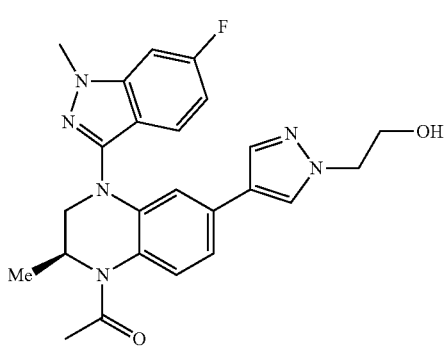 [SMILES: CC(=O)N1c2ccc(-c3cnn(CCO)c3)cc2N(c2nn(C)c3cc(F)ccc23)C[C@@H]1C]

¹H NMR (300 MHz, CD₃OD) δ ppm 1.20-1.32 (m, 3H), 2.35 (s, 3H), 3.69-4.09 (m, 7H), 4.10-4.30(2H), 5.25 (s, 1H), 6.85-6.95 (m, 2H), 7.10 (s, 1H), 7.20-7.47 (m, 3H), 7.54 (s, 1H), 7.77 (s, 1H). MS (ESI, pos. ion) m/z 449 [M+H]+.

Example 223

1-[(2S)-4-(5-fluoro-1-methyl-1H-indazol-3-yl)-6-[1-(2-hydroxyethyl)-1H-pyrazol-4-yl]-2-methyl-1,2,3,4-tetrahydroquinoxalin-1-yl]ethan-1-one (I-189)

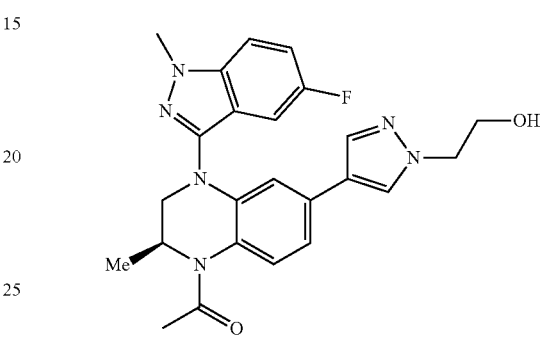

¹H NMR (300 MHz, CD₃OD) δ ppm 1.28-1.35 (m, 4H), 2.34 (s, 3H), 3.61-4.00 (m, 4H), 4.09 (s, 3H), 4.15-4.24 (m, 2H), 5.29 (s, 1H), 6.70 (s, 1H), 6.75-6.90 (m, 1H), 6.95-7.10 (m, 1H), 7.25 (s, 1H), 7.45 (s, 2H), 7.55 (s, 1H), 7.71 (s, 1H). MS (ESI, pos. ion) m/z 449 [M+H]+.

Example 224

1-[(2S)-4-(4-fluoro-1-methyl-1H-indazol-3-yl)-6-[1-(2-hydroxyethyl)-1H-pyrazol-4-yl]-2-methyl-1,2,3,4-tetrahydroquinoxalin-1-yl]ethan-1-one (I-190)

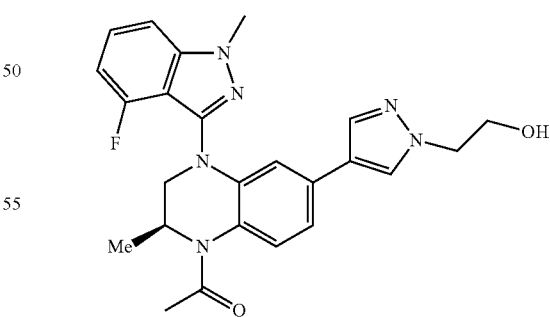

¹H NMR (300 MHz, CD₃OD) δ ppm 1.29 (s, 3H), 2.35 (s, 3H), 3.64-4.00 (m, 4H), 4.07 (s, 3H), 4.15-4.24 (m, 2H), 5.29 (s, 1H), 6.78 (s, 1H), 6.95-7.14 (m, 2H), 7.21-7.40 (m, 2H), 7.61 (s, 1H), 7.59-7.79 (m, 1H), 7.72(1H). MS (ESI, pos. ion) m/z 449 [M+H]+.

Example 225

1-[(2S)-4-(7-fluoro-1-methyl-1H-indazol-3-yl)-6-[1-(2-hydroxyethyl)-1H-pyrazol-4-yl]-2-methyl-1,2,3,4-tetrahydroquinoxalin-1-yl]ethan-1-one (I-180)

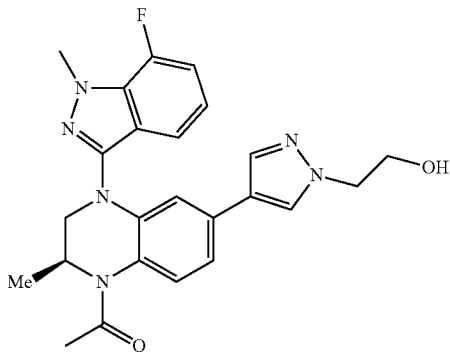 [SMILES: CC(=O)N1c2ccc(-c3cnn(CCO)c3)cc2N(c2nn(C)c3c(F)cccc23)C[C@@H]1C]

$^1$H NMR (300 MHz, CD$_3$OD) δ ppm 1.29 (d, J=6.60 Hz, 3H), 2.35 (s, 3H), 3.71-3.90 (m, 3H), 3.91-3.08 (m, 1H), 4.14-4.21 (m, 2H), 4.23 (s, 3H), 5.29 (s, 1H), 6.83 (s, 1H), 7.01-7.22 (m, 4H), 7.35 (s, 1H), 7.54 (s, 1H), 7.72 (s, 1H). MS (ESI, pos. ion) m/z 449 [M+H]$^+$.

The following examples were prepared according to the procedure outlined for Example 216, with the following changes:

In Step 2, tert-butyl 4-[4-(tetramethyl-1,3,2-dioxaborolan-2-yl)-1H-pyrazol-1-yl]piperidin-1-carboxylate was used in place of 1-cyclopropyl-4-(4,4,5,5-tetramethyl-1,3,2-dioxaborolan-2-yl)-1H-pyrazole. To remove N-tert-butoxycarbonyl group, the product from Step 2 was dissolved in a solution of dichloromethane and trifluoroacetic acid (4:1, 0.1 M reaction concentration) and stirred at rt for 1.5 h. The reaction mixture was concentrated, and the residue was partitioned between dichloromethane and saturated aqueous sodium bicarbonate solution. The layers were separated and the organic phase was washed with brine, dried over anhydrous sodium sulfate, filtered, and concentrated to afford the desired product.

Example 226

1-[(2S)-2-methyl-4-(1-methyl-1H-indazol-3-yl)-6-[1-(piperidin-4-yl)-1H-pyrazol-4-yl]-1,2,3,4-tetrahydroquinoxalin-1-yl]ethan-1-one (I-181)

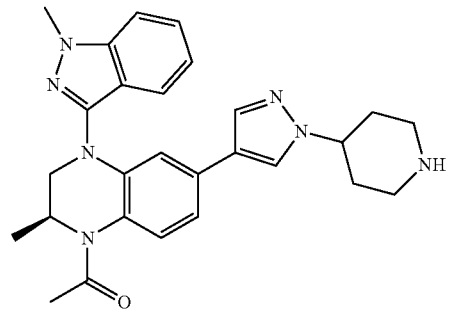 [SMILES: CC(=O)N1c2ccc(-c3cnn(C4CCNCC4)c3)cc2N(c2nn(C)c3ccccc23)C[C@@H]1C]

$^1$H NMR (300 MHz, CD$_3$OD) δ ppm 1.22-1.31 (m, 3H), 1.78-1.91 (m, 2H), 1.94-2.09 (m, 2H), 2.34 (s, 3H), 2.73 (t, J=12.30 Hz, 2H), 3.16 (d, J=12.30 Hz, 2H), 3.76 (d, J=11.70 Hz, 1H), 3.99-3.91 (m, 1H), 4.06 (s, 3H), 4.10-4.21 (m,1H), 5.25 (s, 1H), 6.83 (s, 1H), 7.03-7.21 (m, 2H), 7.39-7.51 (m, 4H), 7.59 (d, J=8.70 Hz, 1H), 7.72 (s, 1H). MS (ESI, pos. ion) m/z 470 [M+H]$^+$.

Example 227

(S)-1-(2-methyl-4-(1-methyl-1H-pyrazolo[3,4-c]pyridin-3-yl)-6-(1-(piperidin-4-yl)-1H-pyrazol-4-yl)-3,4-dihydroquinoxalin-1(2H)-yl)ethanone (I-182)

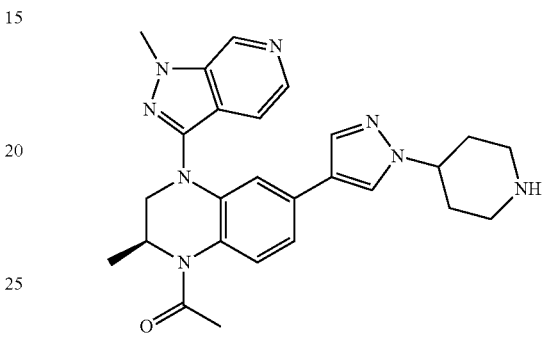

$^1$H NMR (300 MHz, CD$_3$OD) δ ppm 1.18-1.32 (m, 3H), 1.80-2.00 (m, 2H), 2.01-2.12 (m, 2H), 2.36 (s, 3H), 2.69-2.82 (m, 2H), 3.15-3.22 (m, 2H), 3.75-3.88 (m, 1H), 3.95-4.09 (m, 1H), 4.15-4.25 (m, 4H), 5.27 (br s, 1H), 6.94 (d, J=1.50 Hz, 1H), 7.09-7.18 (m, 1H), 7.20-7.45 (m, 2H), 7.55 (s, 1H), 7.91 (s, 1H), 8.16 (d, J=8.70 Hz, 1H), 9.11 (s, 1H). MS (ESI, pos. ion) m/z 471 [M+H]$^+$.

Example 228

2,4-difluorophenyl (S)-4-acetyl-3-methyl-7-(1-(piperidin-4-yl)-1H-pyrazol-4-yl)-3,4-dihydroquinoxaline-1(2H)-carboxylate (I-191)

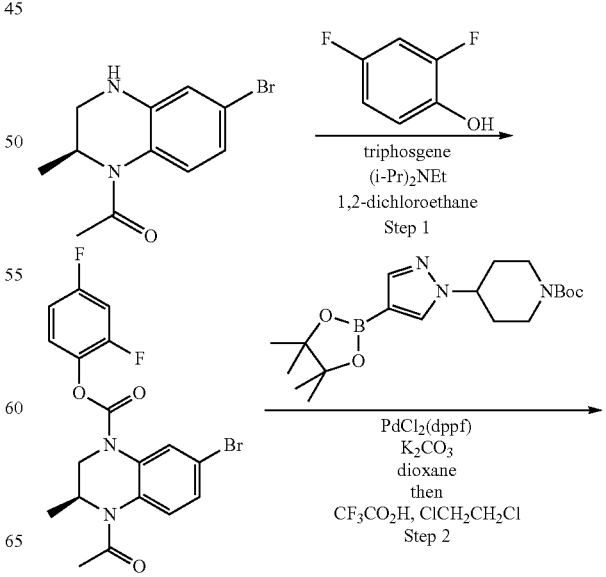

-continued

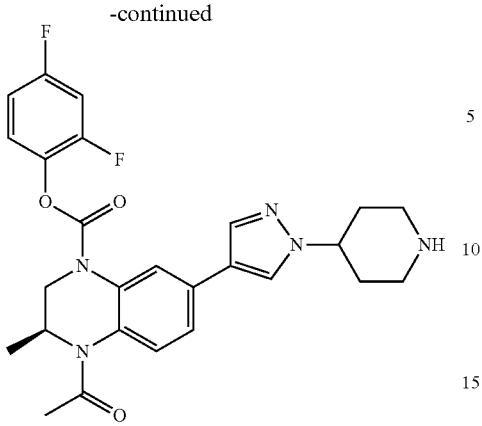

Step 1. 2,4-difluorophenyl (S)-4-acetyl-7-bromo-3-methyl-3,4-dihydroquinoxaline-1(2H)-carboxylate A 1.5 mL reaction vial was charged with (S)-1-(6-bromo-2-methyl-3,4-dihydroquinoxalin-1(2H)-yl)ethan-1-one (0.2 M in 4:1:1,2-dichloroethane/N,N-disopropylethylamine, 100 µL, 0.02 mmol). Triphosgene (0.4 M solution in 1,2-dichloroethane, 20 µL, 0.008 mmol) was then added, and the reaction mixture was placed on a heater shaker at room temperature for 4 h. 2,4-Difluorophenol (0.2 M solution in 1,4-dioxane, 110 µl, 0.022 mmol) was then added, and the reaction was heated to 50° C. on a heater shaker overnight. Methanol (100 µl) was added and the reaction was placed on a heater shaker at 50° C. for 30 minutes. The reaction was diluted with ethyl acetate and washed with a saturated sodium bicarbonate solution. The aqueous layer was separated and washed with ethyl acetate and the combined organic layers were concentrated under a stream of nitrogen and vacuum. The crude product was purified by mass triggered preparatory HPLC. The product, 2,4-difluorophenyl (5)-4-acetyl-7-bromo-3-methyl-3,4-dihydroquinoxaline-1(2H)-carboxylate, was used without further purification.

Step 2. 2,4-difluorophenyl (S)-4-acetyl-3-methyl-7-(1-(piperidin-4-yl)-1H-pyrazol-4-yl)-3,4-dihydroquinoxaline-1(2H)-carboxylate A 1.5 mL reaction vial was charged with 2,4-difluorophenyl (S)-4-acetyl-7-bromo-3-methyl-3,4-dihydroquinoxaline-1(2H)-carboxylate (0.02 mmol), tert-butyl 4-(4-(4,4,5,5-tetramethyl-1,3,2-dioxaborolan-2-yl)-1H-pyrazol-1-yl) piperidin-1-carboxylate (0.2 M solution in 1,4-dioxane, 225 µL, 0.03 mmol), and 1,4-dioxane (100 µL). Potassium carbonate (1 M solution in water, 60 µL, 0.06 mmol) was then added, and the reaction mixture was purged with nitrogen. [1,1'-Bis(diphenylphosphino)ferrocene]dichloropalladium (II) (0.02 M solution in 1,2-dichloroethane, 150 µL, 0.003 mmol) was then added, the reaction was purged with nitrogen and heated to 80° C. on a heater shaker overnight. The reaction was diluted with ethyl acetate and washed with 1 N aqueous sodium hydroxide solution. The aqueous layer was separated and extracted with ethyl acetate (1 mL) and the combined organic layers were concentrated under a stream of nitrogen. The crude product was purified by mass triggered preparatory HPLC. The product-containing fractions were combined and concentrated. The residue was taken up in 1,2-dichloroethane (200 µL) and trifluoroacetic acid (100 µL was added. The reactions stirred at room temperature for 2 h. The reaction was concentrated, and diluted with ethyl acetate (0.5 mL) and saturated aqueous sodium bicarbonate solution (0.5 mL). The aqueous layer was separated and extracted with ethyl acetate (1 mL), and the combined organic layers were concentrated under a stream of nitrogen and vacuum. The crude product was purified by mass triggered preparatory HPLC. The product-containing fractions were combined and concentrated to afford 2,4-difluorophenyl (S)-4-acetyl-3-methyl-7-(1-(piperidin-4-yl)-1H-pyrazol-4-yl)-3,4-dihydroquinoxaline-1(2H)-carboxylate. MS (ESI, pos. ion) m/z 496 [M+H]+.

Example 229

(S)-1-acetyl-6-(1-cyclopropyl-1H-pyrazol-4-yl)-N-(4-fluorophenyl)-2-methyl-2,3-dihydropyrido[2,3-b]pyrazine-4(1H)-carboxamide (I-192)

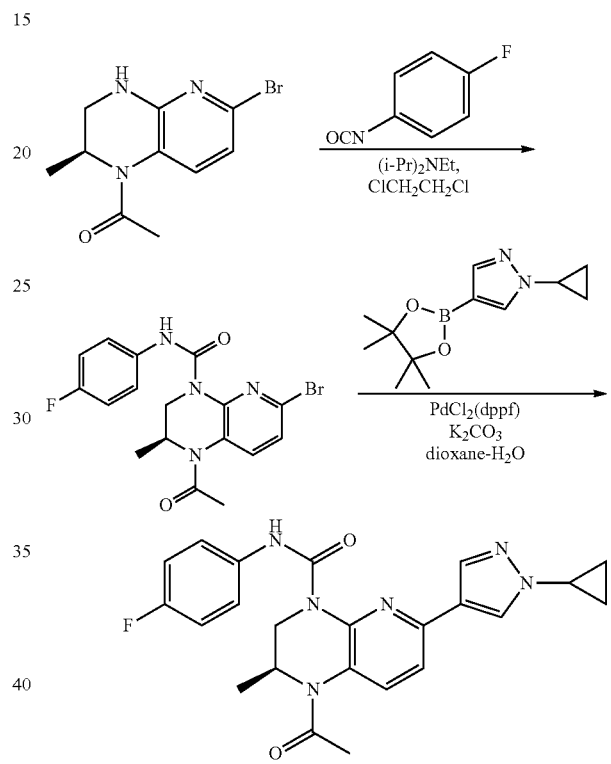

A reaction vial was charged with (S)-1-(6-bromo-2-methyl-3,4-dihydropyrido[2,3-b]pyrazine-1(2H)-yl)ethanone (0.1 M solution in 1,2-dichloroethane, 0.30 mL, 0.03 mmol) and N,N-diisopropylethylamine (0.052 mL, 0.300 mmol) was added. 1-Fluoro-4-isocyanatobenzene (0.017 mL, 0.150 mmol) was added neat, followed by the addition of a catalytic amount of DMAP (~1 mg), and the reaction was shaken at 50° C. overnight. The reaction was diluted with ethyl acetate and washed with saturated aqueous sodium bicarbonate solution. The aqueous layer was separated and extracted with ethyl acetate, and the combined organic layers were concentrated under a stream of nitrogen and vacuum to yield (S)-1-acetyl-6-bromo-N-(4-fluorophenyl)-2-methyl-2,3-dihydropyrido [2,3-b]pyrazine-4(1H)-carboxamide. The crude product was dissolved in 1,4-dioxane (100 µL and 1-cyclopropyl-4-(4,4,5,5-tetramethyl-1,3,2-dioxaborolan-2-yl)-1H-pyrazole (0.2 M solution in 1,4-dioxane, 0.27 mL, 0.054 mmol), potassium carbonate (1.0 M solution in water, 0.090 mL, 0.090 mmol) and [1,1'-bis(diphenylphosphino) ferrocene]dichloropalladium(II) dichloromethane adduct (0.02 M solution in 1,2-dichloroethane, 150 µL, 0.003 mmol) were added. The reaction was purged with nitrogen, and heated to 80° C. on a heater shaker for 4 hours. The reaction was diluted with ethyl acetate and washed with 1 N aqueous sodium hydroxide solution and brine. The combined organic layers were concentrated in a Genevac. The crude product was purified by mass triggered preparatory HPLC. The product-containing fractions were combined and concentrated to afford (S)-1-acetyl-6-(1-cyclopropyl-1H-pyrazol-4-yl)-N-(4-fluorophenyl)-2-methyl-2,3-dihydropyrido[2,3-b]pyrazine-4(1H)-carboxamide. MS (ESI, pos. ion) m/z 435 [M+H]$^+$.

Example 230

(S)-1-acetyl-6-(1-cyclopropyl-1H-pyrazol-4-yl)-N-isopropyl-2-methyl-2,3-dihydropyrido[2,3-b]pyrazine-4(1H)-carboxamide (I-193)

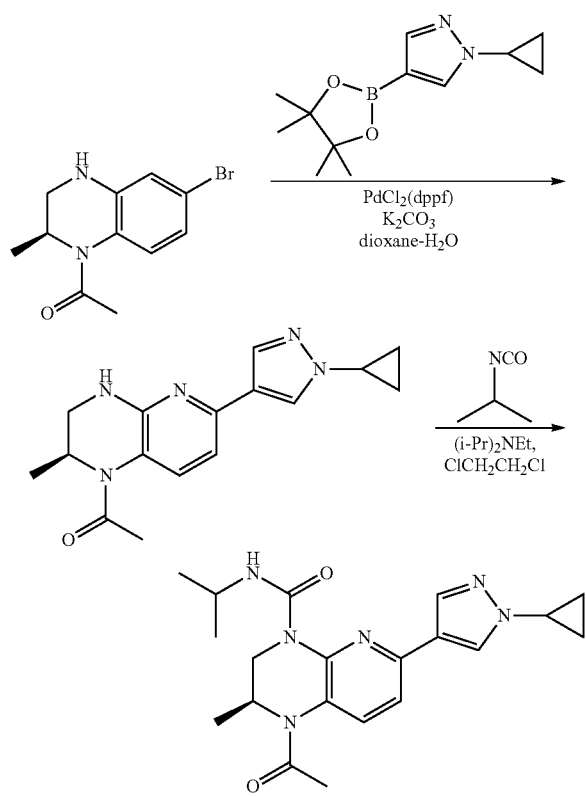

A reaction vial was charged with (S)-1-(6-bromo-2-methyl-3,4-dihydropyrido[2,3-b]pyrazine-1(2H)-yl)ethanone (0.1 M solution in 1,2-dichloroethane, 0.30 mL, 0.03 mmol), 1,4-dioxane (100 µL), 1-cyclopropyl-4-(4,4,5,5-tetramethyl-1,3,2-dioxaborolan-2-yl)-1H-pyrazole (0.2 M solution in 1,4-dioxane, 0.27 mL, 0.054 mmol), potassium carbonate (1.0 M solution in water, 0.090 mL, 0.090 mmol) and [1,1'-bis(diphenylphosphino)ferrocene]dichloropalladium(II) dichloromethane adduct (0.02 M solution in 1,2-dichloroethane, 150 µL, 0.003 mmol). The reaction was purged with nitrogen, and heated to 80° C. on a heater shaker overnight. The reaction was diluted with ethyl acetate and washed with 1 N aqueous sodium hydroxide solution and brine. The combined organic layers were concentrated under a stream of nitrogen and vacuum to yield (S)-1-(6-(1-cyclopropyl-1H-pyrazol-4-yl)-2-methyl-3,4-dihydropyrido[2,3-b]pyrazine-1(2H)-yl)ethanone. The crude product was dissolved in 1,2-dichloroethane (200 µL), and N,N-diisopropylethylamine (0.052 mL, 0.300 mmol) was added. 2-Isocyanatopropane (0.020 mL, 0.200 mmol) was then added along with a catalytic amount of DMAP (~1 mg), and the reaction was shaken at 80° C. for 3 hours. The reaction was diluted with ethyl acetate and washed with saturated aqueous sodium bicarbonate solution. The aqueous layer was separated and extracted with ethyl acetate and the combined organic layers were concentrated in a Genevac. The crude product was purified by mass triggered preparatory HPLC. The product-containing fractions were combined and concentrated to afford (S)-1-acetyl-6-(1-cyclopropyl-1H-pyrazol-4-yl)-N-isopropyl-2-methyl-2,3-dihydropyrido[2,3-b]pyrazine-4(1H)-carboxamide. MS (ESI, pos. ion) m/z 383 [M+H]$^+$.

Example 231

(S)-isopropyl 7-(1-cyclopropyl-1H-pyrazol-4-yl)-3-methyl-4-(methyl carbamoyl)-3,4-dihydropyrido[2,3-b]pyrazine-1(2H)-carboxylate (I-194)

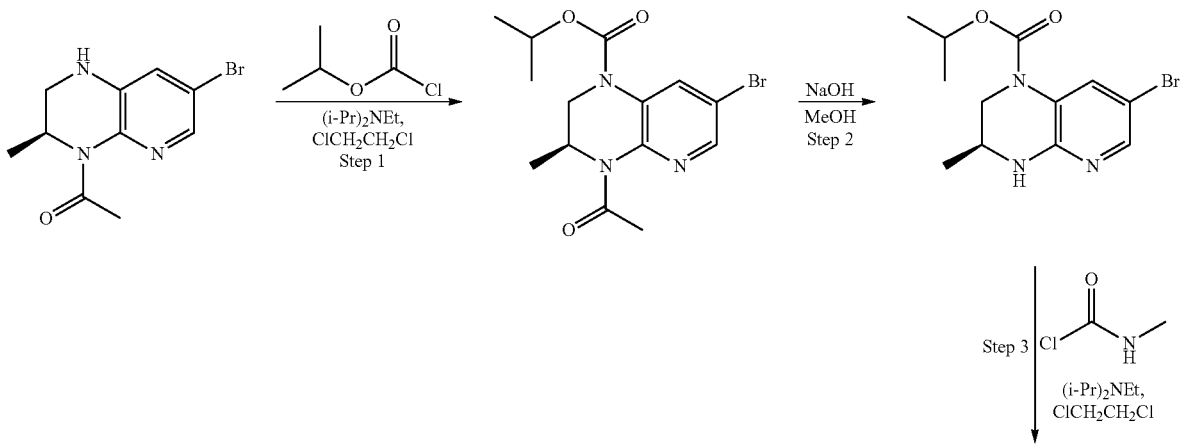

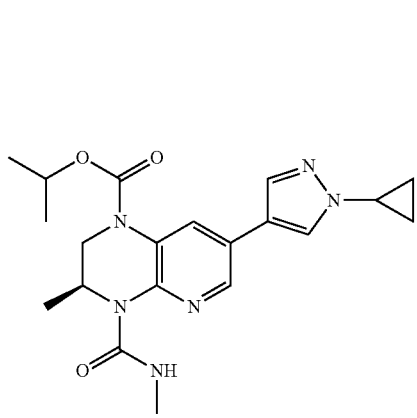
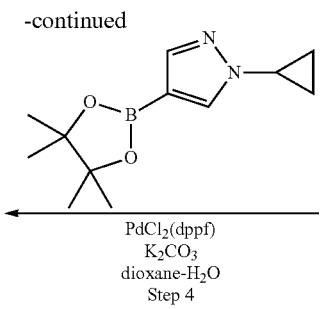
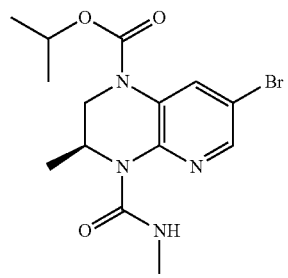

PdCl₂(dppf)
K₂CO₃
dioxane-H₂O
Step 4

Step 1. (S)-isopropyl 4-acetyl-7-bromo-3-methyl-3,4-dihydropyrido[2,3-b]pyrazine-1(2H)-carboxylate A reaction vial was charged with (S)-1-(7-bromo-3-methyl-2,3-dihydropyrido[2,3-b]pyrazin-4(1H)-yl)ethanone (0.054 g, 0.2 mmol) and N,N-diisopropylethylamine (0.245 mL, 1.40 mmol) was added. Isopropyl chloroformate (1.0 M solution in toluene, 1.00 mL, 1.00 mmol) was added, and the reaction was heated at 50° C. overnight. The reaction was diluted with ethyl acetate (3 mL) and washed with saturated aqueous sodium bicarbonate solution (2 mL). The aqueous layer was separated and extracted with ethyl acetate. The combined organic layers were dried over anhydrous sodium sulfate, filtered, and concentrated. The residue was purified via column chromatography on silica gel (eluting with 20% ethyl acetate-hexane) to afford (S)-isopropyl 4-acetyl-7-bromo-3-methyl-3,4-dihydropyrido[2,3-b]pyrazine-1(2H)-carboxylate (0.070 g, 98%) as a colorless oil. MS (ESI, pos. ion) m/z 356, 358 [M+H]⁺.

Step 2. (S)-isopropyl 7-bromo-3-methyl-3,4-dihydropyrido[2,3-b]pyrazine-1(2H)-carboxylate A reaction vial was charged with (S)-isopropyl 4-acetyl-7-bromo-3-methyl-3,4-dihydropyrido[2,3-b]pyrazine-1(2H)-carboxylate (0.2 M in methanol, 0.1 mL, 0.02 mmol). Sodium hydroxide (2.0 M in water, 0.050 mL, 0.10 mmol) was added and the reaction was shaken at room temperature for 6 hours. The reaction mixture was concentrated to afford (S)-isopropyl 7-bromo-3-methyl-3,4-dihydropyrido[2,3-b]pyrazine-1(2H)-carboxylate which was used in the next step without purification. MS (ESI, pos. ion) m/z 314, 316 [M+H]⁺.

Step 3. (S)-isopropyl 7-bromo-3-methyl-4-(methylcarbamoyl)-3,4-dihydropyrido[2,3-b]pyrazine-1(2H)-carboxylate A reaction vial was charged with (S)-isopropyl 7-bromo-3-methyl-3,4-dihydropyrido[2,3-b]pyrazine-1(2H)-carboxylate (0.02 mmol), 1,2-dichloroethane (0.10 mL), and N,N-diisopropylethylamine (0.25 mL, 0.14 mmol). Methylcarbamic chloride (1.0 M solution in 1,2-dichloroethane, 0.120 mL, 0.120 mmol) was added, and the reaction was heated at 50° C. overnight. N,N-Diisopropylethylamine (0.25 mL, 0.14 mmol) and methylcarbamic chloride (1.0 M solution in 1,2-dichloroethane, 0.120 mL, 0.120 mmol) were added, and the reaction was heated at 80° C. overnight. The reaction was diluted with ethyl acetate and washed with saturated aqueous sodium chloride solution. The aqueous layer was separated and extracted with ethyl acetate and the combined organic layers were concentrated under a stream of nitrogen to afford (S)-isopropyl 7-bromo-3-methyl-4-(methylcarbamoyl)-3,4-dihydropyrido[2,3-b]pyrazine-1(2H)-carboxylate which was used in the next step without purification.

Step 4. (S)-isopropyl 7-(1-cyclopropyl-1H-pyrazol-4-yl)-3-methyl-4-(methylcarbamoyl)-3,4-dihydropyrido[2,3-b]pyrazine-1(2H)-carboxylate A reaction vial was charged with (S)-isopropyl 7-bromo-3-methyl-4-(methylcarbamoyl)-3,4-dihydropyrido[2,3-b]pyrazine-1 (2H)-carboxylate (0.015 g, 0.04 mmol), 1-cyclopropyl-4-(4,4,5,5-tetramethyl-1,3,2-dioxaborolan-2-yl)-1H-pyrazole (0.2 M solution in 1,4-dioxane, 0.40 mL, 0.080 mmol), potassium carbonate (1.0 M solution in water, 0.120 mL, 0.120 mmol) and [1,1'-bis(diphenylphosphino)ferrocene]dichloropalladium(II) dichloromethane adduct (0.02 M solution in 1,2-dichloroethane, 0.200 mL, 0.004 mmol). The reaction was purged with nitrogen and heated to 80° C. on a heater shaker overnight. The reaction was diluted with ethyl acetate and washed with brine. The combined organic layers were concentrated under a stream of nitrogen. The crude product was purified by mass triggered preparatory HPLC. The product-containing fractions were combined and concentrated to afford (S)-isopropyl 7-(1-cyclopropyl-1H-pyrazol-4-yl)-3-methyl-4-(methylcarbamoyl)-3,4-dihydropyrido[2,3-b]pyrazine-1(2H)-carboxylate. MS (ESI, pos. ion) m/z 399 [M+H]⁺.

Example 232 isopropyl (S)-4-acetyl-7-(1-cyclopropyl-1H-pyrazol-4-yl)-3-methyl-6-nitro-3,4-dihydroquinoxaline-1(2H)-carboxylate (I-195)

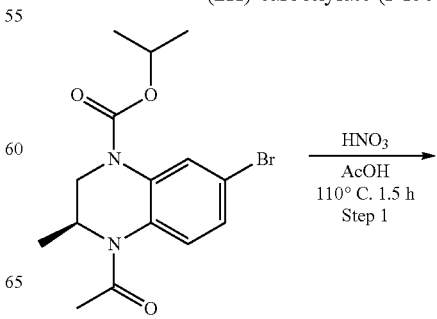

HNO₃
AcOH
110° C. 1.5 h
Step 1

Step 1. isopropyl (S)-4-acetyl-7-bromo-3-methyl-6-nitro-3,4-dihydroquinoxaline-1(2H)-carboxylate

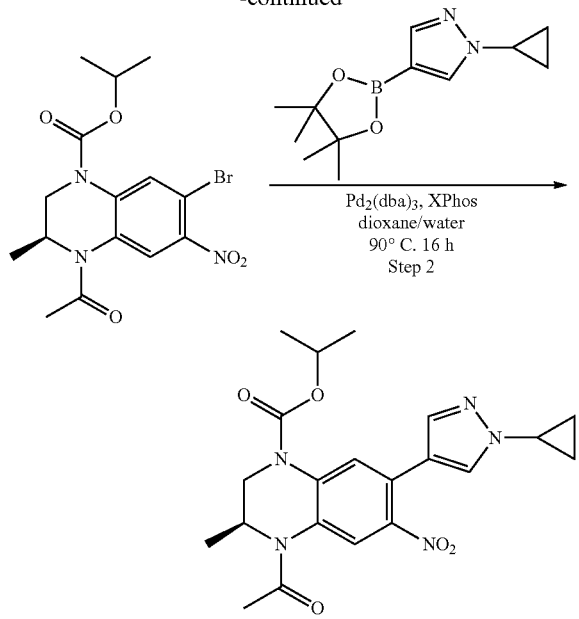

A reaction vial was charged with isopropyl (S)-4-acetyl-7-bromo-3-methyl-3,4-dihydroquinoxaline-1(2H)-carboxylate (0.100 g, 0.282 mmol) and acetic acid (1 mL), and the reaction was heated to 110° C. Nitric acid (37.7 µL, 0.845 mmol) was added dropwise and the reaction was stirred at 110° C. for 1 h. The reaction was cooled to ambient temperature and then added dropwise to an ice/water bath. The resulting slurry was filtered, and the filter cake was dried overnight under vacuum to provide isopropyl (S)-4-acetyl-7-bromo-3-methyl-6-nitro-3,4-dihydroquinoxaline-1(2H)-carboxylate (0.111 g, 99%) as a white solid. MS (ESI, pos. ion) m/z 428 [M+H]+.

Step 2. isopropyl (S)-4-acetyl-7-(1-cyclopropyl-1H-pyrazol-4-yl)-3-methyl-6-nitro-3,4-dihydroquinoxaline-1(2H)-carboxylate A mixture of isopropyl (S)-4-acetyl-7-bromo-3-methyl-6-nitro-3,4-dihydroquinoxaline-1(2H)-carboxylate (0.131 g, 0.327 mmol), 1-cyclopropyl-4-(4,4,5,5-tetramethyl-1,3,2-dioxaborolan-2-yl)-1H-pyrazole (0.092 g, 0.392 mmol), cesium carbonate (0.319 g, 0.980 mmol), XPhos (0.016 g, 0.033 mmol) and tris(dibenzylideneacetone)dipalladium (0.015 g, 0.016 mmol) in 1,4-dioxane (3 mL) and water (0.6 mL) was heated for 16 h at 90° C. The reaction was cooled to rt and concentrated. The residue was diluted with ethyl acetate and washed with saturated aqueous sodium bicarbonate solution. The organic phase was concentrated and the residue was purified by mass triggered preparatory HPLC. The product-containing fractions were combined and concentrated in a Genevac to afford isopropyl (S)-4-acetyl-7-(1-cyclopropyl-1H-pyrazol-4-yl)-3-methyl-6-nitro-3,4-dihydroquinoxaline-1(2H)-carboxylate. MS (ESI, pos. ion) m/z 428 [M+H]+.

Example 233

Isopropyl (S)-4-acetyl-6-amino-7-(1-cyclopropyl-1H-pyrazol-4-yl)-3-methyl-3,4-dihydroquinoxaline-1(2H)-carboxylate (I-206)

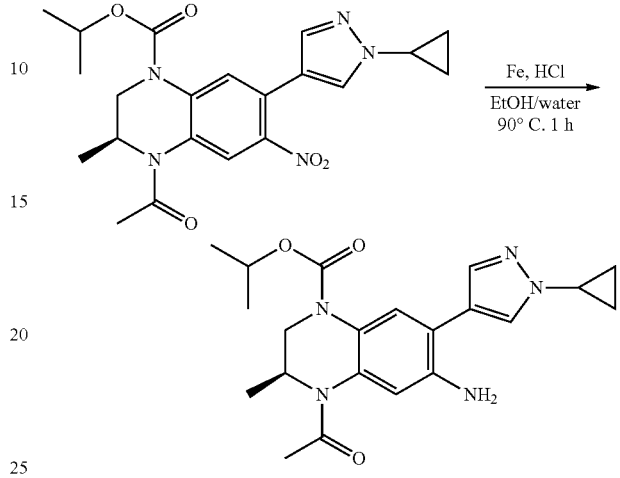

Iron powder (1.010 g, 18.09 mmol) was added to a solution of isopropyl (S)-4-acetyl-7-(1-cyclopropyl-1H-pyrazol-4-yl)-3-methyl-6-nitro-3,4-dihydroquinoxaline-1(2H)-carboxylate (0.86 g, 1.81 mmol) in ethanol (12 mL) and water (2.4 mL). 1 N aqueous HCl (1 drop) was added, and the reaction was heated at 90° C. for 2 h. The mixture was cooled to rt and filtered through a pad of Celite, washing with ethanol. The filtrate was concentrated, and ethyl acetate was added. The solution was washed with saturated aqueous sodium bicarbonate solution and brine, dried over anhydrous sodium sulfate, filtered, and concentrated. The residue was purified by mass triggered preparatory HPLC. The product-containing fractions were combined and concentrated in a Genevac to afford isopropyl (S)-4-acetyl-6-amino-7-(1-cyclopropyl-1H-pyrazol-4-yl)-3-methyl-3,4-dihydroquinoxaline-1(2H)-carboxylate. MS (ESI, pos. ion) m/z 398 [M+H]+.

Example 234

Isopropyl (S)-4-acetyl-7-(1-cyclopropyl-1H-pyrazol-4-yl)-3-methyl-6-(methyl sulfonamido)-3,4-dihydroquinoxaline-1(2H)-carboxylate (I-213)

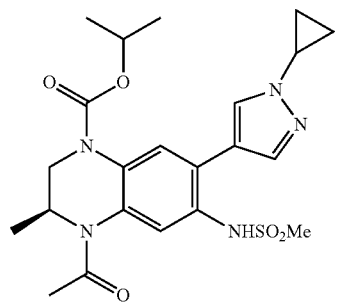

Pyridine (4.07 µL, 0.050 mmol) was added to a solution of isopropyl (S)-4-acetyl-6-amino-7-(1-cyclopropyl-1H-pyrazol-4-yl)-3-methyl-3,4-dihydroquinoxaline-1(2H)-carboxylate (0.010 g, 0.025 mmol) in 1,4-dioxane (200 µL). Methanesulfonyl chloride (1.96 µL, 0.025 mmol) was added, and the mixture stirred at rt for 18 h. The reaction mixture was concentrated and ethyl acetate was added. The solution was

Example 235

Isopropyl (S)-6-acetamido-4-acetyl-7-(1-cyclopropyl-1H-pyrazol-4-yl)-3-methyl-3,4-dihydroquinoxaline-1(2H)-carboxylate (I-214)

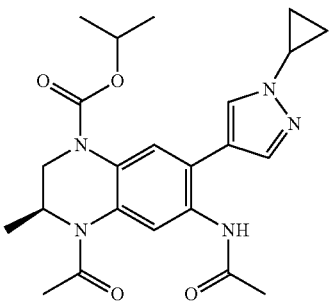 [SMILES: CC(=O)Nc1cc2c(cc1-c1cnn(C3CC3)c1)N(C(=O)OC(C)C)C[C@H](C)N2C(C)=O]

washed with 1 N aqueous HCl, and the organic phase was separated and concentrated to afford isopropyl (S)-4-acetyl-7-(1-cyclopropyl-1H-pyrazol-4-yl)-3-methyl-6-(methylsulfonamido)-3,4-dihydroquinoxaline-1(2H)-carboxylate (0.0087 g, 73% yield). $^1$H NMR (400 MHz, CDCl$_3$) δ ppm 1.07-1.16 (m, 6 H), 1.18-1.36 (m, 8H), 2.30 (s, 3 H), 2.99 (s, 3 H), 3.58-3.80 (m, 2 H), 3.84-3.99 (m, 1 H), 4.99-5.08 (m, 1 H), 6.85 (br s, 1 H), 7.49-7.50 (m, 1 H), 7.71 (d, J=4.40 Hz, 2 H), 7.97 (br s, 1 H). MS (ESI, pos. ion) m/z 476 [M+H]+.

Pyridine (5.09 µL, 0.063 mmol) was added to a solution of isopropyl (S)-4-acetyl-6-amino-7-(1-cyclopropyl-1H-pyrazol-4-yl)-3-methyl-3,4-dihydroquinoxaline-1(2H)-carboxylate (0.010 g, 0.025 mmol) in dichloromethane (200 µL). Acetic anhydride (3.56 µL, 0.038 mmol) was added, and the reaction stirred at rt for 18 h. The reaction mixture was concentrated and ethyl acetate was added. The solution was washed with 1 N aqueous HCl, and the organic phase was separated and concentrated. The residue was purified by mass triggered preparatory HPLC. The product-containing fractions were combined and concentrated in a Genevac to afford isopropyl (S)-6-acetamido-4-acetyl-7-(1-cyclopropyl-1H-pyrazol-4-yl)-3-methyl-3,4-dihydroquinoxaline-1(2H)-carboxylate. MS (ESI, pos. ion) m/z 440 [M+H]+.

Example 236

Isopropyl (S)-4-acetyl-7-(1-cyclopropyl-1H-pyrazol-4-yl)-3-methyl-6-(3-methylureido)-3,4-dihydroquinoxaline-1(2H)-carboxylate (I-215)

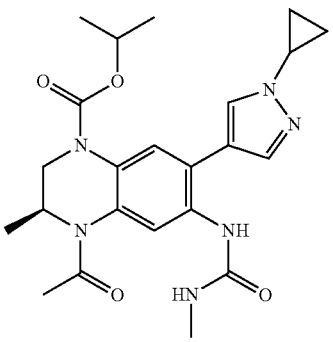 [SMILES: CNC(=O)Nc1cc2c(cc1-c1cnn(C3CC3)c1)N(C(=O)OC(C)C)C[C@H](C)N2C(C)=O]

Pyridine (5.09 µL, 0.063 mmol) was added to a solution of isopropyl (S)-4-acetyl-6-amino-7-(1-cyclopropyl-1H-pyrazol-4-yl)-3-methyl-3,4-dihydroquinoxaline-1(2H)-carboxylate (0.010 g, 0.025 mmol) in dichloromethane (200 µL). Methylcarbamic chloride (0.003 g, 0.030 mmol) was added, and the reaction stirred at rt for 18 h. The reaction mixture was concentrated and ethyl acetate was added. The solution was washed with 1 N aqueous HCl, and the organic phase was separated and concentrated. The residue was purified by mass triggered preparatory HPLC. The product-containing fractions were combined and concentrated in a Genevac to afford isopropyl (S)-4-acetyl-7-(1-cyclopropyl-1H-pyrazol-4-yl)-3-methyl-6-(3-methylureido)-3,4-dihydroquinoxaline-1(2H)-carboxylate. MS (ESI, pos. ion) m/z 455 [M+H]+.

Example 237

Isopropyl (S)-4-acetyl-6-amino-3-methyl-7-(4-(methylsulfonyl)phenyl)-3,4-dihydroquinoxaline-1(2H)-carboxylate (I-216)

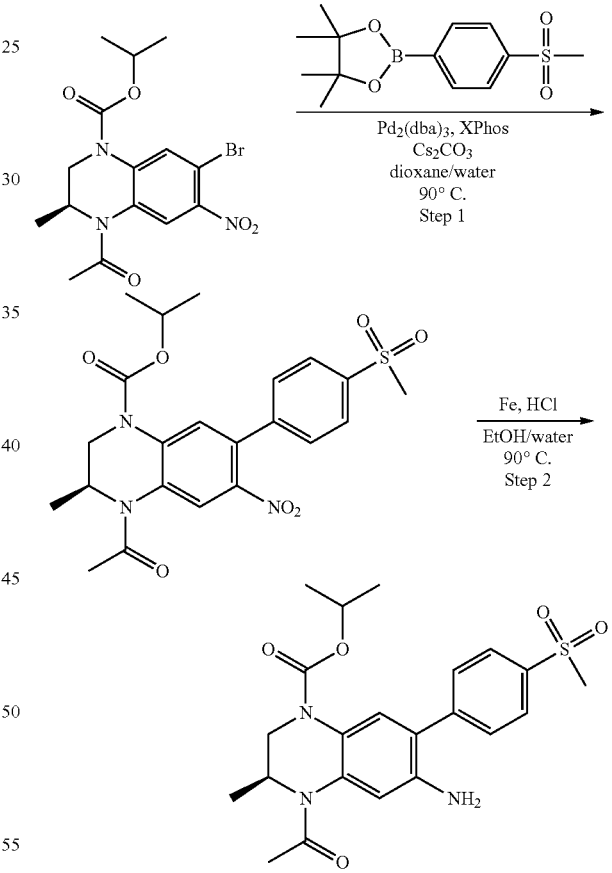

Step 1. isopropyl (S)-4-acetyl-3-methyl-7-(4-(methylsulfonyl)phenyl)-6-nitro-3,4-dihydroquinoxaline-1(2H)-carboxylate A mixture of isopropyl (S)-4-acetyl-7-bromo-3-methyl-6-nitro-3,4-dihydroquinoxaline-1(2H)-carboxylate (0.870 g, 2.17 mmol), 4,4,5,5-tetramethyl-2-(4-(methylsulfonyl)phenyl)-1,3,2-dioxaborolane (0.920 g, 3.26 mmol), cesium carbonate (2.1 g, 6.52 mmol), XPhos (0.104 g, 0.22 mmol) and tris(dibenzylideneacetone)dipalladium (0.100 g, 0.11 mmol) in 1,4-dioxane (12 mL) and water (3 mL) was heated for 16 h at 90° C. The reaction was cooled to rt and concentrated. The residue was diluted with ethyl acetate and washed with saturated aqueous sodium bicarbonate solution. The organic phase was concentrated and the residue was purified by column chromatography on silica gel (eluting with 50% ethyl acetate-hexane) to afford isopropyl (S)-4-acetyl-3-methyl-7-(4-(methylsulfonyl)phenyl)-6-nitro-3,4-dihydroquinoxaline-1(2H)-carboxylate (0.860 g, 83%). MS (ESI, pos. ion) m/z 498 [M+Na]+.

Step 2. isopropyl (S)-4-acetyl-6-amino-3-methyl-7-(4-(methylsulfonyl)phenyl)-3,4-dihydroquinoxaline-1(2H)-carboxylate Iron powder (1.010 g, 18.09 mmol) was added to a solution of isopropyl (S)-4-acetyl-3-methyl-7-(4-(methylsulfonyl)phenyl)-6-nitro-3,4-dihydroquinoxaline-1 (2H)-carboxylate (0.86 g, 1.81 mmol) in ethanol (12 mL) and water (2.4 mL). 1 N aqueous HCl (1 drop) was added, and the reaction was heated at 90° C. for 2 h. The mixture was cooled to rt and filtered through a pad of Celite, washing with ethanol. The filtrate was concentrated, and ethyl acetate was added. The solution was washed with saturated aqueous sodium bicarbonate solution and brine, dried over anhydrous sodium sulfate, filtered, and concentrated. The residue was purified by mass triggered preparatory HPLC. The product-containing fractions were combined and concentrated in a Genevac to afford isopropyl (S)-4-acetyl-6-amino-3-methyl-7-(4-(methylsulfonyl)phenyl)-3,4-dihydroquinoxaline-1(2H)-carboxylate. MS (ESI, pos. ion) m/z 468 [M+Na]+.

Example 238

Isopropyl (S)-4-acetyl-6-bromo-3-methyl-7-(4-(methylsulfonyl)phenyl)-3,4-dihydroquinoxaline-1(2H)-carboxylate (I-217)

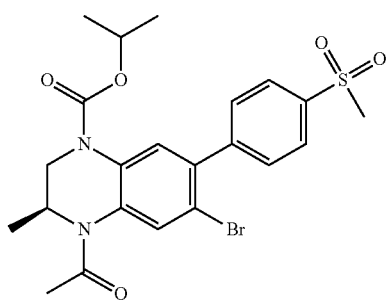 [SMILES: CC(=O)N1c2cc(Br)c(-c3ccc(S(C)(=O)=O)cc3)cc2N(C(=O)OC(C)C)C[C@@H]1C]

tert-Butyl nitrite (0.018 g, 0.155 mmol) was added to a solution of copper(I) bromide (0.008 g, 0.056 mmol) in acetonitrile (1 mL), and the solution was heated at 60° C. for 20 minutes. A solution of (S)-isopropyl 4-acetyl-6-amino-3-methyl-7-(4-(methylsulfonyl)phenyl)-3,4-dihydroquinoxaline-1(2H)-carboxylate (0.025 g, 0.056 mmol) was added, and the reaction was heated at 60° C. for 2 h. The mixture was concentrated and purified via preparative thin layer chromatography (eluting with 3:1 ethyl acetate-hexanes). The material was further purified by mass triggered preparatory HPLC. The product-containing fractions were combined and concentrated in a Genevac to afford isopropyl (S)-4-acetyl-6-bromo-3-methyl-7-(4-(methylsulfonyl)phenyl)-3,4-dihydroquinoxaline-1(2H)-carboxylate. MS (ESI, pos. ion) m/z 531, 533 [M+Na]+.

Example 239

Isopropyl (S)-4-acetyl-6-chloro-3-methyl-7-(4-(methylsulfonyl)phenyl)-3,4-dihydroquinoxaline-1(2H)-carboxylate (I-218)

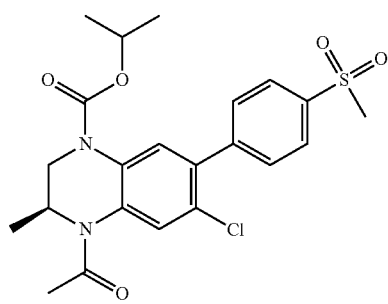 [SMILES: CC(=O)N1c2cc(Cl)c(-c3ccc(S(C)(=O)=O)cc3)cc2N(C(=O)OC(C)C)C[C@@H]1C]

Isopropyl (S)-4-acetyl-6-amino-3-methyl-7-(4-(methylsulfonyl)phenyl)-3,4-dihydroquinoxaline-1(2H)-carboxylate was synthesized according to the procedure described above for isopropyl (S)-4-acetyl-6-bromo-3-methyl-7-(4-(methylsulfonyl)phenyl)-3,4-dihydroquinoxaline-1(2H)-carboxylate (Example 238), substituting copper (I) chloride for copper (I) bromide. MS (ESI, pos. ion) m/z 487 [M+Na]+.

Example 240

Isopropyl (S)-4-acetyl-6-cyano-3-methyl-7-(4-(methylsulfonyl)phenyl)-3,4-dihydroquinoxaline-1(2H)-carboxylate (I-219)

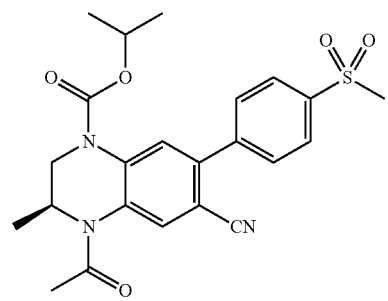

Isopropyl (S)-4-acetyl-6-cyano-3-methyl-7-(4-(methylsulfonyl)phenyl)-3,4-dihydroquinoxaline-1(2H)-carboxylate was synthesized according to the procedure described above for isopropyl (S)-4-acetyl-6-bromo-3-methyl-7-(4-(methylsulfonyl)phenyl)-3,4-dihydroquinoxaline-1(2H)-

Example 241

Isopropyl (S)-4-acetyl-6-fluoro-3-methyl-7-(4-(methylsulfonyl)phenyl)-3,4-dihydroquinoxaline-1(2H)-carboxylate (I-196)

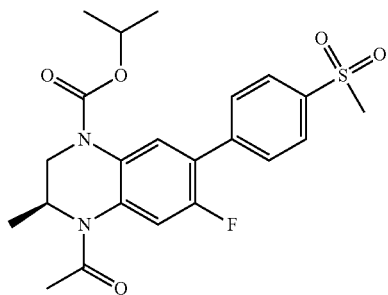 [SMILES: CC(=O)N1c2cc(F)c(-c3ccc(S(C)(=O)=O)cc3)cc2N(C(=O)OC(C)C)C[C@@H]1C]

A solution of (S)-isopropyl 4-acetyl-6-amino-3-methyl-7-(-(4-(methylsulfonyl)phenyl)-3,4-dihydroquinoxaline-1(2H)-carboxylate (0.030 g, 0.067 mmol) in dichloromethane (350 µL) was cooled to −15° C. and then added dropwise to a −15° C. solution of boron trifluoride diethyl etherate (12.8 µL, 0.101 mmol). tert-Butyl nitrite (10.68 µL, 0.081 mmol) was added dropwise, and the reaction was held at −15° C. for 10 min before slowly warming to 5° C. The solution was concentrated, and the resulting solid gently heated with heat gun. The solids expanded as gas was being evolved. The solid was cooled to room temperature and purified via preparative thin layer chromatography (eluting with 50% ethyl acetate-hexanes). The material was further purified by mass triggered preparatory HPLC. The product-containing fractions were combined and concentrated in a Genevac to afford isopropyl (S)-4-acetyl-6-fluoro-3-methyl-7-(4 (methylsulfonyl)phenyl)-3,4-dihydroquinoxaline-1(2H)-carboxylate. MS (ESI, pos. ion) m/z 471 [M+Na]+.

Example 242

Isopropyl (S)-6-acetamido-4-acetyl-3-methyl-7-(4-(methylsulfonyl)phenyl)-3,4-dihydroquinoxaline-1(2H)-carboxylate (I-197)

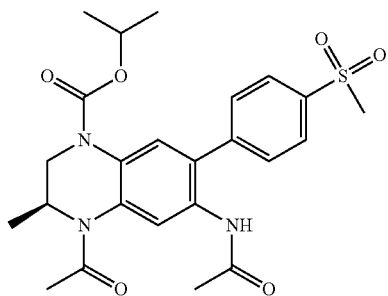 [SMILES: CC(=O)Nc1cc2c(cc1-c1ccc(S(C)(=O)=O)cc1)N(C(=O)OC(C)C)C[C@H](C)N2C(C)=O]

Isopropyl (S)-6-acetamido-4-acetyl-3-methyl-7-(4-(methylsulfonyl)phenyl)-3,4-dihydroquinoxaline-1(2H)-carboxylate was synthesized from isopropyl (S)-4-acetyl-6-amino-3-methyl-7-(4-(methylsulfonyl)phenyl)-3,4-dihydroquinoxaline-1(2H)-carboxylate according to the procedure described above for isopropyl (S)-6-acetamido-4-acetyl-7-(1-cyclopropyl-1H-pyrazol-4-yl)-3-methyl-3,4-dihydroquinoxaline-1(2H)-carboxylate (Example 235). MS (ESI, pos. ion) m/z 510 [M+Na]+.

Example 243

Isopropyl (S)-4-acetyl-6-((methoxycarbonyl)amino)-3-methyl-7-(4-(methylsulfonyl)phenyl)-3,4-dihydroquinoxaline-1(2H)-carboxylate (I-198)

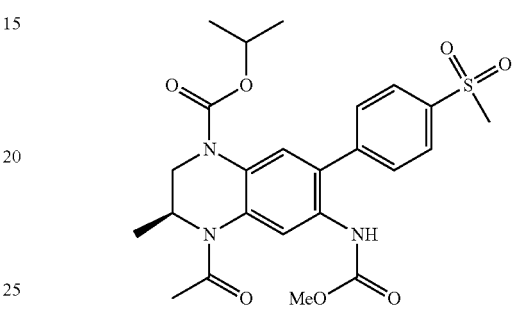

Isopropyl (S)-4-acetyl-6-((methoxycarbonyl)amino)-3-methyl-7-(4-(methylsulfonyl)phenyl)-3,4-dihydroquinoxaline-1(2H)-carboxylate was synthesized from isopropyl (S)-4-acetyl-6-amino-3-methyl-7-(4-(methylsulfonyl)phenyl)-3,4-dihydroquinoxaline-1(2H)-carboxylate and methyl chloroformate (instead of acetic anhydride) according to the procedure described above for isopropyl (S)-6-acetamido-4-acetyl-7-(1-cyclopropyl-1H-pyrazol-4-yl)-3-methyl-3,4-dihydroquinoxaline-1(2H)-carboxylate (Example 235). MS (ESI, pos. ion) m/z 504 [M+H]+.

Example 244

Isopropyl (S)-4-acetyl-6-methoxy-3-methyl-7-(4-(methylsulfonyl)phenyl)-3,4-dihydroquinoxaline-1(2H)-carboxylate (I-199)

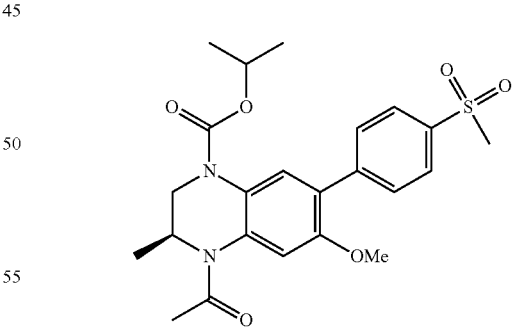

A solution of (S)-isopropyl 4-acetyl-6-amino-3-methyl-7-(-(4-(methylsulfonyl)phenyl)-3,4-dihydroquinoxaline-1(2H)-carboxylate (0.030 g, 0.067 mmol) in dichloromethane (350 µL) was cooled to −15° C. and then added dropwise to a −15° C. solution of boron trifluoride diethyl etherate (12.8 µL, 0.101 mmol). tert-Butyl nitrite (10.68 µL, 0.081 mmol) was added dropwise, and the reaction was held at −15° C. for 10 min before slowly warming to 5° C. The solution was concentrated, and methanol was added. The mixture was heated at 60° C. for 2 h, cooled to rt, and then concentrated. The residue was purified by mass triggered preparatory HPLC. The product-containing fractions were combined and concentrated in a Genevac to afford isopropyl (S)-4-acetyl-6-methoxy-3-methyl-7-(4-(methylsulfonyl)phenyl)-3,4-dihydroquinoxaline-1(2H)-carboxylate. MS (ESI, pos. ion) m/z 483 [M+Na]+.

Example 245

Isopropyl (S)-6-acetamido-4-acetyl-3-methyl-3,4-dihydroquinoxaline-1(2H)-carboxylate (I-200)

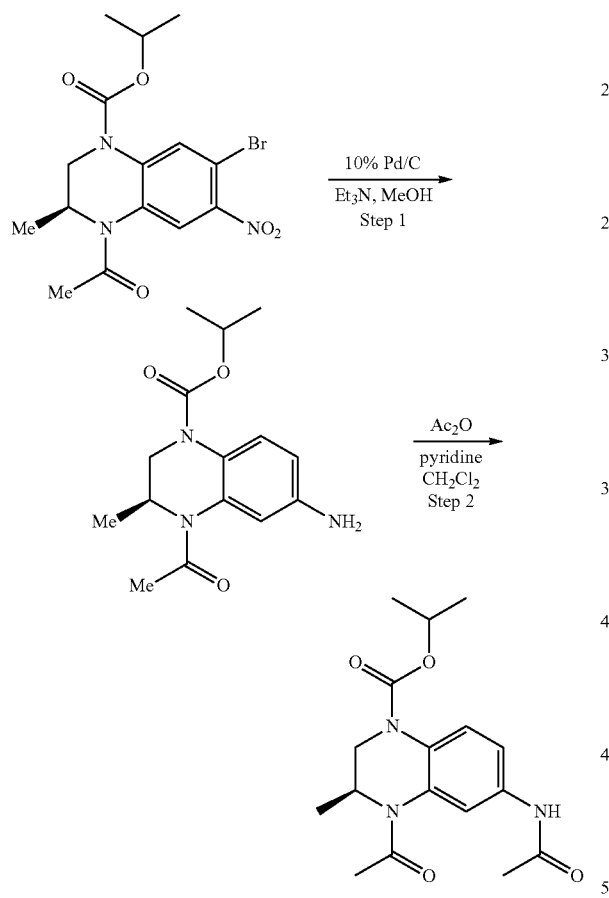

Step 1. isopropyl (S)-4-acetyl-6-amino-3-methyl-3,4-dihydroquinoxaline-1(2H)-carboxylate A mixture of isopropyl (S)-4-acetyl-7-bromo-3-methyl-6-nitro-3,4-dihydroquinoxaline-1(2H)-carboxylate (0.23 g, 0.575 mmol), methanol (23 mL), triethylamine (0.80 mL, 0.575 mmol) and palladium on carbon (10 wt %, 23 mg) was added to a Parr bottle, and the mixture was shaken at room temperature for 3 h under a hydrogen atmosphere (30 psi). The mixture was filtered through Celite and the filter cake was washed with methanol. The filtrate was concentrated to afford isopropyl (S)-4-acetyl-6-amino-3-methyl-3,4-dihydroquinoxaline-1(2H)-carboxylate (0.167 g, 100%). MS (ESI, pos. ion) m/z 314 [M+Na]+.

Step 2. Isopropyl (S)-6-acetamido-4-acetyl-3-methyl-3,4-dihydroquinoxaline-1(2H)-carboxylate Isopropyl (S)-6-acetamido-4-acetyl-3-methyl-3,4-dihydroquinoxaline-1(2H)-carboxylate was synthesized from isopropyl (S)-4-acetyl-6-amino-3-methyl-3,4-dihydroquinoxaline-1(2H)-carboxylate according to the procedure described above for isopropyl (S)-6-acetamido-4-acetyl-7-(1-cyclopropyl-1H-pyrazol-4-yl)-3-methyl-3,4-dihydroquinoxaline-1(2H)-carboxylate (Example 235). MS (ESI, pos. ion) m/z 356 [M+Na]+.

Example 246

Isopropyl (S)-4-acetyl-3-methyl-6-(methylsulfonamido)-3,4-dihydroquinoxaline-1(2H)-carboxylate (I-201)

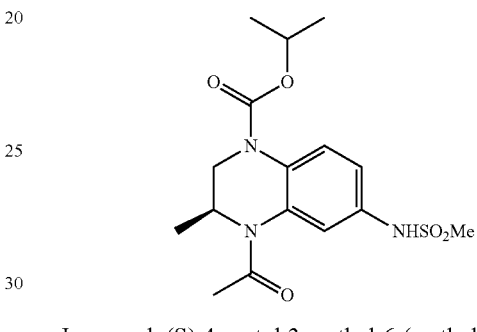

Isopropyl (S)-4-acetyl-3-methyl-6-(methylsulfonamido)-3,4-dihydroquinoxaline-1(2H)-carboxylate was synthesized from isopropyl (S)-4-acetyl-6-amino-3-methyl-3,4-dihydroquinoxaline-1(2H)-carboxylate according to the procedure described above for isopropyl (S)-4-acetyl-7-(1-cyclopropyl-1H-pyrazol-4-yl)-3-methyl-6-(methylsulfonamido)-3,4-dihydroquinoxaline-1(2H)-carboxylate (Example 234). MS (ESI, pos. ion) m/z 392 [M+Na]$^+$.

Example 247

Isopropyl (S)-4-acetyl-6-((methoxycarbonyl)amino)-3-methyl-3,4-dihydro quinoxaline-1(2H)-carboxylate (I-202)

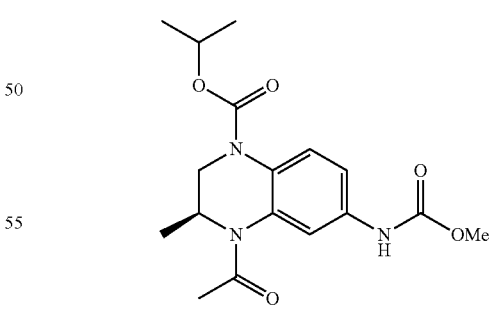

Isopropyl (S)-4-acetyl-6-((methoxycarbonyl)amino)-3-methyl-3,4-dihydroquinoxaline-1(2H)-carboxylate was synthesized from isopropyl (S)-4-acetyl-6-amino-3-methyl-3,4-dihydroquinoxaline-1(2H)-carboxylate and methyl chloroformate (instead of acetic anhydride) according to the procedure described above for isopropyl (S)-6-acetamido-4-acetyl-7-(1-cyclopropyl-1H-pyrazol-4-yl)-3-methyl-3,4-dihydroquinoxaline-1(2H)-carboxylate (Example 235). MS (ESI, pos. ion) m/z 372 [M+Na]$^+$.

Example 248

Isopropyl (S)-6-acetamido-4-acetyl-7-bromo-3-methyl-3,4-dihydro quinoxaline-1(2H)-carboxylate (I-203)

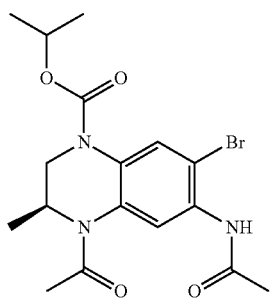 [SMILES: CC(=O)Nc1cc2c(cc1Br)N(C(=O)OC(C)C)C[C@H](C)N2C(C)=O]

Step 1. (S)-isopropyl 4-acetyl-6-amino-7-bromo-3-methyl-3,4-dihydroquinoxaline-1(2H)-carboxylate Isopropyl (S)-4-acetyl-6-amino-7-bromo-3-methyl-3,4-dihydroquinoxaline-1(2H)-carboxylate was prepared from isopropyl (S)-4-acetyl-7-bromo-3-methyl-6-nitro-3,4-dihydroquinoxaline-1(2H)-carboxylate according to the procedure described above for isopropyl (S)-4-acetyl-6-amino-7-(1-cyclopropyl-1H-pyrazol-4-yl)-3-methyl-3,4-dihydroquinoxaline-1(2H)-carboxylate (Example 233). MS (ESI, pos. ion) m/z 392,394 [M+H]+.

Step 2. Isopropyl (S)-6-acetamido-4-acetyl-7-bromo-3-methyl-3,4-dihydroquinoxaline-1(2H)-carboxylate Isopropyl (S)-6-acetamido-4-acetyl-7-bromo-3-methyl-3,4-dihydroquinoxaline-1(2H)-carboxylate was prepared from isopropyl (S)-4-acetyl-6-amino-7-bromo-3-methyl-3,4-dihydroquinoxaline-1(2H)-carboxylate according to the procedure described above for isopropyl (S)-6-acetamido-4-acetyl-7-(1-cyclopropyl-1H-pyrazol-4-yl)-3-methyl-3,4-dihydroquinoxaline-1(2H)-carboxylate (Example 235). MS (ESI, pos. ion) m/z 412, 414 [M+H]+.

Example 249

Isopropyl (S)-4-acetyl-7-(1-cyclopropyl-1H-pyrazol-4-yl)-6-((methoxy carbonyl)amino)-3-methyl-3,4-dihydroquinoxaline-1(2H)-carboxylate (I-204)

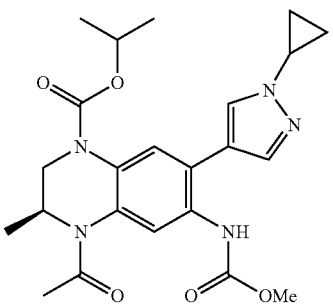 [SMILES: COC(=O)Nc1cc2c(cc1-c1cnn(C3CC3)c1)N(C(=O)OC(C)C)C[C@H](C)N2C(C)=O]

Isopropyl (S)-4-acetyl-7-(1-cyclopropyl-1H-pyrazol-4-yl)-6-((methoxycarbonyl)amino)-3-methyl-3,4-dihydroquinoxaline-1(2H)-carboxylate was synthesized according to the procedure described above for isopropyl (S)-6-acetamido-4-acetyl-7-(1-cyclopropyl-1H-pyrazol-4-yl)-3-methyl-3,4-dihydroquinoxaline-1(2H)-carboxylate (Example 235), substituting methyl chloroformate for acetic anhydride. MS (ESI, pos. ion) m/z 456 [M+H]+.

Example 250

Isopropyl (S)-6-acetamido-4-acetyl-7-(1-(2-hydroxy-2-methylpropyl)-1H-pyrazol-4-yl)-3-methyl-3,4-dihydroquinoxaline-1(2H)-carboxylate (I-205)

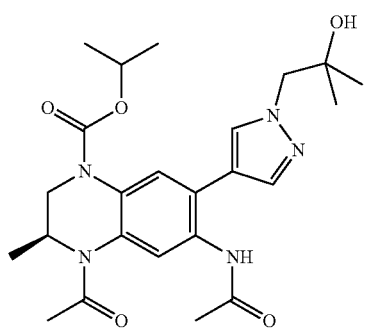 [SMILES: CC(=O)Nc1cc2c(cc1-c1cnn(CC(C)(C)O)c1)N(C(=O)OC(C)C)C[C@H](C)N2C(C)=O]

A mixture of isopropyl (S)-6-acetamido-4-acetyl-7-bromo-3-methyl-3,4-dihydroquinoxaline-1(2H)-carboxylate (0.011 g, 0.027 mmol), 2-methyl-1-(4-(4,4,5,5-tetramethyl-1,3,2-dioxaborolan-2-yl)-1H-pyrazol-1-yl)propan-2-ol (0.0085 g, 0.032 mmol), cesium carbonate (0.026 g, 0.080 mmol), XPhos (0.001 g, 0.003 mmol) and tris(dibenzylideneacetone)dipalladium (0.001 g, 0.002 mmol) in 1,4-dioxane (0.25 mL) and water (0.05 mL) was heated for 16 h at 90° C. The reaction was cooled to rt and concentrated. The residue was diluted with ethyl acetate and washed with saturated aqueous sodium bicarbonate solution. The organic phase was concentrated and the residue was purified by mass triggered preparatory HPLC. The product-containing fractions were combined and concentrated in a Genevac to afford isopropyl (S)-6-acetamido-4-acetyl-7-(1-(2-hydroxy-2-methylpropyl)-1H-pyrazol-4-yl)-3-methyl-3,4-dihydroquinoxaline-1 (2H)-carboxylate. MS (ESI, pos. ion) m/z 472 [M+H]+.

Example 251

Isopropyl (S)-4-acetyl-7-(1-cyclopropyl-1H-pyrazol-4-yl)-6-fluoro-3-methyl-3,4-dihydroquinoxaline-1 (2H)-carboxylate (I-207)

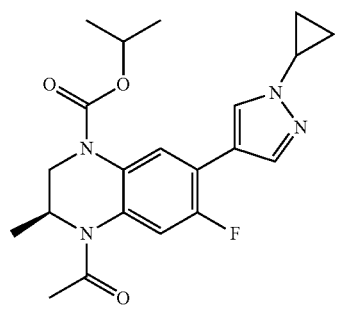 [SMILES: CC(=O)N1c2cc(F)c(-c3cnn(C4CC4)c3)cc2N(C(=O)OC(C)C)C[C@@H]1C]

Isopropyl (S)-4-acetyl-7-(1-cyclopropyl-1H-pyrazol-4-yl)-6-fluoro-3-methyl-3,4-dihydroquinoxaline-1(2H)-carboxylate was synthesized from isopropyl (S)-4-acetyl-6-amino-7-(1-cyclopropyl-1H-pyrazol-4-yl)-3-methyl-3,4-dihydroquinoxaline-1 (2H)-carboxylate according to the procedure described above for isopropyl (S)-4-acetyl-6-fluoro-3-methyl-7-(4-(methylsulfonyl)phenyl)-3,4-dihydroquinoxaline-1(2H)-carboxylate (Example 241). MS (ESI, pos. ion) m/z 401 [M+H]+.

Example 252

Isopropyl (S)-4-acetyl-6-chloro-7-(1-cyclopropyl-1H-pyrazol-4-yl)-3-methyl-3,4-dihydroquinoxaline-1 (2H)-carboxylate (I-208)

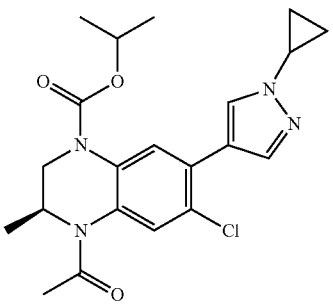 [SMILES: CC(=O)N1c2cc(Cl)c(-c3cnn(C4CC4)c3)cc2N(C(=O)OC(C)C)C[C@@H]1C]

Isopropyl (S)-4-acetyl-6-chloro-7-(1-cyclopropyl-1H-pyrazol-4-yl)-3-methyl-3,4-dihydroquinoxaline-1(2H)-carboxylate was synthesized from isopropyl (S)-4-acetyl-6-amino-7-(1-cyclopropyl-1H-pyrazol-4-yl)-3-methyl-3,4-dihydroquinoxaline-1 (2H)-carboxylate according to the procedure described above for isopropyl (S)-4-acetyl-6-bromo-3-methyl-7-(4-(methylsulfonyl)phenyl)-3,4-dihydroquinoxaline-1 (2H)-carboxylate (Example 238), substituting copper (I) chloride for copper (I) bromide. MS (ESI, pos. ion) m/z 417 [M+H]+.

Example 253

Isopropyl (S)-4-acetyl-6-bromo-7-(1-cyclopropyl-1H-pyrazol-4-yl)-3-methyl-3,4-dihydroquinoxaline-1 (2H)-carboxylate (I-209)

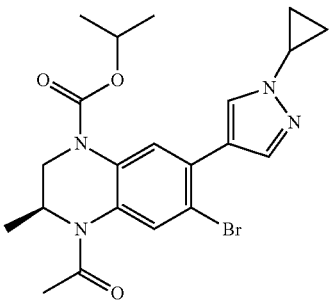 [SMILES: CC(=O)N1c2cc(Br)c(-c3cnn(C4CC4)c3)cc2N(C(=O)OC(C)C)C[C@@H]1C]

Isopropyl (S)-4-acetyl-6-bromo-7-(1-cyclopropyl-1H-pyrazol-4-yl)-3-methyl-3,4-dihydroquinoxaline-1(2H)-carboxylate was synthesized from isopropyl (S)-4-acetyl-6-amino-7-(1-cyclopropyl-1H-pyrazol-4-yl)-3-methyl-3,4-dihydroquinoxaline-1(2H)-carboxylate according to the procedure described above for isopropyl (S)-4-acetyl-6-bromo-3-methyl-7-(4-(methylsulfonyl)phenyl)-3,4-dihydroquinoxaline-1(2H)-carboxylate (Example 238). MS (ESI, pos. ion) m/z 461, 463 [M+H]+.

Example 254

Isopropyl (S)-4-acetyl-7-(1-cyclopropyl-1H-pyrazol-4-yl)-6-methoxy-3-methyl-3,4-dihydroquinoxaline-1 (2H)-carboxylate (I-210)

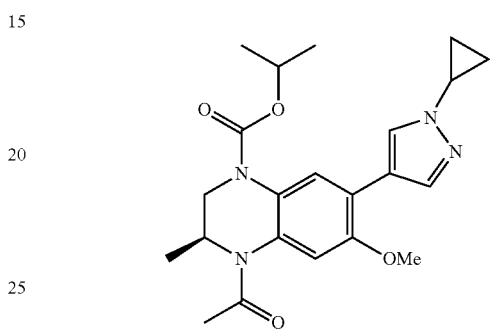

Isopropyl (S)-4-acetyl-7-(1-cyclopropyl-1H-pyrazol-4-yl)-6-methoxy-3-methyl-3,4-dihydroquinoxaline-1(2H)-carboxylate was synthesized from isopropyl (S)-4-acetyl-6-amino-7-(1-cyclopropyl-1H-pyrazol-4-yl)-3-methyl-3,4-dihydroquinoxaline-1(2H)-carboxylate according to the procedure described above for isopropyl (S)-4-acetyl-6-methoxy-3-methyl-7-(4-(methylsulfonyl)phenyl)-3,4-dihydroquinoxaline-1(2H)-carboxylate (Example 244). MS (ESI, pos. ion) m/z 413 [M+H]+.

Example 255

Isopropyl (S)-4-acetyl-6-cyano-7-(1-cyclopropyl-1H-pyrazol-4-yl)-3-methyl-3,4-dihydroquinoxaline-1 (2H)-carboxylate (I-211)

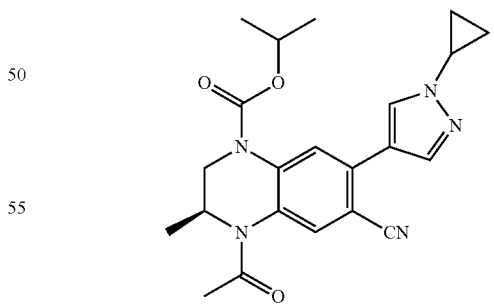

Isopropyl (S)-4-acetyl-6-cyano-7-(1-cyclopropyl-1H-pyrazol-4-yl)-3-methyl-3,4-dihydroquinoxaline-1(2H)-carboxylate was synthesized from isopropyl (S)-4-acetyl-6-amino-7-(1-cyclopropyl-1H-pyrazol-4-yl)-3-methyl-3,4-dihydroquinoxaline-1 (2H)-carboxylate according to the procedure described above for isopropyl (S)-4-acetyl-6-bromo-3-methyl-7-(4-(methylsulfonyl)phenyl)-3,4-dihydroquinoxaline-1(2H)-carboxylate (Example 238), substituting copper (I) cyanide for copper (I) bromide. MS (ESI, pos. ion) m/z 408 [M+H]+.

Example 256

Isopropyl (S)-4-acetyl-6-carbamoyl-7-(1-cyclopropyl-1H-pyrazol-4-yl)-3-methyl-3,4-dihydroquinoxaline-1(2H)-carboxylate (I-212)

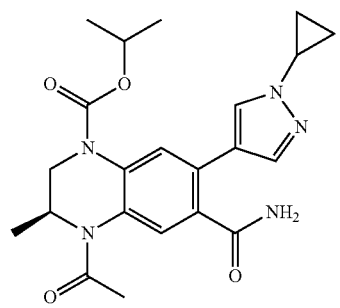 [SMILES: CC(=O)N1c2cc(C(N)=O)c(-c3cnn(C4CC4)c3)cc2N(C(=O)OC(C)C)C[C@@H]1C]

Potassium carbonate (0.002 g, 0.014 mmol) was added to a solution of isopropyl (S)-4-acetyl-6-cyano-7-(1-cyclopropyl-1H-pyrazol-4-yl)-3-methyl-3,4-dihydroquinoxaline-1 (2H)-carboxylate (0.010 g, 0.025 mmol) in dimethyl sulfoxide (2004), and the mixture was cooled in an ice bath. Hydrogen peroxide (30 wt %, 100 µL, 0.979 mmol) was added dropwise, the ice bath removed after 1 minute, and the reaction was allowed to warm to room temperature. Water was added, and the resulting precipitate was filtered and dried. The solid was purified by mass triggered preparatory HPLC. The product-containing fractions were combined and concentrated in a Genevac to afford isopropyl (S)-4-acetyl-6-carbamoyl-7-(1-cyclopropyl-1H-pyrazol-4-yl)-3-methyl-3,4-dihydroquinoxaline-1(2H)-carboxylate. MS (ESI, pos. ion) m/z 426 [M+H]+.

Example 257

Library Protocol A

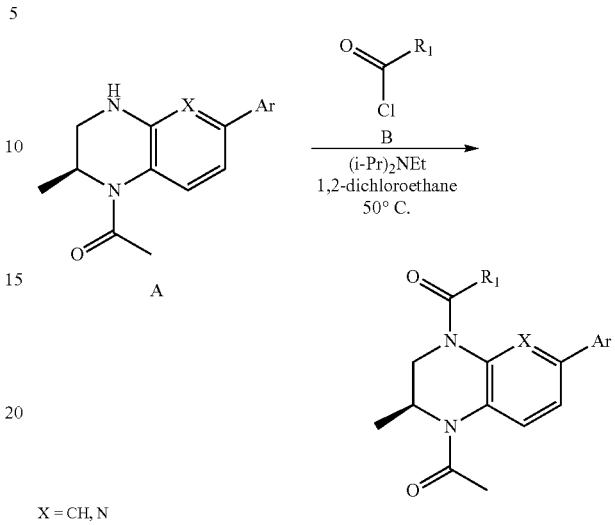

X = CH, N

A reaction vial was charged with piperazine (A) (0.2 M in 1,2-dichloroethane, 100 µL, 0.02 mmol), N,N-diisopropylethyl amine (25 µL, 0.14 mmol), and an acid chloride or chloroformate (B) (0.4 M in 1,2-dichloroethane, 100 µL, 0.04 mmol), and the mixture was shaken at 50° C. for 2 h. Ethyl acetate and water were added and the mixture was shaken. The aqueous layer was separated and extracted with ethyl acetate. The combined organic phases were concentrated to afford the crude product. This material was purified by mass triggered preparatory HPLC. The product-containing fractions were combined and concentrated in a Genevac to afford the desired product.

The following compounds in Table 1 were synthesized according to the above protocol:

TABLE 1

| Compound | Structure | LC-MS [M + 1]+ | HPLC RT (min) |
|---|---|---|---|
| I-223 | 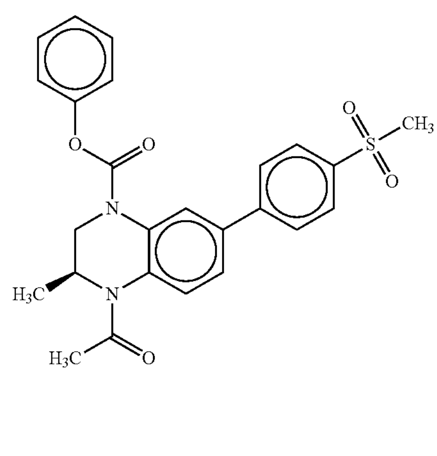 | 465 | 1.44 |

TABLE 1-continued

| Compound | Structure | LC-MS [M + 1]+ | HPLC RT (min) |
|---|---|---|---|
| I-224 | 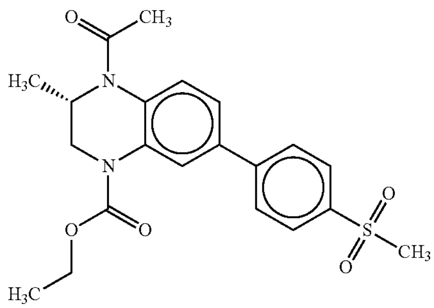 | 417 | 1.28 |
| I-225 | 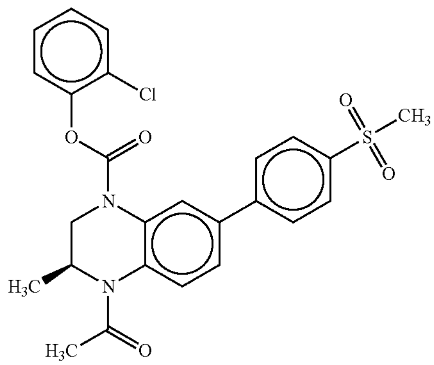 | 499 | 1.48 |
| I-226 | 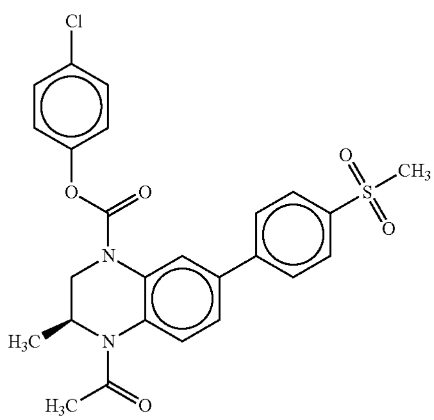 | 499 | 1.54 |
| I-227 | 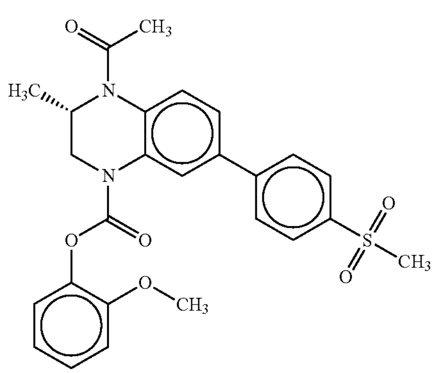 | 495 | 1.4 |

TABLE 1-continued

| Compound | Structure | LC-MS [M + 1]+ | HPLC RT (min) |
|---|---|---|---|
| I-228 | 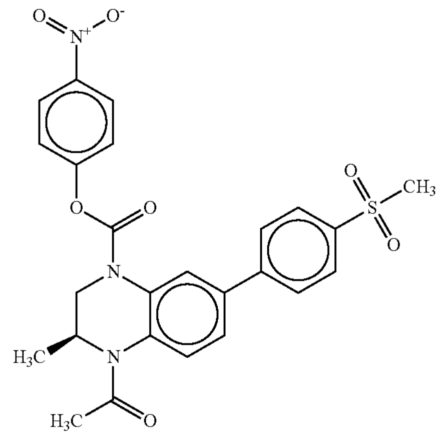 | 527 | 1.43 |
| I-229 | 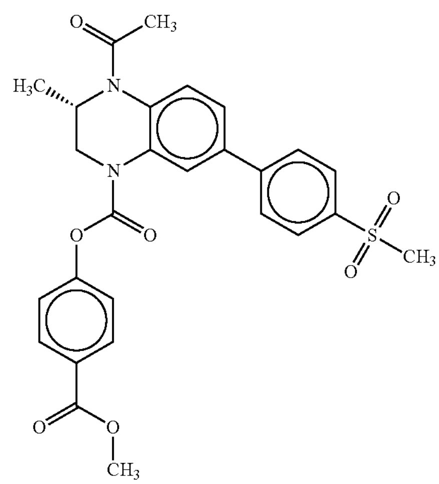 | 523 | 1.41 |
| I-230 | 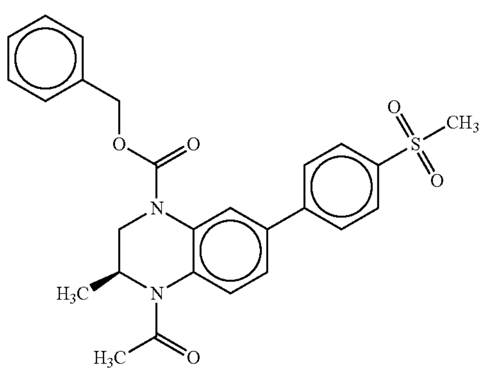 | 479 | 1.45 |
| I-231 | 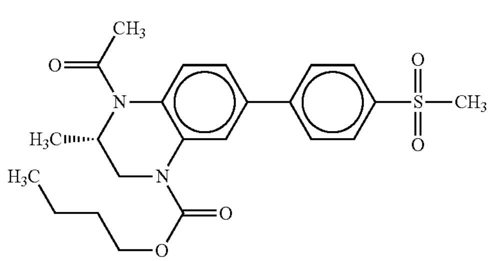 | 445 | 1.47 |

TABLE 1-continued

| Compound | Structure | LC-MS [M + 1]+ | HPLC RT (min) |
|---|---|---|---|
| I-232 | 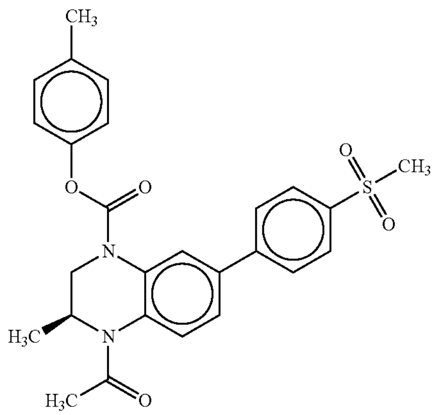 | 479 | 1.51 |
| I-233 | 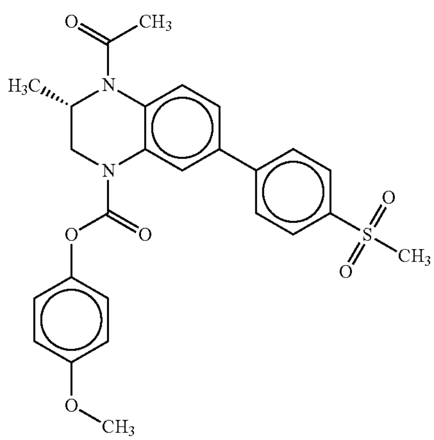 | 495 | 1.42 |
| I-234 | 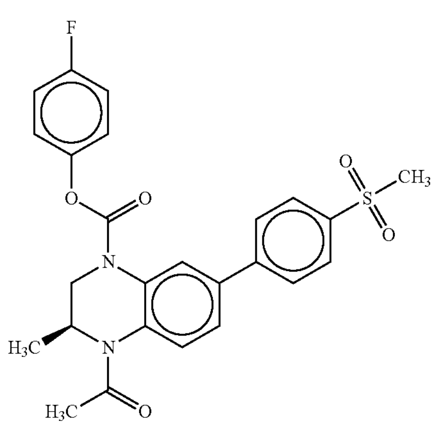 | 483 | 1.44 |

TABLE 1-continued

| Compound | Structure | LC-MS [M + 1]+ | HPLC RT (min) |
|---|---|---|---|
| I-235 | 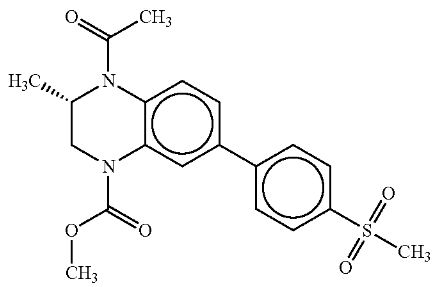 | 403 | 1.16 |
| I-236 | 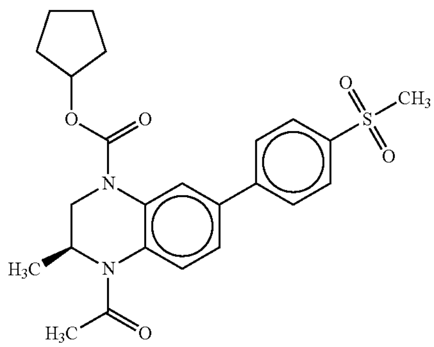 | 457 | 1.48 |
| I-237 | 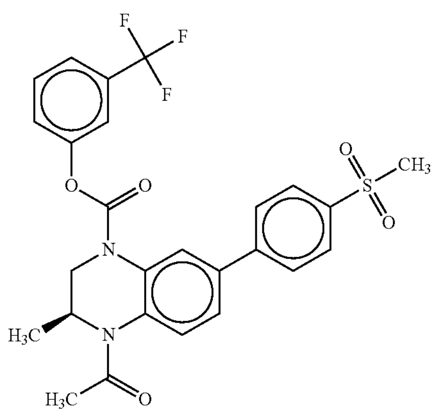 | 533 | 1.58 |
| I-238 | 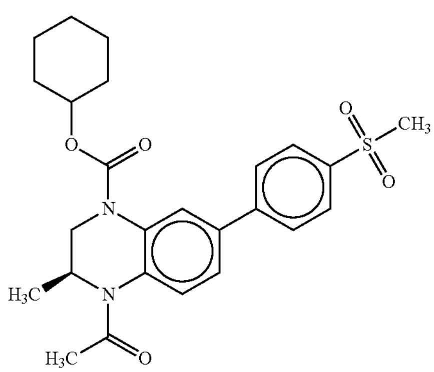 | 471 | 1.57 |

TABLE 1-continued

| Compound | Structure | LC-MS [M + 1]+ | HPLC RT (min) |
|---|---|---|---|
| I-239 | 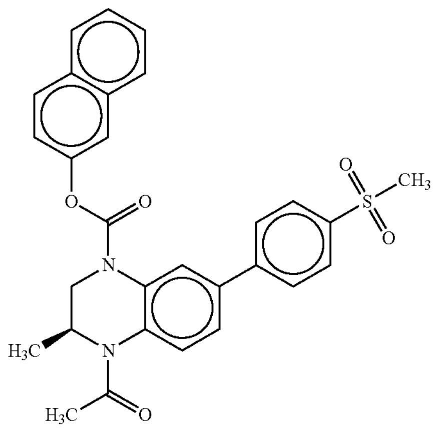 | 515 | 1.6 |
| I-240 | 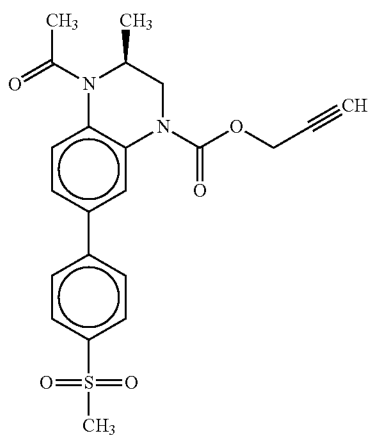 | 427 | 1.24 |
| I-241 | 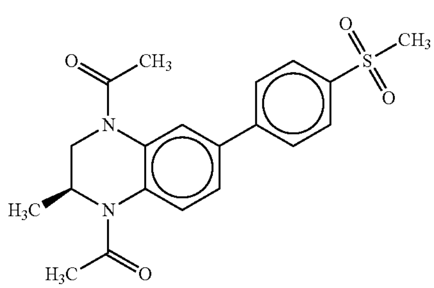 | 387 | 0.99 |
| I-242 | 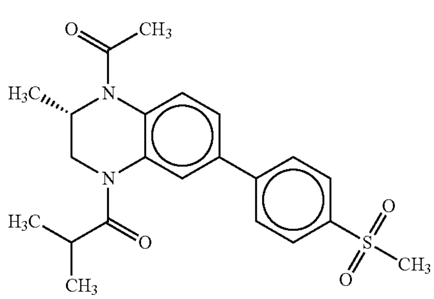 | 415 | 1.18 |

TABLE 1-continued
| Compound | Structure | LC-MS [M + 1]+ | HPLC RT (min) |
|---|---|---|---|
| I-243 | 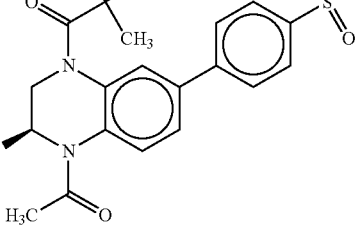 | 429 | 1.26 |
| I-244 | 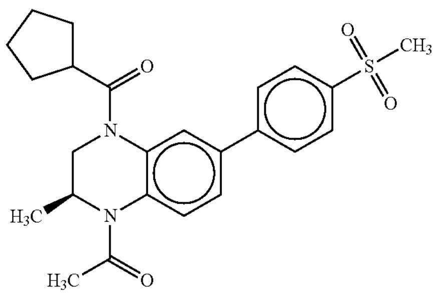 | 441 | 1.3 |
| I-245 | 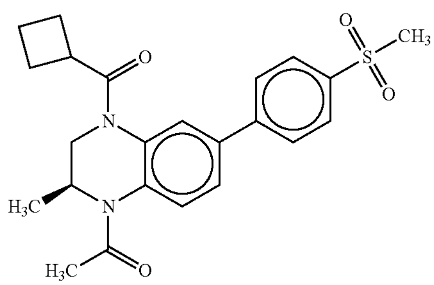 | 427 | 1.23 |
| I-246 | 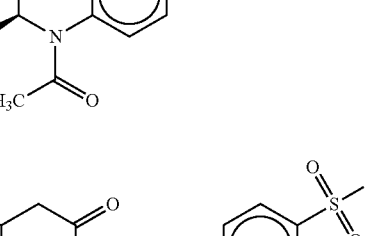 | 455 | 1.37 |
| I-247 | 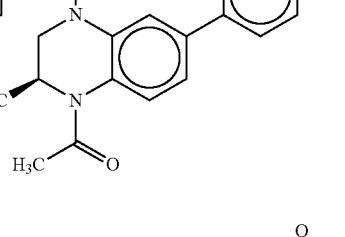 | 412 | 1.05 |

TABLE 1-continued

| Compound | Structure | LC-MS [M + 1]+ | HPLC RT (min) |
|---|---|---|---|
| I-248 | 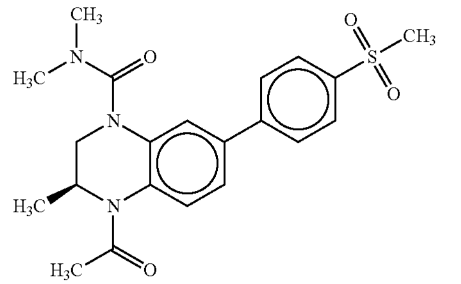 | 416 | 1.03 |
| I-249 | 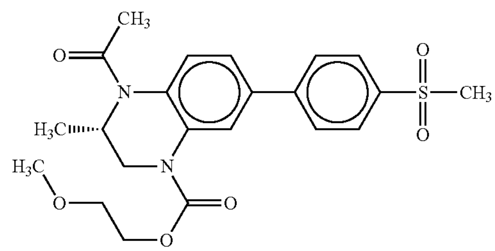 | 447 | 1.17 |
| I-250 | 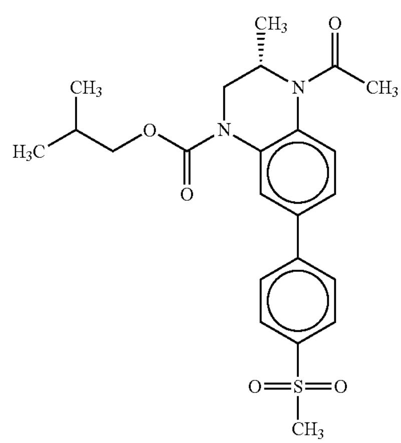 | 445 | 1.46 |
| I-251 | 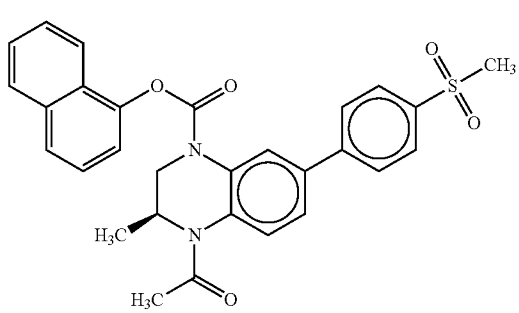 | 515 | 1.58 |

TABLE 1-continued

| Compound | Structure | LC-MS [M + 1]+ | HPLC RT (min) |
|---|---|---|---|
| I-252 | 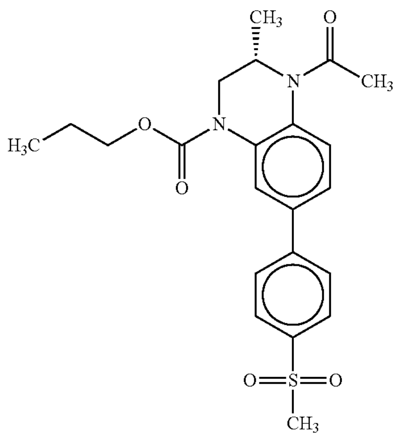 | 431 | 1.38 |
| I-253 | 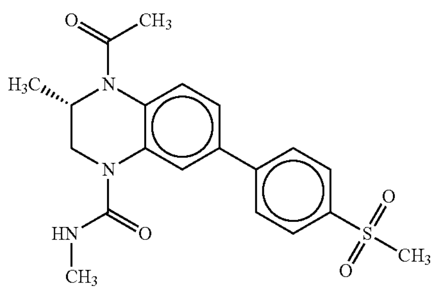 | 402 | 0.96 |
| I-254 | 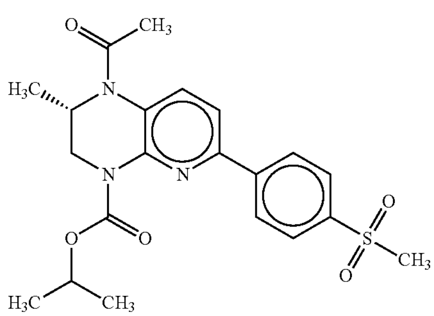 | 432 | 1.26 |
| I-255 | 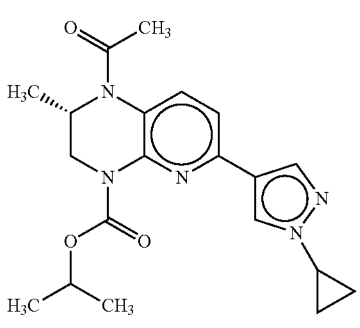 | 384 | 1.18 |

TABLE 1-continued

| Compound | Structure | LC-MS [M + 1]+ | HPLC RT (min) |
|---|---|---|---|
| I-256 | 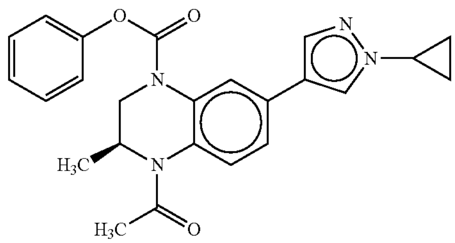 | 417 | 1.33 |
| I-257 | 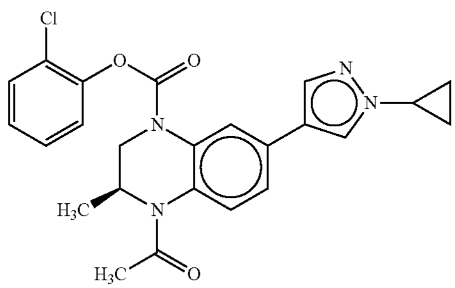 | 451 | 1.4 |
| I-258 | 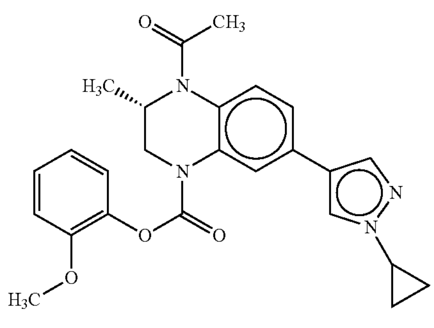 | 447 | 1.4 |
| I-259 | 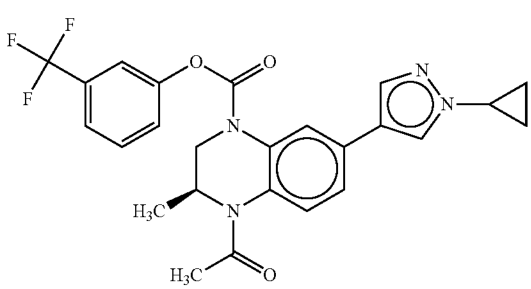 | 485 | 1.6 |
| I-260 | 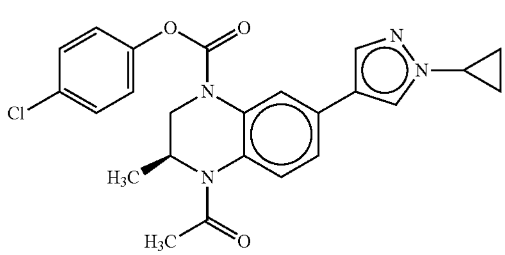 | 451 | 1.56 |

TABLE 1-continued

| Compound | Structure | LC-MS [M + 1]+ | HPLC RT (min) |
|---|---|---|---|
| I-261 | 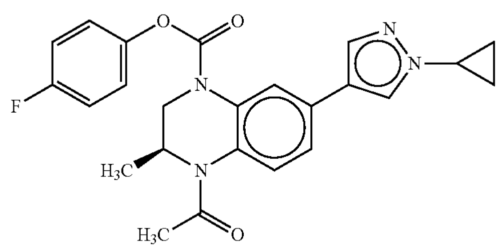 | 435 | 1.45 |
| I-262 | 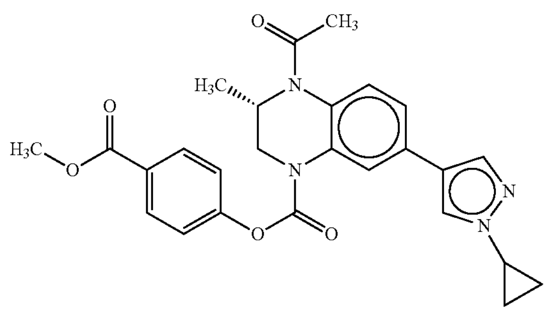 | 475 | 1.32 |
| I-263 | 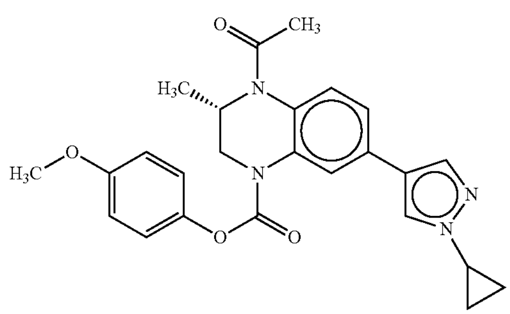 | 447 | 1.32 |
| I-264 | 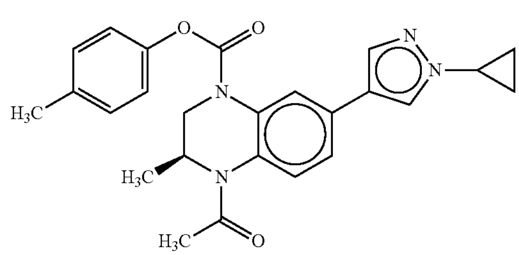 | 431 | 1.52 |
| I-265 | 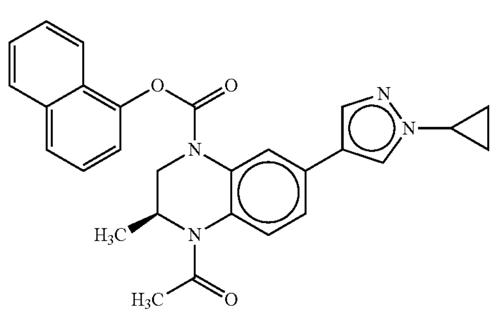 | 467 | 1.58 |

TABLE 1-continued

| Compound | Structure | LC-MS [M + 1]+ | HPLC RT (min) |
|---|---|---|---|
| I-266 | 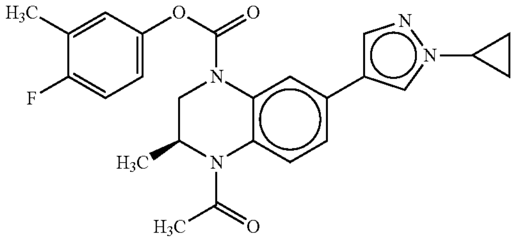 | 449 | 1.55 |
| I-267 | 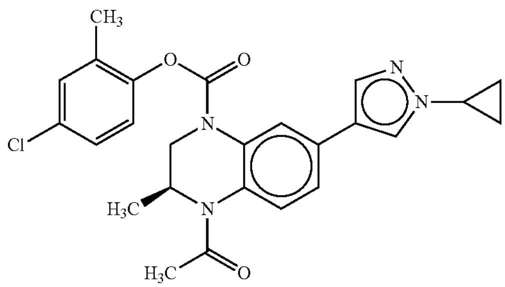 | 465 | 1.61 |

Example 258

Library Protocol B

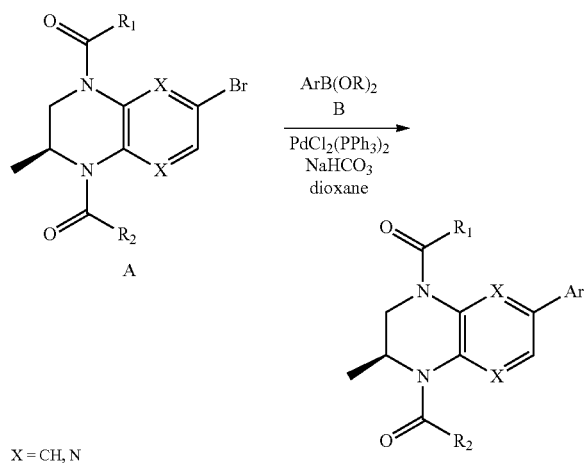

X = CH, N

A reaction vial was charged with aryl bromide (A) (0.2 M in 1,4-dioxane, 100 µL, 0.02 mmol) and a boronic acid or ester (B) (0.2 M in 1,4-dioxane, 150 µL, 0.03 mmol). Sodium bicarbonate (1 M solution in water, 60 µL, 0.06 mmol) was added followed by bis(triphenylphosphine)palladium(II) dichloride (0.02 M in DMF, 100 µL, 0.002 mmol), and the mixture was shaken at 80° C. overnight. Ethyl acetate and water were added and the mixture was shaken. The organic layer was separated and the aqueous phase was extracted with ethyl acetate. The combined organic phases were concentrated to afford the crude product. This material was purified by mass triggered preparatory HPLC. The product-containing fractions were combined and concentrated in a Genevac to afford the desired product.

The following compounds in Table 2 were synthesized according to the above protocol:

TABLE 2

| Example | Structure | LC-MS [M + 1]+ | HPLC RT (min) |
|---|---|---|---|
| I-268 | 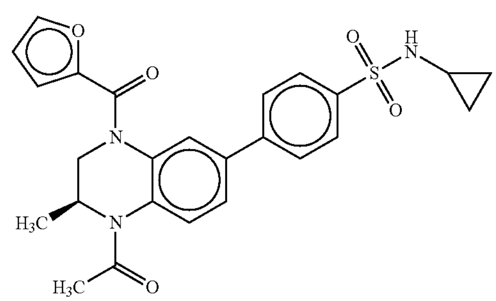 | 480 | 1.26 |

TABLE 2-continued

| Example | Structure | LC-MS [M + 1]+ | HPLC RT (min) |
|---|---|---|---|
| I-269 | 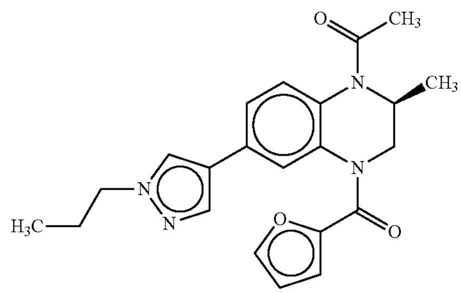 | 393 | 1.2 |
| I-270 | 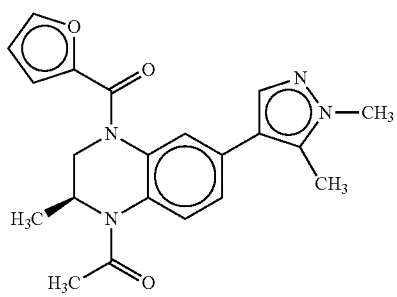 | 379 | 1.02 |
| I-271 | 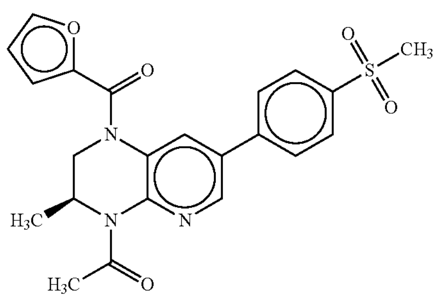 | 440 | 1.18 |
| I-272 | 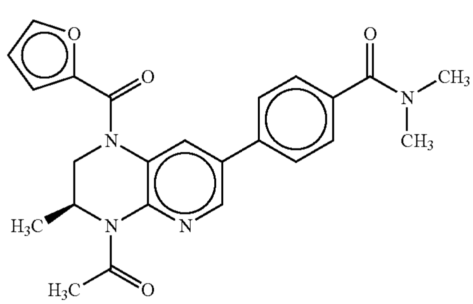 | 433 | 1.12 |
| I-273 | 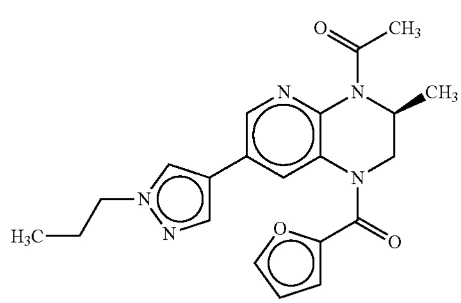 | 394 | 1.21 |

TABLE 2-continued
| Example | Structure | LC-MS [M + 1]+ | HPLC RT (min) |
|---|---|---|---|
| I-274 | 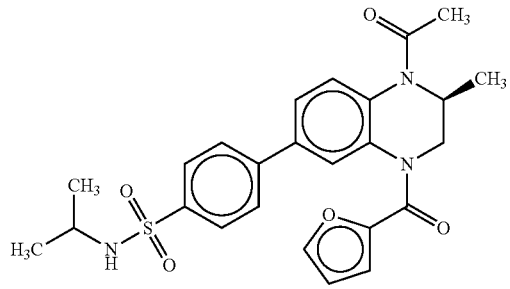 | 482 | 1.31 |
| I-275 | 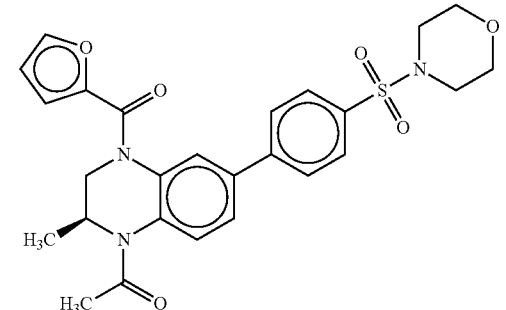 | 510 | 1.28 |
| I-276 | 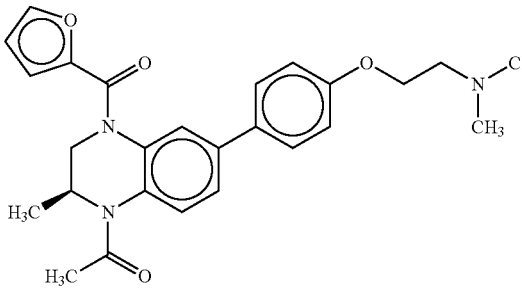 | 448 | 0.85 |
| I-277 | 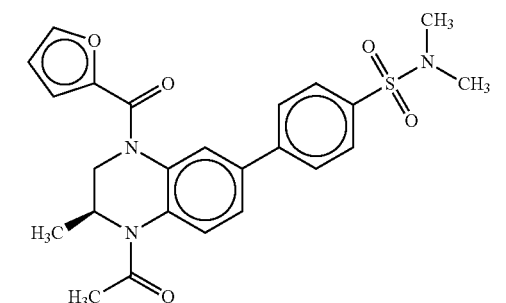 | 468 | 1.31 |

TABLE 2-continued

| Example | Structure | LC-MS [M + 1]+ | HPLC RT (min) |
|---|---|---|---|
| I-278 | 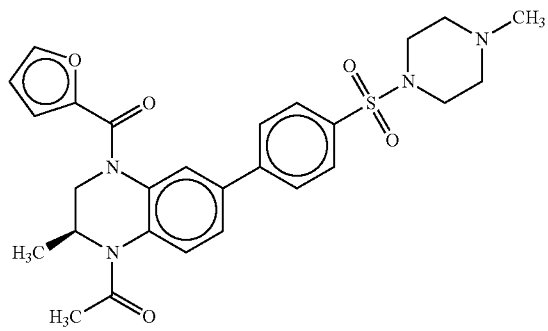 | 523 | 0.93 |
| I-279 | 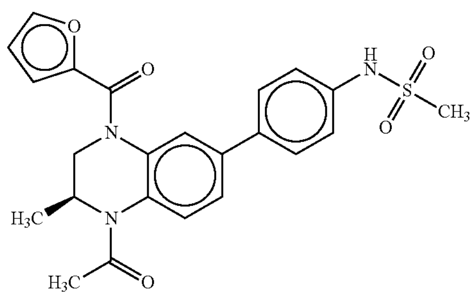 | 454 | 1.12 |
| I-280 | 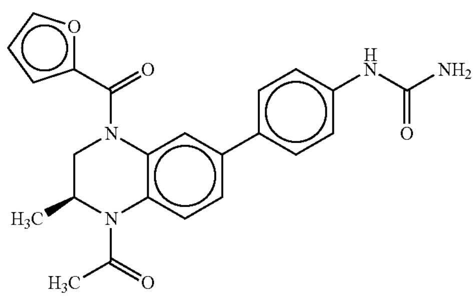 | 419 | 0.94 |
| I-281 | 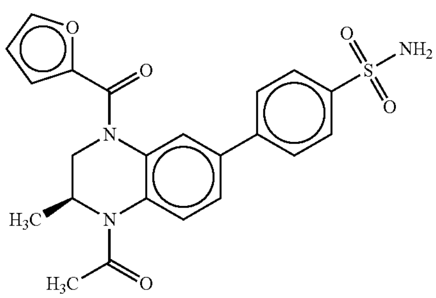 | 440 | 1.02 |
| I-282 | 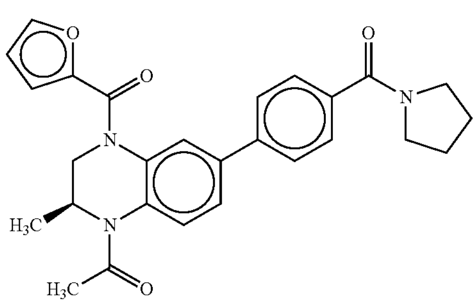 | 458 | 1.2 |

TABLE 2-continued

| Example | Structure | LC-MS [M + 1]+ | HPLC RT (min) |
|---------|-----------|----------------|---------------|
| I-283 | 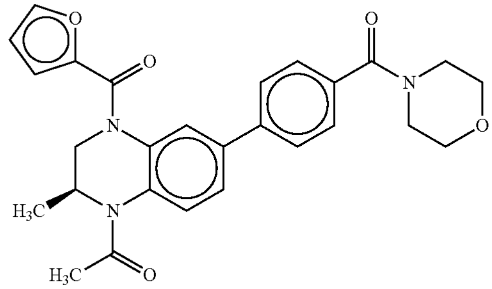 | 474 | 1.07 |
| I-284 | 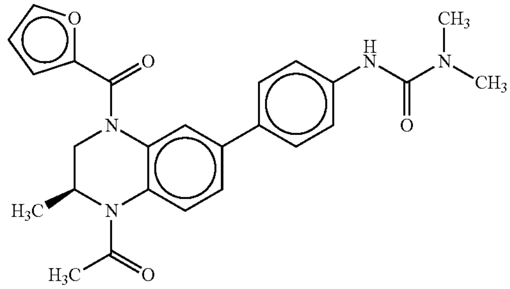 | 447 | 1.11 |
| I-285 | 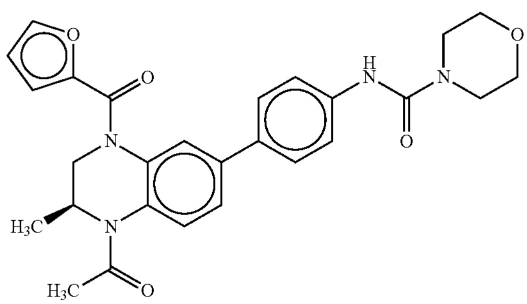 | 489 | 1.08 |
| I-286 | 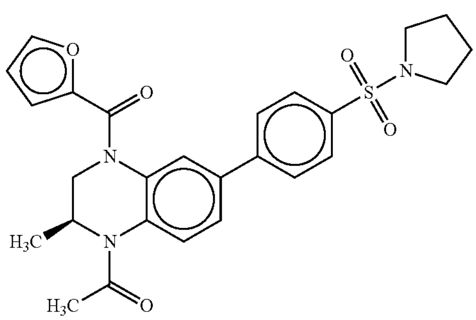 | 494 | 1.38 |
| I-287 | 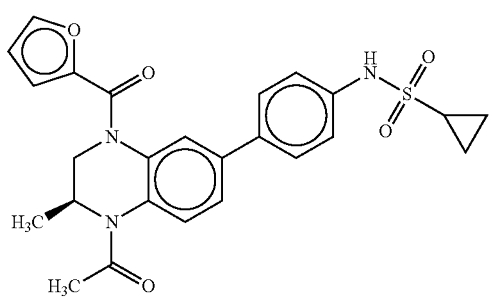 | 480 | 1.22 |

TABLE 2-continued

| Example | Structure | LC-MS [M + 1]+ | HPLC RT (min) |
|---------|-----------|----------------|---------------|
| I-288 | 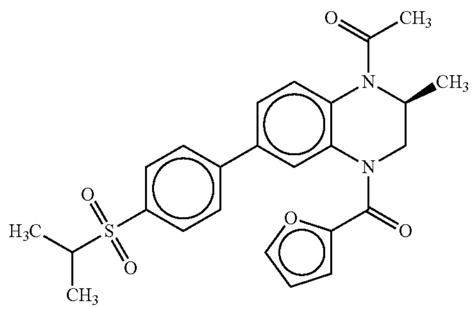 | 467 | 1.29 |
| I-289 | 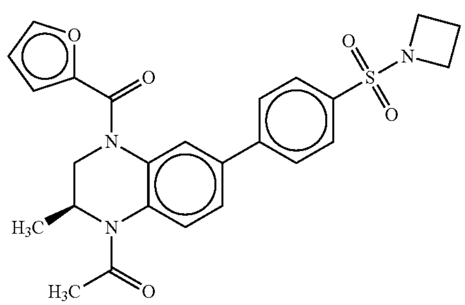 | 480 | 1.29 |
| I-290 | 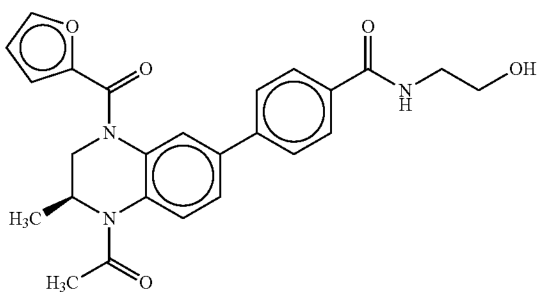 | 448 | 0.9 |
| I-291 | 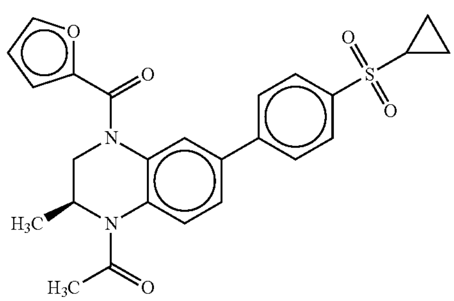 | 465 | 1.26 |
| I-292 | 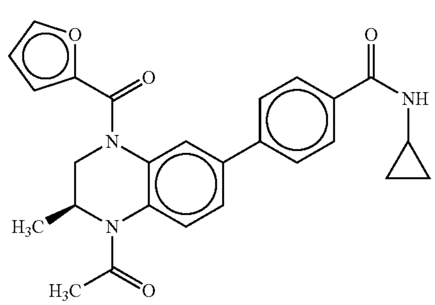 | 444 | 1.13 |

TABLE 2-continued
| Example | Structure | LC-MS [M + 1]+ | HPLC RT (min) |
|---|---|---|---|
| I-293 | 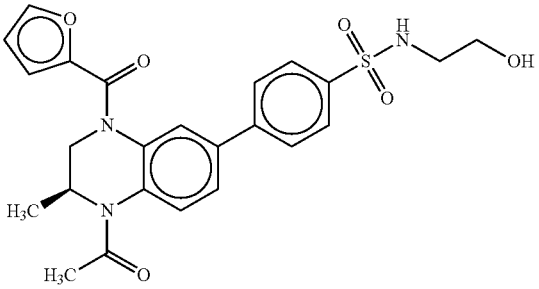 | 484 | 1.01 |
| I-294 | 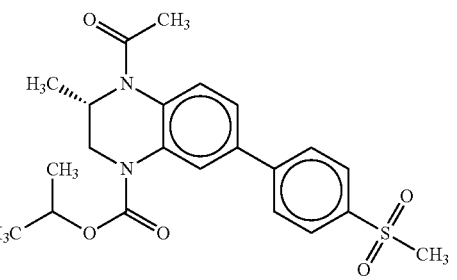 | 431 | 1.32 |
| I-295 | 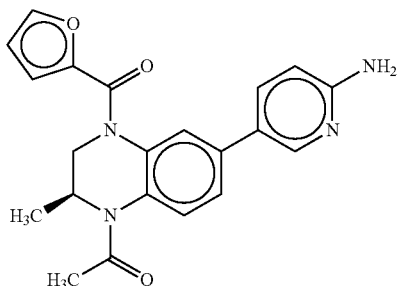 | 377 | 0.7 |
| I-296 | 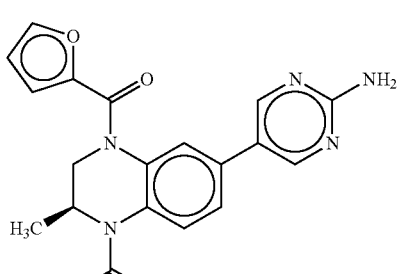 | 378 | 0.83 |
| I-297 | 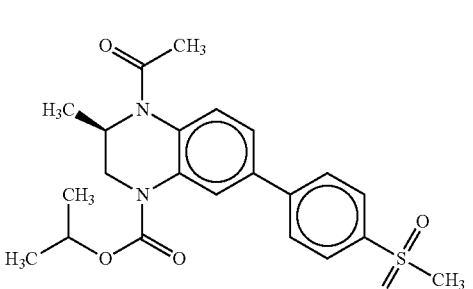 | 431 | 1.35 |

TABLE 2-continued

| Example | Structure | LC-MS [M + 1]+ | HPLC RT (min) |
|---------|-----------|----------------|---------------|
| I-298 | 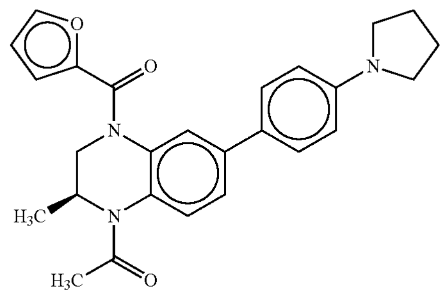 | 430 | 1.76 |
| I-299 | 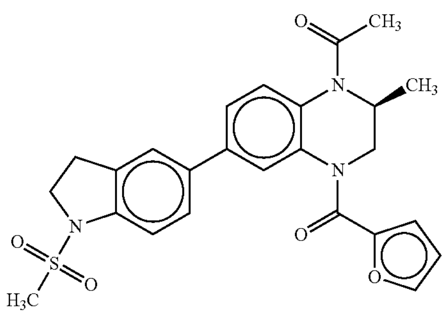 | 480 | 1.28 |
| I-300 | 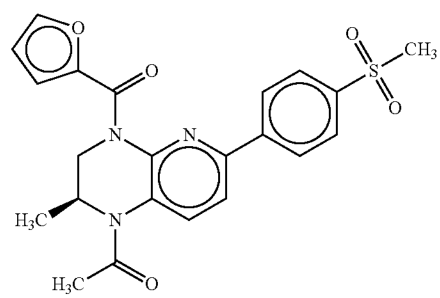 | 440 | 1.15 |
| I-301 | 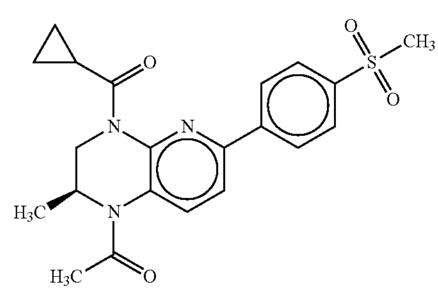 | 414 | 1.17 |
| I-302 | 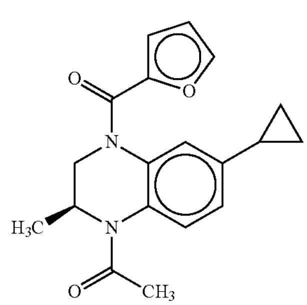 | 342 | 1.91 |

TABLE 2-continued

| Example | Structure | LC-MS [M + 1]+ | HPLC RT (min) |
|---|---|---|---|
| I-303 | 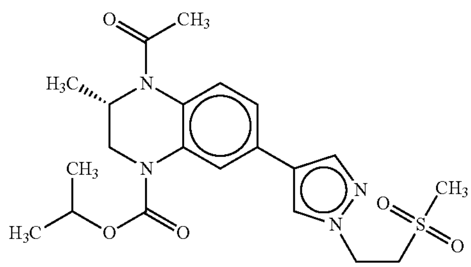 | 449 | 1.13 |
| I-304 | 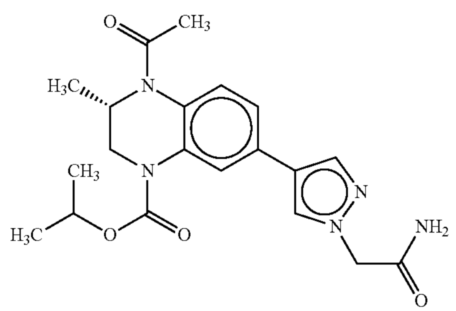 | 400 | 0.98 |
| I-305 | 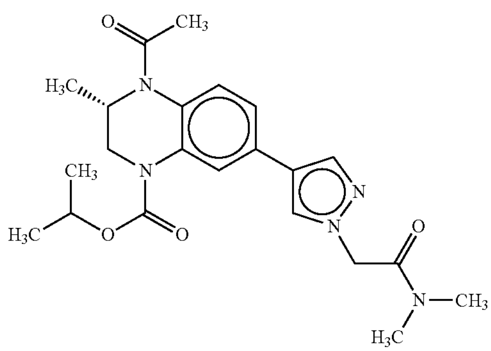 | 428 | 1.08 |
| I-306 | 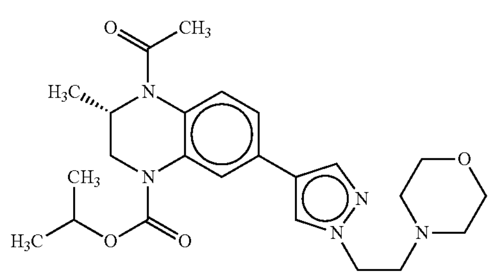 | 456 | 0.92 |
| I-307 | 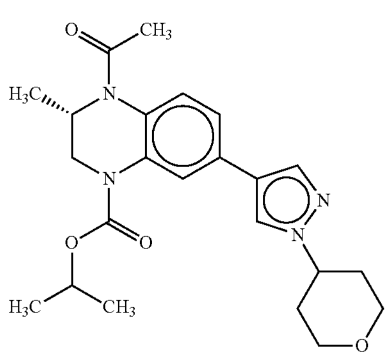 | 427 | 1.27 |

TABLE 2-continued

| Example | Structure | LC-MS [M + 1]+ | HPLC RT (min) |
|---|---|---|---|
| I-308 | 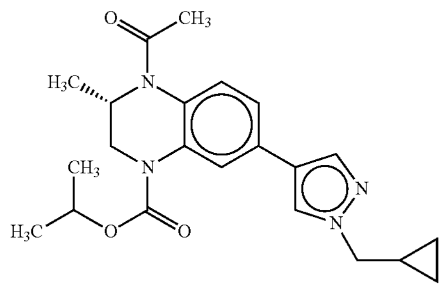 | 397 | 1.44 |
| I-309 | 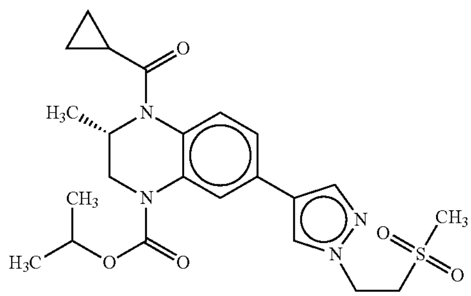 | 475 | 1.29 |
| I-310 | 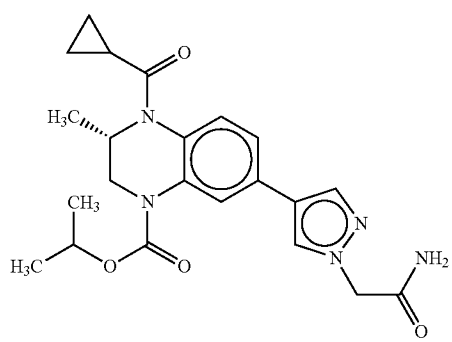 | 426 | 1.14 |
| I-311 | 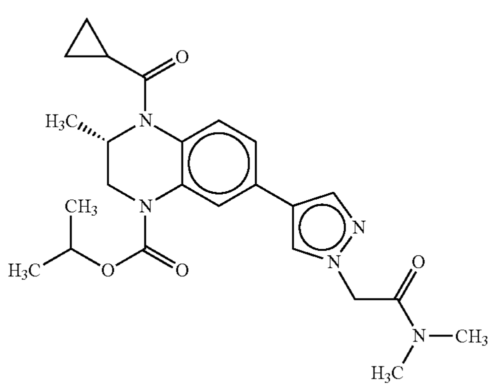 | 454 | 1.24 |

TABLE 2-continued

| Example | Structure | LC-MS [M + 1]+ | HPLC RT (min) |
|---|---|---|---|
| I-312 | 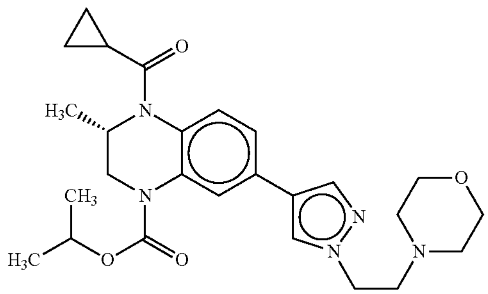 | 482 | 1.08 |
| I-313 | 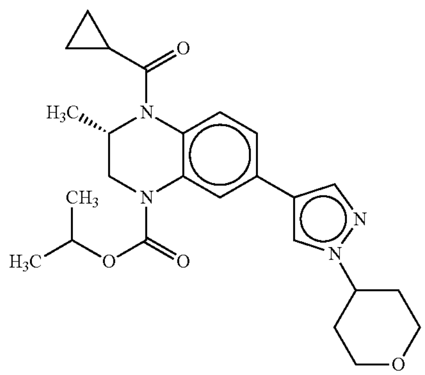 | 453 | 1.45 |
| I-314 | 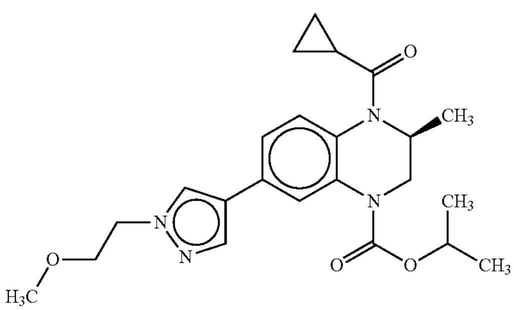 | 427 | 1.42 |
| I-315 | 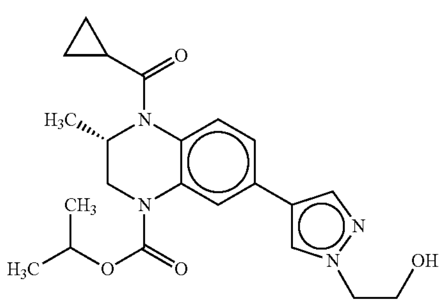 | 413 | 1.21 |

TABLE 2-continued

| Example | Structure | LC-MS [M + 1]+ | HPLC RT (min) |
|---|---|---|---|
| I-316 | 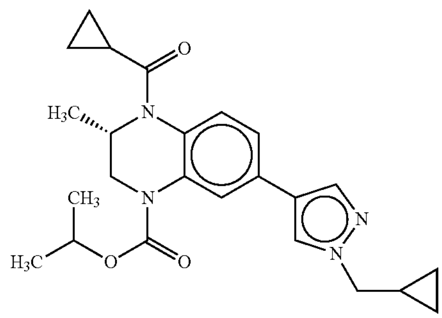 | 423 | 1.62 |
| I-317 | 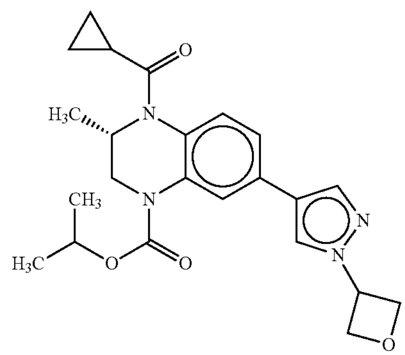 | 425 | 1.34 |
| I-318 | 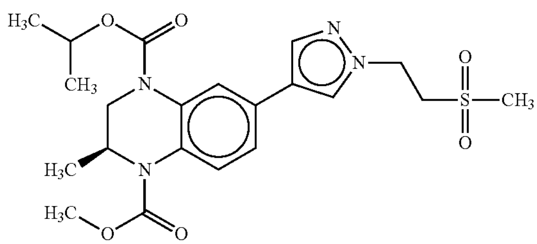 | 465 | 1.33 |
| I-319 | 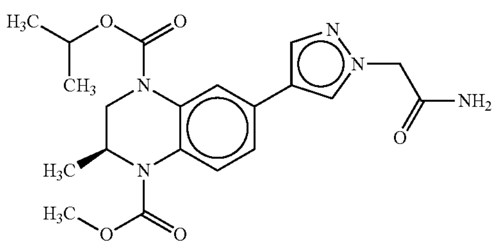 | 416 | 1.17 |
| I-320 | 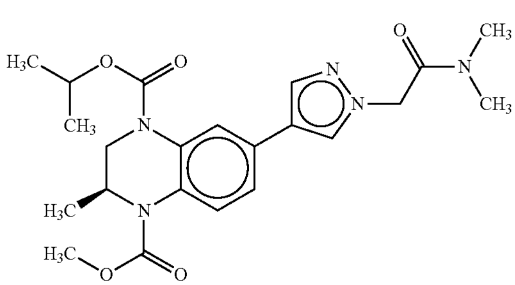 | 444 | 1.27 |

TABLE 2-continued

| Example | Structure | LC-MS [M + 1]+ | HPLC RT (min) |
|---|---|---|---|
| I-321 | 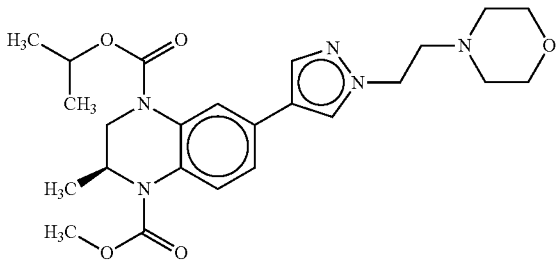 | 472 | 1.11 |
| I-322 | 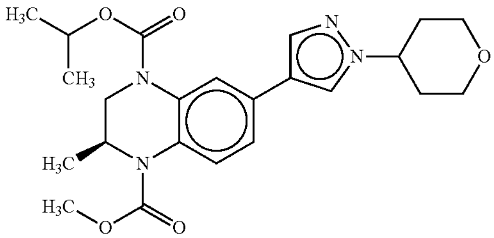 | 443 | 1.48 |
| I-323 | 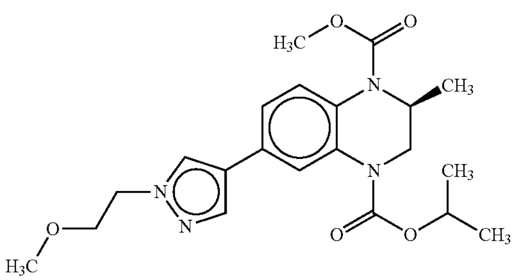 | 417 | 1.45 |
| I-324 | 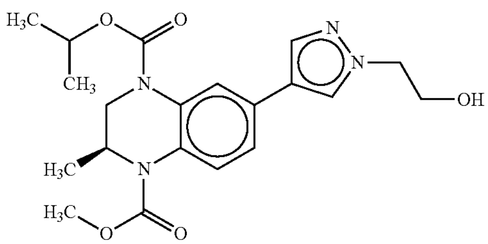 | 403 | 1.24 |
| I-325 | 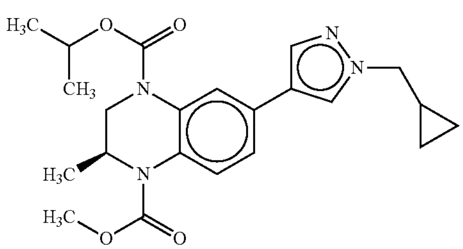 | 413 | 1.64 |
| I-326 | 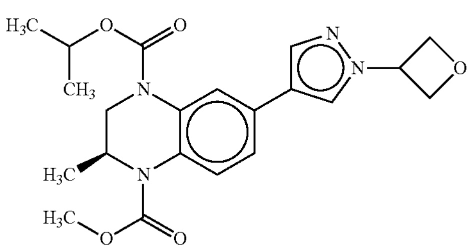 | 415 | 1.39 |

TABLE 2-continued

| Example | Structure | LC-MS [M + 1]+ | HPLC RT (min) |
|---------|-----------|----------------|---------------|
| I-327 | 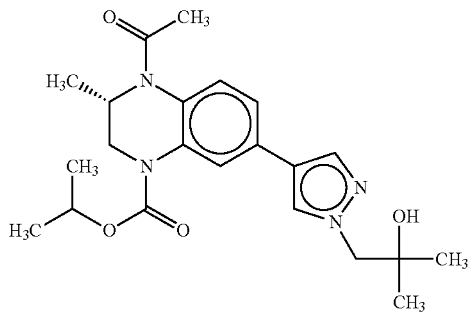 | 415 | 1.15 |
| I-328 | 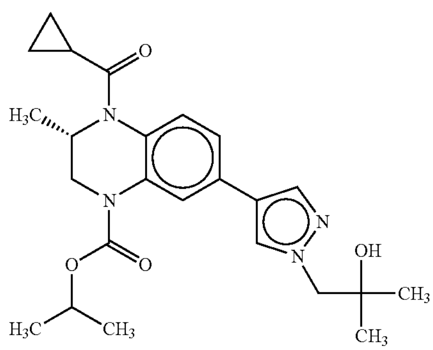 | 441 | 1.33 |
| I-329 | 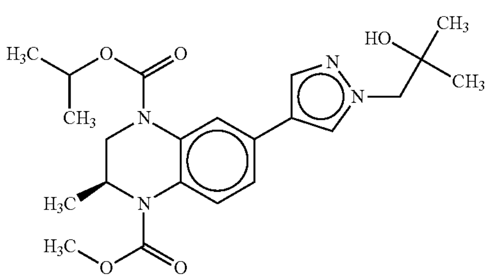 | 431 | 1.36 |
| I-330 | 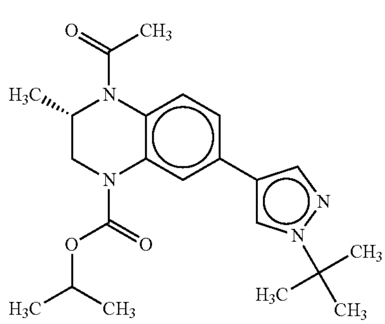 | 399 | 1.51 |

TABLE 2-continued

| Example | Structure | LC-MS [M + 1]+ | HPLC RT (min) |
|---|---|---|---|
| I-331 | 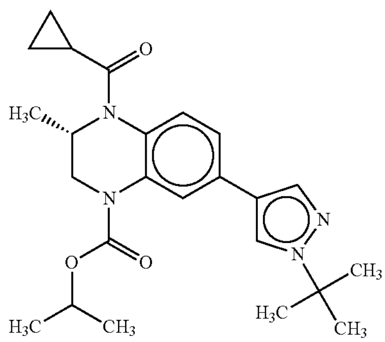 | 425 | 1.7 |
| I-332 | 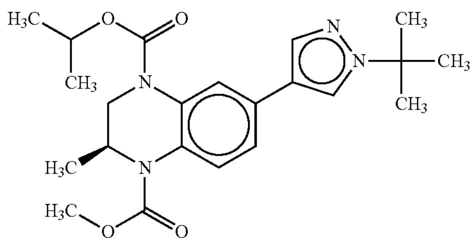 | 415 | 1.71 |
| I-333 | 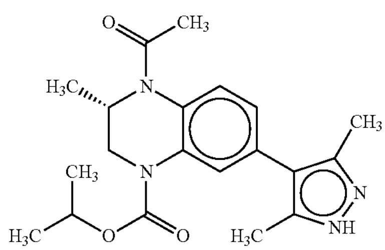 | 371 | 1.09 |
| I-334 | 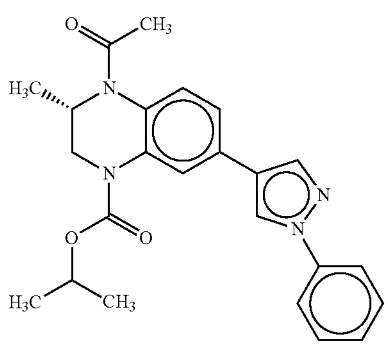 | 419 | 1.66 |
| I-335 | 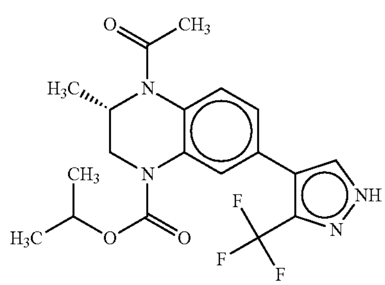 | 411 | 1.29 |

TABLE 2-continued

| Example | Structure | LC-MS [M + 1]+ | HPLC RT (min) |
|---------|-----------|----------------|---------------|
| I-336 | 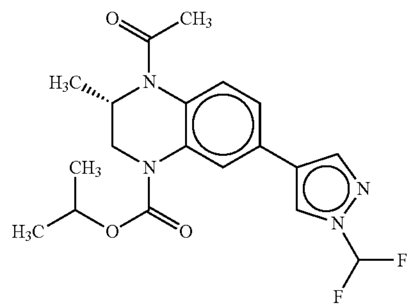 | 393 | 1.39 |
| I-337 | 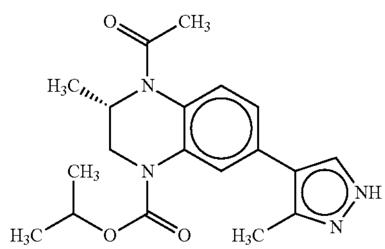 | 357 | 1.07 |
| I-338 | 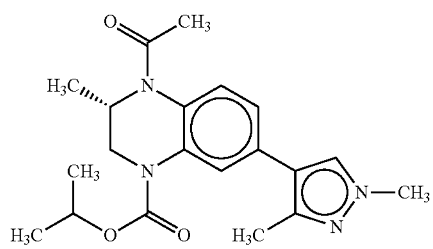 | 371 | 1.19 |
| I-339 | 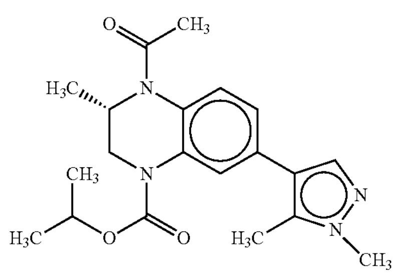 | 371 | 1.2 |
| I-340 | 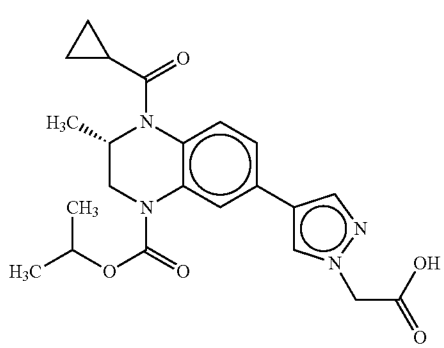 | 427 | 1.12 |

TABLE 2-continued

| Example | Structure | LC-MS [M + 1]+ | HPLC RT (min) |
|---|---|---|---|
| I-341 | 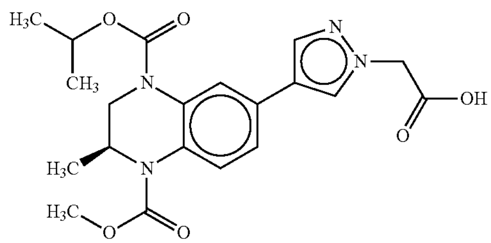 | 417 | 1.15 |
| I-342 | 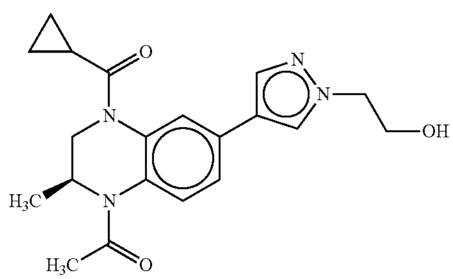 | 369 | 0.8 |
| I-343 | 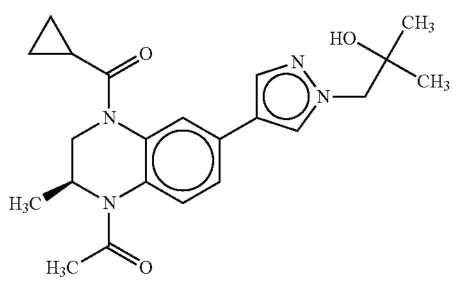 | 397 | 0.94 |
| I-344 | 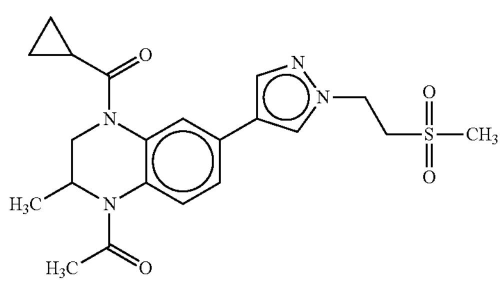 | 431 | 0.88 |
| I-345 | 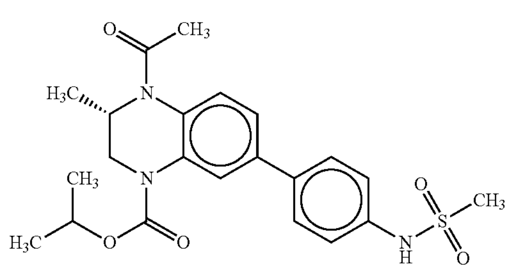 | 446 | 1.3 |

TABLE 2-continued

| Example | Structure | LC-MS [M + 1]+ | HPLC RT (min) |
|---------|-----------|----------------|---------------|
| I-346 | 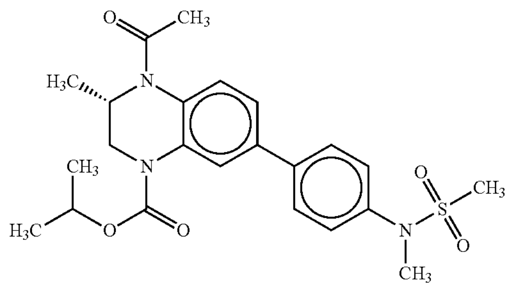 | 460 | 1.42 |
| I-347 | 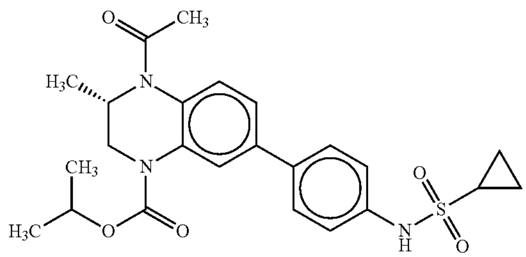 | 472 | 1.4 |
| I-348 | 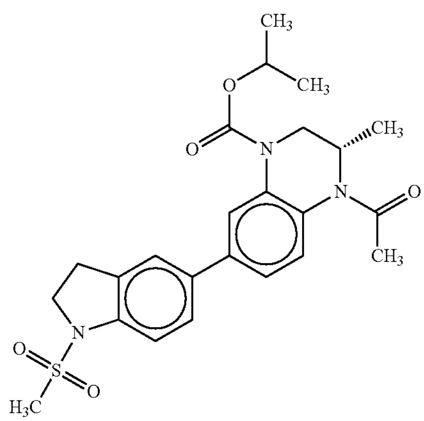 | 472 | 1.47 |
| I-349 | 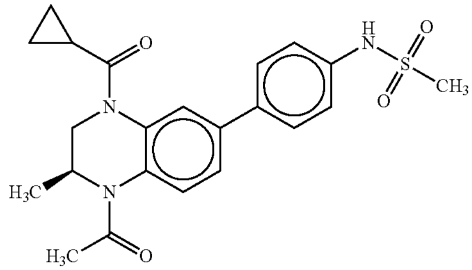 | 428 | 1.12 |
| I-350 | 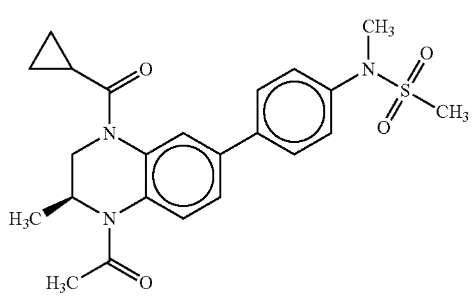 | 442 | 1.23 |

TABLE 2-continued

| Example | Structure | LC-MS [M + 1]+ | HPLC RT (min) |
|---|---|---|---|
| I-351 | 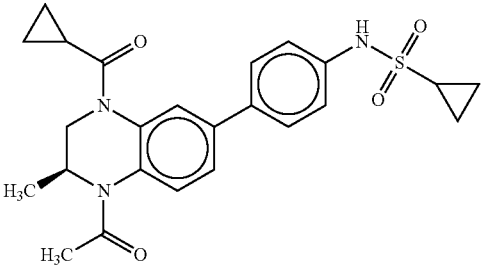 | 454 | 1.22 |
| I-352 | 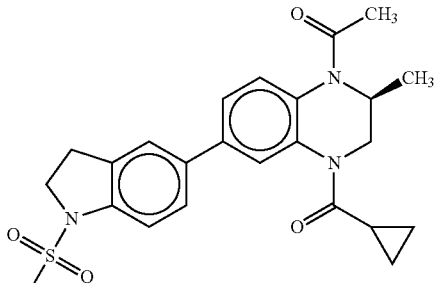 | 454 | 1.28 |

Example 259

Library Protocol B1

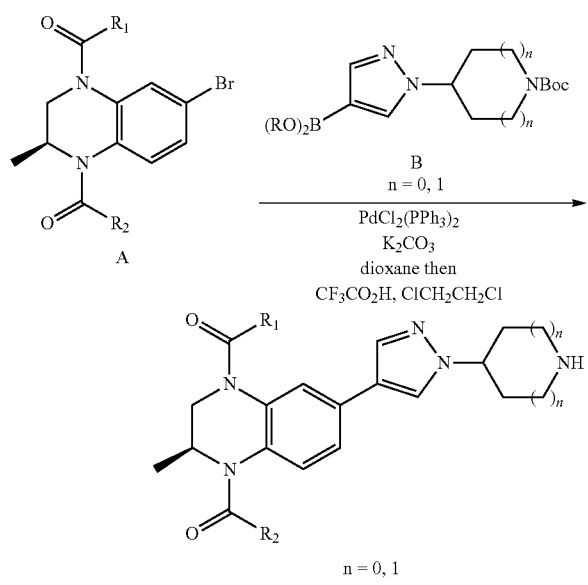

A reaction vial was charged with aryl bromide (A) (0.2 M in 1,4-dioxane, 200 µL, 0.04 mmol) and a boronic acid or ester (B) (0.2 M in 1,4-dioxane, 240 µL, 0.048 mmol). Potassium bicarbonate (1 M solution in water, 40 µL, 0.04 mmol) was added followed by bis(triphenylphosphine)palladium(II) dichloride (0.02 M in DMF, 200 µL, 0.004 mmol), and the mixture was shaken at 80° C. overnight. Ethyl acetate and water were added and the mixture was shaken. The aqueous layer was separated and extracted with ethyl acetate. The combined organic phases were concentrated to afford the crude product. This material was purified by column chromatography on silica gel (eluting with 20-50% ethyl acetate-hexane). The product-containing fractions were combined and concentrated. The residue was taken up in 1,2-dichloroethane (200 µL) and trifluoroacetic acid (100 µL) was added. The reactions stirred at room temperature for 2 h. The reaction was concentrated, and diluted with ethyl acetate (0.5 mL) and saturated aqueous sodium bicarbonate solution (0.5 mL). The aqueous layer was separated and extracted with ethyl acetate (1 mL), and the organic layers were combined and concentrated under a stream of nitrogen. The crude product was purified by mass triggered preparatory HPLC. The product-containing fractions were combined and concentrated to afford the desired product.

The following compounds in Table 3 were synthesized according to the above protocol:

TABLE 3
| Example | Structure | LC-MS [M + 1]+ | HPLC RT (min) |
|---|---|---|---|
| I-353 | 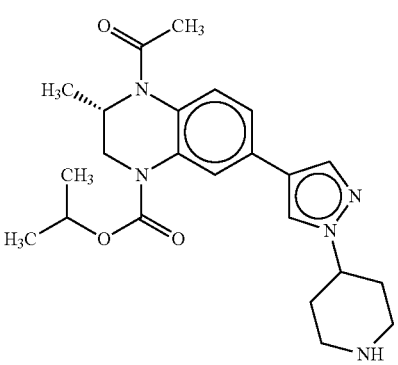 | 426 | 0.91 |
| I-354 | 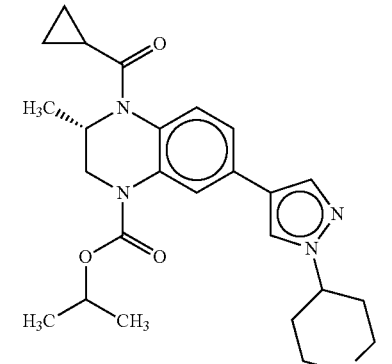 | 452 | 1.02 |
| I-355 | 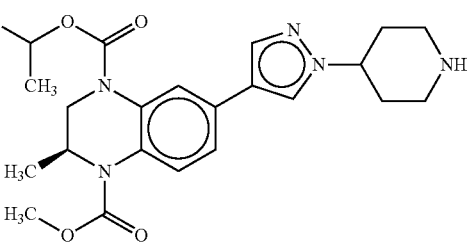 | 442 | 1.09 |
| I-356 | 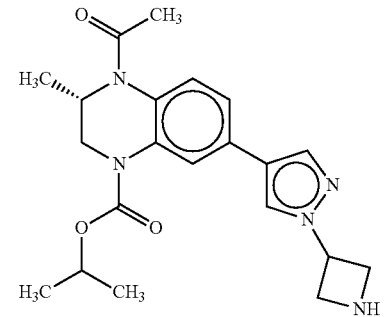 | 398 | 0.83 |

TABLE 3-continued
| Example | Structure | LC-MS [M + 1]+ | HPLC RT (min) |
|---|---|---|---|
| I-357 | 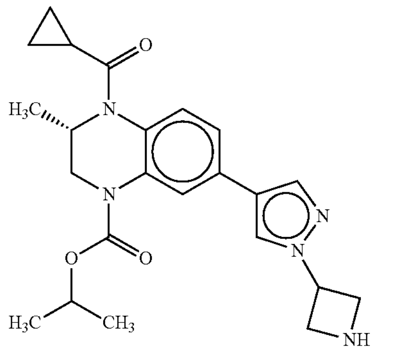 | 424 | 0.98 |
| I-358 | 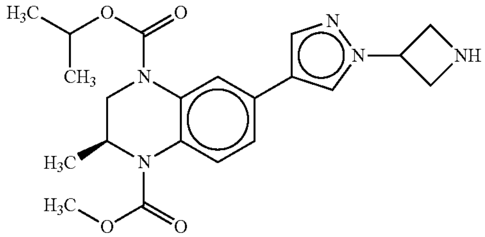 | 414 | 1.02 |
| I-359 | 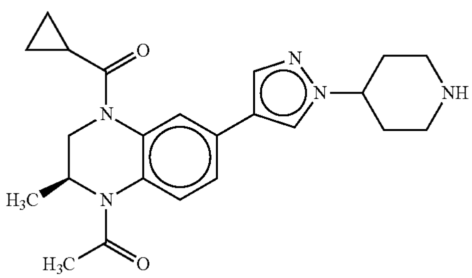 | 408 | 0.68 |
| I-360 | 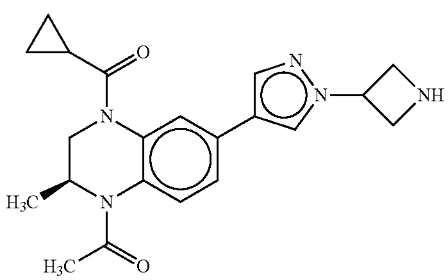 | 380 | 0.65 |
Example 260
Library Protocol C
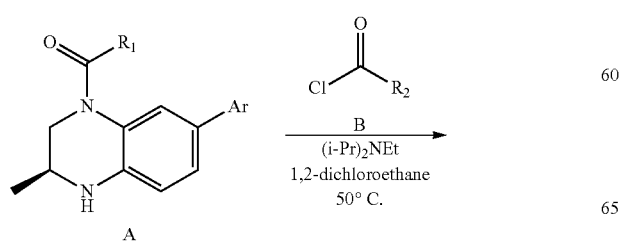
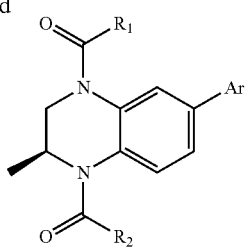
A 1.5 mL reaction vial was charged with benzopiperazine (A) (0.2 M in 1,2-dichloroethane, 100 μL, 0.02 mmol), N,N-diisopropylethylamine (25 μL, 0.143 mmol), and an acid chloride or chloroformate (B) (0.4 M in 1,2-dichloroethane, 150 µL, 0.06 mmol)). The reaction mixture was heated to 50° C. for 2 h on a heater shaker. The reaction was diluted with ethyl acetate (0.5 mL) and washed with brine (0.5 mL). The aqueous layer was separated and extracted with ethyl acetate (1 mL) and the organic layers were combined and concentrated under a stream of nitrogen. The crude product was purified by mass triggered preparatory HPLC. The product-containing fractions were combined and concentrated in a Genevac to afford the desired product.

The following compounds in Table 3 were synthesized according to the above protocol:

TABLE 3

| Example | Structure | LC-MS [M + 1]+ | HPLC RT (min) |
|---------|-----------|----------------|---------------|
| I-361 | 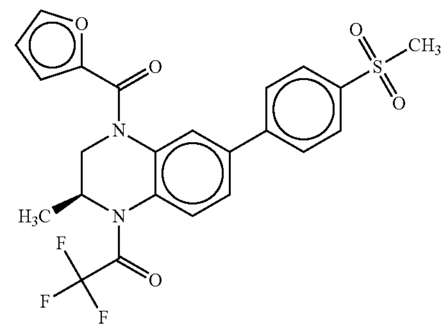 | 493 | 1.44 |
| I-362 | 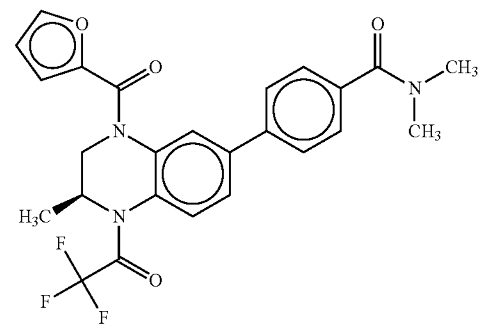 | 486 | 1.39 |
| I-363 | 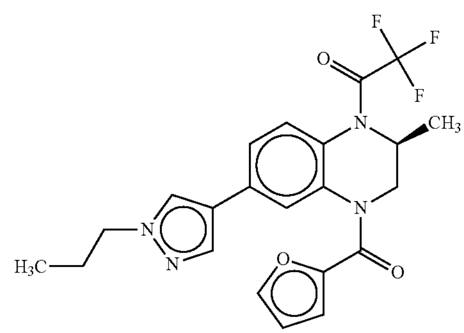 | 447 | 1.52 |
| I-364 | 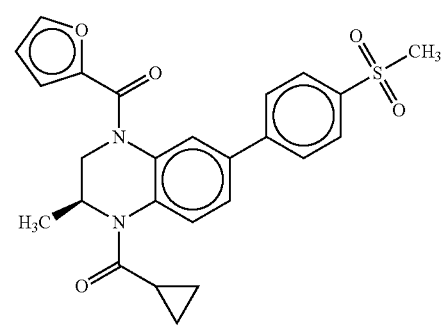 | 465 | 1.3 |

TABLE 3-continued

| Example | Structure | LC-MS [M + 1]+ | HPLC RT (min) |
|---|---|---|---|
| I-365 | 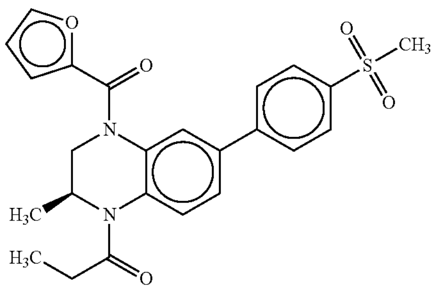 | 453 | 1.24 |
| I-366 | 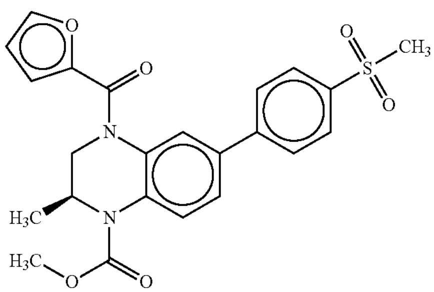 | 455 | 1.33 |
| I-367 | 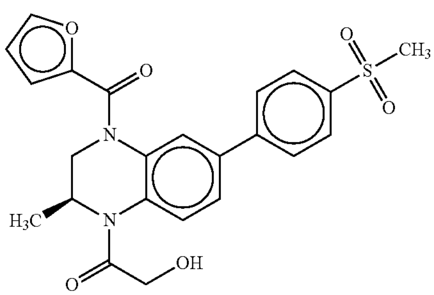 | 455 | 1.02 |
| I-368 | 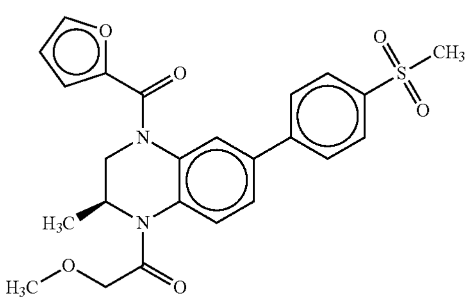 | 469 | 1.13 |
| I-369 | 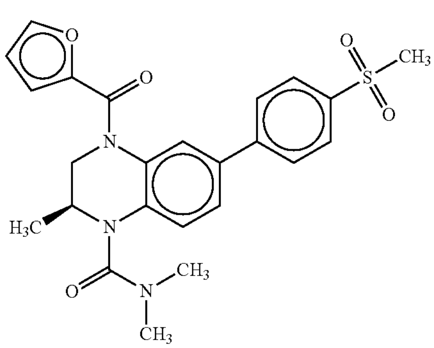 | 468 | 1.16 |

TABLE 3-continued

| Example | Structure | LC-MS [M + 1]+ | HPLC RT (min) |
|---|---|---|---|
| I-370 | 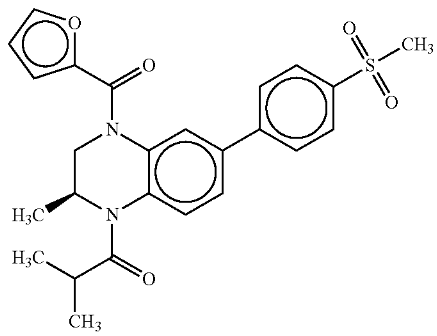 | 467 | 1.35 |
| I-371 | 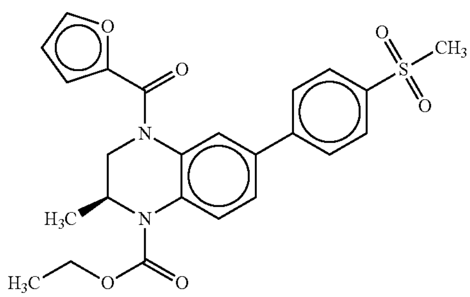 | 469 | 1.46 |
| I-372 | 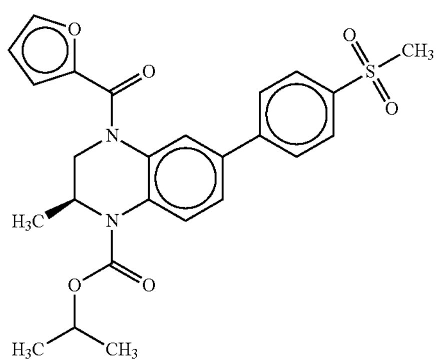 | 483 | 1.57 |
| I-373 | 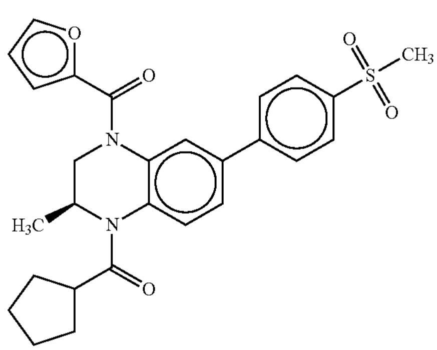 | 493 | 1.49 |

TABLE 3-continued

| Example | Structure | LC-MS [M + 1]+ | HPLC RT (min) |
|---|---|---|---|
| I-374 | 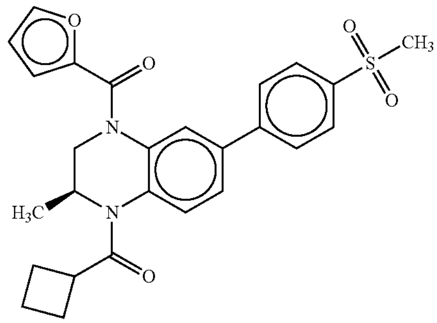 | 479 | 1.4 |
| I-375 | 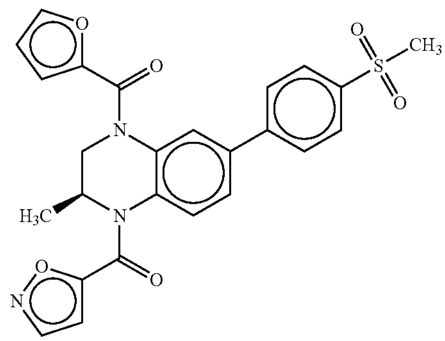 | 492 | 1.23 |
| I-376 | 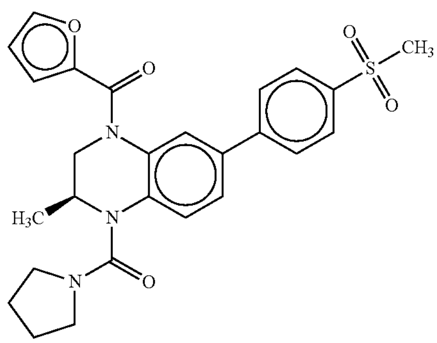 | 494 | 1.25 |
| I-377 | 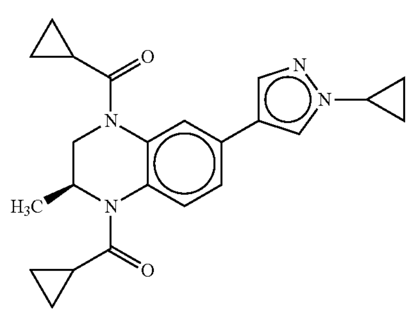 | 391 | 1.32 |

TABLE 3-continued
| Example | Structure | LC-MS [M + 1]+ | HPLC RT (min) |
|---------|-----------|----------------|---------------|
| I-378 | 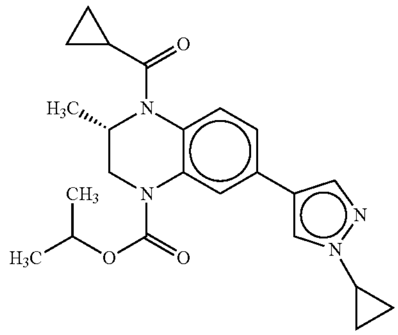 | 409 | 1.52 |
| I-379 | 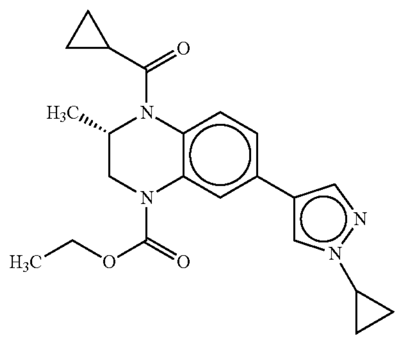 | 395 | 1.43 |
| I-380 | 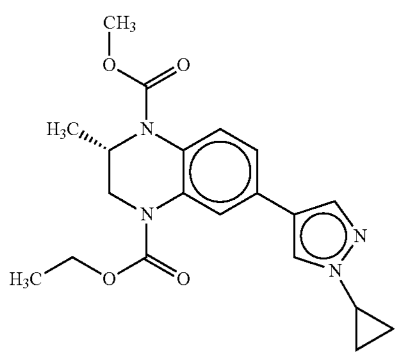 | 385 | 1.44 |
Example 261
Library Protocol D
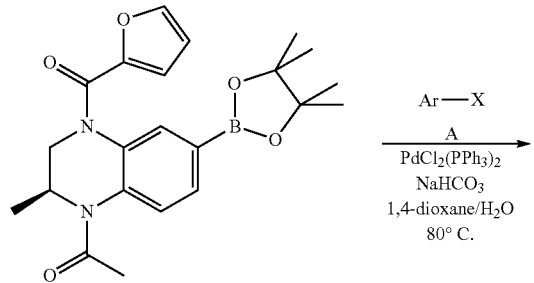
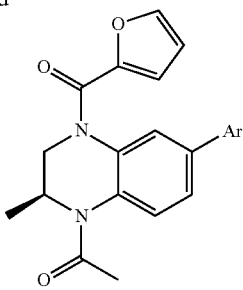
-continued
A 1.5 mL reaction vial was charged with (S)-1-(4-(furan-2-carbonyl)-2-methyl-6-(4,4,5,5-tetramethyl-1,3,2-dioxaborolan-2-yl)-3,4-dihydroquinoxalin-1 (2H)-yl)ethanone (0.2 M solution in 1,4-dioxane, 100 μL, 0.02 mmol) and aryl halide (A) (0.2 M solution in 1,4-dioxane, 120 μL, 0.024 mmol). Sodium bicarbonate (1 M solution in water, 60 μL, 0.06 mmol) was added and the reaction mixture was purged with nitrogen. Bis(triphenylphosphine)palladium(II) dichloride (0.01 M solution in dimethylformamide, 100 μL, 0.002 mmol) was added, and the reaction was purged with nitrogen and heated to 80° C. on a heater shaker overnight. The reaction was diluted with ethyl acetate (0.5 mL) and washed with brine (0.5 mL). The aqueous layer was separated and extracted with ethyl acetate (1 mL) and the organic layers were combined and concentrated under a stream of nitrogen and vacuum. The crude product was purified by mass triggered preparatory HPLC. The product-containing fractions were combined and concentrated in a Genevac to afford the desired product.

The following compounds in Table 5 were synthesized according to the above protocol:

TABLE 5

| Example | Structure | LC-MS [M + 1]+ | HPLC RT (min) |
|---|---|---|---|
| I-381 | 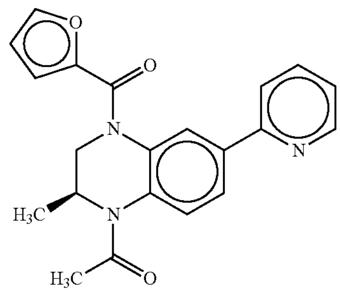 | 362 | 1.13 |
| I-382 | 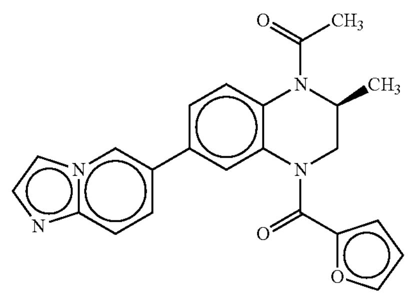 | 401 | 0.72 |
| I-383 | 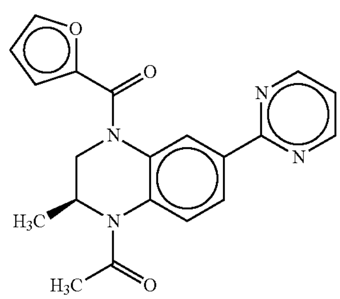 | 363 | 1.11 |
| I-384 | 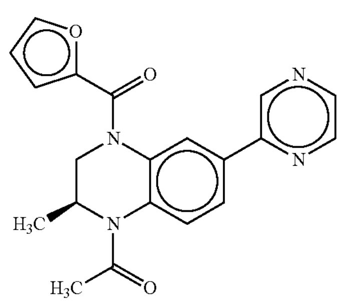 | 363 | 1.03 |

TABLE 5-continued

| Example | Structure | LC-MS [M + 1]+ | HPLC RT (min) |
|---------|-----------|----------------|---------------|
| I-385 | 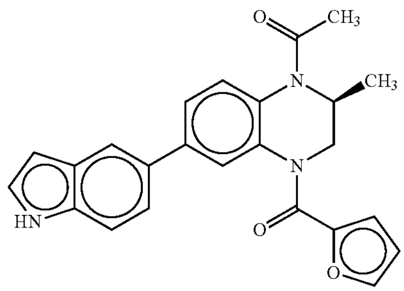 | 400 | 1.31 |
| I-386 | 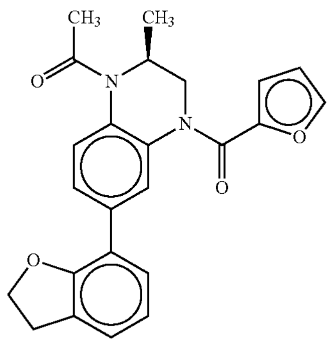 | 403 | 1.46 |
| I-387 | 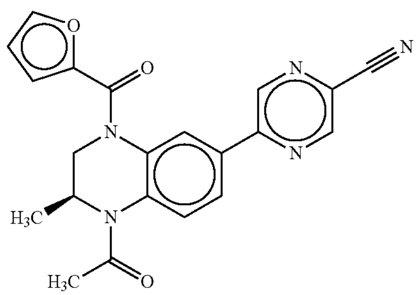 | 405 | 0.7 |
| I-388 | 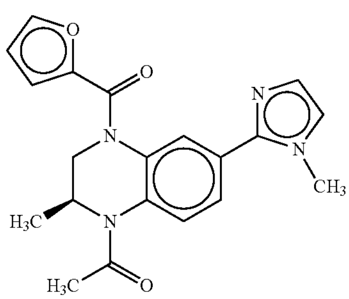 | 365 | 0.62 |
| I-389 | 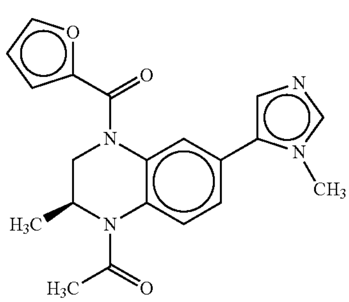 | 365 | 0.63 |

TABLE 5-continued
| Example | Structure | LC-MS [M + 1]+ | HPLC RT (min) |
|---|---|---|---|
| I-390 | 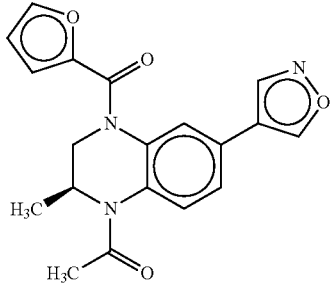 | 352 | 0.97 |
| I-391 | 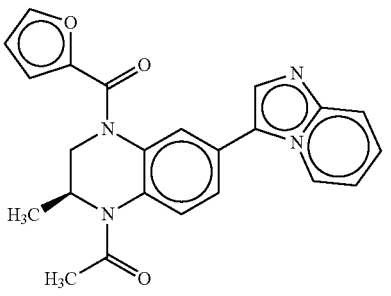 | 401 | 0.73 |
| I-392 | 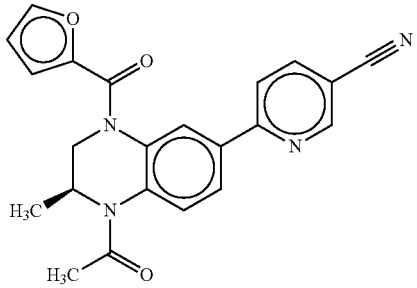 | 387 | 1.24 |
| I-393 | 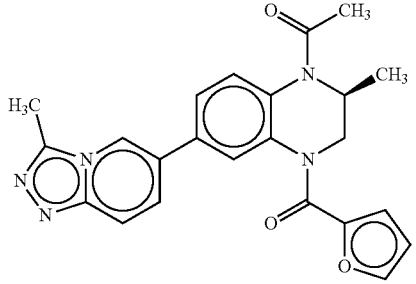 | 416 | 0.85 |
| I-394 | 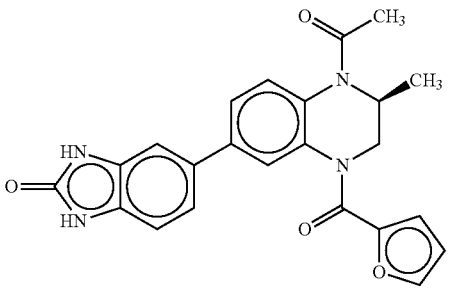 | 417 | 0.9 |

TABLE 5-continued

| Example | Structure | LC-MS [M + 1]+ | HPLC RT (min) |
|---|---|---|---|
| I-395 | 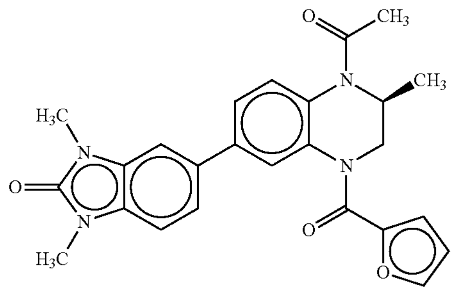 | 445 | 1.15 |
| I-396 | 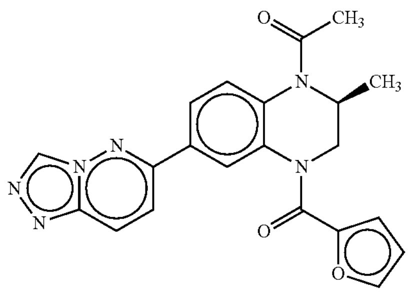 | 403 | 0.86 |
| I-397 | 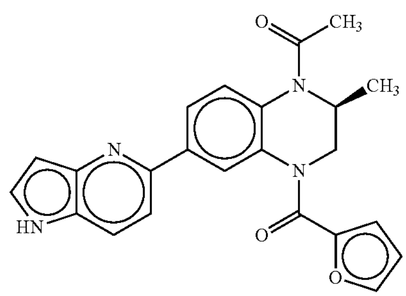 | 401 | 0.78 |
| I-398 | 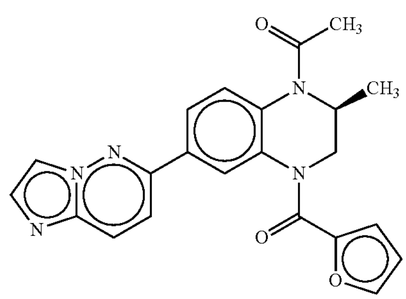 | 402 | 0.92 |
| I-399 | 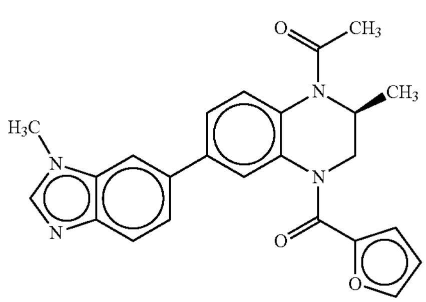 | 415 | 0.85 |

TABLE 5-continued

| Example | Structure | LC-MS [M + 1]+ | HPLC RT (min) |
|---|---|---|---|
| I-400 | 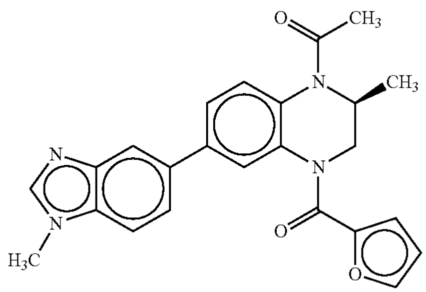 | 415 | 0.87 |
| I-401 | 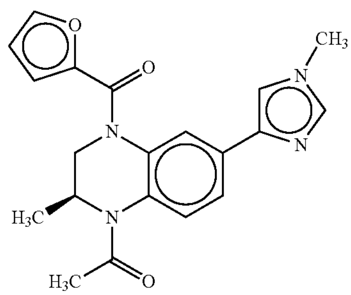 | 365 | 0.66 |
| I-402 | 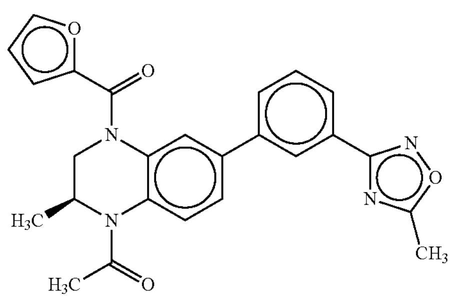 | 443 | 1.42 |
| I-403 | 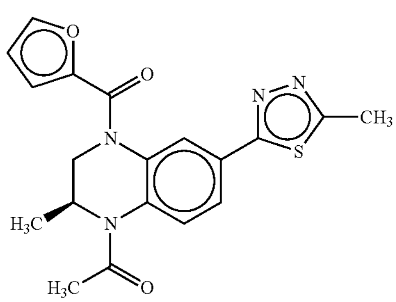 | 383 | 1.03 |
| I-404 | 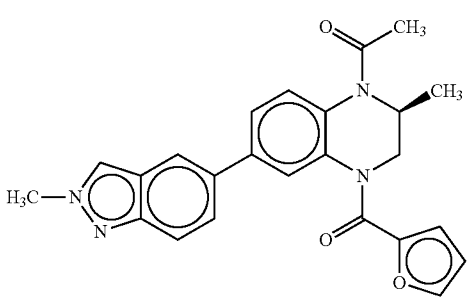 | 415 | 1.13 |

TABLE 5-continued

| Example | Structure | LC-MS [M + 1]+ | HPLC RT (min) |
|---|---|---|---|
| I-405 | 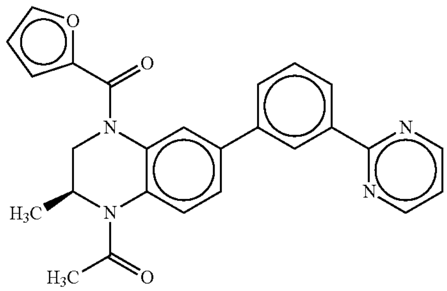 | 439 | 1.4 |
| I-406 | 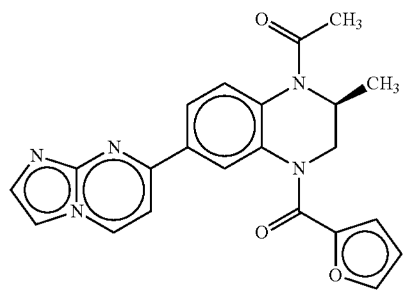 | 402 | 0.76 |
| I-407 | 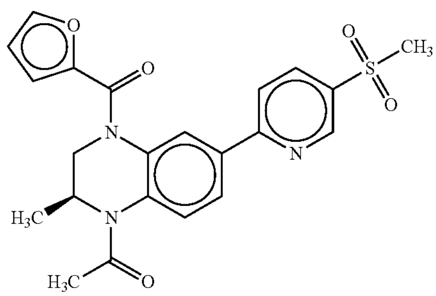 | 440 | 1.05 |
| I-408 | 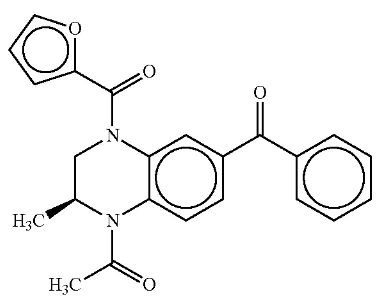 | 389 | 1.33 |
| I-409 | 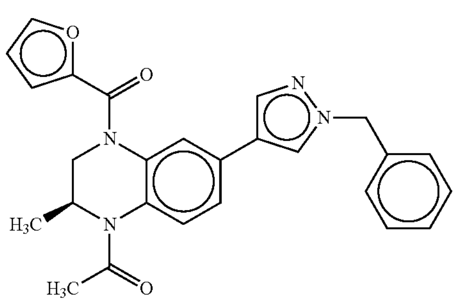 | 441 | 1.33 |

TABLE 5-continued

| Example | Structure | LC-MS [M + 1]+ | HPLC RT (min) |
|---|---|---|---|
| I-410 | 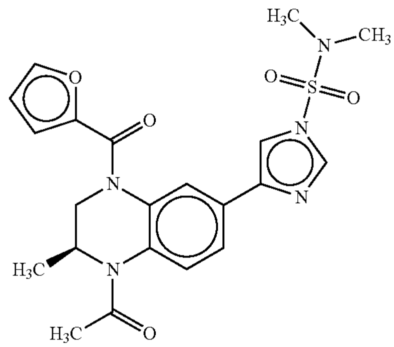 | 458 | 1.2 |
| I-411 | 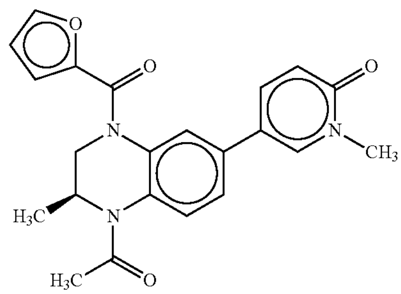 | 392 | 0.86 |
| I-412 | 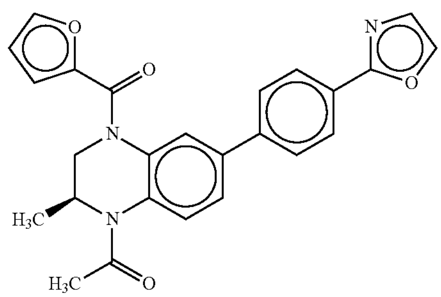 | 428 | 1.35 |
| I-413 | 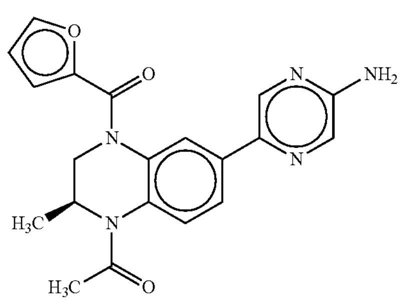 | 378 | 0.87 |
| I-414 | 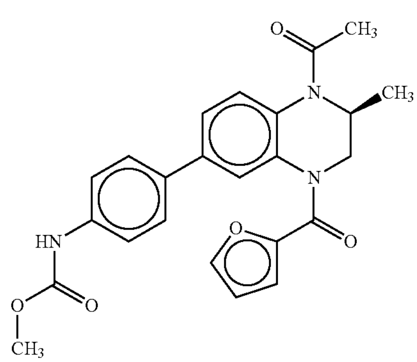 | 434 | 1.25 |

TABLE 5-continued

| Example | Structure | LC-MS [M + 1]+ | HPLC RT (min) |
|---|---|---|---|
| I-415 | 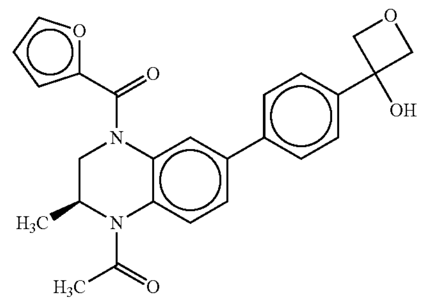 | 433 | 1.05 |
| I-416 | 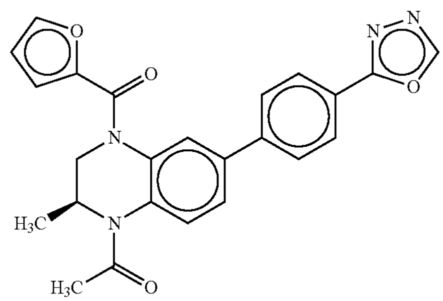 | 429 | 1.17 |
| I-417 | 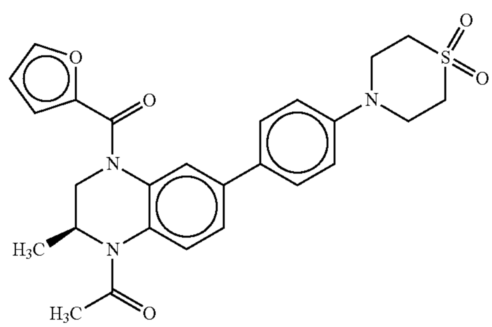 | 494 | 1.18 |
| I-418 | 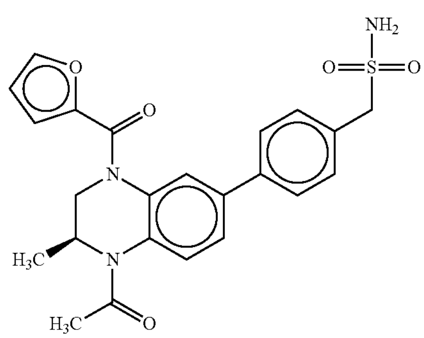 | 454 | 1.02 |
| I-419 | 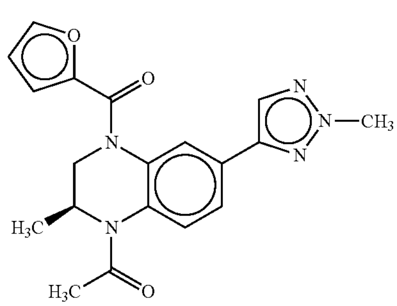 | 366 | 0.9 |

TABLE 5-continued

| Example | Structure | LC-MS [M + 1]+ | HPLC RT (min) |
|---------|-----------|----------------|---------------|
| I-420 | 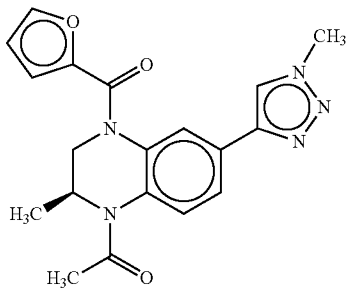 | 366 | 0.89 |
| I-421 | 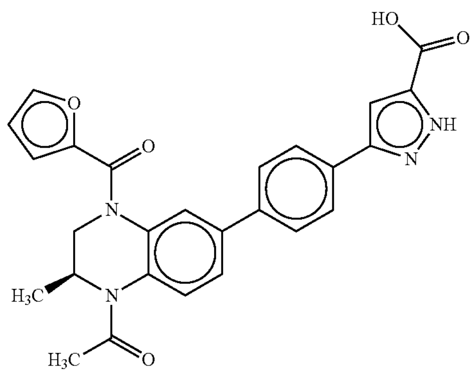 | 471 | 1.03 |
| I-422 | 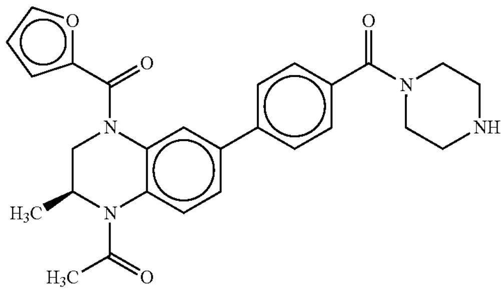 | 473 | 0.77 |
| I-423 | 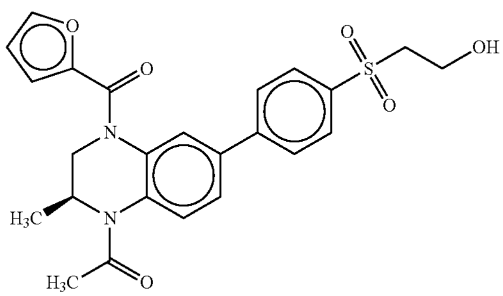 | 469 | 1 |
| I-424 | 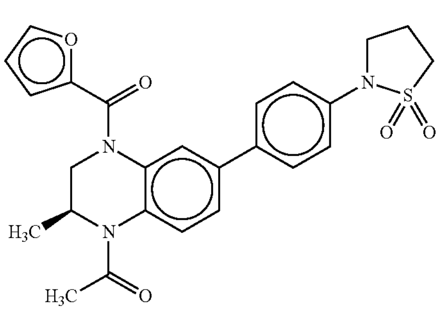 | 480 | 1.2 |

TABLE 5-continued

| Example | Structure | LC-MS [M + 1]+ | HPLC RT (min) |
|---|---|---|---|
| I-425 | 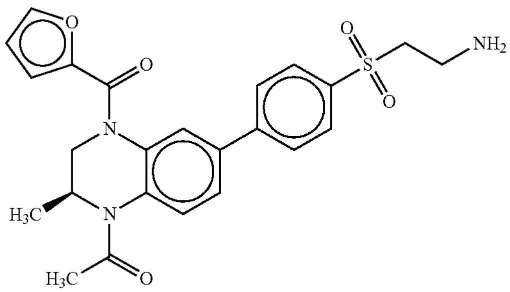 | 468 | 0.83 |
| I-426 | 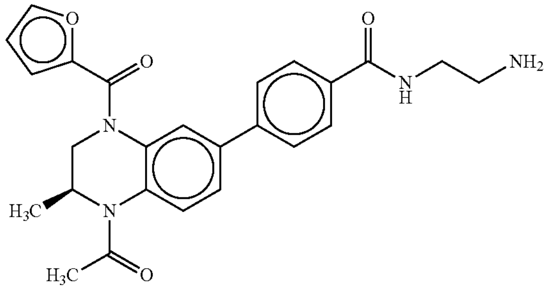 | 447 | 0.78 |
| I-427 | 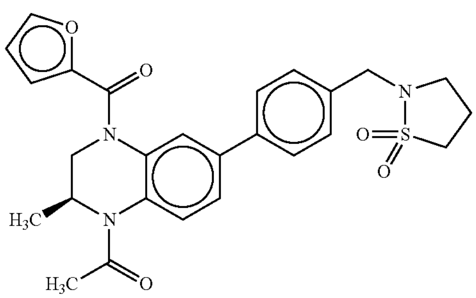 | 494 | 1.24 |
| I-428 | 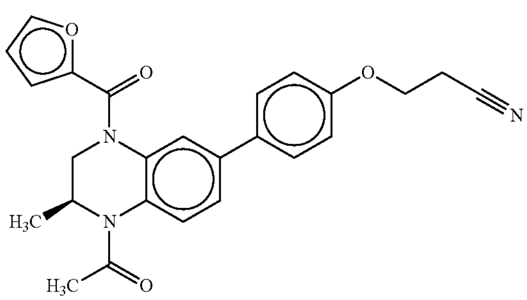 | 430 | 1.31 |
| I-429 | 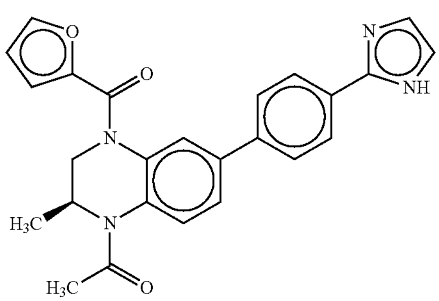 | 427 | 0.81 |

Example 262

Library Protocol D1

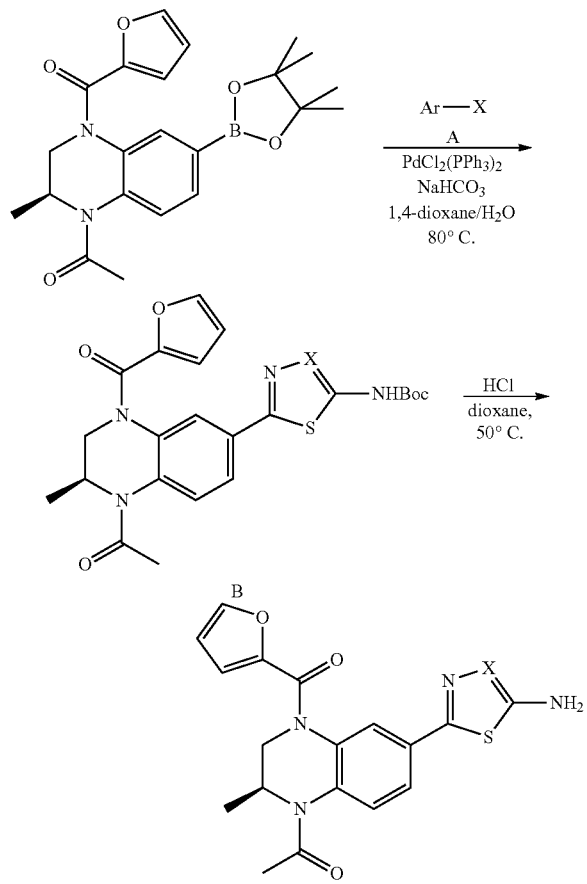

A 1.5 mL reaction vial was charged with (S)-1-(4-(furan-2-carbonyl)-2-methyl-6-(4,4,5,5-tetramethyl-1,3,2-dioxaborolan-2-yl)-3,4-dihydroquinoxalin-1 (2H)-yl)ethanone (0.2 M solution in 1,4-dioxane, 100 µL, 0.02 mmol) and aryl halide (A) (0.2 M solution in 1,4-dioxane, 120 µL, 0.024 mmol). Sodium bicarbonate (1 M solution in water, 60 µL, 0.06 mmol) was added and the reaction mixture was purged with nitrogen. Bis(triphenylphosphine)palladium(II) dichloride (0.01 M solution in dimethylformamide, 100 µL, 0.002 mmol) was then added, and the reaction was purged with nitrogen and heated to 80° C. on a heater shaker overnight. The reaction was diluted with ethyl acetate (0.5 mL) and washed with brine (0.5 mL). The aqueous layer was separated and extracted with ethyl acetate (1 mL), and the organic layers were combined and concentrated under a stream of nitrogen and vacuum. The crude product (B) was dissolved in dioxane (0.3 mL), HCl (4.0 M in 1,4-dioxane, 0.15 mL, 0.6 mmol) was added, and the mixture stirred at 50° C. for 2 h. The reaction was concentrated, and diluted with ethyl acetate (0.5 mL) and saturated aqueous sodium bicarbonate solution (0.5 mL). The aqueous layer was separated and extracted with ethyl acetate (1 mL), and the organic layers were combined and concentrated under a stream of nitrogen and vacuum. The crude product was purified by mass triggered preparatory HPLC. The product-containing fractions were combined and concentrated in a Genevac to afford the desired product.

The following compounds in Table 6 were synthesized according to the above protocol:

TABLE 6

| Example | Structure | LC-MS [M+1]+ | HPLC RT (min) |
|---|---|---|---|
| I-430 | ![structure] | 384 | 0.83 |
| I-431 | ![structure] | 383 | 1.00 |

Example 263

Library Protocol E

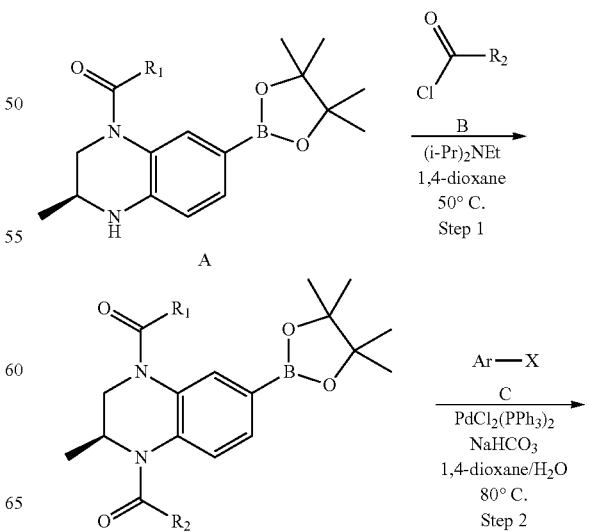

-continued

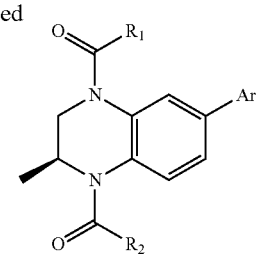

Step 1. A 1.5 mL reaction vial was charged with piperazine (A) (0.4 M solution in 1,4-dioxane, 75 μL, 0.03 mmol), N,N-diisopropylethylamine (25 μL, 0.143 mmol), and an acid chloride or chloroformate (B) (2 M solution in 1,4-dioxane, 120 μL, 0.24 mmol). The reaction mixture was heated to 50° C. for 2 h on a heater shaker. The reaction was quenched with 50 μL of methanol and the reaction mixture was heated to 50° C. for 1 h on a heater shaker. The reaction was then diluted with ethyl acetate (0.5 mL) and washed with brine (0.5 mL). The aqueous layer was separated and extracted with ethyl acetate (1 mL) and the organic layers were combined and concentrated under a stream of nitrogen. The crude product was carried through to the next reaction without purification.

Step 2. To the residue from the previous reaction was added 150 μL of 1,4-dioxane, aryl halide (C) (0.2M solution in 1,4-dioxane, 100 μL, 0.02 mmol), and sodium bicarbonate (1 M solution in water, 60 μL, 0.06 mmol). The reaction mixture was purged with nitrogen. Bis(triphenylphosphine)palladium (II) dichloride (0.01 M solution in dimethylformamide, 50 μL, 0.001 mmol) was added, the reaction was purged with nitrogen and heated to 80° C. on a heater shaker overnight. The reaction was diluted with ethyl acetate (0.5 mL) and washed with brine (0.5 mL). The aqueous layer was separated and extracted with ethyl acetate (1 mL) and the organic layers were combined and concentrated under a stream of nitrogen and vacuum. The crude product was purified by mass triggered preparatory HPLC. The product-containing fractions were combined and concentrated in a Genevac to afford the desired product.

The following compounds in Table 7 were synthesized according to the above protocol:

TABLE 7

| Example | Structure | LC-MS [M + 1]+ | HPLC RT (min) |
|---------|-----------|----------------|---------------|
| I-432 | 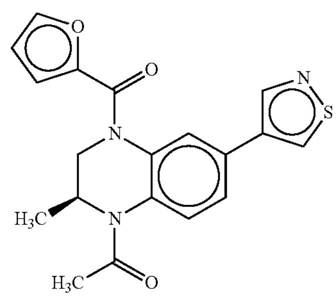 | 368 | 1.16 |
| I-433 | 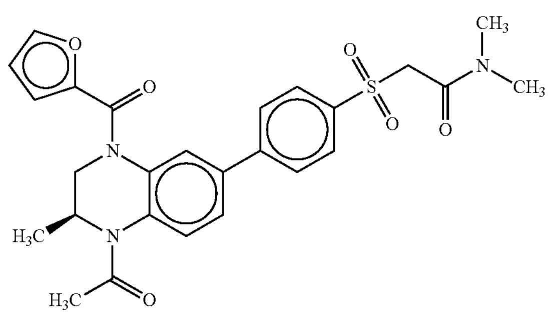 | 510 | 1.07 |
| I-434 | 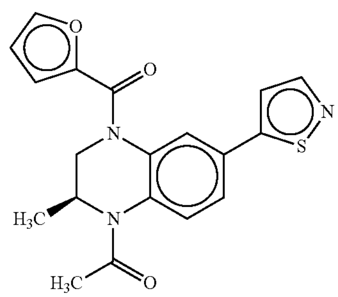 | 368 | 1.19 |

TABLE 7-continued
| Example | Structure | LC-MS [M + 1]+ | HPLC RT (min) |
|---|---|---|---|
| I-435 | 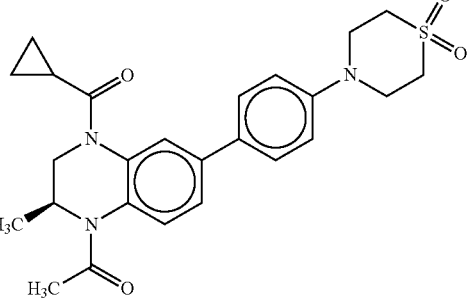 | 468 | 1.19 |
| I-436 | 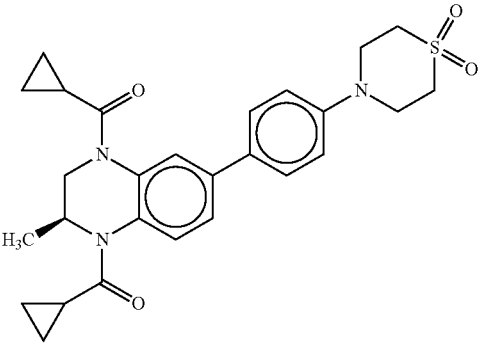 | 494 | 1.34 |
| I-437 | 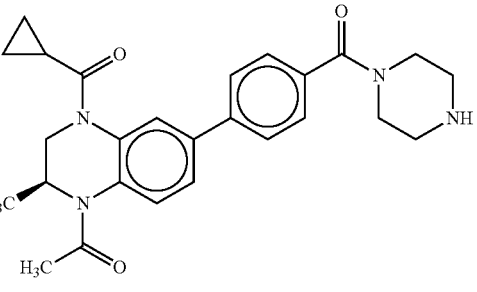 | 447 | 0.74 |
| I-438 | 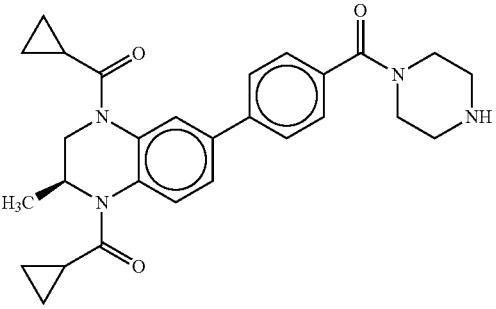 | 473 | 0.88 |

TABLE 7-continued

| Example | Structure | LC-MS [M + 1]+ | HPLC RT (min) |
|---|---|---|---|
| I-439 | 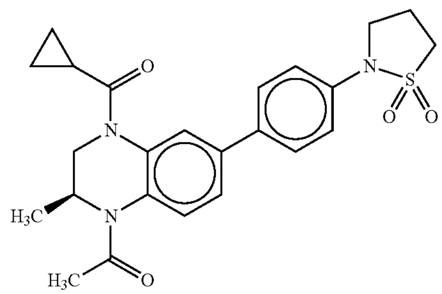 | 454 | 1.21 |
| I-440 | 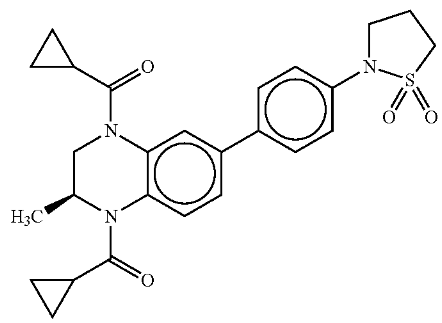 | 480 | 1.37 |
| I-441 | 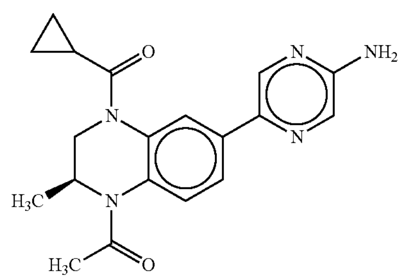 | 352 | 0.87 |
| I-442 | 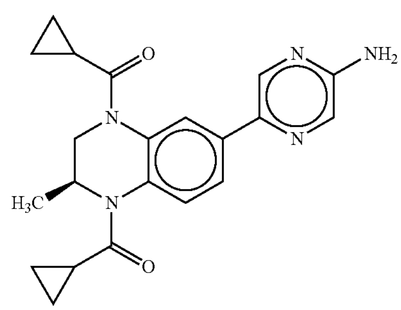 | 378 | 1.06 |
| I-443 | 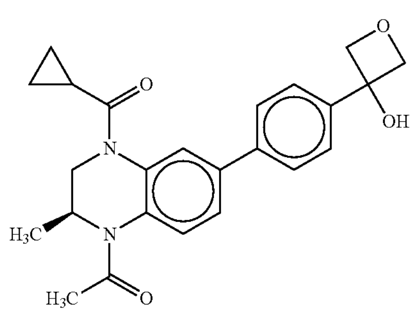 | 407 | 1.04 |

TABLE 7-continued

| Example | Structure | LC-MS [M + 1]+ | HPLC RT (min) |
|---|---|---|---|
| I-444 | 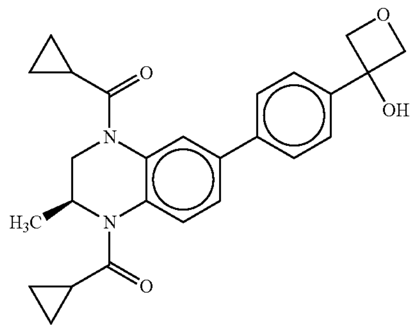 | 433 | 1.23 |
| I-445 | 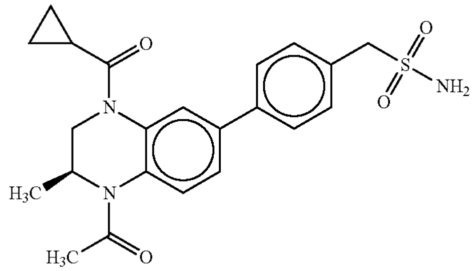 | 428 | 1.01 |
| I-446 | 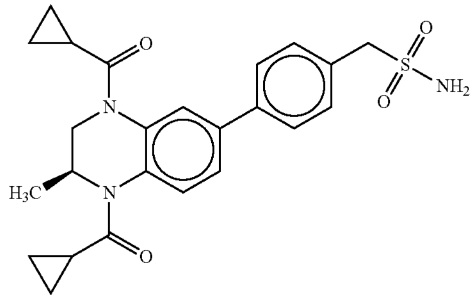 | 454 | 1.2 |
| I-447 | 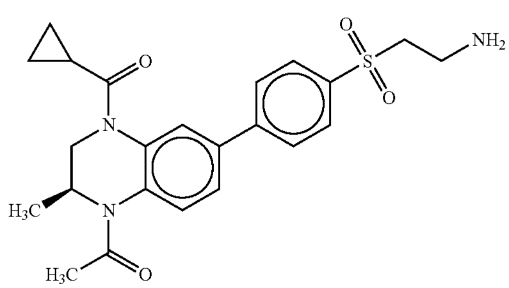 | 442 | 0.82 |
| I-448 | 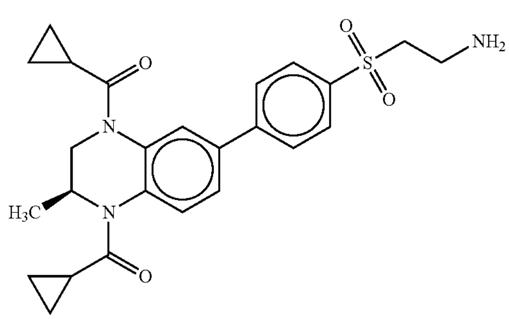 | 468 | 0.96 |

TABLE 7-continued

| Example | Structure | LC-MS [M + 1]+ | HPLC RT (min) |
|---|---|---|---|
| I-449 | 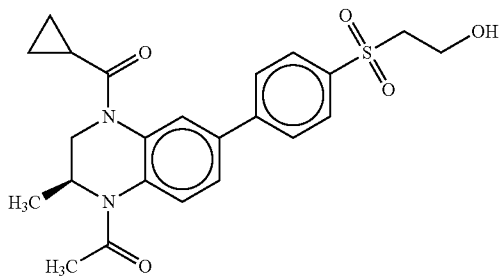 | 443 | 0.99 |
| I-450 | 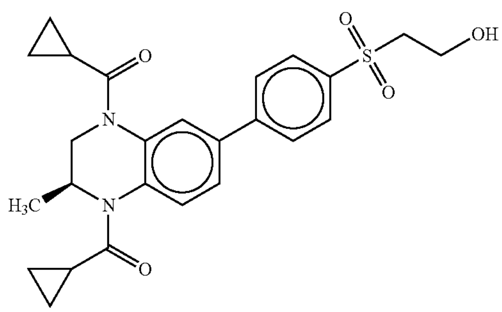 | 469 | 1.17 |
| I-451 | 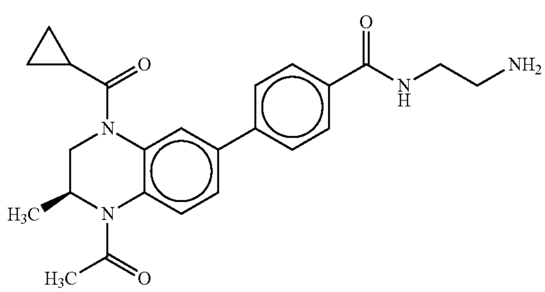 | 421 | 0.75 |
| I-452 | 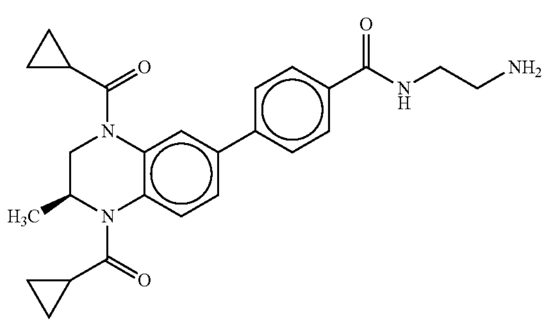 | 447 | 0.9 |
| I-453 | 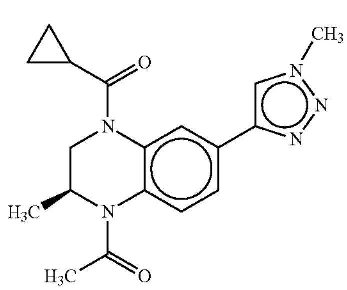 | 340 | 0.89 |

TABLE 7-continued

| Example | Structure | LC-MS [M + 1]+ | HPLC RT (min) |
|---|---|---|---|
| I-454 | 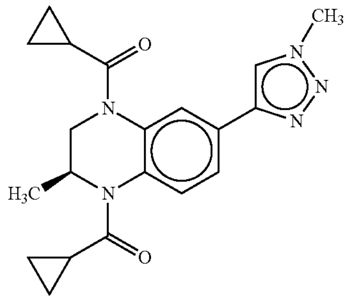 | 366 | 1.07 |
| I-455 | 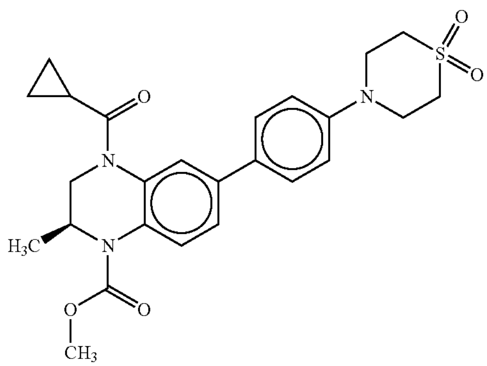 | 484 | 1.37 |
| I-456 | 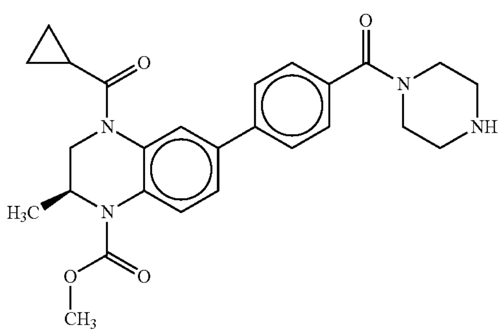 | 463 | 0.89 |
| I-457 | 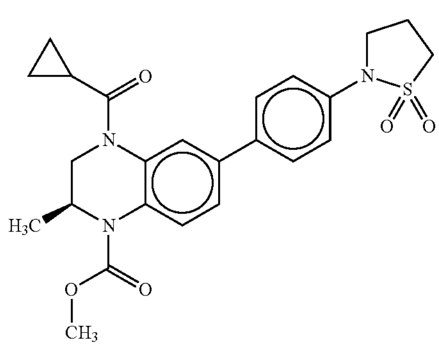 | 470 | 1.4 |

TABLE 7-continued
| Example | Structure | LC-MS [M + 1]+ | HPLC RT (min) |
|---|---|---|---|
| I-458 | 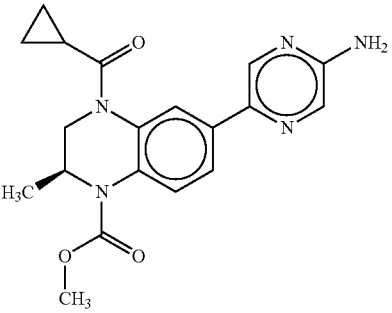 | 368 | 1.06 |
| I-459 | 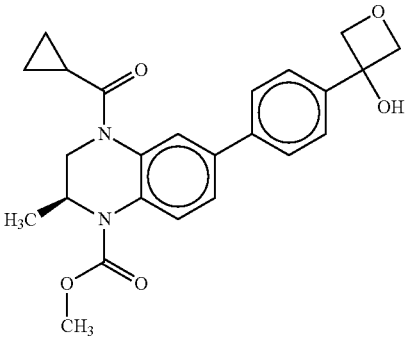 | 423 | 1.25 |
| I-460 | 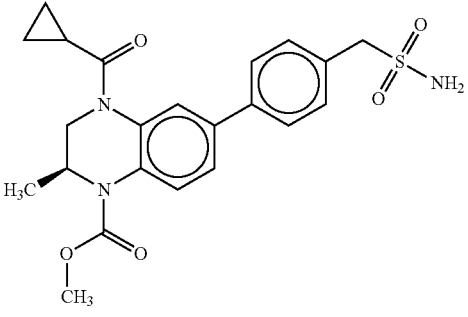 | 444 | 1.23 |
| I-461 | 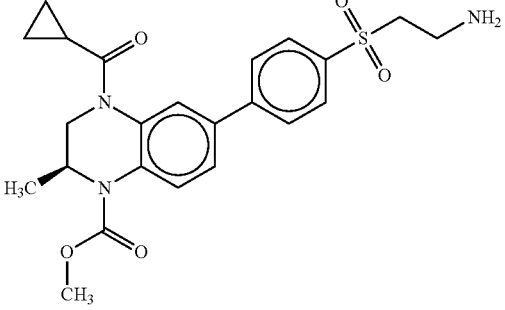 | 458 | 0.98 |

TABLE 7-continued

| Example | Structure | LC-MS [M + 1]+ | HPLC RT (min) |
|---------|-----------|----------------|---------------|
| I-462 | 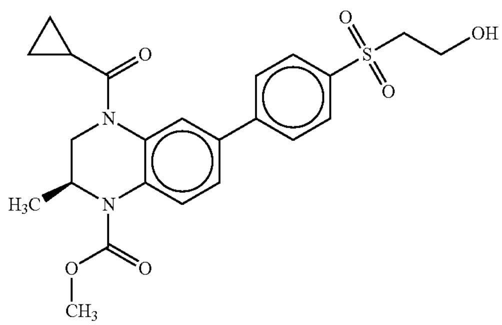 | 459 | 1.2 |
| I-463 | 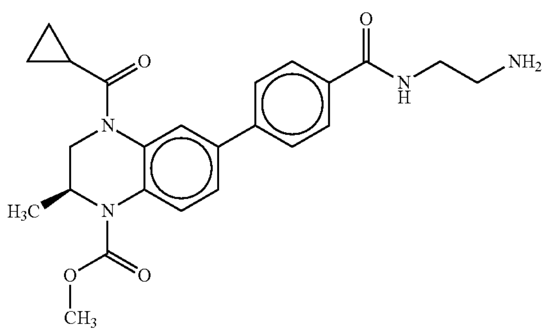 | 437 | 0.93 |
| I-464 | 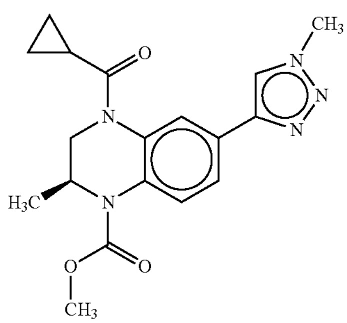 | 356 | 1.08 |
| I-465 | 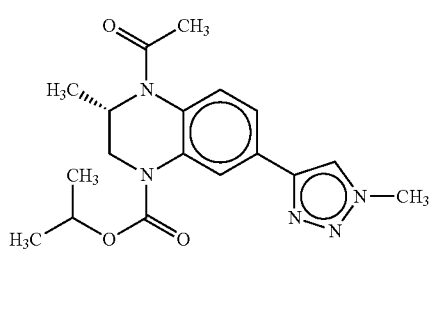 | 358 | 1.12 |

TABLE 7-continued

| Example | Structure | LC-MS [M + 1]+ | HPLC RT (min) |
|---------|-----------|----------------|---------------|
| I-466 | 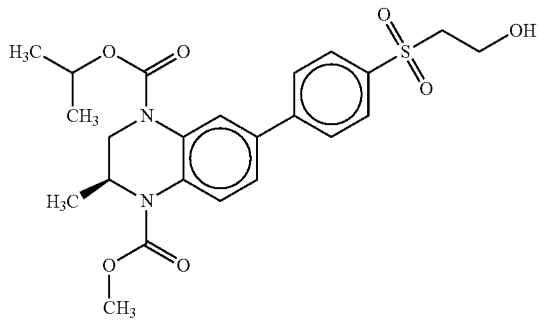 | 494 | 1.41 |
| I-467 | 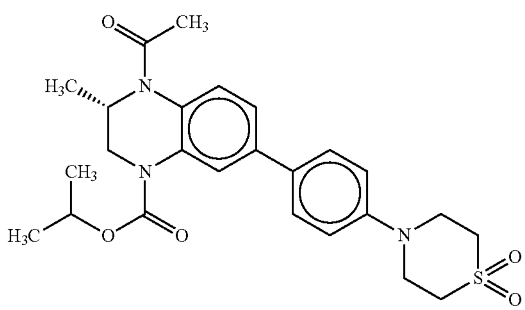 | 486 | 1.37 |
| I-468 | 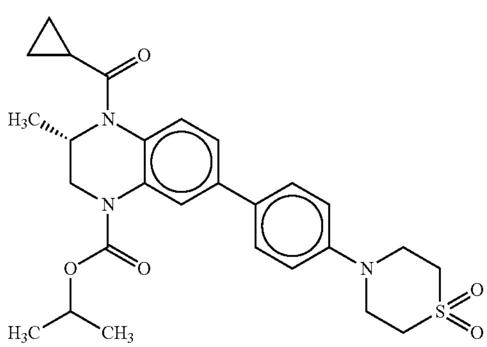 | 512 | 1.54 |
| I-469 | 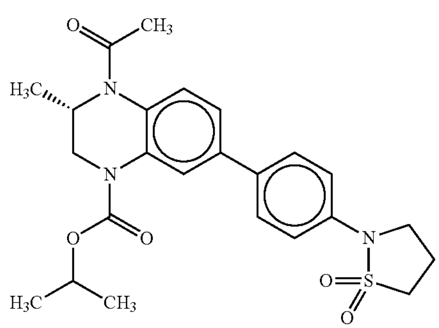 | 472 | 1.36 |

TABLE 7-continued

| Example | Structure | LC-MS [M + 1]+ | HPLC RT (min) |
|---|---|---|---|
| I-470 | 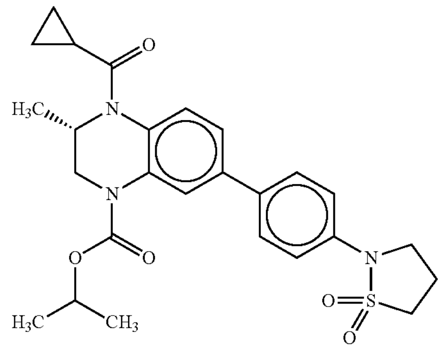 | 498 | 1.57 |
| I-471 | 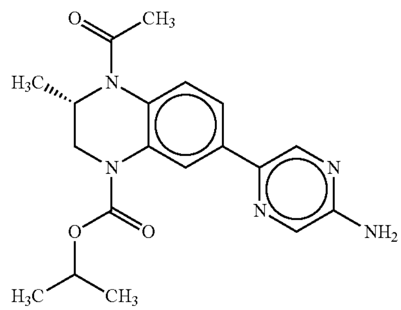 | 370 | 1.09 |
| I-472 | 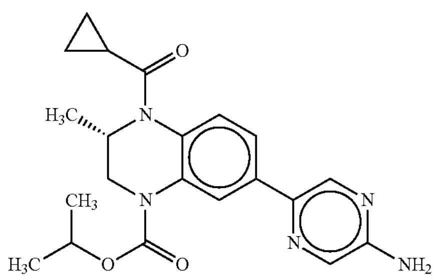 | 396 | 1.26 |
| I-473 | 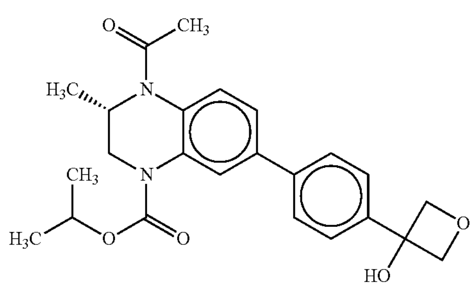 | 425 | 1.25 |
| I-474 | 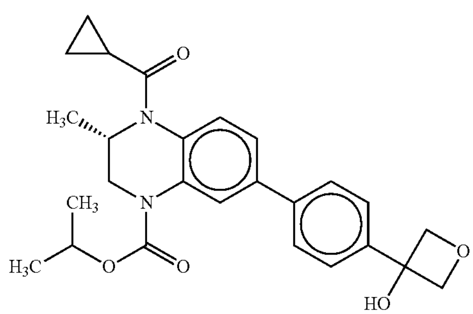 | 451 | 1.43 |

TABLE 7-continued

| Example | Structure | LC-MS [M + 1]+ | HPLC RT (min) |
|---|---|---|---|
| I-475 | 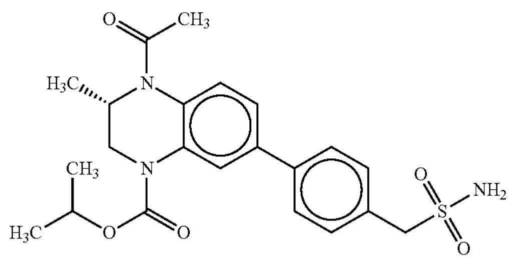 | 446 | 1.22 |
| I-476 | 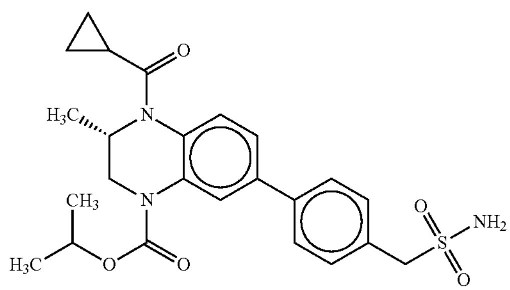 | 472 | 1.38 |
| I-477 | 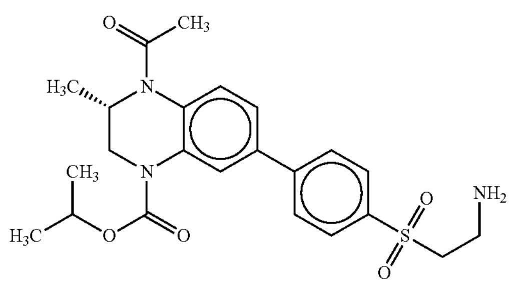 | 460 | 0.99 |
| I-478 | 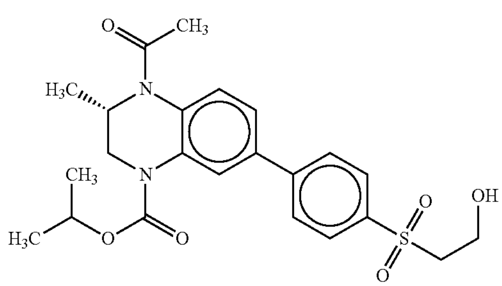 | 461 | 1.21 |
| I-479 | 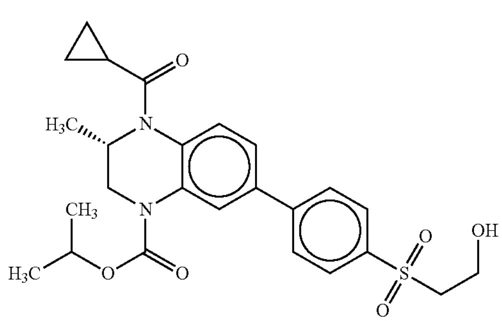 | 487 | 1.38 |

TABLE 7-continued

| Example | Structure | LC-MS [M + 1]+ | HPLC RT (min) |
|---|---|---|---|
| I-480 | 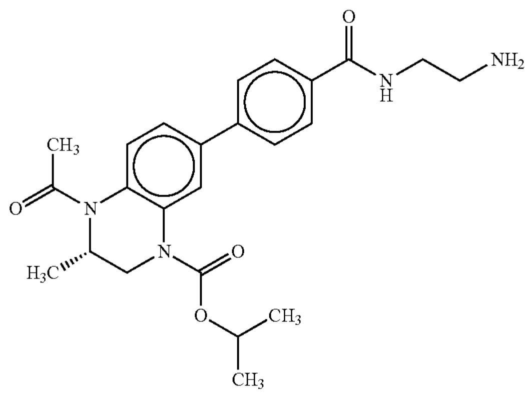 | 439 | 0.92 |
| I-481 | 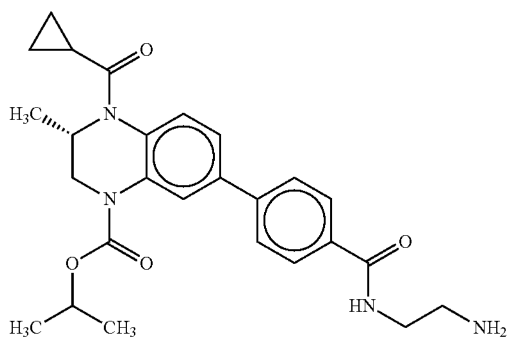 | 465 | 1.07 |
| I-482 | 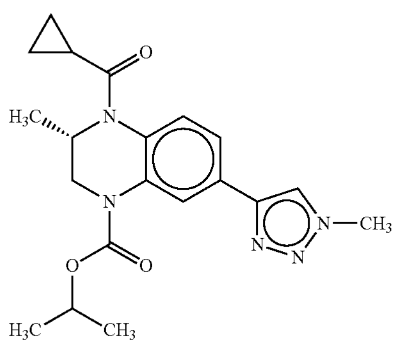 | 384 | 1.29 |
| I-483 | 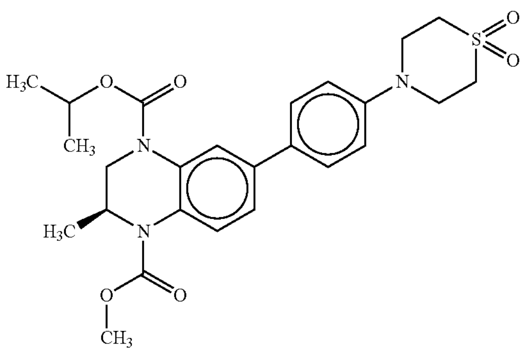 | 502 | 1.58 |

TABLE 7-continued

| Example | Structure | LC-MS [M + 1]+ | HPLC RT (min) |
|---------|-----------|----------------|---------------|
| I-484 | 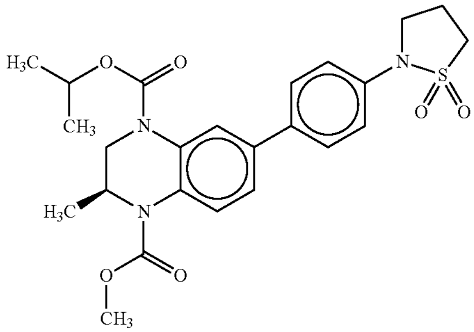 | 505 | 1.6 |
| I-485 | 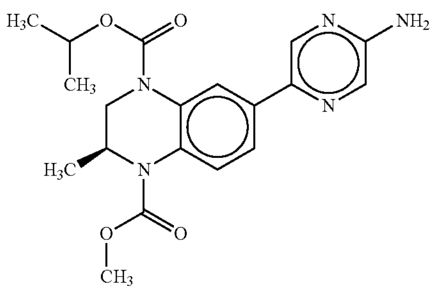 | 386 | 1.3 |
| I-486 | 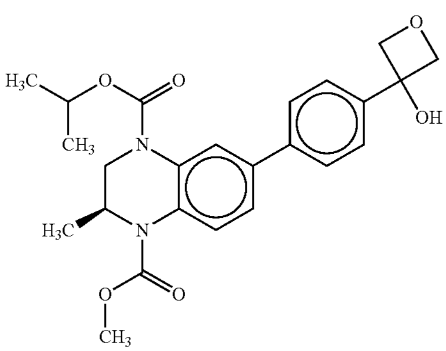 | 458 | 1.46 |
| I-487 | 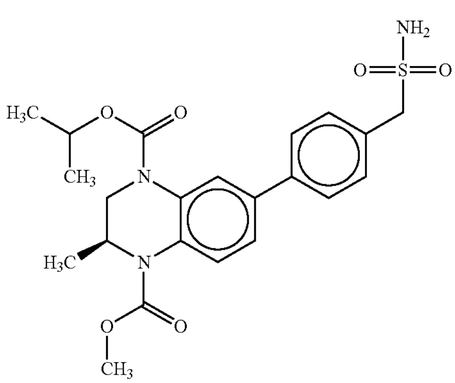 | 479 | 1.42 |

TABLE 7-continued

| Example | Structure | LC-MS [M + 1]+ | HPLC RT (min) |
|---------|-----------|----------------|---------------|
| I-488 | 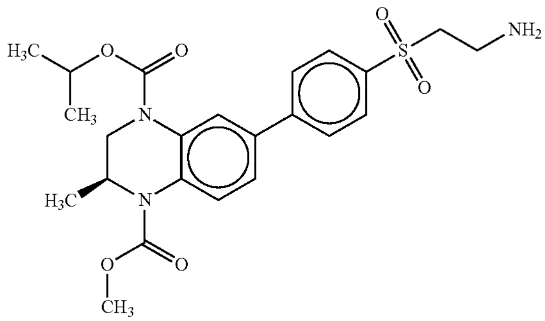 | 476 | 1.17 |
| I-489 | 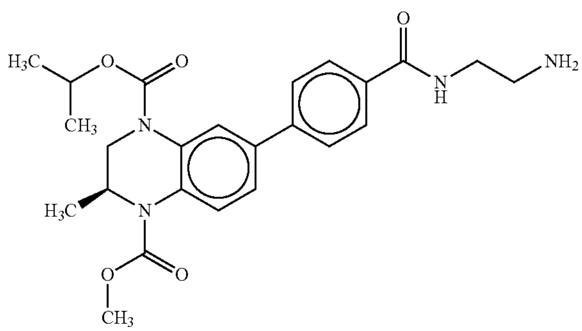 | 455 | 1.11 |
| I-490 | 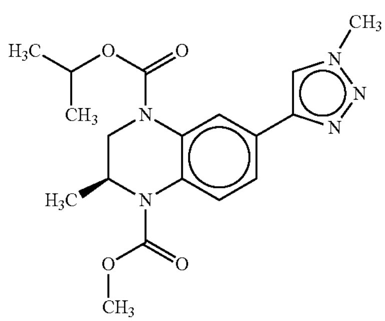 | 374 | 1.31 |
| I-491 | 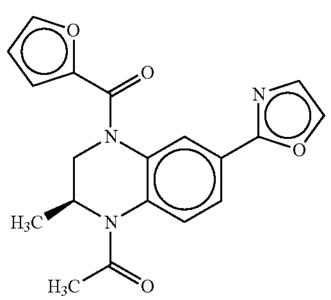 | 352 | 1.06 |

TABLE 7-continued

| Example | Structure | LC-MS [M + 1]+ | HPLC RT (min) |
|---|---|---|---|
| I-492 | 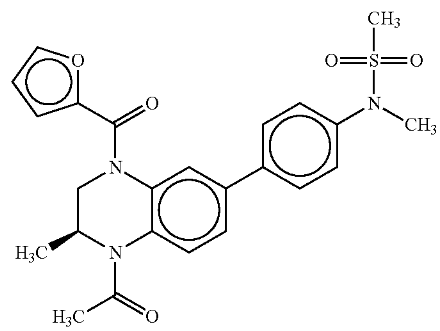 | 468 | 1.22 |

Example 264

Library Protocol F

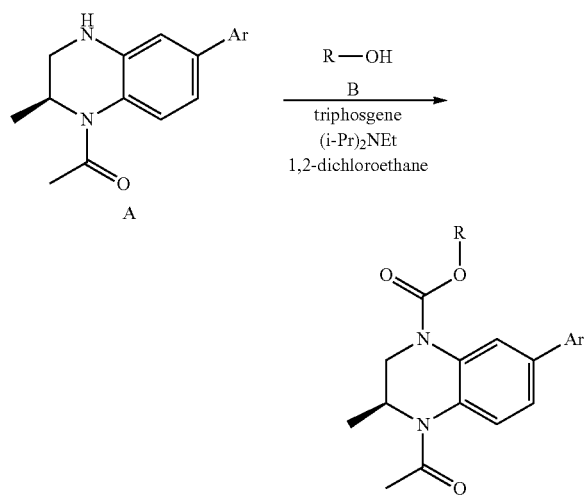

A 1.5 mL reaction vial was charged with (S)-1-(6-aryl-2-methyl-3,4-dihydroquinoxalin-1(2H)-yl)ethan-1-one (A) (0.2 M solution in 3:1:1, 1,2-dichloroethane:N,N-dimethylacetamide:N,N-diisopropylethyl amine, 100 μl, 20 μmol) and triphosgene (0.4 M solution in 1,2-dichloroethane, 20 μL, 8.00 μmol). The reaction mixture was stirred at room temperature for 1 h. The alcohol (B) (0.1 M solution in 1,2-dichloroethane, 110 μL, 22 μmol) was added, and the reaction mixture was heated at 50° C. for 2 h. Methanol (100 μL) was added and the mixture stirred at 50° C. for 15 min. The reaction was diluted with ethyl acetate and washed with saturated aqueous sodium bicarbonate solution. The aqueous layer was separated and extracted with ethyl acetate and the combined organic layers were concentrated under a stream of nitrogen and vacuum. The crude product was purified by mass triggered preparatory HPLC. The product-containing fractions were combined and concentrated in a Genevac to afford the desired product.

The following compounds in Table 8 were synthesized according to the above protocol:

TABLE 8

| Example | Structure | LC-MS [M + 1]+ | HPLC RT (min) |
|---|---|---|---|
| I-493 | 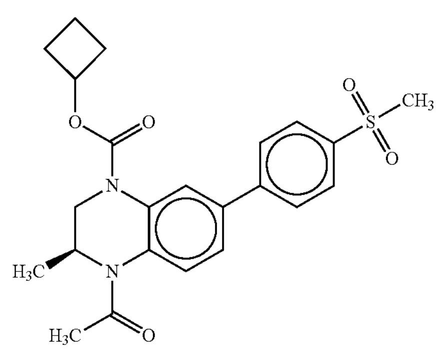 | 443 | 1.42 |

TABLE 8-continued
| Example | Structure | LC-MS [M + 1]+ | HPLC RT (min) |
|---|---|---|---|
| I-494 | 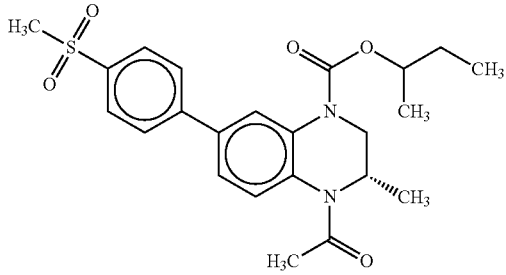 | 445 | 1.46 |
| I-495 | 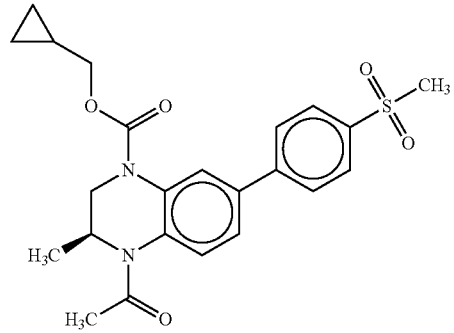 | 443 | 1.39 |
| I-496 | 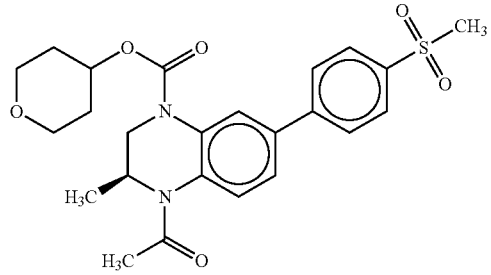 | 473 | 1.22 |
| I-497 | 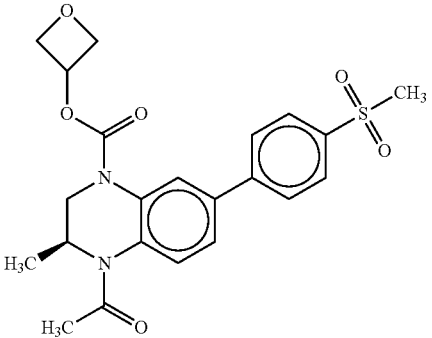 | 445 | 1.13 |

TABLE 8-continued

| Example | Structure | LC-MS [M + 1]+ | HPLC RT (min) |
|---------|-----------|----------------|---------------|
| I-498 | 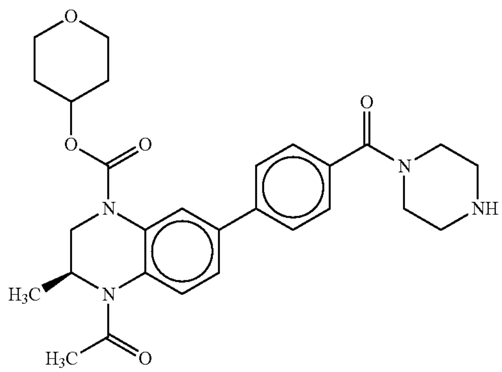 | 507 | 0.82 |
| I-499 | 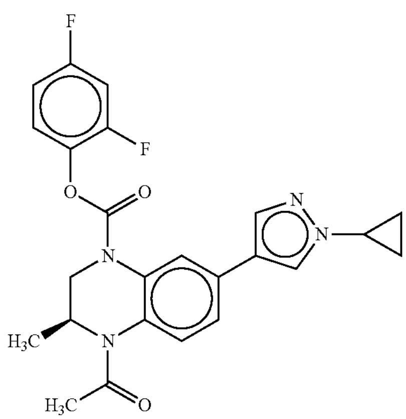 | 453 | 1.44 |
| I-500 | 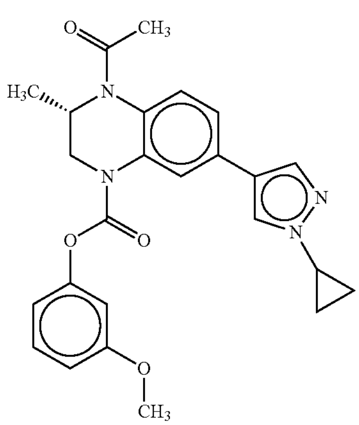 | 447 | 1.41 |

TABLE 8-continued

| Example | Structure | LC-MS [M + 1]+ | HPLC RT (min) |
|---|---|---|---|
| I-501 | 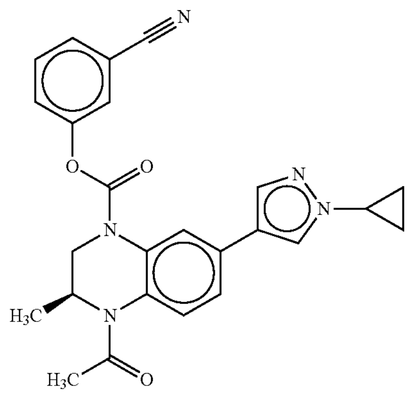 | 442 | 1.33 |
| I-502 | 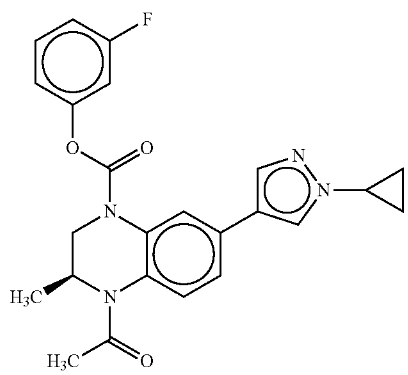 | 435 | 1.43 |
| I-503 | 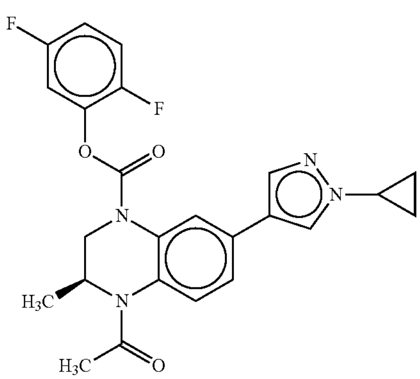 | 453 | 1.44 |
| I-504 | 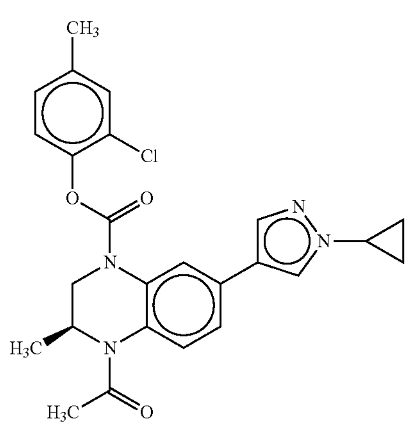 | 465 | 1.58 |

TABLE 8-continued

| Example | Structure | LC-MS [M + 1]+ | HPLC RT (min) |
|---------|-----------|----------------|---------------|
| I-505 | 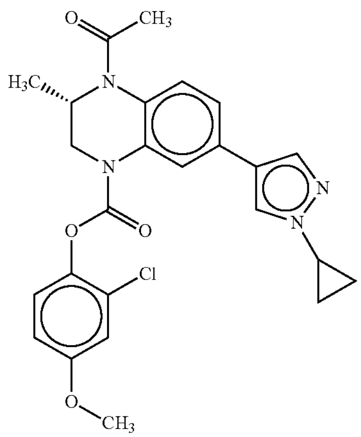 | 481 | 1.49 |
| I-506 | 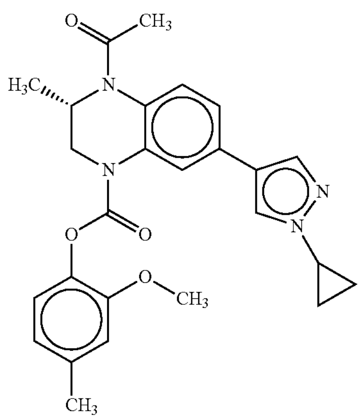 | 461 | 1.47 |
| I-507 | 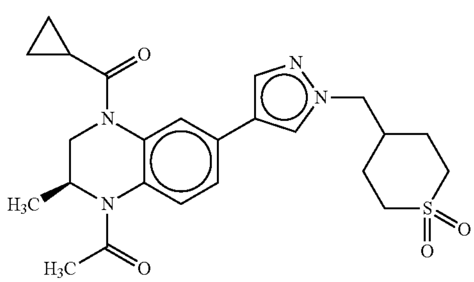 | 472 | 1.35 |
| I-508 | 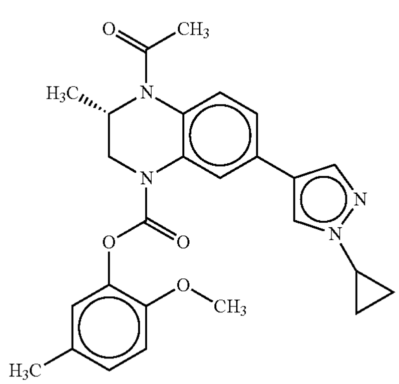 | 461 | 1.47 |

TABLE 8-continued

| Example | Structure | LC-MS [M + 1]+ | HPLC RT (min) |
|---|---|---|---|
| I-509 | 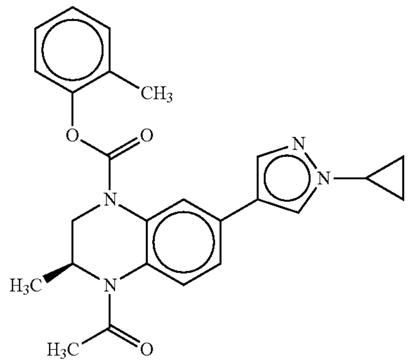 | 431 | 1.47 |
| I-510 | 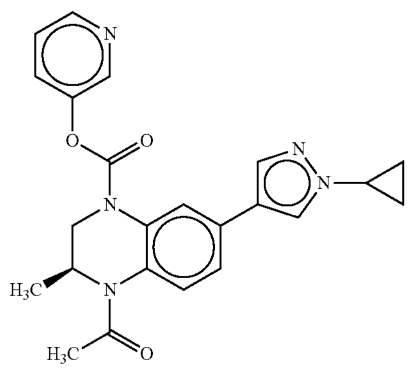 | 418 | 1.1 |
| I-511 | 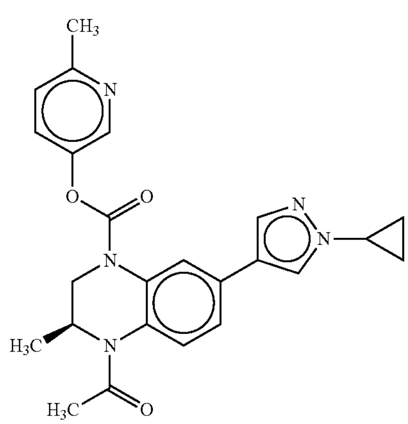 | 432 | 1.13 |

TABLE 8-continued
| Example | Structure | LC-MS [M + 1]+ | HPLC RT (min) |
|---|---|---|---|
| I-512 | 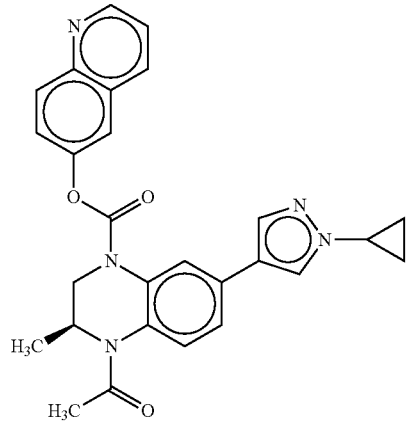 | 468 | 1.19 |
| I-513 | 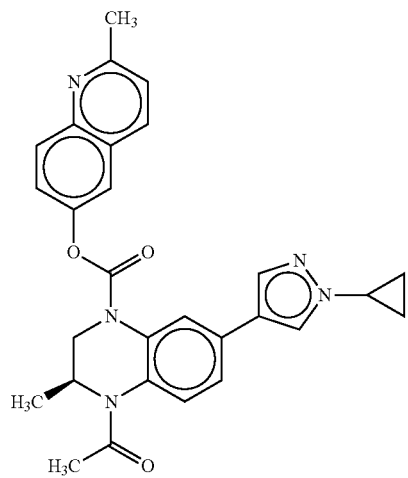 | 482 | 1.12 |
| I-514 | 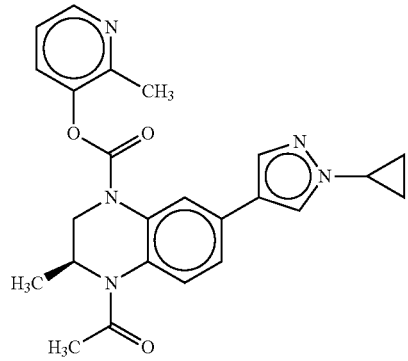 | 432 | 1.1 |

TABLE 8-continued

| Example | Structure | LC-MS [M + 1]+ | HPLC RT (min) |
|---------|-----------|----------------|---------------|
| I-515 | 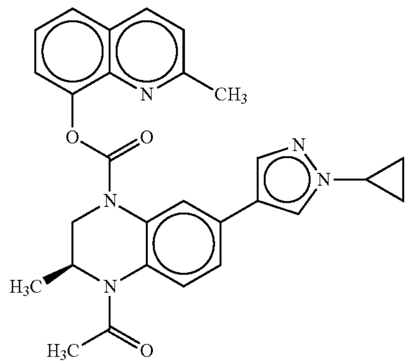 | 482 | 1.41 |
| I-516 | 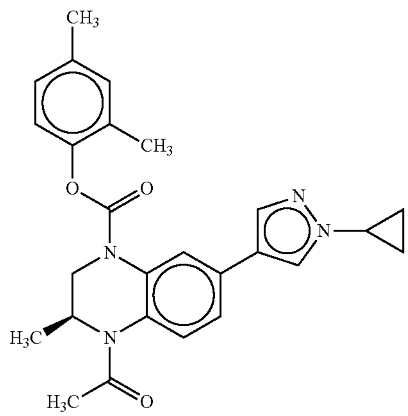 | 445 | 1.57 |
| I-517 | 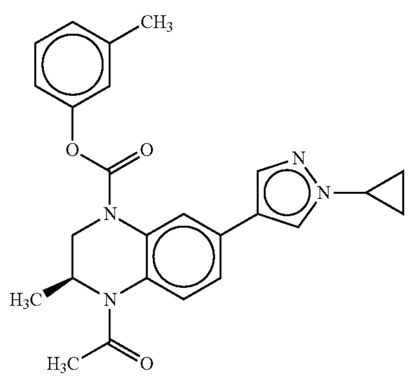 | 431 | 1.49 |
| I-518 | 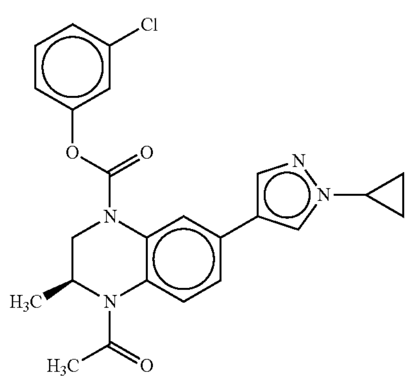 | 451 | 1.54 |

TABLE 8-continued

| Example | Structure | LC-MS [M + 1]+ | HPLC RT (min) |
|---------|-----------|----------------|---------------|
| I-519 | 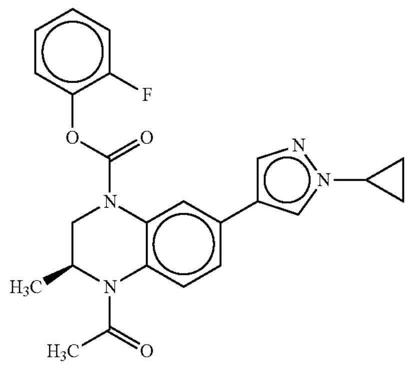 | 435 | 1.41 |
| I-520 | 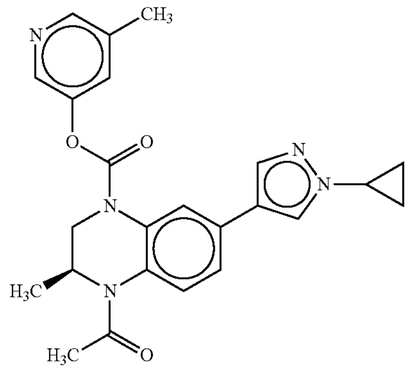 | 432 | 1.17 |
| I-521 | 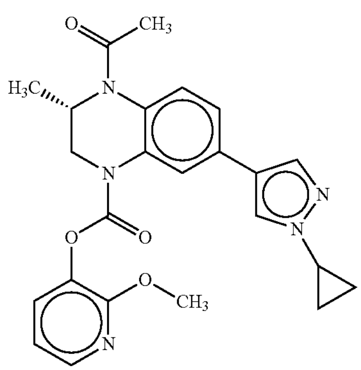 | 448 | 1.27 |
| I-522 | 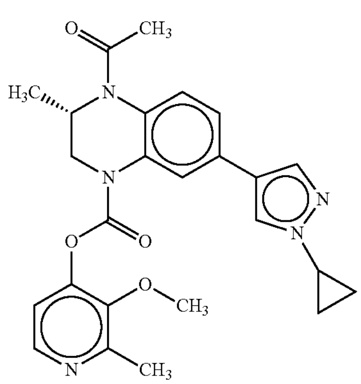 | 462 | 1.1 |

TABLE 8-continued

| Example | Structure | LC-MS [M + 1]+ | HPLC RT (min) |
|---|---|---|---|
| I-523 | 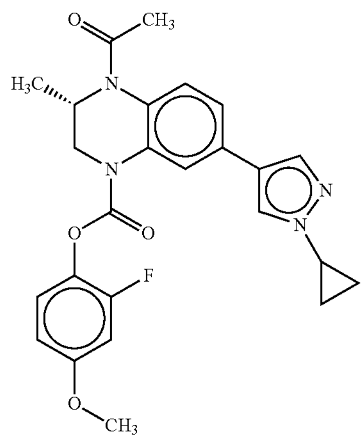 | 465 | 1.43 |
| I-524 | 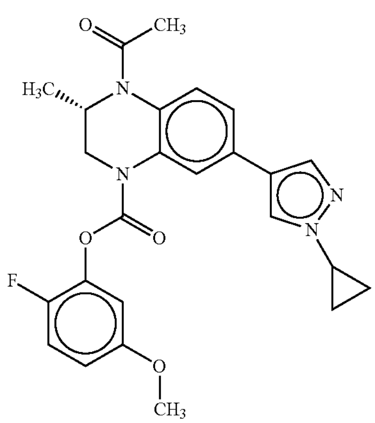 | 465 | 1.43 |
| I-525 | 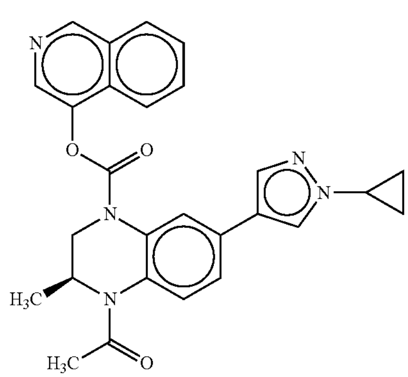 | 468 | 1.25 |

TABLE 8-continued
| Example | Structure | LC-MS [M + 1]+ | HPLC RT (min) |
|---------|-----------|----------------|---------------|
| I-526 | 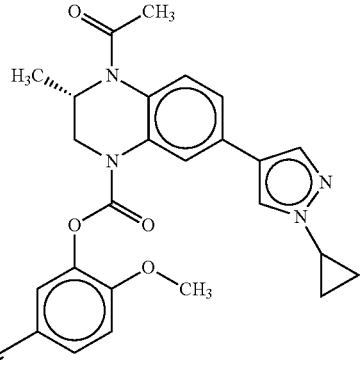 | 472 | 1.31 |
| I-527 | 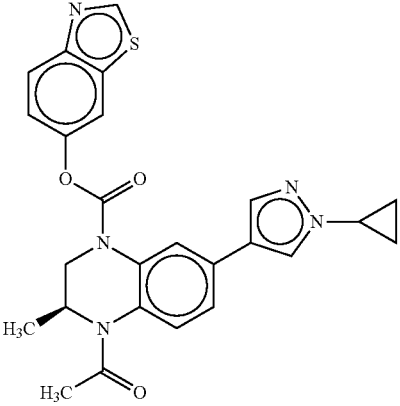 | 474 | 1.26 |
| I-528 | 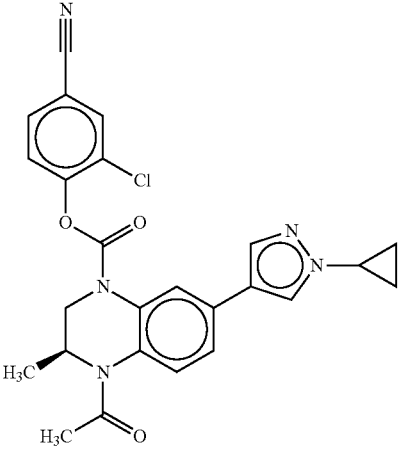 | 476 | 1.43 |

TABLE 8-continued

| Example | Structure | LC-MS [M + 1]+ | HPLC RT (min) |
|---|---|---|---|
| I-529 | 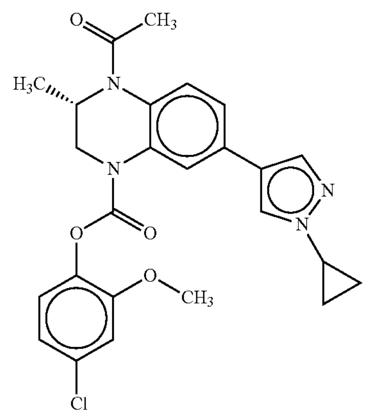 | 481 | 1.52 |
| I-530 | 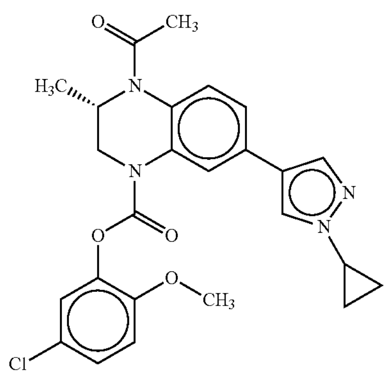 | 481 | 1.51 |
| I-531 | 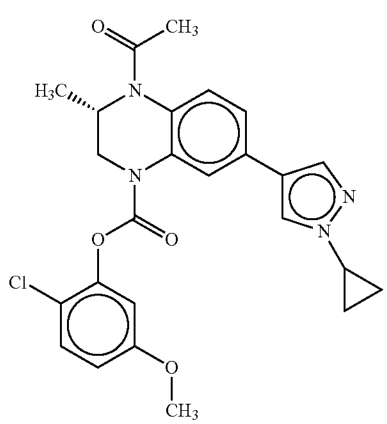 | 481 | 1.5 |

Example 265

Library Protocol G

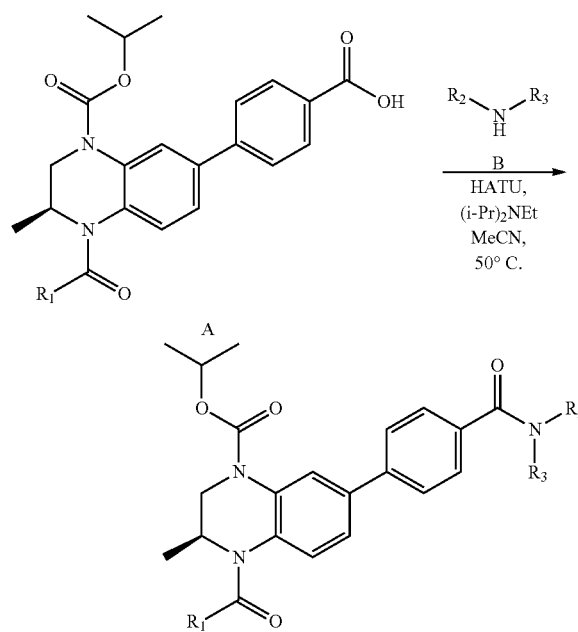

A 1.5 mL reaction vial was charged with benzoic acid (A) (0.2 M solution in 9:1 dichloroethane:N,N-diisopropylethylamine, 150 μL, 0.03 mmol), amine (B) (0.2 M solution in 1,4-dioxane, 225 μL, 0.045 mmol) and O-(7-azabenzotriazol-1-yl)-N,N,N',N'-tetramethyluronium hexafluorophosphate (HATU) (0.2 M solution in acetonitrile, 195 μL, 0.039 mmol). The reaction mixture was heated to 50° C. for 16 h on a heater shaker. The reaction mixture was concentrated, diluted with ethyl acetate (0.5 mL) and washed with brine (0.5 mL). The aqueous layer was separated and extracted with ethyl acetate (1 mL), and the organic layers were combined and concentrated under a stream of nitrogen and vacuum. The crude product was purified by mass triggered preparatory HPLC. The product-containing fractions were combined and concentrated in a Genevac to afford the desired product.

The following compounds Table 9 were synthesized according to the above protocol:

TABLE 9

| Example | Structure | LC-MS [M + 1]+ | HPLC RT (min) |
|---|---|---|---|
| I-532 | 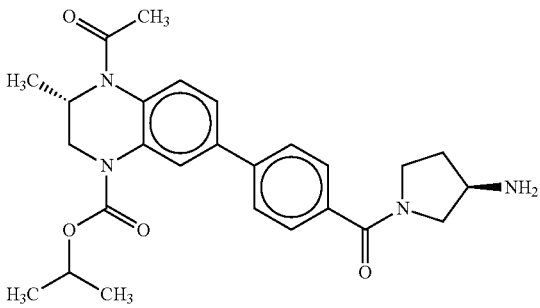 | 465 | 0.91 |
| I-533 | 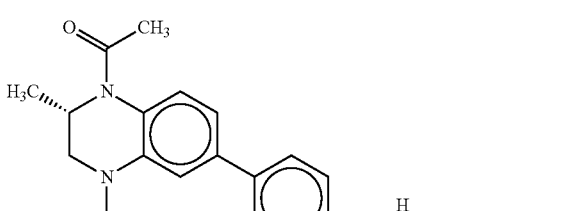 | 467 | 1 |

TABLE 9-continued

| Example | Structure | LC-MS [M + 1]+ | HPLC RT (min) |
|---|---|---|---|
| I-534 | 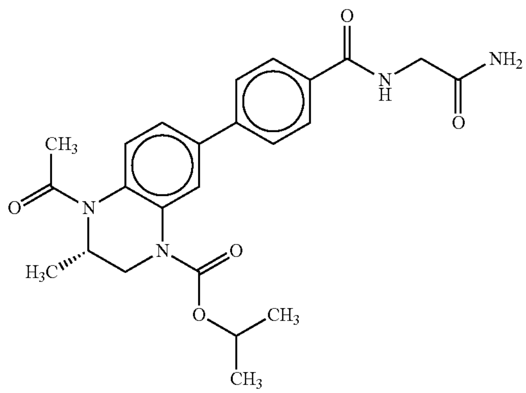 | 453 | 1.06 |
| I-535 | 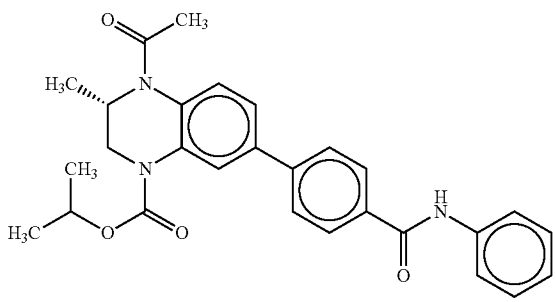 | 472 | 1.63 |
| I-536 | 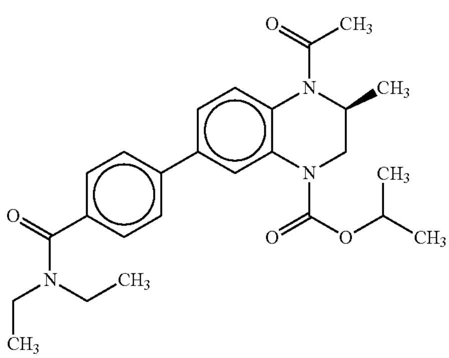 | 452 | 1.51 |
| I-537 | 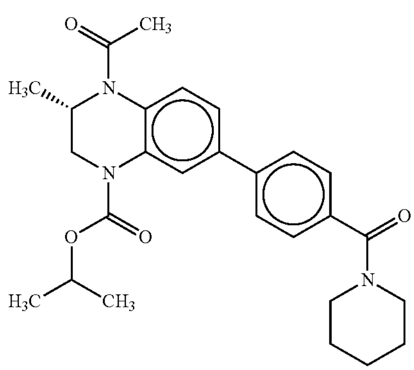 | 464 | 1.55 |

TABLE 9-continued

| Example | Structure | LC-MS [M + 1]+ | HPLC RT (min) |
|---|---|---|---|
| I-538 | 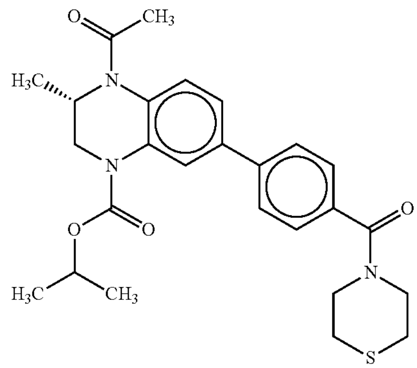 | 482 | 1.48 |
| I-539 | 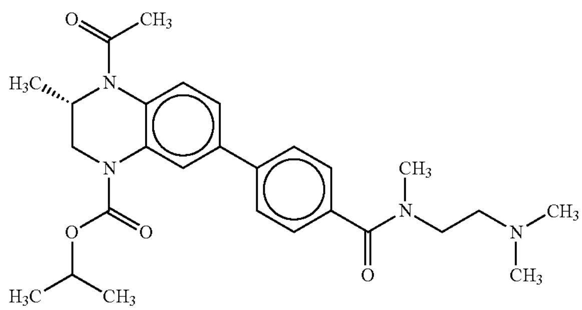 | 481 | 1.01 |
| I-540 | 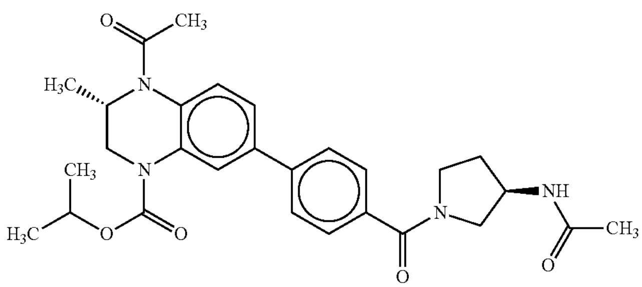 | 507 | 1.1 |
| I-541 | 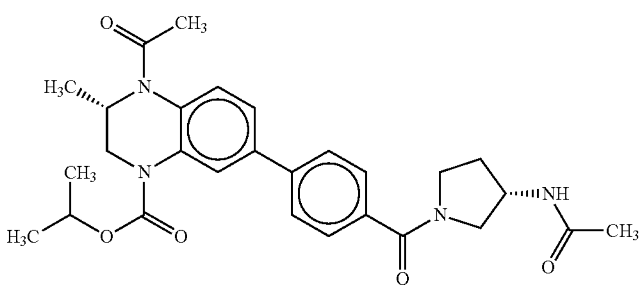 | 507 | 1.1 |
| I-542 | 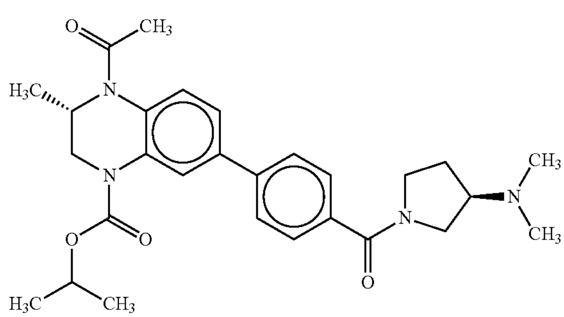 | 493 | 0.97 |

TABLE 9-continued

| Example | Structure | LC-MS [M + 1]+ | HPLC RT (min) |
|---|---|---|---|
| I-543 | 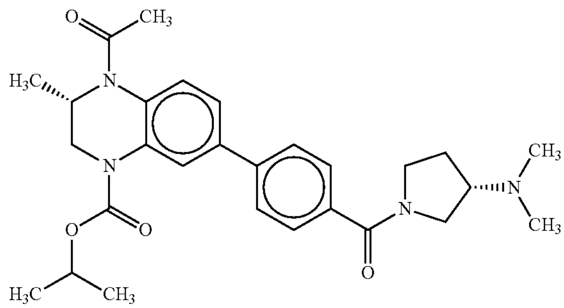 | 493 | 0.96 |
| I-544 | 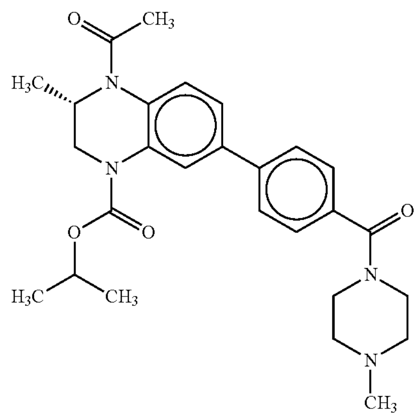 | 479 | 0.97 |
| I-545 | 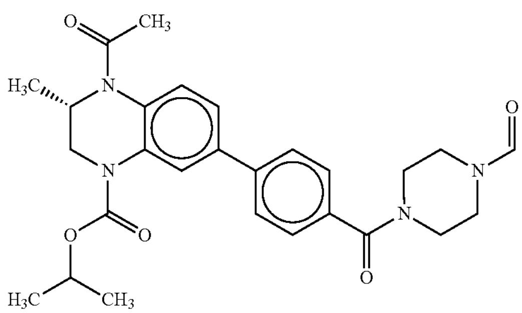 | 493 | 1.14 |
| I-546 | 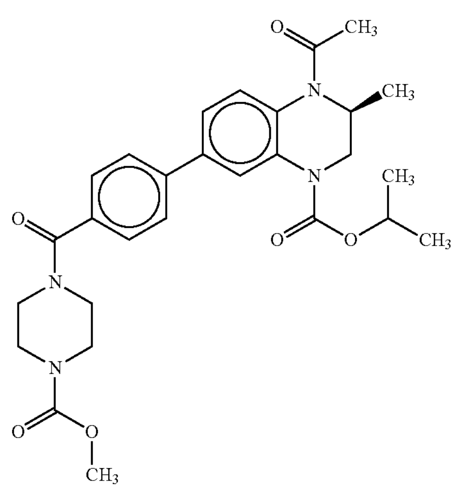 | 523 | 1.32 |

TABLE 9-continued

| Example | Structure | LC-MS [M + 1]+ | HPLC RT (min) |
|---|---|---|---|
| I-547 | 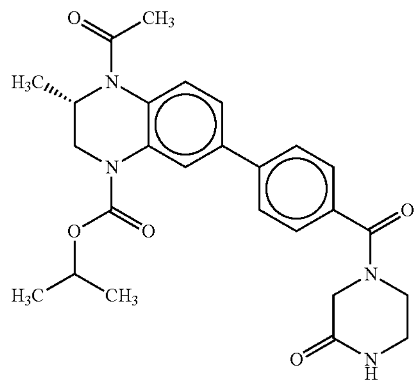 | 479 | 1.07 |
| I-548 | 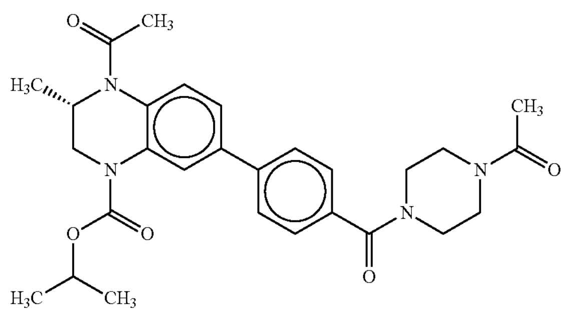 | 507 | 1.15 |
| I-549 | 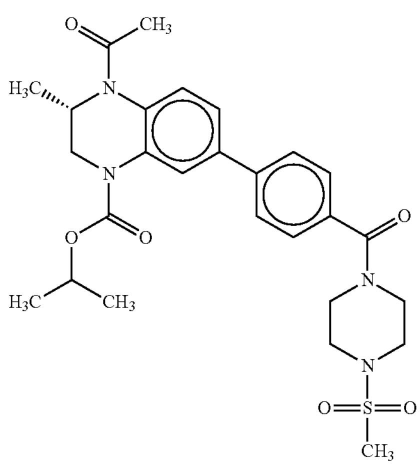 | 543 | 1.28 |
| I-550 | 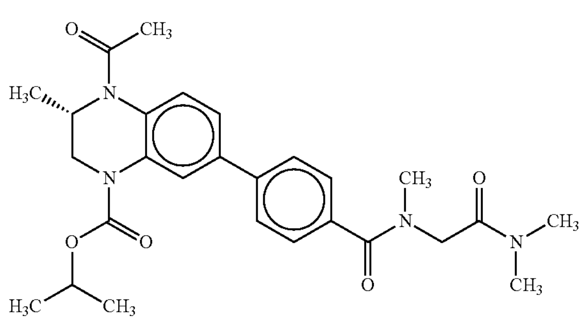 | 495 | 1.18 |

TABLE 9-continued

| Example | Structure | LC-MS [M + 1]+ | HPLC RT (min) |
|---|---|---|---|
| I-551 | 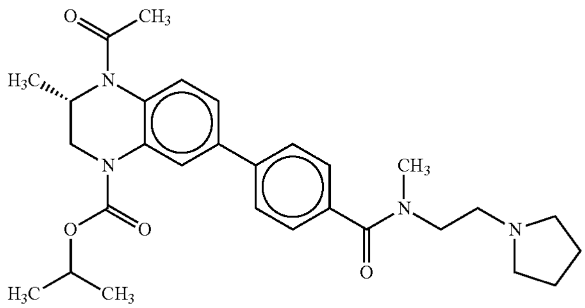 | 507 | 1.05 |
| I-552 | 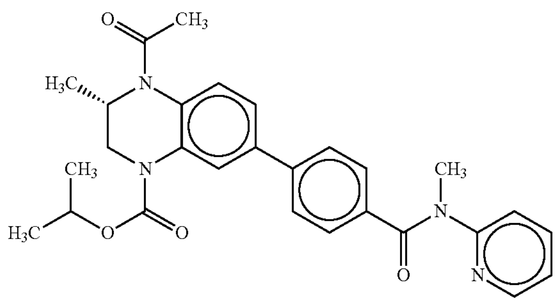 | 487 | 1.39 |
| I-553 | 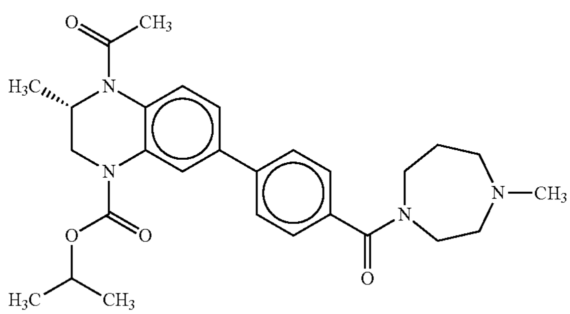 | 493 | 0.98 |
| I-554 | 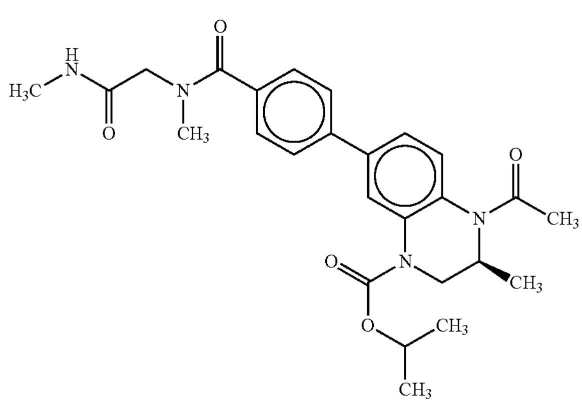 | 481 | 1.11 |

| Example | Structure | LC-MS [M + 1]+ | HPLC RT (min) |
|---------|-----------|----------------|---------------|
| I-555 | 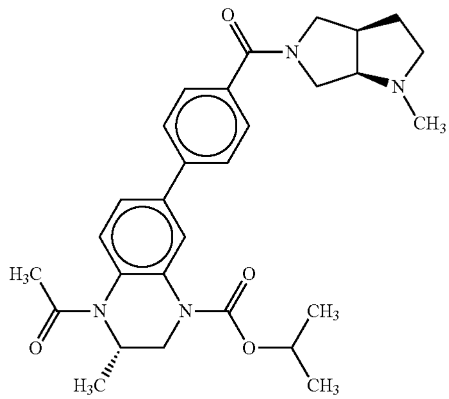 | 505 | 0.98 |
| I-556 | 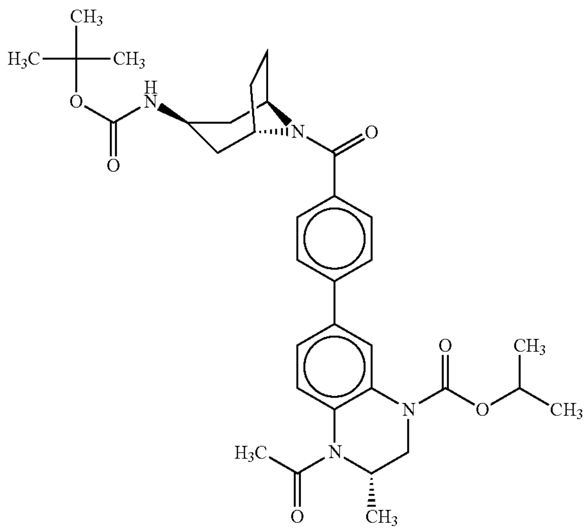 | 505 | 1.02 |
| I-557 | 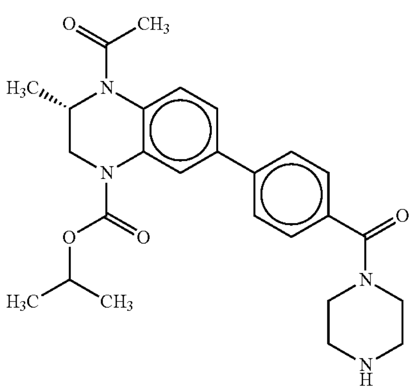 | 465 | 0.91 |

TABLE 9-continued

| Example | Structure | LC-MS [M + 1]+ | HPLC RT (min) |
|---------|-----------|----------------|---------------|
| I-558 | 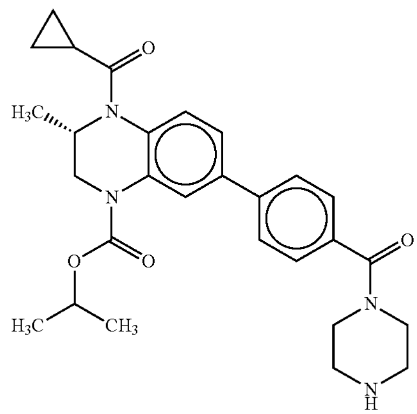 | 491 | 1.07 |
| I-559 | 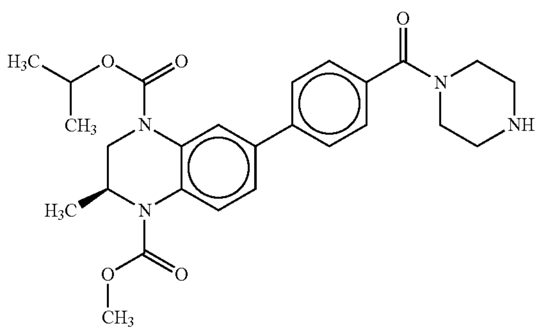 | 481 | 1.11 |
| I-560 | 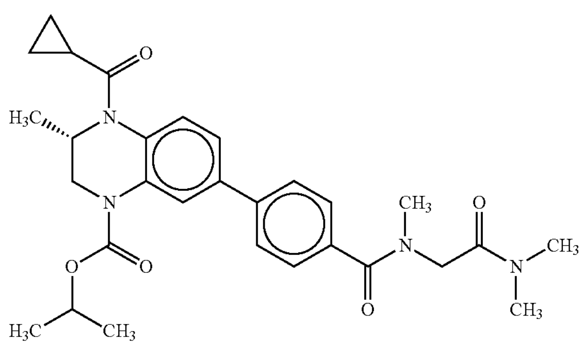 | 521 | 1.33 |
| I-561 | 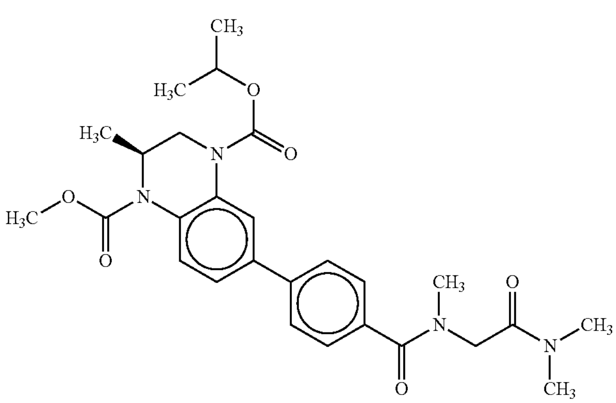 | 511 | 1.37 |

TABLE 9-continued
| Example | Structure | LC-MS [M + 1]+ | HPLC RT (min) |
|---|---|---|---|
| I-562 | 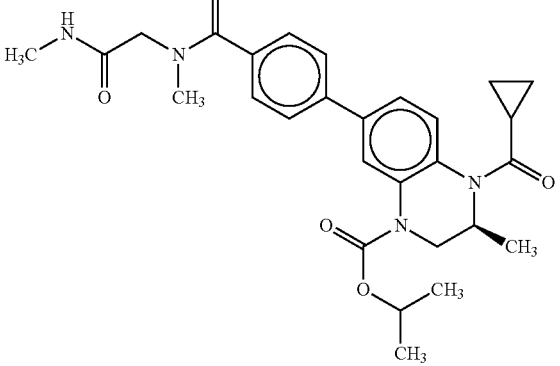 | 507 | 1.27 |
| I-563 | 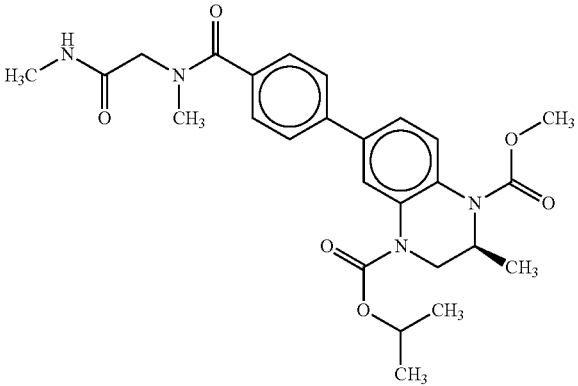 | 497 | 1.3 |
| I-564 | 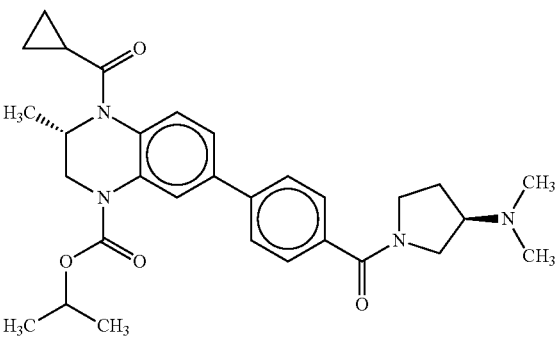 | 519 | 1.08 |
| I-565 | 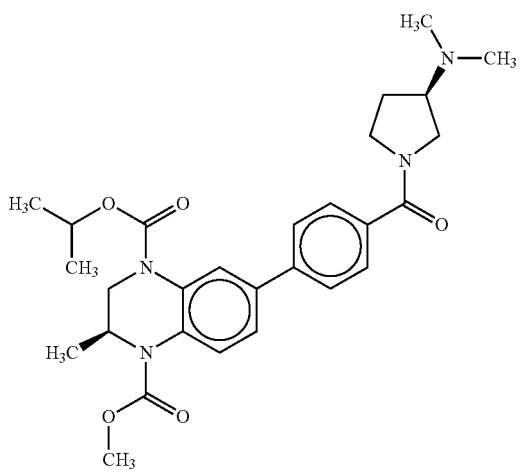 | 509 | 1.12 |

TABLE 9-continued
| Example | Structure | LC-MS [M + 1]+ | HPLC RT (min) |
|---------|-----------|----------------|---------------|
| I-566 | 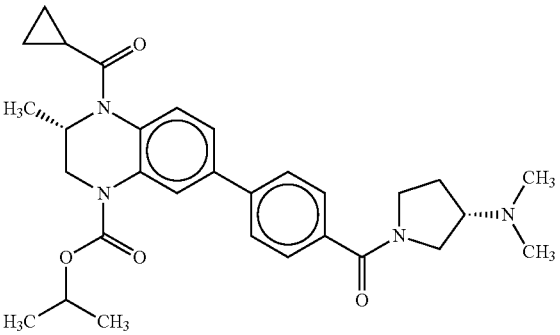 | 519 | 1.08 |
| I-567 | 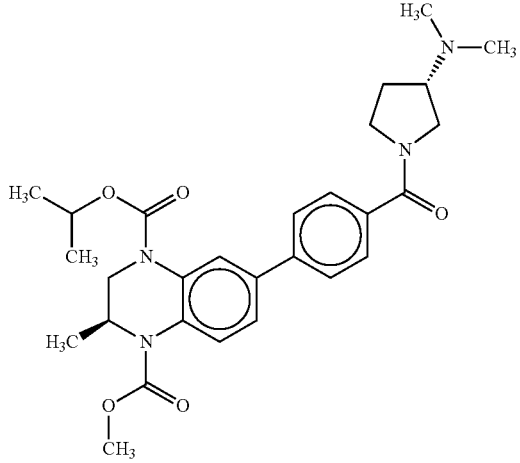 | 509 | 1.12 |
| I-568 | 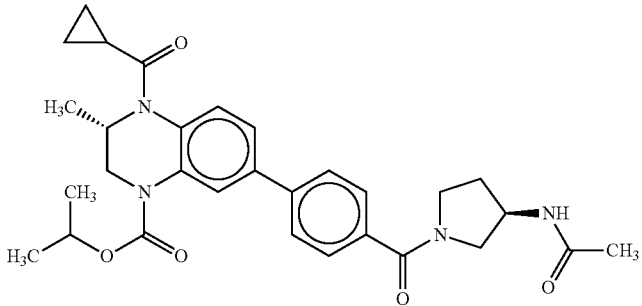 | 533 | 1.25 |

TABLE 9-continued
| Example | Structure | LC-MS [M + 1]+ | HPLC RT (min) |
|---|---|---|---|
| I-569 | 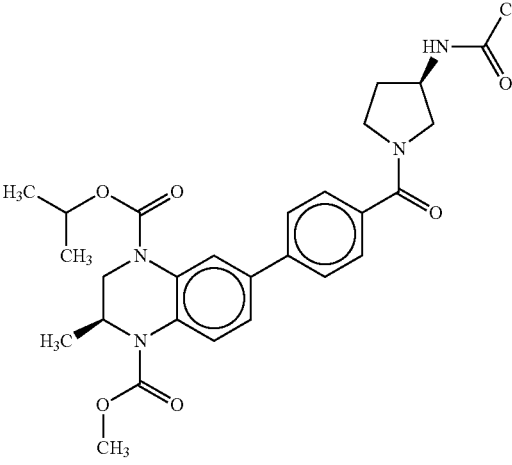 | 523 | 1.29 |
| I-570 | 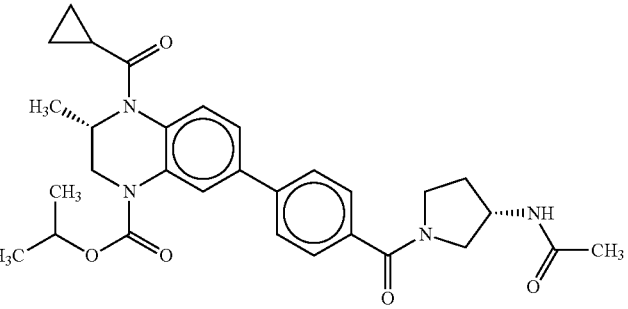 | 533 | 1.25 |
| I-571 | 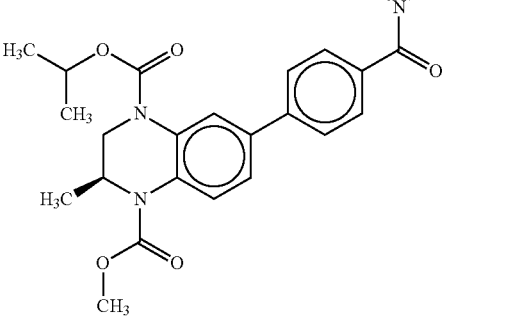 | 523 | 1.28 |

TABLE 9-continued
| Example | Structure | LC-MS [M + 1]+ | HPLC RT (min) |
|---|---|---|---|
| I-572 | 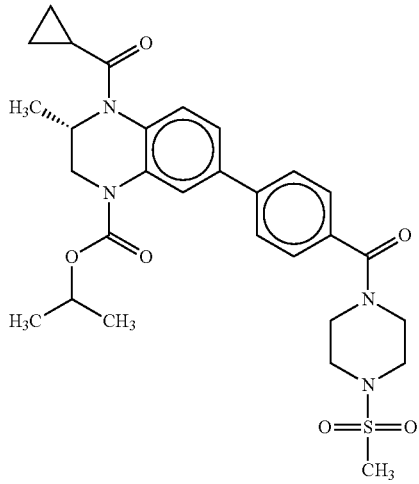 | 569 | 1.44 |
| I-573 | 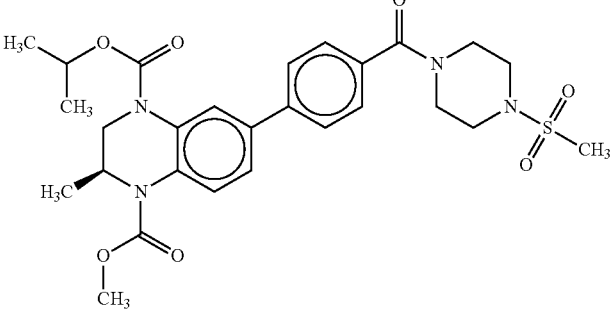 | 559 | 1.48 |
| I-574 | 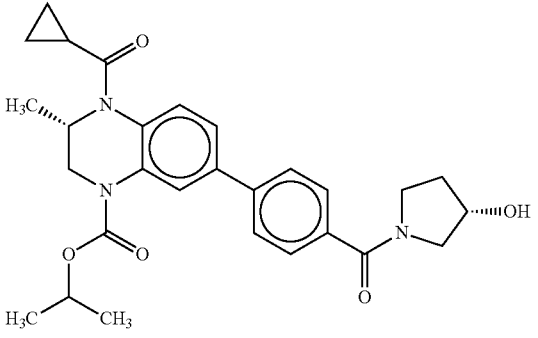 | 492 | 1.27 |
| I-575 | 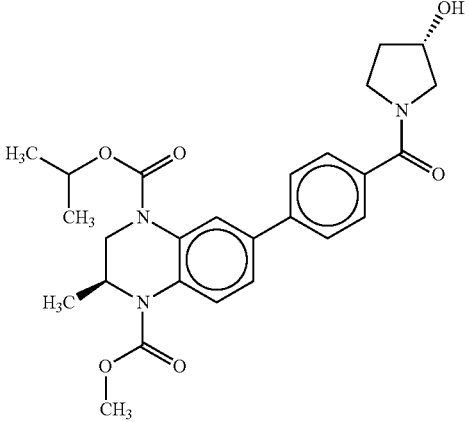 | 482 | 1.31 |

TABLE 9-continued

| Example | Structure | LC-MS [M + 1]+ | HPLC RT (min) |
|---------|-----------|----------------|---------------|
| I-576 | 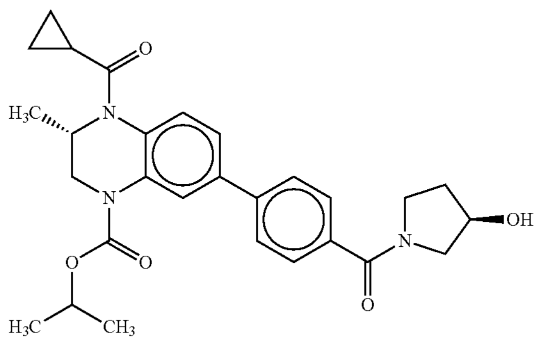 | 492 | 1.28 |
| I-577 | 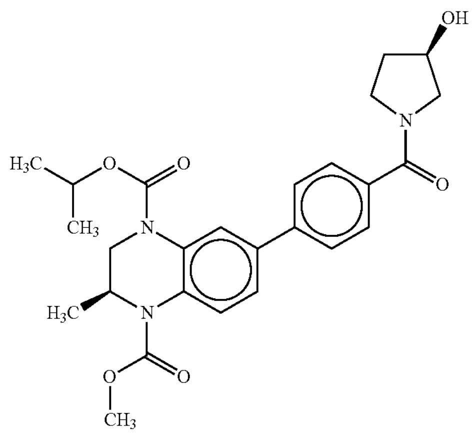 | 482 | 1.3 |
| I-578 | 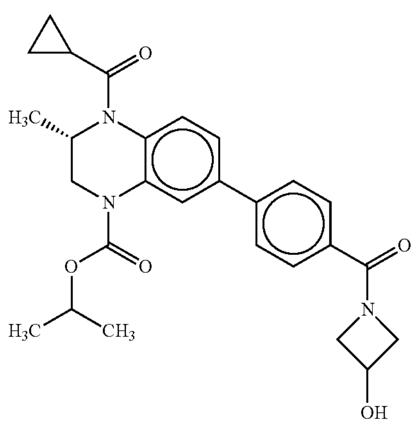 | 478 | 1.27 |
| I-579 | 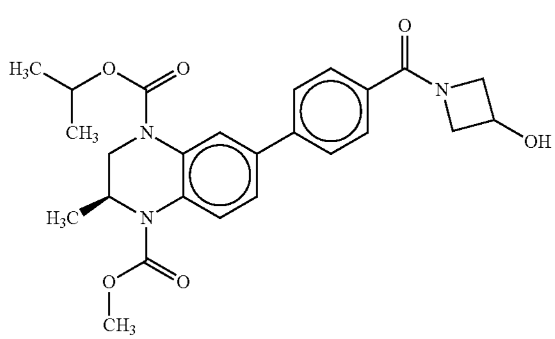 | 468 | 1.3 |

TABLE 9-continued

| Example | Structure | LC-MS [M + 1]+ | HPLC RT (min) |
|---|---|---|---|
| I-580 | 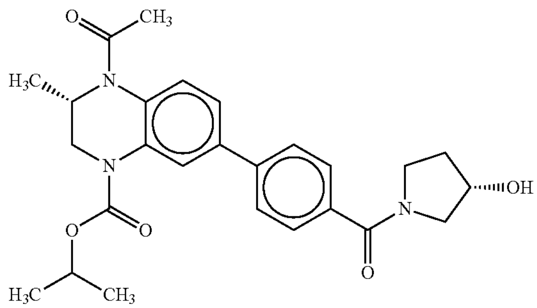 | 466 | 1.09 |
| I-581 | 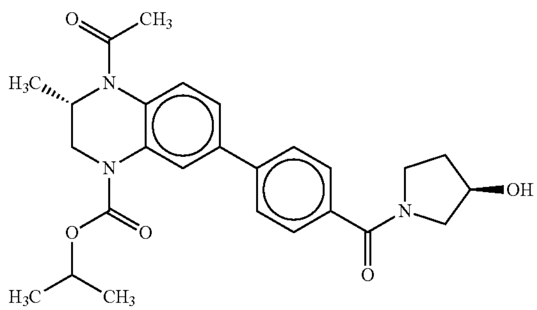 | 466 | 1.09 |
| I-582 | 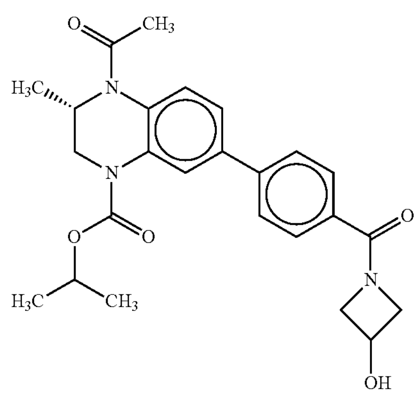 | 452 | 1.09 |
| I-583 | 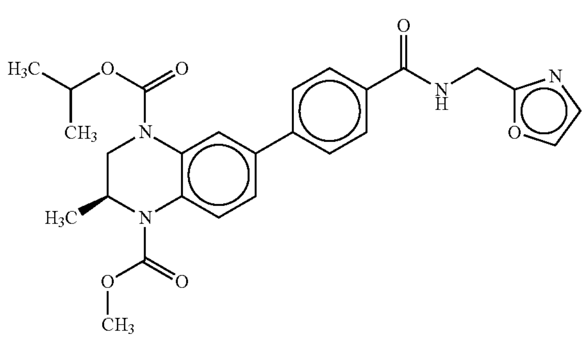 | 493 | 1.42 |

TABLE 9-continued

| Example | Structure | LC-MS [M + 1]+ | HPLC RT (min) |
|---|---|---|---|
| I-584 | 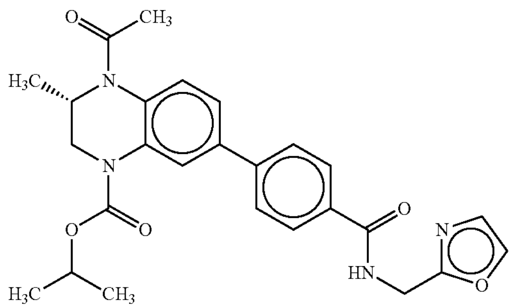 | 477 | 1.21 |
| I-585 | 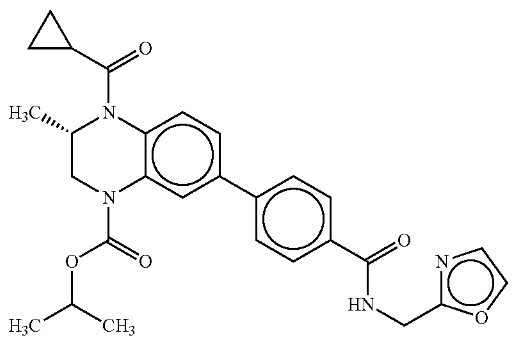 | 503 | 1.38 |

Example 266

Library Protocol G1

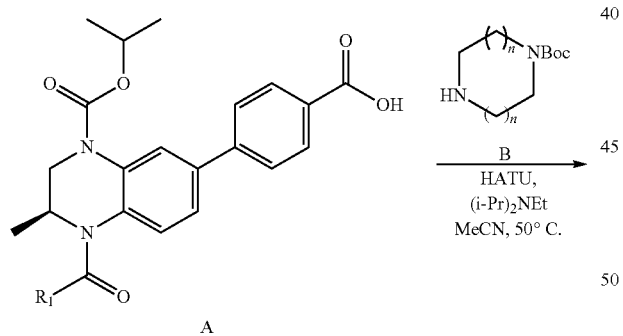

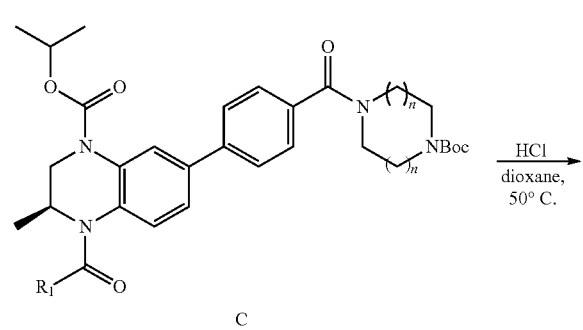

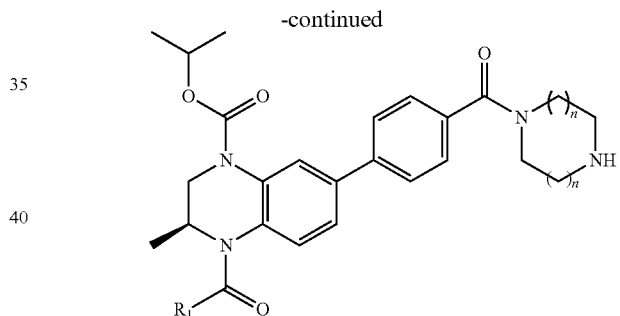

A 1.5 mL reaction vial was charged with benzoic acid (A) (0.2 M solution in 9:1 dichloroethane:N,N-diisopropylethylamine, 150 µL, 0.03 mmol), amine (B) (0.2 M solution in 1,4-dioxane, 225 µL, 0.045 mmol) and O-(7-azabenzotriazol-1-yl)-N,N,N',N'-tetramethyluronium hexafluorophosphate (HATU) (0.2 M solution in acetonitrile, 195 µL, 0.039 mmol). The reaction mixture was heated to 50° C. for 16 h on a heater shaker. The reaction mixture was concentrated, diluted with ethyl acetate (0.5 mL) and washed with brine (0.5 mL). The aqueous layer was separated and extracted with ethyl acetate (1 mL), and the organic layers were combined and concentrated under a stream of nitrogen and vacuum. The crude product (C) was dissolved in dioxane (0.3 mL), HCl (4.0 M in 1,4-dioxane, 0.15 mL, 0.6 mmol) was added, and the mixture stirred at 50° C. for 2 h. The reaction was concentrated, and diluted with ethyl acetate (0.5 mL) and saturated aqueous sodium bicarbonate solution (0.5 mL). The aqueous layer was separated and extracted with ethyl acetate (1 mL), and the organic layers were combined and concentrated under a stream of nitrogen and vacuum. The crude product was purified by mass triggered preparatory HPLC. The product-containing fractions were combined and concentrated in a Genevac to afford the desired product.

The following compounds in Table 10 were synthesized according to the above protocol:

TABLE 10

| Example | Structure | LC-MS [M + 1]+ | HPLC RT (min) |
|---|---|---|---|
| I-586 | 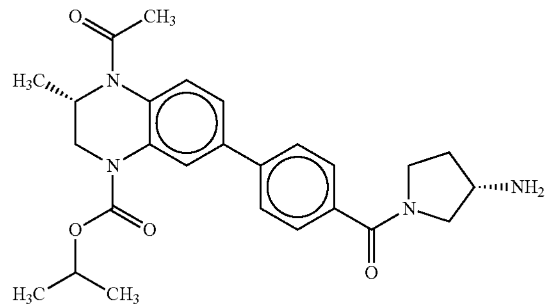 | 465 | 0.93 |
| I-587 | 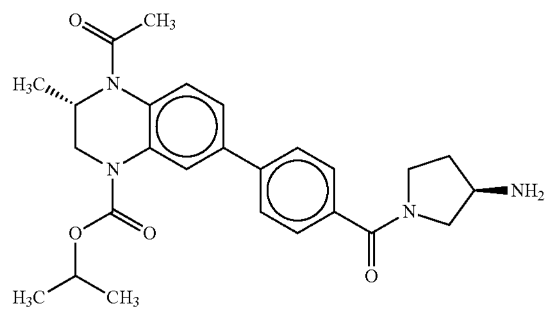 | 465 | 0.93 |
| I-588 | 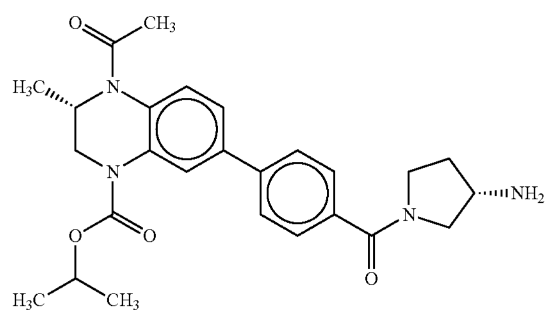 | 465 | 0.93 |
| I-589 | 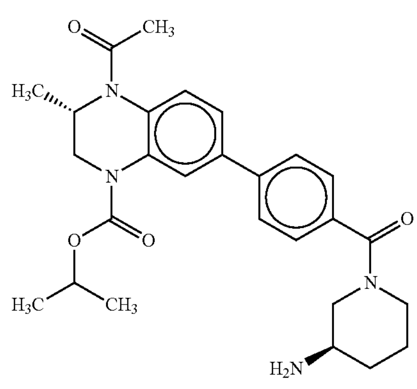 | 479 | 0.99 |

TABLE 10-continued
| Example | Structure | LC-MS [M + 1]+ | HPLC RT (min) |
|---|---|---|---|
| I-590 | 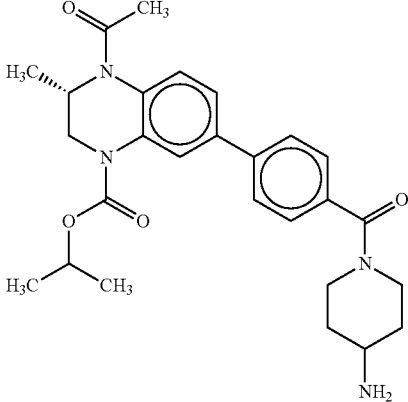 | 479 | 0.96 |
| I-591 | 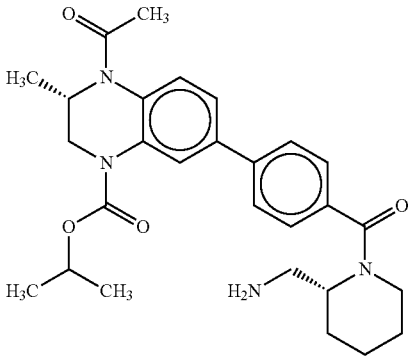 | 493 | 1.06 |
| I-592 | 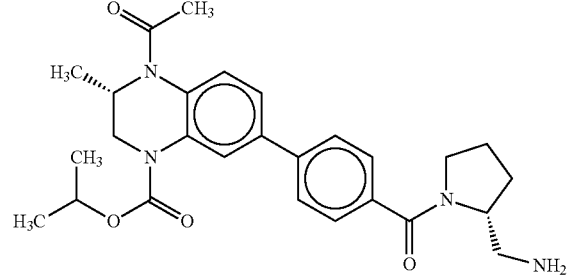 | 479 | 1.07 |
| I-593 | 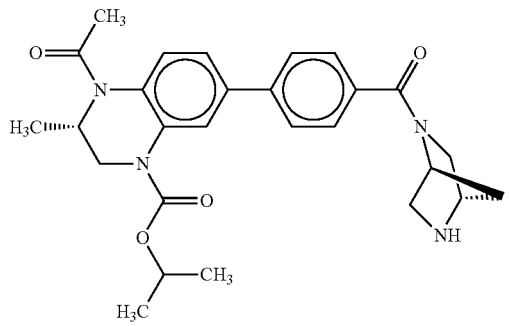 | 477 | 0.95 |

TABLE 10-continued

| Example | Structure | LC-MS [M + 1]+ | HPLC RT (min) |
|---|---|---|---|
| I-594 | 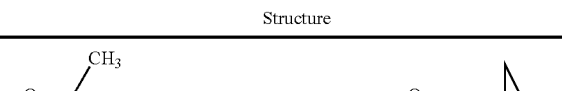 | 505 | 1.02 |

Example 267

Library Protocol H

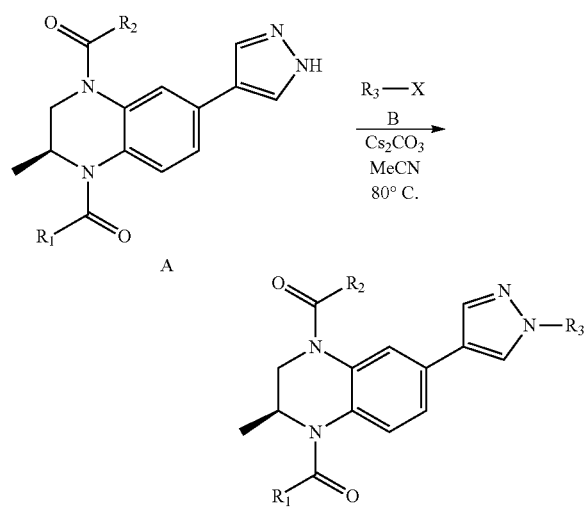

A 1.5 mL reaction vial was charged with pyrazole (A) (0.4 M solution in acetonitrile, 0.050 mL, 0.02 mmol, alkyl halide (B) (0.2 M solution in acetonitrile, 0.150 mL, 0.030 mmol), and cesium carbonate (0.033 g, 0.100 mmol). The reaction mixture was heated to 80° C. for 16 h on a heater shaker. The reaction mixture was concentrated, diluted with ethyl acetate (0.5 mL) and washed with brine (0.5 mL). The aqueous layer was separated and extracted with ethyl acetate (1 mL), and the organic layers were combined and concentrated under a stream of nitrogen and vacuum. The crude product was purified by mass triggered preparatory HPLC. The product-containing fractions were combined and concentrated in a Genevac to afford the desired product.

The following compounds in Table 11 were synthesized according to the above protocol:

TABLE 11

| Example | Structure | LC-MS [M + 1]+ | HPLC RT (min) |
|---|---|---|---|
| I-595 | 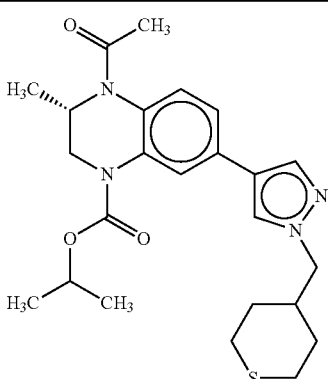 | 489 | 1.13 |

TABLE 11-continued

| Example | Structure | LC-MS [M + 1]+ | HPLC RT (min) |
|---------|-----------|----------------|---------------|
| I-596 | 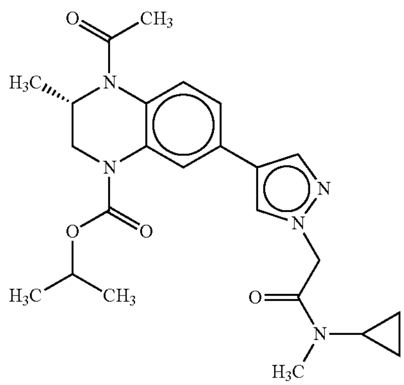 | 454 | 1.2 |
| I-597 | 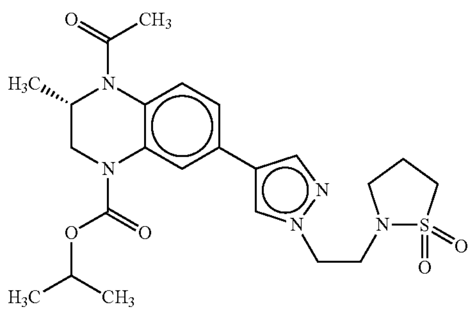 | 490 | 1.12 |
| I-598 | 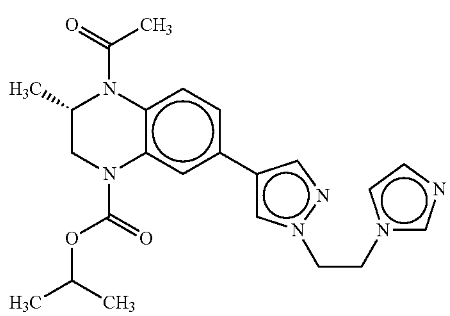 | 437 | 0.85 |
| I-599 | 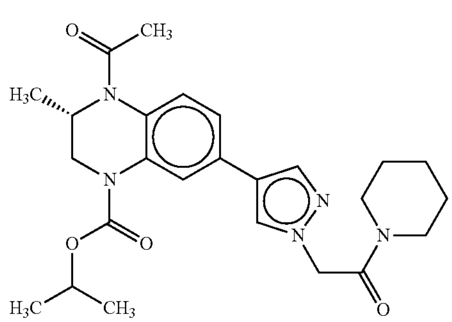 | 468 | 1.25 |

TABLE 11-continued

| Example | Structure | LC-MS [M + 1]+ | HPLC RT (min) |
|---|---|---|---|
| I-600 | 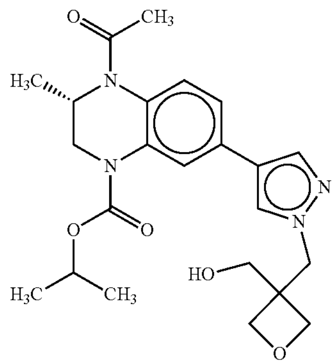 | 443 | 1.02 |
| I-601 | 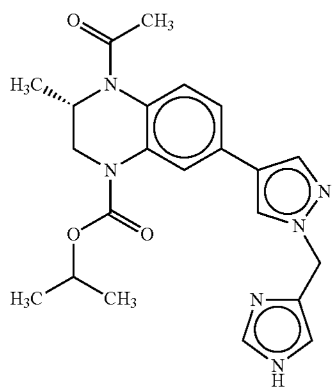 | 423 | 0.84 |
| I-602 | 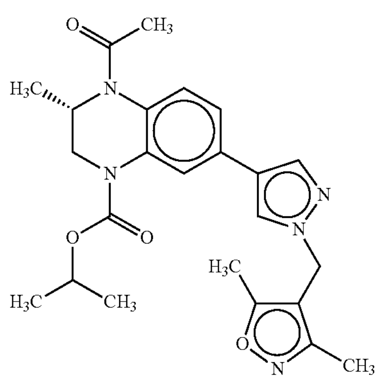 | 452 | 1.31 |
| I-603 | 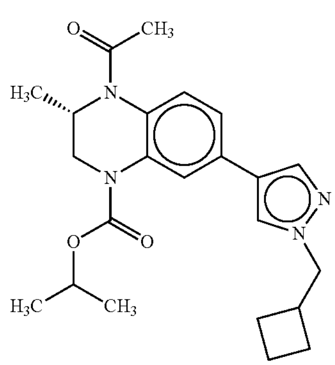 | 411 | 1.56 |

TABLE 11-continued
| Example | Structure | LC-MS [M + 1]+ | HPLC RT (min) |
|---|---|---|---|
| I-604 | 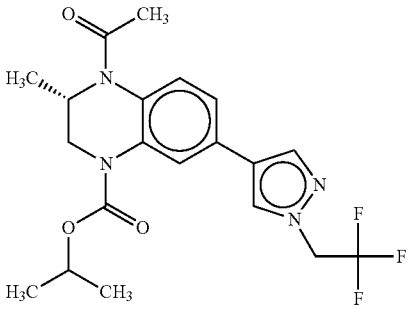 | 425 | 1.39 |
| I-605 | 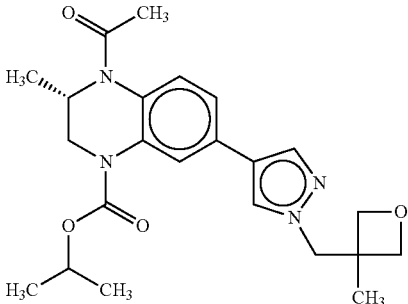 | 427 | 1.22 |
| I-606 | 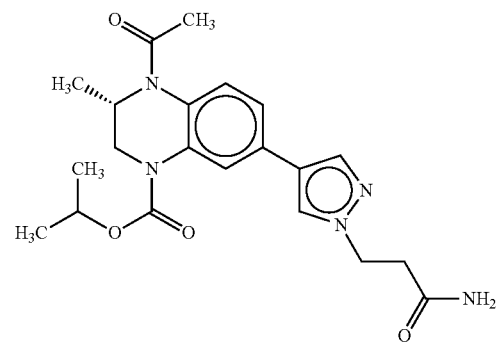 | 414 | 0.95 |
| I-607 | 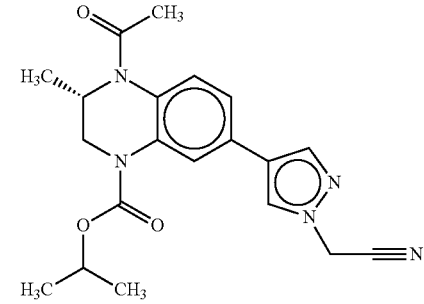 | 382 | 1.19 |

TABLE 11-continued
| Example | Structure | LC-MS [M + 1]+ | HPLC RT (min) |
|---|---|---|---|
| I-608 | 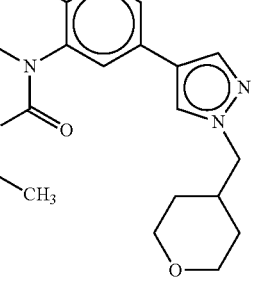 | 441 | 1.25 |
| I-609 | 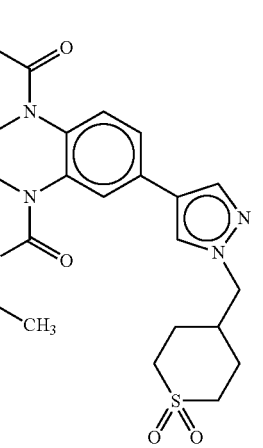 | 515 | 1.29 |
| I-610 | 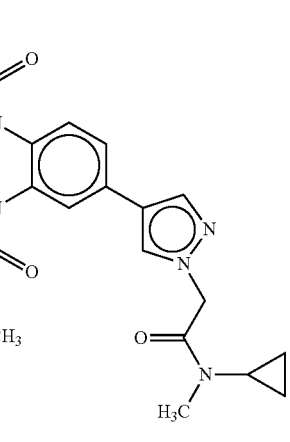 | 480 | 1.36 |
| I-611 | 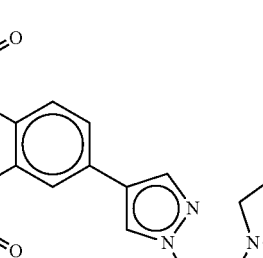 | 516 | 1.29 |

TABLE 11-continued

| Example | Structure | LC-MS [M + 1]+ | HPLC RT (min) |
|---------|-----------|----------------|---------------|
| I-612 | 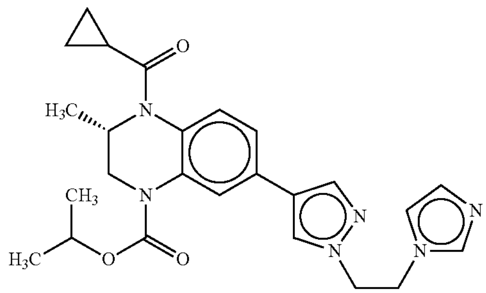 | 463 | 0.99 |
| I-613 | 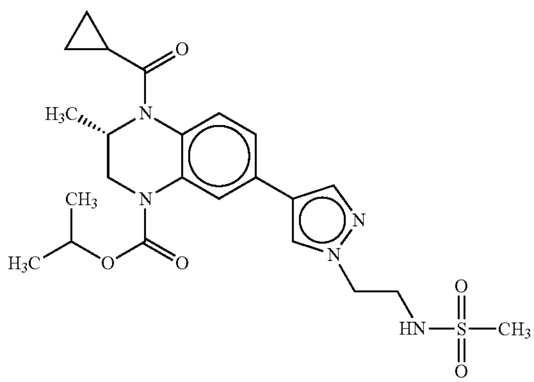 | 490 | 1.23 |
| I-614 | 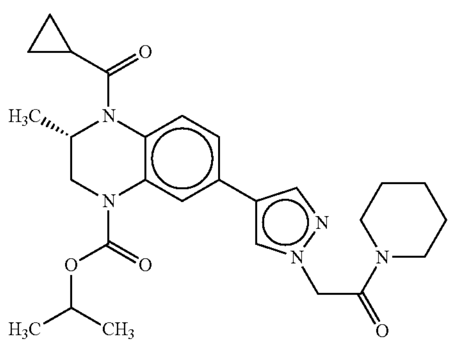 | 494 | 1.41 |
| I-615 | 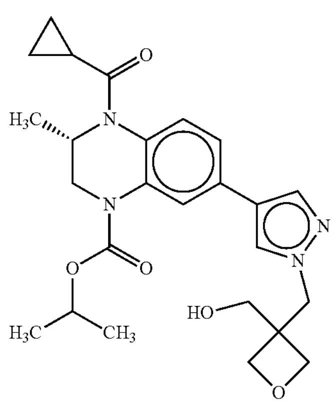 | 469 | 1.19 |

TABLE 11-continued

| Example | Structure | LC-MS [M + 1]+ | HPLC RT (min) |
|---------|-----------|----------------|---------------|
| I-616 | 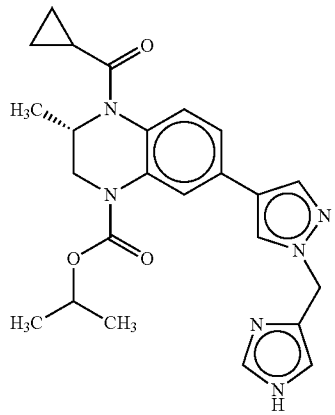 | 449 | 0.99 |
| I-617 | 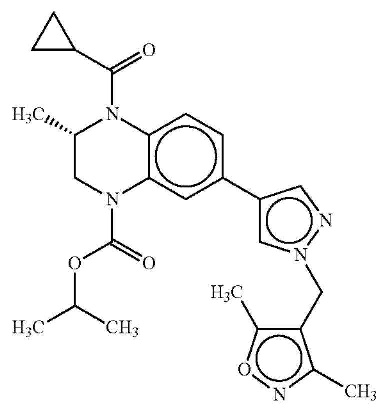 | 478 | 1.48 |
| I-618 | 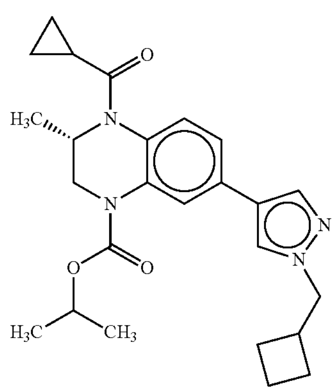 | 437 | 1.75 |
| I-619 | 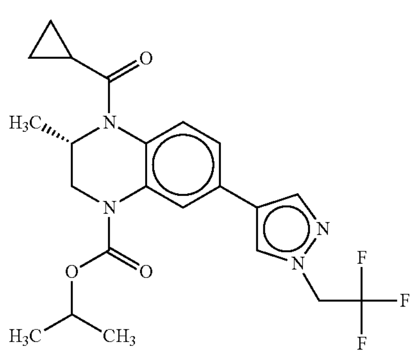 | 451 | 1.57 |

TABLE 11-continued

| Example | Structure | LC-MS [M + 1]+ | HPLC RT (min) |
|---|---|---|---|
| I-620 | 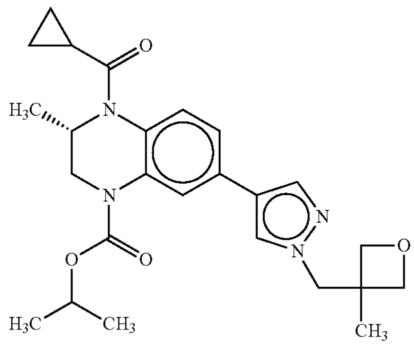 | 453 | 1.4 |
| I-621 | 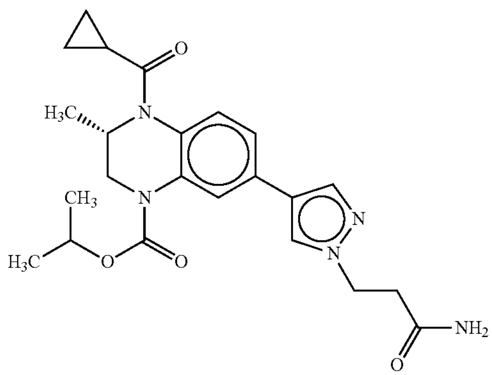 | 440 | 1.11 |
| I-622 | 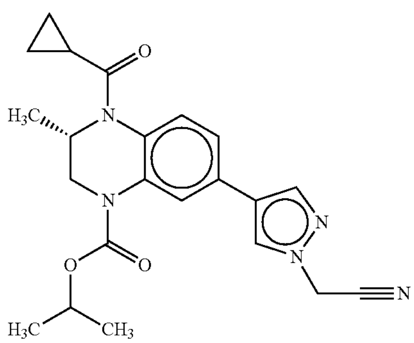 | 408 | 1.38 |
| I-623 | 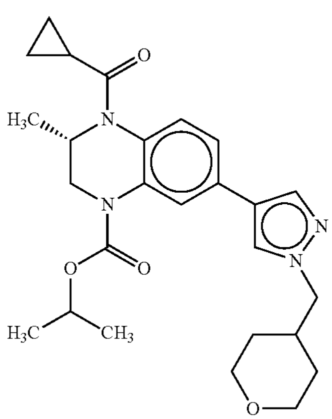 | 467 | 1.44 |

TABLE 11-continued
| Example | Structure | LC-MS [M + 1]+ | HPLC RT (min) |
|---------|-----------|----------------|---------------|
| I-624 | 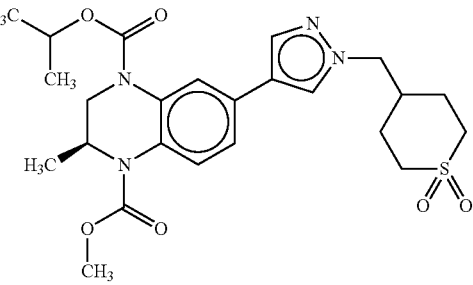 | 505 | 1.32 |
| I-625 | 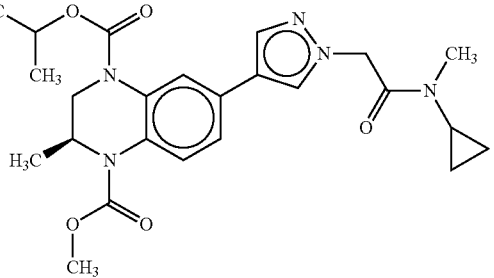 | 470 | 1.38 |
| I-626 | 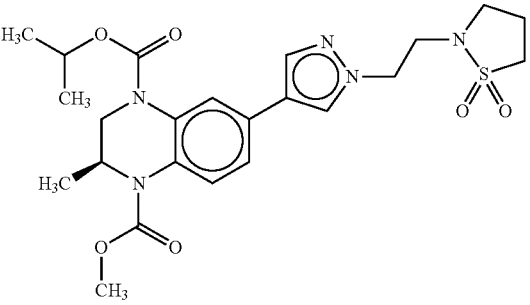 | 506 | 1.32 |
| I-627 | 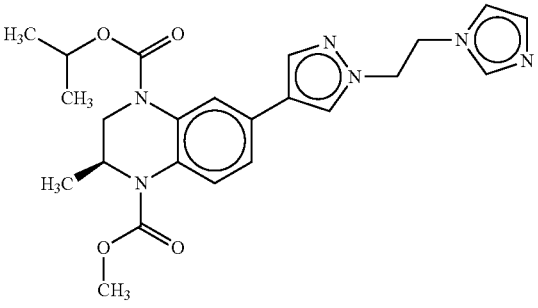 | 453 | 1.03 |
| I-628 | 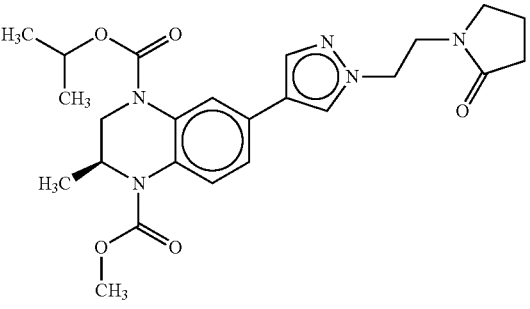 | 470 | 1.25 |

TABLE 11-continued

| Example | Structure | LC-MS [M + 1]+ | HPLC RT (min) |
|---|---|---|---|
| I-629 | 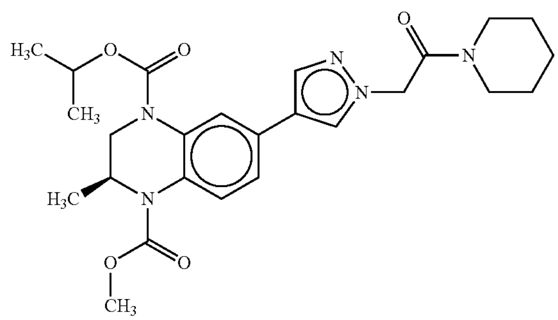 | 484 | 1.44 |
| I-630 | 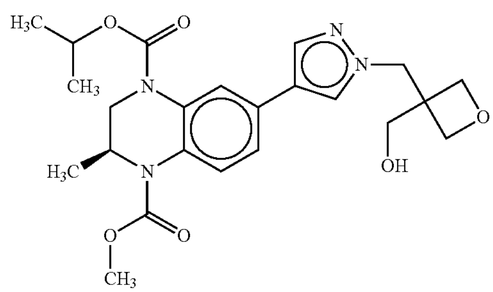 | 459 | 1.22 |
| I-631 | 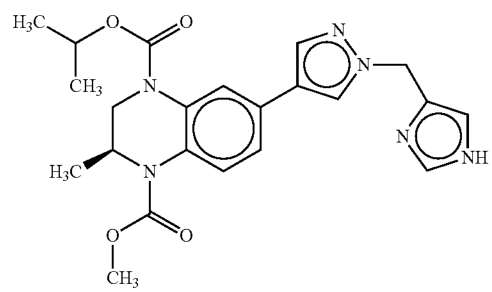 | 439 | 1.02 |
| I-632 | 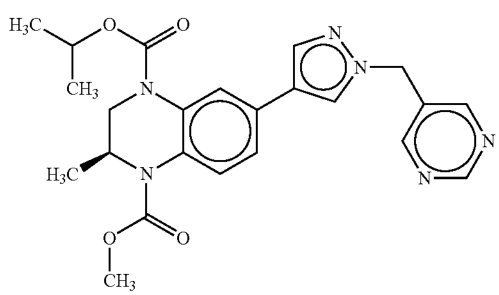 | 451 | 1.27 |
| I-633 | 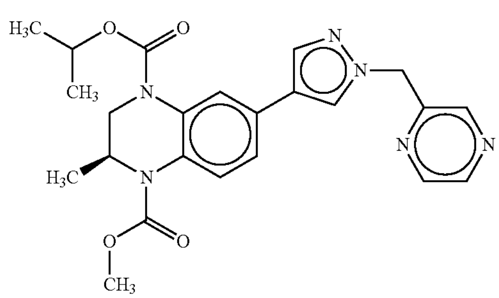 | 451 | 1.32 |

TABLE 11-continued

| Example | Structure | LC-MS [M + 1]+ | HPLC RT (min) |
|---|---|---|---|
| I-634 | 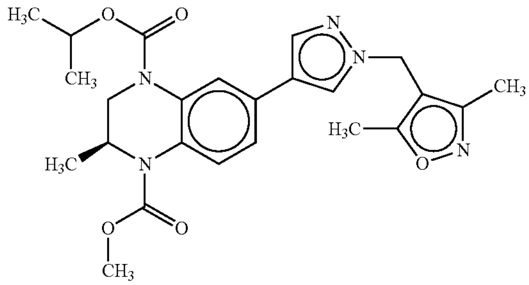 | 468 | 1.51 |
| I-635 | 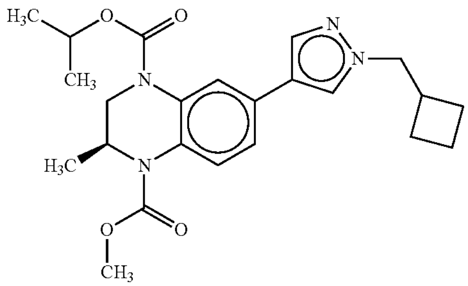 | 427 | 1.75 |
| I-636 | 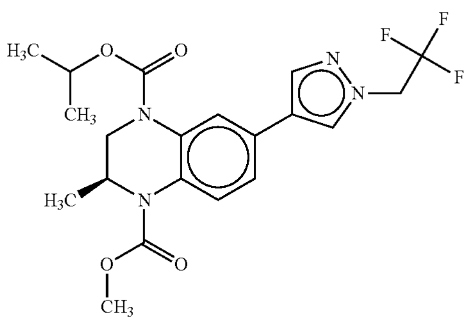 | 441 | 1.6 |
| I-637 | 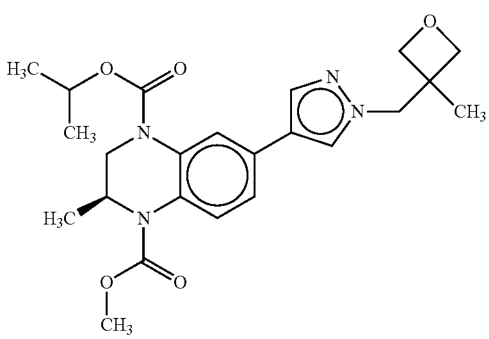 | 443 | 1.43 |
| I-638 | 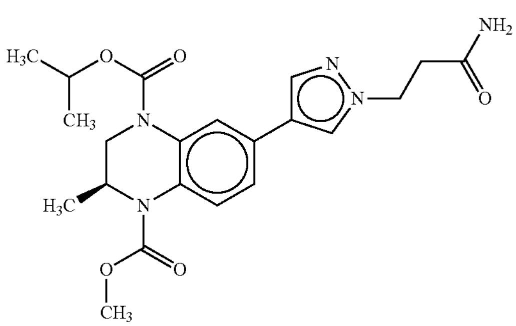 | 430 | 1.14 |

TABLE 11-continued

| Example | Structure | LC-MS [M + 1]+ | HPLC RT (min) |
|---|---|---|---|
| I-639 | 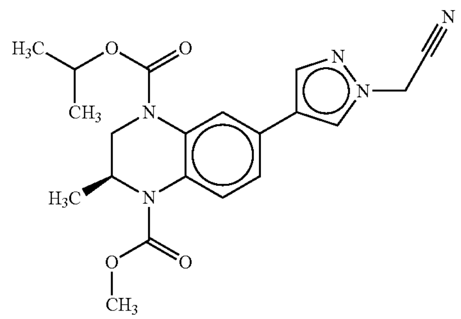 | 398 | 1.41 |
| I-640 | 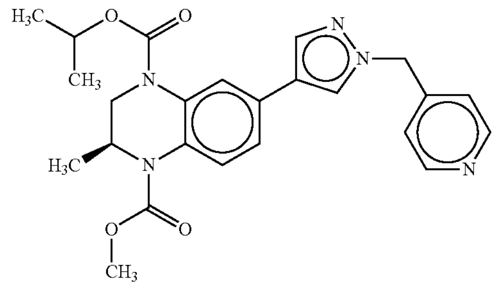 | 450 | 1.23 |
| I-641 | 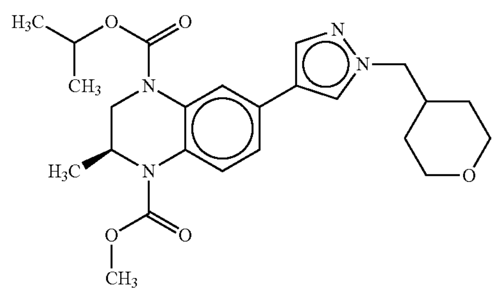 | 457 | 1.46 |
| I-642 | 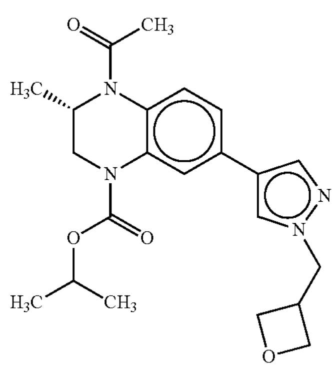 | 413 | 1.13 |

TABLE 11-continued

| Example | Structure | LC-MS [M + 1]+ | HPLC RT (min) |
|---|---|---|---|
| I-643 | 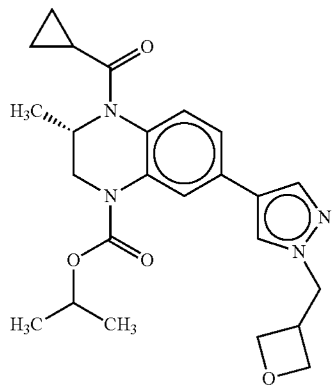 | 439 | 1.3 |
| I-644 | 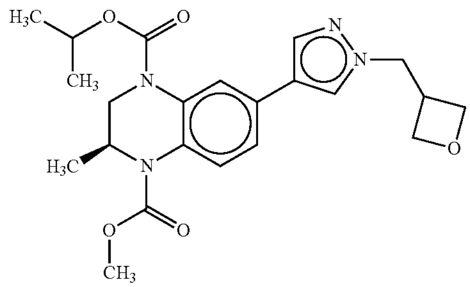 | 429 | 1.34 |
| I-645 | 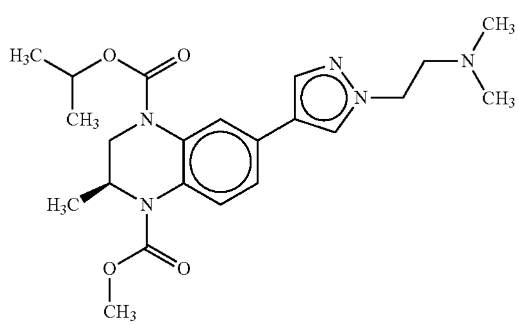 | 430 | 1.02 |
| I-646 | 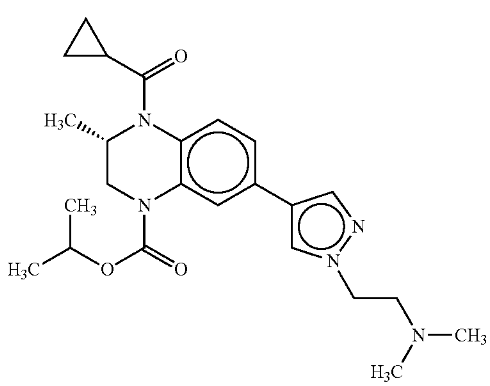 | 440 | 0.99 |

TABLE 11-continued

| Example | Structure | LC-MS [M + 1]+ | HPLC RT (min) |
|---|---|---|---|
| I-647 | 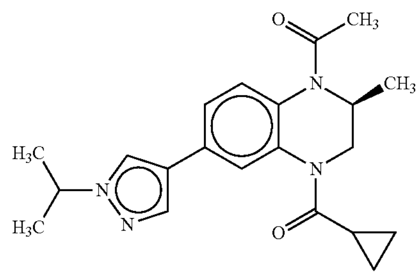 | 367 | 1.17 |
| I-648 | 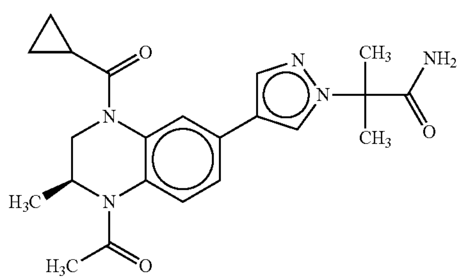 | 410 | 0.9 |
| I-649 | 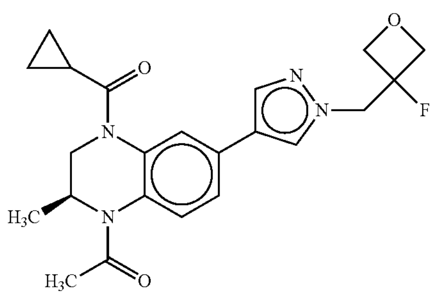 | 413 | 1.01 |
| I-650 | 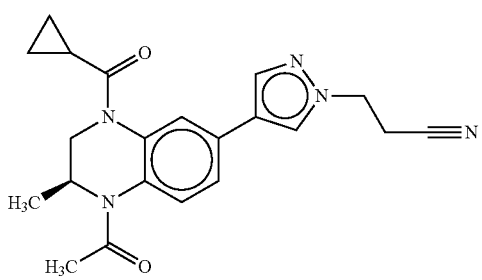 | 378 | 0.95 |
| I-651 | 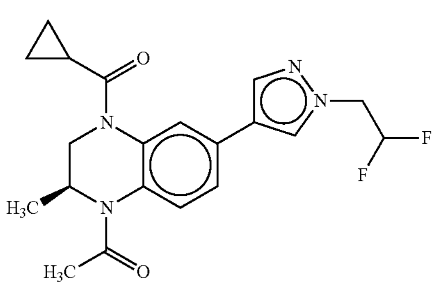 | 389 | 1.09 |

TABLE 11-continued

| Example | Structure | LC-MS [M + 1]+ | HPLC RT (min) |
|---------|-----------|----------------|---------------|
| I-652 | 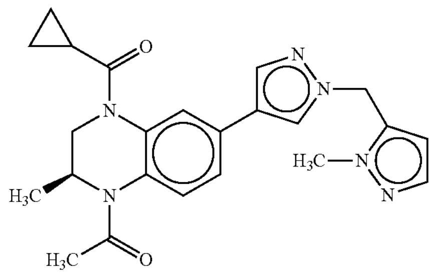 | 419 | 0.97 |
| I-653 | 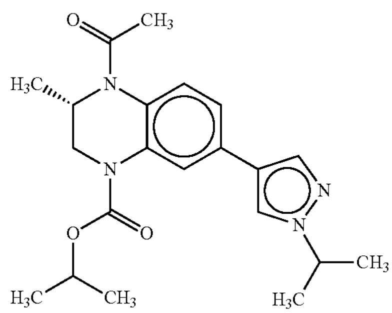 | 385 | 1.38 |
| I-654 | 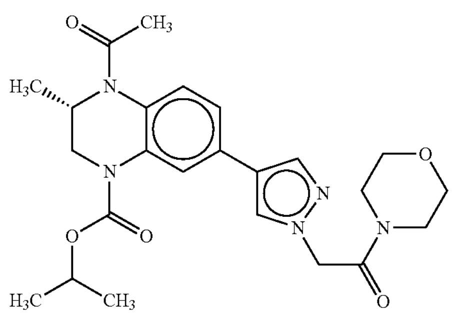 | 470 | 1.04 |
| I-655 | 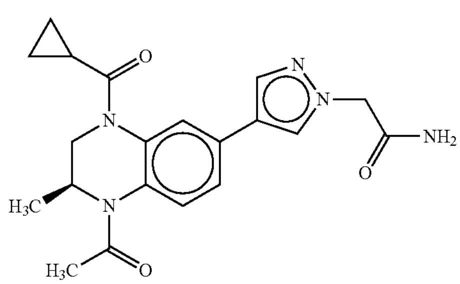 | 382 | 0.74 |
| I-656 | 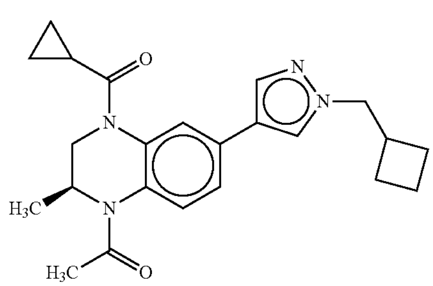 | 393 | 1.36 |

TABLE 11-continued
| Example | Structure | LC-MS [M + 1]+ | HPLC RT (min) |
|---|---|---|---|
| I-657 | 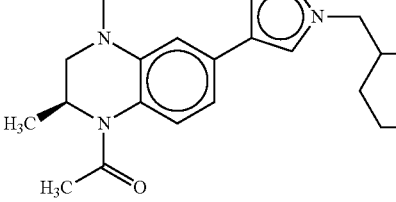 | 423 | 1.06 |
| I-658 | 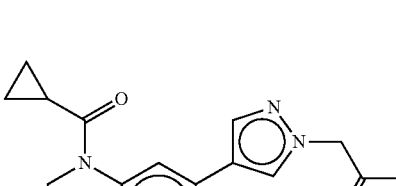 | 436 | 1.01 |
| I-659 | 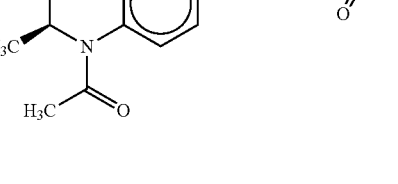 | 472 | 0.93 |
| I-660 | 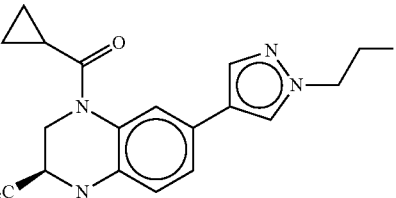 | 436 | 0.87 |
| I-661 | 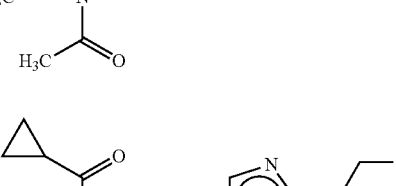 | 450 | 1.06 |

TABLE 11-continued

| Example | Structure | LC-MS [M + 1]+ | HPLC RT (min) |
|---|---|---|---|
| I-662 | 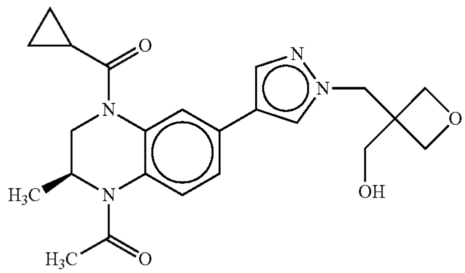 | 425 | 0.84 |
| I-663 | 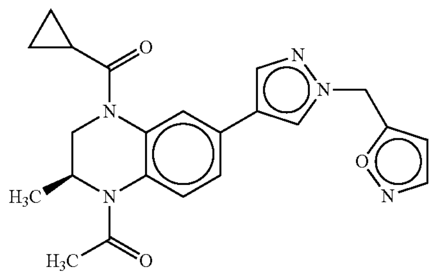 | 406 | 1.01 |
| I-664 | 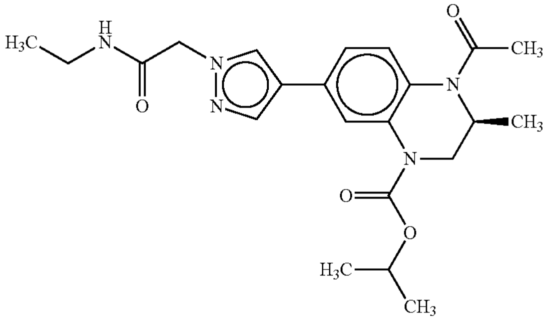 | 428 | 1.06 |
| I-665 | 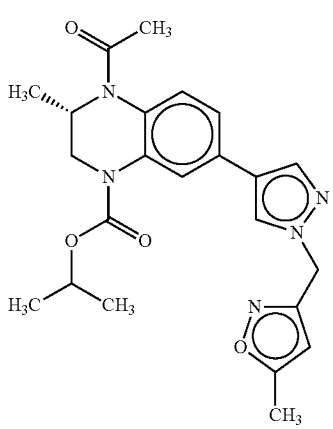 | 438 | 1.3 |

TABLE 11-continued

| Example | Structure | LC-MS [M + 1]+ | HPLC RT (min) |
|---|---|---|---|
| I-666 | 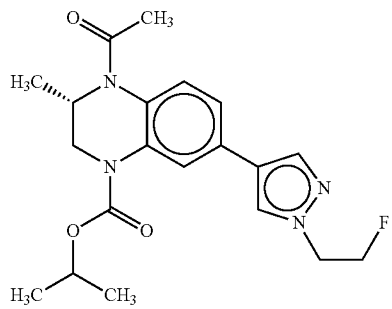 | 389 | 1.21 |
| I-667 | 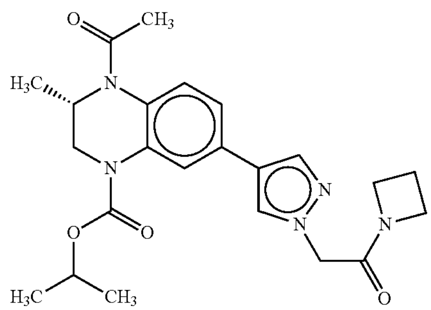 | 440 | 1.05 |
| I-668 | 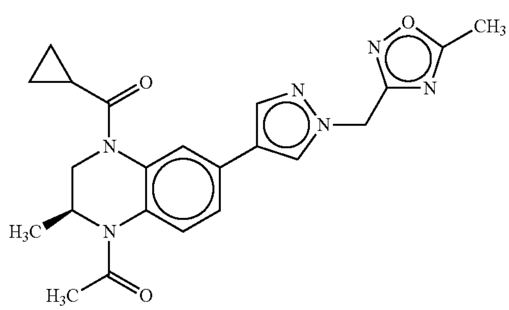 | 421 | 1 |
| I-669 | 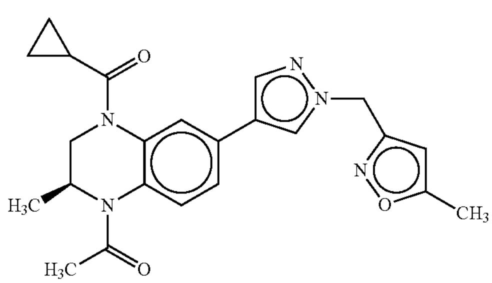 | 420 | 1.12 |
| I-670 | 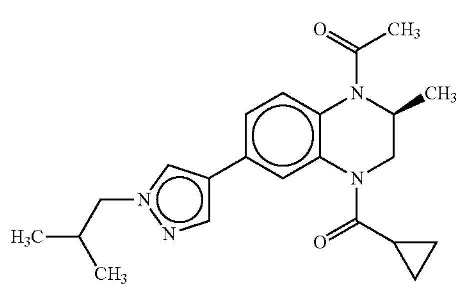 | 381 | 1.3 |

TABLE 11-continued
| Example | Structure | LC-MS [M + 1]+ | HPLC RT (min) |
|---|---|---|---|
| I-671 | 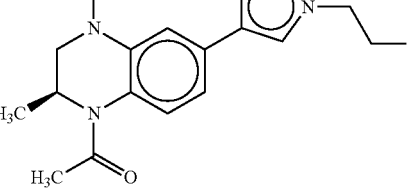 | 371 | 1.01 |
| I-672 | 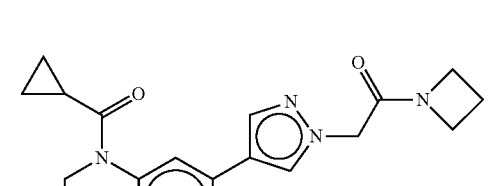 | 422 | 0.86 |
| I-673 | 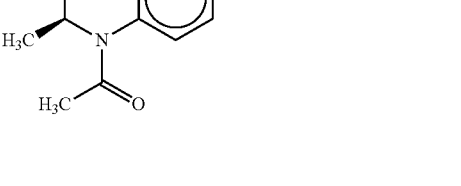 | 383 | 0.85 |
| I-674 | 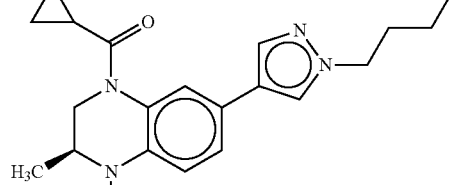 | 396 | 0.77 |
| I-675 | 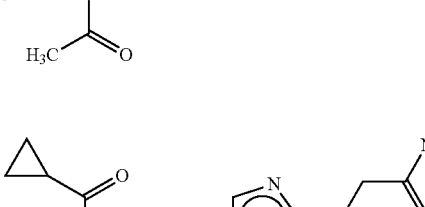 | 364 | 0.98 |

TABLE 11-continued

| Example | Structure | LC-MS [M + 1]+ | HPLC RT (min) |
| --- | --- | --- | --- |
| I-676 | 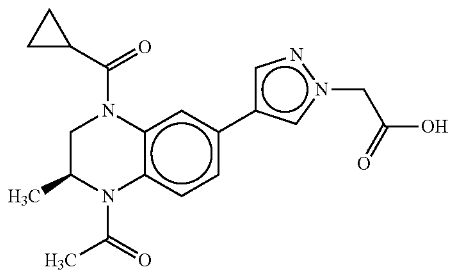 | 383 | 0.76 |
| I-677 | 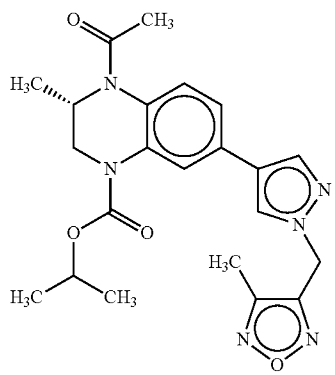 | 439 | 1.37 |
| I-678 | 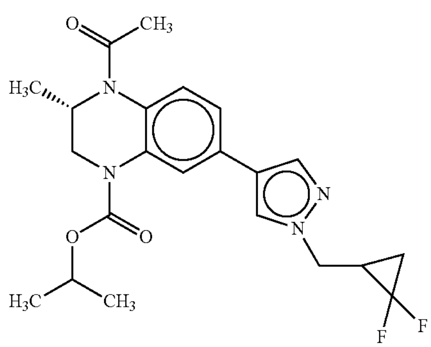 | 433 | 1.41 |
| I-679 | 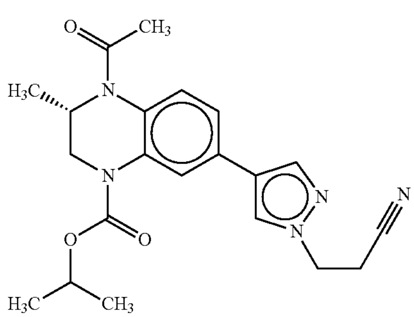 | 396 | 1.15 |

TABLE 11-continued

| Example | Structure | LC-MS [M + 1]+ | HPLC RT (min) |
|---|---|---|---|
| I-680 | 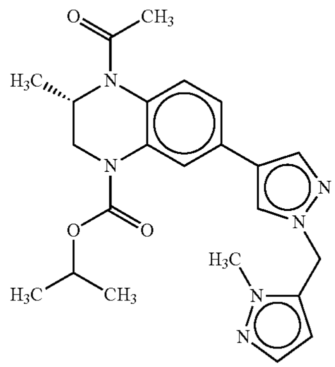 | 437 | 1.16 |
| I-681 | 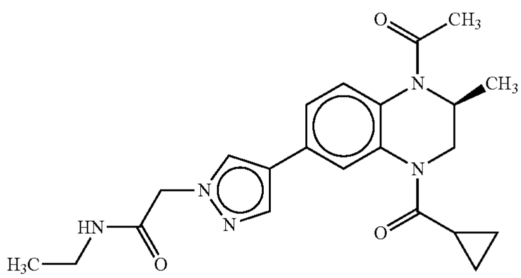 | 410 | 0.86 |
| I-682 | 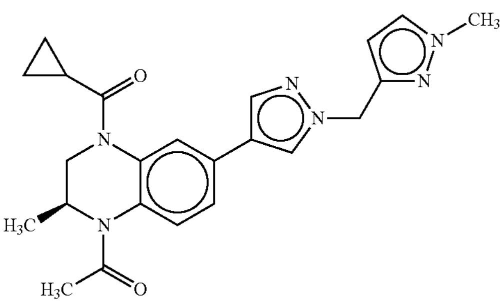 | 419 | 0.97 |
| I-683 | 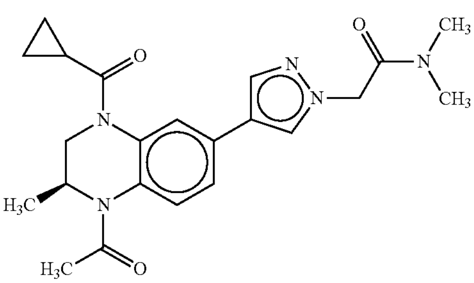 | 410 | 0.84 |
| I-684 | 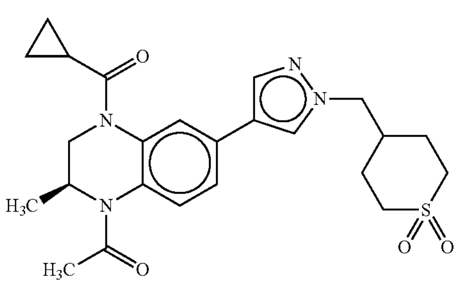 | 471 | 0.93 |

TABLE 11-continued

| Example | Structure | LC-MS [M + 1]+ | HPLC RT (min) |
|---|---|---|---|
| I-685 | 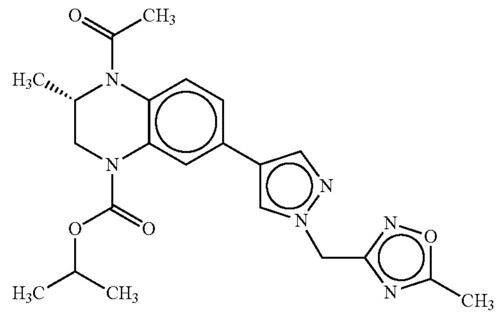 | 439 | 1.2 |
| I-686 | 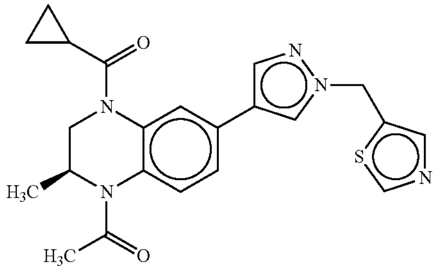 | 422 | 0.98 |

Example 268

Library Protocol H1

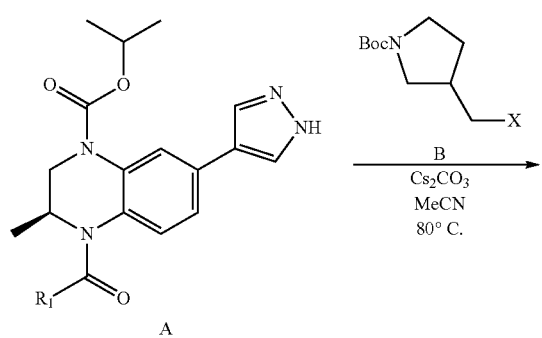

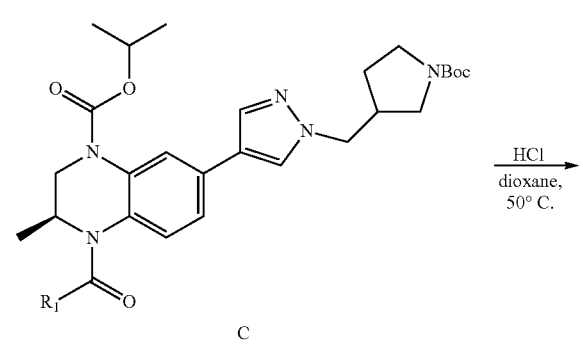

A 1.5 mL reaction vial was charged with pyrazole (A) (0.4 M solution in acetonitrile, 0.050 mL, 0.02 mmol, alkyl halide (B) (0.2 M solution in acetonitrile, 0.150 mL, 0.030 mmol), and cesium carbonate (0.033 g, 0.100 mmol). The reaction mixture was heated to 80° C. for 16 h on a heater shaker. The reaction mixture was concentrated, diluted with ethyl acetate (0.5 mL) and washed with brine (0.5 mL). The aqueous layer was separated and extracted with ethyl acetate (1 mL), and the organic layers were combined and concentrated under a stream of nitrogen and vacuum. The crude product (C) was dissolved in dioxane (0.3 mL), HCl (4.0 M in 1,4-dioxane, 0.15 mL, 0.6 mmol) was added, and the mixture stirred at 50° C. for 2 h. The reaction was concentrated and diluted with ethyl acetate (0.5 mL) and saturated aqueous sodium bicarbonate solution (0.5 mL). The aqueous layer was separated and extracted with ethyl acetate (1 mL), and the organic layers were combined and concentrated under a stream of nitrogen and vacuum. The crude product was purified by mass triggered preparatory HPLC. The product-containing fractions were combined and concentrated in a Genevac to afford the desired product.

The following compounds in Table 12 were synthesized according to the above protocol:

TABLE 12

| Example | Structure | LC-MS [M + 1]+ | HPLC RT (min) |
|---|---|---|---|
| I-687 | 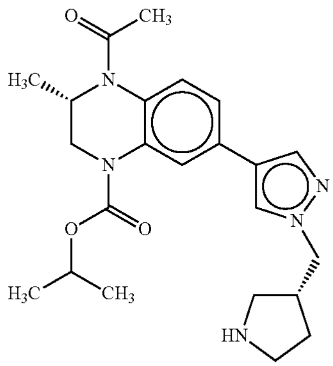 | 426 | 0.86 |
| I-688 | 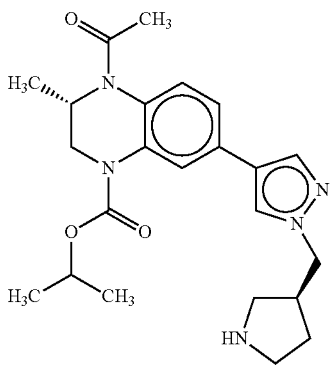 | 426 | 0.86 |
| I-689 | 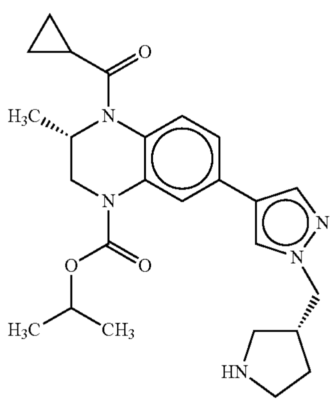 | 452 | 1 |
| I-690 | 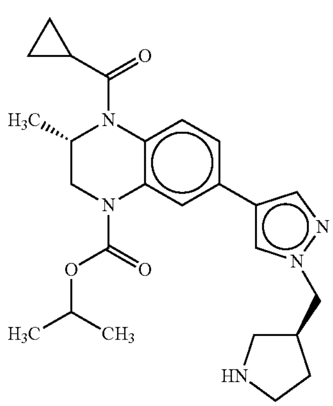 | 452 | 1.01 |

TABLE 12-continued

| Example | Structure | LC-MS [M + 1]+ | HPLC RT (min) |
|---|---|---|---|
| I-691 | 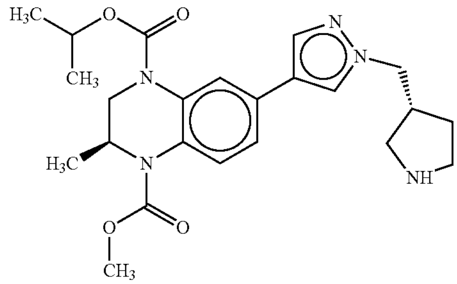 | 442 | 1.03 |
| I-692 | 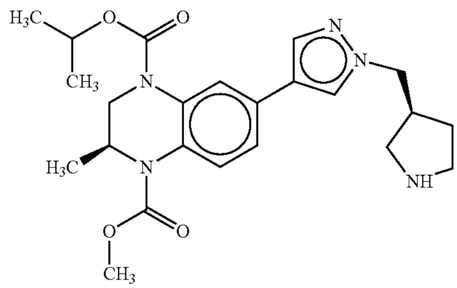 | 442 | 1.04 |

Example 269

Library Protocol I

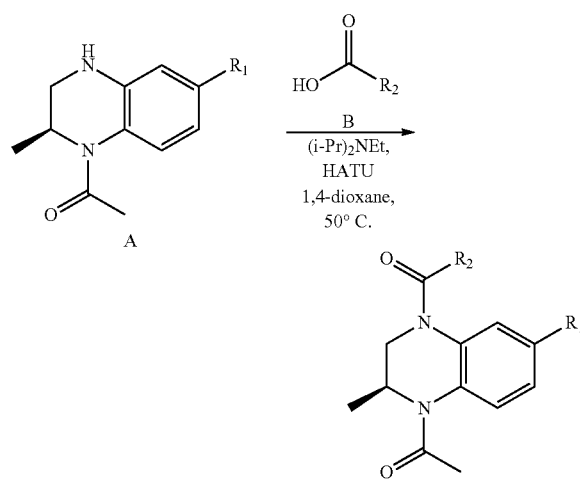

A 1.5 mL reaction vial was charged with benzopiperazine (A) (0.2M solution in 1,4-dioxane, 100 µL, 0.02 mmol) and the carboxylic acid (B) (0.2M solution in 1,4-dioxane with 10% N,N-diisopropylethylamine, 300 µL, 0.06 mmol). HATU (0.2 M solution in acetonitrile, 300 µL, 0.06 mmol) was added and the reaction was heated to 50° C. on a heater shaker for 2 hrs. The reaction was diluted with ethyl acetate and washed with saturated aqueous sodium bicarbonate solution. The aqueous layer was separated and extracted with ethyl acetate and the combined organic layers were concentrated under a stream of nitrogen and vacuum. The crude product was purified by mass triggered preparatory HPLC. The product-containing fractions were combined and concentrated in a Genevac to afford the desired product.

The following compounds in Table 13 were synthesized according to the above protocol:

TABLE 13

| Example | Structure | LC-MS [M + 1]+ | HPLC RT (min) |
|---|---|---|---|
| I-693 | 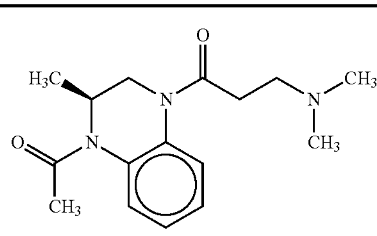 | 290 | 0.61 |

TABLE 13-continued

| Example | Structure | LC-MS [M + 1]+ | HPLC RT (min) |
|---------|-----------|----------------|---------------|
| I-694 | 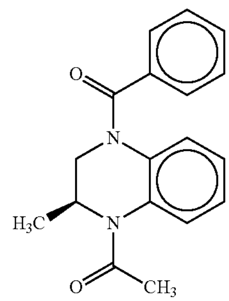 | 295 | 1.2 |
| I-695 | 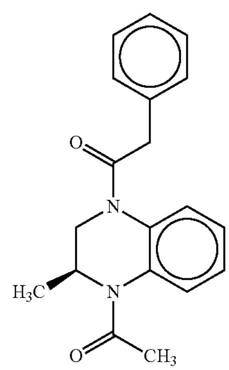 | 309 | 1.25 |
| I-696 | 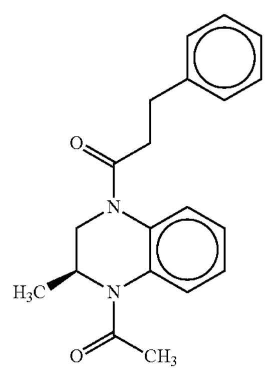 | 323 | 1.36 |
| I-697 | 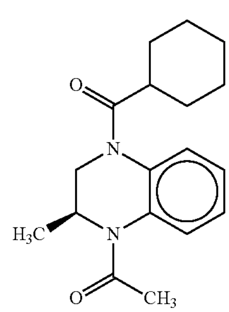 | 301 | 1.37 |

TABLE 13-continued
| Example | Structure | LC-MS [M + 1]+ | HPLC RT (min) |
|---------|-----------|----------------|---------------|
| I-698 | 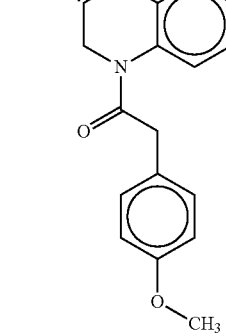 | 339 | 1.24 |
| I-699 | 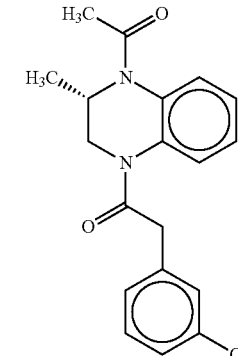 | 339 | 1.24 |
| I-700 | 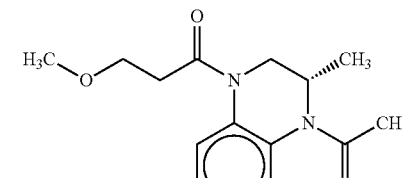 | 277 | 0.92 |
| I-701 | 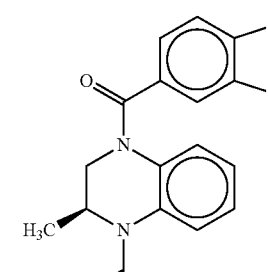 | 339 | 1.19 |

TABLE 13-continued

| Example | Structure | LC-MS [M + 1]+ | HPLC RT (min) |
|---|---|---|---|
| I-702 | 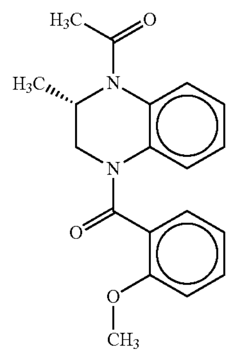 | 325 | 1.19 |
| I-703 | 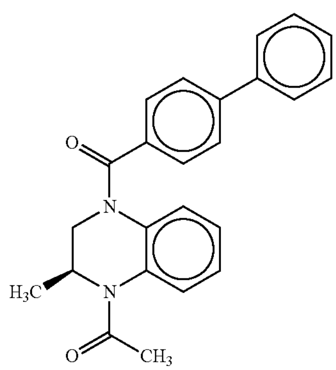 | 371 | 1.56 |
| I-704 | 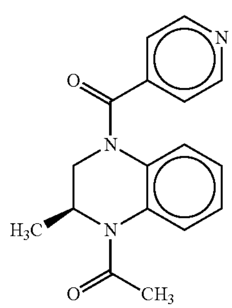 | 296 | 0.84 |
| I-705 | 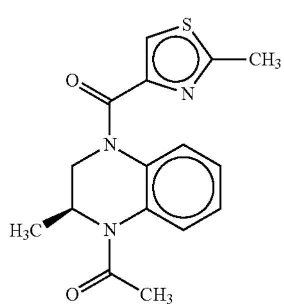 | 316 | 1.02 |

TABLE 13-continued

| Example | Structure | LC-MS [M + 1]+ | HPLC RT (min) |
|---------|-----------|----------------|---------------|
| I-706 | 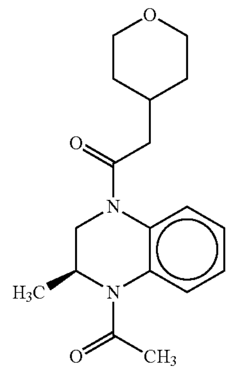 | 317 | 0.98 |
| I-707 | 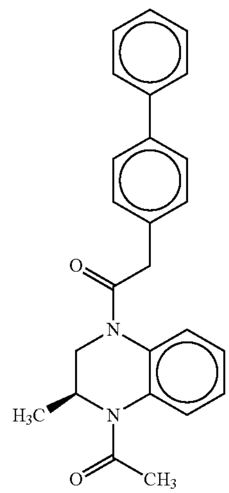 | 385 | 1.59 |
| I-708 | 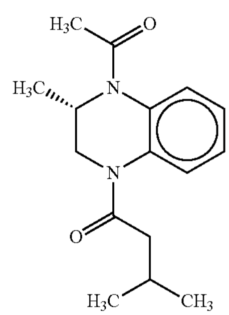 | 275 | 1.21 |
| I-709 | 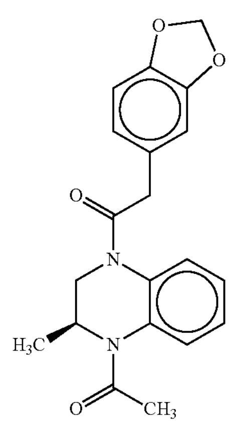 | 353 | 1.22 |

TABLE 13-continued

| Example | Structure | LC-MS [M + 1]+ | HPLC RT (min) |
|---|---|---|---|
| I-710 | 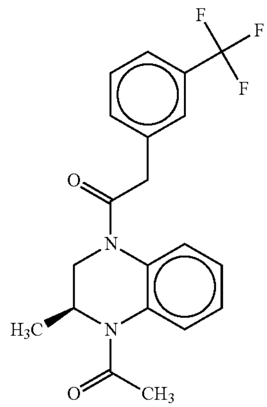 | 377 | 1.46 |
| I-711 | 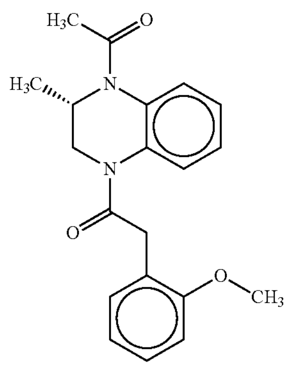 | 339 | 1.27 |
| I-712 | 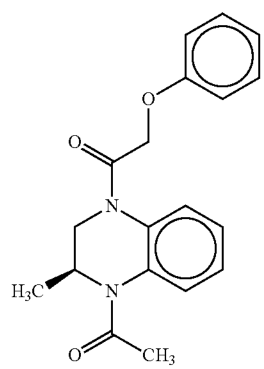 | 325 | 1.25 |
| I-713 | 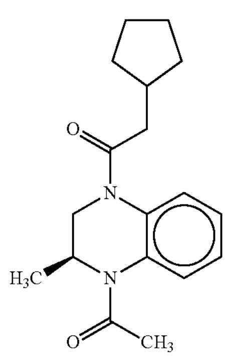 | 301 | 1.37 |

TABLE 13-continued

| Example | Structure | LC-MS [M + 1]+ | HPLC RT (min) |
|---|---|---|---|
| I-714 | 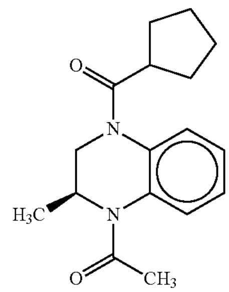 | 287 | 1.28 |
| I-715 | 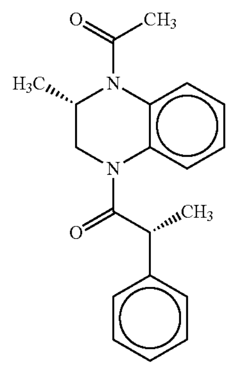 | 323 | 1.35 |
| I-716 | 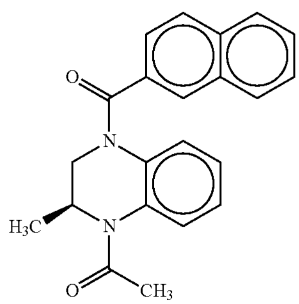 | 345 | 1.43 |
| I-717 | 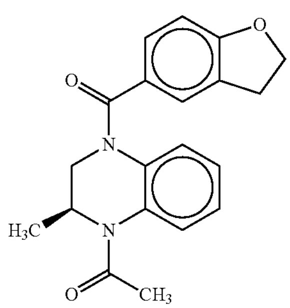 | 337 | 1.21 |
| I-718 | 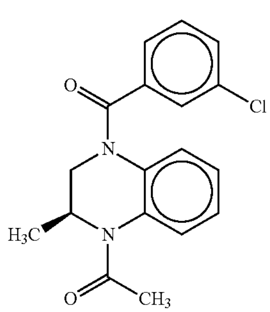 | 329 | 1.37 |

TABLE 13-continued

| Example | Structure | LC-MS [M + 1]+ | HPLC RT (min) |
|---------|-----------|----------------|---------------|
| I-719 | 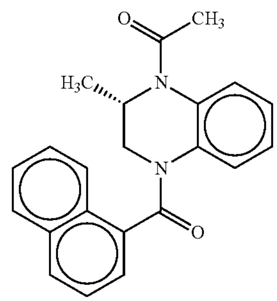 | 345 | 1.38 |
| I-720 | 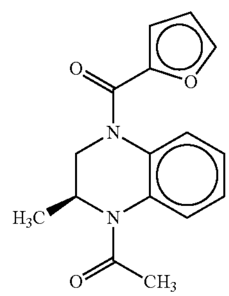 | 285 | 1.06 |
| I-721 | 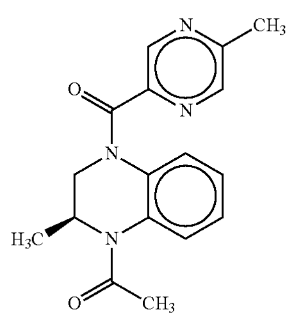 | 311 | 0.94 |
| I-722 | 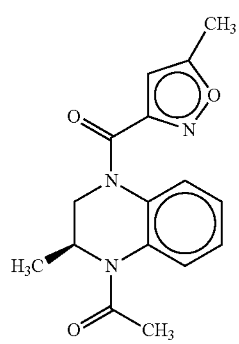 | 300 | 1.09 |

TABLE 13-continued

| Example | Structure | LC-MS [M + 1]+ | HPLC RT (min) |
|---|---|---|---|
| I-723 | 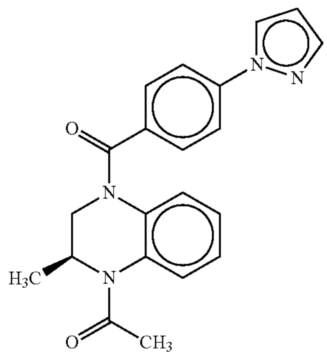 | 361 | 1.22 |
| I-724 | 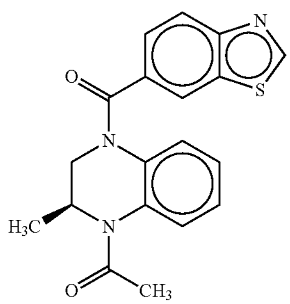 | 352 | 1.08 |
| I-725 | 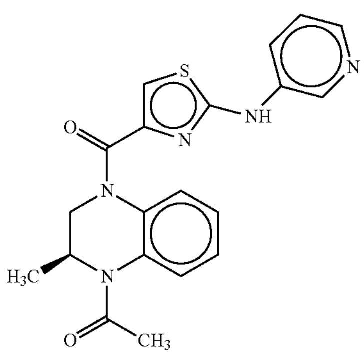 | 394 | 0.85 |
| I-726 | 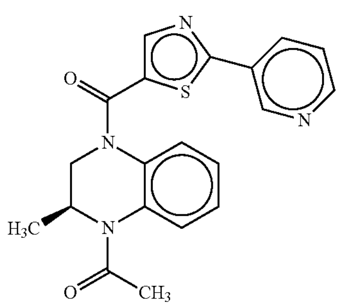 | 379 | 1.06 |

TABLE 13-continued

| Example | Structure | LC-MS [M + 1]+ | HPLC RT (min) |
|---|---|---|---|
| I-727 | 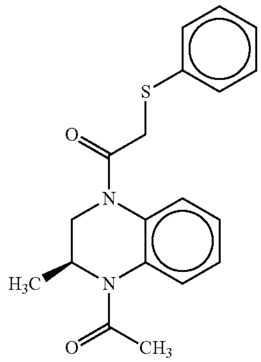 | 341 | 1.34 |
| I-728 | 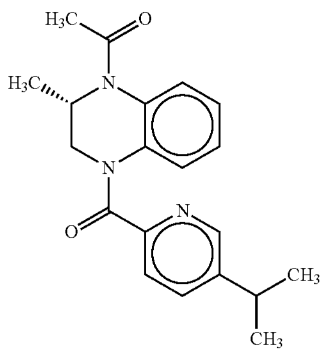 | 338 | 1.3 |
| I-729 | 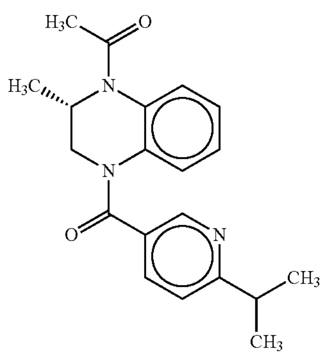 | 338 | 1.19 |
| I-730 | 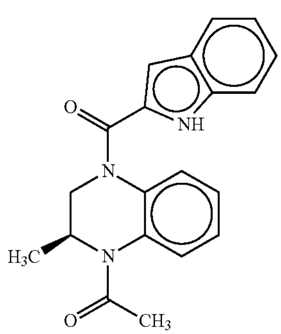 | 334 | 1.32 |

TABLE 13-continued

| Example | Structure | LC-MS [M + 1]+ | HPLC RT (min) |
|---|---|---|---|
| I-731 | 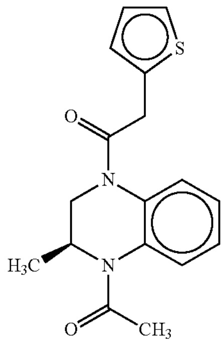 | 315 | 1.21 |
| I-732 | 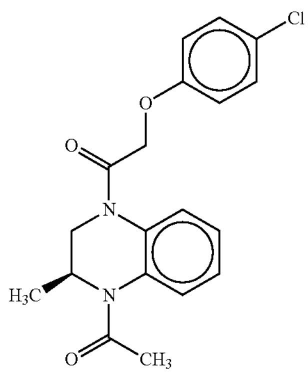 | 359 | 1.41 |
| I-733 | 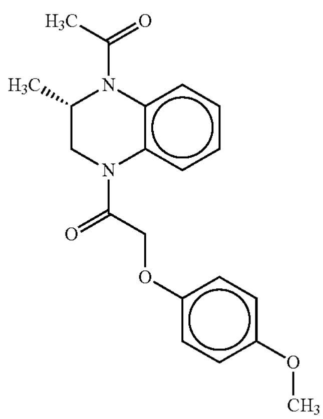 | 355 | 1.23 |
| I-734 | 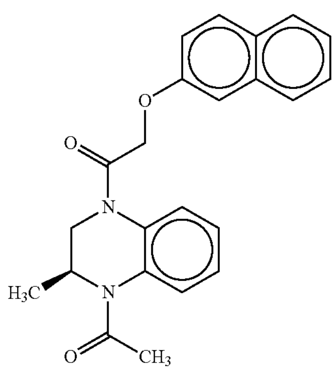 | 375 | 1.47 |

TABLE 13-continued

| Example | Structure | LC-MS [M + 1]+ | HPLC RT (min) |
|---|---|---|---|
| I-735 | 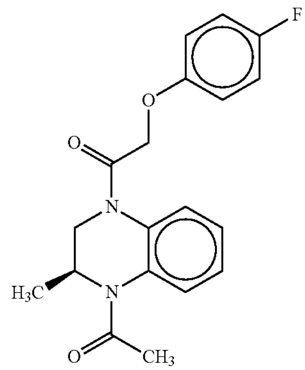 | 343 | 1.28 |
| I-736 | 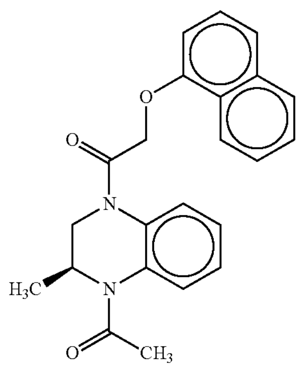 | 375 | 1.49 |
| I-737 | 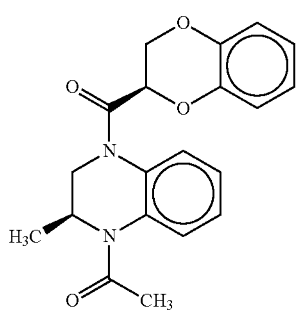 | 353 | 1.37 |
| I-738 | 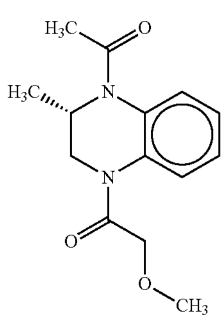 | 263 | 0.84 |

TABLE 13-continued
| Example | Structure | LC-MS [M + 1]+ | HPLC RT (min) |
|---|---|---|---|
| I-739 | 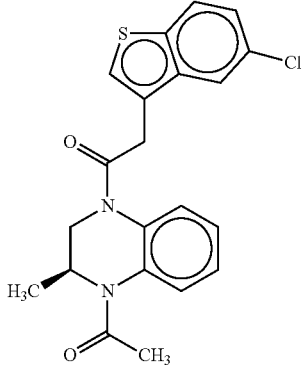 | 399 | 1.55 |
| I-740 | 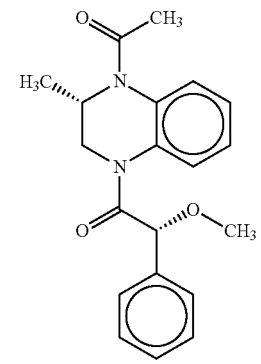 | 339 | 1.13 |
| I-741 | 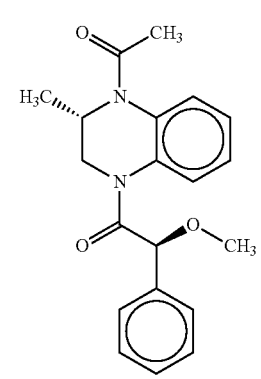 | 339 | 1.23 |
| I-742 | 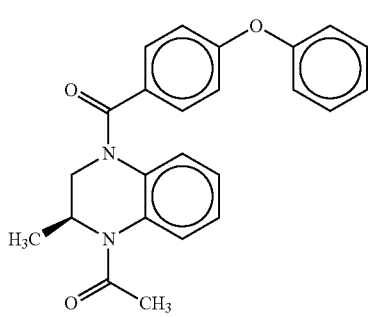 | 387 | 1.57 |

TABLE 13-continued

| Example | Structure | LC-MS [M + 1]+ | HPLC RT (min) |
|---|---|---|---|
| I-743 | 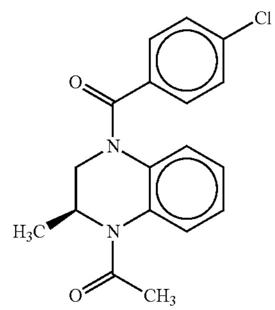 | 329 | 1.37 |
| I-744 | 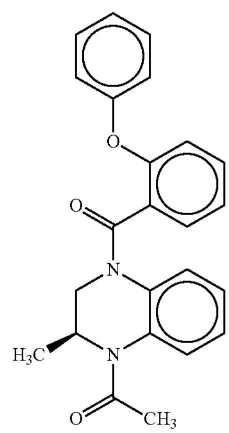 | 387 | 1.5 |
| I-745 | 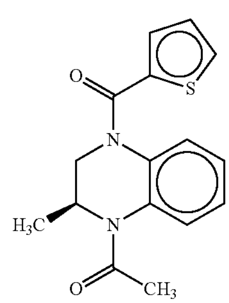 | 301 | 1.18 |
| I-746 | 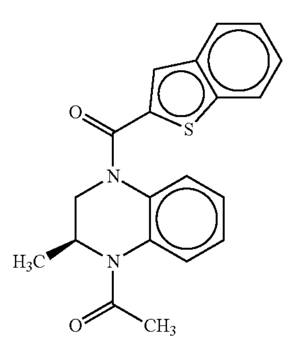 | 351 | 1.45 |

TABLE 13-continued

| Example | Structure | LC-MS [M + 1]+ | HPLC RT (min) |
|---------|-----------|----------------|---------------|
| I-747 | 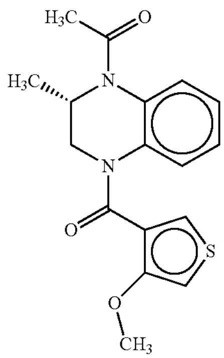 | 331 | 1.15 |
| I-748 | 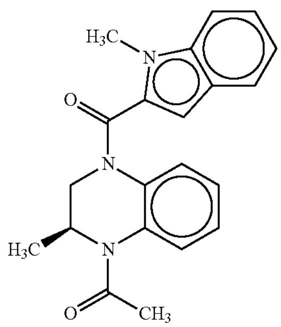 | 348 | 1.41 |
| I-749 | 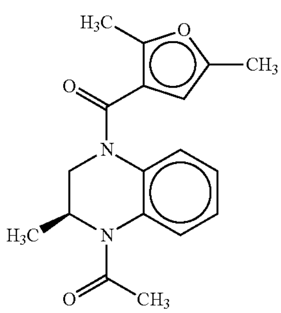 | 313 | 1.28 |
| I-750 | 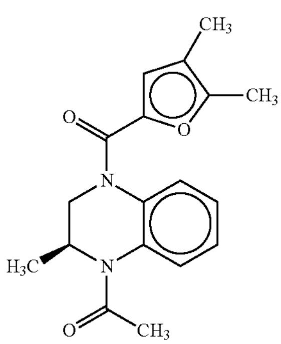 | 313 | 1.28 |

TABLE 13-continued

| Example | Structure | LC-MS [M + 1]+ | HPLC RT (min) |
|---------|-----------|----------------|---------------|
| I-751 | 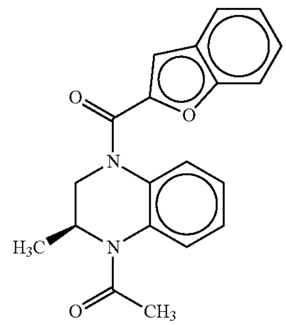 | 335 | 1.36 |
| I-752 | 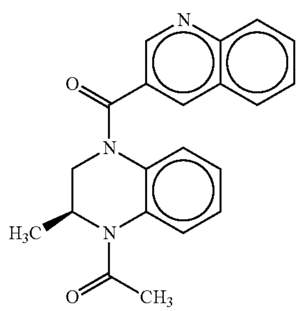 | 346 | 1.14 |
| I-753 | 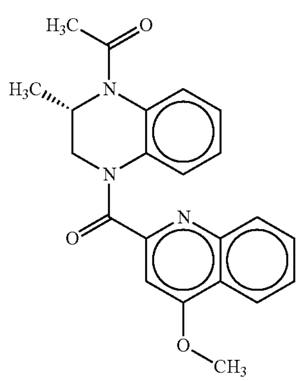 | 376 | 1.32 |
| I-754 | 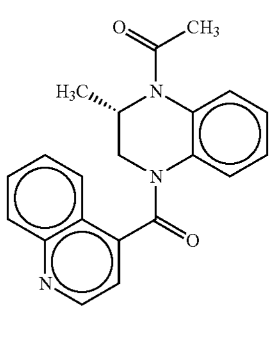 | 346 | 1.06 |

TABLE 13-continued

| Example | Structure | LC-MS [M + 1]+ | HPLC RT (min) |
|---|---|---|---|
| I-755 | 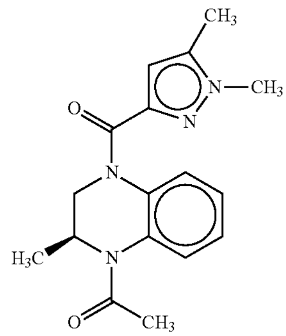 | 313 | 0.97 |
| I-756 | 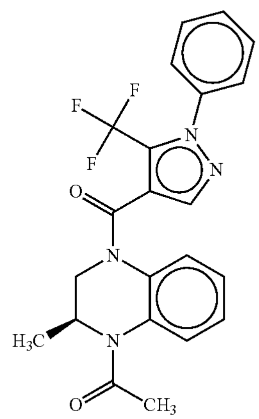 | 429 | 1.44 |
| I-757 | 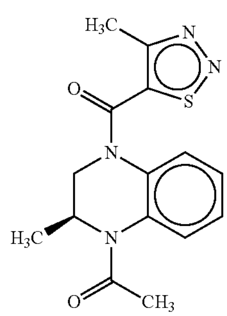 | 317 | 1.08 |
| I-758 | 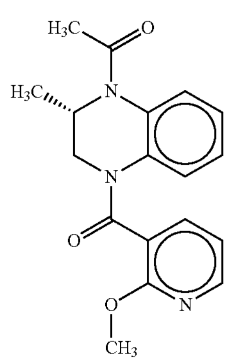 | 326 | 1.05 |

TABLE 13-continued

| Example | Structure | LC-MS [M + 1]+ | HPLC RT (min) |
|---------|-----------|----------------|---------------|
| I-759 | 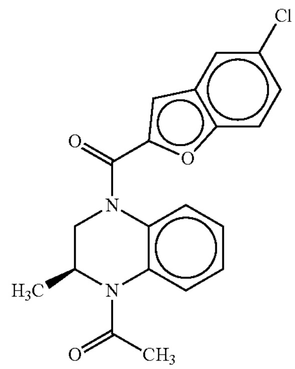 | 369 | 1.51 |
| I-760 | 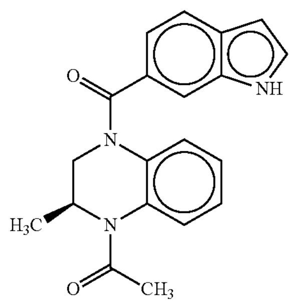 | 334 | 1.2 |
| I-761 | 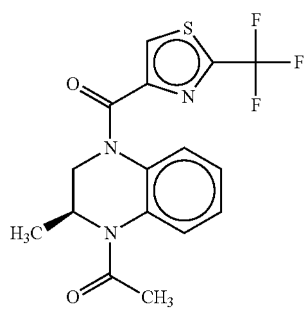 | 370 | 1.34 |
| I-762 | 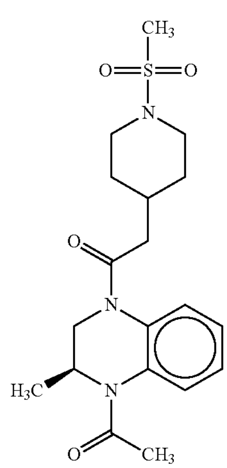 | 394 | 1.03 |

TABLE 13-continued

| Example | Structure | LC-MS [M + 1]+ | HPLC RT (min) |
|---------|-----------|----------------|---------------|
| I-763 | 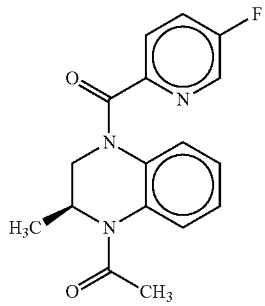 | 314 | 1.07 |
| I-764 | 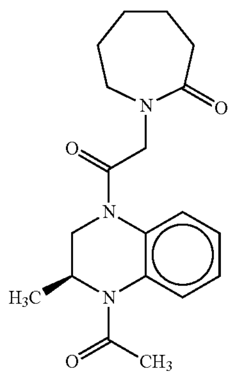 | 344 | 0.97 |
| I-765 | 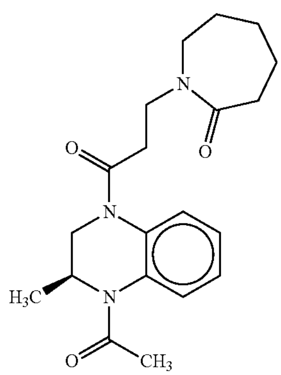 | 358 | 0.97 |
| I-766 | 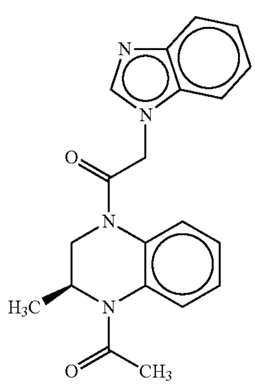 | 349 | 0.87 |

TABLE 13-continued

| Example | Structure | LC-MS [M + 1]+ | HPLC RT (min) |
|---------|-----------|----------------|---------------|
| I-767 | 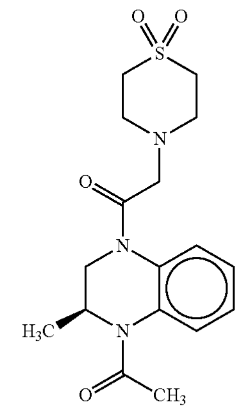 | 366 | 0.83 |
| I-768 | 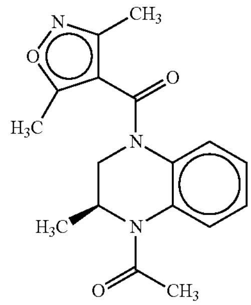 | 314 | 1.06 |
| I-769 | 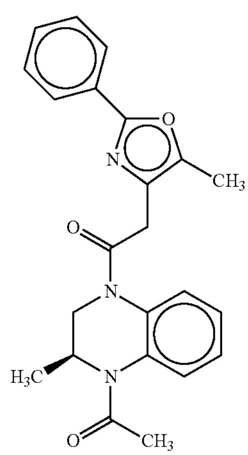 | 390 | 1.39 |
| I-770 | 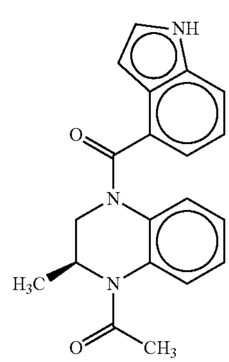 | 334 | 1.12 |

TABLE 13-continued

| Example | Structure | LC-MS [M + 1]+ | HPLC RT (min) |
|---------|-----------|----------------|---------------|
| I-771 | 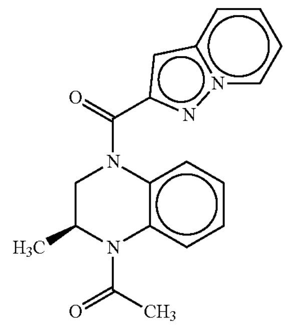 | 335 | 1.11 |
| I-772 | 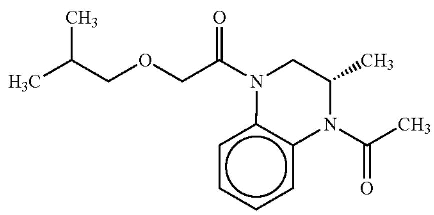 | 305 | 1.27 |
| I-773 | 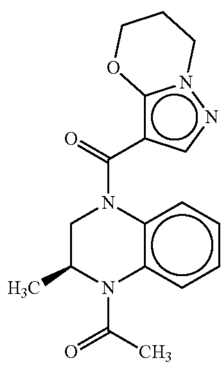 | 341 | 0.86 |
| I-774 | 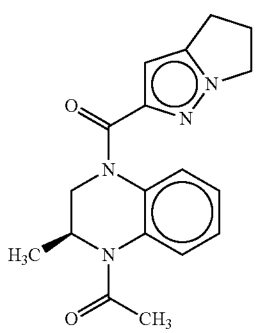 | 325 | 0.99 |
| I-775 | 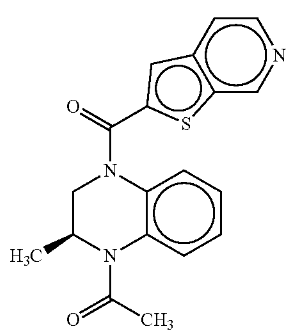 | 352 | 0.93 |

TABLE 13-continued

| Example | Structure | LC-MS [M + 1]+ | HPLC RT (min) |
|---|---|---|---|
| I-776 | 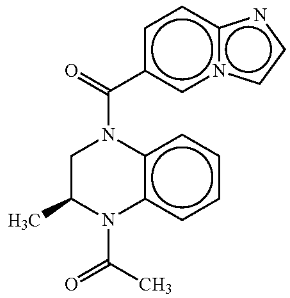 | 335 | 0.67 |
| I-777 | 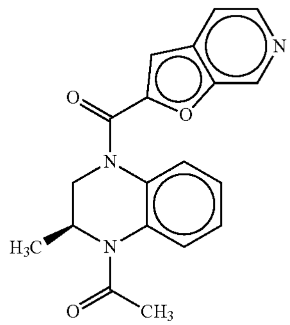 | 336 | 0.91 |
| I-778 | 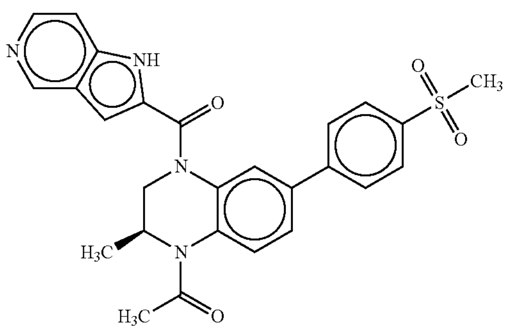 | 489 | 0.84 |
| I-779 | 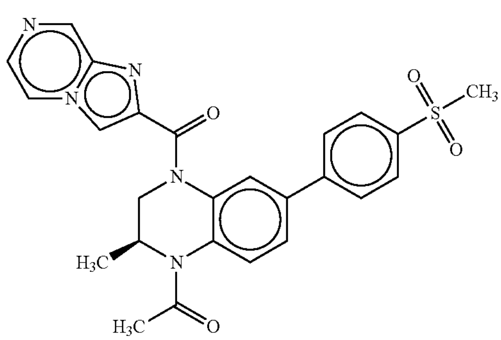 | 490 | 0.96 |

TABLE 13-continued

| Example | Structure | LC-MS [M + 1]+ | HPLC RT (min) |
|---|---|---|---|
| I-780 | 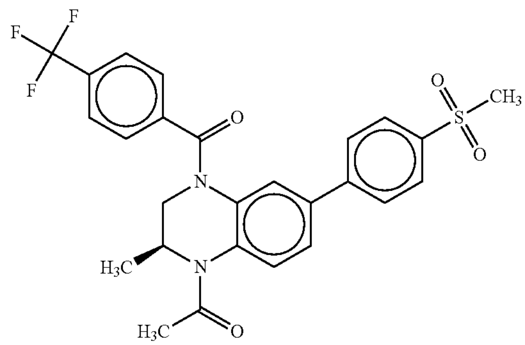 | 534 | 1.42 |
| I-781 | 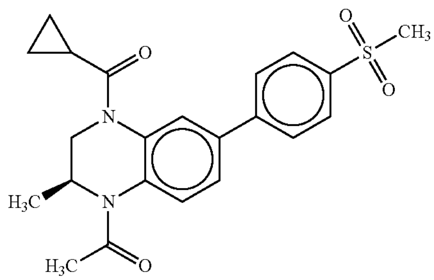 | 413 | 1.15 |
| I-782 | 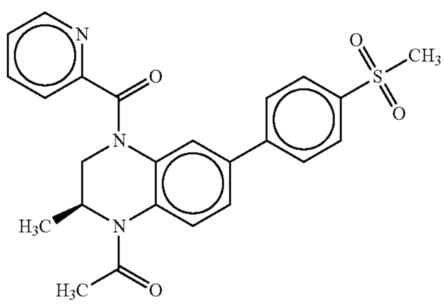 | 450 | 1.08 |
| I-783 | 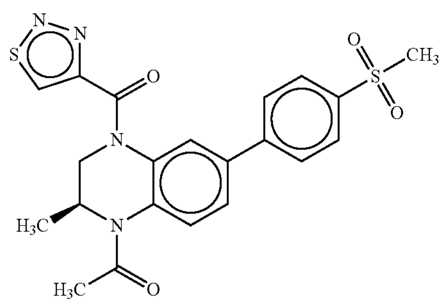 | 457 | 1.1 |
| I-784 | 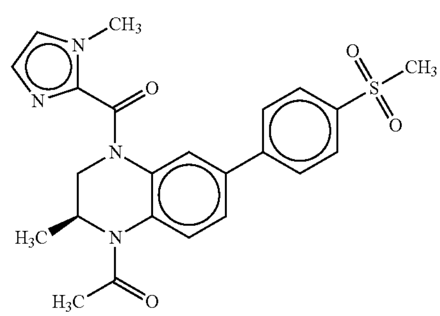 | 453 | 1.01 |

TABLE 13-continued

| Example | Structure | LC-MS [M + 1]+ | HPLC RT (min) |
|---------|-----------|----------------|---------------|
| I-785 | 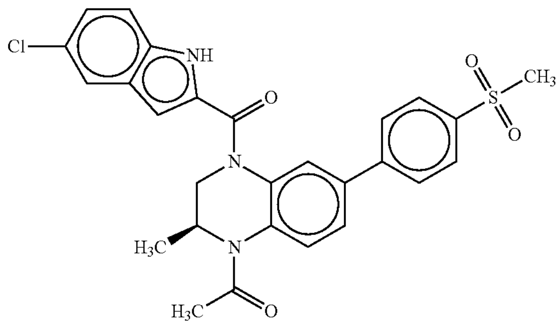 | 522 | 1.44 |
| I-786 | 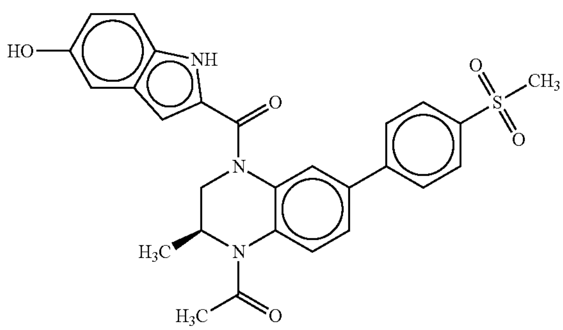 | 504 | 1.1 |
| I-787 | 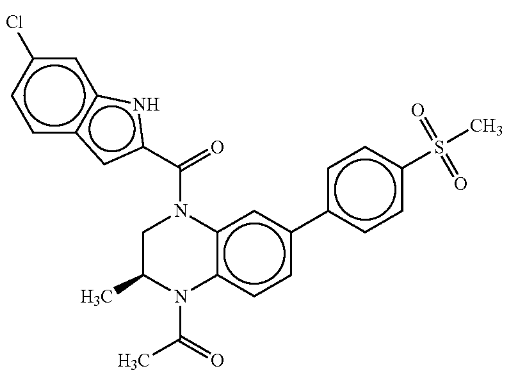 | 522 | 1.45 |
| I-788 | 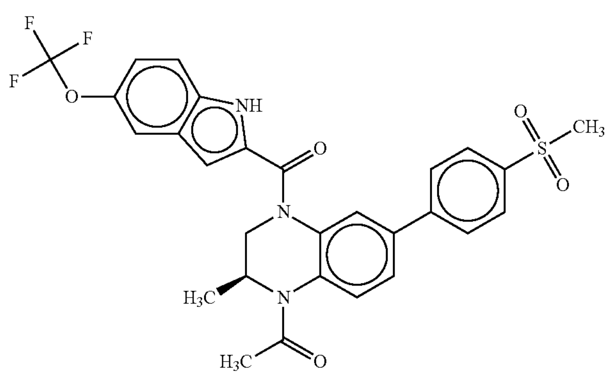 | 572 | 1.52 |

TABLE 13-continued

| Example | Structure | LC-MS [M + 1]+ | HPLC RT (min) |
|---|---|---|---|
| I-789 | 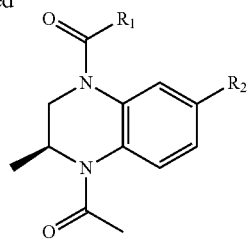 | 489 | 1.12 |
| I-790 | 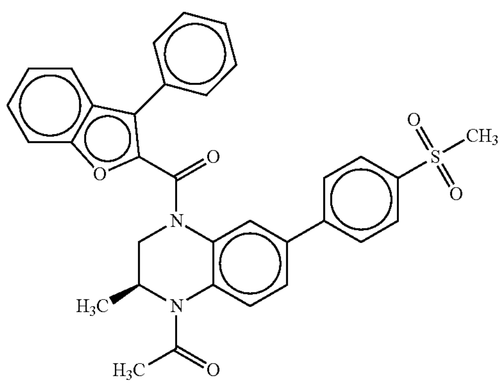 | 565 | 1.59 |

Example 270

Library Protocol J

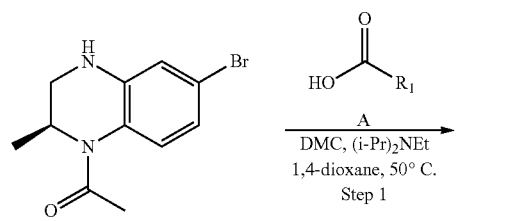

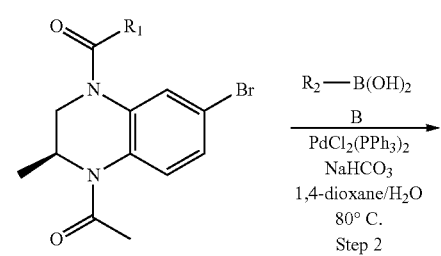

Step 1. A 1.5 mL reaction vial was charged with ((S)-1-(6-bromo-2-methyl-3,4-dihydroquinoxalin-1(2H)-yl)ethanone (0.2M solution in 1,4-dioxane, 150 μL, 0.03 mmol) and the carboxylic acid (A) (0.2M solution in 1,4-dioxane with 10% N,N-diisopropylethylamine, 450 μL, 0.09 mmol). 2-Chloro-1,3-dimethylimidazolidinium chloride (DMC, 0.2M solution in acetonitrile, 450 μL, 0.09 mmol) was added, and the reaction was heated to 50° C. on a heater shaker for 2 hrs. The reaction was diluted with ethyl acetate and washed with saturated aqueous sodium bicarbonate solution. The aqueous layer was separated and washed with ethyl acetate and the combined organic layers were concentrated under a stream of nitrogen and vacuum to yield the crude product which was used without purification.

Step 2. A 1.5 mL reaction vial was charged with the aryl bromide from above, 1,4-dioxane (100 μL), and the boronic acid (B) (0.2M solution in 1,2-dioxane, 180 μL, 0.036 mmol). Sodium bicarbonate (1 M solution in water, 90 μL, 0.09 mmol) was added, and the reaction mixture was purged with nitrogen. Bis(triphenylphosphine)palladium(II) dichloride (0.01M solution in dimethylformamide, 150 μL, 0.003 mmol) was added, the reaction was purged with nitrogen, and heated to 80° C. on a heater shaker overnight. The reaction was diluted with ethyl acetate and washed with a saturated aqueous sodium bicarbonate solution. The aqueous layer was separated and extracted with ethyl acetate and the combined organic layers were concentrated under a stream of nitrogen and vacuum. The crude product was purified by mass triggered preparatory HPLC. The product-containing fractions were combined and concentrated in a Genevac to afford the desired product.

The following compounds in Table 14 were synthesized according to the above protocol:

TABLE 14

| Example | Structure | LC-MS [M + 1]+ | HPLC RT (min) |
|---------|-----------|----------------|---------------|
| I-791 | 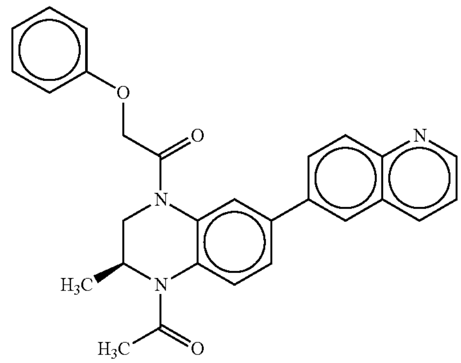 | 452 | 1.3 |
| I-792 | 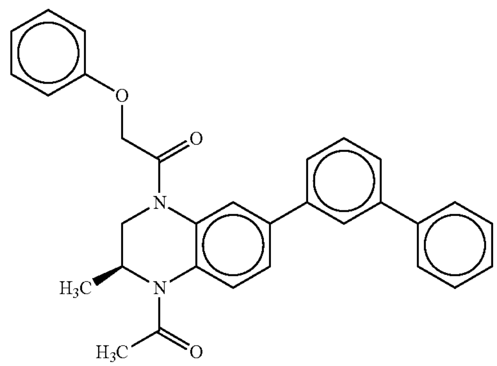 | 477 | 1.9 |
| I-793 | 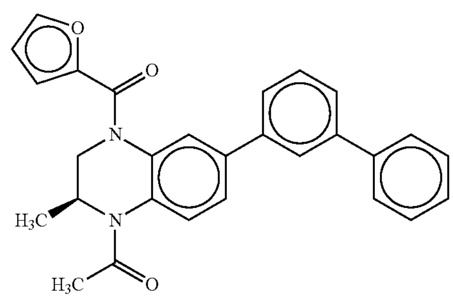 | 437 | 1.76 |
| I-794 | 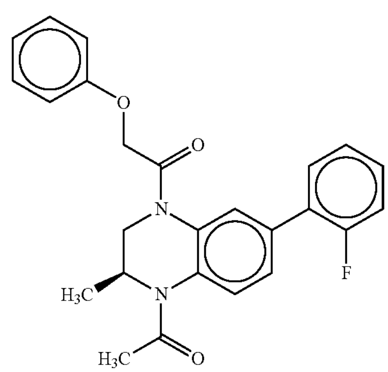 | 419 | 1.61 |

TABLE 14-continued

| Example | Structure | LC-MS [M + 1]+ | HPLC RT (min) |
|---|---|---|---|
| I-795 | 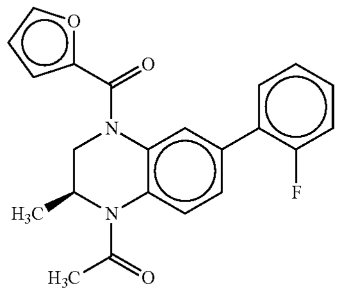 | 379 | 1.45 |
| I-796 | 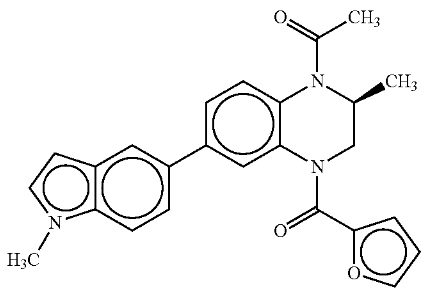 | 414 | 1.47 |
| I-797 | 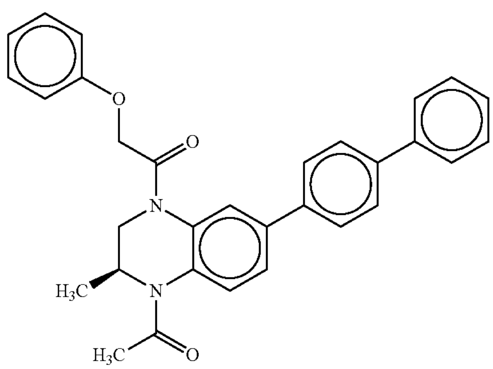 | 477 | 1.91 |
| I-798 | 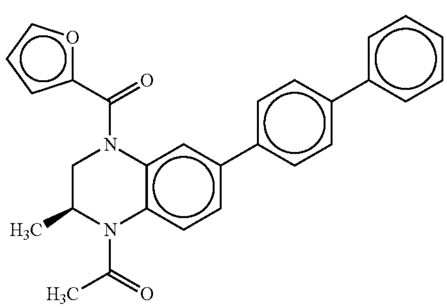 | 437 | 1.78 |
| I-799 | 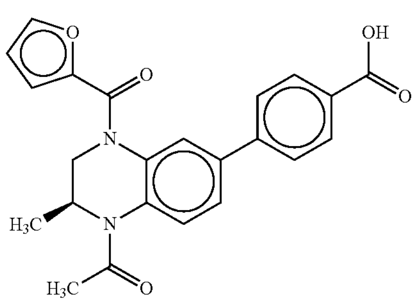 | 405 | 1.09 |

TABLE 14-continued

| Example | Structure | LC-MS [M + 1]+ | HPLC RT (min) |
|---|---|---|---|
| I-800 | 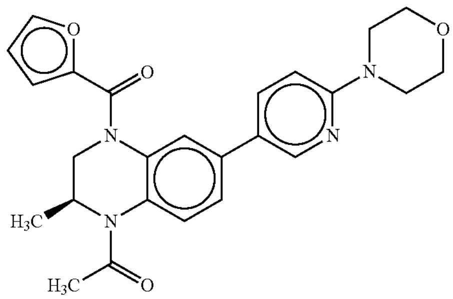 | 447 | 1.09 |
| I-801 | 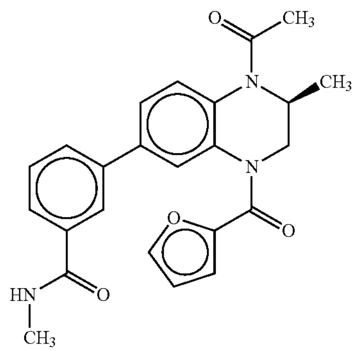 | 418 | 1.05 |
| I-802 | 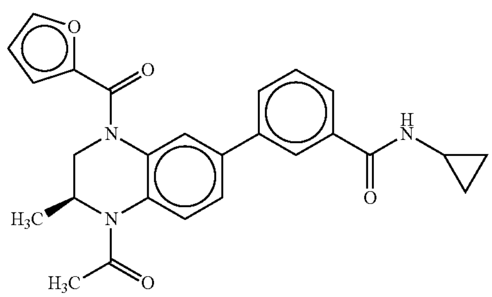 | 444 | 1.15 |
| I-803 | 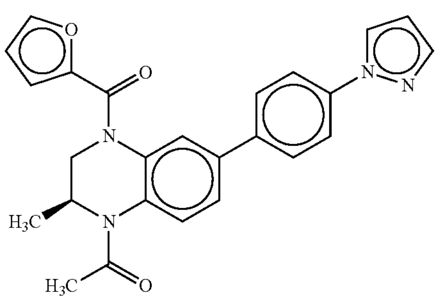 | 427 | 1.36 |
| I-804 | 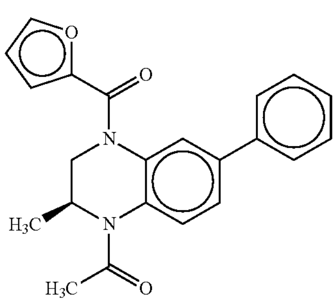 | 361 | 1.46 |

TABLE 14-continued

| Example | Structure | LC-MS [M + 1]+ | HPLC RT (min) |
|---|---|---|---|
| I-805 | 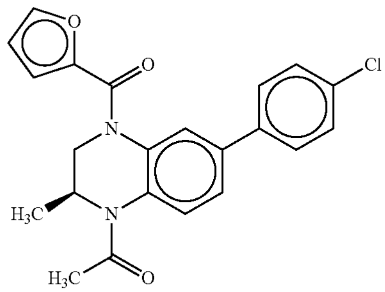 | 395 | 1.63 |
| I-806 | 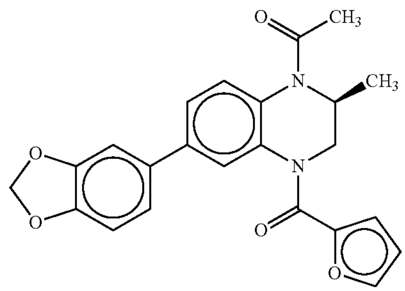 | 405 | 1.39 |
| I-807 | 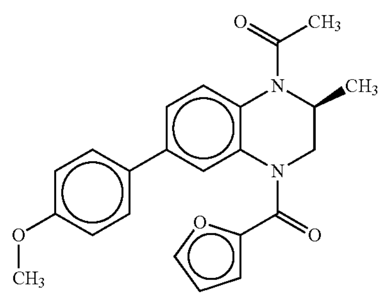 | 391 | 1.43 |
| I-808 | 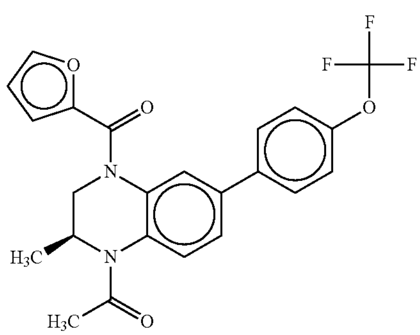 | 445 | 1.69 |
| I-809 | 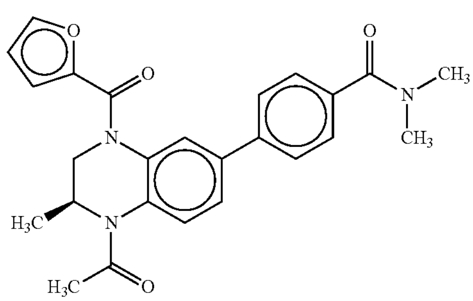 | 432 | 1.09 |

TABLE 14-continued

| Example | Structure | LC-MS [M + 1]+ | HPLC RT (min) |
|---|---|---|---|
| I-810 | 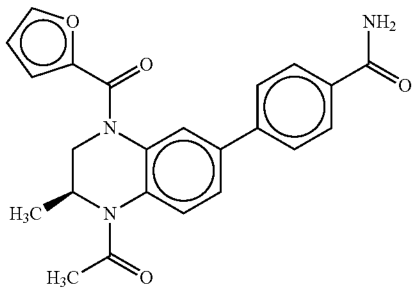 | 404 | 0.93 |
| I-811 | 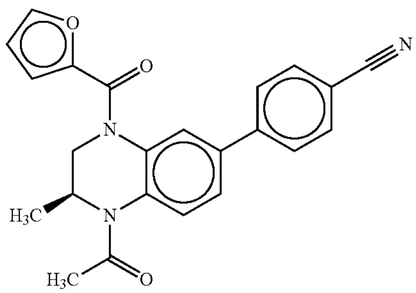 | 386 | 1.34 |
| I-812 | 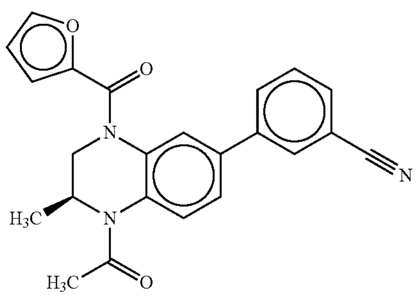 | 386 | 1.34 |
| I-813 | 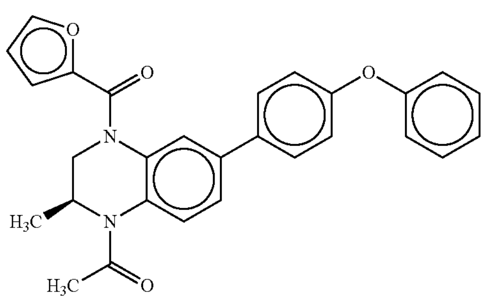 | 453 | 1.77 |
| I-814 | 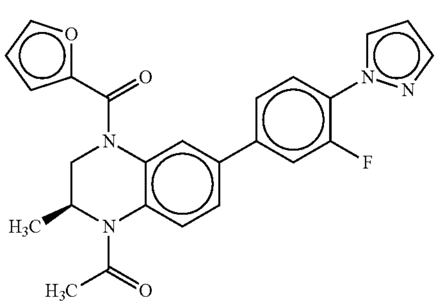 | 445 | 1.44 |

TABLE 14-continued

| Example | Structure | LC-MS [M + 1]+ | HPLC RT (min) |
|---|---|---|---|
| I-815 | 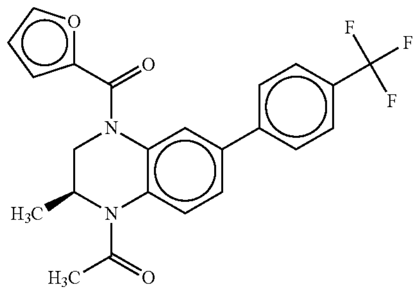 | 429 | 1.66 |
| I-816 | 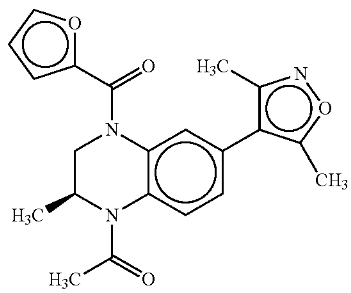 | 380 | 1.18 |
| I-817 | 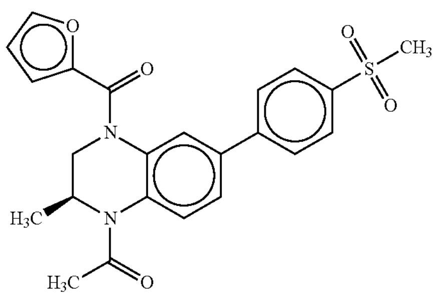 | 439 | 1.14 |
| I-818 | 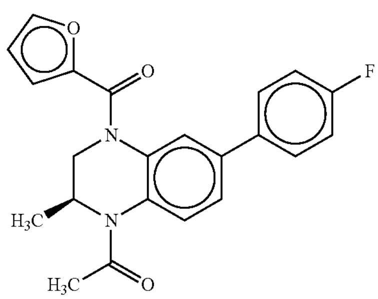 | 379 | 1.48 |
| I-819 | 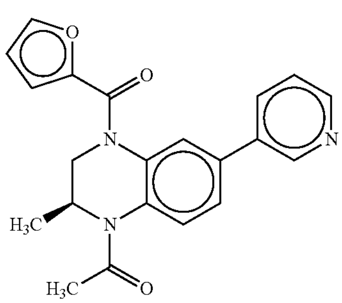 | 362 | 0.9 |

TABLE 14-continued

| Example | Structure | LC-MS [M + 1]+ | HPLC RT (min) |
|---|---|---|---|
| I-820 | 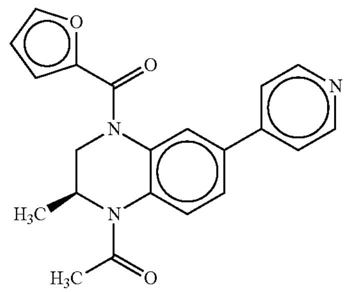 | 362 | 0.77 |
| I-821 | 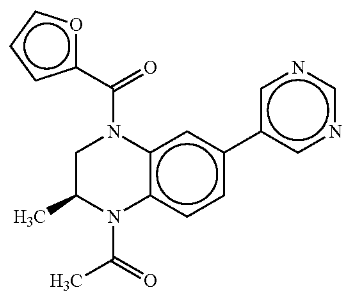 | 363 | 0.9 |
| I-822 | 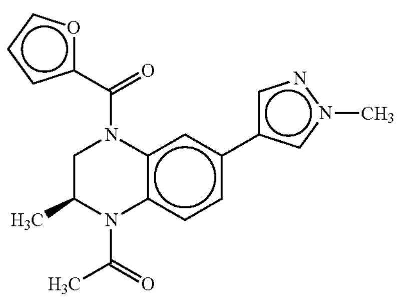 | 365 | 0.97 |
| I-823 | 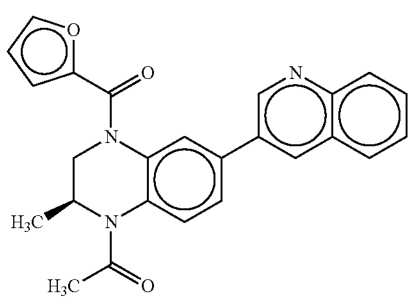 | 412 | 1.26 |
| I-824 | 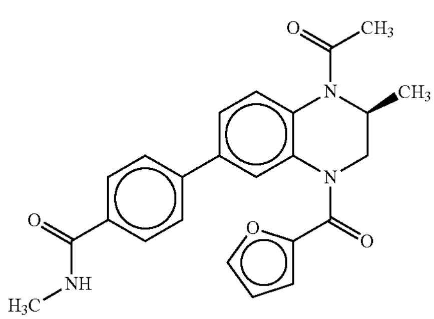 | 418 | 1 |

TABLE 14-continued

| Example | Structure | LC-MS [M + 1]+ | HPLC RT (min) |
|---|---|---|---|
| I-825 | 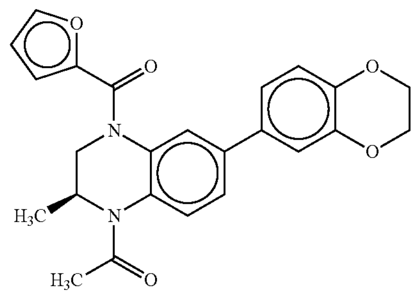 | 419 | 1.37 |
| I-826 | 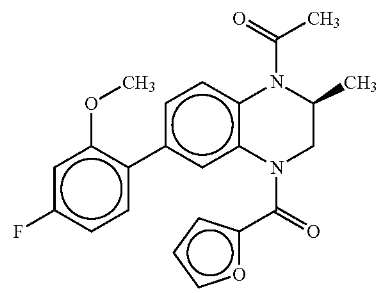 | 409 | 1.48 |
| I-827 | 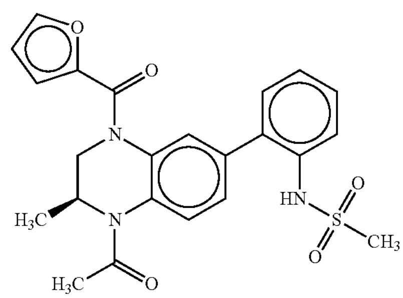 | 454 | 1.2 |
| I-828 | 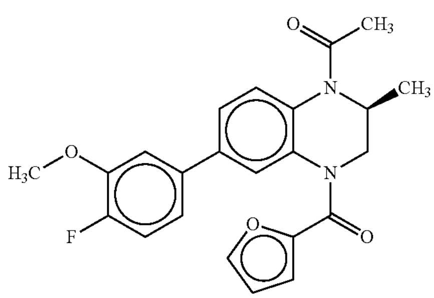 | 409 | 1.46 |
| I-829 | 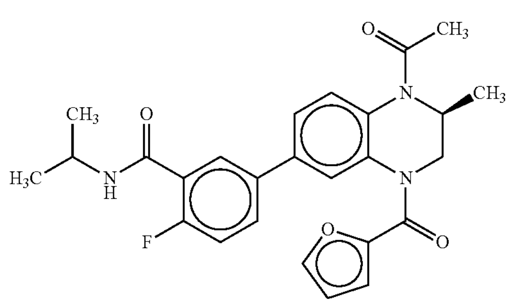 | 464 | 1.32 |

TABLE 14-continued

| Example | Structure | LC-MS [M + 1]+ | HPLC RT (min) |
|---------|-----------|----------------|---------------|
| I-830 | 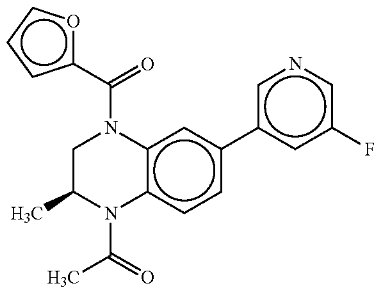 | 380 | 1.18 |
| I-831 | 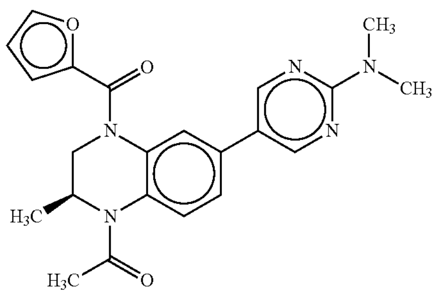 | 406 | 1.24 |
| I-832 | 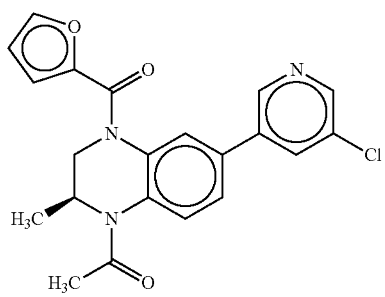 | 396 | 1.29 |
| I-833 | 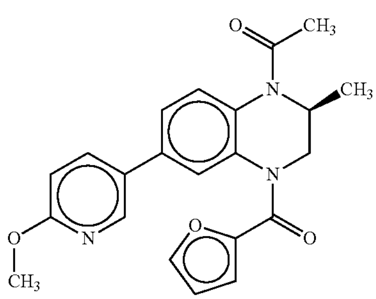 | 392 | 1.3 |
| I-834 | 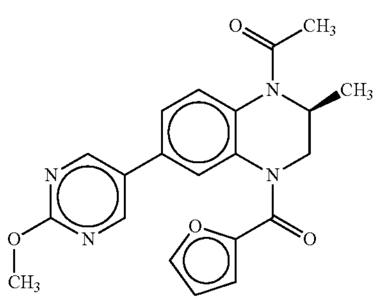 | 393 | 1.08 |

TABLE 14-continued

| Example | Structure | LC-MS [M + 1]+ | HPLC RT (min) |
|---------|-----------|----------------|---------------|
| I-835 | 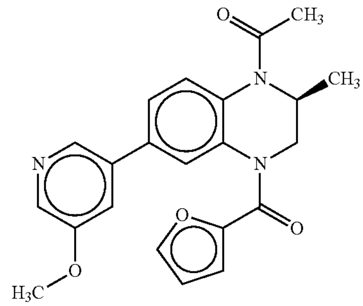 | 392 | 1.06 |
| I-836 | 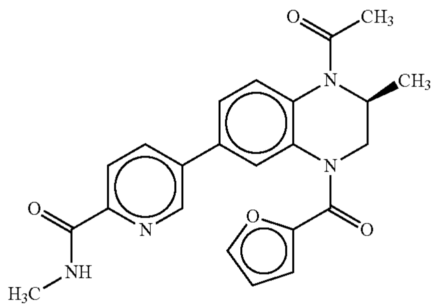 | 419 | 1.02 |
| I-837 | 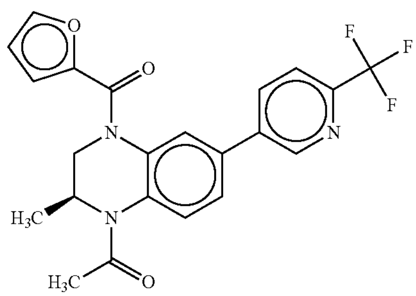 | 430 | 1.39 |
| I-838 | 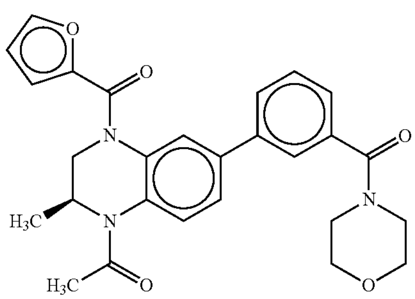 | 474 | 1.1 |
| I-839 | 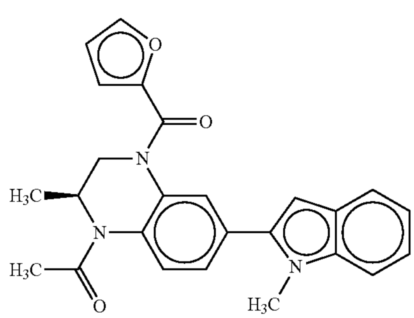 | 414 | 1.6 |

TABLE 14-continued

| Example | Structure | LC-MS [M + 1]+ | HPLC RT (min) |
|---------|-----------|----------------|---------------|
| I-840 | 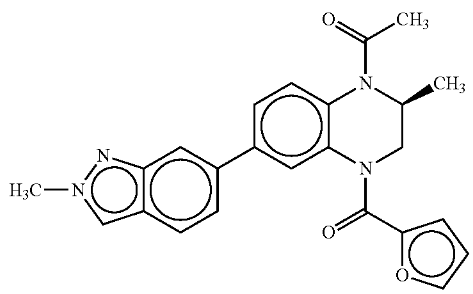 | 415 | 1.14 |
| I-841 | 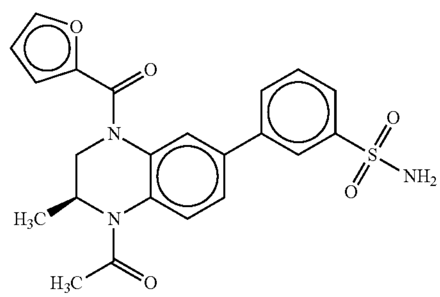 | 440 | 1.05 |
| I-842 | 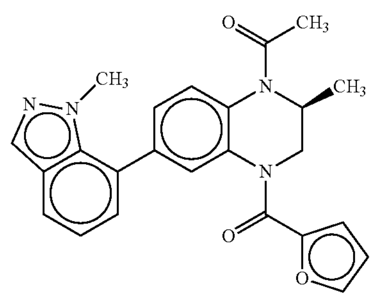 | 415 | 1.32 |
| I-843 | 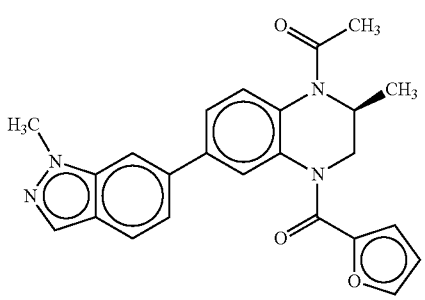 | 415 | 1.28 |
| I-844 | 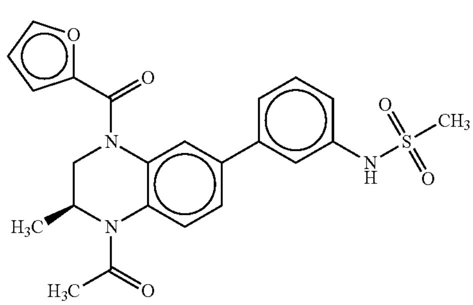 | 454 | 1.15 |

TABLE 14-continued

| Example | Structure | LC-MS [M + 1]+ | HPLC RT (min) |
|---|---|---|---|
| I-845 | 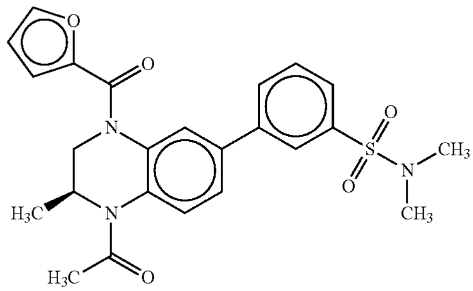 | 468 | 1.3 |
| I-846 | 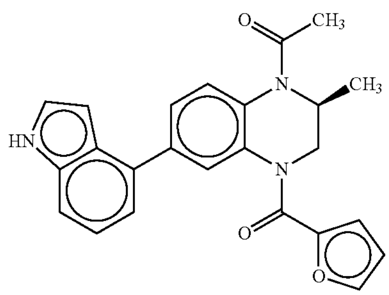 | 400 | 1.29 |
| I-847 | 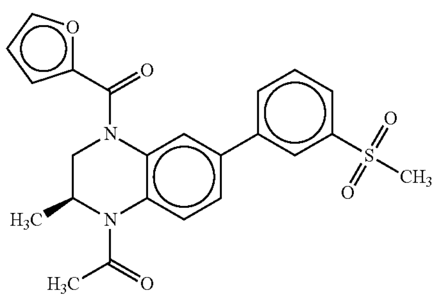 | 439 | 1.12 |
| I-848 | 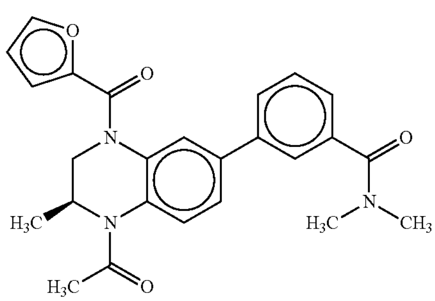 | 432 | 1.12 |
| I-849 | 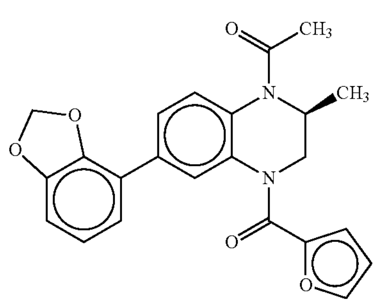 | 405 | 1.43 |

TABLE 14-continued

| Example | Structure | LC-MS [M + 1]+ | HPLC RT (min) |
| --- | --- | --- | --- |
| I-850 | 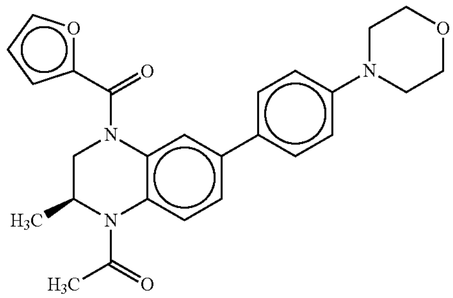 | 446 | 1.33 |
| I-851 | 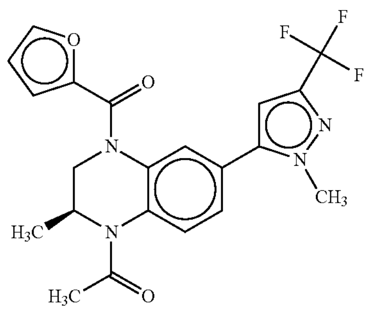 | 433 | 1.39 |
| I-852 | 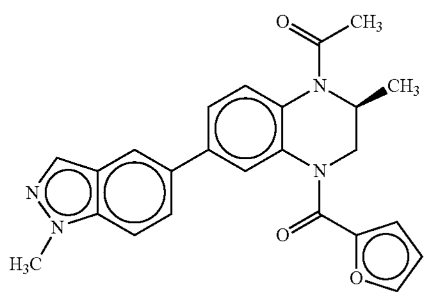 | 415 | 1.24 |
| I-853 | 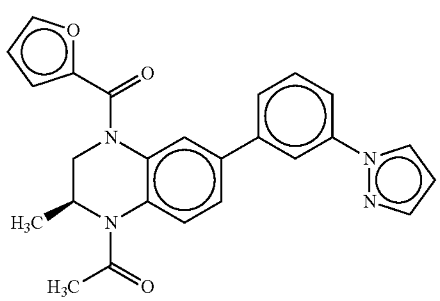 | 427 | 1.39 |
| I-854 | 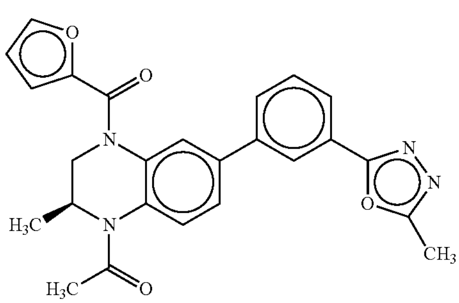 | 443 | 1.21 |

TABLE 14-continued

| Example | Structure | LC-MS [M + 1]+ | HPLC RT (min) |
|---|---|---|---|
| I-855 | 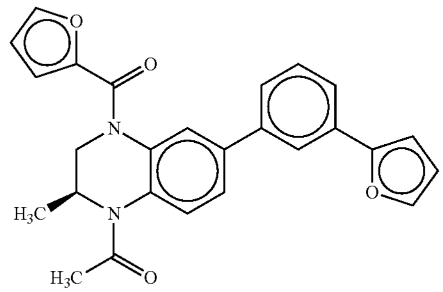 | 427 | 1.66 |
| I-856 | 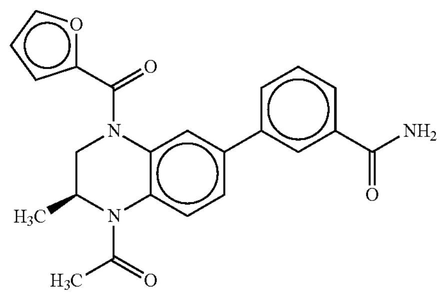 | 404 | 0.97 |
| I-857 | 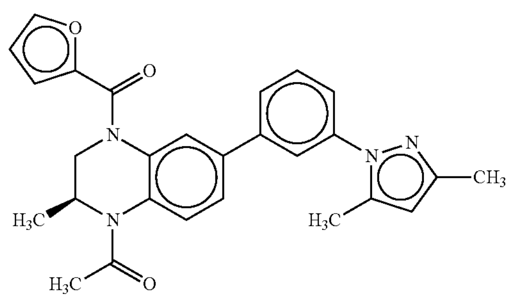 | 455 | 1.44 |
| I-858 | 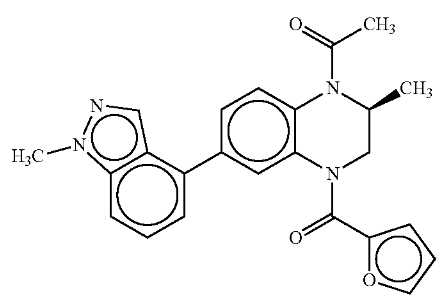 | 415 | 1.28 |
| I-859 | 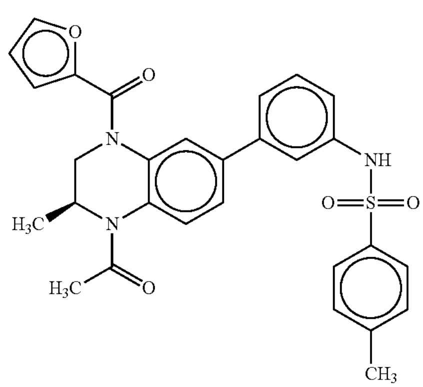 | 530 | 1.44 |

TABLE 14-continued

| Example | Structure | LC-MS [M + 1]+ | HPLC RT (min) |
|---------|-----------|----------------|---------------|
| I-860 | 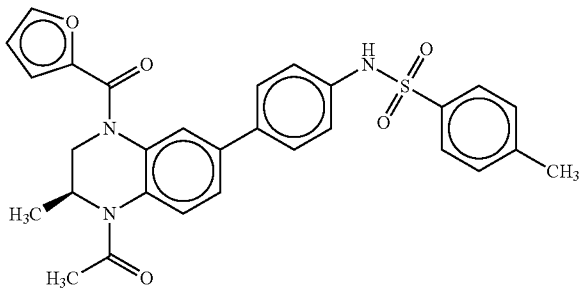 | 530 | 1.43 |
| I-861 | 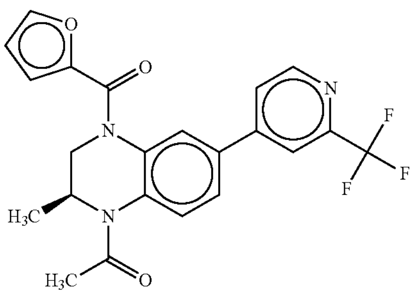 | 430 | 1.38 |
| I-862 | 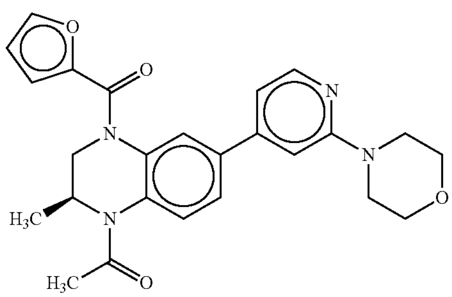 | 447 | 0.95 |
| I-863 | | 392 | 1.27 |
| I-864 | 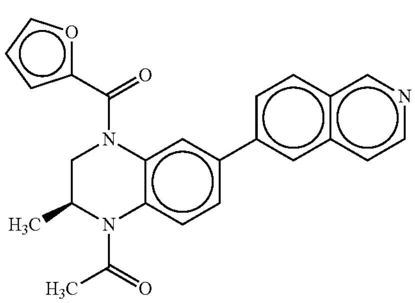 | 412 | 0.93 |

TABLE 14-continued

| Example | Structure | LC-MS [M + 1]+ | HPLC RT (min) |
|---------|-----------|----------------|---------------|
| I-865 | 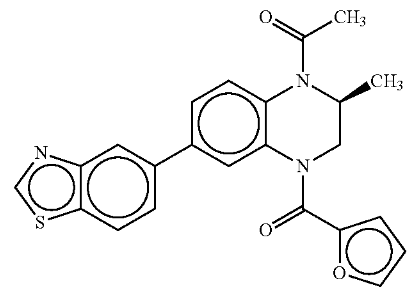 | 418 | 1.3 |
| I-866 | 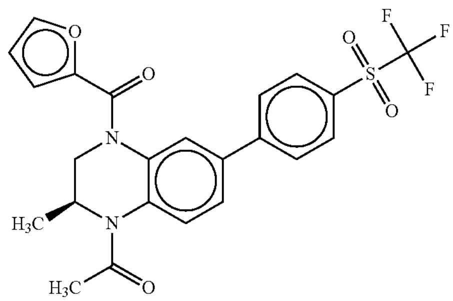 | 493 | 1.6 |
| I-867 | 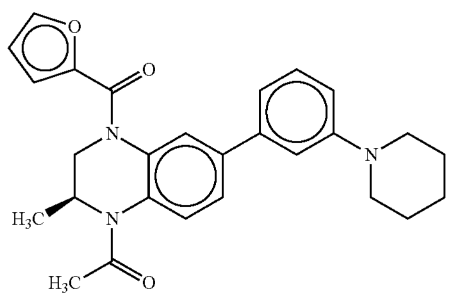 | 444 | 1.52 |
| I-868 | 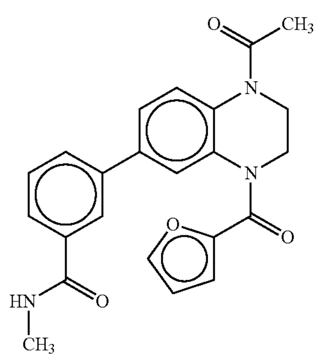 | 404 | 0.97 |
| I-869 | 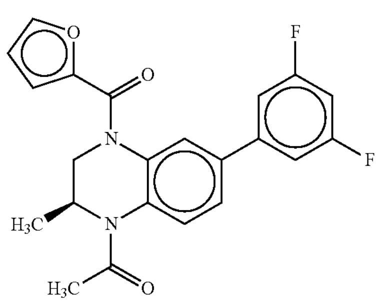 | 397 | 1.54 |

TABLE 14-continued

| Example | Structure | LC-MS [M + 1]+ | HPLC RT (min) |
|---------|-----------|----------------|---------------|
| I-870 | 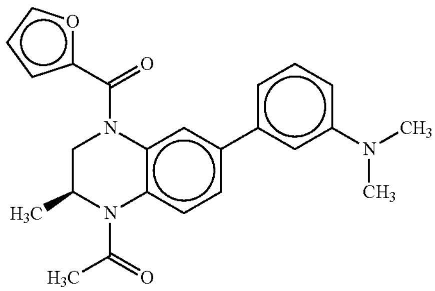 | 404 | 1.49 |
| I-871 | 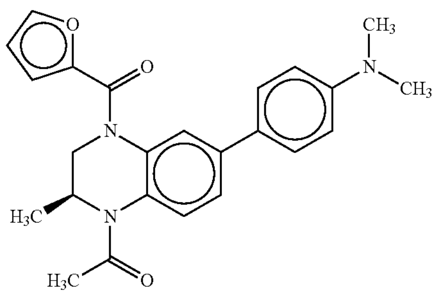 | 404 | 1.48 |
| I-872 | 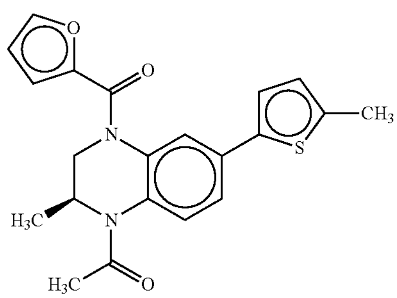 | 381 | 1.55 |
| I-873 | 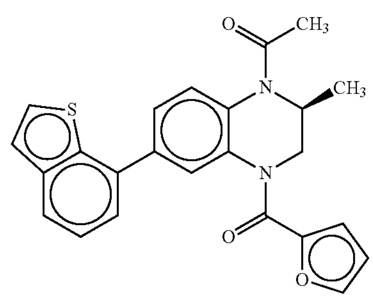 | 417 | 1.57 |
| I-874 | 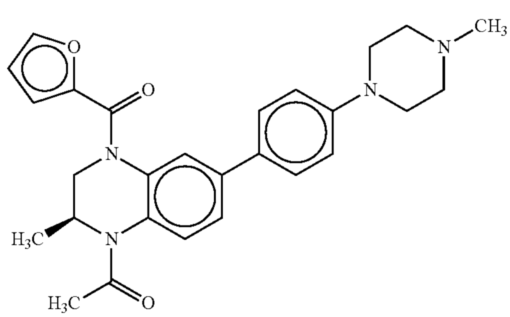 | 459 | 0.83 |

TABLE 14-continued

| Example | Structure | LC-MS [M + 1]+ | HPLC RT (min) |
|---------|-----------|----------------|---------------|
| I-875 | 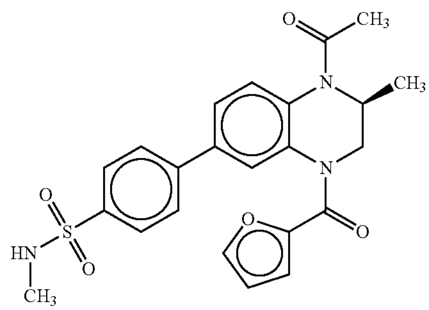 | 454 | 1.15 |
| I-876 | 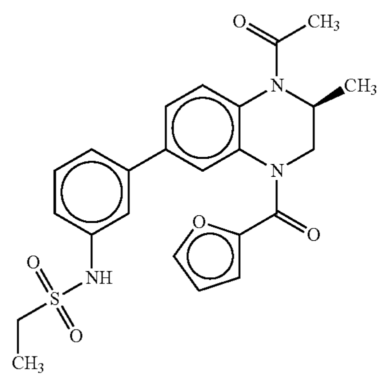 | 468 | 1.22 |
| I-877 | 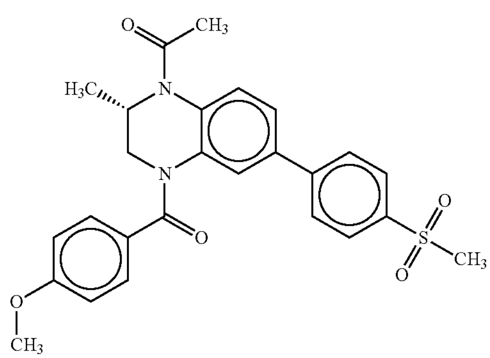 | 479 | 1.21 |
| I-878 | 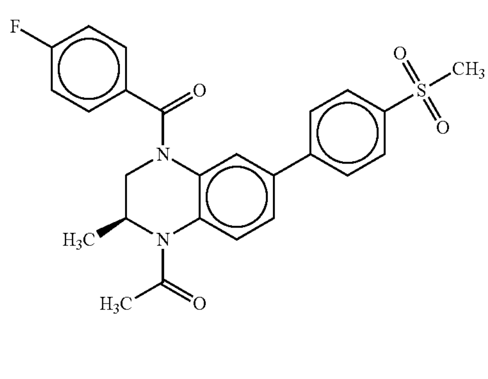 | 467 | 1.23 |

TABLE 14-continued

| Example | Structure | LC-MS [M + 1]+ | HPLC RT (min) |
|---|---|---|---|
| I-879 | 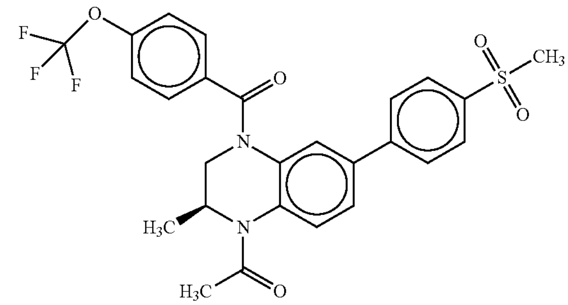 | 533 | 1.44 |
| I-880 | 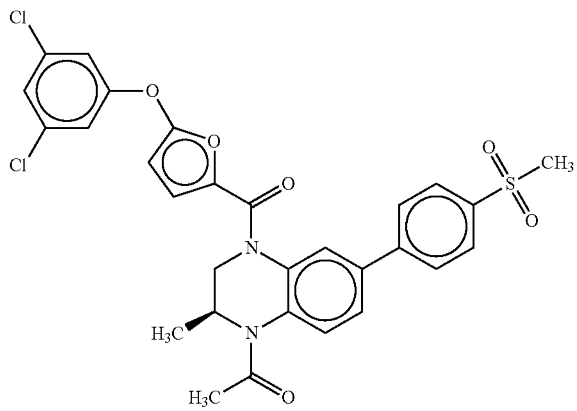 | 599 | 1.59 |
| I-881 | 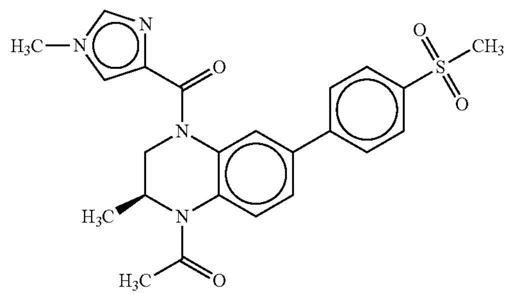 | 453 | 0.92 |
| I-882 | 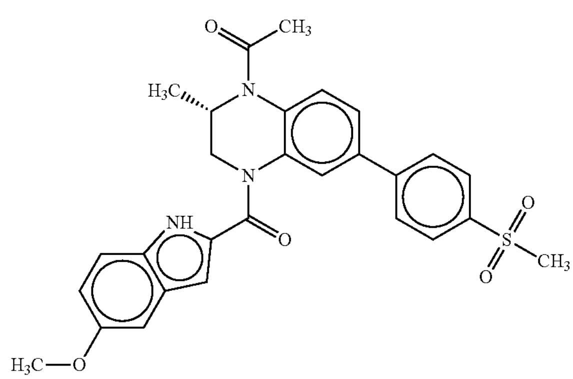 | 518 | 1.3 |

TABLE 14-continued

| Example | Structure | LC-MS [M + 1]+ | HPLC RT (min) |
|---------|-----------|----------------|---------------|
| I-883 | 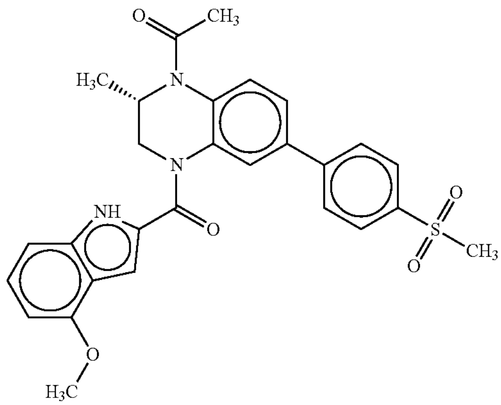 | 518 | 1.31 |
| I-884 | 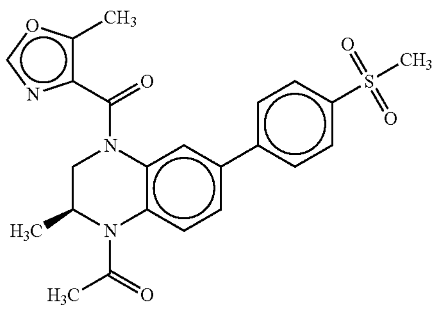 | 454 | 1.07 |
| I-885 | 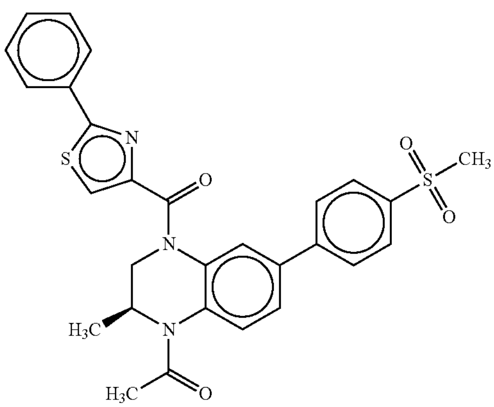 | 532 | 1.41 |
| I-886 | 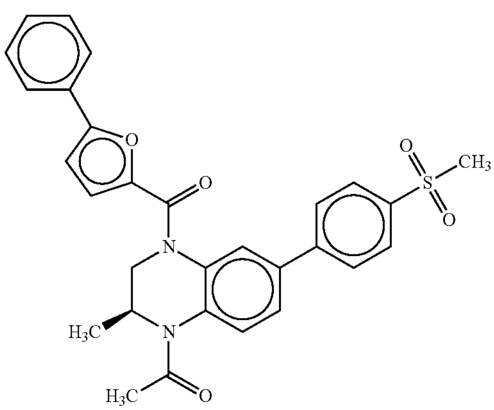 | 515 | 1.39 |

TABLE 14-continued
| Example | Structure | LC-MS [M + 1]+ | HPLC RT (min) |
|---|---|---|---|
| I-887 | 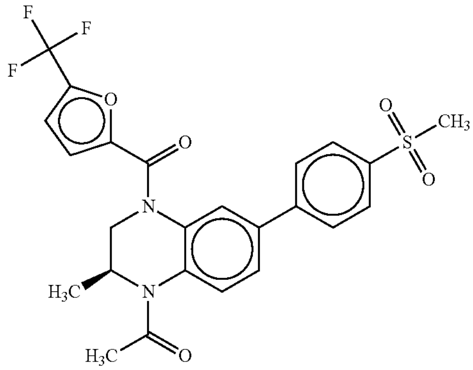 | 507 | 1.36 |
| I-888 | 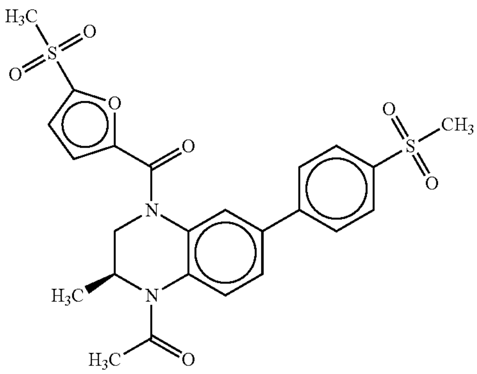 | 517 | 1.12 |
| I-889 | 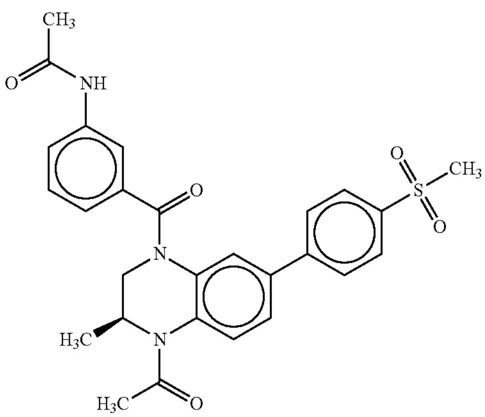 | 506 | 1.05 |
Example 271
Library Protocol J1
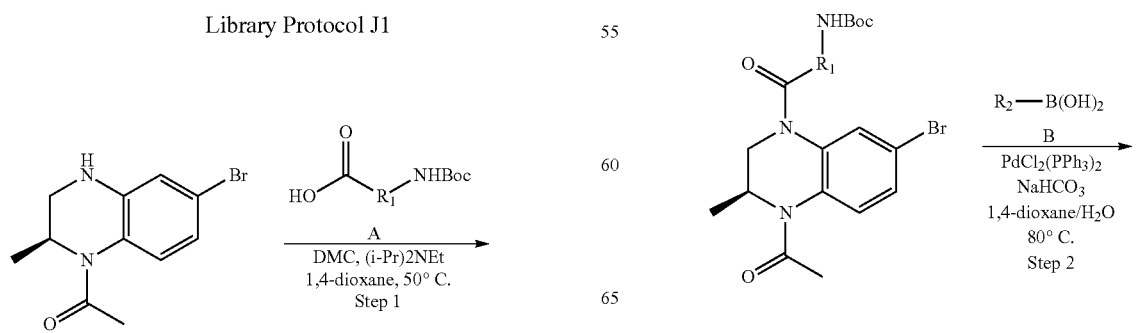

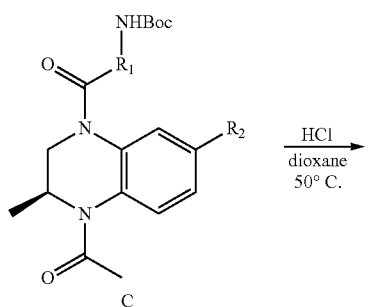

Step 1. A 1.5 mL reaction vial was charged with ((S)-1-(6-bromo-2-methyl-3,4-dihydroquinoxalin-1(2H)-yl)ethanone (0.2M solution in 1,4-dioxane, 150 µL, 0.03 mmol) and the carboxylic acid (A) (0.2M solution in 1,2-dioxane with 10% N,N-diisopropylethylamine, 450 µL, 0.09 mmol). 2-Chloro-1,3-dimethylimidazolidinium chloride (DMC, 0.2 M solution in acetonitrile, 450 µL, 0.09 mmol) was added, and the reaction was heated to 50° C. on a heater shaker for 2 hrs. The reaction was diluted with ethyl acetate and washed with saturated aqueous sodium bicarbonate solution. The aqueous layer was separated and extracted with ethyl acetate, and the combined organic layers were concentrated under a stream of nitrogen and vacuum to yield the crude product which was used without purification.

Step 2. A 1.5 mL reaction vial was charged with the aryl bromide from above, 1,4-dioxane (100 µL), and the boronic acid (B) (0.2M solution in 1,4-dioxane, 180 µL, 0.036 mmol). Sodium bicarbonate (1 M solution in water, 90 µL, 0.09 mmol) was added, and the reaction mixture was purged with nitrogen. Bis(triphenylphosphine)palladium(II) dichloride (0.01M solution in dimethylformamide, 150 µL, 0.003 mmol) was added, the reaction was purged with nitrogen, and heated to 80° C. on a heater shaker overnight. The reaction was diluted with ethyl acetate and washed with a saturated aqueous sodium bicarbonate solution. The aqueous layer was separated and extracted with ethyl acetate, and the combined organic layers were concentrated under a stream of nitrogen and vacuum. The crude product (C) was dissolved in 1,4-dioxane (0.3 mL), HCl (4.0 M in 1,4-dioxane, 0.15 mL, 0.6 mmol) was added, and the mixture stirred at 50° C. for 2 h. The reaction was concentrated, and diluted with ethyl acetate (0.5 mL) and saturated aqueous sodium bicarbonate solution (0.5 mL). The aqueous layer was separated and extracted with ethyl acetate (1 mL), and the organic layers were combined and concentrated under a stream of nitrogen and vacuum. The crude product was purified by mass triggered preparatory HPLC. The product-containing fractions were combined and concentrated in a Genevac to afford the desired product.

The following compound in Table 15 were synthesized according to the above protocol:

TABLE 15

| Example | Structure | LC-MS [M + 1]+ | HPLC RT (min) |
|---|---|---|---|
| I-890 | 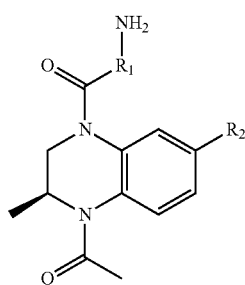 | 468 | 1.29 |

Example 272

Library Protocol K

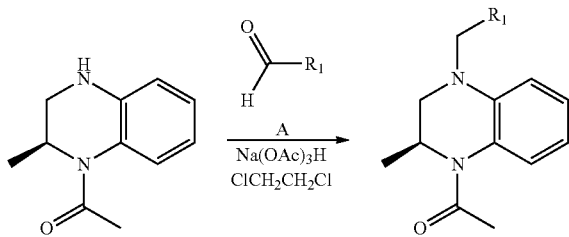

A 1.5 mL reaction vial was charged with (S)-1-(2-methyl-3,4-dihydroquinoxalin-1(2H)-yl)ethanone (0.2M solution in 1,2-dichloroethane, 100 µL, 0.02 mmol), the aldehyde (A) (0.2 M solution in 1,2-dichloroethane, 500 µL, 0.10 mmol), and acetic acid (2 M solution in 1,2-dichloroethane, 18 µL, 0.02 mmol). Sodium triacetoxyborohydride (0.2 M suspension in 1,2-dichloroethane, 500 µL, 0.1 mmol) was added, and the reaction was placed on a heater shaker at room temperature overnight. The reaction was diluted with ethyl acetate and washed with saturated aqueous sodium bicarbonate solution. The aqueous layer was separated and extracted with ethyl acetate, and the combined organic layers were concentrated under a stream of nitrogen and vacuum. The crude product was purified by mass triggered preparatory HPLC. The product-containing fractions were combined and concentrated in a Genevac to afford the desired product.

The following compounds in Table 16 were synthesized according to the above protocol:

TABLE 16

| Example | Structure | LC-MS [M + 1]+ | HPLC RT (min) |
|---|---|---|---|
| I-891 | 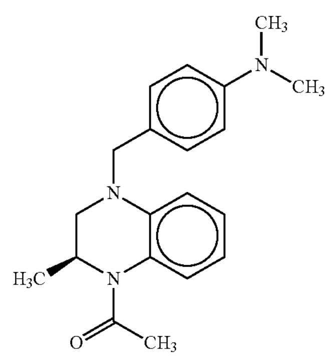 | 324 | 1.43 |
| I-892 | 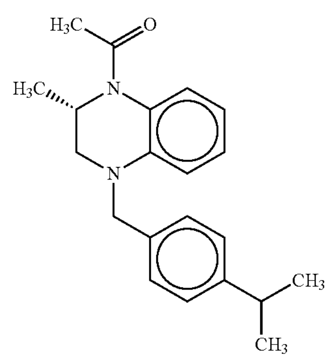 | 323 | 1.91 |
| I-893 | 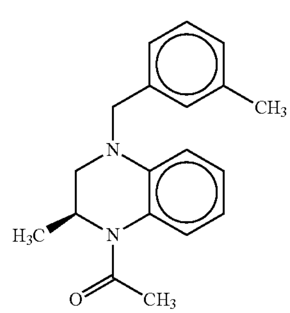 | 295 | 1.7 |

TABLE 16-continued

| Example | Structure | LC-MS [M + 1]+ | HPLC RT (min) |
|---|---|---|---|
| I-894 | 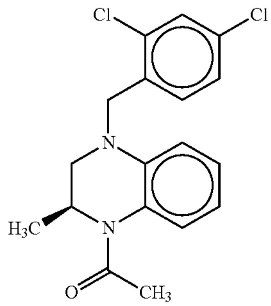 | 349 | 1.93 |
| I-895 | 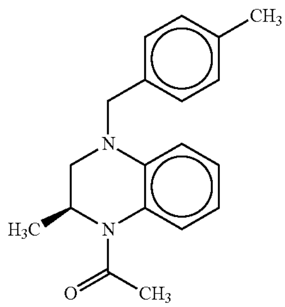 | 295 | 1.71 |
| I-896 | 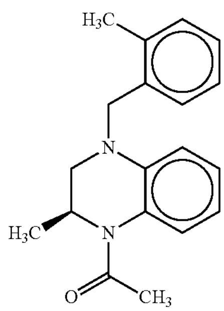 | 295 | 1.68 |
| I-897 | 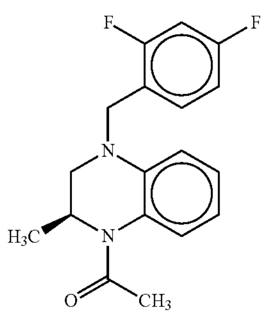 | 317 | 1.63 |
| I-898 | 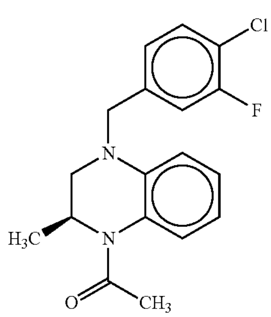 | 333 | 1.73 |

TABLE 16-continued

| Example | Structure | LC-MS [M + 1]+ | HPLC RT (min) |
|---------|-----------|----------------|---------------|
| I-899 | 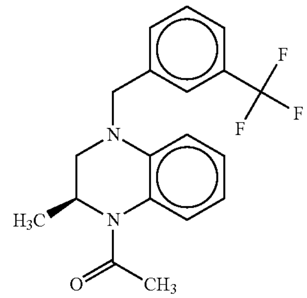 | 349 | 1.72 |
| I-900 | 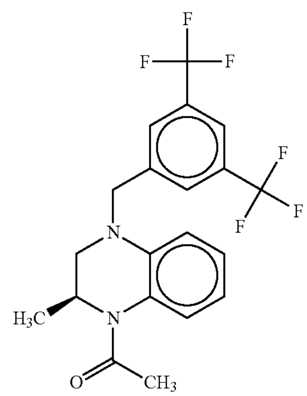 | 417 | 1.87 |
| I-901 | 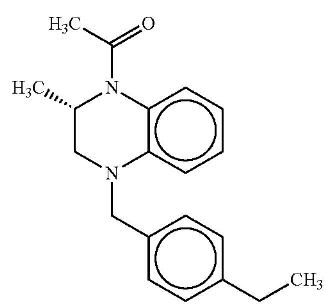 | 309 | 1.82 |
| I-902 | 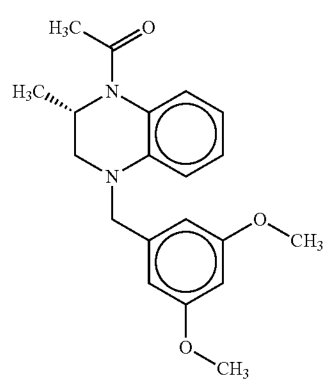 | 341 | 1.55 |

TABLE 16-continued

| Example | Structure | LC-MS [M + 1]+ | HPLC RT (min) |
|---------|-----------|----------------|---------------|
| I-903 | 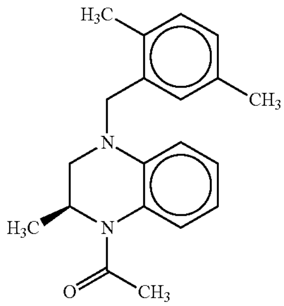 | 309 | 1.8 |
| I-904 | 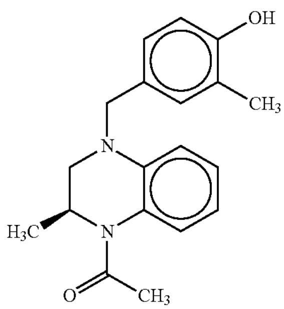 | 311 | 1.36 |
| I-905 | 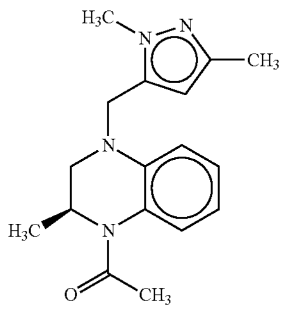 | 299 | 1.13 |
| I-906 | 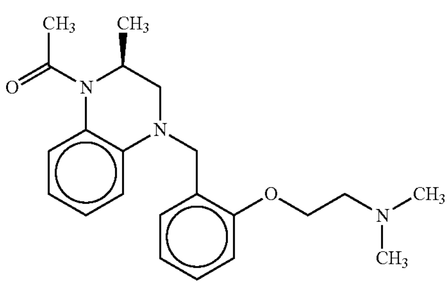 | 368 | 1.02 |
| I-907 | 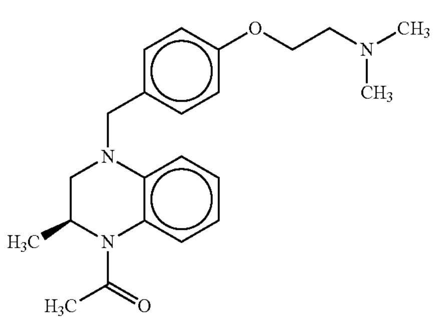 | 368 | 0.98 |

TABLE 16-continued

| Example | Structure | LC-MS [M + 1]+ | HPLC RT (min) |
|---------|-----------|----------------|---------------|
| I-908 | 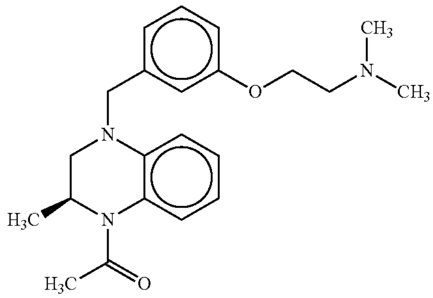 | 368 | 1 |
| I-909 | 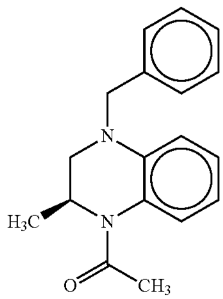 | 281 | 1.58 |
| I-910 | 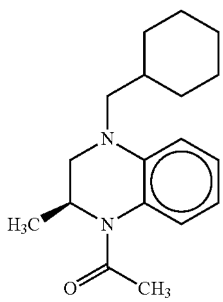 | 287 | 1.94 |
| I-911 | 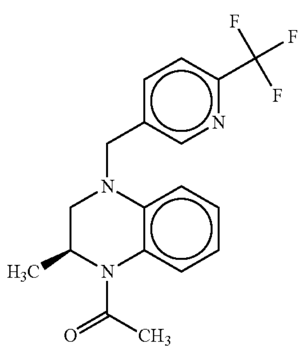 | 350 | 1.46 |
| I-912 | 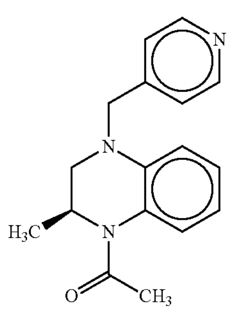 | 282 | 0.77 |

TABLE 16-continued

| Example | Structure | LC-MS [M + 1]+ | HPLC RT (min) |
|---|---|---|---|
| I-913 | 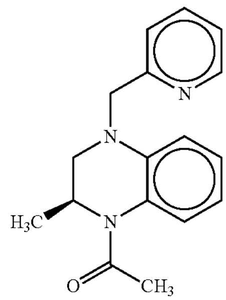 | 282 | 1.03 |
| I-914 | 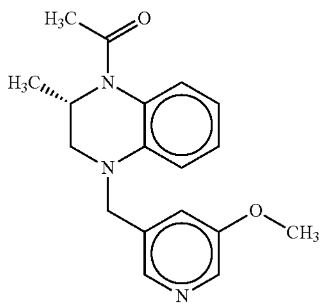 | 312 | 1.06 |
| I-915 | 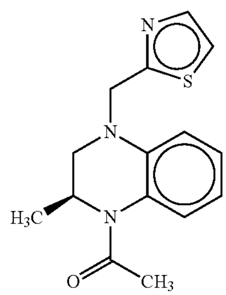 | 288 | 1.16 |
| I-916 | 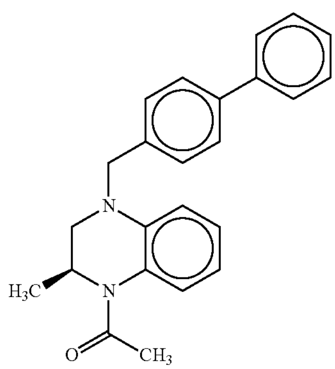 | 357 | 1.89 |
| I-917 | 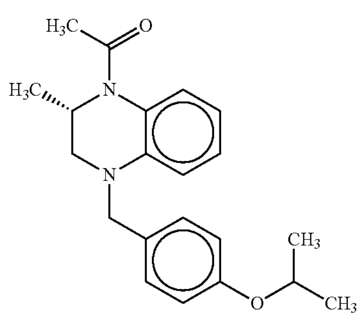 | 339 | 1.77 |

TABLE 16-continued

| Example | Structure | LC-MS [M + 1]+ | HPLC RT (min) |
|---------|-----------|----------------|---------------|
| I-918 | 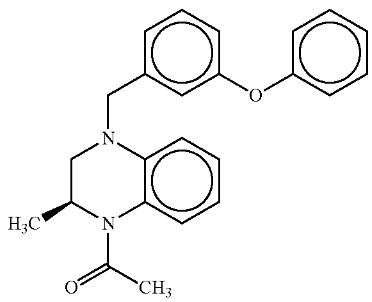 | 373 | 1.86 |
| I-919 | 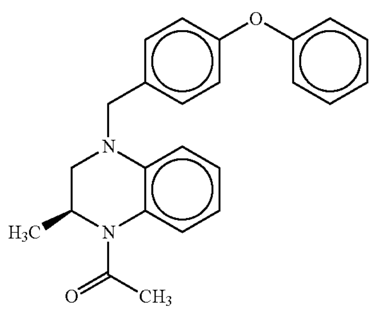 | 373 | 1.88 |
| I-920 | 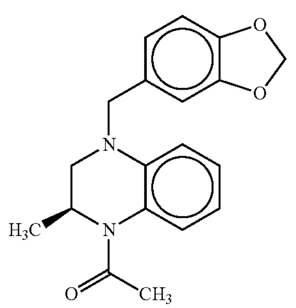 | 325 | 1.52 |
| I-921 | 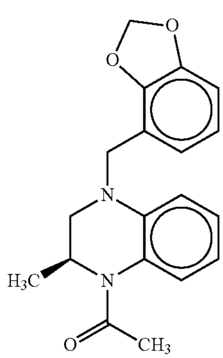 | 325 | 1.54 |

TABLE 16-continued

| Example | Structure | LC-MS [M + 1]+ | HPLC RT (min) |
|---------|-----------|----------------|---------------|
| I-922 | 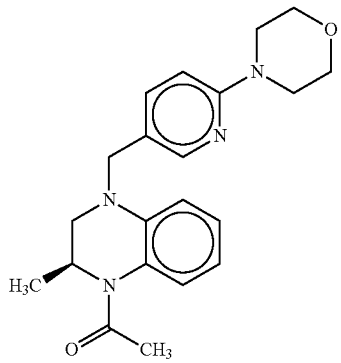 | 367 | 1.02 |
| I-923 | 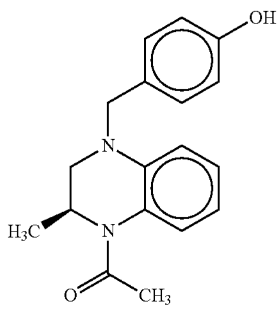 | 297 | 1.25 |
| I-924 | 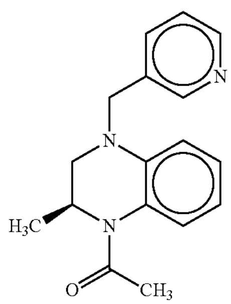 | 282 | 0.85 |
| I-925 | 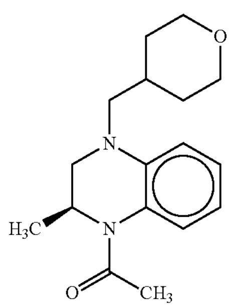 | 289 | 1.28 |
| I-926 | 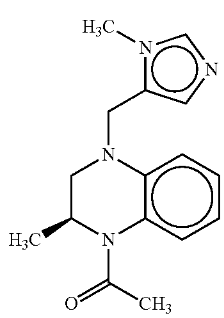 | 285 | 0.69 |

TABLE 16-continued

| Example | Structure | LC-MS [M + 1]+ | HPLC RT (min) |
|---|---|---|---|
| I-927 | 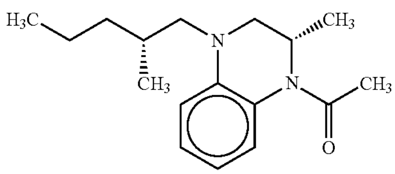 | 275 | 1.9 |
| I-928 | 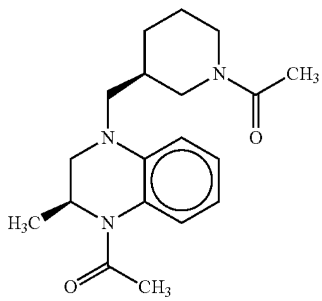 | 330 | 1.14 |
| I-929 | 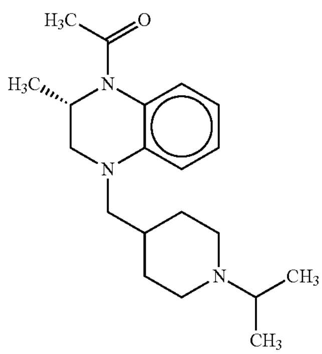 | 330 | 0.84 |

Example 273

Library Protocol L

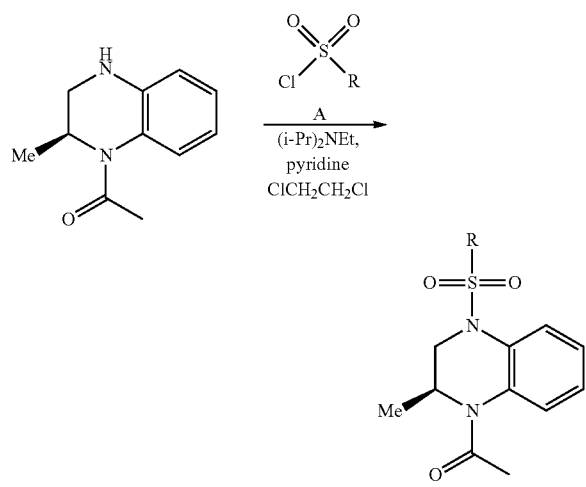

A 1.5 mL reaction vial was charged with (S)-1-(2-methyl-3,4-dihydroquinoxalin-1(2H)-yl)ethanone (0.2 M solution in 1,2-dichloroethane with 5% pyridine and 10% N,N-diisopropylethylamine, 100 µL, 0.02 mmol) and sulfonyl chloride (A) (0.2 M solution in 1,2-dichloroethane, 150 µL, 0.03 mmol). The reaction was placed on a heater shaker at 50° C. for 2 h. The reaction was diluted with ethyl acetate and washed with a saturated aqueous sodium bicarbonate solution. The aqueous layer was separated and extracted with ethyl acetate, and the combined organic layers were concentrated under a stream of nitrogen and vacuum. The crude product was purified by mass triggered preparatory HPLC. The product-containing fractions were combined and concentrated in a Genevac to afford the desired product.

The following compounds in Table 17 were synthesized according to the above protocol:

TABLE 17

| Example | Structure | LC-MS [M + 1]+ | HPLC RT (min) |
|---|---|---|---|
| I-930 | 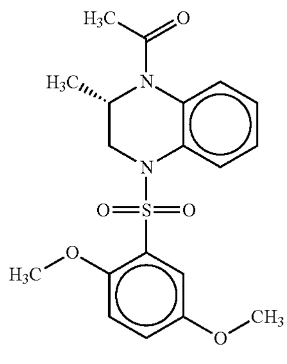 | 391 | 1.34 |
| I-931 | 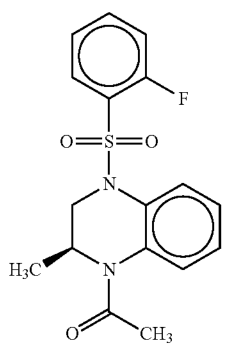 | 349 | 1.33 |
| I-932 | 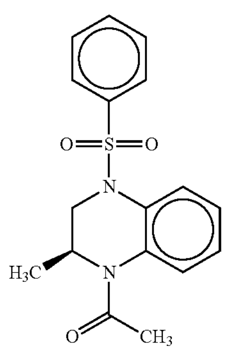 | 331 | 1.31 |
| I-933 | 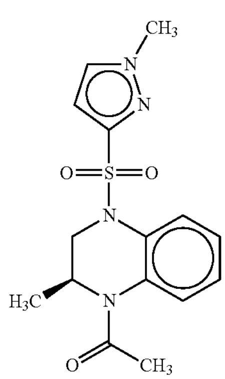 | 335 | 1.09 |

TABLE 17-continued

| Example | Structure | LC-MS [M + 1]+ | HPLC RT (min) |
|---|---|---|---|
| I-934 | 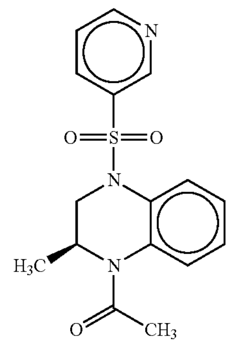 | 332 | 1.1 |
| I-935 | 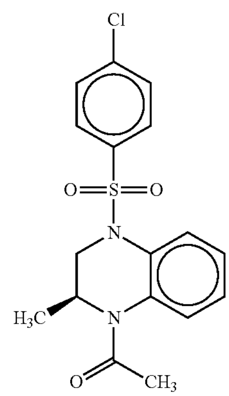 | 365 | 1.47 |
| I-936 | 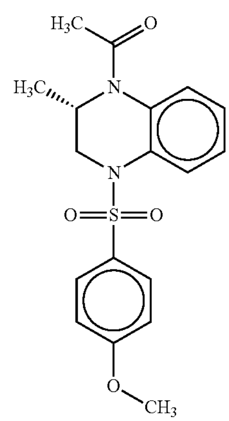 | 361 | 1.35 |
| I-937 | 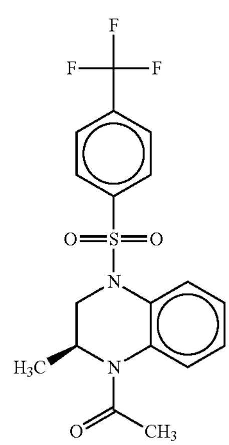 | 399 | 1.56 |

TABLE 17-continued

| Example | Structure | LC-MS [M+1]+ | HPLC RT (min) |
|---|---|---|---|
| I-938 | | 356 | 1.33 |
| I-939 | | 415 | 1.59 |
| I-940 | | 345 | 1.41 |
| I-941 | 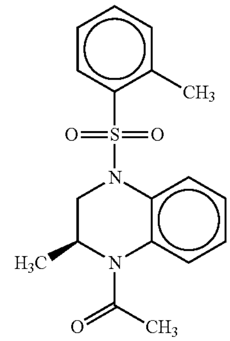 | 345 | 1.41 |
| I-942 | 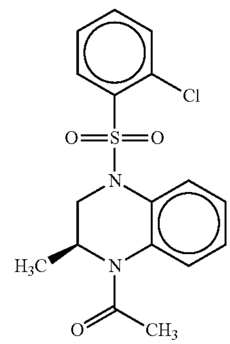 | 365 | 1.39 |
| I-943 | 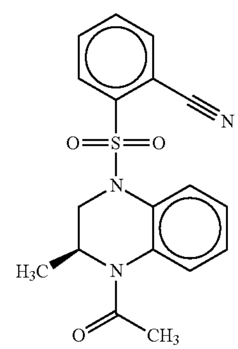 | 356 | 1.24 |
| I-944 | 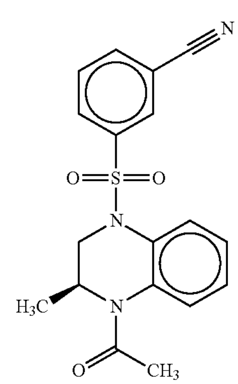 | 356 | 1.31 |

TABLE 17-continued

| Example | Structure | LC-MS [M + 1]+ | HPLC RT (min) |
|---|---|---|---|
| I-945 | 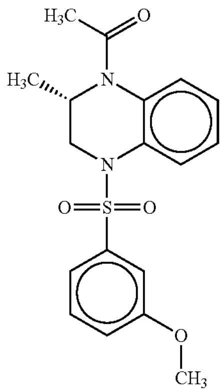 | 361 | 1.37 |
| I-946 | 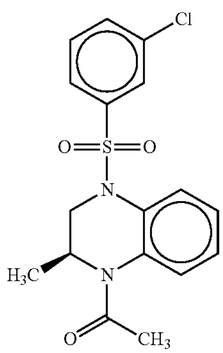 | 365 | 1.47 |
| I-947 | 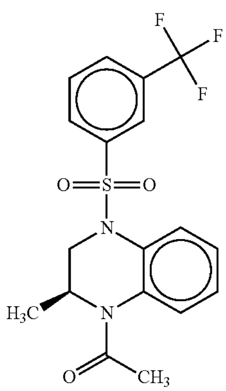 | 399 | 1.55 |
| I-948 | 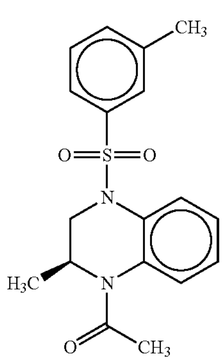 | 345 | 1.41 |
| I-949 | | 359 | 1.51 |
| I-950 | | 391 | 1.34 |
| I-951 | | 400 | 1.47 |
| I-952 | | 295 | 1.14 |

TABLE 17-continued

| Example | Structure | LC-MS [M + 1]+ | HPLC RT (min) |
|---|---|---|---|
| I-953 | 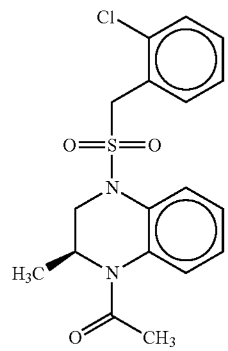 | 379 | 1.47 |
| I-954 | 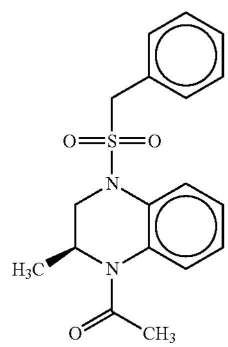 | 345 | 1.37 |
| I-955 | 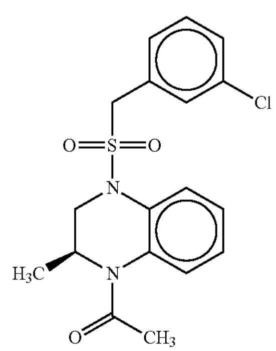 | 379 | 1.49 |
| I-956 | 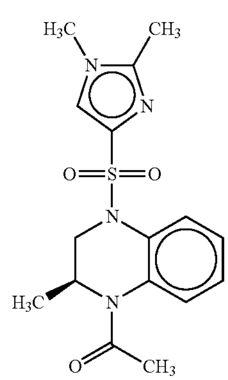 | 349 | 0.94 |
| I-957 | | 373 | 1.3 |
| I-958 | | 370 | 1.29 |
| I-959 | | 395 | 1.49 |
| I-960 | | 375 | 1.44 |

TABLE 17-continued

| Example | Structure | LC-MS [M + 1]+ | HPLC RT (min) |
|---|---|---|---|
| I-961 | 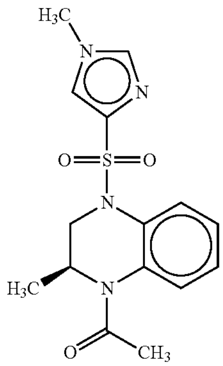 | 335 | 0.93 |
| I-962 | 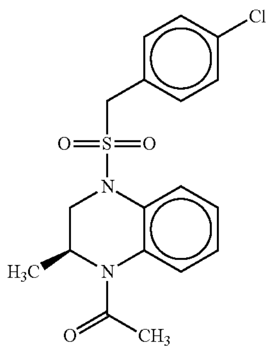 | 379 | 1.5 |
| I-963 | 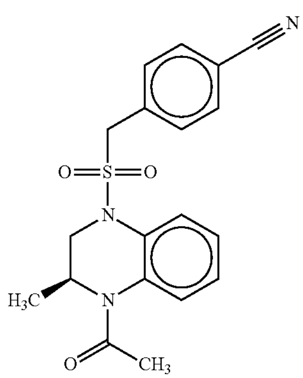 | 370 | 1.3 |

Example 274

Library Protocol M

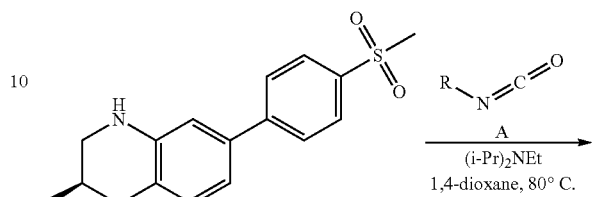

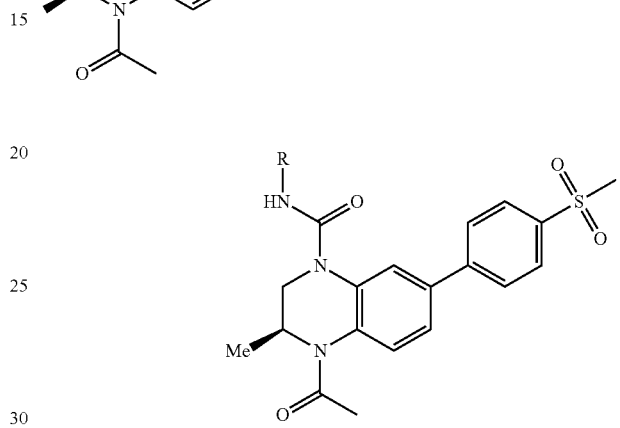

A 1.5 mL reaction vial was charged with (S)-1-(2-methyl-6-(4-(methylsulfonyl)phenyl)-3,4-dihydroquinoxalin-1(2H)-yl)ethanone (0.4M solution in 1,4-dioxane, 50 µL, 0.02 mmol), the isocyanate (A) (0.2M solution in 1,4-dioxane, 150 µL, 0.03 mmol), and N,N-diisopropylethylamine (15 µL, 0.09 mmol). The reaction was placed on a heater shaker at 80° C. for 16 h. The reaction was concentrated and the crude product was purified by mass triggered preparatory HPLC. The product-containing fractions were combined and concentrated in a Genevac to afford the desired product.

The following compounds in Table 18 were synthesized according to the above protocol:

TABLE 18

| Example | Structure | LC-MS [M + 1]+ | HPLC RT (min) |
|---|---|---|---|
| I-964 | 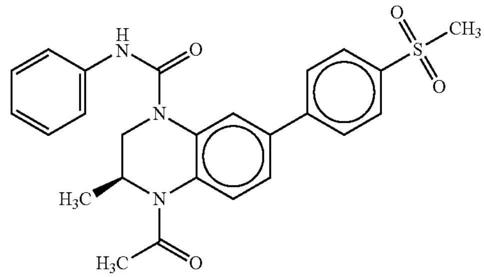 | 464 | 1.28 |

TABLE 18-continued

| Example | Structure | LC-MS [M + 1]+ | HPLC RT (min) |
|---------|-----------|----------------|---------------|
| I-965 | 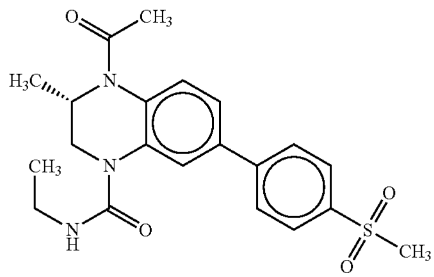 | 416 | 1.05 |
| I-966 | 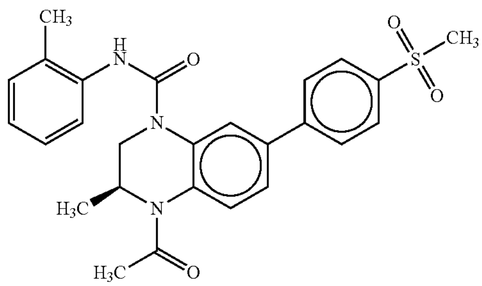 | 478 | 1.27 |
| I-967 | 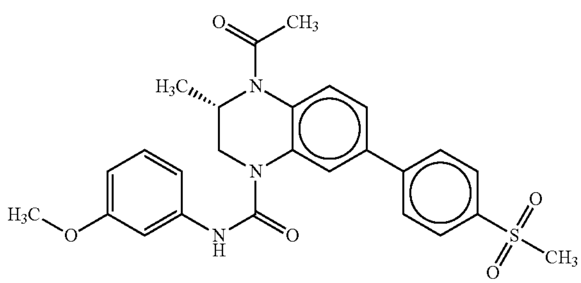 | 494 | 1.27 |
| I-968 | 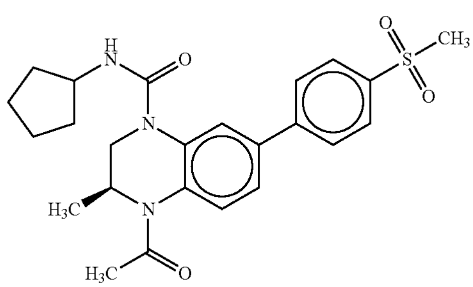 | 456 | 1.23 |
| I-969 | 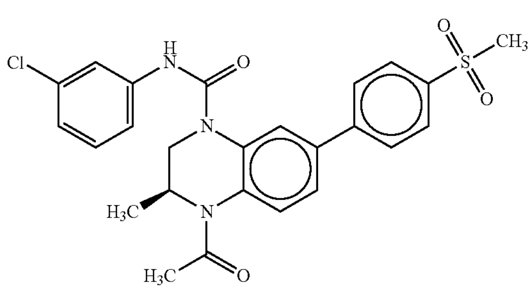 | 498 | 1.41 |

TABLE 18-continued

| Example | Structure | LC-MS [M + 1]+ | HPLC RT (min) |
|---|---|---|---|
| I-970 | 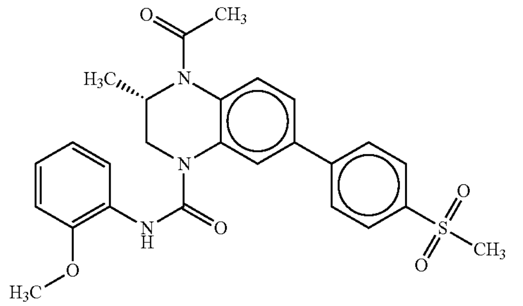 | 494 | 1.33 |
| I-971 | 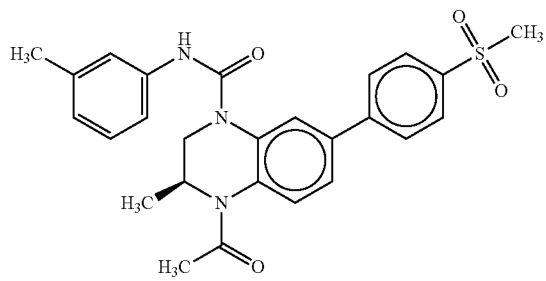 | 478 | 1.34 |
| I-972 | 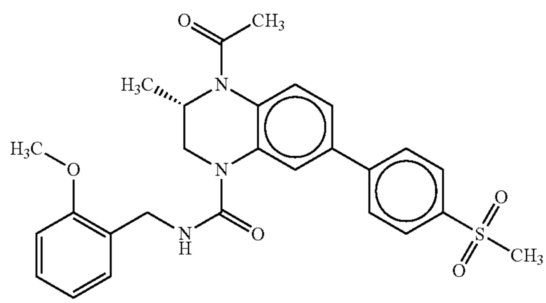 | 508 | 1.27 |
| I-973 | 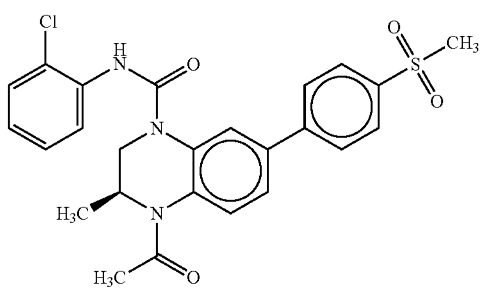 | 498 | 1.34 |
| I-974 | 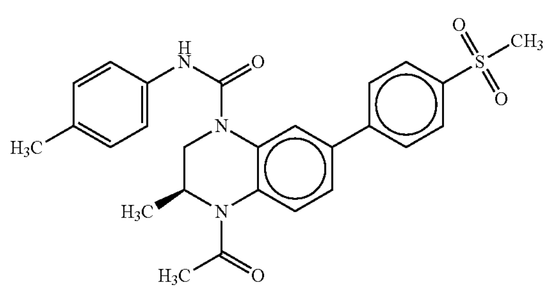 | 478 | 1.34 |

TABLE 18-continued

| Example | Structure | LC-MS [M + 1]+ | HPLC RT (min) |
|---------|-----------|----------------|---------------|
| I-975 | 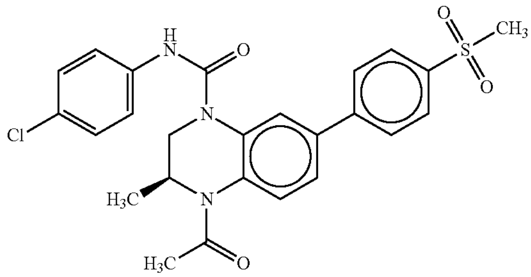 | 498 | 1.4 |
| I-976 | 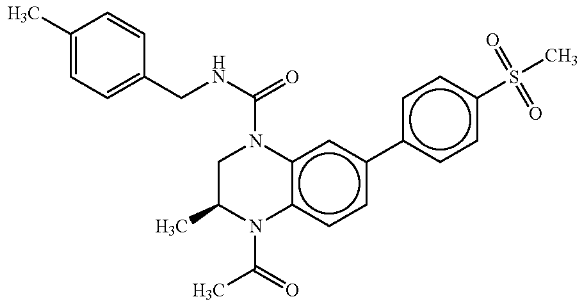 | 492 | 1.33 |
| I-977 | 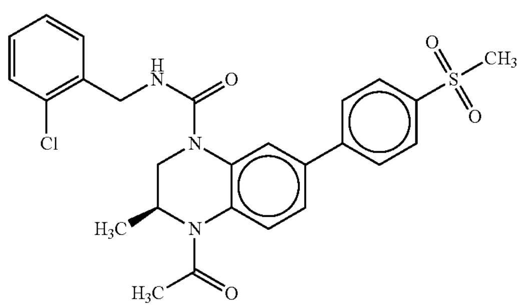 | 512 | 1.32 |
| I-978 | 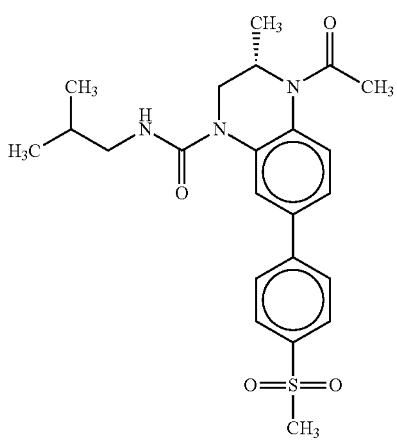 | 444 | 1.21 |

TABLE 18-continued

| Example | Structure | LC-MS [M + 1]+ | HPLC RT (min) |
|---|---|---|---|
| I-979 | 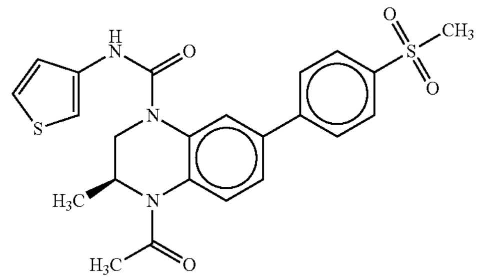 | 470 | 1.25 |
| I-980 | 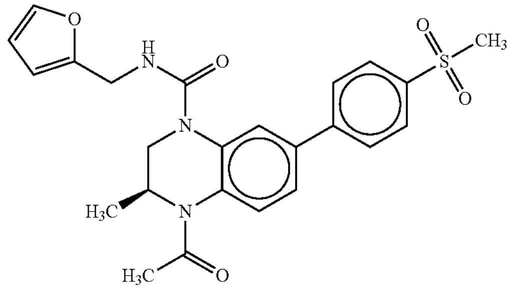 | 468 | 1.14 |

Example 275

Library Protocol N

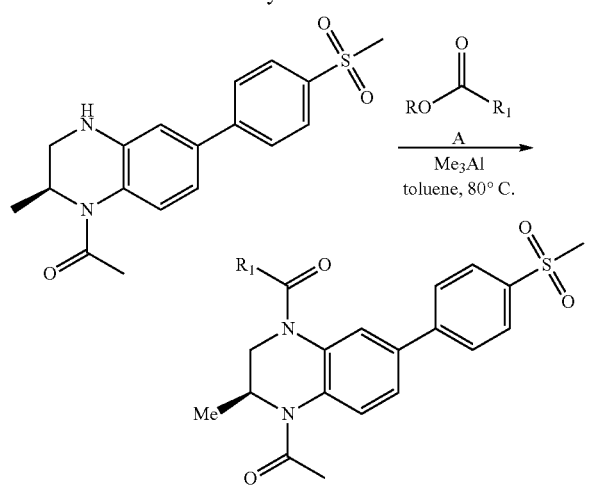

A 1.5 mL reaction vial was charged with (S)-1-(2-methyl-6-(4-(methylsulfonyl)phenyl)-3,4-dihydroquinoxalin-1(2H)-yl)ethanone (0.2M solution in toluene, 100 µL, 0.02 mmol), the ester (A) (0.2M solution in toluene, 200 µL, 0.04 mmol), and trimethylaluminum (2 M solution in toluene, 40 µL, 0.08 mmol). The reaction was placed on a heater shaker at 80° C. for 2 h. The reaction was diluted with ethyl acetate and washed with a saturated aqueous ammonium chloride solution. The aqueous layer was separated and extracted with ethyl acetate, and the combined organic layers were concentrated under a stream of nitrogen and vacuum. The crude product was purified by mass triggered preparatory HPLC. The product-containing fractions were combined and concentrated in a Genevac to afford the desired product.

The following compounds in Table 19 were synthesized according to the above protocol:

TABLE 19

| Example | Structure | LC-MS [M + 1]+ | HPLC RT (min) |
|---|---|---|---|
| I-981 | 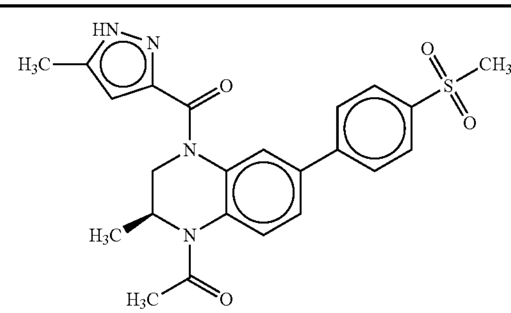 | 453 | 1 |

TABLE 19-continued

| Example | Structure | LC-MS [M + 1]+ | HPLC RT (min) |
|---|---|---|---|
| I-982 | 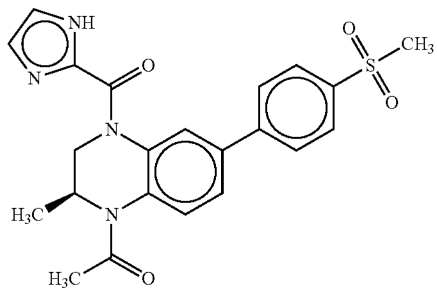 | 439 | 0.95 |

Example 276

Library Protocol O

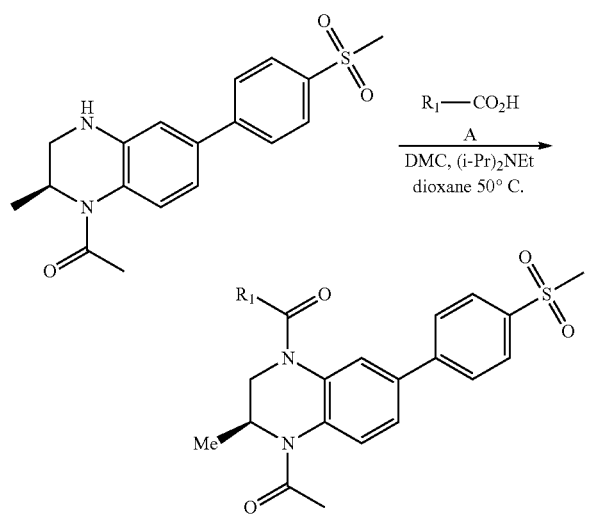

A 1.5 mL reaction vial was charged with (S)-1-(2-methyl-6-(4-(methylsulfonyl)phenyl)-3,4-dihydroquinoxalin-1(2H)-yl)ethanone (0.4 M solution in 1,4-dioxane, 100 μL, 0.04 mmol) and the carboxylic acid (A) (0.4 M solution in 1,4-dioxane with 20% N,N-diisopropylethylamine, 300 μL, 0.12 mmol). 2-Chloro-1,3-dimethylimidazolidinium chloride (DMC) (0.4 M solution in acetonitrile, 300 μL, 0.12 mmol) was added, and the reaction was heated to 50° C. on a heater shaker for 2 hrs. The reaction was diluted with ethyl acetate and washed with saturated aqueous sodium bicarbonate solution. The aqueous layer was separated and extracted with ethyl acetate, and the combined organic layers were concentrated under a stream of nitrogen and vacuum. The crude product was purified by mass triggered preparatory HPLC. The product-containing fractions were combined and concentrated in a Genevac to afford the desired product.

The following compounds in Table 20 were synthesized according to the above protocol:

TABLE 20

| Example | Structure | LC-MS [M + 1]+ | HPLC RT (min) |
|---|---|---|---|
| I-983 | 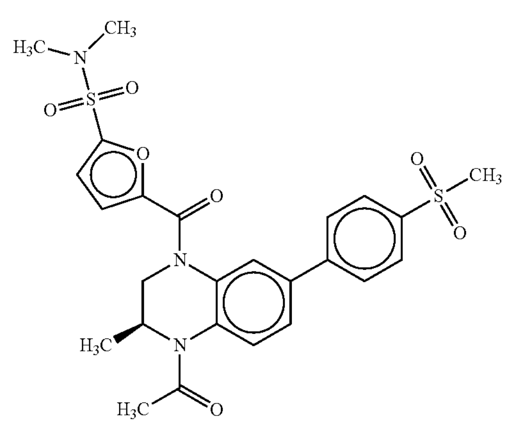 | 546 | 1.18 |

TABLE 20-continued

| Example | Structure | LC-MS [M + 1]+ | HPLC RT (min) |
|---------|-----------|----------------|---------------|
| I-984 | 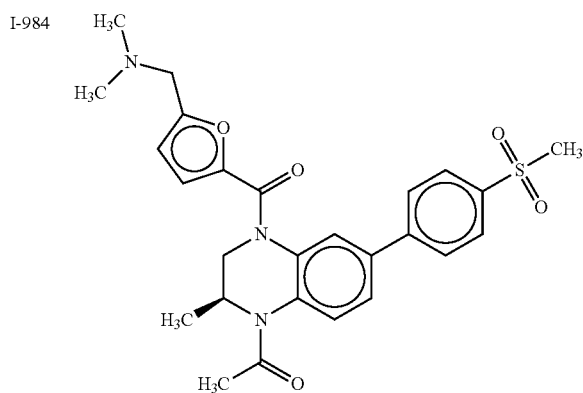 | 496 | 0.82 |

Example 277

Library Protocol O1

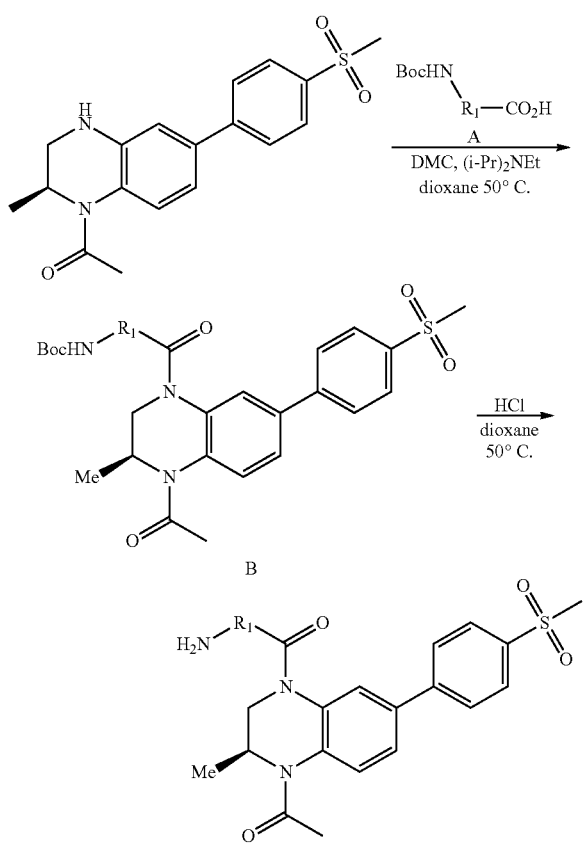

A 1.5 mL reaction vial was charged with (S)-1-(2-methyl-6-(4-(methylsulfonyl)phenyl)-3,4-dihydroquinoxalin-1(2H)-yl)ethanone (0.4 M solution in 1,4-dioxane, 100 μL, 0.04 mmol) and the carboxylic acid (A) (0.4 M solution in 1,4-dioxane with 20% N,N-diisopropylethylamine, 300 μL, 0.12 mmol). 2-Chloro-1,3-dimethylimidazolidinium chloride (DMC) (0.4 M solution in acetonitrile, 300 μL, 0.12 mmol) was added, and the reaction was heated to 50° C. on a heater shaker for 2 h. The reaction was diluted with ethyl acetate and washed with saturated aqueous sodium bicarbonate solution. The aqueous layer was separated and extracted with ethyl acetate, and the combined organic layers were concentrated under a stream of nitrogen and vacuum. The crude product (B) was dissolved in 1,4-dioxane (0.3 mL), HCl (4.0 M in 1,4-dioxane, 0.15 mL, 0.6 mmol) was added, and the mixture was stirred at 50° C. for 2 h. The reaction was concentrated, and diluted with ethyl acetate (0.5 mL) and saturated aqueous sodium bicarbonate solution (0.5 mL). The aqueous layer was separated and extracted with ethyl acetate (1 mL), and the organic layers were combined and concentrated under a stream of nitrogen and vacuum. The crude product was purified by mass triggered preparatory HPLC. The product-containing fractions were combined and concentrated in a Genevac to afford the desired product.

The following compounds in Table 21 were synthesized according to the above protocol:

TABLE 21

| Example | Structure | LC-MS [M + 1]+ | HPLC RT (min) |
|---------|-----------|----------------|---------------|
| I-985 | 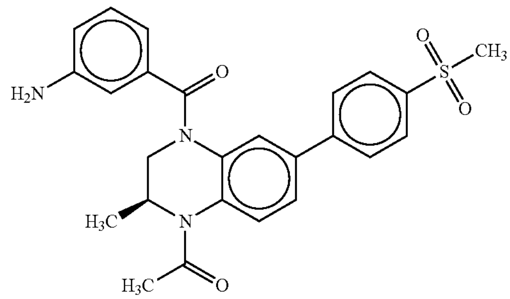 | 464 | 1.07 |
| I-986 | 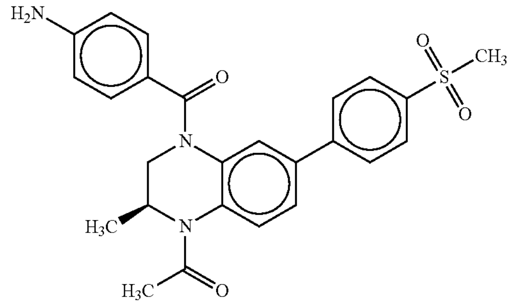 | 464 | 1.06 |

Example 278

Library Protocol P

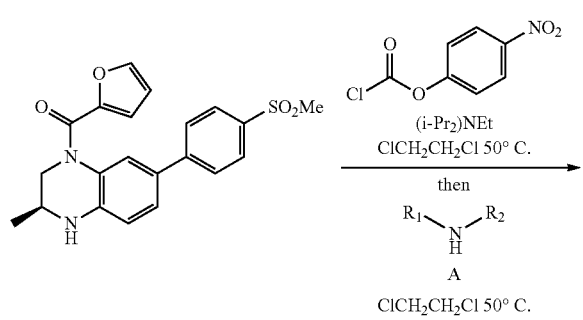

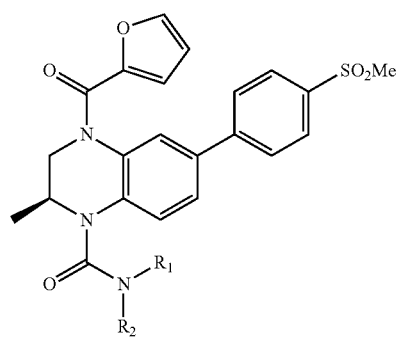

A 1.5 mL reaction vial was charged with (S)-furan-2-yl(3-methyl-7-(4-(methylsulfonyl)phenyl)-3,4-dihydroquinoxaline-1(2H)-yl)methanone (0.2 M solution in 1,4-dioxane, 100 µL, 0.02 mmol). N,N-Diisopropylethylamine (25 µL, 0.143 mmol) was added followed by the addition of 4-nitrophenylchloroformate (0.2 M solution in 1,2-dichloromethane, 100 µL, 0.024 mmol). The reaction was heated to 50° C. for 2 hrs. The amine (A) (2 M solution in methanol, 200 µL, 0.4 mmol) was added and the reaction was heated to 50° C. for 72 hrs. The reaction was diluted with ethyl acetate and washed with saturated aqueous sodium bicarbonate solution. The aqueous layer was separated and extracted with ethyl acetate, and the combined organic layers were concentrated under a stream of nitrogen and vacuum. The crude product was purified by mass triggered preparatory HPLC. The product-containing fractions were combined and concentrated in a Genevac to afford the desired product.

The following compounds Table 22 were synthesized according to the above protocol:

TABLE 22

| Example | Structure | LC-MS [M + 1]+ | HPLC RT (min) |
|---|---|---|---|
| I-987 | 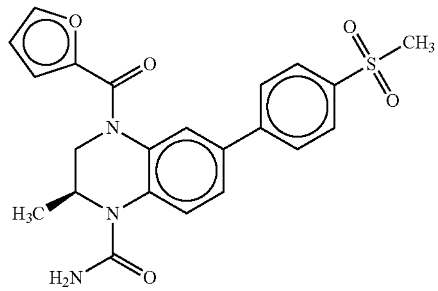 | 440 | 1.00 |
| I-988 | 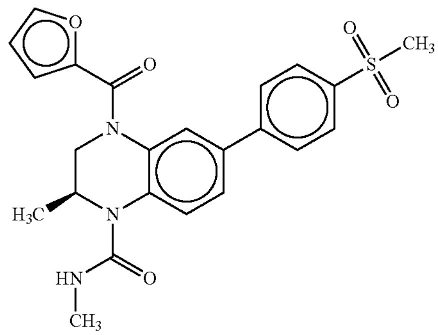 | 454 | 1.08 |

Example 279

Library Protocol Q

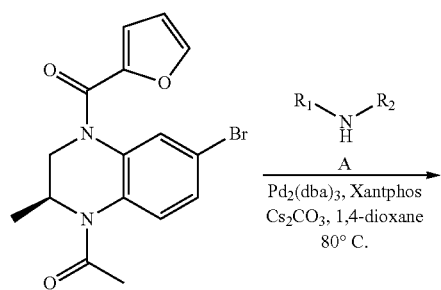

A reaction vial was charged with (S)-1-(6-bromo-4-(furan-2-carbonyl)-2-methyl-3,4-dihydroquinoxalin-1(2H)-yl)ethanone (7.26 mg, 0.02 mmol), amine (A) (6.43 mg, 0.060 mmol) and 1,4-dioxane (0.35 mL). Cesium carbonate (0.013 g, 0.040 mmol), 4,5-bis(diphenylphosphino)-9,9-dimethylxanthene (XANTPHOS) (1.50 mg, 2.60 µmol) and tris(dibenzylideneacetone)dipalladium (1.83 mg, 2.00 µmol) were added, and the reaction mixture was placed on a heater shaker at 80° C. for 4 h. The reaction was diluted with ethyl acetate and washed with water. The aqueous layer was separated and washed with ethyl acetate and the combined organic layers were concentrated under a stream of nitrogen and vacuum. The crude product was purified by mass triggered preparatory HPLC. The crude product was purified by mass triggered preparatory HPLC. The product-containing fractions were combined and concentrated in a Genevac to afford the desired product.

The following compounds in Table 23 were synthesized according to the above protocol:

TABLE 23

| Example | Structure | LC-MS [M + 1]+ | HPLC RT (min) |
|---|---|---|---|
| I-989 | 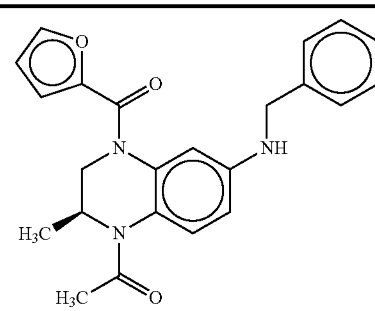 | 390 | 1.34 |

TABLE 23-continued

| Example | Structure | LC-MS [M+1]+ | HPLC RT (min) |
|---|---|---|---|
| I-990 | 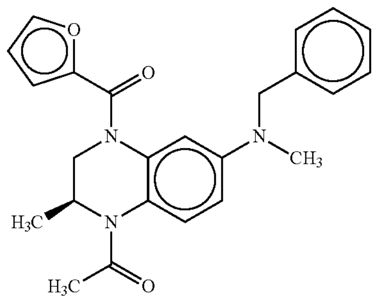 | 404 | 1.5 |
| I-991 | 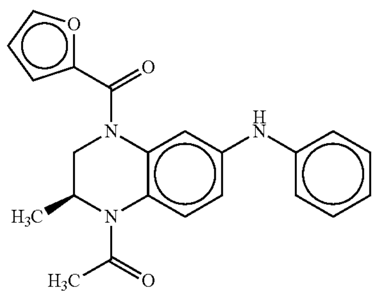 | 376 | 1.32 |
| I-992 | 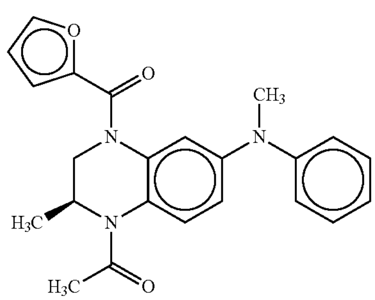 | 390 | 1.48 |
| I-993 | 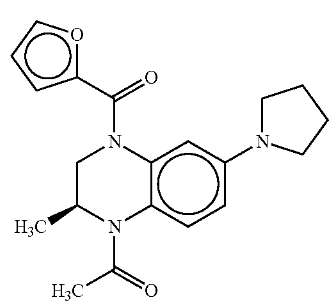 | 354 | 1.37 |

Example 280

Library protocol R

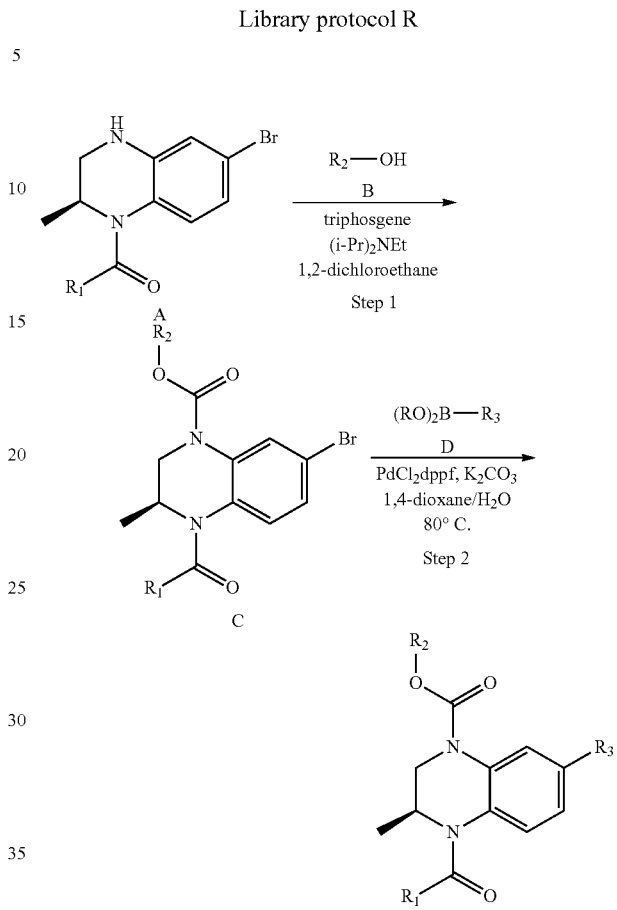

Step 1. A 1.5 mL reaction vial was charged with 6-bromobenzopiperazine (A) (0.2 M in 4:1:1,2-dichloroethane/N,N-disopropylethylamine, 100 μL, 0.02 mmol). Triphosgene (0.4 M solution 1,2-dichloroethane, 20 μL, 0.008 mmol) was added, and the reaction mixture was placed on a heater shaker at room temperature for 4 h. The alcohol (B) (0.2 M solution in 1,4-dioxane, 110 μl, 22.00 μmol) was then added, and the reaction was heated to 50° C. on a heater shaker overnight. Methanol (100 μl) was added and the reaction was placed on a heater shaker at 50° C. for 30 minutes. The reaction was diluted with ethyl acetate and washed with a saturated sodium bicarbonate solution. The aqueous layer was separated and washed with ethyl acetate and the combined organic layers were concentrated under a stream of nitrogen and vacuum. The crude carbamate (C) was used without further purification.

Step 2. A 1.5 mL reaction vial was charged with carbamate (C) from above (0.02 mmol), the boronic acid (D) (0.2M solution in 1,4-dioxane, 225 μL, 0.03 mmol), and 1,4-dioxane (100 μL). Potassium carbonate (1 M solution in water, 60 μL, 0.06 mmol) was added, and the reaction mixture was purged with nitrogen. [1,1'-Bis(diphenylphosphino)ferrocene]dichloropalladium(II) (0.02 M solution in 1,2-dichloroethane, 150 μL, 0.003 mmol) was then added, and the reaction was purged with nitrogen and heated to 80° C. on a heater shaker overnight. The reaction was diluted with ethyl acetate and washed with 1 N aqueous sodium hydroxide solution.

The aqueous layer was separated and washed with ethyl acetate and the combined organic layers were concentrated under a stream of nitrogen and vacuum. The crude product was purified by mass triggered preparatory HPLC. The product-containing fractions were combined and concentrated in a Genevac to afford the desired product.

The following compounds in Table 24 were synthesized according to the above protocol:

TABLE 24

| Example | Structure | LC-MS [M + 1]+ | HPLC RT (min) |
| --- | --- | --- | --- |
| I-994 | 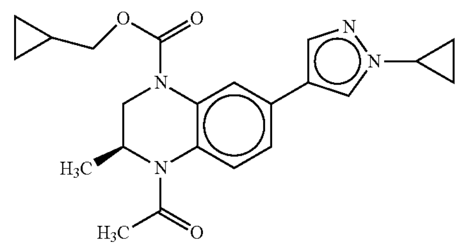 | 395 | 1.36 |
| I-995 | 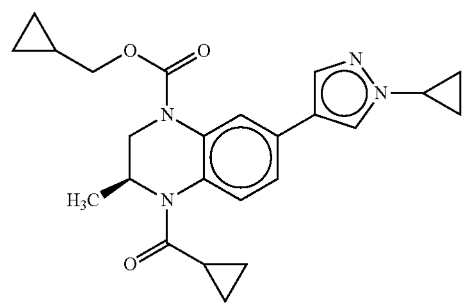 | 421 | 1.54 |
| I-996 | 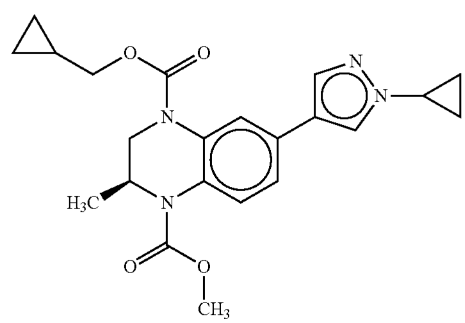 | 411 | 1.56 |
| I-997 | 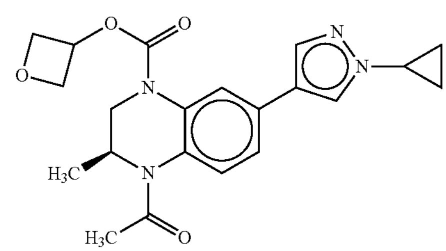 | 397 | 1.07 |
| I-998 | 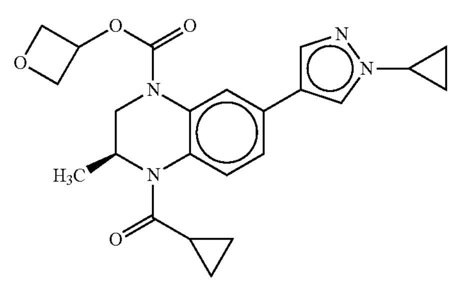 | 423 | 1.25 |

TABLE 24-continued

| Example | Structure | LC-MS [M + 1]+ | HPLC RT (min) |
|---|---|---|---|
| I-999 | 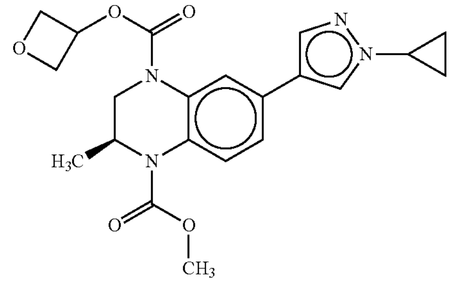 | 413 | 1.27 |
| I-1000 | 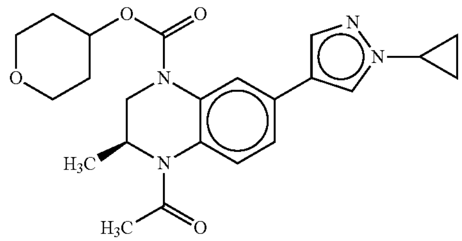 | 425 | 1.17 |
| I-1001 | 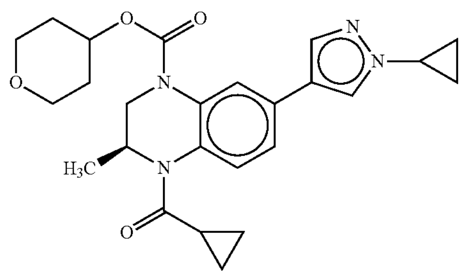 | 451 | 1.35 |
| I-1002 | 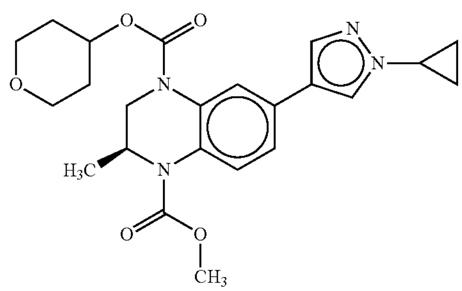 | 441 | 1.37 |
| I-1003 | 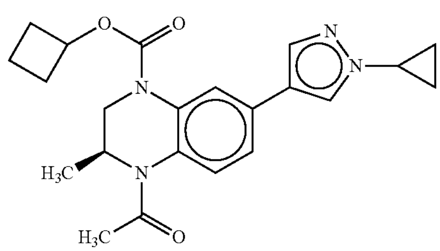 | 395 | 1.39 |

TABLE 24-continued

| Example | Structure | LC-MS [M + 1]+ | HPLC RT (min) |
|---------|-----------|----------------|---------------|
| I-1004 | 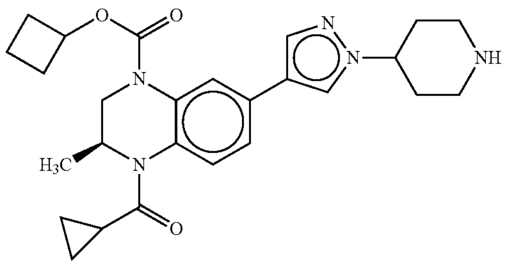 | 421 | 1.58 |
| I-1005 | 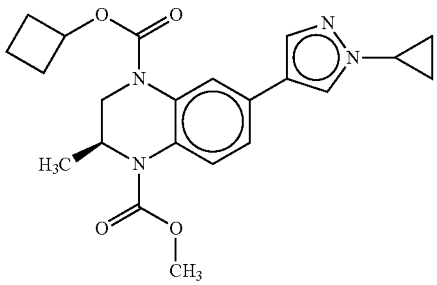 | 411 | 1.6 |
| I-1006 | 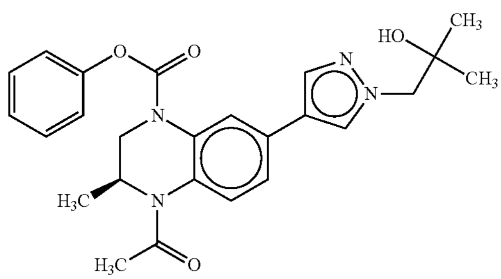 | 449 | 1.22 |
| I-1007 | 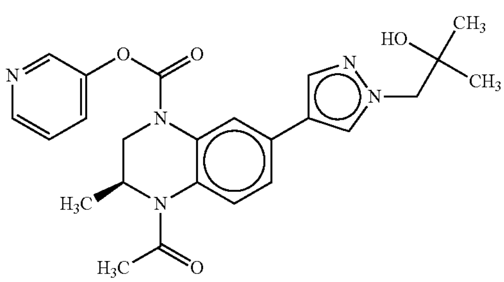 | 450 | 0.95 |
| I-1008 | 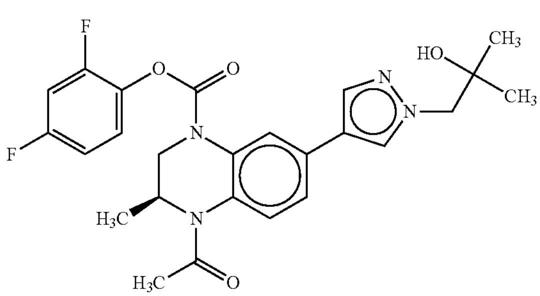 | 485 | 1.28 |

TABLE 24-continued
| Example | Structure | LC-MS [M + 1]+ | HPLC RT (min) |
|---|---|---|---|
| I-1009 | 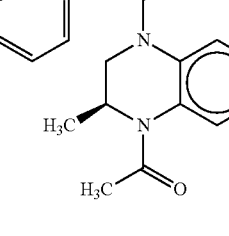 | 457 | 1.16 |
| I-1010 | 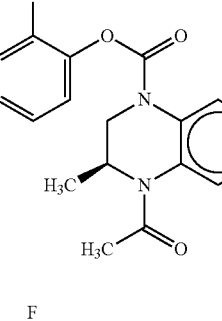 | 501 | 1.46 |
| I-1011 | 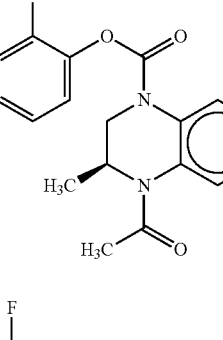 | 542 | 1.49 |
| I-1012 | 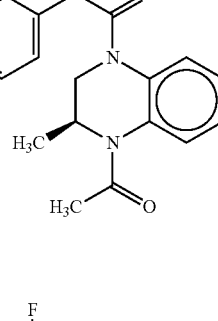 | 466 | 1.31 |
| I-1013 | 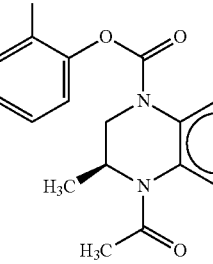 | 516 | 1.42 |

TABLE 24-continued

| Example | Structure | LC-MS [M + 1]+ | HPLC RT (min) |
|---|---|---|---|
| I-1014 | ![structure] | 485 | 1.35 |

Example 281

Library Protocol S

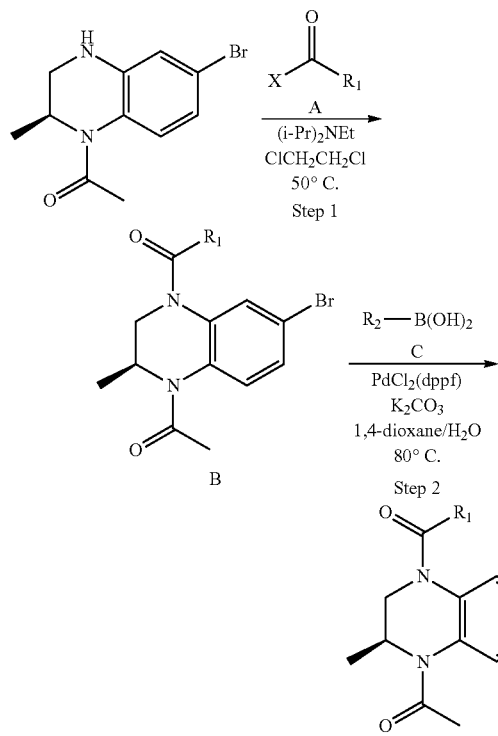

Step 1. A 1.5 mL reaction vial was charged with (S)-1-(6-bromo-2-methyl-3,4-dihydroquinoxalin-1(2H)-yl)ethanone (0.2M solution in 1,2-dichloroethane, 150 μL, 0.03 mmol), N,N-diisopropylethylamine (30 μL, 0.172 mmol), and the acid chloride (A, 0.5 M solution in 1,2-dichloroethane, 120 μL, 0.06 mmol) or chloroformate (A, 1.0 M solution in 1,2-dichloroethane, 120 μL, 0.12 mmol). The reaction was heated to 50° C. on a heater shaker for 2 h. The reaction was diluted with ethyl acetate (500 μL) and washed with saturated aqueous sodium chloride solution (500 μL). The aqueous layer was separated and extracted with ethyl acetate (1 mL), and the combined organic layers were concentrated under a stream of nitrogen and vacuum to yield the crude product (B) which was used without purification.

Step 2. A 1.5 mL reaction vial was charged with the aryl bromide (B) from above, 1,4-dioxane (100 μL), and the boronic acid (C) (0.2M solution in 1,4-dioxane, 225 μL, 0.045 mmol). Potassium carbonate (1 M solution in water, 90 μL, 0.09 mmol) was added, and the reaction mixture was purged with nitrogen. [1,1′-Bis(diphenylphosphino)ferrocene]dichloropalladium(II) dichloromethane adduct (0.02 M solution in 1,2-dichloroethane, 150 μL, 0.003 mmol) was added, the reaction was purged with nitrogen, and heated to 80° C. on a heater shaker overnight. The reaction was diluted with ethyl acetate (500 μL) and washed with a saturated aqueous sodium chloride solution (500 μL). The aqueous layer was separated and extracted with ethyl acetate (1 mL) and the combined organic layers were concentrated under a stream of nitrogen and vacuum. The crude product was purified by mass triggered preparatory HPLC. The product-containing fractions were combined and concentrated in a Genevac to afford the desired product.

The following compounds in Table 25 were synthesized according to the above protocol:

TABLE 25

| Example | Structure | LC-MS [M + 1]+ | HPLC RT (min) |
|---|---|---|---|
| I-1015 | ![structure] | 439 | 1.12 |

TABLE 25-continued

| Example | Structure | LC-MS [M + 1]+ | HPLC RT (min) |
|---|---|---|---|
| I-1016 | 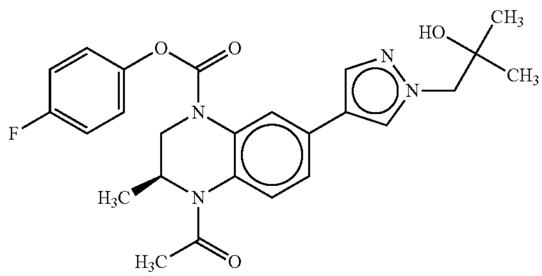 | 467 | 1.25 |
| I-1017 | 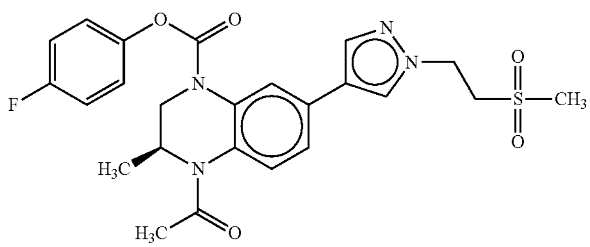 | 501 | 1.20 |
| I-1018 | 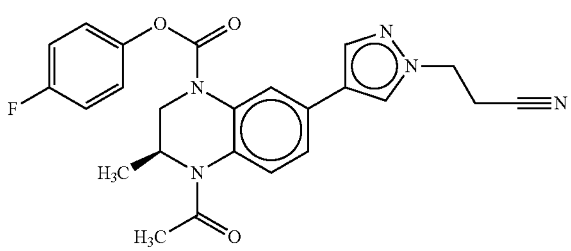 | 448 | 1.26 |
| I-1019 | 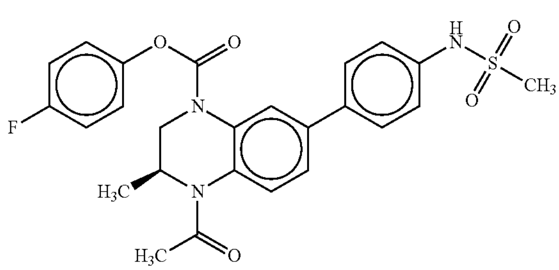 | 498 | 1.39 |
| I-1020 | 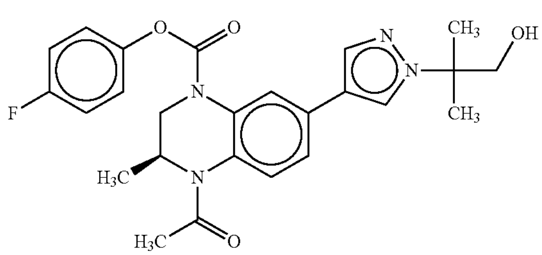 | 467 | 1.28 |

TABLE 25-continued

| Example | Structure | LC-MS [M + 1]+ | HPLC RT (min) |
|---|---|---|---|
| I-1021 | 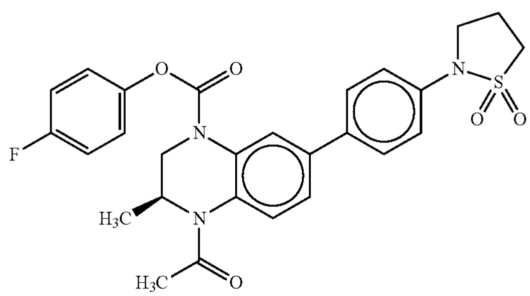 | 524 | 1.47 |
| I-1022 | 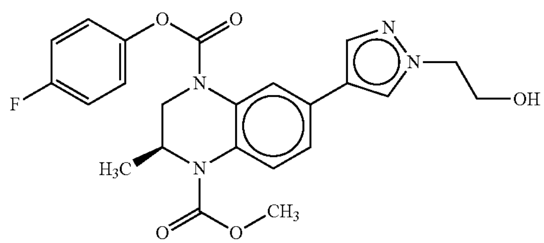 | 455 | 1.33 |
| I-1023 | 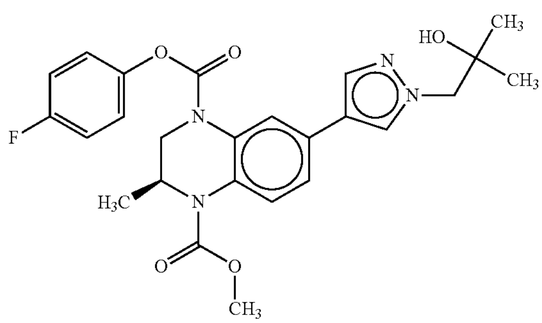 | 483 | 1.46 |
| I-1024 | 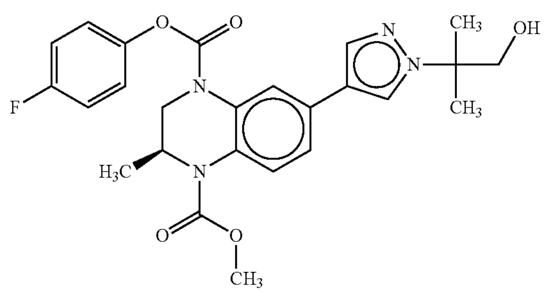 | 483 | 1.50 |
| I-1025 | 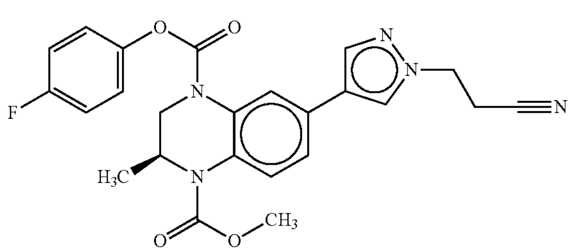 | 464 | 1.48 |

TABLE 25-continued

| Example | Structure | LC-MS [M + 1]+ | HPLC RT (min) |
|---|---|---|---|
| I-1026 | 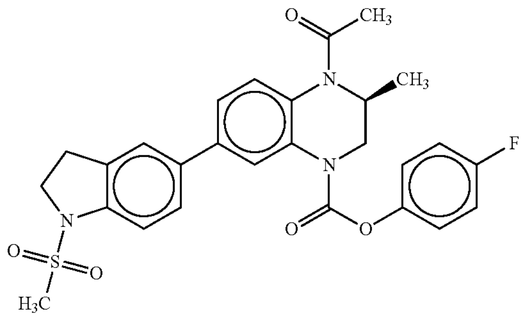 | 524 | 1.56 |
| I-1027 | 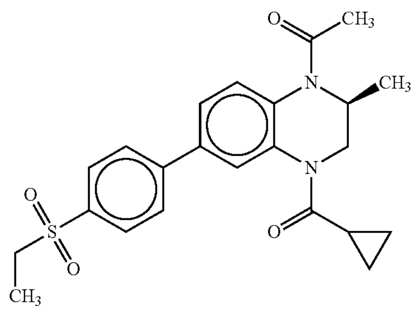 | 427 | 1.3 |
| I-1028 | 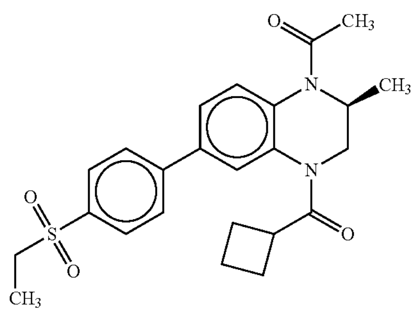 | 441 | 1.38 |
| I-1029 | 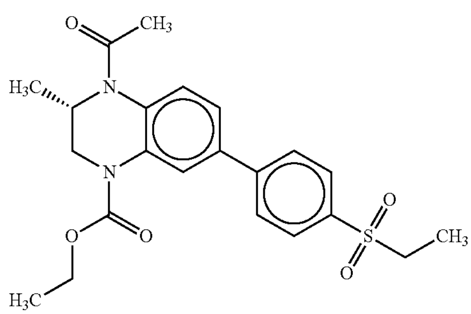 | 431 | 1.43 |
| I-1030 | 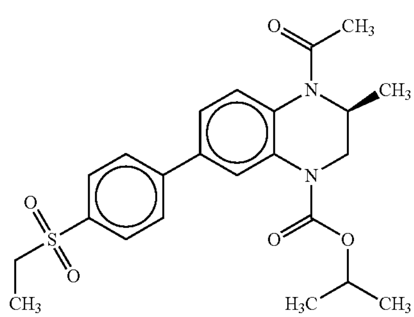 | 445 | 1.53 |

TABLE 25-continued

| Example | Structure | LC-MS [M + 1]+ | HPLC RT (min) |
|---------|-----------|----------------|---------------|
| I-1031 | 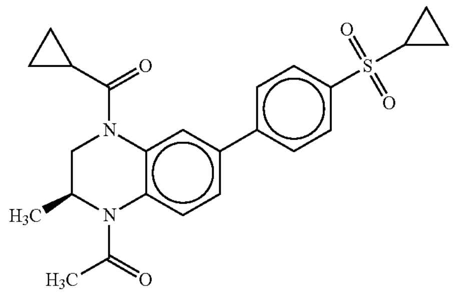 | 439 | 1.36 |
| I-1032 | 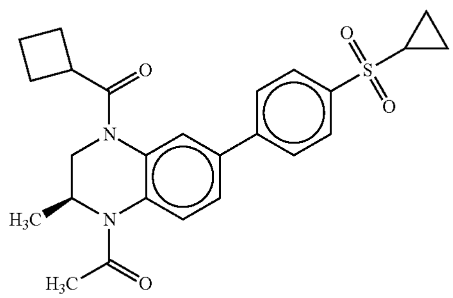 | 453 | 1.44 |
| I-1033 | 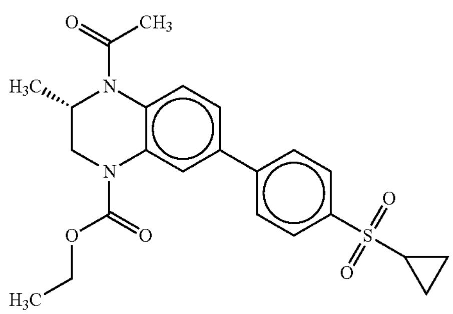 | 443 | 1.48 |
| I-1034 | 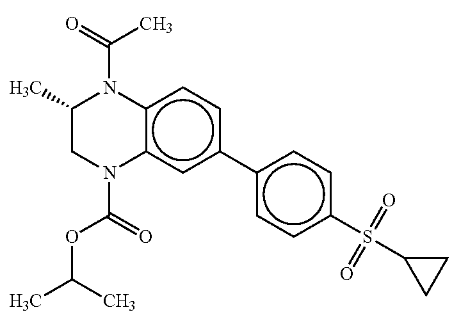 | 457 | 1.58 |
| I-1035 | 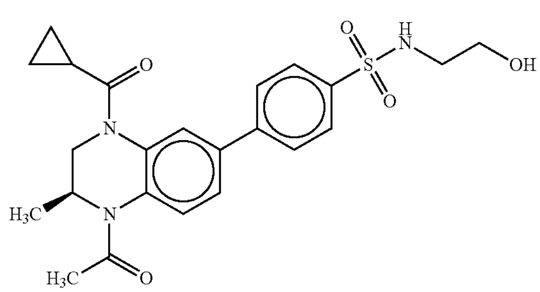 | 458 | 1.07 |

TABLE 25-continued

| Example | Structure | LC-MS [M + 1]+ | HPLC RT (min) |
|---------|-----------|----------------|---------------|
| I-1036 | 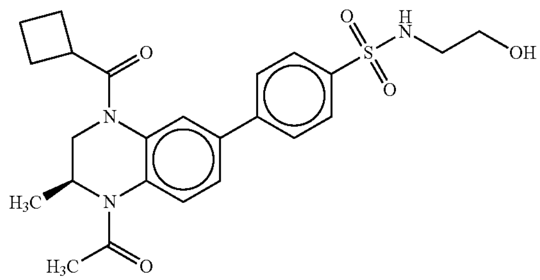 | 472 | 1.15 |
| I-1037 | 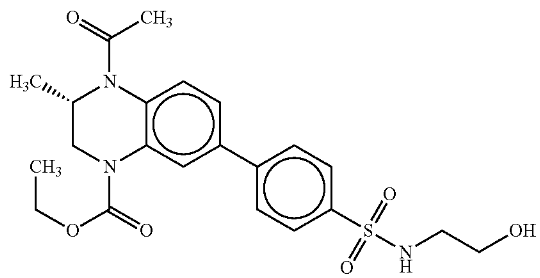 | 462 | 1.19 |
| I-1038 | 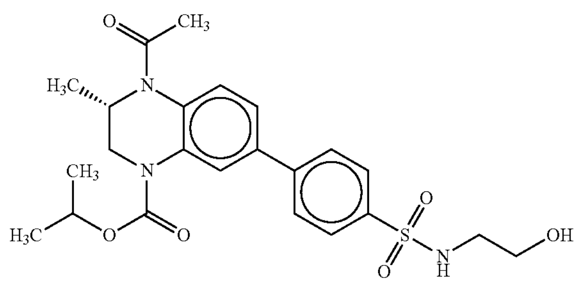 | 476 | 1.28 |
| I-1039 | 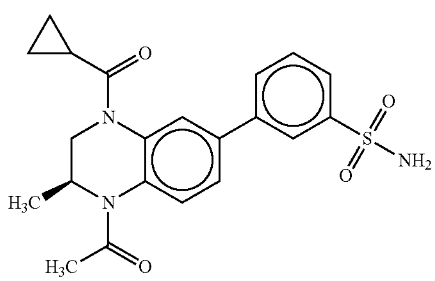 | 414 | 1.12 |
| I-1040 | 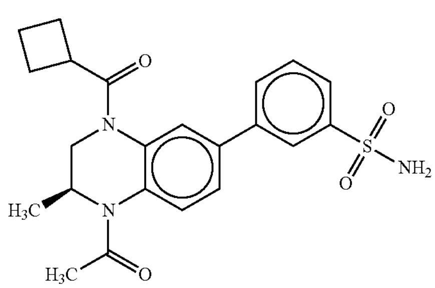 | 428 | 1.2 |

TABLE 25-continued

| Example | Structure | LC-MS [M + 1]+ | HPLC RT (min) |
|---|---|---|---|
| I-1041 | 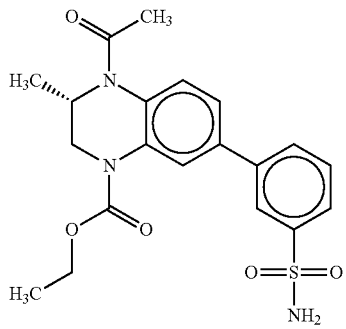 | 418 | 1.24 |
| I-1042 | 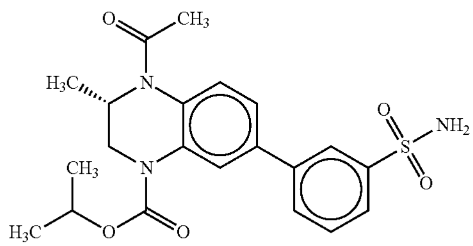 | 432 | 1.33 |
| I-1043 | 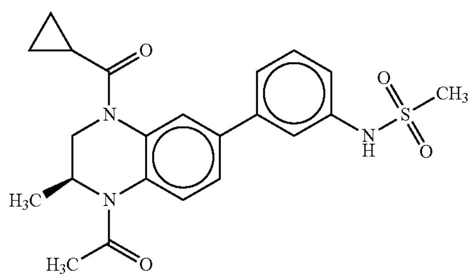 | 428 | 1.24 |
| I-1044 | 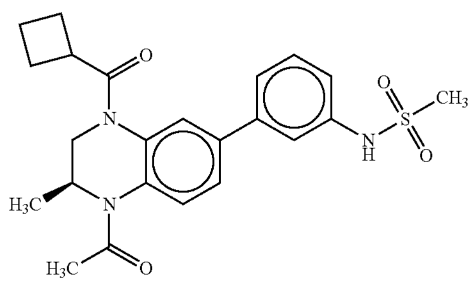 | 442 | 1.32 |
| I-1045 | 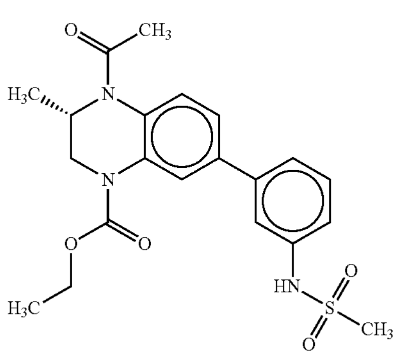 | 432 | 1.36 |

TABLE 25-continued

| Example | Structure | LC-MS [M + 1]+ | HPLC RT (min) |
|---|---|---|---|
| I-1046 | 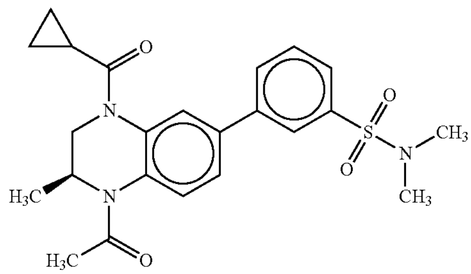 | 442 | 1.42 |
| I-1047 | 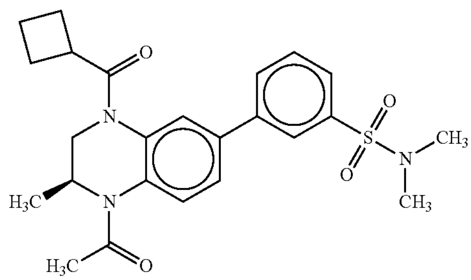 | 456 | 1.5 |
| I-1048 | 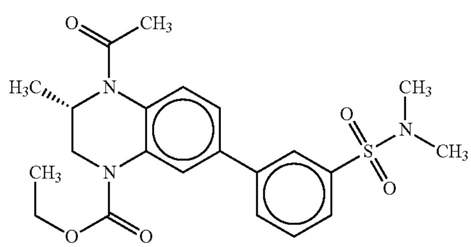 | 446 | 1.54 |
| I-1049 | 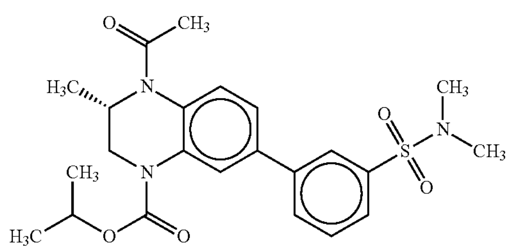 | 460 | 1.63 |
| I-1050 | 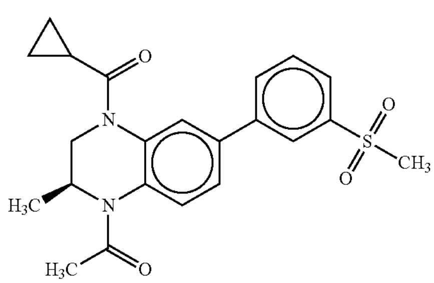 | 413 | 1.23 |

TABLE 25-continued

| Example | Structure | LC-MS [M + 1]+ | HPLC RT (min) |
|---|---|---|---|
| I-1051 | 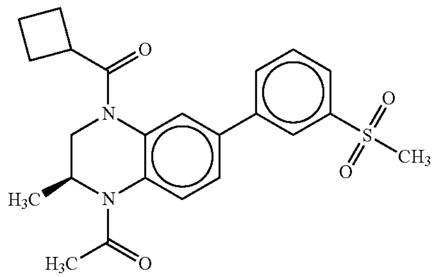 | 427 | 1.32 |
| I-1052 | 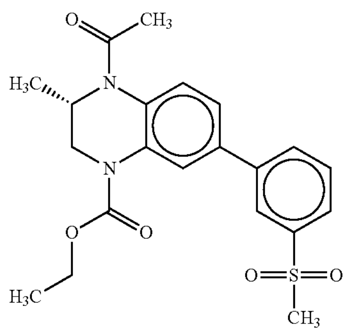 | 417 | 1.36 |
| I-1053 | 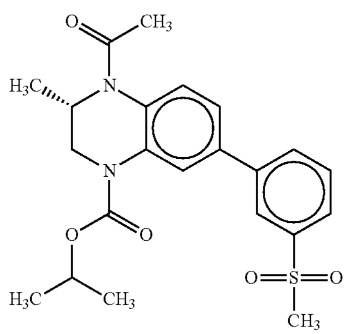 | 431 | 1.46 |
| I-1054 | 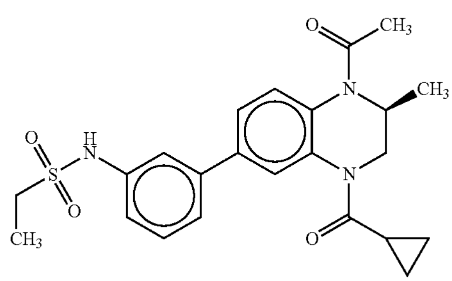 | 442 | 1.3 |
| I-1055 | 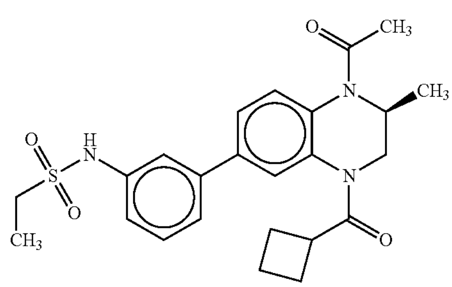 | 456 | 1.38 |

TABLE 25-continued

| Example | Structure | LC-MS [M + 1]+ | HPLC RT (min) |
|---|---|---|---|
| I-1056 | 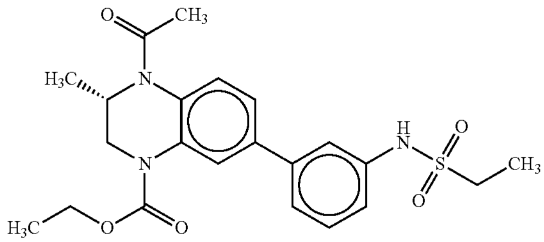 | 446 | 1.42 |
| I-1057 | 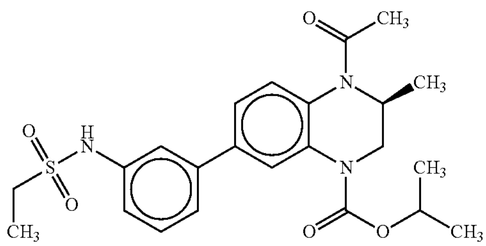 | 460 | 1.51 |
| I-1058 | 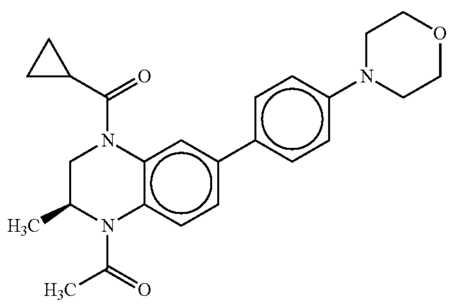 | 420 | 1.44 |
| I-1059 | 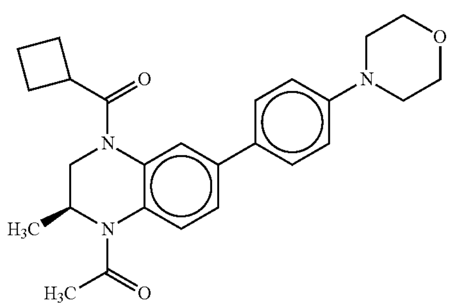 | 434 | 1.54 |
| I-1060 | 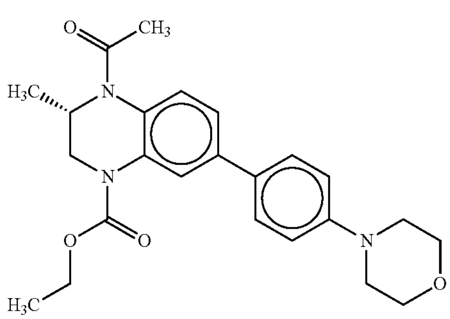 | 424 | 1.57 |

TABLE 25-continued

| Example | Structure | LC-MS [M + 1]+ | HPLC RT (min) |
|---|---|---|---|
| I-1061 | 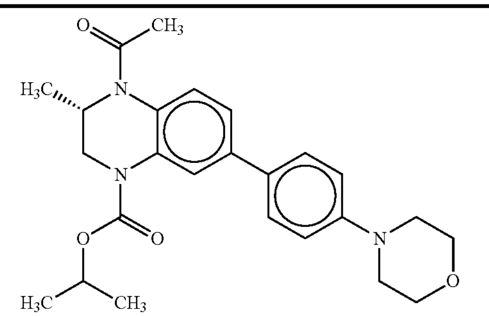 | 438 | 1.67 |
| I-1062 | 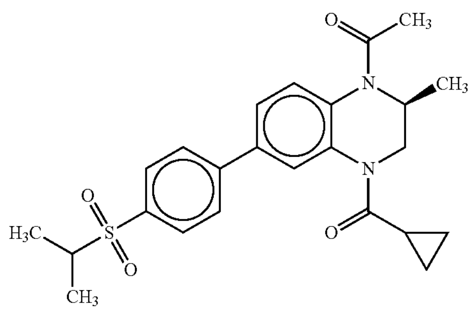 | 441 | 1.39 |
| I-1063 | 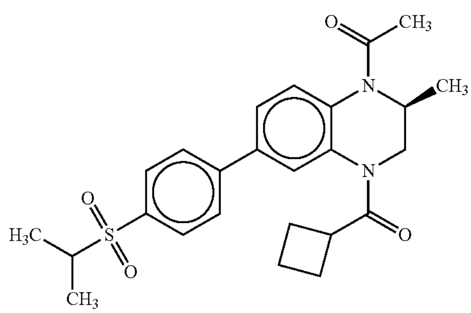 | 455 | 1.48 |
| I-1064 | 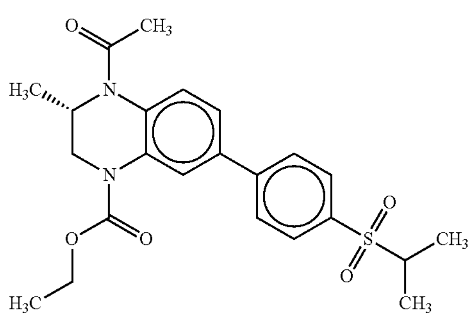 | 445 | 1.52 |
| I-1065 | 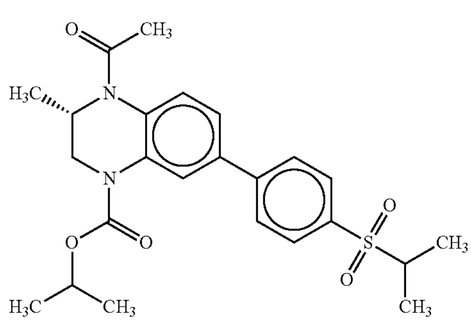 | 459 | 1.62 |

TABLE 25-continued

| Example | Structure | LC-MS [M + 1]+ | HPLC RT (min) |
|---|---|---|---|
| I-1066 | 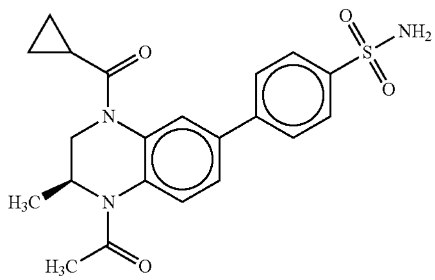 | 414 | 1.09 |
| I-1067 | 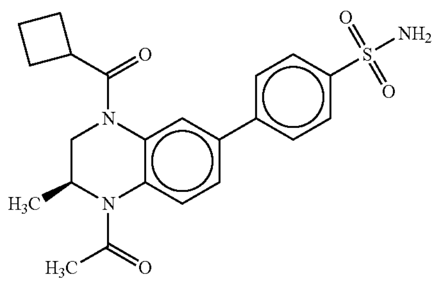 | 428 | 1.17 |
| I-1068 | 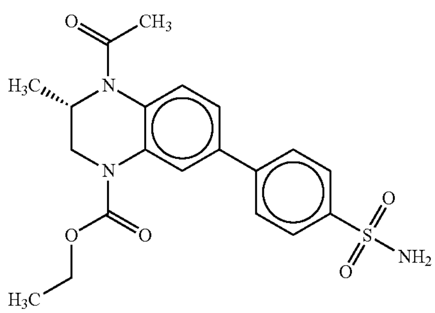 | 418 | 1.21 |
| I-1069 | 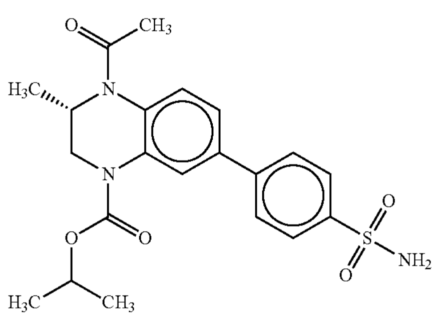 | 432 | 1.3 |
| I-1070 | 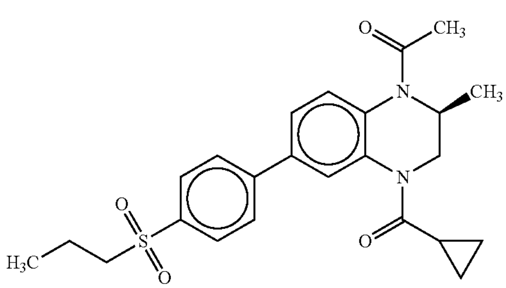 | 441 | 1.42 |

TABLE 25-continued

| Example | Structure | LC-MS [M + 1]+ | HPLC RT (min) |
|---------|-----------|----------------|---------------|
| I-1071 | 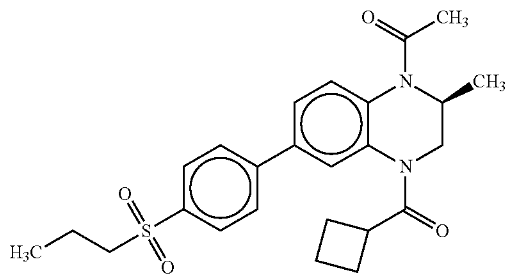 | 455 | 1.51 |
| I-1072 | 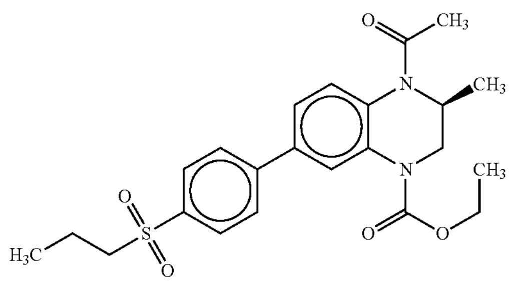 | 445 | 1.56 |
| I-1073 | 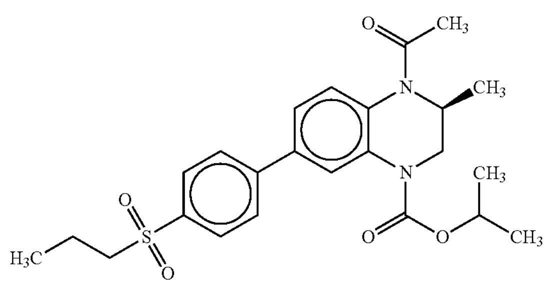 | 459 | 1.65 |
| I-1074 | 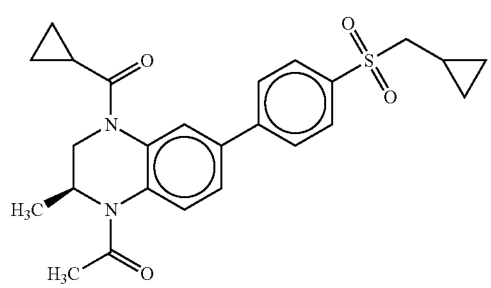 | 453 | 1.42 |
| I-1075 | 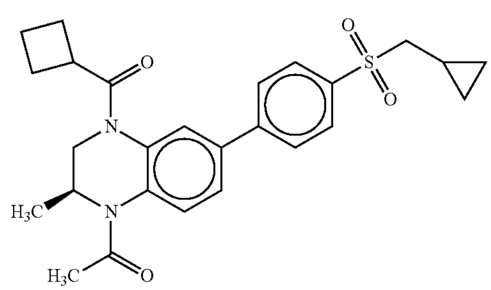 | 467 | 1.5 |

TABLE 25-continued

| Example | Structure | LC-MS [M + 1]+ | HPLC RT (min) |
|---|---|---|---|
| I-1076 | 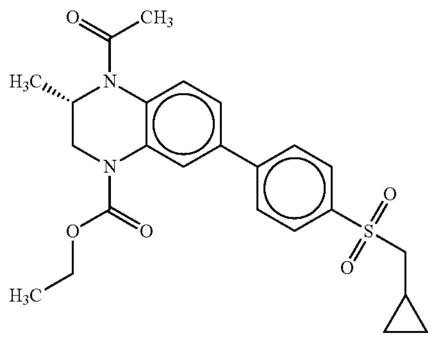 | 457 | 1.55 |
| I-1077 | 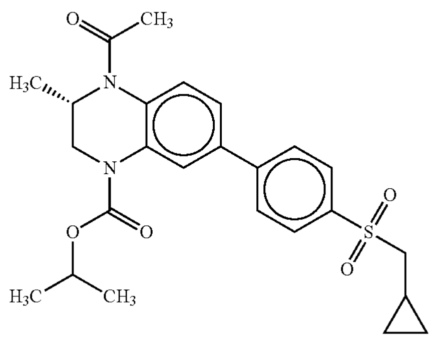 | 471 | 1.64 |
| I-1078 | 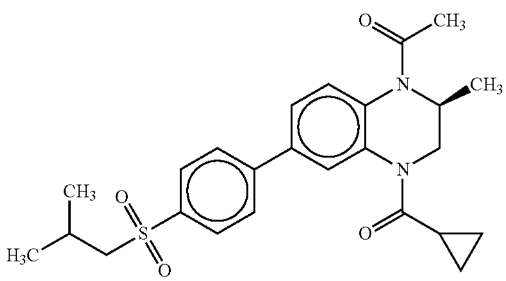 | 455 | 1.54 |
| I-1079 | 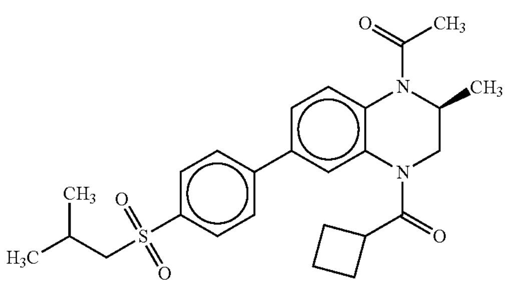 | 469 | 1.62 |
| I-1080 | 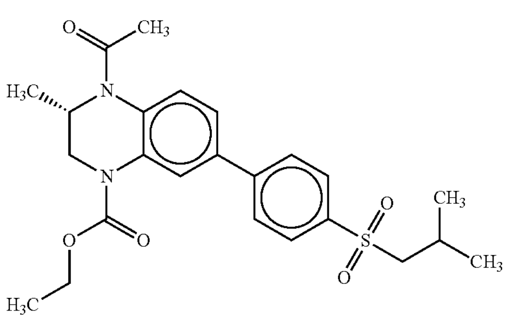 | 459 | 1.67 |

TABLE 25-continued

| Example | Structure | LC-MS [M + 1]+ | HPLC RT (min) |
|---|---|---|---|
| I-1081 | 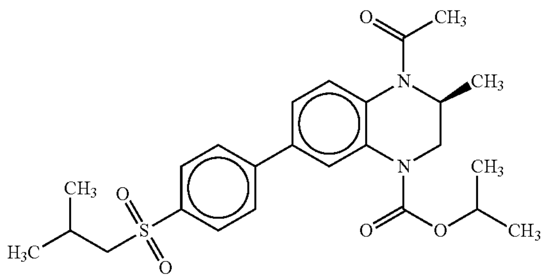 | 473 | 1.76 |
| I-1082 | 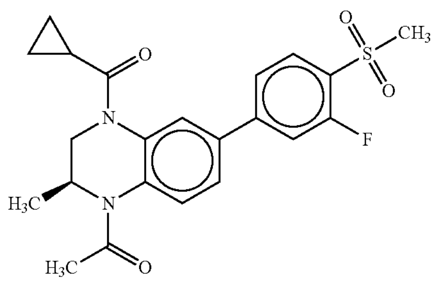 | 431 | 1.28 |
| I-1083 | 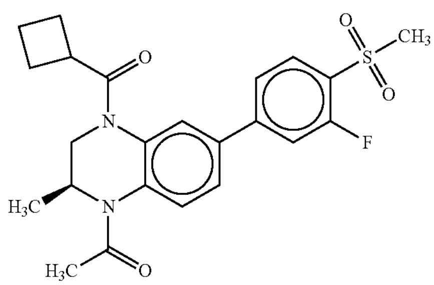 | 445 | 1.36 |
| I-1084 | 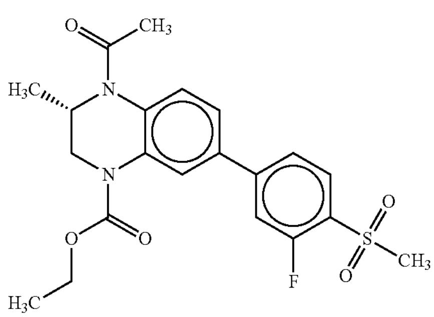 | 435 | 1.41 |
| I-1085 | 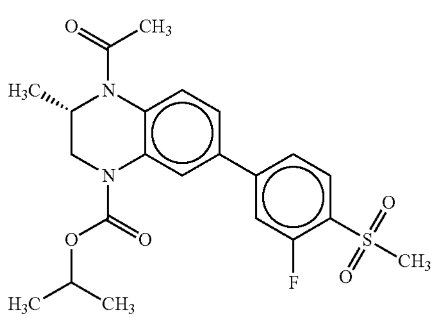 | 449 | 1.51 |

TABLE 25-continued

| Example | Structure | LC-MS [M + 1]+ | HPLC RT (min) |
|---|---|---|---|
| I-1086 | 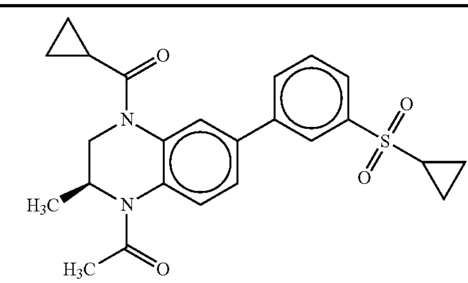 | 439 | 1.37 |
| I-1087 | 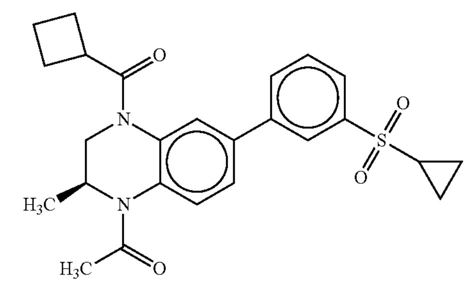 | 453 | 1.45 |
| I-1088 | 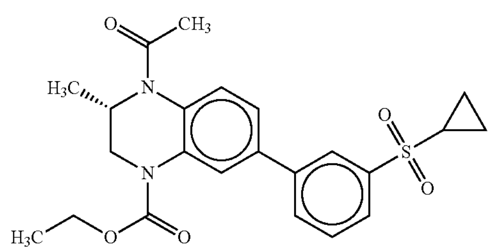 | 443 | 1.5 |
| I-1089 | 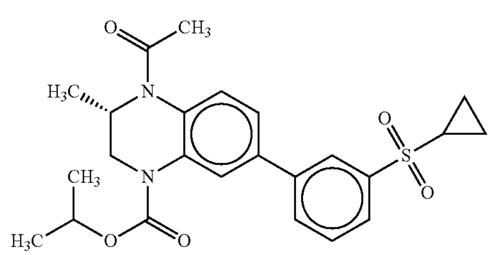 | 457 | 1.59 |
| I-1090 | 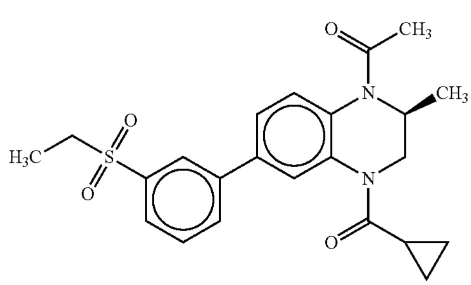 | 427 | 1.32 |

TABLE 25-continued
| Example | Structure | LC-MS [M + 1]+ | HPLC RT (min) |
|---|---|---|---|
| I-1091 | 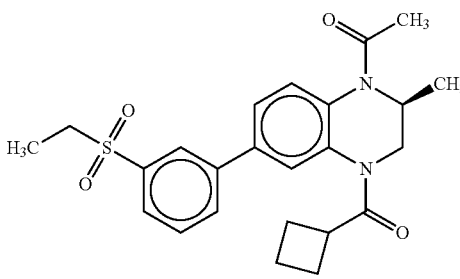 | 441 | 1.4 |
| I-1092 | 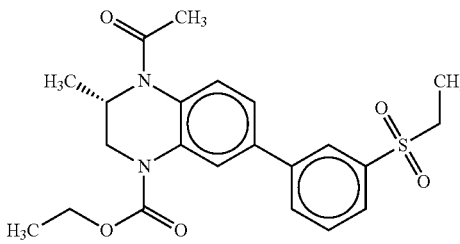 | 431 | 1.44 |
| I-1093 | 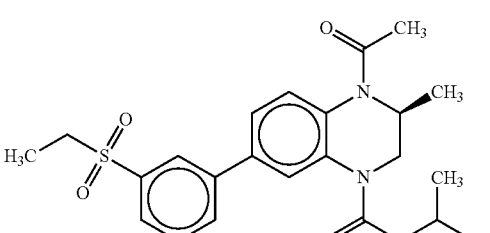 | 445 | 1.54 |
| I-1094 | 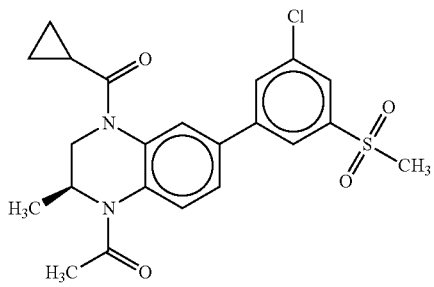 | 447 | 1.43 |
| I-1095 | 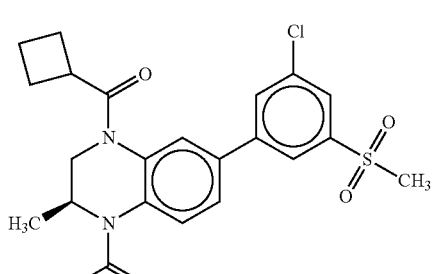 | 461 | 1.52 |

TABLE 25-continued

| Example | Structure | LC-MS [M + 1]+ | HPLC RT (min) |
|---|---|---|---|
| I-1096 | 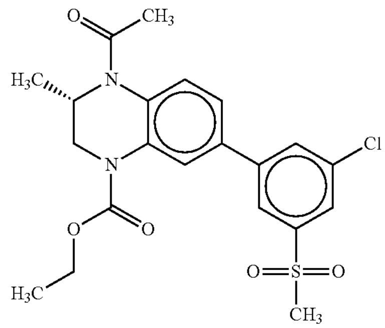 | 451 | 1.58 |
| I-1097 | 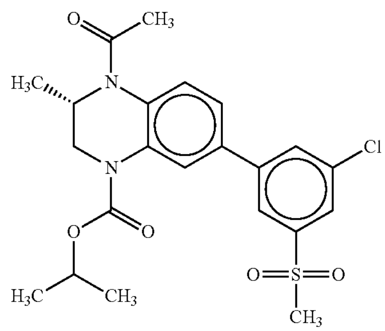 | 465 | 1.67 |
| I-1098 | 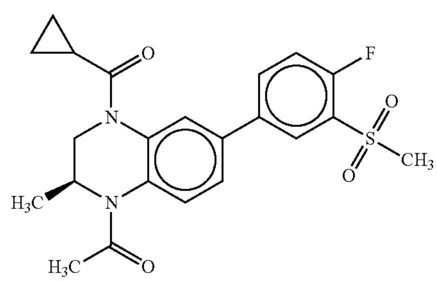 | 431 | 1.28 |
| I-1099 | 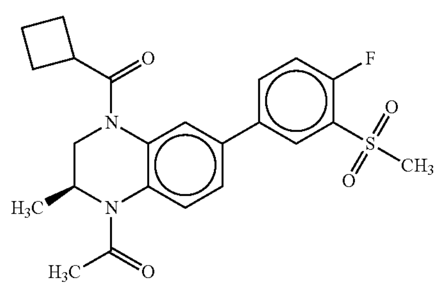 | 445 | 1.37 |
| I-1100 | 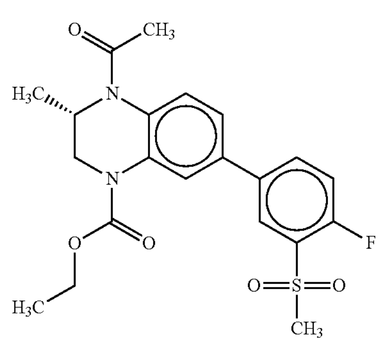 | 435 | 1.41 |

TABLE 25-continued

| Example | Structure | LC-MS [M + 1]+ | HPLC RT (min) |
|---|---|---|---|
| I-1101 | 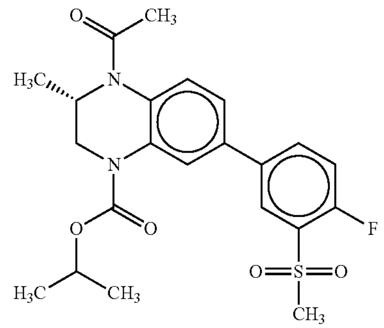 | 449 | 1.5 |
| I-1102 | 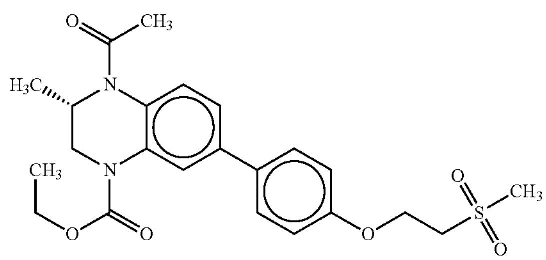 | 461 | 1.37 |
| I-1103 | 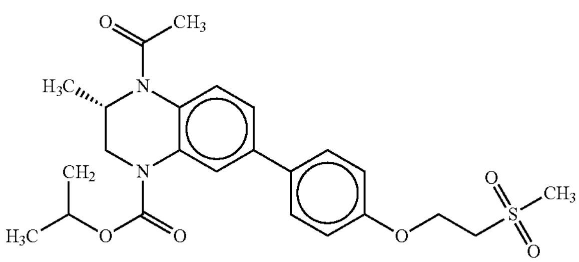 | 475 | 1.45 |
| I-1104 | 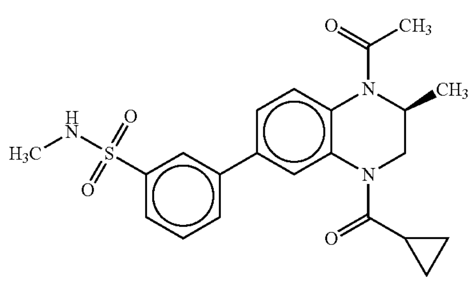 | 428 | 1.25 |
| I-1105 | 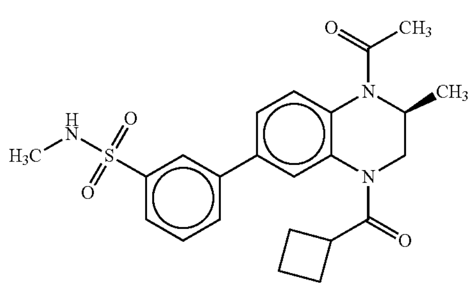 | 442 | 1.34 |

TABLE 25-continued

| Example | Structure | LC-MS [M + 1]+ | HPLC RT (min) |
|---|---|---|---|
| I-1106 | 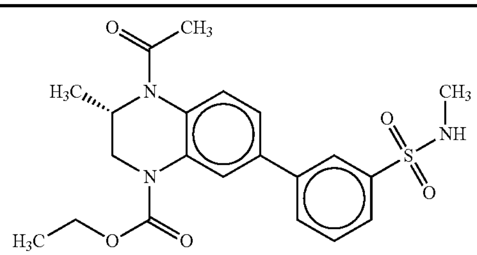 | 432 | 1.38 |
| I-1107 | 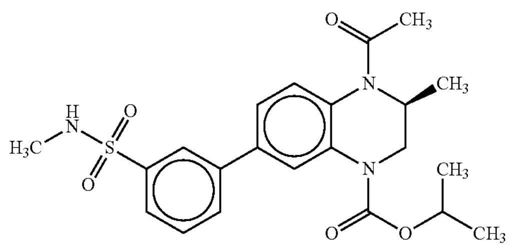 | 446 | 1.46 |
| I-1108 | 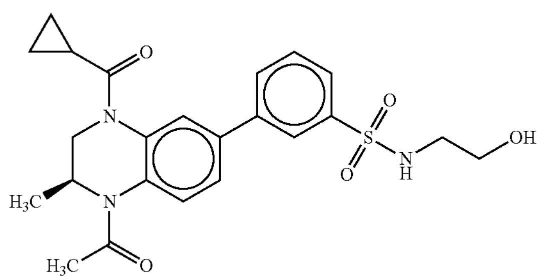 | 458 | 1.02 |
| I-1109 | 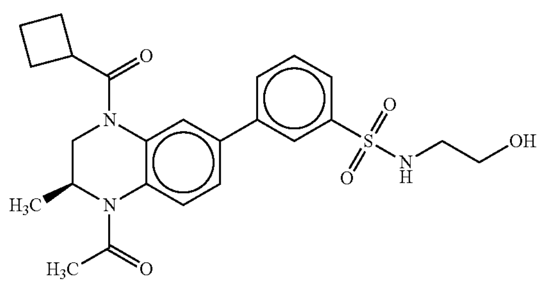 | 472 | 1.09 |
| I-1110 | 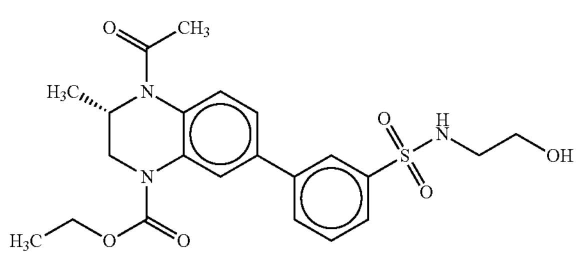 | 462 | 1.13 |
| I-1111 | 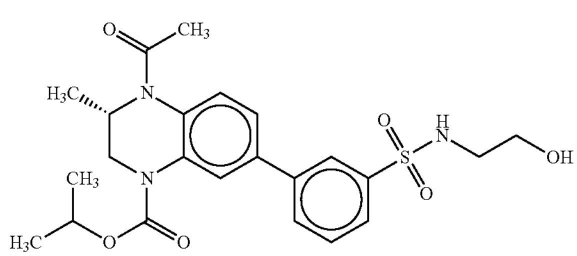 | 476 | 1.2 |

TABLE 25-continued

| Example | Structure | LC-MS [M + 1]+ | HPLC RT (min) |
|---|---|---|---|
| I-1112 | 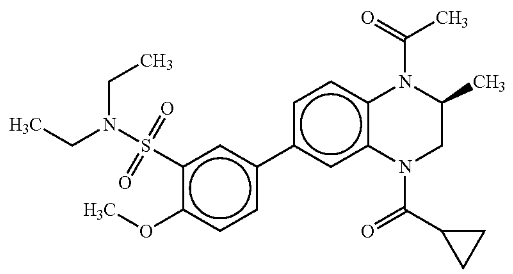 | 500 | 1.45 |
| I-1113 | 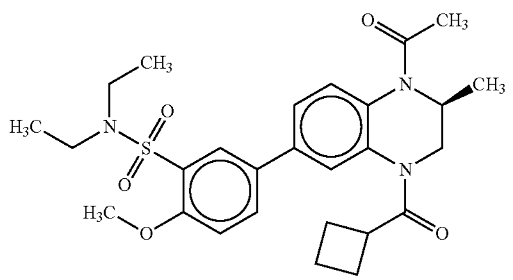 | 514 | 1.52 |
| I-1114 | 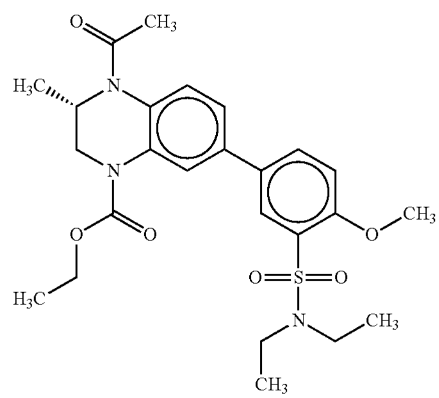 | 504 | 1.55 |
| I-1115 | 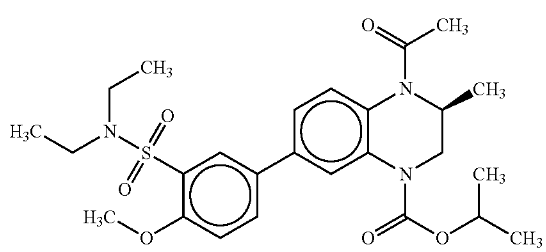 | 518 | 1.64 |
| I-1116 | 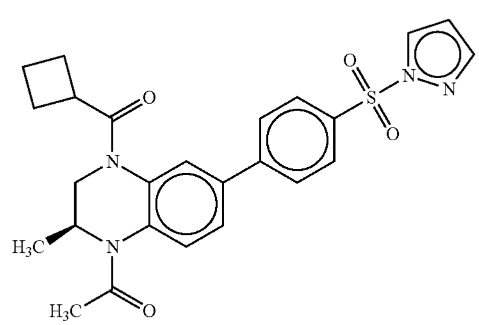 | 479 | 1.44 |

TABLE 25-continued

| Example | Structure | LC-MS [M + 1]+ | HPLC RT (min) |
|---|---|---|---|
| I-1117 | 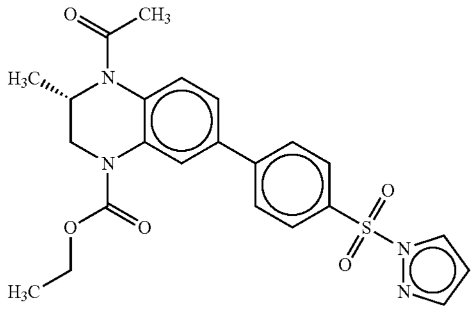 | 469 | 1.48 |
| I-1118 | 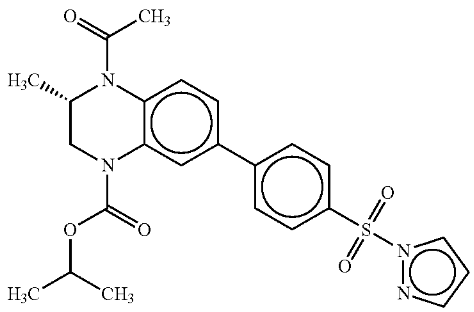 | 483 | 1.57 |
| I-1119 | 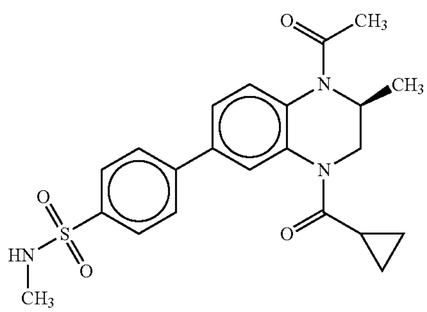 | 428 | 1.13 |
| I-1120 | 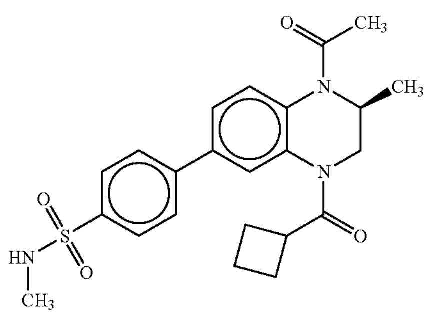 | 442 | 1.21 |
| I-1121 | 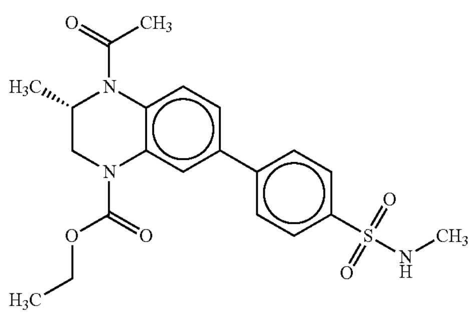 | 432 | 1.25 |

TABLE 25-continued

| Example | Structure | LC-MS [M + 1]+ | HPLC RT (min) |
|---|---|---|---|
| I-1122 | 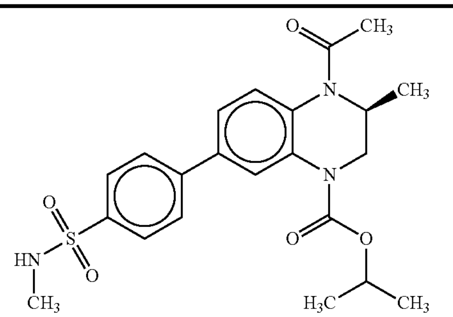 | 446 | 1.35 |
| I-1123 | 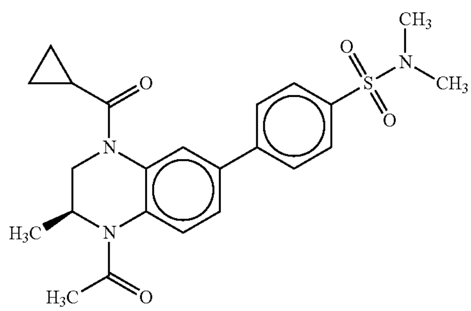 | 442 | 1.3 |
| I-1124 | 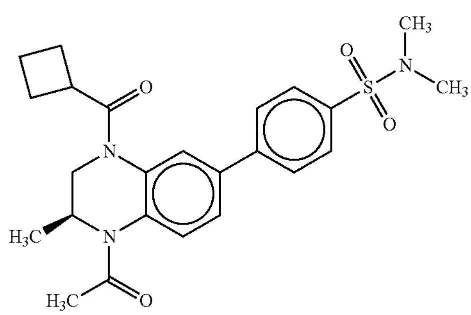 | 456 | 1.38 |
| I-1125 | 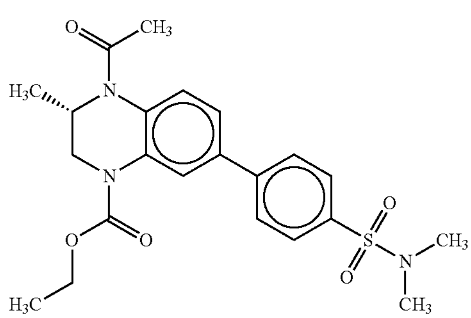 | 446 | 1.43 |
| I-1126 | 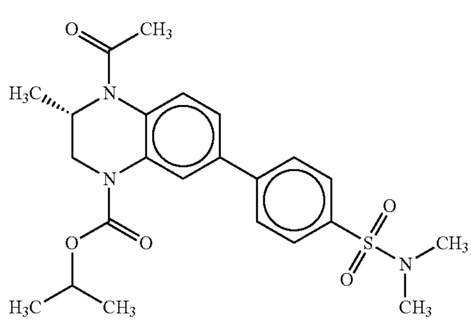 | 460 | 1.52 |

TABLE 25-continued

| Example | Structure | LC-MS [M + 1]+ | HPLC RT (min) |
|---|---|---|---|
| I-1127 | 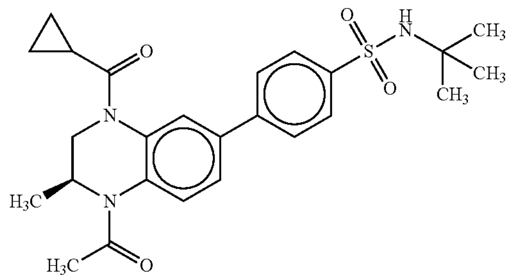 | 470 | 1.39 |
| I-1128 | 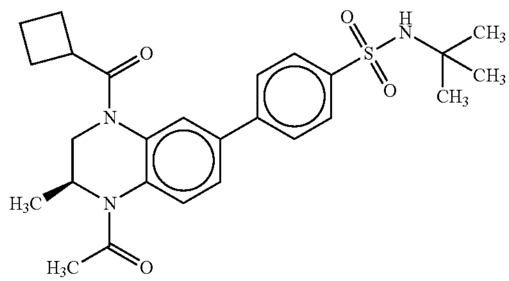 | 484 | 1.47 |
| I-1129 | 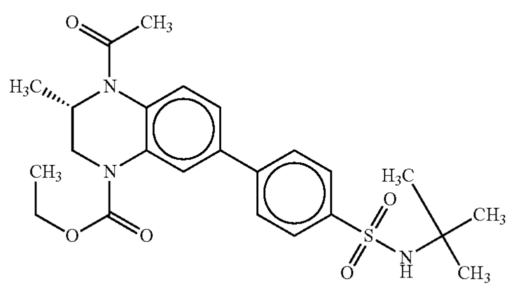 | 474 | 1.52 |
| I-1130 | 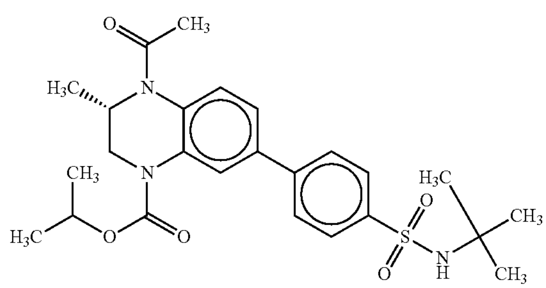 | 488 | 1.6 |
| I-1131 | 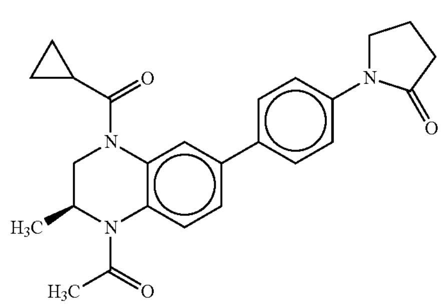 | 418 | 1.19 |

TABLE 25-continued

| Example | Structure | LC-MS [M + 1]+ | HPLC RT (min) |
|---------|-----------|----------------|---------------|
| I-1132 | 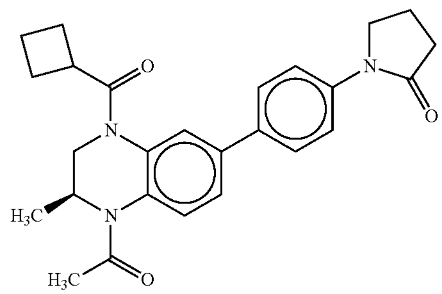 | 432 | 1.28 |
| I-1133 | 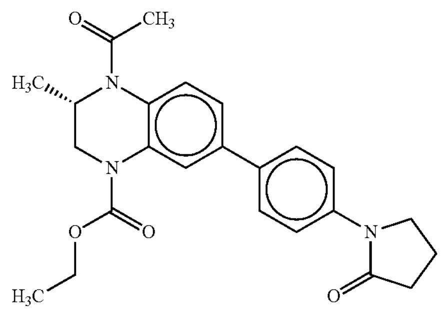 | 422 | 1.31 |
| I-1134 | 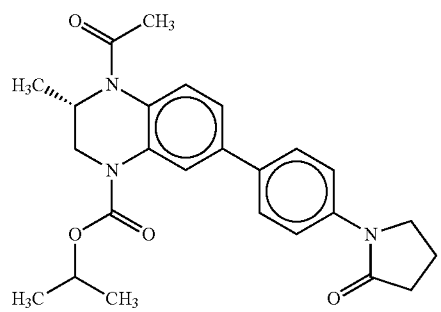 | 436 | 1.41 |
| I-1135 | 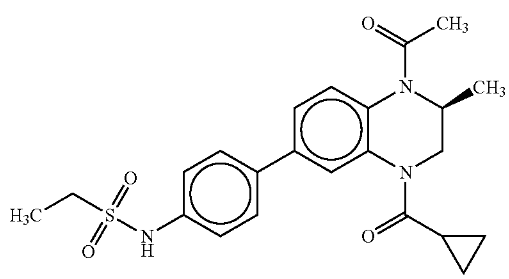 | 442 | 1.17 |
| I-1136 | 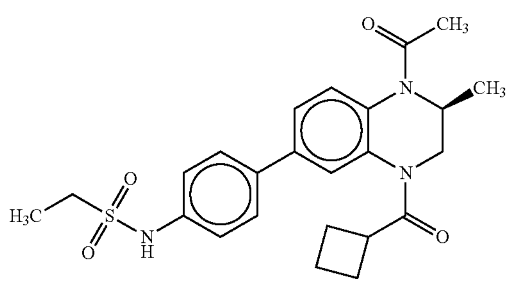 | 456 | 1.25 |

TABLE 25-continued

| Example | Structure | LC-MS [M + 1]+ | HPLC RT (min) |
|---|---|---|---|
| I-1137 | 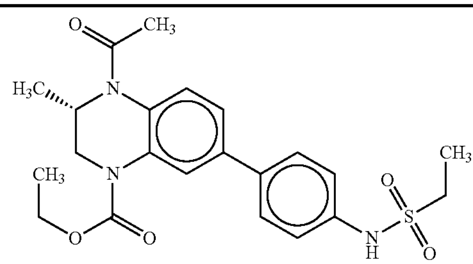 | 446 | 1.28 |
| I-1138 | 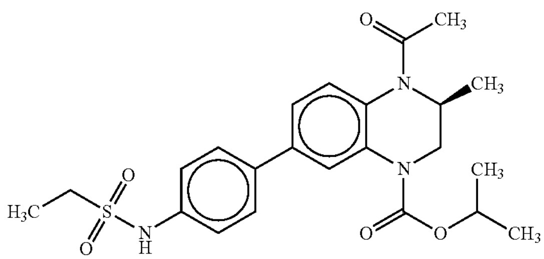 | 460 | 1.37 |
| I-1139 | 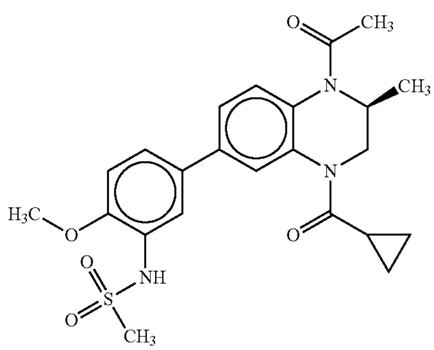 | 458 | 1.16 |
| I-1140 | 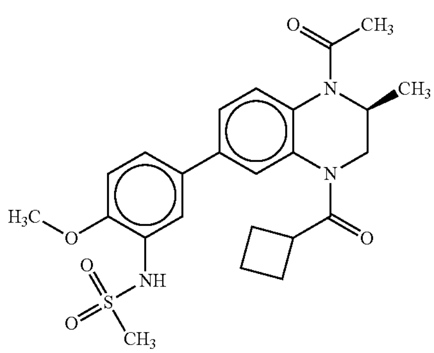 | 472 | 1.23 |
| I-1141 | 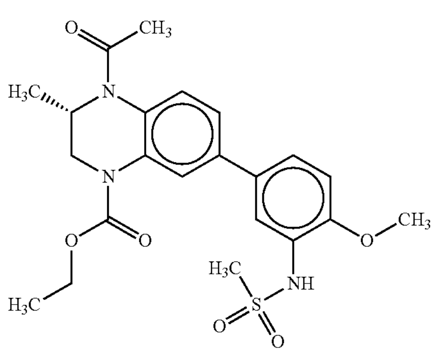 | 462 | 1.26 |

TABLE 25-continued

| Example | Structure | LC-MS [M + 1]+ | HPLC RT (min) |
|---------|-----------|----------------|---------------|
| I-1142 | 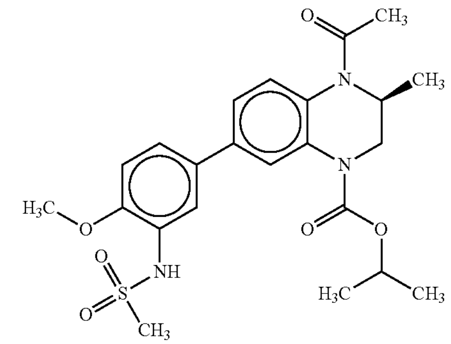 | 476 | 1.35 |
| I-1143 | 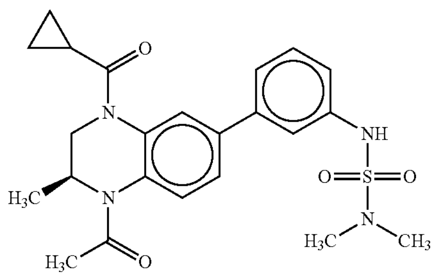 | 457 | 1.25 |
| I-1144 | 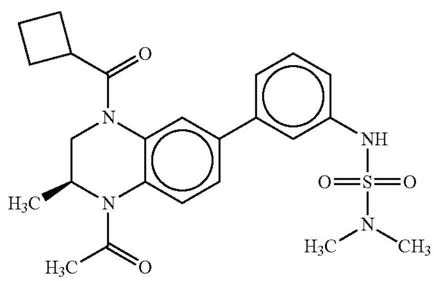 | 471 | 1.33 |
| I-1145 | 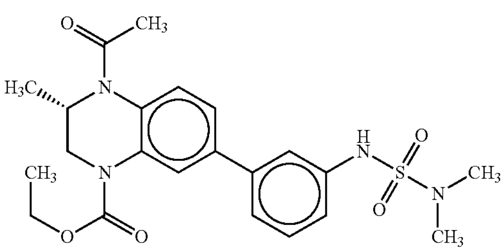 | 461 | 1.37 |
| I-1146 | 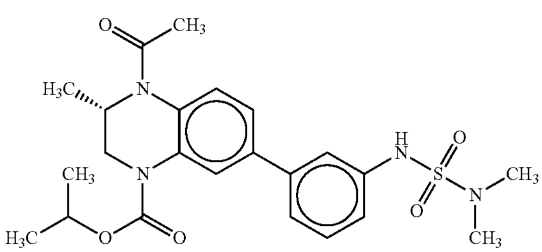 | 475 | 1.45 |

TABLE 25-continued

| Example | Structure | LC-MS [M + 1]+ | HPLC RT (min) |
|---|---|---|---|
| I-1147 | 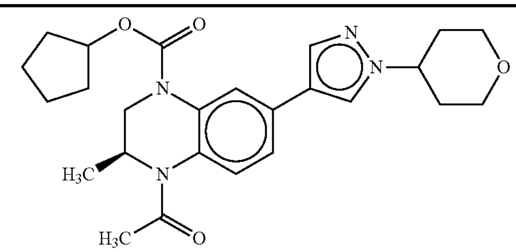 | 453 | 1.35 |
| I-1148 | 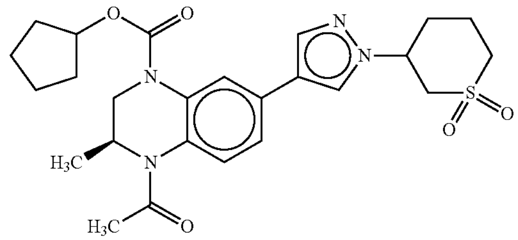 | 501 | 1.31 |

Example 282

Library Protocol S1

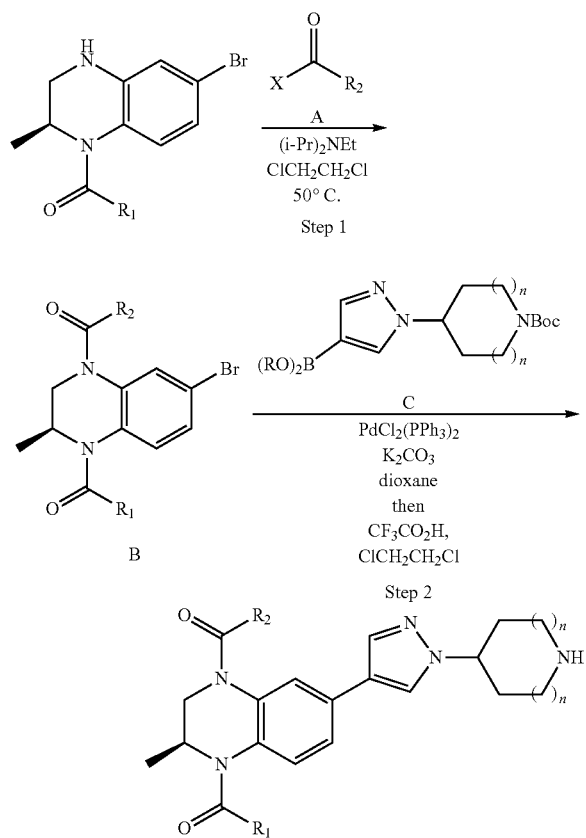

$n = 0, 1$

Step 1. A 1.5 mL reaction vial was charged with (S)-1-(6-bromo-2-methyl-3,4-dihydroquinoxalin-1(2H)-yl)ethanone (0.2 M solution in 1,2-dichloroethane, 150 µL, 0.03 mmol), N,N-diisopropylethylamine (30 µL, 0.172 mmol), and the acid chloride (A, 0.5M solution in 1,2-dichloroethane, 120 µL, 0.06 mmol) or chloroformate (A, 1.0 M solution in 1,2-dichloroethane, 120 µL, 0.12 mmol). The reaction was heated to 50° C. on a heater shaker for 2 h. The reaction was diluted with ethyl acetate (500 µL) and washed with saturated aqueous sodium chloride solution (500 µL). The aqueous layer was separated and extracted with ethyl acetate (1 mL) and the combined organic layers were concentrated under a stream of nitrogen and vacuum to yield the crude product (B) which was used without purification.

Step 2. A 1.5 mL reaction vial was charged with the aryl bromide (B) from above, 1,4-dioxane (100 µL), and the boronic acid (C) (0.2M solution in 1,4-dioxane, 225 µL, 0.045 mmol). Potassium carbonate (1 M solution in water, 90 µL, 0.09 mmol) was added, and the reaction mixture was purged with nitrogen. [1,1'-Bis(diphenylphosphino)ferrocene]dichloropalladium(II) dichloromethane adduct (0.02 M solution in 1,2-dichloroethane, 150 µL, 0.003 mmol) was added, the reaction was purged with nitrogen, and heated to 80° C. on a heater shaker overnight. The reaction was diluted with ethyl acetate (500 µL) and washed with a saturated aqueous sodium chloride solution (500 µL). The aqueous layer was separated and extracted with ethyl acetate (1 mL) and the combined organic layers were concentrated under a stream of nitrogen and vacuum. The residue was taken up in 1,2-dichloroethane (200 µL) and trifluoroacetic acid (100 µL) was added. The reaction was placed on a shaker at room temperature for 2 h. The reaction was concentrated and diluted with ethyl acetate (0.5 mL) and saturated aqueous sodium bicarbonate solution (0.5 mL). The aqueous layer was separated and extracted with ethyl acetate (1 mL), and the organic layers were combined and concentrated under a stream of nitrogen and vacuum. The crude product was purified by mass triggered preparatory HPLC. The product-containing fractions were combined and concentrated in a Genevac to afford the desired product.

The following compounds in Table 26 were synthesized according to the above protocol:

TABLE 26

| Example | Structure | LC-MS [M + 1]+ | HPLC RT (min) |
|---|---|---|---|
| I-1149 | 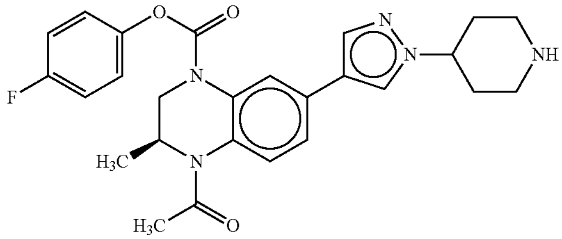 | 478 | 0.96 |
| I-1150 | 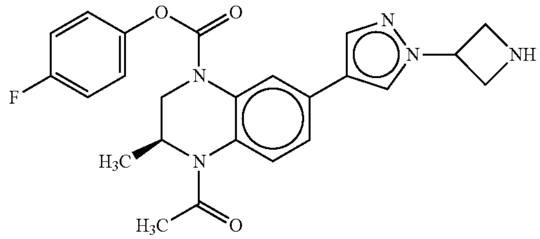 | 450 | 0.95 |
| I-1151 | 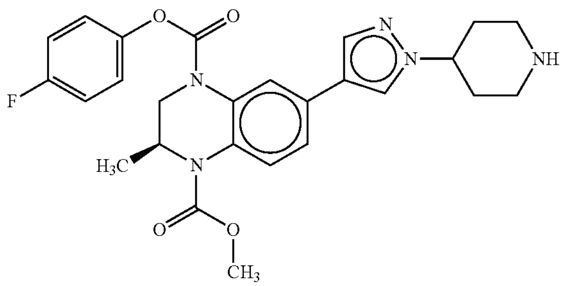 | 494 | 1.16 |

Example 283

Library Protocol T

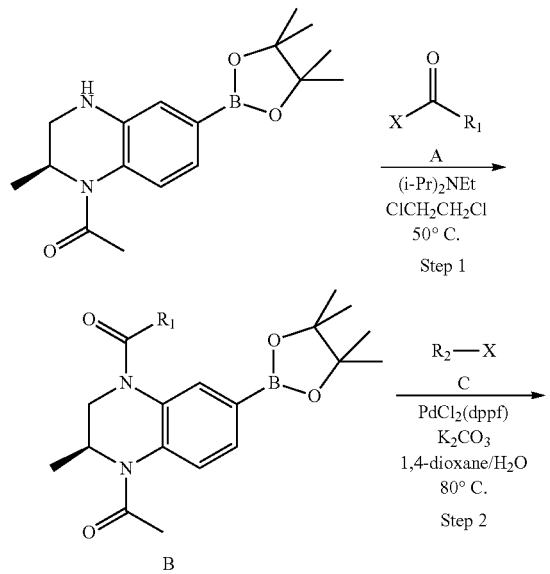

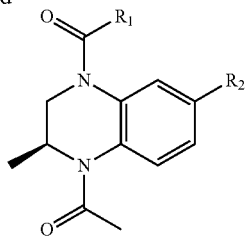

Step 1. A 1.5 mL reaction vial was charged with (S)-1-(2-methyl-6-(4,4,5,5-tetramethyl-1,3,2-dioxaborolan-2-yl)-3,4-dihydroquinoxalin-1(2H)-yl)ethan-1-one (0.4 M solution in 1,2-dichloroethane, 150 µL, 0.06 mmol), N,N-diisopropylethylamine (60 µL, 0.344 mmol), and the acid chloride (A, 0.5M solution in 1,2-dichloroethane, 240 µL, 0.12 mmol) or chloroformate (A, 1.0 M solution in 1,2-dichloroethane, 240 µL, 0.24 mmol). The reaction was heated to 50° C. on a heater shaker for 2 hrs. The reaction was diluted with ethyl acetate (500 µL) and washed with saturated aqueous sodium chloride solution (500 µL). The aqueous layer was separated and extracted with ethyl acetate (1 mL) and the combined organic layers were concentrated under a stream of nitrogen and vacuum to yield the crude product (B) which was used without purification.

Step 2. A 1.5 mL reaction vial was charged with the boronic ester (B) from above, 1,4-dioxane (200 µL), and the aryl halide (C) (0.2 M solution in 1,4-dioxane, 200 µL, 0.040 mmol). Potassium carbonate (1 M solution in water, 120 μL, 0.12 mmol) was added, and the reaction mixture was purged with nitrogen. [1,1'-Bis(diphenylphosphino)ferrocene]dichloropalladium(II) dichloromethane adduct (0.02 M solution in 1,2-dichloroethane, 200 μL, 0.004 mmol) was added, the reaction was purged with nitrogen, and heated to 80° C. on a heater shaker overnight. The reaction was diluted with ethyl acetate (500 μL) and washed with a saturated aqueous sodium chloride solution (500 μL). The aqueous layer was separated and extracted with ethyl acetate (1 mL) and the combined organic layers were concentrated under a stream of nitrogen and vacuum. The crude product was purified by mass triggered preparatory HPLC. The product-containing fractions were combined and concentrated in a Genevac to afford the desired product.

The following compounds in Table 27: were synthesized according to the above protocol:

TABLE 27

| Example | Structure | LC-MS [M + 1]+ | HPLC RT (min) |
|---------|-----------|----------------|---------------|
| I-1152  | 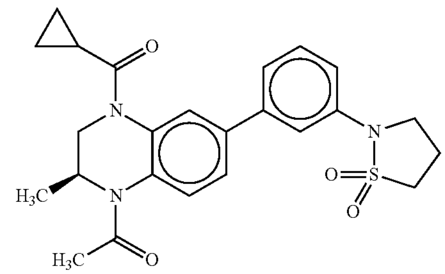          | 454            | 1.3           |
| I-1153  | 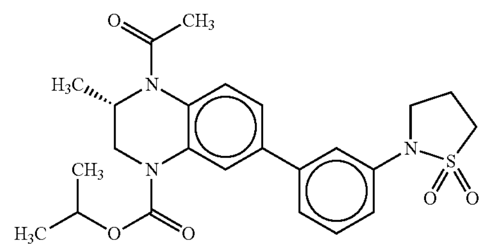          | 472            | 1.49          |
| I-1154  | 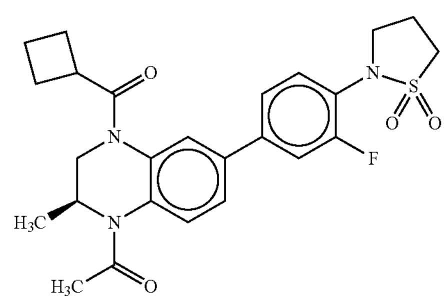          | 486            | 1.28          |
| I-1155  | 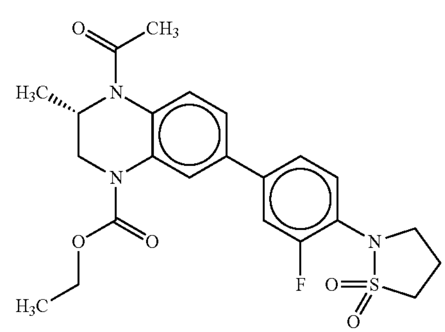          | 476            | 1.32          |

TABLE 27-continued
| Example | Structure | LC-MS [M + 1]+ | HPLC RT (min) |
|---------|-----------|----------------|---------------|
| I-1156 | 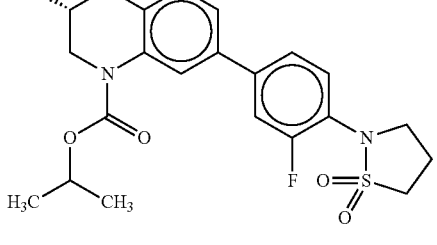 | 490 | 1.41 |
| I-1157 | 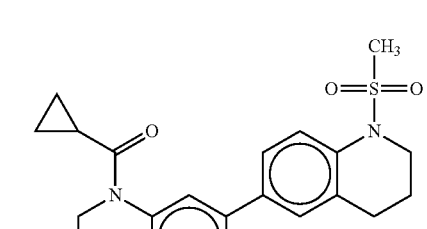 | 468 | 1.35 |
| I-1158 | 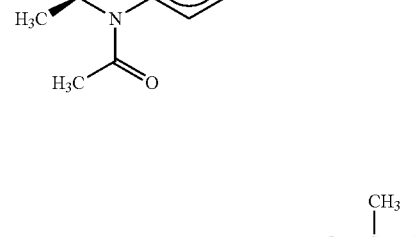 | 482 | 1.42 |
| I-1159 | 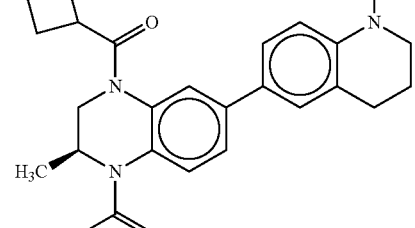 | 472 | 1.46 |

TABLE 27-continued

| Example | Structure | LC-MS [M + 1]+ | HPLC RT (min) |
|---------|-----------|----------------|---------------|
| I-1160  | 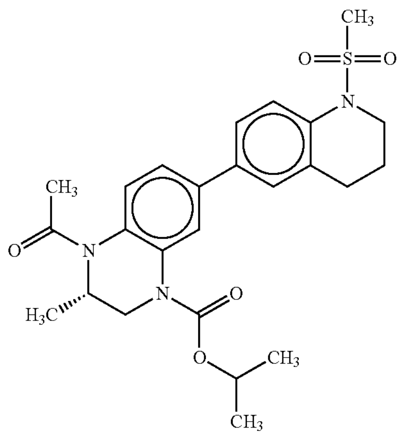          | 486            | 1.55          |
| I-1161  | 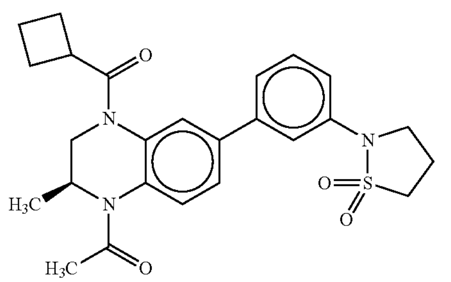          | 468            | 1.29          |
| I-1162  | 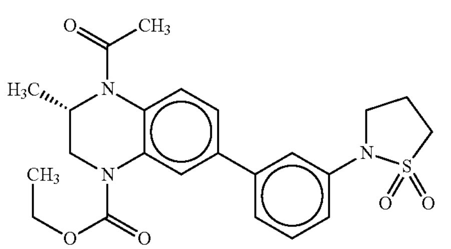          | 458            | 1.33          |
| I-1163  | 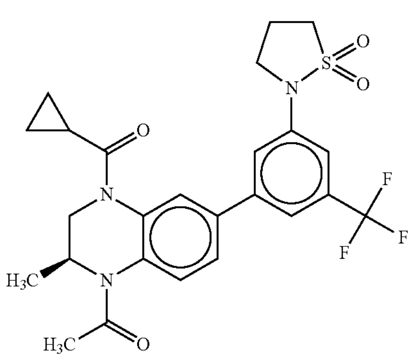          | 522            | 1.46          |

TABLE 27-continued

| Example | Structure | LC-MS [M + 1]+ | HPLC RT (min) |
|---------|-----------|----------------|---------------|
| I-1164  | 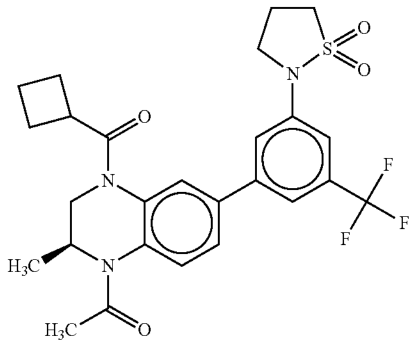          | 536            | 1.52          |
| I-1165  | 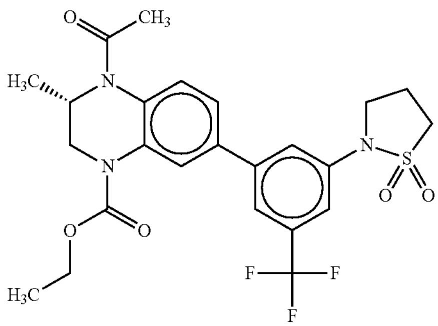          | 526            | 1.56          |
| I-1166  | 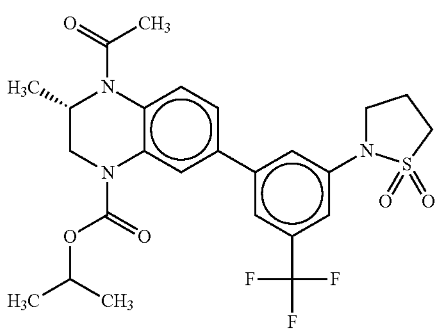          | 540            | 1.64          |
| I-1167  | 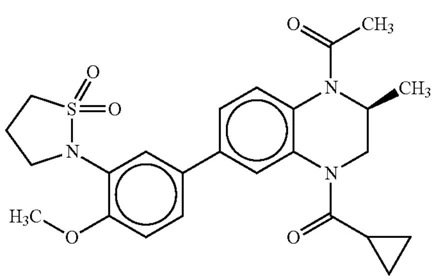          | 484            | 1.18          |
| I-1168  | 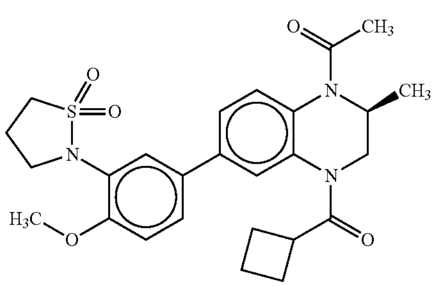          | 498            | 1.25          |

TABLE 27-continued

| Example | Structure | LC-MS [M + 1]+ | HPLC RT (min) |
|---------|-----------|----------------|---------------|
| I-1169 | 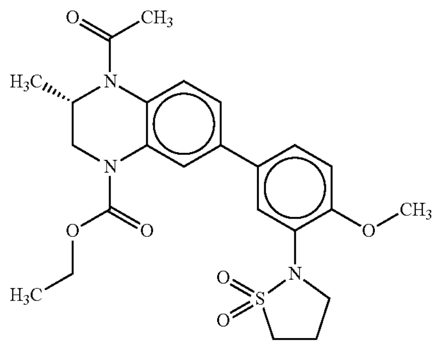 | 488 | 1.29 |
| I-1170 | 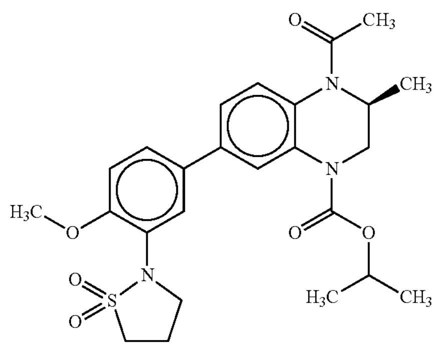 | 502 | 1.38 |
| I-1171 | 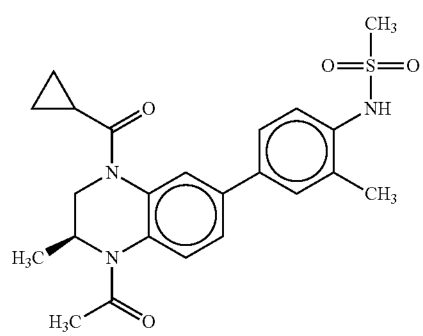 | 442 | 1.14 |
| I-1172 | 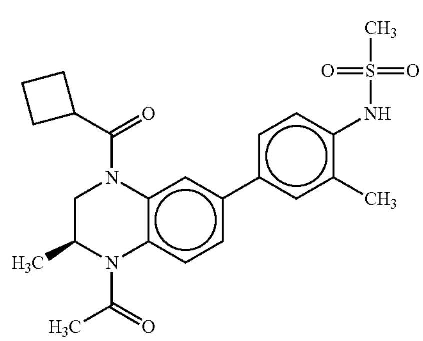 | 456 | 1.21 |

TABLE 27-continued

| Example | Structure | LC-MS [M + 1]+ | HPLC RT (min) |
|---|---|---|---|
| I-1173 | 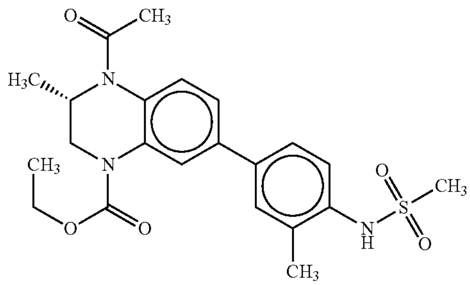 | 446 | 1.25 |
| I-1174 | 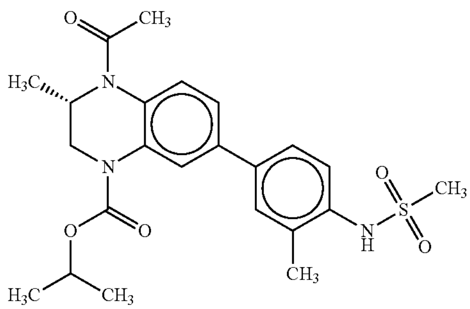 | 460 | 1.34 |
| I-1175 | 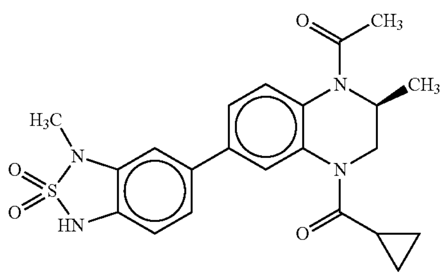 | 441 | 1.14 |
| I-1176 | 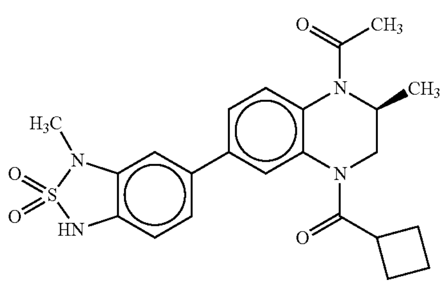 | 455 | 1.2 |
| I-1177 | 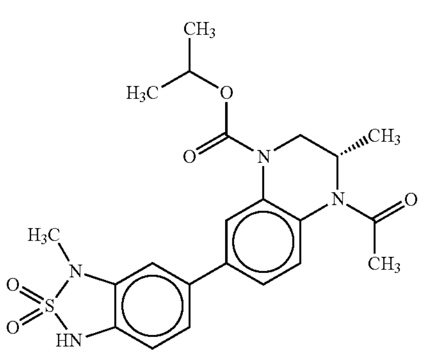 | 459 | 1.31 |

TABLE 27-continued

| Example | Structure | LC-MS [M + 1]+ | HPLC RT (min) |
|---------|-----------|----------------|---------------|
| I-1178 | 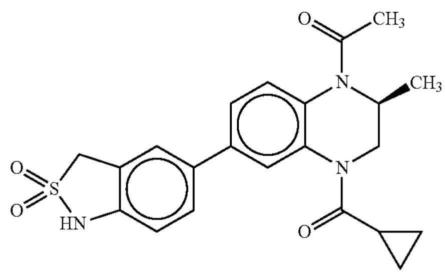 | 426 | 1.06 |
| I-1179 | 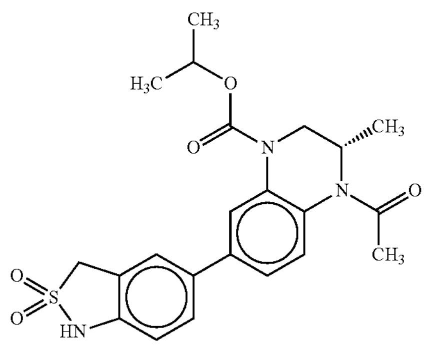 | 444 | 1.27 |
| I-1180 | 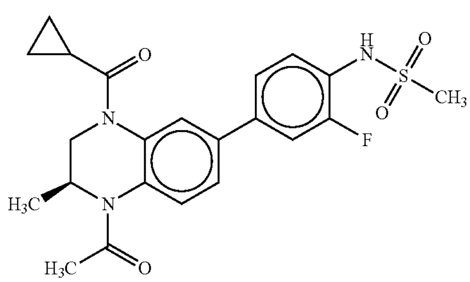 | 446 | 1.12 |
| I-1181 | 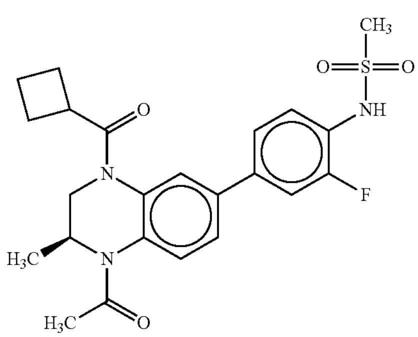 | 460 | 1.2 |
| I-1182 | 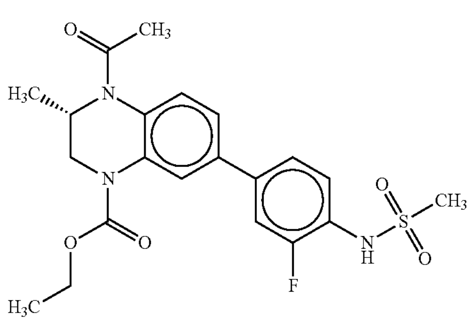 | 450 | 1.24 |

TABLE 27-continued
| Example | Structure | LC-MS [M + 1]+ | HPLC RT (min) |
|---------|-----------|----------------|---------------|
| I-1183  | 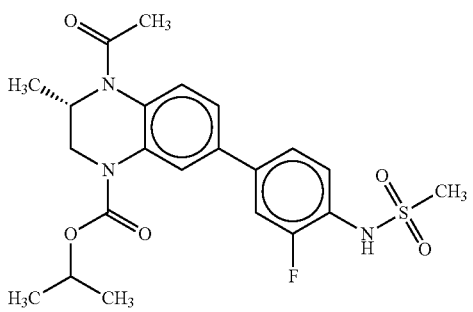 | 464 | 1.33 |
| I-1184  | 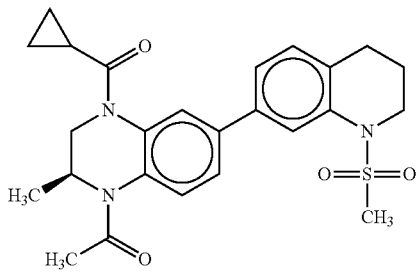 | 468 | 1.4 |
| I-1185  | 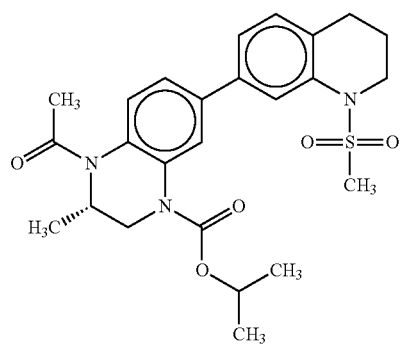 | 486 | 1.59 |
Example 284
Library Protocol U
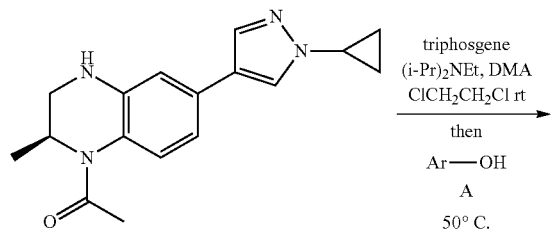
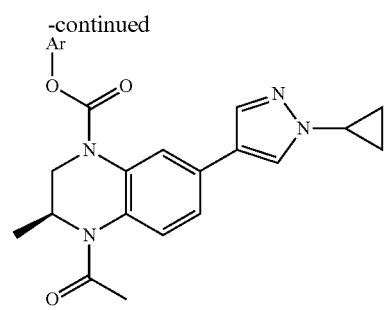
A 1.5 mL reaction vial was charged with (S)-1-(6-(1-cyclopropyl-1H-pyrazol-4-yl)-2-methyl-3,4-dihydroquinoxalin-1(2H)-yl)ethan-1-one (0.2 M solution in 3:1:1, 1,2-dichloroethane/N,N-dimethylacetamide/N,N-diisopropylethylamine, 150 μL, 0.03 mmol). Triphosgene (0.4 M solution in 1,2-dichloroethane, 30 μL, 0.012 mmol) was added slowly, and the vial was sealed and shaken at rt for 24 h. Aryl alcohol (B) (0.2 M solution in 1,2-dichloroethane, 225 μL, 0.045 mmol) was added and the system was sealed and heated to 50° C. on a heater shaker overnight. Methanol (150 μL) was added, and the system was sealed and heated to 50° C. on a heater shaker for 15 minutes. The reaction was concentrated and the residue was diluted with ethyl acetate (500 μL) and washed with saturated aqueous sodium bicarbonate solution (500 μL). The aqueous layer was separated and extracted with ethyl acetate (1 mL) and the combined organic layers were concentrated under a stream of nitrogen and vacuum. The crude product was purified by mass triggered preparatory HPLC. The product-containing fractions were combined and concentrated in a Genevac to afford the desired product.

The following compounds in Table 28 were synthesized according to the above protocol:

TABLE 28

| Example | Structure | LC-MS [M + 1]+ | HPLC RT (min) |
|---------|-----------|----------------|---------------|
| I-1186 | 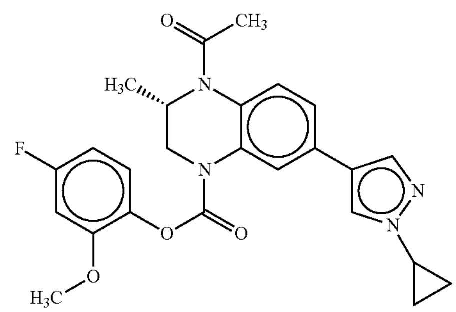 | 465 | 1.41 |
| I-1187 | 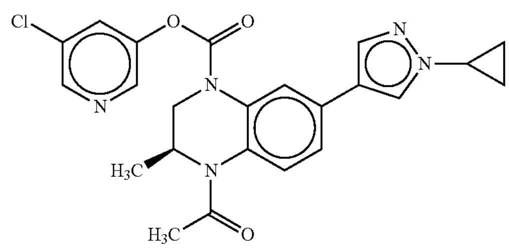 | 452 | 1.31 |
| I-1188 | 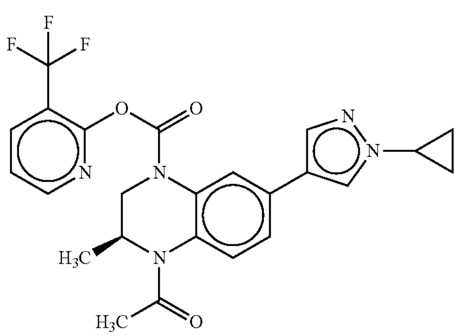 | 486 | 1.22 |
| I-1189 | 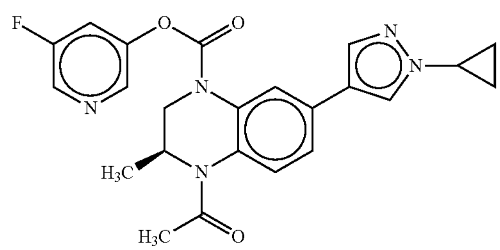 | 436 | 1.22 |

TABLE 28-continued

| Example | Structure | LC-MS [M + 1]+ | HPLC RT (min) |
|---|---|---|---|
| I-1190 | 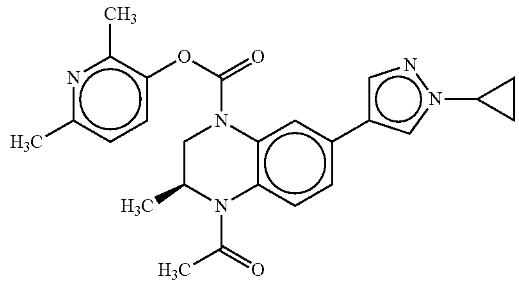 | 446 | 1.08 |
| I-1191 | 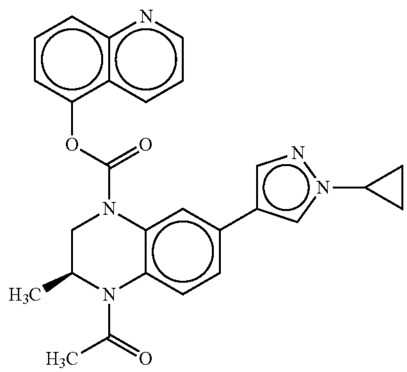 | 468 | 1.215 |
| I-1192 | 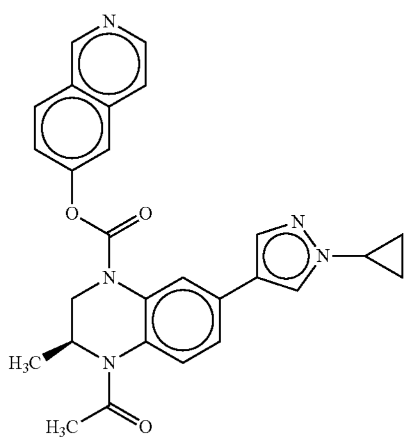 | 468 | 1.0649 |
| I-1193 | 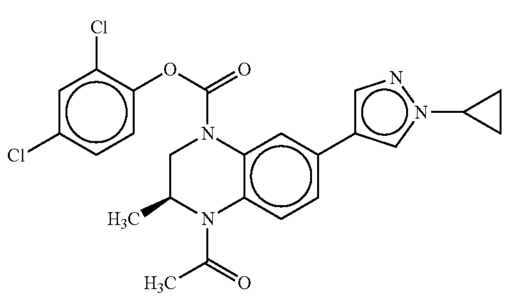 | 485 | 1.6415 |

TABLE 28-continued

| Example | Structure | LC-MS [M + 1]+ | HPLC RT (min) |
|---|---|---|---|
| I-1194 | 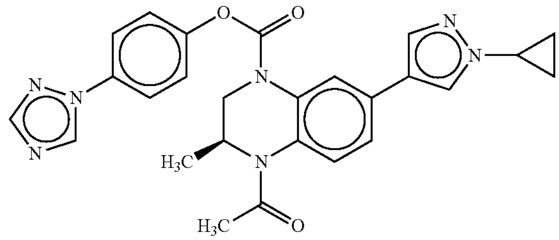 | 484 | 1.1717 |
| I-1195 | 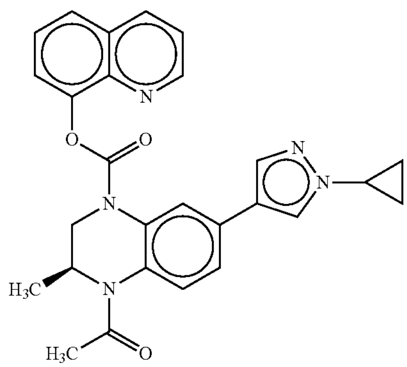 | 468 | 1.3233 |
| I-1196 | 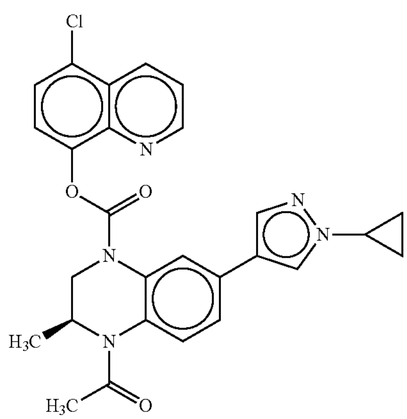 | 502 | 1.5121 |
| I-1197 | 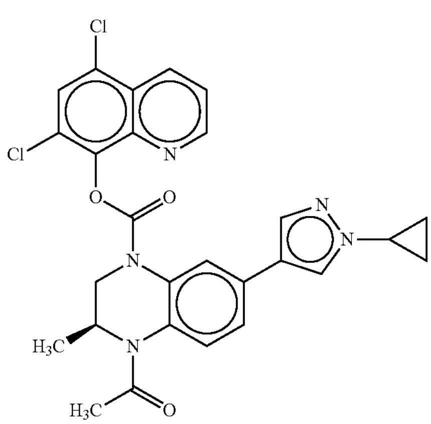 | 536 | 1.6367 |

TABLE 28-continued

| Example | Structure | LC-MS [M + 1]+ | HPLC RT (min) |
|---|---|---|---|
| I-1198 | 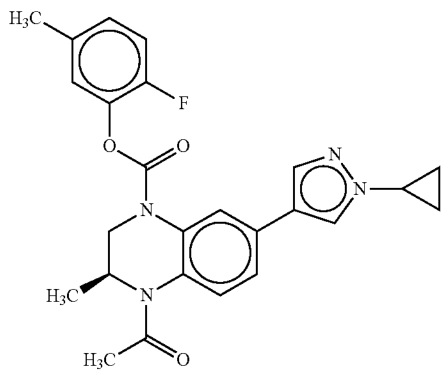 | 449 | 1.51 |
| I-1199 | 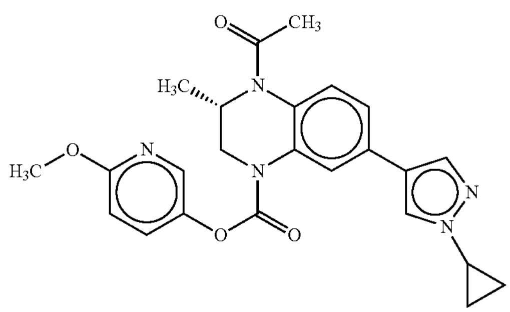 | 448 | 1.3033 |
| I-1200 | 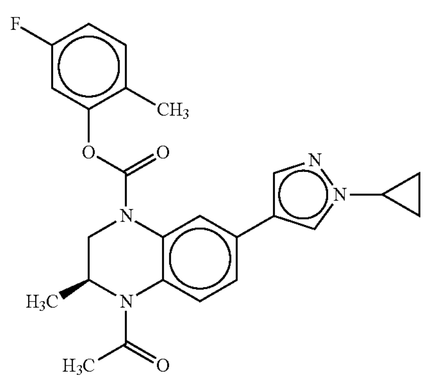 | 449 | 1.5017 |
| I-1201 | 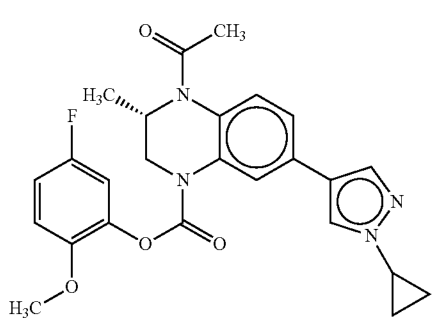 | 465 | 1.4117 |

TABLE 28-continued
| Example | Structure | LC-MS [M + 1]+ | HPLC RT (min) |
|---|---|---|---|
| I-1202 | 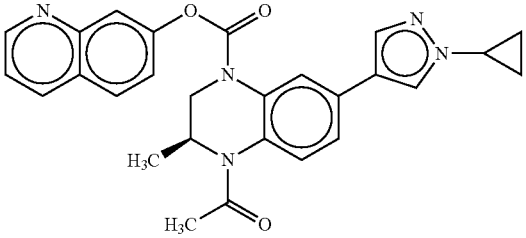 | 468 | 1.212 |
| I-1203 | 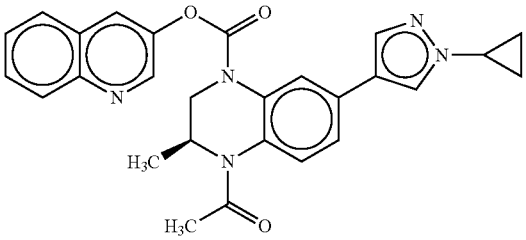 | 468 | 1.3296 |
| I-1204 | 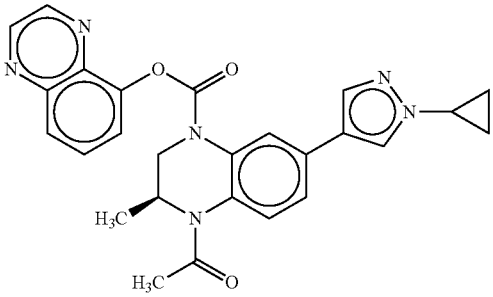 | 469 | 1.2117 |
| I-1205 | 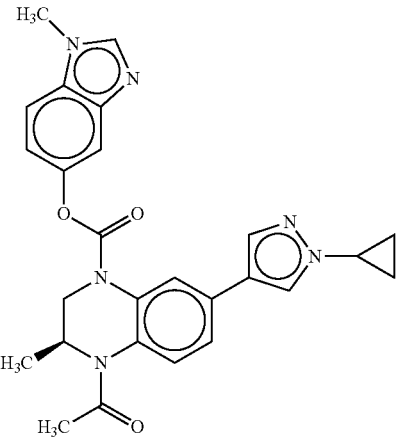 | 471 | 0.985 |

TABLE 28-continued
| Example | Structure | LC-MS [M + 1]+ | HPLC RT (min) |
|---|---|---|---|
| I-1206 | 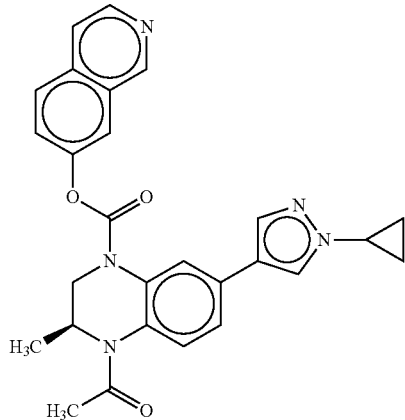 | 468 | 1.11 |
| I-1207 | 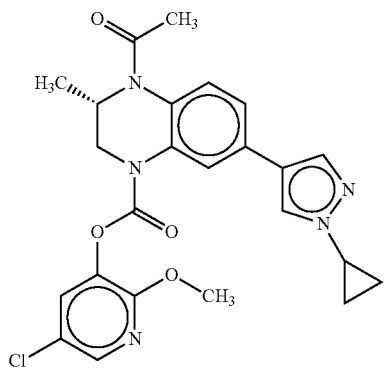 | 482 | 1.52 |
| I-1208 | 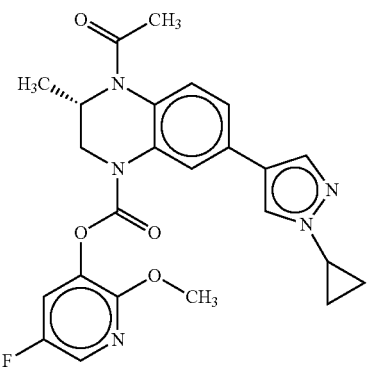 | 466 | 1.41 |

TABLE 28-continued

| Example | Structure | LC-MS [M + 1]+ | HPLC RT (min) |
|---|---|---|---|
| I-1209 | 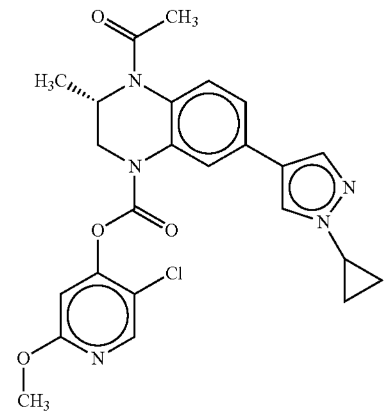 | 482 | 1.49 |
| I-1210 | 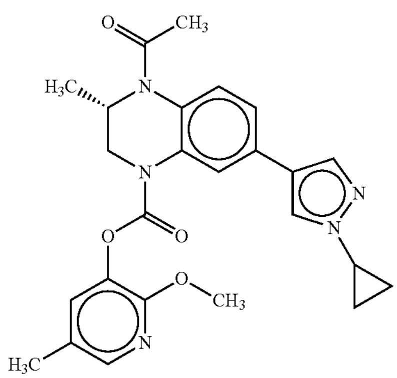 | 462 | 1.38 |

Example 285

Library Protocol V

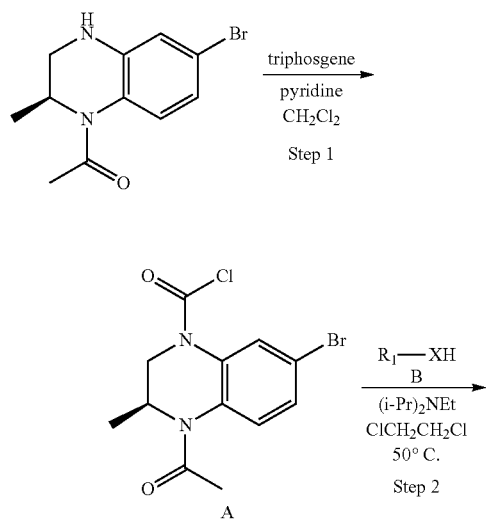

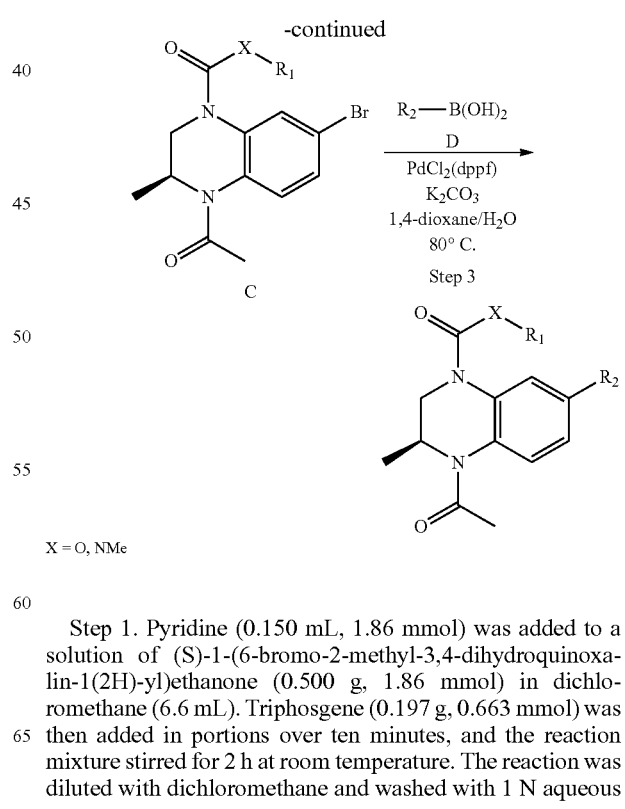

X = O, NMe

Step 1. Pyridine (0.150 mL, 1.86 mmol) was added to a solution of (S)-1-(6-bromo-2-methyl-3,4-dihydroquinoxalin-1(2H)-yl)ethanone (0.500 g, 1.86 mmol) in dichloromethane (6.6 mL). Triphosgene (0.197 g, 0.663 mmol) was then added in portions over ten minutes, and the reaction mixture stirred for 2 h at room temperature. The reaction was diluted with dichloromethane and washed with 1 N aqueous HCl solution. The organic phase was separated and washed with saturated aqueous sodium bicarbonate solution, dried over anhydrous magnesium sulfate, filtered and concentrated in a Genevac to afford (S)-4-acetyl-7-bromo-3-methyl-3,4-dihydroquinoxaline-1(2H)-carbonyl chloride, which was dissolved in 1,2-dichloroethane (9.0 mL) to afford a 0.2 M solution.

Step 2. A 1.5 mL reaction vial was charged with (S)-4-acetyl-7-bromo-3-methyl-3,4-dihydroquinoxaline-1(2H)-carbonyl chloride (A, 0.2M solution in 1,2-dichloroethane, 150 µL, 0.03 mmol), N,N-diisopropylethylamine (25 µL, 0.143 mmol), and the alcohol or amine (B, 0.4 M solution in 1,2-dichloroethane, 150 µL, 0.06 mmol). The reaction was heated to 50° C. on a heater shaker for 2 h. The reaction was diluted with ethyl acetate (500 µL) and washed with saturated aqueous sodium chloride solution (500 µL). The aqueous layer was separated and extracted with ethyl acetate (1 mL) and the combined organic layers were concentrated under a stream of nitrogen and vacuum to yield the crude product (C) which was used without purification.

Step 3. A 1.5 mL reaction vial was charged with the aryl bromide (C) from above, 1,4-dioxane (100 µL), and the boronic acid (D) (0.2M solution in 1,4-dioxane, 225 µL, 0.045 mmol). Potassium carbonate (1 M solution in water, 90 µL, 0.09 mmol) was added, and the reaction mixture was purged with nitrogen. [1,1'-Bis(diphenylphosphino)ferrocene]dichloropalladium(II) dichloromethane adduct (0.02 M solution in 1,2-dichloroethane, 150 µL, 0.003 mmol) was added, the reaction was purged with nitrogen, and heated to 80° C. on a heater shaker overnight. The reaction was diluted with ethyl acetate (500 µL) and washed with a saturated aqueous sodium chloride solution (500 µL). The aqueous layer was separated and extracted with ethyl acetate (1 mL) and the combined organic layers were concentrated under a stream of nitrogen and vacuum. The crude product was purified by mass triggered preparatory HPLC. The product-containing fractions were combined and concentrated in a Genevac to afford the desired product.

The following compounds in Table 29 were synthesized according to the above protocol:

TABLE 29

| Example | Structure | LC-MS [M + 1]+ | HPLC RT (min) |
|---------|-----------|----------------|---------------|
| I-1211  | 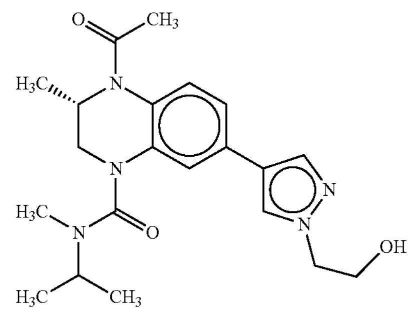          | 400            | 0.88          |
| I-1212  | 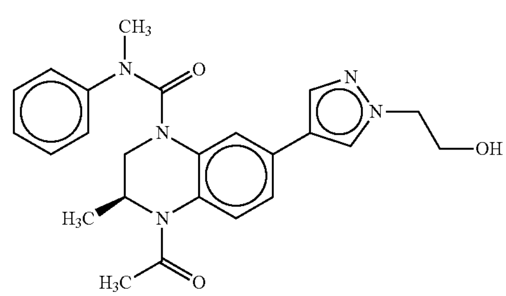          | 434            | 0.93          |
| I-1213  | 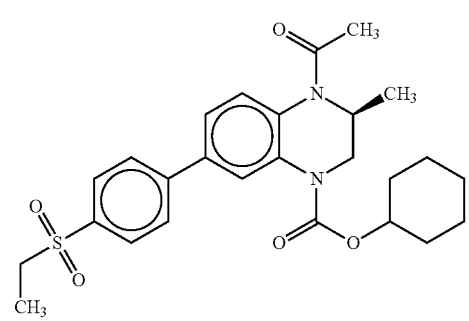          | 485            | 1.65          |

TABLE 29-continued

| Example | Structure | LC-MS [M + 1]+ | HPLC RT (min) |
|---------|-----------|----------------|---------------|
| I-1214 | 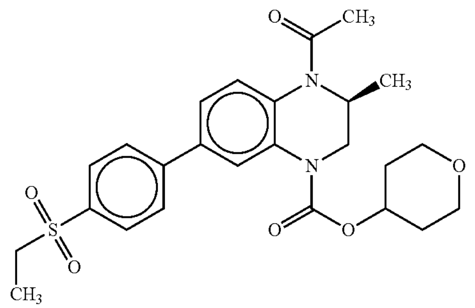 | 487 | 1.26 |
| I-1215 | 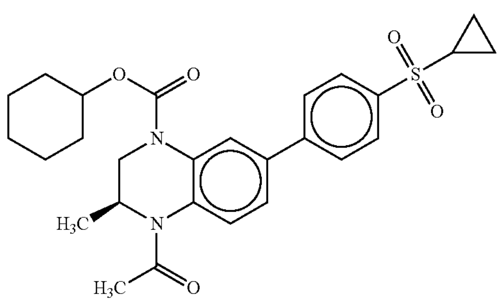 | 497 | 1.69 |
| I-1216 | 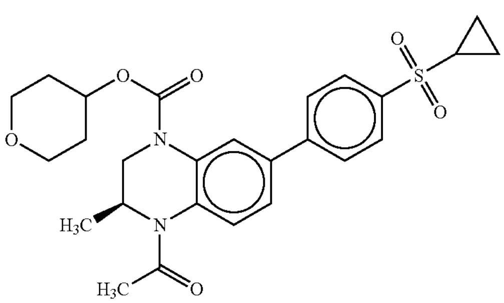 | 499 | 1.3 |
| I-1217 | 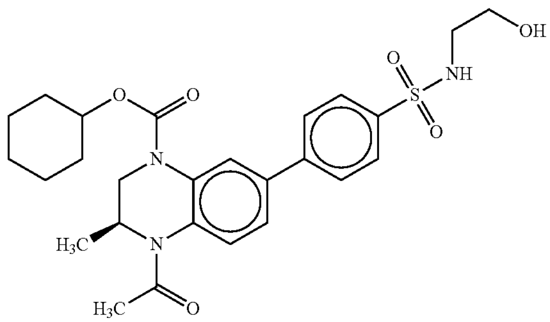 | 516 | 1.39 |

TABLE 29-continued

| Example | Structure | LC-MS [M + 1]+ | HPLC RT (min) |
|---------|-----------|----------------|---------------|
| I-1218  | 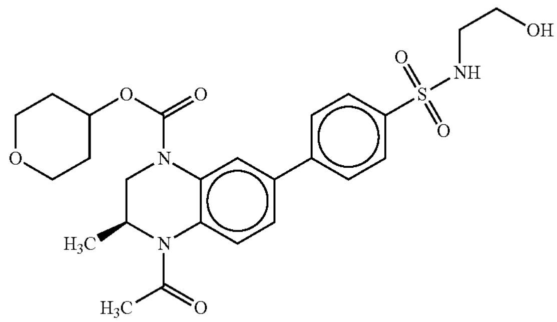          | 518            | 1.05          |
| I-1219  | 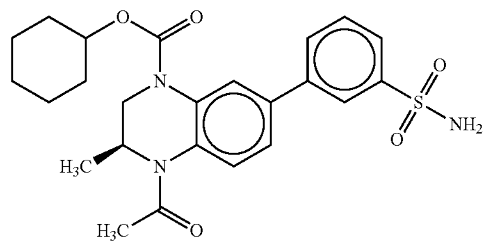          | 472            | 1.44          |
| I-1220  | 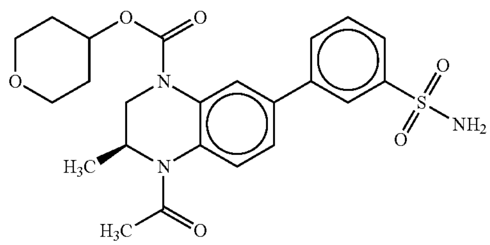          | 474            | 1.09          |
| I-1221  | 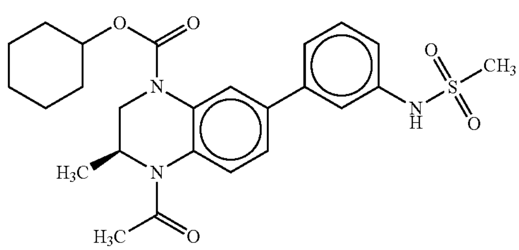          | 486            | 1.55          |
| I-1222  | 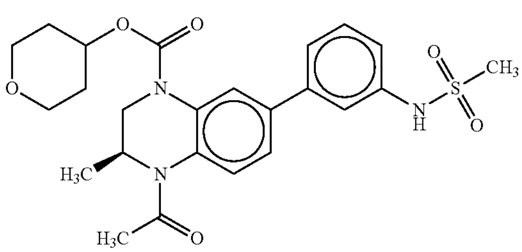          | 488            | 1.19          |

TABLE 29-continued

| Example | Structure | LC-MS [M + 1]+ | HPLC RT (min) |
|---|---|---|---|
| I-1223 | 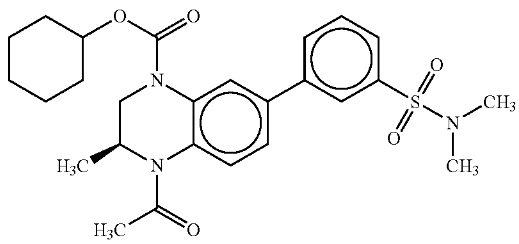 | 500 | 1.74 |
| I-1224 | 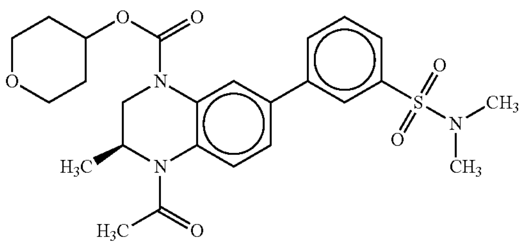 | 502 | 1.36 |
| I-1225 | 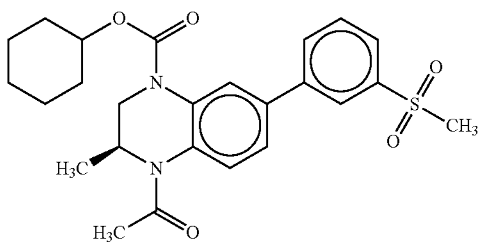 | 471 | 1.58 |
| I-1226 | 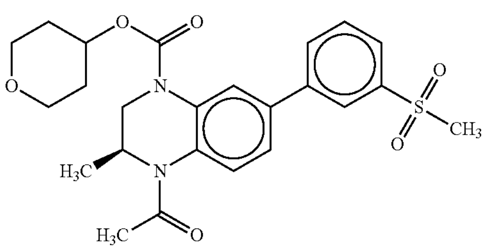 | 473 | 1.19 |
| I-1227 | 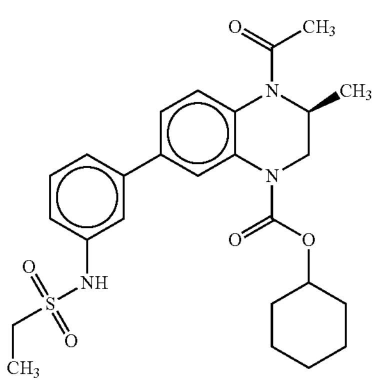 | 500 | 1.62 |

TABLE 29-continued

| Example | Structure | LC-MS [M + 1]+ | HPLC RT (min) |
|---|---|---|---|
| I-1228 | 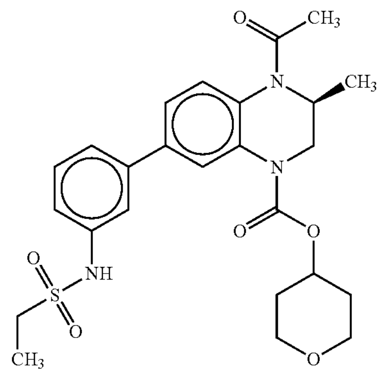 | 502 | 1.25 |
| I-1229 | 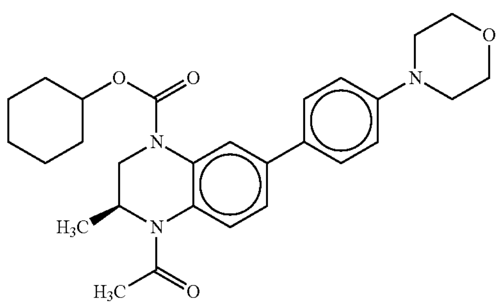 | 478 | 1.8 |
| I-1230 | 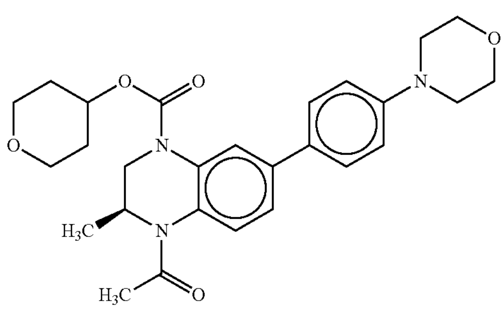 | 480 | 1.38 |
| I-1231 | 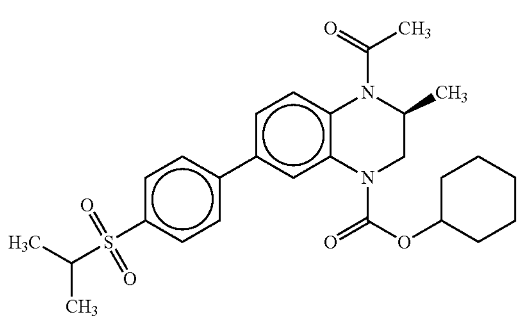 | 499 | 1.74 |

TABLE 29-continued

| Example | Structure | LC-MS [M + 1]+ | HPLC RT (min) |
|---|---|---|---|
| I-1232 | 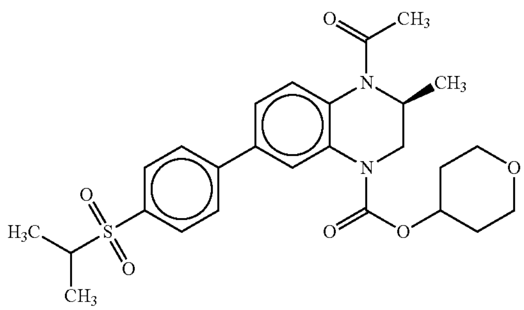 | 501 | 1.34 |
| I-1233 | 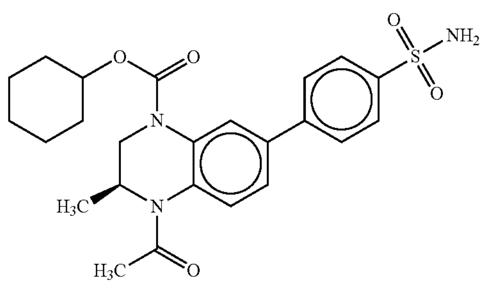 | 472 | 1.42 |
| I-1234 | 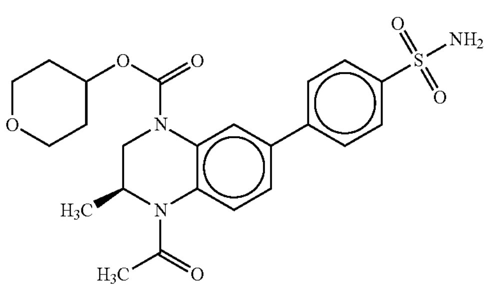 | 474 | 1.06 |
| I-1235 | 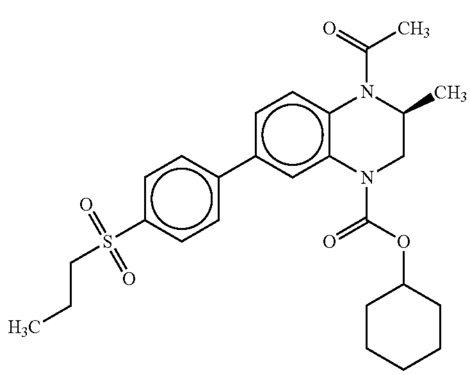 | 499 | 1.76 |

TABLE 29-continued

| Example | Structure | LC-MS [M + 1]+ | HPLC RT (min) |
|---------|-----------|----------------|---------------|
| I-1236 | 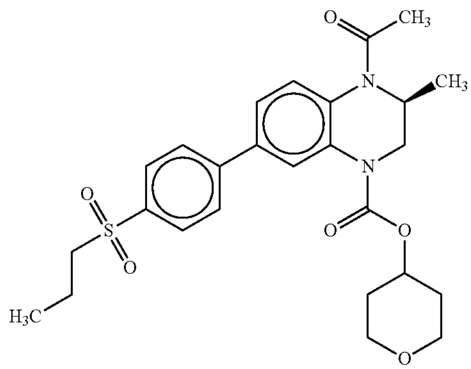 | 501 | 1.38 |
| I-1237 | 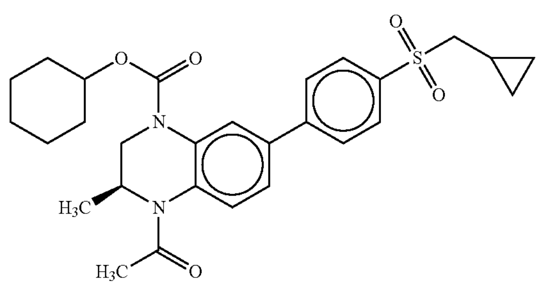 | 511 | 1.75 |
| I-1238 | 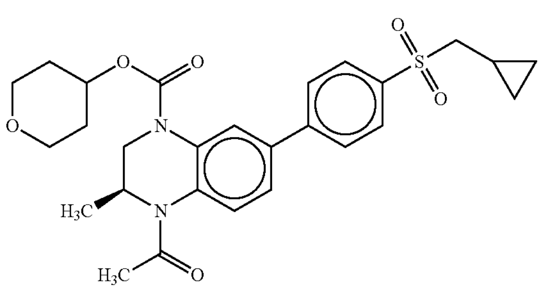 | 513 | 1.37 |
| I-1239 | 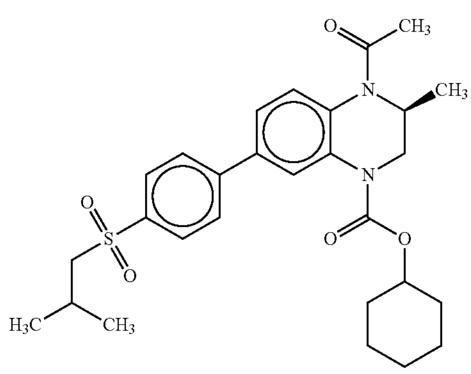 | 513 | 1.86 |

TABLE 29-continued

| Example | Structure | LC-MS [M + 1]+ | HPLC RT (min) |
|---------|-----------|----------------|---------------|
| I-1240 | 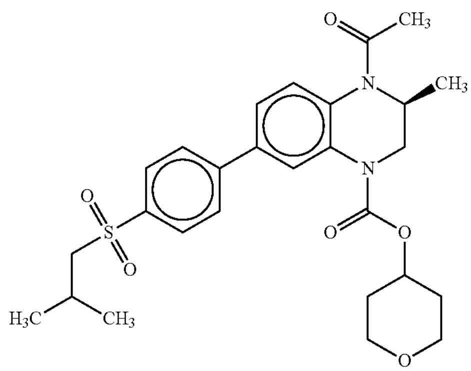 | 515 | 1.48 |
| I-1241 | 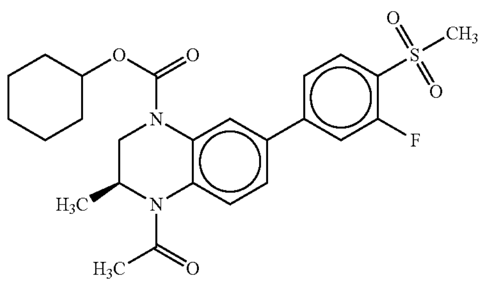 | 489 | 1.63 |
| I-1242 | 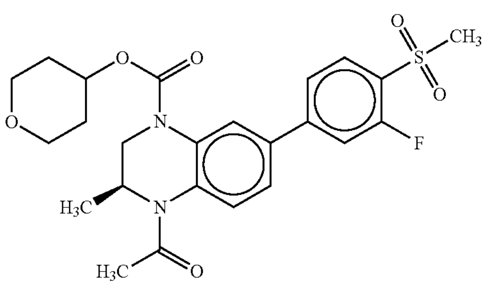 | 491 | 1.24 |
| I-1243 | 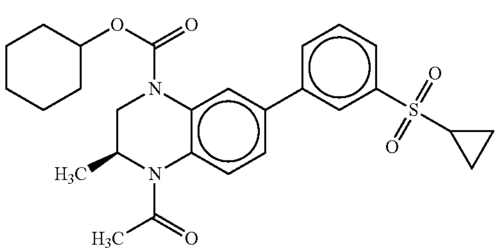 | 497 | 1.7 |
| I-1244 | 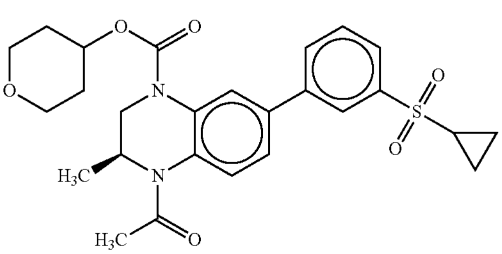 | 499 | 1.32 |

TABLE 29-continued

| Example | Structure | LC-MS [M + 1]+ | HPLC RT (min) |
|---|---|---|---|
| I-1245 | 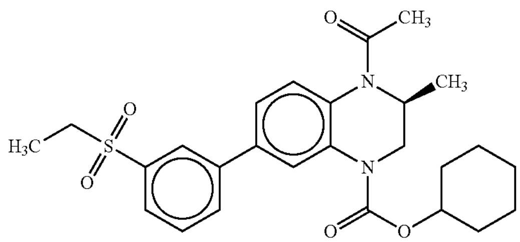 | 485 | 1.65 |
| I-1246 | 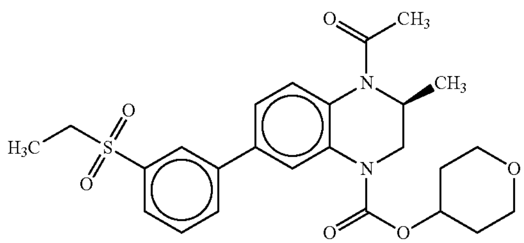 | 487 | 1.27 |
| I-1247 | 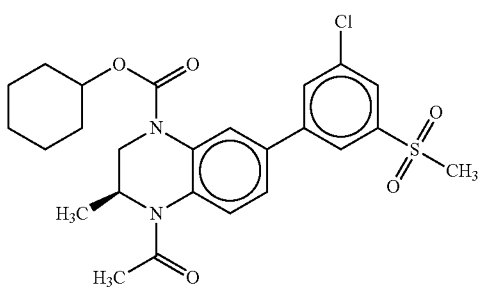 | 505 | 1.78 |
| I-1248 | 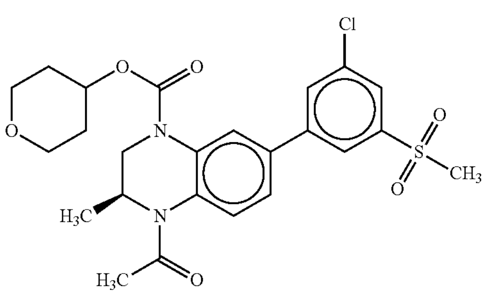 | 507 | 1.39 |
| I-1249 | 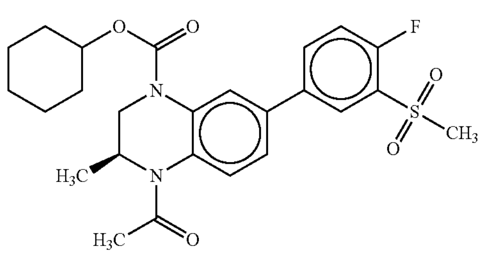 | 489 | 1.62 |

TABLE 29-continued

| Example | Structure | LC-MS [M + 1]+ | HPLC RT (min) |
|---|---|---|---|
| I-1250 | 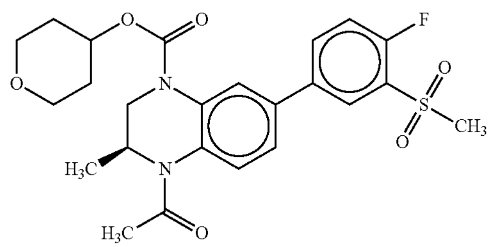 | 491 | 1.24 |
| I-1251 | 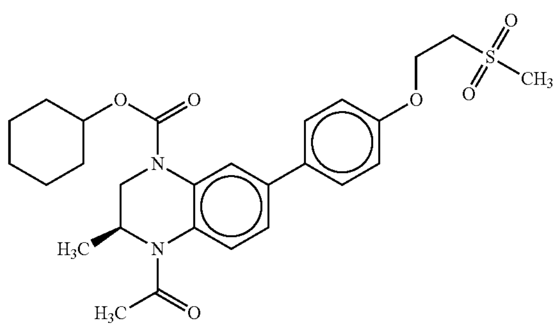 | 515 | 1.56 |
| I-1252 | 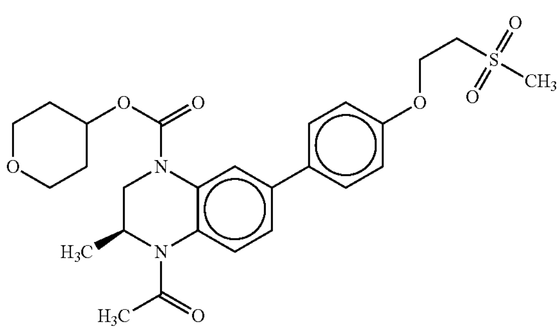 | 517 | 1.2 |
| I-1253 | 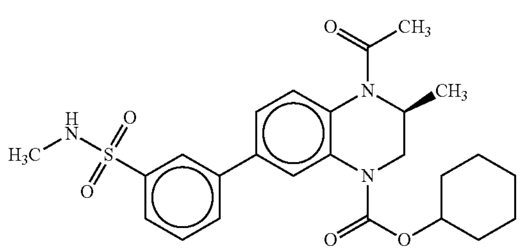 | 486 | 1.58 |
| I-1254 | 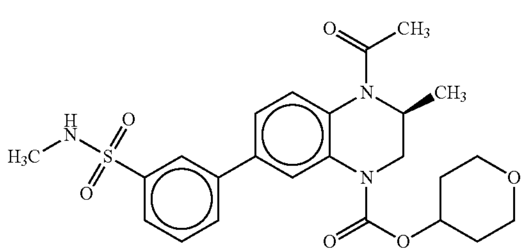 | 488 | 1.21 |

TABLE 29-continued

| Example | Structure | LC-MS [M + 1]+ | HPLC RT (min) |
|---------|-----------|----------------|---------------|
| I-1255 | 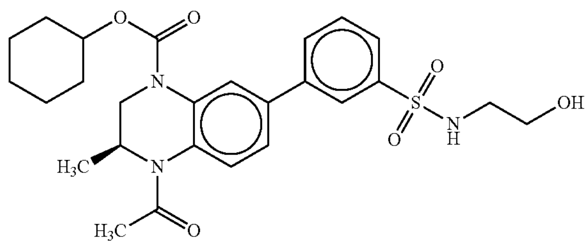 | 516 | 1.41 |
| I-1256 | 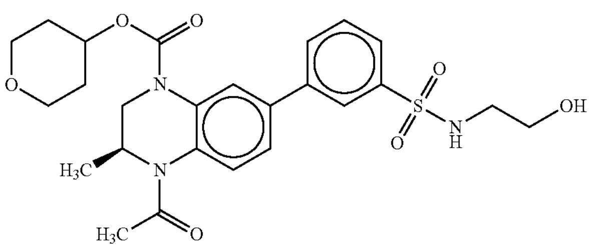 | 518 | 1.07 |
| I-1257 | 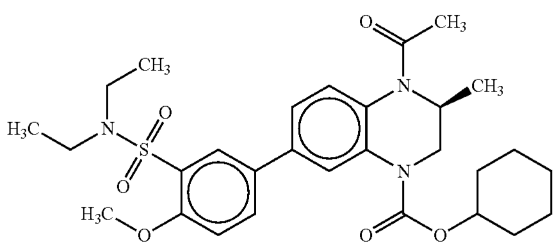 | 558 | 1.84 |
| I-1258 | 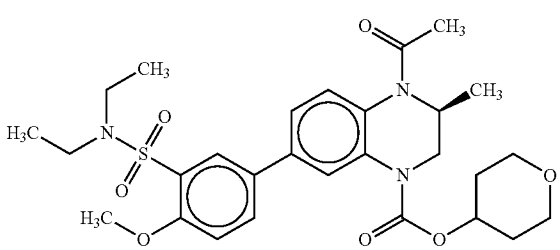 | 560 | 1.48 |
| I-1259 | 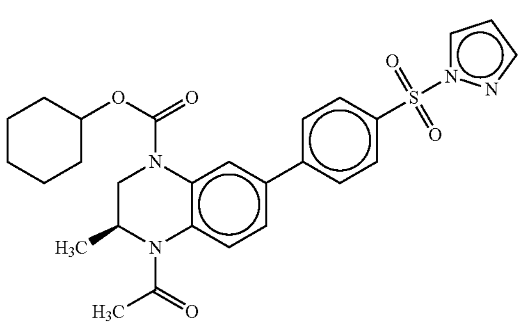 | 523 | 1.78 |

TABLE 29-continued
| Example | Structure | LC-MS [M + 1]+ | HPLC RT (min) |
|---|---|---|---|
| I-1260 | 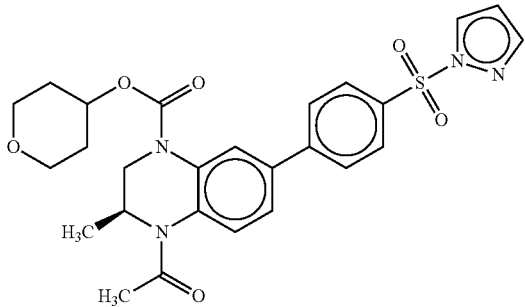 | 525 | 1.41 |
| I-1261 | 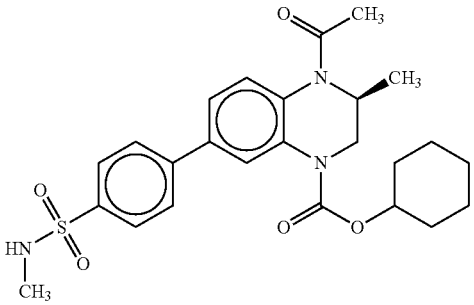 | 486 | 1.56 |
| I-1262 | 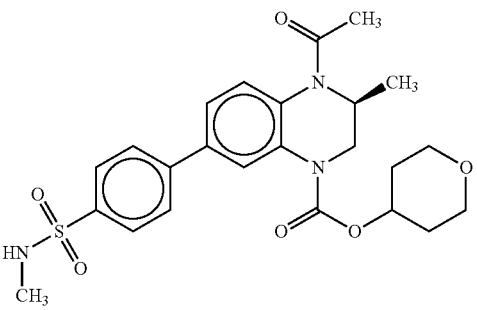 | 488 | 1.19 |
| I-1263 | 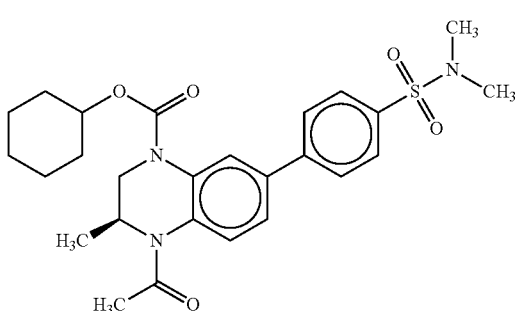 | 500 | 1.74 |

TABLE 29-continued

| Example | Structure | LC-MS [M + 1]+ | HPLC RT (min) |
|---|---|---|---|
| I-1264 | 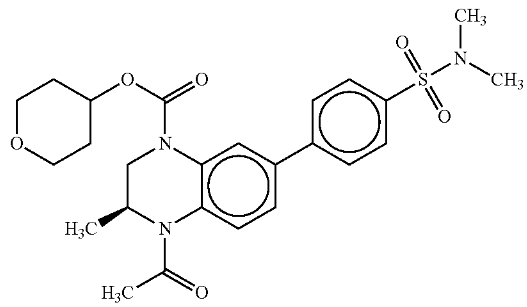 | 502 | 1.35 |
| I-1265 | 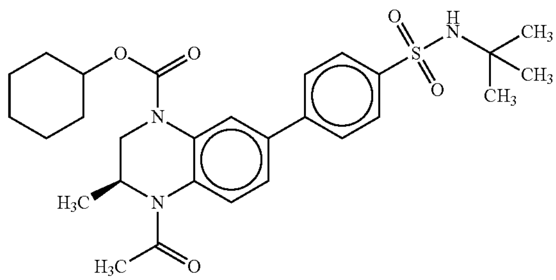 | 528 | 1.81 |
| I-1266 | 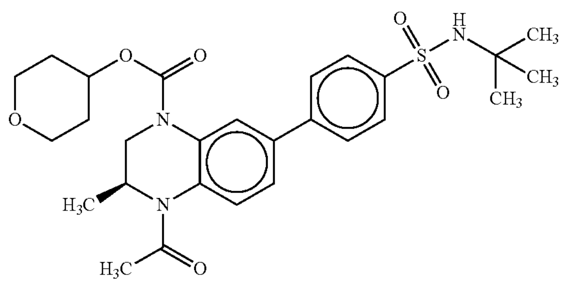 | 530 | 1.43 |
| I-1267 | 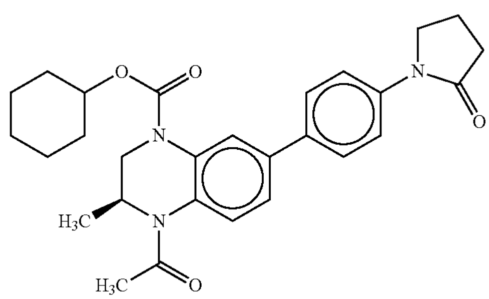 | 476 | 1.63 |
| I-1268 | 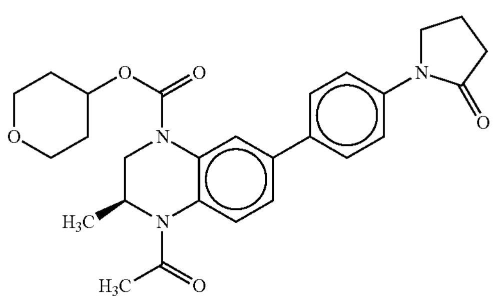 | 478 | 1.24 |

TABLE 29-continued

| Example | Structure | LC-MS [M + 1]+ | HPLC RT (min) |
|---|---|---|---|
| I-1269 | 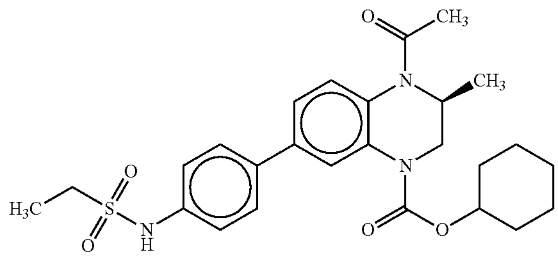 | 500 | 1.57 |
| I-1270 | 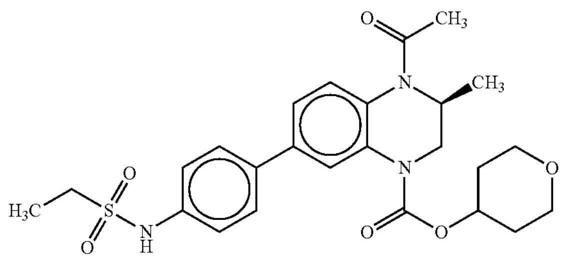 | 502 | 1.22 |
| I-1271 | 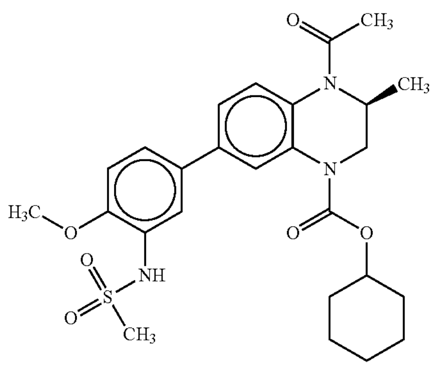 | 516 | 1.55 |
| I-1272 | 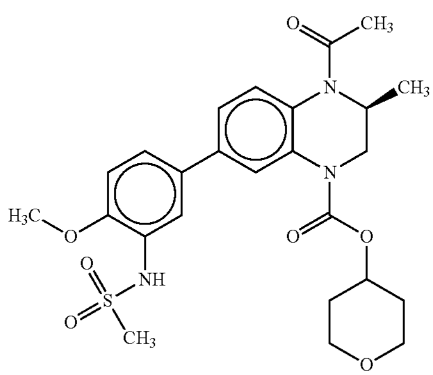 | 518 | 1.2 |
| I-1273 | 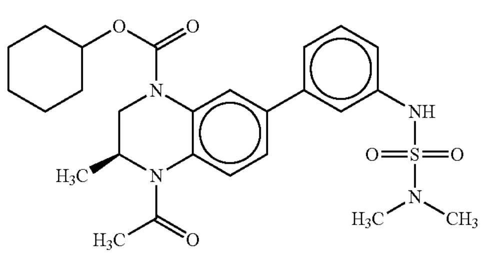 | 515 | 1.66 |

TABLE 29-continued

| Example | Structure | LC-MS [M + 1]+ | HPLC RT (min) |
|---|---|---|---|
| I-1274 | 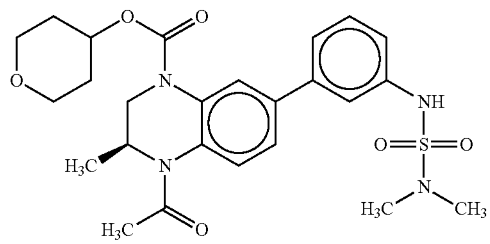 | 517 | 1.3 |

Example 286

Library Protocol W

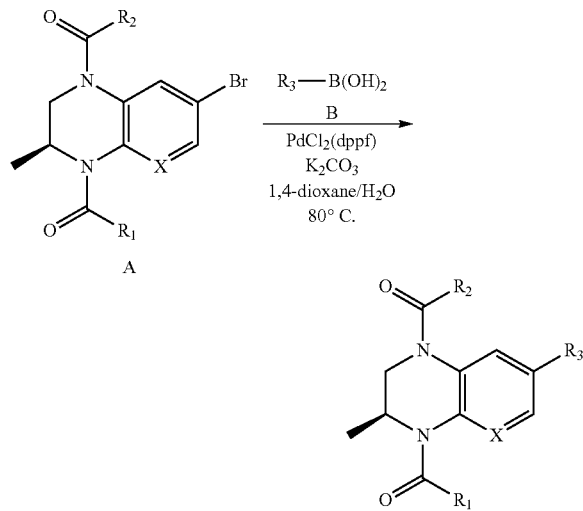

X = CH, N

A 1.5 mL reaction vial was charged with the aryl bromide (A) (0.2 M solution in 3:1:1, 1,2-dichloroethane/N,N-dimethylacetamide/N,N-diisopropylethylamine, 150 µL, 0.03 mmol) and the boronic acid (B) (0.2 M solution in 1,4-dioxane, 270 µL, 0.054 mmol). Potassium carbonate (1 M solution in water, 90 µL, 0.09 mmol) was added, and the reaction mixture was purged with nitrogen. [1,1'-Bis(diphenylphosphino)ferrocene]dichloropalladium(II) dichloromethane adduct (0.02 M solution in 1,2-dichloroethane, 150 µL, 0.003 mmol) was added, the reaction was purged with nitrogen, and heated to 80° C. on a heater shaker overnight. The reaction was diluted with ethyl acetate (500 µL) and washed with a solution of 1 N sodium hydroxide in brine (400 µL). The aqueous layer was separated and extracted with ethyl acetate (1 mL) and the combined organic layers were concentrated under a stream of nitrogen and vacuum. The crude product was purified by mass triggered preparatory HPLC. The product-containing fractions were combined and concentrated in a Genevac to afford the desired product.

The following compounds in Table 30 were synthesized according to the above protocol:

TABLE 30

| Example | Structure | LC-MS [M + 1]+ | HPLC RT (min) |
|---|---|---|---|
| I-1275 | 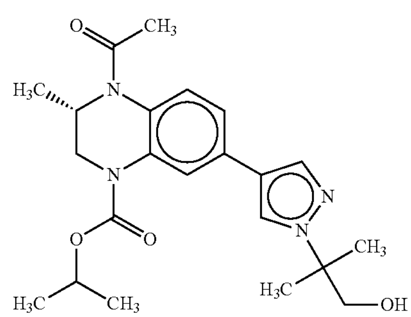 | 415 | 1.1883 |

TABLE 30-continued

| Example | Structure | LC-MS [M + 1]+ | HPLC RT (min) |
|---|---|---|---|
| I-1276 | 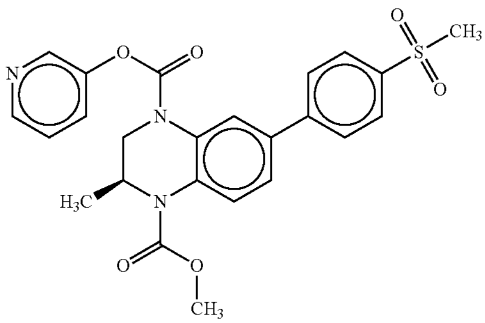 | 482 | 1.31 |
| I-1277 | 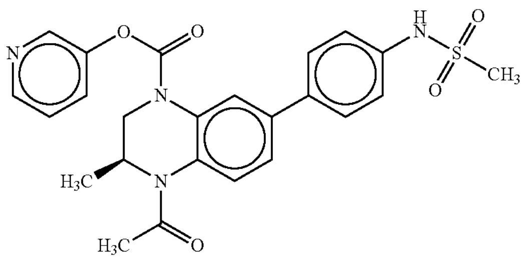 | 481 | 1.11 |
| I-1278 | 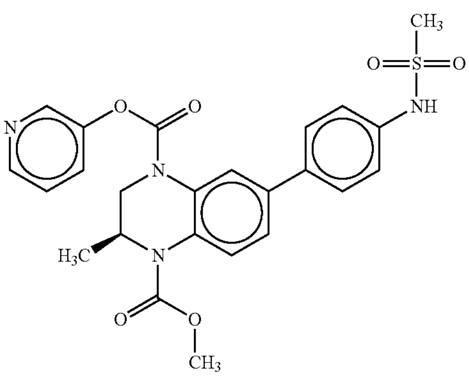 | 497 | 1.3 |
| I-1279 | 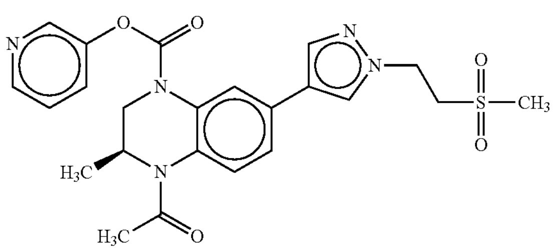 | 484 | 0.93 |
| I-1280 | 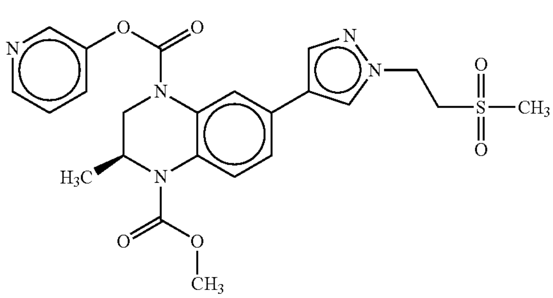 | 500 | 1.11 |

TABLE 30-continued

| Example | Structure | LC-MS [M + 1]+ | HPLC RT (min) |
|---|---|---|---|
| I-1281 | 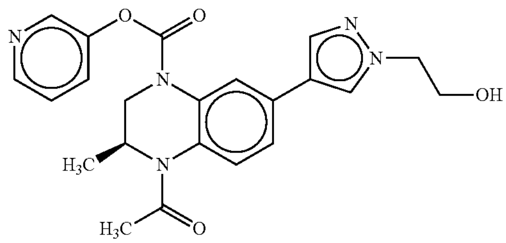 | 422 | 0.86 |
| I-1282 | 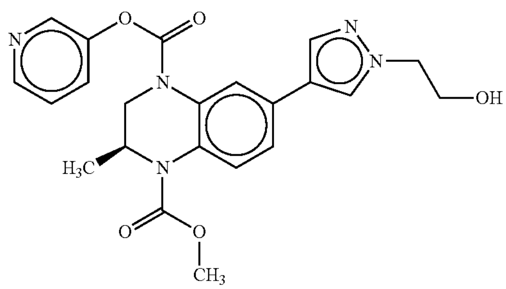 | 438 | 1.03 |
| I-1283 | 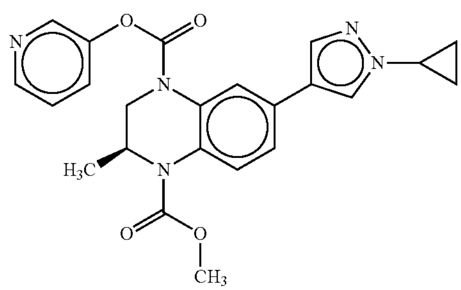 | 434 | 1.3 |
| I-1284 | 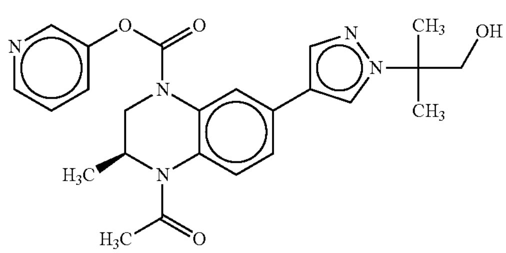 | 450 | 1.01 |
| I-1285 | 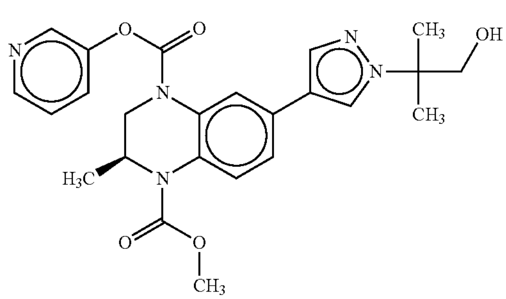 | 466 | 1.18 |

TABLE 30-continued

| Example | Structure | LC-MS [M + 1]+ | HPLC RT (min) |
|---|---|---|---|
| I-1286 | 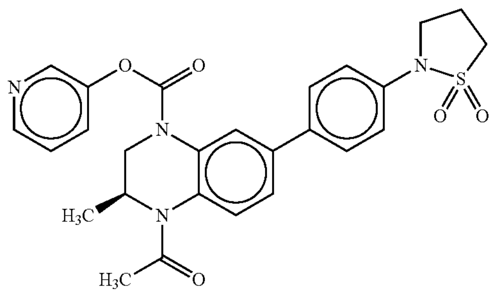 | 507 | 1.18 |
| I-1287 | 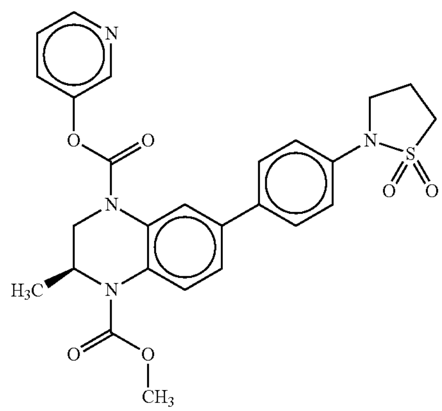 | 523 | 1.37 |
| I-1288 | 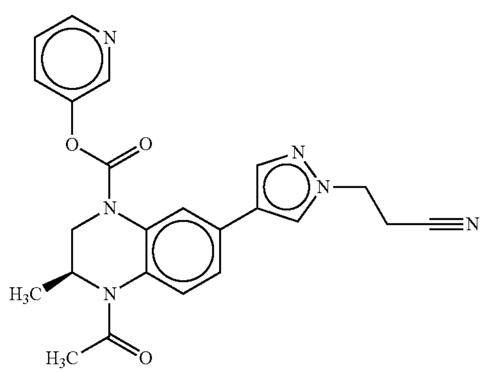 | 431 | 0.98 |
| I-1289 | 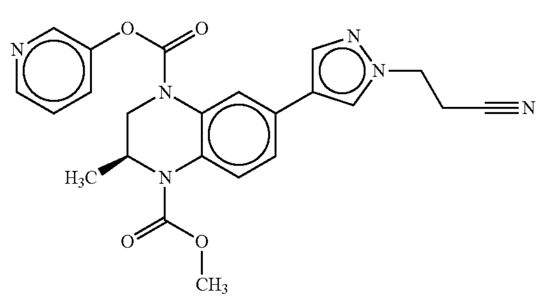 | 447 | 1.17 |

TABLE 30-continued

| Example | Structure | LC-MS [M + 1]+ | HPLC RT (min) |
|---------|-----------|----------------|---------------|
| I-1290 | 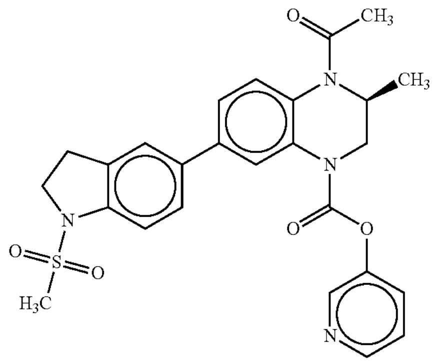 | 507 | 1.27 |
| I-1291 | 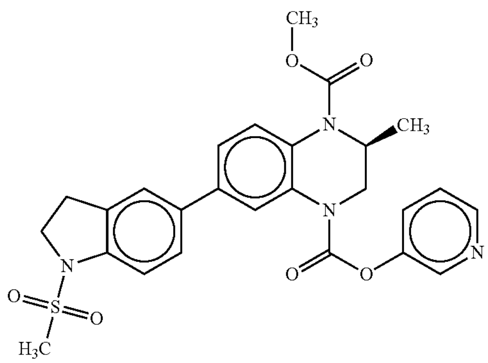 | 523 | 1.45 |
| I-1292 | 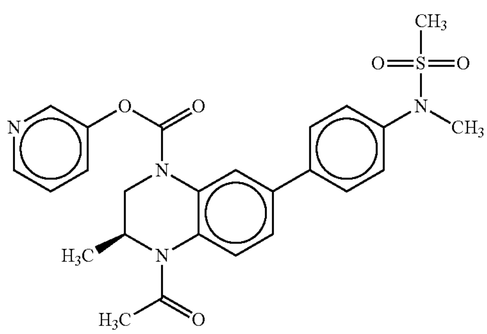 | 495 | 1.22 |
| I-1293 | 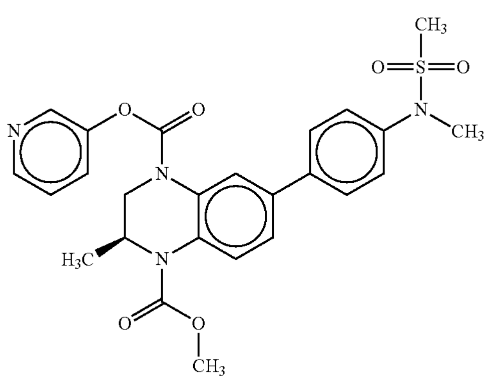 | 511 | 1.4 |

TABLE 30-continued

| Example | Structure | LC-MS [M + 1]+ | HPLC RT (min) |
|---|---|---|---|
| I-1294 | 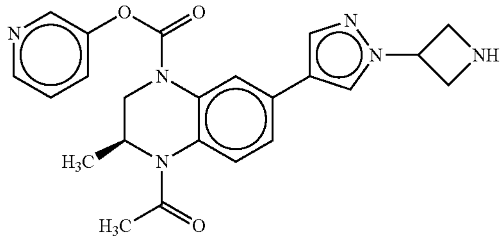 | 433 | 0.73 |
| I-1295 | 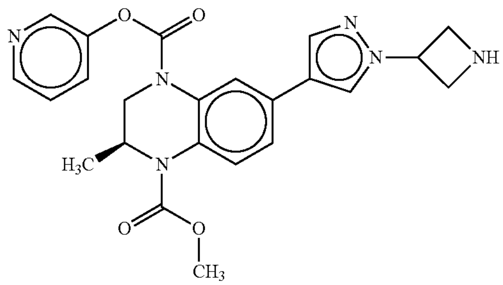 | 449 | 0.9 |
| I-1296 | 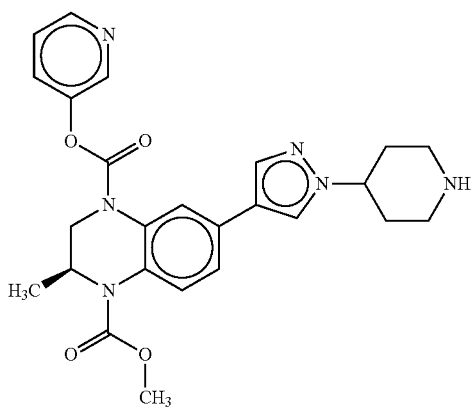 | 477 | 0.91 |
| I-1297 | 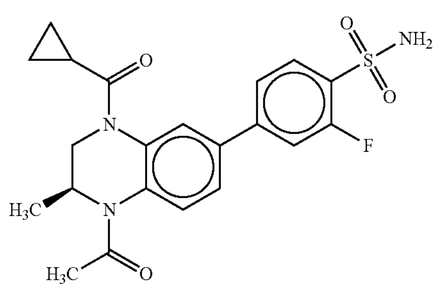 | 432 | 1.04 |
| I-1298 | 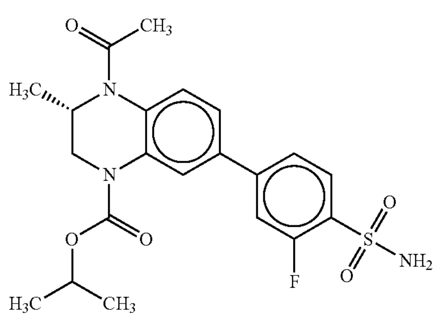 | 450 | 1.26 |

TABLE 30-continued

| Example | Structure | LC-MS [M + 1]+ | HPLC RT (min) |
|---------|-----------|----------------|---------------|
| I-1299  | 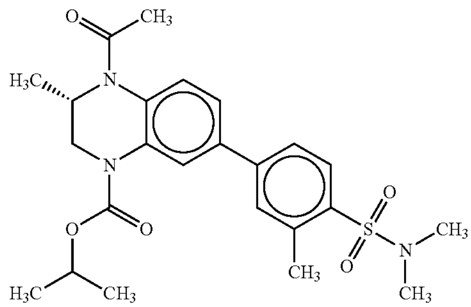          | 474            | 1.59          |
| I-1300  | 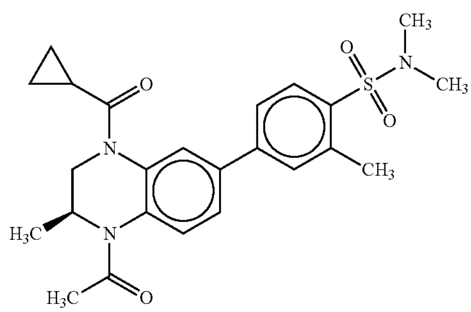          | 456            | 1.39          |
| I-1301  | 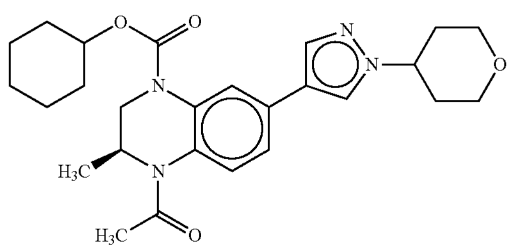          | 467            | 1.45          |
| I-1302  | 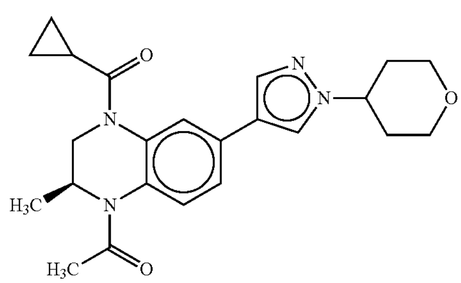          | 409            | 1.02          |
| I-1303  | 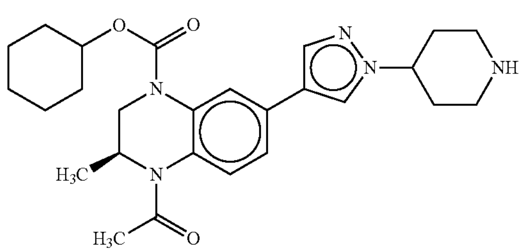          | 466            | 1.03          |

TABLE 30-continued

| Example | Structure | LC-MS [M + 1]+ | HPLC RT (min) |
|---|---|---|---|
| I-1304 | 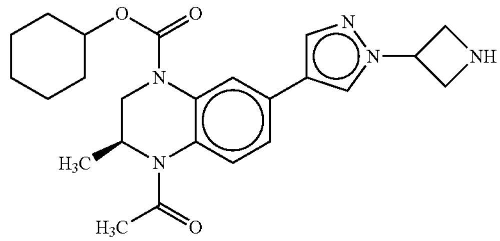 | 438 | 1.01 |
| I-1305 | 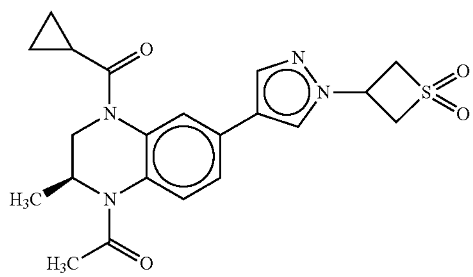 | 429 | 0.97 |
| I-1306 | 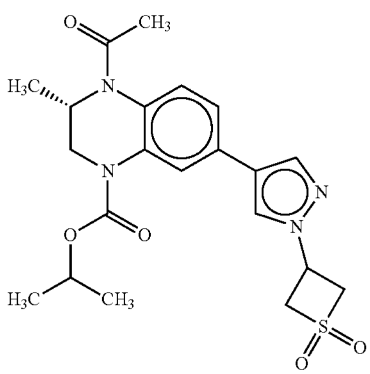 | 447 | 1.19 |
| I-1307 | 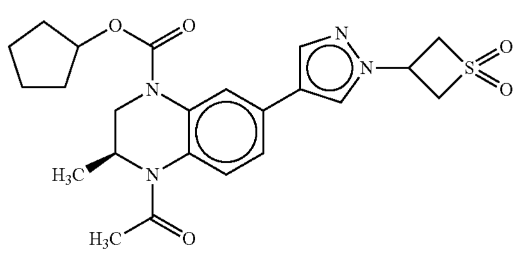 | 473 | 1.31 |
| I-1308 | 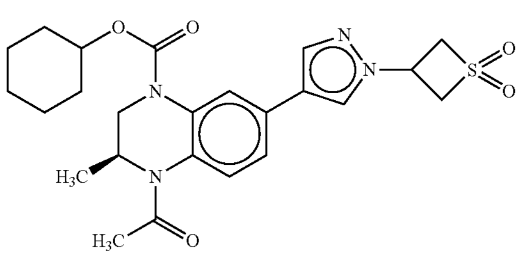 | 487 | 1.41 |

TABLE 30-continued
| Example | Structure | LC-MS [M + 1]+ | HPLC RT (min) |
|---|---|---|---|
| I-1309 | 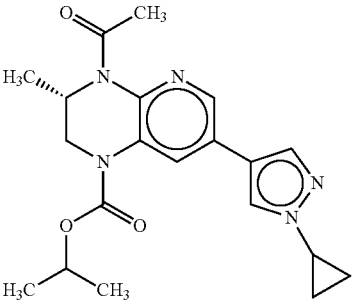 | 384 | 1.36 |
| I-1310 | 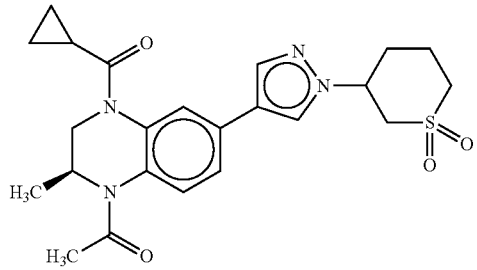 | 457 | 0.98 |
| I-1311 | 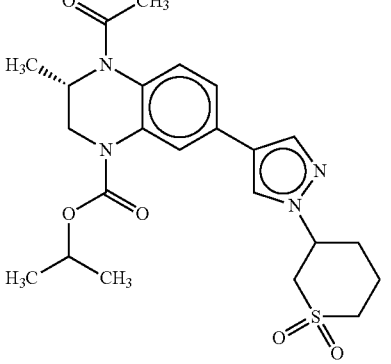 | 475 | 1.19 |
| I-1312 | 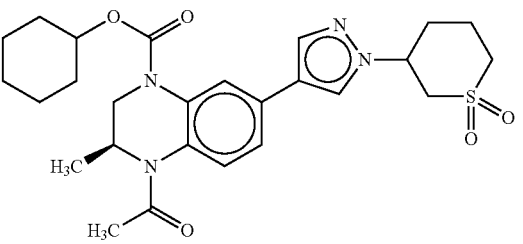 | 515 | 1.41 |

Example 287

Library Protocol X

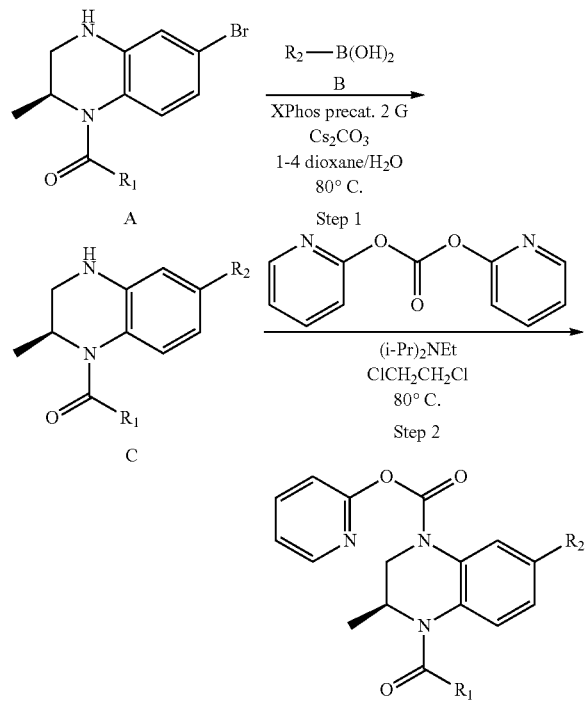

Step 1. A 1.5 mL reaction vial was charged with the aryl bromide (A) (0.2 M solution in 1,4-dioxane, 150 μL, 0.03), the boronic acid (B) (0.2 M solution in 1,4-dioxane, 270 μL, 0.054 mmol), and cesium carbonate (1 M solution in water, 90 μL, 0.09 mmol). XPhos precatalyst 2nd generation (0.02 M solution in 1,2-dichloroethane, 150 μL, 0.003 mmol) was added, the reaction was purged with nitrogen, and heated to 80° C. on a heater shaker overnight. The reaction was diluted with ethyl acetate (500 μL) and washed with a solution of 1 N sodium hydroxide in brine (400 μL). The aqueous layer was separated and extracted with ethyl acetate (1 mL) and the combined organic layers were concentrated to afford benzopiperazine (C), which was used without further purification.

Step 2. A 1.5 mL reaction vial was charged with benzopiperazine (C) from above, N,N-diisopropylethylamine (1.0 M in 1,2-dichloroethane, 180 μL, 0.180 mmol) and di(pyridin-2-yl) carbonate (0.4 M in 1,2-dichloroethane, 225 μL, 0.090 mmol), and the system was sealed and shaken at 80° C. for 2 hours. The reaction was diluted with ethyl acetate (500 μL) and washed with a 1 N aqueous hydrogen chloride solution (500 μL). The aqueous layer was separated and extracted with ethyl acetate (1 mL) and the combined organic layers were concentrated under a stream of nitrogen and vacuum. The crude product was purified by mass triggered preparatory HPLC. The product-containing fractions were combined and concentrated in a Genevac to afford the desired product.

The following compounds in Table 31 were synthesized according to the above protocol:

TABLE 31

| Example | Structure | LC-MS [M + 1]+ | HPLC RT (min) |
|---|---|---|---|
| I-1313 | 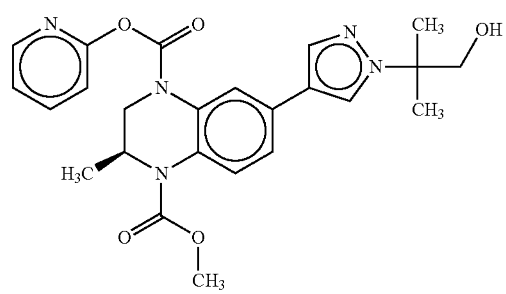 | 466.42 | 1.23 |
| I-1314 | 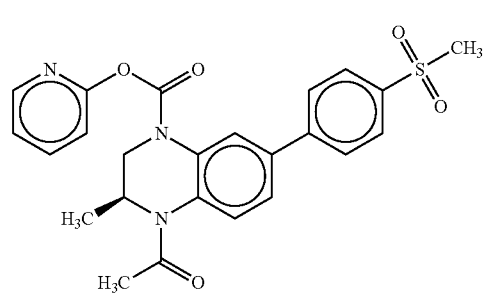 | 466.22 | 1.17 |

TABLE 31-continued

| Example | Structure | LC-MS [M + 1]+ | HPLC RT (min) |
|---------|-----------|----------------|---------------|
| I-1315 | 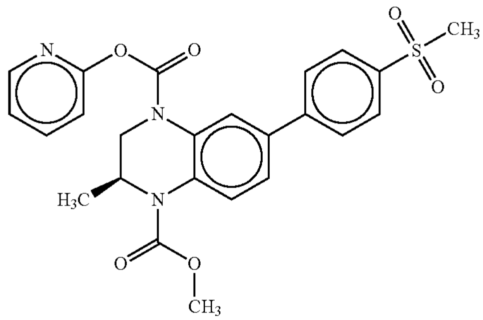 | 482.20 | 1.37 |
| I-1316 | 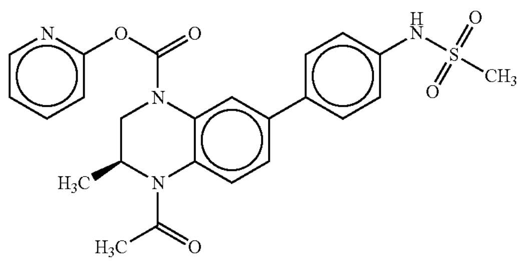 | 481.22 | 1.15 |
| I-1317 | 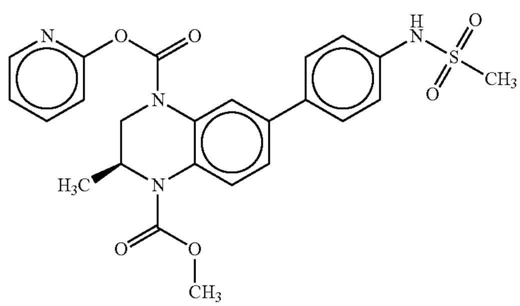 | 497.22 | 1.35 |
| I-1318 | 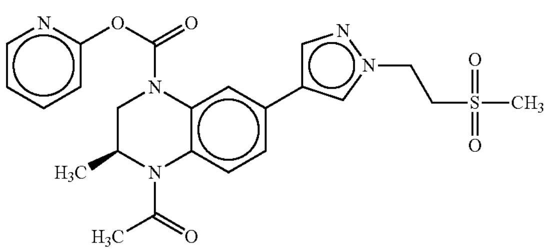 | 484.23 | 0.96 |
| I-1319 | 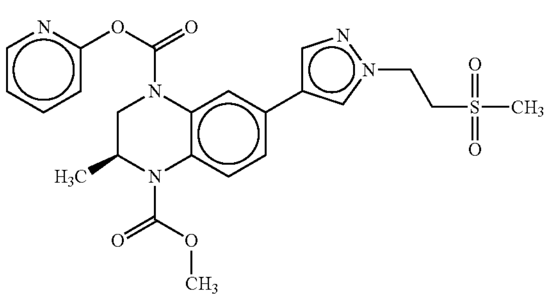 | 500.20 | 1.15 |

TABLE 31-continued

| Example | Structure | LC-MS [M + 1]+ | HPLC RT (min) |
|---|---|---|---|
| I-1320 | 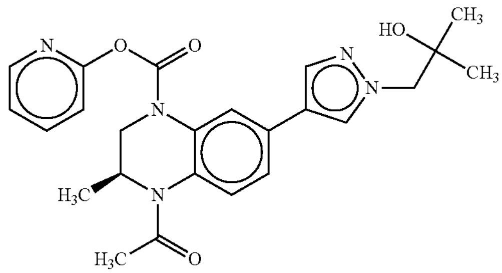 | 450.25 | 1.01 |
| I-1321 | 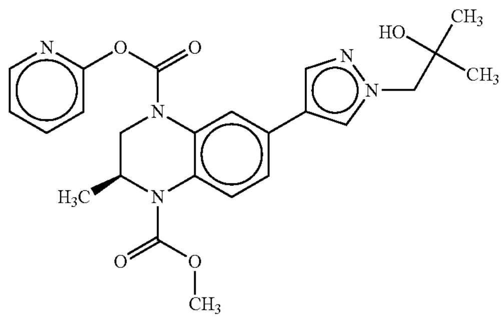 | 466.29 | 1.19 |
| I-1322 | 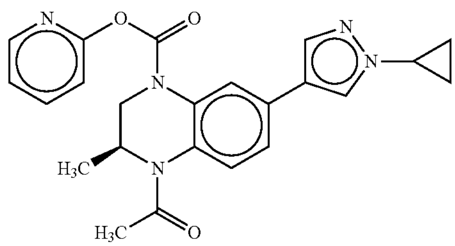 | 418.16 | 1.17 |
| I-1323 | 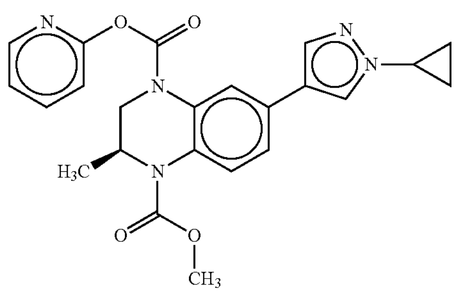 | 434.18 | 1.35 |
| I-1324 | 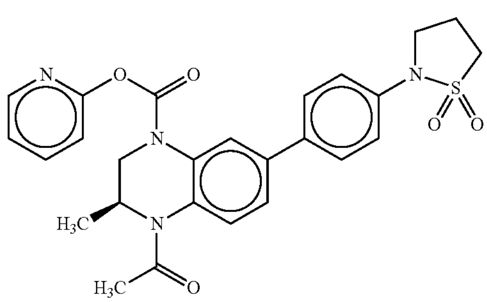 | 507.16 | 1.23 |

TABLE 31-continued

| Example | Structure | LC-MS [M + 1]+ | HPLC RT (min) |
|---------|-----------|----------------|---------------|
| I-1325 | 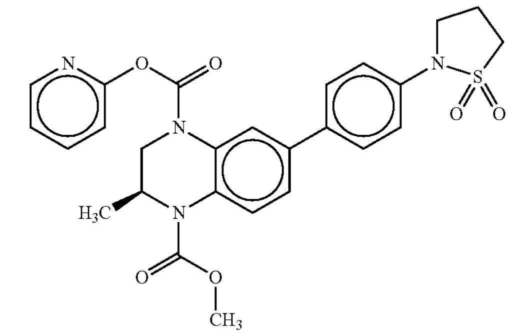 | 523.24 | 1.42 |
| I-1326 | 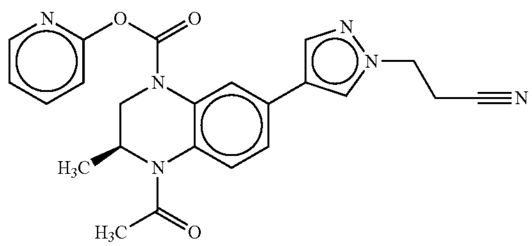 | 431.22 | 1.02 |
| I-1327 | 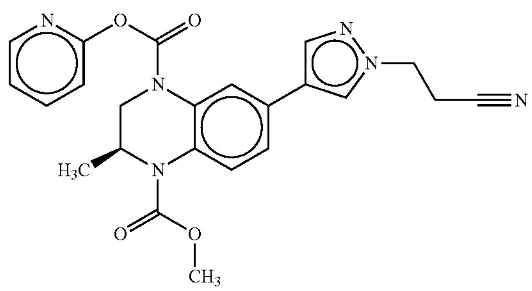 | 447.22 | 1.21 |
| I-1328 | 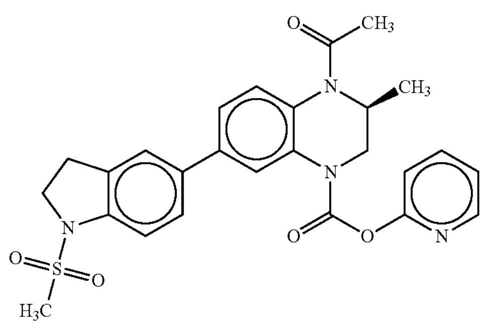 | 507.26 | 1.32 |
| I-1329 | 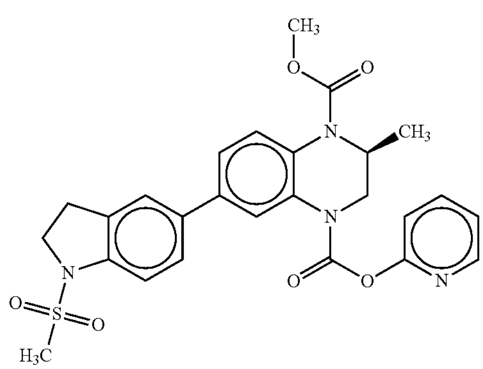 | 523.26 | 1.51 |

TABLE 31-continued

| Example | Structure | LC-MS [M + 1]+ | HPLC RT (min) |
|---|---|---|---|
| I-1330 | 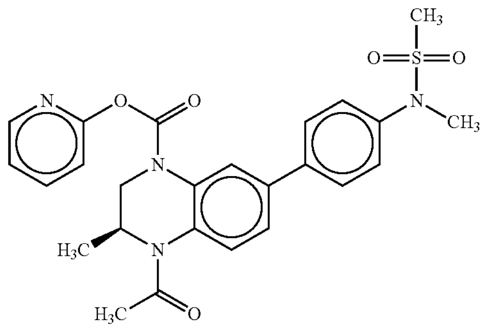 | 495.25 | 1.26 |
| I-1331 | 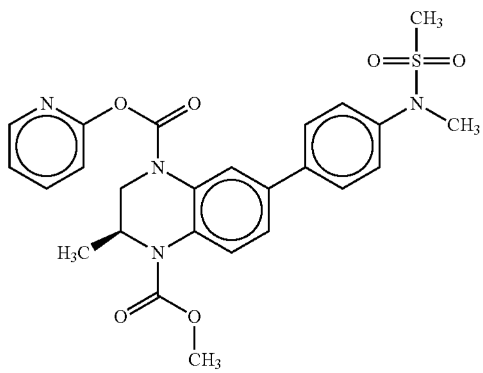 | 511.26 | 1.45 |
| I-1332 | 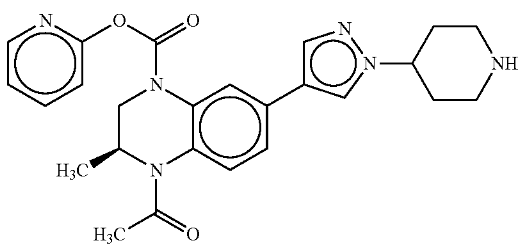 | 461.30 | 0.77 |
| I-1333 | 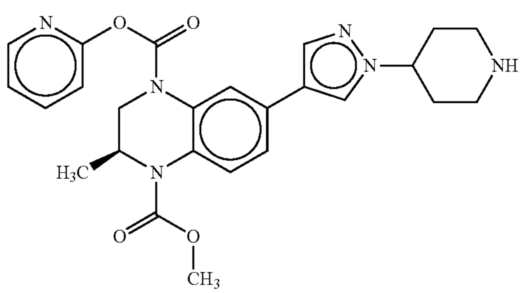 | 477.31 | 0.94 |
| I-1334 | 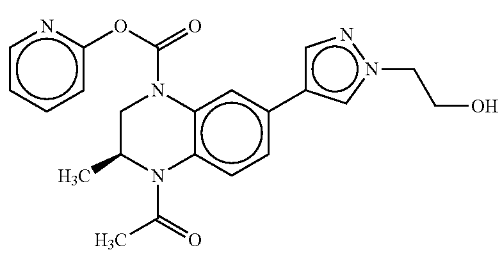 | 422.20 | 0.88 |

TABLE 31-continued

| Example | Structure | LC-MS [M + 1]+ | HPLC RT (min) |
|---|---|---|---|
| I-1335 | 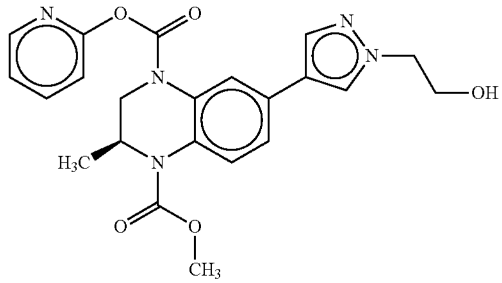 | 438.21 | 1.07 |

Example 288

AlphaScreen Binding Assay

The binding of Example compounds to BRD4 Bromodomain 1 and BRD4 Bromodomain 2 was assessed using 384-well AlphaScreen assay technology. His-epitope tagged BRD4 $BD1_{44-168}$ and BRD4 $BD2_{333-460}$ were cloned, expressed, and purified to homogeneity. BRD4 BD1 and BRD4 BD2 binding and inhibition was assessed by monitoring the engagement of biotinylated Histone H4 (1-21) K5/8/12/16 tetra-acetylated peptide with the targets using the AlphaScreen technology (PerkinElmer). Specifically, in a 384-well black or white flat bottom plate, BRD4 BD1 (50 nM final) or BRD4 BD2 (100 nM final) was combined with peptide (50 nM final for BD1 or 100 nM final for BD2) in 50 mM HEPES (pH 7.3), 100 mM NaCl, 0.1% (w/v) BSA, and 0.01% (w/v) Triton X-100 either in the presence of DMSO (final 1.25% DMSO) or compound dilution series in DMSO. Alpha streptavidin donor beads and Nickel-chelate acceptor beads were added to a final concentration of 10 µg/ml each. After a minimum of 1 hour equilibration, plates were read on a BMG PHERAstar FS multi-label reader (BMG LabTech). The half maximal inhibitory concentration ($IC_{50}$) values were calculated using IDBS Activity Base software with a four parameter logistic curve fit by the equation $y=A+((B-A)/(1+((C/x)^D)))$, wherein A denotes the bottom plateau of the curve, B denotes the top plateau of the curve, C denotes the x value at the middle of the curve, D denotes the slope factor, x denotes the original known x values, and y denotes the original known y values. Data was fitted using the Levenburg Marquardt algorithm.

Table 32. provides the compounds arranged according to Inhibition of BRD4 BD1. The compounds are grouped in four groups; $IC_{50}$<0.1 µM; 0.1≥$IC_{50}$≤1.0 µM; 1.0≥$IC_{50}$≤10.0 µM; and $IC_{50}$>10 µM.

TABLE 32

Exemplary compounds arranged according to inhibition of BRD4 BD1

Compounds with BRD4 BD1 $IC_{50}$ < 0.1 µM

I-12
I-20
I-23
I-24
I-25
I-65

TABLE 32-continued

Exemplary compounds arranged according to inhibition of BRD4 BD1

I-66
I-69
I-71
I-74
I-77
I-85
I-87
I-89
I-90
I-91
I-95
I-99
I-144
I-154
I-174
I-175
I-260
I-303
I-347
I-352
I-360
I-510
I-511
I-512
I-521
I-540
I-542
I-543
I-550
I-554
I-561
I-600
I-604
I-630
I-1000
I-1003
I-1018
I-1147
I-1301
I-1304

Compounds with BRD4 BD1 0.1 µM ≥ $IC_{50}$ ≤ 1.0 µM

I-1
I-2
I-3
I-4
I-5
I-8
I-9
I-10
I-13
I-16
I-17
I-18

TABLE 32-continued

Exemplary compounds arranged according to inhibition of BRD4 BD1

I-21
I-22
I-26
I-27
I-28
I-29
I-30
I-31
I-32
I-33
I-34
I-35
I-37
I-38
I-39
I-40
I-41
I-42
I-43
I-44
I-46
I-51
I-52
I-53
I-54
I-55
I-59
I-60
I-62
I-68
I-72
I-78
I-79
I-80
I-83
I-86
I-88
I-93
I-94
I-98
I-116
I-117
I-119
I-120
I-121
I-122
I-127
I-130
I-131
I-133
I-134
I-135
I-137
I-138
I-139
I-140
I-141
I-143
I-145
I-147
I-148
I-149
I-150
I-152
I-153
I-156
I-158
I-159
I-160
I-161
I-162
I-163
I-164
I-165
I-166
I-167
I-168

TABLE 32-continued

Exemplary compounds arranged according to inhibition of BRD4 BD1

I-169
I-170
I-171
I-172
I-173
I-176
I-177
I-178
I-179
I-181
I-182
I-183
I-184
I-185
I-186
I-188
I-190
I-191
I-195
I-204
I-205
I-206
I-207
I-211
I-212
I-214
I-215
I-220
I-221
I-222
I-223
I-224
I-225
I-227
I-228
I-229
I-231
I-232
I-233
I-234
I-238
I-250
I-252
I-256
I-257
I-258
I-261
I-262
I-263
I-264
I-266
I-267
I-268
I-269
I-279
I-286
I-287
I-289
I-291
I-294
I-299
I-304
I-305
I-306
I-307
I-308
I-309
I-310
I-312
I-313
I-314
I-315
I-316
I-317
I-318
I-319
I-320

TABLE 32-continued

Exemplary compounds arranged according to inhibition of BRD4 BD1

| |
|---|
| I-321 |
| I-322 |
| I-323 |
| I-324 |
| I-325 |
| I-326 |
| I-327 |
| I-328 |
| I-329 |
| I-330 |
| I-331 |
| I-332 |
| I-336 |
| I-337 |
| I-338 |
| I-345 |
| I-346 |
| I-348 |
| I-349 |
| I-351 |
| I-353 |
| I-354 |
| I-355 |
| I-356 |
| I-364 |
| I-366 |
| I-377 |
| I-378 |
| I-379 |
| I-380 |
| I-394 |
| I-395 |
| I-398 |
| I-409 |
| I-410 |
| I-415 |
| I-417 |
| I-419 |
| I-421 |
| I-422 |
| I-424 |
| I-425 |
| I-427 |
| I-428 |
| I-429 |
| I-432 |
| I-433 |
| I-435 |
| I-436 |
| I-437 |
| I-438 |
| I-439 |
| I-440 |
| I-441 |
| I-443 |
| I-444 |
| I-445 |
| I-446 |
| I-448 |
| I-449 |
| I-451 |
| I-455 |
| I-456 |
| I-465 |
| I-466 |
| I-467 |
| I-468 |
| I-469 |
| I-470 |
| I-471 |
| I-472 |
| I-473 |
| I-474 |
| I-475 |
| I-476 |
| I-477 |
| I-478 |

TABLE 32-continued

Exemplary compounds arranged according to inhibition of BRD4 BD1

| |
|---|
| I-479 |
| I-480 |
| I-481 |
| I-482 |
| I-483 |
| I-484 |
| I-485 |
| I-487 |
| I-488 |
| I-490 |
| I-492 |
| I-493 |
| I-494 |
| I-495 |
| I-496 |
| I-498 |
| I-499 |
| I-500 |
| I-501 |
| I-502 |
| I-503 |
| I-504 |
| I-506 |
| I-507 |
| I-508 |
| I-509 |
| I-513 |
| I-515 |
| I-517 |
| I-518 |
| I-519 |
| I-522 |
| I-523 |
| I-524 |
| I-526 |
| I-527 |
| I-529 |
| I-530 |
| I-532 |
| I-533 |
| I-534 |
| I-536 |
| I-537 |
| I-538 |
| I-539 |
| I-541 |
| I-544 |
| I-545 |
| I-546 |
| I-547 |
| I-548 |
| I-549 |
| I-551 |
| I-552 |
| I-553 |
| I-555 |
| I-556 |
| I-557 |
| I-558 |
| I-559 |
| I-560 |
| I-562 |
| I-563 |
| I-564 |
| I-565 |
| I-566 |
| I-567 |
| I-568 |
| I-569 |
| I-570 |
| I-571 |
| I-572 |
| I-573 |
| I-574 |
| I-575 |
| I-576 |
| I-577 |

TABLE 32-continued

Exemplary compounds arranged according to inhibition of BRD4 BD1

I-578
I-579
I-580
I-581
I-582
I-584
I-586
I-587
I-588
I-589
I-590
I-591
I-592
I-593
I-594
I-595
I-596
I-597
I-598
I-599
I-601
I-602
I-603
I-605
I-606
I-607
I-608
I-609
I-611
I-612
I-615
I-616
I-617
I-619
I-620
I-621
I-623
I-624
I-625
I-626
I-627
I-628
I-631
I-632
I-633
I-634
I-636
I-637
I-638
I-640
I-641
I-642
I-643
I-644
I-647
I-649
I-650
I-651
I-652
I-653
I-654
I-656
I-657
I-659
I-662
I-663
I-664
I-665
I-666
I-667
I-668
I-669
I-670
I-671
I-673
I-677
I-678

TABLE 32-continued

Exemplary compounds arranged according to inhibition of BRD4 BD1

I-679
I-680
I-682
I-684
I-685
I-686
I-687
I-688
I-689
I-690
I-692
I-789
I-796
I-801
I-807
I-809
I-810
I-822
I-825
I-838
I-843
I-844
I-845
I-848
I-849
I-850
I-852
I-853
I-857
I-859
I-860
I-862
I-864
I-865
I-870
I-871
I-872
I-874
I-875
I-876
I-994
I-995
I-996
I-997
I-1001
I-1002
I-1004
I-1005
I-1006
I-1008
I-1011
I-1012
I-1013
I-1014
I-1015
I-1016
I-1019
I-1020
I-1021
I-1023
I-1024
I-1025
I-1026
I-1030
I-1033
I-1034
I-1038
I-1057
I-1065
I-1069
I-1072
I-1073
I-1089
I-1093
I-1102
I-1103
I-1107

TABLE 32-continued

Exemplary compounds arranged according
to inhibition of BRD4 BD1

I-1111
I-1114
I-1115
I-1122
I-1130
I-1134
I-1135
I-1136
I-1137
I-1138
I-1141
I-1142
I-1146
I-1148
I-1149
I-1150
I-1151
I-1153
I-1155
I-1156
I-1157
I-1158
I-1159
I-1160
I-1162
I-1166
I-1167
I-1168
I-1169
I-1170
I-1171
I-1172
I-1173
I-1174
I-1175
I-1176
I-1177
I-1178
I-1179
I-1180
I-1182
I-1183
I-1184
I-1185
I-1186
I-1187
I-1189
I-1190
I-1191
I-1192
I-1194
I-1195
I-1196
I-1198
I-1199
I-1201
I-1202
I-1204
I-1205
I-1206
I-1207
I-1213
I-1214
I-1215
I-1216
I-1217
I-1218
I-1219
I-1220
I-1221
I-1222
I-1223
I-1224
I-1225
I-1226
I-1227
I-1228

TABLE 32-continued

Exemplary compounds arranged according
to inhibition of BRD4 BD1

I-1229
I-1230
I-1231
I-1232
I-1233
I-1234
I-1235
I-1236
I-1237
I-1238
I-1239
I-1240
I-1241
I-1243
I-1244
I-1245
I-1246
I-1248
I-1251
I-1252
I-1253
I-1254
I-1255
I-1256
I-1257
I-1258
I-1259
I-1260
I-1261
I-1262
I-1263
I-1264
I-1265
I-1266
I-1267
I-1268
I-1269
I-1270
I-1271
I-1272
I-1273
I-1274
I-1275
I-1279
I-1281
I-1284
I-1286
I-1292
I-1294
I-1299
I-1300
I-1302
I-1303
I-1306
I-1307
I-1308
I-1309
I-1310
I-1311
I-1312
I-1316
I-1322
I-1323
I-1324
I-1326
I-1328
I-1330
I-1332
I-1334

Compounds with BRD4
BD1 $1.0 \mu M \geq IC_{50} \leq 10.0 \geq M$

I-6
I-11
I-14
I-15
I-19

TABLE 32-continued

Exemplary compounds arranged according to inhibition of BRD4 BD1

I-36
I-45
I-47
I-48
I-49
I-50
I-58
I-61
I-63
I-64
I-70
I-73
I-75
I-76
I-81
I-84
I-92
I-107
I-111
I-112
I-118
I-123
I-124
I-125
I-126
I-128
I-129
I-132
I-136
I-142
I-146
I-151
I-180
I-187
I-189
I-194
I-196
I-197
I-198
I-199
I-200
I-203
I-208
I-209
I-210
I-216
I-217
I-218
I-219
I-226
I-235
I-236
I-237
I-239
I-240
I-241
I-244
I-245
I-246
I-249
I-251
I-254
I-255
I-259
I-265
I-270
I-271
I-272
I-273
I-274
I-275
I-276
I-277
I-278
I-280
I-281
I-282

TABLE 32-continued

Exemplary compounds arranged according to inhibition of BRD4 BD1

I-283
I-284
I-285
I-288
I-290
I-292
I-293
I-295
I-296
I-298
I-300
I-301
I-302
I-311
I-333
I-334
I-335
I-339
I-340
I-341
I-342
I-343
I-344
I-350
I-357
I-358
I-359
I-363
I-365
I-374
I-381
I-382
I-383
I-384
I-385
I-386
I-390
I-391
I-392
I-393
I-396
I-397
I-399
I-401
I-402
I-403
I-404
I-405
I-407
I-408
I-411
I-412
I-413
I-414
I-416
I-418
I-420
I-423
I-426
I-430
I-434
I-442
I-447
I-450
I-452
I-453
I-454
I-457
I-458
I-459
I-460
I-461
I-462
I-463
I-464
I-486
I-489

TABLE 32-continued

Exemplary compounds arranged according to inhibition of BRD4 BD1

I-491
I-497
I-505
I-514
I-516
I-520
I-525
I-528
I-531
I-535
I-583
I-585
I-610
I-613
I-614
I-618
I-622
I-629
I-635
I-639
I-645
I-646
I-648
I-655
I-658
I-660
I-661
I-672
I-674
I-675
I-676
I-681
I-683
I-691
I-778
I-781
I-783
I-785
I-786
I-787
I-791
I-793
I-794
I-795
I-798
I-799
I-800
I-802
I-803
I-804
I-805
I-806
I-808
I-811
I-812
I-813
I-814
I-815
I-817
I-818
I-819
I-820
I-823
I-824
I-828
I-829
I-830
I-831
I-832
I-833
I-834
I-835
I-836
I-837
I-840
I-841
I-846

TABLE 32-continued

Exemplary compounds arranged according to inhibition of BRD4 BD1

I-847
I-854
I-855
I-856
I-858
I-861
I-863
I-866
I-867
I-869
I-873
I-877
I-882
I-890
I-964
I-968
I-970
I-973
I-974
I-979
I-981
I-982
I-988
I-989
I-990
I-991
I-992
I-993
I-998
I-999
I-1007
I-1009
I-1010
I-1017
I-1022
I-1027
I-1028
I-1029
I-1031
I-1032
I-1035
I-1036
I-1037
I-1039
I-1040
I-1041
I-1042
I-1043
I-1044
I-1045
I-1046
I-1047
I-1048
I-1049
I-1050
I-1051
I-1052
I-1053
I-1054
I-1055
I-1056
I-1058
I-1059
I-1060
I-1061
I-1062
I-1063
I-1064
I-1066
I-1068
I-1070
I-1071
I-1074
I-1075
I-1076
I-1077
I-1078

TABLE 32-continued

Exemplary compounds arranged according to inhibition of BRD4 BD1

| |
|---|
| I-1079 |
| I-1080 |
| I-1081 |
| I-1082 |
| I-1083 |
| I-1084 |
| I-1085 |
| I-1086 |
| I-1087 |
| I-1088 |
| I-1090 |
| I-1091 |
| I-1092 |
| I-1094 |
| I-1095 |
| I-1096 |
| I-1097 |
| I-1098 |
| I-1099 |
| I-1100 |
| I-1101 |
| I-1104 |
| I-1105 |
| I-1106 |
| I-1108 |
| I-1109 |
| I-1110 |
| I-1112 |
| I-1113 |
| I-1116 |
| I-1117 |
| I-1118 |
| I-1119 |
| I-1120 |
| I-1121 |
| I-1123 |
| I-1124 |
| I-1125 |
| I-1126 |
| I-1127 |
| I-1128 |
| I-1129 |
| I-1131 |
| I-1132 |
| I-1133 |
| I-1139 |
| I-1140 |
| I-1143 |
| I-1144 |
| I-1145 |
| I-1152 |
| I-1154 |
| I-1161 |
| I-1163 |
| I-1164 |
| I-1165 |
| I-1181 |
| I-1193 |
| I-1197 |
| I-1200 |
| I-1203 |
| I-1208 |
| I-1209 |
| I-1210 |
| I-1242 |
| I-1247 |
| I-1249 |
| I-1250 |
| I-1276 |
| I-1277 |
| I-1278 |
| I-1280 |
| I-1282 |
| I-1283 |
| I-1285 |
| I-1287 |
| I-1288 |
| I-1289 |
| I-1290 |
| I-1291 |
| I-1293 |
| I-1295 |
| I-1296 |
| I-1297 |
| I-1298 |
| I-1305 |
| I-1313 |
| I-1314 |
| I-1315 |
| I-1317 |
| I-1318 |
| I-1319 |
| I-1320 |
| I-1321 |
| I-1325 |
| I-1327 |
| I-1329 |
| I-1331 |
| I-1333 |
| I-1335 |

Compounds with BRD4 BD1 $IC_{50} > 10.0$ μM

| |
|---|
| I-7 |
| I-56 |
| I-57 |
| I-67 |
| I-82 |
| I-96 |
| I-97 |
| I-100 |
| I-101 |
| I-102 |
| I-103 |
| I-104 |
| I-105 |
| I-106 |
| I-108 |
| I-109 |
| I-110 |
| I-113 |
| I-114 |
| I-115 |
| I-192 |
| I-193 |
| I-201 |
| I-202 |
| I-213 |
| I-230 |
| I-242 |
| I-243 |
| I-247 |
| I-248 |
| I-253 |
| I-297 |
| I-361 |
| I-362 |
| I-367 |
| I-368 |
| I-369 |
| I-370 |
| I-371 |
| I-372 |
| I-373 |
| I-375 |
| I-376 |
| I-387 |
| I-388 |
| I-389 |
| I-400 |
| I-406 |
| I-431 |
| I-693 |
| I-694 |

TABLE 32-continued

Exemplary compounds arranged according to inhibition of BRD4 BD1

I-695
I-696
I-697
I-698
I-699
I-700
I-701
I-702
I-703
I-704
I-705
I-706
I-707
I-708
I-709
I-710
I-711
I-712
I-713
I-714
I-715
I-716
I-717
I-718
I-719
I-720
I-721
I-722
I-723
I-724
I-725
I-726
I-727
I-728
I-729
I-730
I-731
I-732
I-733
I-734
I-735
I-736
I-737
I-738
I-739
I-740
I-741
I-742
I-743
I-744
I-745
I-746
I-747
I-748
I-749
I-750
I-751
I-752
I-753
I-754
I-755
I-756
I-757
I-758
I-759
I-760
I-761
I-762
I-763
I-764
I-765
I-766
I-767
I-768
I-769
I-770
I-771

TABLE 32-continued

Exemplary compounds arranged according to inhibition of BRD4 BD1

I-772
I-773
I-774
I-775
I-776
I-777
I-779
I-780
I-782
I-784
I-788
I-790
I-792
I-797
I-816
I-821
I-826
I-827
I-839
I-842
I-851
I-868
I-878
I-879
I-880
I-881
I-883
I-884
I-885
I-886
I-887
I-888
I-889
I-891
I-892
I-893
I-894
I-895
I-896
I-897
I-898
I-899
I-900
I-901
I-902
I-903
I-904
I-905
I-906
I-907
I-908
I-909
I-910
I-911
I-912
I-913
I-914
I-915
I-916
I-917
I-918
I-919
I-920
I-921
I-922
I-923
I-924
I-925
I-926
I-927
I-928
I-929
I-930
I-931
I-932
I-933
I-934

TABLE 32-continued

Exemplary compounds arranged according to inhibition of BRD4 BD1

I-935
I-936
I-937
I-938
I-939
I-940
I-941
I-942
I-943
I-944
I-945
I-946
I-947
I-948
I-949
I-950
I-951
I-952
I-953
I-954
I-955
I-956
I-957
I-958
I-959
I-960
I-961
I-962
I-963
I-965
I-966
I-967
I-969
I-971
I-972
I-975
I-976
I-977
I-978
I-980
I-983
I-984
I-985
I-986
I-987
I-1067
I-1188
I-1211
I-1212

Table 33 provides the compounds arranged according to Inhibition of BRD4 BD2. The compounds are grouped in three groups; $IC_{50}<0.05$ µM; $0.05$ µM$\geq IC_{50} \leq 0.5$ µM; and $IC_{50}>0.5$ µM.

TABLE 33

Exemplary compounds arranged according to inhibition of BRD4 BD2

Compounds with BRD4 BD2 $IC_{50} < 0.05$ µM

I-8
I-12
I-13
I-14
I-15
I-16
I-17
I-18
I-25
I-32
I-39

TABLE 33-continued

Exemplary compounds arranged according to inhibition of BRD4 BD2

I-47
I-52
I-53
I-55
I-65
I-66
I-69
I-71
I-72
I-74
I-77
I-85
I-87
I-88
I-89
I-90
I-91
I-95
I-99
I-119
I-120
I-121
I-122
I-124
I-126
I-127
I-128
I-139
I-141
I-144
I-150
I-152
I-158
I-179
I-180
I-181
I-182
I-183
I-185
I-188
I-190
I-191
I-206
I-221
I-223
I-225
I-227
I-228
I-229
I-233
I-234
I-237
I-238
I-239
I-256
I-257
I-258
I-259
I-260
I-261
I-262
I-263
I-264
I-265
I-266
I-267
I-268
I-269
I-274
I-276
I-277
I-278
I-279
I-280
I-281
I-282
I-283

TABLE 33-continued

Exemplary compounds arranged according to inhibition of BRD4 BD2

I-284
I-285
I-287
I-288
I-289
I-290
I-291
I-293
I-294
I-295
I-347
I-348
I-352
I-356
I-359
I-360
I-364
I-365
I-366
I-394
I-395
I-401
I-402
I-407
I-409
I-410
I-412
I-413
I-414
I-415
I-416
I-417
I-418
I-421
I-422
I-424
I-425
I-426
I-427
I-429
I-435
I-443
I-448
I-477
I-492
I-510
I-511
I-512
I-521
I-529
I-536
I-540
I-542
I-543
I-554
I-596
I-599
I-600
I-601
I-602
I-606
I-687
I-789
I-796
I-802
I-804
I-807
I-809
I-811
I-812
I-814
I-817
I-818
I-820
I-822
I-824
I-825

TABLE 33-continued

Exemplary compounds arranged according to inhibition of BRD4 BD2

I-829
I-831
I-836
I-838
I-841
I-843
I-844
I-848
I-850
I-853
I-855
I-856
I-857
I-859
I-860
I-865
I-871
I-872
I-874
I-875
I-876
I-1011
I-1012
I-1014
I-1016
I-1018
I-1019
I-1020
I-1023
I-1024
I-1025
I-1039
I-1040
I-1147
I-1148
I-1150
I-1157
I-1176
I-1183
I-1186
I-1187
I-1191
I-1192
I-1195
I-1201
I-1204
I-1205
I-1206
I-1217
I-1219
I-1275
I-1301
I-1302
I-1304
I-1305
I-1307
I-1308
I-1312
I-1322
I-1323
I-1324
I-1332

Compounds with BRD4
BD2 0.05 µM ≥ $IC_{50}$ ≤ 0.5 µM

I-2
I-3
I-4
I-5
I-6
I-9
I-10
I-11
I-19
I-20
I-21
I-22

TABLE 33-continued

Exemplary compounds arranged
according to inhibition of BRD4 BD2

| |
|---|
| I-23 |
| I-24 |
| I-26 |
| I-27 |
| I-28 |
| I-31 |
| I-33 |
| I-34 |
| I-35 |
| I-36 |
| I-37 |
| I-38 |
| I-40 |
| I-41 |
| I-42 |
| I-43 |
| I-44 |
| I-48 |
| I-51 |
| I-54 |
| I-57 |
| I-59 |
| I-60 |
| I-62 |
| I-63 |
| I-64 |
| I-68 |
| I-73 |
| I-76 |
| I-78 |
| I-79 |
| I-80 |
| I-83 |
| I-86 |
| I-92 |
| I-93 |
| I-94 |
| I-98 |
| I-100 |
| I-105 |
| I-106 |
| I-107 |
| I-108 |
| I-111 |
| I-112 |
| I-114 |
| I-116 |
| I-117 |
| I-118 |
| I-123 |
| I-125 |
| I-129 |
| I-130 |
| I-131 |
| I-132 |
| I-133 |
| I-134 |
| I-135 |
| I-136 |
| I-137 |
| I-138 |
| I-140 |
| I-142 |
| I-143 |
| I-145 |
| I-146 |
| I-147 |
| I-148 |
| I-149 |
| I-151 |
| I-153 |
| I-161 |
| I-162 |
| I-184 |
| I-186 |
| I-187 |
| I-189 |

TABLE 33-continued

Exemplary compounds arranged
according to inhibition of BRD4 BD2

| |
|---|
| I-194 |
| I-200 |
| I-204 |
| I-205 |
| I-207 |
| I-212 |
| I-214 |
| I-215 |
| I-220 |
| I-222 |
| I-224 |
| I-226 |
| I-231 |
| I-232 |
| I-235 |
| I-240 |
| I-241 |
| I-244 |
| I-245 |
| I-246 |
| I-248 |
| I-250 |
| I-251 |
| I-252 |
| I-255 |
| I-270 |
| I-271 |
| I-272 |
| I-275 |
| I-296 |
| I-298 |
| I-299 |
| I-300 |
| I-302 |
| I-303 |
| I-304 |
| I-305 |
| I-306 |
| I-307 |
| I-308 |
| I-309 |
| I-310 |
| I-311 |
| I-312 |
| I-313 |
| I-314 |
| I-315 |
| I-316 |
| I-317 |
| I-318 |
| I-319 |
| I-320 |
| I-321 |
| I-322 |
| I-323 |
| I-324 |
| I-325 |
| I-326 |
| I-327 |
| I-328 |
| I-329 |
| I-330 |
| I-336 |
| I-338 |
| I-339 |
| I-341 |
| I-342 |
| I-343 |
| I-344 |
| I-345 |
| I-346 |
| I-349 |
| I-350 |
| I-351 |
| I-353 |
| I-354 |
| I-355 |

TABLE 33-continued

Exemplary compounds arranged according to inhibition of BRD4 BD2

| |
|---|
| I-357 |
| I-358 |
| I-363 |
| I-377 |
| I-378 |
| I-379 |
| I-381 |
| I-383 |
| I-384 |
| I-386 |
| I-389 |
| I-390 |
| I-391 |
| I-392 |
| I-393 |
| I-396 |
| I-397 |
| I-398 |
| I-399 |
| I-403 |
| I-404 |
| I-405 |
| I-411 |
| I-420 |
| I-423 |
| I-428 |
| I-430 |
| I-432 |
| I-433 |
| I-434 |
| I-436 |
| I-437 |
| I-438 |
| I-439 |
| I-440 |
| I-441 |
| I-442 |
| I-444 |
| I-445 |
| I-446 |
| I-447 |
| I-449 |
| I-450 |
| I-451 |
| I-452 |
| I-453 |
| I-454 |
| I-455 |
| I-456 |
| I-457 |
| I-458 |
| I-459 |
| I-460 |
| I-461 |
| I-462 |
| I-463 |
| I-464 |
| I-465 |
| I-466 |
| I-467 |
| I-468 |
| I-469 |
| I-471 |
| I-473 |
| I-474 |
| I-475 |
| I-478 |
| I-483 |
| I-485 |
| I-486 |
| I-488 |
| I-490 |
| I-491 |
| I-493 |
| I-494 |
| I-496 |
| I-498 |

TABLE 33-continued

Exemplary compounds arranged according to inhibition of BRD4 BD2

| |
|---|
| I-499 |
| I-500 |
| I-501 |
| I-502 |
| I-503 |
| I-504 |
| I-505 |
| I-506 |
| I-507 |
| I-508 |
| I-509 |
| I-513 |
| I-514 |
| I-515 |
| I-516 |
| I-517 |
| I-518 |
| I-519 |
| I-520 |
| I-522 |
| I-523 |
| I-524 |
| I-525 |
| I-526 |
| I-527 |
| I-528 |
| I-530 |
| I-531 |
| I-532 |
| I-533 |
| I-534 |
| I-535 |
| I-537 |
| I-538 |
| I-539 |
| I-541 |
| I-544 |
| I-545 |
| I-546 |
| I-547 |
| I-548 |
| I-549 |
| I-550 |
| I-551 |
| I-552 |
| I-553 |
| I-555 |
| I-556 |
| I-557 |
| I-558 |
| I-559 |
| I-561 |
| I-562 |
| I-563 |
| I-564 |
| I-565 |
| I-566 |
| I-567 |
| I-568 |
| I-569 |
| I-570 |
| I-571 |
| I-573 |
| I-574 |
| I-575 |
| I-576 |
| I-577 |
| I-578 |
| I-579 |
| I-580 |
| I-581 |
| I-582 |
| I-584 |
| I-586 |
| I-587 |
| I-588 |
| I-589 |

TABLE 33-continued

Exemplary compounds arranged
according to inhibition of BRD4 BD2

| |
|---|
| I-590 |
| I-591 |
| I-592 |
| I-593 |
| I-594 |
| I-595 |
| I-597 |
| I-598 |
| I-603 |
| I-604 |
| I-605 |
| I-607 |
| I-608 |
| I-609 |
| I-610 |
| I-611 |
| I-612 |
| I-614 |
| I-615 |
| I-616 |
| I-617 |
| I-619 |
| I-620 |
| I-621 |
| I-623 |
| I-624 |
| I-625 |
| I-626 |
| I-627 |
| I-628 |
| I-629 |
| I-630 |
| I-631 |
| I-632 |
| I-633 |
| I-634 |
| I-637 |
| I-638 |
| I-640 |
| I-641 |
| I-642 |
| I-643 |
| I-644 |
| I-647 |
| I-648 |
| I-649 |
| I-650 |
| I-651 |
| I-652 |
| I-653 |
| I-654 |
| I-655 |
| I-656 |
| I-657 |
| I-658 |
| I-659 |
| I-660 |
| I-661 |
| I-662 |
| I-663 |
| I-664 |
| I-665 |
| I-666 |
| I-667 |
| I-668 |
| I-669 |
| I-670 |
| I-671 |
| I-672 |
| I-673 |
| I-674 |
| I-675 |
| I-677 |
| I-678 |
| I-679 |
| I-680 |
| I-681 |

TABLE 33-continued

Exemplary compounds arranged
according to inhibition of BRD4 BD2

| |
|---|
| I-682 |
| I-683 |
| I-684 |
| I-685 |
| I-686 |
| I-688 |
| I-689 |
| I-690 |
| I-691 |
| I-692 |
| I-720 |
| I-778 |
| I-781 |
| I-782 |
| I-785 |
| I-786 |
| I-787 |
| I-791 |
| I-792 |
| I-793 |
| I-795 |
| I-798 |
| I-799 |
| I-800 |
| I-801 |
| I-803 |
| I-805 |
| I-806 |
| I-808 |
| I-813 |
| I-815 |
| I-819 |
| I-821 |
| I-823 |
| I-828 |
| I-830 |
| I-832 |
| I-833 |
| I-834 |
| I-835 |
| I-837 |
| I-840 |
| I-845 |
| I-846 |
| I-847 |
| I-849 |
| I-852 |
| I-854 |
| I-858 |
| I-861 |
| I-862 |
| I-863 |
| I-864 |
| I-866 |
| I-867 |
| I-869 |
| I-870 |
| I-877 |
| I-878 |
| I-882 |
| I-886 |
| I-887 |
| I-890 |
| I-906 |
| I-908 |
| I-909 |
| I-921 |
| I-964 |
| I-967 |
| I-968 |
| I-970 |
| I-971 |
| I-973 |
| I-974 |
| I-979 |
| I-981 |
| I-984 |

TABLE 33-continued

Exemplary compounds arranged
according to inhibition of BRD4 BD2

| |
|---|
| I-985 |
| I-988 |
| I-989 |
| I-990 |
| I-991 |
| I-993 |
| I-994 |
| I-995 |
| I-997 |
| I-999 |
| I-1000 |
| I-1001 |
| I-1002 |
| I-1003 |
| I-1004 |
| I-1005 |
| I-1006 |
| I-1007 |
| I-1008 |
| I-1009 |
| I-1010 |
| I-1013 |
| I-1015 |
| I-1021 |
| I-1022 |
| I-1026 |
| I-1027 |
| I-1028 |
| I-1029 |
| I-1030 |
| I-1031 |
| I-1032 |
| I-1033 |
| I-1034 |
| I-1035 |
| I-1036 |
| I-1037 |
| I-1038 |
| I-1041 |
| I-1042 |
| I-1043 |
| I-1044 |
| I-1045 |
| I-1046 |
| I-1047 |
| I-1048 |
| I-1049 |
| I-1050 |
| I-1051 |
| I-1052 |
| I-1053 |
| I-1054 |
| I-1055 |
| I-1056 |
| I-1057 |
| I-1058 |
| I-1059 |
| I-1060 |
| I-1061 |
| I-1062 |
| I-1063 |
| I-1064 |
| I-1065 |
| I-1066 |
| I-1067 |
| I-1068 |
| I-1069 |
| I-1070 |
| I-1071 |
| I-1072 |
| I-1073 |
| I-1074 |
| I-1075 |
| I-1076 |
| I-1077 |
| I-1078 |
| I-1079 |

TABLE 33-continued

Exemplary compounds arranged
according to inhibition of BRD4 BD2

| |
|---|
| I-1080 |
| I-1081 |
| I-1082 |
| I-1083 |
| I-1084 |
| I-1085 |
| I-1086 |
| I-1087 |
| I-1088 |
| I-1089 |
| I-1090 |
| I-1091 |
| I-1092 |
| I-1093 |
| I-1098 |
| I-1099 |
| I-1100 |
| I-1101 |
| I-1102 |
| I-1103 |
| I-1104 |
| I-1105 |
| I-1106 |
| I-1107 |
| I-1108 |
| I-1109 |
| I-1110 |
| I-1111 |
| I-1112 |
| I-1113 |
| I-1114 |
| I-1115 |
| I-1116 |
| I-1117 |
| I-1119 |
| I-1120 |
| I-1121 |
| I-1122 |
| I-1123 |
| I-1124 |
| I-1125 |
| I-1126 |
| I-1127 |
| I-1128 |
| I-1129 |
| I-1130 |
| I-1131 |
| I-1132 |
| I-1133 |
| I-1134 |
| I-1135 |
| I-1136 |
| I-1137 |
| I-1138 |
| I-1139 |
| I-1140 |
| I-1141 |
| I-1142 |
| I-1143 |
| I-1144 |
| I-1145 |
| I-1146 |
| I-1149 |
| I-1151 |
| I-1152 |
| I-1153 |
| I-1154 |
| I-1155 |
| I-1156 |
| I-1158 |
| I-1159 |
| I-1160 |
| I-1161 |
| I-1162 |
| I-1163 |
| I-1164 |
| I-1165 |

TABLE 33-continued

Exemplary compounds arranged according to inhibition of BRD4 BD2

I-1166
I-1167
I-1168
I-1169
I-1170
I-1171
I-1172
I-1173
I-1174
I-1175
I-1177
I-1178
I-1179
I-1180
I-1181
I-1182
I-1184
I-1185
I-1189
I-1190
I-1193
I-1194
I-1196
I-1197
I-1198
I-1199
I-1200
I-1202
I-1203
I-1207
I-1208
I-1209
I-1210
I-1211
I-1213
I-1214
I-1215
I-1216
I-1218
I-1220
I-1221
I-1222
I-1223
I-1224
I-1225
I-1226
I-1227
I-1228
I-1229
I-1230
I-1231
I-1232
I-1233
I-1234
I-1235
I-1236
I-1237
I-1238
I-1239
I-1240
I-1241
I-1242
I-1243
I-1244
I-1245
I-1246
I-1249
I-1251
I-1252
I-1253
I-1254
I-1255
I-1256
I-1257
I-1258
I-1259
I-1260

TABLE 33-continued

Exemplary compounds arranged according to inhibition of BRD4 BD2

I-1261
I-1262
I-1263
I-1264
I-1265
I-1266
I-1267
I-1268
I-1269
I-1270
I-1271
I-1272
I-1273
I-1274
I-1276
I-1277
I-1279
I-1280
I-1281
I-1283
I-1284
I-1285
I-1286
I-1288
I-1289
I-1290
I-1292
I-1294
I-1295
I-1296
I-1297
I-1298
I-1299
I-1300
I-1303
I-1306
I-1309
I-1310
I-1311
I-1313
I-1314
I-1315
I-1316
I-1317
I-1318
I-1319
I-1320
I-1321
I-1325
I-1326
I-1327
I-1328
I-1329
I-1330
I-1331
I-1333
I-1334
I-1335

Compounds with BRD4 BD2 IC$_{50}$ > 0.5 µM

I-7
I-29
I-30
I-45
I-46
I-49
I-50
I-56
I-58
I-61
I-67
I-70
I-75
I-81
I-82
I-84

TABLE 33-continued

Exemplary compounds arranged
according to inhibition of BRD4 BD2

I-96
I-97
I-101
I-102
I-103
I-104
I-109
I-110
I-113
I-115
I-192
I-193
I-195
I-196
I-197
I-198
I-199
I-201
I-202
I-203
I-208
I-209
I-210
I-211
I-213
I-216
I-217
I-218
I-219
I-230
I-236
I-242
I-243
I-247
I-249
I-253
I-254
I-273
I-286
I-292
I-297
I-301
I-331
I-332
I-333
I-334
I-335
I-337
I-340
I-361
I-362
I-367
I-368
I-369
I-370
I-371
I-372
I-373
I-374
I-375
I-376
I-380
I-382
I-385
I-387
I-388
I-400
I-406
I-408
I-419
I-431
I-470
I-472
I-476
I-479
I-481
I-482

TABLE 33-continued

Exemplary compounds arranged
according to inhibition of BRD4 BD2

I-484
I-487
I-489
I-495
I-497
I-572
I-583
I-585
I-613
I-618
I-622
I-635
I-636
I-639
I-645
I-646
I-676
I-693
I-694
I-695
I-696
I-697
I-698
I-699
I-700
I-701
I-702
I-703
I-704
I-705
I-706
I-707
I-708
I-709
I-710
I-711
I-712
I-713
I-714
I-715
I-716
I-717
I-718
I-719
I-721
I-722
I-723
I-724
I-725
I-726
I-727
I-728
I-729
I-730
I-731
I-732
I-733
I-734
I-735
I-736
I-737
I-738
I-739
I-740
I-741
I-742
I-743
I-744
I-745
I-746
I-747
I-748
I-749
I-750
I-751
I-752
I-753

TABLE 33-continued

Exemplary compounds arranged
according to inhibition of BRD4 BD2

| |
|---|
| I-754 |
| I-755 |
| I-756 |
| I-757 |
| I-758 |
| I-759 |
| I-760 |
| I-761 |
| I-762 |
| I-763 |
| I-764 |
| I-765 |
| I-766 |
| I-767 |
| I-768 |
| I-769 |
| I-770 |
| I-771 |
| I-772 |
| I-773 |
| I-774 |
| I-775 |
| I-776 |
| I-777 |
| I-779 |
| I-780 |
| I-783 |
| I-784 |
| I-788 |
| I-790 |
| I-794 |
| I-797 |
| I-810 |
| I-816 |
| I-826 |
| I-827 |
| I-839 |
| I-842 |
| I-851 |
| I-868 |
| I-873 |
| I-879 |
| I-880 |
| I-881 |
| I-883 |
| I-884 |
| I-885 |
| I-888 |
| I-889 |
| I-891 |
| I-892 |
| I-893 |
| I-894 |
| I-895 |
| I-896 |
| I-897 |
| I-898 |
| I-899 |
| I-900 |
| I-901 |
| I-902 |
| I-903 |
| I-904 |
| I-905 |
| I-907 |
| I-910 |
| I-911 |
| I-912 |
| I-913 |
| I-914 |
| I-915 |
| I-916 |
| I-917 |
| I-918 |
| I-919 |
| I-920 |
| I-922 |

TABLE 33-continued

Exemplary compounds arranged
according to inhibition of BRD4 BD2

| |
|---|
| I-923 |
| I-924 |
| I-925 |
| I-926 |
| I-927 |
| I-928 |
| I-929 |
| I-930 |
| I-931 |
| I-932 |
| I-933 |
| I-934 |
| I-935 |
| I-936 |
| I-937 |
| I-938 |
| I-939 |
| I-940 |
| I-941 |
| I-942 |
| I-943 |
| I-944 |
| I-945 |
| I-946 |
| I-947 |
| I-948 |
| I-949 |
| I-950 |
| I-951 |
| I-952 |
| I-953 |
| I-954 |
| I-955 |
| I-956 |
| I-957 |
| I-958 |
| I-959 |
| I-960 |
| I-961 |
| I-962 |
| I-963 |
| I-965 |
| I-966 |
| I-969 |
| I-972 |
| I-975 |
| I-976 |
| I-977 |
| I-978 |
| I-980 |
| I-982 |
| I-983 |
| I-986 |
| I-987 |
| I-992 |
| I-996 |
| I-998 |
| I-1017 |
| I-1094 |
| I-1095 |
| I-1096 |
| I-1097 |
| I-1118 |
| I-1188 |
| I-1212 |
| I-1247 |
| I-1248 |
| I-1250 |
| I-1278 |
| I-1282 |
| I-1287 |
| I-1291 |
| I-1293 |

Example 289

Oncology Cell Growth Assay

The impact of Example compounds on cancer cell proliferation was determined using the acute myelocytic leukemia (AML) cell line MV4-11 (ATCC) in a 3-day proliferation assay. MV4-11 cells were maintained in RPMI 1640 media supplemented with 10% FBS at 37° C. and an atmosphere of 5% $CO_2$. For compound testing, compound dilutions series were prepared in DMSO via a 3-fold serial dilution from 2 mM to 0.001 mM in 384-well white flat bottom plates. The final compound concentrations in the wells were 10, 3.3, 1.1, 0.37, 0.12, 0.041, 0.013 and 0.0045 µM. MV4-11 cells were plated at a density of 3000 cells/well in final volume of 50 µl culture media and incubated for 72 hours. The amounts of viable cells were determined using the CellTiter-Glo Luminescent Cell Viability Assay kit (Promega) according to the manufacturer suggested protocol. Luminescent signal from the CellTiter-Glo assay was read on an EnVision multilabel plate reader (PerkinElmer). Values for the concentration that inhibited cell growth by 50% ($gIC_{50}$) between the DMSO control and background control (no cells) were determined using IDBS Activity Base software with a four parameter logistic curve fit by the equation $y=A+((B-A)/(1+((C/x)^D)))$, wherein A denotes the bottom plateau of the curve, B denotes the top plateau of the curve, C denotes the x value at the middle of the curve, D denotes the slope factor, x denotes the original known x values, and y denotes the original known y values. Data was fitted using the Levenburg Marquardt algorithm.

Table 34 provides the compounds arranged according to Inhibition of proliferation of MV4-11 cell line. The compounds are grouped in three groups; $IC_{50}<0.1$ µM; $0.1$ µM$\geq IC_{50}\leq 1.0$ µM; $1.0$ µM$\geq IC_{50}\leq 10.0$ µM; and $IC_{50}>10.0$ µM.

TABLE 34

Exemplary compounds arranged according to inhibition of proliferation of MV4-11 Cell line.

Compounds with MV4-11 $IC_{50} < 0.1$ µM

I-3
I-16
I-22
I-23
I-25
I-39
I-52
I-54
I-86
I-87
I-88
I-93
I-94
I-99
I-154
I-159
I-160
I-173
I-174
I-175
I-181
I-185
I-223
I-225
I-227
I-229
I-232
I-233

TABLE 34-continued

Exemplary compounds arranged according to inhibition of proliferation of MV4-11 Cell line.

I-234
I-256
I-258
I-264
I-268
I-276
I-279
I-286
I-287
I-347
I-352
I-409
I-417
I-506
I-507
I-512
I-513
I-515
I-517
I-519
I-521
I-522
I-523
I-524
I-527
I-529
I-530
I-533
I-540
I-542
I-543
I-548
I-553
I-555
I-556
I-860
I-1003
I-1021
I-1147
I-1149
I-1192
I-1195
I-1204
I-1217
I-1219
I-1254
I-1269
I-1271
I-1301
I-1303
I-1304
I-1322
I-1332

Compounds with MV4-11 $0.1$ µM $\geq IC_{50} \leq 0.5$ µM

I-1
I-2
I-4
I-5
I-8
I-9
I-10
I-12
I-13
I-14
I-15
I-17
I-18
I-19
I-20
I-21
I-24
I-26
I-27
I-31
I-33

TABLE 34-continued

Exemplary compounds arranged according to inhibition of proliferation of MV4-11 Cell line.

I-34
I-35
I-36
I-37
I-38
I-40
I-41
I-42
I-44
I-46
I-51
I-53
I-55
I-60
I-62
I-65
I-66
I-69
I-71
I-72
I-74
I-77
I-78
I-79
I-80
I-81
I-85
I-89
I-90
I-91
I-95
I-98
I-116
I-117
I-119
I-120
I-121
I-122
I-124
I-128
I-129
I-131
I-133
I-135
I-137
I-139
I-140
I-141
I-143
I-144
I-147
I-148
I-149
I-152
I-153
I-158
I-161
I-162
I-163
I-165
I-166
I-167
I-170
I-176
I-177
I-178
I-179
I-180
I-182
I-183
I-184
I-186
I-188
I-189
I-190
I-191
I-206
I-212
I-214
I-215
I-220
I-221
I-228
I-231
I-237
I-238
I-239
I-250
I-252
I-257
I-259
I-260
I-261
I-262
I-263
I-266
I-267
I-269
I-274
I-275
I-277
I-278
I-280
I-281
I-282
I-283
I-284
I-285
I-288
I-289
I-290
I-291
I-292
I-293
I-294
I-295
I-299
I-303
I-304
I-305
I-306
I-307
I-308
I-312
I-313
I-314
I-315
I-316
I-317
I-321
I-322
I-323
I-324
I-327
I-328
I-329
I-330
I-345
I-346
I-348
I-349
I-350
I-351
I-353
I-354
I-355
I-356
I-359
I-360
I-364
I-366
I-377
I-378
I-379

TABLE 34-continued

Exemplary compounds arranged according to
inhibition of proliferation of MV4-11 Cell line.

I-382
I-398
I-401
I-410
I-412
I-413
I-414
I-415
I-422
I-423
I-425
I-426
I-427
I-428
I-429
I-430
I-435
I-436
I-437
I-438
I-439
I-443
I-445
I-455
I-456
I-465
I-467
I-468
I-469
I-471
I-473
I-475
I-477
I-478
I-480
I-493
I-494
I-495
I-496
I-498
I-499
I-500
I-501
I-502
I-503
I-504
I-508
I-509
I-510
I-511
I-518
I-526
I-532
I-534
I-536
I-537
I-538
I-539
I-541
I-544
I-545
I-546
I-547
I-549
I-550
I-551
I-552
I-554
I-557
I-558
I-559
I-560
I-561
I-562
I-563
I-564
I-565

TABLE 34-continued

Exemplary compounds arranged according to
inhibition of proliferation of MV4-11 Cell line.

I-566
I-567
I-568
I-569
I-570
I-571
I-572
I-573
I-575
I-576
I-578
I-579
I-580
I-581
I-582
I-584
I-586
I-587
I-588
I-589
I-590
I-591
I-592
I-593
I-594
I-595
I-596
I-597
I-598
I-599
I-600
I-601
I-602
I-603
I-604
I-605
I-606
I-607
I-608
I-615
I-616
I-617
I-618
I-619
I-620
I-623
I-628
I-630
I-632
I-633
I-634
I-637
I-641
I-642
I-643
I-650
I-653
I-654
I-656
I-657
I-663
I-664
I-665
I-666
I-667
I-668
I-670
I-671
I-673
I-677
I-678
I-679
I-680
I-682
I-685
I-686
I-687

TABLE 34-continued

Exemplary compounds arranged according to
inhibition of proliferation of MV4-11 Cell line.

I-688
I-789
I-796
I-800
I-804
I-806
I-807
I-809
I-810
I-817
I-822
I-824
I-838
I-841
I-843
I-844
I-845
I-848
I-850
I-852
I-859
I-864
I-865
I-871
I-872
I-874
I-875
I-876
I-994
I-995
I-997
I-1000
I-1001
I-1002
I-1004
I-1005
I-1006
I-1007
I-1008
I-1011
I-1012
I-1013
I-1014
I-1015
I-1016
I-1018
I-1019
I-1020
I-1024
I-1026
I-1027
I-1029
I-1030
I-1031
I-1032
I-1033
I-1034
I-1036
I-1037
I-1038
I-1039
I-1040
I-1041
I-1042
I-1049
I-1053
I-1054
I-1057
I-1058
I-1059
I-1065
I-1069
I-1070
I-1071
I-1072
I-1073
I-1077

TABLE 34-continued

Exemplary compounds arranged according to
inhibition of proliferation of MV4-11 Cell line.

I-1078
I-1089
I-1093
I-1104
I-1106
I-1107
I-1108
I-1110
I-1111
I-1112
I-1113
I-1115
I-1119
I-1120
I-1121
I-1122
I-1123
I-1124
I-1125
I-1126
I-1127
I-1128
I-1129
I-1130
I-1131
I-1132
I-1133
I-1134
I-1135
I-1136
I-1137
I-1138
I-1139
I-1140
I-1141
I-1142
I-1143
I-1144
I-1146
I-1148
I-1150
I-1151
I-1152
I-1153
I-1156
I-1157
I-1159
I-1160
I-1167
I-1168
I-1169
I-1170
I-1171
I-1172
I-1173
I-1174
I-1179
I-1183
I-1184
I-1185
I-1186
I-1189
I-1191
I-1194
I-1196
I-1198
I-1199
I-1201
I-1202
I-1205
I-1206
I-1213
I-1214
I-1215
I-1216
I-1218
I-1220

TABLE 34-continued

Exemplary compounds arranged according to inhibition of proliferation of MV4-11 Cell line.

I-1221
I-1222
I-1223
I-1224
I-1225
I-1227
I-1228
I-1229
I-1230
I-1231
I-1232
I-1233
I-1234
I-1235
I-1236
I-1237
I-1239
I-1240
I-1241
I-1243
I-1244
I-1245
I-1246
I-1248
I-1249
I-1251
I-1252
I-1253
I-1255
I-1256
I-1257
I-1258
I-1259
I-1261
I-1262
I-1263
I-1264
I-1265
I-1266
I-1267
I-1268
I-1270
I-1272
I-1273
I-1274
I-1275
I-1279
I-1281
I-1284
I-1286
I-1292
I-1299
I-1302
I-1307
I-1308
I-1311
I-1312
I-1316
I-1323
I-1324
I-1326
I-1328
I-1330
I-1334

Compounds with MV4-11 IC$_{50}$ > 0.5 μM

I-28
I-29
I-30
I-43
I-59
I-82
I-83
I-114
I-123
I-126

TABLE 34-continued

Exemplary compounds arranged according to inhibition of proliferation of MV4-11 Cell line.

I-127
I-130
I-134
I-138
I-145
I-146
I-150
I-156
I-164
I-168
I-169
I-171
I-172
I-187
I-194
I-195
I-196
I-197
I-198
I-199
I-200
I-201
I-202
I-203
I-204
I-205
I-207
I-208
I-209
I-210
I-211
I-213
I-216
I-217
I-218
I-219
I-222
I-224
I-236
I-245
I-251
I-265
I-309
I-310
I-318
I-319
I-320
I-325
I-326
I-331
I-332
I-336
I-337
I-338
I-365
I-407
I-420
I-447
I-449
I-466
I-470
I-472
I-474
I-476
I-479
I-482
I-483
I-485
I-490
I-574
I-577
I-609
I-611
I-612
I-621
I-624
I-625

TABLE 34-continued

Exemplary compounds arranged according to
inhibition of proliferation of MV4-11 Cell line.

I-626
I-627
I-631
I-636
I-638
I-640
I-644
I-647
I-649
I-651
I-652
I-659
I-662
I-669
I-689
I-690
I-692
I-778
I-781
I-786
I-791
I-792
I-793
I-794
I-795
I-798
I-799
I-801
I-825
I-849
I-857
I-862
I-863
I-867
I-868
I-988
I-996
I-1023
I-1025
I-1028
I-1035
I-1043
I-1044
I-1045
I-1046
I-1047
I-1048
I-1050
I-1051
I-1052
I-1055
I-1056
I-1060
I-1061
I-1062
I-1063
I-1064
I-1066
I-1067
I-1068
I-1074
I-1075
I-1076
I-1079
I-1080
I-1081
I-1082
I-1083
I-1084
I-1085
I-1086
I-1087
I-1088
I-1090
I-1091
I-1092
I-1094
I-1095
I-1096
I-1097
I-1098
I-1099
I-1100
I-1101
I-1102
I-1103
I-1105
I-1109
I-1114
I-1116
I-1117
I-1118
I-1145
I-1154
I-1155
I-1158
I-1161
I-1162
I-1163
I-1164
I-1165
I-1166
I-1175
I-1176
I-1177
I-1178
I-1180
I-1181
I-1182
I-1187
I-1190
I-1207
I-1211
I-1212
I-1226
I-1238
I-1242
I-1247
I-1250
I-1260
I-1294
I-1297
I-1298
I-1300
I-1305
I-1306
I-1309
I-1310

It is expected and indicated in the literature, that all BET family inhibitors have some activity for all BET bromodomains. The compounds of this invention have also inhibitory activity for all BET family bromodomains.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A compound of Formula (I)

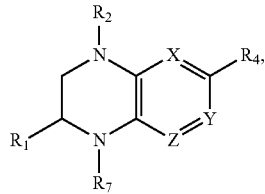

or a pharmaceutically acceptable salt, enantiomer hydrate, solvate, isomer, or tautomer thereof,
wherein:
X is selected from N or $CR_3$;
Y is selected from N or $CR_5$;
Z is selected from N or $CR_6$;
$R_1$ is $C_1$-$C_6$ alkyl, or $C_1$-$C_6$ haloalkyl;
$R_2$ is —C(O)$(CR^kR^l)_n$O$(CR^kR^l)_m R^d$, —C(O)$(CR^kR^l)_n R^e$, —S(O)$_2(CR^kR^l)_n R^f$, —$(CR^kR^l)_n R^g$, —C(O)$(CR^kR^l)_n$N$R^a R^g$ or —C(O)$(CR^kR^l)_n$S$(CR^kR^l)_m R^f$;
$R_3$ and $R_6$ are independently selected from hydrogen or halogen;
$R_4$ is $C_2$-$C_6$ alkyl, F, Cl, I, $C_3$-$C_6$ cycloalkyl, $C_6$-$C_{10}$ aryl, heterocycloalkyl, heteroaryl, —N$R^a R^b$, —C(O)$R^h$, —O$R^h$, $C_1$-$C_6$ haloalkyl, $C_2$-$C_6$ alkenyl, $C_2$-$C_6$ alkynyl, —$C_1$-$C_4$ alkyl(aryl), —$C_1$-$C_4$ alkyl(heteroaryl), or —$C_1$-$C_4$ alkyl(heterocycloalkyl), wherein the cycloalkyl, aryl, heterocycloalkyl, heteroaryl, and alkyl are optionally substituted with one or more $R_{10}$;
$R_5$ is hydrogen, halogen, $C_1$-$C_6$ alkyl, nitro, —NH$_2$, $C_1$-$C_6$ alkylamino, $C_1$-$C_6$ dialkylamino, $C_1$-$C_6$ aminoalkyl, $C_1$-$C_6$ aminoalkoxy, CN, $C_1$-$C_6$ alkoxy, —C(O)N$R^a R^b$, —N$R^a$S(O)$_2 R^b$, —N$R^a$C(O)$R^b$, —N$R^a$C(O)O$R^b$, —N$R^a$C(O)N$R^b R^c$, $C_1$-$C_6$ haloalkyl, $C_1$-$C_6$ haloalkoxy, —S(O)$_2$N$R^a R^b$, or —S(O)$_2 R^a$;
$R_7$ is —C(O)$R_8$, —C(O)O$R_8$, —C(O)N$R_8 R_9$, or —S(O)$_2 R_8$;
$R_8$ and $R_9$ are independently hydrogen, —$(CR^kR^l)_m$O$R^a$, $C_1$-$C_6$ alkyl, $C_1$-$C_6$ haloalkyl, $C_3$-$C_6$ cycloalkyl, heterocycloalkyl, aryl, or heteroaryl;
each $R_{10}$ is independently at each occurrence selected from the group consisting of $C_1$-$C_6$ alkyl, $C_1$-$C_6$ alkoxy, $C_1$-$C_6$ hydroxyalkyl, $C_1$-$C_6$ haloalkyl, $C_1$-$C_6$ haloalkoxy, —O$R^i$, —N$R^a R^i$, CN, oxo, —$(CR^kR^l)_n$S(O)$_2 R^i$, —$(CR^kR^l)_n$N$R^a$S(O)$_2 R^i$, —$(CR^kR^l)_n$S(O)$_2$N$R^a R^i$, —$(CR^kR^l)_n$C(O)O$R^a$, —$(CR^kR^l)_n$C(O)$R^i$, —$(CR^kR^l)_n$C(O)N$R^a R^i$, —$(CR^kR^l)_n R^i$, —$(CR^kR^l)_n$N$R^a$C(O)N$R^b$, —$(CR^kR^l)_n$N$R^a$C(O)O$R^b$, and oxo, wherein each alkyl is substituted with one or more $R_{11}$; or
two $R_{10}$ together when on adjacent carbons form an aryl ring optionally substituted with one or more $R_{11}$; or two $R_{10}$ together when on adjacent carbons form a heteroaryl ring optionally substituted with one or more $R_{11}$; or two $R_{10}$ together when on adjacent carbons form a heterocycloalkyl ring optionally substituted with one or more $R_{11}$;
each $R_{11}$ is independently at each occurrence selected from halogen, $C_1$-$C_6$ alkyl, $C_1$-$C_6$ alkoxy, $C_1$-$C_6$ haloalkyl, $C_1$-$C_6$ haloalkoxy, hydroxy, CN, $C_1$-$C_6$ hydroxyalkyl, —$(CR^kR^l)_m$NH$_2$, $C_1$-$C_6$ alkylamino, $C_1$-$C_6$ dialkylamino, —C(O)N$R^a R^b$, —C(O)O$R^a$, —C(O)$R^a$, —S(O)$_2 R^a$, —C(O)H, —N$R^a$C(O)O$R^a$, —N$R^a$C(O)$C_1$-$C_6$ alkyl, or oxo;
or two $R_{11}$ together can form a heterocycloalkyl ring;
$R^a$, $R^b$, and $R^c$ are each independently at each occurrence hydrogen, $C_1$-$C_6$ alkyl, —$C_1$-$C_4$ alkyl(aryl), or aryl, wherein the alkyl and aryl are optionally substituted with one or more $R_{10}$;
$R^d$ is $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, CN, —C(O)$C_1$-$C_6$ alkyl, $C_3$-$C_7$ cycloalkyl, aryl, heteroaryl, or heterocycloalkyl, wherein cycloalkyl, aryl, heteroaryl, and heterocycloalkyl are optionally substituted with one or more $R_{12}$;
$R^e$ is hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_1$-$C_6$ alkoxy, CN, $C_3$-$C_7$ cycloalkyl, aryl, heteroaryl, or heterocycloalkyl, wherein cycloalkyl, aryl, heteroaryl, and heterocycloalkyl are optionally substituted with one or more $R_{12}$;
$R^f$ is $C_3$-$C_7$ cycloalkyl, aryl, heteroaryl, or heterocycloalkyl, wherein cycloalkyl, aryl, heteroaryl and heterocycloalkyl are optionally substituted with one or more $R_{12}$;
$R^g$ is $C_1$-$C_6$ alkyl, $C_3$-$C_7$ cycloalkyl, —$C_1$-$C_4$ alkyl($C_3$-$C_7$ cycloalkyl), aryl, —$C_1$-$C_4$ alkyl(aryl), heteroaryl, —$C_1$-$C_4$alkyl(heteroaryl), heterocycloalkyl or —$C_1$-$C_4$ alkyl (heterocycloalkyl), wherein cycloalkyl, aryl, heteroaryl, and heterocycloalkyl are optionally substituted with one or more $R_{12}$;
$R^h$ is $C_3$-$C_7$ cycloalkyl, aryl, heteroaryl, or heterocycloalkyl, wherein cycloalkyl, aryl, heteroaryl, and heterocycloalkyl are optionally substituted with one or more $R_{10}$;
$R^i$ is hydrogen, $C_1$-$C_6$ alkyl, $C_1$-$C_6$ alkoxy, $C_1$-$C_6$ hydroxyalkyl, $C_1$-$C_6$ haloalkyl, —$(CH_2)_q$N(H)$C_1$-$C_6$ alkyl, —$(CH_2)_q$N($C_1$-$C_6$ alkyl)$_2$, —$(CR^kR^l)_m C_3$-$C_7$ cycloalkyl, —$(CR^kR^l)_m$aryl, —$(CR^kR^l)_m$heteroaryl, or —$(CR^kR^l)_m$heterocycloalkyl, wherein alkyl, cycloalkyl, aryl, heteroaryl, and heterocycloalkyl are optionally substituted with one or more $R^{11}$;
each $R_{12}$ is independently at each occurrence selected from $C_1$-$C_6$ alkyl, halogen, CN, $C_1$-$C_6$ alkoxy, $C_1$-$C_6$ haloalkyl, $C_1$-$C_6$ haloalkoxy, hydroxy, NO$_2$, —NH$_2$, CH$_2$NH$_2$, —$(CH_2)_q$N($C_1$-$C_6$ alkyl)$_2$, $C_1$-$C_6$ alkylamino, $C_1$-$C_6$ dialkylamino, —O$(CH_2)_q$N(H)$C_1$-$C_6$ alkyl, —O$(CH_2)_q$N($C_1$-$C_6$ alkyl)$_2$, aryl, heteroaryl, —NH-heteroaryl, —O-aryl, —S(O)$_p$—$C_1$-$C_6$ alkyl, —S(O)$_p$—N(H)$C_1$-$C_6$ alkyl, —S(O)$_p$—N($C_1$-$C_6$ alkyl)$_2$, —C(O)$C_1$-$C_6$ alkyl, —C(O)O$C_1$-$C_6$ alkyl, —NHC(O)($C_1$-$C_6$ alkyl), or oxo, wherein aryl and heteroaryl are optionally substituted with one or more substituents selected from $C_1$-$C_6$ alkyl, halogen, CN, $C_1$-$C_6$ alkoxy, hydroxy, NO$_2$, —NH$_2$, $C_1$-$C_6$ alkylamino, or $C_1$-$C_6$ dialkylamino; or
two $R_{12}$ together with the carbon to which they are attached can form a 4- to 6 membered heterospirocycle; or two $R_{12}$ together when on adjacent carbons form a $C_4$-$C_6$ cycloalkyl optionally substituted with one or more $R_{13}$; or two $R_{12}$ together when on adjacent carbons form an aryl optionally substituted with one or more $R_{13}$; or two $R_{12}$ together when on adjacent carbons form a heteroaryl optionally substituted with one or more $R_{13}$; or two $R_{12}$ together when on adjacent carbons form a heterocycloalkyl optionally substituted with one or more $R_{13}$; or $R_{12}$ with the carbon to which it is attached and the adjacent carbon form a $C_3$ cycloalkyl optionally substituted with one or more $R_{13}$;

each $R_{13}$ is independently at each occurrence selected from $C_1$-$C_6$ alkyl, halogen, CN, $C_1$-$C_6$ alkoxy, $C_1$-$C_6$ haloalkyl, $C_1$-$C_6$ haloalkoxy, hydroxy, $NO_2$, —$NH_2$, $CH_2NH_2$, —$(CH_2)_qN(C_1$-$C_6$ alkyl$)_2$, $C_1$-$C_6$ alkylamino, $C_1$-$C_6$ dialkylamino, —$O(CH_2)_qN(H)C_1$-$C_6$ alkyl, —$O(CH_2)_qN(C_1$-$C_6$ alkyl$)_2$, aryl, heteroaryl, —NH-heteroaryl, —O-aryl, —$S(O)_p$—$C_1$-$C_6$ alkyl, —$S(O)_p$—N(H)$C_1$-$C_6$ alkyl, —$S(O)_p$—N($C_1$-$C_6$ alkyl$)_2$, —C(O)$C_1$-$C_6$ alkyl, —NHC(O)($C_1$-$C_6$ alkyl), or oxo, wherein aryl and heteroaryl are optionally substituted with one or more substituents selected from the group consisting of $C_1$-$C_6$ alkyl, halogen, CN, $C_1$-$C_6$ alkoxy, hydroxy, $NO_2$, —$NH_2$, $C_1$-$C_6$ alkylamino, and $C_1$-$C_6$ dialkylamino;

$R^k$ and $R^l$ are each independently at each occurrence selected from H, $C_1$-$C_6$ alkyl, $C_1$-$C_6$ alkoxy, $C_1$-$C_6$ haloalkyl, or halogen;

each m, n, and p is independently at each occurrence 0, 1, or 2; and each q is independently at each occurrence 1, 2, 3 or 4;

provided that when m is 0, $R^d$ is not $C_1$-$C_6$ alkoxy, $C_1$-$C_6$ haloalkoxy, or CN.

2. The compound of claim 1, wherein $R_3$ and $R_6$ are independently selected from hydrogen or F.

3. The compound of claim 1, wherein X and Z are independently selected from N or CH.

4. The compound of claim 1, wherein Y is N or $CR_5$ and $R_5$ is hydrogen, halogen, nitro, —$NH_2$, CN, $C_1$-$C_3$ alkoxy, —C(O)$NR^aR^b$, —$NR^aS(O)_2R^b$, —$NR^aC(O)R^b$, —$NR^aC(O)OR^b$, or —$NR^aC(O)NR^bR^c$.

5. The compound of claim 1, wherein $R_4$ is hydrogen, $C_3$-$C_6$ cycloalkyl, $C_6$-$C_{10}$ aryl, heterocycloalkyl, heteroaryl, —$NR^aR^b$, —C(O)$R^h$, —$OR^h$, wherein the cycloalkyl, aryl, heterocycloalkyl, heteroaryl, and alkyl are optionally substituted with one or more $R_{10}$.

6. The compound of claim 1, wherein $R_1$ is methyl.

7. The compound of claim 1, wherein $R_4$ is selected from the group consisting of:

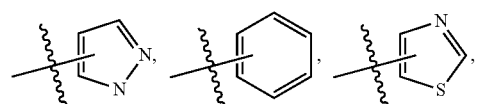

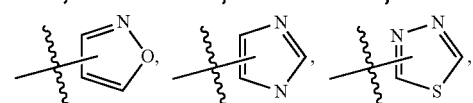

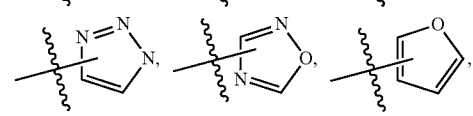

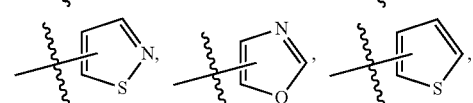

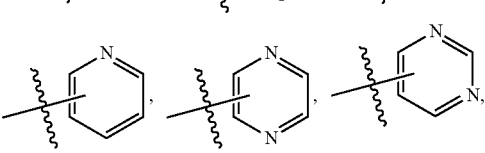

-continued

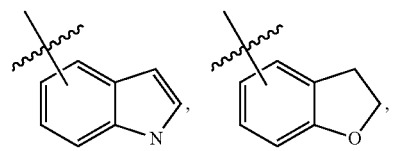

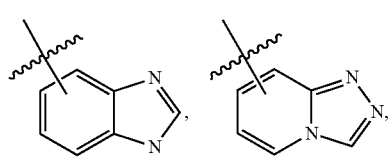

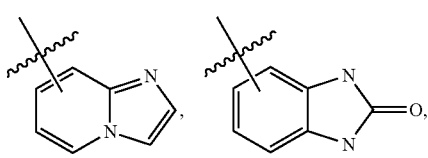

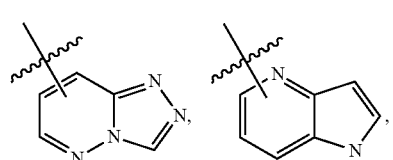

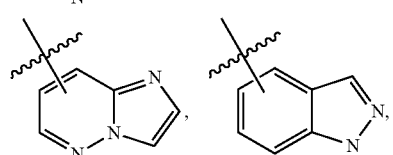

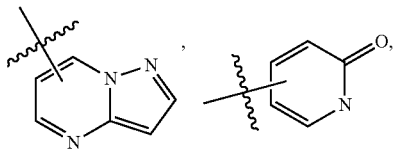

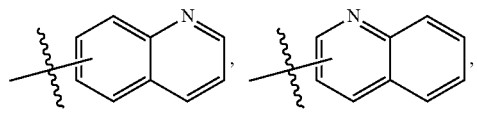

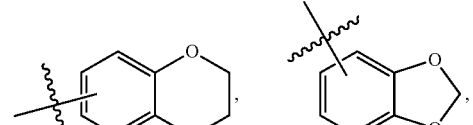

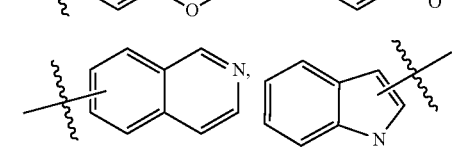

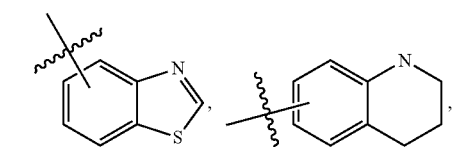

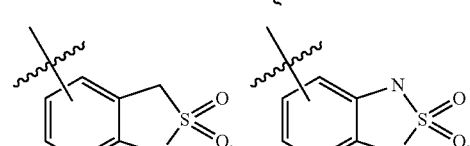

-continued

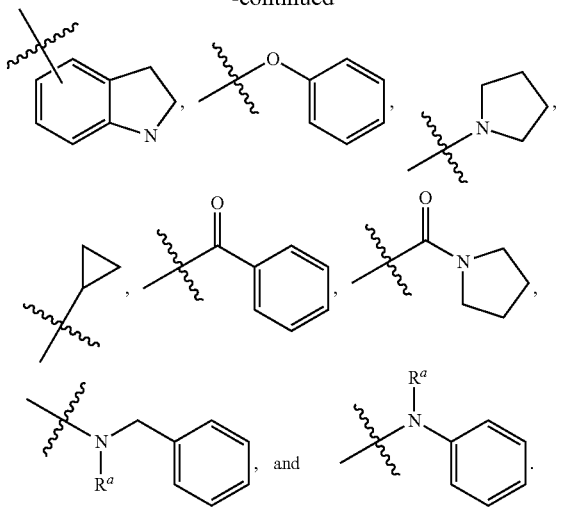

, and

8. The compound of claim 1, wherein $R_4$ is phenyl, pyridine, pyridazine, pyrimidine or pyrazole.

9. The compound of claim 1, wherein $R_7$ is —C(O)$R_8$, —C(O)O$R_8$, or —C(O)N$R_8R_9$.

10. The compound of claim 1, wherein $R_8$ is —CH$_3$, or -cyclopropyl.

11. The compound of claim 1, wherein $R_2$ is —C(O)(CH$_2$)$_n$O(CH$_2$)$_m$R$^d$, —C(O)(CH$_2$)$_n$R$^e$, —S(O)$_2$(CH$_2$)$_n$R$^f$, —(CH$_2$)$_n$R$^g$, —C(O)(CH$_2$)$_n$NR$^a$R$^g$.

12. The compound of claim 1, wherein $R_2$ is —C(O)O(CH$_2$)$_m$R$^d$ or —C(O)(CH$_2$)$_n$R$^e$.

13. The compound of claim 1, wherein R$^d$ and R$^e$ are independently cyclopropyl, cyclobutyl, iso-propyl, or methyl.

14. The compound of claim 1, wherein X is CH, Y is CH, and Z is CH.

15. The compound of claim 1, wherein X is CH, Y is CH, Z is CH, and $R_1$ is methyl.

16. The compound of claim 1, wherein X is CH, Y is CH, Z is CH, $R_1$ is methyl and $R_2$ is —C(O)O(CH$_2$)$_m$R$^d$ or —C(O)(CH$_2$)$_n$R$^e$.

17. The compound of claim 1, wherein X is CH, Y is CH, Z is CH, $R_1$ is methyl, $R_2$ is —C(O)O(CH$_2$)$_m$R$^d$ or —C(O)(CH$_2$)$_n$R$^e$, and $R_4$ is phenyl, pyridine, pyridazine, pyrimidine, or pyrazole.

18. The compound of claim 1, having Formula (II):

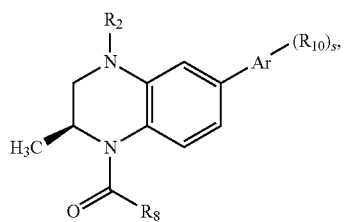

(II)

or a pharmaceutically acceptable salt, enantiomer hydrate, solvate, isomer, or tautomer thereof,
wherein:
Ar is $C_6$-$C_{10}$ aryl or heteroaryl;
$R_2$ is —C(O)(CR$^k$R$^l$)$_n$O(CR$^k$R$^l$)$_m$R$^d$, —C(O)(CR$^k$R$^l$)$_n$R$^e$, —S(O)$_2$(CR$^k$R$^l$)$_n$R$^f$, —(CR$^k$R$^l$)$_n$R$^g$, —C(O)(CR$^k$R$^l$)$_n$NR$^a$R$^g$ or —C(O)(CR$^k$R$^l$)$_n$S(CR$^k$R$^l$)$_m$R$^f$;

$R_8$ is —(CR$^k$R$^l$)$_m$OR$^a$, $C_1$-$C_6$ alkyl, or $C_3$-$C_6$ cycloalkyl;
each $R_{10}$ is independently at each occurrence selected from the group consisting of $C_1$-$C_6$ alkyl, $C_1$-$C_6$ alkoxy, $C_1$-$C_6$ hydroxyalkyl, $C_1$-$C_6$ haloalkyl, $C_1$-$C_6$ haloalkoxy, —OR$^i$, —NR$^a$R$^i$, CN, oxo, —(CR$^k$R$^l$)$_n$S(O)$_2$R$^i$, —(CR$^k$R$^l$)$_n$NR$^a$S(O)$_2$R$^i$, —(CR$^k$R$^l$)$_n$S(O)$_2$NR$^a$R$^i$, —(CR$^k$R$^l$)$_n$NR$^a$R$^i$S(O)$_2$NR$^a$R$^i$, —(CR$^k$R$^l$)$_n$C(O)OR$^a$, —(CR$^k$R$^l$)$_n$C(O)R$^i$, —(CR$^k$R$^l$)$_n$C(O)NR$^a$R$^i$, —(CR$^k$R$^l$)$_n$R$^i$, —(CR$^k$R$^l$)$_n$NR$^a$C(O)NR$^b$, and —(CR$^k$R$^l$)$_n$NR$^a$C(O)OR$^b$, wherein each alkyl is substituted with one or more $R_{11}$; or
two $R_{10}$ together when on adjacent carbons form an aryl ring optionally substituted with one or more $R_{11}$; or two $R_{10}$ together when on adjacent carbons form a heteroaryl ring optionally substituted with one or more $R_{11}$; or two $R_{10}$ together when on adjacent carbons form a heterocycloalkyl ring optionally substituted with one or more $R_{11}$;
each $R_{11}$ is independently at each occurrence selected from halogen, $C_1$-$C_6$ alkyl, $C_1$-$C_6$ alkoxy, $C_1$-$C_6$ haloalkyl, hydroxy, CN, $C_1$-$C_6$ hydroxyalkyl, —(CR$^k$R$^l$)$_m$NH$_2$, $C_1$-$C_6$ alkylamino, $C_1$-$C_6$ dialkylamino, —C(O)NR$^a$R$^b$, —C(O)OR$^a$, —C(O)R$^a$, —S(O)$_2$R$^a$, —C(O)H, —NR$^a$C(O)OR$^a$, —NR$^a$C(O)C$_1$-$C_6$ alkyl, or oxo;
or two $R_{11}$ together can form a heterocycloalkyl ring;
R$^a$ and R$^b$ are each independently at each occurrence hydrogen, $C_1$-$C_6$ alkyl, —$C_1$-$C_4$alkyl(aryl), or aryl, wherein the alkyl and aryl are optionally substituted with one or more $R_{10}$;
R$^d$ is $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, CN, —C(O)$C_1$-$C_6$ alkyl, $C_3$-$C_7$ cycloalkyl, aryl, heteroaryl, or heterocycloalkyl, wherein cycloalkyl, aryl, heteroaryl, and heterocycloalkyl are optionally substituted with one or more $R_{12}$;
R$^e$ is hydrogen, $C_1$-$C_6$ alkyl, $C_2$-$C_6$ alkenyl, $C_2$-$C_6$ alkynyl, $C_1$-$C_6$ haloalkyl, $C_1$-$C_6$ haloalkoxy, $C_1$-$C_6$ alkoxy, CN, $C_3$-$C_7$ cycloalkyl, aryl, heteroaryl, or heterocycloalkyl, wherein cycloalkyl, aryl, heteroaryl, and heterocycloalkyl are optionally substituted with one or more $R_{12}$;
R$^f$ is $C_3$-$C_7$ cycloalkyl, aryl, heteroaryl, or heterocycloalkyl, wherein cycloalkyl, aryl, heteroaryl, and heterocycloalkyl are optionally substituted with one or more $R_{12}$;
R$^g$ is $C_1$-$C_6$ alkyl, $C_3$-$C_7$ cycloalkyl, —$C_1$-$C_4$alkyl($C_3$-$C_7$ cycloalkyl), aryl, —$C_1$-$C_4$alkyl(aryl), heteroaryl, —$C_1$-$C_4$alkyl(heteroaryl), heterocycloalkyl or —$C_1$-$C_4$ alkyl (heterocycloalkyl), wherein cycloalkyl, aryl, heteroaryl, and heterocycloalkyl are optionally substituted with one or more $R_{12}$;
R$^i$ is hydrogen, $C_1$-$C_6$ alkyl, $C_1$-$C_6$ alkoxy, $C_1$-$C_6$ hydroxyalkyl, $C_1$-$C_6$ haloalkyl, —(CH$_2$)$_q$N(H)$C_1$-$C_6$ alkyl, —(CH$_2$)$_q$N($C_1$-$C_6$ alkyl)$_2$, —(CR$^k$R$^l$)$_m$$C_3$-$C_7$ cycloalkyl, —(CR$^k$R$^l$)$_m$aryl, —(CR$^k$R$^l$)$_m$heteroaryl, or —(CR$^k$R$^l$)$_m$heterocycloalkyl, wherein alkyl, cycloalkyl, aryl, heteroaryl, and heterocycloalkyl are optionally substituted with one or more $R^{11}$;
each $R_{12}$ is independently at each occurrence selected from $C_1$-$C_6$ alkyl, halogen, CN, $C_1$-$C_6$ alkoxy, $C_1$-$C_6$ haloalkyl, $C_1$-$C_6$ haloalkoxy, hydroxy, NO$_2$, —NH$_2$, CH$_2$NH$_2$, —(CH$_2$)$_q$N($C_1$-$C_6$ alkyl)$_2$, $C_1$-$C_6$ alkylamino, $C_1$-$C_6$ dialkylamino, —O(CH$_2$)$_q$N(H)$C_1$-$C_6$ alkyl, —O(CH$_2$)$_q$N($C_1$-$C_6$ alkyl)$_2$, aryl, heteroaryl, —NH-heteroaryl, —O-aryl, —S(O)$_p$—$C_1$-$C_6$ alkyl, —S(O)$_p$—N(H)$C_1$-$C_6$ alkyl, —S(O)$_p$—N($C_1$-$C_6$ alkyl)$_2$, —C(O)$C_1$-$C_6$ alkyl, —C(O)O$C_1$-$C_6$ alkyl, —NHC(O)($C_1$-$C_6$ alkyl), or oxo, wherein aryl and heteroaryl are optionally substituted with one or more substituents selected from $C_1$-$C_6$ alkyl, halogen, CN, $C_1$-$C_6$ alkoxy, hydroxy, $NO_2$, —$NH_2$, $C_1$-$C_6$ alkylamino, or $C_1$-$C_6$ dialkylamino; or two $R_{12}$ together with the carbon to which they are attached can form a 4- to 6 membered heterospirocycle; or two $R_{12}$ together when on adjacent carbons form a $C_4$-$C_6$ cycloalkyl optionally substituted with one or more $R_{13}$; or two $R_{12}$ together when on adjacent carbons form an aryl optionally substituted with one or more $R_{13}$; or two $R_{12}$ together when on adjacent carbons form a heteroaryl optionally substituted with one or more $R_{13}$; or two $R_{12}$ together when on adjacent carbons form a heterocycloalkyl optionally substituted with one or more $R_{13}$; or $R_{12}$ with the carbon to which it is attached and the adjacent carbon form a $C_3$ cycloalkyl optionally substituted with one or more $R_{13}$;

each $R_{13}$ is independently at each occurrence selected from $C_1$-$C_6$ alkyl, halogen, CN, $C_1$-$C_6$ alkoxy, $C_1$-$C_6$ haloalkyl, $C_1$-$C_6$ haloalkoxy, hydroxy, $NO_2$, —$NH_2$, $CH_2NH_2$, —$(CH_2)_qN(C_1$-$C_6$ alkyl$)_2$, $C_1$-$C_6$ alkylamino, $C_1$-$C_6$ dialkylamino, —$O(CH_2)_qN(H)C_1$-$C_6$ alkyl, —$O(CH_2)_qN(C_1$-$C_6$ alkyl$)_2$, aryl, heteroaryl, —NH-heteroaryl, —O-aryl, —$S(O)_p$—$C_1$-$C_6$ alkyl, —$S(O)_p$—$N(H)C_1$-$C_6$ alkyl, $S(O)_p$—$N(C_1$-$C_6$ alkyl$)_2$, —$C(O)C_1$-$C_6$ alkyl, —$NHC(O)(C_1$-$C_6$ alkyl), or oxo, wherein aryl and heteroaryl are optionally substituted with one or more substituents selected from the group consisting of $C_1$-$C_6$ alkyl, halogen, CN, $C_1$-$C_6$ alkoxy, hydroxy, $NO_2$, —$NH_2$, $C_1$-$C_6$ alkylamino, and $C_1$-$C_6$ dialkylamino;

$R^k$ and $R^l$ are each independently at each occurrence selected from H, $C_1$-$C_6$ alkyl, $C_1$-$C_6$ alkoxy, $C_1$-$C_6$ haloalkyl, or halogen;

each m, n, and p is independently at each occurrence 0, 1, or 2;

each q is independently at each occurrence 1, 2, 3 or 4; and s is 1, 2, 3, 4, or 5;

provided that when m is 0, $R^d$ is not $C_1$-$C_6$ alkoxy, $C_1$-$C_6$ haloalkoxy, or CN.

19. The compound of claim 1, having Formula (III)

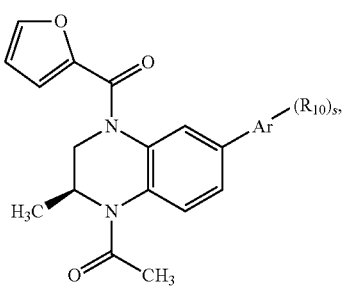

(III)

or a pharmaceutically acceptable salt, enantiomer hydrate, solvate, isomer, or tautomer thereof, wherein:

Ar is $C_6$-$C_{10}$ aryl or heteroaryl;

each $R_{10}$ is independently at each occurrence selected from the group consisting of $C_1$-$C_6$ alkyl, $C_1$-$C_6$ alkoxy, $C_1$-$C_6$ hydroxyalkyl, $C_1$-$C_6$ haloalkyl, $C_1$-$C_6$ haloalkoxy, —$OR^i$, —$NR^aR^i$, CN, oxo, —$(CR^kR^l)_nS(O)_2R^i$, —$(CR^kR^l)_nNR^aS(O)_2R^i$, —$(CR^kR^l)_nS(O)_2NR^aR^i$, —$(CR^kR^l)_nNR^aR^iS(O)_2NR^aR^i$, —$(CR^kR^l)_nC(O)OR^a$, —$(CR^kR^l)_nC(O)R^i$, —$(CR^kR^l)_nC(O)NR^aR^i$, —$(CR^kR^l)_nR^i$, —$(CR^kR^l)_nNR^aC(O)NR^b$, and —$(CR^kR^l)_nNR^aC(O)OR^b$, wherein each alkyl is substituted with one or more $R_{11}$; or two $R_{10}$ together when on adjacent carbons form an aryl ring optionally substituted with one or more $R_{11}$; or two $R_{10}$ together when on adjacent carbons a heteroaryl ring optionally substituted with one or more $R_{11}$; or two $R_{10}$ together when on adjacent carbons form a heterocycloalkyl ring optionally substituted with one or more $R_{11}$;

each $R_{11}$ is independently at each occurrence selected from halogen, $C_1$-$C_6$ alkyl, $C_1$-$C_6$ alkoxy, $C_1$-$C_6$ haloalkyl, hydroxy, CN, $C_1$-$C_6$ hydroxyalkyl, —$(CR^kR^l)_mNH_2$, $C_1$-$C_6$ alkylamino, $C_1$-$C_6$ dialkylamino, —$C(O)NR^aR^b$, —$C(O)OR^a$, —$C(O)R^a$, —$S(O)_2R^a$, —$C(O)H$, —$NR^aC(O)OR^a$, —$NR^aC(O)C_1$-$C_6$ alkyl, or oxo;

or two $R_{11}$ together can form a heterocycloalkyl ring;

$R^a$ and $R^b$ are each independently at each occurrence hydrogen, $C_1$-$C_6$ alkyl, —$C_1$-$C_4$alkyl(aryl), or aryl, wherein the alkyl and aryl are optionally substituted with one or more $R_{10}$;

$R^i$ is hydrogen, $C_1$-$C_6$ alkyl, $C_1$-$C_6$ alkoxy, $C_1$-$C_6$ hydroxyalkyl, $C_1$-$C_6$ haloalkyl, —$(CH_2)$—$N(H)C_1$-$C_6$ alkyl, —$(CH_2)_qN(C_1$-$C_6$ alkyl$)_2$, —$(CR^kR^l)_mC_3$-$C_7$ cycloalkyl, —$(CR^kR^l)_m$aryl, —$(CR^kR^l)_m$heteroaryl, or —$(CR^kR^l)_m$heterocycloalkyl, wherein alkyl, cycloalkyl, aryl, heteroaryl, and heterocycloalkyl are optionally substituted with one or more $R^{11}$;

$R^k$ and $R^l$ are each independently at each occurrence selected from H, $C_1$-$C_6$ alkyl, $C_1$-$C_6$ alkoxy, $C_1$-$C_6$ haloalkyl, or halogen;

each m and n is independently at each occurrence 0, 1, or 2;

each q is independently at each occurrence 1, 2, 3 or 4; and s is 1, 2, 3, 4, or 5.

20. The compound of claim 1, having Formula (IV)

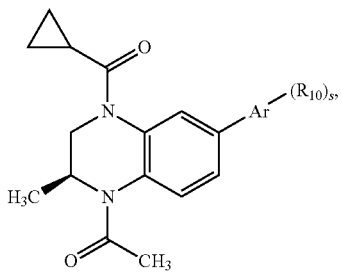

(IV)

or a pharmaceutically acceptable salt, enantiomer hydrate, solvate, isomer, or tautomer thereof, wherein:

Ar is $C_6$-$C_{10}$ aryl or heteroaryl;

each $R_{10}$ is independently at each occurrence selected from the group consisting of $C_1$-$C_6$ alkyl, $C_1$-$C_6$ alkoxy, $C_1$-$C_6$ hydroxyalkyl, $C_1$-$C_6$ haloalkyl, $C_1$-$C_6$ haloalkoxy, —$OR^i$, —$NR^aR^i$, CN, oxo, —$(CR^kR^l)_nS(O)_2R^i$, —$(CR^kR^l)_nNR^aS(O)_2R^i$, —$(CR^kR^l)_nS(O)_2NR^aR^i$, —$(CR^kR^l)_nNR^aR^iS(O)_2NR^aR^i$, —$(CR^kR^l)_nC(O)OR^a$, —$(CR^kR^l)_nC(O)R^i$, —$(CR^kR^l)_nC(O)NR^aR^i$, —$(CR^kR^l)_nR^i$, —$(CR^kR^l)_nNR^aC(O)NR^b$, and —$(CR^kR^l)_nNR^aC(O)OR^b$, wherein each alkyl is substituted with one or more $R_{11}$; or two $R_{10}$ together when on adjacent carbons form an aryl ring optionally substituted with one or more $R_{11}$; or two $R_{10}$ together when on adjacent carbons form a heteroaryl ring optionally substituted with one or more $R_{11}$; or two $R_{10}$ together when on adjacent carbons form a heterocycloalkyl ring optionally substituted with one or more $R_{11}$;

each $R_{11}$ is independently at each occurrence selected from halogen, $C_1$-$C_6$ alkyl, $C_1$-$C_6$ alkoxy, $C_1$-$C_6$ haloalkyl, hydroxy, CN, $C_1$-$C_6$ hydroxyalkyl, —$(CR^kR^l)_m NH_2$, $C_1$-$C_6$ alkylamino, $C_1$-$C_6$ dialkylamino, —$C(O)NR^aR^b$, —$C(O)OR^a$, —$C(O)R^a$, —$S(O)_2R^a$, —$C(O)H$, —$NR^aC(O)OR^a$, —$NR^aC(O)C_1$-$C_6$ alkyl, or oxo;

or two $R_{11}$ together can form a heterocycloalkyl ring;

$R^a$ and $R^b$ are each independently at each occurrence hydrogen, $C_1$-$C_6$ alkyl, —$C_1$-$C_4$ alkyl(aryl), or aryl, wherein the alkyl and aryl are optionally substituted with one to three $R_{10}$;

$R^i$ is hydrogen, $C_1$-$C_6$ alkyl, $C_1$-$C_6$ alkoxy, $C_1$-$C_6$ hydroxyalkyl, $C_1$-$C_6$ haloalkyl, —$(CH_2)_q N(H)C_1$-$C_6$ alkyl, —$(CH_2)_q N(C_1$-$C_6$ alkyl)$_2$, —$(CR^kR^l)_m C_3$-$C_7$ cycloalkyl, —$(CR^kR^l)_m$aryl, —$(CR^kR^l)_m$heteroaryl, or —$(CR^kR^l)_m$heterocycloalkyl, wherein alkyl, cycloalkyl, aryl, heteroaryl, and heterocycloalkyl are optionally substituted with one or more $R^{11}$;

$R^k$ and $R^l$ are each independently at each occurrence selected from H, $C_1$-$C_6$ alkyl, $C_1$-$C_6$ alkoxy, $C_1$-$C_6$ haloalkyl, or halogen;

each m and n is independently at each occurrence 0, 1, or 2;
each q is independently at each occurrence 1, 2, 3 or 4; and
s is 1, 2, 3, 4, or 5.

21. The compound of claim 1, having Formula (V):

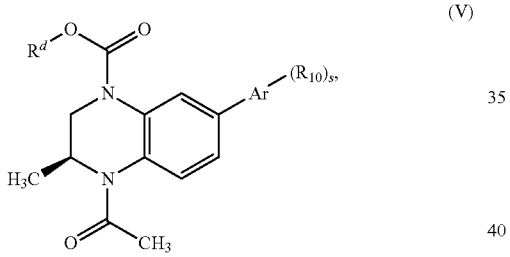

(V)

or a pharmaceutically acceptable salt, enantiomer hydrate, solvate, isomer, or tautomer thereof,
wherein:
Ar is $C_6$-$C_{10}$ aryl or heteroaryl;

each $R_{10}$ is independently at each occurrence selected from the group consisting of $C_1$-$C_6$ alkyl, $C_1$-$C_6$ alkoxy, $C_1$-$C_6$ hydroxyalkyl, $C_1$-$C_6$ haloalkyl, $C_1$-$C_6$ haloalkoxy, —$OR^i$, —$NR^aR^i$, CN, oxo, —$(CR^kR^l)_n S(O)_2R^i$, —$(CR^kR^l)_n NR^a S(O)_2 R^i$, —$(CR^kR^l)_n S(O)_2 NR^aR^i$, —$(CR^kR^l)_n NR^aR^i S(O)_2 NR^aR^i$, —$(CR^kR^l)_n C(O)OR^a$, —$(CR^kR^l)_n C(O)R^i$, —$(CR^kR^l)_n C(O)NR^aR^i$, —$(CR^kR^l)_n R^i$, —$(CR^kR^l)_n NR^aC(O)NR^b$, and —$(CR^kR^l)_n NR^aC(O)OR^b$, wherein each alkyl is substituted with one or more $R_{11}$; or two $R_{10}$ together when on adjacent carbons form an aryl ring optionally substituted with one or more $R_{11}$; or two $R_{10}$ together when on adjacent carbons form a heteroaryl ring optionally substituted with one or more $R_{11}$; or two $R_{10}$ together when on adjacent carbons form a heterocycloalkyl ring optionally substituted with one or more $R_{11}$;

each $R_{11}$ is independently at each occurrence selected from halogen, $C_1$-$C_6$ alkyl, $C_1$-$C_6$ alkoxy, $C_1$-$C_6$ haloalkyl, hydroxy, CN, $C_1$-$C_6$ hydroxyalkyl, —$(CR^kR^l)_m NH_2$, $C_1$-$C_6$ alkylamino, $C_1$-$C_6$ dialkylamino, —$C(O)NR^aR^b$, —$C(O)OR^a$, —$C(O)R^a$, —$S(O)_2R^a$, —$C(O)H$, —$NR^aC(O)OR^a$, —$NR^aC(O)C_1$-$C_6$ alkyl, or oxo;

or two $R_{11}$ together can form a heterocycloalkyl ring;

$R^a$ and $R^b$ are each independently at each occurrence hydrogen, $C_1$-$C_6$ alkyl, —$C_1$-$C_4$ alkyl(aryl), or aryl, wherein the alkyl and aryl are optionally substituted with one or more $R_{10}$;

$R^d$ is $C_1$-$C_6$ alkyl, $C_1$-$C_6$ haloalkyl, $C_3$-$C_7$ cycloalkyl, aryl, heteroaryl, or heterocycloalkyl, wherein cycloalkyl, aryl, heteroaryl, and heterocycloalkyl are optionally substituted with one or more $R_{12}$;

$R^i$ is hydrogen, $C_1$-$C_6$ alkyl, $C_1$-$C_6$ alkoxy, $C_1$-$C_6$ hydroxyalkyl, $C_1$-$C_6$ haloalkyl, —$(CH_2)_q N(H)C_1$-$C_6$ alkyl, —$(CH_2)_q N(C_1$-$C_6$ alkyl)$_2$, —$(CR^kR^l)_m C_3$-$C_7$ cycloalkyl, —$(CR^kR^l)_m$aryl, —$(CR^kR^l)_m$heteroaryl, or —$(CR^kR^l)_m$heterocycloalkyl, wherein alkyl, cycloalkyl, aryl, heteroaryl, and heterocycloalkyl are optionally substituted with one or more $R^{11}$;

each $R_{12}$ is independently at each occurrence selected from $C_1$-$C_6$ alkyl, halogen, CN, $C_1$-$C_6$ alkoxy, $C_1$-$C_6$ haloalkyl, $C_1$-$C_6$ haloalkoxy, hydroxy, $NO_2$, —$NH_2$, $CH_2NH_2$, —$(CH_2)_q N(C_1$-$C_6$ alkyl)$_2$, $C_1$-$C_6$ alkylamino, $C_1$-$C_6$ dialkylamino, —$O(CH_2)_q N(H)C_1$-$C_6$ alkyl, —$O(CH_2)_q N(C_1$-$C_6$ alkyl)$_2$, aryl, heteroaryl, —NH-heteroaryl, —O-aryl, —$S(O)_p$—$C_1$-$C_6$ alkyl, —$S(O)_p$—$N(H)C_1$-$C_6$ alkyl, —$S(O)_p$—$N(C_1$-$C_6$ alkyl)$_2$, —$C(O)C_1$-$C_6$ alkyl, —$C(O)OC_1$-$C_6$ alkyl, —$NHC(O)(C_1$-$C_6$ alkyl), or oxo, wherein aryl and heteroaryl are optionally substituted with one or more substituents selected from $C_1$-$C_6$ alkyl, halogen, CN, $C_1$-$C_6$ alkoxy, hydroxy, $NO_2$, —$NH_2$, $C_1$-$C_6$ alkylamino, or $C_1$-$C_6$ dialkylamino; or two $R_{12}$ together with the carbon to which they are attached may form a 4- to 6 membered heterospirocycle; or two $R_{12}$ together when on adjacent carbons form a $C_4$-$C_6$ cycloalkyl optionally substituted with one or more $R_{13}$; or two $R_{12}$ together when on adjacent carbons form an aryl optionally substituted with one or more $R_{13}$; or two $R_{12}$ together when on adjacent carbons form a heteroaryl optionally substituted with one or more $R_{13}$; or two $R_{12}$ together when on adjacent carbons form a heterocycloalkyl optionally substituted with one or more $R_{13}$; or $R_{12}$ with the carbon to which it is attached and the adjacent carbon form a $C_3$ cycloalkyl optionally substituted with one or more $R_{13}$;

each $R_{13}$ is independently at each occurrence selected from $C_1$-$C_6$ alkyl, halogen, CN, $C_1$-$C_6$ alkoxy, $C_1$-$C_6$ haloalkyl, $C_1$-$C_6$ haloalkoxy, hydroxy, $NO_2$, —$NH_2$, $CH_2NH_2$, —$(CH_2)_q N(C_1$-$C_6$ alkyl)$_2$, $C_1$-$C_6$ alkylamino, $C_1$-$C_6$ dialkylamino, —$O(CH_2)_q N(H)C_1$-$C_6$ alkyl, —$O(CH_2)_q N(C_1$-$C_6$ alkyl)$_2$, aryl, heteroaryl, —NH-heteroaryl, —O-aryl, —$S(O)_p$—$C_1$-$C_6$ alkyl, —$S(O)_p$—$N(H)C_1$-$C_6$ alkyl, —$S(O)_p$—$N(C_1$-$C_6$ alkyl)$_2$, —$C(O)C_1$-$C_6$ alkyl, —$NHC(O)(C_1$-$C_6$ alkyl), or oxo, wherein aryl and heteroaryl are optionally substituted with one or more substituents selected from the group consisting of $C_1$-$C_6$ alkyl, halogen, CN, $C_1$-$C_6$ alkoxy, hydroxy, $NO_2$, —$NH_2$, $C_1$-$C_6$ alkylamino, and $C_1$-$C_6$ dialkylamino;

$R^k$ and $R^l$ are each independently at each occurrence selected from H, $C_1$-$C_6$ alkyl, $C_1$-$C_6$ alkoxy, $C_1$-$C_6$ haloalkyl, or halogen;

each m, n, and p is independently at each occurrence 0, 1, or 2;
each q is independently at each occurrence 1, 2, 3 or 4; and
s is 1, 2, 3, 4, or 5;

provided that when m is 0, $R^d$ is not $C_1$-$C_6$ alkoxy, $C_1$-$C_6$ haloalkoxy, or CN.

22. The compound of claim 1, having Formula (VI):

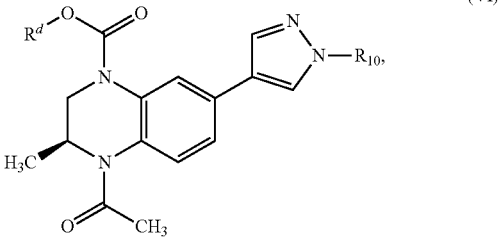

(VI)

or a pharmaceutically acceptable salt, enantiomer hydrate, solvate, isomer, or tautomer thereof,
wherein:
$R_{10}$ is independently selected from the group consisting of $C_1$-$C_6$ alkyl, $C_1$-$C_6$ alkoxy, $C_1$-$C_6$ hydroxyalkyl, $C_1$-$C_6$ haloalkyl, $C_1$-$C_6$ haloalkoxy, CN, oxo, —$(CR^kR^i)_nS(O)_2R^i$, —$(CR^kR^i)_nNR^aS(O)_2R^i$, —$(CR^kR^i)_nS(O)_2NR^aR^i$, —$(CR^kR^i)_nNR^aR^iS(O)_2NR^aR^i$, —$(CR^kR^i)_nC(O)OR^a$, —$(CR^kR^i)_nC(O)R^i$, —$(CR^kR^i)_nC(O)NR^aR^i$, —$(CR^kR^i)_n R^i$, —$(CR^kR^i)_nNR^aC(O)NR^b$, and —$(CR^kR^i)_nNR^aC(O)OR^b$, wherein each alkyl is substituted with one or more $R_{11}$; or
two $R_{10}$ together when on adjacent carbons form an aryl ring optionally substituted with one or more $R_{11}$; or two $R_{10}$ together when on adjacent carbons form a heteroaryl ring optionally substituted with one or more $R_{11}$; or two $R_{10}$ together when on adjacent carbons form a heterocycloalkyl ring optionally substituted with one or more $R_{11}$;
each $R_{11}$ is independently at each occurrence selected from halogen, $C_1$-$C_6$ alkyl, $C_1$-$C_6$ alkoxy, $C_1$-$C_6$ haloalkyl, hydroxy, CN, $C_1$-$C_6$ hydroxyalkyl, —$(CR^kR^i)_mNH_2$, $C_1$-$C_6$ alkylamino, $C_1$-$C_6$ dialkylamino, —$C(O)NR^aR^b$, —$C(O)OR^a$, —$C(O)R^a$, —$S(O)_2R^a$, —$C(O)H$, —$NR^aC(O)OR^a$, —$NR^aC(O)C_1$-$C_6$ alkyl, or oxo;
or two $R_{11}$ together can form a heterocycloalkyl ring;
$R^a$ and $R^b$ are each independently hydrogen, $C_1$-$C_6$ alkyl, —$C_1$-$C_4$ alkyl(aryl), or aryl, wherein the alkyl and aryl are optionally substituted with one or more $R_{10}$;
$R^d$ is $C_1$-$C_6$ alkyl, $C_1$-$C_6$ haloalkyl, $C_3$-$C_7$ cycloalkyl, aryl, heteroaryl, or heterocycloalkyl, wherein cycloalkyl, aryl, heteroaryl, and heterocycloalkyl are optionally substituted with one or more $R_{12}$;
$R^i$ is hydrogen, $C_1$-$C_6$ alkyl, $C_1$-$C_6$ alkoxy, $C_1$-$C_6$ hydroxyalkyl, $C_1$-$C_6$ haloalkyl, —$(CH_2)_qN(H)C_1$-$C_6$ alkyl, —$(CH_2)_qN(C_1$-$C_6$ alkyl)$_2$, —$(CR^kR^i)_mC_3$-$C_7$ cycloalkyl, —$(CR^kR^i)_m$aryl, —$(CR^kR^i)_m$heteroaryl, or —$(CR^kR^i)_m$heterocycloalkyl, wherein alkyl, cycloalkyl, aryl, heteroaryl, and heterocycloalkyl are optionally substituted with one or more $R^{11}$;
each $R_{12}$ is independently at each occurrence selected from $C_1$-$C_6$ alkyl, halogen, CN, $C_1$-$C_6$ alkoxy, $C_1$-$C_6$ haloalkyl, $C_1$-$C_6$ haloalkoxy, hydroxy, $NO_2$, —$NH_2$, $CH_2NH_2$, —$(CH_2)_qN(C_1$-$C_6$ alkyl)$_2$, $C_1$-$C_6$ alkylamino, $C_1$-$C_6$ dialkylamino, —$O(CH_2)_qN(H)C_1$-$C_6$ alkyl, —$O(CH_2)_qN(C_1$-$C_6$ alkyl)$_2$, aryl, heteroaryl, —NH-heteroaryl, —O-aryl, —$S(O)_p$—$C_1$-$C_6$ alkyl, —$S(O)_p$—$N(H)C_1$-$C_6$ alkyl, —$S(O)_p$—$N(C_1$-$C_6$ alkyl)$_2$, —$C(O)C_1$-$C_6$ alkyl, —$C(O)OC_1$-$C_6$ alkyl, —NHC(O)($C_1$-$C_6$ alkyl), or oxo, wherein aryl and heteroaryl are optionally substituted with one or more substituents selected from $C_1$-$C_6$ alkyl, halogen, CN, $C_1$-$C_6$ alkoxy, hydroxy, $NO_2$, —$NH_2$, $C_1$-$C_6$ alkylamino, or $C_1$-$C_6$ dialkylamino; or
two $R_{12}$ together with the carbon to which they are attached may form a 4- to 6 membered heterospirocycle; or two $R_{12}$ together when on adjacent carbons form a $C_4$-$C_6$ cycloalkyl optionally substituted with one or more $R_{13}$; or two $R_{12}$ together when on adjacent carbons form an aryl optionally substituted with one or more $R_{13}$; or two $R_{12}$ together when on adjacent carbons form a heteroaryl optionally substituted with one or more $R_{13}$; or two $R_{12}$ together when on adjacent carbons form a heterocycloalkyl optionally substituted with one or more $R_{13}$; or $R_{12}$ with the carbon to which it is attached and the adjacent carbon form a $C_3$ cycloalkyl optionally substituted with one or more $R_{13}$;
each $R_{13}$ is independently at each occurrence selected from $C_1$-$C_6$ alkyl, halogen, CN, $C_1$-$C_6$ alkoxy, $C_1$-$C_6$ haloalkyl, $C_1$-$C_6$ haloalkoxy, hydroxy, $NO_2$, —$NH_2$, $CH_2NH_2$, —$(CH_2)_qN(C_1$-$C_6$ alkyl)$_2$, $C_1$-$C_6$ alkylamino, $C_1$-$C_6$ dialkylamino, —$O(CH_2)_qN(H)C_1$-$C_6$ alkyl, —$O(CH_2)_qN(C_1$-$C_6$ alkyl)$_2$, aryl, heteroaryl, —NH-heteroaryl, —O-aryl, —$S(O)_p$—$C_1$-$C_6$ alkyl, —$S(O)_p$—$N(H)C_1$-$C_6$ alkyl, —$S(O)_p$—$N(C_1$-$C_6$ alkyl)$_2$, —$C(O)C_1$-$C_6$ alkyl, —NHC(O)($C_1$-$C_6$ alkyl), or oxo, wherein aryl and heteroaryl are optionally substituted with one or more substituents selected from consisting of $C_1$-$C_6$ alkyl, halogen, CN, $C_1$-$C_6$ alkoxy, hydroxy, $NO_2$, —$NH_2$, $C_1$-$C_6$ alkylamino, and $C_1$-$C_6$ dialkylamino;
$R^k$ and $R^l$ are each independently at each occurrence selected from H, $C_1$-$C_6$ alkyl, $C_1$-$C_6$ alkoxy, $C_1$-$C_6$ haloalkyl, or halogen;
each m, n, and p is independently at each occurrence 0, 1, or 2; and
each q is independently at each occurrence 1, 2, 3 or 4;
provided that when m is 0, $R^d$ is not $C_1$-$C_6$ alkoxy, $C_1$-$C_6$ haloalkoxy, or CN.

23. A compound selected from the group consisting of:
3,3-difluorocyclobutyl (3S)-4-acetyl-7-[1-(1,1-dioxo-1λ⁶-thietan-3-yl)-1H-pyrazol-4-yl]-3-methyl-1,2,3,4-tetrahydroquinoxaline-1-carboxylate;
4,4-difluorocyclohexyl (3S)-4-acetyl-3-methyl-7-[1-(oxan-4-yl)-1H-pyrazol-4-yl]-1,2,3,4-tetrahydroquinoxaline-1-carboxylate;
2-methoxyphenyl (3S)-4-acetyl-3-methyl-7-[1-(oxetan-3-yl)-1H-pyrazol-4-yl]-1,2,3,4-tetrahydroquinoxaline-1-carboxylate;
3,3-difluorocyclobutyl (3S)-4-acetyl-3-methyl-7-[1-(oxan-4-yl)-1H-pyrazol-4-yl]-1,2,3,4-tetrahydroquinoxaline-1-carboxylate;
3,3-difluorocyclobutyl (3S)-4-acetyl-7-(4-methanesulfonylphenyl)-3-methyl-1,2,3,4-tetrahydroquinoxaline-1-carboxylate;
1-[(2S)-4-cyclopropanecarbonyl-6-(1-cyclopropyl-1H-pyrazol-4-yl)-2-methyl-1,2,3,4-tetrahydroquinoxalin-1-yl]ethan-1-one;
ethyl (3S)-4-acetyl-3-methyl-7-[1-(oxetan-3-yl)-1H-pyrazol-4-yl]-1,2,3,4-tetrahydroquinoxaline-1-carboxylate;
1-[(2S)-4-cyclopropanecarbonyl-2-methyl-6-[1-(oxetan-3-yl)-1H-pyrazol-4-yl]-1,2,3,4-tetrahydroquinoxalin-1-yl]ethan-1-one;
1-[(2S)-4-cyclobutanecarbonyl-2-methyl-6-[1-(oxetan-3-yl)-1H-pyrazol-4-yl]-1,2,3,4-tetrahydroquinoxalin-1-yl]ethan-1-one;

propan-2-yl (3S)-4-acetyl-7-[1-(2-hydroxyethyl)-1H-pyrazol-4-yl]-3-methyl-1,2,3,4-tetrahydroquinoxaline-1-carboxylate;
1-[(2S)-4-(furan-2-carbonyl)-2-methyl-6-(1H-pyrazol-4-yl)-1,2,3,4-tetrahydroquinoxalin-1-yl]ethan-1-one;
1-[(2S)-4-(furan-2-carbonyl)-2-methyl-6-(1H-pyrazol-3-yl)-1,2,3,4-tetrahydroquinoxalin-1-yl]ethan-1-one;
1-[(2S)-4-(furan-2-carbonyl)-2-methyl-6-(2-methyl-1,3-thiazol-5-yl)-1,2,3,4-tetrahydroquinoxalin-1-yl]ethan-1-one;
phenyl (3S)-4-acetyl-3-methyl-7-(1H-pyrazol-4-yl)-1,2,3,4-tetrahydroquinoxaline-1-carboxylate;
propan-2-yl (3S)-4-acetyl-7-[1-(2-methoxyethyl)-1H-pyrazol-4-yl]-3-methyl-1,2,3,4-tetrahydroquinoxaline-1-carboxylate;
1-[(2S)-4-(furan-2-carbonyl)-6-[1-(2-methoxyethyl)-1H-pyrazol-4-yl]-2-methyl-1,2,3,4-tetrahydroquinoxalin-1-yl]ethan-1-one;
ethyl (3S)-4-acetyl-3-methyl-7-(1H-pyrazol-4-yl)-1,2,3,4-tetrahydroquinoxaline-1-carboxylate;
cyclopentyl (3S)-4-acetyl-3-methyl-7-(1H-pyrazol-4-yl)-1,2,3,4-tetrahydroquinoxaline-1-carboxylate;
ethyl (3S)-4-acetyl-7-(1-cyclopropyl-1H-pyrazol-4-yl)-3-methyl-1,2,3,4-tetrahydroquinoxaline-1-carboxylate;
propan-2-yl (3S)-4-acetyl-7-(1-cyclopropyl-1H-pyrazol-4-yl)-3-methyl-1,2,3,4-tetrahydroquinoxaline-1-carboxylate;
cyclopentyl (3S)-4-acetyl-7-(1-cyclopropyl-1H-pyrazol-4-yl)-3-methyl-1,2,3,4-tetrahydroquinoxaline-1-carboxylate;
propan-2-yl (3S)-4-acetyl-7-(1-cyclobutyl-1H-pyrazol-4-yl)-3-methyl-1,2,3,4-tetrahydroquinoxaline-1-carboxylate;
cyclopentyl (3S)-4-acetyl-7-(1-cyclobutyl-1H-pyrazol-4-yl)-3-methyl-1,2,3,4-tetrahydroquinoxaline-1-carboxylate;
3,3-difluorocyclobutyl (3S)-4-acetyl-7-(1-cyclopropyl-1H-pyrazol-4-yl)-3-methyl-1,2,3,4-tetrahydroquinoxaline-1-carboxylate;
3,3-difluorocyclobutyl (3S)-4-acetyl-7-[1-(2-hydroxyethyl)-1H-pyrazol-4-yl]-3-methyl-1,2,3,4-tetrahydroquinoxaline-1-carboxylate;
3,3-difluorocyclobutyl (3S)-4-acetyl-7-[1-(2-hydroxy-2-methylpropyl)-1H-pyrazol-4-yl]-3-methyl-1,2,3,4-tetrahydroquinoxaline-1-carboxylate;
3,3-difluorocyclobutyl (3S)-4-acetyl-7-[4-(1,1-dioxo-1$\lambda^6$,2-thiazolidin-2-yl)phenyl]-3-methyl-1,2,3,4-tetrahydroquinoxaline-1-carboxylate;
3,3-difluorocyclobutyl (3S)-4-acetyl-7-(4-methanesulfonamidophenyl)-3-methyl-1,2,3,4-tetrahydroquinoxaline-1-carboxylate;
4,4-difluorocyclohexyl (3S)-4-acetyl-7-(4-methanesulfonamidophenyl)-3-methyl-1,2,3,4-tetrahydroquinoxaline-1-carboxylate;
4,4-difluorocyclohexyl (3S)-4-acetyl-7-(4-methanesulfonylphenyl)-3-methyl-1,2,3,4-tetrahydroquinoxaline-1-carboxylate;
4,4-difluorocyclohexyl (3S)-4-acetyl-7-(1-cyclopropyl-1H-pyrazol-4-yl)-3-methyl-1,2,3,4-tetrahydroquinoxaline-1-carboxylate;
4,4-difluorocyclohexyl (3S)-4-acetyl-7-[1-(2-hydroxyethyl)-1H-pyrazol-4-yl]-3-methyl-1,2,3,4-tetrahydroquinoxaline-1-carboxylate;
4,4-difluorocyclohexyl (3S)-4-acetyl-7-[1-(2-hydroxy-2-methylpropyl)-1H-pyrazol-4-yl]-3-methyl-1,2,3,4-tetrahydroquinoxaline-1-carboxylate;
4,4-difluorocyclohexyl (3S)-4-acetyl-7-[4-(1,1-dioxo-1$\lambda^6$,2-thiazolidin-2-yl)phenyl]-3-methyl-1,2,3,4-tetrahydroquinoxaline-1-carboxylate;
oxan-4-yl (3S)-4-acetyl-7-[1-(1,1-dioxo-1$\lambda^6$-thietan-3-yl)-1H-pyrazol-4-yl]-3-methyl-1,2,3,4-tetrahydroquinoxaline-1-carboxylate;
oxan-4-yl (3S)-4-acetyl-3-methyl-7-[1-(oxan-4-yl)-1H-pyrazol-4-yl]-1,2,3,4-tetrahydroquinoxaline-1-carboxylate;
cyclobutyl (3S)-4-acetyl-3-methyl-7-[1-(oxan-4-yl)-1H-pyrazol-4-yl]-1,2,3,4-tetrahydroquinoxaline-1-carboxylate;
4-cyclopentyl 1-methyl (2S)-6-(1-cyclopropyl-1H-pyrazol-4-yl)-2-methyl-1,2,3,4-tetrahydroquinoxaline-1,4-dicarboxylate;
cyclopentyl (3S)-4-cyclopropanecarbonyl-7-(1-cyclopropyl-1H-pyrazol-4-yl)-3-methyl-1,2,3,4-tetrahydroquinoxaline-1-carboxylate;
methyl (2S)-4-cyclopropanecarbonyl-6-(1-cyclopropyl-1H-pyrazol-4-yl)-2-methyl-1,2,3,4-tetrahydroquinoxaline-1-carboxylate;
1-methyl 4-propan-2-yl (2S)-6-(1-cyclopropyl-1H-pyrazol-4-yl)-2-methyl-1,2,3,4-tetrahydroquinoxaline-1,4-dicarboxylate;
1-[(2S)-4-(1,3-benzoxazol-2-yl)-6-(1-cyclopropyl-1H-pyrazol-4-yl)-2-methyl-1,2,3,4-tetrahydroquinoxalin-1-yl]ethan-1-one;
1-[(2S)-6-(4-methanesulfonylphenyl)-2-methyl-4-(pyrimidin-2-yl)-1,2,3,4-tetrahydroquinoxalin-1-yl]ethan-1-one;
1-[(2S)-4-(1,3-benzoxazol-2-yl)-6-(4-methanesulfonylphenyl)-2-methyl-1,2,3,4-tetrahydroquinoxalin-1-yl]ethan-1-one;
1-[(2S)-6-(4-methanesulfonylphenyl)-2-methyl-4-(pyridin-2-yl)-1,2,3,4-tetrahydroquinoxalin-1-yl]ethan-1-one;
1-[(2S)-6-(4-methanesulfonylphenyl)-2-methyl-4-(quinazolin-2-yl)-1,2,3,4-tetrahydroquinoxalin-1-yl]ethan-1-one;
1-[(2S)-6-(4-methanesulfonylphenyl)-2-methyl-4-(4-phenylpyrimidin-2-yl)-1,2,3,4-tetrahydroquinoxalin-1-yl]ethan-1-one;
1-[(2S)-6-(4-methanesulfonylphenyl)-2-methyl-4-(5-phenylpyrimidin-2-yl)-1,2,3,4-tetrahydroquinoxalin-1-yl]ethan-1-one;
1-[(2S)-6-(1-cyclopropyl-1H-pyrazol-4-yl)-2-methyl-4-(quinazolin-2-yl)-1,2,3,4-tetrahydroquinoxalin-1-yl]ethan-1-one;
1-[(2S)-6-(1-cyclopropyl-1H-pyrazol-4-yl)-2-methyl-4-(1-methyl-1H-indazol-3-yl)-1,2,3,4-tetrahydroquinoxalin-1-yl]ethan-1-one;
1-[(2S)-2-methyl-4-(1-methyl-1H-indazol-3-yl)-6-[1-(oxetan-3-yl)-1H-pyrazol-4-yl]-1,2,3,4-tetrahydroquinoxalin-1-yl]ethan-1-one;
1-[(2S)-6-(1-cyclopropyl-1H-pyrazol-4-yl)-4-(6-fluoro-1-methyl-1H-indazol-3-yl)-2-methyl-1,2,3,4-tetrahydroquinoxalin-1-yl]ethan-1-one;
1-[(2S)-6-(1-cyclopropyl-1H-pyrazol-4-yl)-4-(5-fluoro-1-methyl-1H-indazol-3-yl)-2-methyl-1,2,3,4-tetrahydroquinoxalin-1-yl]ethan-1-one;
1-[(2S)-4-(1,3-benzoxazol-2-yl)-6-[1-(1,3-benzoxazol-2-yl)-1H-pyrazol-4-yl]-2-methyl-1,2,3,4-tetrahydroquinoxalin-1-yl]ethan-1-one;
1-[(3S)-1-(furan-2-carbonyl)-7-(4-methanesulfonylphenyl)-3-methyl-1H,2H,3H,4H-pyrido[3,4-b]pyrazin-4-yl]ethan-1-one;

propan-2-yl (3S)-4-acetyl-7-(4-methanesulfonylphenyl)-3-methyl-1H,2H,3H,4H-pyrido[3,4-b]pyrazine-1-carboxylate;
oxetan-3-yl (3S)-4-acetyl-3-methyl-7-[1-(oxetan-3-yl)-1H-pyrazol-4-yl]-1,2,3,4-tetrahydroquinoxaline-1-carboxylate;
cyclobutylmethyl (3S)-4-acetyl-3- methyl-7-[1- (oxetan-3-yl)-1H-pyrazol-4-yl]-1,2,3,4-tetrahydroquinoxaline-1-carboxylate;
(3-methyloxetan-3-yl)methyl (3S)-4-acetyl-3-methyl-7-[1-(oxetan-3-yl)-1H-pyrazol-4-yl]-1,2,3,4-tetrahydroquinoxaline-1-carboxylate;
2,2-dichloroethyl (3S)-4-acetyl-3-methyl-7-[1-(oxetan-3-yl)-1H-pyrazol-4-yl]-1,2,3,4-tetrahydroquinoxaline-1-carboxylate;
(3-ethyl oxetan-3-yl)methyl (3S)-4-acetyl-3-methyl-7-[1-(oxetan-3-yl)-1H-pyrazol-4-yl]-1,2,3,4-tetrahydroquinoxaline-1-carboxylate;
oxetan-3-ylmethyl (3S)-4-acetyl-3-methyl-7-[1-(oxetan-3-yl)-1H-pyrazol-4-yl]-1,2,3,4-tetrahydroquinoxaline-1-carboxylate;
3,3-difluorocyclobutyl (3S)-4-acetyl-3-methyl-7-[1-(oxetan-3-yl)-1H-pyrazol-4-yl]-1,2,3,4-tetrahydroquinoxaline-1-carboxylate;
(3-fluorooxetan-3-yl)methyl (3S)-4-acetyl-3-methyl-7-[1-(oxetan-3-yl)-1H-pyrazol-4-yl]-1,2,3,4-tetrahydroquinoxaline-1-carboxylate;
2-(oxetan-3-yl)ethyl (3S)-4-acetyl-3-methyl-7-[1-(oxetan-3-yl)-1H-pyrazol-4-yl]-1,2,3,4-trahydroquinoxaline-1-carboxylate;
2,2-difluoropropyl (3S)-4-acetyl-3-methyl -7-[1-(oxetan-3-yl)-1H-pyrazol-4-yl]-1,2,3,4-tetrahydroquinoxaline-1-carboxylate;
3,3,3-trifluoropropyl (3S)-4-acetyl-3-methyl-7-[1-(oxetan-3-yl)-1H-pyrazol-4-yl]-1,2,3,4-tetrahydroquinoxaline-1-carboxylate;
2-oxaspiro[3.3]heptan-6-yl (3S)-4-acetyl-3-methyl-7-[1-(oxetan-3-yl)-1H-pyrazol-4-yl]-1,2,3,4-tetrahydroquinoxaline-1-carboxylate;
2,2,2-trifluoroethyl (3S)-4-acetyl-3-methyl-7-[1-(oxetan-3-yl)-1H-pyrazol-4-yl]-1,2,3,4-tetrahydroquinoxaline-1-carboxylate;
1,3-difluoropropan-2-yl (3S)-4-acetyl-3-methyl-7-[1-(oxetan-3-yl)-1H-pyrazol-4-yl]-1,2,3,4-tetrahydroquinoxaline-1-carboxylate;
(2,2-dimethylcyclopropyl)methyl (3S)-4-acetyl-3-methyl-7-[1-(oxetan-3-yl)-1H-pyrazol-4-yl]-1,2,3,4-tetrahydroquinoxaline-1-carboxylate;
bicyclo[3.1.0]hexan-3-yl (3S)-4-acetyl-3-methyl-7-[1-(oxetan-3-yl)-1H-pyrazol-4-yl]-1,2,3,4-tetrahydroquinoxaline-1-carboxylate;
(2,2-difluorocyclopropyl)methyl (3S)-4-acetyl-3-methyl-7-[1-(oxetan-3-yl)-1H-pyrazol-4-yl]-1,2,3,4-tetrahydroquinoxaline-1-carboxylate;
1-methylcyclopropyl (3S)-4-acetyl-3-methyl-7-[1-(oxetan-3-yl)-1H-pyrazol-4-yl]-1,2,3,4-tetrahydroquinoxaline-1-carboxylate;
2-fluoro-2-methylpropyl (3S)-4-acetyl-3-methyl-7-[1-(oxetan-3-yl)-1H-pyrazol-4-yl]-1,2,3,4-tetrahydroquinoxaline-1-carboxylate;
3,3,3-trifluoropropyl (3S)-4-acetyl-7-(1-cyclopropyl-1H-pyrazol-4-yl)-3-methyl-1,2,3,4-tetrahydroquinoxaline-1-carboxylate;
2,2,2-trifluoroethyl (3S)-4-acetyl-7-(1-cyclopropyl-1H-pyrazol-4-yl)-3-methyl-1,2,3,4-tetrahydroquinoxaline-1-carboxylate;
1,3-difluoropropan-2-yl (3S)-4-acetyl-7-(1-cyclopropyl-1H-pyrazol-4-yl)-3-methyl-1,2,3,4-tetrahydroquinoxaline-1-carboxylate;
3,3,3-trifluoropropyl (3S)-4-acetyl-7-[1-(2-hydroxyethyl)-1H-pyrazol-4-yl]-3-methyl-1,2,3,4-tetrahydroquinoxaline-1-carboxylate;
2,2,2-trifluoroethyl (3S)-4-acetyl-7-[1-(2-hydroxyethyl)-1H-pyrazol-4-yl]-3-methyl-1,2,3,4-tetrahydroquinoxaline-1-carboxylate;
1,3-difluoropropan-2-yl (3S)-4-acetyl-7-[1-(2-hydroxyethyl)-1H-pyrazol-4-yl]-3-methyl-1,2,3,4-tetrahydroquinoxaline-1-carboxylate;
2,2-difluoroethyl (3S)-4-acetyl-3-methyl-7-[1-(oxetan-3-yl)-1H-pyrazol-4-yl]-1,2,3,4-tetrahydroquinoxaline-1-carboxylate;
4-fluorophenyl (3S)-4-acetyl-3-methyl-7-[1-(oxetan-3-yl)-1H-pyrazol-4-yl]-1,2,3,4-tetrahydroquinoxaline-1-carboxylate;
cyclohexyl (3S)-4-acetyl-3-methyl-7-[1-(oxetan-3-yl)-1H-pyrazol-4-yl]-1,2,3,4-tetrahydroquinoxaline-1-carboxylate;
4-methoxyphenyl (3S)-4-acetyl-3-methyl-7-[1-(oxetan-3-yl)-1H-pyrazol-4-yl]-1,2,3,4-tetrahydroquinoxaline-1-carboxylate;
phenyl (3S)-4-acetyl-3-methyl-7-[1-(oxetan-3-yl)-1H-pyrazol-4-yl]-1,2,3,4-tetrahydroquinoxaline-1-carboxylate;
pyridin-3-yl (3S)-4-acetyl-3-methyl-7-[1-(oxetan-3-yl)-1H-pyrazol-4-yl]-1,2,3,4-tetrahydroquinoxaline-1-carboxylate;
pyridin-4-yl (3S)-4-acetyl-3-methyl-7-[1-(oxetan-3-yl)-1H-pyrazol-4-yl]-1,2,3,4-tetrahydroquinoxaline-1-carboxylate;
pyridin-2-yl (3S)-4-acetyl-3-methyl-7-[1-(oxetan-3-yl)-1H-pyrazol-4-yl]-1,2,3,4-tetrahydroquinoxaline-1-carboxylate;
(2S)-4-(1,3-benzoxazol-2-yl)-1-cyclopropanecarbonyl-6-(1-cyclopropyl-1H-pyrazol-4-yl)-2-methyl-1,2,3,4-tetrahydroquinoxaline;
1-[(2S)-6-(1-cyclopropyl-1H-pyrazol-4-yl)-4-(1H-indazol-3-yl)-2-methyl-1,2,3,4-tetrahydroquinoxalin-1-yl]ethan-1-one;
1-[(2S)-4-(1H-indazol-3-yl)-6-(4-methanesulfonylphenyl)-2-methyl-1,2,3,4-tetrahydroquinoxalin-1-yl]ethan-1-one;
1-[(2S)-4-(1,2-benzoxazol-3-yl)-6-(1-cyclopropyl-1H-pyrazol-4-yl)-2-methyl-1,2,3,4-tetrahydroquinoxalin-1-yl]ethan-1-one;
(2S)-4-(furan-2-carbonyl)-1-methanesulfonyl-6-(4-methanesulfonylphenyl)-2-methyl-1,2,3,4-tetrahydroquinoxaline;
1-[(2S)-4-cyclopropanecarbonyl-2-methyl-6-phenoxy-1H,2H,3H,4H-pyrido[2,3-b]pyrazin-1-yl]ethan-1-one;
cyclobutyl (3S)-4-acetyl-7-[1-(1,1-dioxo-1$\lambda^6$-thietan-3-yl)-1H-pyrazol-4-yl]-3-methyl-1,2,3,4-tetrahydroquinoxaline-1-carboxylate;
phenyl (3S)-4-acetyl-3-methyl-7-[4-(piperazine-1-carbonyl)phenyl]-1,2,3,4-tetrahydroquinoxaline-1-carboxylate;
1-[(2S)-6-(4-methanesulfonylphenyl)-2-methyl-4-(pyrrolidine-1-carbonyl)-1,2,3,4-tetrahydroquinoxalin-1-yl]ethan-1-one;
1-[(2S)-4-(furan-2-carbonyl)-2-methyl-6-(pyrrolidine-1-carbonyl)-1,2,3,4-tetrahydroquinoxalin-1-yl]ethan-1-one;
(3S)-4-acetyl-7-(4-methanesulfonylphenyl)-3-methyl-1,2,3,4-tetrahydroquinoxaline-1-carbaldehyde;

(2S)-4-(furan-2-carbonyl)-6-(4-methanesulfonylphenyl)-2-methyl-1,2,3,4-tetrahydroquinoxaline-1-carbaldehyde;

1-[(2S)-6-(4-methanesulfonylphenyl)-2,4-dimethyl-1,2,3,4-tetrahydroquinoxalin-1-yl]ethan-1-one;

1-[(3S)-4-acetyl-3-methyl-7-[1-(oxetan-3-yl)-1H-pyrazol-4-yl]-1,2,3,4-tetrahydroquinoxalin-1-yl]-3-methylbutan-1-one;

1-[(3S)-4-acetyl-3-methyl-7-[1-(oxetan-3-yl)-1H-pyrazol-4-yl]-1,2,3,4-tetrahydroquinoxalin-1-yl]-2,2-difluoroethan-1-one;

1-[(3S)-4-acetyl-3-methyl-7-[1-(oxetan-3-yl)-1H-pyrazol-4-yl]-1,2,3,4-tetrahydroquinoxalin-1-yl]-2-cyclopropylethan-1-one;

1-[(3S)-4-acetyl-3-methyl-7-[1-(oxetan-3-yl)-1H-pyrazol-4-yl]-1,2,3,4-tetrahydroquinoxalin-1-yl]-3,3,3-trifluoropropan-1-one;

1-[(3S)-4-acetyl-3-methyl-7-[1-(oxetan-3-yl)-1H-pyrazol-4-yl]-1,2,3,4-tetrahydroquinoxalin-1-yl]-2-methylpropan-1-one;

1-[(2S)-2-methyl-4-(oxane-4-carbonyl)-6-[1-(oxetan-3-yl)-1H-pyrazol-4-yl]-1,2,3,4-tetrahydroquinoxalin-1-yl]ethan-1-one;

1-[(3S)-4-acetyl-3-methyl-7-[1-(oxetan-3-yl)-1H-pyrazol-4-yl]-1,2,3,4-tetrahydroquinoxalin-1-yl]-2-cyclopentylethan-1-one;

1-[(2S)-4-[(1S)-2,2-dichlorocyclopropanecarbonyl]-2-methyl-6-[1-(oxetan-3-yl)-1H-pyrazol-4-yl]-1,2,3,4-tetrahydroquinoxalin-1-yl]ethan-1-one;

1-[(2S)-4-[(1R)-2,2-dichlorocyclopropanecarbonyl]-2-methyl-6-[1-(oxetan-3-yl)-1H-pyrazol-4-yl]-1,2,3,4-tetrahydroquinoxalin-1-yl]ethan-1-one;

1-[(2S)-2-methyl-4-(1-methylcyclopropanecarbonyl)-6-[1-(oxetan-3-yl)-1H-pyrazol-4-yl]-1,2,3,4-tetrahydroquinoxalin-1-yl]ethan-1-one;

1-[(3S)-4-acetyl-3-methyl-7-[1-(oxetan-3-yl)-1H-pyrazol-4-yl]-1,2,3,4-tetrahydroquinoxalin-1-yl]-2-chloro-2-methylpropan-1-one;

propan-2-yl (3S)-4-acetyl-3-methyl-7-[1-(pyrazin-2-ylmethyl)-1H-pyrazol-4-yl]-1,2,3,4-tetrahydroquinoxaline-1-carboxylate;

propan-2-yl (3S)-4-acetyl-3-methyl-7-[1-(pyridin-4-ylmethyl)-1H-pyrazol-4-yl]-1,2,3,4-tetrahydroquinoxaline-1-carboxylate;

1-[(2S)-4-cyclopropanecarbonyl-2-methyl-6-[1-(pyridin-4-ylmethyl)-1H-pyrazol-4-yl]-1,2,3,4-tetrahydroquinoxalin-1-yl]ethan-1-one;

propan-2-yl (3S)-4-acetyl-3-methyl-7-[1-(pyridin-3-ylmethyl)-1H-pyrazol-4-yl]-1,2,3,4-tetrahydroquinoxaline-1-carboxylate;

propan-2-yl (3S)-4-acetyl-3-methyl-7-[1-(pyridin-2-ylmethyl)-1H-pyrazol-4-yl]-1,2,3,4-tetrahydroquinoxaline-1-carboxylate;

1-[(2S)-4-cyclopropanecarbonyl-2-methyl-6-[1-(pyridin-2-ylmethyl)-1H-pyrazol-4-yl]-1,2,3,4-tetrahydroquinoxalin-1-yl]ethan-1-one;

1-[(2S)-4-cyclopropanecarbonyl-2-methyl-6-[1-(pyridin-3-ylmethyl)-1H-pyrazol-4-yl]-1,2,3,4-tetrahydroquinoxalin-1-yl]ethan-1-one;

1-[(2S)-4-cyclopropanecarbonyl-2-methyl-6-[1-(pyrazin-2-ylmethyl)-1H-pyrazol-4-yl]-1,2,3,4-tetrahydroquinoxalin-1-yl]ethan-1-one;

1-[(2S)-4-cyclopropanecarbonyl-2-methyl-6-{1-[(3-methyloxetan-3-yl)methyl]-1H-pyrazol-4-yl}-1,2,3,4-tetrahydroquinoxalin-1-yl]ethan-1-one;

2-{4-[(2S)-1-acetyl-4-cyclopropanecarbonyl-2-methyl-1,2,3,4-tetrahydroquinoxalin-6-yl]-1H-pyrazol-1-yl}-1-(morpholin-4-yl)ethan-1-one;

1-[(2S)-4-cyclopropanecarbonyl-2-methyl-6-[1-(pyrimidin-2-ylmethyl)-1H-pyrazol-4-yl]-1,2,3,4-tetrahydroquinoxalin-1-yl]ethan-1-one;

1-[(2S)-4-cyclopropanecarbonyl-6-[1-(1H-imidazol-4-ylmethyl)-1H-pyrazol-4-yl]-2-methyl-1,2,3,4-tetrahydroquinoxalin-1-yl]ethan-1-one;

1-[(2S)-4-cyclopropanecarbonyl-2-methyl-6-[1-(pyrimidin-5-ylmethyl)-1H-pyrazol-4-yl]-1,2,3,4-tetrahydroquinoxalin-1-yl]ethan-1-one;

propan-2-yl (3S)-4-acetyl-7-{1-[2-(dimethylamino)ethyl]-1H-pyrazol-4-yl}-3-methyl-1,2,3,4-tetrahydroquinoxaline-1-carboxylate;

2-{4-[(2S)-1-acetyl-2-methyl-4-[(propan-2-yloxy)carbonyl]-1,2,3,4-tetrahydroquinoxalin-6-yl]-1H-pyrazol-1-yl}acetic acid;

propan-2-yl (3S)-4-acetyl-3-methyl-7-[1-(1,2-oxazol-5-ylmethyl)-1H-pyrazol-4-yl]-1,2,3,4-tetrahydroquinoxaline-1-carboxylate;

2-{4-[(2S)-1-acetyl-4-cyclopropanecarbonyl-2-methyl-1,2,3,4-tetrahydroquinoxalin-6-yl]-1H-pyrazol-1-yl}-N-methylacetamide;

propan-2-yl (3S)-4-acetyl-7-{1-[(3-fluorooxetan-3-yl)methyl]-1H-pyrazol-4-yl}-3-methyl-1,2,3,4-tetrahydroquinoxaline-1-carboxylate;

propan-2-yl (3S)-4-acetyl-3-methyl-7-{1-[(methylcarbamoyl)methyl]-1H-pyrazol-4-yl}-1,2,3,4-tetrahydroquinoxaline-1-carboxylate;

propan-2-yl (3S)-4-acetyl-7-[1-(2,2-difluoroethyl)-1H-pyrazol-4-yl]-3-methyl-1,2,3,4-tetrahydroquinoxaline-1-carboxylate;

3-{4-[(2S)-1-acetyl-4-cyclopropanecarbonyl-2-methyl-1,2,3,4-tetrahydroquinoxalin-6-yl]-1H-pyrazol-1-yl}propanoic acid;

propan-2-yl (3S)-4-acetyl-7-[1-(3-hydroxypropyl)-1H-pyrazol-4-yl]-3-methyl-1,2,3,4-trahydroquinoxaline-1-carboxylate;

propan-2-yl (3S)-4-acetyl-7-[1-(1-carbamoyl-1-methylethyl)-1H-pyrazol-4-yl]-3-methyl-1,2,3,4-tetrahydroquinoxaline-1-carboxylate;

propan-2-yl (3S)-4-acetyl-3-methyl-7-{1-[2-(1H-1,2,4-triazol-1-yl)ethyl]-1H-pyrazol-4-yl}-1,2,3,4-tetrahydroquinoxaline-1-carboxylate;

propan-2-yl (3S)-4-acetyl-7-[1-(2-fluoro-2-methylpropyl)-1H-pyrazol-4-yl]-3-methyl-1,2,3,4-tetrahydroquinoxaline-1-carboxylate;

propan-2-yl (3S)-4-acetyl-3-methyl-7-{1-[(3-methyl-1,2-oxazol-5-yl)methyl]-1H-pyrazol-4-yl}-1,2,3,4-tetrahydroquinoxaline-1-carboxylate;

propan-2-yl (3S)-4-acetyl-3-methyl-7-[1-(3,3,3-trifluoropropyl)-1H-pyrazol-4-yl]-1,2,3,4-tetrahydroquinoxaline-1-carboxylate;

propan-2-yl (3S)-4-acetyl-3-methyl-7-[1-(1,3-thiazol-5-ylmethyl)-1H-pyrazol-4-yl]-1,2,3,4-tetrahydroquinoxaline-1-carboxylate;

propan-2-yl (3S)-4-acetyl-3-methyl-7-[1-(oxetan-3-yl)-1H-pyrazol-4-yl]-1,2,3,4-tetrahydroquinoxaline-1-carboxylate;

1-[(2S)-4-cyclopropanecarbonyl-6-[1-(2-fluoro-2-methylpropyl)-1H-pyrazol-4-yl]-2-methyl-1,2,3,4-tetrahydroquinoxalin-1-yl]ethan-1-one;

1-[(2S)-4-cyclopropanecarbonyl-6-{1-[2-(dimethylamino)ethyl]-1H-pyrazol-4-yl}-2-methyl-1,2,3,4-tetrahydroquinoxalin-1-yl]ethan-1-one;

1-[(2S)-4-cyclopropanecarbonyl-2-methyl-6-{1-[(4-methyl-1,2,5-oxadiazol-3-yl)methyl]-1H-pyrazol-4-yl}-1,2,3,4-tetrahydroquinoxalin-1-yl]ethan-1-one;
1-[(2S)-4-cyclopropanecarbonyl-6-{1-[(2,2-difluorocyclopropyl)methyl]-1H-pyrazol-4-yl}-2-methyl-1,2,3,4-tetrahydroquinoxalin-1-yl]ethan-1-one;
1-[(2S)-4-cyclopropanecarbonyl-2-methyl-6-{1-[(3-methyl-1,2-oxazol-5-yl)methyl]-1H-pyrazol-4-yl}-1,2,3,4-tetrahydroquinoxalin-1-yl]ethan-1-one;
1-[(2S)-4-cyclopropanecarbonyl-2-methyl-6-[1-(3,3,3-trifluoropropyl)-1H-pyrazol-4-yl]-1,2,3,4-tetrahydroquinoxalin-1-yl]ethan-1-one;
1-[(2S)-4-cyclopropanecarbonyl-2-methyl-6-{1-[2-(morpholin-4-yl)ethyl]-1H-pyrazol-4-yl}-1,2,3,4-tetrahydroquinoxalin-1-yl]ethan-1-one;
4,4-difluorocyclohexyl (3S)-4-acetyl-7-[1-(azetidin-3-yl)-1H-pyrazol-4-yl]-3-methyl-1,2,3,4-tetrahydroquinoxaline-1-carboxylate;
4,4-difluorocyclohexyl (3S)-4-acetyl-3-methyl-7-[1-(piperidin-4-yl)-1H-pyrazol-4-yl]-1,2,3,4-tetrahydroquinoxaline-1-carboxylate;
cyclobutyl (3S)-4-acetyl-7-[1-(1,1-dioxo-1λ⁶-thian-4-yl)-1H-pyrazol-4-yl]-3-methyl-1,2,3,4-tetrahydroquinoxaline-1-carboxylate;
oxan-4-yl (3S)-4-acetyl-7-[1-(1,1-dioxo-1λ⁶-thian-4-yl)-1H-pyrazol-4-yl]-3-methyl-1,2,3,4-tetrahydroquinoxaline-1-carboxylate;
propan-2-yl (3S)-4-acetyl-7-[1-(1,1-dioxo-1λ⁶-thian-4-yl)-1H-pyrazol-4-yl]-3-methyl-1,2,3,4-tetrahydroquinoxaline-1-carboxylate;
4-{4-[(2S)-1-acetyl-4-cyclopropanecarbonyl-2-methyl-1,2,3,4-tetrahydroquinoxalin-6-yl]-1H-pyrazol-1-yl}-1λ⁶-thiane-1,1-dione;
cyclobutyl (3S)-4-acetyl-7-[1-(1,1-dioxo-1λ⁶-thian-3-yl)-1H-pyrazol-4-yl]-3-methyl-1,2,3,4-tetrahydroquinoxaline-1-carboxylate;
propan-2-yl (3S)-4-acetyl-3-methyl-7-{1-[(2S)-2-methylazetidin-3-yl]-1H-pyrazol-4-yl}-1,2,3,4-tetrahydroquinoxaline-1-carboxylate;
1-[(2S)-4-cyclopropanecarbonyl-2-methyl-6-{1-[(2S)-2-methylazetidin-3-yl]-1H-pyrazol-4-yl}-1,2,3,4-tetrahydroquinoxalin-1-yl]ethan-1-one;
oxan-4-yl (3S)-4-acetyl-7-[1-(1,1-dioxo-1λ⁶-thian-3-yl)-1H-pyrazol-4-yl]-3-methyl-1,2,3,4-tetrahydroquinoxaline-1-carboxylate;
3,3-difluorocyclobutyl (3S)-4-acetyl-7-[1-(1,1-dioxo-1λ⁶-thian-3-yl)-1H-pyrazol-4-yl]-3-methyl-1,2,3,4-tetrahydroquinoxaline-1-carboxylate;
oxan-4-yl (3S)-4-acetyl-3-methyl-7-[1-(2-oxopiperidin-4-yl)-1H-pyrazol-4-yl]-1,2,3,4-tetrahydroquinoxaline-1-carboxylate;
3,3-difluorocyclobutyl (3S)-4-acetyl-3-methyl-7-[1-(2-oxopiperidin-4-yl)-1H-pyrazol-4-yl]-1,2,3,4-tetrahydroquinoxaline-1-carboxylate;
4,4-difluorocyclohexyl (3S)-4-acetyl-3-methyl-7-[1-(2-oxopiperidin-4-yl)-1H-pyrazol-4-yl]-1,2,3,4-tetrahydroquinoxaline-1-carboxylate;
propan-2-yl (3S)-4-acetyl-3-methyl-7-[1-(2-oxopiperidin-4-yl)-1H-pyrazol-4-yl]-1,2,3,4-tetrahydroquinoxaline-1-carboxylate;
4-{4-[(2S)-1-acetyl-4-cyclopropanecarbonyl-2-methyl-1,2,3,4-tetrahydroquinoxalin-6-yl]-1H-pyrazol-1-yl}piperidin-2-one;
3,3-difluorocyclobutyl (3S)-4-acetyl-3-methyl-7-{1-[(2S)-2-methylazetidin-3-yl]-1H-pyrazol-4-yl}-1,2,3,4-tetrahydroquinoxaline-1-carboxylate;
cyclopropylmethyl (3S)-4-acetyl-7-[1-(1,1-dioxo-1λ⁶-thian-4-yl)-1H-pyrazol-4-yl]-3-methyl-1,2,3,4-tetrahydroquinoxaline-1-carboxylate;
cyclobutyl (3S)-4-acetyl-3-methyl-7-{1-[(2R)-2-methylazetidin-3-yl]-1H-pyrazol-4-yl}-1,2,3,4-tetrahydroquinoxaline-1-carboxylate;
cyclopropylmethyl (3S)-4-acetyl-7-{1-[(3R)-1,1-dioxo-1λ⁶-thian-3-yl]-1H-pyrazol-4-yl}-3-methyl-1,2,3,4-tetrahydroquinoxaline-1-carboxylate;
cyclopropylmethyl (3S)-4-acetyl-7-{1-[(3S)-1,1-dioxo-1λ⁶-thian-3-yl]-1H-pyrazol-4-yl}-3-methyl-1,2,3,4-tetrahydroquinoxaline-1-carboxylate;
cyclobutyl (3S)-4-acetyl-7-{1-[(3R)-1,1-dioxo-1λ⁶-thian-3-yl]-1H-pyrazol-4-yl}-3-methyl-1,2,3,4-tetrahydroquinoxaline-1-carboxylate;
cyclobutyl (3S)-4-acetyl-7-{1-[(3S)-1,1-dioxo-1λ⁶-thian-3-yl]-1H-pyrazol-4-yl}-3-methyl-1,2,3,4-tetrahydroquinoxaline-1-carboxylate;
cyclobutyl (3S)-4-acetyl-3-methyl-7-[1-(2-oxopiperidin-4-yl)-1H-pyrazol-4-yl]-1,2,3,4-tetrahydroquinoxaline-1-carboxylate;
cyclobutyl (3S)-4-acetyl-3-methyl-7-{1-[(4R)-2-oxopiperidin-4-yl]-1H-pyrazol-4-yl}-1,2,3,4-tetrahydroquinoxaline-1-carboxylate;
cyclobutyl (3S)-4-acetyl-3-methyl-7-{1-[(4 S)-2-oxopiperidin-4-yl]-1H-pyrazol-4-yl}-1,2,3,4-tetrahydroquinoxaline-1-carboxylate;
cyclobutyl (3S)-4-acetyl-3-methyl-7-{1-[(2S)-2-methylazetidin-3-yl]-1H-pyrazol-4-yl}-1,2,3,4-tetrahydroquinoxaline-1-carboxylate;
1-[(2S)-6-(1-cyclopropyl-1H-pyrazol-4-yl)-4-(7-fluoro-1-methyl-1H-indazol-3-yl)-2-methyl-1,2,3,4-tetrahydroquinoxalin-1-yl]ethan-1-one;
1-[(2S)-4-(7-fluoro-1-methyl-1H-indazol-3-yl)-6-[1-(2-hydroxyethyl)-1H-pyrazol-4-yl]-2-methyl-1,2,3,4-tetrahydroquinoxalin-1-yl]ethan-1-one;
1-[(2S)-2-methyl-4-(1-methyl-1 H-indazol-3-yl)-6-[1-(piperidin-4-yl)-1H-pyrazol-4-yl]-1,2,3,4-tetrahydroquinoxalin-1-yl]ethan-1-one;
1-[(2S)-2-methyl-4-{1-methyl-1H-pyrazolo[3,4-c]pyridin-3-yl }-6-[1-(piperidin-4-yl)-1H-pyrazol-4-yl]-1,2,3,4-tetrahydroquinoxalin-1-yl]ethan-1-one;
1-[(2S)-6-(1-cyclopropyl-1H-pyrazol-4-yl)-4-(4-fluoro-1-methyl-1H-indazol-3-yl)-2-methyl-1,2,3,4-tetrahydroquinoxalin-1-yl]ethan-1-one;
1-[(2S)-6-(1-cyclopropyl-1H-pyrazol-4-yl)-2-methyl-4-{1-methyl-1H-pyrazolo[3,4-b]pyridin-3-yl}-1,2,3,4-tetrahydroquinoxalin-1-yl]ethan-1-one;
1-[(2S)-6-(1-cyclopropyl-1H-pyrazol-4-yl)-2-methyl-4-{1-methyl-1H-pyrazolo[3,4-c]pyridin-3-yl}-1,2,3,4-tetrahydroquinoxalin-1-yl]ethan-1-one;
1-[(2S)-6-(1-cyclopropyl-1H-pyrazol-4-yl)-2-methyl-4-{1-methyl-1H-pyrazolo[4,3-c]pyridin-3-yl}-1,2,3,4-tetrahydroquinoxalin-1-yl]ethan-1-one;
1-[(2S)-6-(1-cyclopropyl-1H-pyrazol-4-yl)-2-methyl-4-{1-methyl-1H-pyrazolo[4,3-b]pyridin-3-yl}-1,2,3,4-tetrahydroquinoxalin-1-yl]ethan-1-one;
1-[(2S)-4-(6-fluoro-1-methyl-1H-indazol-3-yl)-6-[1-(2-hydroxyethyl)-1H-pyrazol-4-yl]-2-methyl-1,2,3,4-tetrahydroquinoxalin-1-yl]ethan-1-one;
1-[(2S)-4-(5-fluoro-1-methyl-1H-indazol-3-yl)-6-[1-(2-hydroxyethyl)-1H-pyrazol-4-yl]-2-methyl-1,2,3,4-tetrahydroquinoxalin-1-yl]ethan-1-one;
1-[(2S)-4-(4-fluoro-1-methyl-1H-indazol-3-yl)-6-[1-(2-hydroxyethyl)-1H-pyrazol-4-yl]-2-methyl-1,2,3,4-tetrahydroquinoxalin-1-yl]ethan-1-one;

propan-2-yl (3S)-4-cyclopropanecarbonyl-3-methyl-7-(1H-pyrazol-4-yl)-1,2,3,4-tetrahydroquinoxaline-1-carboxylate;
propan-2-yl (3S)-4-acetyl-3-methyl-7-(1H-pyrazol-4-yl)-1,2,3,4-tetrahydroquinoxaline-1-carboxylate;
1-methyl 4-propan-2-yl (2S)-2-methyl-6-(1H-pyrazol-4-yl)-1,2,3,4-tetrahydroquinoxaline-1,4-dicarboxylate;
phenyl (3S)-4-acetyl-7-(4-methanesulfonylphenyl)-3-methyl-1,2,3,4-tetrahydroquinoxaline-1-carboxylate;
ethyl (3S)-4-acetyl-7-(4-methanesulfonylphenyl)-3-methyl-1,2,3,4-tetrahydroquinoxaline-1-carboxylate;
2-chlorophenyl (3S)-4-acetyl-7-(4-methanesulfonylphenyl)-3-methyl-1,2,3,4-tetrahydroquinoxaline-1-carboxylate;
4-chlorophenyl (3S)-4-acetyl-7-(4-methanesulfonylphenyl)-3-methyl-1,2,3,4-tetrahydroquinoxaline-1-carboxylate;
2-methoxyphenyl (3S)-4-acetyl-7-(4-methanesulfonylphenyl)-3-methyl-1,2,3,4-tetrahydroquinoxaline-1-carboxylate;
4-nitrophenyl (3S)-4-acetyl-7-(4-methanesulfonylphenyl)-3-methyl-1,2,3,4-tetrahydroquinoxaline-1-carboxylate;
4-(methoxycarbonyl)phenyl (3S)-4-acetyl-7-(4-methanesulfonylphenyl)-3-methyl-1,2,3,4-tetrahydroquinoxaline-1-carboxylate;
benzyl (3S)-4-acetyl-7-(4-methanesulfonylphenyl)-3-methyl-1,2,3,4-tetrahydroquinoxaline-1-carboxylate;
butyl (3S)-4-acetyl-7-(4-methanesulfonylphenyl)-3-methyl-1,2,3,4-tetrahydroquinoxaline-1-carboxylate;
4-methylphenyl (3S)-4-acetyl-7-(4-methanesulfonylphenyl)-3-methyl-1,2,3,4-tetrahydroquinoxaline-1-carboxylate;
4-methoxyphenyl (3S)-4-acetyl-7-(4-methanesulfonylphenyl)-3-methyl-1,2,3,4-tetrahydroquinoxaline-1-carboxylate;
4-fluorophenyl (3S)-4-acetyl-7-(4-methanesulfonylphenyl)-3-methyl-1,2,3,4-tetrahydroquinoxaline-1-carboxylate;
methyl (3S)-4-acetyl-7-(4-methanesulfonylphenyl)-3-methyl-1,2,3,4-tetrahydroquinoxaline-1-carboxylate;
cyclopentyl (3S)-4-acetyl-7-(4-methanesulfonylphenyl)-3-methyl-1,2,3,4-tetrahydroquinoxaline-1-carboxylate;
3-(trifluoromethyl)phenyl (3S)-4-acetyl-7-(4-methanesulfonylphenyl)-3-methyl-1,2,3,4-tetrahydroquinoxaline-1-carboxylate;
cyclohexyl (3S)-4-acetyl-7-(4-methanesulfonylphenyl)-3-methyl-1,2,3,4-tetrahydroquinoxaline-1-carboxylate;
naphthalen-2-yl (3S)-4-acetyl-7-(4-methanesulfonylphenyl)-3-methyl-1,2,3,4-tetrahydroquinoxaline-1-carboxylate;
prop-2-yn-1-yl (3S)-4-acetyl-7-(4-methanesulfonylphenyl)-3-methyl-1,2,3,4-tetrahydroquinoxaline-1-carboxylate;
1-[(3S)-4-acetyl-7-(4-methanesulfonylphenyl)-3-methyl-1,2,3,4-tetrahydroquinoxalin-1-yl]ethan-1-one;
1-[(3S)-4-acetyl-7-(4-methanesulfonylphenyl)-3-methyl-1,2,3,4-tetrahydroquinoxalin-1-yl]-2-methylpropan-1-one;
1-[(3S)-4-acetyl-7-(4-methanesulfonylphenyl)-3-methyl-1,2,3,4-tetrahydroquinoxalin-1-yl]-2,2-dimethylpropan-1-one;
1-[(2S)-4-cyclopentanecarbonyl-6-(4-methanesulfonylphenyl)-2-methyl-1,2,3,4-tetrahydroquinoxalin-1-yl]ethan-1-one;
1-[(2S)-4-cyclobutanecarbonyl-6-(4-methanesulfonylphenyl)-2-methyl-1,2,3,4-tetrahydroquinoxalin-1-yl]ethan-1-one;
1-[(3S)-4-acetyl-7-(4-methanesulfonylphenyl)-3-methyl-1,2,3,4-tetrahydroquinoxalin-1-yl]-2-cyclopentylethan-1-one;
3-[(3S)-4-acetyl-7-(4-methanesulfonylphenyl)-3-methyl-1,2,3,4-tetrahydroquinoxalin-1-yl]-3-oxopropanenitrile;
(3S)-4-acetyl-7-(4-methanesulfonylphenyl)-N,N,3-trimethyl-1,2,3,4-tetrahydroquinoxaline-1-carboxamide;
2-methoxyethyl (3S)-4-acetyl-7-(4-methanesulfonylphenyl)-3-methyl-1,2,3,4-tetrahydroquinoxaline-1-carboxylate;
2-methylpropyl (3S)-4-acetyl-7-(4-methanesulfonylphenyl)-3-methyl-1,2,3,4-tetrahydroquinoxaline-1-carboxylate;
naphthalen-1-yl (3S)-4-acetyl-7-(4-methanesulfonylphenyl)-3-methyl-1,2,3,4-tetrahydroquinoxaline-1-carboxylate;
propyl (3S)-4-acetyl-7-(4-methanesulfonylphenyl)-3-methyl-1,2,3,4-tetrahydroquinoxaline-1-carboxylate;
(3S)-4-acetyl-7-(4-methanesulfonylphenyl)-N,3-dimethyl-1,2,3,4-tetrahydroquinoxaline-1-carboxamide;
propan-2-yl (2S)-1-acetyl-6-(4-methanesulfonylphenyl)-2-methyl-1H,2H,3H,4H-pyrido[2,3-b]pyrazine-4-carboxylate;
propan-2-yl (2S)-1-acetyl-6-(1-cyclopropyl-1H-pyrazol-4-yl)-2-methyl-1H,2H,3H,4H-pyrido[2,3-b]pyrazine-4-carboxylate;
phenyl (3S)-4-acetyl-7-(1-cyclopropyl-1H-pyrazol-4-yl)-3-methyl-1,2,3,4-tetrahydroquinoxaline-1-carboxylate;
2-chlorophenyl (3S)-4-acetyl-7-(1-cyclopropyl-1H-pyrazol-4-yl)-3-methyl-1,2,3,4-tetrahydroquinoxaline-1-carboxylate;
2-methoxyphenyl (3S)-4-acetyl-7-(1-cyclopropyl-1H-pyrazol-4-yl)-3-methyl-1,2,3,4-tetrahydroquinoxaline-1-carboxylate;
3-(trifluoromethyl)phenyl (3S)-4-acetyl-7-(1-cyclopropyl-1H-pyrazol-4-yl)-3-methyl-1,2,3,4-tetrahydroquinoxaline-1-carboxylate;
4-chlorophenyl (3S)-4-acetyl-7-(1-cyclopropyl-1H-pyrazol-4-yl)-3-methyl-1,2,3,4-tetrahydroquinoxaline-1-carboxylate;
4-fluorophenyl (3S)-4-acetyl-7-(1-cyclopropyl-1H-pyrazol-4-yl)-3-methyl-1,2,3,4-tetrahydroquinoxaline-1-carboxylate;
4-(methoxycarbonyl)phenyl (3S)-4-acetyl-7-(1-cyclopropyl-1H-pyrazol-4-yl)-3-methyl-1,2,3,4-tetrahydroquinoxaline-1-carboxylate;
4-methoxyphenyl (3S)-4-acetyl-7-(1-cyclopropyl-1H-pyrazol-4-yl)-3-methyl-1,2,3,4-tetrahydroquinoxaline-1-carboxylate;
4-methylphenyl (3S)-4-acetyl-7-(1-cyclopropyl-1H-pyrazol-4-yl)-3-methyl-1,2,3,4-tetrahydroquinoxaline-1-carboxylate;
naphthalen-1-yl (3S)-4-acetyl-7-(1-cyclopropyl-1H-pyrazol-4-yl)-3-methyl-1,2,3,4-tetrahydroquinoxaline-1-carboxylate;
4-fluoro-3-methylphenyl (3S)-4-acetyl-7-(1-cyclopropyl-1H-pyrazol-4-yl)-3-methyl-1,2,3,4-tetrahydroquinoxaline-1-carboxylate;
4-[(2S)-1-acetyl-4-(furan-2-carbonyl)-2-methyl-1,2,3,4-tetrahydroquinoxalin-6-yl]-N-cyclopropylbenzene-1-sulfonamide;

1-[(2S)-4-(furan-2-carbonyl)-2-methyl-6-(1-propyl-1H-pyrazol-4-yl)-1,2,3,4-tetrahydroquinoxalin-1-yl]ethan-1-one;

1-[(2S)-6-(1, 5-dimethyl-1H-pyrazol-4-yl)-4-(furan-2-carbonyl)-2-methyl-1,2,3,4-tetrahydroquinoxalin-1-yl]ethan-1-one;

1-[(3S)-1-(furan-2-carbonyl)-7-(4-methanesulfonylphenyl)-3-methyl-1H,2H,3H,4H-pyrido[2,3-b]pyrazin-4-yl]ethan-1-one;

4-[(3S)-4-acetyl-1-(furan-2-carbonyl)-3-methyl-1H,2H,3H,4H-pyrido[2,3-b]pyrazin-7-yl]-N,N-dimethylbenzamide;

1-[(3S)-1-(furan-2-carbonyl)-3-methyl-7-(1-propyl-1H-pyrazol-4-yl)-1H,2H,3H,4H-pyrido[2,3-b]pyrazin-4-yl]ethan-1-one;

4-[(2S)-1-acetyl-4-(furan-2-carbonyl)-2-methyl-1,2,3,4-tetrahydroquinoxalin-6-yl]-N-(propan-2-yl)benzene-1-sulfonamide;

1-[(2S)-4-(furan-2-carbonyl)-2-methyl-6-[4-(morpholine-4-sulfonyl)phenyl]-1,2,3,4-tetrahydroquinoxalin-1-yl]ethan-1-one;

1-[(2S)-6-{4-[2-(dimethylamino)ethoxy]phenyl}-4-(furan-2-carbonyl)-2-methyl-1,2,3,4-tetrahydroquinoxalin-1-yl]ethan-1-one;

4-[(2S)-1-acetyl-4-(furan-2-carbonyl)-2-methyl-1,2,3,4-tetrahydroquinoxalin-6-yl]-N,N-dimethylbenzene-1-sulfonamide;

1-[(2S)-4-(furan-2-carbonyl)-2-methyl-6-{4-[(4-methylpiperazin-1-yl)sulfonyl]phenyl}-1,2,3,4-tetrahydroquinoxalin-1-yl]ethan-1-one;

N-{4-[(2S)-1-acetyl-4-(furan-2-carbonyl)-2-methyl-1,2,3,4-tetrahydroquinoxalin-6-yl]phenyl}methanesulfonamide;

{4-[(2S)-1-acetyl-4-(furan-2-carbonyl)-2-methyl-1,2,3,4-tetrahydroquinoxalin-6-yl]phenyl}urea;

4-[(2S)-1-acetyl-4-(furan-2-carbonyl)-2-methyl-1,2,3,4-tetrahydroquinoxalin-6-yl]benzene-1-sulfonamide;

1-[(2S)-4-(furan-2-carbonyl)-2-methyl-6-[4-(pyrrolidine-1-carbonyl)phenyl]-1,2,3,4-tetrahydroquinoxalin-1-yl]ethan-1-one;

1-[(2S)-4-(furan-2-carbonyl)-2-methyl-6-[4-(morpholine-4-carbonyl)phenyl]-1,2,3,4-tetrahydroquinoxalin-1-yl]ethan-1-one;

1-{4-[(2S)-1-acetyl-4-(furan-2-carbonyl)-2-methyl-1,2,3,4-tetrahydroquinoxalin-6-yl]phenyl}-3,3-dimethylurea;

N-{4-[(2S)-1-acetyl-4-(furan-2-carbonyl)-2-methyl-1,2,3,4-tetrahydroquinoxalin-6-yl]phenyl}morpholine-4-carboxamide;

1-[(2S)-4-(furan-2-carbonyl)-2-methyl-6-[4-(pyrrolidine-1-sulfonyl)phenyl]-1,2,3,4-tetrahydroquinoxalin-1-yl]ethan-1-one;

N-{4-[(2S)-1-acetyl-4-(furan-2-carbonyl)-2-methyl-1,2,3,4-tetrahydroquinoxalin-6-yl]phenyl}cyclopropanesulfonamide;

1-[(2S)-4-(furan-2-carbonyl)-2-methyl-6-[4-(propane-2-sulfonyl)phenyl]-1,2,3,4-tetrahydroquinoxalin-1-yl]ethan-1-one;

1-[(2S)-6-[4-(azetidine-1-sulfonyl)phenyl]-4-(furan-2-carbonyl)-2-methyl-1,2,3,4-tetrahydroquinoxalin-1-yl]ethan-1-one;

4-[(2S)-1-acetyl-4-(furan-2-carbonyl)-2-methyl-1,2,3,4-tetrahydroquinoxalin-6-yl]-N-(2-hydroxyethyl)benzamide;

1-[(2S)-6-[4-(cyclopropanesulfonyl)phenyl]-4-(furan-2-carbonyl)-2-methyl-1,2,3,4-tetrahydroquinoxalin-1-yl]ethan-1-one;

4-[(2S)-1-acetyl-4-(furan-2-carbonyl)-2-methyl-1,2,3,4-tetrahydroquinoxalin-6-yl]-N-cyclopropylbenzamide;

S-{4-[(2S)-1-acetyl-4-(furan-2-carbonyl)-2-methyl-1,2,3,4-tetrahydroquinoxalin-6-yl]phenyl}-2-hydroxyethane-1-sulfonamido;

propan-2-yl (3S)-4-acetyl-7-(4-methanesulfonylphenyl)-3-methyl-1,2,3,4-tetrahydroquinoxaline-1-carboxylate;

1-[(2S)-6-(6-aminopyridin-3-yl)-4-(furan-2-carbonyl)-2-methyl-1,2,3,4-tetrahydroquinoxalin-1-yl]ethan-1-one;

1-[(2S)-6-(2-aminopyrimidin-5-yl)-4-(furan-2-carbonyl)-2-methyl-1,2,3,4-tetrahydroquinoxalin-1-yl]ethan-1-one;

propan-2-yl (3R)-4-acetyl-7-(4-methanesulfonylphenyl)-3-methyl-1,2,3,4-tetrahydroquinoxaline-1-carboxylate;

1-[(2S)-4-(furan-2-carbonyl)-2-methyl-6-[4-(pyrrolidin-1-yl)phenyl]-1,2,3,4-tetrahydroquinoxalin-1-yl]ethan-1-one;

1-[(2S)-4-(furan-2-carbonyl)-6-(1-methanesulfonyl-2,3-dihydro-1H-indol-5-yl)-2-methyl-1,2,3,4-tetrahydroquinoxalin-1-yl]ethan-1-one;

1-[(2S)-4-(furan-2-carbonyl)-6-(4-methanesulfonylphenyl)-2-methyl-1H,2H,3H,4H-pyrido[2,3-b]pyrazin-1-yl]ethan-1-one;

1-[(2S)-4-cyclopropanecarbonyl-6-(4-methanesulfonylphenyl)-2-methyl-1H,2H,3H,4H-pyrido[2,3-b]pyrazin-1-yl]ethan-1-one;

1-[(2S)-6-cyclopropyl-4-(furan-2-carbonyl)-2-methyl-1,2,3,4-tetrahydroquinoxalin-1-yl]ethan-1-one;

propan-2-yl (3S)-4-acetyl-7-[1-(2-methanesulfonylethyl)-1H-pyrazol-4-yl]-3-methyl-1,2,3,4-tetrahydroquinoxaline-1-carboxylate;

propan-2-yl (3S)-4-acetyl-7-[1-(carbamoylmethyl)-1H-pyrazol-4-yl]-3-methyl-1,2,3,4-tetrahydroquinoxaline-1-carboxylate;

propan-2-yl (3S)-4-acetyl-7-{1-[(dimethylcarbamoyl)methyl]-1H-pyrazol-4-yl}-3-methyl-1,2,3,4-tetrahydroquinoxaline-1-carboxylate;

propan-2-yl (3S)-4-acetyl-3-methyl-7-{1-[2-(morpholin-4-yl)ethyl]-1H-pyrazol-4-yl}-1,2,3,4-tetrahydroquinoxaline-1-carboxylate;

propan-2-yl (3S)-4-acetyl-3-methyl-7-[1-(oxan-4-yl)-1H-pyrazol-4-yl]-1,2,3,4-tetrahydroquinoxaline-1-carboxylate;

propan-2-yl (3S)-4-acetyl-7-[1-(cyclopropylmethyl)-1H-pyrazol-4-yl]-3-methyl-1,2,3,4-tetrahydroquinoxaline-1-carboxylate;

propan-2-yl (3S)-4-cyclopropanecarbonyl-7-[1-(2-methanesulfonylethyl)-1H-pyrazol-4-yl]-3-methyl-1,2,3,4-tetrahydroquinoxaline-1-carboxylate;

propan-2-yl (3S)-7-[1-(carbamoylmethyl)-1H-pyrazol-4-yl]-4-cyclopropanecarbonyl-3-methyl-1,2,3,4-tetrahydroquinoxaline-1-carboxylate;

propan-2-yl (3S)-4-cyclopropanecarbonyl-7-{1-[(dimethylcarbamoyl)methyl]-1H-pyrazol-4-yl}-3-methyl-1,2,3,4-tetrahydroquinoxaline-1-carboxylate;

propan-2-yl (3S)-4-cyclopropanecarbonyl-3-methyl-7-{1-[2-(morpholin-4-yl)ethyl]-1H-pyrazol-4-yl}-1,2,3,4-tetrahydroquinoxaline-1-carboxylate;

propan-2-yl (3S)-4-cyclopropanecarbonyl-3-methyl-7-[1-(oxan-4-yl)-1H-pyrazol-4-yl]-1,2,3,4-tetrahydroquinoxaline-1-carboxylate;

propan-2-yl (3S)-4-cyclopropanecarbonyl-7-[1-(2-methoxyethyl)-1H-pyrazol-4-yl]-3-methyl-1,2,3,4-tetrahydroquinoxaline-1-carboxylate;

propan-2-yl (3S)-4-cyclopropanecarbonyl-7-[1-(2-hydroxyethyl)-1H-pyrazol-4-yl]-3-methyl-1,2,3,4-tetrahydroquinoxaline-1-carboxylate;

propan-2-yl (3S)-4-cyclopropanecarbonyl-7-[1-(cyclopropylmethyl)-1H-pyrazol-4-yl]-3-methyl-1,2,3,4-tetrahydroquinoxaline-1-carboxylate;

propan-2-yl (3S)-4-cyclopropanecarbonyl-3-methyl-7-[1-(oxetan-3-yl)-1H-pyrazol-4-yl]-1,2,3,4-tetrahydroquinoxaline-1-carboxylate;

1-methyl 4-propan-2-yl (2S)-6-[1-(2-methanesulfonylethyl)-1H-pyrazol-4-yl]-2-methyl-1,2,3,4-tetrahydroquinoxaline-1,4-dicarboxylate;

1-methyl 4-propan-2-yl (2S)-6-[1-(carbamoylmethyl)-1H-pyrazol-4-yl]-2-methyl-1,2,3,4-tetrahydroquinoxaline-1,4-dicarboxylate;

1-methyl 4-propan-2-yl (2S)-6-{1-[(dimethylcarbamoyl)methyl]-1H-pyrazol-4-yl}-2-methyl-1,2,3,4-tetrahydroquinoxaline-1,4-dicarboxylate;

1-methyl 4-propan-2-yl (2S)-2-methyl-6-{1-[2-(morpholin-4-yl)ethyl]-1H-pyrazol-4-yl}-1,2,3,4-tetrahydroquinoxaline-1,4-dicarboxylate;

1-methyl 4-propan-2-yl (2S)-2-methyl-6-[1-(oxan-4-yl)-1H-pyrazol-4-yl]-1,2,3,4-tetrahydroquinoxaline-1,4-dicarboxylate;

1-methyl 4-propan-2-yl (2S)-6-[1-(2-methoxyethyl)-1H-pyrazol-4-yl]-2-methyl-1,2,3,4-tetrahydroquinoxaline-1,4-dicarboxylate;

1-methyl 4-propan-2-yl (2S)-6-[1-(2-hydroxyethyl)-1H-pyrazol-4-yl]-2-methyl-1,2,3,4-tetrahydroquinoxaline-1,4-dicarboxylate;

1-methyl 4-propan-2-yl (2S)-6-[1-(cyclopropylmethyl)-1H-pyrazol-4-yl]-2-methyl-1,2,3,4-tetrahydroquinoxaline-1,4-dicarboxylate;

1-methyl 4-propan-2-yl (2S)-2-methyl-6-[1-(oxetan-3-yl)-1H-pyrazol-4-yl]-1,2,3,4-tetrahydroquinoxaline-1,4-dicarboxylate;

propan-2-yl (3S)-4-acetyl-7-[1-(2-hydroxy-2-methylpropyl)-1H-pyrazol-4-yl]-3-methyl-1,2,3,4-tetrahydroquinoxaline-1-carboxylate;

propan-2-yl (3S)-4-cyclopropanecarbonyl-7-[1-(2-hydroxy-2-methylpropyl)-1H-pyrazol-4-yl]-3-methyl-1,2,3,4-tetrahydroquinoxaline-1-carboxylate;

1-methyl 4-propan-2-yl (2S)-6-[1-(2-hydroxy-2-methylpropyl)-1H-pyrazol-4-yl]-2-methyl-1,2,3,4-tetrahydroquinoxaline-1,4-dicarboxylate;

propan-2-yl (3S)-4-acetyl-7-(1-tert-butyl-1H-pyrazol-4-yl)-3-methyl-1,2,3,4-tetrahydroquinoxaline-1-carboxylate;

propan-2-yl (3S)-7-(1-tert-butyl-1H-pyrazol-4-yl)-4-cyclopropanecarbonyl-3-methyl-1,2,3,4-tetrahydroquinoxaline-1-carboxylate;

1-methyl 4-propan-2-yl (2S)-6-(1-tert-butyl-1H-pyrazol-4-yl)-2-methyl-1,2,3,4-tetrahydroquinoxaline-1,4-dicarboxylate;

propan-2-yl (3S)-4-acetyl-7-(3,5-dimethyl-1H-pyrazol-4-yl)-3-methyl-1,2,3,4-tetrahydroquinoxaline-1-carboxylate;

propan-2-yl (3S)-4-acetyl-3-methyl-7-(1-phenyl-1H-pyrazol-4-yl)-1,2,3,4-tetrahydroquinoxaline-1-carboxylate;

propan-2-yl (3S)-4-acetyl-3-methyl-7-[3-(trifluoromethyl)-1H-pyrazol-4-yl]-1,2,3,4-tetrahydroquinoxaline-1-carboxylate;

propan-2-yl (3S)-4-acetyl-7-[1-(difluoromethyl)-1H-pyrazol-4-yl]-3-methyl-1,2,3,4-tetrahydroquinoxaline-1-carboxylate;

propan-2-yl (3S)-4-acetyl-3-methyl-7-(3-methyl-1H-pyrazol-4-yl)-1,2,3,4-tetrahydroquinoxaline-1-carboxylate;

propan-2-yl (3S)-4-acetyl-7-(1,3-dimethyl-1H-pyrazol-4-yl)-3-methyl-1,2,3,4-tetrahydroquinoxaline-1-carboxylate;

propan-2-yl (3S)-4-acetyl-7-(1,5-dimethyl-1H-pyrazol-4-yl)-3-methyl-1,2,3,4-tetrahydroquinoxaline-1-carboxylate;

2-{4-[(2S)-1-cyclopropanecarbonyl-2-methyl-4-[(propan-2-yloxy)carbonyl]-1,2,3,4-tetrahydroquinoxalin-6-yl]-1H-pyrazol-1-yl}acetic acid;

2-{4-[(2S)-1-(methoxycarbonyl)-2-methyl-4-[(propan-2-yloxy)carbonyl]-1,2,3,4-tetrahydroquinoxalin-6-yl]-1H-pyrazol-1-yl}acetic acid;

1-[(2S)-4-cyclopropanecarbonyl-6-[1-(2-hydroxyethyl)-1H-pyrazol-4-yl]-2-methyl-1,2,3,4-tetrahydroquinoxalin-1-yl]ethan-1-one;

1-[(2S)-4-cyclopropanecarbonyl-6-[1-(2-hydroxy-2-methylpropyl)-1H-pyrazol-4-yl]-2-methyl-1,2,3,4-tetrahydroquinoxalin-1-yl]ethan-1-one;

1-{4-cyclopropanecarbonyl-6-[1-(2-methanesulfonylethyl)-1H-pyrazol-4-yl]-2-methyl-1,2,3,4-tetrahydroquinoxalin-1-yl}ethan-1-one;

propan-2-yl (3S)-4-acetyl-7-(4-methanesulfonamidophenyl)-3-methyl-1,2,3,4-tetrahydroquinoxaline-1-carboxylate;

propan-2-yl (3S)-4-acetyl-3-methyl-7-[4-(N-methylmethane sulfonamido)phenyl]-1,2,3,4-tetrahydroquinoxaline-1-carboxylate;

propan-2-yl (3S)-4-acetyl-7-(1-methanesulfonyl-2,3-dihydro-1H-indol-5-yl)-3-methyl-1,2,3,4-tetrahydroquinoxaline-1-carboxylate;

N-{4-[(2S)-1-acetyl-4-cyclopropanecarbonyl-2-methyl-1,2,3,4-tetrahydroquinoxalin-6-yl]phenyl}methanesulfonamide;

N-{4-[(2S)-1-acetyl-4-cyclopropanecarbonyl-2-methyl-1,2,3,4-tetrahydroquinoxalin-6-yl]phenyl}-N-methylmethanesulfonamide;

propan-2-yl (3S)-4-acetyl-3-methyl-7-[1-(piperidin-4-yl)-1H-pyrazol-4-yl]-1,2,3,4-tetrahydroquinoxaline-1-carboxylate;

propan-2-yl (3S)-4-cyclopropanecarbonyl-3-methyl-7-[1-(piperidin-4-yl)-1H-pyrazol-4-yl]-1,2,3,4-tetrahydroquinoxaline-1-carboxylate;

1-methyl 4-propan-2-yl (2S)-2-methyl-6-[1-(piperidin-4-yl)-1H-pyrazol-4-yl]-1,2,3,4-tetrahydroquinoxaline-1,4-dicarboxylate;

propan-2-yl (3S)-4-acetyl-7-[1-(azetidin-3-yl)-1H-pyrazol-4-yl]-3-methyl-1,2,3,4-tetrahydroquinoxaline-1-carboxylate;

propan-2-yl (3S)-7-[1-(azetidin-3-yl)-1H-pyrazol-4-yl]-4-cyclopropanecarbonyl-3-methyl-1,2,3,4-tetrahydroquinoxaline-1-carboxylate;

1-methyl 4-propan-2-yl (2S)-6-[1-(azetidin-3-yl)-1H-pyrazol-4-yl]-2-methyl-1,2,3,4-tetrahydroquinoxaline-1,4-dicarboxylate;

1-[(2S)-4-cyclopropanecarbonyl-2-methyl-6-[1-(piperidin-4-yl)-1H-pyrazol-4-yl]-1,2,3,4-tetrahydroquinoxalin-1-yl]ethan-1-one;

1-[(2S)-6-[1-(azetidin-3-yl)-1H-pyrazol-4-yl]-4-cyclopropanecarbonyl-2-methyl-1,2,3,4-tetrahydroquinoxalin-1-yl]ethan-1-one;

2,2,2-trifluoro-1-[(2S)-4-(furan-2-carbonyl)-6-(4-methanesulfonylphenyl)-2-methyl-1,2,3,4-tetrahydroquinoxalin-1-yl]ethan-1-one;

4-[(2S)-4-(furan-2-carbonyl)-2-methyl-1-(trifluoroacetyl)-1,2,3,4-tetrahydroquinoxalin-6-yl]-N,N-dimethylbenzamide;

2,2,2-trifluoro-1-[(2S)-4-(furan-2-carbonyl)-2-methyl-6-(1-propyl-1H-pyrazol-4-yl)-1,2,3,4-tetrahydroquinoxalin-1-yl]ethan-1-one;

(2S)-1-cyclopropanecarbonyl-4-(furan-2-carbonyl)-6-(4-methanesulfonylphenyl)-2-methyl-1,2,3,4-tetrahydroquinoxaline;

1-[(2S)-4-(furan-2-carbonyl)-6-(4-methanesulfonylphenyl)-2-methyl-1,2,3,4-tetrahydroquinoxalin-1-yl]propan-1-one;

methyl (2S)-4-(furan-2-carbonyl)-6-(4-methanesulfonylphenyl)-2-methyl-1,2,3,4-tetrahydroquinoxaline-1-carboxylate;

1-[(2S)-4-(furan-2-carbonyl)-6-(4-methanesulfonylphenyl)-2-methyl-1,2,3,4-tetrahydroquinoxalin-1-yl]-2-hydroxyethan-1-one;

1-[(2S)-4-(furan-2-carbonyl)-6-(4-methanesulfonylphenyl)-2-methyl-1,2,3,4-tetrahydroquinoxalin-1-yl]-2-methoxyethan-1-one;

(2S)-4-(furan-2-carbonyl)-6-(4-methanesulfonylphenyl)-N,N,2-trimethyl-1,2,3,4-tetrahydroquinoxaline-1-carboxamide;

1-[(2S)-4-(furan-2-carbonyl)-6-(4-methane sulfonylphenyl)-2-methyl-1,2,3,4-tetrahydroquinoxalin-1-yl]-2-methylpropan-1-one;

ethyl (2S)-4-(furan-2-carbonyl)-6-(4-methanesulfonylphenyl)-2-methyl-1,2,3,4-tetrahydroquinoxaline-1-carboxylate;

propan-2-yl (2S)-4-(furan-2-carbonyl)-6-(4-methanesulfonylphenyl)-2-methyl-1,2,3,4-tetrahydroquinoxaline-1-carboxylate;

(2S)-1-cyclopentanecarbonyl-4-(furan-2-carbonyl)-6-(4-methanesulfonylphenyl)-2-methyl-1,2,3,4-tetrahydroquinoxaline;

(2S)-1-cyclobutanecarbonyl-4-(furan-2-carbonyl)-6-(4-methanesulfonylphenyl)-2-methyl-1,2,3,4-tetrahydroquinoxaline;

(2S)-4-(furan-2-carbonyl)-6-(4-methanesulfonylphenyl)-2-methyl-1-(1,2-oxazole-5-carbonyl)-1,2,3,4-tetrahydroquinoxaline;

(2S)-4-(furan-2-carbonyl)-6-(4-methanesulfonylphenyl)-2-methyl-1-(pyrrolidine-1-carbonyl)-1,2,3,4-tetrahydroquinoxaline;

(2S)-1,4-dicyclopropanecarbonyl-6-(1-cyclopropyl-1H-pyrazol-4-yl)-2-methyl-1,2,3,4-tetrahydroquinoxaline;

propan-2-yl (3S)-4-cyclopropanecarbonyl-7-(1-cyclopropyl-1H-pyrazol-4-yl)-3-methyl-1,2,3,4-tetrahydroquinoxaline-1-carboxylate;

ethyl (3S)-4-cyclopropanecarbonyl-7-(1-cyclopropyl-1H-pyrazol-4-yl)-3-methyl-1,2,3,4-tetrahydroquinoxaline-1-carboxylate;

4-ethyl 1-methyl (2S)-6-(1-cyclopropyl-1H-pyrazol-4-yl)-2-methyl-1,2,3,4-tetrahydroquinoxaline-1,4-dicarboxylate;

1-[(2S)-4-(furan-2-carbonyl)-2-methyl-6-(pyridin-2-yl)-1,2,3,4-tetrahydroquinoxalin-1-yl]ethan-1-one;

1-[(2S)-4-(furan-2-carbonyl)-6-{imidazo[1,2-a]pyridin-6-yl}-2-methyl-1,2,3,4-tetrahydroquinoxalin-1-yl]ethan-1-one;

1-[(2S)-4-(furan-2-carbonyl)-2-methyl-6-(pyrimidin-2-yl)-1,2,3,4-tetrahydroquinoxalin-1-yl]ethan-1-one;

1-[(2S)-4-(furan-2-carbonyl)-2-methyl-6-(pyrazin-2-yl)-1,2,3,4-tetrahydroquinoxalin-1-yl]ethan-1-one;

1-[(2S)-4-(furan-2-carbonyl)-6-(1H-indol-5-yl)-2-methyl-1,2,3,4-tetrahydroquinoxalin-1-yl]ethan-1-one 1-[(2S)-6-(2,3-dihydro-1-benzofuran-7-yl)-4-(furan-2-carbonyl)-2-methyl-1,2,3,4-tetrahydroquinoxalin-1-yl]ethan-1-one;

5-[(2S)-1-acetyl-4-(furan-2-carbonyl)-2-methyl-1,2,3,4-tetrahydroquinoxalin-6-yl]pyrazine-2-carbonitrile;

1-[(2S)-4-(furan-2-carbonyl)-2-methyl-6-(1-methyl-1H-imidazol-2-yl)-1,2,3,4-tetrahydroquinoxalin-1-yl]ethan-1-one;

1-[(2S)-4-(furan-2-carbonyl)-2-methyl-6-(1-methyl-1H-imidazol-5-yl)-1,2,3,4-tetrahydroquinoxalin-1-yl]ethan-1-one;

1-[(2S)-4-(furan-2-carbonyl)-2-methyl-6-(1,2-oxazol-4-yl)-1,2,3,4-tetrahydroquinoxalin-1-yl]ethan-1-one;

1-[(2S)-4-(furan-2-carbonyl)-6-{imidazo[1,2-a]pyridin-3-yl}-2-methyl-1,2,3,4-tetrahydroquinoxalin-1-yl]ethan-1-one;

6-[(2S)-1-acetyl-4-(furan-2-carbonyl)-2-methyl-1,2,3,4-tetrahydroquinoxalin-6-yl]pyridine-3-carbonitrile;

1-[(2S)-4-(furan-2-carbonyl)-2-methyl-6-{3-methyl-[1,2,4]triazolo[4,3-a]pyridin-6-yl}-1,2,3,4-tetrahydroquinoxalin-1-yl]ethan-1-one;

5-[(2S)-1-acetyl-4-(furan-2-carbonyl)-2-methyl-1,2,3,4-tetrahydroquinoxalin-6-yl]-2,3-dihydro-1H-1,3-benzodiazol-2-one;

5-[(2S)-1-acetyl-4-(furan-2-carbonyl)-2-methyl-1,2,3,4-tetrahydroquinoxalin-6-yl]-1,3-dimethyl-2,3-dihydro-1H-1,3-benzodiazol-2-one;

1-[(2S)-4-(furan-2-carbonyl)-2-methyl-6-{[1,2,4]triazolo[4,3-b]pyridazin-6-yl}-1,2,3,4-tetrahydroquinoxalin-1-yl]ethan-1-one;

1-[(2S)-4-(furan-2-carbonyl)-2-methyl-6-{1H-pyrrolo[3,2-b]pyridin-5-yl}-1,2,3,4-tetrahydroquinoxalin-1-yl]ethan-1-one;

1-[(2S)-4-(furan-2-carbonyl)-6-{imidazo[1,2-b]pyridazin-6-yl}-2-methyl-1,2,3,4-trahydroquinoxalin-1-yl]ethan-1-one;

1-[(2S)-4-(furan-2-carbonyl)-2-methyl-6-(1-methyl-1H-1,3-benzodiazol-6-yl)-1,2,3,4-tetrahydroquinoxalin-1-yl]ethan-1-one;

1-[(2S)-4-(furan-2-carbonyl)-2-methyl-6-(1-methyl-1H-1,3-benzodiazol-5-yl)-1,2,3,4-tetrahydroquinoxalin-1-yl]ethan-1-one;

1-[(2S)-4-(furan-2-carbonyl)-2-methyl-6-(1-methyl-1H-imidazol-4-yl)-1,2,3,4-tetrahydroquinoxalin-1-yl]ethan-1-one;

1-[(2S)-4-(furan-2-carbonyl)-2-methyl-6-[3-(5-methyl-1,2,4-oxadiazol-3-yl)phenyl]-1,2,3,4-tetrahydroquinoxalin-1-yl]ethan-1-one;

1-[(2S)-4-(furan-2-carbonyl)-2-methyl-6-(5-methyl-1,3,4-thi adi azol-2-yl)-1,2,3,4-tetrahydroquinoxalin-1-yl]ethan-1-one;

1-[(2S)-4-(furan-2-carbonyl)-2-methyl-6-(2-methyl-2H-indazol-5-yl)-1,2,3,4-tetrahydroquinoxalin-1-yl]ethan-1-one;

1-[(2S)-4-(furan-2-carbonyl)-2-methyl-6-[3-(pyrimidin-2-yl)phenyl]-1,2,3,4-tetrahydroquinoxalin-1-yl]ethan-1-one;

1-[(2S)-4-(furan-2-carbonyl)-6-{imidazo[1,2-a]pyrimidin-7-yl}-2-methyl-1,2,3,4-tetrahydroquinoxalin-1-yl]ethan-1-one;

1-[(2S)-4-(furan-2-carbonyl)-6-(5-methanesulfonylpyridin-2-yl)-2-methyl-1,2,3,4-tetrahydroquinoxalin-1-yl]ethan-1-one;

1-[(2S)-6-benzoyl-4-(furan-2-carbonyl)-2-methyl-1,2,3,4-tetrahydroquinoxalin-1-yl]ethan-1-one;

1-[(2S)-6-(1-benzyl-1H-pyrazol-4-yl)-4-(furan-2-carbonyl)-2-methyl-1,2,3,4-tetrahydroquinoxalin-1-yl]ethan-1-one;

4-[(2S)-1-acetyl-4-(furan-2-carbonyl)-2-methyl-1,2,3,4-tetrahydroquinoxalin-6-yl]-N,N-dimethyl-1H-imidazole-1-sulfonamide;

5-[(2S)-1-acetyl-4-(furan-2-carbonyl)-2-methyl-1,2,3,4-tetrahydroquinoxalin-6-yl]-1-methyl-1,2-dihydropyridin-2-one;

1-[(2S)-4-(furan-2-carbonyl)-2-methyl-6-[4-(1,3-oxazol-2-yl)phenyl]-1,2,3,4-tetrahydroquinoxalin-1-yl]ethan-1-one;

1-[(2S)-6-(5-aminopyrazin-2-yl)-4-(furan-2-carbonyl)-2-methyl-1,2,3,4-tetrahydroquinoxalin-1-yl]ethan-1-one;

methyl N-{4-[(2S)-1-acetyl-4-(furan-2-carbonyl)-2-methyl-1,2,3,4-tetrahydroquinoxalin-6-yl]phenyl}carbamate;

1-[(2S)-4-(furan-2-carbonyl)-6-[4-(3-hydroxyoxetan-3-yl)phenyl]-2-methyl-1,2,3,4-tetrahydroquinoxalin-1-yl]ethan-1-one;

1-[(2S)-4-(furan-2-carbonyl)-2-methyl-6-[4-(1,3,4-oxadiazol-2-yl)phenyl]-1,2,3,4-tetrahydroquinoxalin-1-yl]ethan-1-one;

4-{4-[(2S)-1-acetyl-4-(furan-2-carbonyl)-2-methyl-1,2,3,4-tetrahydroquinoxalin-6-yl]phenyl}-1$\lambda^6$-thiomorpholine-1,1-dione;

{4-[(2S)-1-acetyl-4-(furan-2-carbonyl)-2-methyl-1,2,3,4-tetrahydroquinoxalin-6-yl]phenyl}methanesulfonamide;

1-[(2S)-4-(furan-2-carbonyl)-2-methyl-6-(2-methyl-2H-1,2,3-triazol-4-yl)-1,2,3,4-tetrahydroquinoxalin-1-yl]ethan-1-one;

1-[(2S)-4-(furan-2-carbonyl)-2-methyl-6-(1-methyl-1H-1,2,3-triazol-4-yl)-1,2,3,4-tetrahydroquinoxalin-1-yl]ethan-1-one;

3-{4-[(2S)-1-acetyl-4-(furan-2-carbonyl)-2-methyl-1,2,3,4-tetrahydroquinoxalin-6-yl]phenyl}-1H-pyrazole-5-carboxylic acid;

1-[(2S)-4-(furan-2-carbonyl)-2-methyl-6-[4-(piperazine-1-carbonyl)phenyl]-1,2,3,4-tetrahydroquinoxalin-1-yl]ethan-1-one;

1-[(2S)-4-(furan-2-carbonyl)-6-[4-(2-hydroxyethanesulfonyl)phenyl]-2-methyl-1,2,3,4-tetrahydroquinoxalin-1-yl]ethan-1-one;

2-{4-[(2S)-1-acetyl-4-(furan-2-carbonyl)-2-methyl-1,2,3,4-tetrahydroquinoxalin-6-yl]phenyl}-1$\lambda^6$,2-thiazolidine-1,1-dione;

1-[(2S)-6-[4-(2-aminoethanesulfonyl)phenyl]-4-(furan-2-carbonyl)-2-methyl-1,2,3,4-tetrahydroquinoxalin-1-yl]ethan-1-one;

4-[(2S)-1-acetyl-4-(furan-2-carbonyl)-2-methyl-1,2,3,4-tetrahydroquinoxalin-6-yl]-N-(2-aminoethyl)benzamide;

2-({4-[(2S)-1-acetyl-4-(furan-2-carbonyl)-2-methyl-1,2,3,4-tetrahydroquinoxalin-6-yl]phenyl}methyl)-1$\lambda^6$,2-thiazolidine-1,1-dione;

3-{4-[(2S)-1-acetyl-4-(furan-2-carbonyl)-2-methyl-1,2,3,4-tetrahydroquinoxalin-6-yl]phenoxy}propanenitrile;

1-[(2S)-4-(furan-2-carbonyl)-6-[4-(1H-imidazol-2-yl)phenyl]-2-methyl-1,2,3,4-tetrahydroquinoxalin-1-yl]ethan-1-one;

1-[(2S)-6-(5-amino-1,3,4-thi adi azol-2-yl)-4-(furan-2-carbonyl)-2-methyl-1,2,3,4-tetrahydroquinoxalin-1-yl]ethan-1-one;

1-[(2S)-6-(5-amino-1,3-thiazol-2-yl)-4-(furan-2-carbonyl)-2-methyl-1,2,3,4-tetrahydroquinoxalin-1-yl]ethan-1-one;

1-[(2S)-4-(furan-2-carbonyl)-2-methyl-6-(1,2-thiazol-4-yl)-1,2,3,4-tetrahydroquinoxalin-1-yl]ethan-1-one;

2-{4-[(2S)-1-acetyl-4-(furan-2-carbonyl)-2-methyl-1,2,3,4-tetrahydroquinoxalin-6-yl]benzenesulfonyl}-N,N-dimethylacetamide;

1-[(2S)-4-(furan-2-carbonyl)-2-methyl-6-(1,2-thiazol-5-yl)-1,2,3,4-tetrahydroquinoxalin-1-yl]ethan-1-one;

4-{4-[(2S)-1-acetyl-4-cyclopropanecarbonyl-2-methyl-1,2,3,4-tetrahydroquinoxalin-6-yl]phenyl}-1$\lambda^6$-thiomorpholine-1,1-dione;

4-{4-[(2S)-1,4-dicyclopropanecarbonyl-2-methyl-1,2,3,4-tetrahydroquinoxalin-6-yl]phenyl}-1$\lambda^6$-thiomorpholine-1,1-dione;

1-[(2S)-4-cyclopropanecarbonyl-2-methyl-6-[4-(piperazine-1-carbonyl)phenyl]-1,2,3,4-tetrahydroquinoxalin-1-yl]ethan-1-one;

(2S)-1,4-dicyclopropanecarbonyl-2-methyl-6-[4-(piperazine-1-carbonyl)phenyl]-1,2,3,4-tetrahydroquinoxaline;

2-{4-[(2S)-1-acetyl-4-cyclopropanecarbonyl-2-methyl-1,2,3,4-tetrahydroquinoxalin-6-yl]phenyl}-1$\lambda^6$,2-thiazolidine-1,1-dione;

2-{4-[(2S)-1,4-dicyclopropanecarbonyl-2-methyl-1,2,3,4-tetrahydroquinoxalin-6-yl]phenyl}-1$\lambda^6$,2-thiazolidine-1,1-dione;

1-[(2S)-6-(5-aminopyrazin-2-yl)-4-cyclopropanecarbonyl-2-methyl-1,2,3,4-tetrahydroquinoxalin-1-yl]ethan-1-one;

5-[(2S)-1,4-dicyclopropanecarbonyl-2-methyl-1,2,3,4-tetrahydroquinoxalin-6-yl]pyrazin-2-amine;

1-[(2S)-4-cyclopropanecarbonyl-6-[4-(3-hydroxyoxetan-3-yl)phenyl]-2-methyl-1,2,3,4-tetrahydroquinoxalin-1-yl]ethan-1-one;

3-{4-[(2S)-1,4-dicyclopropanecarbonyl-2-methyl-1,2,3,4-tetrahydroquinoxalin-6-yl]phenyl}oxetan-3-ol;

{4-[(2S)-1-acetyl-4-cyclopropanecarbonyl-2-methyl-1,2,3,4-tetrahydroquinoxalin-6-yl]phenyl}methanesulfonamide;

{4-[(2S)-1,4-dicyclopropanecarbonyl-2-methyl-1,2,3,4-tetrahydroquinoxalin-6-yl]phenyl}methanesulfonamide;

1-[(2S)-6-[4-(2-aminoethanesulfonyl)phenyl]-4-cyclopropanecarbonyl-2-methyl-1,2,3,4-tetrahydroquinoxalin-1-yl]ethan-1-one;

2-{4-[(2S)-1,4-dicyclopropanecarbonyl-2-methyl-1,2,3,4-tetrahydroquinoxalin-6-yl]benzenesulfonyl}ethan-1-amine;

1-[(2S)-4-cyclopropanecarbonyl-6-[4-(2-hydroxyethanesulfonyl)phenyl]-2-methyl-1,2,3,4-tetrahydroquinoxalin-1-yl]ethan-1-one;

2-{4-[(2S)-1,4-dicyclopropanecarbonyl-2-methyl-1,2,3,4-tetrahydroquinoxalin-6-yl]benzenesulfonyl}ethan-1-ol;

4-[(2S)-1-acetyl-4-cyclopropanecarbonyl-2-methyl-1,2,3,4-tetrahydroquinoxalin-6-yl]-N-(2-aminoethyl)benzamide;

N-(2-aminoethyl)-4-[(2S)-1,4-dicyclopropanecarbonyl-2-methyl-1,2,3,4-tetrahydroquinoxalin-6-yl]benzamide;

1-[(2S)-4-cyclopropanecarbonyl-2-methyl-6-(1-methyl-1H-1,2,3-triazol-4-yl)-1,2,3,4-tetrahydroquinoxalin-1-yl]ethan-1-one;

(2S)-1,4-dicyclopropanecarbonyl-2-methyl-6-(1-methyl-1H-1,2,3-triazol-4-yl)-1,2,3,4-tetrahydroquinoxaline;

methyl (2S)-4-cyclopropanecarbonyl-6-[4-(1,1-dioxo-1$\lambda^6$-thiomorpholin-4-yl)phenyl]-2-methyl-1,2,3,4-tetrahydroquinoxaline-1-carboxylate;

methyl (2S)-4-cyclopropanecarbonyl-2-methyl-6-[4-(piperazine-1-carbonyl)phenyl]-1,2,3,4-tetrahydroquinoxaline-1-carboxylate;

methyl (2S)-4-cyclopropanecarbonyl-6-[4-(1,1-dioxo-1λ⁶,2-thiazolidin-2-yl)phenyl]-2-methyl-1,2,3,4-tetrahydroquinoxaline-1-carboxylate;
methyl (2S)-6-(5-aminopyrazin-2-yl)-4-cyclopropanecarbonyl-2-methyl-1,2,3,4-tetrahydroquinoxaline-1-carboxylate;
methyl (2S)-4-cyclopropanecarbonyl-6-[4-(3-hydroxyoxetan-3-yl)phenyl]-2-methyl-1,2,3,4-tetrahydroquinoxaline-1-carboxylate;
methyl (2S)-4-cyclopropanecarbonyl-2-methyl-6-[4-(sulfamoylmethyl)phenyl]-1,2,3,4-tetrahydroquinoxaline-1-carboxylate;
methyl (2S)-6-[4-(2-aminoethanesulfonyl)phenyl]-4-cyclopropanecarbonyl-2-methyl-1,2,3,4-tetrahydroquinoxaline-1-carboxylate;
methyl (2S)-4-cyclopropanecarbonyl-6-[4-(2-hydroxyethanesulfonyl)phenyl]-2-methyl-1,2,3,4-tetrahydroquinoxaline-1-carboxylate;
methyl (2S)-6-{4-[(2-aminoethyl)carbamoyl]phenyl}-4-cyclopropanecarbonyl-2-methyl-1,2,3,4-tetrahydroquinoxaline-1-carboxylate;
methyl (2S)-4-cyclopropanecarbonyl-2-methyl-6-(1-methyl-1H-1,2,3-triazol-4-yl)-1,2,3,4-tetrahydroquinoxaline-1-carboxylate;
propan-2-yl (3S)-4-acetyl-3-methyl-7-(1-methyl-1H-1,2,3-triazol-4-yl)-1,2,3,4-tetrahydroquinoxaline-1-carboxylate;
1-methyl 4-propan-2-yl (2S)-6-[4-(2-hydroxyethanesulfonyl)phenyl]-2-methyl-1,2,3,4-tetrahydroquinoxaline-1,4-dicarboxylate;
propan-2-yl (3S)-4-acetyl-7-[4-(1,1-dioxo-1λ⁶-thiomorpholin-4-yl)phenyl]-3-methyl-1,2,3,4-tetrahydroquinoxaline-1-carboxylate;
propan-2-yl (3S)-4-cyclopropanecarbonyl-7-[4-(1,1-dioxo-1λ⁶-thiomorpholin-4-yl)phenyl]-3-methyl-1,2,3,4-tetrahydroquinoxaline-1-carboxylate;
propan-2-yl (3S)-4-acetyl-7-[4-(1,1-dioxo-1λ⁶,2-thiazolidin-2-yl)phenyl]-3-methyl-1,2,3,4-tetrahydroquinoxaline-1-carboxylate;
propan-2-yl (3S)-4-cyclopropanecarbonyl-7-[4-(1,1-dioxo-1λ⁶,2-thiazolidin-2-yl)phenyl]-3-methyl-1,2,3,4-tetrahydroquinoxaline-1-carboxylate propan-2-yl (3S)-4-acetyl-7-(5-aminopyrazin-2-yl)-3-methyl-1,2,3,4-tetrahydroquinoxaline-1-carboxylate;
propan-2-yl (3S)-7-(5-aminopyrazin-2-yl)-4-cyclopropanecarbonyl-3-methyl-1,2,3,4-tetrahydroquinoxaline-1-carboxylate;
propan-2-yl (3S)-4-acetyl-7-[4-(3-hydroxyoxetan-3-yl)phenyl]-3-methyl-1,2,3,4-tetrahydroquinoxaline-1-carboxylate;
propan-2-yl (3S)-4-cyclopropanecarbonyl-7-[4-(3-hydroxyoxetan-3-yl)phenyl]-3-methyl-1,2,3,4-tetrahydroquinoxaline-1-carboxylate;
propan-2-yl (3S)-4-acetyl-3-methyl-7-[4-(sulfamoylmethyl)phenyl]-1,2,3,4-tetrahydroquinoxaline-1-carboxylate;
propan-2-yl (3S)-4-cyclopropanecarbonyl-3-methyl-7-[4-(sulfamoylmethyl)phenyl]-1,2,3,4-tetrahydroquinoxaline-1-carboxylate;
propan-2-yl (3S)-4-acetyl-7-[4-(2-aminoethanesulfonyl)phenyl]-3-methyl-1,2,3,4-tetrahydroquinoxaline-1-carboxylate;
propan-2-yl (3S)-4-acetyl-7-[4-(2-hydroxyethanesulfonyl)phenyl]-3-methyl-1,2,3,4-tetrahydroquinoxaline-1-carboxylate;
propan-2-yl (3S)-4-cyclopropanecarbonyl-7-[4-(2-hydroxyethane sulfonyl)phenyl]-3-methyl-1,2,3,4-tetrahydroquinoxaline-1-carboxylate;
propan-2-yl (3S)-4-acetyl-7-{4-[(2-aminoethyl)carbamoyl]phenyl}-3-methyl-1,2,3,4-tetrahydroquinoxaline-1-carboxylate;
propan-2-yl (3S)-7-{4-[(2-aminoethyl)carbamoyl]phenyl}-4-cyclopropanecarbonyl-3-methyl-1,2,3,4-tetrahydroquinoxaline-1-carboxylate;
propan-2-yl (3S)-4-cyclopropanecarbonyl-3-methyl-7-(1-methyl-1H-1,2,3-triazol-4-yl)-1,2,3,4-tetrahydroquinoxaline-1-carboxylate;
1-methyl 4-propan-2-yl (2S)-6-[4-(1,1-dioxo-1λ⁶-thiomorpholin-4-yl)phenyl]-2-methyl-1,2,3,4-tetrahydroquinoxaline-1,4-dicarboxylate;
1-methyl 4-propan-2-yl (2S)-6-[4-(1,1-dioxo-1λ⁶,2-thiazolidin-2-yl)phenyl]-2-methyl-1,2,3,4-tetrahydroquinoxaline-1,4-dicarboxylate;
1-methyl 4-propan-2-yl (2S)-6-(5-aminopyrazin-2-yl)-2-methyl-1,2,3,4-tetrahydroquinoxaline-1,4-dicarboxylate;
1-methyl 4-propan-2-yl (2S)-6-[4-(3-hydroxyoxetan-3-yl)phenyl]-2-methyl-1,2,3,4-tetrahydroquinoxaline-1,4-dicarboxylate;
1-methyl 4-propan-2-yl (2S)-2-methyl-6-[4-(sulfamoylmethyl)phenyl]-1,2,3,4-tetrahydroquinoxaline-1,4-dicarboxylate;
1-methyl 4-propan-2-yl (2S)-6-[4-(2-aminoethane sulfonyl)phenyl]-2-methyl-1,2,3,4-tetrahydroquinoxaline-1,4-dicarboxylate;
1-methyl 4-propan-2-yl (2S)-6-{4-[(2-aminoethyl)carbamoyl]phenyl}-2-methyl-1,2,3,4-tetrahydroquinoxaline-1,4-dicarboxylate;
1-methyl 4-propan-2-yl (2S)-2-methyl-6-(1-methyl-1H-1,2,3-triazol-4-yl)-1,2,3,4-tetrahydroquinoxaline-1,4-dicarboxylate;
1-[(2S)-4-(furan-2-carbonyl)-2-methyl-6-(1,3-oxazol-2-yl)-1,2,3,4-tetrahydroquinoxalin-1-yl]ethan-1-one;
N-{4-[(2S)-1-acetyl-4-(furan-2-carbonyl)-2-methyl-1,2,3,4-tetrahydroquinoxalin-6-yl]phenyl}-N-methylmethanesulfonamide;
cyclobutyl (3S)-4-acetyl-7-(4-methanesulfonylphenyl)-3-methyl-1,2,3,4-tetrahydroquinoxaline-1-carboxylate;
butan-2-yl (3S)-4-acetyl-7-(4-methanesulfonylphenyl)-3-methyl-1,2,3,4-tetrahydroquinoxaline-1-carboxylate;
cyclopropylmethyl (3S)-4-acetyl-7-(4-methanesulfonylphenyl)-3-methyl-1,2,3,4-tetrahydroquinoxaline-1-carboxylate;
oxan-4-yl (3S)-4-acetyl-7-(4-methanesulfonylphenyl)-3-methyl-1,2,3,4-tetrahydroquinoxaline-1-carboxylate;
oxetan-3-yl (3S)-4-acetyl-7-(4-methanesulfonylphenyl)-3-methyl-1,2,3,4-tetrahydroquinoxaline-1-carboxylate;
oxan-4-yl (3S)-4-acetyl-3-methyl-7-[4-(piperazine-1-carbonyl)phenyl]-1,2,3,4-tetrahydroquinoxaline-1-carboxylate;
2,4-difluorophenyl (3S)-4-acetyl-7-(1-cyclopropyl-1H-pyrazol-4-yl)-3-methyl-1,2,3,4-tetrahydroquinoxaline-1-carboxylate;
3-methoxyphenyl (3S)-4-acetyl-7-(1-cyclopropyl-1H-pyrazol-4-yl)-3-methyl-1,2,3,4-tetrahydroquinoxaline-1-carboxylate;
3-cyanophenyl (3S)-4-acetyl-7-(1-cyclopropyl-1H-pyrazol-4-yl)-3-methyl-1,2,3,4-tetrahydroquinoxaline-1-carboxylate;
3-fluorophenyl (3S)-4-acetyl-7-(1-cyclopropyl-1H-pyrazol-4-yl)-3-methyl-1,2,3,4-tetrahydroquinoxaline-1-carboxylate;

2,5-difluorophenyl (3S)-4-acetyl-7-(1-cyclopropyl-1H-pyrazol-4-yl)-3-methyl-1,2,3,4-tetrahydroquinoxaline-1-carboxylate;
2-chloro-4-methylphenyl (3S)-4-acetyl-7-(1-cyclopropyl-1H-pyrazol-4-yl)-3-methyl-1,2,3,4-tetrahydroquinoxaline-1-carboxylate;
2-chloro-4-methoxyphenyl (3S)-4-acetyl-7-(1-cyclopropyl-1H-pyrazol-4-yl)-3-methyl-1,2,3,4-tetrahydroquinoxaline-1-carboxylate;
2-methoxy-4-methylphenyl (3S)-4-acetyl-7-(1-cyclopropyl-1H-pyrazol-4-yl)-3-methyl-1,2,3,4-tetrahydroquinoxaline-1-carboxylate;
4-cyano-2-methoxyphenyl (3S)-4-acetyl-7-(1-cyclopropyl-1H-pyrazol-4-yl)-3-methyl-1,2,3,4-tetrahydroquinoxaline-1-carboxylate;
2-methoxy-5-methylphenyl (3S)-4-acetyl-7-(1-cyclopropyl-1H-pyrazol-4-yl)-3-methyl-1,2,3,4-tetrahydroquinoxaline-1-carboxylate;
2-methylphenyl (3S)-4-acetyl-7-(1-cyclopropyl-1H-pyrazol-4-yl)-3-methyl-1,2,3,4-tetrahydroquinoxaline-1-carboxylate;
pyridin-3-yl (3S)-4-acetyl-7-(1-cyclopropyl-1H-pyrazol-4-yl)-3-methyl-1,2,3,4-tetrahydroquinoxaline-1-carboxylate;
6-methylpyridin-3-yl (3S)-4-acetyl-7-(1-cyclopropyl-1H-pyrazol-4-yl)-3-methyl-1,2,3,4-tetrahydroquinoxaline-1-carboxylate;
quinolin-6-yl (3S)-4-acetyl-7-(1-cyclopropyl-1H-pyrazol-4-yl)-3-methyl-1,2,3,4-tetrahydroquinoxaline-1-carboxylate;
2-methylquinolin-6-yl (3S)-4-acetyl-7-(1-cyclopropyl-1H-pyrazol-4-yl)-3-methyl-1,2,3,4-tetrahydroquinoxaline-1-carboxylate;
2-methylpyridin-3-yl (3S)-4-acetyl-7-(1-cyclopropyl-1H-pyrazol-4-yl)-3-methyl-1,2,3,4-tetrahydroquinoxaline-1-carboxylate;
2-methylquinolin-8-yl (3S)-4-acetyl-7-(1-cyclopropyl-1H-pyrazol-4-yl)-3-methyl-1,2,3,4-tetrahydroquinoxaline-1-carboxylate;
2,4-dimethylphenyl (3S)-4-acetyl-7-(1-cyclopropyl-1H-pyrazol-4-yl)-3-methyl-1,2,3,4-tetrahydroquinoxaline-1-carboxylate;
3-methylphenyl (3S)-4-acetyl-7-(1-cyclopropyl-1H-pyrazol-4-yl)-3-methyl-1,2,3,4-tetrahydroquinoxaline-1-carboxylate;
3-chlorophenyl (3S)-4-acetyl-7-(1-cyclopropyl-1H-pyrazol-4-yl)-3-methyl-1,2,3,4-tetrahydroquinoxaline-1-carboxylate;
2-fluorophenyl (3S)-4-acetyl-7-(1-cyclopropyl-1H-pyrazol-4-yl)-3-methyl-1,2,3,4-trahydroquinoxaline-1-carboxylate;
5-methylpyridin-3-yl (3S)-4-acetyl-7-(1-cyclopropyl-1H-pyrazol-4-yl)-3-methyl-1,2,3,4-tetrahydroquinoxaline-1-carboxylate;
2-methoxypyridin-3-yl (3S)-4-acetyl-7-(1-cyclopropyl-1H-pyrazol-4-yl)-3-methyl-1,2,3,4-tetrahydroquinoxaline-1-carboxylate;
3-methoxy-2-methylpyridin-4-yl (3S)-4-acetyl-7-(1-cyclopropyl-1H-pyrazol-4-yl)-3-methyl-1,2,3,4-tetrahydroquinoxaline-1-carboxylate;
2-fluoro-4-methoxyphenyl (3S)-4-acetyl-7-(1-cyclopropyl-1H-pyrazol-4-yl)-3-methyl-1,2,3,4-tetrahydroquinoxaline-1-carboxylate;
2-fluoro-5-methoxyphenyl (3S)-4-acetyl-7-(1-cyclopropyl-1H-pyrazol-4-yl)-3-methyl-1,2,3,4-tetrahydroquinoxaline-1-carboxylate;
isoquinolin-4-yl (3S)-4-acetyl-7-(1-cyclopropyl-1H-pyrazol-4-yl)-3-methyl-1,2,3,4-tetrahydroquinoxaline-1-carboxylate;
5-cyano-2-methoxyphenyl (3S)-4-acetyl-7-(1-cyclopropyl-1H-pyrazol-4-yl)-3-methyl-1,2,3,4-tetrahydroquinoxaline-1-carboxylate;
1,3-benzothiazol-6-yl (3S)-4-acetyl-7-(1-cyclopropyl-1H-pyrazol-4-yl)-3-methyl-1,2,3,4-tetrahydroquinoxaline-1-carboxylate;
2-chloro-4-cyanophenyl (3S)-4-acetyl-7-(1-cyclopropyl-1H-pyrazol-4-yl)-3-methyl-1,2,3,4-tetrahydroquinoxaline-1-carboxylate;
4-chloro-2-methoxyphenyl (3S)-4-acetyl-7-(1-cyclopropyl-1H-pyrazol-4-yl)-3-methyl-1,2,3,4-tetrahydroquinoxaline-1-carboxylate;
5-chloro-2-methoxyphenyl (3S)-4-acetyl-7-(1-cyclopropyl-1H-pyrazol-4-yl)-3-methyl-1,2,3,4-tetrahydroquinoxaline-1-carboxylate;
2-chloro-5-methoxyphenyl (3S)-4-acetyl-7-(1-cyclopropyl-1H-pyrazol-4-yl)-3-methyl-1,2,3,4-tetrahydroquinoxaline-1-carboxylate;
propan-2-yl (3S)-4-acetyl-7-{4-[(3R)-3-aminopyrrolidine-1-carbonyl]phenyl}-3-methyl-1,2,3,4-tetrahydroquinoxaline-1-carboxylate;
propan-2-yl (3S)-4-acetyl-7-(4-{[2-(dimethylamino)ethyl]carbamoyl}phenyl)-3-methyl-1,2,3,4-tetrahydroquinoxaline-1-carboxylate;
propan-2-yl (3S)-4-acetyl-7-{4-[(carbamoylmethyl)carbamoyl]phenyl}-3-methyl-1,2,3,4-tetrahydroquinoxaline-1-carboxylate;
propan-2-yl (3S)-4-acetyl-3-methyl-7-[4-(phenylcarbamoyl)phenyl]-1,2,3,4-tetrahydroquinoxaline-1-carboxylate;
propan-2-yl (3S)-4-acetyl-7-[4-(diethylcarbamoyl)phenyl]-3-methyl-1,2,3,4-tetrahydroquinoxaline-1-carboxylate;
propan-2-yl (3S)-4-acetyl-3-methyl-7-[4-(piperidine-1-carbonyl)phenyl]-1,2,3,4-tetrahydroquinoxaline-1-carboxylate;
propan-2-yl (3S)-4-acetyl-3-methyl-7-[4-(thiomorpholine-4-carbonyl)phenyl]-1,2,3,4-tetrahydroquinoxaline-1-carboxylate;
propan-2-yl (3S)-4-acetyl-7-(4-{[2-(dimethylamino)ethyl](methyl)carbamoyl}phenyl)-3-methyl-1,2,3,4-tetrahydroquinoxaline-1-carboxylate;
propan-2-yl (3S)-4-acetyl-7-{4-[(3R)-3-acetamidopyrrolidine-1-carbonyl]phenyl}-3-methyl-1,2,3,4-tetrahydroquinoxaline-1-carboxylate;
propan-2-yl (3S)-4-acetyl-7-{4-[(3S)-3-acetamidopyrrolidine-1-carbonyl]phenyl}-3-methyl-1,2,3,4-tetrahydroquinoxaline-1-carboxylate;
propan-2-yl (3S)-4-acetyl-7-{4-[(3R)-3-(dimethylamino)pyrrolidine-1-carbonyl]phenyl}-3-methyl-1,2,3,4-tetrahydroquinoxaline-1-carboxylate;
propan-2-yl (3S)-4-acetyl-7-{4-[(3S)-3-(dimethylamino)pyrrolidine-1-carbonyl]phenyl}-3-methyl-1,2,3,4-tetrahydroquinoxaline-1-carboxylate;
propan-2-yl (3S)-4-acetyl-3-methyl-7-[4-(4-methylpiperazine-1-carbonyl)phenyl]-1,2,3,4-tetrahydroquinoxaline-1-carboxylate;
propan-2-yl (3S)-4-acetyl-7-[4-(4-formylpiperazine-1-carbonyl)phenyl]-3-methyl-1,2,3,4-tetrahydroquinoxaline-1-carboxylate;
propan-2-yl (3S)-4-acetyl-7-{4-[4-(methoxycarbonyl)piperazine-1-carbonyl]phenyl}-3-methyl-1,2,3,4-tetrahydroquinoxaline-1-carboxylate;

propan-2-yl (3S)-4-acetyl-3-methyl-7-[4-(3-oxopiperazine-1-carbonyl)phenyl]-1,2,3,4-tetrahydroquinoxaline-1-carboxylate;

propan-2-yl (3S)-4-acetyl-7-[4-(4-acetylpiperazine-1-carbonyl)phenyl]-3-methyl-1,2,3,4-tetrahydroquinoxaline-1-carboxylate;

propan-2-yl (3S)-4-acetyl-7-[4-(4-methanesulfonylpiperazine-1-carbonyl)phenyl]-3-methyl-1,2,3,4-tetrahydroquinoxaline-1-carboxylate;

propan-2-yl (3S)-4-acetyl-7-(4-{[(dimethylcarbamoyl)methyl](methyl)carbamoyl}phenyl)-3-methyl-1,2,3,4-tetrahydroquinoxaline-1-carboxylate;

propan-2-yl (3S)-4-acetyl-3-methyl-7-(4-{methyl[2-(pyrrolidin-1-yl)ethyl]carbamoyl}phenyl)-1,2,3,4-tetrahydroquinoxaline-1-carboxylate;

propan-2-yl (3S)-4-acetyl-3-methyl-7-{4-[methyl(pyridin-2-yl)carbamoyl]phenyl}-1,2,3,4-tetrahydroquinoxaline-1-carboxylate;

propan-2-yl (3S)-4-acetyl-3-methyl-7-[4-(4-methyl-1,4-diazepane-1-carbonyl)phenyl]-1,2,3,4-tetrahydroquinoxaline-1-carboxylate;

propan-2-yl (3S)-4-acetyl-3-methyl-7-(4-{methyl[(methylcarbamoyl)methyl]carbamoyl}phenyl)-1,2,3,4-tetrahydroquinoxaline-1-carboxylate;

propan-2-yl (3S)-7-{4-[(3 aR,6aR)-1-methyl-octahydropyrrolo[3,4-b]pyrrole-5-carbonyl]phenyl}-4-acetyl-3-methyl-1,2,3,4-tetrahydroquinoxaline-1-carboxylate;

propan-2-yl (3S)-4-acetyl-7-{4-[(1R,5 S)-3-{[(tert-butoxy)carbonyl]amino}-8-azabicyclo[3.2.1]octane-8-carbonyl]phenyl}-3-methyl-1,2,3,4-tetrahydroquinoxaline-1-carboxylate;

propan-2-yl (3S)-4-acetyl-3-methyl-7-[4-(piperazine-1-carbonyl)phenyl]-1,2,3,4-tetrahydroquinoxaline-1-carboxylate;

propan-2-yl (3S)-4-cyclopropanecarbonyl-3-methyl-7-[4-(piperazine-1-carbonyl)phenyl]-1,2,3,4-tetrahydroquinoxaline-1-carboxylate;

1-methyl 4-propan-2-yl (2S)-2-methyl-6-[4-(piperazine--carbonyl)phenyl]-1,2,3,4-tetrahydroquinoxaline-1,4-dicarboxylate;

propan-2-yl (3S)-4-cyclopropanecarbonyl-7-(4-{[(dimethylcarbamoyl)methyl](methyl)carbamoyl}phenyl)-3-methyl-1,2,3,4-tetrahydroquinoxaline-1-carboxylate;

1-methyl 4-propan-2-yl (2S)-6-(4-{[(dimethylcarbamoyl)methyl](methyl)carbamoyl}phenyl)-2-methyl-1,2,3,4-tetrahydroquinoxaline-1,4-dicarboxylate;

propan-2-yl (3S)-4-cyclopropanecarbonyl-3-methyl-7-(4-{methyl[(methylcarbamoyl)methyl]carbamoyl}phenyl)-1,2,3,4-tetrahydroquinoxaline-1-carboxylate;

1-methyl 4-propan-2-yl (2S)-2-methyl-6-(4-{methyl[(methylcarbamoyl)methyl]carbamoyl}phenyl)-1,2,3,4-tetrahydroquinoxaline-1,4-dicarboxylate;

propan-2-yl (3S)-4-cyclopropanecarbonyl-7-{4-[(3R)-3-(dimethylamino)pyrrolidine-1-carbonyl]phenyl}-3-methyl-1,2,3,4-tetrahydroquinoxaline-1-carboxylate;

1-methyl 4-propan-2-yl (2S)-6-{4-[(3R)-3-(dimethylamino)pyrrolidine-1-carbonyl]phenyl}-2-methyl-1,2,3,4-tetrahydroquinoxaline-1,4-dicarboxylate;

propan-2-yl (3S)-4-cyclopropanecarbonyl-7-{4-[(3S)-3-(dimethylamino)pyrrolidine-1-carbonyl]phenyl}-3-methyl-1,2,3,4-tetrahydroquinoxaline-1-carboxylate;

1-methyl 4-propan-2-yl (2S)-6-{4-[(3S)-3-(dimethylamino)pyrrolidine-1-carbonyl]phenyl}-2-methyl-1,2,3,4-tetrahydroquinoxaline-1,4-dicarboxylate;

propan-2-yl (3S)-4-cyclopropanecarbonyl-7-{4-[(3R)-3-acetamidopyrrolidine-1-carbonyl]phenyl}-3-methyl-1,2,3,4-tetrahydroquinoxaline-1-carboxylate;

1-methyl 4-propan-2-yl (2S)-6-{4-[(3R)-3-acetamidopyrrolidine-1-carbonyl]phenyl}-2-methyl-1,2,3,4-tetrahydroquinoxaline-1,4-dicarboxylate;

propan-2-yl (3S)-4-cyclopropanecarbonyl-7-{4-[(3S)-3-acetamidopyrrolidine-1-carbonyl]phenyl}-3-methyl-1,2,3,4-tetrahydroquinoxaline-1-carboxylate;

1-methyl 4-propan-2-yl (2S)-6-{4-[(3S)-3-acetamidopyrrolidine-1-carbonyl]phenyl}-2-methyl-1,2,3,4-tetrahydroquinoxaline-1,4-dicarboxylate;

propan-2-yl (3S)-4-cyclopropanecarbonyl-7-[4-(4-methanesulfonylpiperazine-1-carbonyl)phenyl]-3-methyl-1,2,3,4-tetrahydroquinoxaline-1-carboxylate;

1-methyl 4-propan-2-yl (2S)-6-[4-(4-methanesulfonylpiperazine-1-carbonyl)phenyl]-2-methyl-1,2,3,4-tetrahydroquinoxaline-1,4-dicarboxylate;

propan-2-yl (3S)-4-cyclopropanecarbonyl-7-{4-[(3S)-3-hydroxypyrrolidine-1-carbonyl]phenyl}-3-methyl-1,2,3,4-tetrahydroquinoxaline-1-carboxylate;

1-methyl 4-propan-2-yl (2S)-6-{4-[(3S)-3-hydroxypyrrolidine-1-carbonyl]phenyl}-2-methyl-1,2,3,4-tetrahydroquinoxaline-1,4-dicarboxylate;

propan-2-yl (3S)-4-cyclopropanecarbonyl-7-{4-[(3R)-3-hydroxypyrrolidine-1-carbonyl]phenyl}-3-methyl-1,2,3,4-tetrahydroquinoxaline-1-carboxylate;

1-methyl 4-propan-2-yl (2S)-6-{4-[(3R)-3-hydroxypyrrolidine-1-carbonyl]phenyl}-2-methyl-1,2,3,4-tetrahydroquinoxaline-1,4-dicarboxylate;

propan-2-yl (3S)-4-cyclopropanecarbonyl-7-[4-(3-hydroxyazetidine-1-carbonyl)phenyl]-3-methyl-1,2,3,4-tetrahydroquinoxaline-1-carboxylate;

1-methyl 4-propan-2-yl (2S)-6-[4-(3-hydroxyazetidine-1-carbonyl)phenyl]-2-methyl-1,2,3,4-tetrahydroquinoxaline-1,4-dicarboxylate;

propan-2-yl (3S)-4-acetyl-7-{4-[(3S)-3-hydroxypyrrolidine-1-carbonyl]phenyl}-3-methyl-1,2,3,4-tetrahydroquinoxaline-1-carboxylate;

propan-2-yl (3S)-4-acetyl-7-{4-[(3R)-3-hydroxypyrrolidine-1-carbonyl]phenyl}-3-methyl-1,2,3,4-tetrahydroquinoxaline-1-carboxylate;

propan-2-yl (3S)-4-acetyl-7-[4-(3-hydroxyazetidine-1-carbonyl)phenyl]-3-methyl-1,2,3,4-tetrahydroquinoxaline-1-carboxylate;

1-methyl 4-propan-2-yl (2S)-2-methyl-6-{4-[(1,3-oxazol-2-ylmethyl)carbamoyl]phenyl}-1,2,3,4-tetrahydroquinoxaline-1,4-dicarboxylate;

propan-2-yl (3S)-4-acetyl-3-methyl-7-{4-[(1,3-oxazol-2-ylmethyl)carbamoyl]phenyl}-1,2,3,4-tetrahydroquinoxaline-1-carboxylate;

propan-2-yl (3S)-4-cyclopropanecarbonyl-3-methyl-7-{4-[(1,3-oxazol-2-ylmethyl)carbamoyl]phenyl}-1,2,3,4-tetrahydroquinoxaline-1-carboxylate;

propan-2-yl (3S)-4-acetyl-7-[4-(3-aminopyrrolidine-1-carbonyl)phenyl]-3-methyl-1,2,3,4-tetrahydroquinoxaline-1-carboxylate;

propan-2-yl (3S)-4-acetyl-7-{4-[(3R)-3-aminopyrrolidine-1-carbonyl]phenyl}-3-methyl-1,2,3,4-tetrahydroquinoxaline-1-carboxylate;

propan-2-yl (3S)-4-acetyl-7-{4-[(3S)-3-aminopyrrolidine-1-carbonyl]phenyl}-3-methyl-1,2,3,4-tetrahydroquinoxaline-1-carboxylate;

propan-2-yl (3S)-4-acetyl-7-{4-[(3R)-3-aminopiperidine-1-carbonyl]phenyl}-3-methyl-1,2,3,4-tetrahydroquinoxaline-1-carboxylate;

propan-2-yl (3S)-4-acetyl-7-[4-(4-aminopiperidine-1-carbonyl)phenyl]-3-methyl-1,2,3,4-tetrahydroquinoxaline-1-carboxylate;

propan-2-yl (3S)-4-acetyl-7-{4-[2-(aminomethyl)piperidine-1-carbonyl]phenyl}-3-methyl-1,2,3,4-tetrahydroquinoxaline-1-carboxylate;

propan-2-yl (3S)-4-acetyl-7-{4-[(2R)-2-(aminomethyl)pyrrolidine-1-carbonyl]phenyl}-3-methyl-1,2,3,4-tetrahydroquinoxaline-1-carboxylate;

propan-2-yl (3S)-4-acetyl-7-{4-[(1 S,4 S)-2,5-diazabicyclo[2.2.1]heptane-2-carbonyl]phenyl}-3-methyl-1,2,3,4-tetrahydroquinoxaline-1-carboxylate;

propan-2-yl (3S)-4-acetyl-7-(4-{[(1R,3 S,5S)-8-azabicyclo[3.2.1]octan-3-yl]carbamoyl}phenyl)-3-methyl-1,2,3,4-tetrahydroquinoxaline-1-carboxylate;

propan-2-yl (3S)-4-acetyl-7-{1-[(1,1-dioxo-1$\lambda^6$-thian-4-yl)methyl]-1H-pyrazol-4-yl}-3-methyl-1,2,3,4-tetrahydroquinoxaline-1-carboxylate;

propan-2-yl (3S)-4-acetyl-7-(1-{[cyclopropyl(methyl)carbamoyl]methyl}-1H-pyrazol-4-yl)-3-methyl-1,2,3,4-tetrahydroquinoxaline-1-carboxylate;

propan-2-yl (3S)-4-acetyl-7-{1-[2-(1,1-dioxo-1$\lambda^6$,2-thiazolidin-2-yl)ethyl]-1H-pyrazol-4-yl}-3-methyl-1,2,3,4-tetrahydroquinoxaline-1-carboxylate;

propan-2-yl (3S)-4-acetyl-7-{1-[2-(1H-imidazol-1-yl)ethyl]-1H-pyrazol-4-yl}-3-methyl-1,2,3,4-tetrahydroquinoxaline-1-carboxylate;

propan-2-yl (3S)-4-acetyl-3-methyl-7-{1-[2-oxo-2-(piperidin-1-yl)ethyl]-1H-pyrazol-4-yl}-1,2,3,4-tetrahydroquinoxaline-1-carboxylate;

propan-2-yl (3S)-4-acetyl-7-(1-{[3-(hydroxymethyl)oxetan-3-yl]methyl}-1H-pyrazol-4-yl)-3-methyl-1,2,3,4-tetrahydroquinoxaline-1-carboxylate;

propan-2-yl (3S)-4-acetyl-7-[1-(1H-imidazol-4-ylmethyl)-1H-pyrazol-4-yl]-3-methyl-1,2,3,4-tetrahydroquinoxaline-1-carboxylate;

propan-2-yl (3S)-4-acetyl-7-{1-[(dimethyl-1,2-oxazol-4-yl)methyl]-1H-pyrazol-4-yl}-3-methyl-1,2,3,4-tetrahydroquinoxaline-1-carboxylate;

propan-2-yl (3S)-4-acetyl-7-[1-(cyclobutylmethyl)-1H-pyrazol-4-yl]-3-methyl-1,2,3,4-tetrahydroquinoxaline-1-carboxylate;

propan-2-yl (3S)-4-acetyl-3-methyl-7-[1-(2,2,2-trifluoroethyl)-1H-pyrazol-4-yl]-1,2,3,4-tetrahydroquinoxaline-1-carboxylate;

propan-2-yl (3S)-4-acetyl-3-methyl-7-{1-[(3-methyloxetan-3-yl)methyl]-1H-pyrazol-4-yl}-1,2,3,4-tetrahydroquinoxaline-1-carboxylate;

propan-2-yl (3S)-4-acetyl-7-[1-(2-carbamoylethyl)-1H-pyrazol-4-yl]-3-methyl-1,2,3,4-tetrahydroquinoxaline-1-carboxylate;

propan-2-yl (3S)-4-acetyl-7-[1-(cyanomethyl)-1H-pyrazol-4-yl]-3-methyl-1,2,3,4-tetrahydroquinoxaline-1-carboxylate;

propan-2-yl (3S)-4-acetyl-3-methyl-7-[1-(oxan-4-ylmethyl)-1H-pyrazol-4-yl]-1,2,3,4-tetrahydroquinoxaline-1-carboxylate;

propan -2-yl (3S)-4-cyclopropanecarbonyl-7-{1-[(1,1-dioxo-1$\lambda^6$-thian-4-yl)methyl]-1H-pyrazol-4-yl}-3-methyl-1,2,3,4-tetrahydroquinoxaline-1-carboxylate;

propan-2-yl (3S)-4-cyclopropanecarbonyl-7-(1-{[cyclopropyl(methyl)carbamoyl]methyl}-1H-pyrazol-4-yl)-3-methyl-1,2,3,4-tetrahydroquinoxaline-1-carboxylate;

propan-2-yl (3S)-4-cyclopropanecarbonyl-7-{1-[2-(1,1-dioxo-1$\lambda^6$,2-thiazolidin-2-yl)ethyl]-1H-pyrazol-4-yl}-3-methyl-1,2,3,4-tetrahydroquinoxaline-1-carboxylate;

propan-2-yl (3S)-4-cyclopropanecarbonyl-7-{1-[2-(1H-imidazol-1-yl)ethyl]-1H-pyrazol-4-yl}-3-methyl-1,2,3,4-tetrahydroquinoxaline-1-carboxylate;

propan-2-yl (3S)-4-cyclopropanecarbonyl-7-[1-(2-methanesulfonamidoethyl)-1H-pyrazol-4-yl]-3-methyl-1,2,3,4-tetrahydroquinoxaline-1-carboxylate;

propan-2-yl (3S)-4-cyclopropanecarbonyl-3-methyl-7-{1-[2-oxo-2-(piperidin-1-yl)ethyl]-1H-pyrazol-4-yl}-1,2,3,4-tetrahydroquinoxaline-1-carboxylate;

propan-2-yl (3S)-4-cyclopropanecarbonyl-7-(1-{[3-(hydroxymethyl)oxetan-3-yl]methyl}-1H-pyrazol-4-yl)-3-methyl-1,2,3,4-tetrahydroquinoxaline-1-carboxylate;

propan-2-yl (3S)-4-cyclopropanecarbonyl-7-[1-(1H-imidazol-4-ylmethyl)-1H-pyrazol-4-yl]-3-methyl-1,2,3,4-tetrahydroquinoxaline-1-carboxylate;

propan-2-yl (3S)-4-cyclopropanecarbonyl-7-{1-[(dimethyl-1,2-oxazol-4-yl)methyl]-1H-pyrazol-4-yl}-3-methyl-1,2,3,4-tetrahydroquinoxaline-1-carboxylate;

propan-2-yl (3S)-7-[1-(cyclobutylmethyl)-1H-pyrazol-4-yl]-4-cyclopropanecarbonyl-3-methyl-1,2,3,4-tetrahydroquinoxaline-1-carboxylate;

propan-2-yl (3S)-4-cyclopropanecarbonyl-3-methyl-7-[1-(2,2,2-trifluoroethyl)-1H-pyrazol-4-yl]-1,2,3,4-tetrahydroquinoxaline-1-carboxylate;

propan-2-yl (3S)-4-cyclopropanecarbonyl-3-methyl-7-{1-[(3-methyloxetan-3-yl)methyl]-1H-pyrazol-4-yl}-1,2,3,4-tetrahydroquinoxaline-1-carboxylate;

propan-2-yl (3S)-7-[1-(2-carbamoylethyl)-1H-pyrazol-4-yl]-4-cyclopropanecarbonyl-3-methyl-1,2,3,4-tetrahydroquinoxaline-1-carboxylate;

propan-2-yl (3S)-7-[1-(cyanomethyl)-1H-pyrazol-4-yl]-4-cyclopropanecarbonyl-3-methyl-1,2,3,4-tetrahydroquinoxaline-1-carboxylate;

propan-2-yl (3S)-4-cyclopropanecarbonyl-3-methyl-7-[1-(oxan-4-ylmethyl)-1H-pyrazol-4-yl]-1,2,3,4-tetrahydroquinoxaline-1-carboxylate;

1-methyl 4-propan-2-yl (2S)-6-{1-[(1,1-dioxo-1$\lambda^6$-thian-4-yl)methyl]-1H-pyrazol-4-yl}-2-methyl-1,2,3,4-tetrahydroquinoxaline-1,4-dicarboxylate;

1-methyl 4-propan-2-yl (2S)-6-(1-{[cyclopropyl(methyl)carbamoyl]methyl}-1H-pyrazol-4-yl)-2-methyl-1,2,3,4-tetrahydroquinoxaline-1,4-dicarboxylate;

1-methyl 4-propan-2-yl (2S)-6-{1-[2-(1,1-dioxo-1$\lambda^6$,2-thiazolidin-2-yl)ethyl]-1H-pyrazol-4-yl}-2-methyl-1,2,3,4-tetrahydroquinoxaline-1,4-dicarboxylate;

1-methyl 4-propan-2-yl (2S)-6-{1-[2-(1H-imidazol-1-yl)ethyl]-1H-pyrazol-4-yl}-2-methyl-1,2,3,4-tetrahydroquinoxaline-1,4-dicarboxylate;

1-methyl 4-propan-2-yl (2S)-2-methyl-6-{1-[2-(2-oxopyrrolidin-1-yl)ethyl]-1H-pyrazol-4-yl}-1,2,3,4-tetrahydroquinoxaline-1,4-dicarboxylate;

1-methyl 4-propan-2-yl (2S)-2-methyl-6-{1-[2-oxo-2-(piperidin-1-yl)ethyl]-1H-pyrazol-4-yl}-1,2,3,4-tetrahydroquinoxaline-1,4-dicarboxylate;

1-methyl 4-propan-2-yl (2S)-6-(1-{[3-(hydroxymethyl)oxetan-3-yl]methyl}-1H-pyrazol-4-yl)-2-methyl-1,2,3,4-tetrahydroquinoxaline-1,4-dicarboxylate;

1-methyl 4-propan-2-yl (2S)-6-[1-(1H-imidazol-4-ylmethyl)-1H-pyrazol-4-yl]-2-methyl-1,2,3,4-tetrahydroquinoxaline-1,4-dicarboxylate;

1-methyl 4-propan-2-yl (2S)-2-methyl-6-[1-(pyrimidin-5-ylmethyl)-1H-pyrazol-4-yl]-1,2,3,4-tetrahydroquinoxaline-1,4-dicarboxylate;

1-methyl 4-propan-2-yl (2S)-2-methyl-6-[1-(pyrazin-2-ylmethyl)-1H-pyrazol-4-yl]-1,2,3,4-tetrahydroquinoxaline-1,4-dicarboxylate;

1-methyl 4-propan-2-yl (2S)-6-{1-[(dimethyl-1,2-oxazol-4-yl)methyl]-1H-pyrazol-4-yl}-2-methyl-1,2,3,4-tetrahydroquinoxaline-1,4-dicarboxylate;

1-methyl 4-propan-2-yl (2S)-6-[1-(cyclobutylmethyl)-1H-pyrazol-4-yl]-2-methyl-1,2,3,4-tetrahydroquinoxaline-1,4-dicarboxylate;

1-methyl 4-propan-2-yl (2S)-2-methyl-6-[1-(2,2,2-trifluoroethyl)-1H-pyrazol-4-yl]-1,2,3,4-tetrahydroquinoxaline-1,4-dicarboxylate;

1-methyl 4-propan-2-yl (2S)-2-methyl-6-{1-[(3-methyloxetan-3-yl)methyl]-1H-pyrazol-4-yl}-1,2,3,4-tetrahydroquinoxaline-1,4-dicarboxylate;

1-methyl 4-propan-2-yl (2S)-6-[1-(2-carbamoylethyl)-1H-pyrazol-4-yl]-2-methyl-1,2,3,4-tetrahydroquinoxaline-1,4-dicarboxylate;

1-methyl 4-propan-2-yl (2S)-6-[1-(cyanomethyl)-1H-pyrazol-4-yl]-2-methyl-1,2,3,4-tetrahydroquinoxaline-1,4-dicarboxylate;

1-methyl 4-propan-2-yl (2S)-2-methyl-6-[1-(pyridin-4-ylmethyl)-1H-pyrazol-4-yl]-1,2,3,4-tetrahydroquinoxaline-1,4-dicarboxylate;

1-methyl 4-propan-2-yl (2S)-2-methyl-6-[1-(oxan-4-ylmethyl)-1H-pyrazol-4-yl]-1,2,3,4-tetrahydroquinoxaline-1,4-dicarboxylate;

propan-2-yl (3S)-4-acetyl-3-methyl-7-[1-(oxetan-3-ylmethyl)-1H-pyrazol-4-yl]-1,2,3,4-tetrahydroquinoxaline-1-carboxylate;

propan-2-yl (3S)-4-cyclopropanecarbonyl-3-methyl-7-[1-(oxetan-3-ylmethyl)-1H-pyrazol-4-yl]-1,2,3,4-tetrahydroquinoxaline-1-carboxylate;

1-methyl 4-propan-2-yl (2S)-2-methyl-6-[1-(oxetan-3-ylmethyl)-1H-pyrazol-4-yl]-1,2,3,4-tetrahydroquinoxaline-1,4-dicarboxylate;

1-methyl 4-propan-2-yl (2S)-6-{1-[2-(dimethyl amino)ethyl]-1H-pyrazol-4-yl}-2-methyl-1,2,3,4-tetrahydroquinoxaline-1,4-dicarboxylate;

propan-2-yl (3S)-4-cyclopropanecarbonyl-7-{1-[2-(dimethylamino)ethyl]-1H-pyrazol-4-yl}-3-methyl-1,2,3,4-tetrahydroquinoxaline-1-carboxylate;

1-[(2S)-4-cyclopropanecarbonyl-2-methyl-6-[1-(propan-2-yl)-1H-pyrazol-4-yl]-1,2,3,4-tetrahydroquinoxalin-1-yl]ethan-1-one;

2-{4-[(2S)-1-acetyl-4-cyclopropanecarbonyl-2-methyl-1,2,3,4-tetrahydroquinoxalin-6-yl]-1H-pyrazol-1-yl}-2-methylpropanamide;

1-[(2S)-4-cyclopropanecarbonyl-6-{1-[(3-fluorooxetan-3-yl)methyl]-1H-pyrazol-4-yl}-2-methyl-1,2,3,4-tetrahydroquinoxalin-1-yl]ethan-1-one;

3-{4-[(2S)-1-acetyl-4-cyclopropanecarbonyl-2-methyl-1,2,3,4-tetrahydroquinoxalin-6-yl]-1H-pyrazol-1-yl}propanenitrile;

1-[(2S)-4-cyclopropanecarbonyl-6-[1-(2,2-difluoroethyl)-1H-pyrazol-4-yl]-2-methyl-1,2,3,4-tetrahydroquinoxalin-1-yl]ethan-1-one;

1-[(2S)-4-cyclopropanecarbonyl-2-methyl-6-{1-[(1-methyl-1H-pyrazol-5-yl)methyl]-1H-pyrazol-4-yl}-1,2,3,4-tetrahydroquinoxalin-1-yl]ethan-1-one;

propan-2-yl (3S)-4-acetyl-3-methyl-7-[1-(propan-2-yl)-1H-pyrazol-4-yl]-1,2,3,4-tetrahydroquinoxaline-1-carboxylate;

propan-2-yl (3S)-4-acetyl-3-methyl-7-{1-[2-(morpholin-4-yl)-2-oxoethyl]-1H-pyrazol-4-yl}-1,2,3,4-tetrahydroquinoxaline-1-carboxylate;

2-{4-[(2S)-1-acetyl-4-cyclopropanecarbonyl-2-methyl-1,2,3,4-tetrahydroquinoxalin-6-yl]-1H-pyrazol-1-yl}acetamide;

1-[(2S)-6-[1-(cyclobutylmethyl)-1H-pyrazol-4-yl]-4-cyclopropanecarbonyl-2-methyl-1,2,3,4-tetrahydroquinoxalin-1-yl]ethan-1-one;

1-[(2S)-4-cyclopropanecarbonyl-2-methyl-6-[1-(oxan-4-ylmethyl)-1H-pyrazol-4-yl]-1,2,3,4-tetrahydroquinoxalin-1-yl]ethan-1-one;

2-{4-[(2S)-1-acetyl-4-cyclopropanecarbonyl-2-methyl-1,2,3,4-tetrahydroquinoxalin-6-yl]-1H-pyrazol-1-yl}-N-cyclopropyl-N-methylacetamide;

2-(2-{4-[(2S)-1-acetyl-4-cyclopropanecarbonyl-2-methyl-1,2,3,4-tetrahydroquinoxalin-6-yl]-1H-pyrazol-1-yl}ethyl)-1$\lambda^6$,2-thiazolidine-1,1-dione;

1-(2-{4-[(2S)-1-acetyl-4-cyclopropanecarbonyl-2-methyl-1,2,3,4-tetrahydroquinoxalin-6-yl]-1H-pyrazol-1-yl}ethyl)pyrrolidin-2-one;

2-{4-[(2S)-1-acetyl-4-cyclopropanecarbonyl-2-methyl-1,2,3,4-tetrahydroquinoxalin-6-yl]-1H-pyrazol-1-yl}-1-(piperidin-1-yl)ethan-1-one;

1-[(2S)-4-cyclopropanecarbonyl-6-(1-{[3-(hydroxymethyl)oxetan-3-yl]methyl}-1H-pyrazol-4-yl)-2-methyl-1,2,3,4-tetrahydroquinoxalin-1-yl]ethan-1-one;

1-[(2S)-4-cyclopropanecarbonyl-2-methyl-6-[1-(1,2-oxazol-5-ylmethyl)-1H-pyrazol-4-yl]-1,2,3,4-tetrahydroquinoxalin-1-yl]ethan-1-one;

propan-2-yl (3S)-4-acetyl-7-{1-[(ethylcarbamoyl)methyl]-1H-pyrazol-4-yl}-3-methyl-1,2,3,4-tetrahydroquinoxaline-1-carboxylate;

propan-2-yl (3S)-4-acetyl-3-methyl-7-{1-[(5-methyl-1,2-oxazol-3-yl)methyl]-1H-pyrazol-4-yl}-1,2,3,4-tetrahydroquinoxaline-1-carboxylate;

propan-2-yl (3S)-4-acetyl-7-[1-(2-fluoroethyl)-1H-pyrazol-4-yl]-3-methyl-1,2,3,4-tetrahydroquinoxaline-1-carboxylate;

propan-2-yl (3S)-4-acetyl-7-{1-[2-(azetidin-1-yl)-2-oxoethyl]-1H-pyrazol-4-yl}-3-methyl-1,2,3,4-tetrahydroquinoxaline-1-carboxylate;

1-[(2S)-4-cyclopropanecarbonyl-2-methyl-6-{1-[(5-methyl-1,2,4-oxadiazol-3-yl)methyl]-1H-pyrazol-4-yl}-1,2,3,4-tetrahydroquinoxalin-1-yl]ethan-1-one;

1-[(2S)-4-cyclopropanecarbonyl-2-methyl-6-{1-[(5-methyl-1,2-oxazol-3-yl)methyl]-1H-pyrazol-4-yl}-1,2,3,4-tetrahydroquinoxalin-1-yl]ethan-1-one;

1-[(2S)-4-cyclopropanecarbonyl-2-methyl-6-[1-(2-methylpropyl)-1H-pyrazol-4-yl]-1,2,3,4-tetrahydroquinoxalin-1-yl]ethan-1-one;

1-[(2S)-4-cyclopropanecarbonyl-6-[1-(2-fluoroethyl)-1H-pyrazol-4-yl]-2-methyl-1,2,3,4-tetrahydroquinoxalin-1-yl]ethan-1-one;

2-{4-[(2S)-1-acetyl-4-cyclopropanecarbonyl-2-methyl-1,2,3,4-tetrahydroquinoxalin-6-yl]-1H-pyrazol-1-yl}-1-(azetidin-1-yl)ethan-1-one;

1-[(2S)-4-cyclopropanecarbonyl-6-[1-(3-hydroxypropyl)-1H-pyrazol-4-yl]-2-methyl-1,2,3,4-tetrahydroquinoxalin-1-yl]ethan-1-one;

3-{4-[(2S)-1-acetyl-4-cyclopropanecarbonyl-2-methyl-1,2,3,4-tetrahydroquinoxalin-6-yl]-1H-pyrazol-1-yl}propanamide;

2-{4-[(2S)-1-acetyl-4-cyclopropanecarbonyl-2-methyl-1,2,3,4-tetrahydroquinoxalin-6-yl]-1H-pyrazol-1-yl}acetonitrile;

2-{4-[(2S)-1-acetyl-4-cyclopropanecarbonyl-2-methyl-1,2,3,4-tetrahydroquinoxalin-6-yl]-1H-pyrazol-1-yl}acetic acid;

propan-2-yl (3S)-4-acetyl-3-methyl-7-{1-[(4-methyl-1,2,5-oxadiazol-3-yl)methyl]-1H-pyrazol-4-yl}-1,2,3,4-tetrahydroquinoxaline-1-carboxylate;

propan-2-yl (3S)-4-acetyl-7-{1-[(2,2-difluorocyclopropyl)methyl]-1H-pyrazol-4-yl}-3-methyl-1,2,3,4-tetrahydroquinoxaline-1-carboxylate;
propan-2-yl (3S)-4-acetyl-7-[1-(2-cyanoethyl)-1H-pyrazol-4-yl]-3-methyl-1,2,3,4-tetrahydroquinoxaline-1-carboxylate;
propan-2-yl (3S)-4-acetyl-3-methyl-7-{1-[(1-methyl-1H-pyrazol-5-yl)methyl]-1H-pyrazol-4-yl}-1,2,3,4-tetrahydroquinoxaline-1-carboxylate;
2-{4-[(2S)-1-acetyl-4-cyclopropanecarbonyl-2-methyl-1,2,3,4-tetrahydroquinoxalin-6-yl]-1H-pyrazol-1-yl}-N-ethylacetamide;
1-[(2S)-4-cyclopropanecarbonyl-2-methyl-6-{1-[(1-methyl-1H-pyrazol-3-yl)methyl]-1H-pyrazol-4-yl}-1,2,3,4-tetrahydroquinoxalin-1-yl]ethan-1-one;
2-{4-[(2S)-1-acetyl-4-cyclopropanecarbonyl-2-methyl-1,2,3,4-tetrahydroquinoxalin-6-yl]-1H-pyrazol-1-yl}-N,N-dimethylacetamide;
4-({4-[(2S)-1-acetyl-4-cyclopropanecarbonyl-2-methyl-1,2,3,4-tetrahydroquinoxalin-6-yl]-1H-pyrazol-1-yl}methyl)-1λ$^6$-thiane-1,1-dione;
propan-2-yl (3S)-4-acetyl-3-methyl-7-{1-[(5-methyl-1,2,4-oxadiazol-3-yl)methyl]-1H-pyrazol-4-yl}-1,2,3,4-tetrahydroquinoxaline-1-carboxylate;
1-[(2S)-4-cyclopropanecarbonyl-2-methyl-6-[1-(1,3-thiazol-5-ylmethyl)-1H-pyrazol-4-yl]-1,2,3,4-tetrahydroquinoxalin-1-yl]ethan-1-one;
propan-2-yl (3S)-4-acetyl-3-methyl-7-{1-[(3R)-pyrrolidin-3-ylmethyl]-1H-pyrazol-4-yl}-1,2,3,4-tetrahydroquinoxaline-1-carboxylate;
propan-2-yl (3S)-4-acetyl-3-methyl-7-{1-[(3S)-pyrrolidin-3-ylmethyl]-1H-pyrazol-4-yl}-1,2,3,4-tetrahydroquinoxaline-1-carboxylate;
propan-2-yl (3S)-4-cyclopropanecarbonyl-3-methyl-7-{1-[(3R)-pyrrolidin-3-ylmethyl]-1H-pyrazol-4-yl}-1,2,3,4-tetrahydroquinoxaline-1-carboxylate;
propan-2-yl (3S)-4-cyclopropanecarbonyl-3-methyl-7-{1-[(3S)-pyrrolidin-3-ylmethyl]-1H-pyrazol-4-yl}-1,2,3,4-tetrahydroquinoxaline-1-carboxylate;
1-methyl 4-propan-2-yl (2S)-2-methyl-6-{1-[(3R)-pyrrolidin-3-ylmethyl]-1H-pyrazol-4-yl}-1,2,3,4-tetrahydroquinoxaline-1,4-dicarboxylate;
1-methyl 4-propan-2-yl (2S)-2-methyl-6-{1-[(3S)-pyrrolidin-3-ylmethyl]-1H-pyrazol-4-yl}-1,2,3,4-tetrahydroquinoxaline-1,4-dicarboxylate;
1-[(3S)-4-acetyl-3-methyl-1,2,3,4-tetrahydroquinoxalin-1-yl]-3-(dimethylamino)propan-1-one;
1-[(2S)-4-benzoyl-2-methyl-1,2,3,4-tetrahydroquinoxalin-1-yl]ethan-1-one;
1-[(3S)-4-acetyl-3-methyl-1,2,3,4-tetrahydroquinoxalin-1-yl]-2-phenylethan-1-one;
1-[(3S)-4-acetyl-3-methyl-1,2,3,4-tetrahydroquinoxalin-1-yl]-3-phenylpropan-1-one;
1-[(2S)-4-cyclohexanecarbonyl-2-methyl-1,2,3,4-tetrahydroquinoxalin-1-yl]ethan-1-one;
1-[(3S)-4-acetyl-3-methyl-1,2,3,4-tetrahydroquinoxalin-1-yl]-2-(4-methoxyphenyl)ethan-1-one;
1-[(3S)-4-acetyl-3-methyl-1,2,3,4-tetrahydroquinoxalin-1-yl]-2-(3-methoxyphenyl)ethan-1-one;
1-[(3S)-4-acetyl-3-methyl-1,2,3,4-tetrahydroquinoxalin-1-yl]-3-methoxypropan-1-one;
1-[(2S)-4-(2H-1,3-benzodioxole-5-carbonyl)-2-methyl-1,2,3,4-tetrahydroquinoxalin-1-yl]ethan-1-one;
1-[(2S)-4-(2-methoxybenzoyl)-2-methyl-1,2,3,4-tetrahydroquinoxalin-1-yl]ethan-1-one;
1-[(2S)-2-methyl-4-(4-phenylbenzoyl)-1,2,3,4-tetrahydroquinoxalin-1-yl]ethan-1-one;
1-[(2S)-2-methyl-4-(pyridine-4-carbonyl)-1,2,3,4-tetrahydroquinoxalin-1-yl]ethan-1-one;
1-[(2S)-2-methyl-4-(2-methyl-1,3-thiazole-4-carbonyl)-1,2,3,4-tetrahydroquinoxalin-1-yl]ethan-1-one;
1-[(3S)-4-acetyl-3-methyl-1,2,3,4-tetrahydroquinoxalin-1-yl]-2-(oxan-4-yl)ethan-1-one
1-[(3S)-4-acetyl-3-methyl-1,2,3,4-tetrahydroquinoxalin-1-yl]-2-(4-phenylphenyl)ethan-1-one;
1-[(3S)-4-acetyl-3-methyl-1,2,3,4-tetrahydroquinoxalin-1-yl]-3-methylbutan-1-one;
1-[(3S)-4-acetyl-3-methyl-1,2,3,4-tetrahydroquinoxalin-1-yl]-2-(2H-1,3-benzodioxol-5-yl)ethan-1-one;
1-[(3S)-4-acetyl-3-methyl-1,2,3,4-tetrahydroquinoxalin-1-yl]-2-[3-(trifluoromethyl)phenyl]ethan-1-one;
1-[(3S)-4-acetyl-3-methyl-1,2,3,4-tetrahydroquinoxalin-1-yl]-2-(2-methoxyphenyl)ethan-1-one;
1-[(3S)-4-acetyl-3-methyl-1,2,3,4-tetrahydroquinoxalin-1-yl]-2-phenoxyethan-1-one;
1-[(3S)-4-acetyl-3-methyl-1,2,3,4-tetrahydroquinoxalin-1-yl]-2-cyclopentyl ethan-1-one;
1-[(2S)-4-cyclopentanecarbonyl-2-methyl-1,2,3,4-tetrahydroquinoxalin-1-yl]ethan-1-one;
(2R)-1-[(3S)-4-acetyl-3-methyl-1,2,3,4-tetrahydroquinoxalin-1-yl]-2-phenylpropan-1-one;
1-[(2S)-2-methyl-4-(naphthalene-2-carbonyl)-1,2,3,4-tetrahydroquinoxalin-1-yl]ethan-1-one;
1-[(2S)-4-(2,3-dihydro-1-benzofuran-5-carbonyl)-2-methyl-1,2,3,4-tetrahydroquinoxalin-1-yl]ethan-1-one;
1-[(2S)-4-(3-chlorobenzoyl)-2-methyl-1,2,3,4-tetrahydroquinoxalin-1-yl]ethan-1-one;
1-[(2S)-2-methyl-4-(naphthalene-1-carbonyl)-1,2,3,4-tetrahydroquinoxalin-1-yl]ethan-1-one;
1-[(2S)-4-(furan-2-carbonyl)-2-methyl-1,2,3,4-tetrahydroquinoxalin-1-yl]ethan-1-one;
1-[(2S)-2-methyl-4-(5-methylpyrazine-2-carbonyl)-1,2,3,4-tetrahydroquinoxalin-1-yl]ethan-1-one;
1-[(2S)-2-methyl-4-(5-methyl-1,2-oxazole-3-carbonyl)-1,2,3,4-tetrahydroquinoxalin-1-yl]ethan-1-one;
1-[(2S)-2-methyl-4-[4-(1H-pyrazol-1-yl)benzoyl]-1,2,3,4-tetrahydroquinoxalin-1-yl]ethan-1-one;
1-[(2S)-4-(1,3-benzothiazole-6-carbonyl)-2-methyl-1,2,3,4-tetrahydroquinoxalin-1-yl]ethan-1-one;
1-[(2S)-2-methyl-4-{2-[(pyridin-3-yl)amino]-1,3-thiazole-4-carbonyl}-1,2,3,4-tetrahydroquinoxalin-1-yl]ethan-1-one;
1-[(2S)-2-methyl-4-[2-(pyridin-3-yl)-1,3-thiazole-5-carbonyl]-1,2,3,4-tetrahydroquinoxalin-1-yl]ethan-1-one;
1-[(3S)-4-acetyl-3-methyl-1,2,3,4-tetrahydroquinoxalin-1-yl]-2-(phenylsulfanyl)ethan-1-one;
1-[(2S)-2-methyl-4-[5-(propan-2-yl)pyridine-2-carbonyl]-1,2,3,4-tetrahydroquinoxalin-1-yl]ethan-1-one;
1-[(2S)-2-methyl-4-[6-(propan-2-yl)pyridine-3-carbonyl]-1,2,3,4-tetrahydroquinoxalin-1-yl]ethan-1-one;
1-[(2S)-4-(1H-indole-2-carbonyl)-2-methyl-1,2,3,4-tetrahydroquinoxalin-1-yl]ethan-1-one;
1-[(3S)-4-acetyl-3-methyl-1,2,3,4-tetrahydroquinoxalin-1-yl]-2-(thiophen-2-yl)ethan-1-one;
1-[(3S)-4-acetyl-3-methyl-1,2,3,4-tetrahydroquinoxalin-1-yl]-2-(4-chlorophenoxy)ethan-1-one;
1-[(3S)-4-acetyl-3-methyl-1,2,3,4-tetrahydroquinoxalin-1-yl]-2-(4-methoxyphenoxy)ethan-1-one;
1-[(3S)-4-acetyl-3-methyl-1,2,3,4-tetrahydroquinoxalin-1-yl]-2-(naphthalen-2-yloxy)ethan-1-one;
1-[(3S)-4-acetyl-3-methyl-1,2,3,4-tetrahydroquinoxalin-1-yl]-2-(4-fluorophenoxy)ethan-1-one;
1-[(3S)-4-acetyl-3-methyl-1,2,3,4-tetrahydroquinoxalin-1-yl]-2-(naphthalen-1-yloxy)ethan-1-one;

1-[(2S)-4-(2,3-dihydro-1,4-benzodioxine-2-carbonyl)-2-methyl-1,2,3,4-tetrahydroquinoxalin-1-yl]ethan-1-one;
1-[(3S)-4-acetyl-3-methyl-1,2,3,4-tetrahydroquinoxalin-1-yl]-2-methoxyethan-1-one;
1-[(3S)-4-acetyl-3-methyl-1,2,3,4-tetrahydroquinoxalin-1-yl]-2-(5-chloro-1-benzothiophen-3-yl)ethan-1-one;
(2R)-1-[(3S)-4-acetyl-3-methyl-1,2,3,4-tetrahydroquinoxalin-1-yl]-2-methoxy-2-phenylethan-1-one;
(2S)-1-[(3S)-4-acetyl-3-methyl-1,2,3,4-tetrahydroquinoxalin-1-yl]-2-methoxy-2-phenylethan-1-one;
1-[(2S)-2-methyl-4-(4-phenoxybenzoyl)-1,2,3,4-tetrahydroquinoxalin-1-yl]ethan-1-one;
1-[(2S)-4-(4-chlorobenzoyl)-2-methyl-1,2,3,4-tetrahydroquinoxalin-1-yl]ethan-1-one;
1-[(2S)-2-methyl-4-(2-phenoxybenzoyl)-1,2,3,4-tetrahydroquinoxalin-1-yl]ethan-1-one;
1-[(2S)-2-methyl-4-(thiophene-2-carbonyl)-1,2,3,4-tetrahydroquinoxalin-1-yl]ethan-1-one;
1-[(2S)-4-(1-benzothiophene-2-carbonyl)-2-methyl-1,2,3,4-tetrahydroquinoxalin-1-yl]ethan-1-one;
1-[(2S)-4-(4-methoxythiophene-3-carbonyl)-2-methyl-1,2,3,4-tetrahydroquinoxalin-1-yl]ethan-1-one;
1-[(2S)-2-methyl-4-(1-methyl-1H-indole-2-carbonyl)-1,2,3,4-tetrahydroquinoxalin-1-yl]ethan-1-one;
1-[(2S)-4-(2,5-dimethylfuran-3-carbonyl)-2-methyl-1,2,3,4-tetrahydroquinoxalin-1-yl]ethan-1-one;
1-[(2S)-4-(4,5-dimethylfuran-2-carbonyl)-2-methyl-1,2,3,4-tetrahydroquinoxalin-1-yl]ethan-1-one;
1-[(2S)-4-(1-benzofuran-2-carbonyl)-2-methyl-1,2,3,4-tetrahydroquinoxalin-1-yl]ethan-1-one;
1-[(2S)-2-methyl-4-(quinoline-3-carbonyl)-1,2,3,4-tetrahydroquinoxalin-1-yl]ethan-1-one;
1-[(2S)-4-(4-methoxyquinoline-2-carbonyl)-2-methyl-1,2,3,4-tetrahydroquinoxalin-1-yl]ethan-1-one;
1-[(2S)-2-methyl-4-(quinoline-4-carbonyl)-1,2,3,4-tetrahydroquinoxalin-1-yl]ethan-1-one;
1-[(2S)-4-(1,5-dimethyl-1H-pyrazole-3-carbonyl)-2-methyl-1,2,3,4-tetrahydroquinoxalin-1-yl]ethan-1-one;
1-[(2S)-2-methyl-4-[1-phenyl-5-(trifluoromethyl)-1H-pyrazole-4-carbonyl]-1,2,3,4-tetrahydroquinoxalin-1-yl]ethan-1-one;
1-[(2S)-2-methyl-4-(4-methyl-1,2,3-thiadiazole-5-carbonyl)-1,2,3,4-tetrahydroquinoxalin-1-yl]ethan-1-one;
1-[(2S)-4-(2-methoxypyridine-3-carbonyl)-2-methyl-1,2,3,4-tetrahydroquinoxalin-1-yl]ethan-1-one;
1-[(2S)-4-(5-chloro-1-benzofuran-2-carbonyl)-2-methyl-1,2,3,4-tetrahydroquinoxalin-1-yl]ethan-1-one;
1-[(2S)-4-(1H-indole-6-carbonyl)-2-methyl-1,2,3,4-tetrahydroquinoxalin-1-yl]ethan-1-one;
1-[(2S)-2-methyl-4-[2-(trifluoromethyl)-1,3-thiazole-4-carbonyl]-1,2,3,4-tetrahydroquinoxalin-1-yl]ethan-1-one;
1-[(3S)-4-acetyl-3-methyl-1,2,3,4-tetrahydroquinoxalin-1-yl]-2-(1-methanesulfonylpiperidin-4-yl)ethan-1-one;
1-[(2S)-4-(5-fluoropyridine-2-carbonyl)-2-methyl-1,2,3,4-tetrahydroquinoxalin-1-yl]ethan-1-one;
1-1-{2-[(3S)-4-acetyl-3-methyl-1,2,3,4-tetrahydroquinoxalin-1-yl]-2-oxoethyl}azepan-2-one;
1-1-{3-[(3S)-4-acetyl-3-methyl-1,2,3,4-tetrahydroquinoxalin-1-yl]-3-oxopropyl}azepan-2-one;
1-[(3S)-4-acetyl-3-methyl-1,2,3,4-tetrahydroquinoxalin-1-yl]-2-(1H-1,3-benzodiazol-1-yl)ethan-1-one;
4-{2-[(3S)-4-acetyl-3-methyl-1,2,3,4-tetrahydroquinoxalin-1-yl]-2-oxoethyl}-1$\lambda^6$-thiomorpholine-1,1-dione;
1-[(2S)-4-(dimethyl-1,2-oxazole-4-carbonyl)-2-methyl-1,2,3,4-tetrahydroquinoxalin-1-yl]ethan-1-one;
1-[(3S)-4-acetyl-3-methyl-1,2,3,4-tetrahydroquinoxalin-1-yl]-2-(5-methyl-2-phenyl-1,3-oxazol-4-yl)ethan-1-one;
1-[(2S)-4-(1H-indole-4-carbonyl)-2-methyl-1,2,3,4-tetrahydroquinoxalin-1-yl]ethan-1-one;
1-[(2S)-2-methyl-4-{pyrazolo[1,5-a]pyridine-2-carbonyl}-1,2,3,4-tetrahydroquinoxalin-1-yl]ethan-1-one;
1-[(3S)-4-acetyl-3-methyl-1,2,3,4-tetrahydroquinoxalin-1-yl]-2-(2-methylpropoxy)ethan-1-one;
1-[(2S)-2-methyl-4-{5H,6H,7H-pyrazolo[3,2-b][1,3]oxazine-3-carbonyl}-1,2,3,4-tetrahydroquinoxalin-1-yl]ethan-1-one;
1-[(2S)-2-methyl-4-{4H,5H,6H-pyrrolo[1,2-b]pyrazole-2-carbonyl}-1,2,3,4-tetrahydroquinoxalin-1-yl]ethan-1-one;
1-[(2S)-2-methyl-4-{thieno[2,3-c]pyridine-2-carbonyl}-1,2,3,4-tetrahydroquinoxalin-1-yl]ethan-1-one;
1-[(2S)-4-{imidazo[1,2-a]pyridine-6-carbonyl}-2-methyl-1,2,3,4-tetrahydroquinoxalin-1-yl]ethan-1-one;
1-[(2S)-4-{furo[2,3-c]pyridine-2-carbonyl}-2-methyl-1,2,3,4-tetrahydroquinoxalin-1-yl]ethan-1-one;
1-[(2S)-6-(4-methanesulfonylphenyl)-2-methyl-4-{1H-pyrrolo[3,2-c]pyridine-2-carbonyl}-1,2,3,4-tetrahydroquinoxalin-1-yl]ethan-1-one;
1-[(2S)-4-{imidazo[1,2-a]pyrazine-2-carbonyl}-6-(4-methanesulfonylphenyl)-2-methyl-1,2,3,4-tetrahydroquinoxalin-1-yl]ethan-1-one;
1-[(2S)-6-(4-methanesulfonylphenyl)-2-methyl-4-[4-(trifluoromethyl)benzoyl]-1,2,3,4-tetrahydroquinoxalin-1-yl]ethan-1-one;
1-[(2S)-4-cyclopropanecarbonyl-6-(4-methanesulfonylphenyl)-2-methyl-1,2,3,4-tetrahydroquinoxalin-1-yl]ethan-1-one;
1-[(2S)-6-(4-methanesulfonylphenyl)-2-methyl-4-(pyridine-2-carbonyl)-1,2,3,4-tetrahydroquinoxalin-1-yl]ethan-1-one;
1-[(2S)-6-(4-methanesulfonylphenyl)-2-methyl-4-(1,2,3-thiadiazole-4-carbonyl)-1,2,3,4-tetrahydroquinoxalin-1-yl]ethan-1-one;
1-[(2S)-6-(4-methanesulfonylphenyl)-2-methyl-4-(1-methyl-1H-imidazole-2-carbonyl)-1,2,3,4-tetrahydroquinoxalin-1-yl]ethan-1-one;
1-[(2S)-4-(5-chloro-1H-indole-2-carbonyl)-6-(4-methanesulfonylphenyl)-2-methyl-1,2,3,4-tetrahydroquinoxalin-1-yl]ethan-1-one;
1-[(2S)-4-(5-hydroxy-1H-indole-2-carbonyl)-6-(4-methanesulfonylphenyl)-2-methyl-1,2,3,4-tetrahydroquinoxalin-1-yl]ethan-1-one;
1-[(2S)-4-(6-chloro-1H-indole-2-carbonyl)-6-(4-methanesulfonylphenyl)-2-methyl-1,2,3,4-tetrahydroquinoxalin-1-yl]ethan-1-one;
1-[(2S)-6-(4-methanesulfonylphenyl)-2-methyl-4-[5-(trifluoromethoxy)-1H-indole-2-carbonyl]-1,2,3,4-tetrahydroquinoxalin-1-yl]ethan-1-one;
1-[(2S)-6-(4-methanesulfonylphenyl)-2-methyl-4-{1H-pyrrolo[2,3-b]pyridine-2-carbonyl}-1,2,3,4-tetrahydroquinoxalin-1-yl]ethan-1-one;
1-[(2S)-6-(4-methanesulfonylphenyl)-2-methyl-4-(3-phenyl-1-benzofuran-2-carbonyl)-1,2,3,4-tetrahydroquinoxalin-1-yl]ethan-1-one;
1-[(3S)-4-acetyl-3-methyl-7-(quinolin-6-yl)-1,2,3,4-tetrahydroquinoxalin-1-yl]-2-phenoxyethan-1-one;
1-[(3S)-4-acetyl-3-methyl-7-(3-phenylphenyl)-1,2,3,4-tetrahydroquinoxalin-1-yl]-2-phenoxyethan-1-one;
1-[(2S)-4-(furan-2-carbonyl)-2-methyl-6-(3-phenylphenyl)-1,2,3,4-tetrahydroquinoxalin-1-yl]ethan-1-one;

1-[(3S)-4-acetyl-7-(2-fluorophenyl)-3-methyl-1,2,3,4-tetrahydroquinoxalin-1-yl]-2-phenoxyethan-1-one;
1-[(2S)-6-(2-fluorophenyl)-4-(furan-2-carbonyl)-2-methyl-1,2,3,4-tetrahydroquinoxalin-1-yl]ethan-1-one;
1-[(2S)-4-(furan-2-carbonyl)-2-methyl-6-(1-methyl-1H-indol-5-yl)-1,2,3,4-tetrahydroquinoxalin-1-yl]ethan-1-one;
1-[(3S)-4-acetyl-3-methyl-7-(4-phenylphenyl)-1,2,3,4-tetrahydroquinoxalin-1-yl]-2-phenoxyethan-1-one;
1-[(2S)-4-(furan-2-carbonyl)-2-methyl-6-(4-phenylphenyl)-1,2,3,4-tetrahydroquinoxalin-1-yl]ethan-1-one;
4-[(2S)-1-acetyl-4-(furan-2-carbonyl)-2-methyl-1,2,3,4-tetrahydroquinoxalin-6-yl]benzoic acid;
1-[(2S)-4-(furan-2-carbonyl)-2-methyl-6-[6-(morpholin-4-yl)pyridin-3-yl]-1,2,3,4-tetrahydroquinoxalin-1-yl]ethan-1-one;
3-[(2S)-1-acetyl-4-(furan-2-carbonyl)-2-methyl-1,2,3,4-tetrahydroquinoxalin-6-yl]-N-methylbenzamide;
3-[(2S)-1-acetyl-4-(furan-2-carbonyl)-2-methyl-1,2,3,4-tetrahydroquinoxalin-6-yl]-N-cyclopropylbenzamide;
1-[(2S)-4-(furan-2-carbonyl)-2-methyl-6-[4-(1H-pyrazol-1-yl)phenyl]-1,2,3,4-tetrahydroquinoxalin-1-yl]ethan-1-one;
1-[(2S)-4-(furan-2-carbonyl)-2-methyl-6-phenyl-1,2,3,4-tetrahydroquinoxalin-1-yl]ethan-1-one;
1-[(2S)-6-(4-chlorophenyl)-4-(furan-2-carbonyl)-2-methyl-1,2,3,4-tetrahydroquinoxalin-1-yl]ethan-1-one;
1-[(2S)-6-(2H-1,3-benzodioxol-5-yl)-4-(furan-2-carbonyl)-2-methyl-1,2,3,4-tetrahydroquinoxalin-1-yl]ethan-1-one;
1-[(2S)-4-(furan-2-carbonyl)-6-(4-methoxyphenyl)-2-methyl-1,2,3,4-tetrahydroquinoxalin-1-yl]ethan-1-one;
1-[(2S)-4-(furan-2-carbonyl)-2-methyl-6-[4-(trifluoromethoxy)phenyl]-1,2,3,4-tetrahydroquinoxalin-1-yl]ethan-1-one;
4-[(2S)-1-acetyl-4-(furan-2-carbonyl)-2-methyl-1,2,3,4-tetrahydroquinoxalin-6-yl]-N,N-dimethylbenzamide;
4-[(2S)-1-acetyl-4-(furan-2-carbonyl)-2-methyl-1,2,3,4-tetrahydroquinoxalin-6-yl]benzamide;
4-[(2S)-1-acetyl-4-(furan-2-carbonyl)-2-methyl-1,2,3,4-tetrahydroquinoxalin-6-yl]benzonitrile;
3-[(2S)-1-acetyl-4-(furan-2-carbonyl)-2-methyl-1,2,3,4-tetrahydroquinoxalin-6-yl]benzonitrile;
1-[(2S)-4-(furan-2-carbonyl)-2-methyl-6-(4-phenoxyphenyl)-1,2,3,4-tetrahydroquinoxalin-1-yl]ethan-1-one;
1-[(2S)-6-[3-fluoro-4-(1H-pyrazol-1-yl)phenyl]-4-(furan-2-carbonyl)-2-methyl-1,2,3,4-tetrahydroquinoxalin-1-yl]ethan-1-one;
1-[(2S)-4-(furan-2-carbonyl)-2-methyl-6-[4-(trifluoromethyl)phenyl]-1,2,3,4-tetrahydroquinoxalin-1-yl]ethan-1-one;
1-[(2S)-6-(dimethyl-1,2-oxazol-4-yl)-4-(furan-2-carbonyl)-2-methyl-1,2,3,4-tetrahydroquinoxalin-1-yl]ethan-1-one;
1-[(2S)-4-(furan-2-carbonyl)-6-(4-methanesulfonylphenyl)-2-methyl-1,2,3,4-tetrahydroquinoxalin-1-yl]ethan-1-one;
1-[(2S)-6-(4-fluorophenyl)-4-(furan-2-carbonyl)-2-methyl-1,2,3,4-tetrahydroquinoxalin-1-yl]ethan-1-one;
1-[(2S)-4-(furan-2-carbonyl)-2-methyl-6-(pyridin-3-yl)-1,2,3,4-tetrahydroquinoxalin-1-yl]ethan-1-one;
1-[(2S)-4-(furan-2-carbonyl)-2-methyl-6-(pyridin-4-yl)-1,2,3,4-tetrahydroquinoxalin-1-yl]ethan-1-one;
1-[(2S)-4-(furan-2-carbonyl)-2-methyl-6-(pyrimidin-5-yl)-1,2,3,4-tetrahydroquinoxalin-1-yl]ethan-1-one;
1-[(2S)-4-(furan-2-carbonyl)-2-methyl-6-(1-methyl-1H-pyrazol-4-yl)-1,2,3,4-tetrahydroquinoxalin-1-yl]ethan-1-one;
1-[(2S)-4-(furan-2-carbonyl)-2-methyl-6-(quinolin-3-yl)-1,2,3,4-tetrahydroquinoxalin-1-yl]ethan-1-one;
4-[(2S)-1-acetyl-4-(furan-2-carbonyl)-2-methyl-1,2,3,4-tetrahydroquinoxalin-6-yl]-N-methylbenzamide;
1-[(2S)-6-(2,3-dihydro-1,4-benzodioxin-6-yl)-4-(furan-2-carbonyl)-2-methyl-1,2,3,4-tetrahydroquinoxalin-1-yl]ethan-1-one;
1-[(2S)-6-(4-fluoro-2-methoxyphenyl)-4-(furan-2-carbonyl)-2-methyl-1,2,3,4-tetrahydroquinoxalin-1-yl]ethan-1-one;
N-{2-[(2S)-1-acetyl-4-(furan-2-carbonyl)-2-methyl-1,2,3,4-tetrahydroquinoxalin-6-yl]phenyl}methanesulfonamide;
1-[(2S)-6-(4-fluoro-3-methoxyphenyl)-4-(furan-2-carbonyl)-2-methyl-1,2,3,4-tetrahydroquinoxalin-1-yl]ethan-1-one;
5-[(2S)-1-acetyl-4-(furan-2-carbonyl)-2-methyl-1,2,3,4-tetrahydroquinoxalin-6-yl]-2-fluoro-N-(propan-2-yl)benzamide;
1-[(2S)-6-(5-fluoropyridin-3-yl)-4-(furan-2-carbonyl)-2-methyl-1,2,3,4-tetrahydroquinoxalin-1-yl]ethan-1-one;
1-[(2S)-6-[2-(dimethylamino)pyrimidin-5-yl]-4-(furan-2-carbonyl)-2-methyl-1,2,3,4-tetrahydroquinoxalin-1-yl]ethan-1-one;
1-[(2S)-6-(5-chloropyridin-3-yl)-4-(furan-2-carbonyl)-2-methyl-1,2,3,4-tetrahydroquinoxalin-1-yl]ethan-1-one;
1-[(2S)-4-(furan-2-carbonyl)-6-(6-methoxypyridin-3-yl)-2-methyl-1,2,3,4-tetrahydroquinoxalin-1-yl]ethan-1-one;
1-[(2S)-4-(furan-2-carbonyl)-6-(2-methoxypyrimidin-5-yl)-2-methyl-1,2,3,4-tetrahydroquinoxalin-1-yl]ethan-1-one;
1-[(2S)-4-(furan-2-carbonyl)-6-(5-methoxypyridin-3-yl)-2-methyl-1,2,3,4-tetrahydroquinoxalin-1-yl]ethan-1-one;
5-[(2S)-1-acetyl-4-(furan-2-carbonyl)-2-methyl-1,2,3,4-tetrahydroquinoxalin-6-yl]-N-methylpyridine-2-carboxamide;
1-[(2S)-4-(furan-2-carbonyl)-2-methyl-6-[6-(trifluoromethyl)pyridin-3-yl]-1,2,3,4-tetrahydroquinoxalin-1-yl]ethan-1-one;
1-[(2S)-4-(furan-2-carbonyl)-2-methyl-6-[3-(morpholine-4-carbonyl)phenyl]-1,2,3,4-tetrahydroquinoxalin-1-yl]ethan-1-one;
1-[(2S)-4-(furan-2-carbonyl)-2-methyl-6-(1-methyl-1H-indol-2-yl)-1,2,3,4-tetrahydroquinoxalin-1-yl]ethan-1-one;
1-[(2S)-4-(furan-2-carbonyl)-2-methyl-6-(2-methyl-2H-indazol-6-yl)-1,2,3,4-tetrahydroquinoxalin-1-yl]ethan-1-one;
3-[(2S)-1-acetyl-4-(furan-2-carbonyl)-2-methyl-1,2,3,4-tetrahydroquinoxalin-6-yl]benzene-1-sulfonamide;
1-[(2S)-4-(furan-2-carbonyl)-2-methyl-6-(1-methyl-1H-indazol-7-yl)-1,2,3,4-tetrahydroquinoxalin-1-yl]ethan-1-one;
1-[(2S)-4-(furan-2-carbonyl)-2-methyl-6-(1-methyl-1H-indazol-6-yl)-1,2,3,4-tetrahydroquinoxalin-1-yl]ethan-1-one;
N-{3-[(2S)-1-acetyl-4-(furan-2-carbonyl)-2-methyl-1,2,3,4-tetrahydroquinoxalin-6-yl]phenyl}methanesulfonamide;
3-[(2S)-1-acetyl-4-(furan-2-carbonyl)-2-methyl-1,2,3,4-tetrahydroquinoxalin-6-yl]-N,N-dimethylbenzene-1-sulfonamide;

1-[(2S)-4-(furan-2-carbonyl)-6-(1H-indol-4-yl)-2-methyl-1,2,3,4-tetrahydroquinoxalin-1-yl]ethan-1-one;
1-[(2S)-4-(furan-2-carbonyl)-6-(3-methanesulfonylphenyl)-2-methyl-1,2,3,4-tetrahydroquinoxalin-1-yl]ethan-1-one;
3-[(2S)-1-acetyl-4-(furan-2-carbonyl)-2-methyl-1,2,3,4-tetrahydroquinoxalin-6-yl]-N,N-dimethylbenzamide;
1-[(2S)-6-(2H-1,3-benzodioxol-4-yl)-4-(furan-2-carbonyl)-2-methyl-1,2,3,4-tetrahydroquinoxalin-1-yl]ethan-1-one;
1-[(2S)-4-(furan-2-carbonyl)-2-methyl-6-[4-(morpholin-4-yl)phenyl]-1,2,3,4-tetrahydroquinoxalin-1-yl]ethan-1-one;
1-[(2S)-4-(furan-2-carbonyl)-2-methyl-6-[1-methyl-3-(trifluoromethyl)-1H-pyrazol-5-yl]-1,2,3,4-tetrahydroquinoxalin-1-yl]ethan-1-one;
1-[(2S)-4-(furan-2-carbonyl)-2-methyl-6-(1-methyl-1H-indazol-5-yl)-1,2,3,4-tetrahydroquinoxalin-1-yl]ethan-1-one;
1-[(2S)-4-(furan-2-carbonyl)-2-methyl-6-[3-(1H-pyrazol-1-yl)phenyl]-1,2,3,4-tetrahydroquinoxalin-1-yl]ethan-1-one;
1-[(2S)-4-(furan-2-carbonyl)-2-methyl-6-[3-(5-methyl-1,3,4-oxadiazol-2-yl)phenyl]-1,2,3,4-tetrahydroquinoxalin-1-yl]ethan-1-one;
1-[(2S)-4-(furan-2-carbonyl)-6-[3-(furan-2-yl)phenyl]-2-methyl-1,2,3,4-tetrahydroquinoxalin-1-yl]ethan-1-one;
3-[(2S)-1-acetyl-4-(furan-2-carbonyl)-2-methyl-1,2,3,4-tetrahydroquinoxalin-6-yl]benzamide;
1-[(2S)-6-[3-(3,5-dimethyl-1H-pyrazol-1-yl)phenyl]-4-(furan-2-carbonyl)-2-methyl-1,2,3,4-tetrahydroquinoxalin-1-yl]ethan-1-one;
1-[(2S)-4-(furan-2-carbonyl)-2-methyl-6-(1-methyl-1H-indazol-4-yl)-1,2,3,4-tetrahydroquinoxalin-1-yl]ethan-1-one;
N-{3-[(2S)-1-acetyl-4-(furan-2-carbonyl)-2-methyl-1,2,3,4-tetrahydroquinoxalin-6-yl]phenyl}-4-methylbenzene-1-sulfonamide;
N-{4-[(2S)-1-acetyl-4-(furan-2-carbonyl)-2-methyl-1,2,3,4-tetrahydroquinoxalin-6-yl]phenyl}-4-methylbenzene-1-sulfonamide;
1-[(2S)-4-(furan-2-carbonyl)-2-methyl-6-[2-(trifluoromethyl)pyridin-4-yl]-1,2,3,4-tetrahydroquinoxalin-1-yl]ethan-1-one;
1-[(2S)-4-(furan-2-carbonyl)-2-methyl-6-[2-(morpholin-4-yl)pyridin-4-yl]-1,2,3,4-tetrahydroquinoxalin-1-yl]ethan-1-one;
1-[(2S)-4-(furan-2-carbonyl)-6-(2-methoxypyridin-4-yl)-2-methyl-1,2,3,4-tetrahydroquinoxalin-1-yl]ethan-1-one;
1-[(2S)-4-(furan-2-carbonyl)-6-(isoquinolin-6-yl)-2-methyl-1,2,3,4-tetrahydroquinoxalin-1-yl]ethan-1-one;
1-[(2S)-6-(1,3-benzothiazol-5-yl)-4-(furan-2-carbonyl)-2-methyl-1,2,3,4-tetrahydroquinoxalin-1-yl]ethan-1-one;
1-[(2S)-4-(furan-2-carbonyl)-2-methyl-6-(4-trifluoromethanesulfonylphenyl)-1,2,3,4-tetrahydroquinoxalin-1-yl]ethan-1-one;
1-[(2S)-4-(furan-2-carbonyl)-2-methyl-6-[3-(piperidin-1-yl)phenyl]-1,2,3,4-tetrahydroquinoxalin-1-yl]ethan-1-one;
3-[1-acetyl-4-(furan-2-carbonyl)-1,2,3,4-tetrahydroquinoxalin-6-yl]-N-methylbenzamide;
1-[(2S)-6-(3, 5-difluorophenyl)-4-(furan-2-carbonyl)-2-methyl-1,2,3,4-tetrahydroquinoxalin-1-yl]ethan-1-one;
1-[(2S)-6-[3-(dimethylamino)phenyl]-4-(furan-2-carbonyl)-2-methyl-1,2,3,4-tetrahydroquinoxalin-1-yl]ethan-1-one;
1-[(2S)-6-[4-(dimethylamino)phenyl]-4-(furan-2-carbonyl)-2-methyl-1,2,3,4-tetrahydroquinoxalin-1-yl]ethan-1-one;
1-[(2S)-4-(furan-2-carbonyl)-2-methyl-6-(5-methylthiophen-2-yl)-1,2,3,4-tetrahydroquinoxalin-1-yl]ethan-1-one;
1-[(2S)-6-(1-benzothiophen-7-yl)-4-(furan-2-carbonyl)-2-methyl-1,2,3,4-tetrahydroquinoxalin-1-yl]ethan-1-one;
1-[(2S)-4-(furan-2-carbonyl)-2-methyl-6-[4-(4-methylpiperazin-1-yl)phenyl]-1,2,3,4-tetrahydroquinoxalin-1-yl]ethan-1-one;
4-[(2S)-1-acetyl-4-(furan-2-carbonyl)-2-methyl-1,2,3,4-tetrahydroquinoxalin-6-yl]-N-methylbenzene-1-sulfonamide;
N-{3-[(2S)-1-acetyl-4-(furan-2-carbonyl)-2-methyl-1,2,3,4-tetrahydroquinoxalin-6-yl]phenyl}ethane-1-sulfonamide;
1-[(2S)-6-(4-methanesulfonylphenyl)-4-(4-methoxybenzoyl)-2-methyl-1,2,3,4-tetrahydroquinoxalin-1-yl]ethan-1-one;
1-[(2S)-4-(4-fluorobenzoyl)-6-(4-methanesulfonylphenyl)-2-methyl-1,2,3,4-tetrahydroquinoxalin-1-yl]ethan-1-one;
1-[(2S)-6-(4-methanesulfonylphenyl)-2-methyl-4-[4-(trifluoromethoxy)benzoyl]-1,2,3,4-tetrahydroquinoxalin-1-yl]ethan-1-one;
1-[(2S)-4-[5-(3,5-dichlorophenoxy)furan-2-carbonyl]-6-(4-methanesulfonylphenyl)-2-methyl-1,2,3,4-tetrahydroquinoxalin-1-yl]ethan-1-one;
1-[(2S)-6-(4-methanesulfonylphenyl)-2-methyl-4-(1-methyl-1H-imidazole-4-carbonyl)-1,2,3,4-tetrahydroquinoxalin-1-yl]ethan-1-one;
1-[(2S)-6-(4-methanesulfonylphenyl)-4-(5-methoxy-1H-indole-2-carbonyl)-2-methyl-1,2,3,4-tetrahydroquinoxalin-1-yl]ethan-1-one;
1-[(2S)-6-(4-methanesulfonylphenyl)-4-(4-methoxy-1H-indole-2-carbonyl)-2-methyl-1,2,3,4-tetrahydroquinoxalin-1-yl]ethan-1-one;
1-[(2S)-6-(4-methanesulfonylphenyl)-2-methyl-4-(5-methyl-1,3-oxazole-4-carbonyl)-1,2,3,4-tetrahydroquinoxalin-1-yl]ethan-1-one;
1-[(2S)-6-(4-methanesulfonylphenyl)-2-methyl-4-(2-phenyl-1,3-thiazole-4-carbonyl)-1,2,3,4-tetrahydroquinoxalin-1-yl]ethan-1-one;
1-[(2S)-6-(4-methanesulfonylphenyl)-2-methyl-4-(5-phenylfuran-2-carbonyl)-1,2,3,4-tetrahydroquinoxalin-1-yl]ethan-1-one;
1-[(2S)-6-(4-methanesulfonylphenyl)-2-methyl-4-[5-(trifluoromethyl)furan-2-carbonyl]-1,2,3,4-tetrahydroquinoxalin-1-yl]ethan-1-one;
1-[(2S)-4-(5-methanesulfonylfuran-2-carbonyl)-6-(4-methanesulfonylphenyl)-2-methyl-1,2,3,4-tetrahydroquinoxalin-1-yl]ethan-1-one;
N-{3-[(3S)-4-acetyl-7-(4-methanesulfonylphenyl)-3-methyl-1,2,3,4-tetrahydroquinoxaline-1-carbonyl]phenyl}acetamide;
1-[(2S)-4-[5-(aminomethyl)furan-2-carbonyl]-6-(4-methanesulfonylphenyl)-2-methyl-1,2,3,4-tetrahydroquinoxalin-1-yl]ethan-1-one;
1-[(2S)-4-{[4-(dimethylamino)phenyl]methyl}-2-methyl-1,2,3,4-tetrahydroquinoxalin-1-yl]ethan-1-one;
1-[(2S)-2-methyl-4-{[4-(propan-2-yl)phenyl]methyl}-1,2,3,4-tetrahydroquinoxalin-1-yl]ethan-1-one;

1-[(2S)-2-methyl-4-[(3-methylphenyl)methyl]-1,2,3,4-tetrahydroquinoxalin-1-yl]ethan-1-one;
1-[(2S)-4-[(2,4-dichlorophenyl)methyl]-2-methyl-1,2,3,4-tetrahydroquinoxalin-1-yl]ethan-1-one;
1-[(2S)-2-methyl-4-[(4-methylphenyl)methyl]-1,2,3,4-tetrahydroquinoxalin-1-yl]ethan-1-one;
1-[(2S)-2-methyl-4-[(2-methylphenyl)methyl]-1,2,3,4-tetrahydroquinoxalin-1-yl]ethan-1-one;
1-[(2S)-4-[(2,4-difluorophenyl)methyl]-2-methyl-1,2,3,4-tetrahydroquinoxalin-1-yl]ethan-1-one;
1-[(2S)-4-[(4-chloro-3-fluorophenyl)methyl]-2-methyl-1,2,3,4-tetrahydroquinoxalin-1-yl]ethan-1-one;
1-[(2S)-2-methyl-4-{[3-(trifluoromethyl)phenyl]methyl}-1,2,3,4-tetrahydroquinoxalin-1-yl]ethan-1-one;
1-[(2S)-4-{[3,5-bis(trifluoromethyl)phenyl]methyl}-2-methyl-1,2,3,4-tetrahydroquinoxalin-1-yl]ethan-1-one;
1-[(2S)-4-[(4-ethylphenyl)methyl]-2-methyl-1,2,3,4-tetrahydroquinoxalin-1-yl]ethan-1-one;
1-[(2S)-4-[(3,5-dimethoxyphenyl)methyl]-2-methyl-1,2,3,4-tetrahydroquinoxalin-1-yl]ethan-1-one;
1-[(2S)-4-[(2,5-dimethylphenyl)methyl]-2-methyl-1,2,3,4-tetrahydroquinoxalin-1-yl]ethan-1-one;
1-[(2S)-4-[(4-hydroxy-3-methylphenyl)methyl]-2-methyl-1,2,3,4-tetrahydroquinoxalin-1-yl]ethan-1-one;
1-[(2S)-4-[(1,3-dimethyl-1H-pyrazol-5-yl)methyl]-2-methyl-1,2,3,4-tetrahydroquinoxalin-1-yl]ethan-1-one;
1-[(2S)-4-({2-[2-(dimethylamino)ethoxy]phenyl}methyl)-2-methyl-1,2,3,4-tetrahydroquinoxalin-1-yl]ethan-1-one;
1-[(2S)-4-({4-[2-(dimethylamino)ethoxy]phenyl}methyl)-2-methyl-1,2,3,4-tetrahydroquinoxalin-1-yl]ethan-1-one;
1-[(2S)-4-({3-[2-(dimethylamino)ethoxy]phenyl}methyl)-2-methyl-1,2,3,4-tetrahydroquinoxalin-1-yl]ethan-1-one;
1-[(2S)-4-benzyl-2-methyl-1,2,3,4-tetrahydroquinoxalin-1-yl]ethan-1-one;
1-[(2S)-4-(cyclohexylmethyl)-2-methyl-1,2,3,4-tetrahydroquinoxalin-1-yl]ethan-1-one;
1-[(2S)-2-methyl-4-{[6-(trifluoromethyl)pyridin-3-yl]methyl}-1,2,3,4-tetrahydroquinoxalin-1-yl]ethan-1-one;
1-[(2S)-2-methyl-4-(pyridin-4-ylmethyl)-1,2,3,4-tetrahydroquinoxalin-1-yl]ethan-1-one;
1-[(2S)-2-methyl-4-(pyridin-2-ylmethyl)-1,2,3,4-tetrahydroquinoxalin-1-yl]ethan-1-one;
1-[(2S)-4-[(5-methoxypyridin-3-yl)methyl]-2-methyl-1,2,3,4-tetrahydroquinoxalin-1-yl]ethan-1-one;
1-[(2S)-2-methyl-4-(1,3-thiazol-2-ylmethyl)-1,2,3,4-tetrahydroquinoxalin-1-yl]ethan-1-one;
1-[(2S)-2-methyl-4-[(4-phenylphenyl)methyl]-1,2,3,4-tetrahydroquinoxalin-1-yl]ethan-1-one;
1-[(2S)-2-methyl-4-{[4-(propan-2-yloxy)phenyl]methyl}-1,2,3,4-tetrahydroquinoxalin-1-yl]ethan-1-one;
1-[(2S)-2-methyl-4-[(3-phenoxyphenyl)methyl]-1,2,3,4-tetrahydroquinoxalin-1-yl]ethan-1-one;
1-[(2S)-2-methyl-4-[(4-phenoxyphenyl)methyl]-1,2,3,4-tetrahydroquinoxalin-1-yl]ethan-1-one;
1-[(2S)-4-(2H-1,3-benzodioxol-5-ylmethyl)-2-methyl-1,2,3,4-tetrahydroquinoxalin-1-yl]ethan-1-one;
1-[(2S)-4-(2H-1,3-benzodioxol-4-ylmethyl)-2-methyl-1,2,3,4-tetrahydroquinoxalin-1-yl]ethan-1-one;
1-[(2S)-2-methyl-4-{[6-(morpholin-4-yl)pyridin-3-yl]methyl}-1,2,3,4-tetrahydroquinoxalin-1-yl]ethan-1-one;
1-[(2S)-4-[(4-hydroxyphenyl)methyl]-2-methyl-1,2,3,4-tetrahydroquinoxalin-1-yl]ethan-1-one;
1-[(2S)-2-methyl-4-(pyridin-3-ylmethyl)-1,2,3,4-tetrahydroquinoxalin-1-yl]ethan-1-one;
1-[(2S)-2-methyl-4-(oxan-4-ylmethyl)-1,2,3,4-tetrahydroquinoxalin-1-yl]ethan-1-one;
1-[(2S)-2-methyl-4-[(1-methyl-1H-imidazol-5-yl)methyl]-1,2,3,4-tetrahydroquinoxalin-1-yl]ethan-1-one;
1-[(2S)-2-methyl-4-(2-methylpentyl)-1,2,3,4-tetrahydroquinoxalin-1-yl]ethan-1-one;
1-[(2S)-4-[(1-acetylpiperidin-3-yl)methyl]-2-methyl-1,2,3,4-tetrahydroquinoxalin-1-yl]ethan-1-one;
1-[(2S)-2-methyl-4-{[1-(propan-2-yl)piperidin-4-yl]methyl}-1,2,3,4-tetrahydroquinoxalin-1-yl]ethan-1-one;
1-[(2S)-4-(2,5-dimethoxybenzenesulfonyl)-2-methyl-1,2,3,4-tetrahydroquinoxalin-1-yl]ethan-1-one;
1-[(2S)-4-(2-fluorobenzenesulfonyl)-2-methyl-1,2,3,4-tetrahydroquinoxalin-1-yl]ethan-1-one;
1-[(2S)-4-(benzenesulfonyl)-2-methyl-1,2,3,4-tetrahydroquinoxalin-1-yl]ethan-1-one;
1-[(2S)-2-methyl-4-[(1-methyl-1H-pyrazol-3-yl)sulfonyl]-1,2,3,4-tetrahydroquinoxalin-1-yl]ethan-1-one;
1-[(2S)-2-methyl-4-(pyridine-3-sulfonyl)-1,2,3,4-tetrahydroquinoxalin-1-yl]ethan-1-one;
1-[(2S)-4-(4-chlorobenzenesulfonyl)-2-methyl-1,2,3,4-tetrahydroquinoxalin-1-yl]ethan-1-one;
1-[(2S)-4-(4-methoxybenzenesulfonyl)-2-methyl-1,2,3,4-tetrahydroquinoxalin-1-yl]ethan-1-one;
1-[(2S)-2-methyl-4-[4-(trifluoromethyl)benzenesulfonyl]-1,2,3,4-tetrahydroquinoxalin-1-yl]ethan-1-one;
4-{[(3S)-4-acetyl-3-methyl-1,2,3,4-tetrahydroquinoxalin-1-yl]sulfonyl}benzonitrile;
1-[(2S)-2-methyl-4-[4-(trifluoromethoxy)benzenesulfonyl]-1,2,3,4-tetrahydroquinoxalin-1-yl]ethan-1-one;
1-[(2S)-2-methyl-4-(4-methylbenzenesulfonyl)-1,2,3,4-tetrahydroquinoxalin-1-yl]ethan-1-one;
1-[(2S)-2-methyl-4-(2-methylbenzenesulfonyl)-1,2,3,4-tetrahydroquinoxalin-1-yl]ethan-1-one;
1-[(2S)-4-(2-chlorobenzenesulfonyl)-2-methyl-1,2,3,4-tetrahydroquinoxalin-1-yl]ethan-1-one;
2-{[(3S)-4-acetyl-3-methyl-1,2,3,4-tetrahydroquinoxalin-1-yl]sulfonyl}benzonitrile;
3-{[(3S)-4-acetyl-3-methyl-1,2,3,4-tetrahydroquinoxalin-1-yl]sulfonyl}benzonitrile;
1-[(2S)-4-(3-methoxybenzenesulfonyl)-2-methyl-1,2,3,4-tetrahydroquinoxalin-1-yl]ethan-1-one;
1-[(2S)-4-(3-chlorobenzenesulfonyl)-2-methyl-1,2,3,4-tetrahydroquinoxalin-1-yl]ethan-1-one;
1-[(2S)-2-methyl-4-[3-(trifluoromethyl)benzenesulfonyl]-1,2,3,4-tetrahydroquinoxalin-1-yl]ethan-1-one;
1-[(2S)-2-methyl-4-(3-methylbenzenesulfonyl)-1,2,3,4-tetrahydroquinoxalin-1-yl]ethan-1-one;
1-[(2S)-4-(2,4-dimethylbenzenesulfonyl)-2-methyl-1,2,3,4-tetrahydroquinoxalin-1-yl]ethan-1-one;
1-[(2S)-4-(2,4-dimethoxybenzenesulfonyl)-2-methyl-1,2,3,4-tetrahydroquinoxalin-1-yl]ethan-1-one;
1-[(2S)-2-methyl-4-{[6-(trifluoromethyl)pyridin-3-yl]sulfonyl}-1,2,3,4-tetrahydroquinoxalin-1-yl]ethan-1-one;
1-[(2S)-4-(cyclopropanesulfonyl)-2-methyl-1,2,3,4-tetrahydroquinoxalin-1-yl]ethan-1-one;
1-[(2S)-4-[(2-chlorophenyl)methanesulfonyl]-2-methyl-1,2,3,4-tetrahydroquinoxalin-1-yl]ethan-1-one;
1-[(2S)-2-methyl-4-phenylmethanesulfonyl-1,2,3,4-tetrahydroquinoxalin-1-yl]ethan-1-one;
1-[(2S)-4-[(3-chlorophenyl)methanesulfonyl]-2-methyl-1,2,3,4-tetrahydroquinoxalin-1-yl]ethan-1-one;
1-[(2S)-4-[(1,2-dimethyl-1H-imidazol-4-yl)sulfonyl]-2-methyl-1,2,3,4-tetrahydroquinoxalin-1-yl]ethan-1-one;

1-[(2S)-4-(4-acetylbenzenesulfonyl)-2-methyl-1,2,3,4-tetrahydroquinoxalin-1-yl]ethan-1-one;
3-({[(3S)-4-acetyl-3-methyl-1,2,3,4-tetrahydroquinoxalin-1-yl]sulfonyl}methyl)benzonitrile;
1-[(2S)-4-(4-chloro-2-methoxybenzenesulfonyl)-2-methyl-1,2,3,4-tetrahydroquinoxalin-1-yl]ethan-1-one;
1-[(2S)-4-(4-methoxy-2-methylbenzenesulfonyl)-2-methyl-1,2,3,4-tetrahydroquinoxalin-1-yl]ethan-1-one;
1-[(2S)-2-methyl-4-[(1-methyl-1H-imidazol-4-yl)sulfonyl]-1,2,3,4-tetrahydroquinoxalin-1-yl]ethan-1-one;
1-[(2S)-4-[(4-chlorophenyl)methanesulfonyl]-2-methyl-1,2,3,4-tetrahydroquinoxalin-1-yl]ethan-1-one;
4-({[(3S)-4-acetyl-3-methyl-1,2,3,4-tetrahydroquinoxalin-1-yl]sulfonyl}methyl)benzonitrile;
(3S)-4-acetyl-7-(4-methanesulfonylphenyl)-3-methyl-N-phenyl-1,2,3,4-tetrahydroquinoxaline-1-carboxamide;
(3S)-4-acetyl-N-ethyl-7-(4-methanesulfonylphenyl)-3-methyl-1,2,3,4-tetrahydroquinoxaline-1-carboxamide;
(3S)-4-acetyl-7-(4-methanesulfonylphenyl)-3-methyl-N-(2-methylphenyl)-1,2,3,4-tetrahydroquinoxaline-1-carboxamide;
(3S)-4-acetyl-7-(4-methanesulfonylphenyl)-N-(3-methoxyphenyl)-3-methyl-1,2,3,4-tetrahydroquinoxaline-1-carboxamide;
(3S)-4-acetyl-N-cyclopentyl-7-(4-methanesulfonylphenyl)-3-methyl-1,2,3,4-tetrahydroquinoxaline-1-carboxamide;
(3S)-4-acetyl-N-(3-chlorophenyl)-7-(4-methanesulfonylphenyl)-3-methyl-1,2,3,4-tetrahydroquinoxaline-1-carboxamide;
(3S)-4-acetyl-7-(4-methanesulfonylphenyl)-N-(2-methoxyphenyl)-3-methyl-1,2,3,4-tetrahydroquinoxaline-1-carboxamide;
(3S)-4-acetyl-7-(4-methanesulfonylphenyl)-3-methyl-N-(3-methylphenyl)-1,2,3,4-tetrahydroquinoxaline-1-carboxamide;
(3S)-4-acetyl-7-(4-methanesulfonylphenyl)-N-[(2-methoxyphenyl)methyl]-3-methyl-1,2,3,4-tetrahydroquinoxaline-1-carboxamide;
(3S)-4-acetyl-N-(2-chlorophenyl)-7-(4-methanesulfonylphenyl)-3-methyl-1,2,3,4-tetrahydroquinoxaline-1-carboxamide;
(3S)-4-acetyl-7-(4-methanesulfonylphenyl)-3-methyl-N-(4-methylphenyl)-1,2,3,4-tetrahydroquinoxaline-1-carboxamide;
(3S)-4-acetyl-N-(4-chlorophenyl)-7-(4-methanesulfonylphenyl)-3-methyl-1,2,3,4-tetrahydroquinoxaline-1-carboxamide;
(3S)-4-acetyl-7-(4-methanesulfonylphenyl)-3-methyl-N-[(4-methylphenyl)methyl]-1,2,3,4-tetrahydroquinoxaline-1-carboxamide;
(3S)-4-acetyl-N-[(2-chlorophenyl)methyl]-7-(4-methanesulfonylphenyl)-3-methyl-1,2,3,4-tetrahydroquinoxaline-1-carboxamide;
(3S)-4-acetyl-7-(4-methanesulfonylphenyl)-3-methyl-N-(2-methylpropyl)-1,2,3,4-tetrahydroquinoxaline-1-carboxamide;
(3S)-4-acetyl-7-(4-methanesulfonylphenyl)-3-methyl-N-(thiophen-3-yl)-1,2,3,4-tetrahydroquinoxaline-1-carboxamide;
(3S)-4-acetyl-N-(furan-2-ylmethyl)-7-(4-methanesulfonylphenyl)-3-methyl-1,2,3,4-tetrahydroquinoxaline-1-carboxamide;
1-[(2S)-6-(4-methanesulfonylphenyl)-2-methyl-4-(5-methyl-1H-pyrazole-3-carbonyl)-1,2,3,4-tetrahydroquinoxalin-1-yl]ethan-1-one;
1-[(2S)-4-(1H-imidazole-2-carbonyl)-6-(4-methanesulfonylphenyl)-2-methyl-1,2,3,4-tetrahydroquinoxalin-1-yl]ethan-1-one;
5-[(3S)-4-acetyl-7-(4-methanesulfonylphenyl)-3-methyl-1,2,3,4-tetrahydroquinoxaline-1-carbonyl]-N,N-dimethylfuran-2-sulfonamide;
1-[(2S)-4-{5-[(dimethylamino)methyl]furan-2-carbonyl}-6-(4-methanesulfonylphenyl)-2-methyl-1,2,3,4-tetrahydroquinoxalin-1-yl]ethan-1-one;
1-[(2S)-4-(3-aminobenzoyl)-6-(4-methanesulfonylphenyl)-2-methyl-1,2,3,4-tetrahydroquinoxalin-1-yl]ethan-1-one;
1-[(2S)-4-(4-aminobenzoyl)-6-(4-methanesulfonylphenyl)-2-methyl-1,2,3,4-tetrahydroquinoxalin-1-yl]ethan-1-one;
(2S)-4-(furan-2-carbonyl)-6-(4-methanesulfonylphenyl)-2-methyl-1,2,3,4-tetrahydroquinoxaline-1-carboxamide;
(2S)-4-(furan-2-carbonyl)-6-(4-methanesulfonylphenyl)-N,2-dimethyl-1,2,3,4-tetrahydroquinoxaline-1-carboxamide;
1-[(2S)-6-(benzylamino)-4-(furan-2-carbonyl)-2-methyl-1,2,3,4-tetrahydroquinoxalin-1-yl]ethan-1-one;
1-[(2S)-6-[benzyl(methyl)amino]-4-(furan-2-carbonyl)-2-methyl-1,2,3,4-tetrahydroquinoxalin-1-yl]ethan-1-one;
1-[(2S)-4-(furan-2-carbonyl)-2-methyl-6-(phenylamino)-1,2,3,4-tetrahydroquinoxalin-1-yl]ethan-1-one;
1-[(2S)-4-(furan-2-carbonyl)-2-methyl-6-[methyl(phenyl)amino]-1,2,3,4-tetrahydroquinoxalin-1-yl]ethan-1-one;
1-[(2S)-4-(furan-2-carbonyl)-2-methyl-6-(pyrrolidin-1-yl)-1,2,3,4-tetrahydroquinoxalin-1-yl]ethan-1-one;
cyclopropylmethyl (3S)-4-acetyl-7-(1-cyclopropyl-1H-pyrazol-4-yl)-3-methyl-1,2,3,4-tetrahydroquinoxaline-1-carboxylate;
cyclopropylmethyl (3S)-4-cyclopropanecarbonyl-7-(1-cyclopropyl-1H-pyrazol-4-yl)-3-methyl-1,2,3,4-tetrahydroquinoxaline-1-carboxylate;
4-cyclopropylmethyl 1-methyl (2S)-6-(1-cyclopropyl-1H-pyrazol-4-yl)-2-methyl-1,2,3,4-tetrahydroquinoxaline-1,4-dicarboxylate;
oxetan-3-yl (3S)-4-acetyl-7-(1-cyclopropyl-1H-pyrazol-4-yl)-3-methyl-1,2,3,4-tetrahydroquinoxaline-1-carboxylate;
oxetan-3-yl (3S)-4-cyclopropanecarbonyl-7-(1-cyclopropyl-1H-pyrazol-4-yl)-3-methyl-1,2,3,4-tetrahydroquinoxaline-1-carboxylate;
1-methyl 4-oxetan-3-yl (2S)-6-(1-cyclopropyl-1H-pyrazol-4-yl)-2-methyl-1,2,3,4-tetrahydroquinoxaline-1,4-dicarboxylate;
oxan-4-yl (3S)-4-acetyl-7-(1-cyclopropyl-1H-pyrazol-4-yl)-3-methyl-1,2,3,4-tetrahydroquinoxaline-1-carboxylate;
oxan-4-yl (3S)-4-cyclopropanecarbonyl-7-(1-cyclopropyl-1H-pyrazol-4-yl)-3-methyl-1,2,3,4-tetrahydroquinoxaline-1-carboxylate;
1-methyl 4-oxan-4-yl (2S)-6-(1-cyclopropyl-1H-pyrazol-4-yl)-2-methyl-1,2,3,4-tetrahydroquinoxaline-1,4-dicarboxylate;
cyclobutyl (3S)-4-acetyl-7-(1-cyclopropyl-1H-pyrazol-4-yl)-3-methyl-1,2,3,4-tetrahydroquinoxaline-1-carboxylate;
cyclobutyl (3S)-4-cyclopropanecarbonyl-7-(1-cyclopropyl-1H-pyrazol-4-yl)-3-methyl-1,2,3,4-tetrahydroquinoxaline-1-carboxylate;

4-cyclobutyl 1-methyl (2S)-6-(1-cyclopropyl-1H-pyrazol-4-yl)-2-methyl-1,2,3,4-tetrahydroquinoxaline-1,4-dicarboxylate;

phenyl (3S)-4-acetyl-7-[1-(2-hydroxy-2-methylpropyl)-1H-pyrazol-4-yl]-3-methyl-1,2,3,4-tetrahydroquinoxaline-1-carboxylate;

pyridin-3-yl (3S)-4-acetyl-7-[1-(2-hydroxy-2-methylpropyl)-1H-pyrazol-4-yl]-3-methyl-1,2,3,4-tetrahydroquinoxaline-1-carboxylate;

1-[(2S)-2-ethyl-4-(furan-2-carbonyl)-6-(4-methanesulfonylphenyl)-1,2,3,4-tetrahydroquinoxalin-1-yl]ethan-1-one;

1-[2-(fluoromethyl)-4-(furan-2-carbonyl)-6-(4-methanesulfonylphenyl)-1,2,3,4-tetrahydroquinoxalin-1-yl]ethan-1-one;

1-[(2S)-4-cyclopropanecarbonyl-6-[4-(ethanesulfonyl)phenyl]-2-methyl-1,2,3,4-tetrahydroquinoxalin-1-yl]ethan-1-one;

1-[(2S)-4-cyclobutanecarbonyl-6-[4-(ethanesulfonyl)phenyl]-2-methyl-1,2,3,4-tetrahydroquinoxalin-1-yl]ethan-1-one;

ethyl (3S)-4-acetyl-7-[4-(ethanesulfonyl)phenyl]-3-methyl-1,2,3,4-tetrahydroquinoxaline-1-carboxylate;

propan-2-yl (3S)-4-acetyl-7-[4-(ethanesulfonyl)phenyl]-3-methyl-1,2,3,4-tetrahydroquinoxaline-1-carboxylate;

1-[(2S)-4-cyclopropanecarbonyl-6-[4-(cyclopropanesulfonyl)phenyl]-2-methyl-1,2,3,4-tetrahydroquinoxalin-1-yl]ethan-1-one;

1-[(2S)-4-cyclobutanecarbonyl-6-[4-(cyclopropanesulfonyl)phenyl]-2-methyl-1,2,3,4-tetrahydroquinoxalin-1-yl]ethan-1-one;

ethyl (3S)-4-acetyl-7-[4-(cyclopropanesulfonyl)phenyl]-3-methyl-1,2,3,4-tetrahydroquinoxaline-1-carboxylate;

propan-2-yl (3S)-4-acetyl-7-[4-(cyclopropanesulfonyl)phenyl]-3-methyl-1,2,3,4-tetrahydroquinoxaline-1-carboxylate;

S-{4-[(2S)-1-acetyl-4-cyclopropanecarbonyl-2-methyl-1,2,3,4-tetrahydroquinoxalin-6-yl]phenyl}-2-hydroxyethane-1-sulfonamido;

S-{4-[(2S)-1-acetyl-4-cyclobutanecarbonyl-2-methyl-1,2,3,4-tetrahydroquinoxalin-6-yl]phenyl}-2-hydroxyethane-1-sulfonamido;

ethyl (3S)-4-acetyl-7-{4-[(2-hydroxyethyl)sulfamoyl]phenyl}-3-methyl-1,2,3,4-tetrahydroquinoxaline-1-carboxylate;

propan-2-yl (3S)-4-acetyl-7-{4-[(2-hydroxyethyl)sulfamoyl]phenyl}-3-methyl-1,2,3,4-tetrahydroquinoxaline-1-carboxylate;

3-[(2S)-1-acetyl-4-cyclopropanecarbonyl-2-methyl-1,2,3,4-tetrahydroquinoxalin-6-yl]benzene-1-sulfonamide;

3-[(2S)-1-acetyl-4-cyclobutanecarbonyl-2-methyl-1,2,3,4-tetrahydroquinoxalin-6-yl]benzene-1-sulfonamide;

ethyl (3S)-4-acetyl-3-methyl-7-(3-sulfamoylphenyl)-1,2,3,4-tetrahydroquinoxaline-1-carboxylate;

propan-2-yl (3S)-4-acetyl-3-methyl-7-(3-sulfamoylphenyl)-1,2,3,4-tetrahydroquinoxaline-1-carboxylate;

N-{3-[(2S)-1-acetyl-4-cyclopropanecarbonyl-2-methyl-1,2,3,4-tetrahydroquinoxalin-6-yl]phenyl}methanesulfonamide;

N-{3-[(2S)-1-acetyl-4-cyclobutanecarbonyl-2-methyl-1,2,3,4-tetrahydroquinoxalin-6-yl]phenyl}methanesulfonamide;

ethyl (3S)-4-acetyl-7-(3-methanesulfonamidophenyl)-3-methyl-1,2,3,4-tetrahydroquinoxaline-1-carboxylate;

3-[(2S)-1-acetyl-4-cyclopropanecarbonyl-2-methyl-1,2,3,4-tetrahydroquinoxalin-6-yl]-N,N-dimethylbenzene-1-sulfonamide;

3-[(2S)-1-acetyl-4-cyclobutanecarbonyl-2-methyl-1,2,3,4-tetrahydroquinoxalin-6-yl]-N,N-dimethylbenzene-1-sulfonamide;

ethyl (3S)-4-acetyl-7-[3-(dimethylsulfamoyl)phenyl]-3-methyl-1,2,3,4-tetrahydroquinoxaline-1-carboxylate;

propan-2-yl (3S)-4-acetyl-7-[3-(dimethylsulfamoyl)phenyl]-3-methyl-1,2,3,4-tetrahydroquinoxaline-1-carboxylate;

1-[(2S)-4-cyclopropanecarbonyl-6-(3-methanesulfonylphenyl)-2-methyl-1,2,3,4-tetrahydroquinoxalin-1-yl]ethan-1-one;

1-[(2S)-4-cyclobutanecarbonyl-6-(3-methanesulfonylphenyl)-2-methyl-1,2,3,4-tetrahydroquinoxalin-1-yl]ethan-1-one;

ethyl (3S)-4-acetyl-7-(3-methanesulfonylphenyl)-3-methyl-1,2,3,4-tetrahydroquinoxaline-1-carboxylate;

propan-2-yl (3S)-4-acetyl-7-(3-methanesulfonylphenyl)-3-methyl-1,2,3,4-tetrahydroquinoxaline-1-carboxylate;

N-{3-[(2S)-1-acetyl-4-cyclopropanecarbonyl-2-methyl-1,2,3,4-tetrahydroquinoxalin-6-yl]phenyl}ethane-1-sulfonamide;

N-{3-[(2S)-1-acetyl-4-cyclobutanecarbonyl-2-methyl-1,2,3,4-tetrahydroquinoxalin-6-yl]phenyl}ethane-1-sulfonamide;

ethyl (3S)-4-acetyl-7-(3-ethanesulfonamidophenyl)-3-methyl-1,2,3,4-tetrahydroquinoxaline-1-carboxylate;

propan-2-yl (3S)-4-acetyl-7-(3-ethanesulfonamidophenyl)-3-methyl-1,2,3,4-tetrahydroquinoxaline-1-carboxylate;

1-[(2S)-4-cyclopropanecarbonyl-2-methyl-6-[4-(morpholin-4-yl)phenyl]-1,2,3,4-tetrahydroquinoxalin-1-yl]ethan-1-one;

1-[(2S)-4-cyclobutanecarbonyl-2-methyl-6-[4-(morpholin-4-yl)phenyl]-1,2,3,4-tetrahydroquinoxalin-1-yl]ethan-1-one;

ethyl (3S)-4-acetyl-3-methyl-7-[4-(morpholin-4-yl)phenyl]-1,2,3,4-tetrahydroquinoxaline-1-carboxylate;

propan-2-yl (3S)-4-acetyl-3-methyl-7-[4-(morpholin-4-yl)phenyl]-1,2,3,4-tetrahydroquinoxaline-1-carboxylate;

1-[(2S)-4-cyclopropanecarbonyl-2-methyl-6-[4-(propane-2-sulfonyl)phenyl]-1,2,3,4-tetrahydroquinoxalin-1-yl]ethan-1-one;

1-[(2S)-4-cyclobutanecarbonyl-2-methyl-6-[4-(propane-2-sulfonyl)phenyl]-1,2,3,4-tetrahydroquinoxalin-1-yl]ethan-1-one;

ethyl (3S)-4-acetyl-3-methyl-7-[4-(propane-2-sulfonyl)phenyl]-1,2,3,4-tetrahydroquinoxaline-1-carboxylate;

propan-2-yl (3S)-4-acetyl-3-methyl-7-[4-(propane-2-sulfonyl)phenyl]-1,2,3,4-tetrahydroquinoxaline-1-carboxylate;

4-[(2S)-1-acetyl-4-cyclopropanecarbonyl-2-methyl-1,2,3,4-tetrahydroquinoxalin-6-yl]benzene-1-sulfonamide;

4-[(2S)-1-acetyl-4-cyclobutanecarbonyl-2-methyl-1,2,3,4-tetrahydroquinoxalin-6-yl]benzene-1-sulfonamide;

ethyl (3S)-4-acetyl-3-methyl-7-(4-sulfamoylphenyl)-1,2,3,4-tetrahydroquinoxaline-1-carboxylate;

propan-2-yl (3S)-4-acetyl-3-methyl-7-(4-sulfamoylphenyl)-1,2,3,4-tetrahydroquinoxaline-1-carboxylate;

1-[(2S)-4-cyclopropanecarbonyl-2-methyl-6-[4-(propane-1-sulfonyl)phenyl]-1,2,3,4-tetrahydroquinoxalin-1-yl]ethan-1-one;

1-[(2S)-4-cyclobutanecarbonyl-2-methyl-6-[4-(propane-1-sulfonyl)phenyl]-1,2,3,4-tetrahydroquinoxalin-1-yl]ethan-1-one;

ethyl (3S)-4-acetyl-3-methyl-7-[4-(propane-1-sulfonyl)phenyl]-1,2,3,4-tetrahydroquinoxaline-1-carboxylate propan-2-yl (3S)-4-acetyl-3-methyl-7-[4-(propane-1-sulfonyl)phenyl]-1,2,3,4-tetrahydroquinoxaline-1-carboxylate;
1-[(2S)-4-cyclopropanecarbonyl-6-(4-cyclopropylmethanesulfonylphenyl)-2-methyl-1,2,3,4-tetrahydroquinoxalin-1-yl]ethan-1-one;
1-[(2S)-4-cyclobutanecarbonyl-6-(4-cyclopropylmethanesulfonylphenyl)-2-methyl-1,2,3,4-tetrahydroquinoxalin-1-yl]ethan-1-one;
ethyl (3S)-4-acetyl-7-(4-cyclopropylmethanesulfonylphenyl)-3-methyl-1,2,3,4-tetrahydroquinoxaline-1-carboxylate;
propan-2-yl (3S)-4-acetyl-7-(4-cyclopropylmethanesulfonylphenyl)-3-methyl-1,2,3,4-tetrahydroquinoxaline-1-carboxylate;
1-[(2S)-4-cyclopropanecarbonyl-2-methyl-6-[4-(2-methylpropanesulfonyl)phenyl]-1,2,3,4-tetrahydroquinoxalin-1-yl]ethan-1-one;
1-[(2S)-4-cyclobutanecarbonyl-2-methyl-6-[4-(2-methylpropanesulfonyl)phenyl]-1,2,3,4-tetrahydroquinoxalin-1-yl]ethan-1-one;
ethyl (3S)-4-acetyl-3-methyl-7-[4-(2-methylpropanesulfonyl)phenyl]-1,2,3,4-tetrahydroquinoxaline-1-carboxylate;
propan-2-yl (3S)-4-acetyl-3-methyl-7-[4-(2-methylpropanesulfonyl)phenyl]-1,2,3,4-tetrahydroquinoxaline-1-carboxylate;
1-[(2S)-4-cyclopropanecarbonyl-6-(3-fluoro-4-methanesulfonylphenyl)-2-methyl-1,2,3,4-tetrahydroquinoxalin-1-yl]ethan-1-one;
1-[(2S)-4-cyclobutanecarbonyl-6-(3-fluoro-4-methanesulfonylphenyl)-2-methyl-1,2,3,4-tetrahydroquinoxalin-1-yl]ethan-1-one;
ethyl (3S)-4-acetyl-7-(3-fluoro-4-methanesulfonylphenyl)-3-methyl-1,2,3,4-tetrahydroquinoxaline-1-carboxylate;
propan-2-yl (3S)-4-acetyl-7-(3-fluoro-4-methanesulfonylphenyl)-3-methyl-1,2,3,4-tetrahydroquinoxaline-1-carboxylate;
1-[(2S)-4-cyclopropanecarbonyl-6-[3-(cyclopropanesulfonyl)phenyl]-2-methyl-1,2,3,4-tetrahydroquinoxalin-1-yl]ethan-1-one;
1-[(2S)-4-cyclobutanecarbonyl-6-[3-(cyclopropanesulfonyl)phenyl]-2-methyl-1,2,3,4-tetrahydroquinoxalin-1-yl]ethan-1-one;
ethyl (3S)-4-acetyl-7-[3-(cyclopropanesulfonyl)phenyl]-3-methyl-1,2,3,4-tetrahydroquinoxaline-1-carboxylate;
propan-2-yl (3S)-4-acetyl-7-[3-(cyclopropanesulfonyl)phenyl]-3-methyl-1,2,3,4-tetrahydroquinoxaline-1-carboxylate;
1-[(2S)-4-cyclopropanecarbonyl-6-[3-(ethanesulfonyl)phenyl]-2-methyl-1,2,3,4-tetrahydroquinoxalin-1-yl]ethan-1-one;
1-[(2S)-4-cyclobutanecarbonyl-6-[3-(ethanesulfonyl)phenyl]-2-methyl-1,2,3,4-tetrahydroquinoxalin-1-yl]ethan-1-one;
ethyl (3S)-4-acetyl-7-[3-(ethanesulfonyl)phenyl]-3-methyl-1,2,3,4-tetrahydroquinoxaline-1-carboxylate;
propan-2-yl (3S)-4-acetyl-7-[3-(ethanesulfonyl)phenyl]-3-methyl-1,2,3,4-tetrahydroquinoxaline-1-carboxylate;
1-[(2S)-6-(3-chloro-5-methanesulfonylphenyl)-4-cyclopropanecarbonyl-2-methyl-1,2,3,4-tetrahydroquinoxalin-1-yl]ethan-1-one;
1-[(2S)-6-(3-chloro-5-methanesulfonylphenyl)-4-cyclobutanecarbonyl-2-methyl-1,2,3,4-tetrahydroquinoxalin-1-yl]ethan-1-one;
ethyl (3S)-4-acetyl-7-(3-chloro-5-methanesulfonylphenyl)-3-methyl-1,2,3,4-tetrahydroquinoxaline-1-carboxylate;
propan-2-yl (3S)-4-acetyl-7-(3-chloro-5-methanesulfonylphenyl)-3-methyl-1,2,3,4-tetrahydroquinoxaline-1-carboxylate;
1-[(2S)-4-cyclopropanecarbonyl-6-(4-fluoro-3-methanesulfonylphenyl)-2-methyl-1,2,3,4-tetrahydroquinoxalin-1-yl]ethan-1-one;
1-[(2S)-4-cyclobutanecarbonyl-6-(4-fluoro-3-methanesulfonylphenyl)-2-methyl-1,2,3,4-trahydroquinoxalin-1-yl]ethan-1-one;
ethyl (3S)-4-acetyl-7-(4-fluoro-3-methanesulfonylphenyl)-3-methyl-1,2,3,4-tetrahydroquinoxaline-1-carboxylate;
propan-2-yl (3S)-4-acetyl-7-(4-fluoro-3-methanesulfonylphenyl)-3-methyl-1,2,3,4-tetrahydroquinoxaline-1-carboxylate;
ethyl (3S)-4-acetyl-7-[4-(2-methanesulfonylethoxy)phenyl]-3-methyl-1,2,3,4-tetrahydroquinoxaline-1-carboxylate;
propan-2-yl (3S)-4-acetyl-7-[4-(2-methanesulfonylethoxy)phenyl]-3-methyl-1,2,3,4-tetrahydroquinoxaline-1-carboxylate;
3-[(2S)-1-acetyl-4-cyclopropanecarbonyl-methyl-1,2,3,4-tetrahydroquinoxalin-6-yl]-N-methylbenzene-1-sulfonamide;
3-[(2S)-1-acetyl-4-cyclobutanecarbonyl-2-methyl-1,2,3,4-tetrahydroquinoxalin-6-yl]-N-methylbenzene-1-sulfonamide;
ethyl (3S)-4-acetyl-3-methyl-7-[3-(methylsulfamoyl)phenyl]-1,2,3,4-tetrahydroquinoxaline-1-carboxylate;
propan-2-yl (3S)-4-acetyl-3-methyl-7-[3-(methylsulfamoyl)phenyl]-1,2,3,4-tetrahydroquinoxaline-1-carboxylate;
S-{3-[(2S)-1-acetyl-4-cyclopropanecarbonyl-2-methyl-1,2,3,4-tetrahydroquinoxalin-6-yl]phenyl}-2-hydroxyethane-1-sulfonamido;
S-{3-[(2S)-1-acetyl-4-cyclobutanecarbonyl-2-methyl-1,2,3,4-tetrahydroquinoxalin-6-yl]phenyl}-2-hydroxyethane-1-sulfonamido;
ethyl (3S)-4-acetyl-7-{3-[(2-hydroxyethyl)sulfamoyl]phenyl}-3-methyl-1,2,3,4-tetrahydroquinoxaline-1-carboxylate;
propan-2-yl (3S)-4-acetyl-7-{3-[(2-hydroxyethyl)sulfamoyl]phenyl}-3-methyl-1,2,3,4-tetrahydroquinoxaline-1-carboxylate;
5-[(2S)-1-acetyl-4-cyclopropanecarbonyl-2-methyl-1,2,3,4-tetrahydroquinoxalin-6-yl]-N,N-di ethyl-2-methoxybenzene-1-sulfonamide;
5-[(2S)-1-acetyl-4-cyclobutanecarbonyl-2-methyl-1,2,3,4-tetrahydroquinoxalin-6-yl]-N,N-di ethyl-2-methoxybenzene-1-sulfonamide;
ethyl (3S)-4-acetyl-7-[3-(diethylsulfamoyl)-4-methoxyphenyl]-3-methyl-1,2,3,4-tetrahydroquinoxaline-1-carboxylate;
propan-2-yl (3S)-4-acetyl-7-[3-(diethylsulfamoyl)-4-methoxyphenyl]-3-methyl-1,2,3,4-tetrahydroquinoxaline-1-carboxylate;
1-[(2S)-4-cyclobutanecarbonyl-2-methyl-6-[4-(1H-pyrazole-1-sulfonyl)phenyl]-1,2,3,4-tetrahydroquinoxalin-1-yl]ethan-1-one;
ethyl (3S)-4-acetyl-3-methyl-7-[4-(1H-pyrazole-1-sulfonyl)phenyl]-1,2,3,4-tetrahydroquinoxaline-1-carboxylate;

propan-2-yl (3S)-4-acetyl-3-methyl-7-[4-(1H-pyrazole-1-sulfonyl)phenyl]-1,2,3,4-tetrahydroquinoxaline-1-carboxylate;
4-[(2S)-1-acetyl-4-cyclopropanecarbonyl-2-methyl-1,2,3,4-tetrahy droquinoxalin-6-yl]-N-methylbenzene-1-sulfonamide;
4-[(2S)-1-acetyl-4-cyclobutanecarbonyl-2-methyl-1,2,3,4-tetrahydroquinoxalin-6-yl]-N-methylbenzene-1-sulfonamide;
ethyl (3S)-4-acetyl-3-methyl-7-[4-(methylsulfamoyl)phenyl]-1,2,3,4-tetrahydroquinoxaline-1-carboxylate;
propan-2-yl (3S)-4-acetyl-3-methyl-7-[4-(methylsulfamoyl)phenyl]-1,2,3,4-tetrahydroquinoxaline-1-carboxylate;
4-[(2S)-1-acetyl-4-cyclopropanecarbonyl-2-methyl-1,2,3,4-tetrahydroquinoxalin-6-yl]-N,N-dimethylbenzene-1-sulfonamide;
4-[(2S)-1-acetyl-4-cyclobutanecarbonyl-2-methyl-1,2,3,4-tetrahydroquinoxalin-6-yl]-N,N-dimethylbenzene-1-sulfonamide;
ethyl (3S)-4-acetyl-7-[4-(dimethylsulfamoyl)phenyl]-3-methyl-1,2,3,4-tetrahydroquinoxaline-1-carboxylate;
propan-2-yl (3S)-4-acetyl-7-[4-(dimethylsulfamoyl)phenyl]-3-methyl-1,2,3,4-tetrahydroquinoxaline-1-carboxylate;
4-[(2S)-1-acetyl-4-cyclopropanecarbonyl-2-methyl-1,2,3,4-tetrahydroquinoxalin-6-yl]-N-tert-butylbenzene-1-sulfonamide;
4-[(2S)-1-acetyl-4-cyclobutanecarbonyl-2-methyl-1,2,3,4-tetrahydroquinoxalin-6-yl]-N-tert-butylbenzene-1-sulfonamide;
ethyl (3S)-4-acetyl-7-[4-(tert-butylsulfamoyl)phenyl]-3-methyl-1,2,3,4-tetrahydroquinoxaline-1-carboxylate;
propan-2-yl (3S)-4-acetyl-7-[4-(tert-butylsulfamoyl)phenyl]-3-methyl-1,2,3,4-tetrahydroquinoxaline-1-carboxylate;
1-{4-[(2S)-1-acetyl-4-cyclopropanecarbonyl-2-methyl-1,2,3,4-tetrahydroquinoxalin-6-yl]phenyl}pyrrolidin-2-one;
1-{4-[(2S)-1-acetyl-4-cyclobutanecarbonyl-2-methyl-1,2,3,4-tetrahydroquinoxalin-6-yl]phenyl}pyrrolidin-2-one;
ethyl (3S)-4-acetyl-3-methyl-7-[4-(2-oxopyrrolidin-1-yl)phenyl]-1,2,3,4-tetrahydroquinoxaline-1-carboxylate;
propan-2-yl (3S)-4-acetyl-3-methyl-7-[4-(2-oxopyrrolidin-1-yl)phenyl]-1,2,3,4-tetrahydroquinoxaline-1-carboxylate;
N-{4-[(2S)-1-acetyl-4-cyclopropanecarbonyl-2-methyl-1,2,3,4-tetrahydroquinoxalin-6-yl]phenyl}ethane-1-sulfonamide;
N-{4-[(2S)-1-acetyl-4-cyclobutanecarbonyl-2-methyl-1,2,3,4-tetrahydroquinoxalin-6-yl]phenyl}ethane-1-sulfonamide;
ethyl (3S)-4-acetyl-7-(4-ethanesulfonamidophenyl)-3-methyl-1,2,3,4-tetrahydroquinoxaline-1-carboxylate;
propan-2-yl (3S)-4-acetyl-7-(4-ethanesulfonamidophenyl)-3-methyl-1,2,3,4-tetrahydroquinoxaline-1-carboxylate;
N-{5-[(2S)-1-acetyl-4-cyclopropanecarbonyl-2-methyl-1,2,3,4-tetrahydroquinoxalin-6-yl]-2-methoxyphenyl}methanesulfonamide;
N-{5-[(2S)-1-acetyl-4-cyclobutanecarbonyl-2-methyl-1,2,3,4-tetrahydroquinoxalin-6-yl]-2-methoxyphenyl}methanesulfonamide;
ethyl (3S)-4-acetyl-7-(3-methanesulfonamido-4-methoxyphenyl)-3-methyl-1,2,3,4-tetrahydroquinoxaline-1-carboxylate;
propan-2-yl (3S)-4-acetyl-7-(3-methanesulfonamido-4-methoxyphenyl)-3-methyl-1,2,3,4-tetrahydroquinoxaline-1-carboxylate;
1-[(2S)-4-cyclopropanecarbonyl-6-{3-[(dimethylsulfamoyl)amino]phenyl}-2-methyl-1,2,3,4-tetrahydroquinoxalin-1-yl]ethan-1-one;
1-[(2S)-4-cyclobutanecarbonyl-6-{3-[(dimethylsulfamoyl)amino]phenyl}-2-methyl-1,2,3,4-tetrahydroquinoxalin-1-yl]ethan-1-one;
ethyl (3S)-4-acetyl-7-{3-[(dimethylsulfamoyl)amino]phenyl}-3-methyl-1,2,3,4-tetrahydroquinoxaline-1-carboxylate;
propan-2-yl (3S)-4-acetyl-7-{3-[(dimethylsulfamoyl)amino]phenyl}-3-methyl-1,2,3,4-tetrahydroquinoxaline-1-carboxylate;
cyclopentyl (3S)-4-acetyl-3-methyl-7-[1-(oxan-4-yl)-1H-pyrazol-4-yl]-1,2,3,4-tetrahydroquinoxaline-1-carboxylate;
cyclopentyl (3S)-4-acetyl-7-[1-(1,1-dioxo-1$\lambda^6$-thian-3-yl)-1H-pyrazol-4-yl]-3-methyl-1,2,3,4-tetrahydroquinoxaline-1-carboxylate;
2-{3-[(2S)-1-acetyl-4-cyclopropanecarbonyl-2-methyl-1,2,3,4-tetrahydroquinoxalin-6-yl]phenyl}-1$\lambda^6$,2-thiazolidine-1,1-dione;
propan-2-yl (3S)-4-acetyl-7-[3-(1,1-dioxo-1$\lambda^6$,2-thiazolidin-2-yl)phenyl]-3-methyl-1,2,3,4-tetrahydroquinoxaline-1-carboxylate;
2-{4-[(2S)-1-acetyl-4-cyclobutanecarbonyl-2-methyl-1,2,3,4-tetrahydroquinoxalin-6-yl]-2-fluorophenyl}-1$\lambda^6$,2-thiazolidine-1,1-dione;
ethyl (3S)-4-acetyl-7-[4-(1,1-dioxo-1$\lambda^6$,2-thiazolidin-2-yl)-3-fluorophenyl]-3-methyl-1,2,3,4-tetrahydroquinoxaline-1-carboxylate;
propan-2-yl (3S)-4-acetyl-7-[4-(1,1-dioxo-1$\lambda^6$,2-thiazolidin-2-yl)-3-fluorophenyl]-3-methyl-1,2,3,4-tetrahydroquinoxaline-1-carboxylate;
1-[(2S)-4-cyclopropanecarbonyl-6-(1-methanesulfonyl-1,2,3,4-tetrahydroquinolin-6-yl)-2-methyl-1,2,3,4-tetrahydroquinoxalin-1-yl]ethan-1-one;
1-[(2S)-4-cyclobutanecarbonyl-6-(1-methanesulfonyl-1,2,3,4-tetrahydroquinolin-6-yl)-2-methyl-1,2,3,4-tetrahydroquinoxalin-1-yl]ethan-1-one;
ethyl (3S)-4-acetyl-7-(1-methanesulfonyl-1,2,3,4-tetrahydroquinolin-6-yl)-3-methyl-1,2,3,4-tetrahydroquinoxaline-1-carboxylate;
propan-2-yl (3S)-4-acetyl-7-(1-methanesulfonyl-1,2,3,4-tetrahydroquinolin-6-yl)-3-methyl-1,2,3,4-tetrahydroquinoxaline-1-carboxylate;
2-{3-[(2S)-1-acetyl-4-cyclobutanecarbonyl-2-methyl-1,2,3,4-tetrahydroquinoxalin-6-yl]phenyl}-1$\lambda^6$,2-thiazolidine-1,1-dione;
ethyl (3S)-4-acetyl-7-[3-(1,1-dioxo-1$\lambda^6$,2-thiazolidin-2-yl)phenyl]-3-methyl-1,2,3,4-tetrahydroquinoxaline-1-carboxylate;
2-{3-[(2S)-1-acetyl-4-cyclopropanecarbonyl-2-methyl-1,2,3,4-tetrahydroquinoxalin-6-yl]-5-(trifluoromethyl)phenyl}-1$\lambda^6$,2-thiazolidine-1,1-dione;
2-{3-[(2S)-1-acetyl-4-cyclobutanecarbonyl-2-methyl-1,2,3,4-tetrahydroquinoxalin-6-yl]-5-(trifluoromethyl)phenyl}-1$\lambda^6$,2-thiazoli dine-1,1-di one;
ethyl (3S)-4-acetyl-7-[3-(1,1-dioxo-1$\lambda^6$,2-thiazolidin-2-yl)-5-(trifluoromethyl)phenyl]-3-methyl-1,2,3,4-tetrahydroquinoxaline-1-carboxylate;
propan-2-yl (3S)-4-acetyl-7-[3-(1,1-dioxo-1$\lambda^6$,2-thiazolidin-2-yl)-5-(trifluoromethyl)phenyl]-3-methyl-1,2,3,4-tetrahydroquinoxaline-1-carboxylate;

2-{5-[(2S)-1-acetyl-4-cyclopropanecarbonyl-2-methyl-1,2,3,4-tetrahydroquinoxalin-6-yl]-2-methoxyphenyl}-1$\lambda^6$,2-thiazolidine-1,1-dione;

2-{5-[(2S)-1-acetyl-4-cyclobutanecarbonyl-2-methyl-1,2,3,4-tetrahydroquinoxalin-6-yl]-2-methoxyphenyl}-1$\lambda^6$,2-thiazolidine-1,1-dione;

ethyl (3S)-4-acetyl-7-[3-(1,1-dioxo-1$\lambda^6$,2-thiazolidin-2-yl)-4-methoxyphenyl]-3-methyl-1,2,3,4-tetrahydroquinoxaline-1-carboxylate;

propan-2-yl (3S)-4-acetyl-7-[3-(1,1-dioxo-1$\lambda^6$,2-thiazolidin-2-yl)-4-methoxyphenyl]-3-methyl-1,2,3,4-tetrahydroquinoxaline-1-carboxylate;

N-{4-[(2S)-1-acetyl-4-cyclopropanecarbonyl-2-methyl-1,2,3,4-tetrahydroquinoxalin-6-yl]-2-methylphenyl}methanesulfonamide;

N-{4-[(2S)-1-acetyl-4-cyclobutanecarbonyl-2-methyl-1,2,3,4-tetrahydroquinoxalin-6-yl]-2-methylphenyl}methanesulfonamide;

ethyl (3S)-4-acetyl-7-(4-methanesulfonamido-3-methylphenyl)-3-methyl-1,2,3,4-tetrahydroquinoxaline-1-carboxylate;

propan-2-yl (3S)-4-acetyl-7-(4-methanesulfonamido-3-methylphenyl)-3-methyl-1,2,3,4-tetrahydroquinoxaline-1-carboxylate;

6-[(2S)-1-acetyl-4-cyclopropanecarbonyl-2-methyl-1,2,3,4-tetrahydroquinoxalin-6-yl]-1-methyl-1,3-dihydro-2$\lambda^6$,1,3-benzothiadiazole-2,2-dione;

6-[(2S)-1-acetyl-4-cyclobutanecarbonyl-2-methyl-1,2,3,4-tetrahydroquinoxalin-6-yl]-1-methyl-1,3-dihydro-2$\lambda^6$,1,3-benzothiadiazole-2,2-dione;

propan-2-yl (3S)-4-acetyl-3-methyl-7-(3-methyl-2,2-dioxo-1,3-dihydro-2$\lambda^6$,1,3-benzothiadiazol-5-yl)-1,2,3,4-tetrahydroquinoxaline-1-carboxylate;

5-[(2S)-1-acetyl-4-cyclopropanecarbonyl-2-methyl-1,2,3,4-tetrahydroquinoxalin-6-yl]-1,3-dihydro-2$\lambda^6$,1-benzothiazole-2,2-dione;

propan-2-yl (3S)-4-acetyl-7-(2,2-dioxo-1,3-dihydro-2$\lambda^6$,1-benzothiazol-5-yl)-3-methyl-1,2,3,4-tetrahydroquinoxaline-1-carboxylate;

N-{4-[(2S)-1-acetyl-4-cyclopropanecarbonyl-2-methyl-1,2,3,4-tetrahydroquinoxalin-6-yl]-2-fluorophenyl}methanesulfonamide;

N-{4-[(2S)-1-acetyl-4-cyclobutanecarbonyl-2-methyl-1,2,3,4-tetrahydroquinoxalin-6-yl]-2-fluorophenyl}methanesulfonamide;

ethyl (3S)-4-acetyl-7-(3-fluoro-4-methanesulfonamidophenyl)-3-methyl-1,2,3,4-tetrahydroquinoxaline-1-carboxylate;

propan-2-yl (3S)-4-acetyl-7-(3-fluoro-4-methanesulfonamidophenyl)-3-methyl-1,2,3,4-tetrahydroquinoxaline-1-carboxylate;

1-[(2S)-4-cyclopropanecarbonyl-6-(1-methanesulfonyl-1,2,3,4-tetrahydroquinolin-7-yl)-2-methyl-1,2,3,4-tetrahydroquinoxalin-1-yl]ethan-1-one;

propan-2-yl (3S)-4-acetyl-7-(1-methanesulfonyl-1,2,3,4-tetrahydroquinolin-7-yl)-3-methyl-1,2,3,4-tetrahydroquinoxaline-1-carboxylate;

5-chloropyridin-3-yl (3S)-4-acetyl-7-(1-cyclopropyl-1H-pyrazol-4-yl)-3-methyl-1,2,3,4-tetrahydroquinoxaline-1-carboxylate;

3-(trifluoromethyl)pyridin-2-yl (3S)-4-acetyl-7-(1-cyclopropyl-1H-pyrazol-4-yl)-3-methyl-1,2,3,4-tetrahydroquinoxaline-1-carboxylate;

5-fluoropyridin-3-yl (3S)-4-acetyl-7-(1-cyclopropyl-1H-pyrazol-4-yl)-3-methyl-1,2,3,4-tetrahydroquinoxaline-1-carboxylate;

2,6-dimethylpyridin-3-yl (3S)-4-acetyl-7-(1-cyclopropyl-1H-pyrazol-4-yl)-3-methyl-1,2,3,4-tetrahydroquinoxaline-1-carboxylate;

quinolin-5-yl (3S)-4-acetyl-7-(1-cyclopropyl-1H-pyrazol-4-yl)-3-methyl-1,2,3,4-tetrahydroquinoxaline-1-carboxylate;

isoquinolin-6-yl (3S)-4-acetyl-7-(1-cyclopropyl-1H-pyrazol-4-yl)-3-methyl-1,2,3,4-tetrahydroquinoxaline-1-carboxylate;

5-chloro-2-methoxypyridin-3-yl (3S)-4-acetyl-7-(1-cyclopropyl-1H-pyrazol-4-yl)-3-methyl-1,2,3,4-tetrahydroquinoxaline-1-carboxylate;

5-fluoro-2-methoxypyridin-3-yl (3S)-4-acetyl-7-(1-cyclopropyl-1H-pyrazol-4-yl)-3-methyl-1,2,3,4-tetrahydroquinoxaline-1-carboxylate;

5-chloro-2-methoxypyridin-4-yl (3S)-4-acetyl-7-(1-cyclopropyl-1H-pyrazol-4-yl)-3-methyl-1,2,3,4-tetrahydroquinoxaline-1-carboxylate;

2-methoxy-5-methylpyridin-3-yl (3S)-4-acetyl-7-(1-cyclopropyl-1H-pyrazol-4-yl)-3-methyl-1,2,3,4-tetrahydroquinoxaline-1-carboxylate;

4-fluoro-2-methoxyphenyl (3S)-4-acetyl-7-(1-cyclopropyl-1H-pyrazol-4-yl)-3-methyl-1,2,3,4-tetrahydroquinoxaline-1-carboxylate;

2,4-dichlorophenyl (3S)-4-acetyl-7-(1-cyclopropyl-1H-pyrazol-4-yl)-3-methyl-1,2,3,4-tetrahydroquinoxaline-1-carboxylate;

4-(1H-1,2,4-triazol-1-yl)phenyl (3S)-4-acetyl-7-(1-cyclopropyl-1H-pyrazol-4-yl)-3-methyl-1,2,3,4-tetrahydroquinoxaline-1-carboxylate;

quinolin-8-yl (3S)-4-acetyl-7-(1-cyclopropyl-1H-pyrazol-4-yl)-3-methyl-1,2,3,4-tetrahydroquinoxaline-1-carboxylate;

5-chloroquinolin-8-yl (3S)-4-acetyl-7-(1-cyclopropyl-1H-pyrazol-4-yl)-3-methyl-1,2,3,4-tetrahydroquinoxaline-1-carboxylate;

5,7-dichloroquinolin-8-yl (3S)-4-acetyl-7-(1-cyclopropyl-1H-pyrazol-4-yl)-3-methyl-1,2,3,4-tetrahydroquinoxaline-1-carboxylate;

2-fluoro-5-methylphenyl (3S)-4-acetyl-7-(1-cyclopropyl-1H-pyrazol-4-yl)-3-methyl-1,2,3,4-tetrahydroquinoxaline-1-carboxylate;

6-methoxypyridin-3-yl (3S)-4-acetyl-7-(1-cyclopropyl-1H-pyrazol-4-yl)-3-methyl-1,2,3,4-tetrahydroquinoxaline-1-carboxylate;

5-fluoro-2-methylphenyl (3S)-4-acetyl-7-(1-cyclopropyl-1H-pyrazol-4-yl)-3-methyl-1,2,3,4-tetrahydroquinoxaline-1-carboxylate;

5-fluoro-2-methoxyphenyl (3S)-4-acetyl-7-(1-cyclopropyl-1H-pyrazol-4-yl)-3-methyl-1,2,3,4-tetrahydroquinoxaline-1-carboxylate;

quinolin-7-yl (3S)-4-acetyl-7-(1-cyclopropyl-1H-pyrazol-4-yl)-3-methyl-1,2,3,4-tetrahydroquinoxaline-1-carboxylate;

quinolin-3-yl (3S)-4-acetyl-7-(1-cyclopropyl-1H-pyrazol-4-yl)-3-methyl-1,2,3,4-tetrahydroquinoxaline-1-carboxylate;

quinoxalin-5-yl (3S)-4-acetyl-7-(1-cyclopropyl-1H-pyrazol-4-yl)-3-methyl-1,2,3,4-tetrahydroquinoxaline-1-carboxylate;

1-methyl-1H-1,3-benzodiazol-5-yl (3S)-4-acetyl-7-(1-cyclopropyl-1H-pyrazol-4-yl)-3-methyl-1,2,3,4-tetrahydroquinoxaline-1-carboxylate;

isoquinolin-7-yl (3S)-4-acetyl-7-(1-cyclopropyl-1H-pyrazol-4-yl)-3-methyl-1,2,3,4-tetrahydroquinoxaline-1-carboxylate;

cyclohexyl (3S)-4-acetyl-7-[4-(ethanesulfonyl)phenyl]-3-methyl-1,2,3,4-tetrahydroquinoxaline-1-carboxylate;
oxan-4-yl (3S)-4-acetyl-7[4-(ethanesulfonyl)phenyl]-3-methyl-1,2,3,4-tetrahydroquinoxaline-1-carboxylate;
cyclohexyl (3S)-4-acetyl-7-[4-(cyclopropanesulfonyl)phenyl]-3-methyl-1,2,3,4-tetrahydroquinoxaline-1-carboxylate;
oxan-4-yl (3S)-4-acetyl-7-[4-(cyclopropanesulfonyl)phenyl]-3-methyl-1,2,3,4-tetrahydroquinoxaline-1-carboxylate;
cyclohexyl (3S)-4-acetyl-7-{4-[(2-hydroxyethyl)sulfamoyl]phenyl}-3-methyl-1,2,3,4-tetrahydroquinoxaline-1-carboxylate;
oxan-4-yl (3S)-4-acetyl-7-{4-[(2-hydroxyethyl)sulfamoyl]phenyl}-3-methyl-1,2,3,4-tetrahydroquinoxaline-1-carboxylate;
cyclohexyl (3S)-4-acetyl-3-methyl-7-(3-sulfamoylphenyl)-1,2,3,4-tetrahydroquinoxaline-1-carboxylate;
oxan-4-yl (3S)-4-acetyl-3-methyl-7-(3-sulfamoylphenyl)-1,2,3,4-tetrahydroquinoxaline-1-carboxylate;
cyclohexyl (3S)-4-acetyl-7-(3-methanesulfonamidophenyl)-3-methyl-1,2,3,4-tetrahydroquinoxaline-1-carboxylate;
oxan-4-yl (3S)-4-acetyl-7-(3-methanesulfonamidophenyl)-3-methyl-1,2,3,4-tetrahydroquinoxaline-1-carboxylate;
cyclohexyl (3S)-4-acetyl-7-[3-(dimethylsulfamoyl)phenyl]-3-methyl-1,2,3,4-tetrahydroquinoxaline-1-carboxylate;
oxan-4-yl (3S)-4-acetyl-7-[3-(dimethylsulfamoyl)phenyl]-3-methyl-1,2,3,4-tetrahydroquinoxaline-1-carboxylate;
cyclohexyl (3S)-4-acetyl-7-(3-methanesulfonylphenyl)-3-methyl-1,2,3,4-tetrahydroquinoxaline-1-carboxylate;
oxan-4-yl (3S)-4-acetyl-7-(3-methanesulfonylphenyl)-3-methyl-1,2,3,4-tetrahydroquinoxaline-1-carboxylate;
cyclohexyl (3S)-4-acetyl-7-(3-ethanesulfonamidophenyl)-3-methyl-1,2,3,4-tetrahydroquinoxaline-1-carboxylate;
oxan-4-yl (3S)-4-acetyl-7-(3-ethanesulfonamidophenyl)-3-methyl-1,2,3,4-tetrahydroquinoxaline-1-carboxylate;
cyclohexyl (3S)-4-acetyl-3-methyl-7-[4-(morpholin-4-yl)phenyl]-1,2,3,4-tetrahydroquinoxaline-1-carboxylate;
oxan-4-yl (3S)-4-acetyl-3-methyl-7-[4-(morpholin-4-yl)phenyl]-1,2,3,4-tetrahydroquinoxaline-1-carboxylate;
cyclohexyl (3S)-4-acetyl-3-methyl-7-[4-(propane-2-sulfonyl)phenyl]-1,2,3,4-tetrahydroquinoxaline-1-carboxylate;
oxan-4-yl (3S)-4-acetyl-3-methyl-7-[4-(propane-2-sulfonyl)phenyl]-1,2,3,4-tetrahydroquinoxaline-1-carboxylate;
cyclohexyl (3S)-4-acetyl-3-methyl-7-(4-sulfamoylphenyl)-1,2,3,4-tetrahydroquinoxaline-1-carboxylate;
oxan-4-yl (3S)-4-acetyl-3-methyl-7-(4-sulfamoylphenyl)-1,2,3,4-tetrahydroquinoxaline-1-carboxylate;
cyclohexyl (3S)-4-acetyl-3-methyl-7-[4-(propane-1-sulfonyl)phenyl]-1,2,3,4-tetrahydroquinoxaline-1-carboxylate;
oxan-4-yl (3S)-4-acetyl-3-methyl-7-[4-(propane-1-sulfonyl)phenyl]-1,2,3,4-tetrahydroquinoxaline-1-carboxylate;
cyclohexyl (3S)-4-acetyl-7-(4-cyclopropylmethanesulfonylphenyl)-3-methyl-1,2,3,4-tetrahydroquinoxaline-1-carboxylate;
oxan-4-yl (3S)-4-acetyl-7-(4-cyclopropylmethanesulfonylphenyl)-3-methyl-1,2,3,4-tetrahydroquinoxaline-1-carboxylate;
cyclohexyl (3S)-4-acetyl-3-methyl-7-[4-(2-methylpropanesulfonyl)phenyl]-1,2,3,4-tetrahydroquinoxaline-1-carboxylate;
oxan-4-yl (3S)-4-acetyl-3-methyl-7-[4-(2-methylpropanesulfonyl)phenyl]-1,2,3,4-tetrahydroquinoxaline-1-carboxylate;
cyclohexyl (3S)-4-acetyl-7-(3-fluoro-4-methanesulfonylphenyl)-3-methyl-1,2,3,4-tetrahydroquinoxaline-1-carboxylate;
oxan-4-yl (3S)-4-acetyl-7-(3-fluoro-4-methanesulfonylphenyl)-3-methyl-1,2,3,4-tetrahydroquinoxaline-1-carboxylate;
cyclohexyl (3S)-4-acetyl-7-[3-(cyclopropanesulfonyl)phenyl]-3-methyl-1,2,3,4-tetrahydroquinoxaline-1-carboxylate;
oxan-4-yl (3S)-4-acetyl-7-[3-(cyclopropanesulfonyl)phenyl]-3-methyl-1,2,3,4-tetrahydroquinoxaline-1-carboxylate;
cyclohexyl (3S)-4-acetyl-7-[3-(ethanesulfonyl)phenyl]-3-methyl-1,2,3,4-tetrahydroquinoxaline-1-carboxylate;
oxan-4-yl (3S)-4-acetyl-7-[3-(ethanesulfonyl)phenyl]-3-methyl-1,2,3,4-tetrahydroquinoxaline-1-carboxylate;
cyclohexyl (3S)-4-acetyl-7-(3-chloro-5-methanesulfonylphenyl)-3-methyl-1,2,3,4-tetrahydroquinoxaline-1-carboxylate;
oxan-4-yl (3S)-4-acetyl-7-(3-chloro-5-methanesulfonylphenyl)-3-methyl-1,2,3,4-tetrahydroquinoxaline-1-carboxylate;
cyclohexyl (3S)-4-acetyl-7-(4-fluoro-3-methanesulfonylphenyl)-3-methyl-1,2,3,4-tetrahydroquinoxaline-1-carboxylate;
oxan-4-yl (3S)-4-acetyl-7-(4-fluoro-3-methanesulfonylphenyl)-3-methyl-1,2,3,4-tetrahydroquinoxaline-1-carboxylate;
cyclohexyl (3S)-4-acetyl-7-[4-(2-methanesulfonylethoxy)phenyl]-3-methyl-1,2,3,4-tetrahydroquinoxaline-1-carboxylate;
oxan-4-yl (3S)-4-acetyl-7-[4-(2-methanesulfonylethoxy)phenyl]-3-methyl-1,2,3,4-tetrahydroquinoxaline-1-carboxylate;
cyclohexyl (3S)-4-acetyl-3-methyl-7-[3-(methylsulfamoyl)phenyl]-1,2,3,4-tetrahydroquinoxaline-1-carboxylate;
oxan-4-yl (3S)-4-acetyl-3-methyl-7-[3-(methylsulfamoyl)phenyl]-1,2,3,4-tetrahydroquinoxaline-1-carboxylate;
cyclohexyl (3S)-4-acetyl-7-{3-[(2-hydroxyethyl)sulfamoyl]phenyl}-3-methyl-1,2,3,4-tetrahydroquinoxaline-1-carboxylate;
oxan-4-yl (3S)-4-acetyl-7-{3-[(2-hydroxyethyl)sulfamoyl]phenyl}-3-methyl-1,2,3,4-tetrahydroquinoxaline-1-carboxylate;
cyclohexyl (3S)-4-acetyl-7-[3-(diethylsulfamoyl)-4-methoxyphenyl]-3-methyl-1,2,3,4-tetrahydroquinoxaline-1-carboxylate;
oxan-4-yl (3S)-4-acetyl-7-[3-(diethylsulfamoyl)-4-methoxyphenyl]-3-methyl-1,2,3,4-tetrahydroquinoxaline-1-carboxylate;
cyclohexyl (3S)-4-acetyl-3-methyl-7-[4-(1H-pyrazole-1-sulfonyl)phenyl]-1,2,3,4-tetrahydroquinoxaline-1-carboxylate;
oxan-4-yl (3S)-4-acetyl-3-methyl-7-[4-(1H-pyrazole-1-sulfonyl)phenyl]-1,2,3,4-tetrahydroquinoxaline-1-carboxylate;
cyclohexyl (3S)-4-acetyl-3-methyl-7-[4-(methylsulfamoyl)phenyl]-1,2,3,4-tetrahydroquinoxaline-1-carboxylate;

oxan-4-yl (3S)-4-acetyl-3-methyl-7-[4-(methylsulfamoyl) phenyl]-1,2,3,4-tetrahydroquinoxaline-1-carboxylate;
cyclohexyl (3S)-4-acetyl-7-[4-(dimethylsulfamoyl)phenyl]-3-methyl-1,2,3,4-tetrahydroquinoxaline-1-carboxylate;
oxan-4-yl (3S)-4-acetyl-7-[4-(dimethylsulfamoyl)phenyl]-3-methyl-1,2,3,4-tetrahydroquinoxaline-1-carboxylate;
cyclohexyl (3S)-4-acetyl-7-[4-(tert-butylsulfamoyl)phenyl]-3-methyl-1,2,3,4-tetrahydroquinoxaline-1-carboxylate;
oxan-4-yl (3S)-4-acetyl-7-[4-(tert-butylsulfamoyl)phenyl]-3-methyl-1,2,3,4-tetrahydroquinoxaline-1-carboxylate;
cyclohexyl (3S)-4-acetyl-3-methyl-7-[4-(2-oxopyrrolidin-1-yl)phenyl]-1,2,3,4-tetrahydroquinoxaline-1-carboxylate;
oxan-4-yl (3S)-4-acetyl-3-methyl-7-[4-(2-oxopyrrolidin-1-yl)phenyl]-1,2,3,4-tetrahydroquinoxaline-1-carboxylate;
cyclohexyl (3S)-4-acetyl-7-(4-ethanesulfonamidophenyl)-3-methyl-1,2,3,4-tetrahydroquinoxaline-1-carboxylate;
oxan-4-yl (3S)-4-acetyl-7-(4-ethanesulfonamidophenyl)-3-methyl-1,2,3,4-tetrahydroquinoxaline-1-carboxylate;
cyclohexyl (3S)-4-acetyl-7-(3-methanesulfonamido-4-methoxyphenyl)-3-methyl-1,2,3,4-tetrahydroquinoxaline-1-carboxylate;
oxan-4-yl (3S)-4-acetyl-7-(3-methanesulfonamido-4-methoxyphenyl)-3-methyl-1,2,3,4-tetrahydroquinoxaline-1-carboxylate;
cyclohexyl (3S)-4-acetyl-7-{3-[(dimethylsulfamoyl)amino]phenyl}-3-methyl-1,2,3,4-tetrahydroquinoxaline-1-carboxylate;
oxan-4-yl (3S)-4-acetyl-7-{3-[(dimethylsulfamoyl)amino]phenyl}-3-methyl-1,2,3,4-tetrahydroquinoxaline-1-carboxylate;
propan-2-yl (3S)-4-acetyl-7-(4-cyclopropanesulfonamidophenyl)-3-methyl-1,2,3,4-tetrahydroquinoxaline-1-carboxylate;
N-{4-[(2S)-1-acetyl-4-cyclopropanecarbonyl-2-methyl-1,2,3,4-tetrahydroquinoxalin-6-yl]phenyl}cyclopropanesulfonamide;
1-[(2S)-4-cyclopropanecarbonyl-6-(1-methanesulfonyl-2,3-dihydro-1H-indol-5-yl)-2-methyl-1,2,3,4-tetrahydroquinoxalin-1-yl]ethan-1-one;
propan-2-yl (3S)-4-acetyl-7-[1-(1-hydroxy-2-methylpropan-2-yl)-1H-pyrazol-4-yl]-3-methyl-1,2,3,4-tetrahydroquinoxaline-1-carboxylate;
1-methyl 4-pyridin-3-yl (2S)-6-(4-methanesulfonylphenyl)-2-methyl-1,2,3,4-tetrahydroquinoxaline-1,4-dicarboxylate;
pyridin-3-yl (3S)-4-acetyl-7-(4-methanesulfonamidophenyl)-3-methyl-1,2,3,4-tetrahydroquinoxaline-1-carboxylate;
1-methyl 4-pyridin-3-yl (2S)-6-(4-methanesulfonamidophenyl)-2-methyl-1,2,3,4-tetrahydroquinoxaline-1,4-dicarboxylate;
pyridin-3-yl (3S)-4-acetyl-7-[1-(2-methanesulfonylethyl)-1H-pyrazol-4-yl]-3-methyl-1,2,3,4-tetrahydroquinoxaline-1-carboxylate;
1-methyl 4-pyridin-3-yl (2S)-6-[1-(2-methanesulfonylethyl)-1H-pyrazol-4-yl]-2-methyl-1,2,3,4-tetrahydroquinoxaline-1,4-dicarboxylate;
pyridin-3-yl (3S)-4-acetyl-7-[1-(2-hydroxyethyl)-1H-pyrazol-4-yl]-3-methyl-1,2,3,4-tetrahydroquinoxaline-1-carboxylate;
1-methyl 4-pyridin-3-yl (2S)-6-[1-(2-hydroxyethyl)-1H-pyrazol-4-yl]-2-methyl-1,2,3,4-tetrahydroquinoxaline-1,4-dicarboxylate;
1-methyl 4-pyridin-3-yl (2S)-6-(1-cyclopropyl-1H-pyrazol-4-yl)-2-methyl-1,2,3,4-tetrahydroquinoxaline-1,4-dicarboxylate;
pyridin-3-yl (3S)-4-acetyl-7-[1-(1-hydroxy-2-methylpropan-2-yl)-1H-pyrazol-4-yl]-3-methyl-1,2,3,4-tetrahydroquinoxaline-1-carboxylate;
1-methyl 4-pyridin-3-yl (2S)-6-[1-(1-hydroxy-2-methylpropan-2-yl)-1H-pyrazol-4-yl]-2-methyl-1,2,3,4-tetrahydroquinoxaline-1,4-dicarboxylate;
pyridin-3-yl (3S)-4-acetyl-7-[4-(1,1-dioxo-1$\lambda^6$,2-thiazolidin-2-yl)phenyl]-3-methyl-1,2,3,4-tetrahydroquinoxaline-1-carboxylate;
1-methyl 4-pyridin-3-yl (2S)-6-[4-(1,1-dioxo-1$\lambda^6$,2-thiazolidin-2-yl)phenyl]-2-methyl-1,2,3,4-tetrahydroquinoxaline-1,4-dicarboxylate;
pyridin-3-yl (3S)-4-acetyl-7-[1-(2-cyanoethyl)-1H-pyrazol-4-yl]-3-methyl-1,2,3,4-tetrahydroquinoxaline-1-carboxylate;
1-methyl 4-pyridin-3-yl (2S)-6-[1-(2-cyanoethyl)-1H-pyrazol-4-yl]-2-methyl-1,2,3,4-tetrahydroquinoxaline-1,4-dicarboxylate;
pyridin-3-yl (3S)-4-acetyl-7-(1-methanesulfonyl-2,3-dihydro-1H-indol-5-yl)-3-methyl-1,2,3,4-tetrahydroquinoxaline-1-carboxylate;
1-methyl 4-pyridin-3-yl (2S)-6-(1-methanesulfonyl-2,3-dihydro-1H-indol-5-yl)-2-methyl-1,2,3,4-tetrahydroquinoxaline-1,4-dicarboxylate;
pyridin-3-yl (3S)-4-acetyl-3-methyl-7-[4-(N-methylmethanesulfonamido)phenyl]-1,2,3,4-tetrahydroquinoxaline-1-carboxylate;
1-methyl 4-pyridin-3-yl (2S)-2-methyl-6-[4-(N-methylmethanesulfonamido)phenyl]-1,2,3,4-tetrahydroquinoxaline-1,4-dicarboxylate;
pyridin-3-yl (3S)-4-acetyl-7-[1-(azetidin-3-yl)-1H-pyrazol-4-yl]-3-methyl-1,2,3,4-tetrahydroquinoxaline-1-carboxylate;
1-methyl 4-pyridin-3-yl (2S)-6-[1-(azetidin-3-yl)-1H-pyrazol-4-yl]-2-methyl-1,2,3,4-tetrahydroquinoxaline-1,4-dicarboxylate;
1-methyl 4-pyridin-3-yl (2S)-2-methyl-6-[1-(piperidin-4-yl)-1H-pyrazol-4-yl]-1,2,3,4-tetrahydroquinoxaline-1,4-dicarboxylate;
4-[(2S)-1-acetyl-4-cyclopropanecarbonyl-2-methyl-1,2,3,4-tetrahydroquinoxalin-6-yl]-2-fluorobenzene-1-sulfonamide;
propan-2-yl (3S)-4-acetyl-7-(3-fluoro-4-sulfamoylphenyl)-3-methyl-1,2,3,4-tetrahydroquinoxaline-1-carboxylate;
propan-2-yl (3S)-4-acetyl-7-[4-(dimethylsulfamoyl)-3-methylphenyl]-3-methyl-1,2,3,4-tetrahydroquinoxaline-1-carboxylate;
4-[(2S)-1-acetyl-4-cyclopropanecarbonyl-2-methyl-1,2,3,4-tetrahydroquinoxalin-6-yl]-N,N,2-trimethylbenzene-1-sulfonamide;
cyclohexyl (3S)-4-acetyl-3-methyl-7-[1-(oxan-4-yl)-1H-pyrazol-4-yl]-1,2,3,4-tetrahydroquinoxaline-1-carboxylate;
1-[(2S)-4-cyclopropanecarbonyl-2-methyl-6-[1-(oxan-4-yl)-1H-pyrazol-4-yl]-1,2,3,4-tetrahydroquinoxalin-1-yl]ethan-1-one;
cyclohexyl (3S)-4-acetyl-3-methyl-7-[1-(piperidin-4-yl)-1H-pyrazol-4-yl]-1,2,3,4-tetrahydroquinoxaline-1-carboxylate;

cyclohexyl (3S)-4-acetyl-7-[1-(azetidin-3-yl)-1H-pyrazol-4-yl]-3-methyl-1,2,3,4-tetrahydroquinoxaline-1-carboxylate;
3-{4-[(2S)-1-acetyl-4-cyclopropanecarbonyl-2-methyl-1,2,3,4-tetrahydroquinoxalin-6-yl]-1H-pyrazol-1-yl}-1$\lambda^6$-thietane-1,1-dione;
propan-2-yl (3S)-4-acetyl-7-[1-(1,1-dioxo-1$\lambda^6$-thietan-3-yl)-1H-pyrazol-4-yl]-3-methyl-1,2,3,4-tetrahydroquinoxaline-1-carboxylate;
cyclopentyl (3S)-4-acetyl-7-[1-(1,1-dioxo-1$\lambda^6$-thietan-3-yl)-1H-pyrazol-4-yl]-3-methyl-1,2,3,4-tetrahydroquinoxaline-1-carboxylate;
cyclohexyl (3S)-4-acetyl-7-[1-(1,1-dioxo-1$\lambda^6$-thietan-3-yl)-1H-pyrazol-4-yl]-3-methyl-1,2,3,4-tetrahydroquinoxaline-1-carboxylate;
propan-2-yl (3S)-4-acetyl-7-(1-cyclopropyl-1H-pyrazol-4-yl)-3-methyl-1H,2H,3H,4H-pyrido[2,3-b]pyrazine-1-carboxylate;
3-{4-[(2S)-1-acetyl-4-cyclopropanecarbonyl-2-methyl-1,2,3,4-tetrahydroquinoxalin-6-yl]-1H-pyrazol-1-yl}-1$\lambda^6$-thiane-1,1-dione;
propan-2-yl (3S)-4-acetyl-7-[1-(1,1-dioxo-1$\lambda^6$-thian-3-yl)-1H-pyrazol-4-yl]-3-methyl-1,2,3,4-tetrahydroquinoxaline-1-carboxylate;
cyclohexyl (3S)-4-acetyl-7-[1-(1,1-dioxo-1$\lambda^6$-thian-3-yl)-1H-pyrazol-4-yl]-3-methyl-1,2,3,4-tetrahydroquinoxaline-1-carboxylate;
1-methyl 4-pyridin-2-yl (2S)-6-[1-(1-hydroxy-2-methylpropan-2-yl)-1H-pyrazol-4-yl]-2-methyl-1,2,3,4-tetrahydroquinoxaline-1,4-dicarboxylate;
pyridin-2-yl (3S)-4-acetyl-7-(4-methanesulfonylphenyl)-3-methyl-1,2,3,4-tetrahydroquinoxaline-1-carboxylate;
1-methyl 4-pyridin-2-yl (2S)-6-(4-methanesulfonylphenyl)-2-methyl-1,2,3,4-tetrahydroquinoxaline-1,4-dicarboxylate;
pyridin-2-yl (3S)-4-acetyl-7-(4-methanesulfonamidophenyl)-3-methyl-1,2,3,4-tetrahydroquinoxaline-1-carboxylate;
1-methyl 4-pyridin-2-yl (2S)-6-(4-methanesulfonamidophenyl)-2-methyl-1,2,3,4-tetrahydroquinoxaline-1,4-dicarboxylate;
pyridin-2-yl (3S)-4-acetyl-7-[1-(2-methanesulfonylethyl)-1H-pyrazol-4-yl]-3-methyl-1,2,3,4-tetrahydroquinoxaline-1-carboxylate;
1-methyl 4-pyridin-2-yl (2S)-6-[1-(2-methanesulfonylethyl)-1H-pyrazol-4-yl]-2-methyl-1,2,3,4-tetrahydroquinoxaline-1,4-dicarboxylate;
pyridin-2-yl (3S)-4-acetyl-7-[1-(2-hydroxy-2-methylpropyl)-1H-pyrazol-4-yl]-3-methyl-1,2,3,4-tetrahydroquinoxaline-1-carboxylate;
1-methyl 4-pyridin-2-yl (2S)-6-[1-(2-hydroxy-2-methylpropyl)-1H-pyrazol-4-yl]-2-methyl-1,2,3,4-tetrahydroquinoxaline-1,4-dicarboxylate;
pyridin-2-yl (3S)-4-acetyl-7-(1-cyclopropyl-1H-pyrazol-4-yl)-3-methyl-1,2,3,4-tetrahydroquinoxaline-1-carboxylate;
1-methyl 4-pyridin-2-yl (2S)-6-(1-cyclopropyl-1H-pyrazol-4-yl)-2-methyl-1,2,3,4-tetrahydroquinoxaline-1,4-dicarboxylate;
pyridin-2-yl (3S)-4-acetyl-7-[4-(1,1-dioxo-1$\lambda^6$,2-thiazolidin-2-yl)phenyl]-3-methyl-1,2,3,4-tetrahydroquinoxaline-1-carboxylate;
1-methyl 4-pyridin-2-yl (2S)-6-[4-(1,1-dioxo-1$^6$,2-thiazolidin-2-yl)phenyl]-2-methyl-1,2,3,4-tetrahydroquinoxaline-1,4-dicarboxylate;
pyridin-2-yl (3S)-4-acetyl-7-[1-(2-cyanoethyl)-1H-pyrazol-4-yl]-3-methyl-1,2,3,4-tetrahydroquinoxaline-1-carboxylate;
1-methyl 4-pyridin-2-yl (2S)-6-[1-(2-cyanoethyl)-1H-pyrazol-4-yl]-2-methyl-1,2,3,4-tetrahydroquinoxaline-1,4-dicarboxylate;
pyridin-2-yl (3S)-4-acetyl-7-(1-methanesulfonyl-2,3-dihydro-1H-indol-5-yl)-3-methyl-1,2,3,4-tetrahydroquinoxaline-1-carboxylate;
1-methyl 4-pyridin-2-yl (2S)-6-(1-methanesulfonyl-2,3-dihydro-1H-indol-5-yl)-2-methyl-1,2,3,4-tetrahydroquinoxaline-1,4-dicarboxylate;
pyridin-2-yl (3S)-4-acetyl-3-methyl-7-[4-(N-methylmethanesulfonamido)phenyl]-1,2,3,4-tetrahydroquinoxaline-1-carboxylate;
1-methyl 4-pyridin-2-yl (2S)-2-methyl-6-[4-(N-methylmethanesulfonamido)phenyl]-1,2,3,4-tetrahydroquinoxaline-1,4-dicarboxylate;
pyridin-2-yl (3S)-4-acetyl-3-methyl-7-[1-(piperidin-4-yl)-1H-pyrazol-4-yl]-1,2,3,4-tetrahydroquinoxaline-1-carboxylate;
1-methyl 4-pyridin-2-yl (2S)-2-methyl-6-[1-(piperidin-4-yl)-1H-pyrazol-4-yl]-1,2,3,4-tetrahydroquinoxaline-1,4-dicarboxylate;
pyridin-2-yl (3S)-4-acetyl-7-[1-(2-hydroxyethyl)-1H-pyrazol-4-yl]-3-methyl-1,2,3,4-tetrahydroquinoxaline-1-carboxylate;
1-methyl 4-pyridin-2-yl (2S)-6-[1-(2-hydroxyethyl)-1H-pyrazol-4-yl]-2-methyl-1,2,3,4-tetrahydroquinoxaline-1,4-dicarboxylate;
2,4-difluorophenyl (3S)-4-acetyl-7-[1-(2-hydroxy-2-methylpropyl)-1H-pyrazol-4-yl]-3-methyl-1,2,3,4-tetrahydroquinoxaline-1-carboxylate;
4-chloro-2-methylphenyl (3S)-4-acetyl-7-(1-cyclopropyl-1H-pyrazol-4-yl)-3-methyl-1,2,3,4-tetrahydroquinoxaline-1-carboxylate;
4-fluorophenyl (3S)-4-acetyl-7-[1-(2-hydroxyethyl)-1H-pyrazol-4-yl]-3-methyl-1,2,3,4-tetrahydroquinoxaline-1-carboxylate;
4-fluorophenyl (3S)-4-acetyl-7-[1-(2-hydroxy-2-methylpropyl)-1H-pyrazol-4-yl]-3-methyl-1,2,3,4-tetrahydroquinoxaline-1-carboxylate;
4-fluorophenyl (3S)-4-acetyl-7-[1-(2-methanesulfonylethyl)-1H-pyrazol-4-yl]-3-methyl-1,2,3,4-tetrahydroquinoxaline-1-carboxylate;
4-fluorophenyl (3S)-4-acetyl-7-[1-(2-cyanoethyl)-1H-pyrazol-4-yl]-3-methyl-1,2,3,4-tetrahydroquinoxaline-1-carboxylate;
4-fluorophenyl (3S)-4-acetyl-7-(4-methanesulfonamidophenyl)-3-methyl-1,2,3,4-tetrahydroquinoxaline-1-carboxylate;
4-fluorophenyl (3S)-4-acetyl-3-methyl-7-[1-(piperidin-4-yl)-1H-pyrazol-4-yl]-1,2,3,4-tetrahydroquinoxaline-1-carboxylate;
4-fluorophenyl (3S)-4-acetyl-7-[1-(azetidin-3-yl)-1H-pyrazol-4-yl]-3-methyl-1,2,3,4-tetrahydroquinoxaline-1-carboxylate;
4-fluorophenyl (3S)-4-acetyl-7-[1-(1-hydroxy-2-methylpropan-2-yl)-1H-pyrazol-4-yl]-3-methyl-1,2,3,4-tetrahydroquinoxaline-1-carboxylate;
2,4-difluorophenyl (3S)-4-acetyl-7-[1-(2-hydroxyethyl)-1H-pyrazol-4-yl]-3-methyl-1,2,3,4-tetrahydroquinoxaline-1-carboxylate;
2,4-difluorophenyl (3S)-4-acetyl-7-(4-methanesulfonylphenyl)-3-methyl-1,2,3,4-tetrahydroquinoxaline-1-carboxylate;

2,4-difluorophenyl (3S)-4-acetyl-7-[4-(1,1-dioxo-1λ$^6$,2-thiazolidin-2-yl)phenyl]-3-methyl-1,2,3,4-tetrahydroquinoxaline-1-carboxylate;

2,4-difluorophenyl (3S)-4-acetyl-7-[1-(2-cyanoethyl)-1H-pyrazol-4-yl]-3-methyl-1,2,3,4-tetrahydroquinoxaline-1-carboxylate;

2,4-difluorophenyl (3S)-4-acetyl-7-(4-methanesulfonamidophenyl)-3-methyl-1,2,3,4-tetrahydroquinoxaline-1-carboxylate;

2,4-difluorophenyl (3S)-4-acetyl-7-[1-(1-hydroxy-2-methylpropan-2-yl)-1H-pyrazol-4-yl]-3-methyl-1,2,3,4-tetrahydroquinoxaline-1-carboxylate;

4-fluorophenyl (3S)-4-acetyl-7-[4-(1,1-dioxo-1λ$^6$,2-thiazolidin-2-yl)phenyl]-3-methyl-1,2,3,4-tetrahydroquinoxaline-1-carboxylate;

2,4-difluorophenyl (3S)-4-acetyl-3-methyl-7-[1-(piperidin-4-yl)-1H-pyrazol-4-yl]-1,2,3,4-tetrahydroquinoxaline-1-carboxylate;

4-(4-fluorophenyl) 1-methyl (2S)-6-[1-(2-hydroxyethyl)-1H-pyrazol-4-yl]-2-methyl-1,2,3,4-tetrahydroquinoxaline-1,4-dicarboxylate;

4-(4-fluorophenyl) 1-methyl (2S)-6-[1-(2-hydroxy-2-methylpropyl)-1H-pyrazol-4-yl]-2-methyl-1,2,3,4-tetrahydroquinoxaline-1,4-dicarboxylate;

4-(4-fluorophenyl) 1-methyl (2S)-6-[1-(1-hydroxy-2-methylpropan-2-yl)-1H-pyrazol-4-yl]-2-methyl-1,2,3,4-tetrahydroquinoxaline-1,4-dicarboxylate;

4-(4-fluorophenyl) 1-methyl (2S)-6-[1-(2-cyanoethyl)-1H-pyrazol-4-yl]-2-methyl-1,2,3,4-tetrahydroquinoxaline-1,4-dicarboxylate;

4-(4-fluorophenyl) 1-methyl (2S)-2-methyl-6-[1-(piperidin-4-yl)-1H-pyrazol-4-yl]-1,2,3,4-tetrahydroquinoxaline-1,4-dicarboxylate;

2 S)-1-acetyl-6-(1-cyclopropyl-1H-pyrazol-4-yl)-N-(4-fluorophenyl)-2-methyl-1H,2H,3H,4H-pyrido[2,3-b]pyrazine-4-carboxamide;

(2S)-1-acetyl-6-(1-cyclopropyl-1H-pyrazol-4-yl)-2-methyl-N-(propan-2-yl)-1H,2H,3H,4H-pyrido[2,3-b]pyrazine-4-carboxamide;

4-fluorophenyl (3S)-4-acetyl-7-(1-methanesulfonyl-2,3-dihydro-1H-indol-5-yl)-3-methyl-1,2,3,4-tetrahydroquinoxaline-1-carboxylate;

propan-2-yl (3S)-4-acetyl-7-(1-cyclopropyl-1H-pyrazol-4-yl)-3-methyl-6-nitro-1,2,3,4-tetrahydroquinoxaline-1-carboxylate;

propan-2-yl (3S)-4-acetyl-6-amino-7-(1-cyclopropyl-1H-pyrazol-4-yl)-3-methyl-1,2,3,4-tetrahydroquinoxaline-1-carboxylate;

propan-2-yl (3S)-4-acetyl-7-(1-cyclopropyl-1H-pyrazol-4-yl)-6-methanesulfonamido-3-methyl-1,2,3,4-tetrahydroquinoxaline-1-carboxylate;

propan-2-yl (3S)-4-acetyl-7-(1-cyclopropyl-1H-pyrazol-4-yl)-6-acetamido-3-methyl-1,2,3,4-tetrahydroquinoxaline-1-carboxylate;

propan-2-yl (3S)-4-acetyl-7-(1-cyclopropyl-1H-pyrazol-4-yl)-3-methyl-6-[(methylcarbamoyl)amino]-1,2,3,4-tetrahydroquinoxaline-1-carboxylate;

(3S)-4-acetyl-7-[1-(2-hydroxyethyl)-1H-pyrazol-4-yl]-N,3-dimethyl-N-(propan-2-yl)-1,2,3,4-tetrahydroquinoxaline-1-carboxamide;

(3S)-4-acetyl-7-[1-(2-hydroxyethyl)-1H-pyrazol-4-yl]-N,3-dimethyl-N-phenyl-1,2,3,4-tetrahydroquinoxaline-1-carboxamide;

propan-2-yl (3S)-4-acetyl-6-bromo-7-(4-methanesulfonylphenyl)-3-methyl-1,2,3,4-tetrahydroquinoxaline-1-carboxylate;

propan-2-yl (3S)-4-acetyl-6-chloro-7-(4-methanesulfonylphenyl)-3-methyl-1,2,3,4-tetrahydroquinoxaline-1-carboxylate;

propan-2-yl (3S)-4-acetyl-6-cyano-7-(4-methanesulfonylphenyl)-3-methyl-1,2,3,4-tetrahydroquinoxaline-1-carboxylate;

propan-2-yl (3S)-4-acetyl-6-fluoro-7-(4-methanesulfonylphenyl)-3-methyl-1,2,3,4-tetrahydroquinoxaline-1-carboxylate;

propan-2-yl (3S)-4-acetyl-6-acetamido-7-(4-methanesulfonylphenyl)-3-methyl-1,2,3,4-tetrahydroquinoxaline-1-carboxylate;

propan-2-yl (3S)-4-acetyl-7-(4-methanesulfonylphenyl)-6-[(methoxycarbonyl)amino]-3-methyl-1,2,3,4-tetrahydroquinoxaline-1-carboxylate;

propan-2-yl (3S)-4-acetyl-6-amino-7-(4-methanesulfonylphenyl)-3-methyl-1,2,3,4-tetrahydroquinoxaline-1-carboxylate;

propan-2-yl (3S)-4-acetyl-7-(4-methanesulfonylphenyl)-6-methoxy-3-methyl-1,2,3,4-tetrahydroquinoxaline-1-carboxylate;

propan-2-yl (3S)-4-acetyl-6-acetamido-3-methyl-1,2,3,4-tetrahydroquinoxaline-1-carboxylate;

propan-2-yl (3S)-4-acetyl-6-methanesulfonamido-3-methyl-1,2,3,4-tetrahydroquinoxaline-1-carboxylate;

propan-2-yl (3S)-4-acetyl-6-[(methoxycarbonyl)amino]-3-methyl-1,2,3,4-tetrahydroquinoxaline-1-carboxylate propan-2-yl (3S)-4-acetyl-7-bromo-6-acetamido-3-methyl-1,2,3,4-tetrahydroquinoxaline-1-carboxylate;

propan-2-yl (3S)-4-acetyl-7-(1-cyclopropyl-1H-pyrazol-4-yl)-6-[(methoxycarbonyl)amino]-3-methyl-1,2,3,4-tetrahydroquinoxaline-1-carboxylate;

propan-2-yl (3S)-4-acetyl-6-acetamido-7-[1-(2-hydroxy-2-methylpropyl)-1H-pyrazol-4-yl]-3-methyl-1,2,3,4-tetrahydroquinoxaline-1-carboxylate;

propan-2-yl (3S)-4-acetyl-7-(1-cyclopropyl-1H-pyrazol-4-yl)-6-fluoro-3-methyl-1,2,3,4-tetrahydroquinoxaline-1-carboxylate;

propan-2-yl (3S)-4-acetyl-6-chloro-7-(1-cyclopropyl-1H-pyrazol-4-yl)-3-methyl-1,2,3,4-tetrahydroquinoxaline-1-carboxylate;

propan-2-yl (3S)-4-acetyl-6-bromo-7-(1-cyclopropyl-1H-pyrazol-4-yl)-3-methyl-1,2,3,4-tetrahydroquinoxaline-1-carboxylate;

propan-2-yl (3S)-4-acetyl-7-(1-cyclopropyl-1H-pyrazol-4-yl)-6-methoxy-3-methyl-1,2,3,4-tetrahydroquinoxaline-1-carboxylate;

propan-2-yl (3S)-4-acetyl-6-cyano-7-(1-cyclopropyl-1H-pyrazol-4-yl)-3-methyl-1,2,3,4-tetrahydroquinoxaline-1-carboxylate;

propan-2-yl (3S)-4-acetyl-6-carbamoyl-7-(1-cyclopropyl-1H-pyrazol-4-yl)-3-methyl-1,2,3,4-tetrahydroquinoxaline-1-carboxylate; and propan-2-yl (3S)-7-(1-cyclopropyl-1H-pyrazol-4-yl)-3-methyl-4-(methylcarbamoyl)-1H,2H,3H,4H-pyrido[2,3-b]pyrazine-1-carboxylate.

24. The compound of claim 23 selected from the group consisting of:

cyclobutyl (3S)-4-acetyl-7-[1-(1,1-dioxo-1λ$^6$-thian-4-yl)-1H-pyrazol-4-yl]-3-methyl-1,2,3,4-tetrahydroquinoxaline-1-carboxylate;

cyclobutyl (3S)-4-acetyl-3-methyl-7-{1-[(4S)-2-oxopiperidin-4-yl]-1H-pyrazol-4-yl}-1,2,3,4-tetrahydroquinoxaline-1-carboxylate;

cyclobutyl (3S)-4-acetyl-3-methyl-7-{1-[(4R)-2-oxopiperidin-4-yl]-1H-pyrazol-4-yl}-1,2,3,4-tetrahydroquinoxaline-1-carboxylate;

propan-2-yl (3S)-4-acetyl-3-methyl-7-{1-[(2S)-2-methylazetidin-3-yl]-1H-pyrazol-4-yl}-1,2,3,4-tetrahydroquinoxaline-1-carboxylate;
cyclobutyl (3S)-4-acetyl-7-[1-(1,1-dioxo-1$\lambda^6$-thietan-3-yl)-1H-pyrazol-4-yl]-3-methyl-1,2,3,4-tetrahydroquinoxaline-1-carboxylate;
1-[(2S)-4-cyclopropanecarbonyl-2-methyl-6-[1-(oxan-4-yl)-1H-pyrazol-4-yl]-1,2,3,4-tetrahydroquinoxalin-1-yl]ethan-1-one;
oxan-4-yl (3S)-4-acetyl-3-methyl-7-[1-(oxan-4-yl)-1H-pyrazol-4-yl]-1,2,3,4-tetrahydroquinoxaline-1-carboxylate;
1-[(2S)-2-methyl-4-(1-methyl-1H-indazol-3-yl)-6-[1-(piperidin-4-yl)-1H-pyrazol-4-yl]-1,2,3,4-tetrahydroquinoxalin-1-yl]ethan-1-one;
1-[(2S)-4-cyclopropanecarbonyl-6-(1-methanesulfonyl-2,3-dihydro-1H-indol-5-yl)-2-methyl-1,2,3,4-tetrahydroquinoxalin-1-yl]ethan-1-one;
4-{4-[(2S)-1-acetyl-4-cyclopropanecarbonyl-2-methyl-1,2,3,4-tetrahydroquinoxalin-6-yl]phenyl}-1$\lambda^6$-thiomorpholine-1,1-dione;
cyclobutyl (3S)-4-acetyl-7-{1-[(3R)-1,1-dioxo-1$\lambda^6$-thian-3-yl]-1H-pyrazol-4-yl}-3-methyl-1,2,3,4-tetrahydroquinoxaline-1-carboxylate;
cyclobutyl (3S)-4-acetyl-7-{1-[(3S)-1,1-dioxo-1$\lambda^6$-thian-3-yl]-1H-pyrazol-4-yl}-3-methyl-1,2,3,4-tetrahydroquinoxaline-1-carboxylate;
3-[(2S)-1-acetyl-4-cyclopropanecarbonyl-2-methyl-1,2,3,4-tetrahydroquinoxalin-6-yl]benzene-1-sulfonamide;
1,3-difluoropropan-2-yl (3S)-4-acetyl-7-(1-cyclopropyl-1H-pyrazol-4-yl)-3-methyl-1,2,3,4-tetrahydroquinoxaline-1-carboxylate;
acetyl-4-cyclopropanecarbonyl-2-methyl-1,2,3,4-tetrahydroquinoxalin-6-yl]phenyl}methanesulfonamide;
1-[(2S)-4-cyclopropanecarbonyl-6-{1-[(2,2-difluorocyclopropyl)methyl]-1H-pyrazol-4-yl}-2-methyl-1,2,3,4-tetrahydroquinoxalin-1-yl]ethan-1-one;
propan-2-yl (3S)-4-acetyl-7-[1-(2-cyanoethyl)-1H-pyrazol-4-yl]-3-methyl-1,2,3,4-tetrahydroquinoxaline-1-carboxylate;
1-[(2S)-4-cyclopropanecarbonyl-2-methyl-6-[1-(oxan-4-ylmethyl)-1H-pyrazol-4-yl]-1,2,3,4-tetrahydroquinoxalin-1-yl]ethan-1-one;
3-{4-[(2S)-1-acetyl-4-cyclopropanecarbonyl-2-methyl-1,2,3,4-tetrahydroquinoxalin-6-yl]-1H-pyrazol-1-yl}propanenitrile;
propan-2-yl (3S)-4-cyclopropanecarbonyl-3-methyl-7-[1-(2,2,2-trifluoroethyl)-1H-pyrazol-4-yl]-1,2,3,4-tetrahydroquinoxaline-1-carboxylate;
propan-2-yl (3S)-4-acetyl-7-[1-(2-hydroxy-2-methylpropyl)-1H-pyrazol-4-yl]-3-methyl-1,2,3,4-tetrahydroquinoxaline-1-carboxylate;
propan-2-yl (3S)-4-acetyl-3-methyl-7-[1-(piperidin-4-yl)-1H-pyrazol-4-yl]-1,2,3,4-tetrahydroquinoxaline-1-carboxylate;
propan-2-yl (3S)-4-acetyl-7-[1-(2-hydroxyethyl)-1H-pyrazol-4-yl]-3-methyl-1,2,3,4-tetrahydroquinoxaline-1-carboxylate;
propan-2-yl (3S)-4-acetyl-7-[1-(2-methanesulfonylethyl)-1H-pyrazol-4-yl]-3-methyl-1,2,3,4-tetrahydroquinoxaline-1-carboxylate;
1-[(2S)-4-cyclopropanecarbonyl-6-(1-cyclopropyl-1H-pyrazol-4-yl)-2-methyl-1,2,3,4-tetrahydroquinoxalin-1-yl]ethan-1-one;
propan-2-yl (3S)-4-acetyl-7-{4-[(2-aminoethyl)carbamoyl]phenyl}-3-methyl-1,2,3,4-tetrahydroquinoxaline-1-carboxylate;
propan-2-yl (3S)-4-acetyl-7-[4-(1,1-dioxo-1$\lambda^6$,2-thiazolidin-2-yl)phenyl]-3-methyl-1,2,3,4-tetrahydroquinoxaline-1-carboxylate;
propan-2-yl (3S)-4-acetyl-7-[4-(1,1-dioxo-1$\lambda^6$-thiomorpholin-4-yl)phenyl]-3-methyl-1,2,3,4-tetrahydroquinoxaline-1-carboxylate;
2-{4-[(2S)-1-acetyl-4-cyclopropanecarbonyl-2-methyl-1,2,3,4-tetrahydroquinoxalin-6-yl]phenyl}-1$\lambda^6$,2-thiazolidine-1,1-dione;
ethyl (3S)-4-acetyl-7-(1-cyclopropyl-1H-pyrazol-4-yl)-3-methyl-1,2,3,4-tetrahydroquinoxaline-1-carboxylate;
propan-2-yl (3S)-4-acetyl-7-(4-methanesulfonylphenyl)-3-methyl-1,2,3,4-tetrahydroquinoxaline-1-carboxylate;
1-[(2S)-4-(furan-2-carbonyl)-2-methyl-6-(1-methyl-1H-pyrazol-4-yl)-1,2,3,4-tetrahydroquinoxalin-1-yl]ethan-1-one;
1-[(2S)-4-(furan-2-carbonyl)-6-(4-methanesulfonylphenyl)-2-methyl-1,2,3,4-tetrahydroquinoxalin-1-yl]ethan-1-one;
4-[(2S)-1-acetyl-4-(furan-2-carbonyl)-2-methyl-1,2,3,4-tetrahydroquinoxalin-6-yl]benzamide; and
4-[(2S)-1-acetyl-4-(furan-2-carbonyl)-2-methyl-1,2,3,4-tetrahydroquinoxalin-6-yl]-N,N-dimethylbenzamide.

25. A pharmaceutical composition comprising a compound of claim 1 and a pharmaceutically acceptable carrier.

26. A method of modulating one or more of BET-family bromodomains, comprising administering to a patient in need thereof a therapeutically effective amount of a compound of claim 1.

27. A method of inhibiting one or more of BET-family bromodomains, comprising administering to a patient in need thereof a therapeutically effective amount of a compound of claim 1.

28. A method of inhibiting one or more of BET-family bromodomains, comprising administering to a patient in need thereof a therapeutically effective amount of the pharmaceutical composition of claim 25.

29. A method of treating, a cancer in a patient associated with the inhibition of one or more of BET-family bromodomains, the method comprising administering a therapeutically effective amount of a compound of claim 1, wherein the cancer is selected from the group consisting of lung cancer, cervix cancer, colon cancer, breast cancer, stomach cancers, hematologic cancers, leukemia, lymphoma, multiple myeloma, midline carcinomas, mesenchymal tumors, hepatic tumors, renal tumors, and neurological tumors, melanoma, actinic keratosis, squamous cell carcinoma, and cutaneous T-cell lymphoma.

30. The pharmaceutical composition of claim 25, further comprising a therapeutically effective amount of one or more additional therapeutic agents.

31. The pharmaceutical composition of claim 30, wherein said one or more additional therapeutic agents are selected from the group consisting of cytotoxic agent, cisplatin, doxorubicin, etoposide, irinotecan, topotecan, paclitaxel, docetaxel, the epothilones, tamoxifen, 5-fluorouracil, methotrexate, temozolomide, cyclophosphamide, lonafarnib, tipifarnib, 4-[[-5-[[-4-(3-Chlorophenyl)-3-oxo-1-piperazinyl]methyl]-1H-imidazol-1-yl]methyl]benzonitrile monohydrochloride, (3R)-3-benzyl-1-(1H-imidazol-5-ylmethyl)-4-thiophen-2-ylsulfonyl-3,5-dihydro-2H-1,4-benzodiazepine-7-carbonitrile, gefitinib, erlotinib hydrochloride, cetuximab, imatinib, interferon alfa 2b, pegylated interferon alfa-2b, aromatase combinations, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, leucovorin, oxaliplatin, pentostatine, vinblastine, vincristine, vindesine, bleomycin, dactinomycin, daunorubicin, epirubicin, idarubicin, plicamycin, deoxycoformycin, mitomycin-C, L-asparaginase, teniposide, 17α-ethinylestradiol, diethylstilbestrol, testosterone, prednisone, fluoxymesterone, dromostanolone propionate, testolactone, megestrol acetate, methylprednisolone, methyltestosterone, prednisolone, triamcinolone, chlorotrianisene, 17α-hydroxyprogesterone, aminoglutethimide, estramustine, medroxyprogesteroneacetate, leuprolide acetate, flutamide, toremifene, goserelin acetate, carboplatin, hydroxyurea, amsacrine, procarbazine, mitotane, mitoxantrone, levamisole, vinorelbine, anastrazole, letrazole, capecitabine, reloxafine, droloxafine, hexamethylmelamine, bevacizumab, trastuzumab, tositumomab, bortezomib, ibritumomab tiuxetan, arsenic trioxide, porfimer sodium, cetuximab, thiotepa, altretamine, melphalan, fulvestrant, exemestane, rituximab, alemtuzumab, dexamethasone, bicalutamide, megestrol, or valrubicin.

32. A method of treating an inflammatory disorder in a patient associated with the inhibition of one or more of BET-family bromodomains, the method comprising administering a therapeutically effective amount of a compound of claim 1, wherein the inflammatory disorder is a chronic autoimmune inflammatory condition or an acute inflammatory condition selected from the group consisting of systemic lupus erythematosus, rheumatoid arthritis, atherosclerosis, psoriasis, and alopecia.

33. The method of claim 32, wherein the inflammatory disorder is rheumatoid arthritis.

34. A method of treating leukaemia comprising administering to a patient in need thereof a therapeutically effective amount of the compound of claim 24.

35. A method of treating lymphoma comprising administering to a patient in need thereof a therapeutically effective amount of the compound of claim 24.

* * * * *